US012624034B2

(12) United States Patent
Chu et al.

(10) Patent No.: US 12,624,034 B2
(45) Date of Patent: May 12, 2026

(54) NON-COVALENT MODIFIERS OF AKT1 AND USES THEREOF

(71) Applicant: Terremoto Biosciences, Inc., South San Francisco, CA (US)

(72) Inventors: Hang Chu, San Mateo, CA (US); Kin S. Yang, San Mateo, CA (US); Solomon H. Reisberg, Contra Costa, CA (US); Adam Zajdlik, San Francisco, CA (US); Jordan D. Carelli, San Francisco, CA (US); Brian P. Bestvater, South San Francisco, CA (US); Timothy R. Hansen, San Francisco, CA (US); Peter A. Thompson, Kirkland, WA (US)

(73) Assignee: TERREMOTO BIOSCIENCES, INC., South San Francisco, CA (US)

( * ) Notice: Subject to any disclaimer, the term of this patent is extended or adjusted under 35 U.S.C. 154(b) by 0 days.

(21) Appl. No.: 19/225,802

(22) Filed: Jun. 2, 2025

(65) Prior Publication Data

US 2025/0289820 A1 Sep. 18, 2025

Related U.S. Application Data

(63) Continuation of application No. PCT/US2024/040866, filed on Aug. 2, 2024.

(60) Provisional application No. 63/650,658, filed on May 22, 2024, provisional application No. 63/517,760, filed on Aug. 4, 2023.

(51) Int. Cl.

| | |
|---|---|
| ***C07D 471/04*** | (2006.01) |
| ***A61K 31/437*** | (2006.01) |
| ***A61K 31/444*** | (2006.01) |
| ***A61K 31/4545*** | (2006.01) |
| ***A61K 31/4725*** | (2006.01) |
| ***A61K 31/497*** | (2006.01) |
| ***A61K 31/501*** | (2006.01) |
| ***A61K 31/5025*** | (2006.01) |
| ***A61K 31/506*** | (2006.01) |
| ***A61K 31/519*** | (2006.01) |
| ***A61K 31/53*** | (2006.01) |
| ***A61K 31/5377*** | (2006.01) |
| ***A61K 31/5386*** | (2006.01) |
| ***A61P 35/00*** | (2006.01) |
| ***C07D 519/00*** | (2006.01) |

(52) U.S. Cl.

CPC .......... *C07D 471/04* (2013.01); *A61K 31/437* (2013.01); *A61K 31/444* (2013.01); *A61K 31/4545* (2013.01); *A61K 31/4725* (2013.01); *A61K 31/497* (2013.01); *A61K 31/501* (2013.01); *A61K 31/5025* (2013.01); *A61K 31/506* (2013.01); *A61K 31/519* (2013.01); *A61K 31/53* (2013.01); *A61K 31/5377* (2013.01); *A61K 31/5386* (2013.01); *A61P 35/00* (2018.01); *C07D 519/00* (2013.01)

(58) Field of Classification Search

CPC .. C07D 471/04; C07D 519/00; A61K 31/437; A61K 31/444; A61K 31/4545; A61K 31/4725; A61K 31/497; A61K 31/501; A61K 31/5025; A61K 31/506; A61K 31/519; A61K 31/53; A61K 31/5377; A61K 31/5386; A61P 35/00

See application file for complete search history.

(56) References Cited

U.S. PATENT DOCUMENTS

2022/0098205 A1* 3/2022 Bae .................... A61K 31/4545

FOREIGN PATENT DOCUMENTS

| | | | |
|---|---|---|---|
| WO | WO-2012177844 | A2 | 12/2012 |
| WO | WO-2016037044 | A1 | 3/2016 |
| WO | WO-2017161028 | A1 | 9/2017 |
| WO | WO-2024178390 | A1 | 8/2024 |
| WO | WO-2025034613 | A1 | 2/2025 |

OTHER PUBLICATIONS

Ashwell, Mark A. et al. Discovery And Optimization Of A Series Of 3-(3-phenyl-3h-imidazo[4,5-b]pyridin-2-yl)pyridin-2-amines: Orally Bioavailable, Selective, And Potent ATP-independent Akt Inhibitors. Journal of Medicinal Chemistry 55(11):5291-5310 (2012).

Hinz, Nico, and Manfred Jucker. Distinct functions of AKT isoforms in breast cancer: a comprehensive review. Cell Communication and Signaling 17(1):154, 1-29 (2019).

Klein, Karen A. et al. Progression of metastatic human prostate cancer to androgen independence in immunodeficient SCID mice. Nature medicine 3(4):402-408 (1997).

Lapierre, Jean-Marc et al. Discovery of 3-(3-(4-(1-Aminocyclobutyl) phenyl)-5-phenyl-3 H-imidazo [4, 5-b] pyridin-2-yl) pyridin-2-amine (ARQ 092): An orally bioavailable, selective, and potent allosteric AKT inhibitor. Journal of medicinal chemistry 59(13):6455-6469 (2016).

Pascual, J, and N C Turner. Targeting the PI3-kinase pathway in triple-negative breast cancer. Annals of Oncology 30(7):1051-1060 (2019).

PCT/US2024/040866 International Search Report and Written Opinion dated Nov. 8, 2024.

(Continued)

*Primary Examiner* — Kamal A Saeed

*Assistant Examiner* — Jalisa Holmes Ferguson

(74) *Attorney, Agent, or Firm* — WILSON SONSINI GOODRICH & ROSATI

(57) ABSTRACT

Provided herein are non-covalent modifiers of AKT1 of Formula (I), (II), (II-A), (III), (III-A), (III-B), (IV), (IV-A), (IV-B), (V), (V-A), (V-B), (VI), (VI-A), or (VI-B), and pharmaceutical compositions thereof. In some embodiments, the present disclosure provides methods of modulating wild-type AKT1 using a compound or salt of Formula (I), (II), (II-A), (III), (III-A), (III-B), (IV), (IV-A), (IV-B), (V), (V-A), (V-B), (VI), (VI-A), or (VI-B), and pharmaceutical compositions thereof.

55 Claims, No Drawings

(56) References Cited

OTHER PUBLICATIONS

Song et al., AKT as a Therapeutic Target for Cancer. Cancer Research; 79(6), 1019-1031 (2019).
Vasta, James D. et al. Quantitative, Wide-Spectrum Kinase Profiling in Live Cells for Assessing the Effect of Cellular ATP on Target Engagement. Cell chemical biology 25(2):206-214_e1-e11 (2018). Published Online Nov. 22, 2017.
Yu, Yi et al. Targeting AKT1-E17K and the PI3K/AKT pathway with an allosteric AKT inhibitor, ARQ 092. PLoS One 10(10):e0140479, 1-26 (2015).
Co-pending U.S. Appl. No. 19/224,601, inventors Chu; Hang et al., filed May 30, 2025.

* cited by examiner

NON-COVALENT MODIFIERS OF AKT1 AND USES THEREOF

CROSS-REFERENCE

This application is a continuation application of International Patent Application No. PCT/US2024/040866, filed Aug. 2, 2024, which claims the benefit of U.S. Provisional Application No. 63/517,760 filed Aug. 4, 2023, and U.S. Provisional Application No. 63/650,658 filed May 22, 2024, each of which is incorporated herein by reference in its entirety.

BACKGROUND OF THE INVENTION

The AKT or Protein Kinase B (PKB) family of serine/threonine protein kinases is comprised of 3 highly homologous members, AKT1, AKT2 and AKT3. The family of AKT proteins are involved in signal transduction pathways that regulate cellular processes including apoptosis, proliferation, differentiation, and metabolism. The AKT1 pathway is the most frequently dysregulated signaling pathways in human cancers. Enhanced activation of all the isoforms can be implicated in tumor development and progression, and has been demonstrated in breast, ovarian, pancreatic, and prostate cancers among others (Song et al., 2019). In cancer cells, AKT1 is involved in proliferation and growth, promoting tumor initiation, and suppressing apoptosis, whereas AKT2 regulates cytoskeleton dynamics, favoring local tissue invasion and metastasis. The role of AKT3 hyperactivation in cancer is hypothesized to be involved with possible stimulation of cell proliferation (Hinz et al., *Cell Commun Signal* 2019, 17(1), 154; Pascual et al., *Ann. Oncol.* 2019, 30(7), 1051-1060). Expression of these AKT family members is altered in many human malignant carcinomas including gastric, breast, prostate, ovarian, and pancreatic. AKT family members are rarely mutated however, the most common mutation is AKT1 E17K which has been reported in 6-8% of breast cancers, 2-6% of colorectal cancers, and in 6% of meningiomas, in humans (Yu et al., *PLoS One* 2015, 10 (10), No. e0140479). Thus, there is a need to develop new treatments for the modulation of AKT1 and mutants thereof.

SUMMARY OF THE INVENTION

In one aspect, the present disclosure provides a compound represented by the structure of Formula (I):

(I)

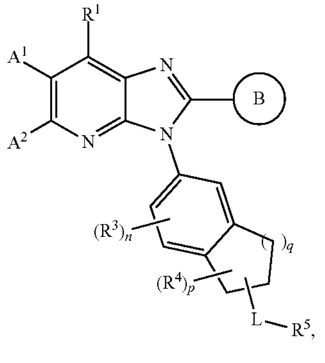

or a pharmaceutically acceptable salt thereof, wherein:

Ring B is selected from:

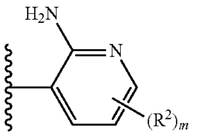

and

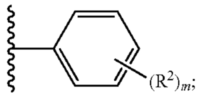

$R^1$ is selected from hydrogen, halogen, $-OR^{10}$, $-SR^{10}$, $-N(R^{10})_2$, $-NO_2$, and $-CN$; and $C_{1-6}$ alkyl optionally substituted with one or more substituents independently selected from: halogen, $C_{3-8}$ carbocycle which is optionally substituted with one or more substituents independently selected from: halogen, $C_{1-4}$ alkyl, $C_{1-4}$ haloalkyl, $-OR^{20}$, $-SR^{20}$, $-N(R^{20})_2$, $-C(O)R^{20}$, $-C(O)OR^{20}$, $-OC(O)R^{20}$, $-C(O)N(R^{20})_2$, $-N(R^{20})C(O)R^{20}$, $-N(R^{20})C(O)N(R^{20})_2$, $-N(R^{20})C(O)OR^{20}$, $-OC(O)N(R^{20})_2$, $-S(O)R^{20}$, $-S(O)_2R^{20}$, $-N(R^{20})S(O)_2R^{20}$, $-S(O)_2N(R^{20})_2$, $-NO_2$, and $-CN$, 4- to 8-membered heterocycle, which is optionally substituted with one or more substituents independently selected from: halogen, $C_{1-4}$ alkyl, $C_{1-4}$ haloalkyl, $-OR^{20}$, $-SR^{20}$, $-N(R^{20})_2$, $-C(O)R^{20}$, $-C(O)OR^{20}$, $-OC(O)R^{20}$, $-C(O)N(R^{20})_2$, $-N(R^{20})C(O)R^{20}$, $-N(R^{20})C(O)N(R^{20})_2$, $-N(R^{20})C(O)OR^{20}$, $-OC(O)N(R^{20})_2$, $-S(O)R^{20}$, $-S(O)_2R^{20}$, $-N(R^{20})S(O)_2R^{20}$, $-S(O)_2N(R^{20})_2$, $-NO_2$, and $-CN$;

$A^1$ and $A^2$ are each independently selected from (i), (ii), and (iii):

(i) hydrogen, halogen, $C_{1-4}$ haloalkyl, $-OR^{11}$, $-SR^{11}$, $-N(R^{11})_2$, $-C(O)N(R^{11})_2$, $-N(R^{11})C(O)R^{11}$, $-C(O)OR^{11}$, $-OC(O)R^{11}$, $-N(R^{11})C(O)OR^{11}$, $-OC(O)N(R^{11})_2$, $-N(R^{11})C(O)N(R^{11})_2$, $-S(O)R^{11}$, $-S(O)_2R^{11}$, $-N(R^{11})S(O)_2R^{11}$, $-S(O)_2N(R^{11})_2$, $-NO_2$, and $-CN$;

(ii) $C_{1-6}$ alkyl, $C_{2-6}$ alkenyl, and $C_{2-6}$ alkynyl, any of which is optionally substituted with one or more substituents independently selected from:

halogen, $-OR^{11}$, $-SR^{11}$, $-N(R^{11})_2$, $-C(O)N(R^{11})_2$, $-N(R^{11})C(O)R^{11}$, $-C(O)OR^{11}$, $-OC(O)R^{11}$, $-N(R^{11})C(O)OR^{11}$, $-OC(O)N(R^{11})_2$, $-N(R^{11})C(O)N(R^{11})_2$, $-S(O)R^{11}$, $-S(O)_2R^{11}$, $-N(R^{11})S(O)_2R^{11}$, $-S(O)_2N(R^{11})_2$, $-NO_2$, $=O$, $=S$, $=N(R^{11})$, and $-CN$; and $C_{3-10}$ carbocycle and 4- to 10-membered heterocycle, any of which is optionally substituted with one or more substituents independently selected from:

halogen, $-OR^{11A}$, $-N(R^{11A})_2$$-C(O)R^{11A}$, $-C(O)N(R^{11A})_2$$-N(R^{11A})C(O)R^{11A}$, $-C(O)OR^{11A}$, $-OC(O)R^{11A}$, $-NO_2$, $=O$, $=S$, $=N(R^{11A})$, $-CN$; and $C_{1-6}$ alkyl $C_{2-6}$ alkenyl, and $C_{2-6}$ alkynyl, any one of which is optionally substituted with one or more substituents independently selected from: halogen, $-OR^{11A}$, $-SR^{11A}$, $-N(R^{11A})_2$$-C(O)R^{11A}$, $-C(O)N(R^{11A})_2$$-N(R^{11A})C(O)R^{11A}$, $-N(R^{11A})S(O)_2R^{11A}$, $-C(O)OR^{11A}$, $-OC(O)R^{11A}$$-NO_2$, $=O$, $=S$, $=N(R^{11A})$, and $-CN$; and (iii) 5- to 10-membered heterocycle and $C_{3-10}$ carbocycle, any of which is optionally substituted with one or more substituents independently selected from:

halogen, $-OR^{11}$, $-SR^{11}$, $-N(R^{11})_2$, $-C(O)R^{11}$, $-C(O)N(R^{11})_2$, $-N(R^{11})C(O)R^{11}$, $-N(R^{11})S(O)_2R^{11}$, $-NS(O)_2N(R^{11})_2$, $-C(O)OR^{11}$, $-OC(O)R^{11}$, $-N(R^{11})C(O)OR^{11}$, $-OC(O)N(R^{11})_2$, —$N(R^{11})C(O)N(R^{11})_2$, —$S(O)R^{11}$, —$S(O)_2R^{11}$, —$S(O)_2N(R^{11})_2$, —$NO_2$, =O, =S, =$N(R^{11})$, and —CN; and $C_{1-6}$ alkyl, $C_{2-6}$ alkenyl, and $C_{3-6}$ alkynyl, any one of which is optionally substituted with one or more substituents independently selected from: halogen, —$OR^{11}$, —$SR^{11}$, —$N(R^{11})_2$, —$C(O)R^{11}$, —$C(O)N(R^{11})_2$, —$N(R^{11})C(O)R^{11}$, —$C(O)OR^{11}$, —$OC(O)R^{11}$, —$N(R^{11})C(O)OR^{11}$, —$OC(O)N(R^{11})_2$, —$N(R^{11})C(O)N(R^{11})_2$, —$S(O)R^{11}$, —$S(O)_2R^{11}$, —$N(R^{11})S(O)_2R^{11}$, —$S(O)_2N(R^{11})_2$, —$NO_2$, =O, =S, =$N(R^{11})$, and —CN; and $C_{3-10}$ carbocycle and 4- to 10-membered heterocycle, any of which is optionally substituted with one or more substituents independently selected from:

halogen, —$OR^{11}$, —$N(R^{11})_2$, —$C(O)R^{11}$, —$C(O)N(R^{11})_2$, —$N(R^{11})C(O)R^{11}$, —$C(O)OR^{11}$, —$OC(O)R^{11}$, —$NO_2$, =O, =S, =$N(R^{11})$, —CN; and $C_{1-6}$ alkyl, $C_{2-6}$ alkenyl, $C_{3-6}$ alkynyl, $C_{3-8}$ carbocycle, or 4- to 8-membered heterocycle, any one of which is optionally substituted with one or more substituents independently selected from: halogen, —$OR^{11}$, —$SR^{11}$, —$N(R^{11})_2$, —$C(O)R^{11}$, —$C(O)N(R^{11})_2$, —$N(R^{11})C(O)R^{11}$, —$N(R^{11})S(O)_2R^{11}$, —$C(O)OR^{11}$, —$OC(O)R^{11}$, —$NO_2$, =O, =S, =$N(R^{11})$, and —CN;

q is selected from 1, 2, and 3;

m and n are each independently selected from 0, 1, 2, and 3;

$R^2$ is independently selected at each instance from halogen, $C_{1-4}$ alkyl, $C_{1-4}$ haloalkyl, —$OR^{12}$, —$SR^{12}$, —$N(R^{12})_2$, —$NO_2$, and —CN;

$R^3$ is independently selected at each instance from:

halogen, —$OR^{13}$, —$SR^{13}$, —$N(R^{13})_2$, —$C(O)R^{13}$, —$C(O)N(R^{13})_2$, —$N(R^{13})C(O)R^{13}$, —$C(O)OR^{13}$, —$OC(O)R^{13}$, —$NO_2$, and —CN; and $C_{1-6}$ alkyl optionally substituted with one or more substituents independently selected from:

halogen, —$OR^{13}$, —$SR^{13}$, —$N(R^{13})_2$, —$C(O)R^{13}$, —$C(O)N(R^{13})_2$, —$N(R^{13})C(O)R^{13}$, —$C(O)OR^{13}$, —$OC(O)R^{13}$, —$NO_2$, =O, =S, =$N(R^{13})$, and —CN;

p is selected from 0, 1, 2, 3, 4, and 5;

$R^4$ is independently selected at each instance from:

halogen, —$OR^{14}$, —$SR^{14}$, —$N(R^{14})_2$, —$C(O)R^{14}$, —$C(O)N(R^{14})_2$, —$N(R^{14})C(O)R^{14}$, —$C(O)OR^{14}$, —$OC(O)R^{14}$, —$NO_2$, and —CN; and $C_{1-6}$ alkyl, $C_{2-6}$ alkenyl, $C_{2-6}$ alkynyl, any one of which is optionally substituted with one or more substituents independently selected from halogen, —$OR^{14}$, —$SR^{14}$, —$N(R^{14})_2$, —$C(O)R^{14}$, —$C(O)N(R^{14})_2$, —$N(R^{14})C(O)R^{14}$, —$C(O)OR^{14}$, —$OC(O)R^{14}$, —$NO_2$, =O, =S, =$N(R^{14})$, and —CN; or two $R^4$ attached to the same atom are taken together to form a group selected from: =O, =S, and =$N(R^{14})$; or two $R^4$ attached to the same atom or to adjacent atoms are taken together with the carbons to which they are attached to form a group selected from 4- to 8-membered heterocycle and $C_{3-8}$ carbocycle, any of which is optionally substituted with one or more substituents independently selected from: halogen, $C_{1-4}$ alkyl, $C_{1-4}$ haloalkyl, —$OR^{14}$, —$SR^{14}$, —$N(R^{14})_2$, —$NO_2$, and —CN;

L is represented by -$L^1$-$L^2$-$L^3$-$L^4$-, wherein $L^1$, $L^2$, $L^3$, and $L^4$ are each independently selected from (a) and (b):

(a) —O—, —$N(R^{15})$—, —S—, —S(O)—, —$S(O)_2$—, —$S(O)(NR^{15})$—, —$N(R^{15})C(O)$—, —$N(R^{15})C(O)O$—, —$N(R^{15})S(O)_2$—, —$N(R^{15})S(O)_2N(R^{15})$—, —$S(O)(NR^{15})N(R^{15})$—, —$N(R^{15})N(R^{15})$—, —$(R^{15})NC(O)N(R^{15})$—, and —$(R^{15})NC(O)N(R^{15})N(R^{15})$—; and (b) $C_{1-6}$ alkylene, $C_{2-6}$ alkenylene, $C_{2-6}$ alkynylene, $C_{3-8}$ carbocyclene, and 4- to 8-membered heterocyclene, any of which is optionally substituted with one or more substituents independently selected from halogen, —$OR^5$, —$SR^{15}$, =O, =S, and —CN;

wherein $L^1$, $L^2$, $L^3$, and $L^4$ are each optionally absent;

wherein no more than two of $L^1$, $L^2$, $L^3$, and $L^4$ are selected from (a) and the two selected are not adjacent;

$R^5$ is selected from 4- to 10-membered heterocycle and $C_{3-10}$ carbocycle, any of which is optionally substituted with one or more substituents independently selected from:

halogen, $C_{1-4}$ haloalkyl, —$OR^{16}$, —$SR^{16}$, —$N(R^{16})_2$, —$C(O)N(R^{16})_2$, —$C(O)OR^{16}$, —$OC(O)R^{16}$, —$N(R^{16})C(O)R^{16}$, —$N(R^{16})S(O)_2R^{16}$, —$S(O)_2N(R^{16})_2$, —$N(R^{16})C(O)N(R^{16})_2$, —$N(R^{16})C(O)OR^{16}$, —$OC(O)N(R^{16})_2$, —$S(O)R^{16}$, —$S(O)_2R^{16}$, —$NO_2$, =O, =S, =$N(R^{16})$, and —CN;

$C_{1-6}$ alkyl, $C_{2-6}$ alkenyl, and $C_{2-6}$ alkynyl, each of which is optionally substituted with one or more substituents independently selected from: halogen, —$OR^{16}$, —$SR^{16}$, —$N(R^{16})_2$, —$NO_2$, and —CN; and 4- to 6-membered heterocycle and $C_{3-8}$ carbocycle, each of which is optionally substituted with one or more substituents independently selected from: halogen, $C_{1-4}$ alkyl, $C_{1-4}$ haloalkyl, —$OR^{16}$, —$SR^{16}$, —$N(R^{16})_2$, —$NO_2$, and —CN;

$R^{10}$, $R^{11}$, $R^{11A}$, $R^{12}$, $R^{13}$, $R^{14}$, and $R^{15}$ are each independently selected at each occurrence from:

hydrogen, $C_{1-4}$ alkyl, $C_{3-8}$ carbocycle, 3- to 8-membered heterocycle, and $C_{1-4}$ haloalkyl;

$R^{16}$ is independently selected at each occurrence from (iv), (v), and (vi):

(iv) hydrogen;

(v) $C_{1-4}$ alkyl, wherein the $C_{1-4}$ alkyl is optionally substituted with one or more substituents independently selected from:

halogen, —$OR^{20}$, —$SR^{20}$, —$N(R^{20})_2$, —$C(O)R^{20}$, —$C(O)OR^{20}$, —$OC(O)R^{20}$, —$C(O)N(R^{20})_2$, —$N(R^{20})C(O)R^{20}$, —$N(R^{20})C(O)N(R^{20})_2$, —$N(R^{20})C(O)OR^{20}$, $OC(O)N(R^{20})_2$, —$S(O)R^{20}$, —$S(O)_2R^{20}$, —$N(R^{20})S(O)_2R^{20}$, —$S(O)_2N(R^{20})_2$, —$NO_2$, and —CN; and $C_{3-8}$ carbocycle and 3- to 8-membered heterocycle, either of which is optionally substituted with one or more substituents independently selected from: halogen, $C_{1-4}$ alkyl, $C_{1-4}$ haloalkyl, —$OR^{20}$, —$SR^{20}$, —$N(R^{20})_2$, —$C(O)R^{20}$, —$C(O)OR^{20}$, —$OC(O)R^{20}$, —$C(O)N(R^{20})_2$, —$N(R^{20})C(O)R^{20}$, —$N(R^{20})C(O)N(R^{20})_2$, —$N(R^{20})C(O)OR^{20}$, —$OC(O)N(R^{20})_2$, —$S(O)R^{20}$, —$S(O)_2R^{20}$, —$N(R^{20})S(O)_2R^{20}$, —$S(O)_2N(R^{20})_2$, —$NO_2$, and —CN; and $C_{3-8}$ carbocycle and 4- to 8-membered heterocycle, either of which is optionally substituted with one or more substituents independently selected from halogen, $C_{1-4}$ alkyl, $C_{1-4}$ haloalkyl, —$OR^{20}$, —$SR^{20}$, —$N(R^{20})_2$, —$C(O)R^{20}$, —$C(O)N(R^{20})_2$, —$C(O)OR^{20}$, —$OC(O)R^{20}$, —$N(R^{20})C$ (O)$R^{20}$, —N($R^{20}$)S(O)$_2R^{20}$, —N($R^{20}$)C(O)N($R^{20}$)$_2$, —N($R^{20}$)C(O)O$R^{20}$, —OC(O)N($R^{20}$)$_2$, —S(O)$R^{20}$, —S(O)$_2R^{20}$, —NO$_2$, —CN, and $C_{3-8}$ carbocycle or 4- to 8-membered heterocycle, either of which is optionally further substituted with one or more substituents independently selected from halogen, $C_{1-4}$ alkyl, $C_{1-4}$ haloalkyl, —O$R^{20}$, —S$R^{20}$, —N($R^{20}$)$_2$, —C(O)$R^{20}$, —C(O)N($R^{20}$)$_2$, —C(O)O$R^{20}$, —OC(O)$R^{20}$, —N($R^{20}$)C(O)$R^{20}$, —N($R^{20}$)S(O)$_2R^{20}$, —N($R^{20}$)C(O)N($R^{20}$)$_2$, —N($R^{20}$)C(O)O$R^{20}$, —OC(O)N($R^{20}$)$_2$, —S(O)$R^{20}$, —S(O)$_2R^{20}$, —NO$_2$, and —CN; and $R^{20}$ is independently selected at each occurrence from hydrogen, $C_{1-4}$ alkyl, $C_{1-4}$ haloalkyl, $C_{3-8}$ carbocycle, and 4- to 8-membered heterocycle.

In one other aspect, the present disclosure provides a compound represented by the structure of Formula (II):

(II)

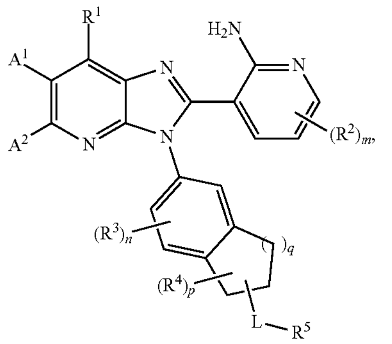

or a pharmaceutically acceptable salt thereof, wherein:

$R^1$ is selected from hydrogen, halogen, —O$R^{10}$, —S$R^{10}$, —N($R^{10}$)$_2$, —NO$_2$, and —CN; and $C_{1-6}$ alkyl optionally substituted with one or more substituents independently selected from: halogen, —O$R^{10}$, —S$R^{10}$, —N($R^{10}$)$_2$, —NO$_2$, and —CN;

$A^1$ and $A^2$ are each independently selected from (i), (ii), and (iii):

(i) hydrogen, halogen, $C_{1-4}$ haloalkyl, —O$R^{11}$, —S$R^{11}$, —N($R^{11}$)$_2$, —C(O)N($R^{11}$)$_2$, —N($R^{11}$)C(O)$R^{11}$, —C(O)O$R^{11}$, —OC(O)$R^{11}$, —N($R^{11}$)C(O)O$R^{11}$, —OC(O)N($R^{11}$)$_2$, —N($R^{11}$)C(O)N($R^{11}$)$_2$, —S(O)$R^{11}$, —S(O)$_2R^{11}$, —N($R^{11}$)S(O)$_2R^{11}$, —S(O)$_2$N($R^{11}$)$_2$, —NO$_2$, and —CN;

(ii) $C_{1-6}$ alkyl, $C_{2-6}$ alkenyl, and $C_{2-6}$ alkynyl, any of which is optionally substituted with one or more substituents independently selected from halogen, —O$R^{11}$, —S$R^{11}$, —N($R^{11}$)$_2$, —C(O)N($R^{11}$)$_2$, —N($R^{11}$)C(O)$R^{11}$, —C(O)O$R^{11}$, —OC(O)$R^{11}$, —N($R^{11}$)C(O)O$R^{11}$, —OC(O)N($R^{11}$)$_2$, —N($R^{11}$)C(O)N($R^{11}$)$_2$, —S(O)$R^{11}$, —S(O)$_2R^{11}$, —N($R^{11}$)S(O)$_2$ $R^{11}$, —S(O)$_2$N($R^{11}$)$_2$, —NO$_2$, =O, =S, =N($R^{11}$), and —CN; and (iii) 5- to 10-membered heterocycle and $C_{3-10}$ carbocycle, any of which is optionally substituted with one or more substituents independently selected from:

halogen, —O$R^{11}$, —S$R^{11}$, —N($R^{11}$)$_2$, —C(O)$R^{11}$, —C(O)N($R^{11}$)$_2$, —N($R^{11}$)C(O)$R^{11}$, —N($R^{11}$)S(O)$_2R^{11}$, —C(O)O$R^{11}$, —OC(O)$R^{11}$, —N($R^{11}$)C(O)O$R^{11}$, —OC(O)N($R^{11}$)$_2$, —N($R^{11}$)C(O)N($R^{11}$)$_2$, —S(O)$R^{11}$, —S(O)$_2R^{11}$, —S(O)$_2$N($R^{11}$)$_2$, —NO$_2$, =O, =S, =N($R^{11}$), and —CN; and $C_{1-6}$ alkyl, $C_{2-6}$ alkenyl, and $C_{3-6}$ alkynyl, any one of which is optionally substituted with one or more substituents independently selected from: halogen, —O$R^{11}$, —S$R^{11}$, —N($R^{11}$)$_2$, —C(O)$R^{11}$, —C(O)N($R^{11}$)$_2$, —N($R^{11}$)C(O)$R^{11}$, —C(O)O$R^{11}$, —OC(O)$R^{11}$, —N($R^{11}$)C(O)O$R^{11}$, —OC(O)N($R^{11}$)$_2$, —N($R^{11}$)C(O)N($R^{11}$)$_2$, —S(O)$R^{11}$, —S(O)$_2R^{11}$, —N($R^{11}$)S(O)$_2R^{11}$, —S(O)$_2$N($R^{11}$)$_2$, —NO$_2$, =O, =S, =N($R^{11}$), and —CN; and $C_{3-10}$ carbocycle and 4- to 10-membered heterocycle, any of which is optionally substituted with one or more substituents independently selected from:

halogen, —O$R^{11}$, —N($R^{11}$)$_2$, —C(O)$R^{11}$, —C(O)N($R^{11}$)$_2$, —N($R^{11}$)C(O)$R^{11}$, —C(O)O$R^{11}$, —OC(O)$R^{11}$, —NO$_2$, =O, =S, =N($R^{11}$), —CN; and $C_{1-6}$ alkyl $C_{2-6}$ alkenyl, and $C_{3-6}$ alkynyl, any one of which is optionally substituted with one or more substituents independently selected from: halogen, —O$R^{11}$, —S$R^{11}$, —N($R^{11}$)$_2$, —C(O)$R^{11}$, —C(O)N($R^{11}$)$_2$, —N($R^{11}$)C(O)$R^{11}$, —N($R^{11}$)S(O)$_2R^{11}$, —C(O)O$R^{11}$, —OC(O)$R^{11}$, —NO$_2$, =O, =S, =N($R^{11}$), and —CN;

q is selected from 1, 2, and 3;

m and n are each independently selected from 0, 1, 2, and 3;

$R^2$ is independently selected at each instance from halogen, $C_{1-4}$ alkyl, $C_{1-4}$ haloalkyl, —O$R^{12}$, —S$R^{12}$, —N($R^{12}$)$_2$, —NO$_2$, and —CN;

$R^3$ is independently selected at each instance from:

halogen, —O$R^{13}$, —S$R^{13}$, —N($R^{13}$)$_2$, —C(O)$R^{13}$, —C(O)N($R^{13}$)$_2$, —N($R^{13}$)C(O)$R^{13}$, —C(O)O$R^{13}$, —OC(O)$R^{13}$, —NO$_2$, and —CN; and $C_{1-6}$ alkyl optionally substituted with one or more substituents independently selected from:

halogen, —O$R^{13}$, —S$R^{13}$, —N($R^{13}$)$_2$, —C(O)$R^{13}$, —C(O)N($R^{13}$)$_2$, —N($R^{13}$)C(O)$R^{13}$, —C(O)O$R^{13}$, —OC(O)$R^{13}$, —NO$_2$, =O, =S, =N($R^{13}$), and —CN;

p is selected from 0, 1, 2, 3, 4, and 5;

$R^4$ is independently selected at each instance from:

halogen, —O$R^{14}$, —S$R^{14}$, —N($R^{14}$)$_2$, —C(O)$R^{14}$, —C(O)N($R^{14}$)$_2$, —N($R^{14}$)C(O)$R^{14}$, —C(O)O$R^{14}$, —OC(O)$R^{14}$, —NO$_2$, and —CN; and $C_{1-6}$ alkyl, $C_{2-6}$ alkenyl, $C_{2-6}$ alkynyl, any one of which is optionally substituted with one or more substituents independently selected from halogen, —O$R^{14}$, —S$R^{14}$, —N($R^{14}$)$_2$, —C(O)$R^{14}$, —C(O)N($R^{14}$)$_2$, —N($R^{14}$)C(O)$R^{14}$, —C(O)O$R^{14}$, —OC(O)$R^{14}$, —NO$_2$, =O, =S, =N($R^{14}$), and —CN; or two $R^4$ attached to the same atom are taken together to form a group selected from: =O, =S, and =N($R^{14}$); or two $R^4$ attached to the same atom or to adjacent atoms are taken together with the carbons to which they are attached to form a group selected from 4- to 8-membered heterocycle and $C_{3-8}$ carbocycle, any of which is optionally substituted with one or more substituents independently selected from: halogen, $C_{1-4}$ alkyl, $C_{1-4}$ haloalkyl, —O$R^{14}$, —S$R^{14}$, —N($R^{14}$)$_2$, —NO$_2$, and —CN;

L is represented by -$L^1$-$L^2$-$L^3$-$L^4$-, wherein $L^1$, $L^2$, $L^3$, and $L^4$ are each independently selected from (a) and (b):

(a) —O—, —N($R^{15}$)—, —S—, —S(O)—, —S(O)$_2$—, —S(O)(N$R^{15}$)—, —N($R^{15}$)C(O)—, —N($R^{15}$)C(O)O—, —N($R^{15}$)S(O)$_2$—, —N($R^{15}$)S(O)$_2$N($R^{15}$)—,

—S(O)(NR$^{15}$)N(R$^{15}$)—, —N(R$^{15}$)N(R$^{15}$)—, —(R$^{15}$)NC(O)N(R$^{15}$)—, and —(R$^{15}$)NC(O)N(R$^{15}$)N(R$^{15}$)—; and (b) $C_{1-6}$ alkylene, $C_{2-6}$ alkenylene, $C_{2-6}$ alkynylene, $C_{3-8}$ carbocyclene, and 4- to 8-membered heterocyclene, any of which is optionally substituted with one or more substituents independently selected from halogen, —OR$^1$, —SR$^{15}$, =O, =S, and —CN;

wherein $L^2$, $L^3$, and $L^4$ are each optionally absent;

wherein no more than two of $L^1$, $L^2$, $L^3$, and $L^4$ are selected from (a) and the two selected are not adjacent;

$R^5$ is selected from 4- to 10-membered heterocycle and $C_{3-10}$ carbocycle, any of which is optionally substituted with one or more substituents independently selected from:

halogen, $C_{1-4}$ haloalkyl, —OR$^{16}$, —SR$^{16}$, —N(R$^{16}$)$_2$, —C(O)N(R$^{16}$)$_2$, —C(O)OR$^{16}$, —OC(O)R$^{16}$, —N(R$^{16}$)C(O)R$^{16}$, —N(R$^{16}$)S(O)$_2$R$^{16}$, —S(O)$_2$N(R$^{16}$)$_2$, —N(R$^{16}$)C(O)N(R$^{16}$)$_2$, —N(R$^{16}$)C(O)OR$^{16}$, —OC(O)N(R$^{16}$)$_2$, —S(O)R$^{16}$, —S(O)$_2$R$^{16}$, —NO$_2$, =O, =S, =N(R$^{16}$), and —CN;

$C_{1-4}$ alkyl, $C_{2-6}$ alkenyl, and $C_{2-6}$ alkynyl, each of which is optionally substituted with one or more substituents independently selected from: halogen, $C_{1-4}$ alkyl, $C_{1-4}$ haloalkyl, —OR$^{16}$, —SR$^{16}$, —N(R$^{16}$)$_2$, —NO$_2$, and —CN; and 4- to 6-membered heterocycle and $C_{3-8}$ carbocycle, each of which is optionally substituted with one or more substituents independently selected from: halogen, $C_{1-4}$ alkyl, $C_{1-4}$ haloalkyl, —OR$^{16}$, —SR$^{16}$, —N(R$^{16}$)$_2$, —NO$_2$, and —CN;

$R^{10}$, $R^{11}$, $R^{12}$, $R^{13}$, $R^{14}$, and $R^{15}$ are each independently selected at each occurrence from: hydrogen, $C_{1-4}$ alkyl, $C_{3-8}$ carbocycle, 4- to 8-membered heterocycle, and $C_{1-4}$ haloalkyl;

$R^{16}$ is independently selected at each occurrence from (iv), (v), and (vi):

(iv) hydrogen;

(v) $C_{1-4}$ alkyl, wherein the $C_{1-4}$ alkyl is optionally substituted with one or more substituents independently selected from:

halogen, —OR$^{20}$, —SR$^{20}$, —N(R$^{20}$)$_2$, —C(O)R$^{20}$, —C(O)OR$^{20}$, —OC(O)R$^{20}$, —C(O)N(R$^{20}$)$_2$, —N(R$^{20}$)C(O)R$^{20}$, —N(R$^{20}$)C(O)N(R$^{20}$)$_2$, —N(R$^{20}$)C(O)OR$^{20}$, OC(O)N(R$^{20}$)$_2$, —S(O)R$^{20}$, —S(O)$_2$R$^{20}$, —N(R$^{20}$)S(O)$_2$R$^{20}$, —S(O)$_2$N(R$^{20}$)$_2$, —NO$_2$, and —CN;

$C_{3-8}$ carbocycle and 4- to 8-membered heterocycle, either of which is optionally substituted with one or more substituents independently selected from: halogen, $C_{1-4}$ alkyl, $C_{1-4}$ haloalkyl, —OR$^{20}$, —SR$^{20}$, —N(R$^{20}$)$_2$, —C(O)R$^{20}$, —C(O)OR$^{20}$, —OC(O)R$^{20}$, —C(O)N(R$^{20}$)$_2$, —N(R$^{20}$)C(O)R$^{20}$, —N(R$^{20}$)C(O)N(R$^{20}$)$_2$, —N(R$^{20}$)C(O)OR$^{20}$, —OC(O)N(R$^{20}$)$_2$, —S(O)R$^{20}$, —S(O)$_2$R$^{20}$, —N(R$^{20}$)S(O)$_2$R$^{20}$, —S(O)$_2$N(R$^{20}$)$_2$, —NO$_2$, and —CN; and (vi) $C_{3-8}$ carbocycle and 4- to 8-membered heterocycle, either of which is optionally substituted with one or more substituents independently selected from halogen, $C_{1-4}$ alkyl, $C_{1-4}$ haloalkyl, —OR$^{20}$, —SR$^{20}$, —N(R$^{20}$)$_2$, —C(O)R$^{20}$, —C(O)N(R$^{20}$)$_2$, —C(O)OR$^{20}$, —OC(O)R$^{20}$, —N(R$^{20}$)C(O)R$^{20}$, —N(R$^{20}$)S(O)$_2$R$^{20}$, —N(R$^{20}$)C(O)N(R$^{20}$)$_2$, —N(R$^{20}$)C(O)OR$^{20}$, —OC(O)N(R$^{20}$)$_2$, —S(O)R$^{20}$, —S(O)$_2$R$^{20}$, —NO$_2$, and —CN; and $R^{20}$ is independently selected at each occurrence from hydrogen, $C_{1-4}$ alkyl, $C_{1-4}$ haloalkyl, $C_{3-8}$ carbocycle, and 4- to 8-membered heterocycle.

In some embodiments, the compound or salt of Formula (II) is represented by the structure of Formula (III):

(III)

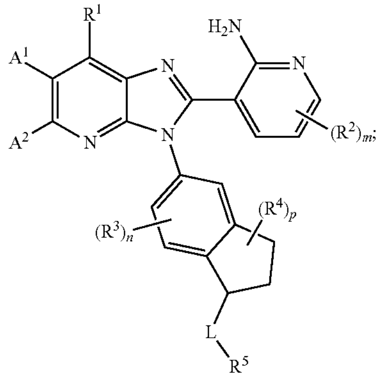

or a pharmaceutically acceptable salt thereof.

In some embodiments, the compound or salt of Formula (II) is represented by the structure of Formula (III-A):

(III-A)

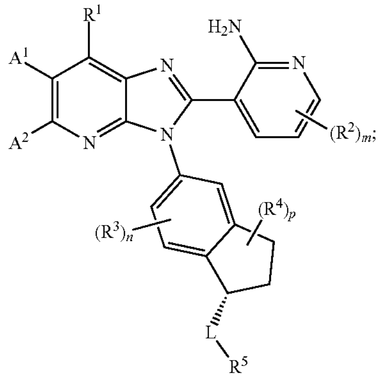

or a pharmaceutically acceptable salt thereof.

In some embodiments, the compound or salt of Formula (II) is represented by the structure of Formula (IV):

(IV)

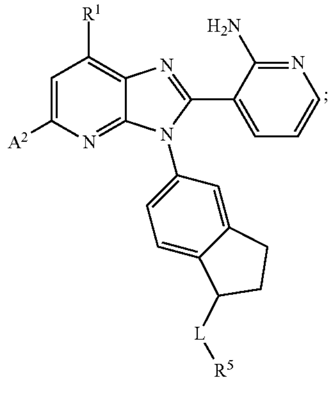

or a pharmaceutically acceptable salt thereof.

In some embodiments, the compound or salt of Formula (II) is represented by the structure of Formula (IV-A):

(IV-A)

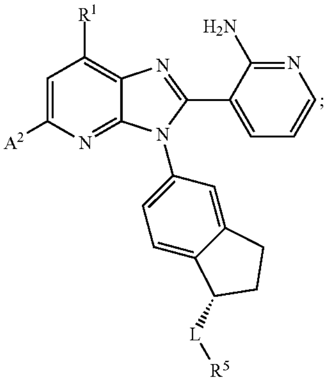

or a pharmaceutically acceptable salt thereof.

In some embodiments, the compound or salt of Formula (II) is represented by the structure of Formula (V):

(V)

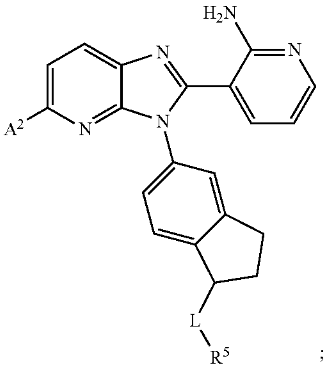

or a pharmaceutically acceptable salt thereof.

In some embodiments, the compound or salt of Formula (II) is represented by the structure of Formula (V-A):

(V-A)

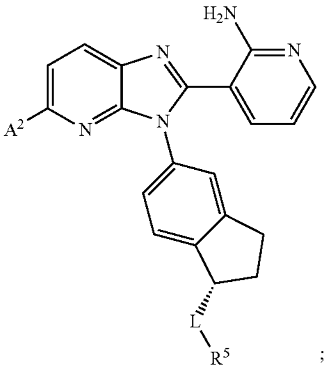

or a pharmaceutically acceptable salt thereof.

In one aspect, the present disclosure provides a pharmaceutical composition comprising a pharmaceutically acceptable excipient and a compound of Formula (I), (II), (III), (III-A), (IV), (IV-A), (V), (V-A), or a pharmaceutically acceptable salt thereof.

In one aspect, the present disclosure provides a method of modulating activity of wild-type AKT1 comprising, administering to a subject in need thereof a compound of Formula (I), (II), (III), (III-A), (IV), (IV-A), (V), (V-A), or a pharmaceutically acceptable salt thereof, or a pharmaceutical composition of the present disclosure comprising a pharmaceutically acceptable excipient and a compound of Formula (I), (II), (III), (III-A), (IV), (IV-A), (V), (V-A), or a pharmaceutically acceptable salt thereof. In one aspect, the present disclosure provides a method of modulating activity of a mutant AKT1 comprising, administering to a subject in need thereof a compound of Formula (I), (II), (III), (III-A), (IV), (IV-A), (V), (V-A), or a pharmaceutically acceptable salt thereof, or a pharmaceutical composition of the present disclosure comprising a pharmaceutically acceptable excipient and a compound of Formula (I), (II), (III), (III-A), (IV), (IV-A), (V), (V-A), or a pharmaceutically acceptable salt thereof. In some embodiments, the mutant AKT1 is AKT1 E17K.

In one aspect, the present disclosure provides a method of selectively modulating activity of wild-type AKT1 over wild-type AKT2 comprising administering to a subject in need thereof a compound of Formula (I), (II), (III), (III-A), (IV), (IV-A), (V), (V-A), or pharmaceutically acceptable salt thereof, or a pharmaceutical composition of the present disclosure comprising a pharmaceutically acceptable excipient and a compound of Formula (I), (II), (III), (III-A), (IV), (IV-A), (V), (V-A), or a pharmaceutically acceptable salt thereof.

In one aspect, the present disclosure provides a method of selectively modulating activity of a mutant AKT1 over wild-type AKT2 comprising administering to a subject in need thereof a compound of Formula (I), (II), (III), (III-A), (IV), (IV-A), (V), (V-A), or pharmaceutically acceptable salt thereof, or a pharmaceutical composition of the present disclosure comprising a pharmaceutically acceptable excipient and a compound of Formula (I), (II), (III), (III-A), (IV), (IV-A), (V), (V-A), or a pharmaceutically acceptable salt thereof. In some embodiments, the mutant AKT1 is AKT1 E17K.

In one aspect, the present disclosure provides a method of treating cancer in a subject in need thereof, the method comprising administering to the subject a compound of Formula (I), (II), (III), (III-A), (IV), (IV-A), (V), (V-A), or pharmaceutically acceptable salt thereof, or a pharmaceutical composition of the present disclosure comprising a pharmaceutically acceptable excipient and a compound of Formula (I), (II), (III), (III-A), (IV), (IV-A), (V), (V-A), or a pharmaceutically acceptable salt thereof. In some embodiments, the cancer is selected from breast cancer, colorectal cancer, and meningioma. In some embodiments, the administration modulates activity of wild-type AKT1. In some embodiments, the administration modulates activity of a mutant AKT1. In some embodiments, the mutant AKT1 is AKT1 E17K.

INCORPORATION BY REFERENCE

All publications, patents, and patent applications mentioned in this specification are herein incorporated by reference for the specific purposes identified herein.

DETAILED DESCRIPTION OF THE INVENTION

The AKT or Protein Kinase B (PKB) family of serine/threonine protein kinases regulate a myriad of key cellular functions, including apoptosis, proliferation, differentiation and metabolism. The AKT family is comprised of 3 highly homologous members, AKT1, AKT2 and AKT3, and each member possesses a unique tissue distribution and may perform a unique set of biological functions. Aberrant expression and/or activation of all AKT isoforms has been implicated in tumor development, including breast, ovarian, pancreatic, and prostate cancers among others.

Inhibitors of AKT proteins have been developed for the treatment of cancer, including the two major classes of small-molecule AKT inhibitors being investigated in the clinic: allosteric and ATP-competitive inhibitors. First, allosteric inhibitors (such as miransertib (ARQ 092) and MK-2206) interfere with PH-domain mediated membrane recruitment (the first step in AKT activation) and inhibit AKT kinase activation and AKT phosphorylation. Second, ATP-competitive inhibitors of AKT (such as ipatasertib and capivasertib) bind to the active kinase, in which the PH-domain has shifted from the kinase domain and exposed the ATP-binding pocket site, thus inhibiting ATP binding.

Provided herein are compounds for modulating (e.g., inhibiting) AKT1 function, as well as methods and compositions for using compounds of the present disclosure in the treatment of cancer. In some embodiments, the compounds selectively inhibit (e.g., 2×, 5×, 10×, 50×, 100×, etc.) an AKT1 protein over an AKT2 and/or AKT3 protein.

Definitions

Unless defined otherwise, all technical and scientific terms used herein have the same meaning as is commonly understood by one of skill in the art to which this invention belongs. All patents and publications referred to herein are incorporated by reference.

As used in the specification and claims, the singular form "a," "an," and "the" includes plural references unless the context clearly dictates otherwise.

"Alkyl" refers to a straight or branched hydrocarbon chain monovalent radical consisting solely of carbon and hydrogen atoms, containing no unsaturation, and preferably having from one to twelve carbon atoms (i.e., $C_{1-12}$ alkyl). The alkyl is attached to the remainder of the molecule through a single bond. An alkyl chain may be optionally substituted by one or more substituents such as those substituents described herein. In certain embodiments, an alkyl comprises one to twelve carbon atoms (i.e., $C_{1-12}$ alkyl). In certain embodiments, an alkyl comprises one to eight carbon atoms (i.e., $C_{1-8}$ alkyl). In other embodiments, an alkyl comprises one to five carbon atoms (i.e., $C_{1-5}$ alkyl). In other embodiments, an alkyl comprises one to four carbon atoms (i.e., $C_{1-4}$ alkyl). In other embodiments, an alkyl comprises one to three carbon atoms (i.e., $C_{1-3}$ alkyl). In other embodiments, an alkyl comprises one to two carbon atoms (i.e., $C_{1-2}$ alkyl). In other embodiments, an alkyl comprises one carbon atom (i.e., $C_1$ alkyl). In other embodiments, an alkyl comprises five to fifteen carbon atoms (i.e., $C_{5-15}$ alkyl). In other embodiments, an alkyl comprises five to eight carbon atoms (i.e., $C_{5-8}$ alkyl). In other embodiments, an alkyl comprises two to five carbon atoms (i.e., $C_{2-5}$ alkyl). In other embodiments, an alkyl comprises three to five carbon atoms (i.e., $C_{3-5}$ alkyl). For example, the alkyl group may be attached to the rest of the molecule by a single bond, such as, methyl, ethyl, 1-propyl (n-propyl), 1-methylethyl (iso-propyl), 1-butyl (n-butyl), 1-methylpropyl (sec-butyl), 2-methylpropyl (iso-butyl), 1,1-dimethylethyl (tert-butyl), 1-pentyl (n-pentyl), and the like.

"Alkenyl" refers to a straight or branched hydrocarbon chain radical group consisting solely of carbon and hydrogen atoms, containing at least one carbon-carbon double bond, and preferably having from two to twelve carbon atoms (i.e., $C_{2-12}$ alkenyl). An alkenyl chain may be optionally substituted by one or more substituents such as those substituents described herein. In certain embodiments, an alkenyl comprises two to eight carbon atoms (i.e., $C_{2-8}$ alkenyl). In certain embodiments, an alkenyl comprises two to six carbon atoms (i.e., $C_{2-6}$ alkenyl). In other embodiments, an alkenyl comprises two to four carbon atoms (i.e., $C_{2-4}$ alkenyl). The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like.

"Alkynyl" refers to a straight or branched hydrocarbon chain radical group consisting solely of carbon and hydrogen atoms, containing at least one carbon-carbon triple bond, and preferably having from two to twelve carbon atoms (i.e., $C_{2-12}$ alkynyl). An alkylnyl chain may be optionally substituted by one or more substituents such as those substituents described herein. In certain embodiments, an alkynyl comprises two to eight carbon atoms (i.e., $C_{2-8}$ alkynyl). In other embodiments, an alkynyl comprises two to six carbon atoms (i.e., $C_{2-6}$ alkynyl). In other embodiments, an alkynyl comprises two to four carbon atoms (i.e., $C_{2-4}$ alkynyl). The alkynyl is attached to the rest of the molecule by a single bond, for example, ethynyl, propynyl, butynyl, pentynyl, hexynyl, and the like.

"Alkylene" refers to a straight or branched divalent hydrocarbon chain linking the rest of the molecule to a radical group, consisting solely of carbon and hydrogen, containing no unsaturation, and preferably having from one to twelve carbon atoms, for example, methylene, ethylene, propylene, (methyl)ethylene, butylene, and the like. The alkylene chain is attached to the rest of the molecule through a single bond and to the radical group through a single bond. An alkylene chain may be optionally substituted by one or more substituents such as those substituents described herein. In certain embodiments, an alkylene comprises one to ten carbon atoms (i.e., $C_{1-10}$ alkylene). In certain embodiments, an alkylene comprises one to eight carbon atoms (i.e., $C_{1-8}$ alkylene). In other embodiments, an alkylene comprises one to five carbon atoms (i.e., $C_{1-5}$ alkylene). In other embodiments, an alkylene comprises one to four carbon atoms (i.e., $C_{1-4}$ alkylene). In other embodiments, an alkylene comprises one to three carbon atoms (i.e., $C_{1-3}$ alkylene). In other embodiments, an alkylene comprises one to two carbon atoms (i.e., $C_{1-2}$ alkylene). In other embodiments, an alkylene comprises one carbon atom (i.e., $C_1$ alkylene). In other embodiments, an alkylene comprises five to eight carbon atoms (i.e., $C_{5-8}$ alkylene). In other embodiments, an alkylene comprises two to five carbon atoms (i.e., $C_{2-5}$ alkylene). In other embodiments, an alkylene comprises three to five carbon atoms (i.e., $C_{3-5}$ alkylene).

"Alkenylene" refers to a straight or branched divalent hydrocarbon chain linking the rest of the molecule to a radical group, consisting solely of carbon and hydrogen, containing at least one carbon-carbon double bond, and preferably having from two to twelve carbon atoms. The alkenylene chain is attached to the rest of the molecule through a single bond and to the radical group through a single bond. An alkenylene chain may be optionally substituted by one or more substituents such as those substituents described herein. In certain embodiments, an alkenylene comprises two to ten carbon atoms (i.e., $C_{2-10}$ alkenylene). In certain embodiments, an alkenylene comprises two to eight carbon atoms (i.e., $C_{2-8}$ alkenylene). In other embodiments, an alkenylene comprises two to five carbon atoms (i.e., $C_{2-5}$ alkenylene). In other embodiments, an alkenylene comprises two to four carbon atoms (i.e., $C_{2-4}$ alkenylene). In other embodiments, an alkenylene comprises two to three carbon atoms (i.e., $C_{2-3}$ alkenylene). In other embodiments, an alkenylene comprises two carbon atoms (i.e., $C_2$ alkenylene). In other embodiments, an alkenylene comprises five to eight carbon atoms (i.e., $C_{5-8}$ alkenylene). In other embodiments, an alkenylene comprises three to five carbon atoms (i.e., $C_{3-5}$ alkenylene).

"Alkynylene" refers to a straight or branched divalent hydrocarbon chain linking the rest of the molecule to a radical group, consisting solely of carbon and hydrogen, containing at least one carbon-carbon triple bond, and preferably having from two to twelve carbon atoms. The alkynylene chain is attached to the rest of the molecule through a single bond and to the radical group through a single bond. An alkynylene chain may be optionally substituted by one or more substituents such as those substituents described herein. In certain embodiments, an alkynylene comprises two to ten carbon atoms (i.e., $C_{2-10}$ alkynylene). In certain embodiments, an alkynylene comprises two to eight carbon atoms (i.e., $C_{2-8}$ alkynylene). In other embodiments, an alkynylene comprises two to five carbon atoms (i.e., $C_{2-5}$ alkynylene). In other embodiments, an alkynylene comprises two to four carbon atoms (i.e., $C_{2-4}$ alkynylene). In other embodiments, an alkynylene comprises two to three carbon atoms (i.e., $C_{2-3}$ alkynylene). In other embodiments, an alkynylene comprises two carbon atoms (i.e., $C_2$ alkynylene). In other embodiments, an alkynylene comprises five to eight carbon atoms (i.e., $C_{2-3}$ alkynylene). In other embodiments, an alkynylene comprises three to five carbon atoms (i.e., $C_{3-5}$ alkynylene).

The term "$C_{x-y}$" when used in conjunction with a chemical moiety, such as alkyl, alkenyl, or alkynyl is meant to include groups that contain from x to y carbons in the chain. For example, the term "$C_{1-6}$ alkyl" refers to saturated hydrocarbon groups, including straight-chain alkyl and branched-chain alkyl groups that contain from 1 to 6 carbons. The term $—C_{x-y}$ alkylene- refers to an alkylene chain with from x to y carbons in the alkylene chain. For example, $—C_{1-6}$ alkylene- may be selected from methylene, ethylene, propylene, butylene, pentylene, and hexylene, any one of which may be optionally substituted.

The terms "$C_{x-y}$ alkenyl" and "$C_{x-y}$ alkynyl" refer to unsaturated aliphatic groups analogous in length and possible substitution to the alkyls described above, but that contain at least one double or triple bond, respectively. The term $—C_{x-y}$ alkenylene- refers to a alkenylene chain with from x to y carbons in the alkenylene chain. For example, $—C_{2-6}$ alkenylene- may be selected from ethenylene, propenylene, butenylene, pentenylene, and hexenylene, any one of which may be optionally substituted. An alkenylene chain may have one double bond or more than one double bond in the alkenylene chain. The term $—C_{x-y}$ alkynylene- refers to a alkynylene chain with from x to y carbons in the alkynylene chain. For example, $—C_{2-6}$ alkynylene- may be selected from ethynylene, propynylene, butynylene, pentynylene, and hexynylene, any one of which may be optionally substituted. An alkynylene chain may have one triple bond or more than one triple bond in the alkynylene chain.

The term "carbocycle" as used herein refers to a saturated, unsaturated or aromatic ring in which each atom of the ring is carbon. Carbocycle includes 3- to 10-membered monocyclic rings and polycyclic rings (e.g., 6- to 12-membered bicyclic rings). Each ring of a polycyclic carbocycle may be selected from saturated, unsaturated, and aromatic rings. Polycyclic carbocycles may be fused, bridged or spiro-ring systems. Each ring of a bicyclic carbocycle may be selected from saturated, unsaturated, and aromatic rings. Bicyclic carbocycles may be fused, bridged or spiro-ring systems. In some embodiments, the carbocycle is an aryl. In some embodiments, the carbocycle is a cycloalkyl. In some embodiments, the carbocycle is a cycloalkenyl. In an exemplary embodiment, an aromatic ring, e.g., phenyl, may be fused to a saturated or unsaturated ring, e.g., cyclohexane, cyclopentane, or cyclohexene. Any combination of saturated, unsaturated and aromatic bicyclic rings, as valence permits, are included in the definition of carbocyclic. Exemplary carbocycles include cyclopentyl, cyclohexyl, cyclohexenyl, adamantyl, phenyl, indanyl, and naphthyl. Carbocycle may be optionally substituted by one or more substituents such as those substituents described herein.

The term "carbocyclene" as used herein refers to a divalent saturated, unsaturated or aromatic ring in which each atom of the ring is carbon. The carbocyclene is attached to the rest of the molecule through a single bond and to the radical group through a single bond. A carbocyclene may be optionally substituted by one or more substituents such as those substituents described herein. Carbocyclene includes divalent 3- to 10-membered monocyclic rings and divalent polycyclic rings (e.g., 6- to 12-membered bicyclic rings). Each ring of a polycyclic carbocyclene may be selected from saturated, unsaturated, and aromatic rings. Polycyclic carbocyclenes may be fused, bridged or spiro-ring systems. Polycyclic carbocyclenes may be fused, bridged or spiro-ring systems. The single bond connecting the carbocyclene to the rest of the molecule and the single bond connecting the carbocyclene to the radical group may be located on the same ring or different rings of a polycyclic carbocyclene. In some embodiments, the carbocycle is an arylene, for example, a phenylene. A "phenylene" as used herein refers to a divalent benzene group. The phenylene is attached to the rest of the molecule through a single bond and to the radical group through a single bond. A phenylene may be optionally substituted by one or more substituents such as those substituents described herein.

"Cycloalkyl" refers to a stable fully saturated monocyclic or polycyclic hydrocarbon radical consisting solely of carbon and hydrogen atoms, which includes fused, bridged, or spiro-ring systems, and preferably having from three to twelve carbon atoms (i.e., $C_{3-12}$ cycloalkyl). In certain embodiments, a cycloalkyl comprises three to ten carbon atoms (i.e., $C_{3-10}$ cycloalkyl). In other embodiments, a cycloalkyl comprises five to seven carbon atoms (i.e., $C_{5-7}$ cycloalkyl). The cycloalkyl may be attached to the rest of the molecule by a single bond. Examples of monocyclic cycloalkyls include, e.g., cyclopropyl, cyclobutyl, cyclopentyl, cyclohexyl, cycloheptyl, and cyclooctyl. Polycyclic cycloalkyl radicals include, for example, adamantyl, norbornyl (i.e., bicyclo[2.2.1]heptanyl), norbornenyl, decalinyl, 7,7-dimethyl-bicyclo[2.2.1]heptanyl, and the like. Cycloalkyl may be optionally substituted by one or more substituents such as those substituents described herein.

"Aryl" refers to a radical derived from an aromatic monocyclic or aromatic polycyclic hydrocarbon ring system by removing a hydrogen atom from a ring carbon atom. The aromatic monocyclic or aromatic multicyclic hydrocarbon ring system contains only hydrogen and carbon and from five to eighteen carbon atoms, where at least one of the rings in the ring system is aromatic, i.e., it contains a cyclic, delocalized (4n+2) p-electron system in accordance with the Hückel theory. The ring system from which aryl groups are derived include, but are not limited to, groups such as benzene, fluorene, indane, indene, tetralin and naphthalene. Aryl may be optionally substituted by one or more substituents such as those substituents described herein.

A "$C_{x-y}$ carbocycle" is meant to include groups that contain from x to y carbons in a ring. For example, the term "$C_{3-6}$ carbocycle" can be a saturated, unsaturated or aromatic ring system that contains from 3 to 6 carbon atoms-any one of which may be optionally substituted as provided herein.

The term "heterocycle" as used herein refers to a saturated, unsaturated, non-aromatic or aromatic ring comprising one or more heteroatoms. Exemplary heteroatoms include N, O, Si, P, B, and S atoms. Heterocycles include 3- to 10-membered monocyclic rings and polycyclic rings (e.g., 6- to 12-membered bicyclic rings). Polycyclic heterocycles may be fused, bridged or spiro-ring systems. Each ring of a polycyclic heterocycle may be selected from saturated, unsaturated, and aromatic rings. In some embodiments, the heterocycle comprises at least one heteroatom selected from oxygen, nitrogen, sulfur, or any combination thereof. In some embodiments, the heterocycle comprises at least one heteroatom selected from oxygen, nitrogen, or any combination thereof. In some embodiments, the heterocycle comprises at least one heteroatom selected from oxygen, sulfur, or any combination thereof. In some embodiments, the heterocycle comprises at least one heteroatom selected from nitrogen, sulfur, or any combination thereof. The heterocycle may be attached to the rest of the molecule through any atom of the heterocycle, valence permitting, such as a carbon or nitrogen atom of the heterocycle. In some embodiments, the heterocycle is a heteroaryl. In some embodiments, the heterocycle is a heterocycloalkyl. Exemplary heterocycles include pyrrolidinyl, pyrrolyl, imidazolyl, pyrazolyl, triazolyl, piperidinyl, pyridinyl, pyrimidinyl, pyridazinyl, pyrazinyl, thiophenyl, oxazolyl, thiazolyl, morpholinyl, indazolyl, indolyl, and quinolinyl. Heterocycle may be optionally substituted by one or more substituents such as those substituents described herein. Bicyclic heterocycles may be fused, bridged or spiro-ring systems. In an exemplary embodiment, a heterocycle, e.g., pyridyl, may be fused to a saturated or unsaturated ring, e.g., cyclohexane, cyclopentane, or cyclohexene. Heterocycle may be optionally substituted by one or more substituents such as those substituents described herein.

The term "heterocyclene" as used herein refers to a divalent saturated, unsaturated, non-aromatic or aromatic ring comprising one or more heteroatoms. Exemplary heteroatoms include N, O, Si, P, B, and S atoms. The heterocyclene is attached to the rest of the molecule through a single bond and to the radical group through a single bond. The single bond attaching the heterocyclene group to the rest of the molecule and the single bond attaching the heterocyclene group to the radical group may be each independently connected through any atom of the heterocyclene as valency permits, including a carbon atom in the heterocyclene ring or a heteroatom in the heterocyclene ring. A heterocyclene may be optionally substituted by one or more substituents such as those substituents described herein. Heterocyclenes include 3- to 10-membered monocyclic rings and polycyclic rings (e.g., 6- to 12-membered bicyclic rings). Each ring of a polycyclic heterocyclene may be selected from saturated, unsaturated, and aromatic rings. Polycyclic heterocyclenes may be fused, bridged or spiro-ring systems. The single bond connecting the heterocyclene to the rest of the molecule and the single bond connecting the heterocyclene to the radical group may be located on the same ring or different rings of a polycyclic heterocyclene and may be attached to the rest of the molecule or the radical group through any atom of the heterocyclene, valence permitting, such as a carbon or nitrogen atom of the heterocycle. In some embodiments, the heterocyclene comprises at least one heteroatom selected from oxygen, nitrogen, sulfur, or any combination thereof. In some embodiments, the heterocyclene comprises at least one heteroatom selected from oxygen, nitrogen, or any combination thereof. In some embodiments, the heterocyclene comprises at least one heteroatom selected from oxygen, sulfur, or any combination thereof. In some embodiments, the heterocyclene comprises at least one heteroatom selected from nitrogen, sulfur, or any combination thereof. In some embodiments, the heterocyclene is a heteroarylene. In some embodiments, the heterocyclene is a heterocycloalkylene.

"Heterocycloalkyl" refers to a stable 3 to 12 membered non-aromatic ring radical that comprises two to twelve carbon atoms and at least one heteroatom wherein each heteroatom may be selected from N, O, Si, P, B, and S atoms. In some embodiments, the heterocycloalkyl comprises at least one heteroatom selected from oxygen, nitrogen, sulfur, or any combination thereof. In some embodiments, the heterocycloalkyl comprises at least one heteroatom selected from oxygen, nitrogen, or any combination thereof. In some embodiments, the heterocycloalkyl comprises at least one heteroatom selected from oxygen, sulfur, or any combination thereof. In some embodiments, the heterocycloalkyl comprises at least one heteroatom selected from nitrogen, sulfur, or any combination thereof. The heterocycloalkyl may be selected from monocyclic or bicyclic, and fused, bridged, or spiro-ring systems. The heteroatoms in the heterocycloalkyl radical are optionally oxidized. One or more nitrogen atoms, if present, are optionally quaternized. The heterocycloalkyl radical is partially or fully saturated. The heterocycloalkyl is attached to the rest of the molecule through any atom of the heterocycloalkyl, valence permitting, such as any carbon or nitrogen atoms of the heterocycloalkyl. Examples of heterocycloalkyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxothiomorpholinyl, and 1,1-dioxothiomorpholinyl. Heterocycloalkyl may be optionally substituted by one or more substituents such as those substituents described herein.

The term "heteroaryl" refers to a radical derived from a 5- to 12-membered aromatic ring radical whose ring structure comprise at least one heteroatom, preferably between one to four heteroatoms. In some embodiments, the heteroaryl comprises at least one heteroatom selected from oxygen, nitrogen, sulfur, or any combination thereof. In some embodiments, the heteroaryl comprises at least one heteroatom selected from oxygen, nitrogen, or any combination thereof. In some embodiments, the heteroaryl comprises at least one heteroatom selected from oxygen, sulfur, or any combination thereof. In some embodiments, the heteroaryl comprises at least one heteroatom selected from nitrogen, sulfur, or any combination thereof. As used herein, the heteroaryl ring may be selected from monocyclic or bicyclic and fused or bridged ring systems wherein at least one of the rings in the ring system is aromatic, i.e., it contains a cyclic, delocalized (4n+2) p-electron system in accordance with the Hückel theory. The heteroatom(s) in the heteroaryl radical may be optionally oxidized. One or more nitrogen atoms, if present, are optionally quaternized. The heteroaryl may be attached to the rest of the molecule through any atom of the heteroaryl, valence permitting, such as a carbon or nitrogen atom of the heteroaryl. Heteroaryl includes aromatic single ring structures, preferably 5- to 6-membered rings, whose ring structures include at least one heteroatom, preferably one to four heteroatoms, more preferably one or two heteroatoms. Heteroaryl groups include, for example, pyrrole, furan, thiophene, imidazole, oxazole, thiazole, pyrazole, pyridine, pyrazine, pyridazine, and pyrimidine, and the like. Heteroaryl may be optionally substituted by one or more substituents such as those substituents described herein. Heteroaryl also includes polycyclic ring systems having two or more rings in which two or more atoms are common to two adjoining rings wherein at least one of the rings is heteroaromatic, e.g., the other rings can be aromatic or non-aromatic carbocyclic, or heterocyclic. Heteroaryl may be optionally substituted by one or more substituents such as those substituents described herein.

An "X-membered heterocycle" refers to the number of endocyclic atoms, i.e., X, in the ring. For example, a 5-membered heteroaryl ring or 5-membered aromatic heterocycle has 5 endocyclic atoms, e.g., triazole, oxazole, thiophene, etc.

"Alkoxy" refers to a radical bonded through an oxygen atom of the formula: —O-alkyl, where alkyl is an alkyl chain as defined above.

"Halo" or "halogen" refers to halogen substituents such as bromo, chloro, fluoro, and iodo substituents.

As used herein, the term "haloalkyl" or "haloalkane" refers to an alkyl radical, as defined above, that is substituted by one or more halogen radicals, for example, trifluoromethyl, dichloromethyl, bromomethyl, 2,2,2-trifluoroethyl, 1-fluoromethyl-2-fluoroethyl, and the like. In some embodiments, the alkyl part of the fluoroalkyl radical is optionally further substituted. Examples of halogen substituted alkanes ("haloalkanes") include halomethane (e.g., chloromethane, bromomethane, fluoromethane, iodomethane), di- and trihalomethane (e.g., trichloromethane, tribromomethane, trifluoromethane, triiodomethane), 1-haloethane, 2-haloethane, 1,2-dihaloethane, 1-halopropane, 2-halopropane, 3-halopropane, 1,2-dihalopropane, 1,3-dihalopropane, 2,3-dihalopropane, 1,2,3-trihalopropane, and any other suitable combinations of alkanes (or substituted alkanes) and halogens (e.g., Cl, Br, F, and I). When an alkyl group is substituted with more than one halogen radical, each halogen may be independently selected for example, 1-chloro,2-fluoroethane.

The term "substituted" refers to moieties having substituents replacing a hydrogen on one or more carbons or substitutable heteroatoms, e.g., an NH or $NH_2$ of a compound. Unless specified otherwise (e.g., by using the terms "substituted" or "optionally substituted," or by the inclusion of an "—R" group), chemical groups described herein are unsubstituted. It will be understood that "substitution" or "substituted with" includes the implicit proviso that such substitution is in accordance with permitted valence of the substituted atom and the substituent, and that the substitution results in a stable compound, i.e., a compound which does not spontaneously undergo transformation such as by rearrangement, cyclization, elimination, etc. In certain embodiments, substituted refers to moieties having substituents replacing two hydrogen atoms on the same carbon atom, such as substituting the two hydrogen atoms on a single carbon with an oxo, imino, or thioxo group. As used herein, the term "substituted" is contemplated to include all permissible substituents of organic compounds. In a broad aspect, the permissible substituents include acyclic and cyclic, branched and unbranched, carbocyclic and heterocyclic, and aromatic and non-aromatic substituents of organic compounds. The permissible substituents can be one or more and the same or different for appropriate organic compounds.

In some embodiments, substituents may include any substituents described herein, for example: halogen, hydroxy, oxo (=O), thioxo (=S), cyano (—CN), nitro (—$NO_2$), imino (=N—H), oximo (=N—OH), hydrazino (=N—$NH_2$), —$R^b$—$OR^a$, —$R^b$—OC(O)$R^a$, —$R^b$—OC(O)$OR^a$, —$R^b$—OC(O)N($R^a$)$_2$, —$R^b$—N($R^a$)$_2$, —$R^b$—C(O)$R^a$, —$R^b$—C(O)$OR^a$, —$R^b$—C(O)N($R^a$)$_2$, —$R^b$—O—$R^c$—C(O)N($R^a$)$_2$, —$R^b$—N($R^a$)C(O)$OR^a$, —$R^b$—N($R^a$)C(O)$R^a$, —$R^b$—N($R^a$)S(O)$_t$$R^a$ (where t is 1 or 2), —$R^b$—S(O)$_t$$R^a$ (where t is 0, 1, or 2), —$R^b$—S(O)$OR^a$ (where t is 1 or 2), —$R^b$—S(O)$_t$N($R^a$)$_2$ (where t is 1 or 2), and —P(O)($R^a$)$_2$; and alkyl, alkenyl, alkynyl, aryl, aralkyl, aralkenyl, aralkynyl, cycloalkyl, cycloalkylalkyl, heterocycloalkyl, heterocycloalkylalkyl, heteroaryl, and heteroarylalkyl any one of which may be optionally substituted by alkyl, alkenyl, alkynyl, halogen, haloalkyl, haloalkenyl, haloalkynyl, oxo (=O), thioxo (=S), cyano (—CN), nitro (—$NO_2$), imino (=N—H), oximo(=N—OH), hydrazine(=N—$NH_2$), —$R^b$—$OR^a$, —$R^b$—OC(O)$R^a$, —$R^b$—OC(O)$OR^a$, —$R^b$—OC(O)N($R^a$)$_2$, —$R^b$—N($R^a$)$_2$, —$R^b$—C(O)$R^a$, —$R^b$—C(O)$OR^a$, —$R^b$—C(O)N($R^a$)$_2$, —$R^b$—O—$R^c$—C(O)N($R^a$)$_2$, —$R^b$—N($R^a$)C(O)$OR^a$, —$R^b$—N($R^a$)C(O)$R^a$, —$R^b$—N($R^a$)S(O)$_t$$R^a$ (where t is 1 or 2), —$R^b$—S(O)$_t$$R^a$ (where t is 0, 1, or 2), —$R^b$—S(O)$OR^a$ (where t is 1 or 2), —$R^b$—S(O)$_t$N($R^a$)$_2$ (where t is 1 or 2), and —P(O)($R^a$)$_2$; wherein each $R^a$ is independently selected from hydrogen, alkyl, cycloalkyl, cycloalkylalkyl, aryl, aralkyl, heterocycloalkyl, heterocycloalkylalkyl, heteroaryl, or heteroarylalkyl, wherein each $R^a$, valence permitting, may be optionally substituted with alkyl, alkenyl, alkynyl, halogen, haloalkyl, haloalkenyl, haloalkynyl, oxo (=O), thioxo (=S), cyano (—CN), nitro (—$NO_2$), imino (=N—H), oximo (=N—OH), hydrazine (=N—$NH_2$), —$R^b$—$OR^a$, —$R^b$—OC(O)—$R^a$, —$R^b$—OC(O)—$OR^a$, —$R^b$—OC(O)—N($R^a$)$_2$, —$R^b$—N($R^a$)$_2$, —$R^b$—C(O)$R^a$, —$R^b$—C(O)$OR^a$, —$R^b$—C(O)N($R^a$)$_2$, —$R^b$—O—$R^c$—C(O)N($R^a$)$_2$, —$R^b$—N($R^a$)C(O)$OR^a$, —$R^b$—N($R^a$)C(O)$R^a$, —$R^b$—N($R^a$)S(O)$_t$$R^a$ (where t is 1 or 2), —$R^b$—S(O)$R^a$ (where t is 0, 1, or 2), —$R^b$—S(O)$OR^a$ (where t is 1 or 2), —$R^b$—S(O)$_t$N($R^a$)$_2$ (where t is 1 or 2), and —P(O)($R^a$)$_2$; and wherein each $R^b$ is independently selected from a direct bond or a straight or branched alkylene, alkenylene, or alkynylene chain, and each $R^c$ is a straight or branched alkylene, alkenylene or alkynylene chain. It will be understood by those skilled in the art that substituents can themselves be substituted, if appropriate.

The term "salt" or "pharmaceutically acceptable salt" refers to salts derived from a variety of organic and inorganic counter ions well known in the art. Pharmaceutically acceptable acid addition salts can be formed with inorganic acids and organic acids. Pharmaceutically acceptable base addition salts can be formed with inorganic and organic bases.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable excipient" or "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the patient.

The terms "subject," "individual," and "patient" may be used interchangeably and refer to humans as well as non-human mammals (e.g., non-human primates, canines, equines, felines, porcines, bovines, ungulates, lagomorphs, and the like). In various embodiments, the subject can be a human (e.g., adult male, adult female, adolescent male, adolescent female, male child, female child) under the care of a physician or other health worker in a hospital, as an outpatient, or other clinical context. In certain embodiments, the subject may not be under the care or prescription of a physician or other health worker.

As used herein, the phrase "a subject in need thereof" refers to a subject, as described infra, that suffers from, or is at risk for, a pathology to be prophylactically or therapeutically treated with a compound or salt described herein.

The terms "administer," "administered," "administers," and "administering" are defined as providing a composition to a subject via a route known in the art, including but not limited to intravenous, intraarterial, oral, parenteral, buccal, topical, transdermal, rectal, intramuscular, subcutaneous, intraosseous, transmucosal, or intraperitoneal routes of administration. In certain embodiments, oral routes of administering a composition can be used. The terms "administer," "administered," "administers," and "administering" a compound should be understood to mean providing a compound or salt of the invention or a prodrug of a compound or salt of the invention to the individual in need.

As used herein, "treatment" or "treating" refers to an approach for obtaining beneficial or desired results with respect to a disease, disorder, or medical condition including, but not limited to, a therapeutic benefit and/or a prophylactic benefit. In certain embodiments, treatment or treating involves administering a compound or composition disclosed herein to a subject. A therapeutic benefit may include the eradication or amelioration of the underlying disorder being treated. Also, a therapeutic benefit may be achieved with the eradication or amelioration of one or more of the physiological symptoms associated with the underlying disorder, such as observing an improvement in the subject, notwithstanding that the subject may still be afflicted with the underlying disorder. In certain embodiments, for prophylactic benefit, the compositions are administered to a subject at risk of developing a particular disease, or to a subject reporting one or more of the physiological symptoms of a disease, even though a diagnosis of this disease may not have been made. Treating can include, for example, reducing, delaying or alleviating the severity of one or more symptoms of the disease or condition, or it can include reducing the frequency with which symptoms of a disease, defect, disorder, or adverse condition, and the like, are experienced by a patient. Treating can be used herein to refer to a method that results in some level of treatment or amelioration of the disease or condition and can contemplate a range of results directed to that end, including but not limited to prevention of the condition entirely.

In certain embodiments, the term "prevent" or "preventing" as related to a disease or disorder may refer to a compound that, in a statistical sample, reduces the occurrence of the disorder or condition in the treated sample relative to an untreated control sample, or delays the onset or reduces the severity of one or more symptoms of the disorder or condition relative to the untreated control sample.

A "therapeutic effect," as that term is used herein, encompasses a therapeutic benefit and/or a prophylactic benefit as described above. A prophylactic effect includes delaying or eliminating the appearance of a disease or condition, delaying or eliminating the onset of symptoms of a disease or condition, slowing, halting, or reversing the progression of a disease or condition, or any combination thereof.

Compounds

In some aspects, the present disclosure provides compounds represented by the structure of Formula (I):

(I)

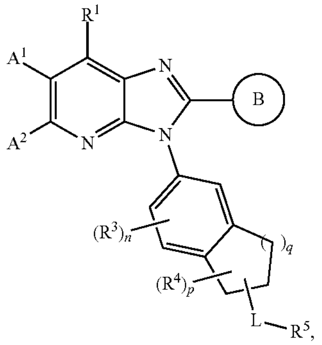

or a pharmaceutically acceptable salt thereof, wherein:

Ring B is selected from:

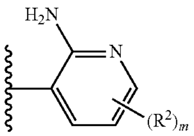 and 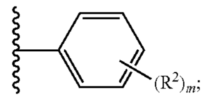;

$R^1$ is selected from hydrogen, halogen, $—OR^{10}$, $—SR^{10}$, $—N(R^{10})_2$, $—NO_2$, and —CN; and $C_{1-6}$ alkyl optionally substituted with one or more substituents independently selected from: halogen, $—OR^{10}$, $—SR^{10}$, $—N(R^{10})_2$, $—NO_2$, and —CN;

$A^1$ and $A^2$ are each independently selected from (i), (ii), and (iii):

(i) hydrogen, halogen, $C_{1-4}$ haloalkyl, $—OR^{11}$, $—SR^{11}$, $—N(R^{11})_2$, $—C(O)N(R^{11})_2$, $—N(R^{11})C(O)R^{11}$, $—C(O)OR^{11}$, $—OC(O)R^{11}$, $—N(R^{11})C(O)OR^{11}$, $—OC(O)N(R^{11})_2$, $—N(R^{11})C(O)N(R^{11})_2$, $—S(O)R^{11}$, $—S(O)_2R^{11}$, $—N(R^{11})S(O)_2R^{11}$, $—S(O)_2N(R^{11})_2$, $—NO_2$, and —CN;

(ii) $C_{1-6}$ alkyl, $C_{2-6}$ alkenyl, and $C_{2-6}$ alkynyl, any of which is optionally substituted with one or more substituents independently selected from:

halogen, $—OR^{11}$, $—SR^{11}$, $—N(R^{11})_2$, $—C(O)N(R^{11})_2$, $—N(R^{11})C(O)R^{11}$, $—C(O)OR^{11}$, $—OC(O)R^{11}$, $—N(R^{11})C(O)OR^{11}$, $—OC(O)N(R^{11})_2$, $—N(R^{11})C(O)N(R^{11})_2$, $—S(O)R^{11}$, $—S(O)_2R^{11}$, $—N(R^{11})S(O)_2R^{11}$, $—S(O)_2N(R^{11})_2$, $—NO_2$, =O, =S, $=N(R^{11})$, and —CN; and $C_{3-10}$ carbocycle and 4- to 10-membered heterocycle, any of which is optionally substituted with one or more substituents independently selected from:

halogen, $—OR^{11A}$, $—N(R^{11A})_2—C(O)R^{11A}$, $—C(O)N(R^{11A})_2—N(R^{11A})C(O)R^{11A}$, $—C(O)OR^{11A}$, $—OC(O)R^{11A}—NO_2$, =O, =S, $=N(R^{11A})$, —CN; and $C_{1-6}$ alkyl $C_{2-6}$ alkenyl, and $C_{2-6}$ alkynyl, any one of which is optionally substituted with one or more substituents independently selected from: halogen, $—OR^{11A}$, $—SR^{11A}$, $—N(R^{11A})_2$, $—C(O)R^{11A}$, $—C(O)N(R^{11A})_2$, $—N(R^{11A})C(O)R^{11A}$, $—N(R^{11A})S(O)_2R^{11A}$, $—C(O)OR^{11A}$, $—OC(O)R^{11A}—NO_2$, =O, =S, $=N(R^{11A})$, and —CN; and (iii) 5- to 10-membered heterocycle and $C_{3-10}$ carbocycle, any of which is optionally substituted with one or more substituents independently selected from:

halogen, $—OR^{11}$, $—SR^{11}$, $—N(R^{11})_2$, $—C(O)R^{11}$, $—C(O)N(R^{11})_2$, $—N(R^{11})C(O)R^{11}$, $—N(R^{11})S(O)_2R^{11}$, $—C(O)OR^{11}$, $—OC(O)R^{11}$, $—N(R^{11})C(O)OR^{11}$, $—OC(O)N(R^{11})_2$, $—N(R^{11})C(O)N(R^{11})_2$, $—S(O)R^{11}$, $—S(O)_2R^{11}$, $—S(O)_2N(R^{11})_2$, $—NO_2$, =O, =S, $=N(R^{11})$, and —CN; and $C_{1-6}$ alkyl, $C_{2-6}$ alkenyl, and $C_{3-6}$ alkynyl, any one of which is optionally substituted with one or more substituents independently selected from: halogen, $—OR^{11}$, $—SR^{11}$, $—N(R^{11})_2$, $—C(O)R^{11}$, $—C(O)N(R^{11})_2$, $—N(R^{11})C(O)R^{11}$, $—C(O)OR^{11}$, $—OC(O)R^{11}$, $—N(R^{11})C(O)OR^{11}$, $—OC(O)N(R^{11})_2$, $—N(R^{11})C(O)N(R^{11})_2$, $—S(O)R^{11}$, $—S(O)_2R^{11}$, $—N(R^{11})S(O)_2R^{11}$, $—S(O)_2N(R^{11})_2$, $—NO_2$, =O, =S, $=N(R^{11})$, and —CN; and $C_{3-10}$ carbocycle and 4- to 10-membered heterocycle, any of which is optionally substituted with one or more substituents independently selected from:

halogen, $—OR^{11}$, $—N(R^{11})_2$, $—C(O)R^{11}$, $—C(O)N(R^{11})_2$, $—N(R^{11})C(O)R^{11}$, $—C(O)OR^{11}$, $—OC(O)R^{11}$, $—NO_2$, =O, =S, $=N(R^{11})$, —CN; and $C_{1-6}$ alkyl $C_{2-6}$ alkenyl, and $C_{3-6}$ alkynyl, any one of which is optionally substituted with one or more substituents independently selected from: halogen, $—OR^{11}$, $—SR^{11}$, $—N(R^{11})_2$, $—C(O)R^{11}$, $—C(O)N(R^{11})_2$, $—N(R^{11})C(O)R^{11}$, $—N(R^{11})S(O)_2R^{11}$, $—C(O)OR^{11}$, $—OC(O)R^{11}$, $—NO_2$, =O, =S, $=N(R^{11})$, and —CN;

q is selected from 1, 2, and 3;

m and n are each independently selected from 0, 1, 2, and 3;

$R^2$ is independently selected at each instance from halogen, $C_{1-4}$ alkyl, $C_{1-4}$ haloalkyl, $—OR^{12}$, $—SR^{12}$, $—N(R^{12})_2$, $—NO_2$, and —CN;

$R^3$ is independently selected at each instance from:

halogen, $—OR^{13}$, $—SR^{13}$, $—N(R^{13})_2$, $—C(O)R^{13}$, $—C(O)N(R^{13})_2$, $—N(R^{13})C(O)R^{13}$, $—C(O)OR^{13}$, $—OC(O)R^{13}$, $—NO_2$, and —CN; and $C_{1-6}$ alkyl optionally substituted with one or more substituents independently selected from:

halogen, $—OR^{13}$, $—SR^{13}$, $—N(R^{13})_2$, $—C(O)R^{13}$, $—C(O)N(R^{13})_2$, $—N(R^{13})C(O)R^{13}$, $—C(O)OR^{13}$, $—OC(O)R^{13}$, $—NO_2$, =O, =S, $=N(R^{13})$, and —CN;

p is selected from 0, 1, 2, 3, 4, and 5;

$R^4$ is independently selected at each instance from:

halogen, $—OR^{14}$, $—SR^{14}$, $—N(R^{14})_2$, $—C(O)R^{14}$, $—C(O)N(R^{14})_2$, $—N(R^{14})C(O)R^{14}$, $—C(O)OR^{14}$, $—OC(O)R^{14}$, $—NO_2$, and —CN; and $C_{1-6}$ alkyl, $C_{2-6}$ alkenyl, $C_{2-6}$ alkynyl, any one of which is optionally substituted with one or more substituents independently selected from halogen, $—OR^{14}$, $—SR^{14}$, $—N(R^{14})_2$, $—C(O)R^{14}$, $—C(O)N(R^{14})_2$, $—N(R^{14})C(O)R^{14}$, $—C(O)OR^{14}$, $—OC(O)R^{14}$, $—NO_2$, =O, =S, $=N(R^{14})$, and —CN; or two $R^4$ attached to the same atom are taken together to form a group selected from: =O, =S, and $=N(R^{14})$; or two $R^4$ attached to the same atom or to adjacent atoms are taken together with the carbons to which they are attached to form a group selected from 4- to 8-membered heterocycle and $C_{3-8}$ carbocycle, any of which is optionally substituted with one or more substituents independently selected from: halogen, $C_{1-4}$ alkyl, $C_{1-4}$ haloalkyl, $—OR^{14}$, $—SR^{14}$, $—N(R^{14})_2$, $—NO_2$, and —CN;

L is represented by $-L^1-L^2-L^3-L^4-$, wherein $L^1$, $L^2$, $L^3$, and $L^4$ are each independently selected from (a) and (b):

(a) —O—, $—N(R^{15})—$, —S—, —S(O)—, $—S(O)_2—$, $—S(O)(NR^{15})—$, $—N(R^{15})C(O)—$, $—N(R^{15})C(O)O—$, $—N(R^{11})S(O)_2—$, $—N(R^{11})S(O)_2N(R^{11})—$, $—S(O)(NR^{11})N(R^{11})—$, $—N(R^{15})N(R^{15})—$, $—(R^{15})NC(O)N(R^{15})—$, and $—(R^{15})NC(O)N(R^{15})N(R^{15})—$; and (b) $C_{1-6}$ alkylene, $C_{2-6}$ alkenylene, $C_{2-6}$ alkynylene, $C_{3-8}$ carbocyclene, and 4- to 8-membered heterocyclene, any of which is optionally substituted with one or more substituents independently selected from halogen, $—OR^5$, $—SR^{15}$, =O, =S, and —CN;

wherein $L^1$, $L^2$, $L^3$, and $L^4$ are each optionally absent;

wherein no more than two of $L^1$, $L^2$, $L^3$, and $L^4$ are selected from (a) and the two selected are not adjacent;

$R^5$ is selected from 4- to 10-membered heterocycle and $C_{3-10}$ carbocycle, any of which is optionally substituted with one or more substituents independently selected from:

halogen, $C_{1-4}$ haloalkyl, $—OR^{16}$, $—SR^{16}$, $—N(R^{16})_2$, $—C(O)N(R^{16})_2$, $—C(O)OR^{16}$, $—OC(O)R^{16}$, $—N(R^{16})C(O)R^{16}$, $—N(R^{16})S(O)_2R^{16}$, $—S(O)_2N(R^{16})_2$, $—N(R^{16})C(O)N(R^{16})_2$, $—N(R^{16})C(O)OR^{16}$, $—OC(O)N(R^{16})_2$, $—S(O)R^{16}$, $—S(O)_2R^{16}$, $—NO_2$, =O, =S, $=N(R^{16})$, and —CN;

$C_{1-6}$ alkyl, $C_{2-6}$ alkenyl, and $C_{2-6}$ alkynyl, each of which is optionally substituted with one or more substituents independently selected from: halogen, $—OR^{16}$, $—SR^{16}$, $—N(R^{16})_2$, $—NO_2$, and —CN; and 4- to 6-membered heterocycle and $C_{3-8}$ carbocycle, each of which is optionally substituted with one or more substituents independently selected from: halogen, $C_{1-4}$ alkyl, $C_{1-4}$ haloalkyl, $—OR^{16}$, $—SR^{16}$, $—N(R^{16})_2$, $—NO_2$, and —CN;

$R^{10}$, $R^{11}$, $R^{11A}$, $R^{12}$, $R^{13}$, $R^{14}$, and $R^{15}$ are each independently selected at each occurrence from:

hydrogen, $C_{1-4}$ alkyl, $C_{3-8}$ carbocycle, 4- to 8-membered heterocycle, and $C_{1-4}$ haloalkyl;

$R^{16}$ is independently selected at each occurrence from (iv), (v), and (vi):

(iv) hydrogen;

(v) $C_{1-4}$ alkyl, wherein the $C_{1-4}$ alkyl is optionally substituted with one or more substituents independently selected from:

halogen, $—OR^{20}$, $—SR^{20}$, $—N(R^{20})_2$, $—C(O)R^{20}$, $—C(O)OR^{20}$, $—OC(O)R^{20}$, $—C(O)N(R^{20})_2$, $—N(R^{20})C(O)R^{20}$, $—N(R^{20})C(O)N(R^{20})_2$, $—N(R^{20})C(O)OR^{20}$, $OC(O)N(R^{20})_2$, $—S(O)R^{20}$, $—S(O)_2R^{20}$, $—N(R^{20})S(O)_2R^{20}$, $—S(O)_2N(R^{20})_2$, $—NO_2$, and —CN; and $C_{3-8}$ carbocycle and 4- to 8-membered heterocycle, either of which is optionally substituted with one or more substituents independently selected from: halogen, $C_{1-4}$ alkyl, $C_{1-4}$ haloalkyl, —$OR^{20}$, —$SR^{20}$, —$N(R^{20})_2$, —$C(O)R^{20}$, —$C(O)OR^{20}$, —$OC(O)R^{20}$, —$C(O)N(R^{20})_2$, —$N(R^{20})C(O)R^{20}$, —$N(R^{20})C(O)N(R^{20})_2$, —$N(R^{20})C(O)OR^{20}$, —$OC(O)N(R^{20})_2$, —$S(O)R^{20}$, —$S(O)_2R^{20}$, —$N(R^{20})S(O)_2R^{20}$, —$S(O)_2N(R^{20})_2$, —$NO_2$, and —CN; and (vi) $C_{3-8}$ carbocycle and 4- to 8-membered heterocycle, either of which is optionally substituted with one or more substituents independently selected from halogen, $C_{1-4}$ alkyl, $C_{1-4}$ haloalkyl, —$OR^{20}$, —$SR^{20}$, —$N(R^{20})_2$, —$C(O)R^{20}$, —$C(O)N(R^{20})_2$, —$C(O)OR^{20}$, —$OC(O)R^{20}$, —$N(R^{20})C(O)R^{20}$, —$N(R^{20})S(O)_2R^{20}$, —$N(R^{20})C(O)N(R^{20})_2$, —$N(R^{20})C(O)OR^{20}$, —$OC(O)N(R^{20})_2$, —$S(O)R^{20}$, —$S(O)_2R^{20}$, —$NO_2$, and —CN; and $R^{20}$ is independently selected at each occurrence from hydrogen, $C_{1-4}$ alkyl, $C_{1-4}$ haloalkyl, $C_{3-8}$ carbocycle, and 4- to 8-membered heterocycle.

In some embodiments, for the compound or salt of Formula (II), $A^2$ is selected from $C_{1-6}$ alkyl, $C_{2-6}$ alkenyl, and $C_{2-6}$ alkynyl, each of which is optionally substituted with one or more substituents independently selected from:

halogen, —$OR^{11}$, —$N(R^{11})_2$, —$C(O)N(R^{11})_2$, —$N(R^{11})C(O)R^{11}$, —$N(R^{11})S(O)_2R^{11}$, —$S(O)_2N(R^{11})_2$, =O, and —$NO_2$, —CN; and $C_{3-10}$ carbocycle and 4- to 10-membered heterocycle, any of which is optionally substituted with one or more substituents independently selected from:

halogen, —$OR^{11A}$, —$N(R^{11A})_2$, —$C(O)R^{11A}$, —$C(O)N(R^{11A})_2$, —$N(R^{11A})C(O)R^{11A}$—$NO_2$, =O, and —CN; and $C_{1-6}$ alkyl, $C_{2-6}$ alkenyl, and $C_{3-6}$ alkynyl, any one of which is optionally substituted with one or more substituents independently selected from: halogen, —$OR^{11A}$, —$N(R^{11A})_2$, —$C(O)R^{11A}$, —$C(O)N(R^{11A})_2$, —$N(R^{11A})C(O)R^{11A}$, —$N(R^{11A})S(O)_2R^{11A}$, —$NO_2$, =O, and —CN.

In some embodiments, for the compound or salt of Formula (I), $A^2$ is selected from $C_{2-6}$ alkynyl optionally substituted with one or more substituents independently selected from:

halogen, —$OR^{11}$, —$N(R^{11})_2$, —$C(O)N(R^{11})_2$, —$N(R^{11})C(O)R^{11}$, —$N(R^{11})S(O)_2R^{11}$, —$S(O)_2N(R^{11})_2$, —$NO_2$, and —CN; and $C_{3-10}$ carbocycle and 4- to 10-membered heterocycle, any of which is optionally substituted with one or more substituents independently selected from:

halogen, —$OR^{11A}$, —$N(R^{11A})_2$, —$C(O)R^{11A}$, —$C(O)N(R^{11A})_2$, —$N(R^{11A})C(O)R^{11A}$—$NO_2$, =O, and —CN; and $C_{1-6}$ alkyl, $C_{2-6}$ alkenyl, and $C_{3-6}$ alkynyl, any one of which is optionally substituted with one or more substituents independently selected from: halogen, —$OR^{11A}$, —$N(R^{11A})_2$, —$C(O)R^{11A}$, —$C(O)N(R^{11A})_2$, —$N(R^{11A})C(O)R^{11A}$, —$N(R^{11A})S(O)_2R^{11A}$, —$NO_2$, =O, and —CN.

In some embodiments, for the compound or salt of Formula (I), $A^2$ is $C_{2-6}$ alkynyl optionally substituted with one or more substituents independently selected from halogen, —$OR^{11}$, —$N(R^{11})_2$, —$NO_2$, —CN; $C_{3-10}$ carbocycle and 4- to 10-membered heterocycle, the $C_{3-10}$ carbocycle and 4- to 10-membered heterocycle are each optionally substituted with one or more substituents independently selected from: halogen, —$OR^{11A}$, —$N(R^{11A})_2$—$NO_2$, =O, and —CN; and $C_{1-6}$ alkyl optionally substituted with one or more substituents independently selected from: halogen, —$OR^{11A}$, —$N(R^{11A})_2$, —$NO_2$, =O, and —CN.

In some embodiments, for the compound or salt of Formula (I), $A^2$ is $C_{2-6}$ alkynyl optionally substituted with one or more substituents independently selected from $C_{3-6}$ carbocycle and 4- to 6-membered heterocycle, each of which is optionally substituted with one or more substituents independently selected from: halogen, —$OR^{11A}$, —$N(R^{11A})_2$, —$C(O)R^{11A}$, —$C(O)N(R^{11A})_2$, —$N(R^{11A})C(O)R^{11A}$, —$NO_2$, =O, and —CN; and $C_{1-6}$ alkyl optionally substituted with one or more substituents independently selected from: —$OR^{11A}$, —$N(R^{11A})_2$, —$C(O)R^{11A}$, —$C(O)N(R^{11A})_2$, —$N(R^{11A})C(O)R^{11A}$, —$NO_2$, =O, and —CN.

In some embodiments, for the compound or salt of Formula (I), $A^2$ is $C_{2-6}$ alkynyl optionally substituted with one or more substituents independently selected from: $C_{3-6}$ carbocycle and 4- to 6-membered heterocycle, any of which is optionally substituted with one or more substituents independently selected from: halogen, —$OR^{11A}$, —$N(R^{11A})_2$, —$C(O)R^{11A}$, —$C(O)N(R^{11A})_2$, —$N(R^{11A})C(O)R^{11A}$, —$NO_2$, =O, and —CN; and $C_{1-6}$ alkyl optionally substituted with one or more substituents independently selected from: halogen, —$OR^{11A}$, and —$N(R^{11A})_2$.

In some embodiments, for the compound or salt of Formula (I), $A^2$ is $C_{2-6}$ alkynyl optionally substituted with one or more substituents independently selected from: $C_{3-6}$ carbocycle and 4- to 6-membered heterocycle, any of which is optionally substituted with one or more substituents independently selected from: halogen, —$OR^{11A}$, —$N(R^{11A})_2$, —$NO_2$, =O, and —CN; and $C_{1-6}$ alkyl optionally substituted with one or more substituents independently selected from: halogen, —$OR^{11A}$ and —$N(R^{11A})_2$.

In some embodiments, for the compound or salt of Formula (I), $A^2$ is $C_{2-6}$ alkynyl optionally substituted with one or more substituents independently selected from: $C_{3-6}$ carbocycle and 4- to 6-membered heterocycle, any of which is optionally substituted with one or more substituents independently selected from: halogen, —$OR^{11A}$, and —$N(R^{11A})_2$; and $C_{1-6}$ alkyl optionally substituted with one or more substituents independently selected from: halogen, —$OR^{11A}$, and —$N(R^{11A})_2$.

In some embodiments, for the compound or salt of Formula (I), $A^2$ is $C_{2-6}$ alkynyl optionally substituted with one or more substituents independently selected from: $C_{3-6}$ carbocycle and 4- to 6-membered heterocycle, any of which is optionally substituted with one or more substituents independently selected from: halogen, —$OR^{11A}$, —$N(R^{11A})_2$, $C_{1-6}$ alkyl and $C_{1-6}$ haloalkyl.

In some embodiments, for the compound or salt of Formula (I), $A^2$ is $C_{2-6}$ alkynyl optionally substituted with one or more substituents independently selected from: $C_{3-6}$ carbocycle and 4- to 6-membered heterocycle, any of which is optionally substituted with one or more substituents independently selected from: halogen, $C_{1-6}$ alkyl and $C_{1-6}$ haloalkyl.

In some embodiments, for the compound or salt of Formula (I), $A^2$ is $C_{2-6}$ alkynyl optionally substituted with cyclopropyl, cyclopentyl, oxetanyl, azetidinyl, and oxazolyl, each of which is optionally substituted with one or more substituents independently selected from: halogen, —$OR^{11A}$, —$N(R^{11A})_2$, —$C(O)R^{11A}$, —$C(O)N(R^{11A})_2$—$N(R^{11A})C(O)R^{11A}$—$NO_2$, =O, —CN; and $C_{1-6}$ alkyl optionally substituted with one or more substituents independently selected from: halogen, —$OR^{11A}$, and —$N(R^{11A})_2$.

In some embodiments, for the compound or salt of Formula (I), $A^2$ is $C_{2-6}$ alkynyl optionally substituted with cyclopropyl, cyclopentyl, oxetanyl, azetidinyl, and oxazolyl, each of which is optionally substituted with one or more substituents independently selected from: halogen, $—OR^{11A}—N(R^{11A})_2$, $—NO_2$, $=O$, —CN; and $C_{1-6}$ alkyl optionally substituted with one or more substituents independently selected from: halogen, $—OR^{11A}$, and $—N(R^{11A})_2$.

In some embodiments, for the compound or salt of Formula (I), $A^2$ is $C_{2-6}$ alkynyl optionally substituted with cyclopropyl, cyclopentyl, oxetanyl, azetidinyl, and oxazolyl, each of which is optionally substituted with one or more substituents independently selected from: halogen, $—OR^{11A}$ and $—N(R^{11A})_2$; and $C_{1-6}$ alkyl optionally substituted with one or more substituents independently selected from: halogen, $—OR^{11A}$, and $—N(R^{11A})_2$.

In some embodiments, for the compound or salt of Formula (I), $A^2$ is selected from

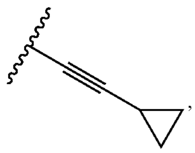,
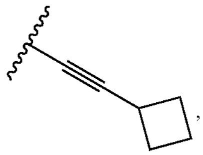,
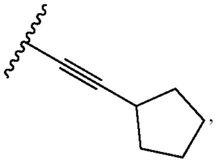,
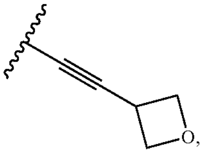,
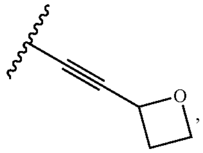,
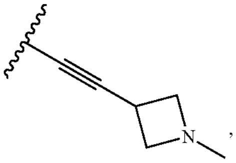, and
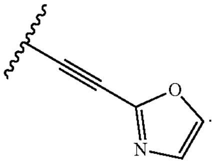.

In some embodiments, for the compound or salt of Formula (I), $A^2$ is

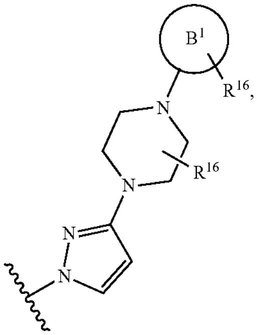

wherein ring $B^1$ is $C_{3-8}$ carbocycle or 4- to 8-membered heterocycle, either of which is optionally substituted with one or more substituents independently selected from halogen, $C_{1-4}$ alkyl, $C_{1-4}$ haloalkyl, $—OR^{20}$, $—SR^{20}$, $—N(R^{20})_2$, $—C(O)R^{20}$, $—C(O)N(R^{20})_2$, $—C(O)OR^{20}$, $—OC(O)R^{20}$, $—N(R^{20})C(O)R^{20}$, $—N(R^{20})S(O)_2R^{20}$, $—N(R^{20})C(O)N(R^{20})_2$, $—N(R^{20})C(O)OR^{20}$, $—OC(O)N(R^{20})_2$, $—S(O)R^{20}$, $—S(O)_2R^{20}$, $—NO_2$, and —CN.

In some embodiments, for the compound or salt of Formula (I), $L^1$, $L^2$, $L^3$, and $L^4$ are all absent.

In some embodiments, for the compound or salt of Formula (I), $R^5$ is selected from 4- to 10-membered heterocycle and $C_{3-10}$ carbocycle, any of which is optionally substituted with one or more substituents independently selected from:

halogen, $C_{1-4}$ haloalkyl, $—OR^{16}$, $—SR^{16}$, $—N(R^{16})_2$, $—C(O)N(R^{16})_2$, $—C(O)OR^{16}$, $—OC(O)R^{16}$, $—N(R^{16})C(O)R^{16}$, $—N(R^{16})S(O)_2R^{16}$, $—S(O)_2N(R^{16})_2$, $—N(R^{16})C(O)N(R^{16})_2$, $—N(R^{16})C(O)OR^{16}$, $—OC(O)N(R^{16})_2$, $—S(O)R^{16}$, $—S(O)_2R^{16}$, $—NO_2$, $=O$, $=S$, $=N(R^{16})$, and —CN;

$C_{1-6}$ alkyl optionally substituted with one or more substituents independently selected from:

halogen, $—OR^{16}$, $—SR^{16}$, $—N(R^{16})_2$, $—NO_2$, and —CN; and 4- to 6-membered heterocycle and $C_{3-8}$ carbocycle, each of which is optionally substituted with one or more substituents independently selected from: halogen, $C_{1-4}$ alkyl, $C_{1-4}$ haloalkyl, $—OR^{16}$, $—SR^{16}$, $—N(R^{16})_2$, $—NO_2$, and —CN.

In some embodiments, for the compound or salt of Formula (I), $R^5$ is selected from 4- to 10-membered heterocycle and $C_{3-10}$ carbocycle, any of which is optionally substituted with one or more substituents independently selected from:

halogen, $—OR^{16}$, $—SR^{16}$, $—N(R^{16})_2$, $—C(O)N(R^{16})_2$, $—C(O)OR^{16}$, $—OC(O)R^{16}$, $—N(R^{16})C(O)R^{16}$, $—N(R^{16})S(O)_2R^{16}$, $—S(O)_2N(R^{16})_2$, $—N(R^{16})C(O)N(R^{16})_2$, $—N(R^{16})C(O)OR^{16}$, $—OC(O)N(R^{16})_2$, $—S(O)R^{16}$, $—S(O)_2R^{16}$, $—NO_2$, $=O$, $=S$, $=N(R^{16})$, and —CN;

$C_{1-4}$ alkyl optionally substituted with one or more substituents independently selected from:

halogen, $C_{1-4}$ alkyl, $C_{1-4}$ haloalkyl, $—OR^{16}$, $—SR^{16}$, $—N(R^{16})_2$, $—NO_2$, and —CN; and 4- to 6-membered heterocycle and $C_{3-8}$ carbocycle, each of which is optionally substituted with one or more substituents independently selected from: halogen, $C_{1-4}$ alkyl, $C_{1-4}$ haloalkyl, $—OR^{16}$, $—SR^{16}$, $—N(R^{16})_2$, $—NO_2$, and —CN.

In some embodiments, for the compound or salt of Formula (I), $R^5$ is selected from 4- to 10-membered heterocycle and $C_{3-10}$ carbocycle, any of which is optionally substituted with one or more substituents independently selected from:

halogen, $—OR^{16}$, $—N(R^{16})_2$, $—C(O)N(R^{16})_2$, $—C(O)OR^{16}$, $—OC(O)R^{16}$, $—N(R^{16})C(O)R^{16}$, $—NO_2$, $=O$, and —CN;

$C_{1-4}$ alkyl optionally substituted with one or more substituents independently selected from:

halogen, $—OR^{16}$, $—SR^{16}$, $—N(R^{16})_2$, $—NO_2$, and —CN; and 4- to 6-membered heterocycle and $C_{3-8}$ carbocycle, each of which is optionally substituted with one or more substituents independently selected from: halogen, $C_{1-4}$ alkyl, $C_{1-4}$ haloalkyl, $—OR^{16}$, $—SR^{16}$, $—N(R^{16})_2$, $—NO_2$, and —CN.

In some embodiments, for the compound or salt of Formula (I), $R^5$ is selected from 4- to 10-membered heterocycle and $C_{3-10}$ carbocycle, any of which is optionally substituted with one or more substituents independently selected from:

halogen, $—OR^{16}$, $—N(R^{16})_2$, $—NO_2$, =O, and —CN;

$C_{1-4}$ alkyl optionally substituted with one or more substituents independently selected from:

halogen, $—OR^{16}$, $—N(R^{16})_2$, $—NO_2$, and —CN; and 4- to 6-membered heterocycle and $C_{3-8}$ carbocycle, each of which is optionally substituted with one or more substituents independently selected from: halogen, $C_{1-4}$ alkyl, $C_{1-4}$ haloalkyl, $—OR^{16}$, $—N(R^{16})_2$, $—NO_2$, and —CN.

In some embodiments, for the compound or salt of Formula (I), $R^5$ is selected from 4- to 10-membered heterocycle and $C_{3-10}$ carbocycle, any of which is optionally substituted with one or more substituents independently selected from:

halogen, $—OR^{16}$, $—N(R^{16})_2$, $—NO_2$, =O, and —CN; and $C_{1-4}$ alkyl optionally substituted with one or more substituents independently selected from:

halogen, $—OR^{16}$, $—N(R^{16})_2$, $—NO_2$, and —CN.

In some embodiments, for the compound or salt of Formula (I), $R^5$ is selected from 4- to 10-membered heterocycle and $C_{3-10}$ carbocycle, any of which is optionally substituted with one or more substituents independently selected from:

halogen, $—OR^{16}$, and $—N(R^{16})_2$; and $C_{1-4}$ alkyl optionally substituted with one or more substituents independently selected from:

halogen, $—OR^{16}$, and $—N(R^{16})_2$.

In some embodiments, for the compound or salt of Formula (I), $R^5$ is 4- to 10-membered heterocycle optionally substituted with one or more substituents independently selected from:

halogen, $—OR^{16}$, $—SR^{16}$, $—N(R^{16})_2$, $—C(O)N(R^{16})_2$, $—C(O)OR^{16}$, $—OC(O)R^{16}$, $—N(R^{16})C(O)R^{16}$, $—N(R^{16})S(O)_2R^{16}$, $—S(O)_2N(R^{16})_2$, $—N(R^{16})C(O)N(R^{16})_2$, $—N(R^{16})C(O)OR^{16}$, $—OC(O)N(R^{16})_2$, $—S(O)R^{16}$, $—S(O)_2R^{16}$, $—NO_2$, =O, =S, $=N(R^{16})$, and —CN;

$C_{1-4}$ alkyl optionally substituted with one or more substituents independently selected from:

halogen, $C_{1-4}$ alkyl, $C_{1-4}$ haloalkyl, $—OR^{16}$, $—SR^{16}$, $—N(R^{16})_2$, $—NO_2$, and —CN; and 4- to 6-membered heterocycle and $C_{3-8}$ carbocycle, each of which is optionally substituted with one or more substituents independently selected from: halogen, $C_{1-4}$ alkyl, $C_{1-4}$ haloalkyl, $—OR^{16}$, $—SR^{16}$, $—N(R^{16})_2$, $—NO_2$, and —CN.

In some embodiments, for the compound or salt of Formula (I), $R^5$ is 4- to 10-membered heterocycle optionally substituted with one or more substituents independently selected from:

halogen, $—OR^{16}$, $—SR^{16}$, $—N(R^{16})_2$, $—C(O)N(R^{16})_2$, $—C(O)OR^{16}$, $—OC(O)R^{16}$, $—N(R^{16})C(O)R^{16}$, $—N(R^{16})S(O)_2R^{16}$, $—S(O)_2N(R^{16})_2$, $—N(R^{16})C(O)N(R^{16})_2$, $—N(R^{16})C(O)OR^{16}$, $—OC(O)N(R^{16})_2$, $—S(O)R^{16}$, $—S(O)_2R^{16}$, $—NO_2$, =O, =S, $=N(R^{16})$, and —CN;

$C_{1-4}$ alkyl optionally substituted with one or more substituents independently selected from:

halogen, $C_{1-4}$ alkyl, $C_{1-4}$ haloalkyl, $—OR^{16}$, $—SR^{16}$, $—N(R^{16})_2$, $—NO_2$, and —CN.

In some embodiments, for the compound or salt of Formula (I), $R^5$ is 4- to 10-membered heterocycle optionally substituted with one or more substituents independently selected from:

halogen, $—OR^{16}$, $—N(R^{16})_2$, $—C(O)N(R^{16})_2$, $—C(O)OR^{16}$, $—OC(O)R^{16}$, $—N(R^{16})C(O)R^{16}$, $—NO_2$, =O, and —CN;

$C_{1-4}$ alkyl optionally substituted with one or more substituents independently selected from:

halogen, $—OR^{16}$, $—SR^{16}$, $—N(R^{16})_2$, $—NO_2$, and —CN; and 4- to 6-membered heterocycle and $C_{3-8}$ carbocycle, each of which is optionally substituted with one or more substituents independently selected from: halogen, $C_{1-4}$ alkyl, $C_{1-4}$ haloalkyl, $—OR^{16}$, $—SR^{16}$, $—N(R^{16})_2$, $—NO_2$, and —CN.

In some embodiments, for the compound or salt of Formula (I), $R^5$ is 4- to 10-membered heterocycle optionally substituted with one or more substituents independently selected from:

halogen, $—OR^{16}$, $—N(R^{16})_2$, $—NO_2$, =O, and —CN;

$C_{1-4}$ alkyl optionally substituted with one or more substituents independently selected from:

halogen, $—OR^{16}$, $—N(R^{16})_2$, $—NO_2$, and —CN; and 4- to 6-membered heterocycle and $C_{3-8}$ carbocycle, each of which is optionally substituted with one or more substituents independently selected from: halogen, $C_{1-4}$ alkyl, $C_{1-4}$ haloalkyl, $—OR^{16}$, $—N(R^{16})_2$, $—NO_2$, and —CN.

In some embodiments, for the compound or salt of Formula (I), $R^5$ is 4- to 10-membered heterocycle optionally substituted with one or more substituents independently selected from:

halogen, $—OR^{16}$, $—N(R^{16})_2$, $—NO_2$, =O, and —CN; and $C_{1-4}$ alkyl optionally substituted with one or more substituents independently selected from:

halogen, $—OR^{16}$, $—N(R^{16})_2$, $—NO_2$, and —CN.

In some embodiments, for the compound or salt of Formula (I), $R^5$ is 4- to 10-membered heterocycle optionally substituted with one or more substituents independently selected from:

halogen, $—OR^{16}$, and $—N(R^{16})_2$; and $C_{1-4}$ alkyl optionally substituted with one or more substituents independently selected from:

halogen, $—OR^{16}$, and $—N(R^{16})_2$.

In some embodiments, for the compound or salt of Formula (I), $R^5$ is selected from azetidinyl, cyclopentyl, cyclohexyl, imidazolyl, pyrazolyl, 1H-1,2,3-triazolyl, 4H-1,2,4-triazolyl, 1,4-dihydropyridinyl, 3,4-dihydropyrido[3,4-d]pyrimidinyl, 1H-benzo[d][1,2,3]triazolyl, each of which is optionally substituted with one or more substituents independently selected from:

halogen, $—OR^{16}$, $—SR^{16}$, $—N(R^{16})_2$, $—C(O)N(R^{16})_2$, $—C(O)OR^{16}$, $—OC(O)R^{16}$, $—N(R^{16})C(O)R^{16}$, $—N(R^{16})S(O)_2R^{16}$, $—S(O)_2N(R^{16})_2$, $—N(R^{16})C(O)N(R^{16})_2$, $—N(R^{16})C(O)OR^{16}$, $—OC(O)N(R^{16})_2$, $—S(O)R^{16}$, $—S(O)_2R^{16}$, $—NO_2$, =O, =S, $=N(R^{16})$, and —CN;

$C_{1-4}$ alkyl optionally substituted with one or more substituents independently selected from: halogen, $C_{1-4}$ alkyl, $C_{1-4}$ haloalkyl, $—OR^{16}$, $—SR^{16}$, $—N(R^{16})_2$, $—NO_2$, and —CN.

In some embodiments, for the compound or salt of Formula (I), $R^5$ is selected from azetidinyl, cyclopentyl, cyclohexyl, imidazolyl, pyrazolyl, 1H-1,2,3-triazolyl, 4H-1,2,4-triazolyl, 1,4-dihydropyridinyl, 3,4-dihydropyrido[3,4- d]pyrimidinyl, 1H-benzo[d][1,2,3]triazolyl, each of which is optionally substituted with one or more substituents independently selected from:

halogen, —$OR^{16}$, —$N(R^{16})_2$, —$C(O)N(R^{16})_2$, —C(O)$OR^{16}$, —$OC(O)R^{16}$, —$N(R^{16})C(O)R^{16}$—$NO_2$, =O, and —CN; and $C_{1-4}$ alkyl optionally substituted with one or more substituents independently selected from:

halogen, —$OR^{16}$, —$N(R^{16})_2$, —$NO_2$, and —CN.

In some embodiments, for the compound or salt of Formula (I), $R^5$ is selected from azetidinyl, cyclopentyl, cyclohexyl, imidazolyl, pyrazolyl, 1H-1,2,3-triazolyl, 4H-1,2,4-triazolyl, 1,4-dihydropyridinyl, 3,4-dihydropyrido[3,4-d]pyrimidinyl, 1H-benzo[d][1,2,3]triazolyl, each of which is optionally substituted with one or more substituents independently selected from:

halogen, —$OR^{16}$, —$N(R^{16})_2$, and =O; and $C_{1-4}$ alkyl optionally substituted with one or more substituents independently selected from:

halogen, —$OR^{16}$, and —$N(R^{16})_2$.

In some embodiments, for the compound or salt of Formula (I), $R^5$ is selected from

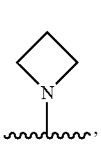,
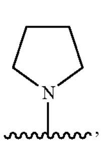,
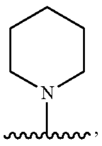,
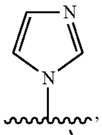,
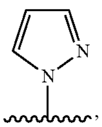,
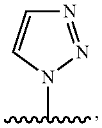,
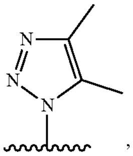,
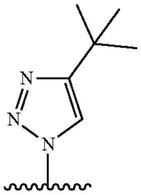,
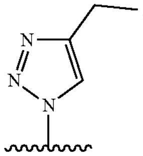,
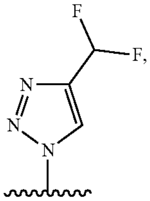,
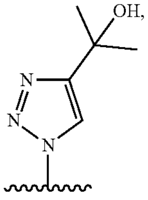
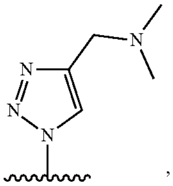,
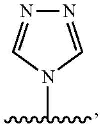,
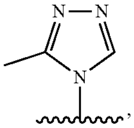,
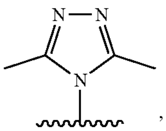,
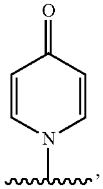,
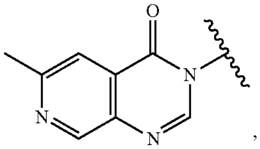, and
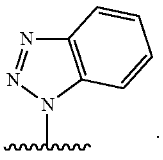.

In some embodiments, for the compound or salt of Formula (I), Ring B is

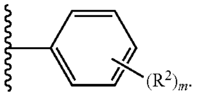

In some embodiments, for the compound or salt of Formula (I), $R^2$ is independently selected at each instance from halogen, $C_{1-4}$ alkyl, $C_{1-4}$ haloalkyl. In some embodiments, $R^2$ is halogen. In some embodiments, $R^2$ is fluoro.

In some embodiments, for the compound or salt of Formula (I), Ring B is selected from and

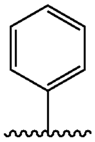 and 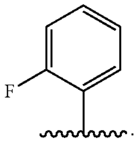.

In some embodiments, for the compound or salt of Formula (I), Ring B is

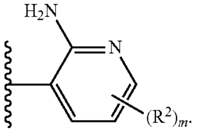

In some embodiments, for the compound or salt of Formula (I), Ring B is

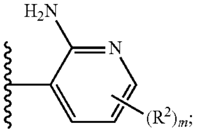

and the compound or salt of Formula (I) is represented by the structure of Formula (II):

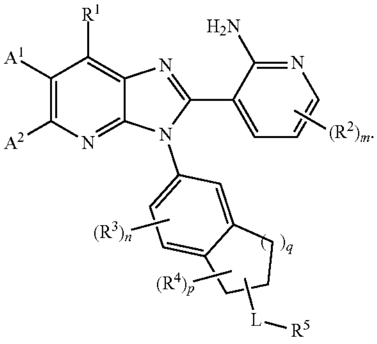

In some aspect, the present disclosure provides compounds represented by the structure of Formula (II):

(II)

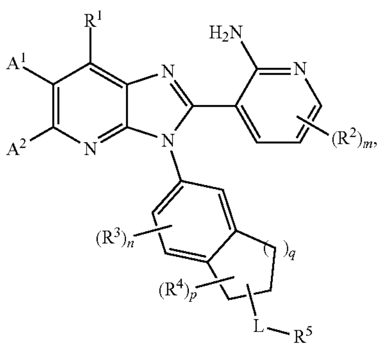

or a pharmaceutically acceptable salt thereof, wherein:

$R^1$ is selected from hydrogen, halogen, —$OR^{10}$, —$SR^{10}$, —$N(R^{10})_2$, —$NO_2$, and —CN; and $C_{1-6}$ alkyl optionally substituted with one or more substituents independently selected from: halogen, —$OR^{10}$, —$SR^{10}$, —$N(R^{10})_2$, —$NO_2$, and —CN;

$A^1$ and $A^2$ are each independently selected from (i), (ii), and (iii):

(i) hydrogen, halogen, $C_{1-4}$ haloalkyl, —$OR^{11}$, —$SR^{11}$, —$N(R^{11})_2$, —$C(O)N(R^{11})_2$, —$N(R^{11})C(O)R^{11}$, —$C(O)OR^{11}$, —$OC(O)R^{11}$, —$N(R^{11})C(O)OR^{11}$, —$OC(O)N(R^{11})_2$, —$N(R^{11})C(O)N(R^{11})_2$, —$S(O)R^{11}$, —$S(O)_2R^{11}$, —$N(R^{11})S(O)_2R^{11}$, —$S(O)_2N(R^{11})_2$, —$NO_2$, and —CN;

(ii) $C_{1-6}$ alkyl, $C_{2-6}$ alkenyl, and $C_{2-6}$ alkynyl, any of which is optionally substituted with one or more substituents independently selected from halogen, —$OR^{11}$, —$SR^{11}$, —$N(R^{11})_2$, —$C(O)N(R^{11})_2$, —$N(R^{11})C(O)R^{11}$, —$C(O)OR^{11}$, —$OC(O)R^{11}$, —$N(R^{11})C(O)OR^{11}$, —$OC(O)N(R^{11})_2$, —$N(R^{11})C(O)N(R^{11})_2$, —$S(O)R^{11}$, —$S(O)_2R^{11}$, —$N(R^{11})S(O)_2 R^{11}$, —$S(O)_2N(R^{11})_2$, —$NO_2$, =O, =S, =$N(R^{11})$, and —CN; and (iii) 5- to 10-membered heterocycle and $C_{3-10}$ carbocycle, any of which is optionally substituted with one or more substituents independently selected from:

halogen, —$OR^{11}$, —$SR^{11}$, —$N(R^{11})_2$, —$C(O)R^{11}$, —$C(O)N(R^{11})_2$, —$N(R^{11})C(O)R^{11}$, —$N(R^{11})S(O)_2R^{11}$, —$C(O)OR^{11}$, —$OC(O)R^{11}$, —$N(R^{11})C(O)OR^{11}$, —$OC(O)N(R^{11})_2$, —$N(R^{11})C(O)N(R^{11})_2$, —$S(O)R^{11}$, —$S(O)_2R^{11}$, —$S(O)_2N(R^{11})_2$, —$NO_2$, =O, =S, =$N(R^{11})$, and —CN; and $C_{1-6}$ alkyl, $C_{2-6}$ alkenyl, and $C_{3-6}$ alkynyl, any one of which is optionally substituted with one or more substituents independently selected from: halogen, —$OR^{11}$, —$SR^{11}$, —$N(R^{11})_2$, —$C(O)R^{11}$, —$C(O)N(R^{11})_2$, —$N(R^{11})C(O)R^{11}$, —$C(O)OR^{11}$, —$OC(O)R^{11}$, —$N(R^{11})C(O)OR^{11}$, —$OC(O)N(R^{11})_2$, —$N(R^{11})C(O)N(R^{11})_2$, —$S(O)R^{11}$, —$S(O)_2R^{11}$, —$N(R^{11})S(O)_2R^{11}$, —$S(O)_2N(R^{11})_2$, —$NO_2$, =O, =S, =$N(R^{11})$, and —CN; and $C_{3-10}$ carbocycle and 4- to 10-membered heterocycle, any of which is optionally substituted with one or more substituents independently selected from:

halogen, —$OR^{11}$, —$N(R^{11})_2$, —$C(O)R^{11}$, —$C(O)N(R^{11})_2$, —$N(R^{11})C(O)R^{11}$, —$C(O)OR^{11}$, —$OC(O)R^{11}$, —$NO_2$, =O, =S, =$N(R^{11})$, —CN; and $C_{1-6}$ alkyl $C_{2-6}$ alkenyl, and $C_{3-6}$ alkynyl, any one of which is optionally substituted with one or more substituents independently selected from: halogen, —$OR^{11}$, —$SR^{11}$, —$N(R^{11})_2$, —$C(O)R^{11}$, —$C(O)N(R^{11})_2$, —$N(R^{11})C(O)R^{11}$, —$N(R^{11})S(O)_2R^{11}$, —$C(O)OR^{11}$, —$OC(O)R^{11}$, —$NO_2$, =O, =S, =$N(R^{11})$, and —CN;

q is selected from 1, 2, and 3;

m and n are each independently selected from 0, 1, 2, and 3;

$R^2$ is independently selected at each instance from halogen, $C_{1-4}$ alkyl, $C_{1-4}$ haloalkyl, —$OR^{12}$, —$SR^{12}$, —$N(R^{12})_2$, —$NO_2$, and —CN;

$R^3$ is independently selected at each instance from:

halogen, —$OR^{13}$, —$SR^{13}$, —$N(R^{13})_2$, —$C(O)R^{13}$, —$C(O)N(R^{13})_2$, —$N(R^{13})C(O)R^{13}$, —$C(O)OR^{13}$, —$OC(O)R^{13}$, —$NO_2$, and —CN; and $C_{1-6}$ alkyl optionally substituted with one or more substituents independently selected from:

halogen, —$OR^{13}$, —$SR^{13}$, —$N(R^{13})_2$, —$C(O)R^{13}$, —$C(O)N(R^{13})_2$, —$N(R^{13})C(O)R^{13}$, —$C(O)OR^{13}$, —$OC(O)R^{13}$, —$NO_2$, =O, =S, =$N(R^{13})$, and —CN;

p is selected from 0, 1, 2, 3, 4, and 5;

$R^4$ is independently selected at each instance from:

halogen, —$OR^{14}$, —$SR^{14}$, —$N(R^{14})_2$, —$C(O)R^{14}$, —$C(O)N(R^{14})_2$, —$N(R^{14})C(O)R^{14}$, —$C(O)OR^{14}$, —$OC(O)R^{14}$, —$NO_2$, and —CN; and $C_{1-6}$ alkyl, $C_{2-6}$ alkenyl, $C_{2-6}$ alkynyl, any one of which is optionally substituted with one or more substituents independently selected from halogen, —$OR^{14}$, —$SR^{14}$, —$N(R^{14})_2$, —$C(O)R^{14}$, —$C(O)N(R^{14})_2$, —$N(R^{14})C(O)R^{14}$, —$C(O)OR^{14}$, —$OC(O)R^{14}$, —$NO_2$, =O, =S, =$N(R^{14})$, and —CN; or two $R^4$ attached to the same atom are taken together to form a group selected from: =O, =S, and =$N(R^{14})$; or two $R^4$ attached to the same atom or to adjacent atoms are taken together with the carbons to which they are attached to form a group selected from 4- to 8-membered heterocycle and $C_{3-8}$ carbocycle, any of which is optionally substituted with one or more substituents independently selected from: halogen, $C_{1-4}$ alkyl, $C_{1-4}$ haloalkyl, —$OR^{14}$, —$SR^{14}$, —$N(R^{14})_2$, —$NO_2$, and —CN;

L is represented by -$L^1$-$L^2$-$L^3$-$L^4$-, wherein $L^1$, $L^2$, $L^3$, and $L^4$ are each independently selected from (a) and (b):

(a) —O—, —$N(R^{15})$—, —S—, —S(O)—, —$S(O)_2$—, —$S(O)(NR^{15})$—, —$N(R^{15})C(O)$—, —$N(R^{15})C(O)O$—, —$N(R^{15})S(O)_2$—, —$N(R^{15})S(O)_2N(R^{15})$—, —$S(O)(NR^{15})N(R^{15})$—, —$N(R^{15})N(R^{15})$—, —$(R^{15})NC(O)N(R^{15})$—, and —$(R^{15})NC(O)N(R^{15})N(R^{15})$—; and (b) $C_{1-6}$ alkylene, $C_{2-6}$ alkenylene, $C_{2-6}$ alkynylene, $C_{3-8}$ carbocyclene, and 4- to 8-membered heterocyclene, any of which is optionally substituted with one or more substituents independently selected from halogen, —$OR^1$, —$SR^{15}$, =O, =S, and —CN;

wherein $L^2$, $L^3$, and $L^4$ are each optionally absent;

wherein no more than two of $L^1$, $L^2$, $L^3$, and $L^4$ are selected from (a) and the two selected are not adjacent;

$R^5$ is selected from 4- to 10-membered heterocycle and $C_{3-10}$ carbocycle, any of which is optionally substituted with one or more substituents independently selected from:

halogen, $C_{1-4}$ haloalkyl, —$OR^{16}$, —$SR^{16}$, —$N(R^{16})_2$, —$C(O)N(R^{16})_2$, —$C(O)OR^{16}$, —$OC(O)R^{16}$, —$N(R^{16})C(O)R^{16}$, —$N(R^{16})S(O)_2R^{16}$, —$S(O)_2N(R^{16})_2$, —$N(R^{16})C(O)N(R^{16})_2$, —$N(R^{16})C(O)OR^{16}$, —OC(O)N($R^{16}$)$_2$, —S(O)$R^{16}$, —S(O)$_2R^{16}$, —$NO_2$, =O, =S, =N($R^{16}$), and —CN;

$C_{1-4}$ alkyl, $C_{2-6}$ alkenyl, and $C_{2-6}$ alkynyl, each of which is optionally substituted with one or more substituents independently selected from: halogen, $C_{1-4}$ alkyl, $C_{1-4}$ haloalkyl, —$OR^{16}$, —$SR^{16}$, —N($R^{16}$)$_2$, —$NO_2$, and —CN; and 4- to 6-membered heterocycle and $C_{3-8}$ carbocycle, each of which is optionally substituted with one or more substituents independently selected from: halogen, $C_{1-4}$ alkyl, $C_{1-4}$ haloalkyl, —$OR^{16}$, —$SR^{16}$, —N($R^{16}$)$_2$, —$NO_2$, and —CN;

$R^{10}$, $R^{11}$, $R^{12}$, $R^{13}$, $R^{14}$, and $R^{15}$ are each independently selected at each occurrence from: hydrogen, $C_{1-4}$ alkyl, $C_{3-8}$ carbocycle, 4- to 8-membered heterocycle, and $C_{1-4}$ haloalkyl;

$R^{16}$ is independently selected at each occurrence from (iv), (v), and (vi):

(iv) hydrogen;

(v) $C_{1-4}$ alkyl, wherein the $C_{1-4}$ alkyl is optionally substituted with one or more substituents independently selected from:

halogen, —$OR^{20}$, —$SR^{20}$, —N($R^{20}$)$_2$, —C(O)$R^{20}$, —C(O)$OR^{20}$, —OC(O)$R^{20}$, —C(O)N($R^{20}$)$_2$, —N($R^{20}$)C(O)$R^{20}$, —N($R^{20}$)C(O)N($R^{20}$)$_2$, —N($R^{20}$)C(O)$OR^{20}$, OC(O)N($R^{20}$)$_2$, —S(O)$R^{20}$, —S(O)$_2R^{20}$, —N($R^{20}$)S(O)$_2R^{20}$, —S(O)$_2$ N($R^{20}$)$_2$, —$NO_2$, and —CN;

$C_{3-8}$ carbocycle and 4- to 8-membered heterocycle, either of which is optionally substituted with one or more substituents independently selected from: halogen, $C_{1-4}$ alkyl, $C_{1-4}$ haloalkyl, —$OR^{20}$, —$SR^{20}$, —N($R^{20}$)$_2$, —C(O)$R^{20}$, —C(O)$OR^{20}$, —OC(O)$R^{20}$, —C(O)N($R^{20}$)$_2$, —N($R^{20}$)C(O)$R^{20}$, —N($R^{20}$)C(O)N($R^{20}$)$_2$, —N($R^{20}$)C(O)$OR^{20}$, —OC(O)N($R^{20}$)$_2$, —S(O)$R^{20}$, —S(O)$_2R^{20}$, —N($R^{20}$)S(O)$_2R^{20}$, —S(O)$_2$N($R^{20}$)$_2$, —$NO_2$, and —CN; and (vi) $C_{3-8}$ carbocycle and 4- to 8-membered heterocycle, either of which is optionally substituted with one or more substituents independently selected from halogen, $C_{1-4}$ alkyl, $C_{1-4}$ haloalkyl, —$OR^{20}$, —$SR^{20}$, —N($R^{20}$)$_2$, —C(O)$R^{20}$, —C(O)N($R^{20}$)$_2$, —C(O) $OR^{20}$, —OC(O)$R^{20}$, —N($R^{20}$)C(O)$R^{20}$, —N($R^{20}$)S (O)$_2R^{20}$, —N($R^{20}$)C(O)N($R^{20}$)$_2$, —N($R^{20}$)C(O) $OR^{20}$, —OC(O)N($R^{20}$)$_2$, —S(O)$R^{20}$, —S(O)$_2R^{20}$, —$NO_2$, and —CN; and $R^{20}$ is independently selected at each occurrence from hydrogen, $C_{1-4}$ alkyl, $C_{1-4}$ haloalkyl, $C_{3-8}$ carbocycle, and 4- to 8-membered heterocycle.

In some embodiments, for the compound or salt of Formula (I) or Formula (II), q is selected from 1, 2, and 3. In some embodiments, q is selected from 1 and 2. In some embodiments, q is selected from 1 and 3. In some embodiments, q is selected from 2 and 3. In some embodiments, q is selected from 1 and 2. In some embodiments, q is 1.

In some embodiments, the compound or salt of Formula (II) is represented by the structure of Formula (II-A):

(II-A)

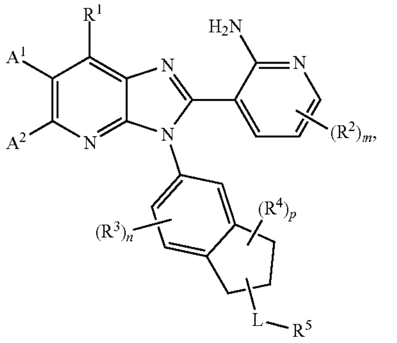

or a pharmaceutically acceptable salt thereof, wherein $A^1$, $A^2$, $R^1$, $R^2$, $R^3$, $R^4$, $R^5$, m, n, p, and L are each defined as in Formula (II).

In some embodiments, the compound or salt of Formula (II) is represented by the structure of Formula (III):

(III)

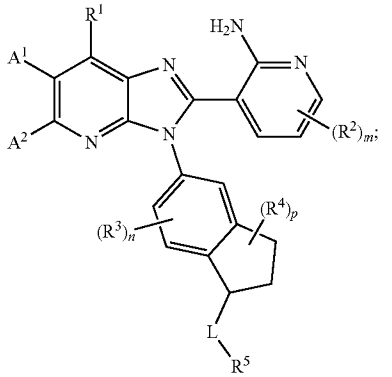

or a pharmaceutically acceptable salt thereof, wherein $A^1$, $A^2$, $R^1$, $R^2$, $R^3$, $R^4$, $R^5$, m, n, p, and L are each defined as in Formula (II).

In some embodiments, the compound or salt of Formula (II) is represented by the structure of Formula (III-A):

(III-A)

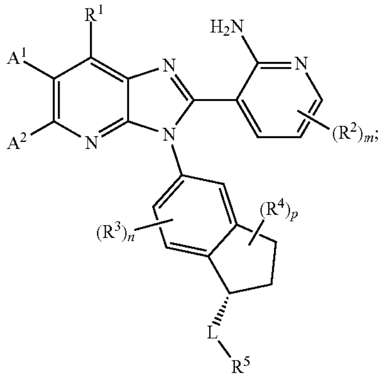

or a pharmaceutically acceptable salt thereof, wherein $A^1$, $A^2$, $R^1$, $R^2$, $R^3$, $R^4$, $R^5$, m, n, p, and L are each defined as in Formula (II).

In some embodiments, the compound or salt of Formula (II) is represented by the structure of Formula (III-B):

(III-B)

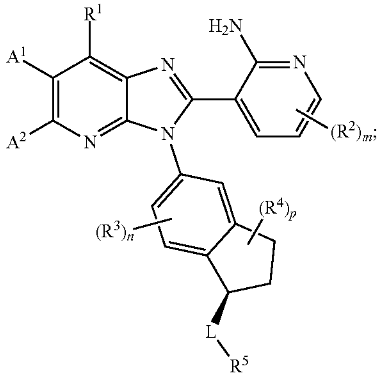

or a pharmaceutically acceptable salt thereof, wherein $A^1$, $A^2$, $R^1$, $R^2$, $R^3$, $R^4$, $R^5$, m, n, p, and L are each defined as in Formula (II).

In some embodiments, for the compound or salt of Formula (I), (II), (II-A), (III), (III-A), or (III-B), m is selected from 0, 1, 2, and 3. In some embodiments, m is selected from 0, 1, and 2. In some embodiments, m is selected from 0 and 1. In some embodiments, m is 0.

In some embodiments, for the compound or salt of Formula (I), (II), (II-A), (III), (III-A), or (III-B), n is selected from 0, 1, 2, and 3. In some embodiments, n is selected from 0, 1, and 2. In some embodiments, n is selected from 0 and 1. In some embodiments, n is 0.

In some embodiments, for the compound or salt of Formula (I), (II), (II-A), (III), (III-A), or (III-B), p is selected from 0, 1, 2, 3, 4, and 5. In some embodiments, p is selected from 0, 1, 2, 3, and 4. In some embodiments, p is selected from 0, 1, 2, and 3. In some embodiments, p is selected from 0, 1, and 2. In some embodiments, p is selected from 0 and 1. In some embodiments, p is 0.

In some embodiments, for the compound or salt of Formula (I), (II), (II-A), (III), (III-A), or (III-B), $A^1$ and $A^2$ are each independently selected from selected from (i), (ii), and (iii):

(i) hydrogen, halogen, $C_{1-4}$ haloalkyl, —$OR^{11}$, —$SR^{11}$, —$N(R^{11})_2$, —$C(O)N(R^{11})_2$, —$N(R^{11})C(O)R^{11}$, —$C(O)OR^{11}$, —$OC(O)R^{11}$, —$N(R^{11})C(O)OR^{11}$, —$OC(O)N(R^{11})_2$, —$N(R^{11})C(O)N(R^{11})_2$, —$S(O)R^{11}$, —$S(O)_2R^{11}$, —$N(R^{11})S(O)_2R^{11}$, —$S(O)_2N(R^{11})_2$, —$NO_2$, and —CN;

(ii) $C_{1-6}$ alkyl, $C_{2-6}$ alkenyl, and $C_{2-6}$ alkynyl, any of which is optionally substituted with one or more substituents independently selected from:

halogen, —$OR^{11}$, —$SR^{11}$, —$N(R^{11})_2$, —$C(O)N(R^{11})_2$, —$N(R^{11})C(O)R^{11}$, —$C(O)OR^{11}$, —$OC(O)R^{11}$, —$N(R^{11})C(O)OR^{11}$, —$OC(O)N(R^{11})_2$, —$N(R^{11})C(O)N(R^{11})_2$, —$S(O)R^{11}$, —$S(O)_2R^{11}$, —$N(R^{11})S(O)_2R^{11}$, —$S(O)_2N(R^{11})_2$, —$NO_2$, =O, =S, =$N(R^{11})$, and —CN; and (iii) 5- to 10-membered heterocycle and $C_{3-10}$ carbocycle, any of which is optionally substituted with one or more substituents independently selected from:

halogen, —$OR^{11}$, —$SR^{11}$, —$N(R^{11})_2$, —$C(O)R^{11}$, —$C(O)N(R^{11})_2$, —$N(R^{11})C(O)R^{11}$, —$N(R^{11})S(O)_2R^{11}$, —$C(O)OR^{11}$, —$OC(O)R^{11}$, —$N(R^{11})C(O)OR^{11}$, —$OC(O)N(R^{11})_2$, —$N(R^{11})C(O)N(R^{11})_2$, —$S(O)R^{11}$, —$S(O)_2R^{11}$, —$S(O)_2N(R^{11})_2$, —$NO_2$, =O, =S, =$N(R^{11})$, and —CN;

$C_{1-6}$ alkyl, $C_{2-6}$ alkenyl, and $C_{3-6}$ alkynyl, any one of which is optionally substituted with one or more substituents independently selected from:

halogen, —$OR^{11}$, —$SR^{11}$, —$N(R^{11})_2$, —$C(O)R^{11}$, —$C(O)N(R^{11})_2$, —$N(R^{11})C(O)R^{11}$, —$C(O)OR^{11}$, —$OC(O)R^{11}$, —$N(R^{11})C(O)OR^{11}$, —$OC(O)N(R^{11})_2$, —$N(R^{11})C(O)N(R^{11})_2$, —$S(O)R^{11}$, —$S(O)_2R^{11}$, —$N(R^{11})S(O)_2R^{11}$, —$S(O)_2N(R^{11})_2$, —$NO_2$, =O, =S, =$N(R^{11})$, and —CN; and $C_{3-10}$ carbocycle and 4- to 10-membered heterocycle; wherein the $C_{3-10}$ carbocycle and 4 to 10-membered heterocycle are each optionally substituted with one or more substituents independently selected from:

halogen, —$OR^{11}$, —$N(R^{11})_2$, —$C(O)R^{11}$, —$C(O)N(R^{11})_2$, —$N(R^{11})C(O)R^{11}$, —$C(O)OR^{11}$, —$OC(O)R^{11}$, —$NO_2$, =O, =S, =$N(R^{11})$, and —CN;

$C_{1-6}$ alkyl, $C_{2-6}$ alkenyl, and $C_{3-6}$ alkynyl, any one of which is optionally substituted with one or more substituents independently selected from:

halogen, —$OR^{11}$, —$SR^{11}$, —$N(R^{11})_2$, —$C(O)R^{11}$, —$C(O)N(R^{11})_2$, —$N(R^{11})C(O)R^{11}$, —$N(R^{11})S(O)_2R^{11}$, —$C(O)OR^{11}$, —$OC(O)R^{11}$, —$NO_2$, =O, =S, =$N(R^{11})$, and —CN.

In some embodiments, for the compound or salt of Formula (I), (II), (I1-A), (III), (I11-A), or (III-B), $A^1$ and $A^2$ are each independently selected from selected from (i), (ii), and (iii):

(i) hydrogen, halogen, $C_{1-4}$ haloalkyl, —$OR^{11}$, —$SR^{11}$, —$N(R^{11})_2$, —$C(O)N(R^{11})_2$, —$N(R^{11})C(O)R^{11}$, —$C(O)OR^{11}$, —$OC(O)R^{11}$, —$N(R^{11})C(O)OR^{11}$, —$OC(O)N(R^{11})_2$, —$N(R^{11})C(O)N(R^{11})_2$, —$S(O)R^{11}$, —$S(O)_2R^{11}$, —$N(R^{11})S(O)_2R^{11}$, —$S(O)_2N(R^{11})_2$, —$NO_2$, and —CN;

(ii) $C_{1-6}$ alkyl, $C_{2-6}$ alkenyl, and $C_{2-6}$ alkynyl, any of which is optionally substituted with one or more substituents independently selected from:

halogen, —$OR^{11}$, —$SR^{11}$, —$N(R^{11})_2$, —$C(O)N(R^{11})_2$, —$N(R^{11})C(O)R^{11}$, —$C(O)OR^{11}$, —$OC(O)R^{11}$, —$N(R^{11})C(O)OR^{11}$, —$OC(O)N(R^{11})_2$, —$N(R^{11})C(O)N(R^{11})_2$, —$S(O)R^{11}$, —$S(O)_2R^{11}$, —$N(R^{11})S(O)_2R^{11}$, —$S(O)_2N(R^{11})_2$, —$NO_2$, =O, =S, =$N(R^{11})$, and —CN; and (iii) 5- to 10-membered heterocycle and $C_{3-10}$ carbocycle, any of which is optionally substituted with one or more substituents independently selected from:

halogen, —$OR^{11}$, —$SR^{11}$, —$N(R^{11})_2$, —$C(O)R^{11}$, —$C(O)N(R^{11})_2$, —$N(R^{11})C(O)R^{11}$, —$N(R^{11})S(O)_2R^{11}$, —$C(O)OR^{11}$, —$OC(O)R^{11}$, —$N(R^{11})C(O)OR^{11}$, —$OC(O)N(R^{11})_2$, —$N(R^{11})C(O)N(R^{11})_2$, —$S(O)R^{11}$, —$S(O)_2R^{11}$, —$S(O)_2N(R^{11})_2$, —$NO_2$, =O, =S, =$N(R^{11})$, and —CN;

$C_{1-6}$ alkyl, $C_{2-6}$ alkenyl, and $C_{3-6}$ alkynyl, any one of which is optionally substituted with one or more substituents independently selected from: halogen, —$OR^{11}$, —$SR^{11}$, —$N(R^{11})_2$, —$C(O)R^{11}$, —$C(O)N(R^{11})_2$, —$N(R^{11})C(O)R^{11}$, —$C(O)OR^{11}$, —$OC(O)R^{11}$, —$N(R^{11})C(O)OR^{11}$, —$OC(O)N(R^{11})_2$, —$N(R^{11})C(O)N(R^{11})_2$, —$S(O)R^{11}$, —$S(O)_2R^{11}$, —$N(R^{11})S(O)_2R^{11}$, —$S(O)_2N(R^{11})_2$, —$NO_2$, =O, =S, =$N(R^{11})$, and —CN; and $C_{3-10}$ carbocycle and 4- to 10-membered heterocycle; wherein the $C_{3-10}$ carbocycle and 4 to 10-membered heterocycle are each optionally substituted with one or more substituents independently selected from:

halogen, —$OR^{11}$, —$N(R^{11})_2$, —$C(O)R^{11}$, —$C(O)N(R^{11})_2$, —$N(R^{11})C(O)R^{11}$, —$C(O)OR^{11}$, —$OC(O)R^{11}$, —$NO_2$, =O, =S, =$N(R^{11})$, and —CN;

$C_{1-6}$ alkyl, $C_{2-6}$ alkenyl, and $C_{3-6}$ alkynyl, any one of which is optionally substituted with one or more substituents independently selected from:

halogen, —$OR^{11}$, —$SR^{11}$, —$N(R^{11})_2$, —$C(O)R^{11}$, —$C(O)N(R^{11})_2$, —$N(R^{11})C(O)R^{11}$, —$N(R^{11})S(O)_2R^{11}$, —$C(O)OR^{11}$, —$OC(O)R^{11}$, —$NO_2$, =O, =S, =$N(R^{11})$, and —CN; and $R^{11}$ is independently selected at each occurrence from hydrogen, $C_{1-4}$ alkyl, $C_{3-8}$ carbocycle, 4- to 8-membered heterocycle, and $C_{1-4}$ haloalkyl.

In some embodiments, for the compound or salt of Formula (I), (II), (II-A), (III), (III-A), or (III-B), $A^1$ and $A^2$ are each independently selected from (i), (ii), and (iii):

(i) hydrogen, halogen, $C_{1-4}$ haloalkyl, —$OR^{11}$, —$N(R^{11})_2$, —$C(O)N(R^{11})_2$, —$N(R^{11})C(O)R^{11}$, and —CN;

(ii) $C_{1-6}$ alkyl, $C_{2-6}$ alkenyl, and $C_{2-6}$ alkynyl, any of which is optionally substituted with one or more substituents independently selected from:

halogen, —$OR^{11}$, —$N(R^{11})_2$, —$C(O)N(R^{11})_2$, —$N(R^{11})C(O)R^{11}$, =O, and —CN; and (iii) 5- to 10-membered heterocycle and $C_{3-10}$ carbocycle, any of which is optionally substituted with one or more substituents independently selected from:

halogen, —$OR^{11}$, —$N(R^{11})_2$, —$C(O)R^{11}$, —$C(O)N(R^{11})_2$, —$N(R^{11})C(O)R^{11}$, —$N(R^{11})S(O)_2R^{11}$, =O, and —CN;

$C_{1-6}$ alkyl, $C_{2-6}$ alkenyl, and $C_{3-6}$ alkynyl, any one of which is optionally substituted with one or more substituents independently selected from:

halogen, —$OR^{11}$, —$N(R^{11})_2$, —$C(O)R^{11}$, —$C(O)N(R^{11})_2$, —$N(R^{11})C(O)R^{11}$, —$N(R^{11})S(O)_2R^{11}$, —$NO_2$, =O, and —CN; and $C_{3-10}$ carbocycle and 4- to 10-membered heterocycle; wherein the $C_{3-10}$ carbocycle and 4 to 10-membered heterocycle are each optionally substituted with one or more substituents independently selected from:

halogen, —$OR^{11}$, —$N(R^{11})_2$, —$C(O)R^{11}$, —$C(O)N(R^{11})_2$, —$N(R^{11})C(O)R^{11}$, =O, and —CN; and $C_{1-6}$ alkyl, $C_{2-6}$ alkenyl, and $C_{3-6}$ alkynyl, any one of which is optionally substituted with one or more substituents independently selected from:

halogen, —$OR^{11}$, —$N(R^{11})_2$, —$C(O)R^{11}$, —$C(O)N(R^{11})_2$, —$N(R^{11})C(O)R^{11}$, —$N(R^{11})S(O)_2R^{11}$, =O, and —CN.

In some embodiments, for the compound or salt of Formula (I), (II), (II-A), (III), (III-A), or (III-B), $A^1$ and $A^2$ are each independently selected from (i), (ii), and (iii):

(i) hydrogen, halogen, $C_{1-4}$ haloalkyl, —$OR^{11}$, —$N(R^{11})_2$, and —CN;

(ii) $C_{1-6}$ alkyl and $C_{2-6}$ alkynyl, any of which is optionally substituted with one or more halogen; and (iii) 5- to 10-membered heterocycle and $C_{3-10}$ carbocycle, any of which is optionally substituted with one or more substituents independently selected from:

halogen, —$OR^{11}$, $C_{1-6}$ alkyl, $C_{1-6}$ haloalkyl, $C_{3-10}$ carbocycle and 4- to 10-membered heterocycle; wherein the $C_{3-10}$ carbocycle and 4- to 10-membered heterocycle are each optionally substituted with one or more $C_{1-6}$ alkyl.

In some embodiments, for the compound or salt of Formula (I), (II), (II-A), (III), (III-A), or (III-B), $A^1$ and $A^2$ are each independently selected from (i) and (iii):

(i) hydrogen, halogen, —$OR^{11}$, $C_{1-6}$ alkyl and $C_{2-6}$ alkynyl; and (iii) 5- to 10-membered heterocycle and $C_{3-10}$ carbocycle, any of which is optionally substituted with one or more substituents independently selected from:

halogen, $C_{1-6}$ alkyl, $C_{1-6}$ haloalkyl, and 4- to 10-membered heterocycle; wherein the 4- to 10-membered heterocycle is optionally substituted with one or more $C_{1-6}$ alkyl.

In some embodiments, for the compound or salt of Formula (I), (II), (II-A), (III), (III-A), or (III-B), $A^1$ and $A^2$ are each independently selected from: hydrogen, 5- to 10-membered heterocycle, and $C_{3-10}$ carbocycle, any of which is optionally substituted with one or more substituents independently selected from: halogen, $C_{1-6}$ alkyl, and $C_{1-6}$ haloalkyl.

In some embodiments, for the compound or salt of Formula (I), (II), (II-A), (III), (III-A), or (III-B), $A^1$ and $A^2$ are each independently selected from: hydrogen, and 5- to 10-membered heterocycle, any of which is optionally substituted with one or more substituents independently selected from: halogen, $C_{1-6}$ alkyl, and $C_{1-6}$ haloalkyl.

In some embodiments, for the compound or salt of Formula (I), (II), (II-A), (III), (III-A), or (III-B), $A^1$ and $A^2$ are each independently selected from: hydrogen, and 5- to 10-membered heterocycle, any of which is optionally substituted with one or more substituents independently selected from: halogen.

In some embodiments, for the compound or salt of Formula (I), (II), (II-A), (III), (III-A), or (III-B), $A^1$ is selected from selected from (i), (ii), and (iii):

(i) hydrogen, halogen, $C_{1-4}$ haloalkyl, —$OR^{11}$, —$SR^{11}$, —$N(R^{11})_2$, —$C(O)N(R^{11})_2$, —$N(R^{11})C(O)R^{11}$, —$C(O)OR^{11}$, —$OC(O)R^{11}$, —$N(R^{11})C(O)OR^{11}$, —$OC(O)N(R^{11})_2$, —$N(R^{11})C(O)N(R^{11})_2$, —$S(O)R^{11}$, —$S(O)_2R^{11}$, —$N(R^{11})S(O)_2R^{11}$, —$S(O)_2N(R^{11})_2$, —$NO_2$, and —CN;

(ii) $C_{1-6}$ alkyl, $C_{2-6}$ alkenyl, and $C_{2-6}$ alkynyl, any of which is optionally substituted with one or more substituents independently selected from:

halogen, —$OR^{11}$, —$SR^{11}$, —$N(R^{11})_2$, —$C(O)N(R^{11})_2$, —$N(R^{11})C(O)R^{11}$, —$C(O)OR^{11}$, —$OC(O)R^{11}$, —$N(R^{11})C(O)OR^{11}$, —$OC(O)N(R^{11})_2$, —$N(R^{11})C(O)N(R^{11})_2$, —$S(O)R^{11}$, —$S(O)_2R^{11}$, —$N(R^{11})S(O)_2R^{11}$, —$S(O)_2N(R^{11})_2$, —$NO_2$, =O, =S, =$N(R^{11})$, and —CN; and (iii) 5- to 10-membered heterocycle and $C_{3-10}$ carbocycle, any of which is optionally substituted with one or more substituents independently selected from:

halogen, —$OR^{11}$, —$SR^{11}$, —$N(R^{11})_2$, —$C(O)R^{11}$, —$C(O)N(R^{11})_2$, —$N(R^{11})C(O)R^{11}$, —$N(R^{11})S(O)_2R^{11}$, —$C(O)OR^{11}$, —$OC(O)R^{11}$, —$N(R^{11})C(O)OR^{11}$, —$OC(O)N(R^{11})_2$, —$N(R^{11})C(O)N(R^{11})_2$, —$S(O)R^{11}$, —$S(O)_2R^{11}$, —$S(O)_2N(R^{11})_2$, —$NO_2$, =O, =S, =$N(R^{11})$, and —CN;

$C_{1-6}$ alkyl, $C_{2-6}$ alkenyl, and $C_{3-6}$ alkynyl, any one of which is optionally substituted with one or more substituents independently selected from:

halogen, —$OR^{11}$, —$SR^{11}$, —$N(R^{11})_2$, —$C(O)R^{11}$, —$C(O)N(R^{11})_2$, —$N(R^{11})C(O)R^{11}$, —$C(O)OR^{11}$, —$OC(O)R^{11}$, —$N(R^{11})C(O)OR^{11}$, —$OC(O)N(R^{11})_2$, —$N(R^{11})C(O)N(R^{11})_2$, —$S(O)R^{11}$, —$S(O)_2R^{11}$, —$N(R^{11})S(O)_2R^{11}$, —$S(O)_2N(R^{11})_2$, —$NO_2$, =O, =S, =$N(R^{11})$, and —CN; and $C_{3-10}$ carbocycle and 4- to 10-membered heterocycle; wherein the $C_{3-10}$ carbocycle and 4 to 10-membered heterocycle are each optionally substituted with one or more substituents independently selected from:

halogen, —$OR^{11}$, —$N(R^{11})_2$, —$C(O)R^{11}$, —$C(O)N(R^{11})_2$, —$N(R^{11})C(O)R^{11}$, —$C(O)OR^{11}$, —$OC(O)R^{11}$, —$NO_2$, =O, =S, =$N(R^{11})$, and —CN;

$C_{1-6}$ alkyl, $C_{2-6}$ alkenyl, and $C_{3-6}$ alkynyl, any one of which is optionally substituted with one or more substituents independently selected from:

halogen, —$OR^{11}$, —$SR^{11}$, —$N(R^{11})_2$, —$C(O)R^{11}$, —$C(O)N(R^{11})_2$, —$N(R^{11})C(O)R^{11}$, —$N(R^{11})S(O)_2R^{11}$, —$C(O)OR^{11}$, —$OC(O)R^{11}$, —$NO_2$, ═O, ═S, ═$N(R^{11})$, and —CN.

In some embodiments, for the compound or salt of Formula (I), (II), (II-A), (III), (III-A), or (III-B), $A^1$ is selected from selected from (i), (ii), and (iii):

(i) hydrogen, halogen, $C_{1-4}$ haloalkyl, —$OR^{11}$, —$SR^{11}$, —$N(R^{11})_2$, —$C(O)N(R^{11})_2$, —$N(R^{11})C(O)R^{11}$, —$C(O)OR^{11}$, —$OC(O)R^{11}$, —$N(R^{11})C(O)OR^{11}$, —$OC(O)N(R^{11})_2$, —$N(R^{11})C(O)N(R^{11})_2$, —$S(O)R^{11}$, —$S(O)_2R^{11}$, —$N(R^{11})S(O)_2R^{11}$, —$S(O)_2N(R^{11})_2$, —$NO_2$, and —CN;

(ii) $C_{1-6}$ alkyl, $C_{2-6}$ alkenyl, and $C_{2-6}$ alkynyl, any of which is optionally substituted with one or more substituents independently selected from:

halogen, —$OR^{11}$, —$SR^{11}$, —$N(R^{11})_2$, —$C(O)N(R^{11})_2$, —$N(R^{11})C(O)R^{11}$, —$C(O)OR^{11}$, —$OC(O)R^{11}$, —$N(R^{11})C(O)OR^{11}$, —$OC(O)N(R^{11})_2$, —$N(R^{11})C(O)N(R^{11})_2$, —$S(O)R^{11}$, —$S(O)_2R^{11}$, —$N(R^{11})S(O)_2R^1$, —$S(O)_2N(R^{11})_2$, —$NO_2$, ═O, ═S, ═$N(R^{11})$, and —CN; and (iii) 5- to 10-membered heterocycle and $C_{3-10}$ carbocycle, any of which is optionally substituted with one or more substituents independently selected from:

halogen, —$OR^{11}$, —$SR^{11}$, —$N(R^{11})_2$, —$C(O)R^{11}$, —$C(O)N(R^{11})_2$, —$N(R^{11})C(O)R^{11}$, —$N(R^{11})S(O)_2R^{11}$, —$C(O)OR^{11}$, —$OC(O)R^{11}$, —$N(R^{11})C(O)OR^{11}$, —$OC(O)N(R^{11})_2$, —$N(R^{11})C(O)N(R^{11})_2$, —$S(O)R^{11}$, —$S(O)_2R^{11}$, —$S(O)_2N(R^{11})_2$, —$NO_2$, ═O, ═S, ═$N(R^{11})$, and —CN;

$C_{1-6}$ alkyl, $C_{2-6}$ alkenyl, and $C_{3-6}$ alkynyl, any one of which is optionally substituted with one or more substituents independently selected from: halogen, —$OR^{11}$, —$SR^{11}$, —$N(R^{11})_2$, —$C(O)R^{11}$, —$C(O)N(R^{11})_2$, —$N(R^{11})C(O)R^{11}$, —$C(O)OR^{11}$, —$OC(O)R^{11}$, —$N(R^{11})C(O)OR^{11}$, —$OC(O)N(R^{11})_2$, —$N(R^{11})C(O)N(R^{11})_2$, —$S(O)R^{11}$, —$S(O)_2R^{11}$, —$N(R^{11})S(O)_2R^{11}$, —$S(O)_2N(R^{11})_2$, —$NO_2$, ═O, ═S, ═$N(R^{11})$, and —CN; and $C_{3-10}$ carbocycle and 4- to 10-membered heterocycle; wherein the $C_{3-10}$ carbocycle and 4 to 10-membered heterocycle are each optionally substituted with one or more substituents independently selected from:

halogen, —$OR^{11}$, —$N(R^{11})_2$, —$C(O)R^{11}$, —$C(O)N(R^{11})_2$, —$N(R^{11})C(O)R^{11}$, —$C(O)OR^{11}$, —$OC(O)R^{11}$, —$NO_2$, ═O, ═S, ═$N(R^{11})$, and —CN;

$C_{1-6}$ alkyl, $C_{2-6}$ alkenyl, and $C_{3-6}$ alkynyl, any one of which is optionally substituted with one or more substituents independently selected from:

halogen, —$OR^{11}$, —$SR^{11}$, —$N(R^{11})_2$, —$C(O)R^{11}$, —$C(O)N(R^{11})_2$, —$N(R^{11})C(O)R^1$ 1, —$N(R^{11})S(O)_2R^{11}$, —$C(O)OR^{11}$, —$OC(O)R^{11}$, —$NO_2$, ═O, ═S, ═$N(R^{11})$, and —CN; and $R^{11}$ is independently selected at each occurrence from hydrogen, $C_{1-4}$ alkyl, $C_{3-8}$ carbocycle, 4- to 8-membered heterocycle, and $C_{1-4}$ haloalkyl.

In some embodiments, for the compound or salt of Formula (I), (II), (II-A), (III), (III-A), or (III-B), $A^1$ is selected from (i), (ii), and (iii):

(i) hydrogen, halogen, $C_{1-4}$ haloalkyl, —$OR^{11}$, —$N(R^{11})_2$, —$C(O)N(R^{11})_2$, —$N(R^{11})C(O)R^{11}$, and —CN;

(ii) $C_{1-6}$ alkyl, $C_{2-6}$ alkenyl, and $C_{2-6}$ alkynyl, any of which is optionally substituted with one or more substituents independently selected from:

halogen, —$OR^{11}$, —$N(R^{11})_2$, —$C(O)N(R^{11})_2$, —$N(R^{11})C(O)R^{11}$, ═O, and —CN; and (iii) 5- to 10-membered heterocycle and $C_{3-10}$ carbocycle, any of which is optionally substituted with one or more substituents independently selected from:

halogen, —$OR^{11}$, —$N(R^{11})_2$, —$C(O)R^{11}$, —$C(O)N(R^{11})_2$, —$N(R^{11})C(O)R^{11}$, —$N(R^{11})S(O)_2R^{11}$, ═O, and —CN;

$C_{1-6}$ alkyl, $C_{2-6}$ alkenyl, and $C_{3-6}$ alkynyl, any one of which is optionally substituted with one or more substituents independently selected from:

halogen, —$OR^{11}$, —$N(R^{11})_2$, —$C(O)R^{11}$, —$C(O)N(R^{11})_2$, —$N(R^{11})C(O)R^{11}$, —$N(R^{11})S(O)_2R^{11}$, —$NO_2$, ═O, and —CN; and $C_{3-10}$ carbocycle and 4- to 10-membered heterocycle; wherein the $C_{3-10}$ carbocycle and 4 to 10-membered heterocycle are each optionally substituted with one or more substituents independently selected from:

halogen, —$OR^{11}$, —$N(R^{11})_2$, —$C(O)R^{11}$, —$C(O)N(R^{11})_2$, —$N(R^{11})C(O)R^{11}$, ═O, and —CN; and $C_{1-6}$ alkyl, $C_{2-6}$ alkenyl, and $C_{3-6}$ alkynyl, any one of which is optionally substituted with one or more substituents independently selected from:

halogen, —$OR^{11}$, —$N(R^{11})_2$, —$C(O)R^{11}$, —$C(O)N(R^{11})_2$, —$N(R^{11})C(O)R^{11}$, —$N(R^{11})S(O)_2R^{11}$, ═O, and —CN.

In some embodiments, for the compound or salt of Formula (I), (II), (II-A), (III), (III-A), or (III-B), $A^1$ is selected from (i), (ii), and (iii):

(i) hydrogen, halogen, $C_{1-4}$ haloalkyl, —$OR^{11}$, —$N(R^{11})_2$, and —CN;

(ii) $C_{1-6}$ alkyl and $C_{2-6}$ alkynyl, any of which is optionally substituted with one or more halogen; and (iii) 5- to 10-membered heterocycle and $C_{3-10}$ carbocycle, any of which is optionally substituted with one or more substituents independently selected from:

halogen, —$OR^{11}$, $C_{1-6}$ alkyl, $C_{1-6}$ haloalkyl, $C_{3-10}$ carbocycle and 4- to 10-membered heterocycle; wherein the $C_{3-10}$ carbocycle and 4- to 10-membered heterocycle are each optionally substituted with one or more $C_{1-6}$ alkyl.

In some embodiments, for the compound or salt of Formula (I), (II), (II-A), (III), (III-A), or (III-B), $A^1$ is selected from (i) and (iii):

(i) hydrogen, halogen, —$OR^{11}$, $C_{1-6}$ alkyl and $C_{2-6}$ alkynyl; and (iii) 5- to 10-membered heterocycle and $C_{3-10}$ carbocycle, any of which is optionally substituted with one or more substituents independently selected from:

halogen, $C_{1-6}$ alkyl, $C_{1-6}$ haloalkyl, and 4- to 10-membered heterocycle; wherein the 4- to 10-membered heterocycle is optionally substituted with one or more $C_{1-6}$ alkyl.

In some embodiments, for the compound or salt of Formula (I), (II), (II-A), (III), (III-A), or (III-B), $A^1$ is selected from: hydrogen, 5- to 10-membered heterocycle, and $C_{3-10}$ carbocycle, any of which is optionally substituted with one or more substituents independently selected from: halogen, $C_{1-6}$ alkyl, and $C_{1-6}$ haloalkyl. In some embodiments, $A^1$ is selected from: hydrogen, and 5 to 10-membered heterocycle, any of which is optionally substituted with one or more substituents independently selected from: halogen, $C_{1-6}$ alkyl, and $C_{1-6}$ haloalkyl. In some embodiments, $A^1$ is selected from: hydrogen and 5- to 10-membered heterocycle, any of which is optionally substituted with one or more substituents independently selected from: halogen. In some embodiments, $A^1$ is hydrogen.

In some embodiments, for the compound or salt of Formula (I), (II), (II-A), (III), (III-A), or (III-B), $A^1$ is selected from hydrogen, halogen, $C_{1-4}$ alkyl, $C_{1-4}$ haloalkyl, —$OR^{11}$, —$N(R^{11})_2$ and —CN. In some embodiments, $A^1$ is selected from hydrogen, halogen, $C_{1-4}$ alkyl, and $C_{1-4}$ haloalkyl. In some embodiments, $A^1$ is selected from hydrogen, fluoro, and methyl. In some embodiments, $A^1$ is hydrogen.

In some embodiments, for the compound or salt of Formula (I), (II), (II-A), (III), (III-A), or (III-B), $R^2$ is independently selected at each instance from halogen, $C_{1-4}$ alkyl, $C_{1-4}$ haloalkyl, —$OR^{12}$, —$SR^{12}$, —$N(R^{12})_2$, —$NO_2$, and —CN. In some embodiments, $R^2$ is independently selected at each instance from: halogen, $C_{1-4}$ alkyl, $C_{1-4}$ haloalkyl, —$OR^{12}$, —$SR^{12}$, —$N(R^{12})_2$, —$NO_2$, and —CN; and $R^{12}$ is independently selected at each occurrence from hydrogen and $C_{1-4}$ alkyl. In some embodiments, $R^2$ is independently selected at each instance from halogen, $C_{1-4}$ alkyl, and $C_{1-4}$ haloalkyl.

In some embodiments, for the compound or salt of Formula (I), (II), (II-A), (III), (III-A), or (III-B), $R^3$ is independently selected at each instance from:

halogen, —$OR^{13}$, —$SR^{13}$, —$N(R^{13})_2$, —$C(O)R^{13}$, —$C(O)N(R^{13})_2$, —$N(R^{13})C(O)R^{13}$, —$C(O)OR^{13}$, —$OC(O)R^{13}$, —$NO_2$, and —CN; and $C_{1-6}$ alkyl optionally substituted with one or more substituents independently selected from:

halogen, —$OR^{13}$, —$SR^{13}$, —$N(R^{13})_2$, —$C(O)R^{13}$, —$C(O)N(R^{13})_2$, —$N(R^{13})C(O)R^{13}$, —$C(O)OR^{13}$, —$OC(O)R^{13}$, —$NO_2$, =O, =S, =$N(R^{13})$, and —CN.

In some embodiments, for the compound or salt of Formula (I), (II), (II-A), (III), (III-A), or (III-B), $R^3$ is independently selected at each instance from:

halogen, —$OR^{13}$, —$N(R^{13})_2$, —$C(O)R^{13}$, —$C(O)N(R^{13})_2$, —$N(R^{13})C(O)R^{13}$, —$C(O)OR^{13}$, —$OC(O)R^{13}$, —$NO_2$, and —CN; and $C_{1-6}$ alkyl optionally substituted with one or more substituents independently selected from: halogen, —$OR^{13}$, —$SR^{13}$, —$N(R^{13})_2$, —$C(O)R^{13}$, —$C(O)N(R^{13})_2$, —$N(R^{13})C(O)R^{13}$, —$C(O)OR^{13}$, —$OC(O)R^{13}$, —$NO_2$, =O, =S, =$N(R^{13})$, and —CN.

In some embodiments, for the compound or salt of Formula (I), (II), (II-A), (III), (III-A), or (III-B), $R^3$ is independently selected at each instance from:

halogen, —$OR^{13}$, —$N(R^{13})_2$, —$C(O)R^{13}$, —$C(O)N(R^{13})_2$, —$N(R^{13})C(O)R^{13}$, —$C(O)OR^{13}$, —$OC(O)R^{13}$, —$NO_2$, and —CN; and $C_{1-6}$ alkyl optionally substituted with one or more substituents independently selected from: halogen, —$OR^{13}$, —$SR^{13}$, —$N(R^{13})_2$, —$C(O)R^{13}$, —$C(O)N(R^{13})_2$, —$N(R^{13})C(O)R^{13}$, —$C(O)OR^{13}$, —$OC(O)R^{13}$, —$NO_2$, =O, =S, =$N(R^{13})$, and —CN; and $R^{13}$ is independently selected at each occurrence from hydrogen and $C_{1-4}$ alkyl, $C_{3-8}$ carbocycle, 4- to 8-membered heterocycle, and $C_{1-4}$ haloalkyl.

In some embodiments, for the compound or salt of Formula (I), (II), (II-A), (III), (III-A), or (III-B), $R^3$ is independently selected at each instance from:

halogen, —$OR^{13}$, —$SR^{13}$, —$N(R^{13})_2$, —$C(O)R^{13}$, —$C(O)N(R^{13})_2$, —$N(R^{13})C(O)R^{13}$, and —CN; and $C_{1-6}$ alkyl optionally substituted with one or more substituents independently selected from:

halogen, —$OR^{13}$, —$N(R^{13})_2$, —$C(O)R^{13}$, —$C(O)N(R^{13})_2$, —$N(R^{13})C(O)R^{13}$, =O, and —CN.

In some embodiments, for the compound or salt of Formula (I), (II), (II-A), (III), (III-A), or (III-B), $R^3$ is independently selected at each instance from halogen, —$OR^{13}$, —$N(R^{13})_2$, —CN, $C_{1-6}$ alkyl, and $C_{1-6}$ haloalkyl. In some embodiments, $R^3$ is independently selected at each instance from halogen, —$OR^{13}$, —$N(R^{13})_2$, —CN, $C_{1-6}$ alkyl, and $C_{1-6}$ haloalkyl; and $R^{13}$ is independently selected at each occurrence from hydrogen and $C_{1-4}$ alkyl. In some embodiments, $R^3$ is independently selected at each instance from halogen, $C_{1-4}$ alkyl, $C_{1-4}$haloalkyl, and —CN.

In some embodiments, for the compound or salt of Formula (I), (II), (II-A), (III), (III-A), or (III-B), $R^4$ is independently selected at each instance from:

halogen, —$OR^{14}$, —$SR^{14}$, —$N(R^{14})_2$, —$C(O)R^{14}$, —$C(O)N(R^{14})_2$, —$N(R^{14})C(O)R^{14}$, —$C(O)OR^{14}$, —$OC(O)R^{14}$, —$NO_2$, and —CN; and $C_{1-6}$ alkyl, $C_{2-6}$ alkenyl, $C_{2-6}$ alkynyl, any one of which is optionally substituted with one or more substituents selected from halogen, —$OR^{14}$, —$SR^{14}$, —$N(R^{14})_2$, —$C(O)R^{14}$, —$C(O)N(R^{14})_2$, —$N(R^{14})C(O)R^{14}$, —$C(O)OR^{14}$, —$OC(O)R^{14}$, —$NO_2$, =O, =S, =$N(R^{14})$, and —CN; or two $R^4$ attached to the same atom are taken together to form a group selected from: =O, =S, and =$N(R^{14})$; or two $R^4$ attached to the same atom or to adjacent atoms are taken together with the carbons to which they are attached to form a group selected from 4- to 8-membered heterocycle and $C_{3-8}$ carbocycle, any of which is optionally substituted with one or more substituents independently selected from halogen, $C_{1-4}$ alkyl, $C_{1-4}$ haloalkyl, —$OR^{14}$, —$SR^{14}$, —$N(R^{14})_2$, —$NO_2$, and —CN.

In some embodiments, for the compound or salt of Formula (I), (II), (II-A), (III), (III-A), or (III-B), $R^4$ is independently selected at each instance from:

halogen, —$OR^{14}$, —$SR^{14}$, —$N(R^{14})_2$, —$C(O)R^{14}$, —$C(O)N(R^{14})_2$, —$N(R^{14})C(O)R^{14}$, —$C(O)OR^{14}$, —$OC(O)R^{14}$, —$NO_2$, and —CN; and $C_{1-6}$ alkyl, $C_{2-6}$ alkenyl, $C_{2-6}$ alkynyl, any one of which is optionally substituted with one or more substituents selected from halogen, —$OR^{14}$, —$SR^{14}$, —$N(R^{14})_2$, —$C(O)R^{14}$, —$C(O)N(R^{14})_2$, —$N(R^{14})C(O)R^{14}$, —$C(O)OR^{14}$, —$OC(O)R^{14}$, —$NO_2$, =O, =S, =$N(R^{14})$, and —CN; or two $R^4$ attached to the same atom are taken together to form a group selected from: =O, =S, and =$N(R^{14})$; or two $R^4$ attached to the same atom or to adjacent atoms are taken together with the carbons to which they are attached to form a group selected from 4- to 8-membered heterocycle and $C_{3-8}$ carbocycle, any of which is optionally substituted with one or more substituents independently selected from halogen, $C_{1-4}$ alkyl, $C_{1-4}$ haloalkyl, —$OR^{14}$, —$SR^{14}$, —$N(R^{14})_2$, —$NO_2$, and —CN; and $R^{14}$ is independently selected at each occurrence from hydrogen, $C_{1-4}$ alkyl, $C_{3-8}$ carbocycle, 4- to 8-membered heterocycle, and $C_{1-4}$ haloalkyl.

In some embodiments, for the compound or salt of Formula (I), (II), (II-A), (III), (III-A), or (III-B), $R^4$ is independently selected at each instance from:

halogen, —$OR^{14}$, —$N(R^{14})_2$, —$C(O)R^{14}$, —$C(O)N(R^{14})_2$, and —CN; and $C_{1-6}$ alkyl, $C_{2-6}$ alkenyl, $C_{2-6}$ alkynyl, any one of which is optionally substituted with one or more substituents selected from halogen, —$OR^{14}$, —$N(R^{14})_2$, —C(O)$R^{14}$, —$C(O)N(R^{14})_2$, —$N(R^{14})C(O)R^{14}$, =O, and —CN; or two $R^4$ attached to the same atom are taken together to form a group selected from: =O, =S, and =$N(R^{14})$; or two $R^4$ attached to the same atom or to adjacent atoms are taken together with the carbons to which they are attached to form a group selected from 4- to 8-membered heterocycle and $C_{3-8}$ carbocycle, any of which is optionally substituted with one or more substituents independently selected from halogen, $C_{1-4}$ alkyl, $C_{1-4}$ haloalkyl, —$OR^{14}$, —$N(R^{14})_2$, and —CN.

In some embodiments, for the compound or salt of Formula (I), (II), (II-A), (III), (III-A), or (III-B), $R^4$ is independently selected at each instance from:

halogen, —$OR^{14}$, —$SR^{14}$, —$N(R^{14})_2$, —CN, $C_{1-6}$ alkyl, $C_{2-6}$ alkenyl, and $C_{2-6}$ alkynyl, wherein the $C_{1-6}$ alkyl, $C_{2-6}$ alkenyl, and $C_{2-6}$ alkynyl are each optionally substituted with one or more substituents selected from halogen, —$OR^{14}$, —$N(R^{14})_2$, =O, and —CN; or two $R^4$ attached to the same atom are taken together to form =O; or two $R^4$ attached to the same atom or to adjacent atoms are taken together with the carbons to which they are attached to form a group selected from 4- to 8-membered heterocycle and $C_{3-8}$ carbocycle; and $R^{14}$ is selected from hydrogen and $C_{1-4}$ alkyl.

In some embodiments, for the compound or salt of Formula (I), (II), (II-A), (III), (III-A), or (III-B), $R^4$ is independently selected at each instance from:

halogen, —$OR^{14}$, $C_{1-6}$ alkyl, and $C_{2-6}$ alkynyl; or two $R^4$ attached to the same atom are taken together to form =O; or two $R^4$ attached to the same atom or to adjacent atoms are taken together with the carbons to which they are attached to form a group selected from 4- to 8-membered heterocycle and $C_{3-8}$ carbocycle; and $R^{14}$ is selected from hydrogen and $C_{1-4}$ alkyl.

In some embodiments, for the compound or salt of Formula (I), (II), (II-A), (III), (III-A), or (III-B), $R^4$ is independently selected at each instance from:

halogen, —OH, $C_{1-6}$ alkyl, and $C_{2-6}$ alkynyl; or two $R^4$ attached to the same atom are taken together to form =O; or two $R^4$ attached to the same atom or to adjacent atoms are taken together with the carbons to which they are attached to form a $C_{3-8}$ carbocycle.

In some embodiments, for the compound or salt of Formula (I), (II), (II-A), (III), (III-A), or (III-B), $R^4$ is independently selected at each instance from:

halogen, —$OR^{14}$, —$SR^{14}$, —$N(R^{14})_2$, —$C(O)R^{14}$, —$C(O)N(R^{14})_2$, —$N(R^{14})C(O)R^{14}$, —$C(O)OR^{14}$, —$OC(O)R^{14}$, —$NO_2$, and —CN; and $C_{1-6}$ alkyl, $C_{2-6}$ alkenyl, $C_{2-6}$ alkynyl, any one of which is optionally substituted with one or more substituents selected from halogen, —$OR^{14}$, —$SR^{14}$, —$N(R^{14})_2$, —$C(O)R^{14}$, —$C(O)N(R^{14})_2$, —$N(R^{14})C(O)R^{14}$, —$C(O)OR^{14}$, —$OC(O)R^{14}$, —$NO_2$, =O, =S, =$N(R^{14})$, and —CN.

In some embodiments, for the compound or salt of Formula (I), (II), (II-A), (III), (III-A), or (III-B), $R^4$ is independently selected at each instance from:

halogen, —$OR^{14}$, —$N(R^{14})_2$, —$C(O)R^{14}$, —C(O)$N(R^{14})_2$, and —CN; and $C_{1-6}$ alkyl, $C_{2-6}$ alkenyl, $C_{2-6}$ alkynyl, any one of which is optionally substituted with one or more substituents selected from halogen, —$OR^{14}$, —$N(R^{14})_2$, —C(O)$R^{14}$, —$C(O)N(R^{14})_2$, —$N(R^{14})C(O)R^{14}$, =O, and —CN.

In some embodiments, for the compound or salt of Formula (I), (II), (II-A), (III), (III-A), or (III-B), $R^4$ is independently selected at each instance from halogen, —$OR^{14}$, —$SR^{14}$, —$N(R^{14})_2$, —CN, $C_{1-6}$ alkyl, $C_{2-6}$ alkenyl, and $C_{2-6}$ alkynyl, wherein the $C_{1-6}$ alkyl, $C_{2-6}$ alkenyl, and $C_{2-6}$ alkynyl are each optionally substituted with one or more substituents selected from halogen, —$OR^{14}$, —$N(R^{14})_2$, =O, and —CN. In some embodiments, $R^4$ is independently selected at each instance from halogen, —$OR^{14}$, $C_{1-6}$ alkyl, and $C_{2-6}$ alkynyl. In some embodiments, $R^4$ is independently selected at each instance from halogen, —OH, $C_{1-6}$ alkyl, and $C_{2-6}$ alkynyl.

In some embodiments, for the compound or salt of Formula (I), (II), (II-A), (III), (III-A), or (III-B), $R^4$ is independently selected at each instance from halogen, —$OR^{14}$, —$SR^{14}$, —$N(R^{14})_2$, —$C(O)R^{14}$, —$C(O)N(R^{14})_2$, —$N(R^{14})C(O)R^{14}$, —$C(O)OR^{14}$, —$OC(O)R^{14}$, —$NO_2$, and —CN. In some embodiments, $R^4$ is independently selected at each instance from halogen, —$OR^{14}$, —$N(R^{14})_2$, —C(O)$R^{14}$, —$C(O)N(R^{14})_2$, and —CN. In some embodiments, $R^4$ is independently selected at each instance from halogen, —$OR^{14}$, —$SR^{14}$, —$N(R^{14})_2$, and —CN. In some embodiments, $R^4$ is independently selected at each instance from halogen and —$OR^{14}$. In some embodiments, $R^4$ is halogen. In some embodiments, $R^4$ is independently selected at each instance from fluoro, chloro, and bromo.

In some embodiments, for the compound or salt of Formula (II) is represented as the structure of Formula (IV):

(IV)

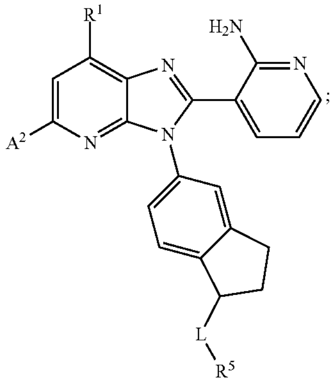

or a pharmaceutically acceptable salt thereof, wherein $A^2$, $R^1$, $R^5$, and L are each defined as in Formula (II).

In some embodiments, for the compound or salt of Formula (II) is represented as the structure of Formula (IV-A):

(IV-A)

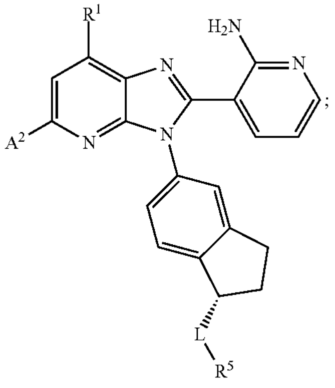

or a pharmaceutically acceptable salt thereof, wherein $A^2$, $R^1$, $R^5$, and L are each defined as in Formula (II).

In some embodiments, for the compound or salt of Formula (II) is represented as the structure of Formula (IV-B):

(IV-B)

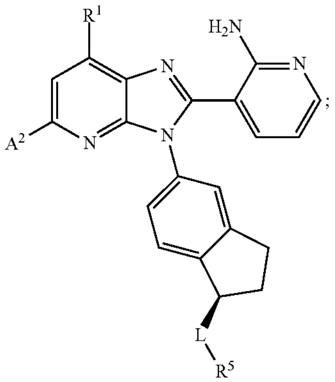

or a pharmaceutically acceptable salt thereof, wherein $A^2$, $R^1$, $R^5$, and L are each defined as in Formula (II).

In some embodiments, for the compound or salt of Formula (I), (II), (II-A), (III), (III-A), (III-B), (IV), (IV-A), or (IV-B), $R^1$ is selected from hydrogen, halogen, —$OR^{10}$, —$N(R^{10})_2$, —$NO_2$, —CN; and $C_{1-6}$ alkyl optionally substituted with one or more substituents independently selected from halogen, —$OR^{10}$, and —$N(R^{10})_2$. In some embodiments, $R^1$ is selected from hydrogen, halogen, —$OR^{10}$, —$N(R^{10})_2$, —CN; and $C_{1-6}$ alkyl optionally substituted with one or more substituents independently selected from halogen, —$OR^{10}$, and —$N(R^{10})_2$. In some embodiments, $R^1$ is selected from hydrogen, —$OR^{10}$, and —CN; and $C_{1-6}$ alkyl optionally substituted with one or more —$OR^{10}$. In some embodiments, $R^1$ is selected from hydrogen, methoxy, —CN, methyl, ethyl, and (methoxy)methyl. In some embodiments, $R^1$ is hydrogen. In some embodiments, $R^1$ is selected from methoxy, —CN, methyl, ethyl, and (methoxy) methyl.

In some embodiments, for the compound or salt of Formula (I), (II), (II-A), (III), (III-A), (III-B), (IV), (IV-A), or (IV-B), $R^1$ is selected from hydrogen, halogen, —$OR^{10}$, —CN; and $C_{1-6}$ alkyl optionally substituted with one or more substituents independently selected from halogen, —$OR^{10}$. In some embodiments, $R^1$ is selected from hydrogen, fluoro, methoxy, —CN, methyl, ethyl, (methoxy)methyl, and

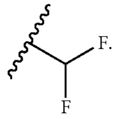 [SMILES: *C(F)F]

In some embodiments, for the compound or salt of Formula (II) is represented as the structure of Formula (V):

(V)

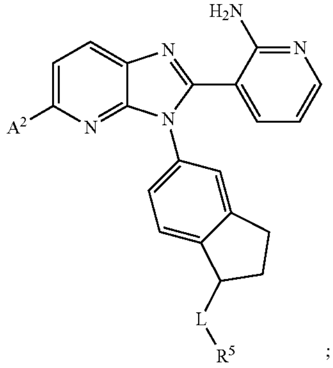

or a pharmaceutically acceptable salt thereof, wherein $A^2$, $R^5$, and L are each defined as in Formula (II).

In some embodiments, for the compound or salt of Formula (II) is represented as the structure of Formula (V-A):

(V-A)

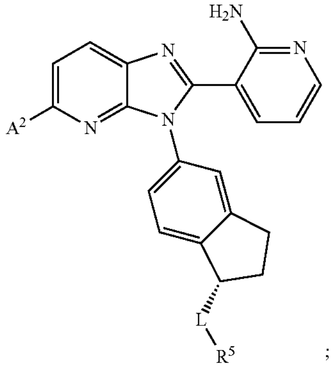

or a pharmaceutically acceptable salt thereof, wherein $A^2$, $R^5$, and L are each defined as in Formula (II).

In some embodiments, for the compound or salt of Formula (II) is represented as the structure of Formula (V-B):

(V-B)

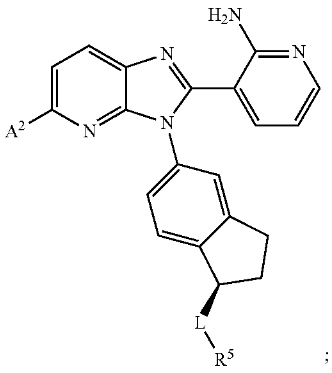

;

or a pharmaceutically acceptable salt thereof, wherein $A^2$, $R^5$, and L are each defined as in Formula (II).

In some embodiments, for the compound or salt of Formula (I), (II), (II-A), (III), (III-A), (III-B), (IV), (IV-A), (IV-B), (V), (V-A), or (V-B), $A^2$ is selected from selected from (i), (ii), and (iii):

(i) hydrogen, halogen, $C_{1-4}$ haloalkyl, —$OR^{11}$, —$SR^{11}$, —$N(R^{11})_2$, —$C(O)N(R^{11})_2$, —$N(R^{11})C(O)R^{11}$, —$C(O)OR^{11}$, —$OC(O)R^{11}$, —$N(R^{11})C(O)OR^{11}$, —$OC(O)N(R^{11})_2$, —$N(R^{11})C(O)N(R^{11})_2$, —$S(O)R^{11}$, —$S(O)_2R^{11}$, —$N(R^{11})S(O)_2R^{11}$, —$S(O)_2N(R^{11})_2$, —$NO_2$, and —CN;

(ii) $C_{1-6}$ alkyl, $C_{2-6}$ alkenyl, and $C_{2-6}$ alkynyl, any of which is optionally substituted with one or more substituents independently selected from:

halogen, —$OR^{11}$, —$SR^{11}$, —$N(R^{11})_2$, —$C(O)N(R^{11})_2$, —$N(R^{11})C(O)R^{11}$, —$C(O)OR^{11}$, —$OC(O)R^{11}$, —$N(R^{11})C(O)OR^{11}$, —$OC(O)N(R^{11})_2$, —$N(R^{11})C(O)N(R^{11})_2$, —$S(O)R^{11}$, —$S(O)_2R^{11}$, —$N(R^{11})S(O)_2R^{11}$, —$S(O)_2N(R^{11})_2$, —$NO_2$, =O, =S, =$N(R^{11})$, and —CN; and (iii) 5- to 10-membered heterocycle and $C_{3-10}$ carbocycle, any of which is optionally substituted with one or more substituents independently selected from:

halogen, —$OR^{11}$, —$SR^{11}$, —$N(R^{11})_2$, —$C(O)R^{11}$, —$C(O)N(R^{11})_2$, —$N(R^{11})C(O)R^{11}$, —$N(R^{11})S(O)_2R^{11}$, —$C(O)OR^{11}$, —$OC(O)R^{11}$, —$N(R^{11})C(O)OR^{11}$, —$OC(O)N(R^{11})_2$, —$N(R^{11})C(O)N(R^{11})_2$, —$S(O)R^{11}$, —$S(O)_2R^{11}$, —$S(O)_2N(R^{11})_2$, —$NO_2$, =O, =S, =$N(R^{11})$, and —CN;

$C_{1-6}$ alkyl, $C_{2-6}$ alkenyl, and $C_{3-6}$ alkynyl, any one of which is optionally substituted with one or more substituents independently selected from:

halogen, —$OR^{11}$, —$SR^{11}$, —$N(R^{11})_2$, —$C(O)R^{11}$, —$C(O)N(R^{11})_2$, —$N(R^{11})C(O)R^{11}$, —$C(O)OR^{11}$, —$OC(O)R^{11}$, —$N(R^{11})C(O)OR^{11}$, —$OC(O)N(R^{11})_2$, —$N(R^{11})C(O)N(R^{11})_2$, —$S(O)R^{11}$, —$S(O)_2R^{11}$, —$N(R^{11})S(O)_2R^{11}$, —$S(O)_2N(R^{11})_2$, —$NO_2$, =O, =S, =$N(R^{11})$, and —CN; and $C_{3-10}$ carbocycle and 4- to 10-membered heterocycle; wherein the $C_{3-10}$ carbocycle and 4 to 10-membered heterocycle are each optionally substituted with one or more substituents independently selected from:

halogen, —$OR^{11}$, —$N(R^{11})_2$, —$C(O)R^{11}$, —$C(O)N(R^{11})_2$, —$N(R^{11})C(O)R^{11}$, —$C(O)OR^{11}$, —$OC(O)R^{11}$, —$NO_2$, =O, =S, =$N(R^{11})$, and —CN;

$C_{1-6}$ alkyl, $C_{2-6}$ alkenyl, and $C_{3-6}$ alkynyl, any one of which is optionally substituted with one or more substituents independently selected from:

halogen, —$OR^{11}$, —$SR^{11}$, —$N(R^{11})_2$, —$C(O)R^{11}$, —$C(O)N(R^{11})_2$, —$N(R^{11})C(O)R^{11}$, —$N(R^{11})S(O)_2R^{11}$, —$C(O)OR^{11}$, —$OC(O)R^{11}$, —$NO_2$, =O, =S, =$N(R^{11})$, and —CN.

In some embodiments, for the compound or salt of Formula (I), (II), (II-A), (III), (III-A), (III-B), (IV), (IV-A), (IV-B), (V), (V-A), or (V-B), $A^2$ is selected from selected from (i), (ii), and (iii):

(i) hydrogen, halogen, —$OR^{11}$, —$N(R^{11})_2$, —$C(O)N(R^{11})_2$, —$N(R^{11})C(O)R^{11}$, —$N(R^{11})S(O)_2R^{11}$, —$S(O)_2N(R^{11})_2$, —$NO_2$, and —CN;

(ii) $C_{1-6}$ alkyl, $C_{2-6}$ alkenyl, and $C_{2-6}$ alkynyl, any of which is optionally substituted with one or more substituents independently selected from: halogen, —$OR^{11}$, —$N(R^{11})_2$, —$C(O)N(R^{11})_2$, —$N(R^{11})C(O)R^{11}$, —$N(R^{11})S(O)_2R^{11}$, —$S(O)_2N(R^{11})_2$, —$NO_2$, =O, and —CN; and (iii) 5- to 10-membered heterocycle and $C_{3-10}$ carbocycle, any of which is optionally substituted with one or more substituents independently selected from:

halogen, —$OR^{11}$, —$N(R^{11})_2$, —$C(O)R^{11}$, —$C(O)N(R^{11})_2$, —$N(R^{11})C(O)R^{11}$, —$N(R^{11})S(O)_2R^{11}$, —$NO_2$, =O, and —CN;

$C_{1-6}$ alkyl, $C_{2-6}$ alkenyl, and $C_{3-6}$ alkynyl, any one of which is optionally substituted with one or more substituents independently selected from:

halogen, —$OR^{11}$, —$N(R^{11})_2$, —$C(O)R^{11}$, —$C(O)N(R^{11})_2$, —$N(R^{11})C(O)R^{11}$, —$N(R^{11})S(O)_2R^{11}$, —$NO_2$, —$NO_2$, =O, and —CN; and $C_{3-10}$ carbocycle and 4- to 10-membered heterocycle, any of which is optionally substituted with one or more substituents independently selected from halogen, —$OR^{11}$, —$N(R^{11})_2$, —$C(O)R^{11}$, —$C(O)N(R^{11})_2$, —$N(R^{11})C(O)R^{11}$, —$NO_2$, =O, —CN; $C_{1-6}$ alkyl, $C_{2-6}$ alkenyl, and $C_{2-6}$ alkynyl, the $C_{1-6}$ alkyl, $C_2$-6 alkenyl, and $C_{3-6}$ alkynyl, are each optionally substituted with one or more substituents independently selected from: halogen, —$OR^{11}$, —$N(R^{11})_2$, —$C(O)R^{11}$, —$C(O)N(R^{11})_2$, —$N(R^{11})C(O)R^{11}$, —$N(R^{11})S(O)_2R^{11}$, —$NO_2$, =O, and —CN.

In some embodiments, for the compound or salt of Formula (I), (II), (II-A), (III), (III-A), (III-B), (IV), (IV-A), (IV-B), (V), (V-A), or (V-B), $A^2$ is selected from:

$C_{1-6}$ alkyl, $C_{2-6}$ alkenyl, and $C_{2-6}$ alkynyl, any of which is optionally substituted with one or more substituents independently selected from halogen, —$OR^{11}$, —$N(R^{11})_2$, —$C(O)N(R^{11})_2$, —$N(R^{11})C(O)R^{11}$, —$N(R^{11})S(O)_2R^{11}$, —$S(O)_2N(R^{11})_2$, —$NO_2$, =O, and —CN; and 5- to 10-membered heterocycle and $C_{3-10}$ carbocycle, any of which is optionally substituted with one or more substituents independently selected from:

halogen, —$OR^{11}$, —$N(R^{11})_2$, —$C(O)R^{11}$, —$C(O)N(R^{11})_2$, —$N(R^{11})C(O)R^{11}$, —$N(R^{11})S(O)_2R^{11}$, —$NO_2$, =O, and —CN;

$C_{1-6}$ alkyl, $C_{2-6}$ alkenyl, and $C_{3-6}$ alkynyl, any one of which is optionally substituted with one or more substituents independently selected from:

halogen, —$OR^{11}$, —$N(R^{11})_2$, —$C(O)R^{11}$, —$C(O)N(R^{11})_2$, —$N(R^{11})C(O)R^{11}$, —$N(R^{11})S(O)_2R^{11}$, —$NO_2$, —$NO_2$, =O, and —CN; and $C_{3-10}$ carbocycle and 3- to 10-membered heterocycle, any of which is optionally substituted with one or more substituents independently selected from halogen, —$OR^{11}$, —$N(R^{11})_2$, —$C(O)R^{11}$, —$C(O)N(R^{11})_2$, —$N(R^{11})C(O)R^{11}$, —$NO_2$, =O, —CN; $C_{1-6}$ alkyl, $C_{2-6}$ alkenyl, and $C_{2-6}$ alkynyl, the $C_{1-6}$ alkyl, $C_2$-6 alkenyl, and $C_{3-6}$ alkynyl, are each optionally substituted with one or more substituents independently selected from: halogen, —$OR^{11}$, —$N(R^{11})_2$, —$C(O)R^{11}$, —$C(O)N(R^{11})_2$, —$N(R^{11})C(O)R^{11}$, —$N(R^{11})S(O)_2R^{11}$, —$NO_2$, =O, and —CN.

In some embodiments, for the compound or salt of Formula (I), (II), (II-A), (III), (III-A), (III-B), (IV), (IV-A), (IV-B), (V), (V-A), or (V-B), $A^2$ is selected from:

- $C_{1-6}$ alkyl and $C_{2-6}$ alkynyl, each of which is optionally substituted with one or more substituents independently selected from halogen, —$OR^{11}$, —$N(R^{11})_2$, —$C(O)N(R^{11})_2$, —$N(R^{11})C(O)R^{11}$, —$N(R^{11})S(O)_2R^{11}$, —$S(O)_2N(R^{11})_2$, —$NO_2$, =O, and —CN; and
- 5- to 10-membered heterocycle and $C_{3-10}$ carbocycle, any of which is optionally substituted with one or more substituents independently selected from:
  - halogen, —$OR^{11}$, —$N(R^{11})_2$, —$C(O)R^{11}$, —$C(O)N(R^{11})_2$, —$N(R^{11})C(O)R^{11}$, —$N(R^{11})S(O)_2R^{11}$, —$NO_2$, =O, and —CN;
  - $C_{1-6}$ alkyl, $C_{2-6}$ alkenyl, and $C_{2-6}$ alkynyl, any one of which is optionally substituted with one or more substituents independently selected from:
    - halogen, —$OR^{11}$, —$N(R^{11})_2$, —$C(O)R^{11}$, —$C(O)N(R^{11})_2$, —$N(R^{11})C(O)R^{11}$, —$N(R^{11})S(O)_2R^{11}$, —$NO_2$, =O, and —CN; and
  - $C_{3-8}$ carbocycle and 4- to 10-membered heterocycle, any of which is optionally substituted with one or more substituents independently selected from halogen, —$OR^{11}$, —$N(R^{11})_2$, —$C(O)R^{11}$, —$C(O)N(R^{11})_2$, —$N(R^{11})C(O)R^{11}$, —$NO_2$, =O, —CN; $C_{1-6}$ alkyl, $C_{2-6}$ alkenyl, and $C_{2-6}$ alkynyl, the $C_{1-6}$ alkyl, $C_{2-6}$ alkenyl, and $C_{2-6}$ alkynyl, are each optionally substituted with one or more substituents independently selected from: halogen, —$OR^{11}$, —$N(R^{11})_2$, —$C(O)R^{11}$, —$C(O)N(R^{11})_2$, —$N(R^{11})C(O)R^{11}$, —$N(R^{11})S(O)_2R^{11}$, —$NO_2$, =O, and —CN.

In some embodiments, for the compound or salt of Formula (I), (II), (II-A), (III), (III-A), (III-B), (IV), (IV-A), (IV-B), (V), (V-A), or (V-B), $A^2$ is selected from $C_{1-6}$ alkyl and $C_{2-6}$ alkynyl, each of which is optionally substituted with one or more substituents independently selected from halogen, —$OR^{11}$, —$N(R^{11})_2$, —$C(O)N(R^{11})_2$, —$N(R^{11})C(O)R^{11}$, —$N(R^{11})S(O)_2R^{11}$, —$S(O)_2N(R^{11})_2$, —$NO_2$, =O, and —CN. In some embodiments, $A^2$ is selected from $C_{1-6}$ alkyl and $C_{2-6}$ alkynyl, each of which is optionally substituted with one or more substituents independently selected from halogen, —$OR^{11}$, —$N(R^{11})_2$, —$NO_2$, =O, and —CN. In some embodiments, $A^2$ is selected from $C_{1-4}$ alkyl and $C_{2-4}$ alkynyl, each of which is optionally substituted with one or more substituents independently selected from halogen, —$OR^{11}$, —$N(R^{11})_2$, —$NO_2$, =O, and —CN. In some embodiments, $A^2$ is selected from $C_{1-4}$ alkyl and $C_{2-4}$ alkynyl, each of which is optionally substituted with one or more substituents independently selected from halogen, —$OR^{11}$, and —$N(R^{11})_2$. In some embodiments, $A^2$ is selected from $C_{1-4}$ alkyl and $C_{2-4}$ alkynyl, each of which is optionally substituted with one or more substituents independently selected from —$OR^{11}$ and —$N(R^{11})_2$. In some embodiments, $A^2$ is selected from methyl, ethyl, propyl, isopropyl, ethylnyl, propylnyl, and isopropylnyl, each of which is optionally substituted with one or more substituents independently selected from halogen, —$OR^{11}$, —$N(R^{11})_2$, —$NO_2$, =O, and —CN. In some embodiments, $A^2$ is selected from methyl, ethyl, propyl, isopropyl, ethylnyl, propylnyl, and isopropylnyl, each of which is optionally substituted with one or more substituents independently selected from halogen, —$OR^{11}$, and —$N(R^{11})_2$.

In some embodiments, for the compound or salt of Formula (I), (II), (II-A), (III), (III-A), (III-B), (IV), (IV-A), (IV-B), (V), (V-A), or (V-B), $A^2$ is selected from: —$CH_3$,

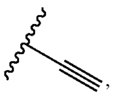,
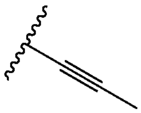,
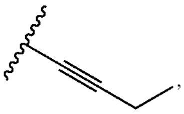,
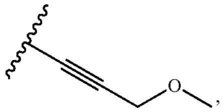,
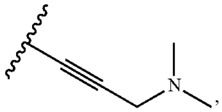, and
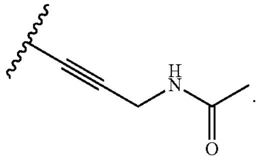.

In some embodiments, for the compound or salt of Formula (I), (II), (II-A), (III), (III-A), (III-B), (IV), (IV-A), (IV-B), (V), (V-A), or (V-B), $A^2$ is selected from 5- to 10-membered heteroaryl, 5- to 10-membered heterocycloalkyl, $C_{4-8}$ aryl, and $C_{3-10}$ cycloalkyl, each of which is optionally substituted with one or more substituents independently selected from:

- halogen, —$OR^{11}$, —$SR^{11}$, —$N(R^{11})_2$, —$C(O)R^{11}$, —$C(O)N(R^{11})_2$, —$N(R^{11})C(O)R^{11}$, —$N(R^{11})S(O)_2R^{11}$, —$C(O)OR^{11}$, —$OC(O)R^{11}$, —$N(R^{11})C(O)OR^{11}$, —$OC(O)N(R^{11})_2$, —$N(R^{11})C(O)N(R^{11})_2$, —$S(O)R^{11}$, —$S(O)_2R^{11}$, —$S(O)_2N(R^{11})_2$, —$NO_2$, =O, =S, =$N(R^{11})$, and —CN;
- $C_{1-6}$ alkyl, $C_{2-6}$ alkenyl, and $C_{3-6}$ alkynyl, any one of which is optionally substituted with one or more substituents independently selected from: halogen, —$OR^{11}$, —$SR^{11}$, —$N(R^{11})_2$, —$C(O)R^{11}$, —$C(O)N(R^{11})_2$, —$N(R^{11})C(O)R^{11}$, —$C(O)OR^{11}$, —$OC(O)R^{11}$, —$N(R^{11})C(O)OR^{11}$, —$OC(O)N(R^{11})_2$, —$N(R^{11})C(O)N(R^{11})_2$, —$S(O)R^{11}$, —$S(O)_2R^{11}$, —$N(R^{11})S(O)_2R^{11}$, —$S(O)_2N(R^{11})_2$, —$NO_2$, =O, =S, =$N(R^{11})$, and —CN; and
- $C_{3-10}$ carbocycle and 4- to 10-membered heterocycle; wherein the $C_{3-10}$ carbocycle and 4- to 10-membered heterocycle are each optionally substituted with one or more substituents independently selected from: halogen, —$OR^{11}$, —$N(R^{11})_2$, —$C(O)R^{11}$, —$C(O)N(R^{11})_2$, —$N(R^{11})C(O)R^1$, —$C(O)OR^1$, —$OC(O)R^{11}$, —$NO_2$, =O, =S, =$N(R^{11})$, and —CN; $C_{1-6}$ alkyl, $C_{2-6}$ alkenyl, and $C_{2-6}$ alkynyl, the $C_{1-6}$ alkyl, $C_{2-6}$ alkenyl, and $C_{2-6}$ alkynyl, are each optionally substituted with one or more substituents independently selected from: halogen, —$OR^{11}$, —$SR^{11}$, —$N(R^{11})_2$, —$C(O)R^{11}$, —$C(O)N(R^{11})_2$, —$N(R^{11})C(O)R^{11}$, —$N(R^{11})S(O)_2R^{11}$, —$C(O)OR^{11}$, —$OC(O)R^{11}$, —$NO_2$, =O, =S, =$N(R^{11})$, and —CN.

In some embodiments, for the compound or salt of Formula (I), (II), (II-A), (III), (III-A), (III-B), (IV), (IV-A), (IV-B), (V), (V-A), or (V-B), $A^2$ is selected from 5- to 10-membered heteroaryl, 5- to 10-membered heterocycloalkyl, $C_{4-8}$ aryl, and $C_{3-10}$ cycloalkyl, each of which is optionally substituted with one or more substituents independently selected from:

- halogen, —$OR^{11}$, —$N(R^{11})_2$, —$C(O)R^{11}$, —$C(O)N(R^{11})_2$, —$N(R^{11})C(O)R^{11}$, —$N(R^{11})S(O)_2R^{11}$, —$NO_2$, =O, and —CN;

$C_{1-6}$ alkyl, $C_{2-6}$ alkenyl, and $C_{3-6}$ alkynyl, any one of which is optionally substituted with one or more substituents independently selected from: halogen, —$OR^{11}$, —$N(R^{11})_2$, —$C(O)R^{11}$, —$C(O)N(R^{11})_2$, —$N(R^{11})C(O)R^{11}$, —$N(R^{11})S(O)_2R^{11}$, —$NO_2$, —$NO_2$, =O, and —CN; and $C_{3-10}$ carbocycle and 4- to 10-membered heterocycle, any of which is optionally substituted with one or more substituents independently selected from halogen, —$OR^{11}$, —$N(R^{11})_2$, —$C(O)R^{11}$, —$C(O)N(R^{11})_2$, —$N(R^{11})C(O)R^{11}$, —$NO_2$, =O, —CN; $C_{1-6}$ alkyl, $C_{2-6}$ alkenyl, and $C_{2-6}$ alkynyl, the $C_{1-6}$ alkyl, $C_{2-6}$ alkenyl, and $C_{3-6}$ alkynyl, are each optionally substituted with one or more substituents independently selected from: halogen, —$OR^{11}$, —$N(R^{11})_2$, —$C(O)R^{11}$, —$C(O)N(R^{11})_2$, —$N(R^{11})C(O)R^{11}$, —$N(R^{11})S(O)_2R^{11}$, —$NO_2$, =O, and —CN.

In some embodiments, for the compound or salt of Formula (I), (II), (II-A), (III), (III-A), (III-B), (IV), (IV-A), (IV-B), (V), (V-A), or (V-B), $A^2$ is selected from pyrazolyl, triazolyl, oxazolyl, thiazolyl, morpholinyl, phenyl, and cyclopropyl, each of which is optionally substituted with one or more substituents independently selected from:

halogen, —$OR^{11}$, —$N(R^{11})_2$, —$C(O)R^{11}$, —$C(O)N(R^{11})_2$, —$N(R^{11})C(O)R^{11}$, —$N(R^{11})S(O)_2R^{11}$, —$NO_2$, =O, and —CN;

$C_{1-6}$ alkyl, $C_{2-6}$ alkenyl, and $C_{3-6}$ alkynyl, any one of which is optionally substituted with one or more substituents independently selected from: halogen, —$OR^{11}$, —$N(R^{11})_2$, —$C(O)R^{11}$, —$C(O)N(R^{11})_2$, —$N(R^{11})C(O)R^{11}$, —$N(R^{11})S(O)_2R^{11}$, —$NO_2$, —$NO_2$, =O, and —CN; and $C_{3-10}$ carbocycle and 4- to 10-membered heterocycle, any of which is optionally substituted with one or more substituents independently selected from halogen, —$OR^{11}$, —$N(R^{11})_2$, —$C(O)R^{11}$, —$C(O)N(R^{11})_2$, —$N(R^{11})C(O)R^{11}$, —$NO_2$, =O, —CN; $C_{1-6}$ alkyl, $C_{2-6}$ alkenyl, and $C_{2-6}$ alkynyl, the $C_{1-6}$ alkyl, $C_{2-6}$ alkenyl, and $C_{2-6}$ alkynyl, are each optionally substituted with one or more substituents independently selected from: halogen, —$OR^{11}$, —$N(R^{11})_2$, —$C(O)R^{11}$, —$C(O)N(R^{11})_2$, —$N(R^{11})C(O)R^{11}$, —$N(R^{11})S(O)_2R^{11}$, —$NO_2$, =O, and —CN.

In some embodiments, for the compound or salt of Formula (I), (II), (II-A), (III), (III-A), (III-B), (IV), (IV-A), (IV-B), (V), (V-A), or (V-B), $A^2$ is selected from 5- to 10-membered heteroaryl, 5- to 10-membered heterocycloalkyl, $C_{4-8}$ aryl, and $C_{3-10}$ cycloalkyl, each of which is optionally substituted with one or more substituents independently selected from:

halogen, —$OR^{11}$, —$N(R^{11})_2$, —$NO_2$, =O, and —CN;

$C_{1-6}$ alkyl optionally substituted with one or more substituents independently selected from:

halogen, —$OR^{11}$, —$N(R^{11})_2$, —$NO_2$, =O, and —CN; and $C_{3-10}$ carbocycle and 4- to 10-membered heterocycle, any of which is optionally substituted with one or more substituents independently selected from halogen, —$OR^{11}$, —$N(R^{11})_2$, —$NO_2$, =O, —CN, $C_{1-6}$ alky, and $C_{1-6}$ haloalkyl.

In some embodiments, for the compound or salt of Formula (I), (II), (II-A), (III), (III-A), (III-B), (IV), (IV-A), (IV-B), (V), (V-A), or (V-B), $A^2$ is selected from pyrazolyl, triazolyl, oxazolyl, thiazolyl, morpholinyl, phenyl, and cyclopropyl, each of which is optionally substituted with one or more substituents independently selected from:

halogen, —$OR^{11}$, —$N(R^{11})_2$, —$NO_2$, =O, and —CN;

$C_{1-6}$ alkyl optionally substituted with one or more substituents independently selected from:

halogen, —$OR^{11}$, —$N(R^{11})_2$, —$NO_2$, =O, and —CN; and $C_{3-10}$ carbocycle and 4- to 10-membered heterocycle, any of which is optionally substituted with one or more substituents independently selected from halogen, —$OR^{11}$, —$N(R^{11})_2$, —$NO_2$, =O, —CN, $C_{1-6}$ alky, and $C_{1-6}$ haloalkyl.

In some embodiments, for the compound or salt of Formula (I), (II), (II-A), (III), (III-A), (III-B), (IV), (IV-A), (IV-B), (V), (V-A), or (V-B), $A^2$ is selected from:

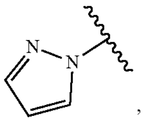
,
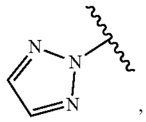
,
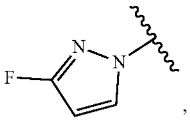
,
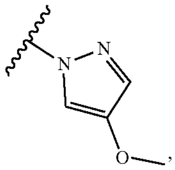
,
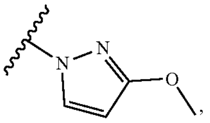
,
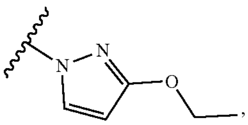
,
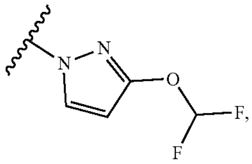
,
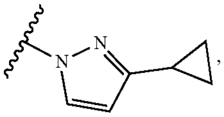
,
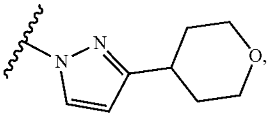
,
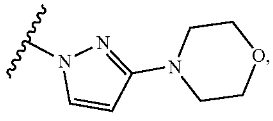
,
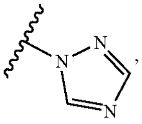
,
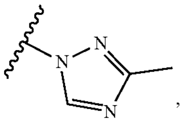
,
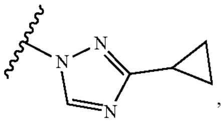
,
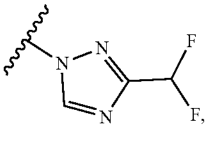
,
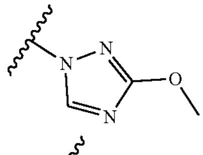
,
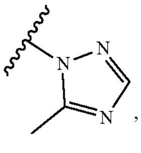
, and
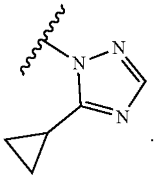
.

In some embodiments, for the compound or salt of Formula (I), (II), (II-A), (III), (III-A), (III-B), (IV), (IV-A), (IV-B), (V), (V-A), or (V-B), $A^2$ is selected from:

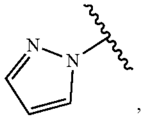,
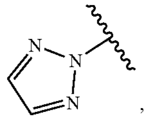,
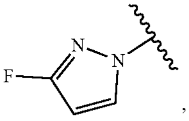,
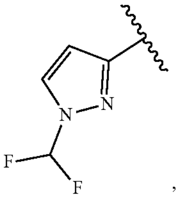,
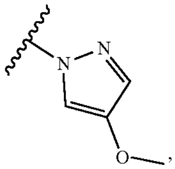,
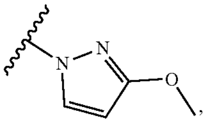,
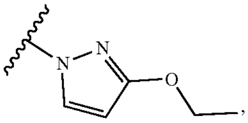,
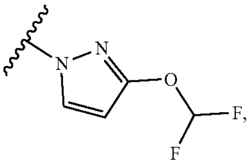,
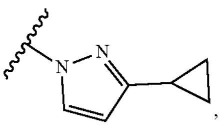,
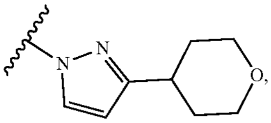,
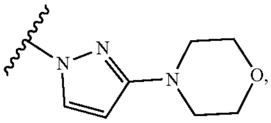,
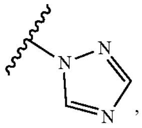,
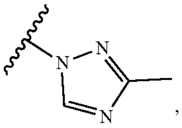,
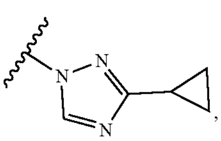,
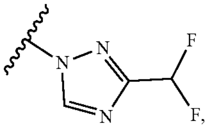,
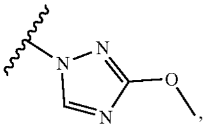,
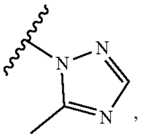,
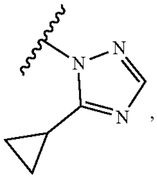,
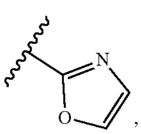,
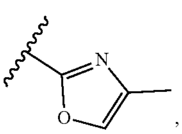,
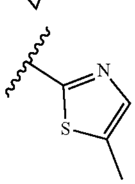,
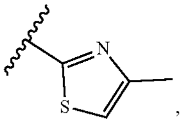,
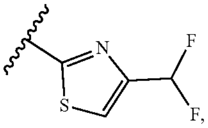,
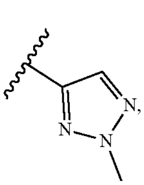,
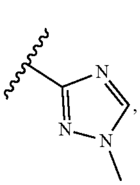,
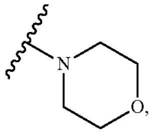, -continued

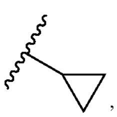,
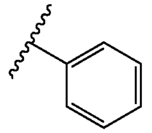
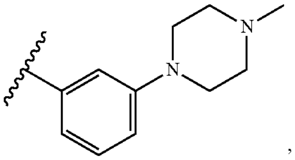, $-CH_3$,
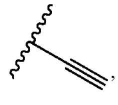,
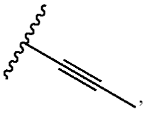,
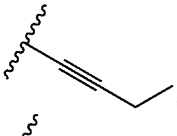,
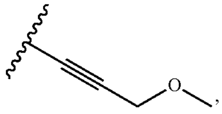,
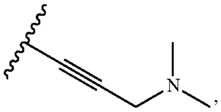, and
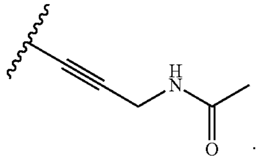.

In some embodiments, for the compound or salt of Formula (I), (II), (II-A), (III), (III-A), (III-B), (IV), (IV-A), (IV-B), (V), (V-A), or (V-B), $A^2$ is 5- to 10-membered heterocycle optionally substituted with one or more substituents independently selected from (i), (ii), and (iii):

(i) halogen, $—OR^{11}$, $—N(R^{11})_2$, $—C(O)R^{11}$, $—C(O)N(R^{11})_2$, $—N(R^{11})C(O)R^{11}$, $—N(R^{11})S(O)_2R^{11}$, $=O$, and —CN;

(ii) $C_{1-6}$ alkyl, $C_{2-6}$ alkenyl, and $C_{3-6}$ alkynyl, any one of which is optionally substituted with one or more substituents independently selected from: halogen, $—OR^{11}$, $—N(R^{11})_2$, $—C(O)R^{11}$, $—C(O)N(R^{11})_2$, $—N(R^{11})C(O)R^{11}$, $—N(R^{11})S(O)_2R^{11}$, $—NO_2$, $=O$, and —CN; and (iii) $C_{3-10}$ carbocycle and 4- to 10-membered heterocycle, any of which is each optionally substituted with one or more substituents independently selected from:

halogen, $—OR^{11}$, $—N(R^{11})_2$, $—C(O)R^{11}$, $—C(O)N(R^{11})_2$, $—N(R^{11})C(O)R^{11}$, $=O$, and —CN; and $C_{1-6}$ alkyl, $C_{2-6}$ alkenyl, and $C_{3-6}$ alkynyl, any one of which is optionally substituted with one or more substituents independently selected from: halogen, $—OR^{11}$, $—N(R^{11})_2$, $—C(O)R^{11}$, $—C(O)N(R^{11})_2$, $—N(R^{11})C(O)R^{11}$, $—N(R^{11})S(O)_2R^{11}$, $=O$, and —CN.

In some embodiments, for the compound or salt of Formula (I), (II), (II-A), (III), (III-A), (III-B), (IV), (IV-A), (IV-B), (V), (V-A), or (V-B), $A^2$ is selected from 5- to 10-membered heterocycle and $C_{3-10}$ carbocycle, any of which is optionally substituted with one or more substituents independently selected from (i), (ii), and (iii):

(i) halogen, $—OR^{11}$, $—SR^{11}$, $—N(R^{11})_2$, $—C(O)R^{11}$, $—C(O)N(R^{11})_2$, $—N(R^{11})C(O)R^{11}$, $—N(R^{11})S(O)_2R^{11}$, $—C(O)OR^{11}$, $—OC(O)R^{11}$, $—N(R^{11})C(O)OR^{11}$, $—OC(O)N(R^{11})_2$, $—N(R^{11})C(O)N(R^{11})_2$, $—S(O)R^{11}$, $—S(O)_2R^{11}$, $—S(O)_2N(R^{11})_2$, $—NO_2$, $=O$, $=S$, $=N(R^{11})$, and —CN;

(ii) $C_{1-6}$ alkyl, $C_{2-6}$ alkenyl, and $C_{3-6}$ alkynyl, any one of which is optionally substituted with one or more substituents independently selected from: halogen, —$OR^{11}$, —$SR^{11}$, —$N(R^{11})_2$, —$C(O)R^{11}$, —$C(O)N(R^{11})_2$, —$N(R^{11})C(O)R^{11}$, —$C(O)OR^{11}$, —$OC(O)R^{11}$, —$N(R^{11})C(O)OR^{11}$, —$OC(O)N(R^{11})_2$, —$N(R^{11})C(O)N(R^{11})_2$, —$S(O)R^{11}$, —$S(O)_2R^{11}$, —$N(R^{11})S(O)_2R^{11}$, —$S(O)_2N(R^{11})_2$, —$NO_2$, =O, =S, =$N(R^{11})$, and —CN; and (iii) $C_{3-10}$ carbocycle and 4- to 10-membered heterocycle; wherein the $C_{3-10}$ carbocycle and 4 to 10-membered heterocycle are each optionally substituted with one or more substituents independently selected from:

halogen, —$OR^{11}$, —$N(R^{11})_2$, —$C(O)R^{11}$, —$C(O)N(R^{11})_2$, —$N(R^{11})C(O)R^{11}$, —$C(O)OR^{11}$, —$OC(O)R^{11}$, —$NO_2$, =O, =S, =$N(R^{11})$, and —CN;

$C_{1-6}$ alkyl, $C_{2-6}$ alkenyl, and $C_{3-6}$ alkynyl, any one of which is optionally substituted with one or more substituents independently selected from:

halogen, —$OR^{11}$, —$SR^{11}$, —$N(R^{11})_2$, —$C(O)R^{11}$, —$C(O)N(R^{11})_2$, —$N(R^{11})C(O)R^{11}$, —$N(R^{11})S(O)_2R^{11}$, —$C(O)OR^{11}$, —$OC(O)R^{11}$, —$NO_2$, =O, =S, =$N(R^{11})$, and —CN; and $R^{11}$ is independently selected at each occurrence from hydrogen, $C_{1-4}$ alkyl, $C_{3-8}$ carbocycle, 4 to 8-membered heterocycle, and $C_{1-4}$ haloalkyl.

In some embodiments, for the compound or salt of Formula (I), (II), (II-A), (III), (III-A), (III-B), (IV), (IV-A), (IV-B), (V), (V-A), or (V-B), $A^2$ is selected from 5- to 10-membered heterocycle and $C_{3-10}$ carbocycle, any of which is optionally substituted with one or more substituents independently selected from (i), (ii), and (iii):

(i) halogen, —$OR^{11}$, —$N(R^{11})_2$, —$C(O)R^{11}$, —$C(O)N(R^{11})_2$, —$N(R^{11})C(O)R^{11}$, —$N(R^{11})S(O)_2R^{11}$, =O, and —CN;

(ii) $C_{1-6}$ alkyl, $C_{2-6}$ alkenyl, and $C_{3-6}$ alkynyl, any one of which is optionally substituted with one or more substituents independently selected from:

halogen, —$OR^{11}$, —$N(R^{11})_2$, —$C(O)R^{11}$, —$C(O)N(R^{11})_2$, —$N(R^{11})C(O)R^{11}$, —$N(R^{11})S(O)_2R^{11}$, —$NO_2$, =O, and —CN; and (iii) $C_{3-10}$ carbocycle and 4- to 10-membered heterocycle; wherein the $C_{3-10}$ carbocycle and 4 to 10-membered heterocycle are each optionally substituted with one or more substituents independently selected from:

halogen, —$OR^{11}$, —$N(R^{11})_2$, —$C(O)R^{11}$, —$C(O)N(R^{11})_2$, —$N(R^{11})C(O)R^{11}$, =O, and —CN; and $C_{1-6}$ alkyl, $C_{2-6}$ alkenyl, and $C_{3-6}$ alkynyl, any one of which is optionally substituted with one or more substituents independently selected from:

halogen, —$OR^{11}$, —$N(R^{11})_2$, —$C(O)R^{11}$, —$C(O)N(R^{11})_2$, —$N(R^{11})C(O)R^{11}$, —$N(R^{11})S(O)_2R^{11}$, =O, and —CN.

In some embodiments, for the compound or salt of Formula (I), (II), (II-A), (III), (III-A), (III-B), (IV), (IV-A), (IV-B), (V), (V-A), or (V-B), $A^2$ is selected from 5- to 10-membered heterocycle optionally substituted with one or more substituents independently selected from (i), (ii), and (iii):

(i) halogen, —$OR^{11}$, —$N(R^{11})_2$, —$C(O)R^{11}$, —$C(O)N(R^{11})_2$, —$N(R^{11})C(O)R^{11}$, =O, and —CN;

(ii) $C_{1-6}$ alkyl optionally substituted with one or more substituents independently selected from: halogen, —$OR^{11}$, —$N(R^{11})_2$, —$C(O)R^{11}$, —$C(O)N(R^{11})_2$, —$N(R^{11})C(O)R^{11}$, and =O; and (iii) $C_{3-10}$ carbocycle and 4- to 10-membered heterocycle; wherein the $C_{3-10}$ carbocycle and 4 to 10-membered heterocycle are each optionally substituted with one or more substituents independently selected from halogen, —$OR^{11}$, —$N(R^{11})_2$, —$C(O)R^{11}$, —$C(O)N(R^{11})_2$, —$N(R^{11})C(O)R^{11}$, =O, and —CN; and $C_{1-6}$ alkyl optionally substituted with one or more substituents independently selected from: halogen, —$OR^{11}$, —$N(R^{11})_2$, —$C(O)R^{11}$, —$C(O)N(R^{11})_2$, —$N(R^{11})C(O)R^{1}$, and =O.

In some embodiments, for the compound or salt of Formula (I), (II), (II-A), (III), (III-A), (III-B), (IV), (IV-A), (IV-B), (V), (V-A), or (V-B), $A^2$ is selected from 5- to 10-membered heterocycle and $C_{3-10}$ carbocycle, any of which is optionally substituted with one or more substituents independently selected from halogen, —$OR^{11}$, $C_{1-6}$ alkyl, $C_{1-6}$ haloalkyl, $C_{3-10}$ carbocycle and 4- to 10-membered heterocycle; wherein the $C_{3-10}$ carbocycle and 3- to 10-membered heterocycle are each optionally substituted with one or more $C_{1-6}$ alkyl.

In some embodiments, for the compound or salt of Formula (I), (II), (II-A), (III), (III-A), (III-B), (IV), (IV-A), (IV-B), (V), (V-A), or (V-B), $A^2$ is 5- to 10-membered heterocycle optionally substituted with one or more substituents independently selected from: halogen, —$OR^{11}$, —$N(R^{11})_2$, —$C(O)R^{11}$, —$C(O)N(R^{11})_2$, —$N(R^{11})C(O)R^{11}$, =O, and —CN; and $C_{1-6}$ alkyl optionally substituted with one or more substituents independently selected from halogen, —$OR^{11}$, —$N(R^{11})_2$, —$C(O)R^{11}$, —$C(O)N(R^{11})_2$, —$N(R^{11})C(O)R^{11}$, and =O. In some embodiments, $A^2$ is selected from 5- to 10-membered heterocycle and $C_{3-10}$ carbocycle, any of which is optionally substituted with one or more substituents independently selected from: halogen, $C_{1-6}$ alkyl, $C_{1-6}$ haloalkyl, and 4- to 10-membered heterocycle; wherein the 4- to 10-membered heterocycle is optionally substituted with one or more $C_{1-6}$ alkyl. In some embodiments, $A^2$ is 5- to 10-membered heterocycle optionally substituted with one or more substituents independently selected from halogen, —$OR^{11}$, —$N(R^{11})_2$, —$C(O)R^{11}$, —$C(O)N(R^{11})_2$, —$N(R^{11})C(O)R^{11}$, =O, and —CN; and $C_{1-6}$ alkyl optionally substituted with one or more substituents independently selected from: halogen, —$OR^{11}$, and —$N(R^{11})_2$. In some embodiments, $A^2$ is selected from 5- to 10-membered heterocycle and $C_{3-10}$ carbocycle, any of which is optionally substituted with one or more substituents independently selected from halogen, $C_{1-6}$ alkyl, and $C_{1-6}$ haloalkyl. In some embodiments, $A^2$ is 5- to 10-membered heterocycle optionally substituted with one or more substituents independently selected from halogen; and $C_{1-6}$ alkyl optionally substituted with one or more substituents independently selected from: halogen. In some embodiments, $A^2$ is 5- to 10-membered heterocycle optionally substituted with one or more substituents independently selected from: halogen, $C_{1-6}$ alkyl, and $C_{1-6}$ haloalkyl. In some embodiments, $A^2$ is 5- to 10-membered heterocycle optionally substituted with one or more substituents independently selected from: halogen. In some embodiments, $A^2$ is 5- to 10-membered heterocycle optionally substituted with one or more substituents independently selected from fluoro. In some embodiments, $A^2$ is optionally substituted 5- to 10-membered heteroaryl. In some embodiments, $A^2$ is optionally substituted 5-membered heteroaryl. In some embodiments, $A^2$ is selected from optionally substituted pyrazolyl and optionally substituted triazolyl. In some embodiments, $A^2$ is selected from

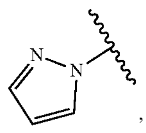,
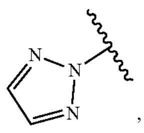,
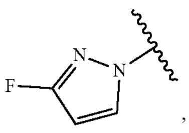, and

-continued

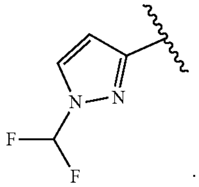.

embodiments, $A^2$ is selected from

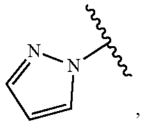, 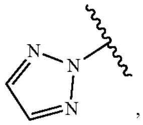, and

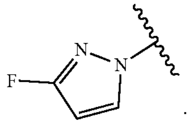.

In some embodiments, for the compound or salt of Formula (I), (II), (II-A), (III), (III-A), (III-B), (IV), (IV-A), (IV-B), (V), (V-A), or (V-B), $A^2$ is selected from

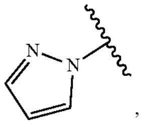, 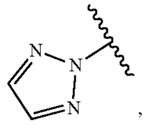, 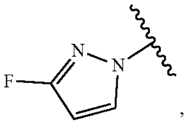, and

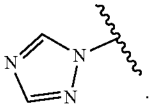.

In some embodiments, for the compound or salt of Formula (I), (II), (II-A), (III), (III-A), (III-B), (IV), (IV-A), (IV-B), (V), (V-A), or (V-B), L is represented by $-L^1-L^2-L^3-L^4-$, wherein $L^1$, $L^2$, $L^3$, and $L^4$ are each independently selected from (a) and (b):

(a) —O—, —N($R^{15}$)—, —S—, —S(O)—, —S(O)$_2$—, —S(O)(N$R^{15}$)—, —N($R^{15}$)C(O)—, —N($R^{15}$)C(O)O—, —N($R^{15}$)S(O)$_2$—, —N($R^{15}$)S(O)$_2$N($R^{15}$)—, —S(O)(N$R^{15}$)N($R^{15}$)—, —N($R^{15}$)N($R^{15}$)—, —($R^{15}$)NC (O)N($R^{15}$)—, and —($R^{15}$)NC(O)N($R^{15}$)N($R^{15}$)—; and (b) $C_{1-6}$ alkylene, $C_{2-6}$ alkenylene, $C_{2-6}$ alkynylene, $C_{3-8}$ carbocyclene, and 4- to 8-membered heterocyclene, any of which is optionally substituted with one or more substituents independently selected from halogen, —O$R^{15}$, —S$R^{15}$, ═O, ═S, and —CN;

wherein $L^2$, $L^3$, and $L^4$ are each optionally absent; and wherein no more than two of $L^1$, $L^2$, $L^3$, and $L^4$ are selected from (a) and the two selected are not adjacent.

In some embodiments, for the compound or salt of Formula (I), (II), (I1-A), (III), (I11-A), (III-B), (IV), (IV-A), (IV-B), (V), (V-A), or (V-B), L is represented by $-L^1-L^2-L^3-L^4-$, wherein $L^1$, $L^2$, $L^3$, and $L^4$ are each independently selected from (a) and (b):

(a) —O—, —N($R^{15}$)—, —S—, —S(O)—, —S(O)$_2$—, —S(O)(N$R^{15}$)—, —N($R^{15}$)C(O)—, —N($R^{15}$)C(O)O—, —N($R^{15}$)S(O)$_2$—, —N($R^{15}$)S(O)$_2$N($R^{15}$)—, —S(O)(N$R^{15}$)N($R^{15}$)—, —N($R^{15}$)N($R^{15}$)—, —($R^{15}$)NC (O)N($R^{15}$)—, and —($R^{15}$)NC(O)N($R^{15}$)N($R^{15}$)—; and (b) $C_{1-6}$ alkylene, $C_{2-6}$ alkenylene, $C_{2-6}$ alkynylene, $C_{3-8}$ carbocyclene, and 4- to 8-membered heterocyclene, any of which is optionally substituted with one or more substituents independently selected from halogen, —O$R^{15}$, —S$R^{15}$, ═O, ═S, and —CN; and $R^{15}$ is independently selected at each occurrence from hydrogen and $C_{1-4}$ alkyl, $C_{3-8}$ carbocycle, 4- to 8-membered heterocycle, and $C_{1-4}$ haloalkyl;

wherein $L^2$, $L^3$, and $L^4$ are each optionally absent; and wherein no more than two of $L^1$, $L^2$, $L^3$, and $L^4$ are selected from (a) and the two selected are not adjacent.

In some embodiments, for the compound or salt of Formula (I), (II), (II-A), (III), (III-A), (III-B), (IV), (IV-A), (IV-B), (V), (V-A), or (V-B), L is represented by $-L^1-L^2-L^3-L^4-$, wherein $L^1$, $L^2$, $L^3$, and $L^4$ are each independently selected from (a) and (b):

(a) —O—, —N($R^{15}$)—, —S—, —N($R^{15}$)C(O)—, —N($R^{15}$)C(O)O—, —N($R^{15}$)S(O)$_2$—N($R^{15}$)N($R^{15}$)—, and —($R^{15}$)NC(O)N($R^{15}$)—; and (b) $C_{1-6}$ alkylene, $C_{2-6}$ alkenylene, $C_{2-6}$ alkynylene, $C_{3-6}$ carbocyclene, and 4- to 6-membered heterocyclene, any of which is optionally substituted with one or more substituents independently selected from halogen, —O$R^{15}$, ═O, and —CN;

wherein $L^2$, $L^3$, and $L^4$ are each optionally absent; and wherein no more than two of $L^1$, $L^2$, $L^3$, and $L^4$ are selected from (a) and the two selected are not adjacent.

In some embodiments, for the compound or salt of Formula (I), (II), (II-A), (III), (III-A), (III-B), (IV), (IV-A), (IV-B), (V), (V-A), or (V-B), L is represented by $-L^1-L^2-L^3-L^4-$, wherein $L^1$, $L^2$, $L^3$, and $L^4$ are each independently selected from (a) and (b):

(a) —O—, —N($R^{15}$)—, and —N($R^{15}$)C(O)—; and (b) $C_{1-6}$ alkylene, $C_{2-6}$ alkynylene, and $C_{3-6}$ carbocyclene;

wherein $L^2$, $L^3$, and $L^4$ are each optionally absent;

wherein no more than two of $L^1$, $L^2$, $L^3$, and $L^4$ are selected from (a) and the two selected are not adjacent; and $R^{15}$ is selected from hydrogen and $C_{1-4}$ alkyl.

In some embodiments, for the compound or salt of Formula (I), (II), (II-A), (III), (III-A), (III-B), (IV), (IV-A), (IV-B), (V), (V-A), or (V-B), L is represented by $-L^1-L^2-L^3-L^4-$, wherein $L^1$, $L^2$, $L^3$, and $L^4$ are each independently selected from (a) and (b):

(a) —O—, —N($R^{15}$)—, and —N($R^{15}$)C(O)—; and (b) $C_{1-6}$ alkylene and $C_{3-6}$ carbocyclene;

wherein $L^2$, $L^3$, and $L^4$ are each optionally absent;

wherein no more than two of $L^1$, $L^2$, $L^3$, and $L^4$ are selected from (a) and the two selected are not adjacent; and $R^{15}$ is selected from hydrogen and $C_{1-4}$ alkyl.

In some embodiments, for the compound or salt of Formula (I), (II), (II-A), (III), (III-A), (III-B), (IV), (IV-A), (IV-B), (V), (V-A), or (V-B), L is represented by $-L^1-L^2-L^3-L^4-$, wherein $L^1$, $L^2$, $L^3$, and $L^4$ are each independently selected from (a) and (b):

(a) —O—, —NH—, and —N(H)C(O)—; and (b) methylene;

wherein $L^2$, $L^3$, and $L^4$ are each optionally absent; and wherein no more than two of $L^1$, $L^2$, $L^3$, and $L^4$ are selected from (a) and the two selected are not adjacent.

In some embodiments, for the compound or salt of Formula (I), (II), (II-A), (III), (III-A), (III-B), (IV), (IV-A), (IV-B), (V), (V-A), or (V-B), L is represented by $-L^1-L^2-L^3-L^4-$, wherein $L^2$, $L^3$, and $L^4$ are absent; and $L^1$ is selected from:

(a) —O—, —$N(R^{15})$—, —S—, —S(O)—, —$S(O)_2$—, —$S(O)(NR^{15})$—, —$N(R^{15})C(O)$—, —$N(R^{15})C(O)O$—, —$N(R^{15})S(O)_2$—, —$N(R^{15})S(O)_2N(R^{15})$—, —$S(O)(NR^{15})N(R^{15})$—, —$N(R^{15})N(R^{15})$—, —$(R^{15})NC(O)N(R^{15})$—, and —$(R^{15})NC(O)N(R^{15})N(R^{15})$—; and (b) $C_{1-6}$ alkylene, $C_{2-6}$ alkenylene, $C_{2-6}$ alkynylene.

In some embodiments, for the compound or salt of Formula (I), (II), (II-A), (III), (III-A), (III-B), (IV), (IV-A), (IV-B), (V), (V-A), or (V-B), L is represented by $-L^1-L^2-L^3-L^4-$, wherein $L^2$, $L^3$, and $L^4$ are absent; and $L^1$ is selected from:

(a) —O—, —$N(R^{15})$—, —S—, —S(O)—, —$S(O)_2$—, —$S(O)(NR^{15})$—, —$N(R^{15})C(O)$—, —$N(R^{15})C(O)O$—, —$N(R^{15})S(O)_2$—, —$N(R^{15})S(O)_2N(R^{15})$—, —$S(O)(NR^{15})N(R^{15})$—, —$N(R^{15})N(R^{15})$—, —$(R^{15})NC(O)N(R^{15})$—, and —$(R^{15})NC(O)N(R^{15})N(R^{15})$—; and (b) $C_{1-6}$ alkylene, $C_{2-6}$ alkenylene, $C_{2-6}$ alkynylene; and $R^{11}$ is selected from hydrogen and $C_{1-4}$ alkyl, and $C_{1-4}$ haloalkyl.

In some embodiments, for the compound or salt of Formula (I), (II), (II-A), (III), (III-A), (III-B), (IV), (IV-A), (IV-B), (V), (V-A), or (V-B), L is represented by $-L^1-L^2-L^3-L^4-$, wherein $L^2$, $L^3$, and $L^4$ are absent; and $L^1$ is selected from —$N(R^{11})$— and —$N(R^{11})C(O)$—. In some embodiments, L is represented by $-L^1-L^2-L^3-L^4-$, wherein $L^2$, $L^3$, and $L^4$ are absent; and $L^1$ is selected from —$N(R^{15})$— and —$N(R^{15})C(O)$—; and $R^{15}$ is selected from hydrogen and $C_{1-4}$ alkyl. In some embodiments, L is represented by $-L^1-L^2-L^3-L^4-$, wherein $L^2$, $L^3$, and $L^4$ are absent; and $L^1$ is selected from —$N(R^{15})$— and —$N(R^{15})C(O)$—; and $R^{15}$ is selected from hydrogen and methyl. In some embodiments, L is represented by $-L^1-L^2-L^3-L^4-$, wherein $L^2$, $L^3$, and $L^4$ are absent; and $L^1$ is —N(H)C(O)—.

In some embodiments, for the compound or salt of Formula (I), (II), (II-A), (III), (III-A), (III-B), (IV), (IV-A), (IV-B), (V), (V-A), or (V-B), L is represented by $-L^1-L^2-L^3-L^4-$, wherein $L^3$ and $L^4$ are absent; and $L^1$ is selected from —O—, —$N(R^{15})$—, —S—, —S(O)—, —$S(O)_2$—, —$S(O)(NR^{15})$—, —$N(R^{15})C(O)$—, —$N(R^{15})C(O)O$—, —$N(R^{15})S(O)_2$—, —$N(R^{15})S(O)_2N(R^{15})$—, —$S(O)(NR^{15})N(R^{15})$—, —$N(R^{15})N(R^{15})$—, —$(R^{15})NC(O)N(R^{15})$—, and —$(R^{15})NC(O)N(R^{15})N(R^{15})$—; and $L^2$ is selected from $C_{1-6}$ alkylene, $C_{2-6}$ alkenylene, $C_{2-6}$ alkynylene, $C_{3-8}$ carbocyclene, and 4 to 8-membered heterocyclene, any of which is optionally substituted with one or more substituents independently selected from halogen, —$OR^{15}$, —$SR^{15}$, =O, =S, and —CN.

In some embodiments, for the compound or salt of Formula (I), (II), (II-A), (III), (III-A), (III-B), (IV), (IV-A), (IV-B), (V), (V-A), or (V-B), L is represented by $-L^1-L^2-L^3-L^4-$, wherein $L^3$ and $L^4$ are absent; and $L^1$ is selected from —O—, —$N(R^{15})$—, —S—, —S(O)—, —$S(O)_2$—, —$S(O)(NR^{15})$—, —$N(R^{15})C(O)$—, —$N(R^{15})C(O)O$—, —$N(R^{15})S(O)_2$—, —$N(R^{15})S(O)_2N(R^{15})$—, —$S(O)(NR^{15})N(R^{15})$—, —$N(R^{15})N(R^{15})$—, —$(R^{15})NC(O)N(R^{15})$—, and —$(R^{15})NC(O)N(R^{15})N(R^{15})$—; and $L^2$ is selected from $C_{1-6}$ alkylene, $C_{2-6}$ alkenylene, $C_{2-6}$ alkynylene, $C_{3-8}$ carbocyclene, and 4 to 8-membered heterocyclene, any of which is optionally substituted with one or more substituents independently selected from halogen, —$OR^{15}$, —$SR^{15}$, =O, =S, and —CN; and $R^{15}$ is independently selected at each occurrence from hydrogen and $C_{1-4}$ alkyl, and $C_{1-4}$ haloalkyl.

In some embodiments, for the compound or salt of Formula (I), (II), (II-A), (III), (III-A), (III-B), (IV), (IV-A), (IV-B), (V), (V-A), or (V-B), L is represented by $-L^1-L^2-L^3-L^4-$, wherein $L^3$ and $L^4$ are absent; $L^1$ is selected from —$N(R^{11})$— and —$N(R^{11})C(O)$—; and $L^2$ is selected from $C_{1-6}$ alkylene, $C_{2-6}$ alkenylene, $C_{3-8}$ carbocyclene. In some embodiments, L is represented by $-L^1-L^2-L^3-L^4-$, wherein $L^3$ and $L^4$ are absent; $L^1$ is selected from —$N(R^{11})$— and —$N(R^{11})C(O)$—; and $L^2$ is selected from $C_{1-6}$ alkylene and $C_{3-6}$ carbocyclene. In some embodiments, L is represented by $-L^1-L^2-L^3-L^4-$, wherein $L^3$ and $L^4$ are absent; $L^1$ is selected from —$N(R^{11})$— and —$N(R^{11})C(O)$—; $L^2$ is selected from $C_{1-6}$ alkylene and $C_{3-6}$ carbocyclene; and $R^{11}$ is selected from hydrogen and $C_{1-4}$ alkyl. In some embodiments, L is represented by $-L^1-L^2-L^3-L^4-$, wherein $L^3$ and $L^4$ are absent; $L^1$ is —N(H)C(O)—; and $L^2$ is selected from methylene.

In some embodiments, for the compound or salt of Formula (I), (II), (II-A), (III), (III-A), (III-B), (IV), (IV-A), (IV-B), (V), (V-A), or (V-B), L is represented by $-L^1-L^2-L^3-L^4-$, wherein $L^4$ is absent; and $L^1$ is selected from —O—, —$N(R^{11})$—, —S—, —S(O)—, —$S(O)_2$—, —$S(O)(NR^{11})$—, —$N(R^{11})C(O)$—, —$N(R^{11})C(O)O$—, —$N(R^{15})S(O)_2$—, —$N(R^{15})S(O)_2N(R^{15})$—, —$S(O)(NR^{15})N(R^{15})$—, —$N(R^{15})N(R^{15})$—, —$(R^{15})NC(O)N(R^{15})$—, and —$(R^{15})NC(O)N(R^{15})N(R^{15})$—;

$L^2$ is selected from $C_{1-6}$ alkylene, $C_{2-6}$ alkenylene, $C_{2-6}$ alkynylene, $C_{3-8}$ carbocyclene, and 4- to 8-membered heterocyclene, any of which is optionally substituted with one or more substituents independently selected from halogen, —$OR^{15}$, —$SR^{15}$, =O, =S, and —CN; and $L^3$ is selected from —O—, —$N(R^{15})$—, —S—, —S(O)—, —$S(O)_2$—, —$S(O)(NR^{15})$—, —$N(R^{15})C(O)$—, —$N(R^{15})C(O)O$—, —$N(R^{15})S(O)_2$—, —$N(R^{15})S(O)_2N(R^{15})$—, —$S(O)(NR^{15})N(R^{15})$—, —$N(R^{15})N(R^{15})$—, —$(R^{15})NC(O)N(R^{15})$—, and —$(R^{15})NC(O)N(R^{15})N(R^{15})$—.

In some embodiments, for the compound or salt of Formula (I), (II), (II-A), (III), (III-A), (III-B), (IV), (IV-A), (IV-B), (V), (V-A), or (V-B), L is represented by $-L^1-L^2-L^3-L^4-$, wherein $L^4$ is absent; and $L^1$ is selected from —O—, —$N(R^{15})$—, —S—, —S(O)—, —$S(O)_2$—, —$S(O)(NR^{15})$—, —$N(R^{15})C(O)$—, —$N(R^{15})C(O)O$—, —$N(R^{15})S(O)_2$—, —$N(R^{15})S(O)_2N(R^{15})$—, —$S(O)(NR^{15})N(R^{15})$—, —$N(R^{15})N(R^{15})$—, —$(R^{15})NC(O)N(R^{15})$—, and —$(R^{15})NC(O)N(R^{15})N(R^{15})$—;

$L^2$ is selected from $C_{1-6}$ alkylene, $C_{2-6}$ alkenylene, $C_{2-6}$ alkynylene, $C_{3-8}$ carbocyclene, and 4- to 8-membered heterocyclene, any of which is optionally substituted with one or more substituents independently selected from halogen, —$OR^{11}$, —$SR^{11}$, =O, =S, and —CN;

$L^3$ is selected from —O—, —$N(R^{11})$—, —S—, —S(O)—, —$S(O)_2$—, —$S(O)(NR^{11})$—, —$N(R^{11})C(O)$—, —$N(R^{11})C(O)O$—, —$N(R^{11})S(O)_2$—, —$N(R^{11})S(O)_2N(R^{11})$—, —$S(O)(NR^{15})N(R^{15})$—, —$N(R^{15})N(R^{15})$—, —$(R^{15})NC(O)N(R^{15})$—, and —$(R^{15})NC(O)N(R^{15})N(R^{15})$—; and $R^{11}$ is independently selected at each occurrence from hydrogen and $C_{1-4}$ alkyl, and $C_{1-4}$ haloalkyl.

In some embodiments, for the compound or salt of Formula (I), (II), (II-A), (III), (III-A), (III-B), (IV), (IV-A), (IV-B), (V), (V-A), or (V-B), L is represented by $-L^1-L^2-L^3-L^4-$, wherein $L^4$ is absent; $L^1$ is selected from $—N(R^{11})—$ and $—N(R^{15})C(O)—$; $L^2$ is selected from $C_{1-6}$ alkylene, $C_{2-6}$ alkenylene, $C_{3-8}$ carbocyclene; and $L^3$ is —O—. In some embodiments, L is represented by $-L^1-L^2-L^3-L^4-$, wherein $L^4$ is absent; $L^1$ is selected from $—N(R^{15})—$ and $—N(R^{15})C(O)—$; $L^2$ is selected from $C_{1-6}$ alkylene and $C_{3-6}$ carbocyclene; and $L^3$ is —O—. In some embodiments, L is represented by $-L^1-L^2-L^3-L^4-$, wherein $L^4$ is absent; $L^1$ is selected from $—N(R^{15})—$ and $—N(R^{15})C(O)—$; $L^2$ is selected from $C_{1-6}$ alkylene and $C_{3-6}$ carbocyclene; $L^3$ is —O—; and $R^{15}$ is selected from hydrogen and $C_{1-4}$ alkyl. In some embodiments, L is represented by $-L^1-L^2-L^3-L^4-$, wherein $L^4$ is absent; $L^1$ is —N(H)C(O)—; $L^2$ is methylene; and $L^3$ is —O—.

In some embodiments, for the compound or salt of Formula (I), (II), (II-A), (III), (III-A), (III-B), (IV), (IV-A), (IV-B), (V), (V-A), or (V-B), L is selected from —N(H)C(O)—,

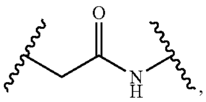, and 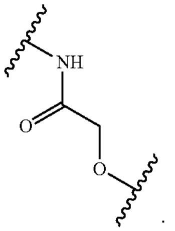.

In some embodiments, for the compound or salt of Formula (I), (II), (II-A), (III), (III-A), (III-B), (IV), (IV-A), (IV-B), (V), (V-A), or (V-B), L is represented by $-L^1-L^2-L^3-L^4$. In some embodiments, $L^4$ is absent. In some embodiments, $L^3$ is absent, —O—, ethynyl, or methylene substituted with =O. In some embodiments, $L^3$ is absent or —O—. In some embodiments, $L^2$ is absent or methylene. In some embodiments, $L^2$ is absent, methylene, (methyl)methylene, ethylene, or —O—. In some embodiments, The compound or salt of any one of claims 9-18, wherein $L^1$ is $—N(R^{15})C(O)—$. In some embodiments $L^1$ is selected from $—N(R^{15})C(O)—$, $—N(R^{15})—$, $—N(R^{15})S(O)—$, $—(R^{15})NC(O)N(R^{15})—$, and 4- to 6-membered heterocyclene optionally substituted with one or more halogen atoms. In some embodiment, $R^{15}$ is hydrogen. In some embodiments, $R^{11}$ is selected from hydrogen and $—CH_3$.

In some embodiments, for the compound or salt of Formula (I), (II), (II-A), (III), (III-A), (III-B), (IV), (IV-A), (IV-B), (V), (V-A), or (V-B), L is selected from

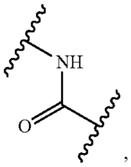, 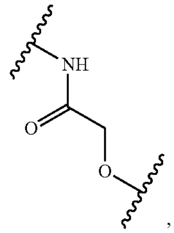, 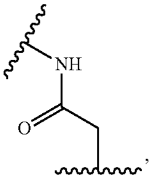,

-continued

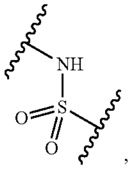, 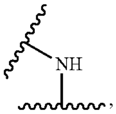, 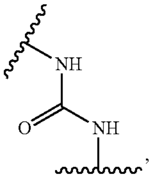,

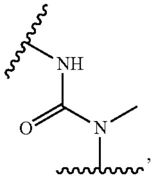, 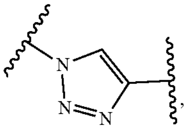, 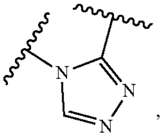,

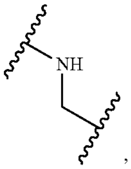, 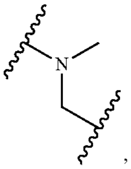, 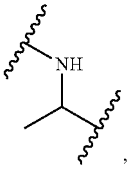,

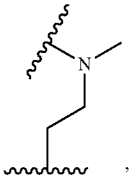, 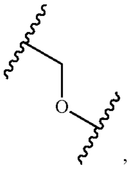, 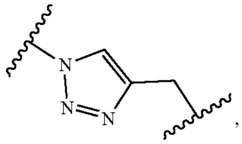,

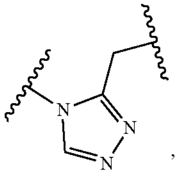, 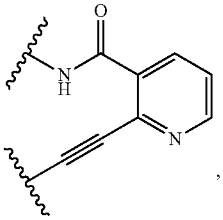,

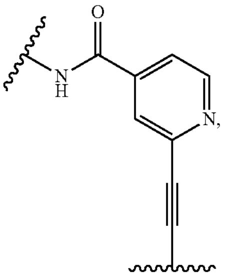, 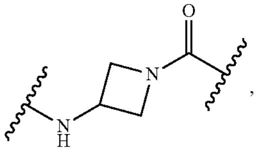,

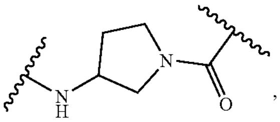,

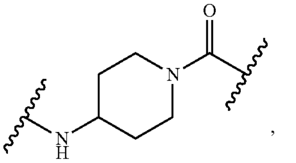, and

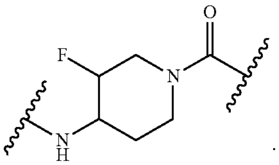 [SMILES: *NC1CCN(C(*)=O)CC1F].

In some embodiments, the compound or salt of Formula (II) is represented by the structure of Formula (VI):

(VI)

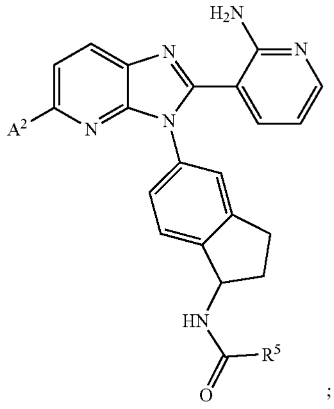

;

or a pharmaceutically acceptable salt thereof, wherein $A^2$ and $R^5$ are each defined as in Formula (II).

In some embodiments, the compound or salt of Formula (II) is represented by the structure of Formula (VI-A):

(VI-A)

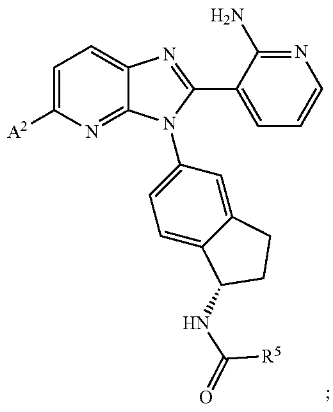

;

or a pharmaceutically acceptable salt thereof, wherein $A^2$ and $R^5$ are each defined as in Formula (II).

In some embodiments, the compound or salt of Formula (II) is represented by the structure of Formula (VI-B):

(VI-B)

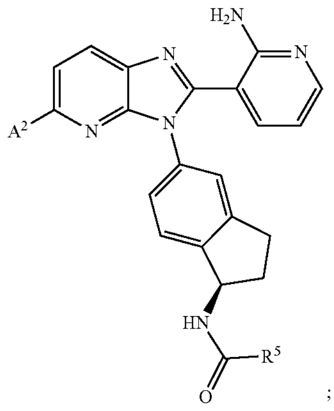

;

or a pharmaceutically acceptable salt thereof, wherein $A^2$ and $R^5$ are each defined as in Formula (II).

In some embodiments, for the compound or salt of Formula (I), (II), (II-A), (III), (III-A), (III-B), (IV), (IV-A), (IV-B), (V), (V-A), (V-B), (VI), (VI-A), or (VI-B), $R^5$ is selected from 4- to 10-membered heterocycle and $C_{3-10}$ carbocycle, any of which is optionally substituted with one or more substituents independently selected from:

halogen, $C_{1-4}$ haloalkyl, —$OR^{16}$, —$SR^{16}$, —$N(R^{16})_2$, —$C(O)N(R^{16})_2$, —$C(O)OR^{16}$, —$OC(O)R^{16}$, —$N(R^{16})C(O)R^{16}$, —$N(R^{16})S(O)_2R^{16}$, —$S(O)_2N(R^{16})_2$, —$N(R^{16})C(O)N(R^{16})_2$, —$N(R^{16})C(O)OR^{16}$, —$OC(O)N(R^{16})_2$, —$S(O)R^{16}$, —$S(O)_2R^{16}$, —$NO_2$, =O, =S, =$N(R^{16})$, and —CN;

$C_{1-4}$ alkyl, $C_{2-6}$ alkenyl, and $C_{2-6}$ alkynyl, each of which is optionally substituted with one or more substituents independently selected from: halogen, $C_{1-4}$ alkyl, $C_{1-4}$ haloalkyl, —$OR^{16}$, —$SR^{16}$, —$N(R^{16})_2$, —$NO_2$, and —CN; and 4- to 6-membered heterocycle and $C_{3-8}$ carbocycle, any of which is optionally substituted with one or more substituents independently selected from: halogen, $C_{1-4}$ alkyl, $C_{1-4}$ haloalkyl, —$OR^{16}$, —$SR^{16}$, —$N(R^{16})_2$, —$NO_2$, and —CN.

In some embodiments, for the compound or salt of Formula (I), (II), (II-A), (III), (III-A), (III-B), (IV), (IV-A), (IV-B), (V), (V-A), (V-B), (VI), (VI-A), or (VI-B), $R^5$ is selected from 4- to 10-membered heterocycle and $C_{3-10}$ carbocycle, any of which is optionally substituted by one or more substituents independently selected from:

halogen, $C_{1-4}$ haloalkyl, —$OR^{16}$, —$SR^{16}$, —$N(R^{16})_2$, —$C(O)N(R^{16})_2$, —$N(R^{16})C(O)R^{16}$, —$N(R^{16})S(O)_2R^{16}$, —$S(O)_2N(R^{16})_2$, —$N(R^{16})C(O)N(R^{16})_2$, =O, and —CN;

$C_{1-4}$ alkyl, $C_{2-6}$ alkenyl, and $C_{2-6}$ alkynyl, each of which is optionally substituted with one or more substituents independently selected from: halogen, $C_{1-4}$ alkyl, $C_{1-4}$ haloalkyl, —$OR^{16}$, —$SR^{16}$, —$N(R^{16})_2$, —$NO_2$, and —CN; and 4- to 6-membered heterocycle and $C_{3-8}$ carbocycle, any of which is optionally substituted with one or more substituents independently selected from halogen, $C_{1-4}$ alkyl, $C_{1-4}$ haloalkyl, —$OR^{16}$, —$SR^{16}$, —$N(R^{16})_2$, —$NO_2$, and —CN.

In some embodiments, for the compound or salt of Formula (I), (II), (II-A), (III), (III-A), (III-B), (IV), (IV-A), (IV-B), (V), (V-A), (V-B), (VI), (VI-A), or (VI-B), $R^5$ is selected from 4- to 10-membered heterocycle and $C_{3-10}$ carbocycle, any of which is optionally substituted with one or more substituents independently selected from:

halogen, $C_{1-4}$ haloalkyl, —$OR^{16}$, —$N(R^{16})_2$, —$C(O)N(R^{16})_2$, —$C(O)OR^{16}$, —$OC(O)R^{16}$, —$N(R^{16})C(O)R^{16}$, —$N(R^{16})S(O)_2R^{16}$, —$S(O)_2R^{16}$, —$S(O)_2N(R^{16})_2$, —$NO_2$, =O, and —CN;

$C_{1-4}$ alkyl, $C_{2-6}$ alkenyl, and $C_{2-6}$ alkynyl, each of which is optionally substituted with one or more substituents independently selected from: halogen, $C_{1-4}$ alkyl, $C_{1-4}$ haloalkyl, —$OR^{16}$, —$SR^{16}$, —$N(R^{16})_2$, —$NO_2$, and —CN; and 4- to 6-membered heterocycle and $C_{3-8}$ carbocycle, each of which is optionally substituted with one or more substituents independently selected from: halogen, $C_{1-4}$ alkyl, $C_{1-4}$ haloalkyl, —$OR^{16}$, —$N(R^{16})_2$, —$NO_2$, and —CN.

In some embodiments, for the compound or salt of Formula (I), (II), (II-A), (III), (III-A), (III-B), (IV), (IV-A), (IV-B), (V), (V-A), (V-B), (VI), (VI-A), or (VI-B), $R^5$ is selected from 4- to 10-membered heterocycle and $C_{3-10}$ carbocycle, any of which is optionally substituted with one or more substituents independently selected from:

halogen, $C_{1-4}$ haloalkyl, —$OR^{16}$, —$N(R^{16})_2$, —$C(O)N(R^{16})_2$, —$C(O)OR^{16}$, —$OC(O)R^{16}$, —$N(R^{16})C(O)R^{16}$, —$NO_2$, =O, and —CN;

$C_{1-4}$ alkyl, $C_{2-6}$ alkenyl, and $C_{2-6}$ alkynyl, each of which is optionally substituted with one or more substituents independently selected from: halogen, $C_{1-4}$ alkyl, $C_{1-4}$ haloalkyl, —$OR^{16}$, —$SR^{16}$, —$N(R^{16})_2$, —$NO_2$, and —CN; and 4- to 6-membered heterocycle and $C_{3-8}$ carbocycle, each of which is optionally substituted with one or more substituents independently selected from: halogen, $C_{1-4}$ alkyl, $C_{1-4}$ haloalkyl, —$OR^{16}$, —$N(R^{16})_2$, —$NO_2$, and —CN.

In some embodiments, for the compound or salt of Formula (I), (II), (II-A), (III), (III-A), (III-B), (IV), (IV-A), (IV-B), (V), (V-A), (V-B), (VI), (VI-A), or (VI-B), $R^5$ is selected from 4- to 10-membered heterocycle and $C_{3-10}$ carbocycle, any of which is optionally substituted with one or more substituents independently selected from:

halogen, $C_{1-4}$ haloalkyl, —$OR^{16}$, —$N(R^{16})_2$, —$C(O)N(R^{16})_2$, —$C(O)OR^{16}$, —$OC(O)R^{16}$, —$N(R^{16})C(O)R^{16}$, —$NO_2$, =O, and —CN;

$C_{1-4}$ alkyl, $C_{2-6}$ alkenyl, and $C_{2-6}$ alkynyl, any of which is optionally substituted with one or more substituents independently selected from: halogen, $C_{1-4}$ alkyl, $C_{1-4}$ haloalkyl, —$OR^{16}$, and —$N(R^{16})_2$; and 4- to 6-membered heterocycle and $C_{3-8}$ carbocycle, each of which is optionally substituted with one or more substituents independently selected from: halogen, $C_{1-4}$ alkyl, $C_{1-4}$ haloalkyl, —$OR^{16}$, —$N(R^{16})_2$, —$NO_2$, and —CN.

In some embodiments, for the compound or salt of Formula (I), (II), (II-A), (III), (III-A), (III-B), (IV), (IV-A), (IV-B), (V), (V-A), (V-B), (VI), (VI-A), or (VI-B), $R^5$ is selected from 4- to 10-membered heterocycle and $C_{3-10}$ carbocycle, any of which is optionally substituted with one or more substituents independently selected from:

halogen, $C_{2-6}$ alkynyl, $C_{1-4}$ haloalkyl, —$OR^{16}$, —$N(R^{16})_2$, =O, and —CN;

$C_{1-4}$ alkyl optionally substituted with one or more substituents independently selected from: —$N(R^{16})_2$; and 4- to 6-membered heterocycle and $C_{3-8}$ carbocycle, each of which is optionally substituted with one or more substituents independently selected from: halogen.

In some embodiments, for the compound or salt of Formula (I), (II), (II-A), (III), (III-A), (III-B), (IV), (IV-A), (IV-B), (V), (V-A), (V-B), (VI), (VI-A), or (VI-B), $R^5$ is selected from 4- to 10-membered heterocycle and $C_{3-10}$ carbocycle, any of which is optionally substituted with one or more substituents independently selected from: fluoro, chloro, methyl, ethyl, ethynyl, difluoromethyl, hydroxy, methoxy, trifluoromethoxy, dimethylamino, =O, —CN, cyclopropyl, and pyrazolyl.

In some embodiments, for the compound or salt of Formula (I), (II), (II-A), (III), (III-A), (III-B), (IV), (IV-A), (IV-B), (V), (V-A), (V-B), (VI), (VI-A), or (VI-B), $R^5$ is selected from 4- to 10-membered heterocycle and $C_{3-10}$ carbocycle, any of which is optionally substituted with one or more substituents independently selected from halogen, $C_{1-4}$ alkyl, $C_{2-6}$ alkynyl, $C_{1-4}$ haloalkyl, —$OR^{16}$, —$N(R^{16})_2$, =O, —CN, and $C_{3-8}$ carbocycle. In some embodiments, $R^5$ is selected from 4- to 10-membered heterocycle and $C_{3-10}$ carbocycle, any of which is optionally substituted with one or more substituents independently selected from: fluoro, chloro, methyl, ethyl, ethynyl, difluoromethyl, hydroxy, methoxy, trifluoromethoxy, dimethylamino, =O, —CN, cyclopropyl, and pyrazolyl.

In some embodiments, for the compound or salt of Formula (I), (II), (II-A), (III), (III-A), (III-B), (IV), (IV-A), (IV-B), (V), (V-A), (V-B), (VI), (VI-A), or (VI-B), $R^5$ is selected from 4- to 10-membered heterocycle and $C_{3-10}$ carbocycle, any of which is optionally substituted with one or more substituents independently selected from halogen, $C_{1-4}$ alkyl, $C_{2-6}$ alkynyl, $C_{1-4}$ haloalkyl, —$OR^{16}$, —$N(R^{16})_2$, —$C(O)N(R^{16})_2$, =O, —CN, $C_{3-8}$ carbocycle, and 3- to 8-membered heterocycle, wherein the $C_{3-8}$ carbocycle and 4- to 8-membered heterocycle are each optionally substituted with one or more substituents selected from halogen, $C_{1-4}$ alkyl, and $C_{1-4}$ haloalkyl. In some embodiments, $R^5$ is selected from 4- to 10-membered heterocycle and $C_{3-10}$ carbocycle, any of which is optionally substituted with one or more substituents independently selected from: fluoro, chloro, methyl, ethyl, ethynyl, propynyl, fluoromethyl, difluoromethyl, trifluoromethyl, hydroxy, —$CH_2OH$, methoxy, —$CH_2OCH_3$,

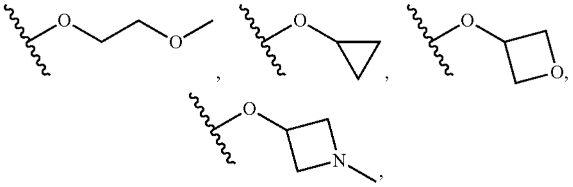

difluoromethoxy, trifluoromethoxy, —$NH_2$, dimethylamino, —$CH_2N(CH_3)_2$,

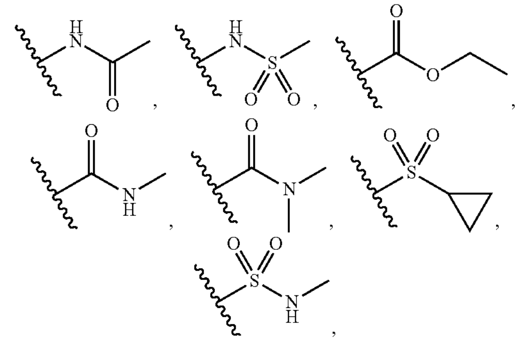

=O, —CN, cyclopropyl, phenyl, morpholinyl, pyrazolyl,

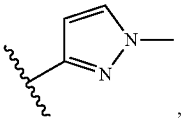 [SMILES: *c1ccn(C)n1]

and pyridinyl.

In some embodiments, for the compound or salt of Formula (I), (II), (II-A), (III), (III-A), (III-B), (IV), (IV-A), (IV-B), (V), (V-A), (V-B), (VI), (VI-A), or (VI-B), $R^5$ is optionally substituted 3- to 10-membered heteroaryl. In some embodiments, $R^5$ is optionally substituted 5- to 10-membered heteroaryl. In some embodiments, $R^5$ is optionally substituted 5- to 6-membered heteroaryl. In some embodiments, $R^5$ is selected from: optionally substituted pyrazolyl, optionally substituted thiazolyl, optionally substituted oxazolyl, optionally substituted pyridyl, optionally substituted pyrimidyl, optionally substituted pyrazinyl, optionally substituted pyridazinyl, optionally substituted benzo[d]isoxazolyl, optionally substituted imidazo[1,2-a]pyridinyl, optionally substituted 1H-benzo[d]imidazolyl, optionally substituted 1H-pyrazolo[3,4-b]pyridinyl, optionally substituted 2H-pyrrolo[3,4-c]pyridinyl, and optionally substituted isoquinolinyl. In some embodiments, $R^5$ is selected from: optionally substituted pyrazolyl, optionally substituted thiazolyl, optionally substituted oxazolyl, optionally substituted pyridyl, optionally substituted pyrimidyl, optionally substituted pyrazinyl, optionally substituted pyridazinyl, optionally substituted benzo[d]isoxazolyl, optionally substituted imidazo[1,2-a]pyridinyl, optionally substituted 1H-benzo[d]imidazolyl, optionally substituted 1H-pyrazolo[3,4-b]pyridinyl, optionally substituted 2H-pyrrolo[3,4-c]pyridinyl, and optionally substituted isoquinolinyl. In some embodiments, $R^5$ is selected from: optionally substituted pyrazolyl, optionally substituted thiazolyl, optionally substituted oxazolyl, optionally substituted pyridyl, optionally substituted pyrimidyl, optionally substituted pyrazinyl, optionally substituted pyridazinyl, optionally substituted benzo[d]isoxazolyl, optionally substituted imidazo[1,2-a]pyridinyl, optionally substituted 1H-benzo[d]imidazolyl, optionally substituted 1H-pyrazolo[3,4-b]pyridinyl, optionally substituted 2H-pyrrolo[3,4-c]pyridinyl, and optionally substituted isoquinolinyl.

In some embodiments, for the compound or salt of Formula (I), (II), (II-A), (III), (III-A), (III-B), (IV), (IV-A), (IV-B), (V), (V-A), (V-B), (VI), (VI-A), or (VI-B), $R^5$ is optionally substituted 4- to 10-membered heterocycle. In some embodiments, $R^5$ is optionally substituted 4- to 10-membered heteroaryl.

In some embodiments, for the compound or salt of Formula (I), (II), (II-A), (III), (III-A), (III-B), (IV), (IV-A), (IV-B), (V), (V-A), (V-B), (VI), (VI-A), or (VI-B), $R^5$ is optionally substituted 3- to 8-membered heterocycloalkyl. In some embodiments, $R^5$ is optionally substituted 3- to 6-membered heterocycloalkyl. In some embodiments, $R^5$ is optionally substituted 4- to 6-membered heterocycloalkyl. In some embodiments, $R^5$ is selected from optionally substituted oxetanyl, optionally substituted pyrrolyl, and optionally substituted morpholinyl.

In some embodiments, for the compound or salt of Formula (I), (II), (II-A), (III), (III-A), (III-B), (IV), (IV-A), (IV-B), (V), (V-A), (V-B), (VI), (VI-A), or (VI-B), $R^5$ is selected from optionally substituted $C_{3-6}$ cycloalkyl and optionally substituted phenyl. In some embodiments, $R^5$ is optionally substituted $C_{3-5}$ cycloalkyl and optionally substituted phenyl. In some embodiments, $R^5$ is selected from optionally substituted cyclopropyl, optionally substituted cyclobutyl, and optionally substituted phenyl. In some embodiments, $R^5$ is optionally substituted $C_{3-6}$ cycloalkyl. In some embodiments, $R^5$ is optionally substituted $C_{3-5}$ cycloalkyl. In some embodiments, $R^5$ is selected from optionally substituted cyclopropyl and optionally substituted cyclobutyl. In some embodiments, $R^5$ is optionally substituted phenyl.

In some embodiments, for the compound or salt of Formula (I), (II), (II-A), (III), (III-A), (III-B), (IV), (IV-A), (IV-B), (V), (V-A), (V-B), (VI), (VI-A), or (VI-B), $R^5$ is selected from:

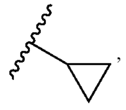
,
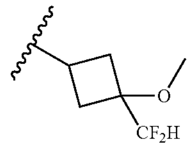
,
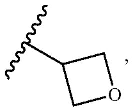
,
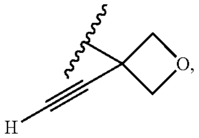
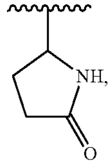
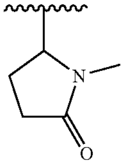
,
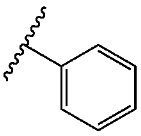
,
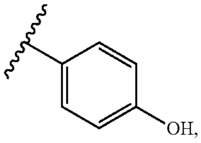
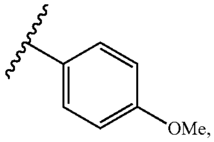
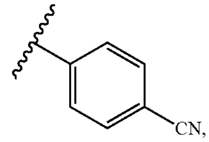
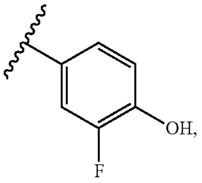
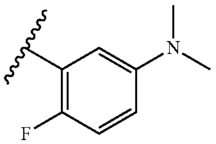
,
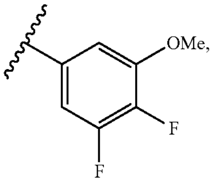
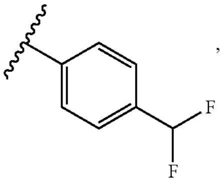
,
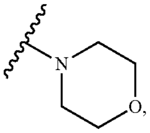
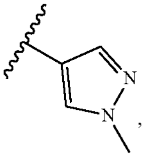
,
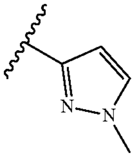
,
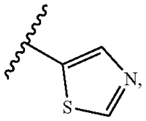
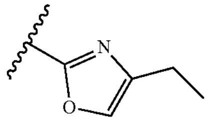
,
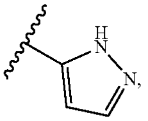
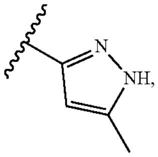
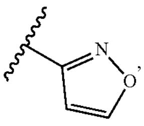
,
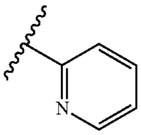
,
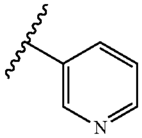
,
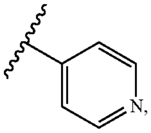
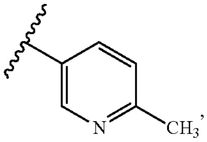
,
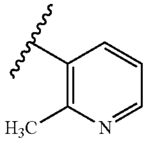
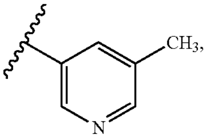
,
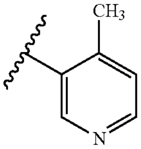
, -continued

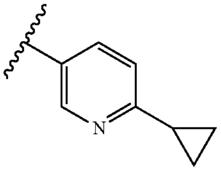, 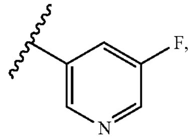

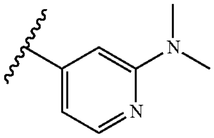, 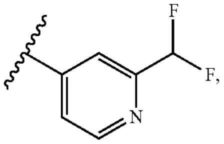

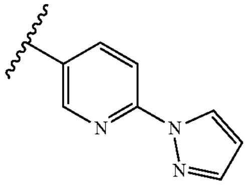, 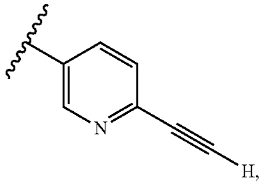

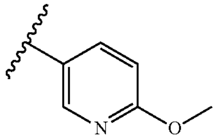, 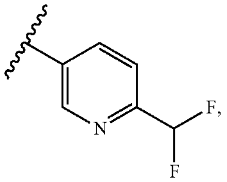

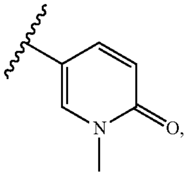 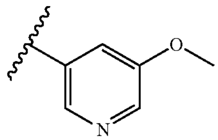,

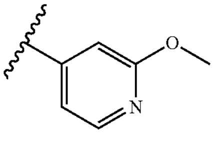, 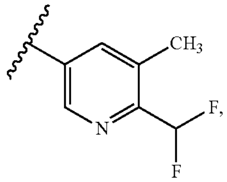

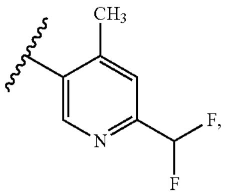 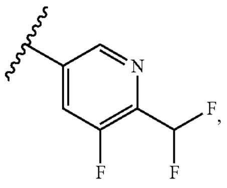

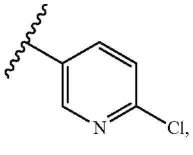 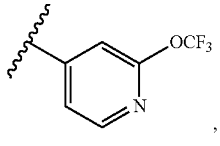,

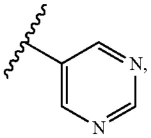 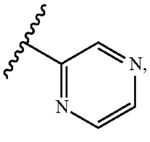 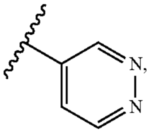

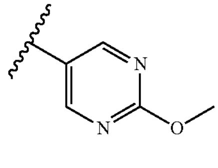, 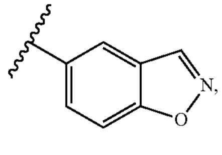

-continued

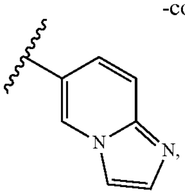 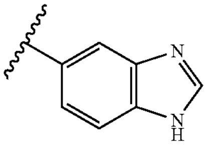,

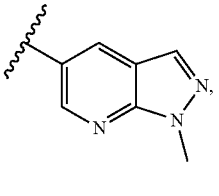 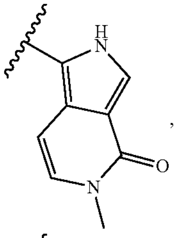,

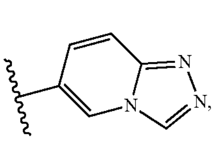 and 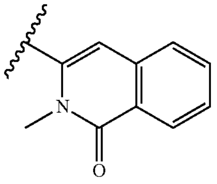.

In some embodiments, for the compound or salt of Formula (I), (II), (II-A), (III), (III-A), (III-B), (IV), (IV-A), (IV-B), (V), (V-A), (V-B), (VI), (VI-A), or (VI-B), $R^5$ is selected from optionally substituted pyrazolyl, optionally substituted thiazolyl, optionally substituted oxazolyl, optionally substituted pyridyl, optionally substituted pyrimidyl, optionally substituted pyrazinyl, optionally substituted pyridazinyl, optionally substituted benzo[d]isoxazolyl, optionally substituted imidazo[1,2-a]pyridinyl, optionally substituted 1H-benzo[d]imidazolyl, optionally substituted 1H-pyrazolo[3,4-b]pyridinyl, optionally substituted 2H-pyrrolo[3,4-c]pyridinyl, and optionally substituted isoquinolinyl.

In some embodiments, for the compound or salt of Formula (I), (II), (II-A), (III), (III-A), (III-B), (IV), (IV-A), (IV-B), (V), (V-A), (V-B), (VI), (VI-A), or (VI-B), $R^5$ is selected from optionally substituted pyrazolyl, optionally substituted thiazolyl, optionally substituted oxazolyl, optionally substituted pyridyl, optionally substituted pyrimidyl, optionally substituted pyrazinyl, optionally substituted pyridazinyl, optionally substituted benzo[d]isoxazolyl, optionally substituted imidazo[1,2-a]pyridinyl, optionally substituted 1H-benzo[d]imidazolyl, optionally substituted 1H-pyrazolo[3,4-b]pyridinyl, optionally substituted 2H-pyrrolo[3,4-c]pyridinyl, and optionally substituted isoquinolinyl, optionally substituted isoxazolyl, optionally substituted isothiazole, optionally substituted 1,2,3-thiadiazolyl, optionally substituted 5,6-dihydro-4H-pyrrolo[1,2-b]pyrazolyl, optionally substituted 2,3-dihydropyrazolo[5,1-b]oxazolyl, optionally substituted 5,6-dihydro-3H-furo[2,3-d]imidazolyl, optionally substituted indolizinyl, optionally substituted pyrazolo[1,5-a]pyridinyl, optionally substituted pyrrolo[1,2-a]pyrimidinyl, optionally substituted pyrazolo[1,5-a]pyrimidinyl, optionally substituted imidazo[1,2-a]pyrimidinyl, optionally substituted imidazo[1,2-b]pyridazinyl, optionally substituted [1,2,4]triazolo[1,5-a]pyridinyl, optionally substituted 6,7-dihydro-5H-cyclopenta[b]pyridinyl, optionally substituted 6,7-dihydro-5H-cyclopenta[c]pyridinyl, optionally substituted 5,6,7,8-tetrahydroisoquinolinyl, optionally substituted 3,4-dihydro-2H-pyrano[2,3-b]pyridinyl, optionally substituted 2,3-dihydro-[1,4]dioxino[2,3-b]pyridinyl, optionally substituted 5,7-dihydrofuro[3,4-b]pyridinyl, optionally substituted 2,3-dihydrofuro[2,3-c]pyridinyl, optionally substituted 2,3-dihydrofuro[2,3-b]pyridinyl, optionally substituted [1,3]dioxolo[4,5-b]pyridinyl, optionally substituted furo[2,3-b]pyridinyl, optionally substituted thieno[2,3-b]pyridinyl, optionally substituted 1,2-dihydro-3H-indazol-3-onyl, optionally substituted 1H-benzo[d][1,2,3]triazolyl, optionally substituted 1,3-dihydro-2H-benzo[d]imidazol-2-onyl, optionally substituted benzo[d]oxazol-2(3H)-onyl, optionally substituted benzo[d]thiazol-2(3H)-onyl, optionally substituted 1H-indazolyl, optionally substituted indolin-2-onyl, and optionally substituted 1,3-dihydro-2H-pyrrolo[2,3-b]pyridin-2-onyl.

In some embodiments, for the compound or salt of Formula (I), (II), (II-A), (III), (III-A), (III-B), (IV), (IV-A), (IV-B), (V), (V-A), (V-B), (VI), (VI-A), or (VI-B), $R^5$ is an optionally substituted 6- to 10-membered bicyclic heterocycle selected from optionally substituted 6- to 10-membered fused heterocycle, optionally substituted 6- to 10-membered bridged heterocycle, and optionally substituted 6- to 10-membered spirocyclic heterocycle.

In some embodiments, for the compound or salt of Formula (I), (II), (II-A), (III), (III-A), (III-B), (IV), (IV-A), (IV-B), (V), (V-A), (V-B), (VI), (VI-A), or (VI-B), $R^5$ is optionally substituted 6- to 10-membered spirocyclic heterocycle selected from optionally substituted 2-azaspiro[3.3]heptanyl, optionally substituted 6-azaspiro[3.4]octanyl, optionally substituted 5-azaspiro[3.4]octanyl, optionally substituted 2-azaspiro[3.5]nonanyl, optionally substituted 7-azaspiro[3.5]nonanyl, and optionally substituted 6-azaspiro[3.5]nonanyl.

In some embodiments, for the compound or salt of Formula (I), (II), (II-A), (III), (III-A), (III-B), (IV), (IV-A), (IV-B), (V), (V-A), (V-B), (VI), (VI-A), or (VI-B), $R^5$ is selected from optionally substituted oxetanyl, optionally substituted pyrrolyl, optionally substituted morpholinyl, optionally substituted azetidinyl, optionally substituted pyrrolidinyl, optionally substituted tetrahydro-2H-thiopyranyl, and optionally substituted piperidinyl.

In some embodiments, for the compound or salt of Formula (I), (II), (II-A), (III), (III-A), (III-B), (IV), (IV-A), (IV-B), (V), (V-A), (V-B), (VI), (VI-A), or (VI-B), $R^5$ is selected from:

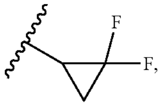
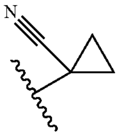
,
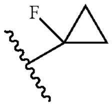
,
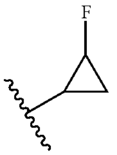
,
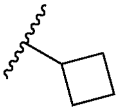
,
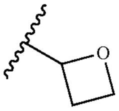
,
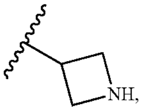
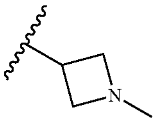
,
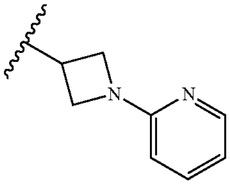
,
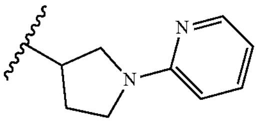
,
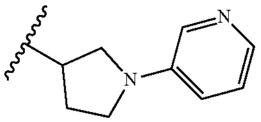
, -continued

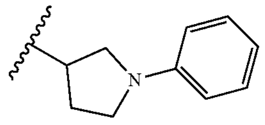
,
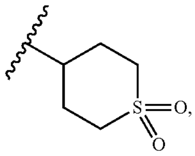
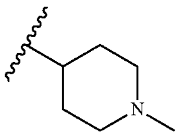
,
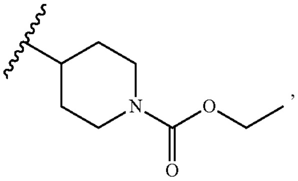
,
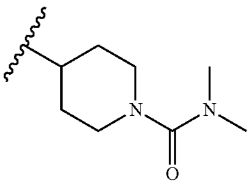
,
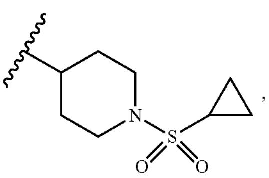
,
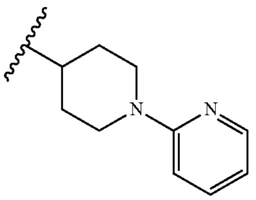
,
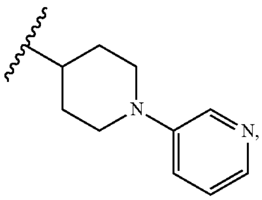
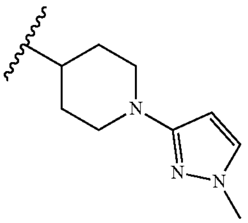
,
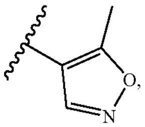
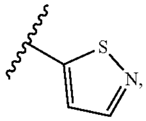
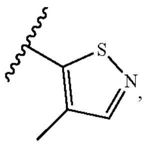
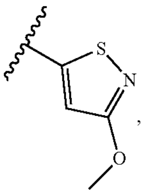
,
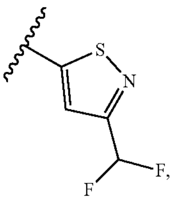
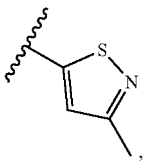
,
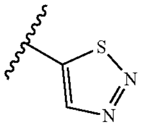
,
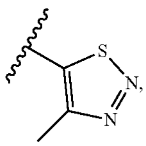
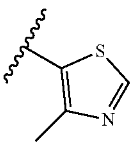
,
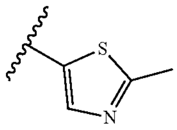
,
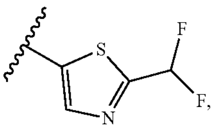
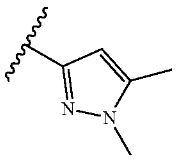
, -continued
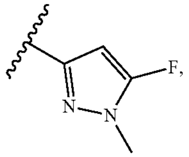
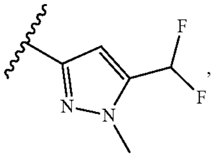
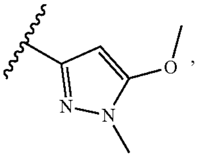
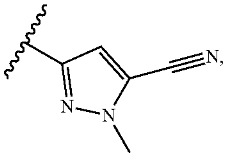
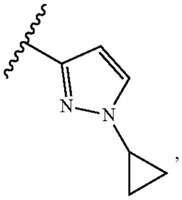
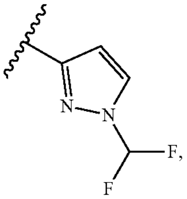
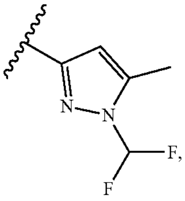
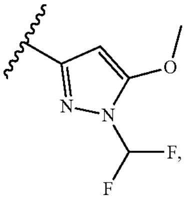
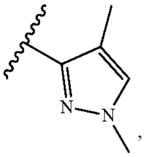
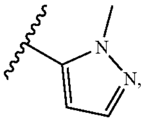
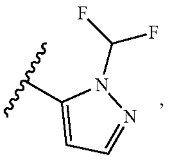
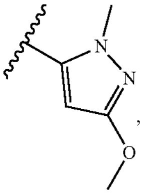
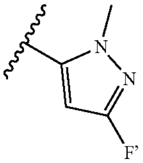
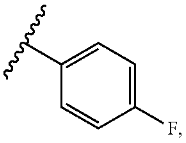
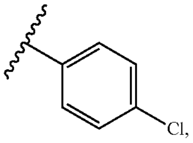
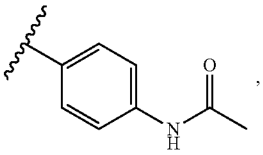
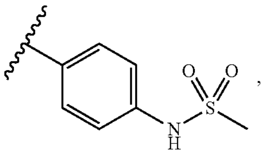
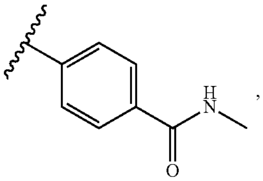
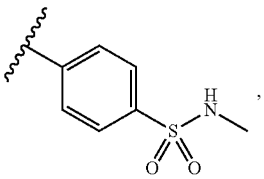
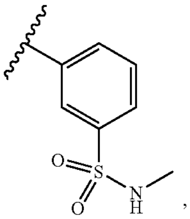
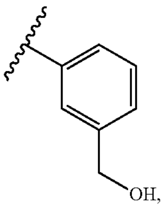
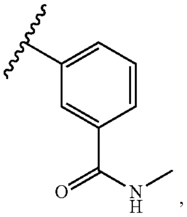
-continued
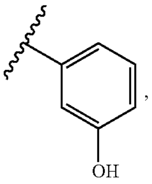
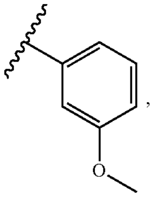
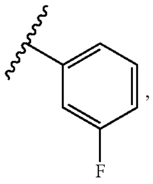
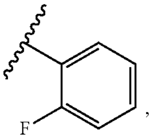
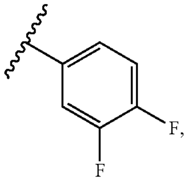
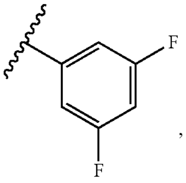
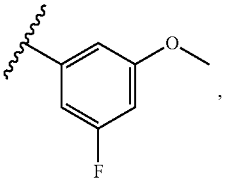
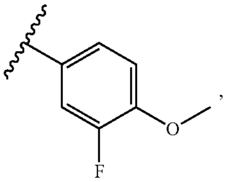
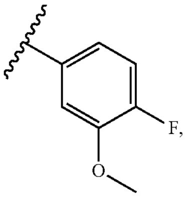
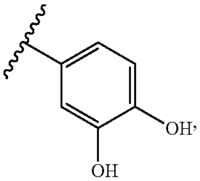
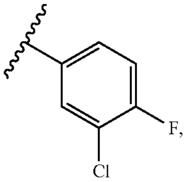
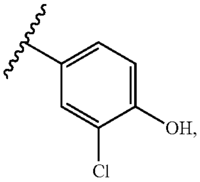
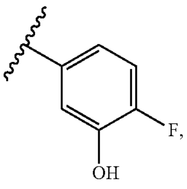
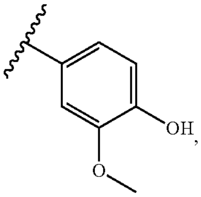
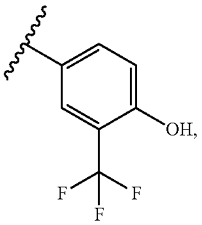
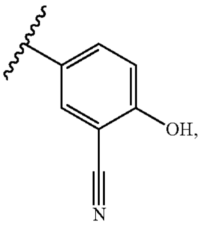
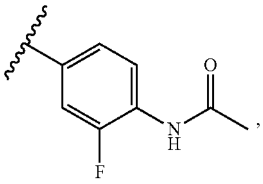
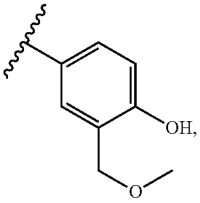

-continued
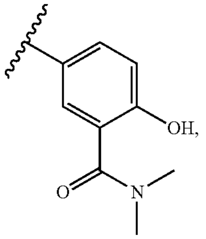
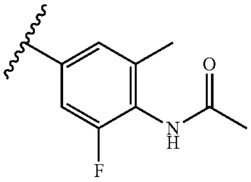
,
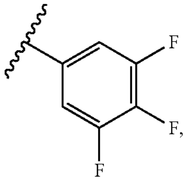
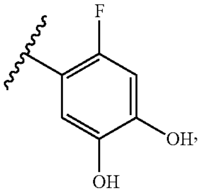
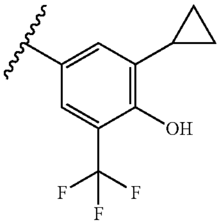
,
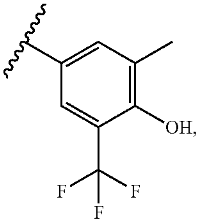
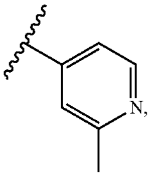
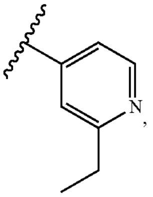
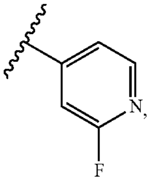
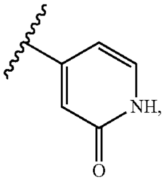
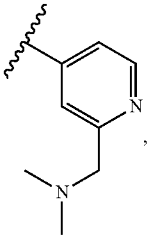
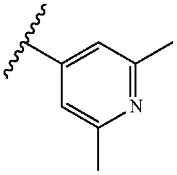
,
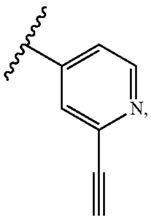
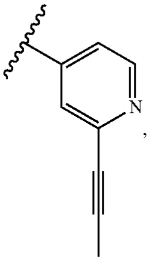
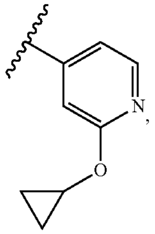
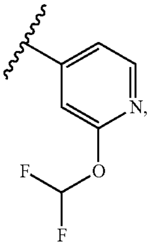
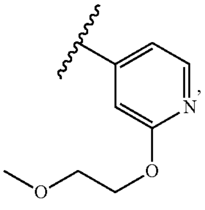
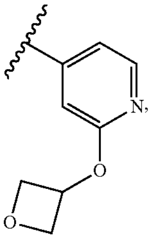
-continued
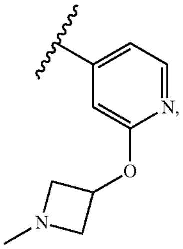
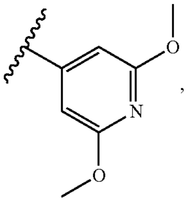
,
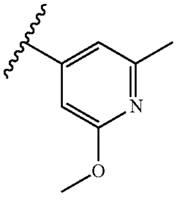
,
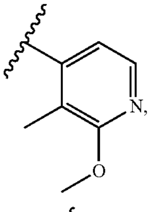
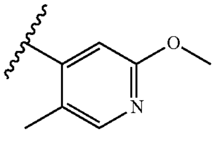
,
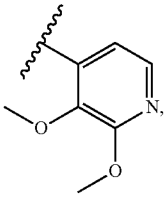
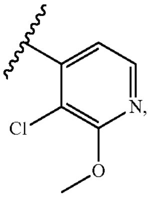
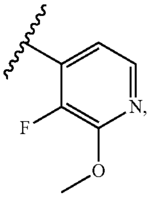
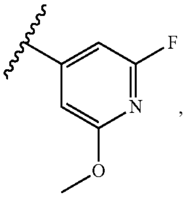
,
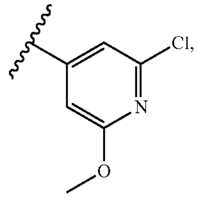
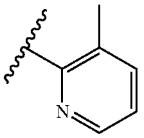
,
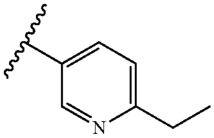
,
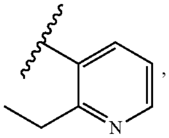
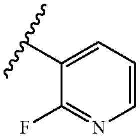
,
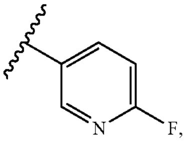
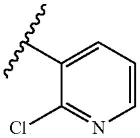
,
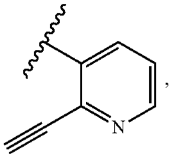
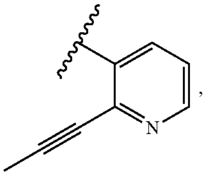
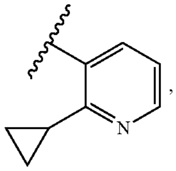
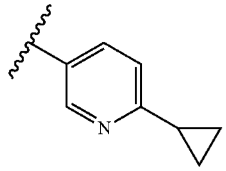
, -continued
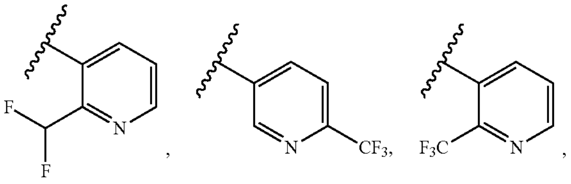
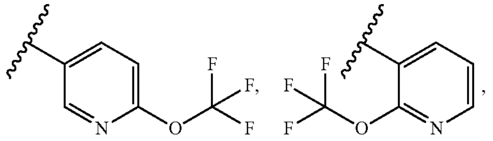
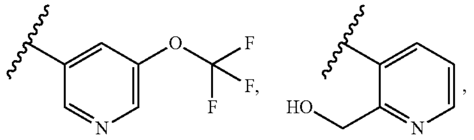
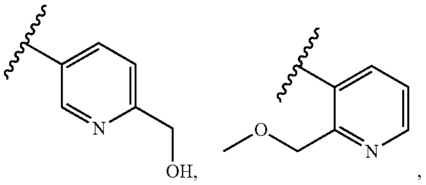
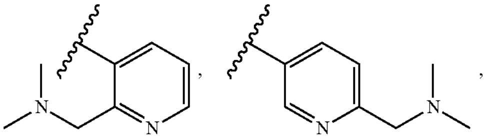
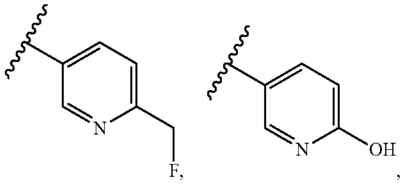
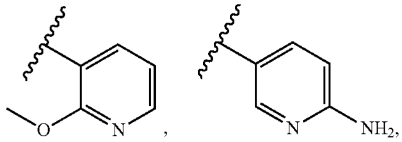
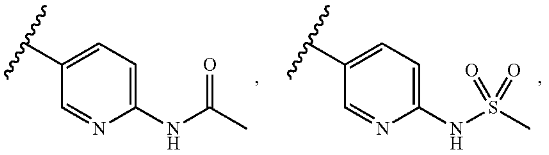
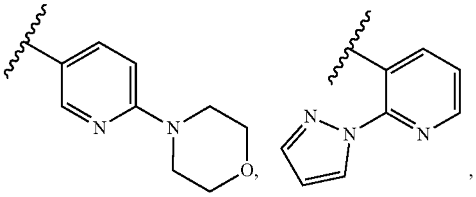
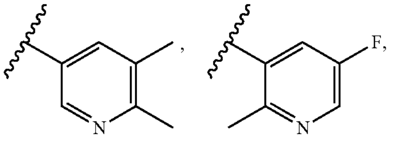
-continued
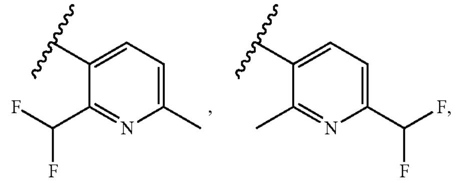
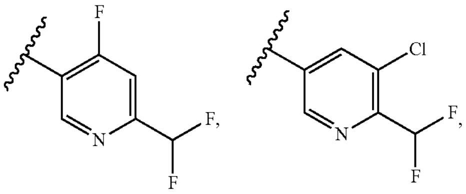
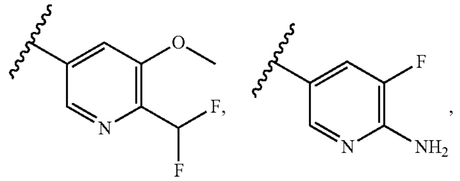
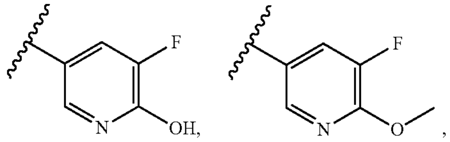
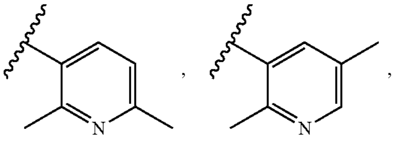
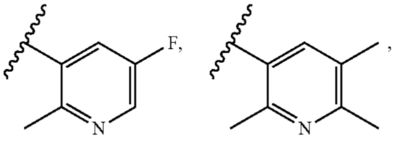
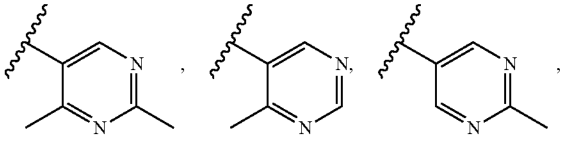
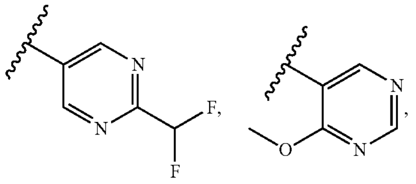
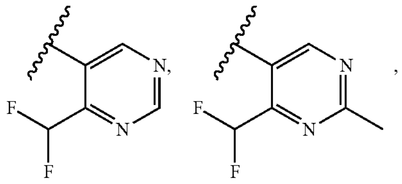
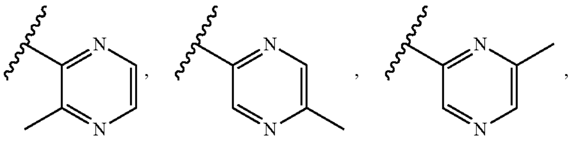

-continued
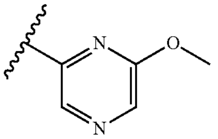 ,
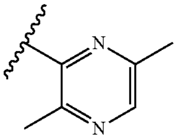 ,
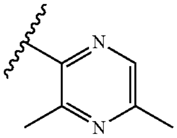 ,
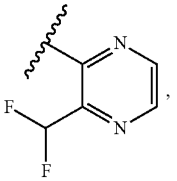
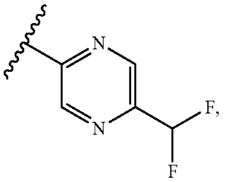
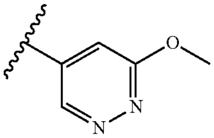 ,
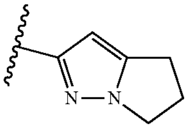 ,
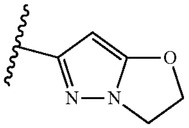 ,
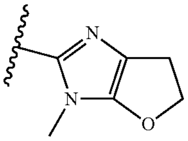 ,
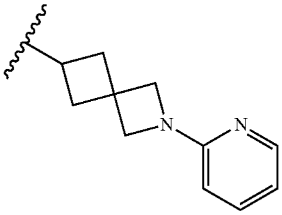 ,
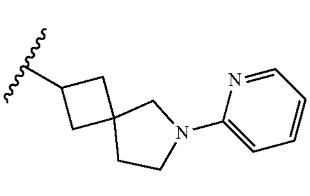 ,
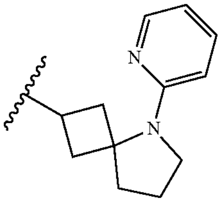 ,
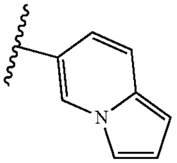 ,
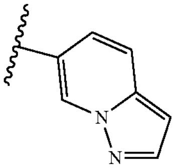 ,
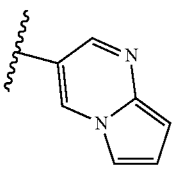 ,
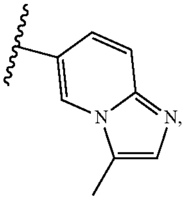
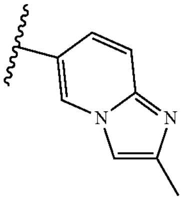 ,
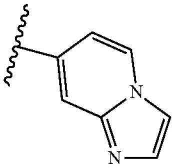 ,
-continued
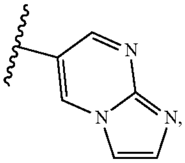
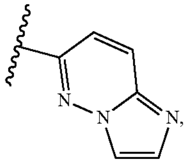
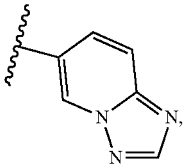
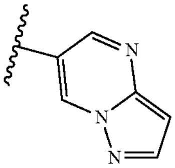 ,
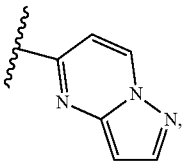
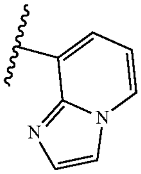 ,
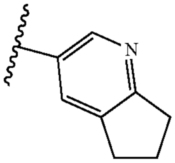 ,
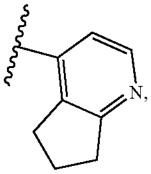
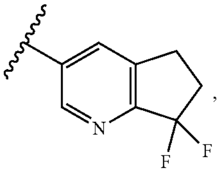 ,
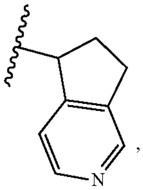
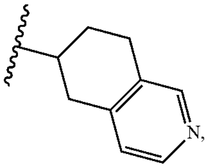
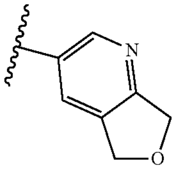 ,
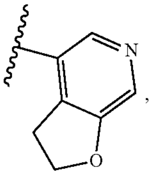 ,
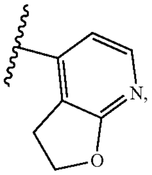
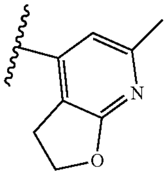 ,
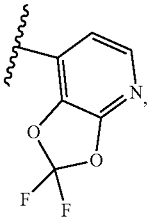
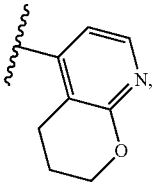
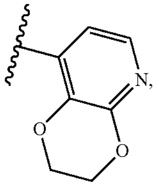
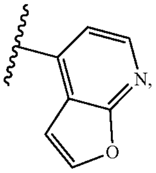
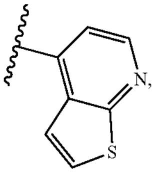
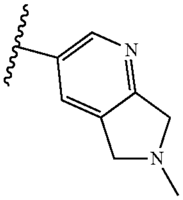 ,
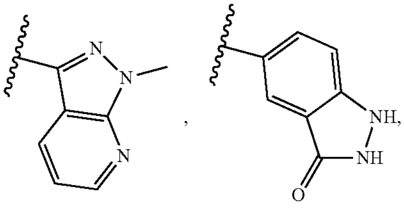

-continued
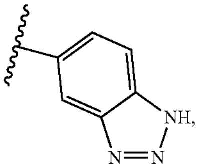
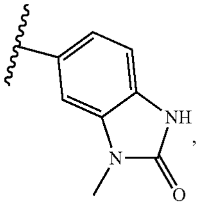
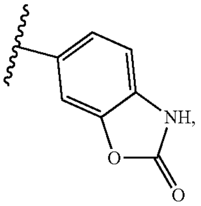
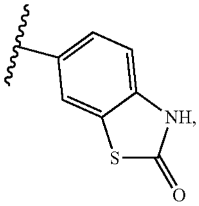
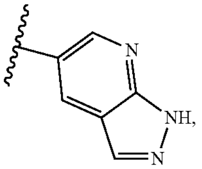
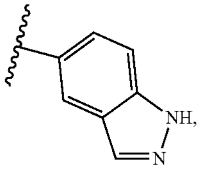
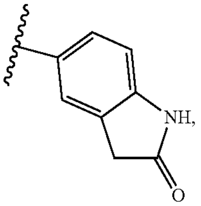
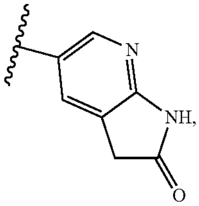
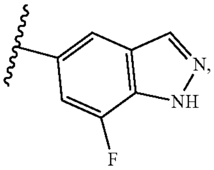
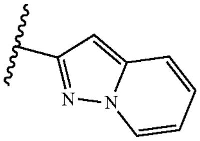,
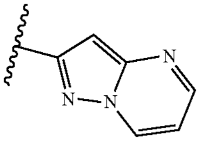,
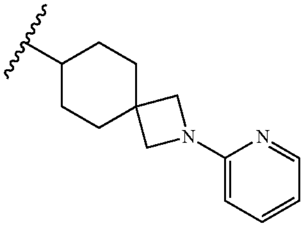,
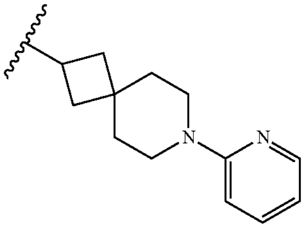, and
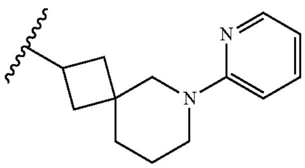.
In some embodiments, for the compound or salt of Formula (I), (II), (II-A), (III), (III-A), (III-B), (IV), (IV-A), (IV-B), (V), (V-A), (V-B), (VI), (VI-A), or (VI-B), $R^5$ is selected from:
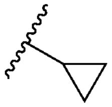,
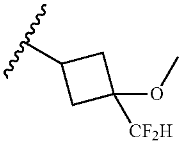
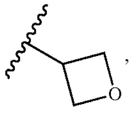
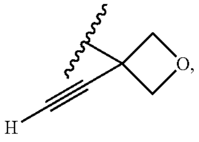
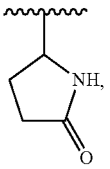
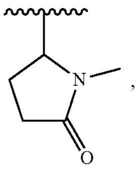
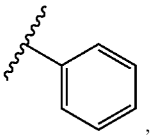
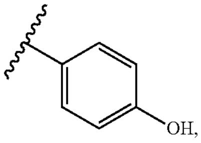
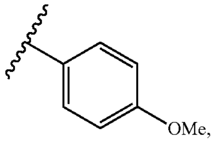
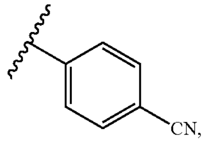
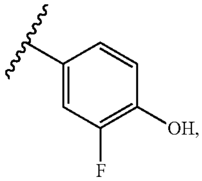
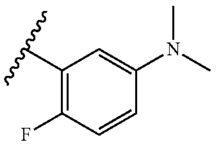,
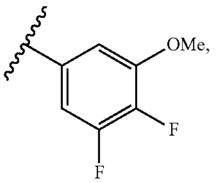
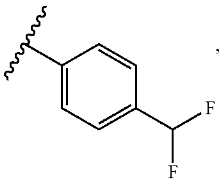,
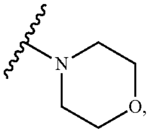
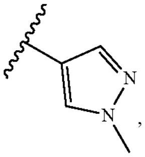
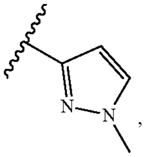
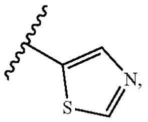
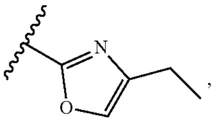
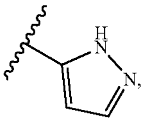
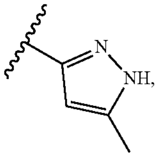
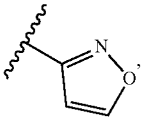
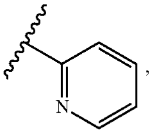
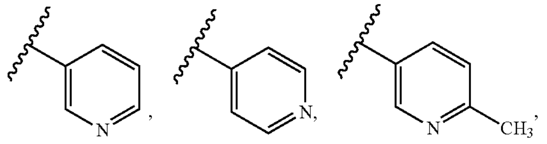
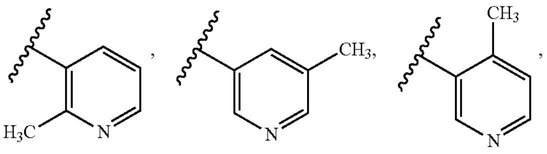

-continued
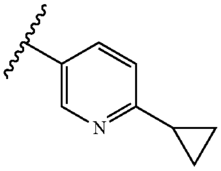 , 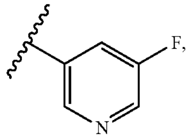
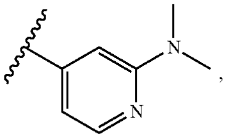 , 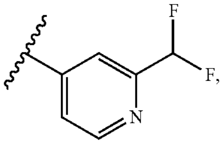
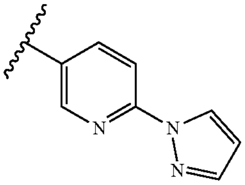 , 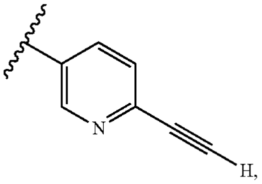
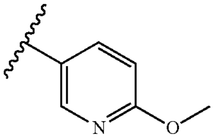 , 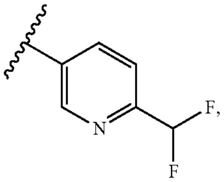
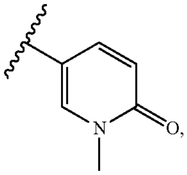 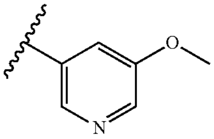 ,
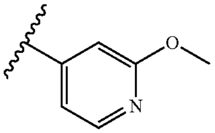 , 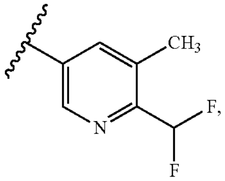
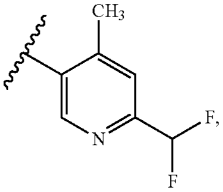 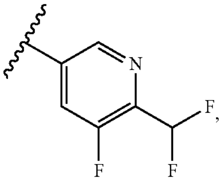
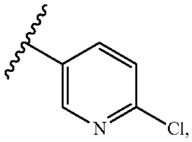 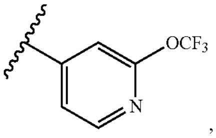 ,
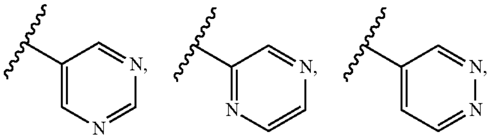
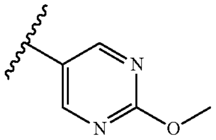 , 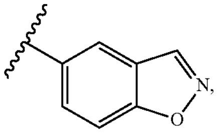
-continued
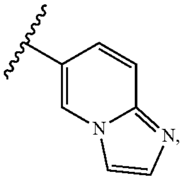 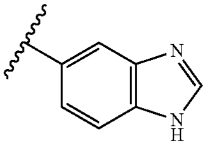 ,
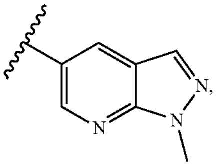 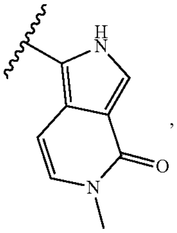 ,
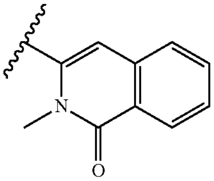 , 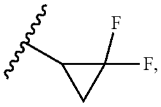
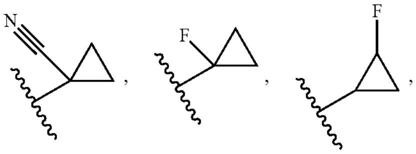
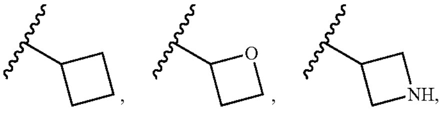
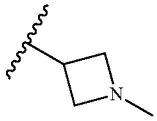 , 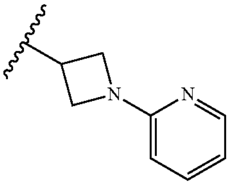 ,
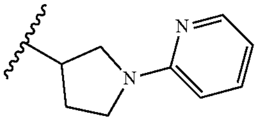 , 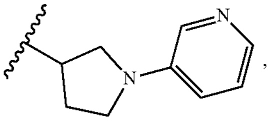 ,
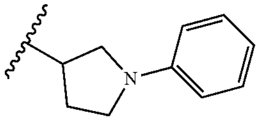 , 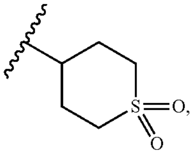
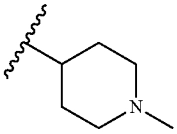 , 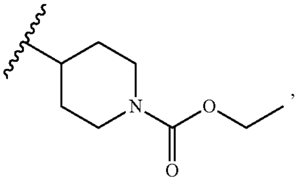 ,
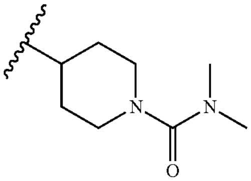 , 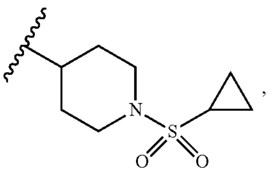 , -continued
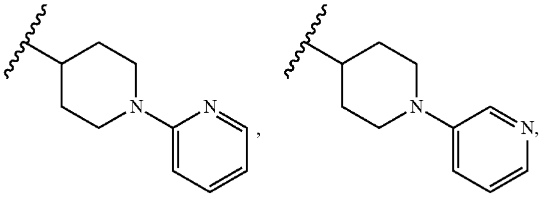
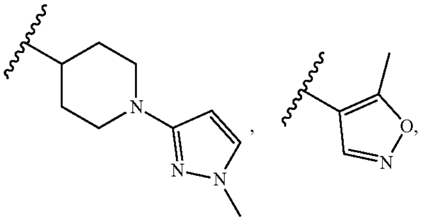
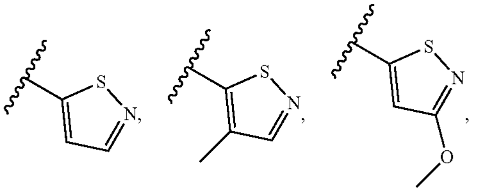
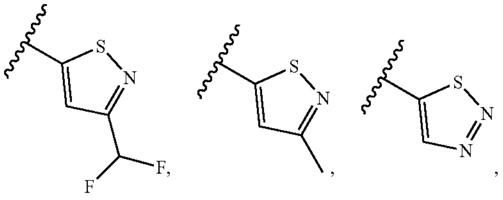
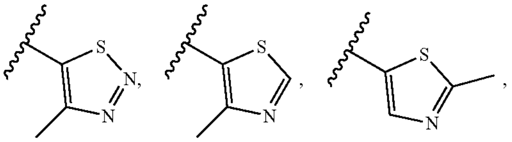
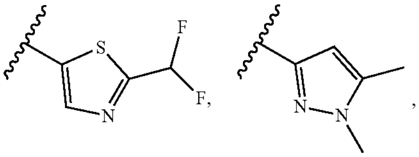
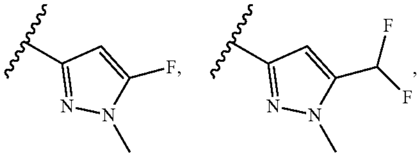
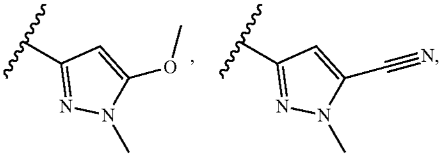
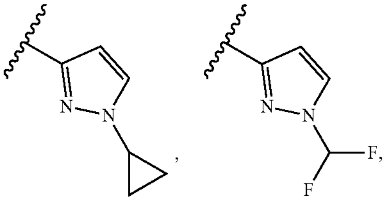
-continued
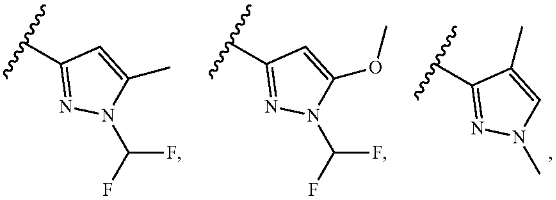
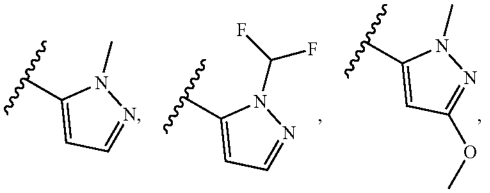
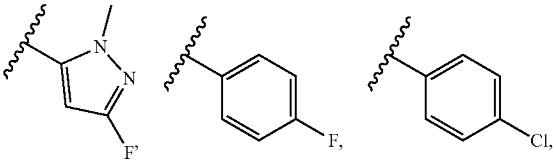
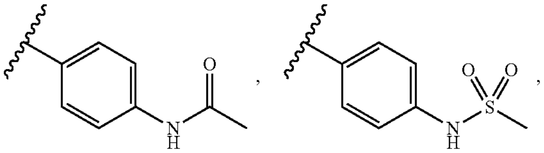
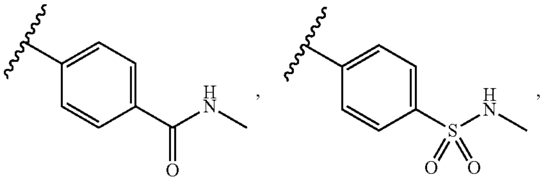
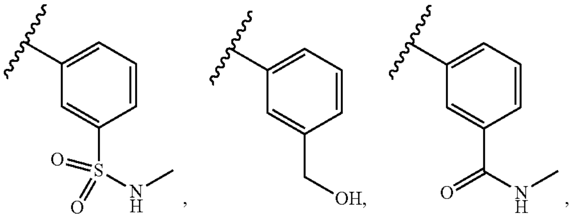
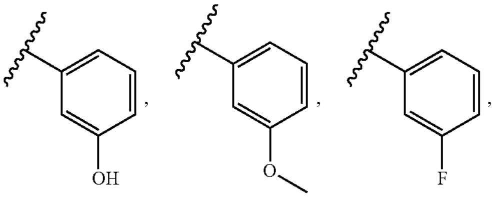
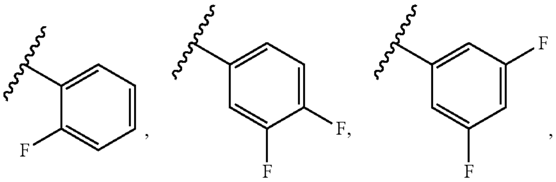
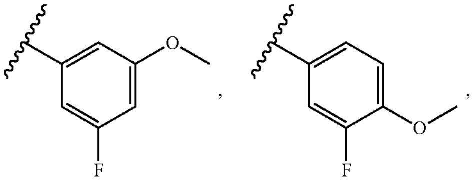

-continued
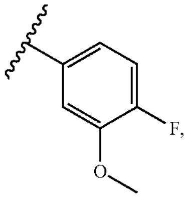 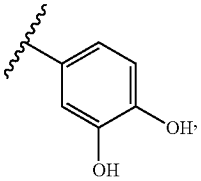
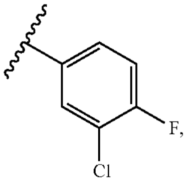 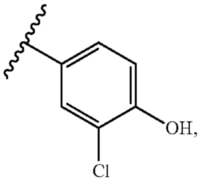
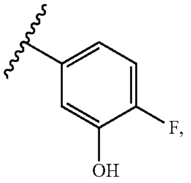 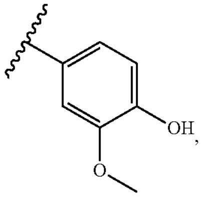
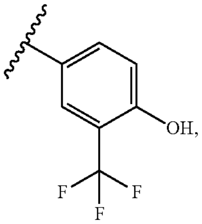 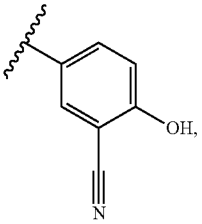
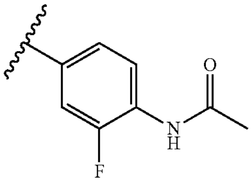 , 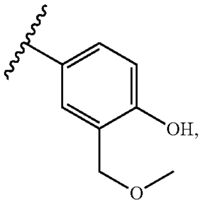
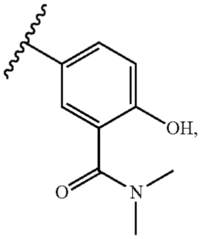 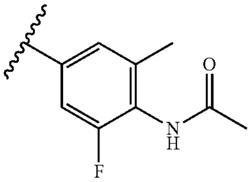 ,
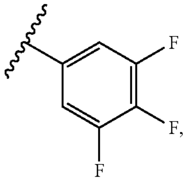 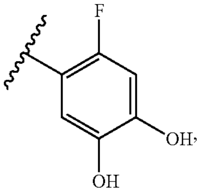
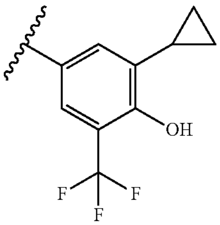 , 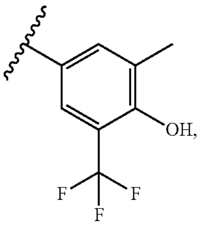
-continued
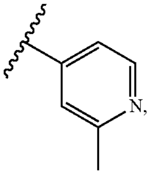 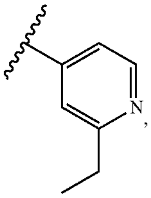 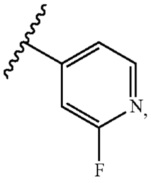
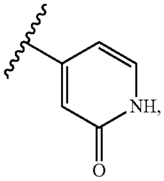 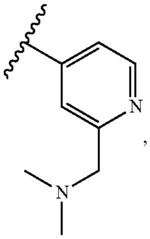 , 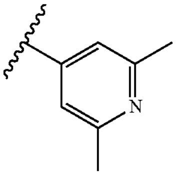 ,
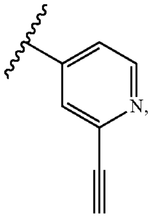 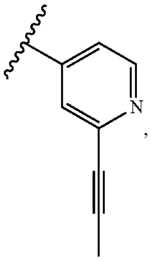 , 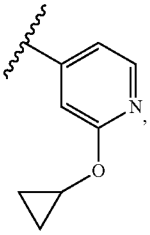
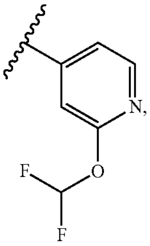 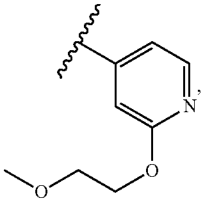 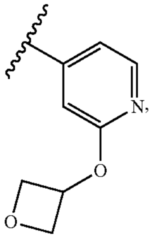
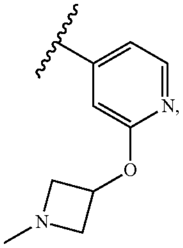 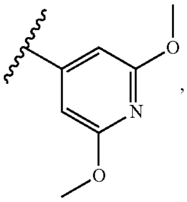 ,
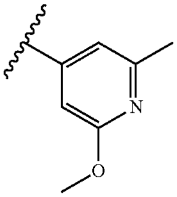 , 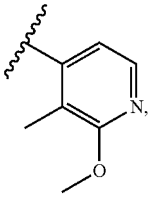
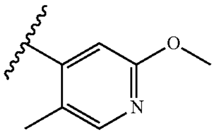 , 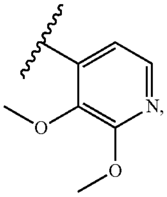

-continued
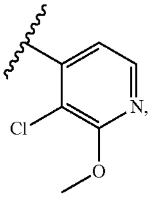 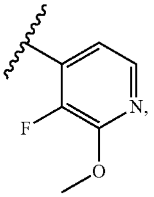 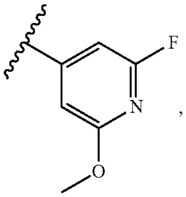 ,
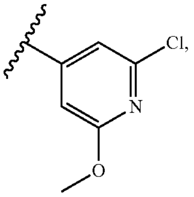 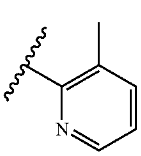 ,
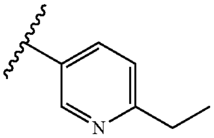 , 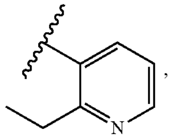 ,
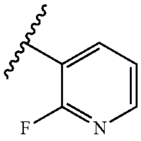 , 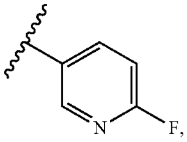 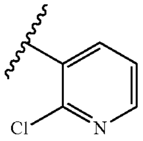 ,
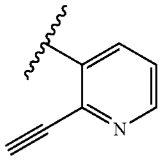 , 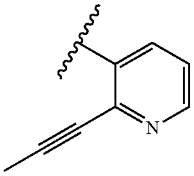 ,
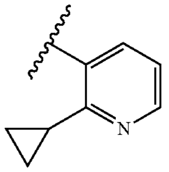 , 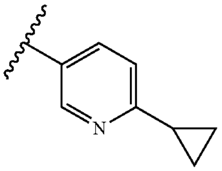 ,
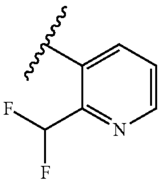 , 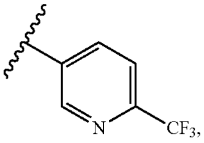 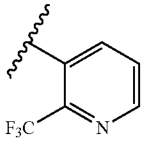 ,
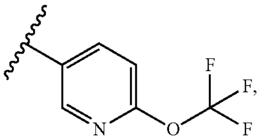 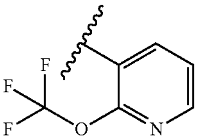 ,
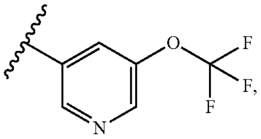 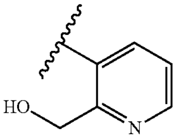 ,
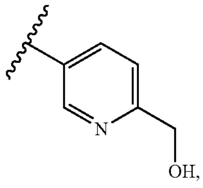 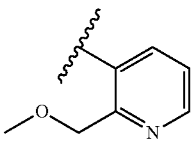 ,
-continued
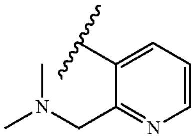 , 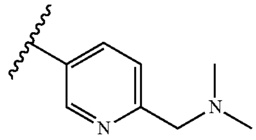 ,
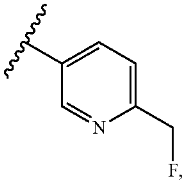 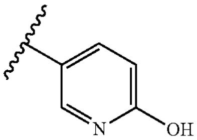 ,
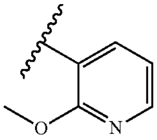 , 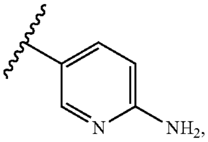
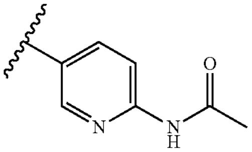 , 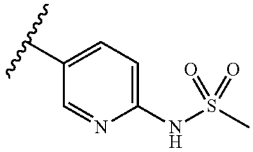 ,
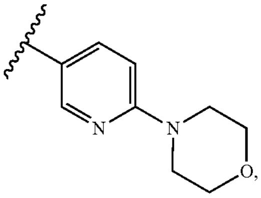 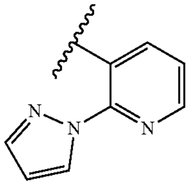 ,
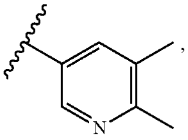 , 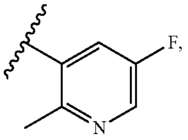
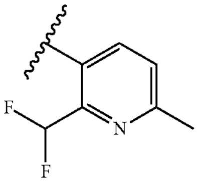 , 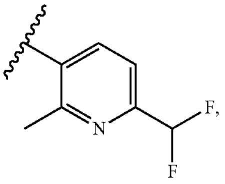
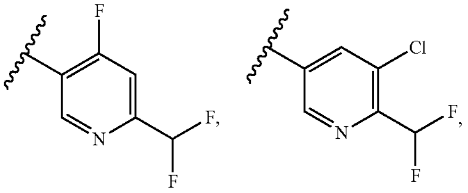
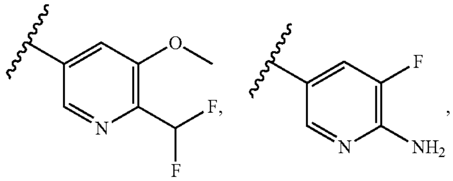 ,
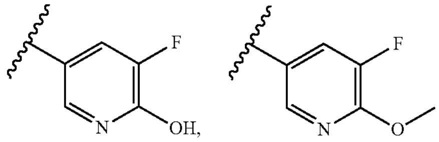 , -continued
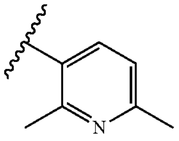, 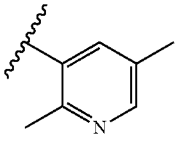,
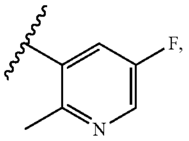 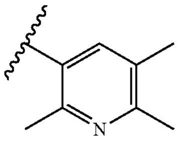,
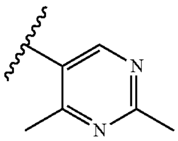, 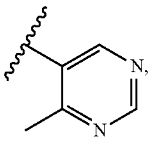 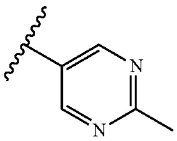,
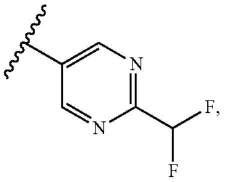 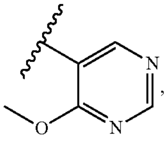
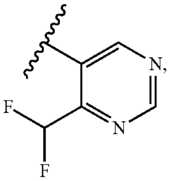 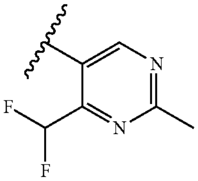,
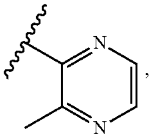 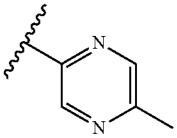, 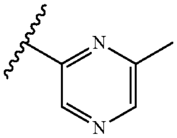,
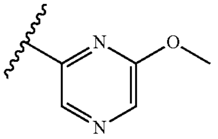, 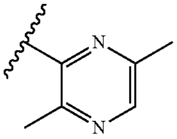,
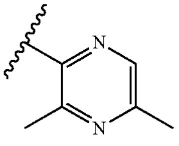, 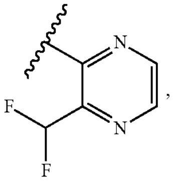
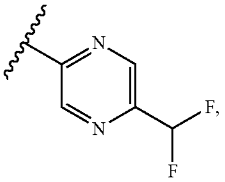 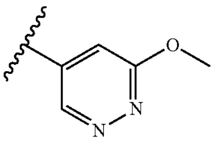,
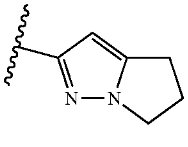, 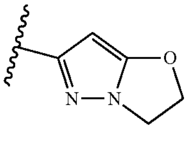,
-continued
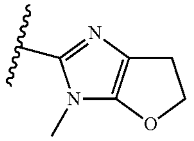, 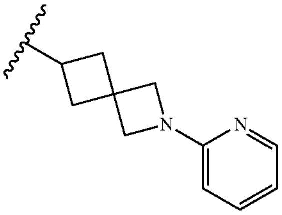,
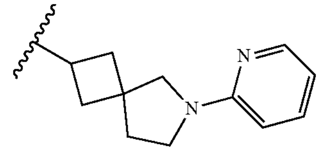, 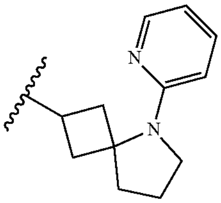,
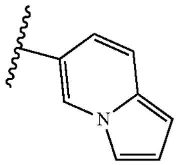, 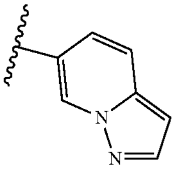,
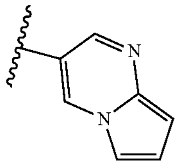, 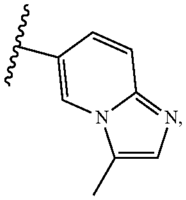
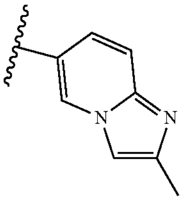 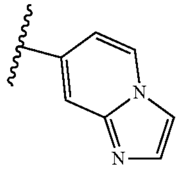,
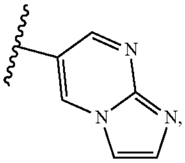 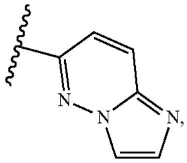
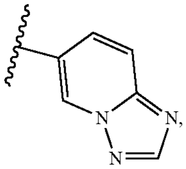 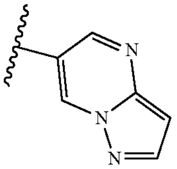,
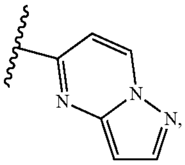 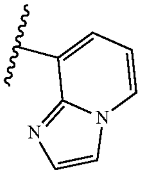, 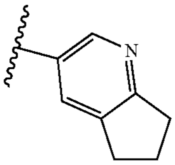,
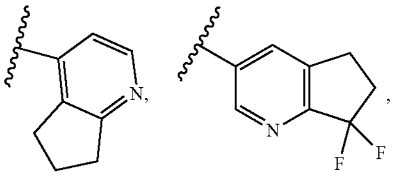

-continued

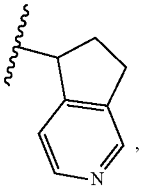,
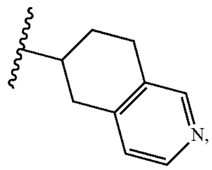
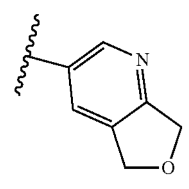,
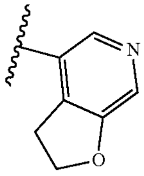,
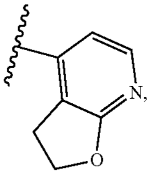
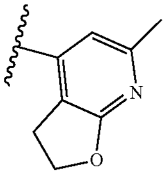,
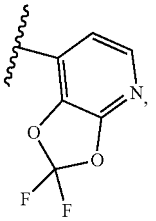
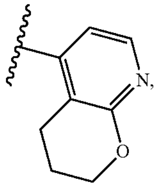
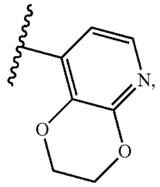
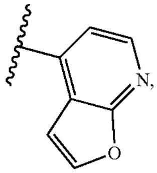
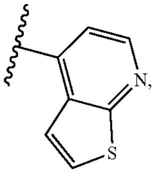
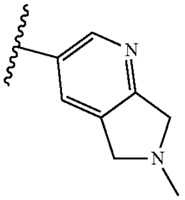,
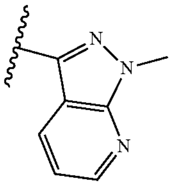,
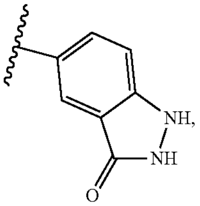
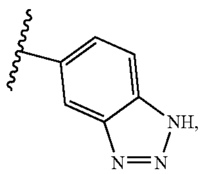
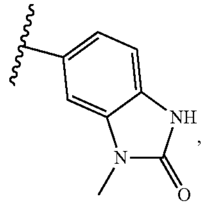,
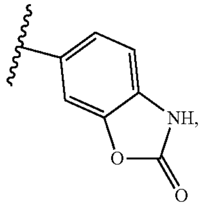
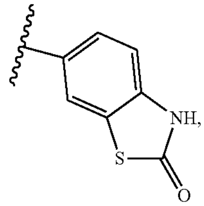
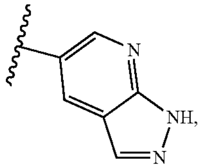
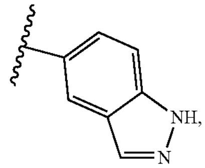

-continued

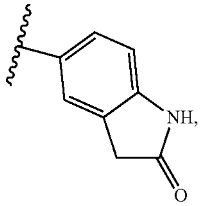
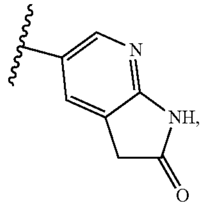
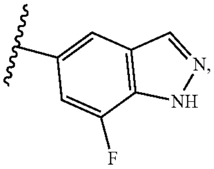
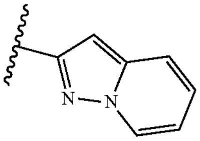,
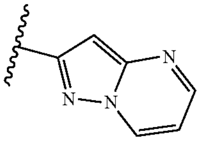,
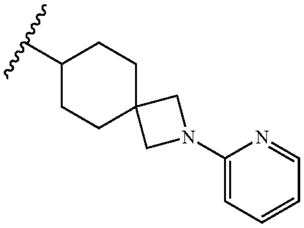,
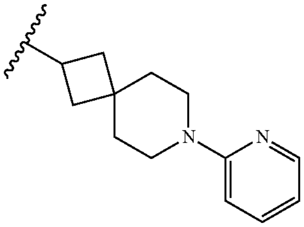, and
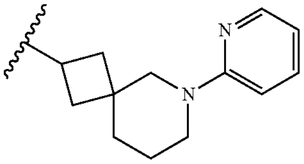.

In some embodiments, for the compound or salt of Formula (I), (II), (II-A), (III), (III-A), (III-B), (IV), (IV-A), (IV-B), (V), (V-A), (V-B), (VI), (VI-A), or (VI-B), $R^{10}$, $R^{11}$, $R^{12}$, $R^{13}$, $R^{14}$, and $R^{11}$ are each independently selected at each occurrence from: hydrogen, $C_{1-4}$ alkyl, $C_{3-6}$ carbocycle, 4- to 6-membered heterocycle, and $C_{1-4}$ haloalkyl. In some embodiments, $R^{10}$, $R^{11}$, $R^{12}$, $R^{13}$, $R^{14}$, and $R^{11}$ are each independently selected at each occurrence from: hydrogen, $C_{1-4}$ alkyl, and $C_{1-4}$ haloalkyl.

In some embodiments, for the compound or salt of Formula (I), (II), (II-A), (III), (III-A), (III-B), (IV), (IV-A), (IV-B), (V), (V-A), (V-B), (VI), (VI-A), or (VI-B), $R^{16}$ is independently selected at each occurrence from (iv), (v), and (vi):

(iv) hydrogen;

(v) $C_{1-4}$ alkyl, wherein the $C_{1-4}$ alkyl is optionally substituted with one or more substituents independently selected from:

halogen, $—OR^{20}$, $—SR^{20}$, $—N(R^{20})_2$, $—C(O)R^{20}$, $—C(O)OR^{20}$, $—OC(O)R^{20}$, $—C(O)N(R^{20})_2$, $—N(R^{20})C(O)R^{20}$, $—N(R^{20})C(O)N(R^{20})_2$, $—N(R^{20})C(O)OR^{20}$, $OC(O)N(R^{20})_2$, $—S(O)R^{20}$, $—S(O)_2R^{20}$, $—N(R^{20})S(O)_2R^{20}$, $—S(O)_2N(R^{20})_2$, $—NO_2$, and —CN; and $C_{3-8}$ carbocycle and 4- to 8-membered heterocycle, either of which is optionally substituted with one or more substituents independently selected from: halogen, $C_{1-4}$ alkyl, $C_{1-4}$ haloalkyl, —$OR^{20}$, —$SR^{20}$, —$N(R^{20})_2$, —$C(O)R^{20}$, —$C(O)OR^{20}$, —$OC(O)R^{20}$, —$C(O)N(R^{20})_2$, —$N(R^{20})C(O)R^{20}$, —$N(R^{20})C(O)N(R^{20})_2$, —$N(R^{20})C(O)OR^{20}$, —$OC(O)N(R^{20})_2$, —$S(O)R^{20}$, —$S(O)_2R^{20}$, —$N(R^{20})S(O)_2R^{20}$, —$S(O)_2N(R^{20})_2$, —$NO_2$, and —CN; and (vi) $C_{3-8}$ carbocycle and 4- to 8-membered heterocycle, either of which is optionally substituted with one or more substituents independently selected from halogen, $C_{1-4}$ alkyl, $C_{1-4}$ haloalkyl, —$OR^{20}$, —$SR^{20}$, —$N(R^{20})_2$, —$C(O)R^{20}$, —$C(O)N(R^{20})_2$, —$C(O)OR^{20}$, —$OC(O)R^{20}$, —$N(R^{20})C(O)R^{20}$, —$N(R^{20})S(O)_2R^{20}$, —$N(R^{20})C(O)N(R^{20})_2$, —$N(R^{20})C(O)OR^{20}$, —$OC(O)N(R^{20})_2$, —$S(O)R^{20}$, —$S(O)_2R^{20}$, —$NO_2$, and —CN.

In some embodiments, for the compound or salt of Formula (I), (II), (II-A), (III), (III-A), (III-B), (IV), (IV-A), (IV-B), (V), (V-A), (V-B), (VI), (VI-A), or (VI-B), $R^{16}$ is independently selected at each occurrence from hydrogen; and $C_{3-8}$ carbocycle and 4- to 8-membered heterocycle, either of which is optionally substituted with one or more substituents independently selected from halogen, $C_{1-4}$ alkyl, $C_{1-4}$ haloalkyl, —$OR^{20}$, —$SR^{20}$, —$N(R^{20})_2$, —$C(O)R^{20}$, —$C(O)N(R^{20})_2$, —$C(O)OR^{20}$, —$OC(O)R^{20}$, —$N(R^{20})C(O)R^{20}$, —$N(R^{20})S(O)_2R^{20}$, —$N(R^{20})C(O)N(R^{20})_2$, —$N(R^{20})C(O)OR^{20}$, —$OC(O)N(R^{20})_2$, —$S(O)R^{20}$, —$S(O)_2R^{20}$, —$NO_2$, and —CN.

In some embodiments, for the compound or salt of Formula (I), (II), (II-A), (III), (III-A), (III-B), (IV), (IV-A), (IV-B), (V), (V-A), (V-B), (VI), (VI-A), or (VI-B), $R^{16}$ is independently selected at each occurrence from (iv) and (v):

(iv) hydrogen; and (v) $C_{1-4}$ alkyl, wherein the $C_{1-4}$ alkyl is optionally substituted with one or more substituents independently selected from:

halogen, —$OR^{20}$, —$SR^{20}$, —$N(R^{20})_2$, —$C(O)R^{20}$, —$C(O)OR^{20}$, —$OC(O)R^{20}$, —$C(O)N(R^{20})_2$, —$N(R^{20})C(O)R^{20}$, —$N(R^{20})C(O)N(R^{20})_2$, —$N(R^{20})C(O)OR^{20}$, —$OC(O)N(R^{20})_2$, —$S(O)R^{20}$, —$S(O)_2R^{20}$, —$N(R^{20})S(O)_2R^{20}$, —$S(O)_2N(R^{20})_2$, —$NO_2$, and —CN; and $C_{3-8}$ carbocycle and 4- to 8-membered heterocycle, either of which is optionally substituted with one or more substituents independently selected from:

halogen, $C_{1-4}$ alkyl, $C_{1-4}$ haloalkyl, —$OR^{20}$, —$SR^{20}$, —$N(R^{20})_2$, —$C(O)R^{20}$, —$C(O)OR^{20}$, —$OC(O)R^{20}$, —$C(O)N(R^{20})_2$, —$N(R^{20})C(O)R^{20}$, —$N(R^{20})C(O)N(R^{20})_2$, —$N(R^{20})C(O)OR^{20}$, —$OC(O)N(R^{20})_2$, —$S(O)R^{20}$, —$S(O)_2R^{20}$, —$N(R^{20})S(O)_2R^{20}$, —$S(O)_2N(R^{20})_2$, —$NO_2$, and —CN.

In some embodiments, for the compound or salt of Formula (I), (II), (I1-A), (III), (I11-A), (III-B), (IV), (IV-A), (IV-B), (V), (V-A), (V-B), (VI), (VI-A), or (VI-B), $R^{16}$ is independently selected at each occurrence from hydrogen; and $C_{1-4}$ alkyl, wherein the $C_{1-4}$ alkyl is optionally substituted with one or more substituents independently selected from: halogen, —$OR^{20}$, —$SR^{20}$, —$N(R^{20})_2$, —$C(O)R^{20}$, —$C(O)OR^{20}$, —$OC(O)R^{20}$, —$C(O)N(R^{20})_2$, —$N(R^{20})C(O)R^{20}$, —$N(R^{20})C(O)N(R^{20})_2$, —$N(R^{20})C(O)OR^{20}$, —$OC(O)N(R^{20})_2$, —$S(O)R^{20}$, —$S(O)_2R^{20}$, —$N(R^{20})S(O)_2R^{20}$, —$S(O)_2N(R^{20})_2$, —$NO_2$, and —CN. In some embodiments, $R^{16}$ is independently selected at each occurrence from hydrogen and $C_{1-4}$ alkyl, wherein the $C_{1-4}$ alkyl is optionally substituted with one or more substituents independently selected from halogen. In some embodiments, $R^{16}$ is independently selected at each occurrence from hydrogen and $C_{1-4}$ alkyl, wherein the $C_{1-4}$ alkyl is optionally substituted with one or more substituents independently selected from fluoro. In some embodiments, $R^{16}$ is independently selected at each occurrence from hydrogen and methyl, wherein the methyl is optionally substituted with one or more substituents independently selected from halogen. In some embodiments, $R^{16}$ is independently selected at each occurrence from hydrogen and methyl, wherein the methyl is optionally substituted with one or more substituents independently selected from fluoro. In some embodiments, $R^{16}$ is independently selected at each occurrence from hydrogen. In some embodiments, $R^{16}$ is independently selected at each occurrence from $C_{1-4}$ alkyl. In some embodiments, $R^{16}$ is independently selected at each occurrence from methyl. In some embodiments, $R^{16}$ is independently selected at each occurrence from $C_{1-4}$ alkyl optionally substituted with one or more substituents independently selected at each occurrence from halogen. In some embodiments, $R^{16}$ is independently selected at each occurrence from $C_{1-4}$ alkyl optionally substituted with one or more substituents independently selected at each occurrence from fluoro. In some embodiments, $R^{16}$ is independently selected at each occurrence from methyl optionally substituted with one or more substituents independently selected at each occurrence from fluoro. In some embodiments, $R^{16}$ is independently selected at each occurrence from trifluoromethyl. In some embodiments, $R^{16}$ is independently selected at each occurrence from hydrogen, methyl, and trifluoromethyl.

In some embodiments, for the compound or salt of Formula (I), (II), (II-A), (III), (III-A), (III-B), (IV), (IV-A), (IV-B), (V), (V-A), (V-B), (VI), (VI-A), or (VI-B), $R^{20}$ is independently selected at each occurrence from hydrogen, $C_{1-4}$ alkyl, $C_{1-4}$ haloalkyl, $C_{3-6}$ carbocycle, and 4- to 6-membered heterocycle. In some embodiments, $R^{20}$ is independently selected at each occurrence from hydrogen, $C_{1-4}$ alkyl, and $C_{1-4}$ haloalkyl.

In some embodiments, the compound or salt of Formula (I) or Formula (II) is a compound of Table 1.

TABLE 1
| Chemical structures of selected compounds. | |
|---|---|
| Cpd ID | Structure |
| 1 | 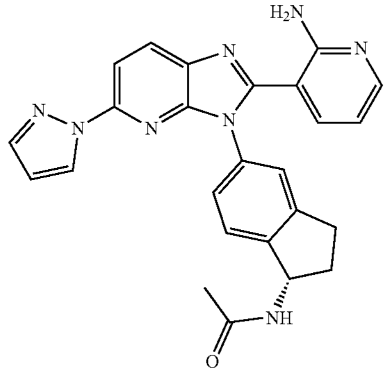 [SMILES: CC(=O)N[C@H]1CCc2cc(-n3c(-c4cccnc4N)nc4ccc(-n5cccn5)nc43)ccc21] |
| 2 | 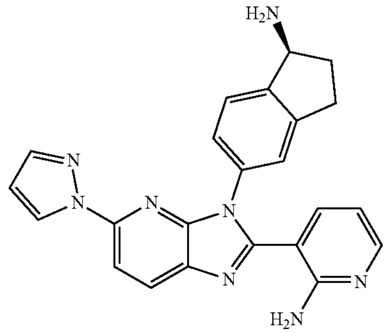 [SMILES: Nc1ncccc1-c1nc2ccc(-n3cccn3)nc2n1-c1ccc2c(c1)CC[C@@H]2N] |
| 3 | 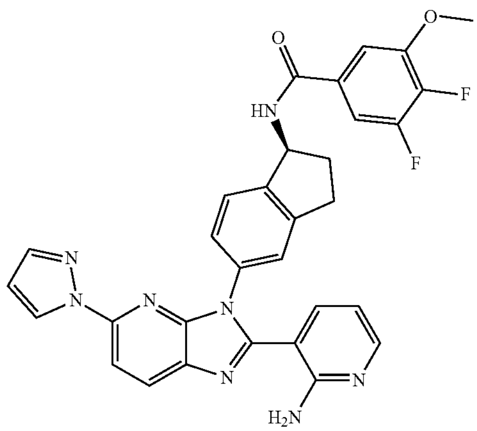 [SMILES: COc1cc(C(=O)N[C@H]2CCc3cc(-n4c(-c5cccnc5N)nc5ccc(-n6cccn6)nc54)ccc32)cc(F)c1F] |
| 4 | 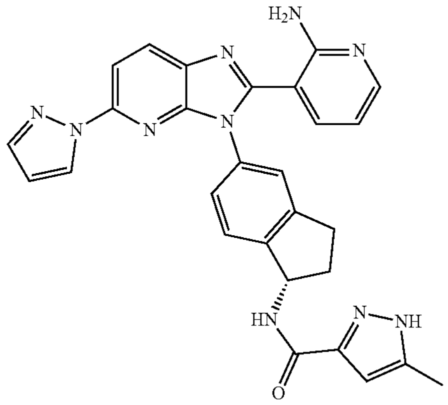 [SMILES: Cc1cc(C(=O)N[C@H]2CCc3cc(-n4c(-c5cccnc5N)nc5ccc(-n6cccn6)nc54)ccc32)n[nH]1] |

TABLE 1-continued
| Chemical structures of selected compounds. | |
|---|---|
| Cpd ID | Structure |
| 5 | 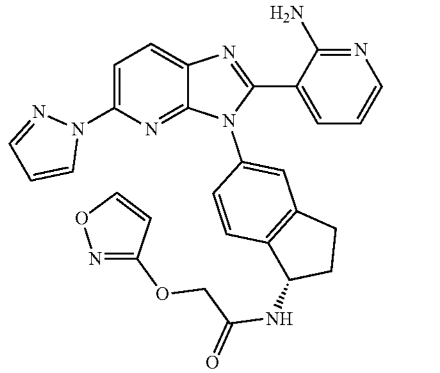 [SMILES: Nc1ncccc1-c1nc2ccc(-n3cccn3)nc2n1-c1ccc2c(c1)CC[C@@H]2NC(=O)COc1ccon1] |
| 6 | 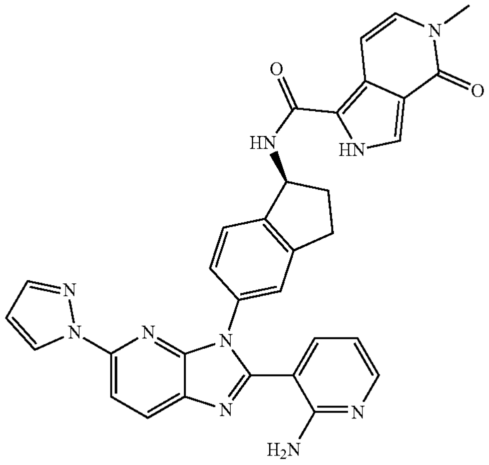 [SMILES: Cn1ccc2c(C(=O)N[C@H]3CCc4cc(-n5c(-c6cccnc6N)nc6ccc(-n7cccn7)nc65)ccc43)[nH]cc2c1=O] |
| 7 | 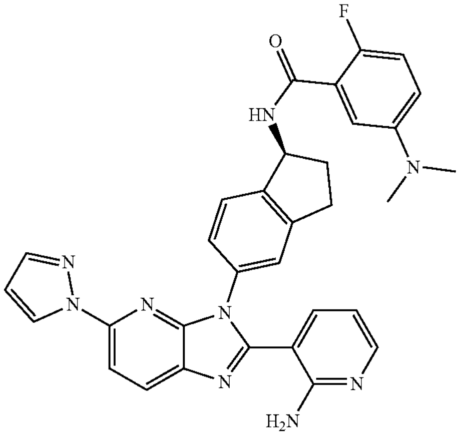 [SMILES: CN(C)c1ccc(F)c(C(=O)N[C@H]2CCc3cc(-n4c(-c5cccnc5N)nc5ccc(-n6cccn6)nc54)ccc32)c1] |

TABLE 1-continued
| Chemical structures of selected compounds. | |
|---|---|
| Cpd ID | Structure |
| 8 | 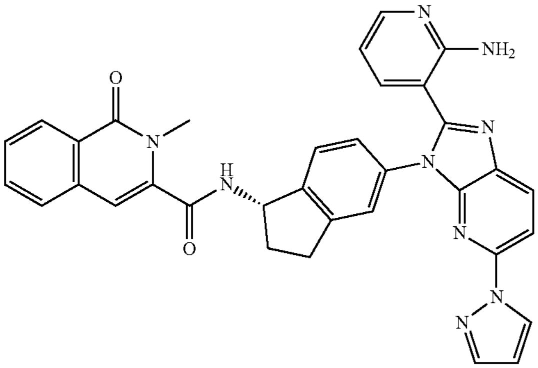 [SMILES: Cn1c(C(=O)N[C@H]2CCc3cc(-n4c(-c5cccnc5N)nc5ccc(-n6cccn6)nc54)ccc32)cc2ccccc2c1=O] |
| 9 | 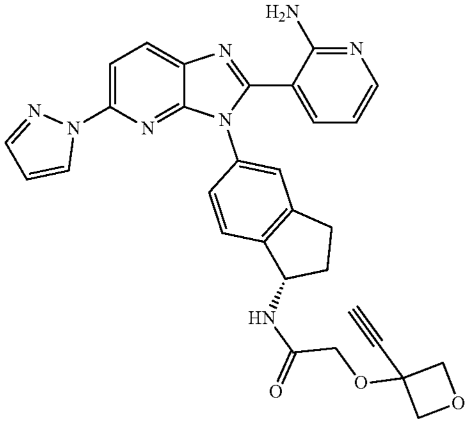 [SMILES: C#CC1(OCC(=O)N[C@H]2CCc3cc(-n4c(-c5cccnc5N)nc5ccc(-n6cccn6)nc54)ccc32)COC1] |
| 10 | 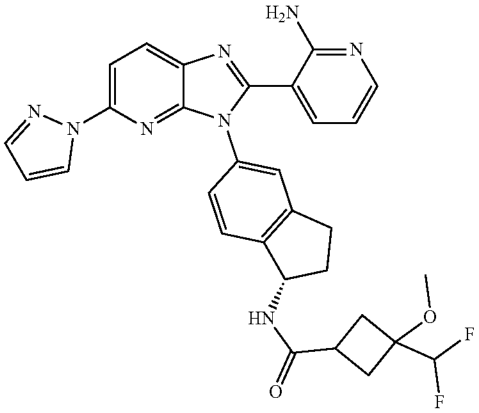 [SMILES: COC1(C(F)F)CC(C(=O)N[C@H]2CCc3cc(-n4c(-c5cccnc5N)nc5ccc(-n6cccn6)nc54)ccc32)C1] |

TABLE 1-continued
| Chemical structures of selected compounds. | |
|---|---|
| Cpd ID | Structure |
| 11 | 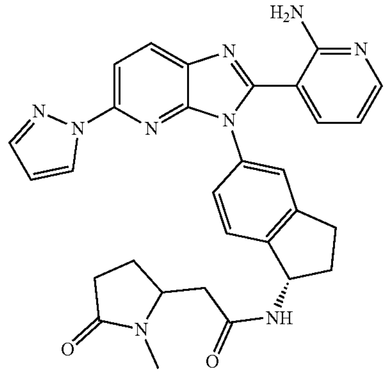 [SMILES: CN1C(=O)CCC1CC(=O)N[C@H]1CCc2cc(-n3c(-c4cccnc4N)nc4ccc(-n5cccn5)nc43)ccc21] |
| 12 | 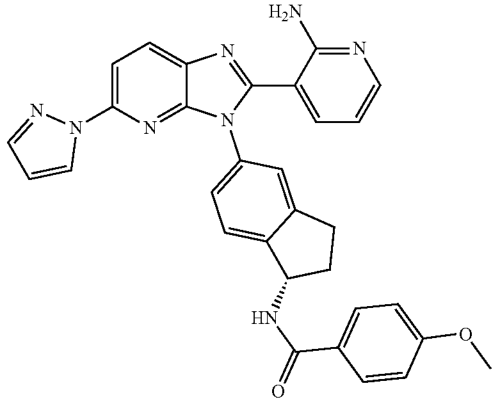 [SMILES: COc1ccc(C(=O)N[C@H]2CCc3cc(-n4c(-c5cccnc5N)nc5ccc(-n6cccn6)nc54)ccc32)cc1] |
| 13 | 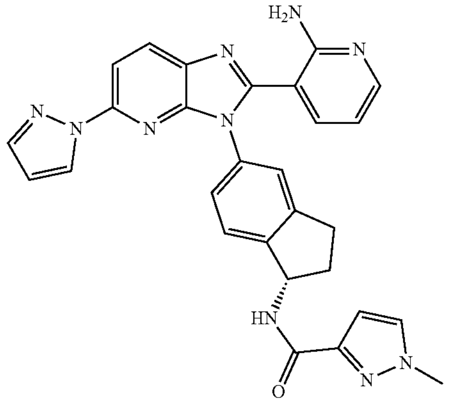 [SMILES: Cn1ccc(C(=O)N[C@H]2CCc3cc(-n4c(-c5cccnc5N)nc5ccc(-n6cccn6)nc54)ccc32)n1] |

TABLE 1-continued
| Chemical structures of selected compounds. | |
|---|---|
| Cpd ID | Structure |
| 14 | 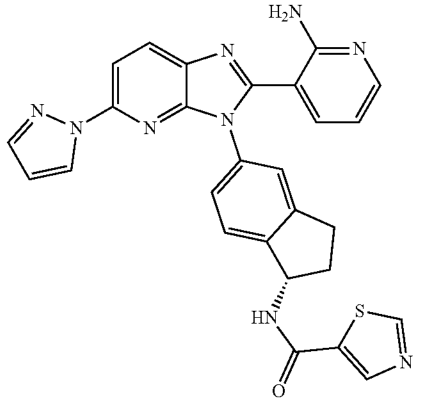 [SMILES: Nc1ncccc1-c1nc2ccc(-n3cccn3)nc2n1-c1ccc2c(c1)CC[C@@H]2NC(=O)c1cncs1] |
| 15 | 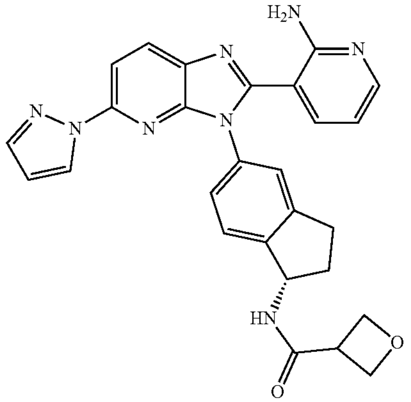 [SMILES: Nc1ncccc1-c1nc2ccc(-n3cccn3)nc2n1-c1ccc2c(c1)CC[C@@H]2NC(=O)C1COC1] |
| 16 | 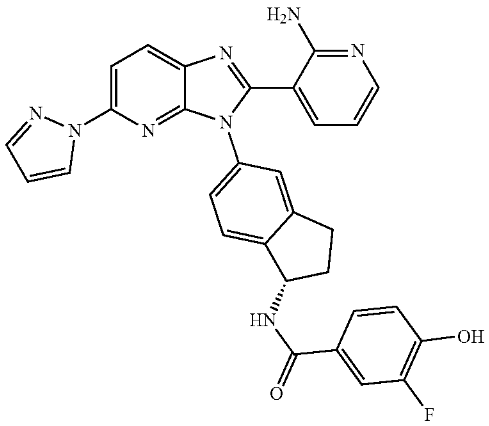 [SMILES: Nc1ncccc1-c1nc2ccc(-n3cccn3)nc2n1-c1ccc2c(c1)CC[C@@H]2NC(=O)c1ccc(O)c(F)c1] |

TABLE 1-continued
| Chemical structures of selected compounds. | |
|---|---|
| Cpd ID | Structure |
| 17 | 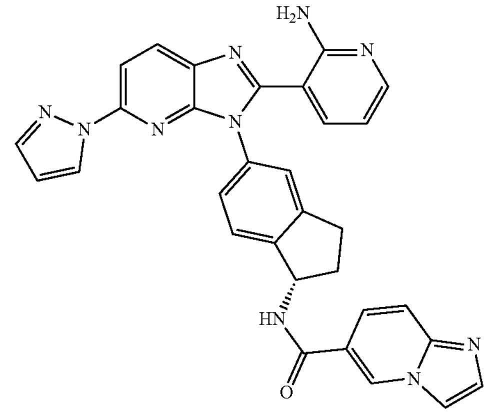 [SMILES: Nc1ncccc1-c1nc2ccc(-n3cccn3)nc2n1-c1ccc2c(c1)CC[C@@H]2NC(=O)c1ccc2nccn2c1] |
| 18 | 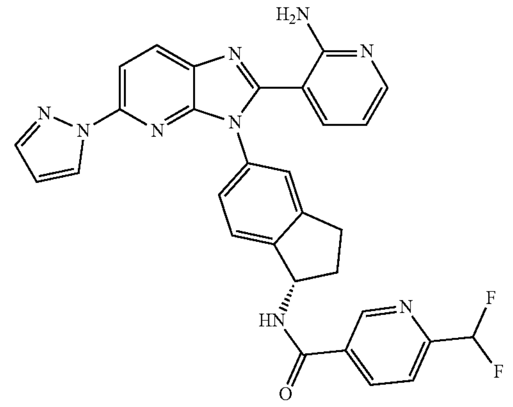 [SMILES: Nc1ncccc1-c1nc2ccc(-n3cccn3)nc2n1-c1ccc2c(c1)CC[C@@H]2NC(=O)c1ccc(C(F)F)nc1] |
| 19 | 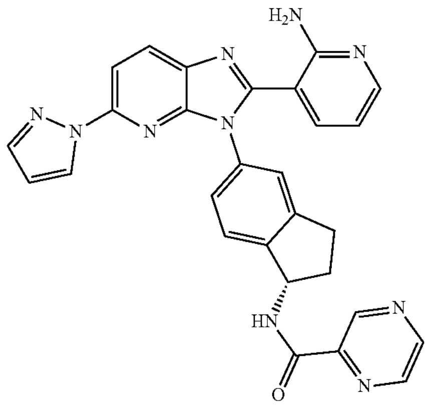 [SMILES: Nc1ncccc1-c1nc2ccc(-n3cccn3)nc2n1-c1ccc2c(c1)CC[C@@H]2NC(=O)c1cnccn1] |

TABLE 1-continued
| Chemical structures of selected compounds. | |
|---|---|
| Cpd ID | Structure |
| 20 | 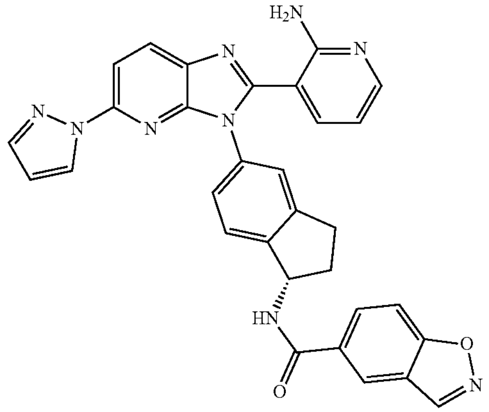 [SMILES: Nc1ncccc1-c1nc2ccc(-n3cccn3)nc2n1-c1ccc2c(c1)CC[C@@H]2NC(=O)c1ccc2oncc2c1] |
| 21 | 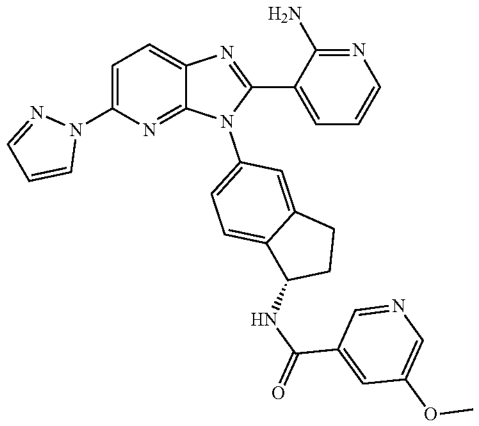 [SMILES: COc1cncc(C(=O)N[C@H]2CCc3cc(-n4c(-c5cccnc5N)nc5ccc(-n6cccn6)nc54)ccc32)c1] |
| 22 | 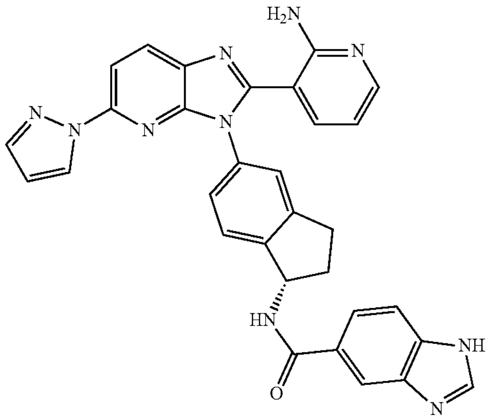 [SMILES: Nc1ncccc1-c1nc2ccc(-n3cccn3)nc2n1-c1ccc2c(c1)CC[C@@H]2NC(=O)c1ccc2[nH]cnc2c1] |

TABLE 1-continued
| Chemical structures of selected compounds. | |
|---|---|
| Cpd ID | Structure |
| 23 | 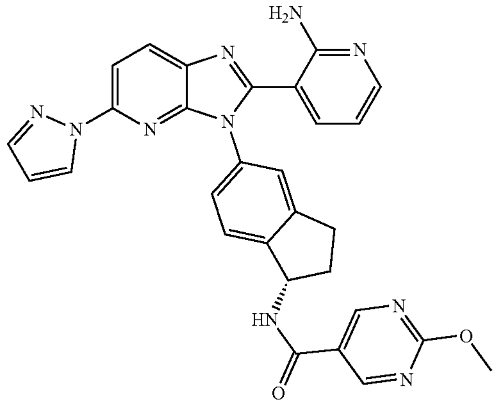 [SMILES: COc1ncc(C(=O)N[C@H]2CCc3cc(-n4c(-c5cccnc5N)nc5ccc(-n6cccn6)nc54)ccc32)cn1] |
| 24 | 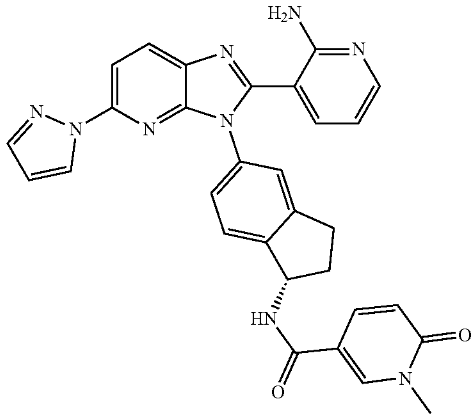 [SMILES: Cn1cc(C(=O)N[C@H]2CCc3cc(-n4c(-c5cccnc5N)nc5ccc(-n6cccn6)nc54)ccc32)ccc1=O] |
| 25 | 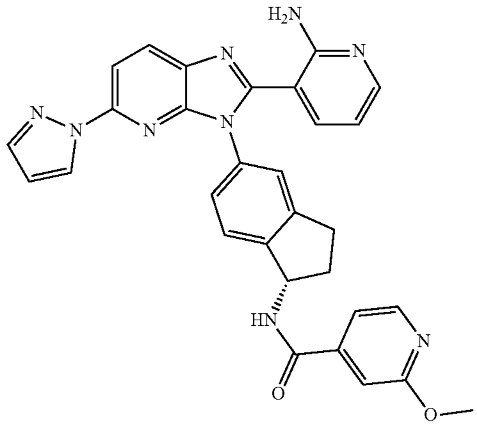 [SMILES: COc1cc(C(=O)N[C@H]2CCc3cc(-n4c(-c5cccnc5N)nc5ccc(-n6cccn6)nc54)ccc32)ccn1] |

TABLE 1-continued
| Chemical structures of selected compounds. | |
|---|---|
| Cpd ID | Structure |
| 26 | 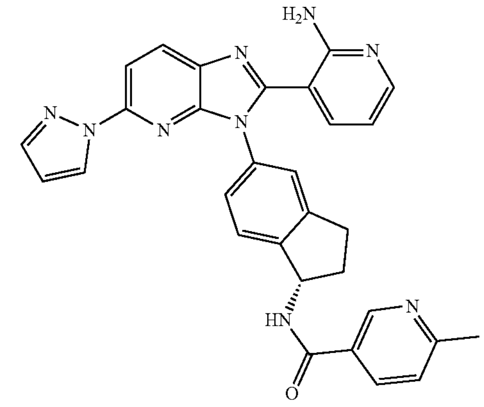 [SMILES: Cc1ccc(C(=O)N[C@H]2CCc3cc(-n4c(-c5cccnc5N)nc5ccc(-n6cccn6)nc54)ccc32)cn1] |
| 27 | 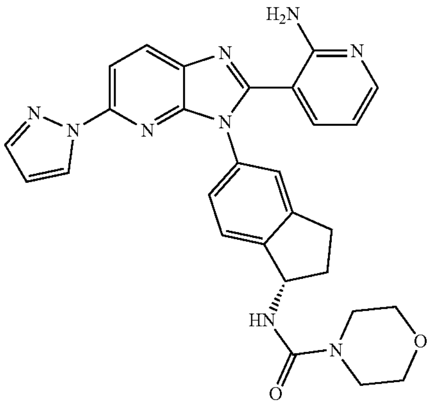 [SMILES: Nc1ncccc1-c1nc2ccc(-n3cccn3)nc2n1-c1ccc2c(c1)CC[C@@H]2NC(=O)N1CCOCC1] |
| 28 | 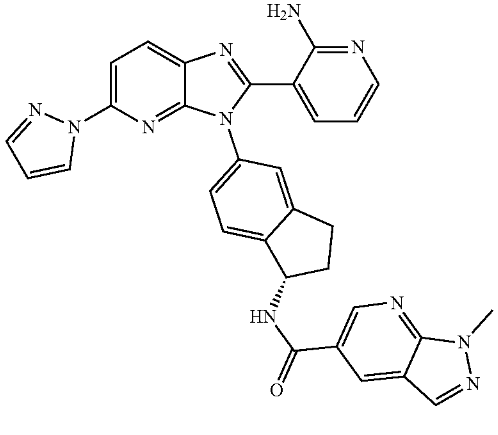 [SMILES: Cn1ncc2cc(C(=O)N[C@H]3CCc4cc(-n5c(-c6cccnc6N)nc6ccc(-n7cccn7)nc65)ccc43)cnc21] |

TABLE 1-continued
| Chemical structures of selected compounds. | |
|---|---|
| Cpd ID | Structure |
| 29 | 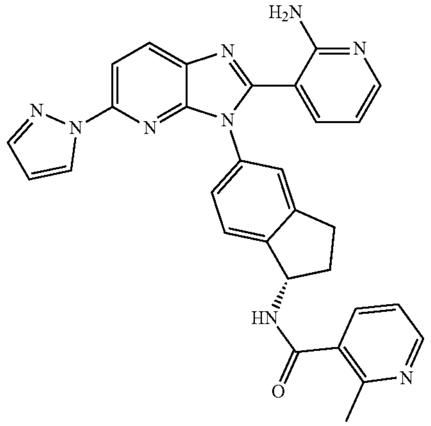 [SMILES: Cc1ncccc1C(=O)N[C@H]1CCc2cc(-n3c(-c4cccnc4N)nc4ccc(-n5cccn5)nc43)ccc21] |
| 30 | 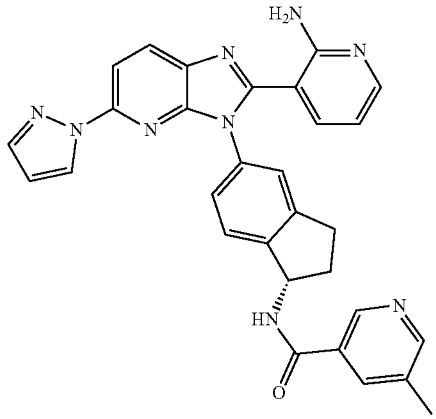 [SMILES: Cc1cncc(C(=O)N[C@H]2CCc3cc(-n4c(-c5cccnc5N)nc5ccc(-n6cccn6)nc54)ccc32)c1] |
| 31 | 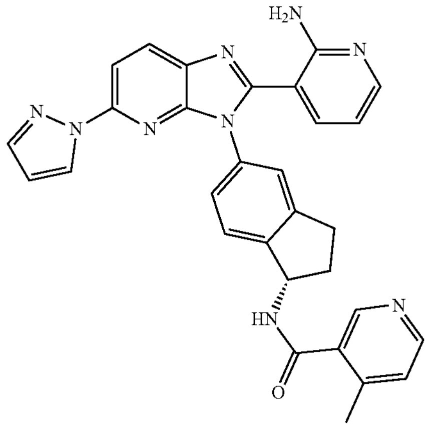 [SMILES: Cc1ccncc1C(=O)N[C@H]1CCc2cc(-n3c(-c4cccnc4N)nc4ccc(-n5cccn5)nc43)ccc21] |

TABLE 1-continued
| Chemical structures of selected compounds. | |
|---|---|
| Cpd ID | Structure |
| 32 | 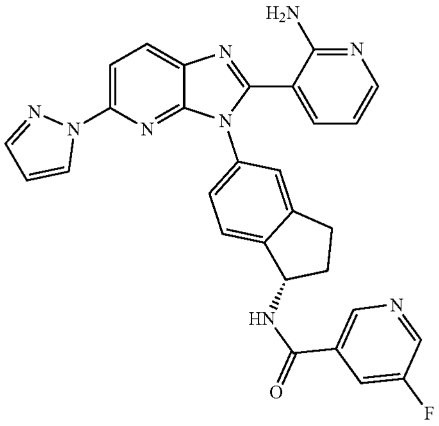 [SMILES: Nc1ncccc1-c1nc2ccc(-n3cccn3)nc2n1-c1ccc2c(c1)CC[C@@H]2NC(=O)c1cncc(F)c1] |
| 33 | 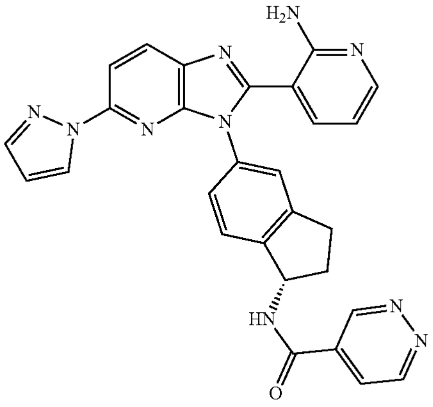 [SMILES: Nc1ncccc1-c1nc2ccc(-n3cccn3)nc2n1-c1ccc2c(c1)CC[C@@H]2NC(=O)c1ccnnc1] |
| 34 | 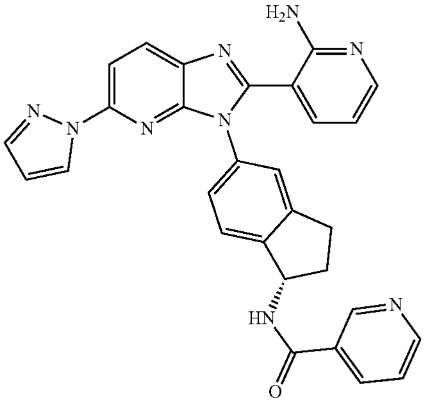 [SMILES: Nc1ncccc1-c1nc2ccc(-n3cccn3)nc2n1-c1ccc2c(c1)CC[C@@H]2NC(=O)c1cccnc1] |

TABLE 1-continued
| Chemical structures of selected compounds. | |
|---|---|
| Cpd ID | Structure |
| 35 | 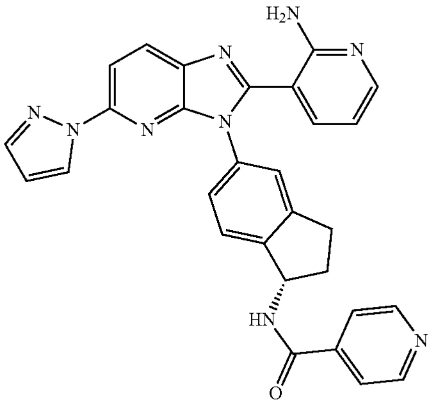 [SMILES: Nc1ncccc1-c1nc2ccc(-n3cccn3)nc2n1-c1ccc2c(c1)CC[C@@H]2NC(=O)c1ccncc1] |
| 36 | 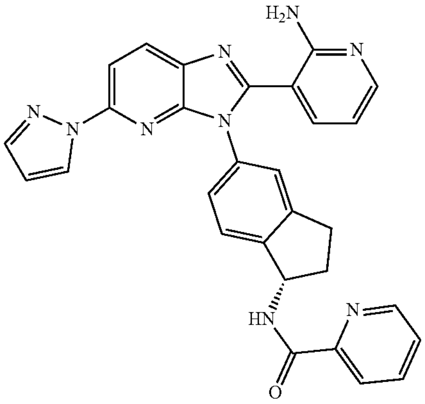 [SMILES: Nc1ncccc1-c1nc2ccc(-n3cccn3)nc2n1-c1ccc2c(c1)CC[C@@H]2NC(=O)c1ccccn1] |
| 37 | 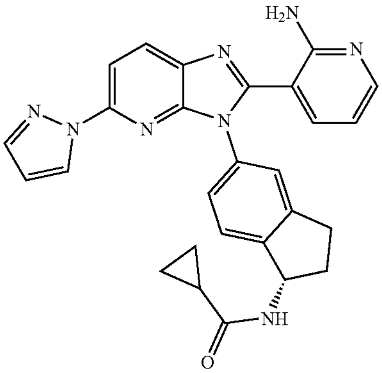 [SMILES: Nc1ncccc1-c1nc2ccc(-n3cccn3)nc2n1-c1ccc2c(c1)CC[C@@H]2NC(=O)C1CC1] |

TABLE 1-continued
| Chemical structures of selected compounds. | |
|---|---|
| Cpd ID | Structure |
| 38 | 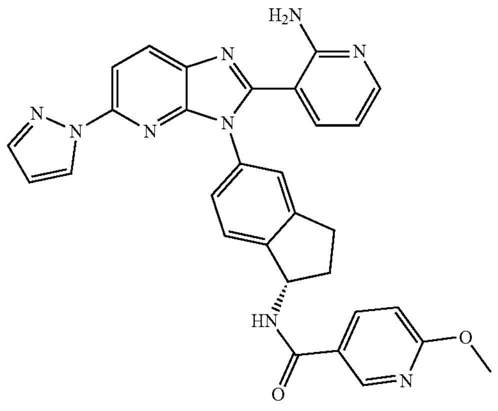 [SMILES: COc1ccc(C(=O)N[C@H]2CCc3cc(-n4c(-c5cccnc5N)nc5ccc(-n6cccn6)nc54)ccc32)cn1] |
| 39 | 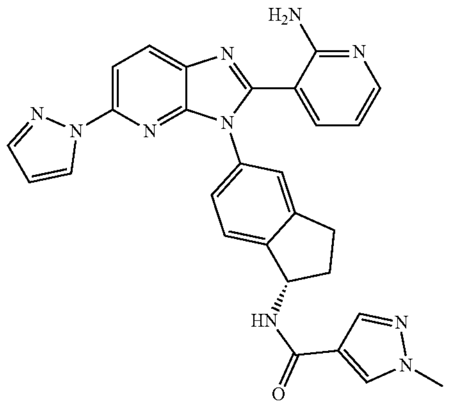 [SMILES: Cn1cc(C(=O)N[C@H]2CCc3cc(-n4c(-c5cccnc5N)nc5ccc(-n6cccn6)nc54)ccc32)cn1] |
| 40 | 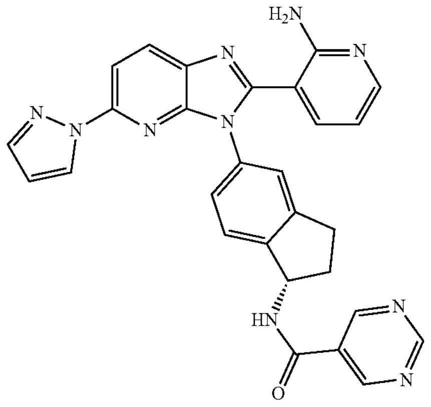 [SMILES: Nc1ncccc1-c1nc2ccc(-n3cccn3)nc2n1-c1ccc2c(c1)CC[C@@H]2NC(=O)c1cncnc1] |

TABLE 1-continued
| Cpd ID | Structure |
|---|---|
| | Chemical structures of selected compounds. |
| 41 | 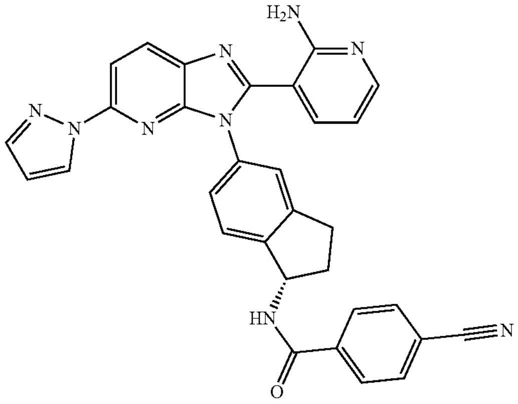 [SMILES: N#Cc1ccc(C(=O)N[C@H]2CCc3cc(-n4c(-c5cccnc5N)nc5ccc(-n6cccn6)nc54)ccc32)cc1] |
| 42 | 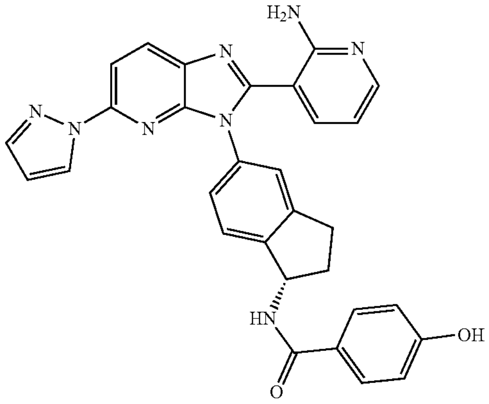 |
| 43 | 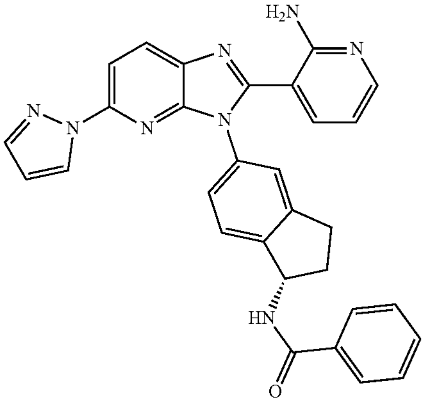 [SMILES: Nc1ncccc1-c1nc2ccc(-n3cccn3)nc2n1-c1ccc2c(c1)CC[C@@H]2NC(=O)c1ccccc1] |

TABLE 1-continued
| Cpd ID | Structure |
| --- | --- |
| | Chemical structures of selected compounds. |
| 44 | 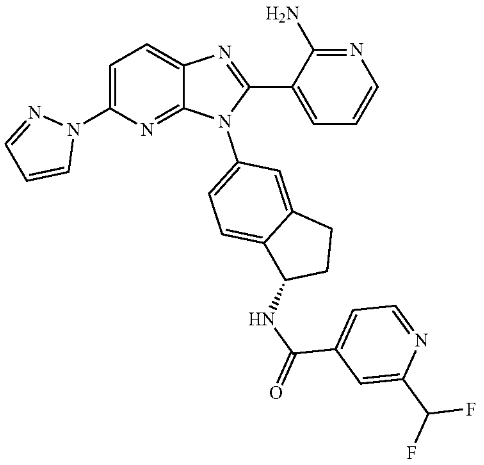 [SMILES: Nc1ncccc1-c1nc2ccc(-n3cccn3)nc2n1-c1ccc2c(c1)CC[C@@H]2NC(=O)c1ccnc(C(F)F)c1] |
| 45 | 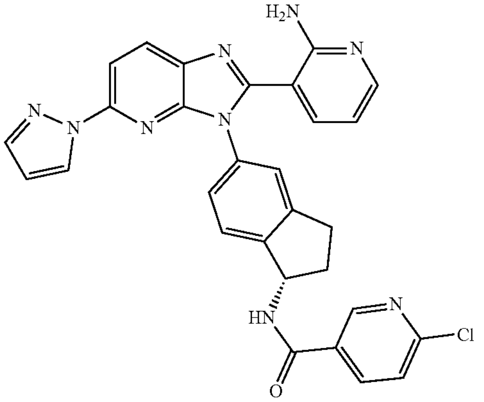 [SMILES: Nc1ncccc1-c1nc2ccc(-n3cccn3)nc2n1-c1ccc2c(c1)CC[C@@H]2NC(=O)c1ccc(Cl)nc1] |
| 46 | 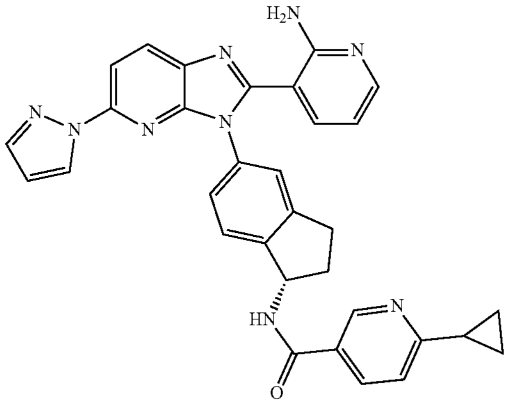 [SMILES: Nc1ncccc1-c1nc2ccc(-n3cccn3)nc2n1-c1ccc2c(c1)CC[C@@H]2NC(=O)c1ccc(C2CC2)nc1] |

TABLE 1-continued
| Chemical structures of selected compounds. | |
|---|---|
| Cpd ID | Structure |
| 47 | 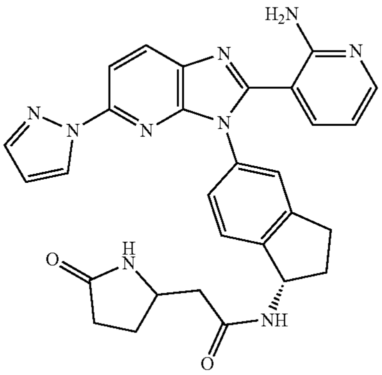 [SMILES: Nc1ncccc1-c1nc2ccc(-n3cccn3)nc2n1-c1ccc2c(c1)CC[C@@H]2NC(=O)CC1CCC(=O)N1] |
| 48 | 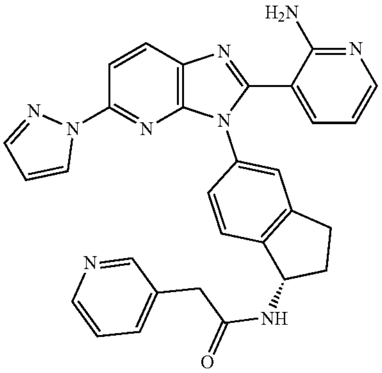 [SMILES: Nc1ncccc1-c1nc2ccc(-n3cccn3)nc2n1-c1ccc2c(c1)CC[C@@H]2NC(=O)Cc1cccnc1] |
| 49 | 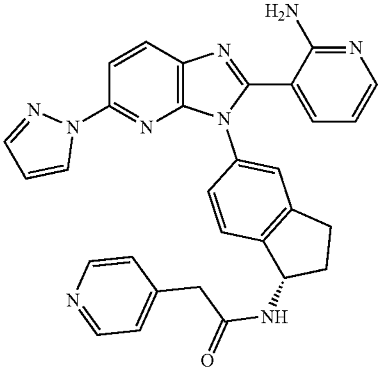 [SMILES: Nc1ncccc1-c1nc2ccc(-n3cccn3)nc2n1-c1ccc2c(c1)CC[C@@H]2NC(=O)Cc1ccncc1] |
| 50 | 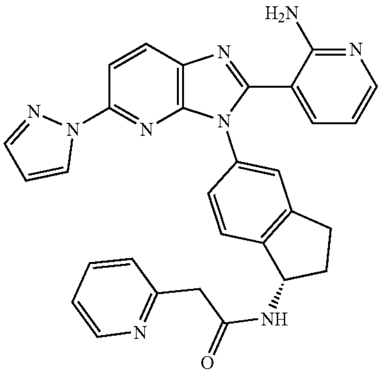 [SMILES: Nc1ncccc1-c1nc2ccc(-n3cccn3)nc2n1-c1ccc2c(c1)CC[C@@H]2NC(=O)Cc1ccccn1] |

TABLE 1-continued
| Chemical structures of selected compounds. | |
|---|---|
| Cpd ID | Structure |
| 51 | 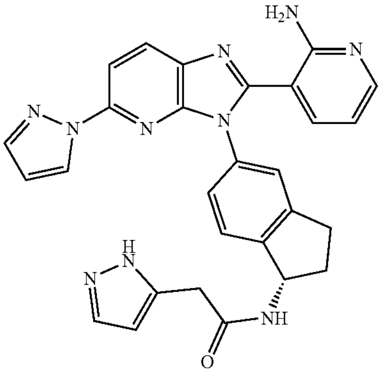 [SMILES: Nc1ncccc1-c1nc2ccc(-n3cccn3)nc2n1-c1ccc2c(c1)CC[C@@H]2NC(=O)Cc1ccn[nH]1] |
| 52 | 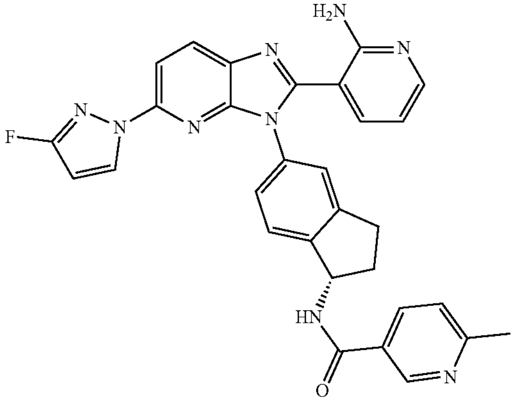 [SMILES: Cc1ccc(C(=O)N[C@H]2CCc3cc(-n4c(-c5cccnc5N)nc5ccc(-n6ccc(F)n6)nc54)ccc32)cn1] |
| 53 | 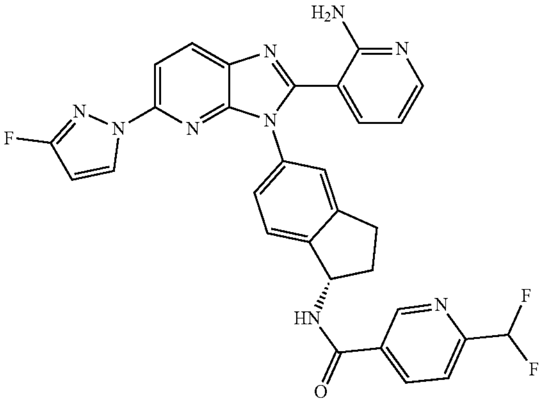 [SMILES: Nc1ncccc1-c1nc2ccc(-n3ccc(F)n3)nc2n1-c1ccc2c(c1)CC[C@@H]2NC(=O)c1ccc(C(F)F)nc1] |

TABLE 1-continued
| Chemical structures of selected compounds. | |
|---|---|
| Cpd ID | Structure |
| 54 | 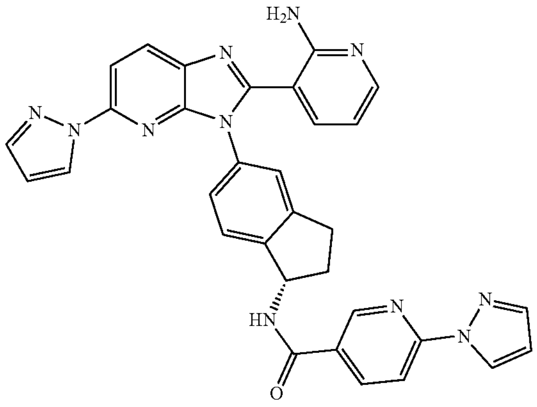 [SMILES: Nc1ncccc1-c1nc2ccc(-n3cccn3)nc2n1-c1ccc2c(c1)CC[C@@H]2NC(=O)c1ccc(-n2cccn2)nc1] |
| 55 | 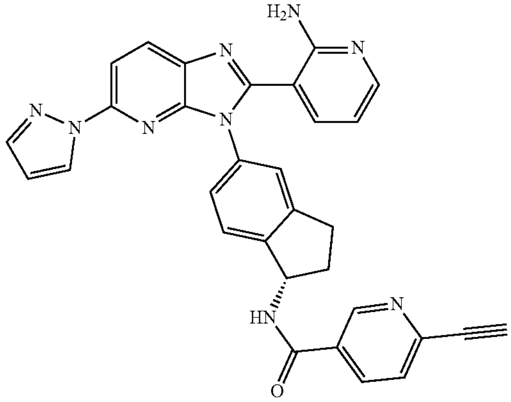 [SMILES: C#Cc1ccc(C(=O)N[C@H]2CCc3cc(-n4c(-c5cccnc5N)nc5ccc(-n6cccn6)nc54)ccc32)cn1] |
| 56 | 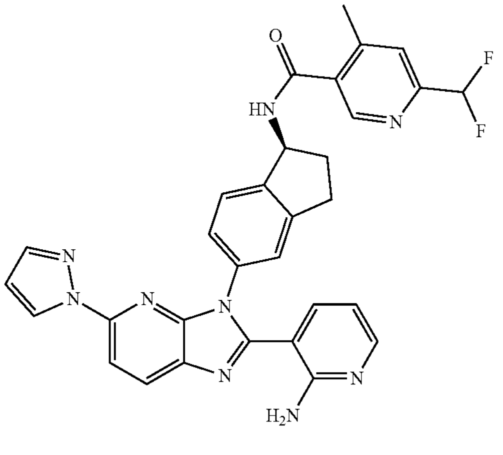 [SMILES: Cc1cc(C(F)F)ncc1C(=O)N[C@H]1CCc2cc(-n3c(-c4cccnc4N)nc4ccc(-n5cccn5)nc43)ccc21] |

TABLE 1-continued
| Chemical structures of selected compounds. | |
|---|---|
| Cpd ID | Structure |
| 57 | 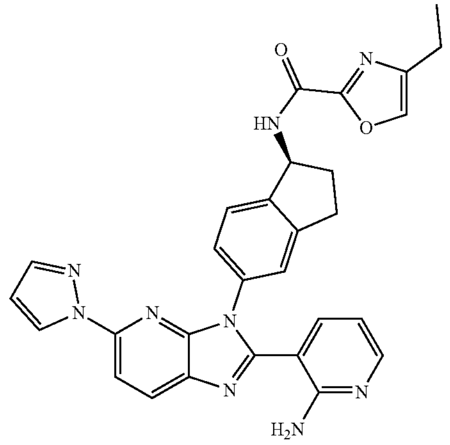 [SMILES: CCc1coc(C(=O)N[C@H]2CCc3cc(-n4c(-c5cccnc5N)nc5ccc(-n6cccn6)nc54)ccc32)n1] |
| 58 | 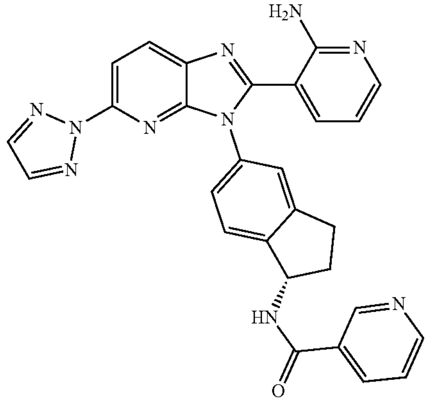 [SMILES: Nc1ncccc1-c1nc2ccc(-n3nccn3)nc2n1-c1ccc2c(c1)CC[C@@H]2NC(=O)c1cccnc1] |
| 59 | 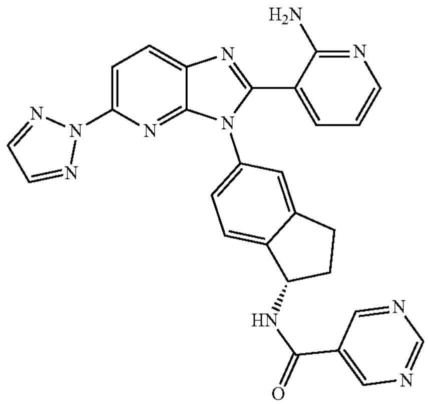 [SMILES: Nc1ncccc1-c1nc2ccc(-n3nccn3)nc2n1-c1ccc2c(c1)CC[C@@H]2NC(=O)c1cncnc1] |

TABLE 1-continued
| Chemical structures of selected compounds. | |
|---|---|
| Cpd ID | Structure |
| 60 | 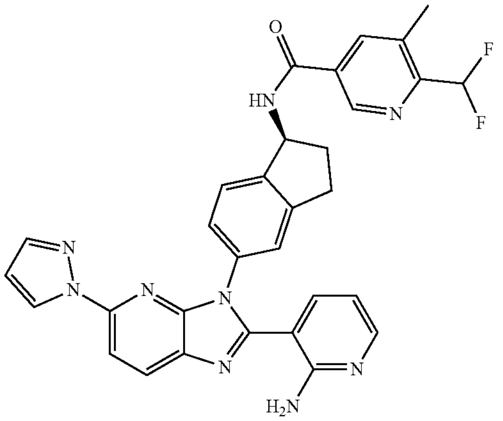 [SMILES: Cc1cc(C(=O)N[C@H]2CCc3cc(-n4c(-c5cccnc5N)nc5ccc(-n6cccn6)nc54)ccc32)cnc1C(F)F] |
| 61 | 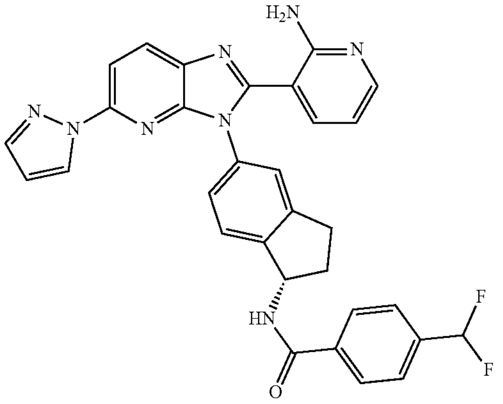 [SMILES: Nc1ncccc1-c1nc2ccc(-n3cccn3)nc2n1-c1ccc2c(c1)CC[C@@H]2NC(=O)c1ccc(C(F)F)cc1] |
| 62 | 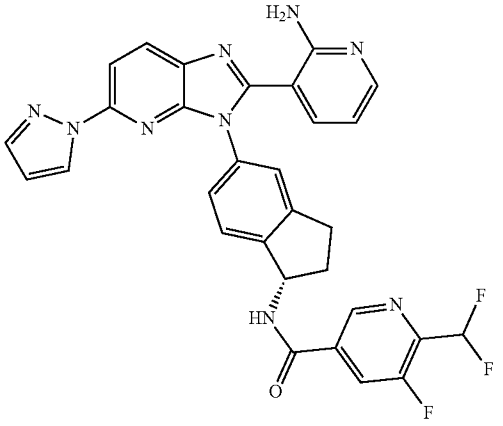 [SMILES: Nc1ncccc1-c1nc2ccc(-n3cccn3)nc2n1-c1ccc2c(c1)CC[C@@H]2NC(=O)c1cnc(C(F)F)c(F)c1] |

TABLE 1-continued
| Cpd ID | Structure |
| --- | --- |
| Chemical structures of selected compounds. | |
| 63 | 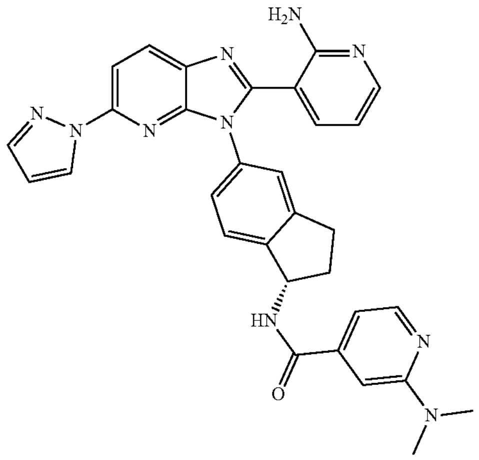 [SMILES: CN(C)c1cc(C(=O)N[C@H]2CCc3cc(-n4c(-c5cccnc5N)nc5ccc(-n6cccn6)nc54)ccc32)ccn1] |
| 64 | 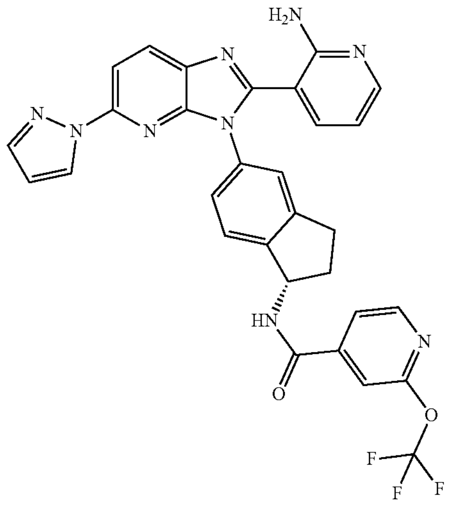 [SMILES: Nc1ncccc1-c1nc2ccc(-n3cccn3)nc2n1-c1ccc2c(c1)CC[C@@H]2NC(=O)c1ccnc(OC(F)(F)F)c1] |
| 65 | 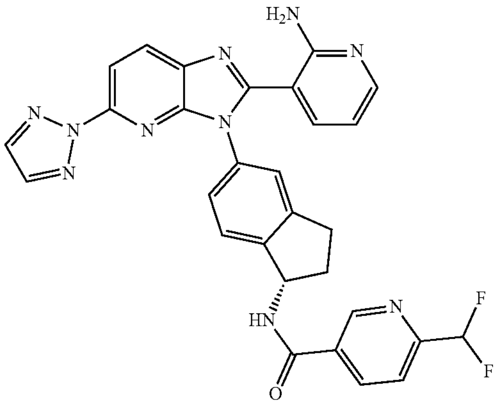 [SMILES: Nc1ncccc1-c1nc2ccc(-n3nccn3)nc2n1-c1ccc2c(c1)CC[C@@H]2NC(=O)c1ccc(C(F)F)nc1] |

TABLE 1-continued
| Chemical structures of selected compounds. | |
|---|---|
| Cpd ID | Structure |
| 66 | 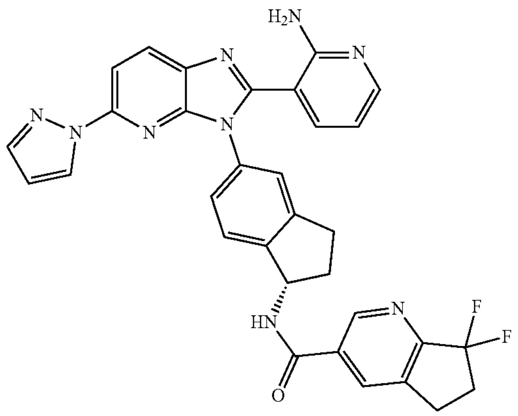 [SMILES: Nc1ncccc1-c1nc2ccc(-n3cccn3)nc2n1-c1ccc2c(c1)CC[C@@H]2NC(=O)c1cnc2c(c1)CCC2(F)F] |
| 67 | 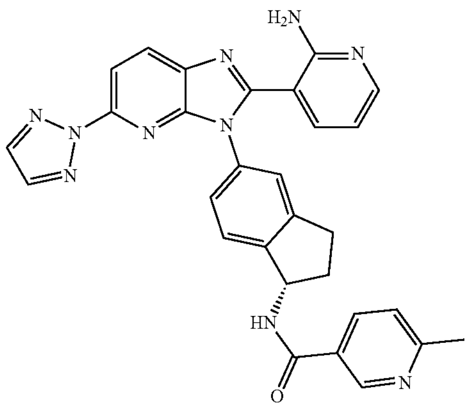 [SMILES: Cc1ccc(C(=O)N[C@H]2CCc3cc(-n4c(-c5cccnc5N)nc5ccc(-n6nccn6)nc54)ccc32)cn1] |
| 68 | 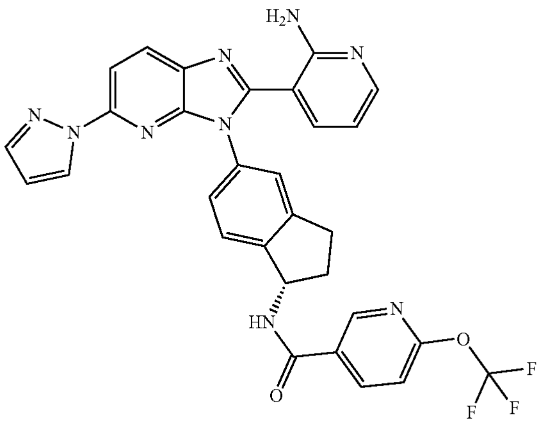 [SMILES: Nc1ncccc1-c1nc2ccc(-n3cccn3)nc2n1-c1ccc2c(c1)CC[C@@H]2NC(=O)c1ccc(OC(F)(F)F)nc1] |

TABLE 1-continued
| Cpd ID | Structure |
| --- | --- |
| Chemical structures of selected compounds. | |
| 69 | 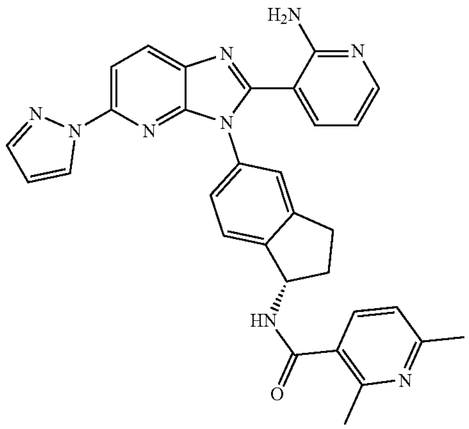 |
| 70 | 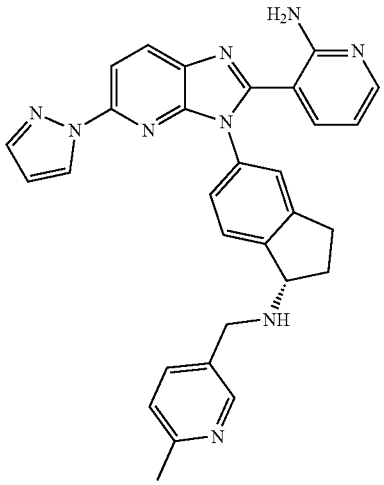 [SMILES: Cc1ccc(CN[C@H]2CCc3cc(-n4c(-c5cccnc5N)nc5ccc(-n6cccn6)nc54)ccc32)cn1] |
| 71 | 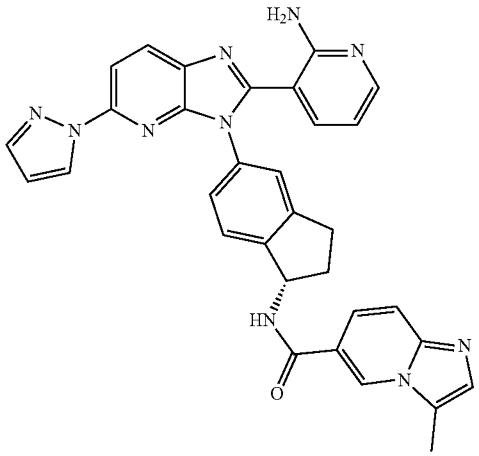 |

TABLE 1-continued
| Chemical structures of selected compounds. | |
|---|---|
| Cpd ID | Structure |
| 72 | 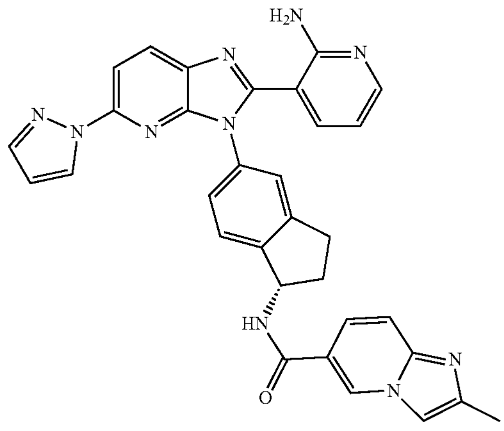 [SMILES: Cc1cn2cc(C(=O)N[C@H]3CCc4cc(-n5c(-c6cccnc6N)nc6ccc(-n7cccn7)nc65)ccc43)ccc2n1] |
| 73 | 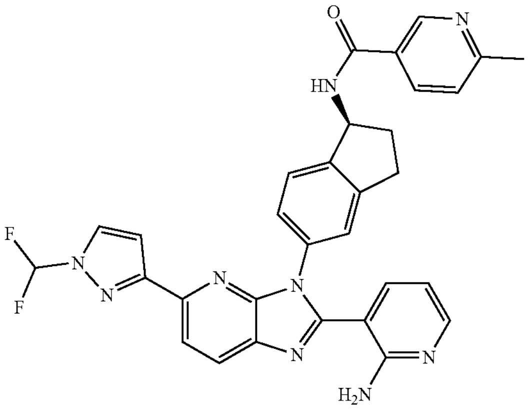 [SMILES: Cc1ccc(C(=O)N[C@H]2CCc3cc(-n4c(-c5cccnc5N)nc5ccc(-c6ccn(C(F)F)n6)nc54)ccc32)cn1] |
| 74 | 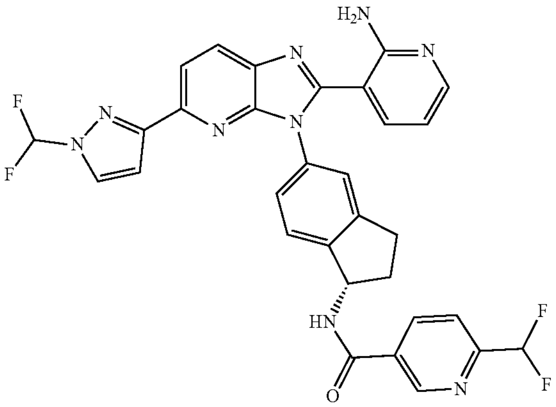 [SMILES: Nc1ncccc1-c1nc2ccc(-c3ccn(C(F)F)n3)nc2n1-c1ccc2c(c1)CC[C@@H]2NC(=O)c1ccc(C(F)F)nc1] |

TABLE 1-continued
| Chemical structures of selected compounds. | |
|---|---|
| Cpd ID | Structure |
| 75 | 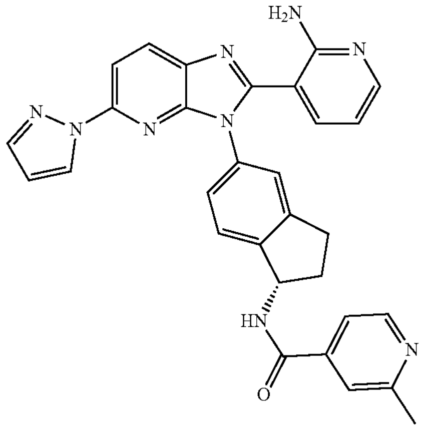 [SMILES: Cc1cc(C(=O)N[C@H]2CCc3cc(-n4c(-c5cccnc5N)nc5ccc(-n6cccn6)nc54)ccc32)ccn1] |
| 76 | 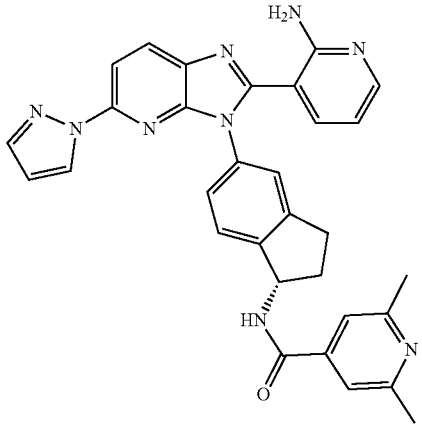 [SMILES: Cc1cc(C(=O)N[C@H]2CCc3cc(-n4c(-c5cccnc5N)nc5ccc(-n6cccn6)nc54)ccc32)cc(C)n1] |
| 77 | 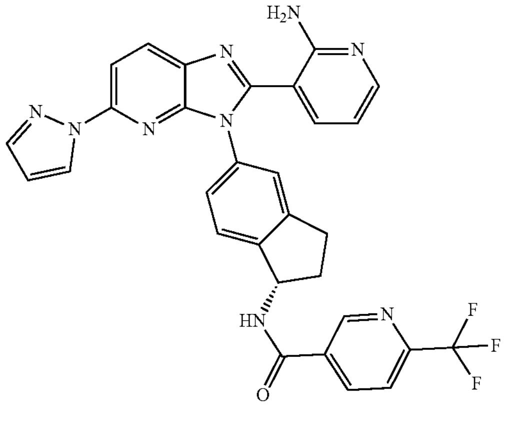 [SMILES: Nc1ncccc1-c1nc2ccc(-n3cccn3)nc2n1-c1ccc2c(c1)CC[C@@H]2NC(=O)c1ccc(C(F)(F)F)nc1] |

TABLE 1-continued
| Chemical structures of selected compounds. | |
|---|---|
| Cpd ID | Structure |
| 78 | 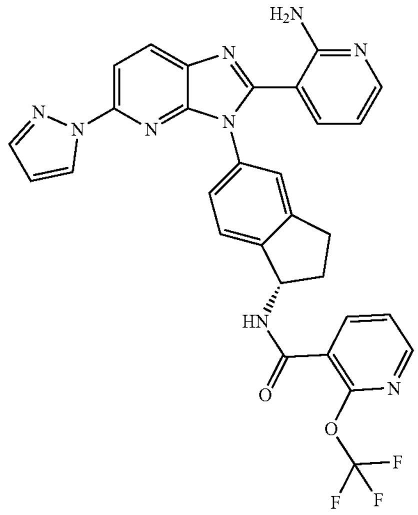 [SMILES: Nc1ncccc1-c1nc2ccc(-n3cccn3)nc2n1-c1ccc2c(c1)CC[C@@H]2NC(=O)c1cccnc1OC(F)(F)F] |
| 79 | 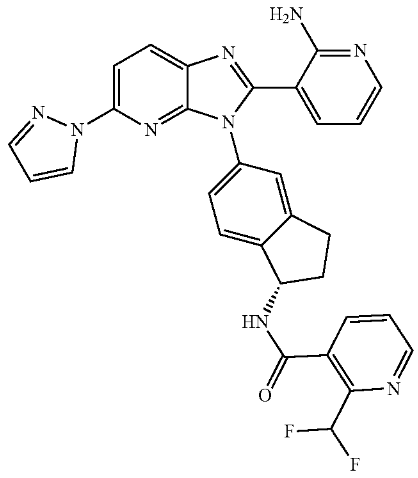 [SMILES: Nc1ncccc1-c1nc2ccc(-n3cccn3)nc2n1-c1ccc2c(c1)CC[C@@H]2NC(=O)c1cccnc1C(F)F] |
| 80 | 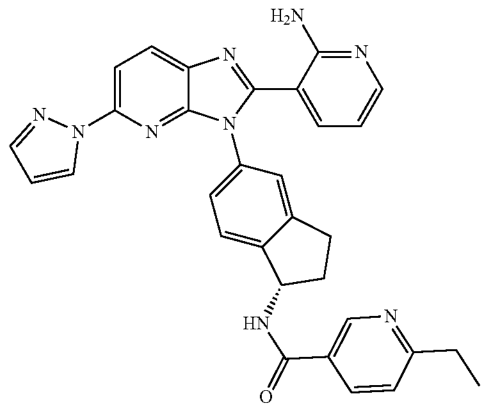 [SMILES: CCc1ccc(C(=O)N[C@H]2CCc3cc(-n4c(-c5cccnc5N)nc5ccc(-n6cccn6)nc54)ccc32)cn1] |

TABLE 1-continued
| Chemical structures of selected compounds. | |
|---|---|
| Cpd ID | Structure |
| 81 | 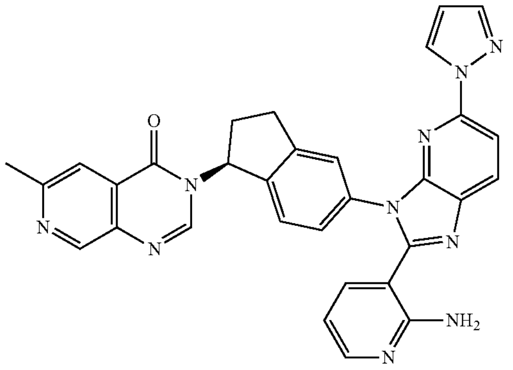 [SMILES: Cc1cc2c(=O)n([C@H]3CCc4cc(-n5c(-c6cccnc6N)nc6ccc(-n7cccn7)nc65)ccc43)cnc2cn1] |
| 82 | 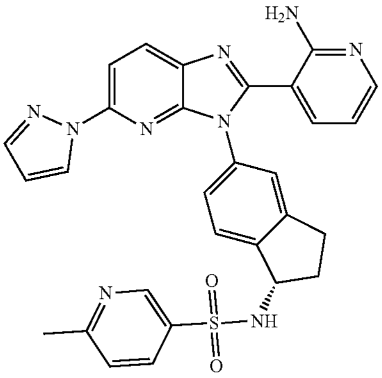 [SMILES: Cc1ccc(S(=O)(=O)N[C@H]2CCc3cc(-n4c(-c5cccnc5N)nc5ccc(-n6cccn6)nc54)ccc32)cn1] |
| 83 | 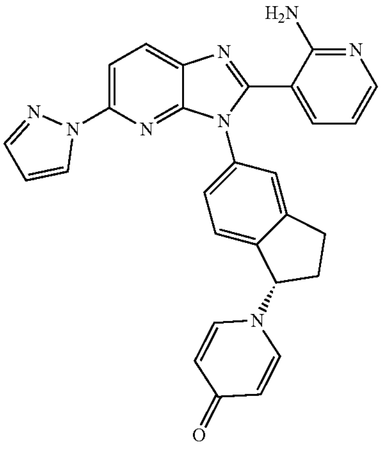 [SMILES: Nc1ncccc1-c1nc2ccc(-n3cccn3)nc2n1-c1ccc2c(c1)CC[C@@H]2n1ccc(=O)cc1] |

TABLE 1-continued
| Chemical structures of selected compounds. | |
|---|---|
| Cpd ID | Structure |
| 84 | 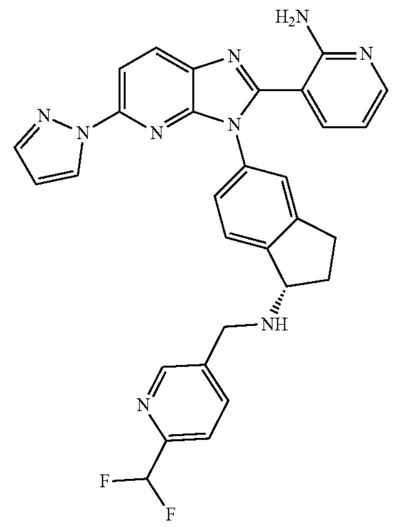 |
| 85 | 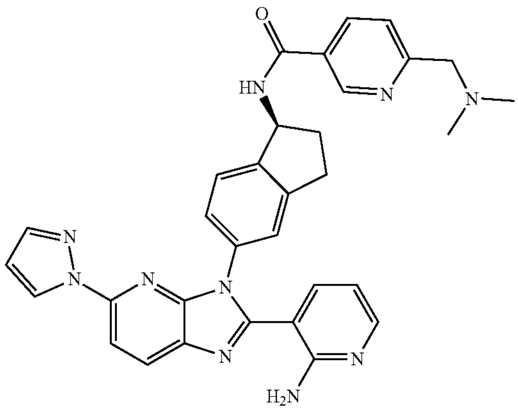 [SMILES: CN(C)Cc1ccc(C(=O)N[C@H]2CCc3cc(-n4c(-c5cccnc5N)nc5ccc(-n6cccn6)nc54)ccc32)cn1] |
| 86 | 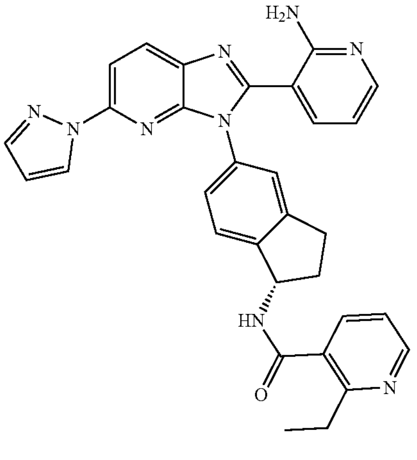 [SMILES: CCc1ncccc1C(=O)N[C@H]1CCc2cc(-n3c(-c4cccnc4N)nc4ccc(-n5cccn5)nc43)ccc21] |

TABLE 1-continued
| Chemical structures of selected compounds. | |
|---|---|
| Cpd ID | Structure |
| 87 | 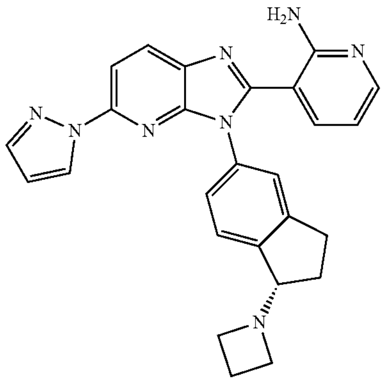 [SMILES: Nc1ncccc1-c1nc2ccc(-n3cccn3)nc2n1-c1ccc2c(c1)CC[C@@H]2N1CCC1] |
| 88 | 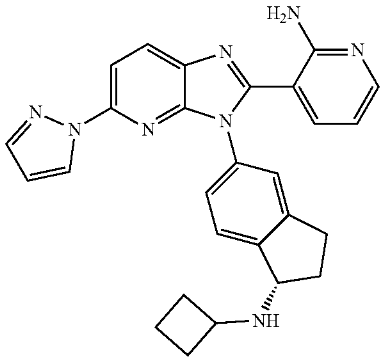 [SMILES: Nc1ncccc1-c1nc2ccc(-n3cccn3)nc2n1-c1ccc2c(c1)CC[C@@H]2NC1CCC1] |
| 89 | 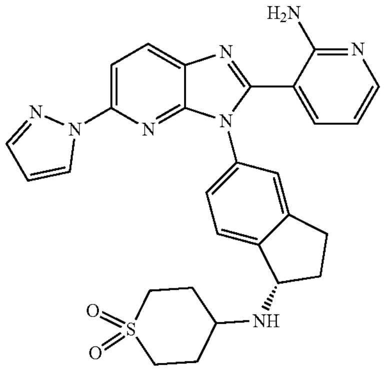 [SMILES: Nc1ncccc1-c1nc2ccc(-n3cccn3)nc2n1-c1ccc2c(c1)CC[C@@H]2NC1CCS(=O)(=O)CC1] |

TABLE 1-continued
| Cpd ID | Structure |
|---|---|
| Chemical structures of selected compounds. | |
| 90 | 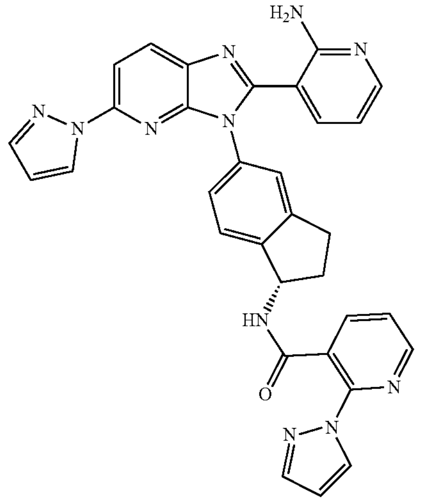 [SMILES: Nc1ncccc1-c1nc2ccc(-n3cccn3)nc2n1-c1ccc2c(c1)CC[C@@H]2NC(=O)c1cccnc1-n1cccn1] |
| 91 | 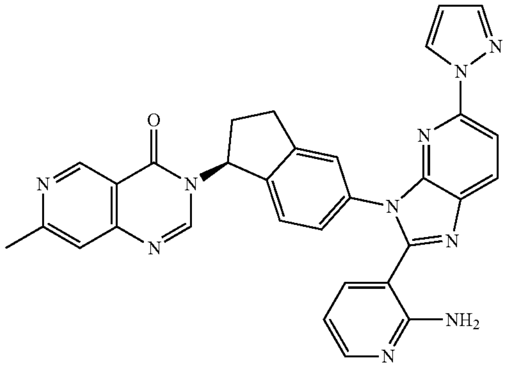 [SMILES: Cc1cc2ncn([C@H]3CCc4cc(-n5c(-c6cccnc6N)nc6ccc(-n7cccn7)nc65)ccc43)c(=O)c2cn1] |
| 92 | 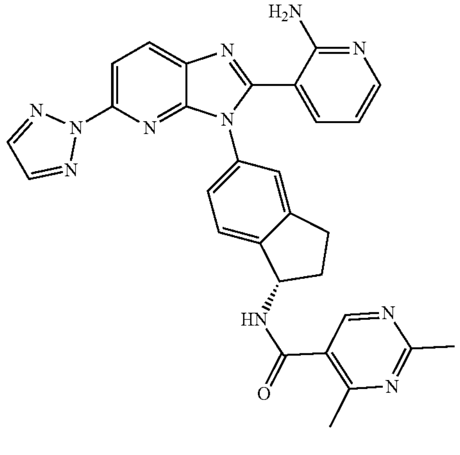 [SMILES: Cc1ncc(C(=O)N[C@H]2CCc3cc(-n4c(-c5cccnc5N)nc5ccc(-n6nccn6)nc54)ccc32)c(C)n1] |

TABLE 1-continued
| Chemical structures of selected compounds. | |
|---|---|
| Cpd ID | Structure |
| 93 | 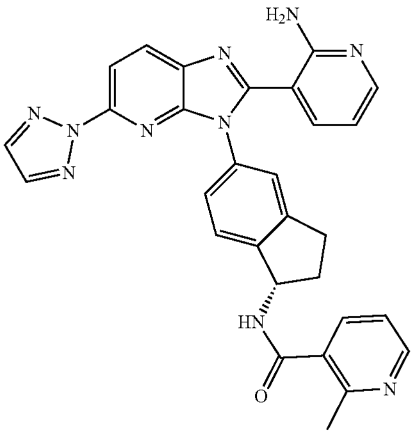 [SMILES: Cc1ncccc1C(=O)N[C@H]1CCc2cc(-n3c(-c4cccnc4N)nc4ccc(-n5nccn5)nc43)ccc21] |
| 94 | 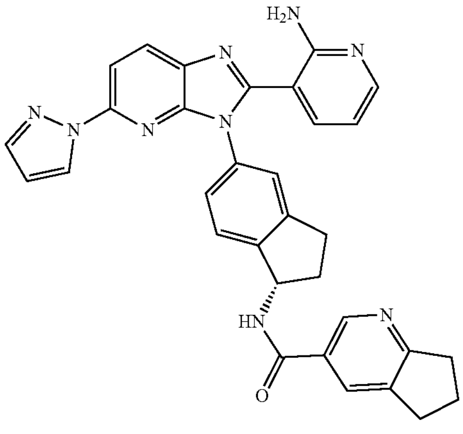 [SMILES: Nc1ncccc1-c1nc2ccc(-n3cccn3)nc2n1-c1ccc2c(c1)CC[C@@H]2NC(=O)c1cnc2c(c1)CCC2] |
| 95 | 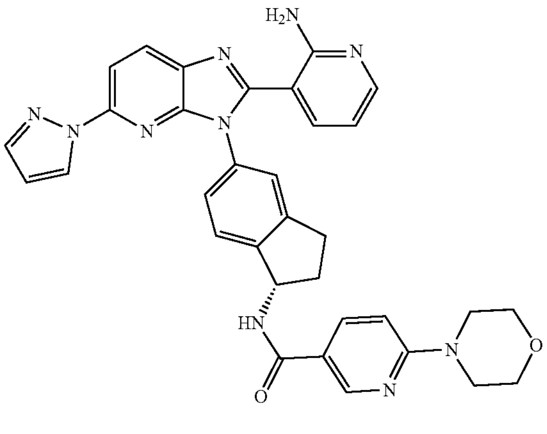 [SMILES: Nc1ncccc1-c1nc2ccc(-n3cccn3)nc2n1-c1ccc2c(c1)CC[C@@H]2NC(=O)c1ccc(N2CCOCC2)nc1] |

TABLE 1-continued
| Cpd ID | Structure |
| --- | --- |
| 96 | 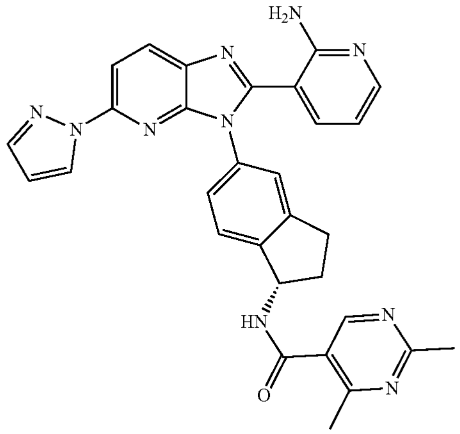 |
| 97 | 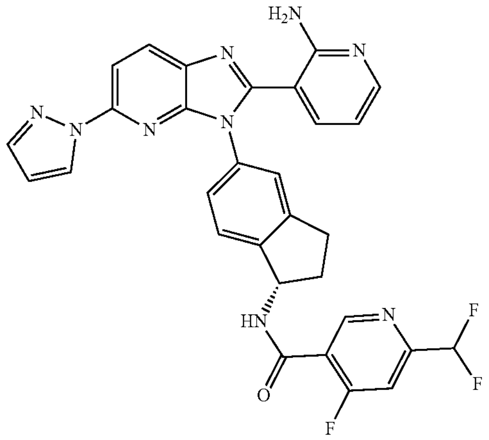 [SMILES: Nc1ncccc1-c1nc2ccc(-n3cccn3)nc2n1-c1ccc2c(c1)CC[C@@H]2NC(=O)c1cnc(C(F)F)cc1F] |
| 98 | 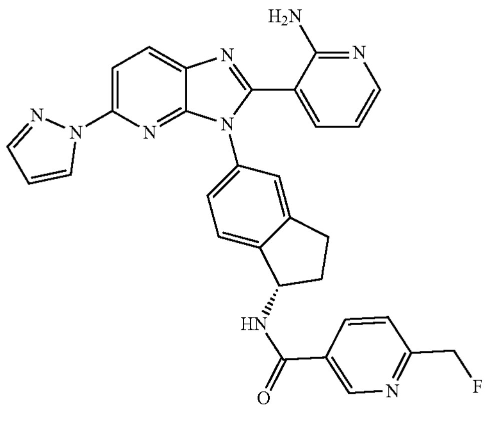 [SMILES: Nc1ncccc1-c1nc2ccc(-n3cccn3)nc2n1-c1ccc2c(c1)CC[C@@H]2NC(=O)c1ccc(CF)nc1] |
Chemical structures of selected compounds.

TABLE 1-continued
| Chemical structures of selected compounds. | |
|---|---|
| Cpd ID | Structure |
| 99 | 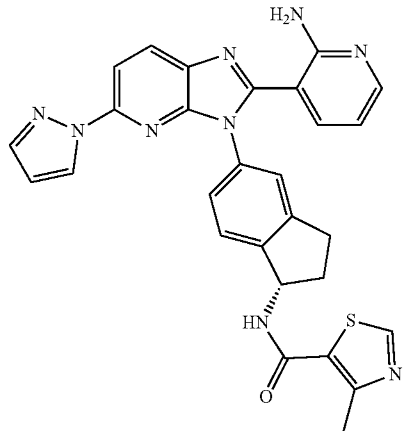 [SMILES: Cc1ncsc1C(=O)N[C@H]1CCc2cc(-n3c(-c4cccnc4N)nc4ccc(-n5cccn5)nc43)ccc21] |
| 100 | 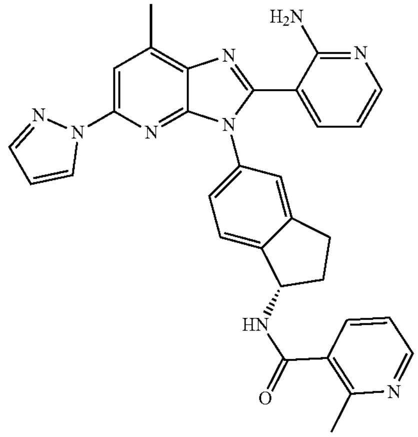 [SMILES: Cc1ncccc1C(=O)N[C@H]1CCc2cc(-n3c(-c4cccnc4N)nc4c(C)cc(-n5cccn5)nc43)ccc21] |
| 101 | 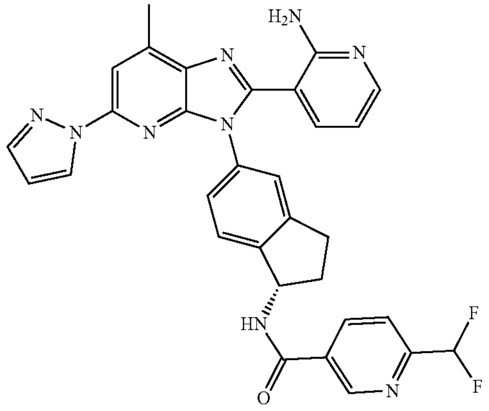 [SMILES: Cc1cc(-n2cccn2)nc2c1nc(-c1cccnc1N)n2-c1ccc2c(c1)CC[C@@H]2NC(=O)c1ccc(C(F)F)nc1] |

TABLE 1-continued
| Chemical structures of selected compounds. | |
|---|---|
| Cpd ID | Structure |
| 102 | 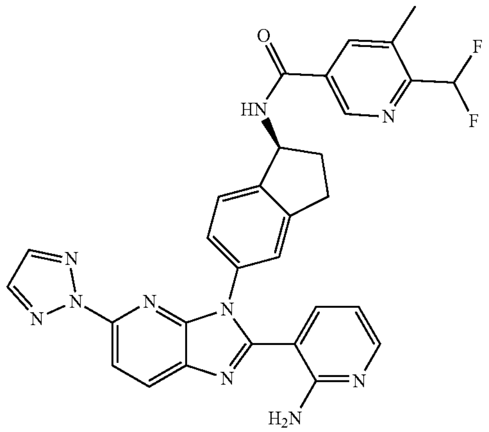 [SMILES: Cc1cc(C(=O)N[C@H]2CCc3cc(-n4c(-c5cccnc5N)nc5ccc(-n6nccn6)nc54)ccc32)cnc1C(F)F] |
| 103 | 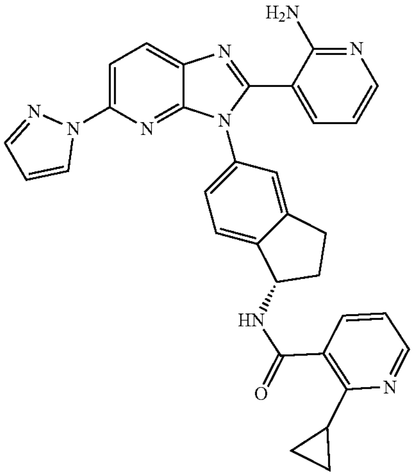 [SMILES: Nc1ncccc1-c1nc2ccc(-n3cccn3)nc2n1-c1ccc2c(c1)CC[C@@H]2NC(=O)c1cccnc1C1CC1] |
| 104 | 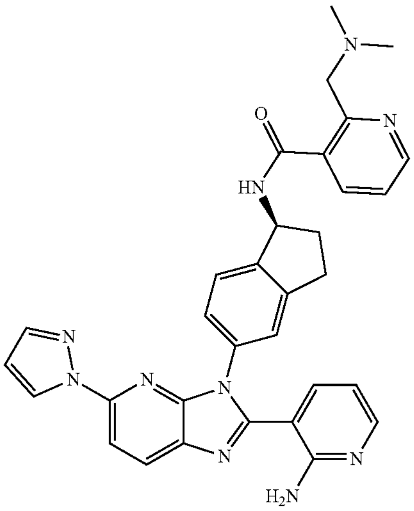 [SMILES: CN(C)Cc1ncccc1C(=O)N[C@H]1CCc2cc(-n3c(-c4cccnc4N)nc4ccc(-n5cccn5)nc43)ccc21] |

TABLE 1-continued
| Chemical structures of selected compounds. | |
|---|---|
| Cpd ID | Structure |
| 105 | 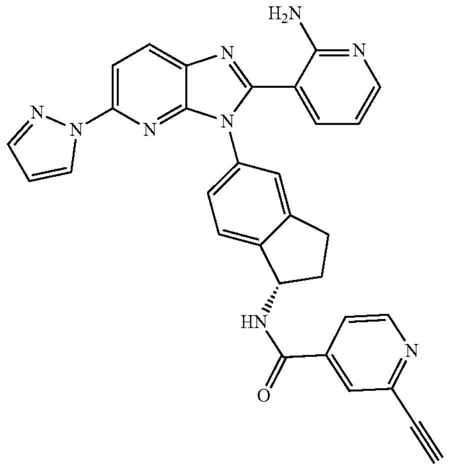 [SMILES: C#Cc1cc(C(=O)N[C@H]2CCc3cc(-n4c(-c5cccnc5N)nc5ccc(-n6cccn6)nc54)ccc32)ccn1] |
| 106 | 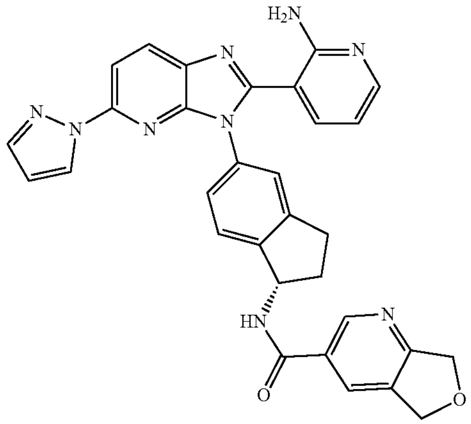 [SMILES: Nc1ncccc1-c1nc2ccc(-n3cccn3)nc2n1-c1ccc2c(c1)CC[C@@H]2NC(=O)c1cnc2c(c1)COC2] |
| 107 | 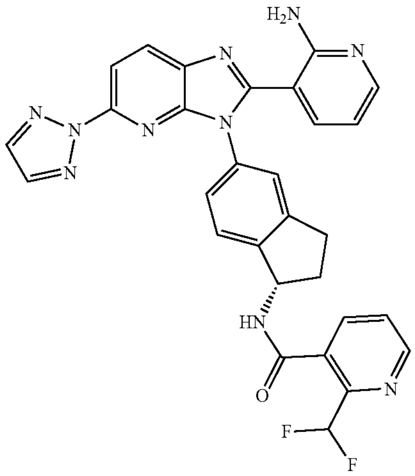 [SMILES: Nc1ncccc1-c1nc2ccc(-n3nccn3)nc2n1-c1ccc2c(c1)CC[C@@H]2NC(=O)c1cccnc1C(F)F] |

TABLE 1-continued
| Chemical structures of selected compounds. | |
|---|---|
| Cpd ID | Structure |
| 108 | 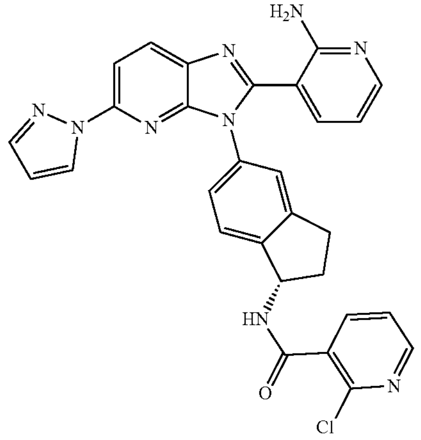 [SMILES: Nc1ncccc1-c1nc2ccc(-n3cccn3)nc2n1-c1ccc2c(c1)CC[C@@H]2NC(=O)c1cccnc1Cl] |
| 110 | 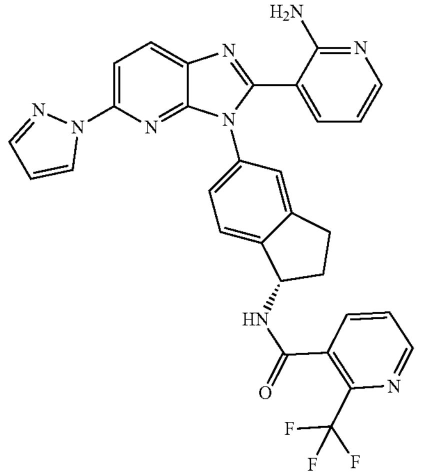 [SMILES: Nc1ncccc1-c1nc2ccc(-n3cccn3)nc2n1-c1ccc2c(c1)CC[C@@H]2NC(=O)c1cccnc1C(F)(F)F] |
| 111 | 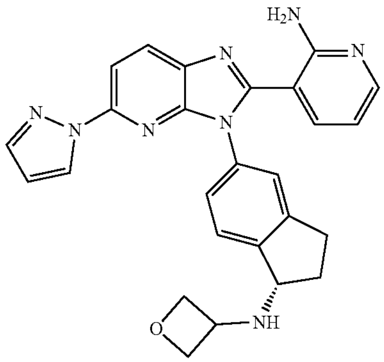 [SMILES: Nc1ncccc1-c1nc2ccc(-n3cccn3)nc2n1-c1ccc2c(c1)CC[C@@H]2NC1COC1] |

TABLE 1-continued
| Chemical structures of selected compounds. | |
|---|---|
| Cpd ID | Structure |
| 112 | 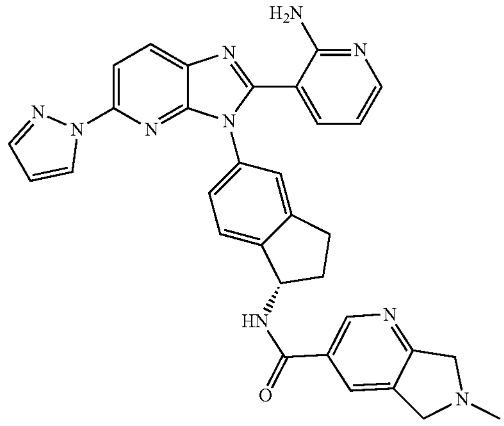 [SMILES: CN1Cc2cc(C(=O)N[C@H]3CCc4cc(-n5c(-c6cccnc6N)nc6ccc(-n7cccn7)nc65)ccc43)cnc2C1] |
| 113 | 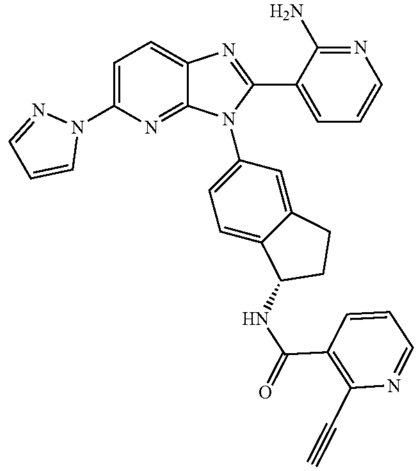 [SMILES: C#Cc1ncccc1C(=O)N[C@H]1CCc2cc(-n3c(-c4cccnc4N)nc4ccc(-n5cccn5)nc43)ccc21] |
| 114 | 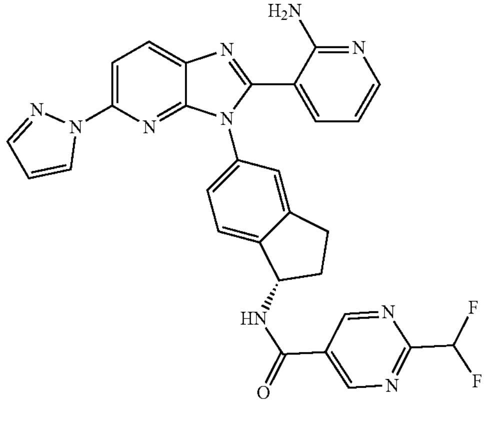 [SMILES: Nc1ncccc1-c1nc2ccc(-n3cccn3)nc2n1-c1ccc2c(c1)CC[C@@H]2NC(=O)c1cnc(C(F)F)nc1] |

TABLE 1-continued
| Cpd ID | Structure |
|---|---|
| 115 | 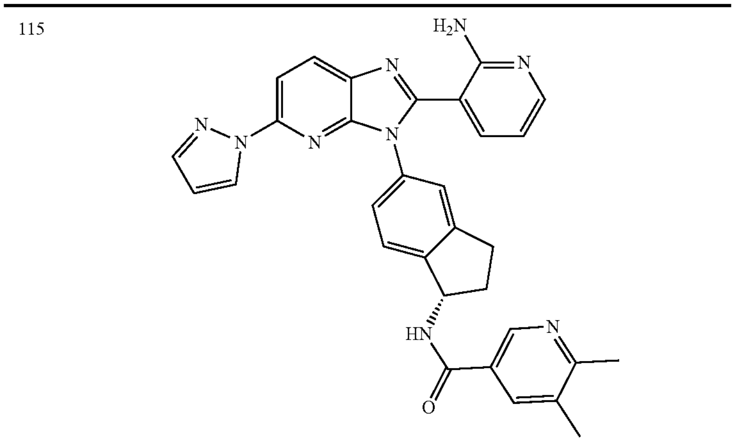 |
| 116 | 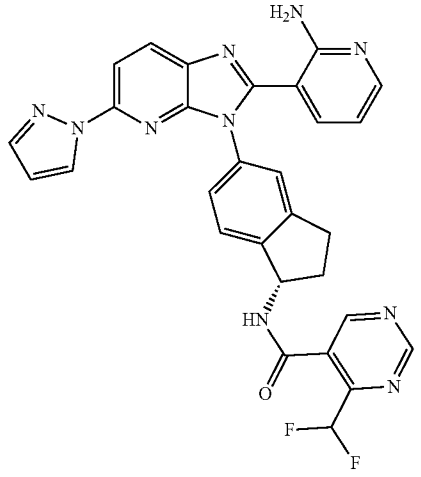 [SMILES: Nc1ncccc1-c1nc2ccc(-n3cccn3)nc2n1-c1ccc2c(c1)CC[C@@H]2NC(=O)c1cncnc1C(F)F] |
| 117 | 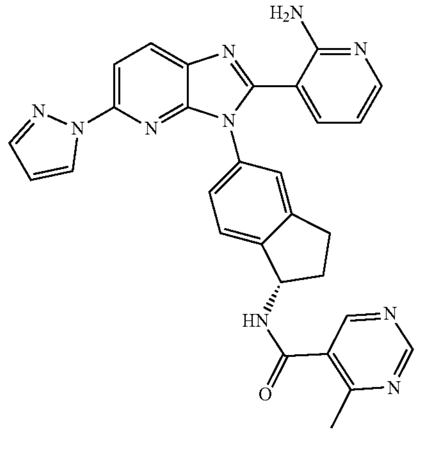 [SMILES: Cc1ncncc1C(=O)N[C@H]1CCc2cc(-n3c(-c4cccnc4N)nc4ccc(-n5cccn5)nc43)ccc21] |
Chemical structures of selected compounds.

TABLE 1-continued
| Chemical structures of selected compounds. | |
|---|---|
| Cpd ID | Structure |
| 118 | 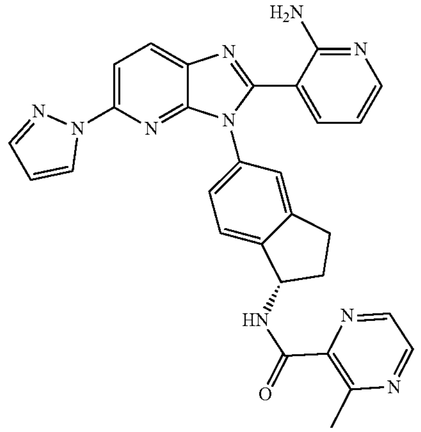 [SMILES: Cc1nccnc1C(=O)N[C@H]1CCc2cc(-n3c(-c4cccnc4N)nc4ccc(-n5cccn5)nc43)ccc21] |
| 119 | 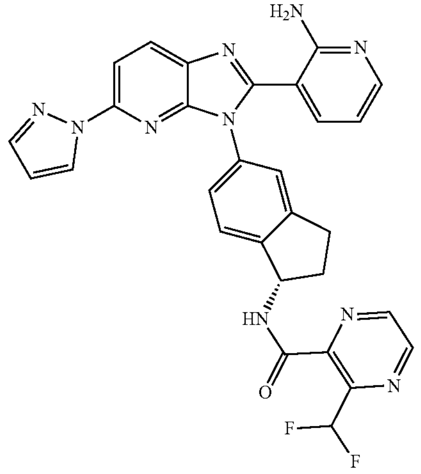 [SMILES: Nc1ncccc1-c1nc2ccc(-n3cccn3)nc2n1-c1ccc2c(c1)CC[C@@H]2NC(=O)c1nccnc1C(F)F] |
| 120 | 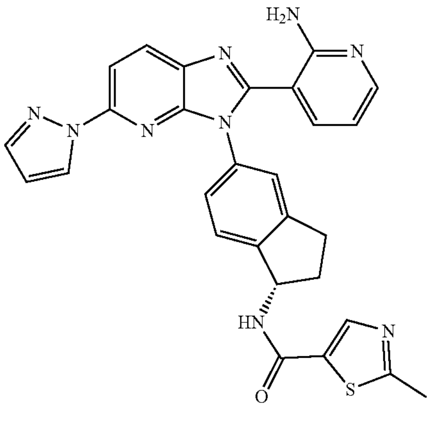 [SMILES: Cc1ncc(C(=O)N[C@H]2CCc3cc(-n4c(-c5cccnc5N)nc5ccc(-n6cccn6)nc54)ccc32)s1] |

TABLE 1-continued
| Chemical structures of selected compounds. | |
|---|---|
| Cpd ID | Structure |
| 121 | 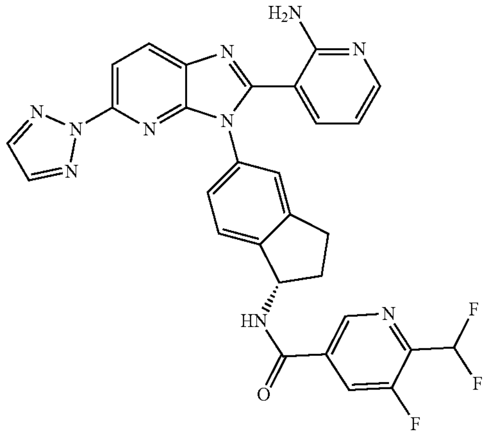 [SMILES: Nc1ncccc1-c1nc2ccc(-n3nccn3)nc2n1-c1ccc2c(c1)CC[C@@H]2NC(=O)c1cnc(C(F)F)c(F)c1] |
| 122 | 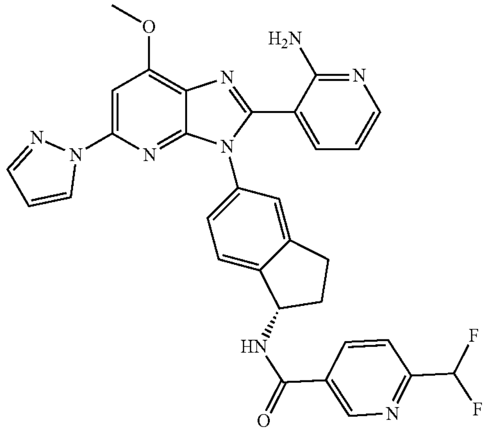 [SMILES: COc1cc(-n2cccn2)nc2c1nc(-c1cccnc1N)n2-c1ccc2c(c1)CC[C@@H]2NC(=O)c1ccc(C(F)F)nc1] |
| 123 | 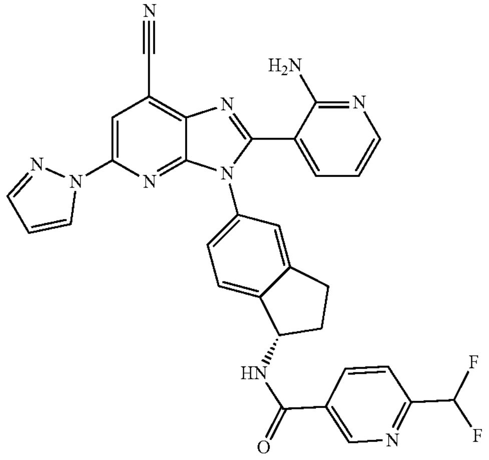 [SMILES: N#Cc1cc(-n2cccn2)nc2c1nc(-c1cccnc1N)n2-c1ccc2c(c1)CC[C@@H]2NC(=O)c1ccc(C(F)F)nc1] |

TABLE 1-continued
| Chemical structures of selected compounds. | |
|---|---|
| Cpd ID | Structure |
| 124 | 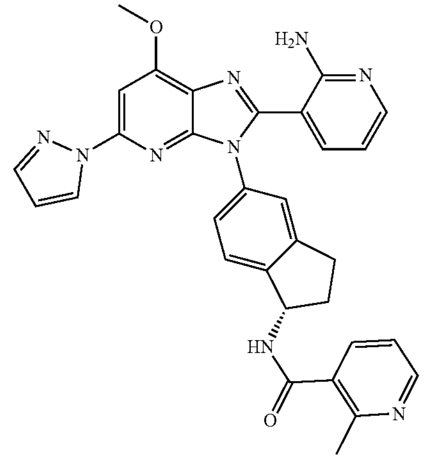 [SMILES: COc1cc(-n2cccn2)nc2c1nc(-c1cccnc1N)n2-c1ccc2c(c1)CC[C@@H]2NC(=O)c1cccnc1C] |
| 125 | 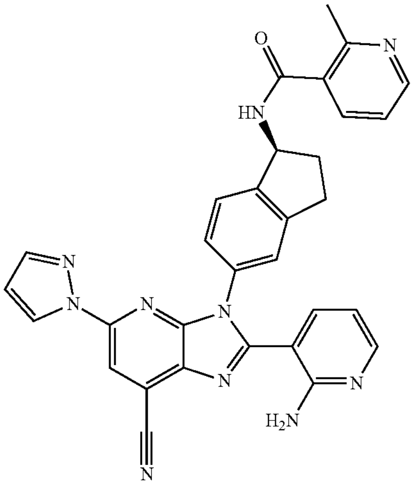 [SMILES: Cc1ncccc1C(=O)N[C@H]1CCc2cc(-n3c(-c4cccnc4N)nc4c(C#N)cc(-n5cccn5)nc43)ccc21] |
| 126 | 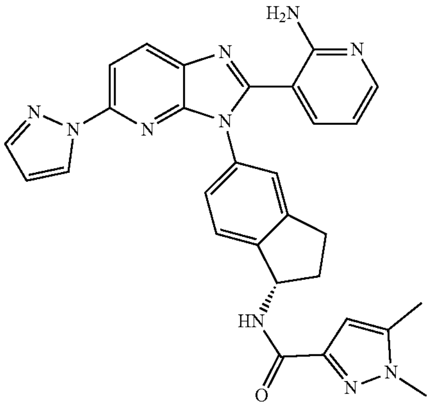 |

TABLE 1-continued
| Chemical structures of selected compounds. | |
|---|---|
| Cpd ID | Structure |
| 127 | 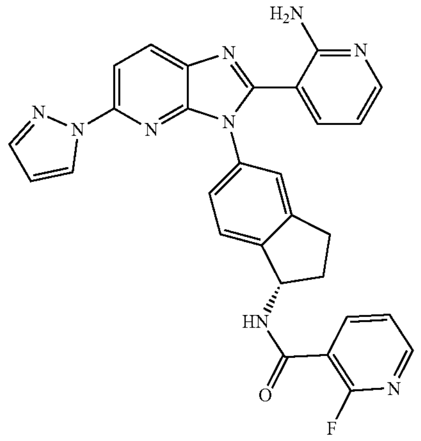 [SMILES: Nc1ncccc1-c1nc2ccc(-n3cccn3)nc2n1-c1ccc2c(c1)CC[C@@H]2NC(=O)c1cccnc1F] |
| 128 | 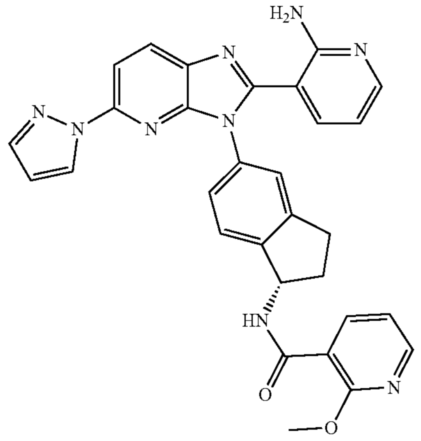 [SMILES: COc1ncccc1C(=O)N[C@H]1CCc2cc(-n3c(-c4cccnc4N)nc4ccc(-n5cccn5)nc43)ccc21] |
| 129 | 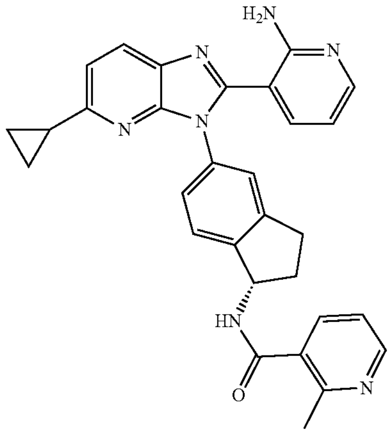 [SMILES: Cc1ncccc1C(=O)N[C@H]1CCc2cc(-n3c(-c4cccnc4N)nc4ccc(C5CC5)nc43)ccc21] |

TABLE 1-continued
| Chemical structures of selected compounds. | |
|---|---|
| Cpd ID | Structure |
| 130 | 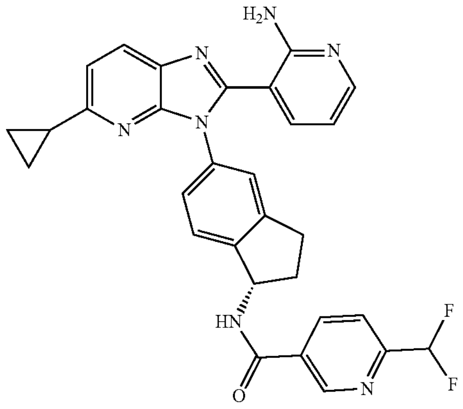 [SMILES: Nc1ncccc1-c1nc2ccc(C3CC3)nc2n1-c1ccc2c(c1)CC[C@@H]2NC(=O)c1ccc(C(F)F)nc1] |
| 131 | 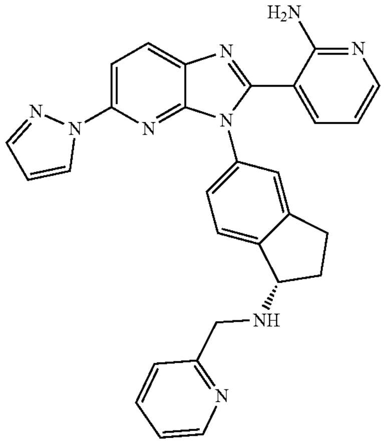 [SMILES: Nc1ncccc1-c1nc2ccc(-n3cccn3)nc2n1-c1ccc2c(c1)CC[C@@H]2NCc1ccccn1] |
| 132 | 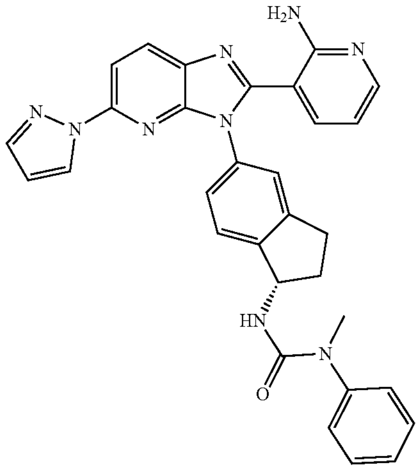 [SMILES: CN(C(=O)N[C@H]1CCc2cc(-n3c(-c4cccnc4N)nc4ccc(-n5cccn5)nc43)ccc21)c1ccccc1] |

TABLE 1-continued
| Chemical structures of selected compounds. | |
|---|---|
| Cpd ID | Structure |
| 133 | 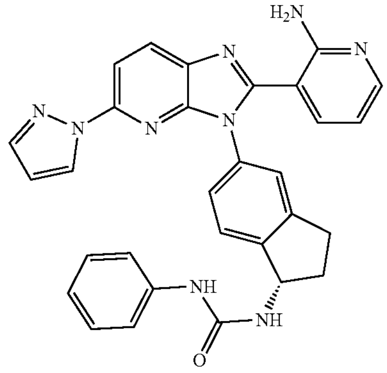 [SMILES: Nc1ncccc1-c1nc2ccc(-n3cccn3)nc2n1-c1ccc2c(c1)CC[C@@H]2NC(=O)Nc1ccccc1] |
| 135 | 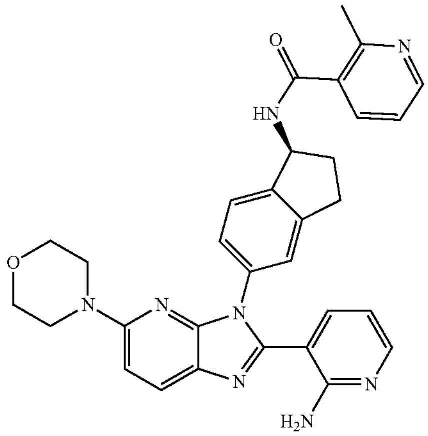 [SMILES: Cc1ncccc1C(=O)N[C@H]1CCc2cc(-n3c(-c4cccnc4N)nc4ccc(N5CCOCC5)nc43)ccc21] |
| 136 | 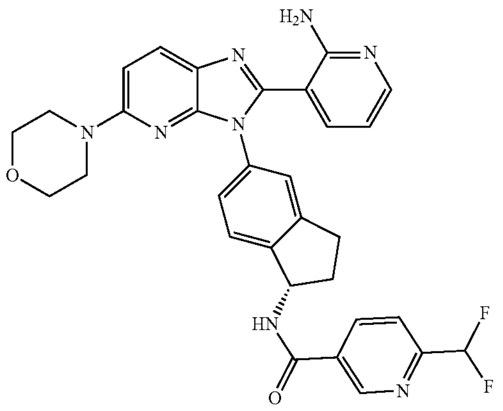 [SMILES: Nc1ncccc1-c1nc2ccc(N3CCOCC3)nc2n1-c1ccc2c(c1)CC[C@@H]2NC(=O)c1ccc(C(F)F)nc1] |

TABLE 1-continued
Chemical structures of selected compounds.
| Cpd ID | Structure |
| --- | --- |
| 137 | 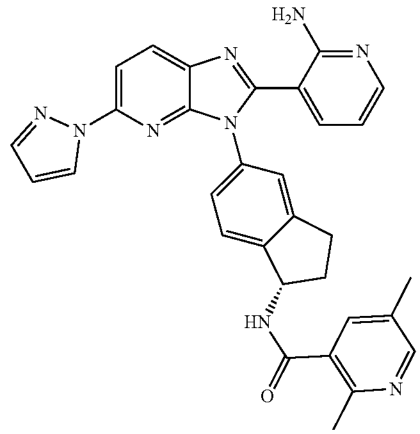 |
| 138 | 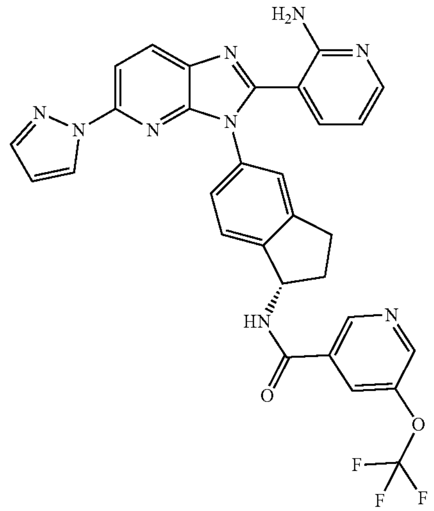 [SMILES: Nc1ncccc1-c1nc2ccc(-n3cccn3)nc2n1-c1ccc2c(c1)CC[C@@H]2NC(=O)c1cncc(OC(F)(F)F)c1] |
| 139 | 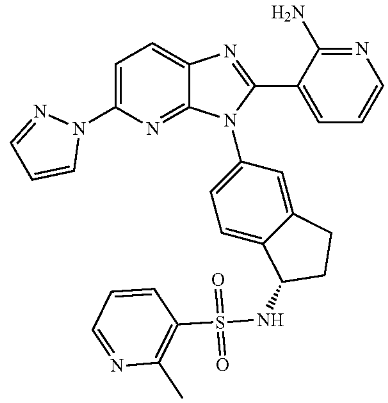 [SMILES: Cc1ncccc1S(=O)(=O)N[C@H]1CCc2cc(-n3c(-c4cccnc4N)nc4ccc(-n5cccn5)nc43)ccc21] |

TABLE 1-continued
| Chemical structures of selected compounds. | |
|---|---|
| Cpd ID | Structure |
| 140 | 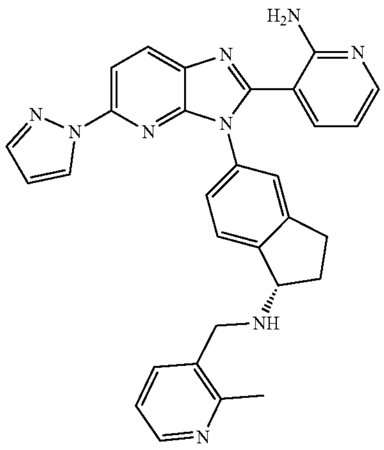 [SMILES: Cc1ncccc1CN[C@H]1CCc2cc(-n3c(-c4cccnc4N)nc4ccc(-n5cccn5)nc43)ccc21] |
| 141 | 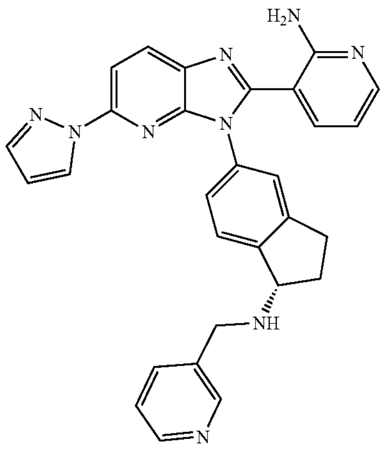 [SMILES: Nc1ncccc1-c1nc2ccc(-n3cccn3)nc2n1-c1ccc2c(c1)CC[C@@H]2NCc1cccnc1] |
| 142 | 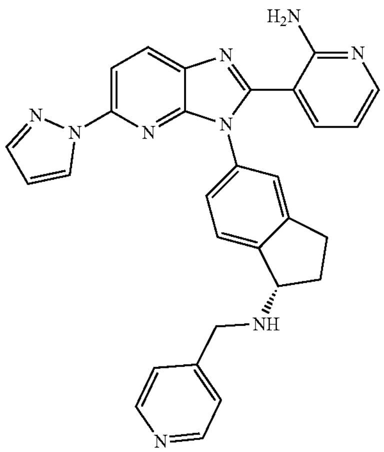 [SMILES: Nc1ncccc1-c1nc2ccc(-n3cccn3)nc2n1-c1ccc2c(c1)CC[C@@H]2NCc1ccncc1] |

TABLE 1-continued
| Chemical structures of selected compounds. | |
|---|---|
| Cpd ID | Structure |
| 143 | 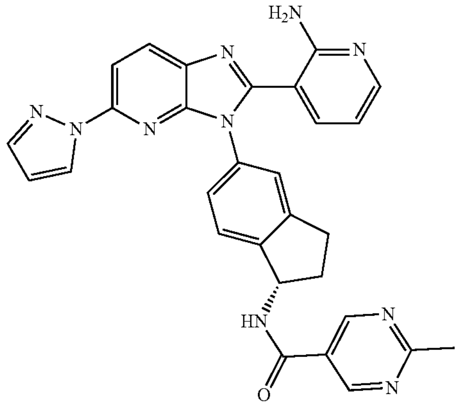 [SMILES: Cc1ncc(C(=O)N[C@H]2CCc3cc(-n4c(-c5cccnc5N)nc5ccc(-n6cccn6)nc54)ccc32)cn1] |
| 144 | 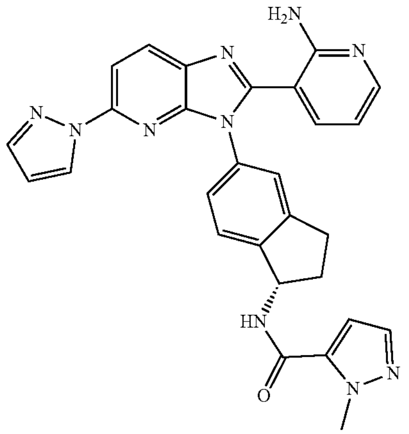 [SMILES: Cn1nccc1C(=O)N[C@H]1CCc2cc(-n3c(-c4cccnc4N)nc4ccc(-n5cccn5)nc43)ccc21] |
| 145 | 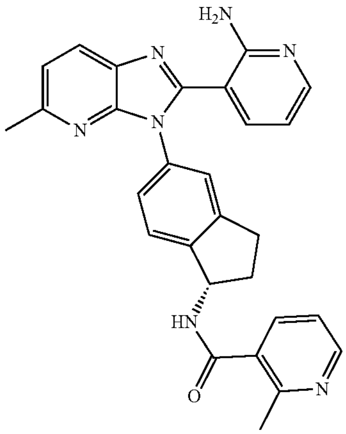 [SMILES: Cc1ccc2nc(-c3cccnc3N)n(-c3ccc4c(c3)CC[C@@H]4NC(=O)c3cccnc3C)c2n1] |

TABLE 1-continued
| Cpd ID | Structure |
|---|---|
| 146 | 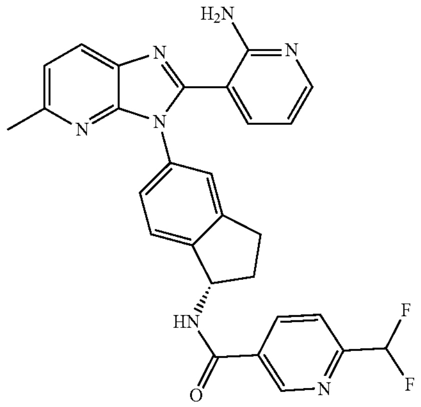 [SMILES: Cc1ccc2nc(-c3cccnc3N)n(-c3ccc4c(c3)CC[C@@H]4NC(=O)c3ccc(C(F)F)nc3)c2n1] |
| 147 | 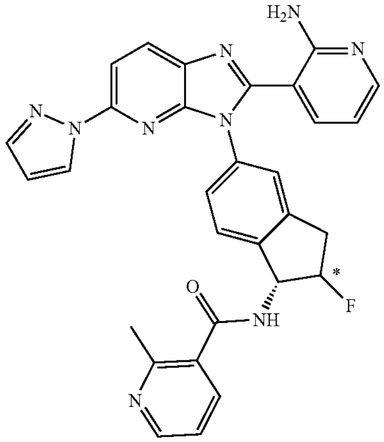 [SMILES: Cc1ncccc1C(=O)N[C@@H]1c2ccc(-n3c(-c4cccnc4N)nc4ccc(-n5cccn5)nc43)cc2CC1F] |
| 148 | 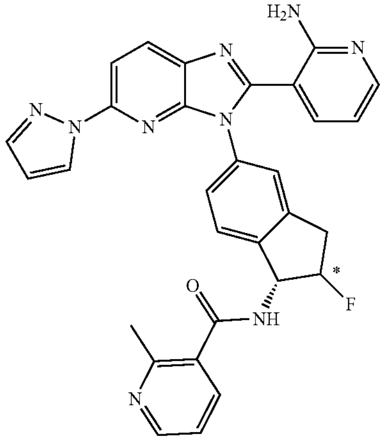 [SMILES: Cc1ncccc1C(=O)N[C@@H]1c2ccc(-n3c(-c4cccnc4N)nc4ccc(-n5cccn5)nc43)cc2CC1F] |

TABLE 1-continued
| Chemical structures of selected compounds. | |
|---|---|
| Cpd ID | Structure |
| 149 | 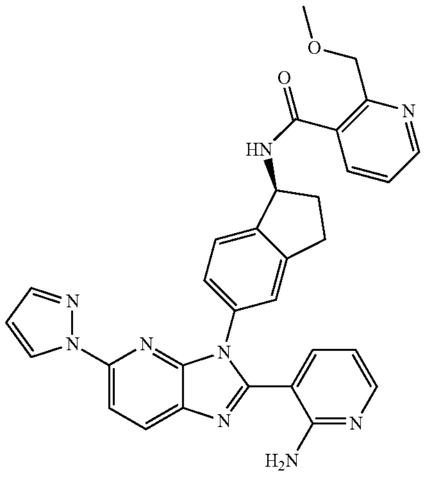 [SMILES: COCc1ncccc1C(=O)N[C@H]1CCc2cc(-n3c(-c4cccnc4N)nc4ccc(-n5cccn5)nc43)ccc21] |
| 150 | 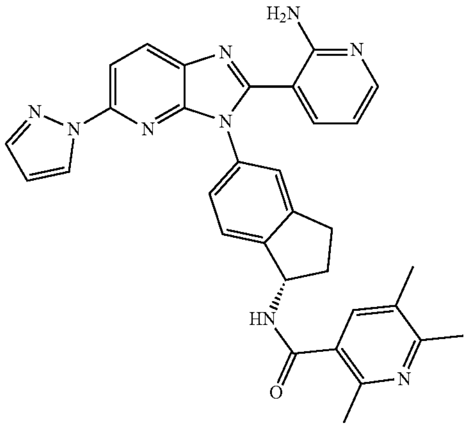 [SMILES: Cc1cc(C(=O)N[C@H]2CCc3cc(-n4c(-c5cccnc5N)nc5ccc(-n6cccn6)nc54)ccc32)c(C)nc1C] |
| 151 | 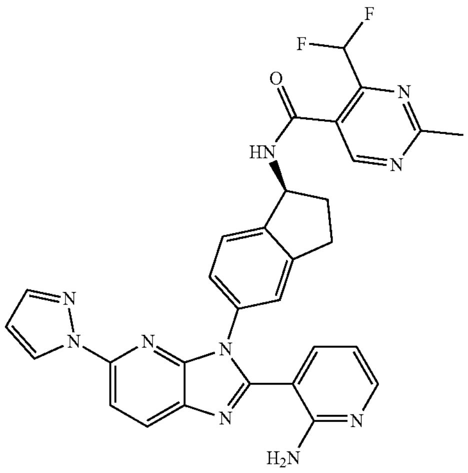 |

TABLE 1-continued
| Chemical structures of selected compounds. | |
|---|---|
| Cpd ID | Structure |
| 152 | 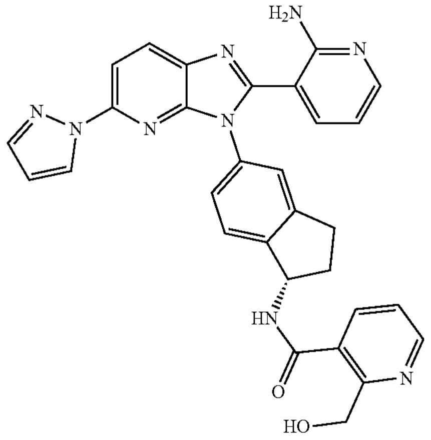 [SMILES: Nc1ncccc1-c1nc2ccc(-n3cccn3)nc2n1-c1ccc2c(c1)CC[C@@H]2NC(=O)c1cccnc1CO] |
| 153 | 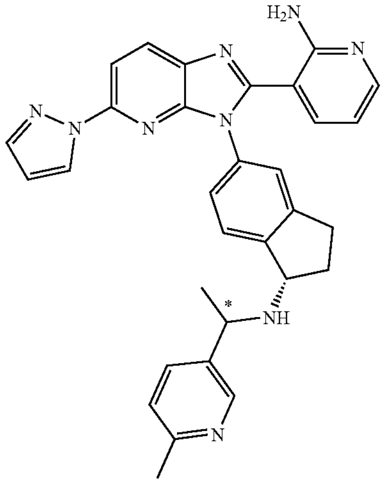 [SMILES: Cc1ccc(C(C)N[C@H]2CCc3cc(-n4c(-c5cccnc5N)nc5ccc(-n6cccn6)nc54)ccc32)cn1] |
| 154 | 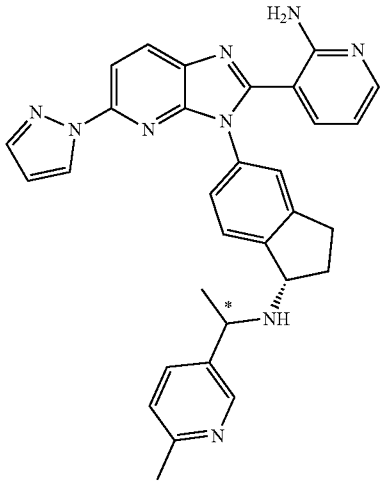 [SMILES: Cc1ccc(C(C)N[C@H]2CCc3cc(-n4c(-c5cccnc5N)nc5ccc(-n6cccn6)nc54)ccc32)cn1] |

TABLE 1-continued
| Chemical structures of selected compounds. | |
|---|---|
| Cpd ID | Structure |
| 155 | 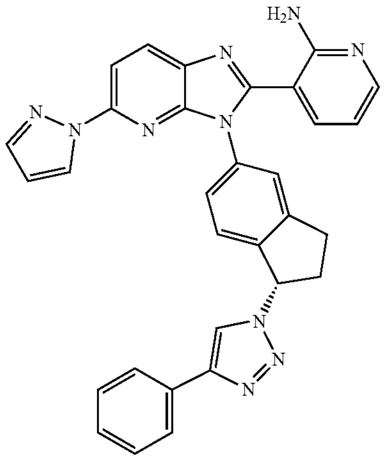 [SMILES: Nc1ncccc1-c1nc2ccc(-n3cccn3)nc2n1-c1ccc2c(c1)CC[C@@H]2n1cc(-c2ccccc2)nn1] |
| 156 | 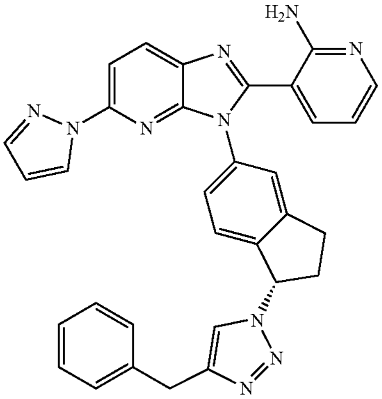 [SMILES: Nc1ncccc1-c1nc2ccc(-n3cccn3)nc2n1-c1ccc2c(c1)CC[C@@H]2n1cc(Cc2ccccc2)nn1] |
| 157 | 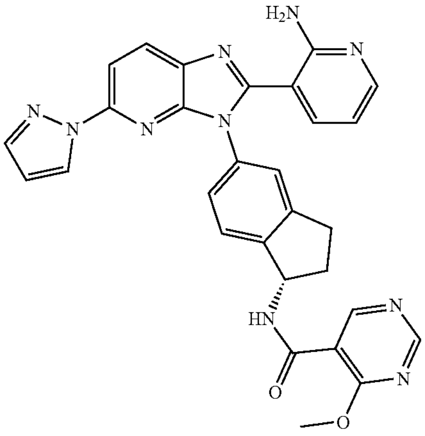 [SMILES: COc1ncncc1C(=O)N[C@H]1CCc2cc(-n3c(-c4cccnc4N)nc4ccc(-n5cccn5)nc43)ccc21] |

TABLE 1-continued
| Chemical structures of selected compounds. | |
|---|---|
| Cpd ID | Structure |
| 158 | 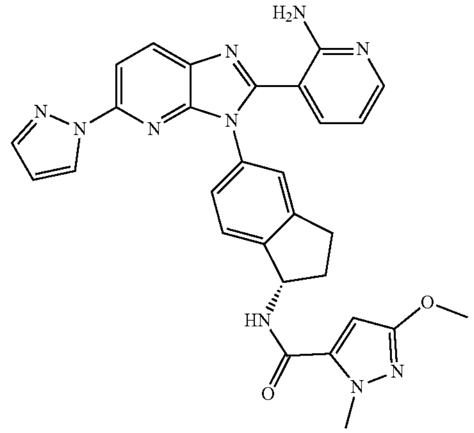 [SMILES: COc1cc(C(=O)N[C@H]2CCc3cc(-n4c(-c5cccnc5N)nc5ccc(-n6cccn6)nc54)ccc32)n(C)n1] |
| 159 | 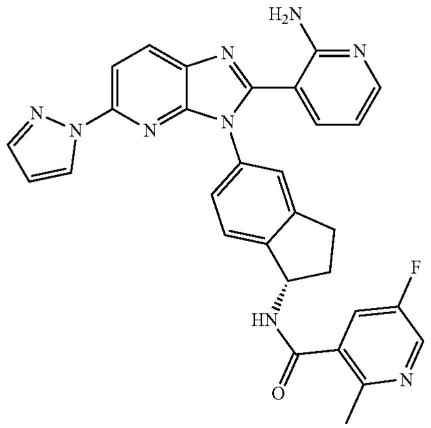 [SMILES: Cc1ncc(F)cc1C(=O)N[C@H]1CCc2cc(-n3c(-c4cccnc4N)nc4ccc(-n5cccn5)nc43)ccc21] |
| 160 | 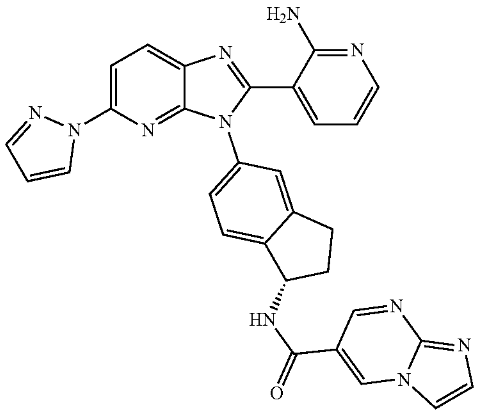 [SMILES: Nc1ncccc1-c1nc2ccc(-n3cccn3)nc2n1-c1ccc2c(c1)CC[C@@H]2NC(=O)c1cnc2nccn2c1] |

TABLE 1-continued
| Cpd ID | Structure |
|---|---|
| 161 | 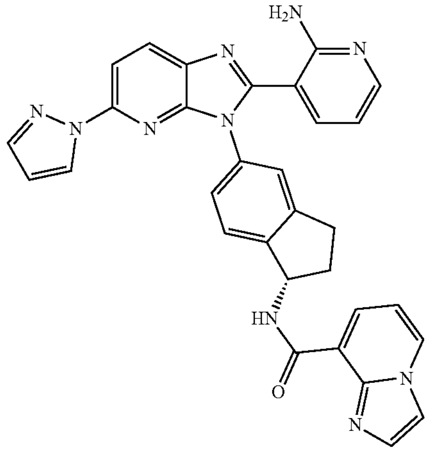 [SMILES: Nc1ncccc1-c1nc2ccc(-n3cccn3)nc2n1-c1ccc2c(c1)CC[C@@H]2NC(=O)c1cccn2ccnc12] |
| 162 | 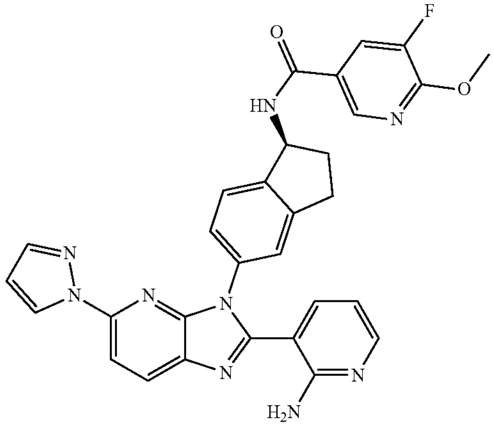 [SMILES: COc1ncc(C(=O)N[C@H]2CCc3cc(-n4c(-c5cccnc5N)nc5ccc(-n6cccn6)nc54)ccc32)cc1F] |
| 163 | 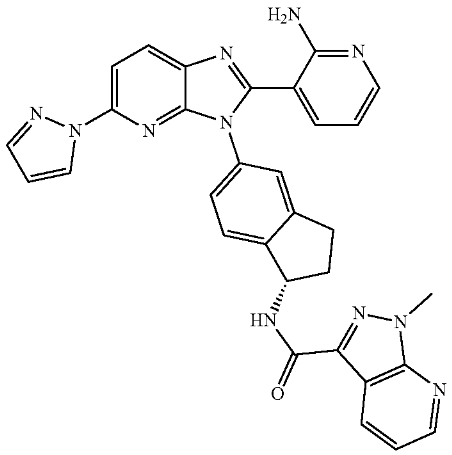 [SMILES: Cn1nc(C(=O)N[C@H]2CCc3cc(-n4c(-c5cccnc5N)nc5ccc(-n6cccn6)nc54)ccc32)c2cccnc21] |
Chemical structures of selected compounds.

TABLE 1-continued
| Chemical structures of selected compounds. | |
|---|---|
| Cpd ID | Structure |
| 164 | 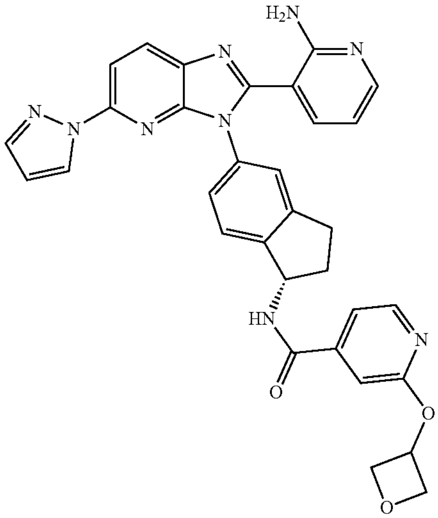 [SMILES: Nc1ncccc1-c1nc2ccc(-n3cccn3)nc2n1-c1ccc2c(c1)CC[C@@H]2NC(=O)c1ccnc(OC2COC2)c1] |
| 165 | 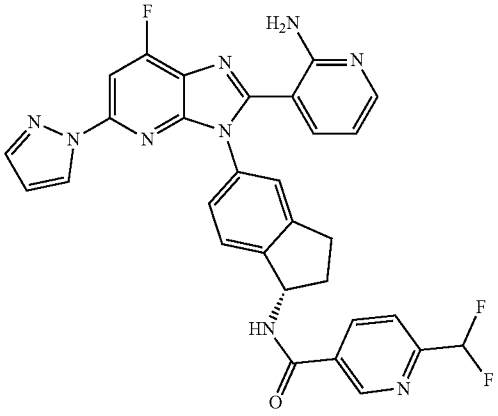 [SMILES: Nc1ncccc1-c1nc2c(F)cc(-n3cccn3)nc2n1-c1ccc2c(c1)CC[C@@H]2NC(=O)c1ccc(C(F)F)nc1] |
| 166 | 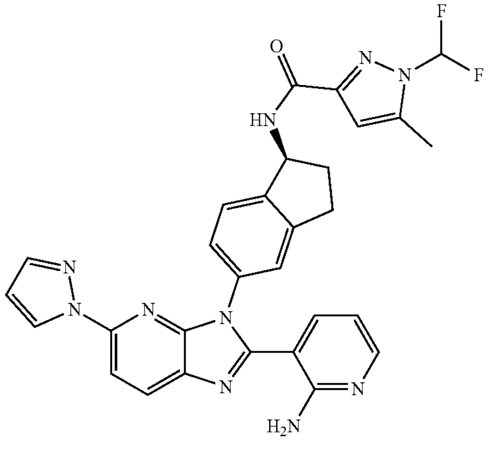 [SMILES: Cc1cc(C(=O)N[C@H]2CCc3cc(-n4c(-c5cccnc5N)nc5ccc(-n6cccn6)nc54)ccc32)nn1C(F)F] |

TABLE 1-continued
| Chemical structures of selected compounds. | |
|---|---|
| Cpd ID | Structure |
| 167 | 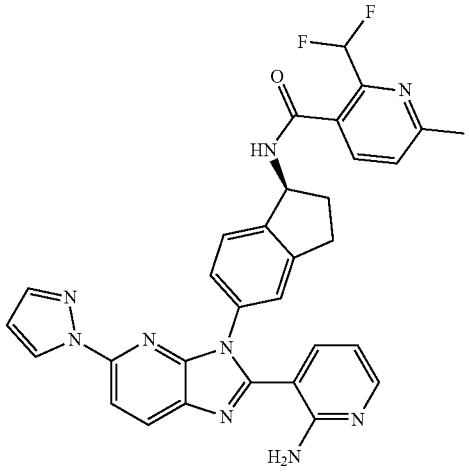 [SMILES: Cc1ccc(C(=O)N[C@H]2CCc3cc(-n4c(-c5cccnc5N)nc5ccc(-n6cccn6)nc54)ccc32)c(C(F)F)n1] |
| 168 | 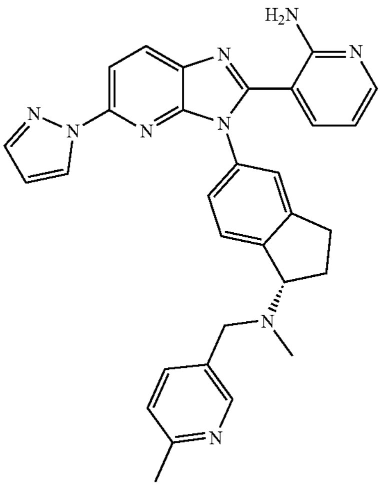 [SMILES: Cc1ccc(CN(C)[C@H]2CCc3cc(-n4c(-c5cccnc5N)nc5ccc(-n6cccn6)nc54)ccc32)cn1] |
| 169 | 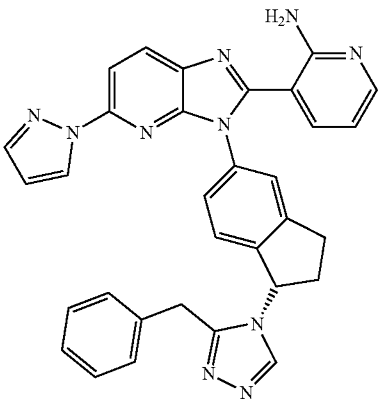 |

TABLE 1-continued
| Chemical structures of selected compounds. | |
|---|---|
| Cpd ID | Structure |
| 170 | 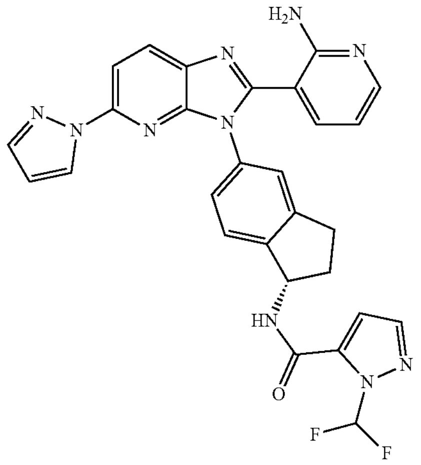 [SMILES: Nc1ncccc1-c1nc2ccc(-n3cccn3)nc2n1-c1ccc2c(c1)CC[C@@H]2NC(=O)c1ccnn1C(F)F] |
| 171 | 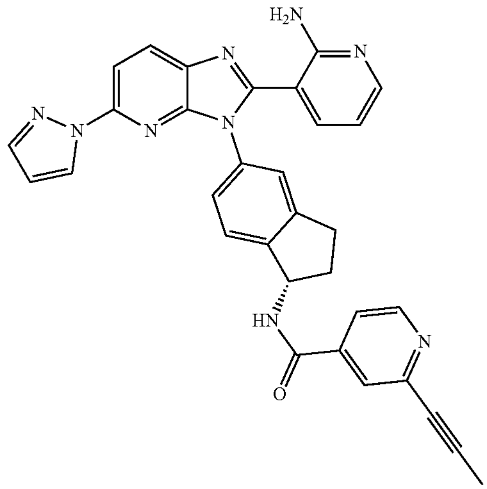 [SMILES: CC#Cc1cc(C(=O)N[C@H]2CCc3cc(-n4c(-c5cccnc5N)nc5ccc(-n6cccn6)nc54)ccc32)ccn1] |
| 172 | 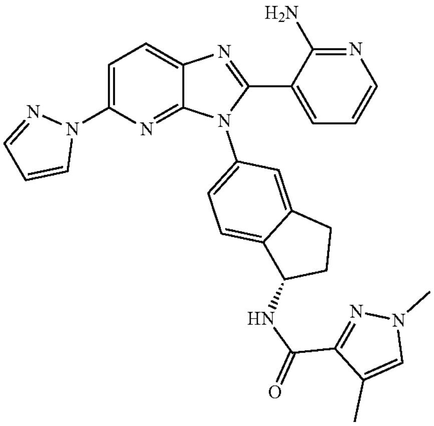 [SMILES: Cc1cn(C)nc1C(=O)N[C@H]1CCc2cc(-n3c(-c4cccnc4N)nc4ccc(-n5cccn5)nc43)ccc21] |

TABLE 1-continued
| Chemical structures of selected compounds. | |
|---|---|
| Cpd ID | Structure |
| 173 | 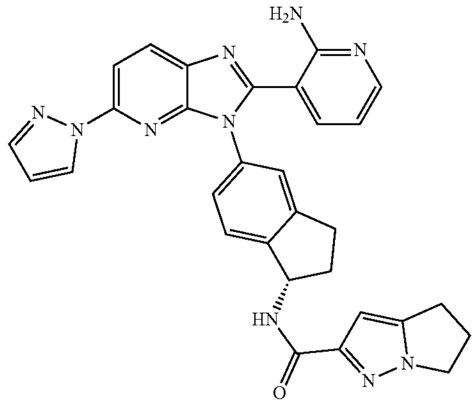 [SMILES: Nc1ncccc1-c1nc2ccc(-n3cccn3)nc2n1-c1ccc2c(c1)CC[C@@H]2NC(=O)c1cc2n(n1)CCC2] |
| 174 | 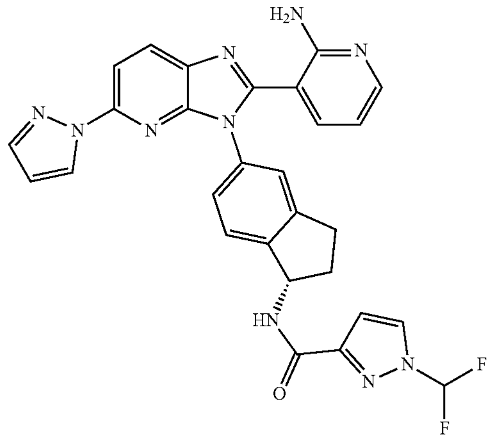 [SMILES: Nc1ncccc1-c1nc2ccc(-n3cccn3)nc2n1-c1ccc2c(c1)CC[C@@H]2NC(=O)c1ccn(C(F)F)n1] |
| 175 | 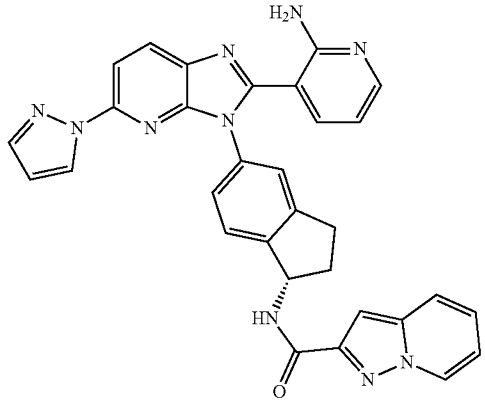 [SMILES: Nc1ncccc1-c1nc2ccc(-n3cccn3)nc2n1-c1ccc2c(c1)CC[C@@H]2NC(=O)c1cc2ccccn2n1] |

TABLE 1-continued
| Chemical structures of selected compounds. | |
|---|---|
| Cpd ID | Structure |
| 176 | 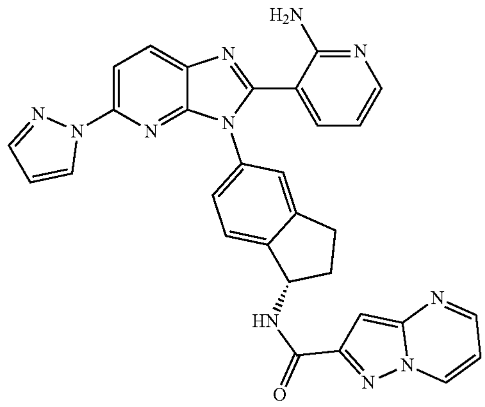 [SMILES: Nc1ncccc1-c1nc2ccc(-n3cccn3)nc2n1-c1ccc2c(c1)CC[C@@H]2NC(=O)c1cc2ncccn2n1] |
| 177 | 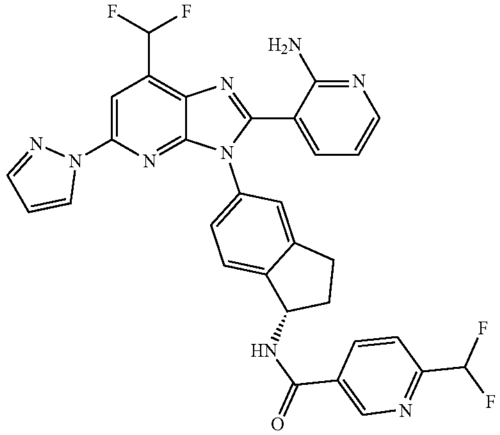 [SMILES: Nc1ncccc1-c1nc2c(C(F)F)cc(-n3cccn3)nc2n1-c1ccc2c(c1)CC[C@@H]2NC(=O)c1ccc(C(F)F)nc1] |
| 178 | 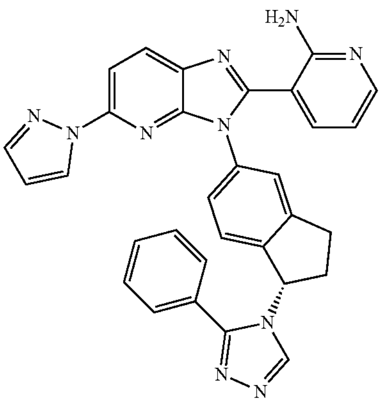 [SMILES: Nc1ncccc1-c1nc2ccc(-n3cccn3)nc2n1-c1ccc2c(c1)CC[C@@H]2n1cnnc1-c1ccccc1] |

TABLE 1-continued
| Chemical structures of selected compounds. | |
|---|---|
| Cpd ID | Structure |
| 179 | 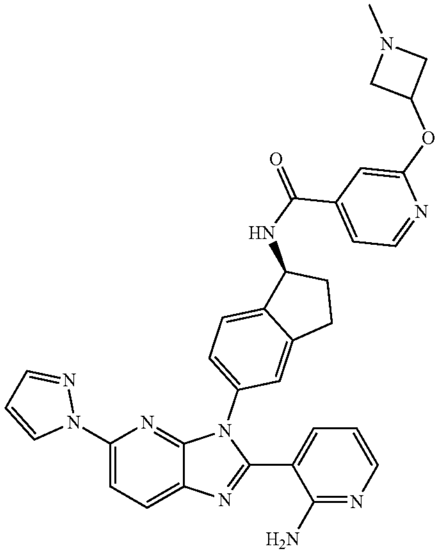 [SMILES: CN1CC(Oc2cc(C(=O)N[C@H]3CCc4cc(-n5c(-c6cccnc6N)nc6ccc(-n7cccn7)nc65)ccc43)ccn2)C1] |
| 180 | 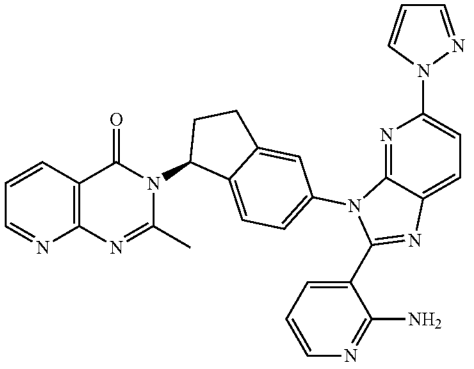 [SMILES: Cc1nc2ncccc2c(=O)n1[C@H]1CCc2cc(-n3c(-c4cccnc4N)nc4ccc(-n5cccn5)nc43)ccc21] |
| 181 | 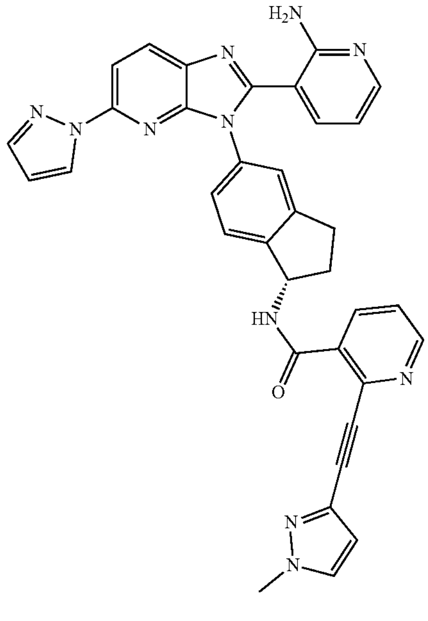 [SMILES: Cn1ccc(C#Cc2ncccc2C(=O)N[C@H]2CCc3cc(-n4c(-c5cccnc5N)nc5ccc(-n6cccn6)nc54)ccc32)n1] |

TABLE 1-continued
| Chemical structures of selected compounds. | |
|---|---|
| Cpd ID | Structure |
| 182 | 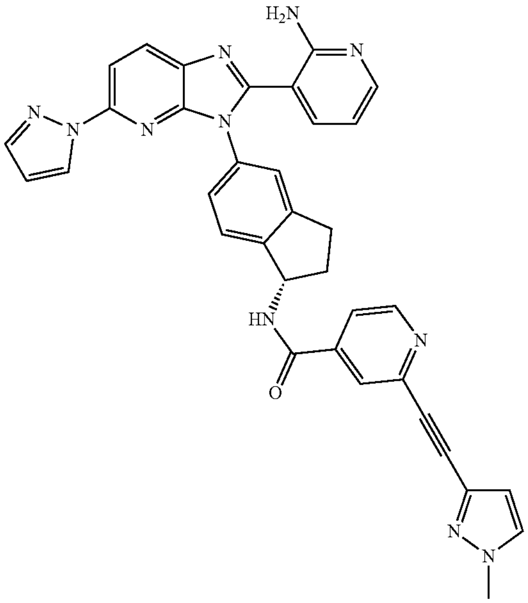 [SMILES: Cn1ccc(C#Cc2cc(C(=O)N[C@H]3CCc4cc(-n5c(-c6cccnc6N)nc6ccc(-n7cccn7)nc65)ccc43)ccn2)n1] |
| 183 | 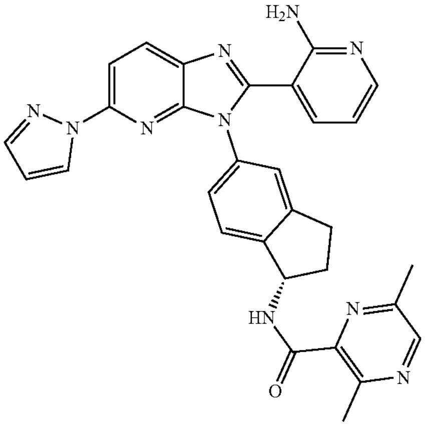 [SMILES: Cc1cnc(C)c(C(=O)N[C@H]2CCc3cc(-n4c(-c5cccnc5N)nc5ccc(-n6cccn6)nc54)ccc32)n1] |
| 184 | 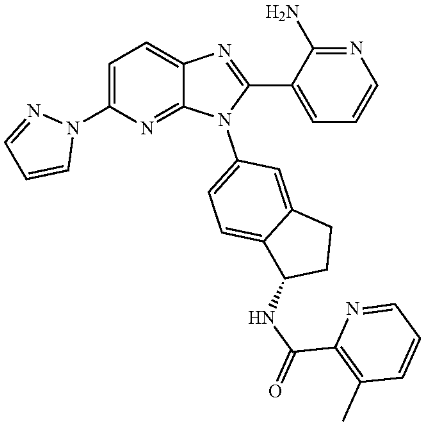 [SMILES: Cc1cccnc1C(=O)N[C@H]1CCc2cc(-n3c(-c4cccnc4N)nc4ccc(-n5cccn5)nc43)ccc21] |

TABLE 1-continued
| Chemical structures of selected compounds. | |
|---|---|
| Cpd ID | Structure |
| 185 | 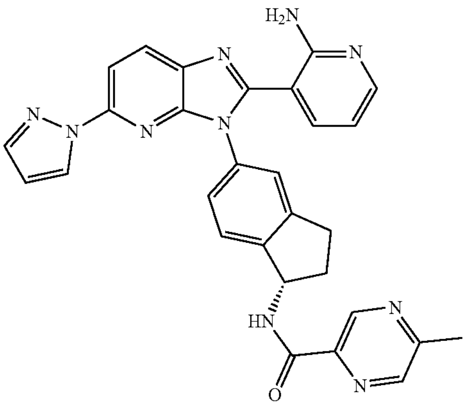 [SMILES: Cc1cnc(C(=O)N[C@H]2CCc3cc(-n4c(-c5cccnc5N)nc5ccc(-n6cccn6)nc54)ccc32)cn1] |
| 186 | 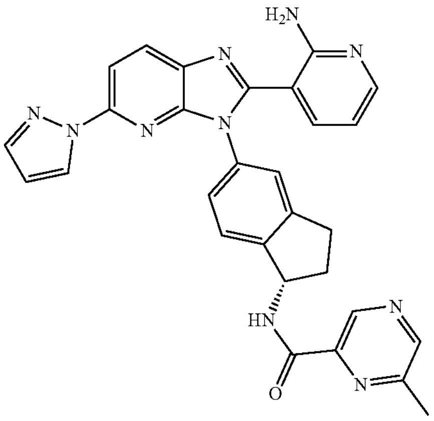 [SMILES: Cc1cncc(C(=O)N[C@H]2CCc3cc(-n4c(-c5cccnc5N)nc5ccc(-n6cccn6)nc54)ccc32)n1] |
| 187 | 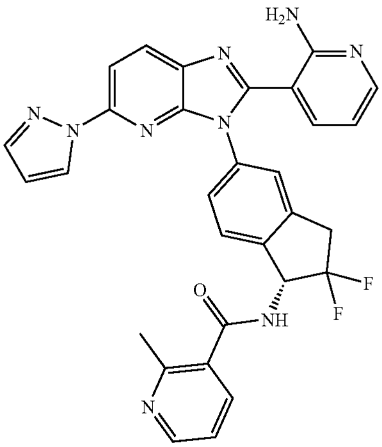 [SMILES: Cc1ncccc1C(=O)N[C@@H]1c2ccc(-n3c(-c4cccnc4N)nc4ccc(-n5cccn5)nc43)cc2CC1(F)F] |

TABLE 1-continued
| Chemical structures of selected compounds. | |
|---|---|
| Cpd ID | Structure |
| 188 | 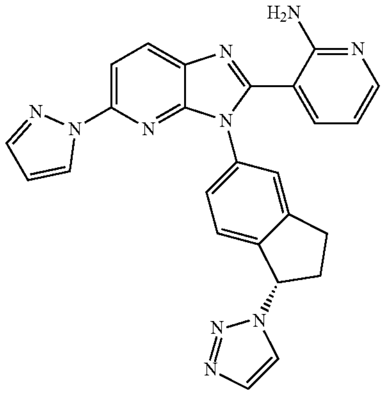 |
| 189 | 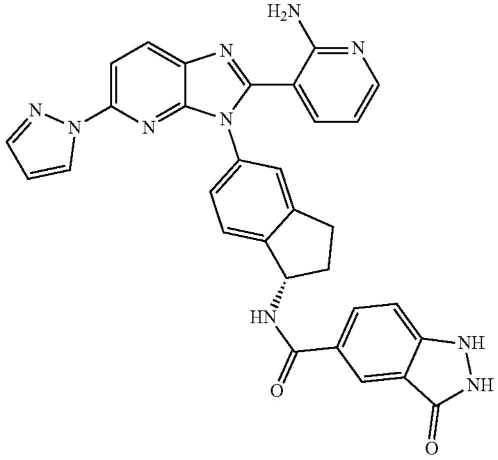 [SMILES: Nc1ncccc1-c1nc2ccc(-n3cccn3)nc2n1-c1ccc2c(c1)CC[C@@H]2NC(=O)c1ccc2[nH][nH]c(=O)c2c1] |
| 190 | 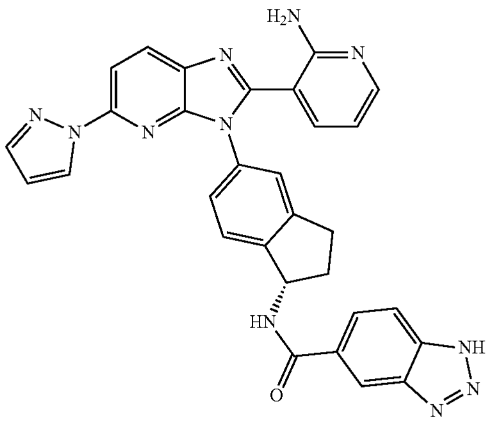 [SMILES: Nc1ncccc1-c1nc2ccc(-n3cccn3)nc2n1-c1ccc2c(c1)CC[C@@H]2NC(=O)c1ccc2[nH]nnc2c1] |

TABLE 1-continued
| Chemical structures of selected compounds. | |
|---|---|
| Cpd ID | Structure |
| 191 | 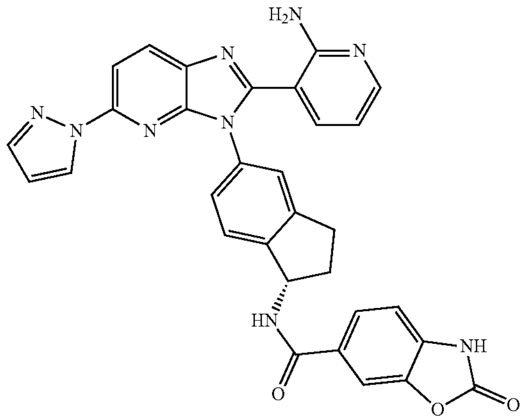 [SMILES: Nc1ncccc1-c1nc2ccc(-n3cccn3)nc2n1-c1ccc2c(c1)CC[C@@H]2NC(=O)c1ccc2[nH]c(=O)oc2c1] |
| 192 | 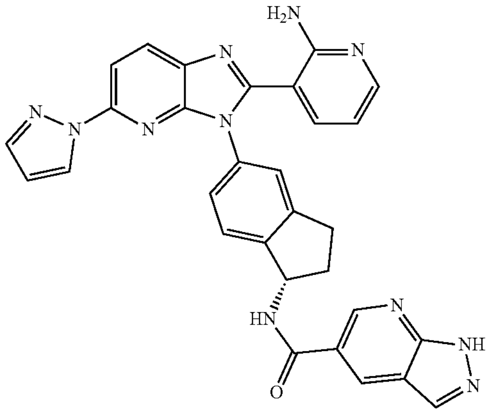 [SMILES: Nc1ncccc1-c1nc2ccc(-n3cccn3)nc2n1-c1ccc2c(c1)CC[C@@H]2NC(=O)c1cnc2[nH]ncc2c1] |
| 193 | 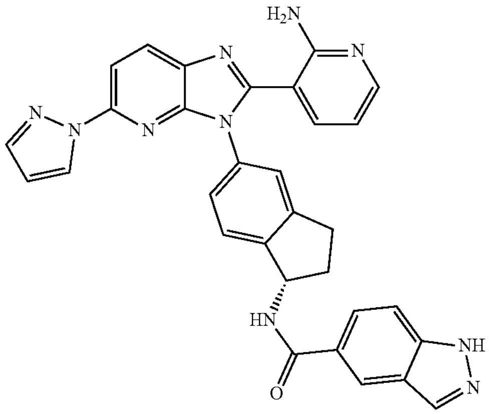 [SMILES: Nc1ncccc1-c1nc2ccc(-n3cccn3)nc2n1-c1ccc2c(c1)CC[C@@H]2NC(=O)c1ccc2[nH]ncc2c1] |

TABLE 1-continued
| Chemical structures of selected compounds. | |
|---|---|
| Cpd ID | Structure |
| 194 | 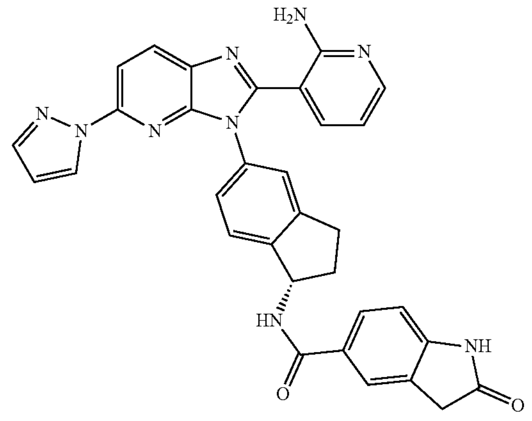 [SMILES: Nc1ncccc1-c1nc2ccc(-n3cccn3)nc2n1-c1ccc2c(c1)CC[C@@H]2NC(=O)c1ccc2c(c1)CC(=O)N2] |
| 195 | 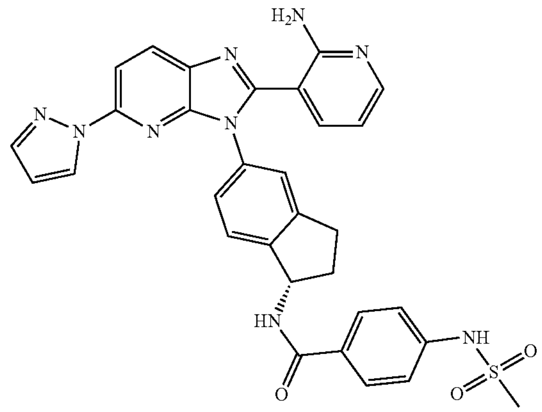 [SMILES: CS(=O)(=O)Nc1ccc(C(=O)N[C@H]2CCc3cc(-n4c(-c5cccnc5N)nc5ccc(-n6cccn6)nc54)ccc32)cc1] |
| 196 | 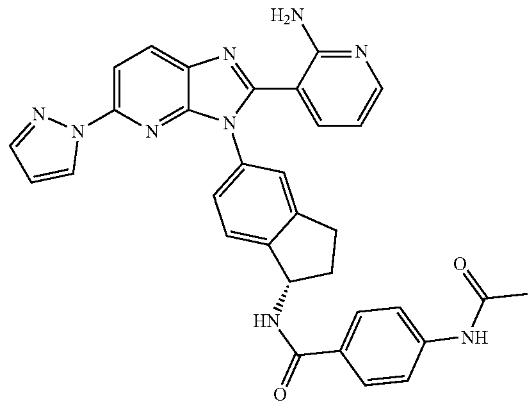 [SMILES: CC(=O)Nc1ccc(C(=O)N[C@H]2CCc3cc(-n4c(-c5cccnc5N)nc5ccc(-n6cccn6)nc54)ccc32)cc1] |

TABLE 1-continued
| Chemical structures of selected compounds. | |
|---|---|
| Cpd ID | Structure |
| 197 | 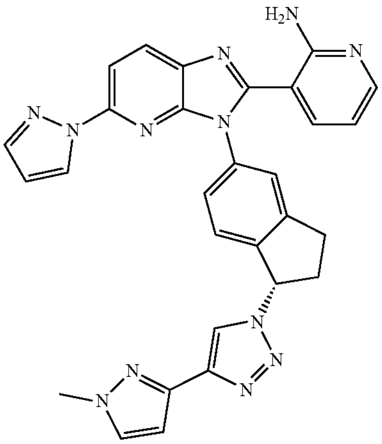 [SMILES: Cn1ccc(-c2cn([C@H]3CCc4cc(-n5c(-c6cccnc6N)nc6ccc(-n7cccn7)nc65)ccc43)nn2)n1] |
| 198 | 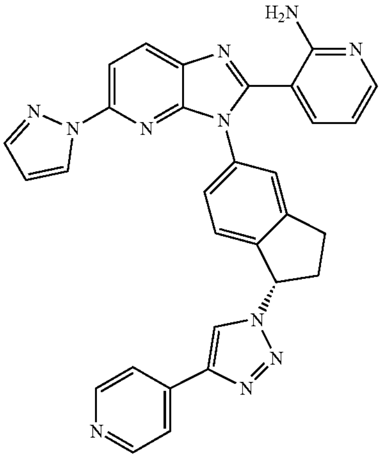 |
| 199 | 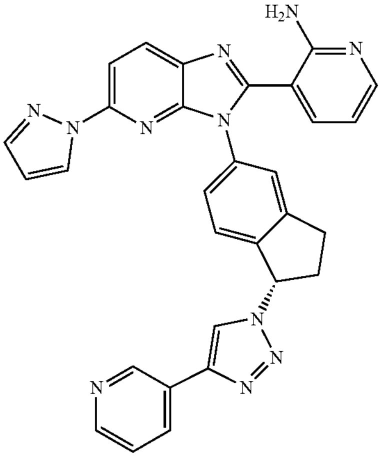 |

TABLE 1-continued
| Chemical structures of selected compounds. | |
|---|---|
| Cpd ID | Structure |
| 200 | 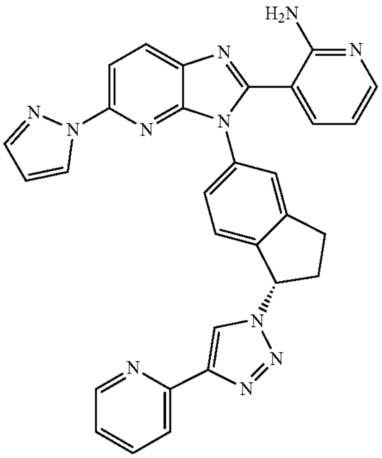 |
| 201 | 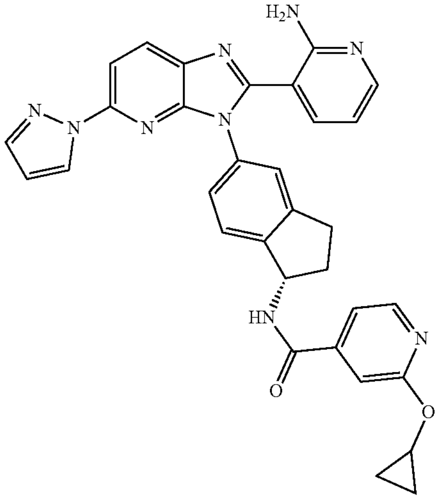 [SMILES: Nc1ncccc1-c1nc2ccc(-n3cccn3)nc2n1-c1ccc2c(c1)CC[C@@H]2NC(=O)c1ccnc(OC2CC2)c1] |
| 202 | 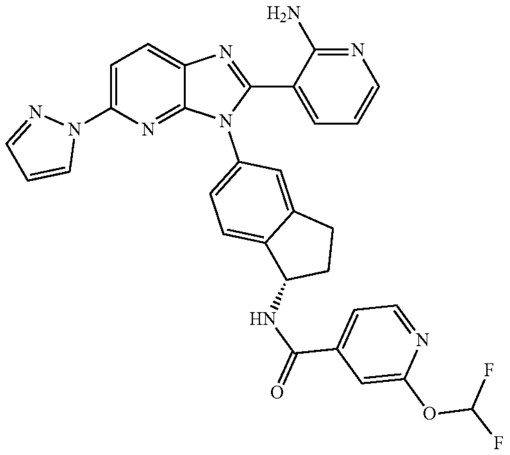 [SMILES: Nc1ncccc1-c1nc2ccc(-n3cccn3)nc2n1-c1ccc2c(c1)CC[C@@H]2NC(=O)c1ccnc(OC(F)F)c1] |

TABLE 1-continued
| Chemical structures of selected compounds. | |
|---|---|
| Cpd ID | Structure |
| 203 | 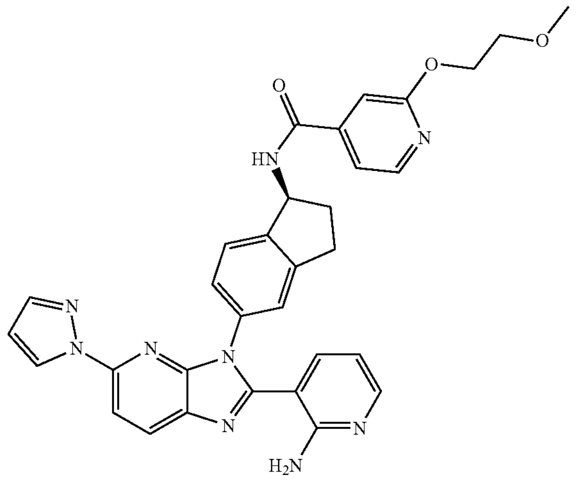 [SMILES: COCCOc1cc(C(=O)N[C@H]2CCc3cc(-n4c(-c5cccnc5N)nc5ccc(-n6cccn6)nc54)ccc32)ccn1] |
| 204 | 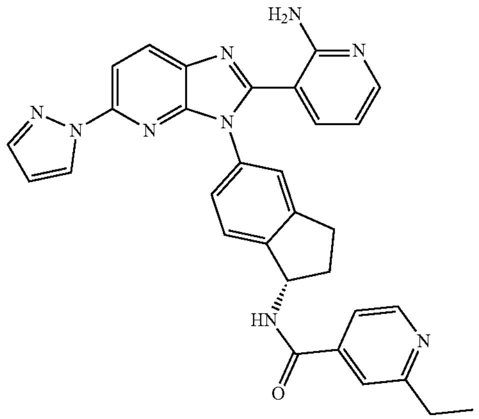 [SMILES: CCc1cc(C(=O)N[C@H]2CCc3cc(-n4c(-c5cccnc5N)nc5ccc(-n6cccn6)nc54)ccc32)ccn1] |
| 205 | 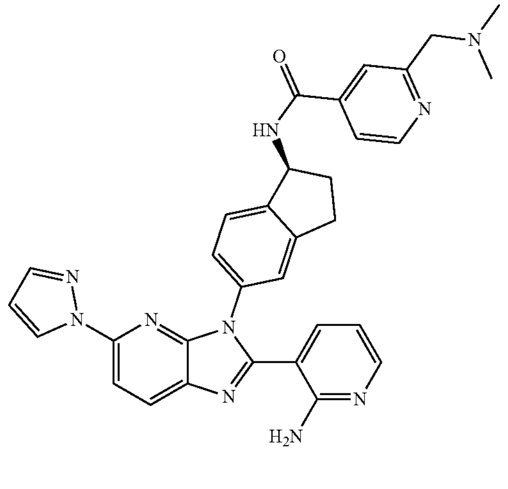 [SMILES: CN(C)Cc1cc(C(=O)N[C@H]2CCc3cc(-n4c(-c5cccnc5N)nc5ccc(-n6cccn6)nc54)ccc32)ccn1] |

TABLE 1-continued
| Chemical structures of selected compounds. | |
|---|---|
| Cpd ID | Structure |
| 206 | 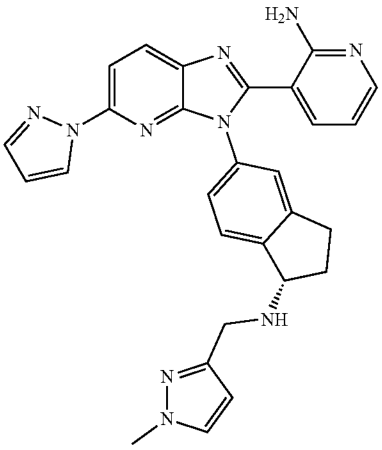 [SMILES: Cn1ccc(CN[C@H]2CCc3cc(-n4c(-c5cccnc5N)nc5ccc(-n6cccn6)nc54)ccc32)n1] |
| 207 | 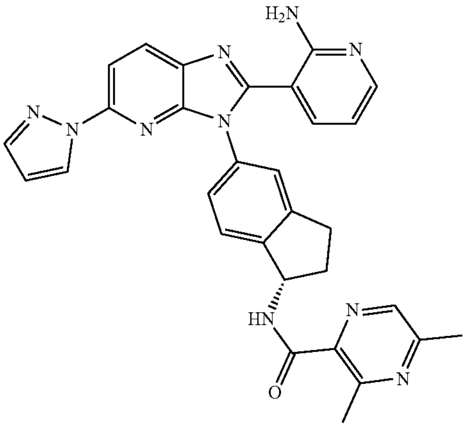 [SMILES: Cc1cnc(C(=O)N[C@H]2CCc3cc(-n4c(-c5cccnc5N)nc5ccc(-n6cccn6)nc54)ccc32)c(C)n1] |
| 208 | 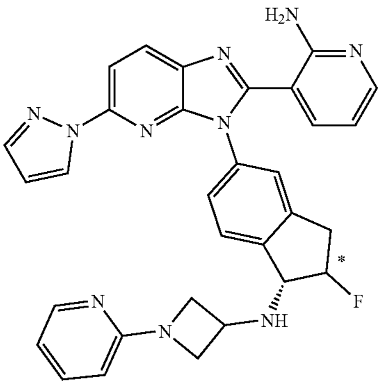 [SMILES: Nc1ncccc1-c1nc2ccc(-n3cccn3)nc2n1-c1ccc2c(c1)CC(F)[C@@H]2NC1CN(c2ccccn2)C1] |

TABLE 1-continued
| Chemical structures of selected compounds. | |
|---|---|
| Cpd ID | Structure |
| 209 | 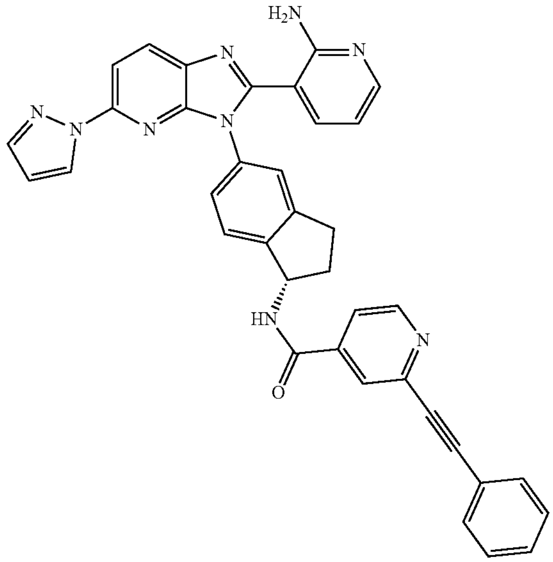 [SMILES: Nc1ncccc1-c1nc2ccc(-n3cccn3)nc2n1-c1ccc2c(c1)CC[C@@H]2NC(=O)c1ccnc(C#Cc2ccccc2)c1] |
| 210 | 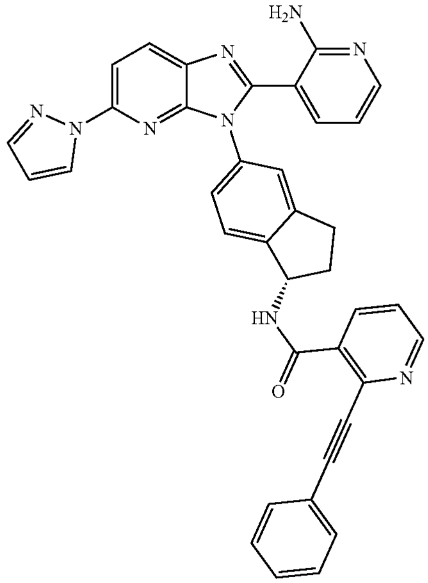 [SMILES: Nc1ncccc1-c1nc2ccc(-n3cccn3)nc2n1-c1ccc2c(c1)CC[C@@H]2NC(=O)c1cccnc1C#Cc1ccccc1] |

TABLE 1-continued
Chemical structures of selected compounds.
| Cpd ID | Structure |
| --- | --- |
| 211 | 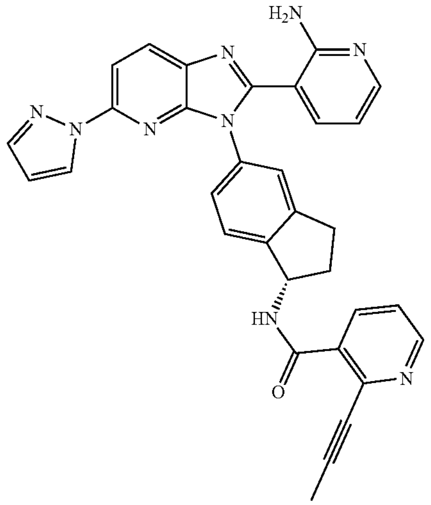 [SMILES: CC#Cc1ncccc1C(=O)N[C@H]1CCc2cc(-n3c(-c4cccnc4N)nc4ccc(-n5cccn5)nc43)ccc21] |
| 212 | 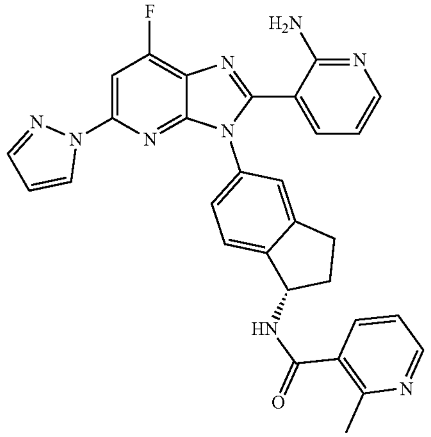 [SMILES: Cc1ncccc1C(=O)N[C@H]1CCc2cc(-n3c(-c4cccnc4N)nc4c(F)cc(-n5cccn5)nc43)ccc21] |
| 213 | 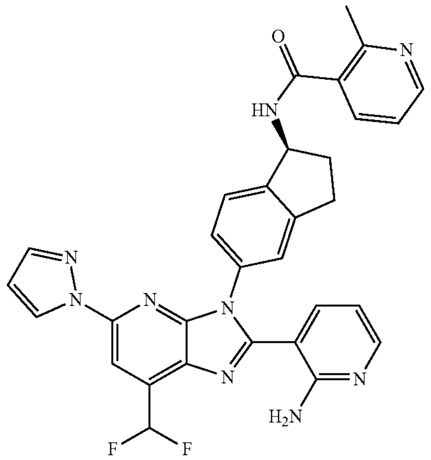 [SMILES: Cc1ncccc1C(=O)N[C@H]1CCc2cc(-n3c(-c4cccnc4N)nc4c(C(F)F)cc(-n5cccn5)nc43)ccc21] |

TABLE 1-continued
| Chemical structures of selected compounds. | |
|---|---|
| Cpd ID | Structure |
| 214 | 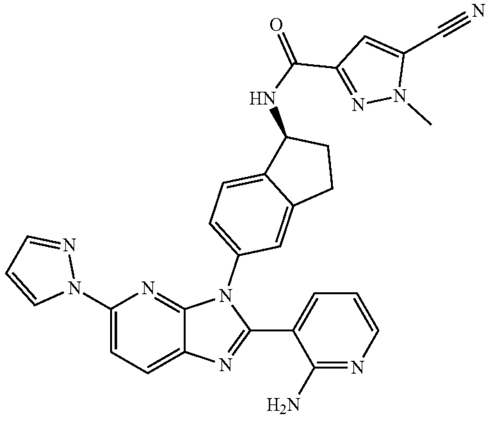 [SMILES: Cn1nc(C(=O)N[C@H]2CCc3cc(-n4c(-c5cccnc5N)nc5ccc(-n6cccn6)nc54)ccc32)cc1C#N] |
| 215 | 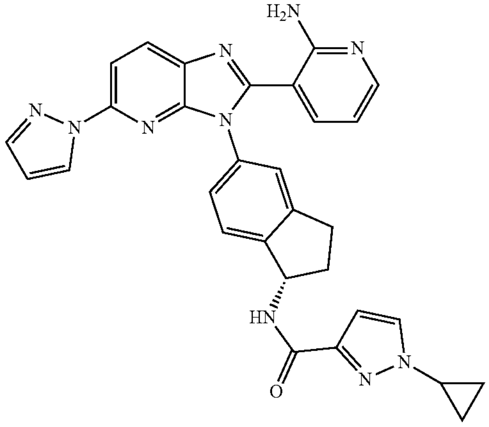 [SMILES: Nc1ncccc1-c1nc2ccc(-n3cccn3)nc2n1-c1ccc2c(c1)CC[C@@H]2NC(=O)c1ccn(C2CC2)n1] |
| 216 | 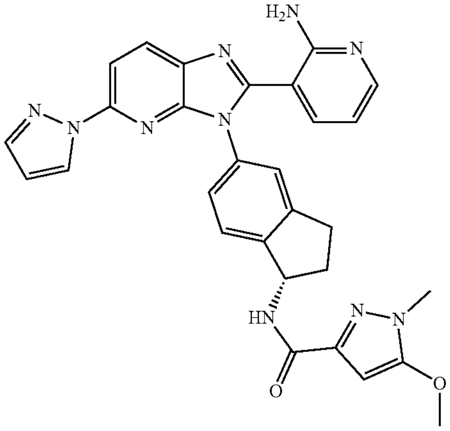 [SMILES: COc1cc(C(=O)N[C@H]2CCc3cc(-n4c(-c5cccnc5N)nc5ccc(-n6cccn6)nc54)ccc32)nn1C] |

TABLE 1-continued
| Chemical structures of selected compounds. | |
|---|---|
| Cpd ID | Structure |
| 217 | 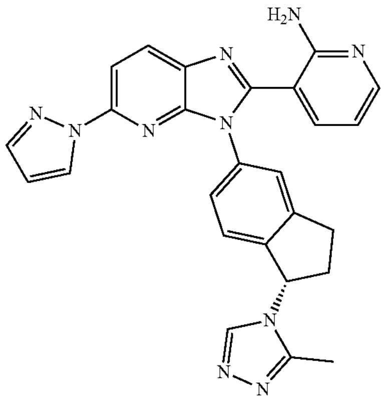 [SMILES: Cc1nncn1[C@H]1CCc2cc(-n3c(-c4cccnc4N)nc4ccc(-n5cccn5)nc43)ccc21] |
| 218 | 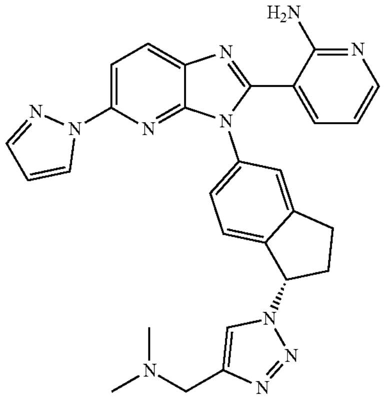 [SMILES: CN(C)Cc1cn([C@H]2CCc3cc(-n4c(-c5cccnc5N)nc5ccc(-n6cccn6)nc54)ccc32)nn1] |
| 219 | 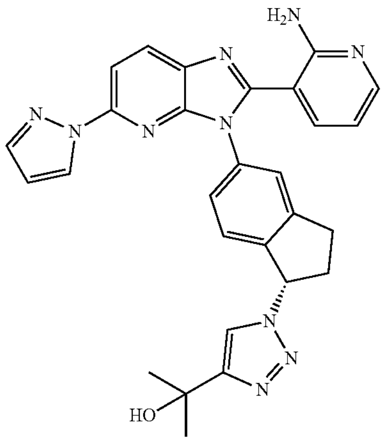 [SMILES: CC(C)(O)c1cn([C@H]2CCc3cc(-n4c(-c5cccnc5N)nc5ccc(-n6cccn6)nc54)ccc32)nn1] |

TABLE 1-continued
| Chemical structures of selected compounds. | |
|---|---|
| Cpd ID | Structure |
| 220 | 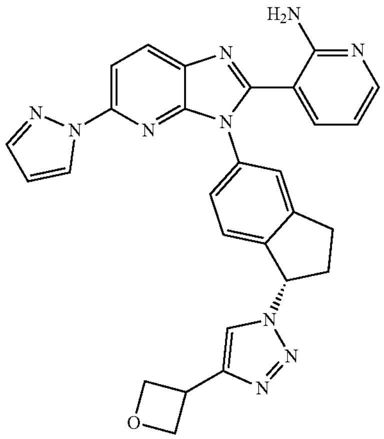 [SMILES: Nc1ncccc1-c1nc2ccc(-n3cccn3)nc2n1-c1ccc2c(c1)CC[C@@H]2n1cc(C2COC2)nn1] |
| 221 | 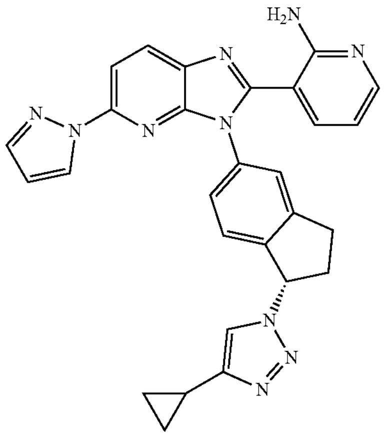 [SMILES: Nc1ncccc1-c1nc2ccc(-n3cccn3)nc2n1-c1ccc2c(c1)CC[C@@H]2n1cc(C2CC2)nn1] |
| 222 | 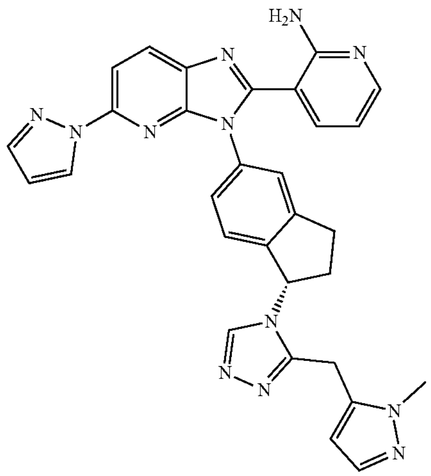 [SMILES: Cn1nccc1Cc1nncn1[C@H]1CCc2cc(-n3c(-c4cccnc4N)nc4ccc(-n5cccn5)nc43)ccc21] |

TABLE 1-continued
| Chemical structures of selected compounds. | |
|---|---|
| Cpd ID | Structure |
| 223 | 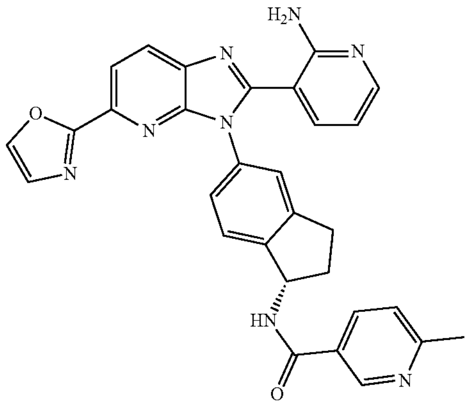 [SMILES: Cc1ccc(C(=O)N[C@H]2CCc3cc(-n4c(-c5cccnc5N)nc5ccc(-c6ncco6)nc54)ccc32)cn1] |
| 224 | 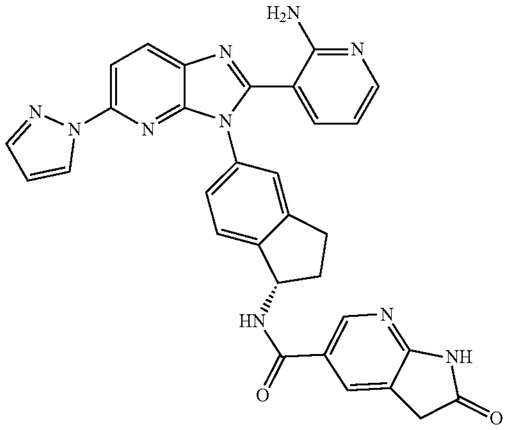 [SMILES: Nc1ncccc1-c1nc2ccc(-n3cccn3)nc2n1-c1ccc2c(c1)CC[C@@H]2NC(=O)c1cnc2c(c1)CC(=O)N2] |
| 225 | 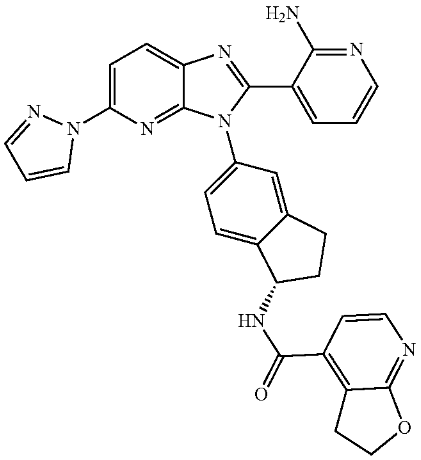 [SMILES: Nc1ncccc1-c1nc2ccc(-n3cccn3)nc2n1-c1ccc2c(c1)CC[C@@H]2NC(=O)c1ccnc2c1CCO2] |

TABLE 1-continued
| Chemical structures of selected compounds. | |
|---|---|
| Cpd ID | Structure |
| 226 | 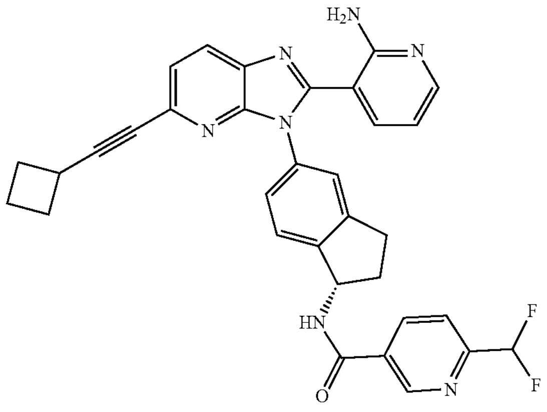 [SMILES: Nc1ncccc1-c1nc2ccc(C#CC3CCC3)nc2n1-c1ccc2c(c1)CC[C@@H]2NC(=O)c1ccc(C(F)F)nc1] |
| 227 | 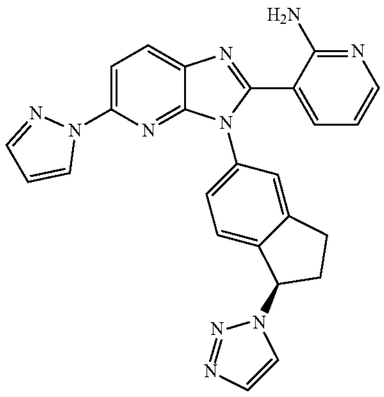 [SMILES: Nc1ncccc1-c1nc2ccc(-n3cccn3)nc2n1-c1ccc2c(c1)CC[C@H]2n1ccnn1] |
| 228 | 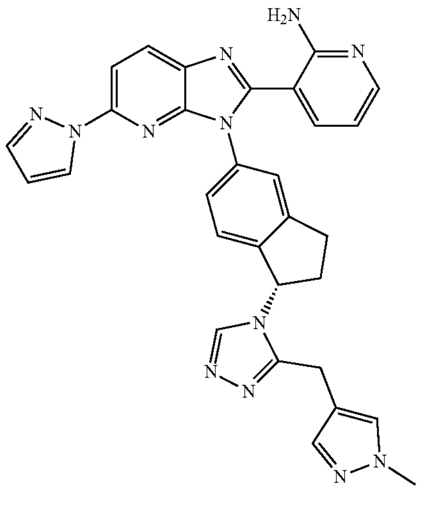 [SMILES: Cn1cc(Cc2nncn2[C@H]2CCc3cc(-n4c(-c5cccnc5N)nc5ccc(-n6cccn6)nc54)ccc32)cn1] |

TABLE 1-continued
| Chemical structures of selected compounds. | |
|---|---|
| Cpd ID | Structure |
| 229 | 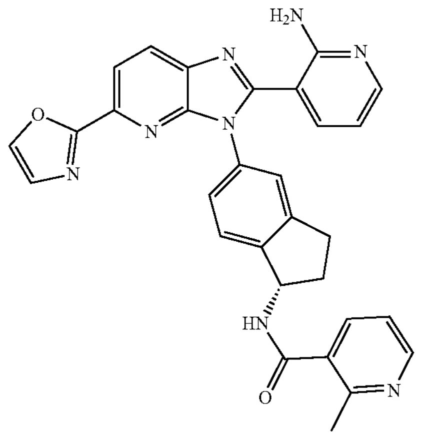 [SMILES: Cc1ncccc1C(=O)N[C@H]1CCc2cc(-n3c(-c4cccnc4N)nc4ccc(-c5ncco5)nc43)ccc21] |
| 230 | 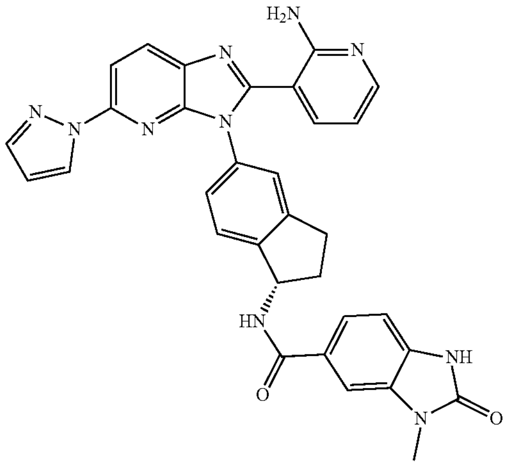 [SMILES: Cn1c(=O)[nH]c2ccc(C(=O)N[C@H]3CCc4cc(-n5c(-c6cccnc6N)nc6ccc(-n7cccn7)nc65)ccc43)cc21] |
| 231 | 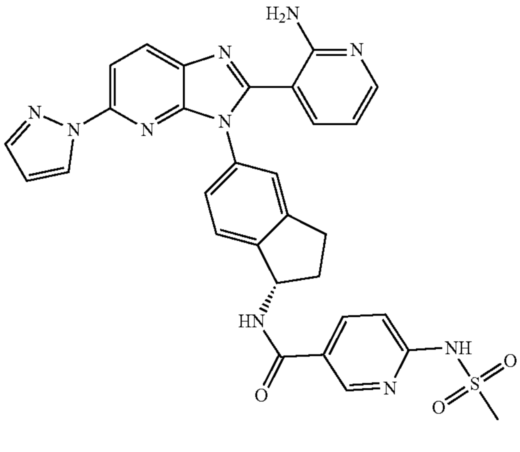 [SMILES: CS(=O)(=O)Nc1ccc(C(=O)N[C@H]2CCc3cc(-n4c(-c5cccnc5N)nc5ccc(-n6cccn6)nc54)ccc32)cn1] |

TABLE 1-continued
| Chemical structures of selected compounds. | |
|---|---|
| Cpd ID | Structure |
| 232 | 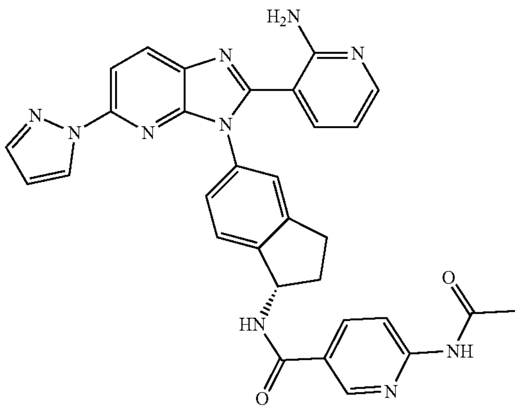 [SMILES: CC(=O)Nc1ccc(C(=O)N[C@H]2CCc3cc(-n4c(-c5cccnc5N)nc5ccc(-n6cccn6)nc54)ccc32)cn1] |
| 233 | 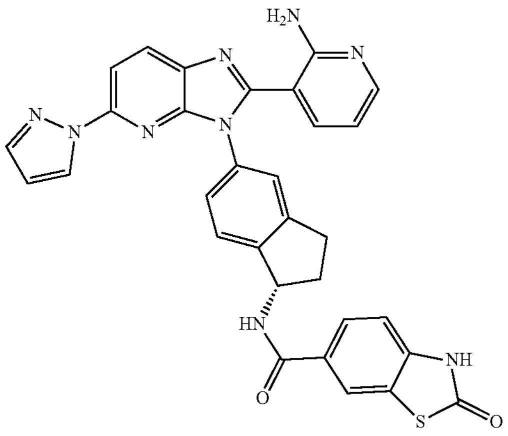 [SMILES: Nc1ncccc1-c1nc2ccc(-n3cccn3)nc2n1-c1ccc2c(c1)CC[C@@H]2NC(=O)c1ccc2[nH]c(=O)sc2c1] |
| 234 | 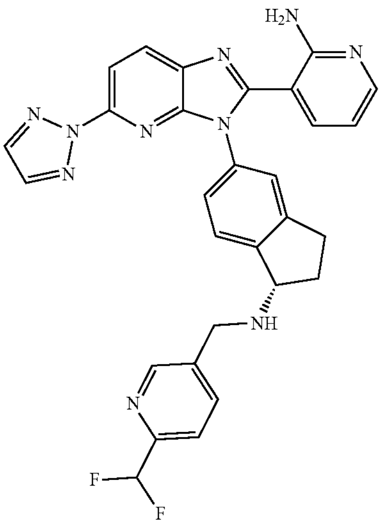 |

TABLE 1-continued
| Chemical structures of selected compounds. | |
|---|---|
| Cpd ID | Structure |
| 235 | 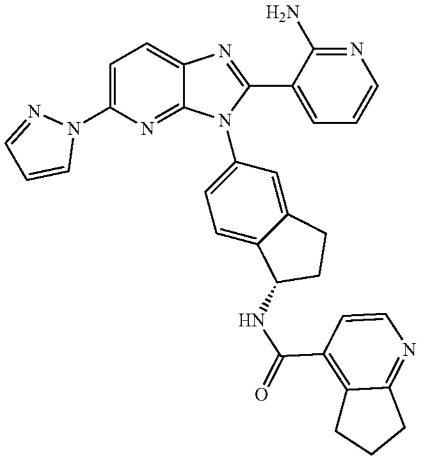 [SMILES: Nc1ncccc1-c1nc2ccc(-n3cccn3)nc2n1-c1ccc2c(c1)CC[C@@H]2NC(=O)c1ccnc2c1CCC2] |
| 236 | 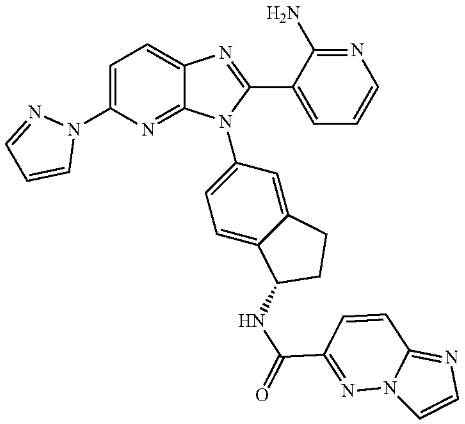 |
| 237 | 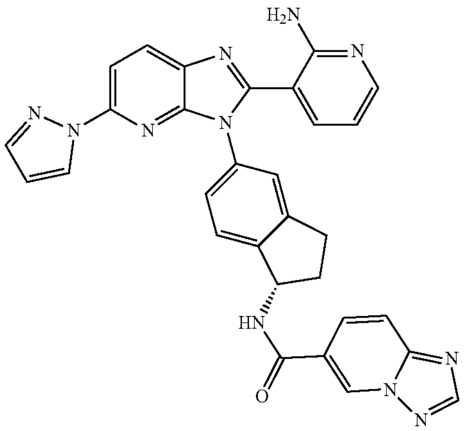 [SMILES: Nc1ncccc1-c1nc2ccc(-n3cccn3)nc2n1-c1ccc2c(c1)CC[C@@H]2NC(=O)c1ccc2ncnn2c1] |

TABLE 1-continued
| Chemical structures of selected compounds. | |
|---|---|
| Cpd ID | Structure |
| 238 | 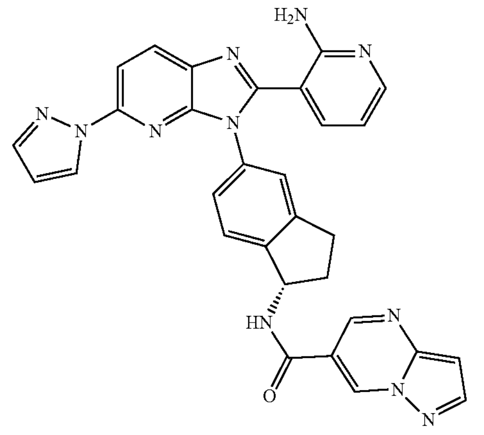 [SMILES: Nc1ncccc1-c1nc2ccc(-n3cccn3)nc2n1-c1ccc2c(c1)CC[C@@H]2NC(=O)c1cnc2ccnn2c1] |
| 239 | 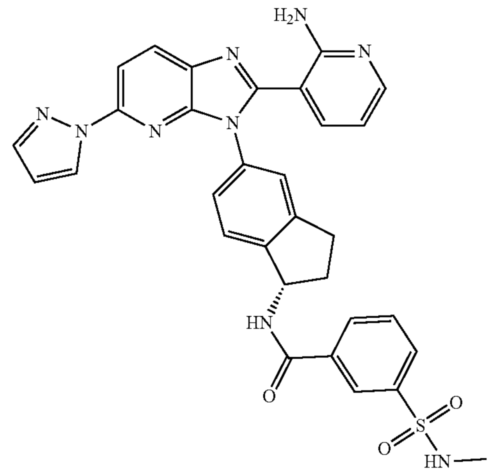 [SMILES: CNS(=O)(=O)c1cccc(C(=O)N[C@H]2CCc3cc(-n4c(-c5cccnc5N)nc5ccc(-n6cccn6)nc54)ccc32)c1] |
| 240 | 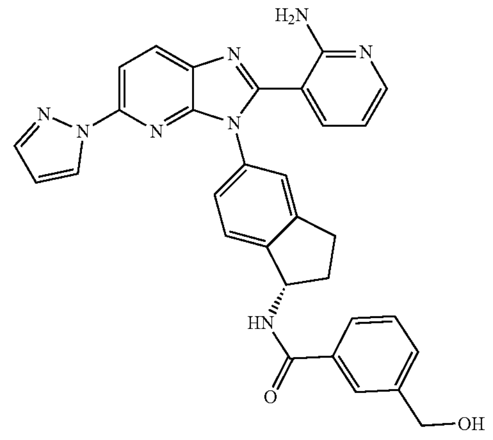 [SMILES: Nc1ncccc1-c1nc2ccc(-n3cccn3)nc2n1-c1ccc2c(c1)CC[C@@H]2NC(=O)c1cccc(CO)c1] |

TABLE 1-continued
| Chemical structures of selected compounds. | |
|---|---|
| Cpd ID | Structure |
| 241 | 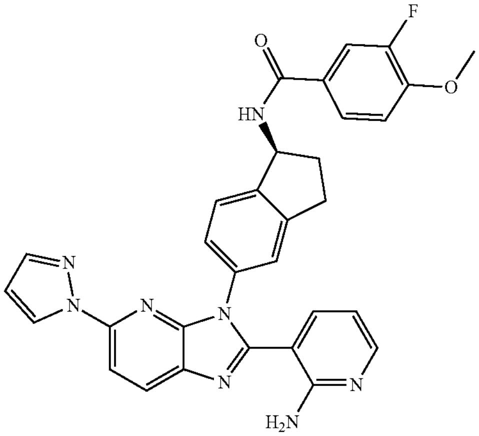 [SMILES: COc1ccc(C(=O)N[C@H]2CCc3cc(-n4c(-c5cccnc5N)nc5ccc(-n6cccn6)nc54)ccc32)cc1F] |
| 242 | 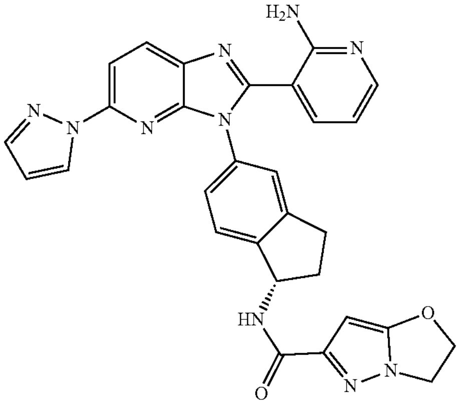 [SMILES: Nc1ncccc1-c1nc2ccc(-n3cccn3)nc2n1-c1ccc2c(c1)CC[C@@H]2NC(=O)c1cc2n(n1)CCO2] |
| 243 | 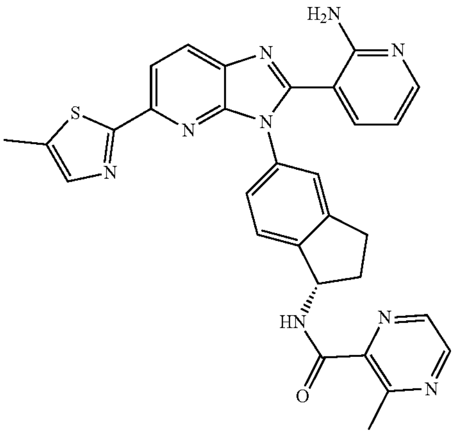 [SMILES: Cc1cnc(-c2ccc3nc(-c4cccnc4N)n(-c4ccc5c(c4)CC[C@@H]5NC(=O)c4nccnc4C)c3n2)s1] |

TABLE 1-continued
| Chemical structures of selected compounds. | |
|---|---|
| Cpd ID | Structure |
| 244 | 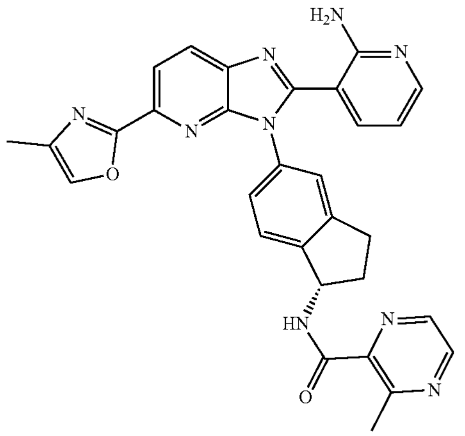 |
| 245 | 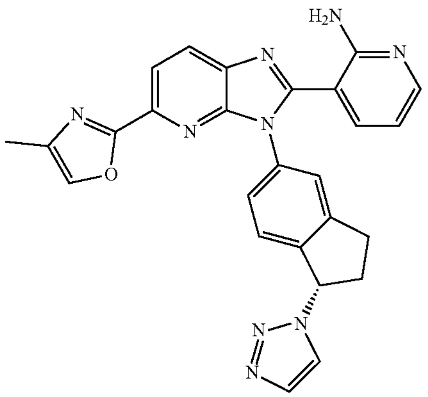 [SMILES: Cc1coc(-c2ccc3nc(-c4cccnc4N)n(-c4ccc5c(c4)CC[C@@H]5n4ccnn4)c3n2)n1] |
| 246 | 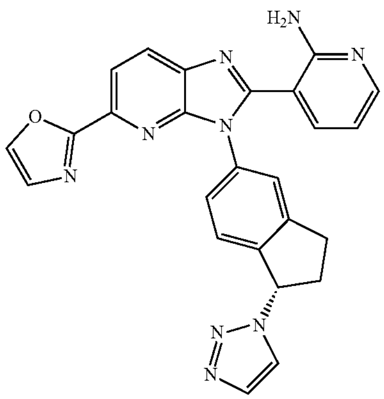 [SMILES: Nc1ncccc1-c1nc2ccc(-c3ncco3)nc2n1-c1ccc2c(c1)CC[C@@H]2n1ccnn1] |

TABLE 1-continued
| Chemical structures of selected compounds. | |
|---|---|
| Cpd ID | Structure |
| 247 | 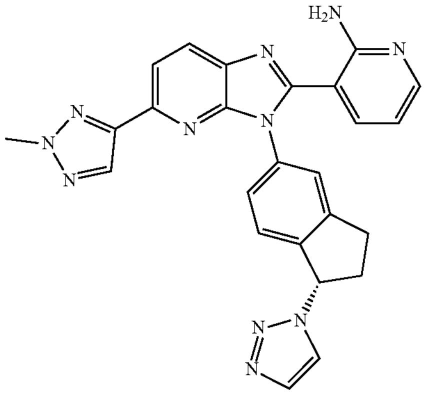 [SMILES: Cn1ncc(-c2ccc3nc(-c4cccnc4N)n(-c4ccc5c(c4)CC[C@@H]5n4ccnn4)c3n2)n1] |
| 248 | 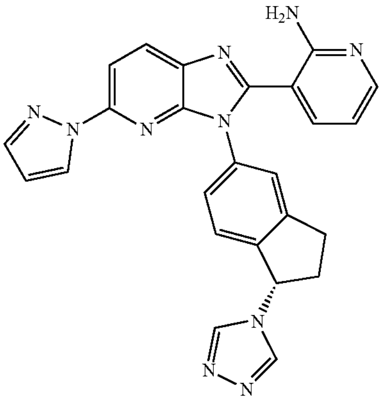 [SMILES: Nc1ncccc1-c1nc2ccc(-n3cccn3)nc2n1-c1ccc2c(c1)CC[C@@H]2n1cnnc1] |
| 249 | 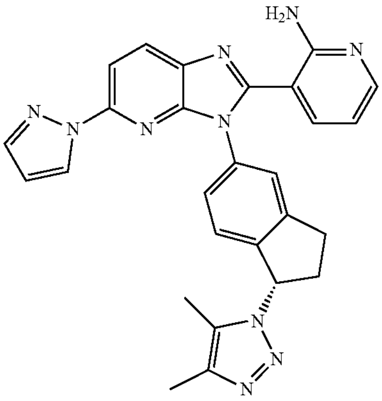 [SMILES: Cc1nnn([C@H]2CCc3cc(-n4c(-c5cccnc5N)nc5ccc(-n6cccn6)nc54)ccc32)c1C] |

TABLE 1-continued
Chemical structures of selected compounds.
| Cpd ID | Structure |
|---|---|
| 250 | 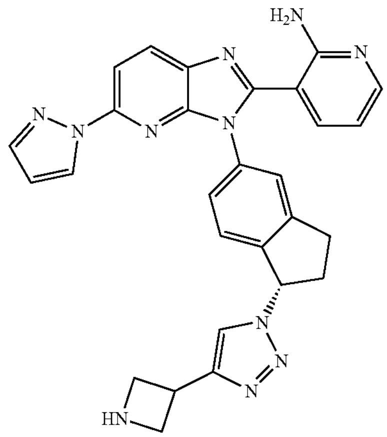 [SMILES: Nc1ncccc1-c1nc2ccc(-n3cccn3)nc2n1-c1ccc2c(c1)CC[C@@H]2n1cc(C2CNC2)nn1] |
| 251 | 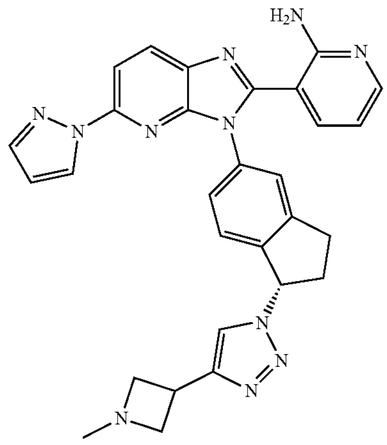 [SMILES: CN1CC(c2cn([C@H]3CCc4cc(-n5c(-c6cccnc6N)nc6ccc(-n7cccn7)nc65)ccc43)nn2)C1] |
| 252 | 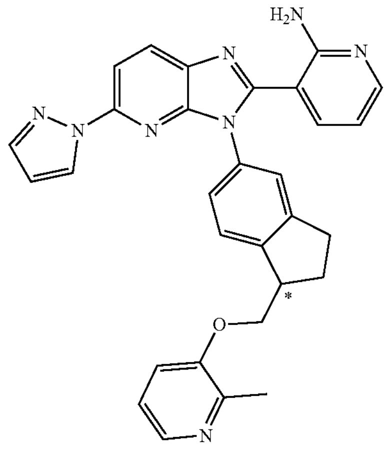 [SMILES: Cc1ncccc1OCC1CCc2cc(-n3c(-c4cccnc4N)nc4ccc(-n5cccn5)nc43)ccc21] |

TABLE 1-continued
| Chemical structures of selected compounds. | |
|---|---|
| Cpd ID | Structure |
| 253 | 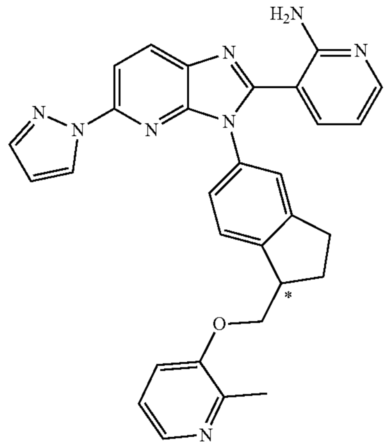 [SMILES: Cc1ncccc1OCC1CCc2cc(-n3c(-c4cccnc4N)nc4ccc(-n5cccn5)nc43)ccc21] |
| 254 | 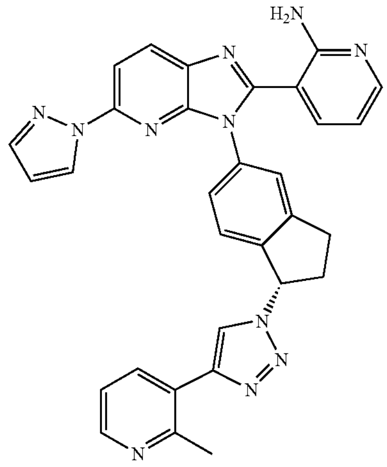 [SMILES: Cc1ncccc1-c1cn([C@H]2CCc3cc(-n4c(-c5cccnc5N)nc5ccc(-n6cccn6)nc54)ccc32)nn1] |
| 255 | 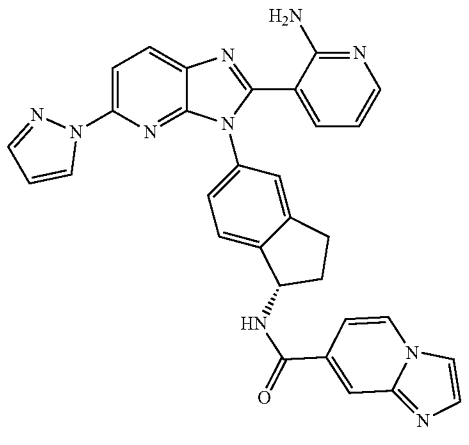 [SMILES: Nc1ncccc1-c1nc2ccc(-n3cccn3)nc2n1-c1ccc2c(c1)CC[C@@H]2NC(=O)c1ccn2ccnc2c1] |

TABLE 1-continued
| Cpd ID | Structure |
|---|---|
| | Chemical structures of selected compounds. |
| 256 | 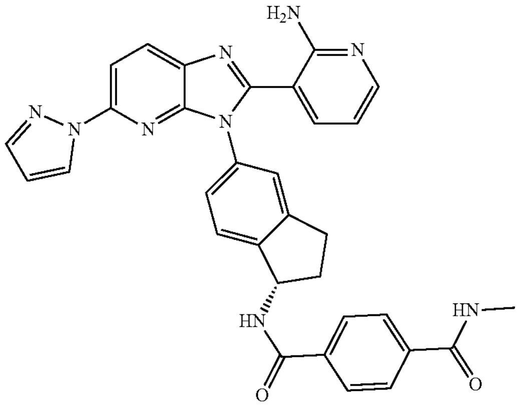 [SMILES: CNC(=O)c1ccc(C(=O)N[C@H]2CCc3cc(-n4c(-c5cccnc5N)nc5ccc(-n6cccn6)nc54)ccc32)cc1] |
| 257 | 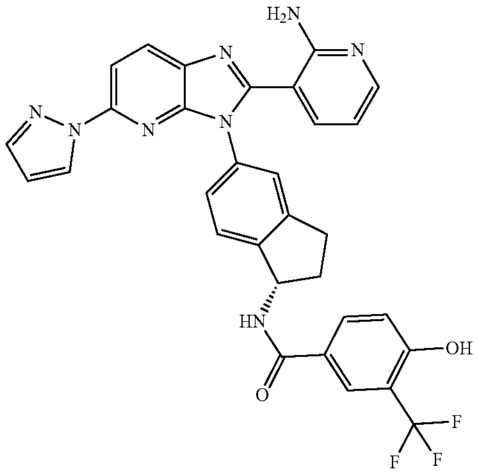 [SMILES: Nc1ncccc1-c1nc2ccc(-n3cccn3)nc2n1-c1ccc2c(c1)CC[C@@H]2NC(=O)c1ccc(O)c(C(F)(F)F)c1] |
| 258 | 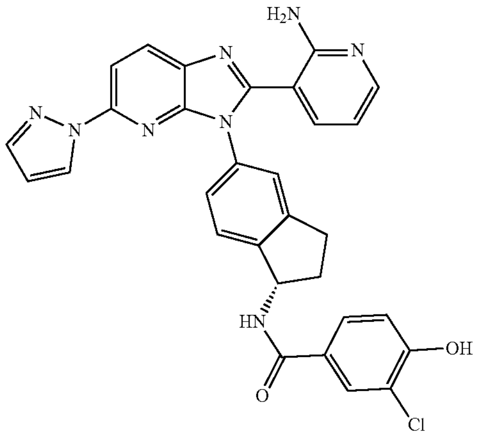 [SMILES: Nc1ncccc1-c1nc2ccc(-n3cccn3)nc2n1-c1ccc2c(c1)CC[C@@H]2NC(=O)c1ccc(O)c(Cl)c1] |

TABLE 1-continued
| Chemical structures of selected compounds. | |
|---|---|
| Cpd ID | Structure |
| 259 | 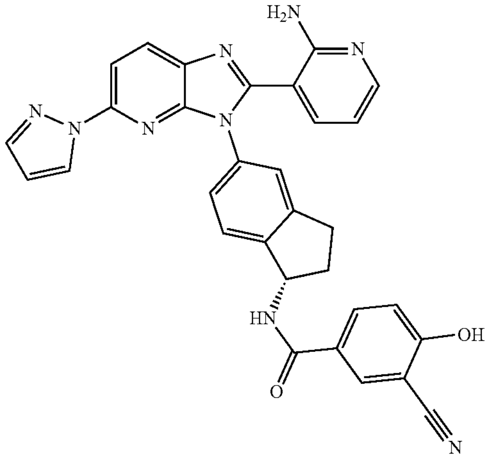 [SMILES: N#Cc1cc(C(=O)N[C@H]2CCc3cc(-n4c(-c5cccnc5N)nc5ccc(-n6cccn6)nc54)ccc32)ccc1O] |
| 260 | 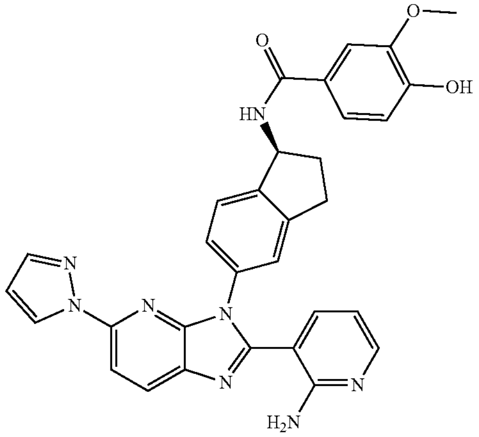 [SMILES: COc1cc(C(=O)N[C@H]2CCc3cc(-n4c(-c5cccnc5N)nc5ccc(-n6cccn6)nc54)ccc32)ccc1O] |
| 261 | 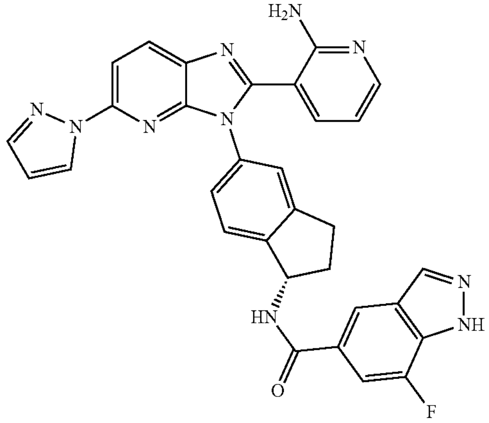 [SMILES: Nc1ncccc1-c1nc2ccc(-n3cccn3)nc2n1-c1ccc2c(c1)CC[C@@H]2NC(=O)c1cc(F)c2[nH]ncc2c1] |

TABLE 1-continued
| Chemical structures of selected compounds. | |
|---|---|
| Cpd ID | Structure |
| 262 | 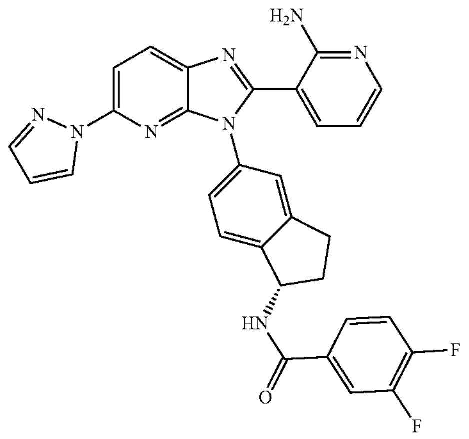 [SMILES: Nc1ncccc1-c1nc2ccc(-n3cccn3)nc2n1-c1ccc2c(c1)CC[C@@H]2NC(=O)c1ccc(F)c(F)c1] |
| 263 | 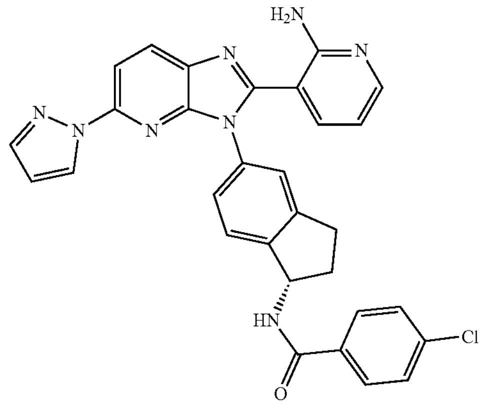 [SMILES: Nc1ncccc1-c1nc2ccc(-n3cccn3)nc2n1-c1ccc2c(c1)CC[C@@H]2NC(=O)c1ccc(Cl)cc1] |
| 264 | 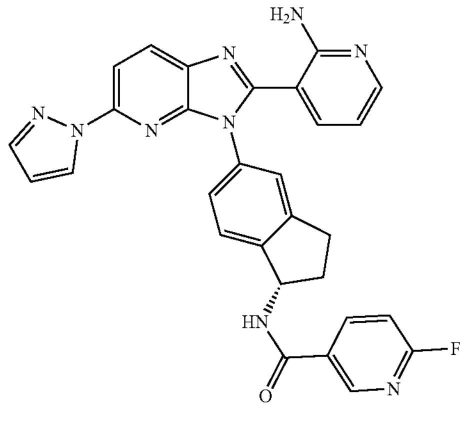 [SMILES: Nc1ncccc1-c1nc2ccc(-n3cccn3)nc2n1-c1ccc2c(c1)CC[C@@H]2NC(=O)c1ccc(F)nc1] |

TABLE 1-continued
| Chemical structures of selected compounds. | |
|---|---|
| Cpd ID | Structure |
| 265 | 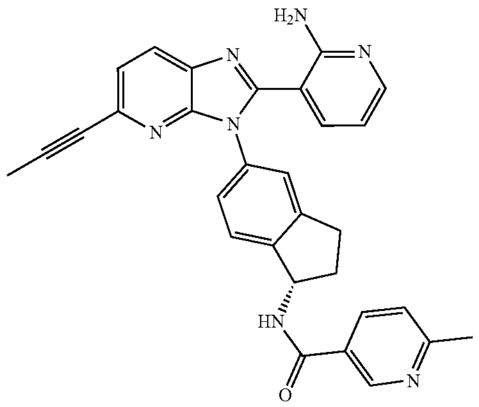 [SMILES: CC#Cc1ccc2nc(-c3cccnc3N)n(-c3ccc4c(c3)CC[C@@H]4NC(=O)c3ccc(C)nc3)c2n1] |
| 266 | 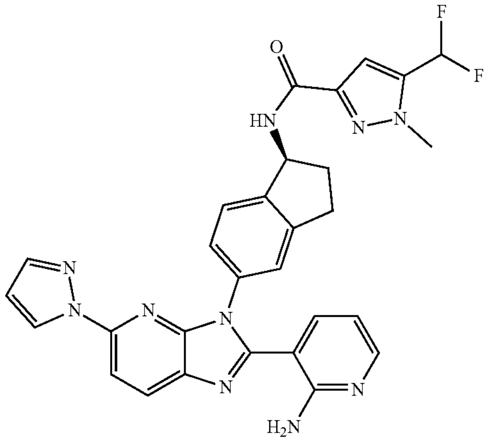 [SMILES: Cn1nc(C(=O)N[C@H]2CCc3cc(-n4c(-c5cccnc5N)nc5ccc(-n6cccn6)nc54)ccc32)cc1C(F)F] |
| 267 | 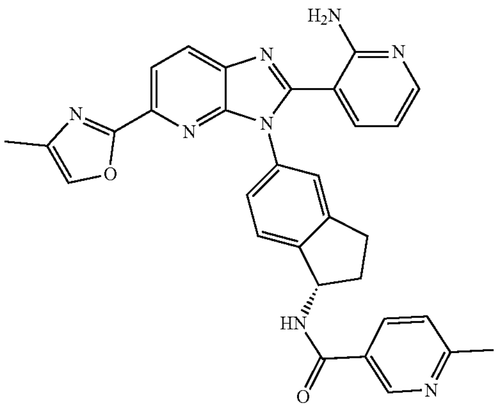 |

TABLE 1-continued
| Chemical structures of selected compounds. | |
|---|---|
| Cpd ID | Structure |
| 268 | 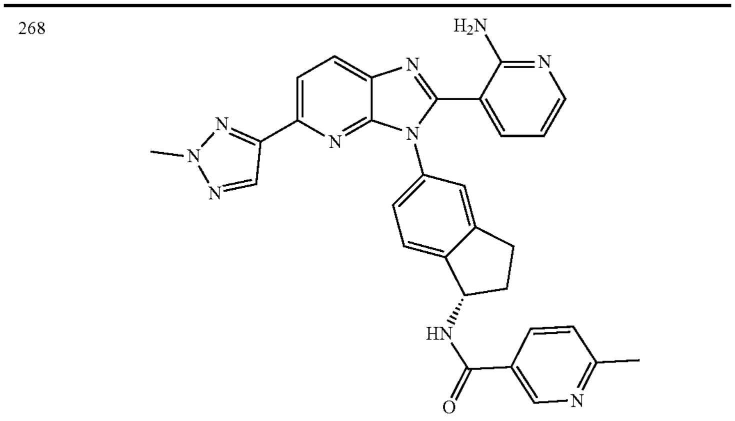 |
| 269 | 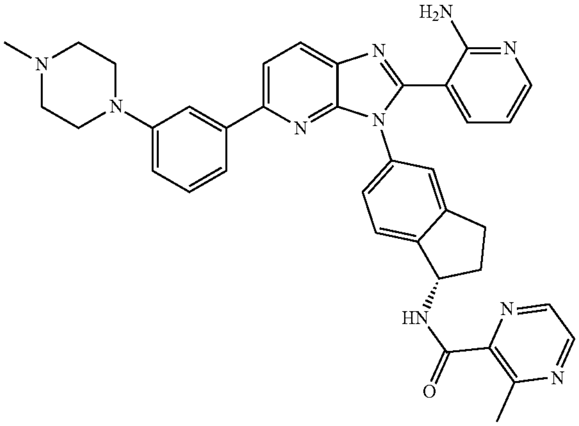 [SMILES: Cc1nccnc1C(=O)N[C@H]1CCc2cc(-n3c(-c4cccnc4N)nc4ccc(-c5cccc(N6CCN(C)CC6)c5)nc43)ccc21] |
| 270 | 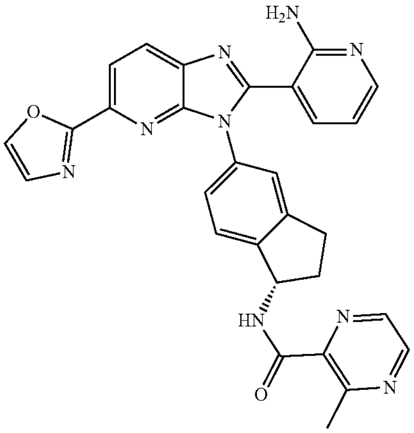 [SMILES: Cc1nccnc1C(=O)N[C@H]1CCc2cc(-n3c(-c4cccnc4N)nc4ccc(-c5ncco5)nc43)ccc21] |

TABLE 1-continued
| Chemical structures of selected compounds. | |
|---|---|
| Cpd ID | Structure |
| 271 | 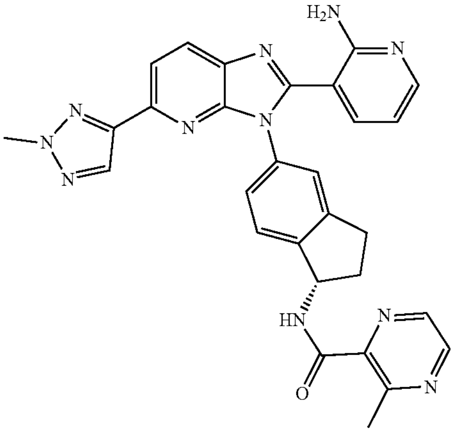 [SMILES: Cc1nccnc1C(=O)N[C@H]1CCc2cc(-n3c(-c4cccnc4N)nc4ccc(-c5cnn(C)n5)nc43)ccc21] |
| 272 | 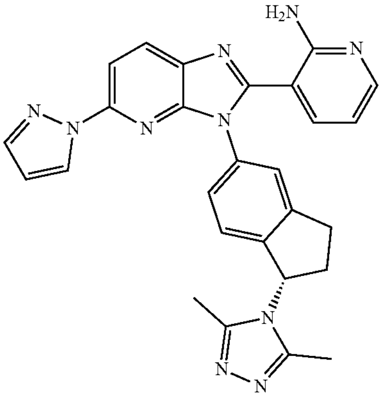 [SMILES: Cc1nnc(C)n1[C@H]1CCc2cc(-n3c(-c4cccnc4N)nc4ccc(-n5cccn5)nc43)ccc21] |
| 273 | 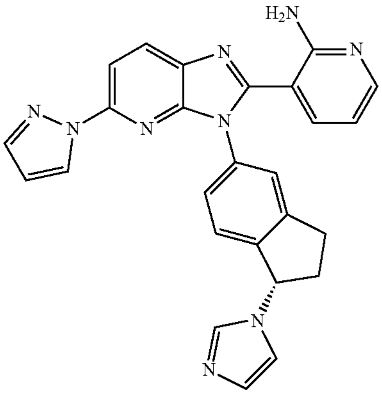 [SMILES: Nc1ncccc1-c1nc2ccc(-n3cccn3)nc2n1-c1ccc2c(c1)CC[C@@H]2n1ccnc1] |

TABLE 1-continued
| Cpd ID | Structure |
|---|---|
| Chemical structures of selected compounds. | |
| 274 | 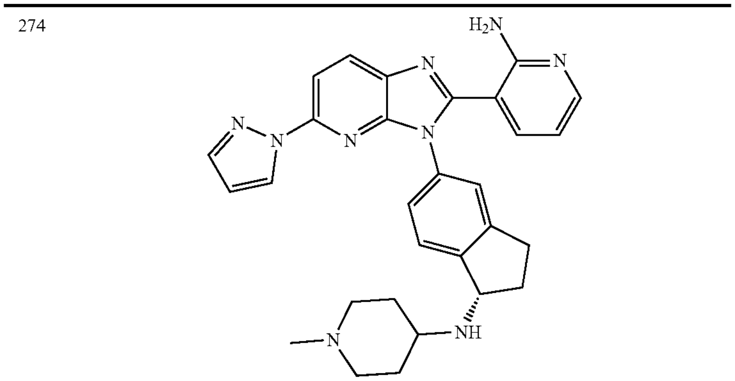 |
| 275 | 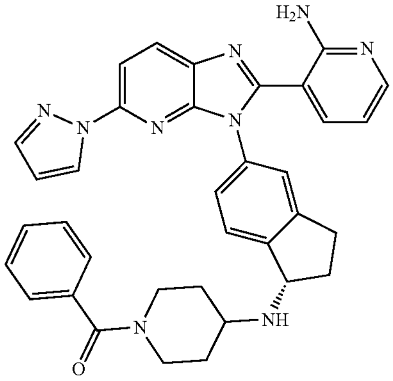 [SMILES: Nc1ncccc1-c1nc2ccc(-n3cccn3)nc2n1-c1ccc2c(c1)CC[C@@H]2NC1CCN(C(=O)c2ccccc2)CC1] |
| 276 | 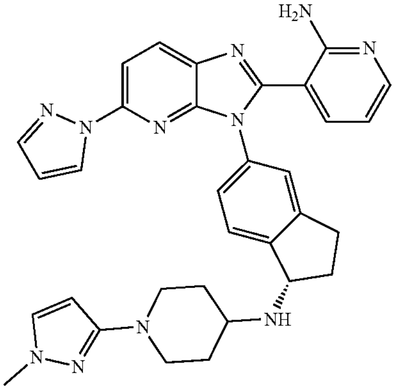 [SMILES: Cn1ccc(N2CCC(N[C@H]3CCc4cc(-n5c(-c6cccnc6N)nc6ccc(-n7cccn7)nc65)ccc43)CC2)n1] |
| 277 | 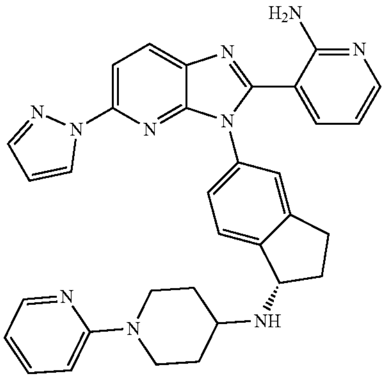 [SMILES: Nc1ncccc1-c1nc2ccc(-n3cccn3)nc2n1-c1ccc2c(c1)CC[C@@H]2NC1CCN(c2ccccn2)CC1] |

TABLE 1-continued
| Chemical structures of selected compounds. | |
|---|---|
| Cpd ID | Structure |
| 279 | 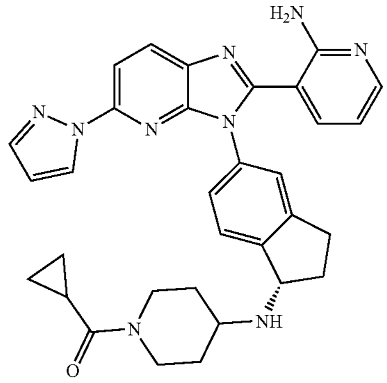 [SMILES: Nc1ncccc1-c1nc2ccc(-n3cccn3)nc2n1-c1ccc2c(c1)CC[C@@H]2NC1CCN(C(=O)C2CC2)CC1] |
| 280 | 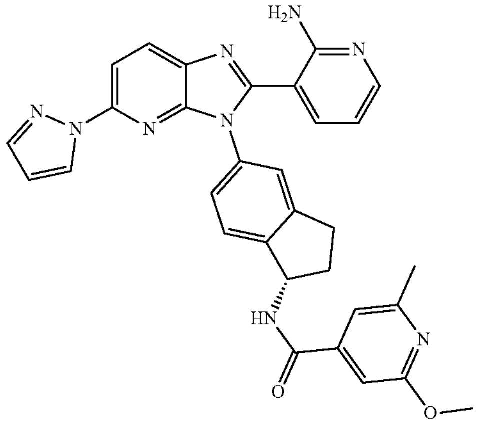 [SMILES: COc1cc(C(=O)N[C@H]2CCc3cc(-n4c(-c5cccnc5N)nc5ccc(-n6cccn6)nc54)ccc32)cc(C)n1] |
| 281 | 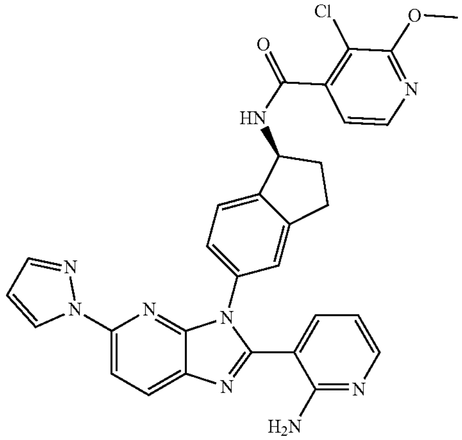 [SMILES: COc1nccc(C(=O)N[C@H]2CCc3cc(-n4c(-c5cccnc5N)nc5ccc(-n6cccn6)nc54)ccc32)c1Cl] |

TABLE 1-continued
| Cpd ID | Structure |
|---|---|
| 282 | 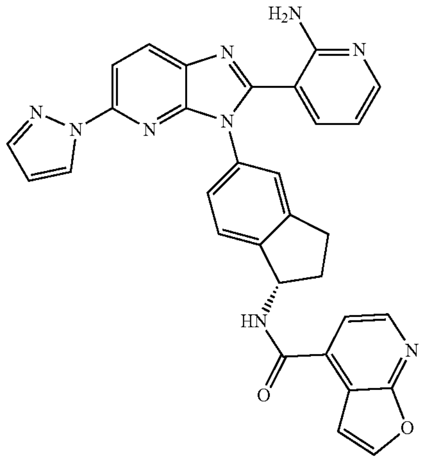 [SMILES: Nc1ncccc1-c1nc2ccc(-n3cccn3)nc2n1-c1ccc2c(c1)CC[C@@H]2NC(=O)c1ccnc2occc12] |
| 283 | 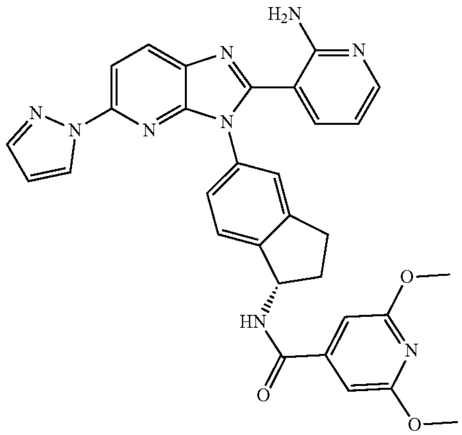 [SMILES: COc1cc(C(=O)N[C@H]2CCc3cc(-n4c(-c5cccnc5N)nc5ccc(-n6cccn6)nc54)ccc32)cc(OC)n1] |
| 284 | 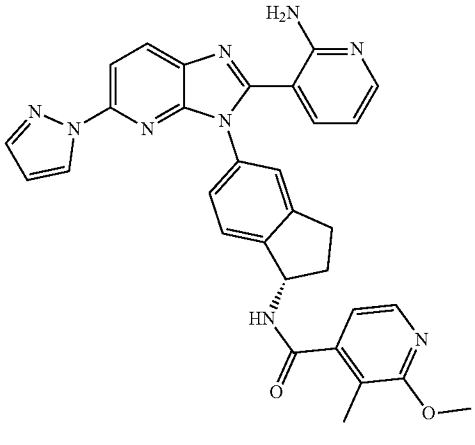 [SMILES: COc1nccc(C(=O)N[C@H]2CCc3cc(-n4c(-c5cccnc5N)nc5ccc(-n6cccn6)nc54)ccc32)c1C] |

TABLE 1-continued
| Chemical structures of selected compounds. | |
|---|---|
| Cpd ID | Structure |
| 285 | 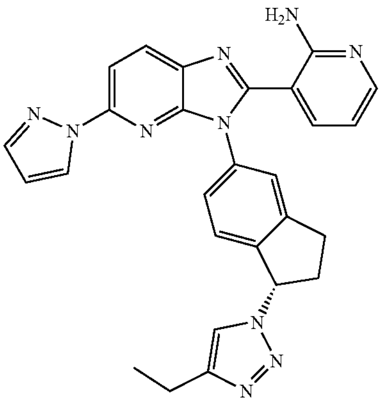 [SMILES: CCc1cn([C@H]2CCc3cc(-n4c(-c5cccnc5N)nc5ccc(-n6cccn6)nc54)ccc32)nn1] |
| 286 | 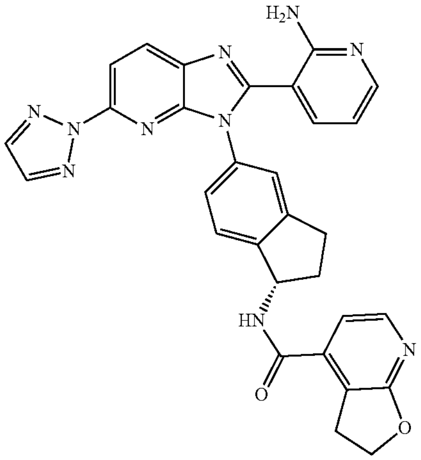 [SMILES: Nc1ncccc1-c1nc2ccc(-n3nccn3)nc2n1-c1ccc2c(c1)CC[C@@H]2NC(=O)c1ccnc2c1CCO2] |
| 287 | 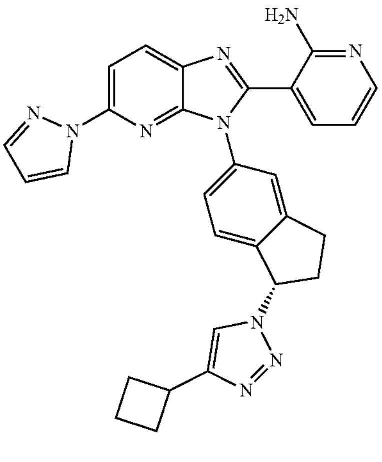 [SMILES: Nc1ncccc1-c1nc2ccc(-n3cccn3)nc2n1-c1ccc2c(c1)CC[C@@H]2n1cc(C2CCC2)nn1] |

TABLE 1-continued
| Chemical structures of selected compounds. | |
|---|---|
| Cpd ID | Structure |
| 288 | 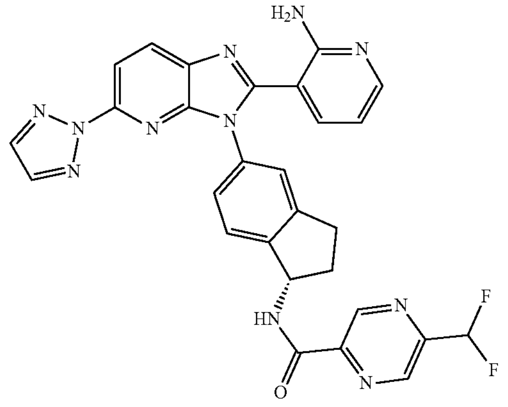 [SMILES: Nc1ncccc1-c1nc2ccc(-n3nccn3)nc2n1-c1ccc2c(c1)CC[C@@H]2NC(=O)c1cnc(C(F)F)cn1] |
| 289 | 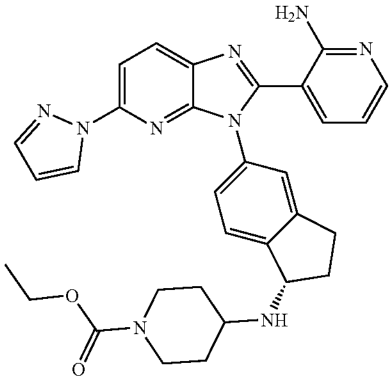 [SMILES: CCOC(=O)N1CCC(N[C@H]2CCc3cc(-n4c(-c5cccnc5N)nc5ccc(-n6cccn6)nc54)ccc32)CC1] |
| 290 | 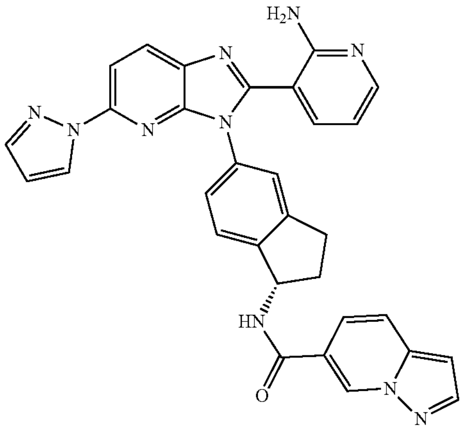 [SMILES: Nc1ncccc1-c1nc2ccc(-n3cccn3)nc2n1-c1ccc2c(c1)CC[C@@H]2NC(=O)c1ccc2ccnn2c1] |

TABLE 1-continued
| Chemical structures of selected compounds. | |
|---|---|
| Cpd ID | Structure |
| 291 | 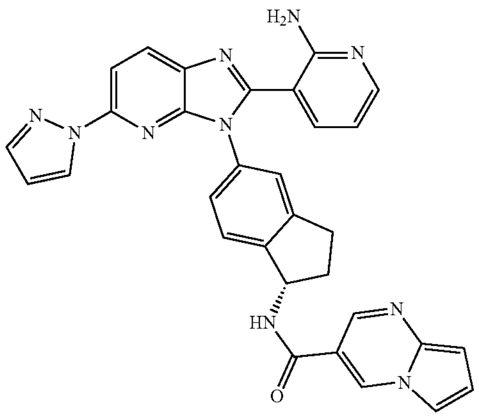 [SMILES: Nc1ncccc1-c1nc2ccc(-n3cccn3)nc2n1-c1ccc2c(c1)CC[C@@H]2NC(=O)c1cnc2cccn2c1] |
| 292 | 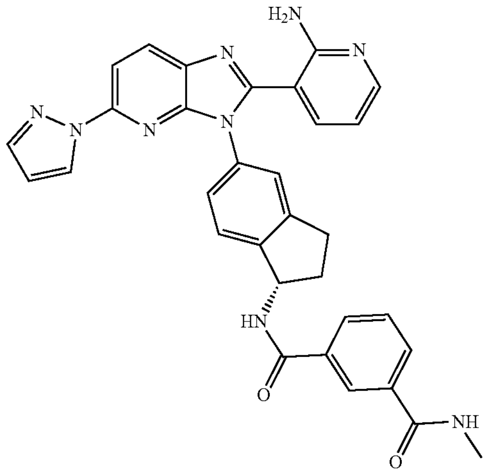 [SMILES: CNC(=O)c1cccc(C(=O)N[C@H]2CCc3cc(-n4c(-c5cccnc5N)nc5ccc(-n6cccn6)nc54)ccc32)c1] |
| 293 | 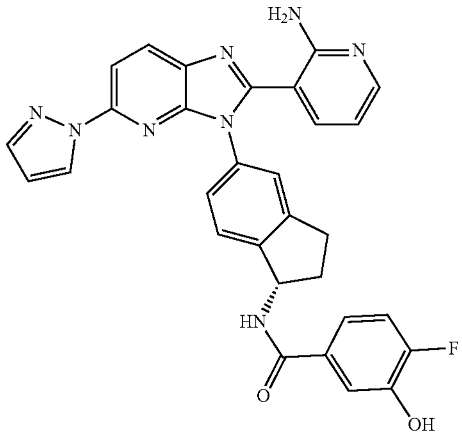 [SMILES: Nc1ncccc1-c1nc2ccc(-n3cccn3)nc2n1-c1ccc2c(c1)CC[C@@H]2NC(=O)c1ccc(F)c(O)c1] |

TABLE 1-continued
Chemical structures of selected compounds.
| Cpd ID | Structure |
|---|---|
| 294 | 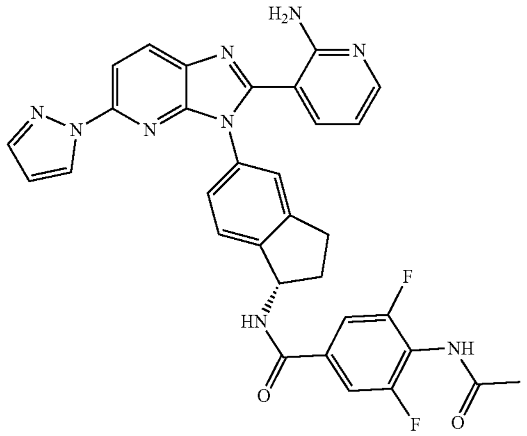 [SMILES: CC(=O)Nc1c(F)cc(C(=O)N[C@H]2CCc3cc(-n4c(-c5cccnc5N)nc5ccc(-n6cccn6)nc54)ccc32)cc1F] |
| 295 | 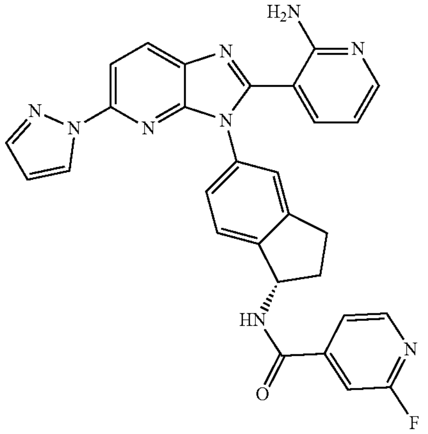 [SMILES: Nc1ncccc1-c1nc2ccc(-n3cccn3)nc2n1-c1ccc2c(c1)CC[C@@H]2NC(=O)c1ccnc(F)c1] |
| 296 | 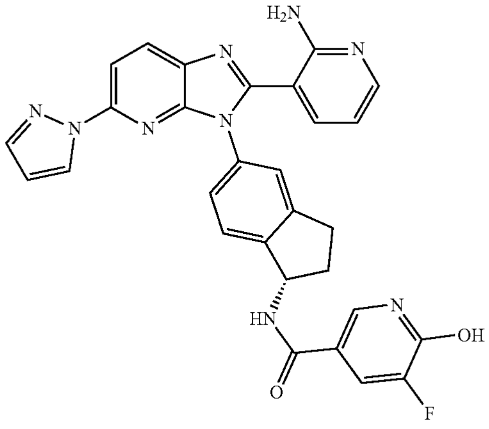 [SMILES: Nc1ncccc1-c1nc2ccc(-n3cccn3)nc2n1-c1ccc2c(c1)CC[C@@H]2NC(=O)c1cnc(O)c(F)c1] |

TABLE 1-continued
| Chemical structures of selected compounds. | |
|---|---|
| Cpd ID | Structure |
| 297 | 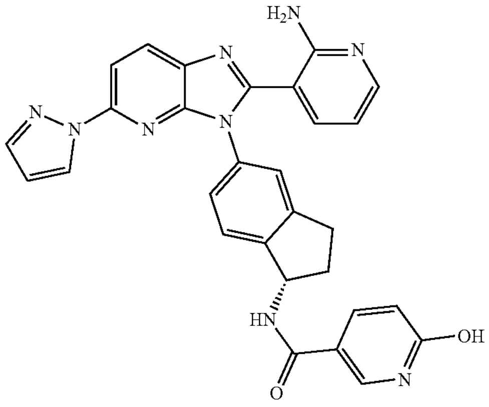 [SMILES: Nc1ncccc1-c1nc2ccc(-n3cccn3)nc2n1-c1ccc2c(c1)CC[C@@H]2NC(=O)c1ccc(O)nc1] |
| 298 | 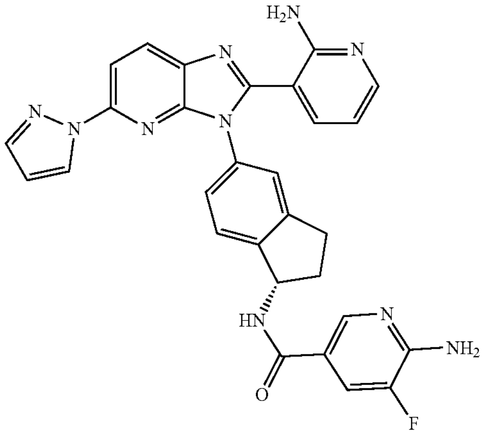 [SMILES: Nc1ncc(C(=O)N[C@H]2CCc3cc(-n4c(-c5cccnc5N)nc5ccc(-n6cccn6)nc54)ccc32)cc1F] |
| 299 | 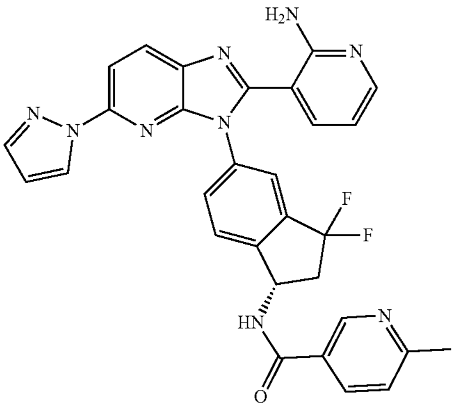 [SMILES: Cc1ccc(C(=O)N[C@H]2CC(F)(F)c3cc(-n4c(-c5cccnc5N)nc5ccc(-n6cccn6)nc54)ccc32)cn1] |

TABLE 1-continued
| Chemical structures of selected compounds. | |
|---|---|
| Cpd ID | Structure |
| 300 | 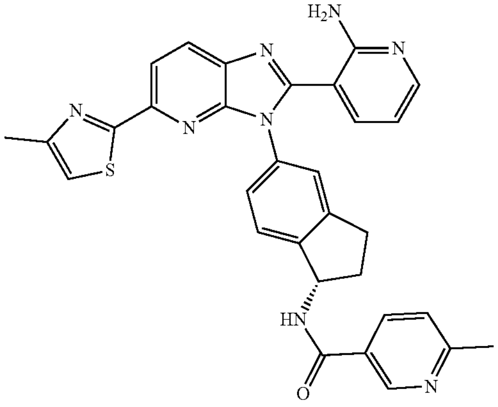 |
| 301 | 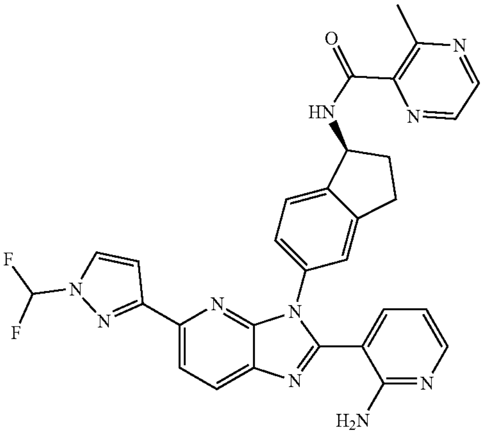 [SMILES: Cc1nccnc1C(=O)N[C@H]1CCc2cc(-n3c(-c4cccnc4N)nc4ccc(-c5ccn(C(F)F)n5)nc43)ccc21] |
| 302 | 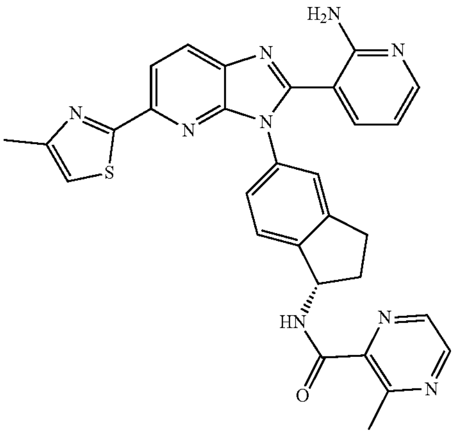 [SMILES: Cc1csc(-c2ccc3nc(-c4cccnc4N)n(-c4ccc5c(c4)CC[C@@H]5NC(=O)c4nccnc4C)c3n2)n1] |

TABLE 1-continued
| Cpd ID | Structure |
| --- | --- |
| | Chemical structures of selected compounds. |
| 303 | 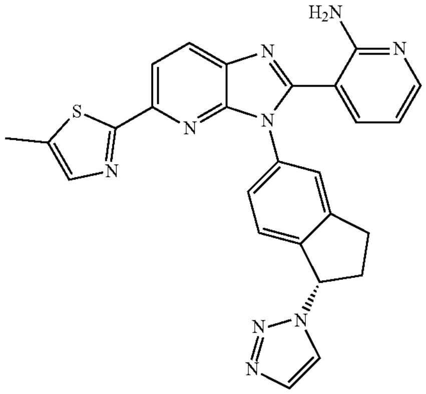 [SMILES: Cc1cnc(-c2ccc3nc(-c4cccnc4N)n(-c4ccc5c(c4)CC[C@@H]5n4ccnn4)c3n2)s1] |
| 304 | 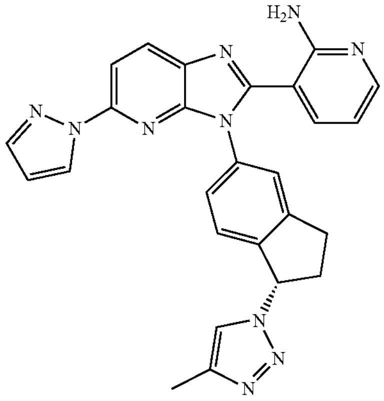 [SMILES: Cc1cn([C@H]2CCc3cc(-n4c(-c5cccnc5N)nc5ccc(-n6cccn6)nc54)ccc32)nn1] |
| 305 | 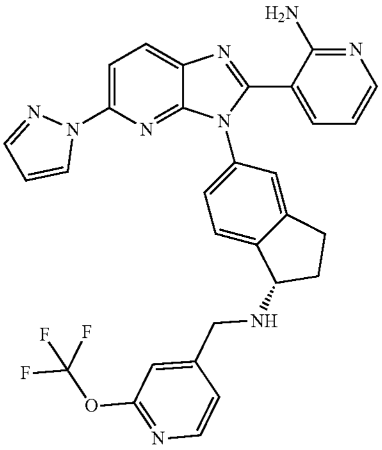 [SMILES: Nc1ncccc1-c1nc2ccc(-n3cccn3)nc2n1-c1ccc2c(c1)CC[C@@H]2NCc1ccnc(OC(F)(F)F)c1] |

TABLE 1-continued
Chemical structures of selected compounds.
| Cpd ID | Structure |
|---|---|
| 306 | 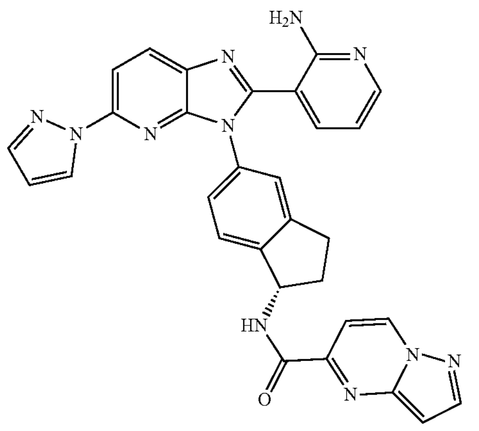 [SMILES: Nc1ncccc1-c1nc2ccc(-n3cccn3)nc2n1-c1ccc2c(c1)CC[C@@H]2NC(=O)c1ccn2nccc2n1] |
| 307 | 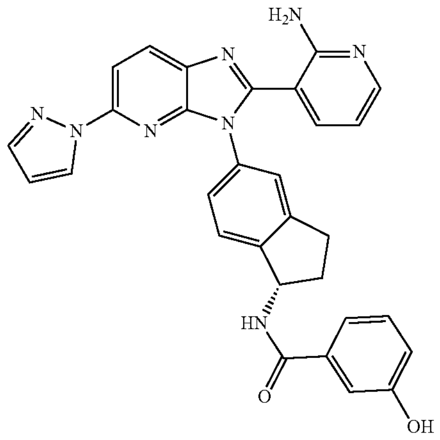 [SMILES: Nc1ncccc1-c1nc2ccc(-n3cccn3)nc2n1-c1ccc2c(c1)CC[C@@H]2NC(=O)c1cccc(O)c1] |
| 308 | 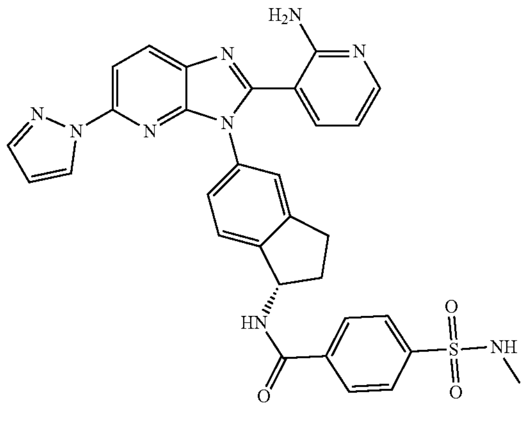 [SMILES: CNS(=O)(=O)c1ccc(C(=O)N[C@H]2CCc3cc(-n4c(-c5cccnc5N)nc5ccc(-n6cccn6)nc54)ccc32)cc1] |

TABLE 1-continued
| Chemical structures of selected compounds. | |
|---|---|
| Cpd ID | Structure |
| 309 | 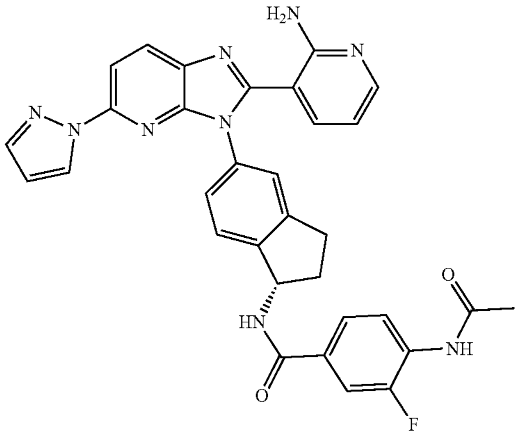 [SMILES: CC(=O)Nc1ccc(C(=O)N[C@H]2CCc3cc(-n4c(-c5cccnc5N)nc5ccc(-n6cccn6)nc54)ccc32)cc1F] |
| 310 | 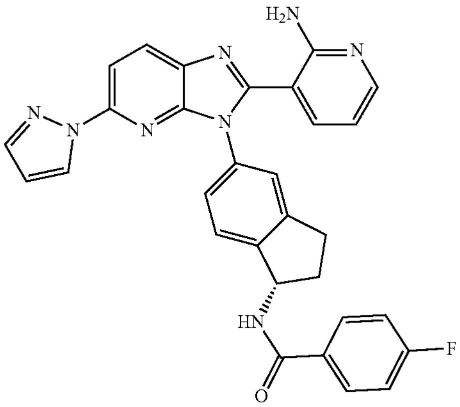 [SMILES: Nc1ncccc1-c1nc2ccc(-n3cccn3)nc2n1-c1ccc2c(c1)CC[C@@H]2NC(=O)c1ccc(F)cc1] |
| 311 | 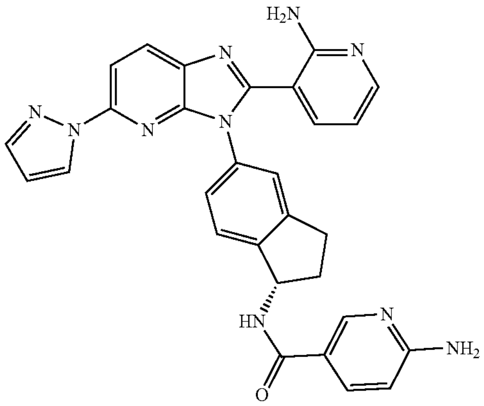 [SMILES: Nc1ccc(C(=O)N[C@H]2CCc3cc(-n4c(-c5cccnc5N)nc5ccc(-n6cccn6)nc54)ccc32)cn1] |

TABLE 1-continued
| Cpd ID | Structure |
|---|---|
| 312 | 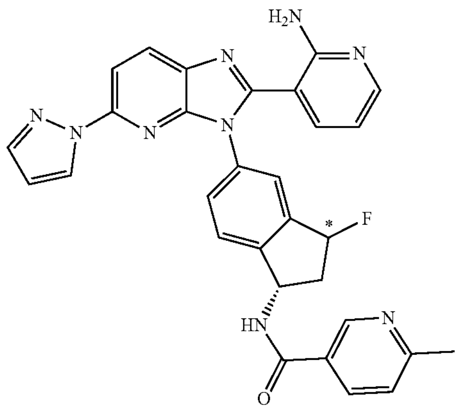 [SMILES: Cc1ccc(C(=O)N[C@H]2CC(F)c3cc(-n4c(-c5cccnc5N)nc5ccc(-n6cccn6)nc54)ccc32)cn1] |
| 313 | 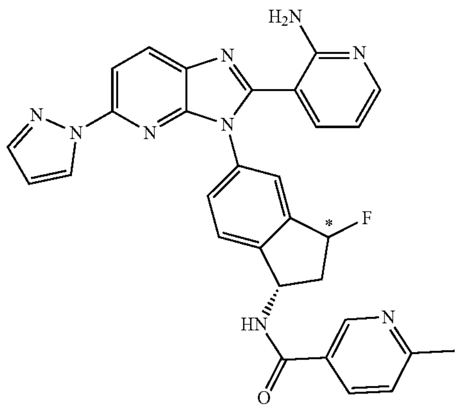 [SMILES: Cc1ccc(C(=O)N[C@H]2CC(F)c3cc(-n4c(-c5cccnc5N)nc5ccc(-n6cccn6)nc54)ccc32)cn1] |
| 314 | 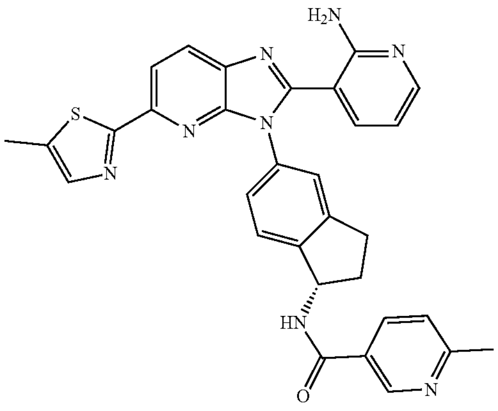 |
Chemical structures of selected compounds.

TABLE 1-continued
| Chemical structures of selected compounds. | |
|---|---|
| Cpd ID | Structure |
| 315 | 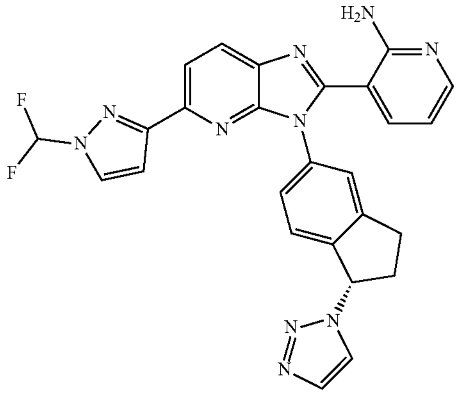 [SMILES: Nc1ncccc1-c1nc2ccc(-c3ccn(C(F)F)n3)nc2n1-c1ccc2c(c1)CC[C@@H]2n1ccnn1] |
| 316 | 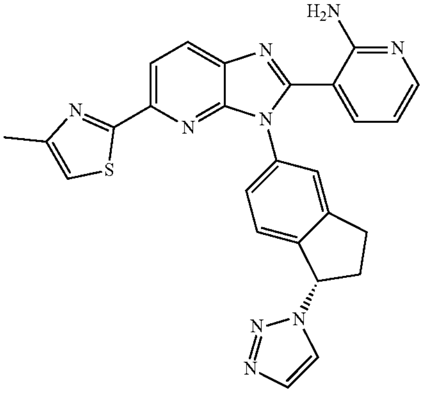 |
| 317 | 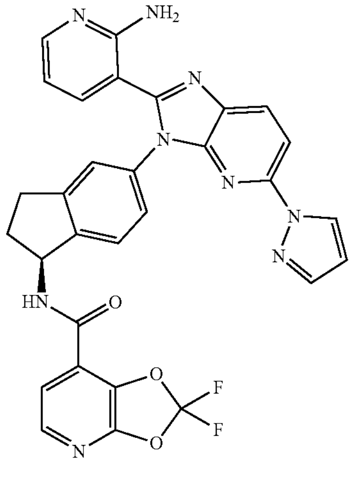 [SMILES: Nc1ncccc1-c1nc2ccc(-n3cccn3)nc2n1-c1ccc2c(c1)CC[C@@H]2NC(=O)c1ccnc2c1OC(F)(F)O2] |

TABLE 1-continued
| Cpd ID | Structure |
|---|---|
| | Chemical structures of selected compounds. |
| 318 | 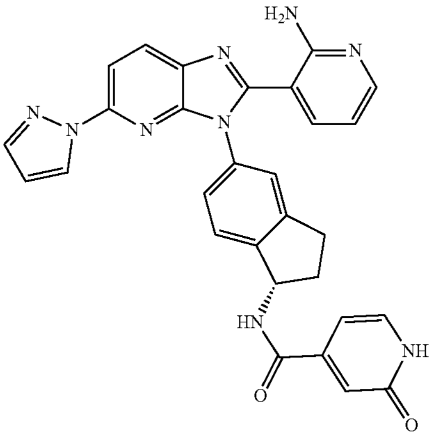 [SMILES: Nc1ncccc1-c1nc2ccc(-n3cccn3)nc2n1-c1ccc2c(c1)CC[C@@H]2NC(=O)c1cc[nH]c(=O)c1] |
| 319 | 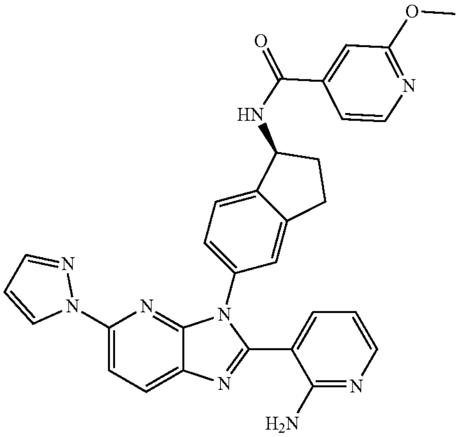 [SMILES: COc1cc(C(=O)N[C@H]2CCc3cc(-n4c(-c5cccnc5N)nc5ccc(-n6cccn6)nc54)ccc32)ccn1] |
| 320 | 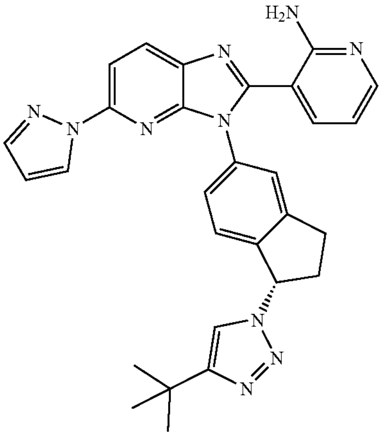 [SMILES: CC(C)(C)c1cn([C@H]2CCc3cc(-n4c(-c5cccnc5N)nc5ccc(-n6cccn6)nc54)ccc32)nn1] |

TABLE 1-continued
| Chemical structures of selected compounds. | |
|---|---|
| Cpd ID | Structure |
| 321 | 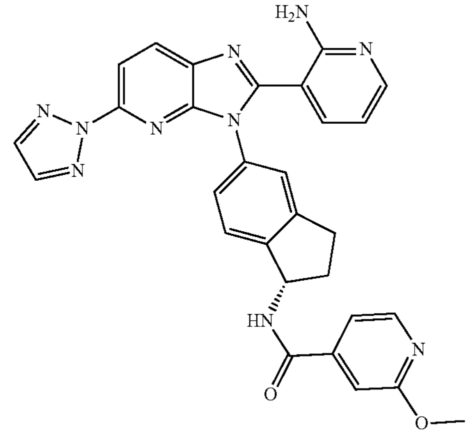 [SMILES: COc1cc(C(=O)N[C@H]2CCc3cc(-n4c(-c5cccnc5N)nc5ccc(-n6nccn6)nc54)ccc32)ccn1] |
| 322 | 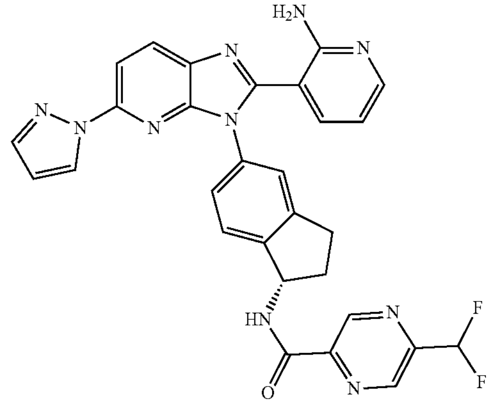 [SMILES: Nc1ncccc1-c1nc2ccc(-n3cccn3)nc2n1-c1ccc2c(c1)CC[C@@H]2NC(=O)c1cnc(C(F)F)cn1] |
| 323 | 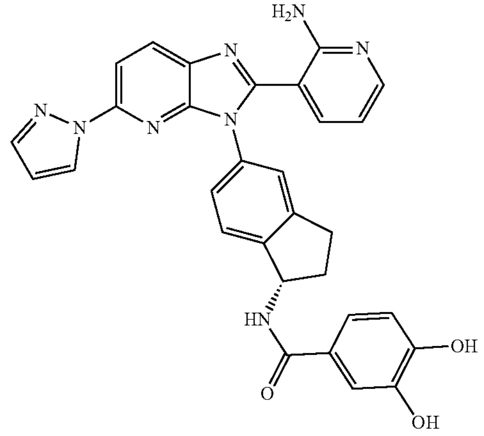 |

TABLE 1-continued
| Cpd ID | Structure |
|---|---|
| 324 | 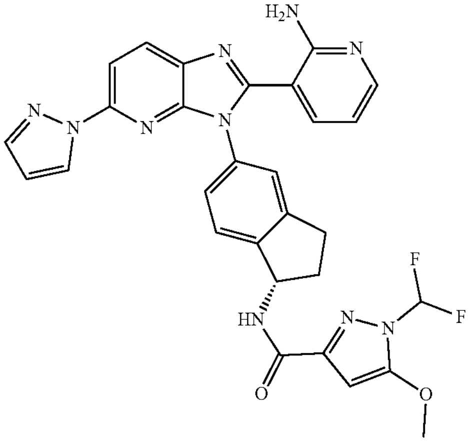 [SMILES: COc1cc(C(=O)N[C@H]2CCc3cc(-n4c(-c5cccnc5N)nc5ccc(-n6cccn6)nc54)ccc32)nn1C(F)F] |
| 325 | 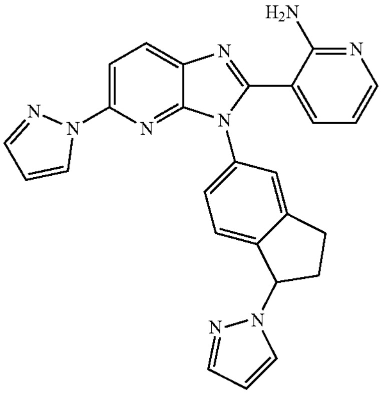 [SMILES: Nc1ncccc1-c1nc2ccc(-n3cccn3)nc2n1-c1ccc2c(c1)CCC2n1cccn1] |
| 326 | 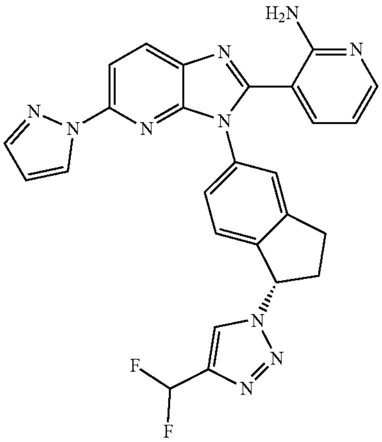 [SMILES: Nc1ncccc1-c1nc2ccc(-n3cccn3)nc2n1-c1ccc2c(c1)CC[C@@H]2n1cc(C(F)F)nn1] |

TABLE 1-continued
Chemical structures of selected compounds.
| Cpd ID | Structure |
|---|---|
| 327 | 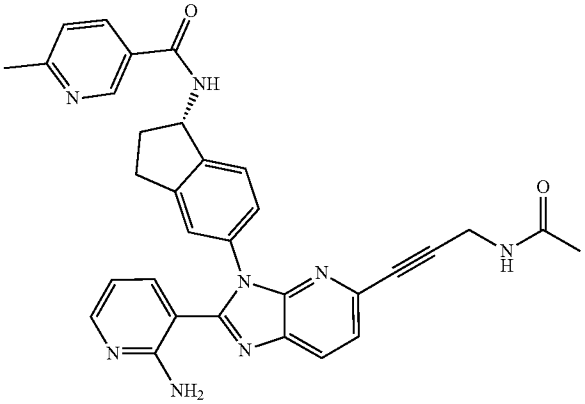 [SMILES: CC(=O)NCC#Cc1ccc2nc(-c3cccnc3N)n(-c3ccc4c(c3)CC[C@@H]4NC(=O)c3ccc(C)nc3)c2n1] |
| 328 | 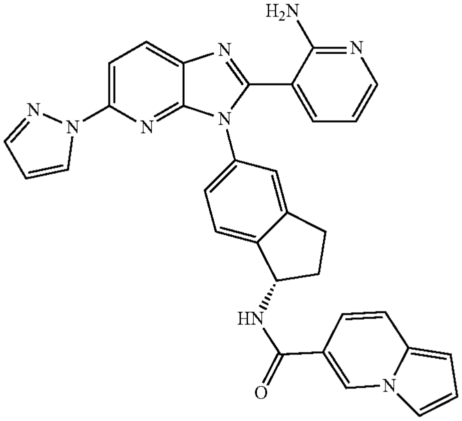 [SMILES: Nc1ncccc1-c1nc2ccc(-n3cccn3)nc2n1-c1ccc2c(c1)CC[C@@H]2NC(=O)c1ccc2cccn2c1] |
| 329 | 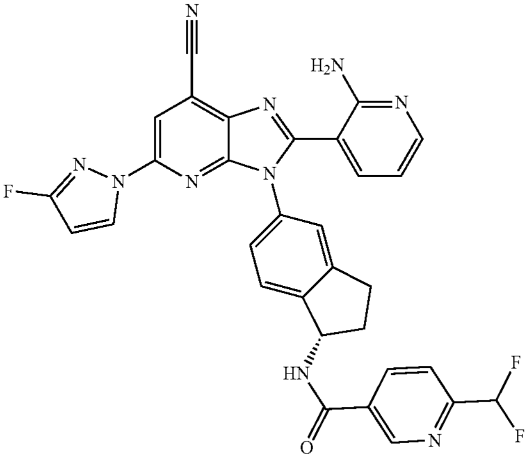 [SMILES: N#Cc1cc(-n2ccc(F)n2)nc2c1nc(-c1cccnc1N)n2-c1ccc2c(c1)CC[C@@H]2NC(=O)c1ccc(C(F)F)nc1] |

TABLE 1-continued
| Chemical structures of selected compounds. | |
|---|---|
| Cpd ID | Structure |
| 330 | 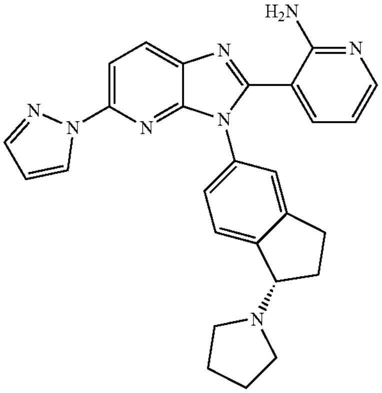 [SMILES: Nc1ncccc1-c1nc2ccc(-n3cccn3)nc2n1-c1ccc2c(c1)CC[C@@H]2N1CCCC1] |
| 331 | 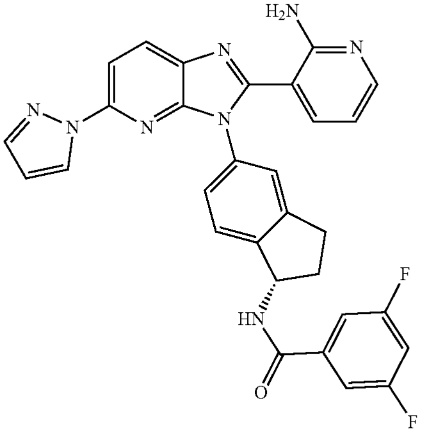 [SMILES: Nc1ncccc1-c1nc2ccc(-n3cccn3)nc2n1-c1ccc2c(c1)CC[C@@H]2NC(=O)c1cc(F)cc(F)c1] |
| 332 | 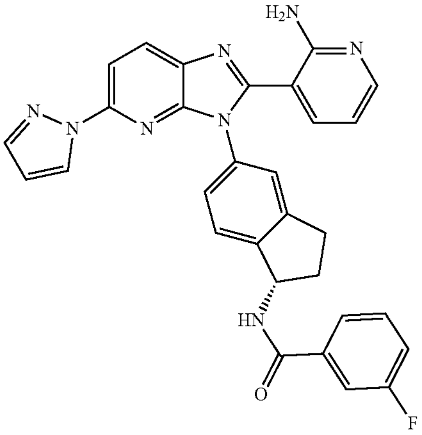 |

TABLE 1-continued
| Chemical structures of selected compounds. | |
|---|---|
| Cpd ID | Structure |
| 333 | 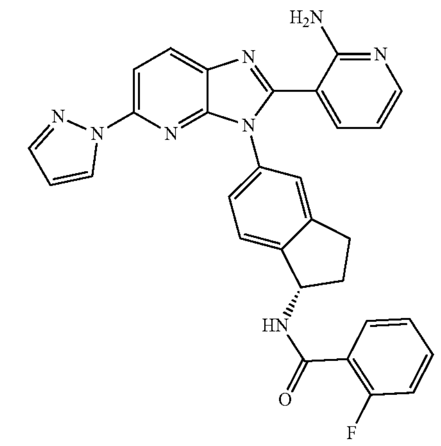 [SMILES: Nc1ncccc1-c1nc2ccc(-n3cccn3)nc2n1-c1ccc2c(c1)CC[C@@H]2NC(=O)c1ccccc1F] |
| 334 | 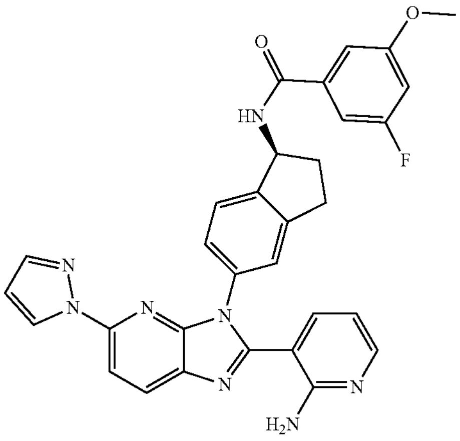 [SMILES: COc1cc(F)cc(C(=O)N[C@H]2CCc3cc(-n4c(-c5cccnc5N)nc5ccc(-n6cccn6)nc54)ccc32)c1] |
| 335 | 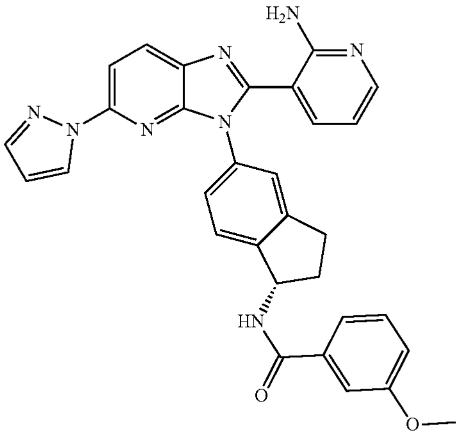 [SMILES: COc1cccc(C(=O)N[C@H]2CCc3cc(-n4c(-c5cccnc5N)nc5ccc(-n6cccn6)nc54)ccc32)c1] |

TABLE 1-continued
| Chemical structures of selected compounds. | |
|---|---|
| Cpd ID | Structure |
| 336 | 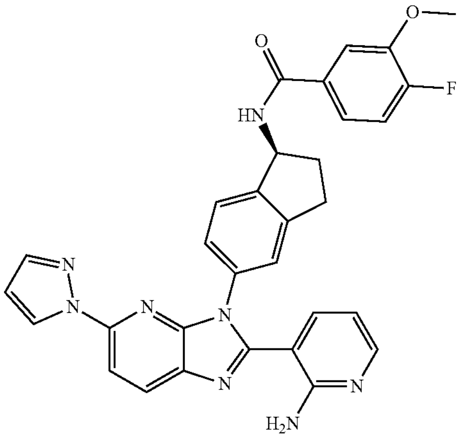 [SMILES: COc1cc(C(=O)N[C@H]2CCc3cc(-n4c(-c5cccnc5N)nc5ccc(-n6cccn6)nc54)ccc32)ccc1F] |
| 337 | 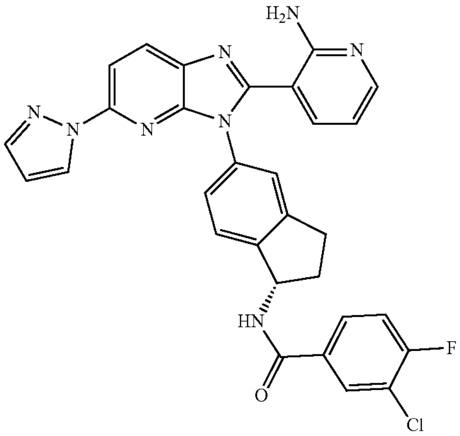 [SMILES: Nc1ncccc1-c1nc2ccc(-n3cccn3)nc2n1-c1ccc2c(c1)CC[C@@H]2NC(=O)c1ccc(F)c(Cl)c1] |
| 338 | 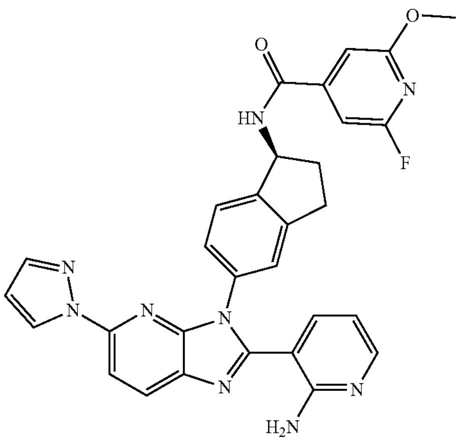 [SMILES: COc1cc(C(=O)N[C@H]2CCc3cc(-n4c(-c5cccnc5N)nc5ccc(-n6cccn6)nc54)ccc32)cc(F)n1] |

TABLE 1-continued
| Chemical structures of selected compounds. | |
|---|---|
| Cpd ID | Structure |
| 341 | 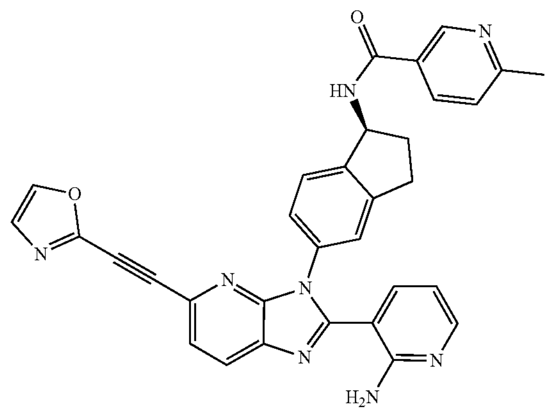 [SMILES: Cc1ccc(C(=O)N[C@H]2CCc3cc(-n4c(-c5cccnc5N)nc5ccc(C#Cc6ncco6)nc54)ccc32)cn1] |
| 342 | 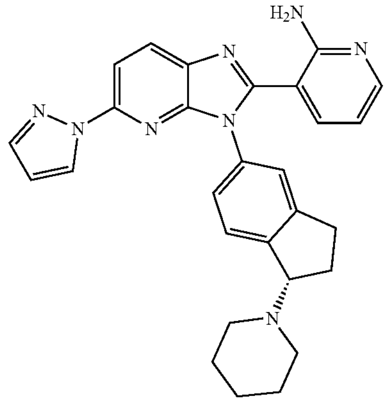 [SMILES: Nc1ncccc1-c1nc2ccc(-n3cccn3)nc2n1-c1ccc2c(c1)CC[C@@H]2N1CCCCC1] |
| 343 | 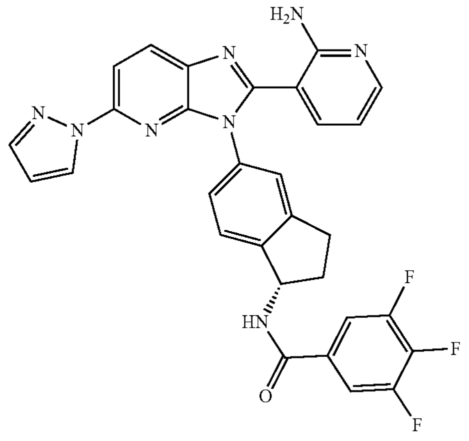 [SMILES: Nc1ncccc1-c1nc2ccc(-n3cccn3)nc2n1-c1ccc2c(c1)CC[C@@H]2NC(=O)c1cc(F)c(F)c(F)c1] |

TABLE 1-continued
Chemical structures of selected compounds.
| Cpd ID | Structure |
| --- | --- |
| 344 | 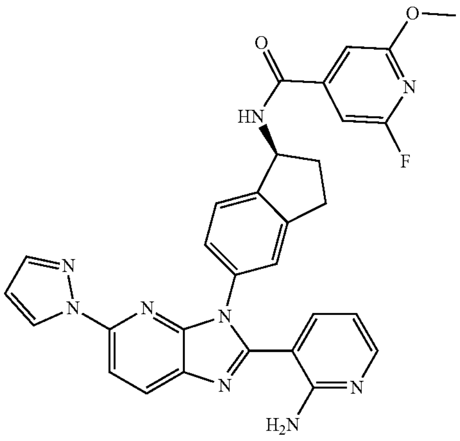 [SMILES: COc1cc(C(=O)N[C@H]2CCc3cc(-n4c(-c5cccnc5N)nc5ccc(-n6cccn6)nc54)ccc32)cc(F)n1] |
| 345 | 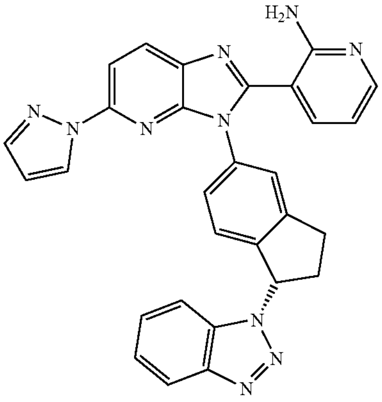 |
| 346 | 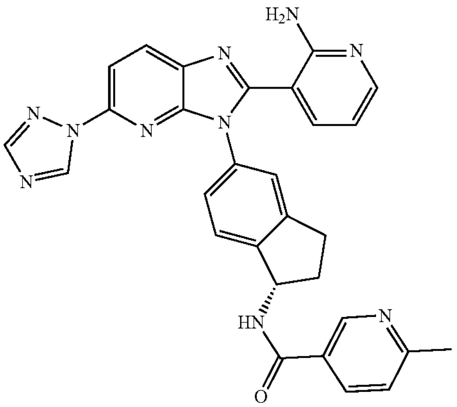 [SMILES: Cc1ccc(C(=O)N[C@H]2CCc3cc(-n4c(-c5cccnc5N)nc5ccc(-n6cncn6)nc54)ccc32)cn1] |

TABLE 1-continued
| Chemical structures of selected compounds. | |
|---|---|
| Cpd ID | Structure |
| 347 | 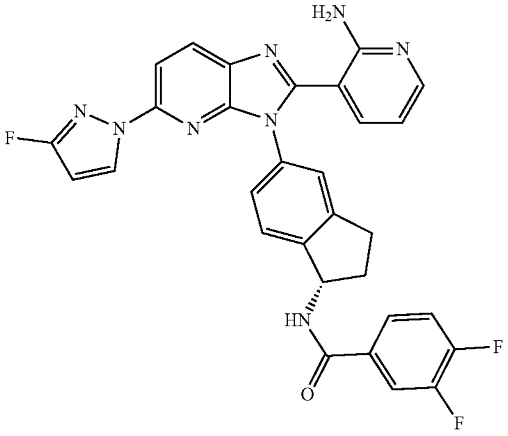 [SMILES: Nc1ncccc1-c1nc2ccc(-n3ccc(F)n3)nc2n1-c1ccc2c(c1)CC[C@@H]2NC(=O)c1ccc(F)c(F)c1] |
| 348 | 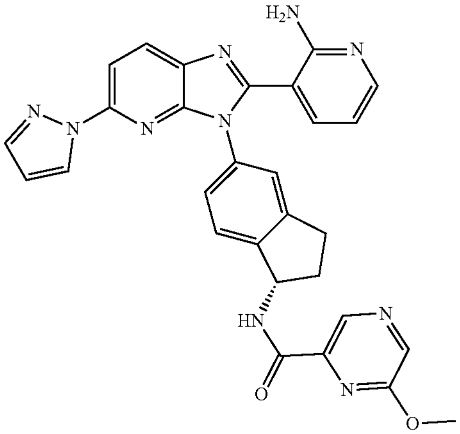 [SMILES: COc1cncc(C(=O)N[C@H]2CCc3cc(-n4c(-c5cccnc5N)nc5ccc(-n6cccn6)nc54)ccc32)n1] |
| 349 | 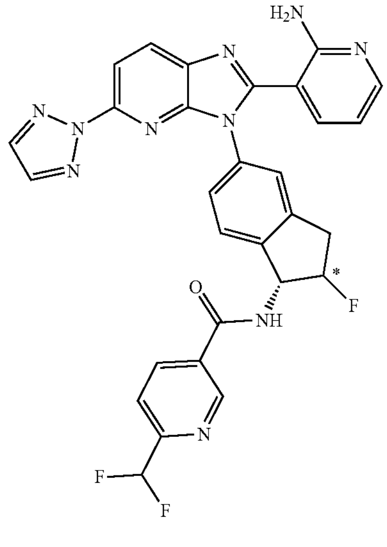 [SMILES: Nc1ncccc1-c1nc2ccc(-n3nccn3)nc2n1-c1ccc2c(c1)CC(F)[C@@H]2NC(=O)c1ccc(C(F)F)nc1] |

TABLE 1-continued
| Chemical structures of selected compounds. | |
|---|---|
| Cpd ID | Structure |
| 350 | 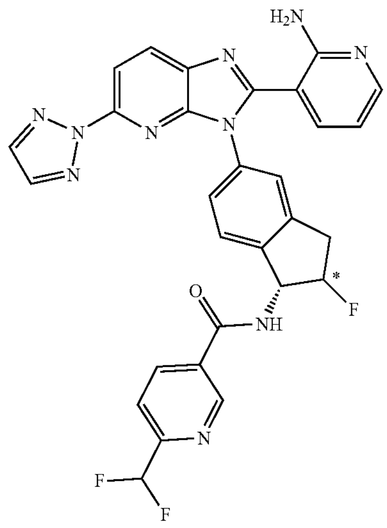 [SMILES: Nc1ncccc1-c1nc2ccc(-n3nccn3)nc2n1-c1ccc2c(c1)CC(F)[C@@H]2NC(=O)c1ccc(C(F)F)nc1] |
| 351 | 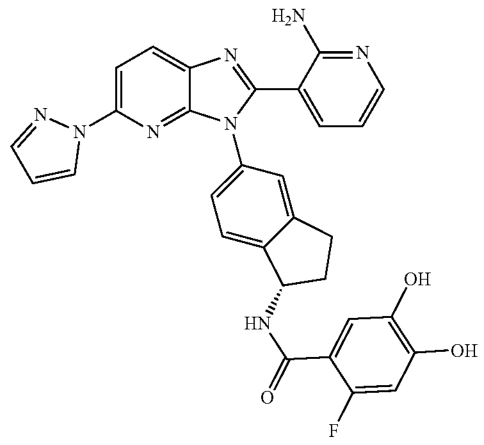 [SMILES: Nc1ncccc1-c1nc2ccc(-n3cccn3)nc2n1-c1ccc2c(c1)CC[C@@H]2NC(=O)c1cc(O)c(O)cc1F] |
| 352 | 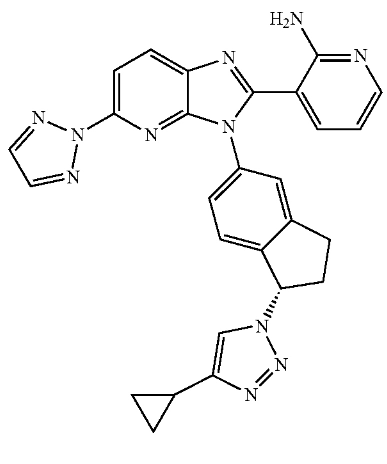 [SMILES: Nc1ncccc1-c1nc2ccc(-n3nccn3)nc2n1-c1ccc2c(c1)CC[C@@H]2n1cc(C2CC2)nn1] |

TABLE 1-continued
| Cpd ID | Structure |
|---|---|
| Chemical structures of selected compounds. | |
| 353 | 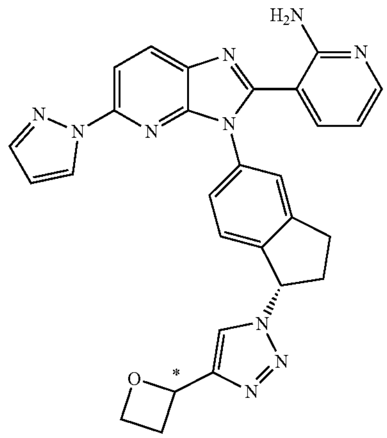 |
| 354 | 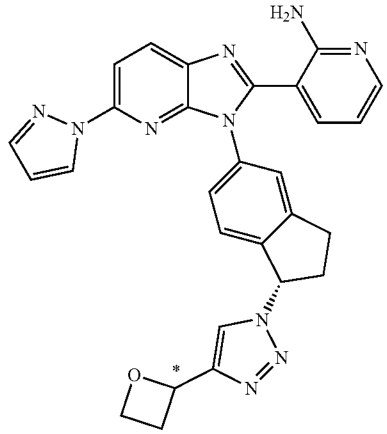 |
| 355 | 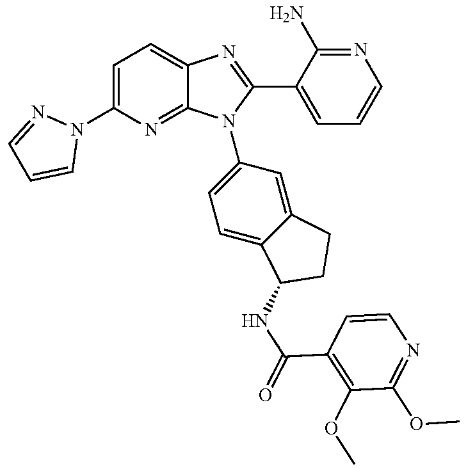 [SMILES: COc1nccc(C(=O)N[C@H]2CCc3cc(-n4c(-c5cccnc5N)nc5ccc(-n6cccn6)nc54)ccc32)c1OC] |

TABLE 1-continued
| Chemical structures of selected compounds. | |
|---|---|
| Cpd ID | Structure |
| 356 | 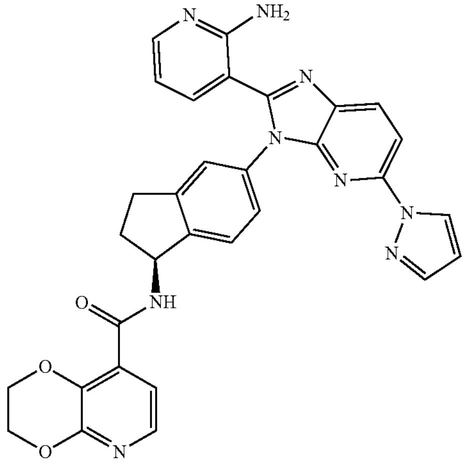 [SMILES: Nc1ncccc1-c1nc2ccc(-n3cccn3)nc2n1-c1ccc2c(c1)CC[C@@H]2NC(=O)c1ccnc2c1OCCO2] |
| 357 | 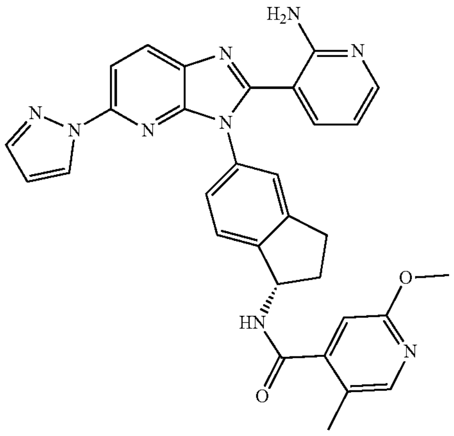 [SMILES: COc1cc(C(=O)N[C@H]2CCc3cc(-n4c(-c5cccnc5N)nc5ccc(-n6cccn6)nc54)ccc32)c(C)cn1] |
| 358 | 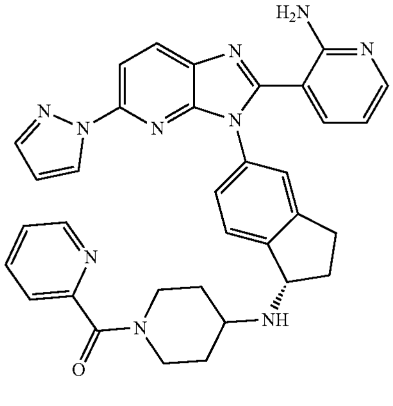 [SMILES: Nc1ncccc1-c1nc2ccc(-n3cccn3)nc2n1-c1ccc2c(c1)CC[C@@H]2NC1CCN(C(=O)c2ccccn2)CC1] |

TABLE 1-continued
Chemical structures of selected compounds.
| Cpd ID | Structure |
| --- | --- |
| 359 | 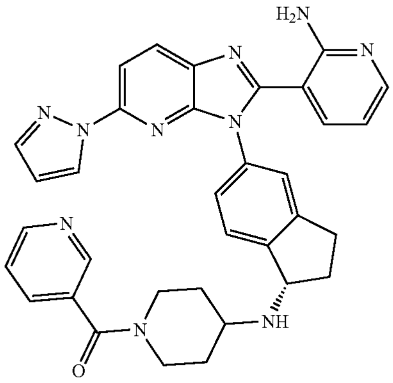 [SMILES: Nc1ncccc1-c1nc2ccc(-n3cccn3)nc2n1-c1ccc2c(c1)CC[C@@H]2NC1CCN(C(=O)c2cccnc2)CC1] |
| 360 | 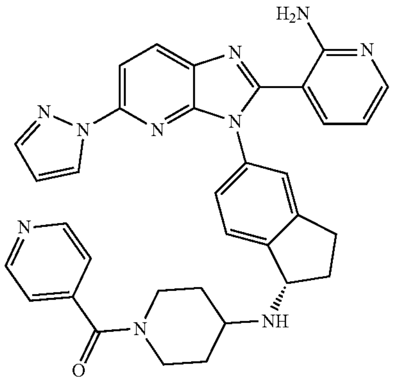 [SMILES: Nc1ncccc1-c1nc2ccc(-n3cccn3)nc2n1-c1ccc2c(c1)CC[C@@H]2NC1CCN(C(=O)c2ccncc2)CC1] |
| 361 | 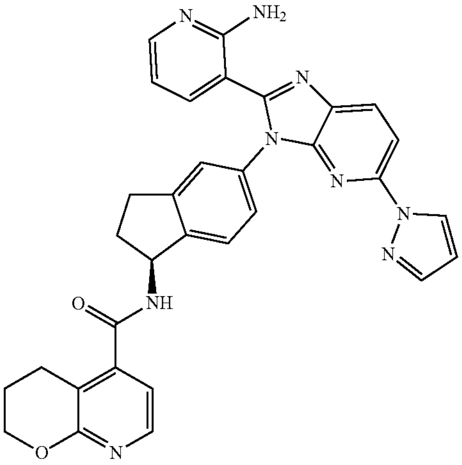 [SMILES: Nc1ncccc1-c1nc2ccc(-n3cccn3)nc2n1-c1ccc2c(c1)CC[C@@H]2NC(=O)c1ccnc2c1CCCO2] |

TABLE 1-continued
| Chemical structures of selected compounds. | |
|---|---|
| Cpd ID | Structure |
| 362 | 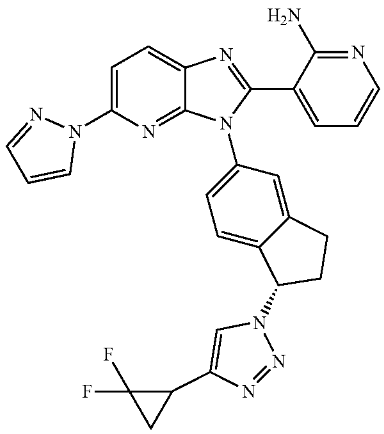 [SMILES: Nc1ncccc1-c1nc2ccc(-n3cccn3)nc2n1-c1ccc2c(c1)CC[C@@H]2n1cc(C2CC2(F)F)nn1] |
| 363 | 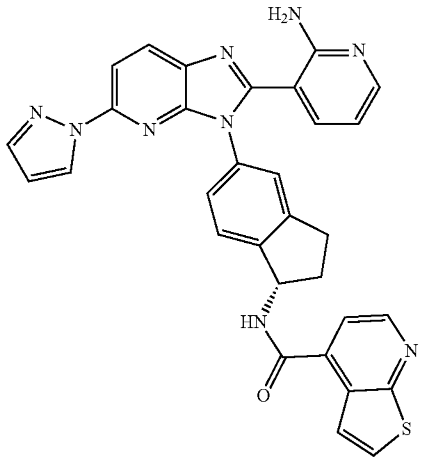 [SMILES: Nc1ncccc1-c1nc2ccc(-n3cccn3)nc2n1-c1ccc2c(c1)CC[C@@H]2NC(=O)c1ccnc2sccc12] |
| 364 | 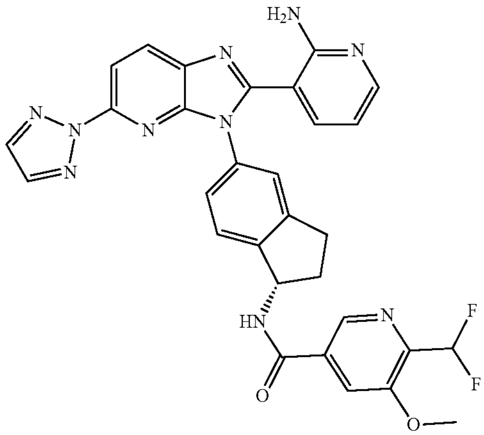 [SMILES: COc1cc(C(=O)N[C@H]2CCc3cc(-n4c(-c5cccnc5N)nc5ccc(-n6nccn6)nc54)ccc32)cnc1C(F)F] |

TABLE 1-continued
| Chemical structures of selected compounds. | |
|---|---|
| Cpd ID | Structure |
| 365 | 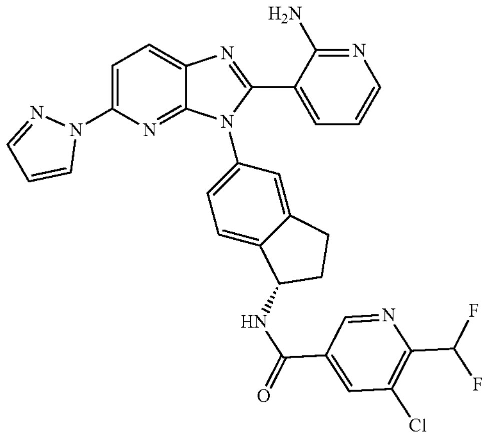 [SMILES: Nc1ncccc1-c1nc2ccc(-n3cccn3)nc2n1-c1ccc2c(c1)CC[C@@H]2NC(=O)c1cnc(C(F)F)c(Cl)c1] |
| 366 | 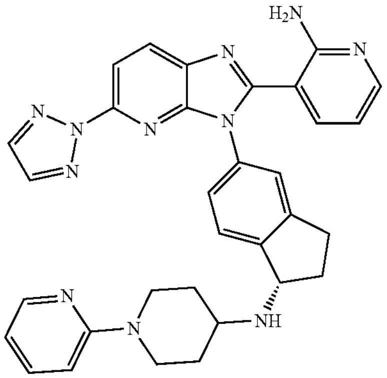 |
| 367 | 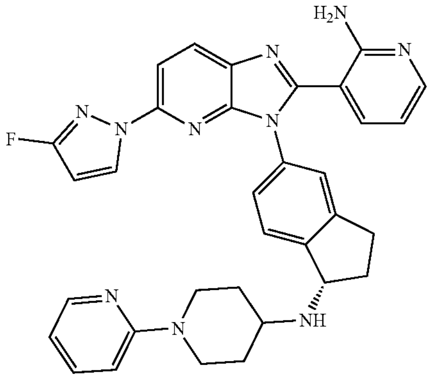 [SMILES: Nc1ncccc1-c1nc2ccc(-n3ccc(F)n3)nc2n1-c1ccc2c(c1)CC[C@@H]2NC1CCN(c2ccccn2)CC1] |

TABLE 1-continued
| Chemical structures of selected compounds. | |
|---|---|
| Cpd ID | Structure |
| 368 | 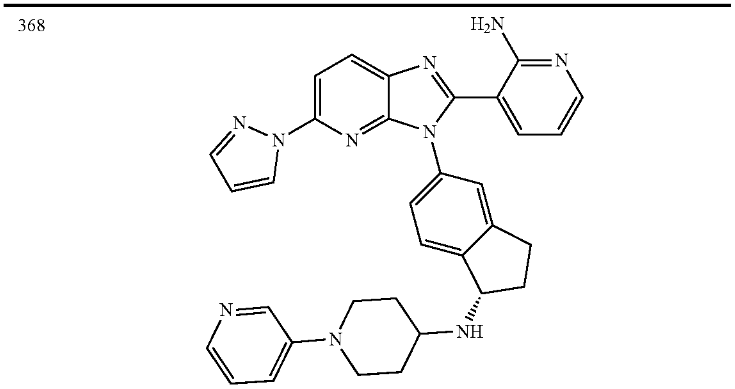 |
| 369 | 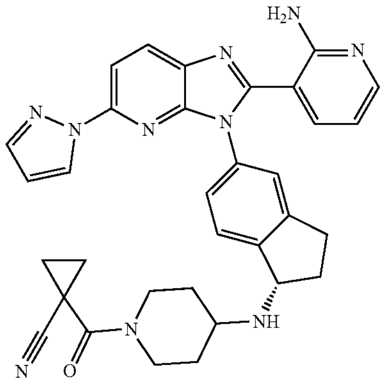 [SMILES: N#CC1(C(=O)N2CCC(N[C@H]3CCc4cc(-n5c(-c6cccnc6N)nc6ccc(-n7cccn7)nc65)ccc43)CC2)CC1] |
| 370 | 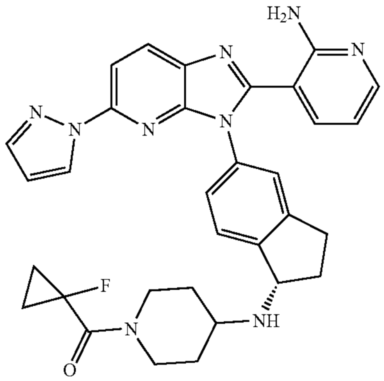 [SMILES: Nc1ncccc1-c1nc2ccc(-n3cccn3)nc2n1-c1ccc2c(c1)CC[C@@H]2NC1CCN(C(=O)C2(F)CC2)CC1] |
| 371 | 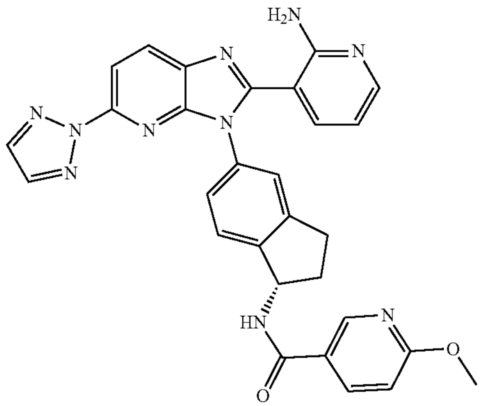 [SMILES: COc1ccc(C(=O)N[C@H]2CCc3cc(-n4c(-c5cccnc5N)nc5ccc(-n6nccn6)nc54)ccc32)cn1] |

TABLE 1-continued
| Chemical structures of selected compounds. | |
|---|---|
| Cpd ID | Structure |
| 372 | 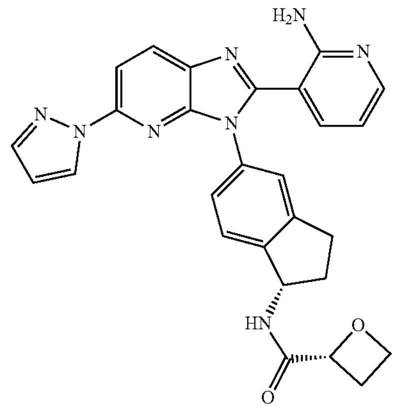 [SMILES: Nc1ncccc1-c1nc2ccc(-n3cccn3)nc2n1-c1ccc2c(c1)CC[C@@H]2NC(=O)[C@H]1CCO1] |
| 373 | 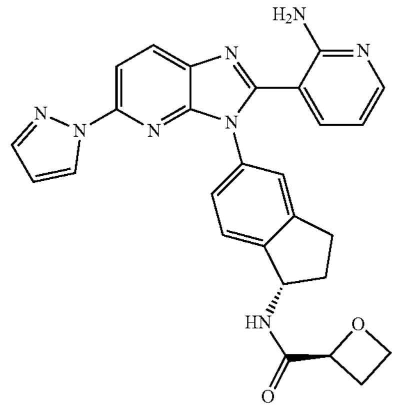 [SMILES: Nc1ncccc1-c1nc2ccc(-n3cccn3)nc2n1-c1ccc2c(c1)CC[C@@H]2NC(=O)[C@@H]1CCO1] |
| 374 | 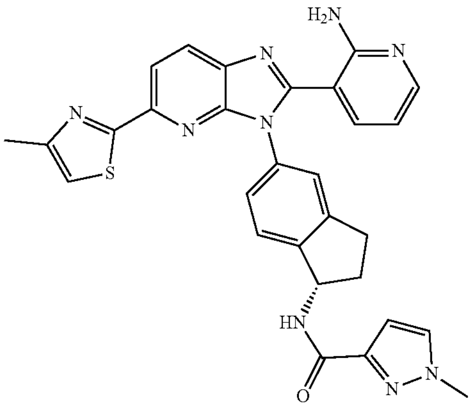 |

TABLE 1-continued
| Cpd ID | Structure |
| --- | --- |
| 375 | 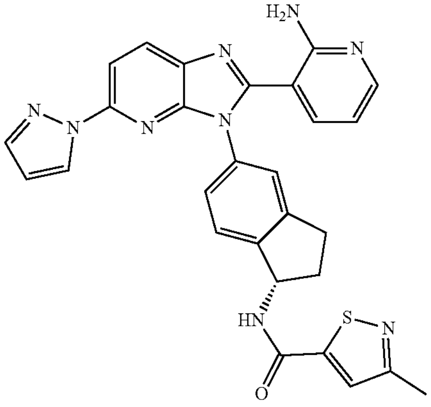 [SMILES: Cc1cc(C(=O)N[C@H]2CCc3cc(-n4c(-c5cccnc5N)nc5ccc(-n6cccn6)nc54)ccc32)sn1] |
| 376 | 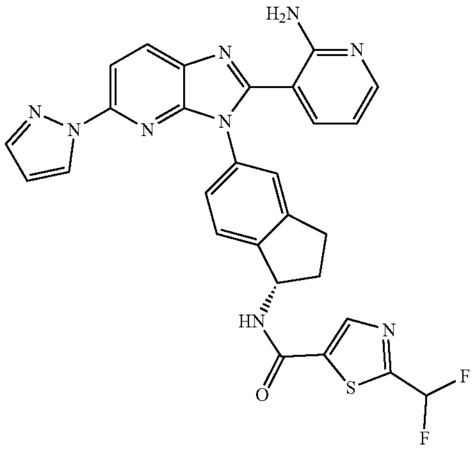 [SMILES: Nc1ncccc1-c1nc2ccc(-n3cccn3)nc2n1-c1ccc2c(c1)CC[C@@H]2NC(=O)c1cnc(C(F)F)s1] |
| 377 | 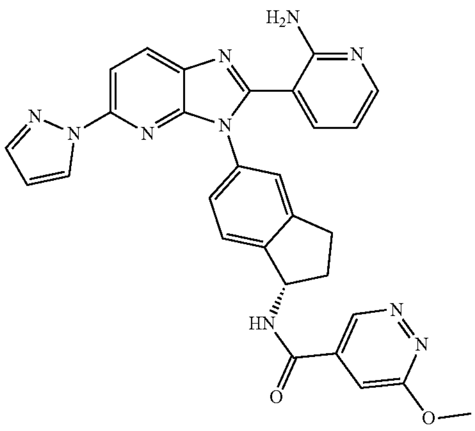 [SMILES: COc1cc(C(=O)N[C@H]2CCc3cc(-n4c(-c5cccnc5N)nc5ccc(-n6cccn6)nc54)ccc32)cnn1] |
Chemical structures of selected compounds.

TABLE 1-continued
| Chemical structures of selected compounds. | |
|---|---|
| Cpd ID | Structure |
| 378 | 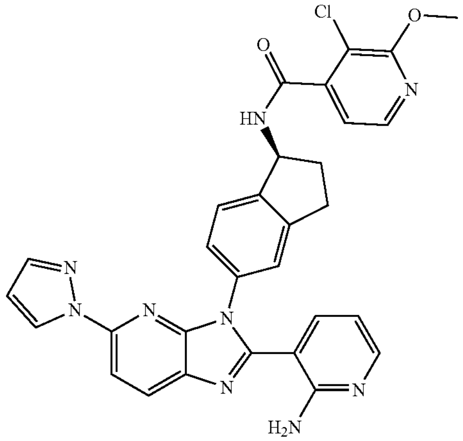 [SMILES: COc1nccc(C(=O)N[C@H]2CCc3cc(-n4c(-c5cccnc5N)nc5ccc(-n6cccn6)nc54)ccc32)c1Cl] |
| 379 | 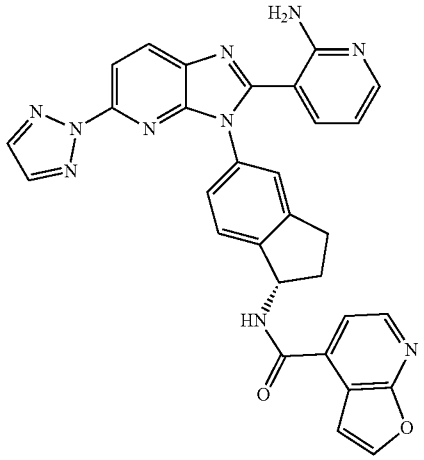 [SMILES: Nc1ncccc1-c1nc2ccc(-n3nccn3)nc2n1-c1ccc2c(c1)CC[C@@H]2NC(=O)c1ccnc2occc12] |
| 380 | 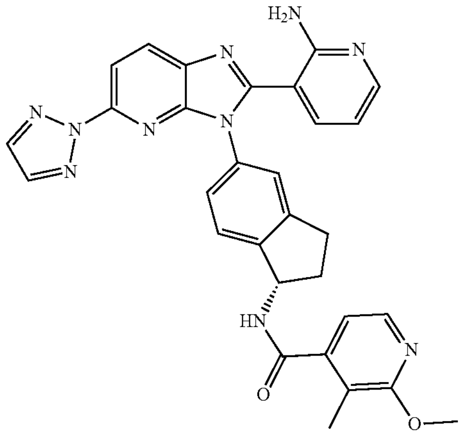 [SMILES: COc1nccc(C(=O)N[C@H]2CCc3cc(-n4c(-c5cccnc5N)nc5ccc(-n6nccn6)nc54)ccc32)c1C] |

TABLE 1-continued
| Chemical structures of selected compounds. | |
|---|---|
| Cpd ID | Structure |
| 381 | 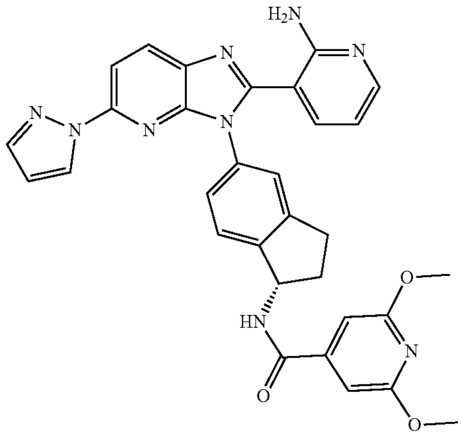 [SMILES: COc1cc(C(=O)N[C@H]2CCc3cc(-n4c(-c5cccnc5N)nc5ccc(-n6cccn6)nc54)ccc32)cc(OC)n1] |
| 382 | 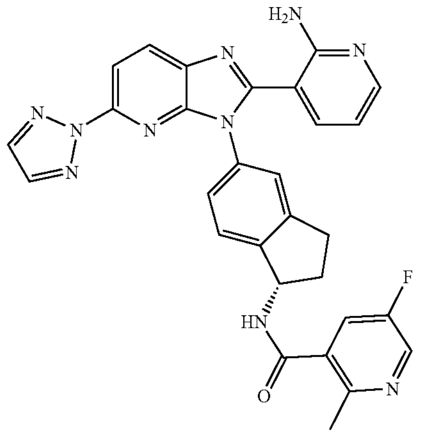 [SMILES: Cc1ncc(F)cc1C(=O)N[C@H]1CCc2cc(-n3c(-c4cccnc4N)nc4ccc(-n5nccn5)nc43)ccc21] |
| 383 | 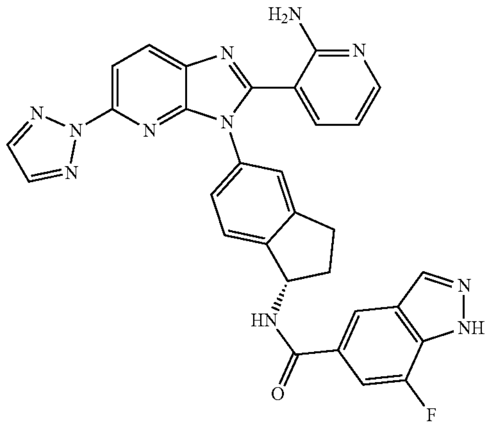 |

TABLE 1-continued
| Cpd ID | Structure |
|---|---|
| 384 | 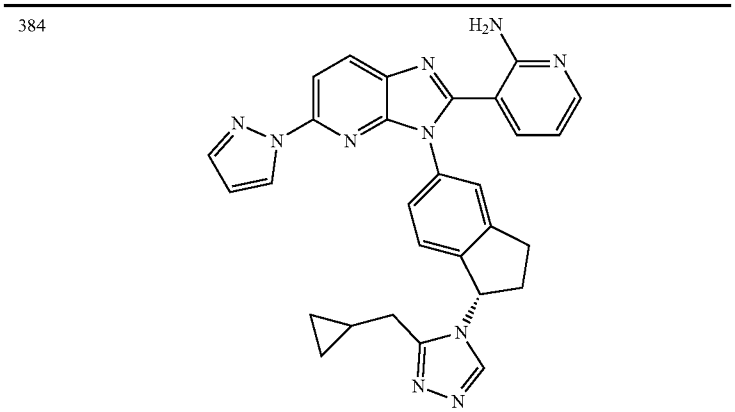 |
| 385 | 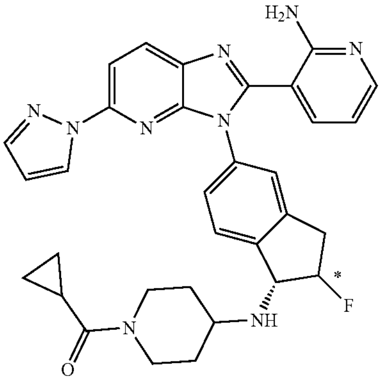 [SMILES: Nc1ncccc1-c1nc2ccc(-n3cccn3)nc2n1-c1ccc2c(c1)CC(F)[C@@H]2NC1CCN(C(=O)C2CC2)CC1] |
| 386 | 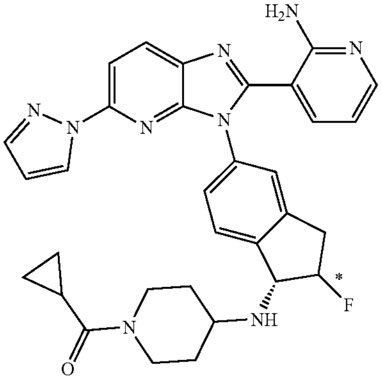 [SMILES: Nc1ncccc1-c1nc2ccc(-n3cccn3)nc2n1-c1ccc2c(c1)CC(F)[C@@H]2NC1CCN(C(=O)C2CC2)CC1] |
| 387 | 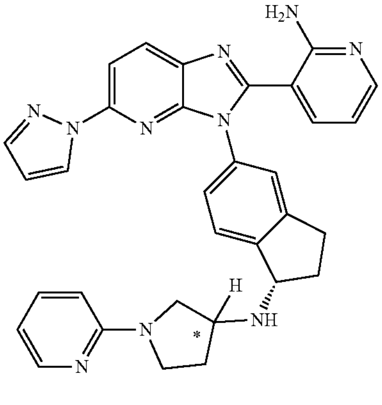 [SMILES: Nc1ncccc1-c1nc2ccc(-n3cccn3)nc2n1-c1ccc2c(c1)CC[C@@H]2NC1CCN(c2ccccn2)C1] |
Chemical structures of selected compounds.

TABLE 1-continued
| Chemical structures of selected compounds. | |
|---|---|
| Cpd ID | Structure |
| 388 | 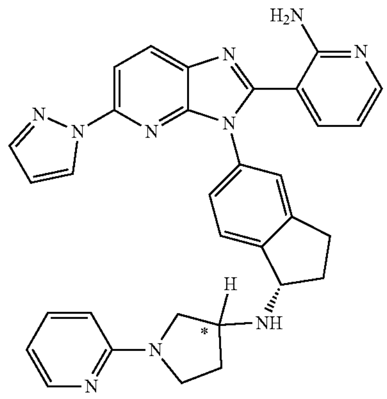 [SMILES: Nc1ncccc1-c1nc2ccc(-n3cccn3)nc2n1-c1ccc2c(c1)CC[C@@H]2NC1CCN(c2ccccn2)C1] |
| 389 | 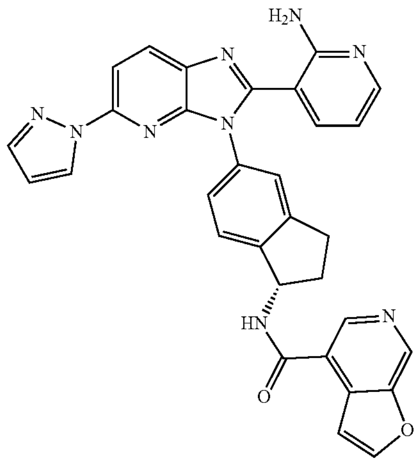 [SMILES: Nc1ncccc1-c1nc2ccc(-n3cccn3)nc2n1-c1ccc2c(c1)CC[C@@H]2NC(=O)c1cncc2occc12] |
| 390 | 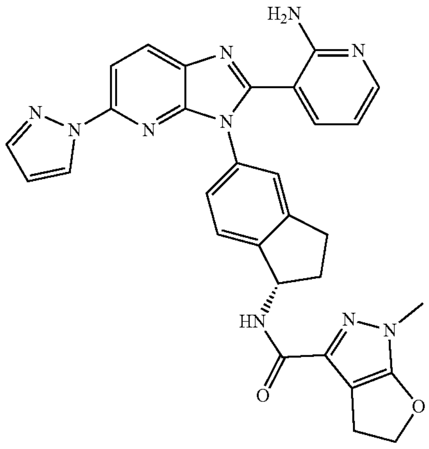 [SMILES: Cn1nc(C(=O)N[C@H]2CCc3cc(-n4c(-c5cccnc5N)nc5ccc(-n6cccn6)nc54)ccc32)c2c1OCC2] |

TABLE 1-continued
| Chemical structures of selected compounds. | |
|---|---|
| Cpd ID | Structure |
| 391 | 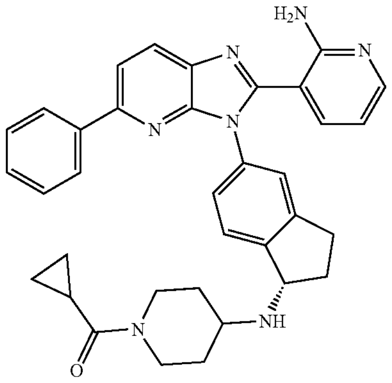 [SMILES: Nc1ncccc1-c1nc2ccc(-c3ccccc3)nc2n1-c1ccc2c(c1)CC[C@@H]2NC1CCN(C(=O)C2CC2)CC1] |
| 392 | 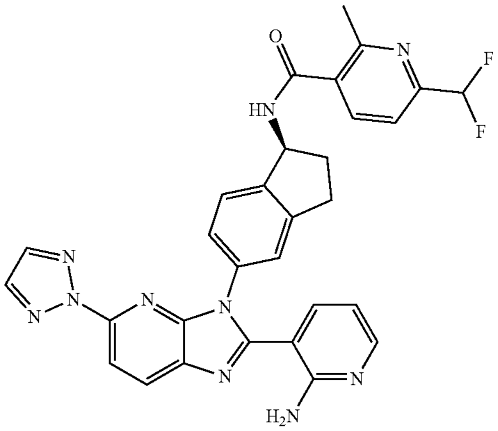 |
| 393 | 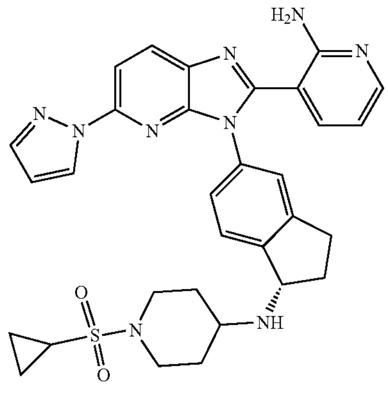 [SMILES: Nc1ncccc1-c1nc2ccc(-n3cccn3)nc2n1-c1ccc2c(c1)CC[C@@H]2NC1CCN(S(=O)(=O)C2CC2)CC1] |

TABLE 1-continued
| Chemical structures of selected compounds. | |
|---|---|
| Cpd ID | Structure |
| 394 | 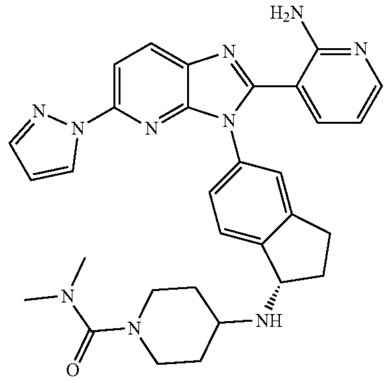 [SMILES: CN(C)C(=O)N1CCC(N[C@H]2CCc3cc(-n4c(-c5cccnc5N)nc5ccc(-n6cccn6)nc54)ccc32)CC1] |
| 395 | 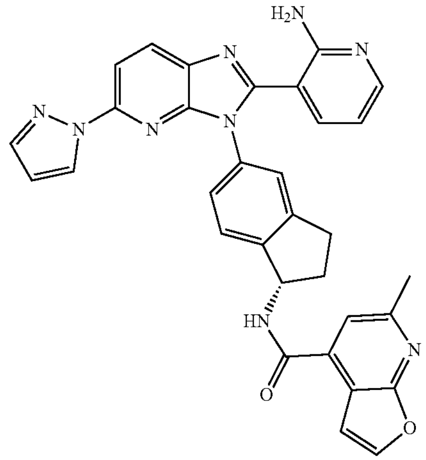 [SMILES: Cc1cc(C(=O)N[C@H]2CCc3cc(-n4c(-c5cccnc5N)nc5ccc(-n6cccn6)nc54)ccc32)c2ccoc2n1] |
| 396 | 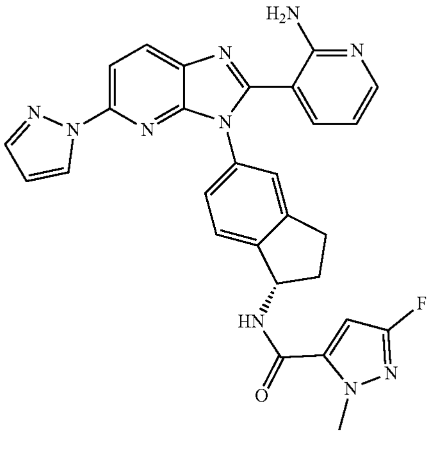 [SMILES: Cn1nc(F)cc1C(=O)N[C@H]1CCc2cc(-n3c(-c4cccnc4N)nc4ccc(-n5cccn5)nc43)ccc21] |

TABLE 1-continued
| Cpd ID | Structure |
|---|---|
| | Chemical structures of selected compounds. |
| 397 | 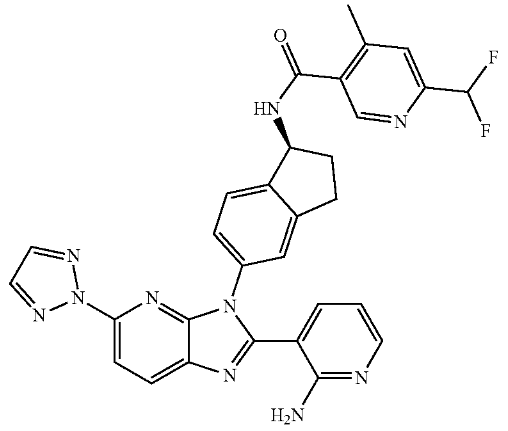 |
| 398 | 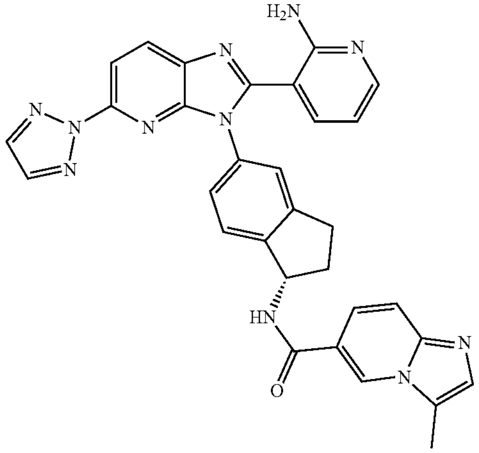 [SMILES: Cc1cnc2ccc(C(=O)N[C@H]3CCc4cc(-n5c(-c6cccnc6N)nc6ccc(-n7nccn7)nc65)ccc43)cn12] |
| 399 | 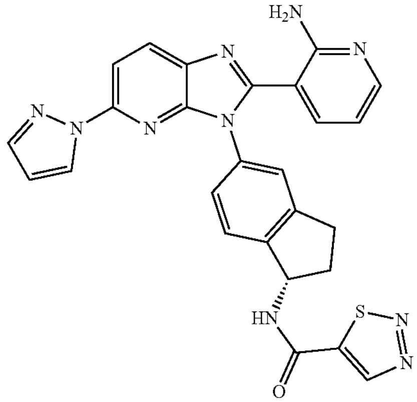 [SMILES: Nc1ncccc1-c1nc2ccc(-n3cccn3)nc2n1-c1ccc2c(c1)CC[C@@H]2NC(=O)c1cnns1] |

TABLE 1-continued
Chemical structures of selected compounds.
| Cpd ID | Structure |
|---|---|
| 400 | 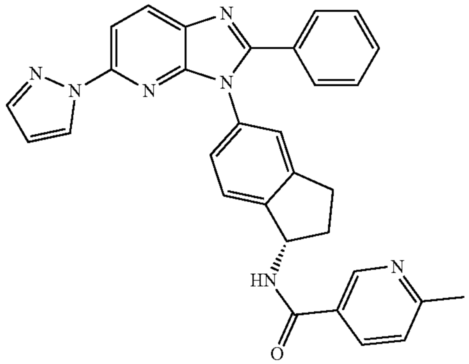 [SMILES: Cc1ccc(C(=O)N[C@H]2CCc3cc(-n4c(-c5ccccc5)nc5ccc(-n6cccn6)nc54)ccc32)cn1] |
| 401 | 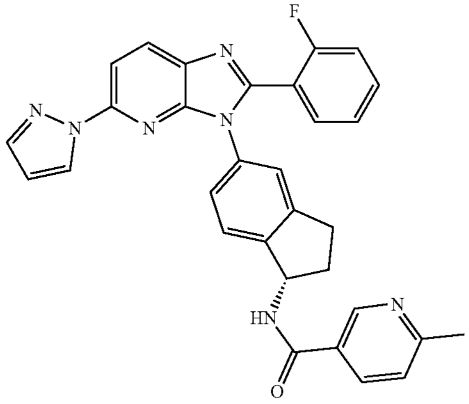 [SMILES: Cc1ccc(C(=O)N[C@H]2CCc3cc(-n4c(-c5ccccc5F)nc5ccc(-n6cccn6)nc54)ccc32)cn1] |
| 402 | 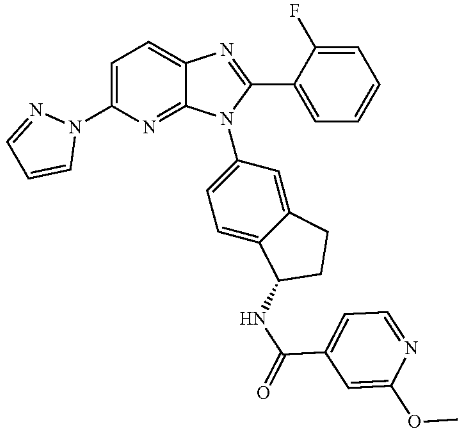 [SMILES: COc1cc(C(=O)N[C@H]2CCc3cc(-n4c(-c5ccccc5F)nc5ccc(-n6cccn6)nc54)ccc32)ccn1] |

TABLE 1-continued
| Chemical structures of selected compounds. | |
|---|---|
| Cpd ID | Structure |
| 403 | 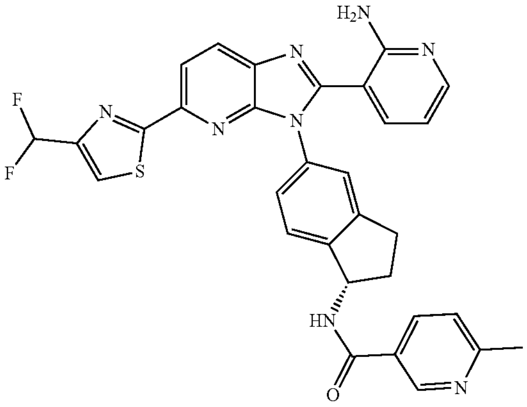 [SMILES: Cc1ccc(C(=O)N[C@H]2CCc3cc(-n4c(-c5cccnc5N)nc5ccc(-c6nc(C(F)F)cs6)nc54)ccc32)cn1] |
| 404 | 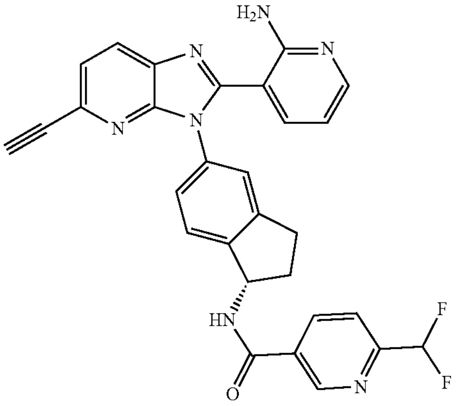 [SMILES: C#Cc1ccc2nc(-c3cccnc3N)n(-c3ccc4c(c3)CC[C@@H]4NC(=O)c3ccc(C(F)F)nc3)c2n1] |
| 405 | 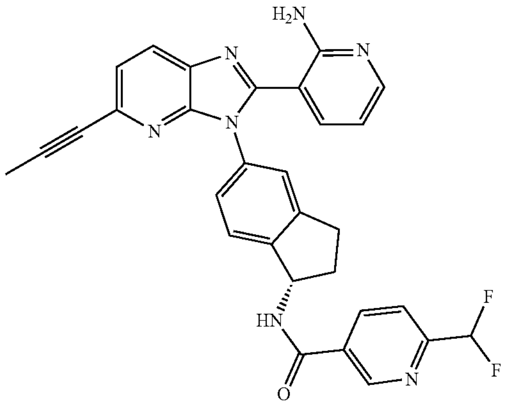 [SMILES: CC#Cc1ccc2nc(-c3cccnc3N)n(-c3ccc4c(c3)CC[C@@H]4NC(=O)c3ccc(C(F)F)nc3)c2n1] |

TABLE 1-continued
| Chemical structures of selected compounds. | |
|---|---|
| Cpd ID | Structure |
| 406 | 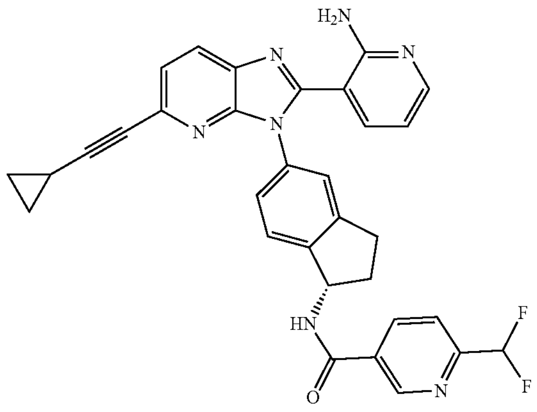 [SMILES: Nc1ncccc1-c1nc2ccc(C#CC3CC3)nc2n1-c1ccc2c(c1)CC[C@@H]2NC(=O)c1ccc(C(F)F)nc1] |
| 407 | 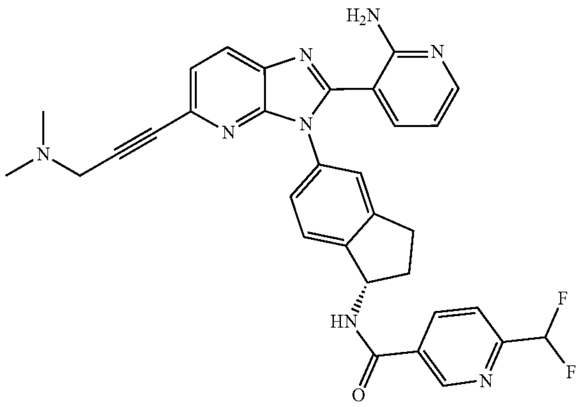 [SMILES: CN(C)CC#Cc1ccc2nc(-c3cccnc3N)n(-c3ccc4c(c3)CC[C@@H]4NC(=O)c3ccc(C(F)F)nc3)c2n1] |
| 408 | 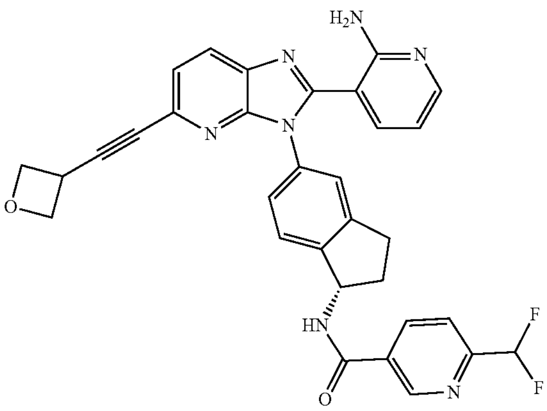 [SMILES: Nc1ncccc1-c1nc2ccc(C#CC3COC3)nc2n1-c1ccc2c(c1)CC[C@@H]2NC(=O)c1ccc(C(F)F)nc1] |

TABLE 1-continued
| Chemical structures of selected compounds. | |
|---|---|
| Cpd ID | Structure |
| 409 | 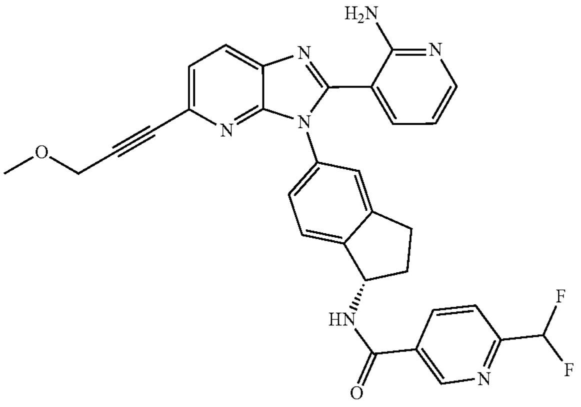 [SMILES: COCC#Cc1ccc2nc(-c3cccnc3N)n(-c3ccc4c(c3)CC[C@@H]4NC(=O)c3ccc(C(F)F)nc3)c2n1] |
| 410 | 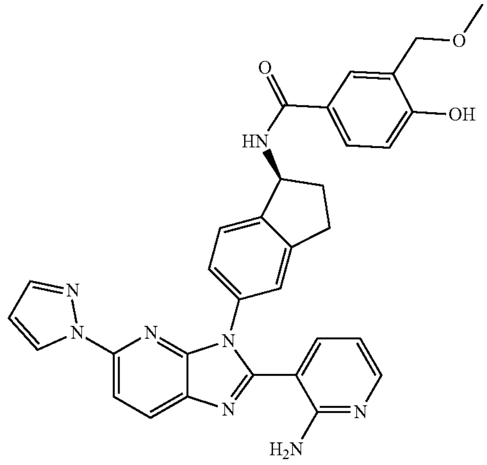 [SMILES: COCc1cc(C(=O)N[C@H]2CCc3cc(-n4c(-c5cccnc5N)nc5ccc(-n6cccn6)nc54)ccc32)ccc1O] |
| 411 | 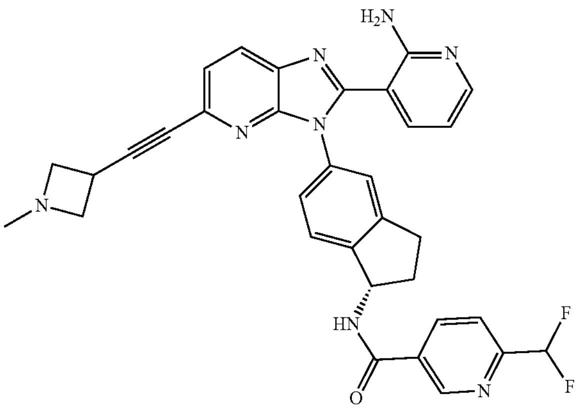 [SMILES: CN1CC(C#Cc2ccc3nc(-c4cccnc4N)n(-c4ccc5c(c4)CC[C@@H]5NC(=O)c4ccc(C(F)F)nc4)c3n2)C1] |

TABLE 1-continued
| Chemical structures of selected compounds. | |
|---|---|
| Cpd ID | Structure |
| 412 | 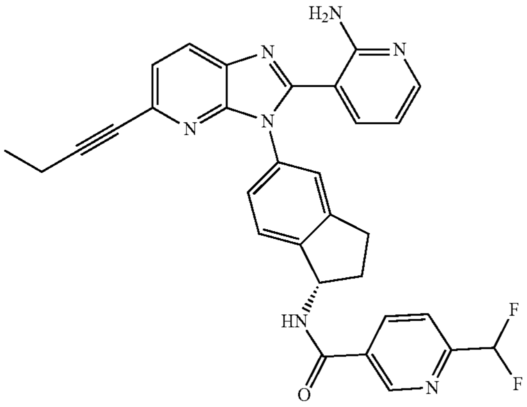 [SMILES: CCC#Cc1ccc2nc(-c3cccnc3N)n(-c3ccc4c(c3)CC[C@@H]4NC(=O)c3ccc(C(F)F)nc3)c2n1] |
| 413 | 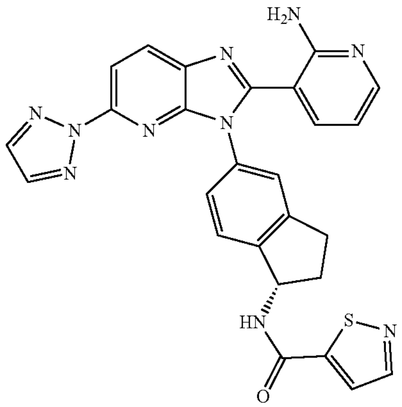 [SMILES: Nc1ncccc1-c1nc2ccc(-n3nccn3)nc2n1-c1ccc2c(c1)CC[C@@H]2NC(=O)c1ccns1] |
| 414 | 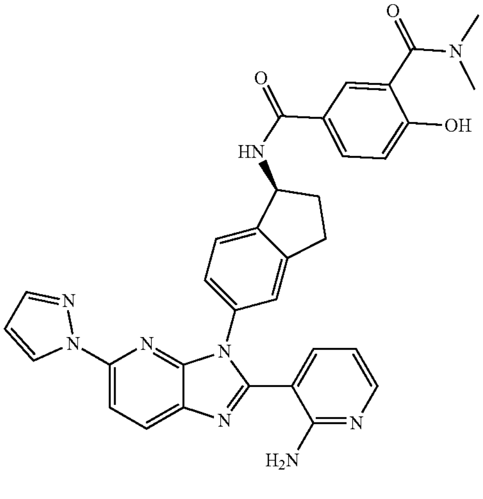 [SMILES: CN(C)C(=O)c1cc(C(=O)N[C@H]2CCc3cc(-n4c(-c5cccnc5N)nc5ccc(-n6cccn6)nc54)ccc32)ccc1O] |

TABLE 1-continued
| Chemical structures of selected compounds. | |
|---|---|
| Cpd ID | Structure |
| 415 | 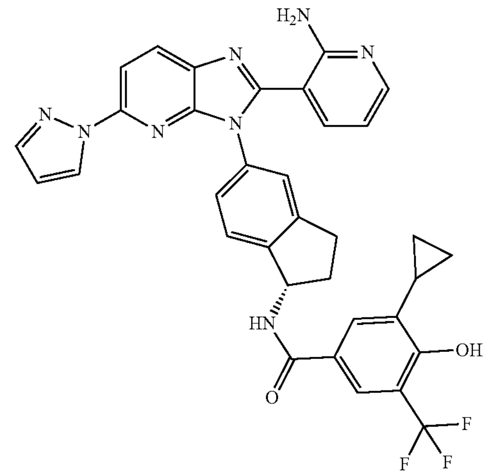 [SMILES: Nc1ncccc1-c1nc2ccc(-n3cccn3)nc2n1-c1ccc2c(c1)CC[C@@H]2NC(=O)c1cc(C2CC2)c(O)c(C(F)(F)F)c1] |
| 416 | 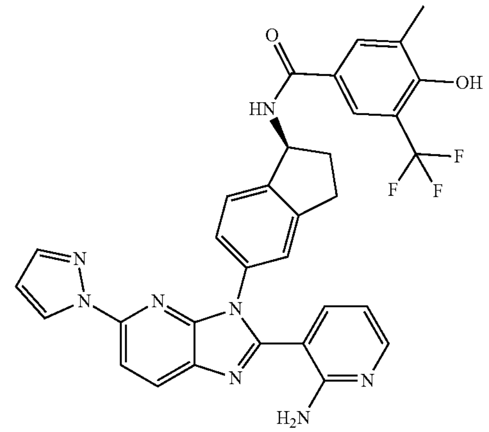 [SMILES: Cc1cc(C(=O)N[C@H]2CCc3cc(-n4c(-c5cccnc5N)nc5ccc(-n6cccn6)nc54)ccc32)cc(C(F)(F)F)c1O] |
| 417 | 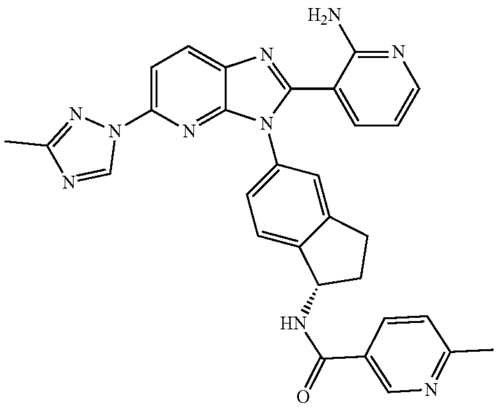 |

TABLE 1-continued
| Chemical structures of selected compounds. | |
|---|---|
| Cpd ID | Structure |
| 418 | 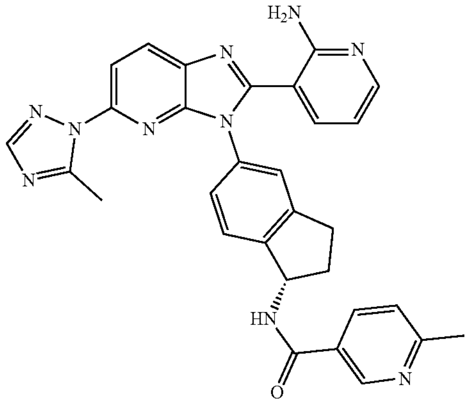 [SMILES: Cc1ccc(C(=O)N[C@H]2CCc3cc(-n4c(-c5cccnc5N)nc5ccc(-n6ncnc6C)nc54)ccc32)cn1] |
| 419 | 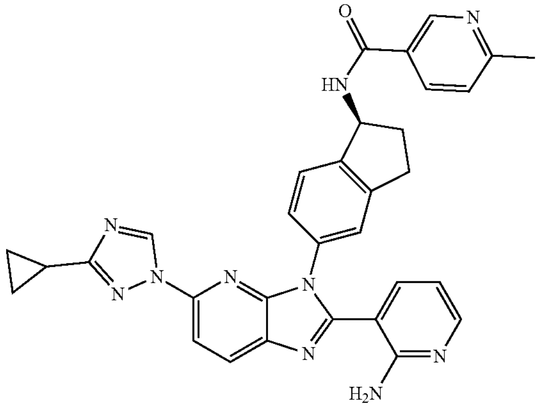 [SMILES: Cc1ccc(C(=O)N[C@H]2CCc3cc(-n4c(-c5cccnc5N)nc5ccc(-n6cnc(C7CC7)n6)nc54)ccc32)cn1] |
| 420 | 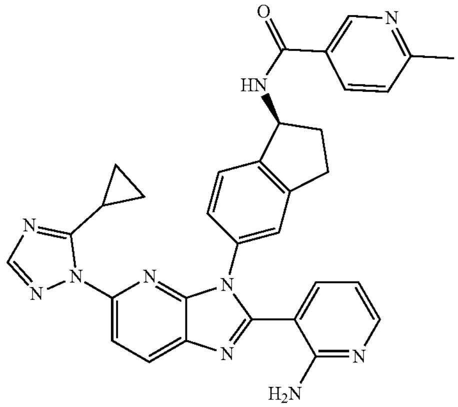 [SMILES: Cc1ccc(C(=O)N[C@H]2CCc3cc(-n4c(-c5cccnc5N)nc5ccc(-n6ncnc6C6CC6)nc54)ccc32)cn1] |

TABLE 1-continued
| Chemical structures of selected compounds. | |
|---|---|
| Cpd ID | Structure |
| 421 | 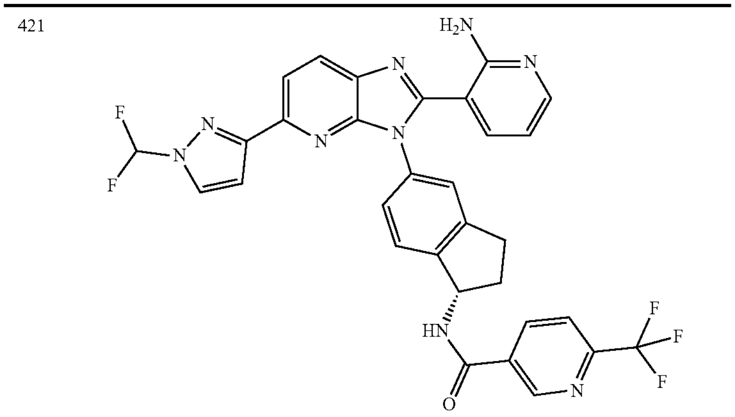 |
| 422 | 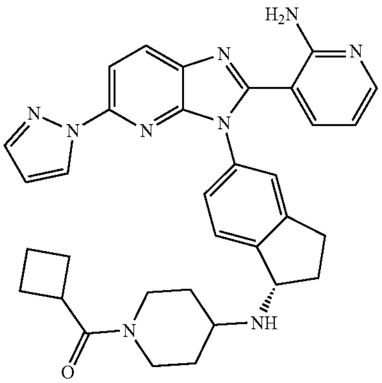 [SMILES: Nc1ncccc1-c1nc2ccc(-n3cccn3)nc2n1-c1ccc2c(c1)CC[C@@H]2NC1CCN(C(=O)C2CCC2)CC1] |
| 423 | 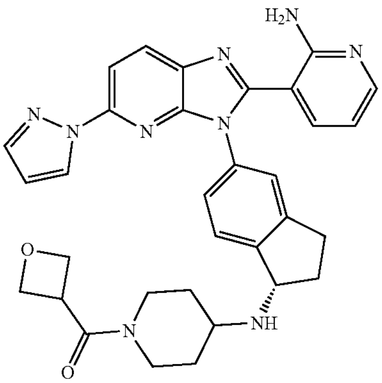 [SMILES: Nc1ncccc1-c1nc2ccc(-n3cccn3)nc2n1-c1ccc2c(c1)CC[C@@H]2NC1CCN(C(=O)C2COC2)CC1] |
| 424 | 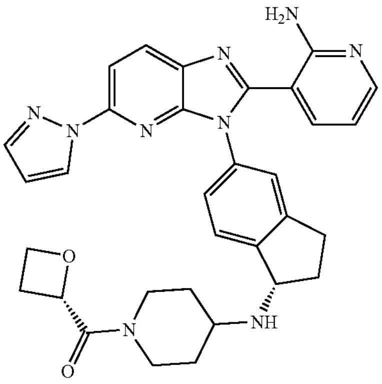 [SMILES: Nc1ncccc1-c1nc2ccc(-n3cccn3)nc2n1-c1ccc2c(c1)CC[C@@H]2NC1CCN(C(=O)[C@@H]2CCO2)CC1] |

TABLE 1-continued
| Chemical structures of selected compounds. | |
|---|---|
| Cpd ID | Structure |
| 425 | 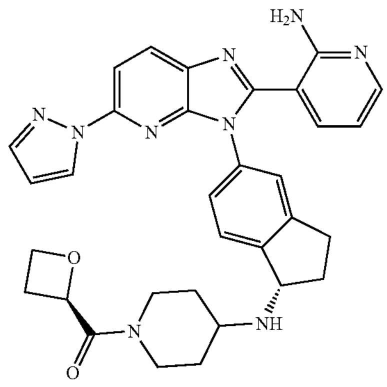 [SMILES: Nc1ncccc1-c1nc2ccc(-n3cccn3)nc2n1-c1ccc2c(c1)CC[C@@H]2NC1CCN(C(=O)[C@H]2CCO2)CC1] |
| 426 | 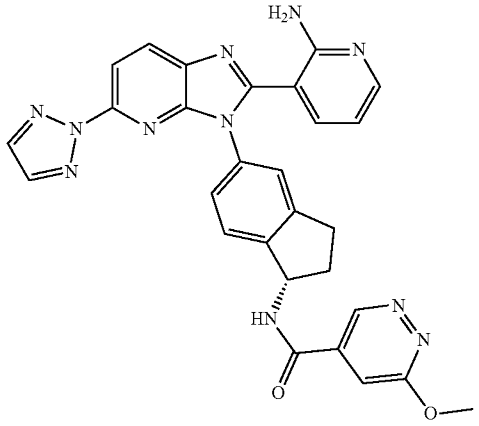 [SMILES: COc1cc(C(=O)N[C@H]2CCc3cc(-n4c(-c5cccnc5N)nc5ccc(-n6nccn6)nc54)ccc32)cnn1] |
| 427 | 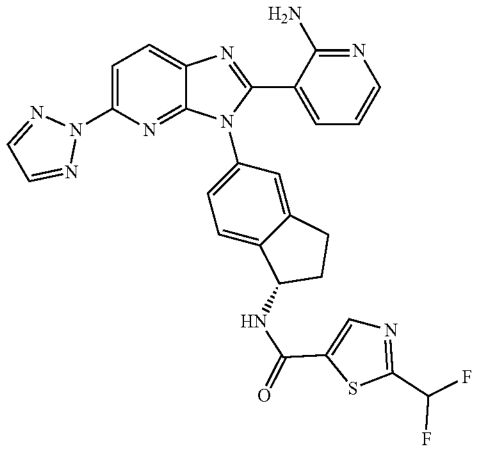 [SMILES: Nc1ncccc1-c1nc2ccc(-n3nccn3)nc2n1-c1ccc2c(c1)CC[C@@H]2NC(=O)c1cnc(C(F)F)s1] |

TABLE 1-continued
| Chemical structures of selected compounds. | |
|---|---|
| Cpd ID | Structure |
| 428 | 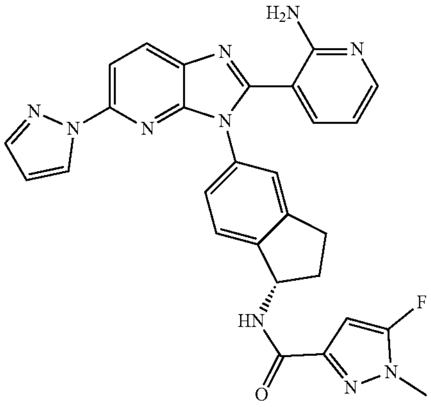 [SMILES: Cn1nc(C(=O)N[C@H]2CCc3cc(-n4c(-c5cccnc5N)nc5ccc(-n6cccn6)nc54)ccc32)cc1F] |
| 429 | 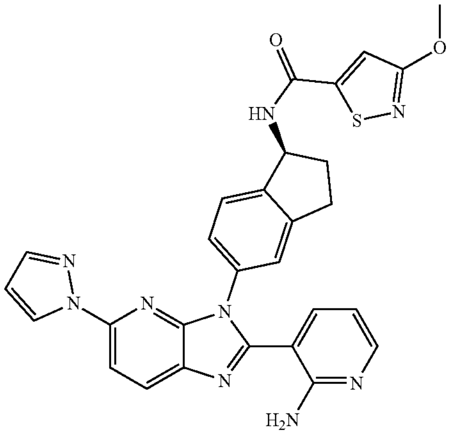 [SMILES: COc1cc(C(=O)N[C@H]2CCc3cc(-n4c(-c5cccnc5N)nc5ccc(-n6cccn6)nc54)ccc32)sn1] |
| 430 | 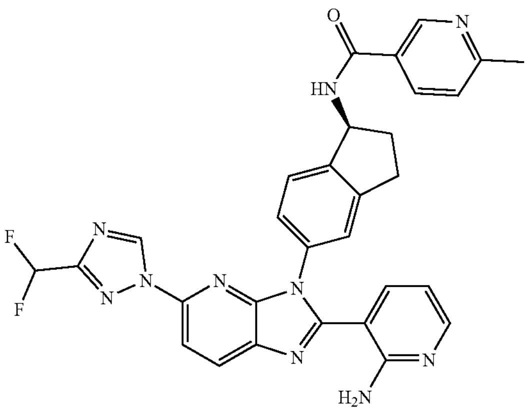 [SMILES: Cc1ccc(C(=O)N[C@H]2CCc3cc(-n4c(-c5cccnc5N)nc5ccc(-n6cnc(C(F)F)n6)nc54)ccc32)cn1] |

TABLE 1-continued
| Chemical structures of selected compounds. | |
|---|---|
| Cpd ID | Structure |
| 431 | 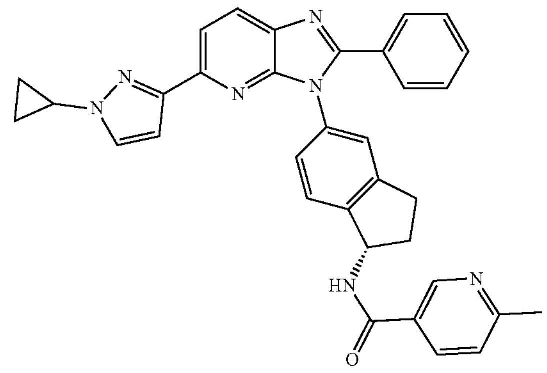 [SMILES: Cc1ccc(C(=O)N[C@H]2CCc3cc(-n4c(-c5ccccc5)nc5ccc(-c6ccn(C7CC7)n6)nc54)ccc32)cn1] |
| 432 | 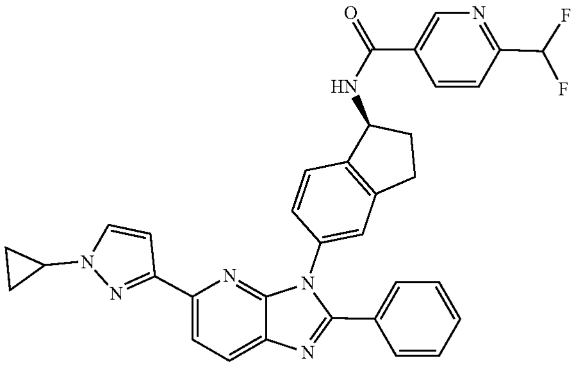 [SMILES: O=C(N[C@H]1CCc2cc(-n3c(-c4ccccc4)nc4ccc(-c5ccn(C6CC6)n5)nc43)ccc21)c1ccc(C(F)F)nc1] |
| 433 | 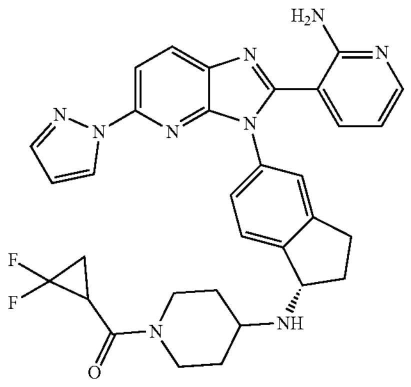 [SMILES: Nc1ncccc1-c1nc2ccc(-n3cccn3)nc2n1-c1ccc2c(c1)CC[C@@H]2NC1CCN(C(=O)C2CC2(F)F)CC1] |
| 434 | 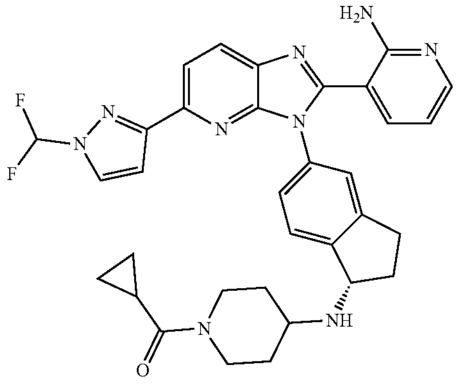 [SMILES: Nc1ncccc1-c1nc2ccc(-c3ccn(C(F)F)n3)nc2n1-c1ccc2c(c1)CC[C@@H]2NC1CCN(C(=O)C2CC2)CC1] |

TABLE 1-continued
| Chemical structures of selected compounds. | |
|---|---|
| Cpd ID | Structure |
| 435 | 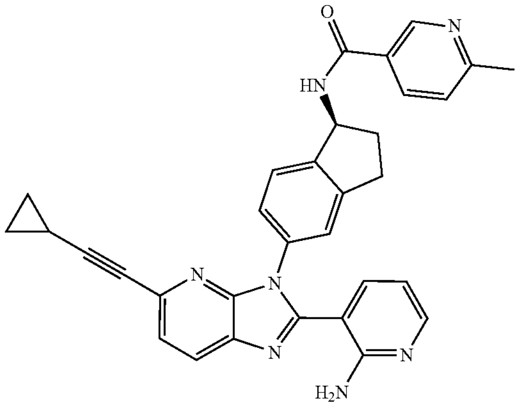 [SMILES: Cc1ccc(C(=O)N[C@H]2CCc3cc(-n4c(-c5cccnc5N)nc5ccc(C#CC6CC6)nc54)ccc32)cn1] |
| 436 | 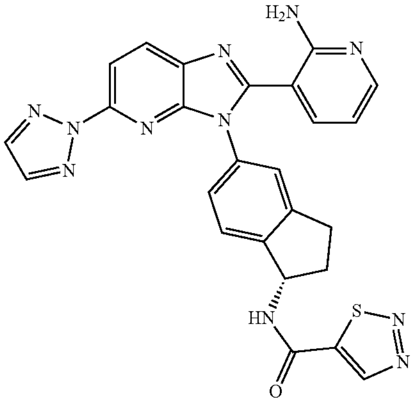 [SMILES: Nc1ncccc1-c1nc2ccc(-n3nccn3)nc2n1-c1ccc2c(c1)CC[C@@H]2NC(=O)c1cnns1] |
| 437 | 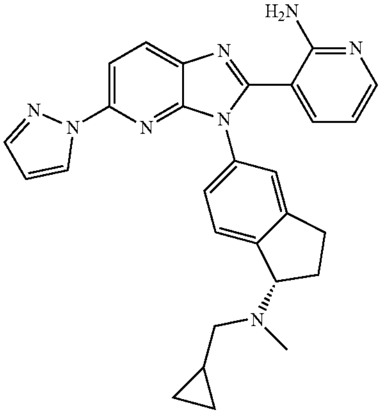 [SMILES: CN(CC1CC1)[C@H]1CCc2cc(-n3c(-c4cccnc4N)nc4ccc(-n5cccn5)nc43)ccc21] |

TABLE 1-continued
| Chemical structures of selected compounds. | |
|---|---|
| Cpd ID | Structure |
| 438 | 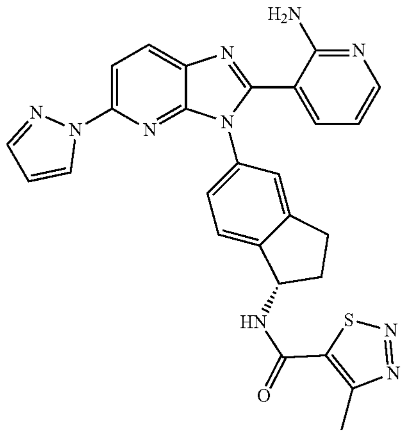 [SMILES: Cc1nnsc1C(=O)N[C@H]1CCc2cc(-n3c(-c4cccnc4N)nc4ccc(-n5cccn5)nc43)ccc21] |
| 439 | 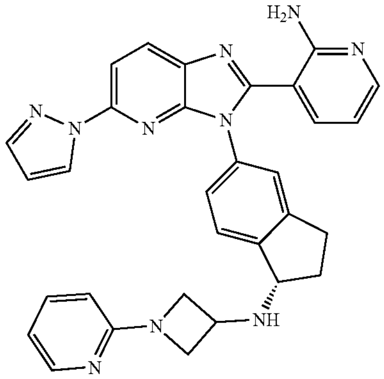 [SMILES: Nc1ncccc1-c1nc2ccc(-n3cccn3)nc2n1-c1ccc2c(c1)CC[C@@H]2NC1CN(c2ccccn2)C1] |
| 440 | 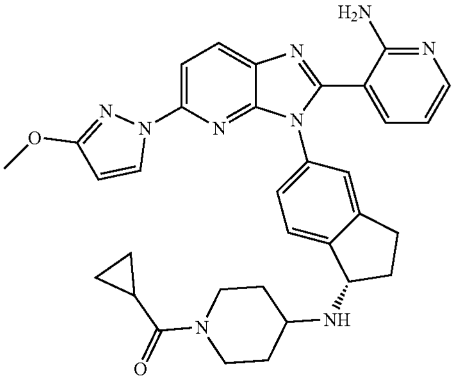 [SMILES: COc1ccn(-c2ccc3nc(-c4cccnc4N)n(-c4ccc5c(c4)CC[C@@H]5NC4CCN(C(=O)C5CC5)CC4)c3n2)n1] |

TABLE 1-continued
| Cpd ID | Structure |
| --- | --- |
| 441 | 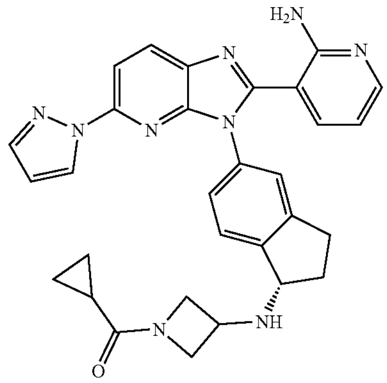 [SMILES: Nc1ncccc1-c1nc2ccc(-n3cccn3)nc2n1-c1ccc2c(c1)CC[C@@H]2NC1CN(C(=O)C2CC2)C1] |
| 442 | 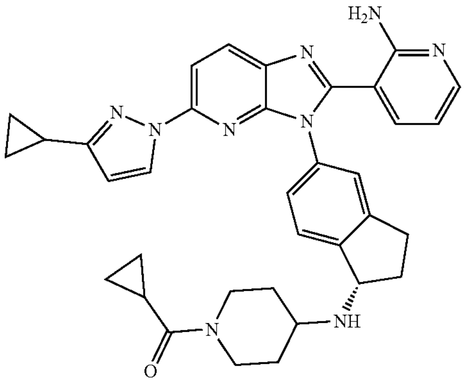 [SMILES: Nc1ncccc1-c1nc2ccc(-n3ccc(C4CC4)n3)nc2n1-c1ccc2c(c1)CC[C@@H]2NC1CCN(C(=O)C2CC2)CC1] |
| 443 | 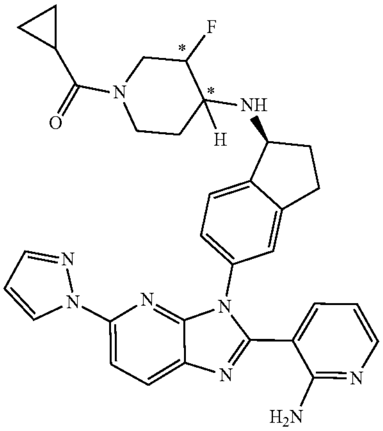 [SMILES: Nc1ncccc1-c1nc2ccc(-n3cccn3)nc2n1-c1ccc2c(c1)CC[C@@H]2NC1CCN(C(=O)C2CC2)CC1F] |
Chemical structures of selected compounds.

TABLE 1-continued
| Chemical structures of selected compounds. | |
|---|---|
| Cpd ID | Structure |
| 444 | 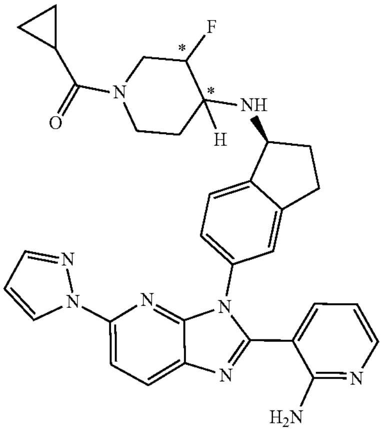 [SMILES: Nc1ncccc1-c1nc2ccc(-n3cccn3)nc2n1-c1ccc2c(c1)CC[C@@H]2NC1CCN(C(=O)C2CC2)CC1F] |
| 445 | 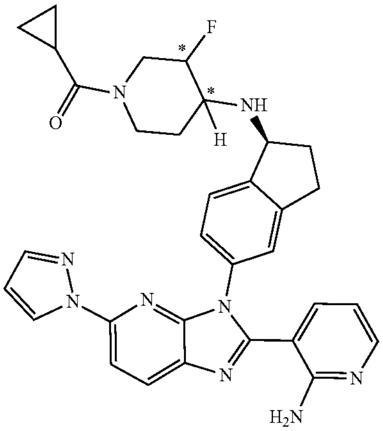 [SMILES: Nc1ncccc1-c1nc2ccc(-n3cccn3)nc2n1-c1ccc2c(c1)CC[C@@H]2NC1CCN(C(=O)C2CC2)CC1F] |
| 446 | 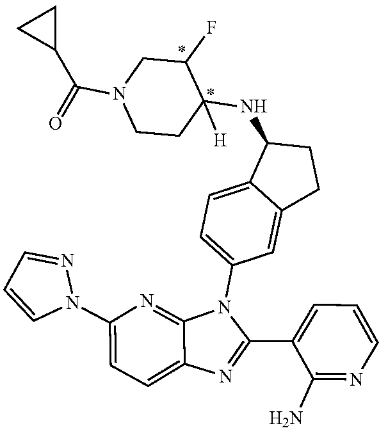 [SMILES: Nc1ncccc1-c1nc2ccc(-n3cccn3)nc2n1-c1ccc2c(c1)CC[C@@H]2NC1CCN(C(=O)C2CC2)CC1F] |

TABLE 1-continued
| Chemical structures of selected compounds. | |
|---|---|
| Cpd ID | Structure |
| 447 | 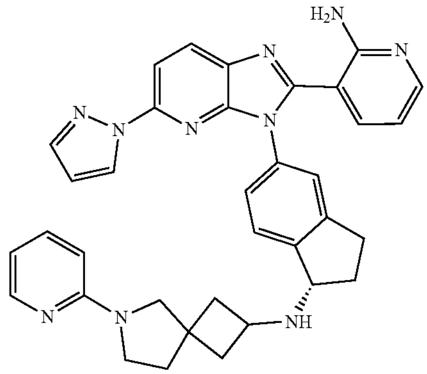 [SMILES: Nc1ncccc1-c1nc2ccc(-n3cccn3)nc2n1-c1ccc2c(c1)CC[C@@H]2NC1CC2(CCN(c3ccccn3)C2)C1] |
| 448 | 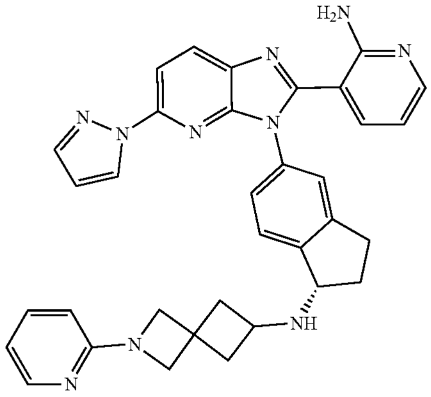 [SMILES: Nc1ncccc1-c1nc2ccc(-n3cccn3)nc2n1-c1ccc2c(c1)CC[C@@H]2NC1CC2(C1)CN(c1ccccn1)C2] |
| 449 | 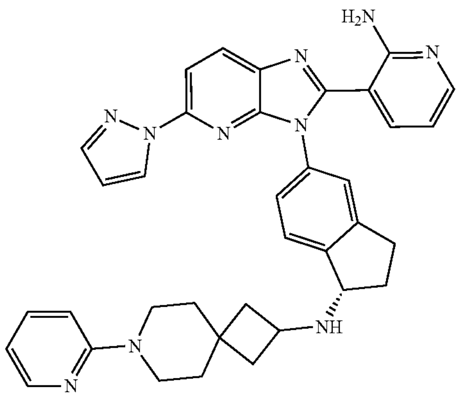 [SMILES: Nc1ncccc1-c1nc2ccc(-n3cccn3)nc2n1-c1ccc2c(c1)CC[C@@H]2NC1CC2(CCN(c3ccccn3)CC2)C1] |

TABLE 1-continued
| Chemical structures of selected compounds. | |
|---|---|
| Cpd ID | Structure |
| 450 | 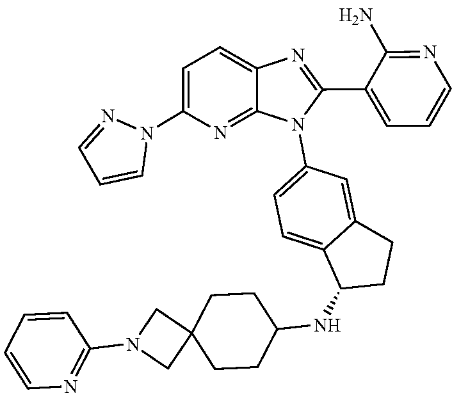 [SMILES: Nc1ncccc1-c1nc2ccc(-n3cccn3)nc2n1-c1ccc2c(c1)CC[C@@H]2NC1CCC2(CC1)CN(c1ccccn1)C2] |
| 451 | 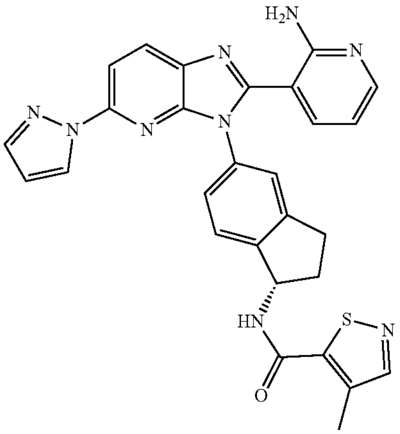 [SMILES: Cc1cnsc1C(=O)N[C@H]1CCc2cc(-n3c(-c4cccnc4N)nc4ccc(-n5cccn5)nc43)ccc21] |
| 452 | 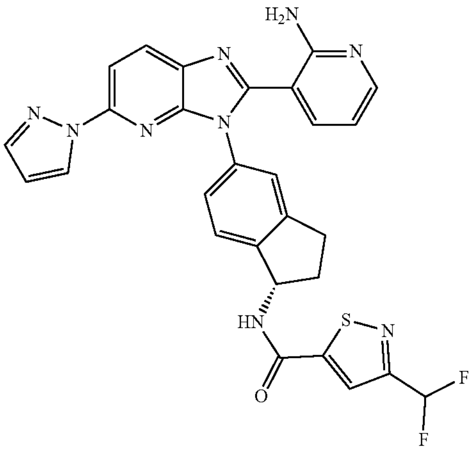 [SMILES: Nc1ncccc1-c1nc2ccc(-n3cccn3)nc2n1-c1ccc2c(c1)CC[C@@H]2NC(=O)c1cc(C(F)F)ns1] |

TABLE 1-continued
| Cpd ID | Structure |
|---|---|
| 453 | 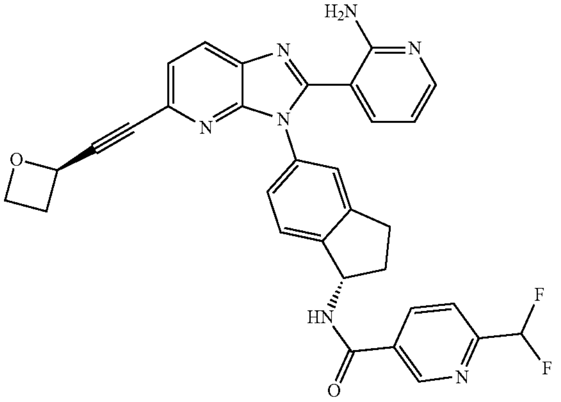 [SMILES: Nc1ncccc1-c1nc2ccc(C#C[C@H]3CCO3)nc2n1-c1ccc2c(c1)CC[C@@H]2NC(=O)c1ccc(C(F)F)nc1] |
| 454 | 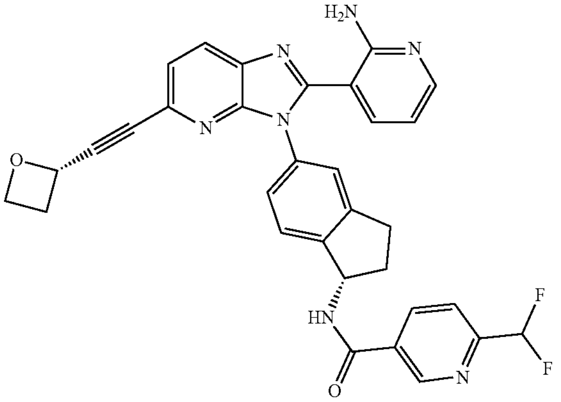 [SMILES: Nc1ncccc1-c1nc2ccc(C#C[C@@H]3CCO3)nc2n1-c1ccc2c(c1)CC[C@@H]2NC(=O)c1ccc(C(F)F)nc1] |
| 455 | 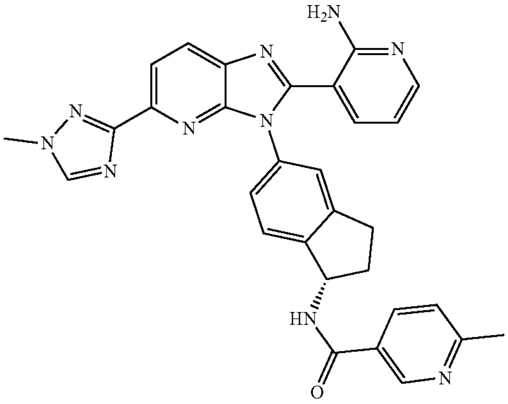 |
Chemical structures of selected compounds.

TABLE 1-continued
| Chemical structures of selected compounds. | |
|---|---|
| Cpd ID | Structure |
| 456 | 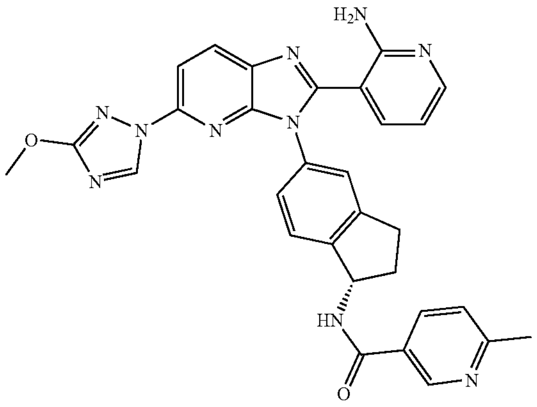 |
| 459 | 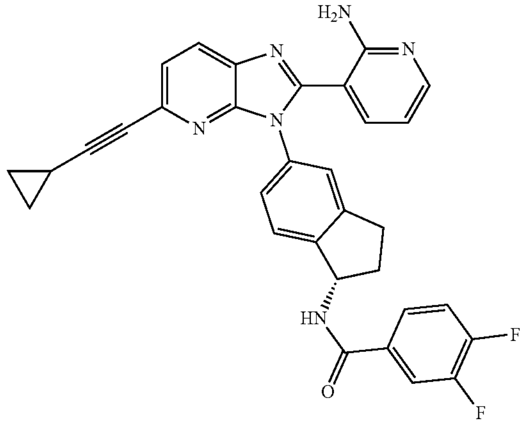 [SMILES: Nc1ncccc1-c1nc2ccc(C#CC3CC3)nc2n1-c1ccc2c(c1)CC[C@@H]2NC(=O)c1ccc(F)c(F)c1] |
| 460 | 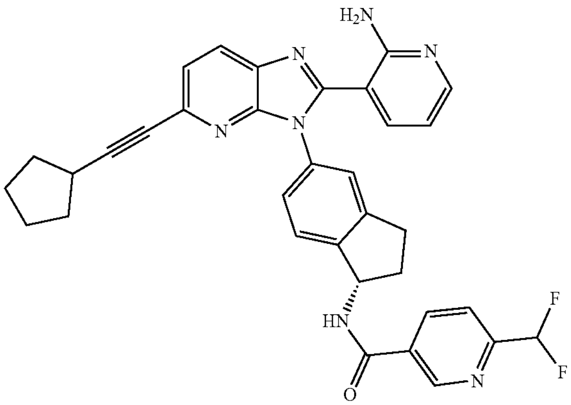 [SMILES: Nc1ncccc1-c1nc2ccc(C#CC3CCCC3)nc2n1-c1ccc2c(c1)CC[C@@H]2NC(=O)c1ccc(C(F)F)nc1] |

TABLE 1-continued
| Cpd ID | Structure |
|---|---|
| 461 | 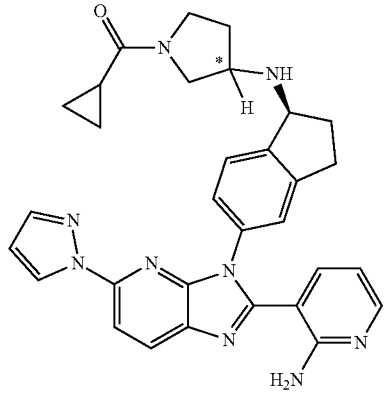 [SMILES: Nc1ncccc1-c1nc2ccc(-n3cccn3)nc2n1-c1ccc2c(c1)CC[C@@H]2NC1CCN(C(=O)C2CC2)C1] |
| 462 | 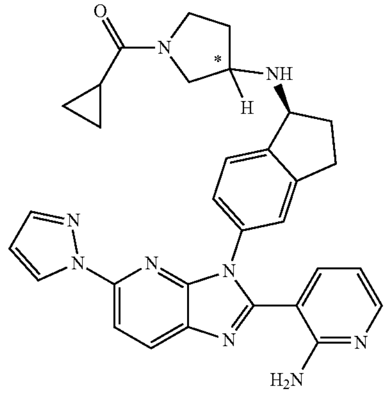 [SMILES: Nc1ncccc1-c1nc2ccc(-n3cccn3)nc2n1-c1ccc2c(c1)CC[C@@H]2NC1CCN(C(=O)C2CC2)C1] |
| 463 | 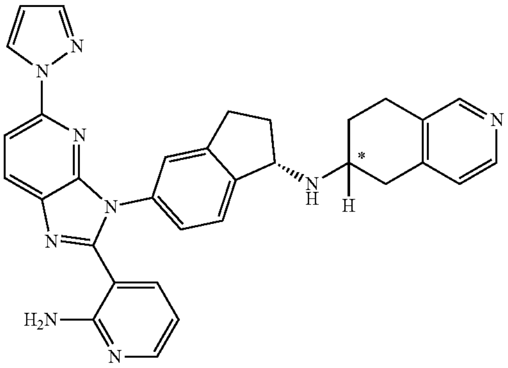 [SMILES: Nc1ncccc1-c1nc2ccc(-n3cccn3)nc2n1-c1ccc2c(c1)CC[C@@H]2NC1CCc2cnccc2C1] |
| 464 | 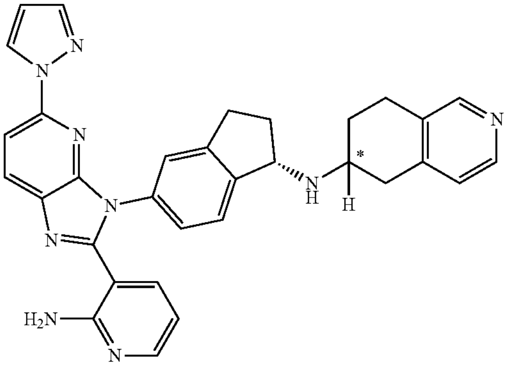 [SMILES: Nc1ncccc1-c1nc2ccc(-n3cccn3)nc2n1-c1ccc2c(c1)CC[C@@H]2NC1CCc2cnccc2C1] |
Chemical structures of selected compounds.

TABLE 1-continued
Chemical structures of selected compounds.
| Cpd ID | Structure |
|---|---|
| 465 | 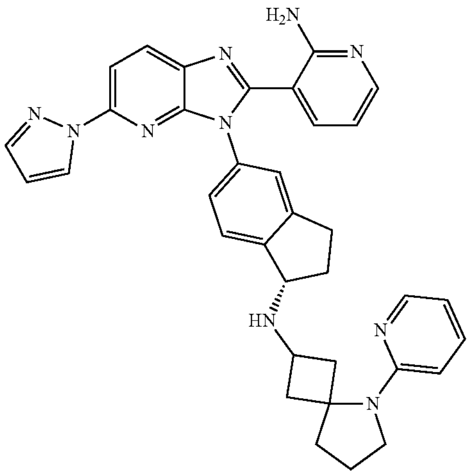 [SMILES: Nc1ncccc1-c1nc2ccc(-n3cccn3)nc2n1-c1ccc2c(c1)CC[C@@H]2NC1CC2(CCCN2c2ccccn2)C1] |
| 466 | 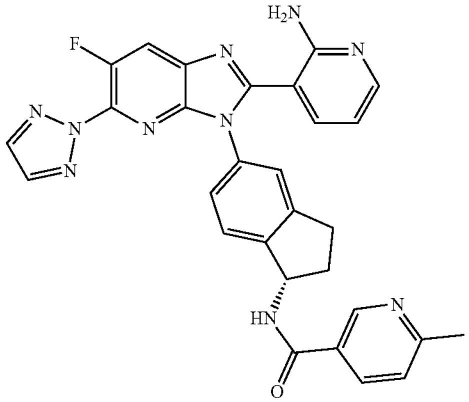 [SMILES: Cc1ccc(C(=O)N[C@H]2CCc3cc(-n4c(-c5cccnc5N)nc5cc(F)c(-n6nccn6)nc54)ccc32)cn1] |
| 467 | 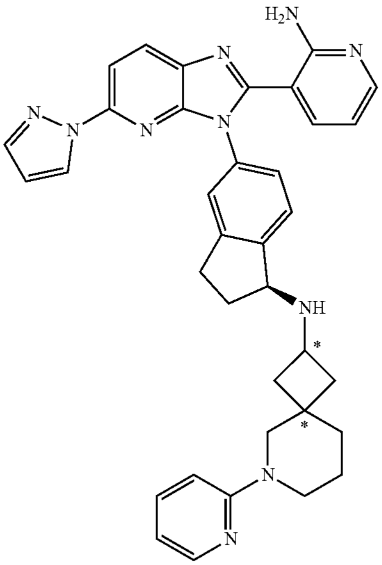 [SMILES: Nc1ncccc1-c1nc2ccc(-n3cccn3)nc2n1-c1ccc2c(c1)CC[C@@H]2NC1CC2(CCCN(c3ccccn3)C2)C1] |

TABLE 1-continued
| Chemical structures of selected compounds. | |
|---|---|
| Cpd ID | Structure |
| 468 | 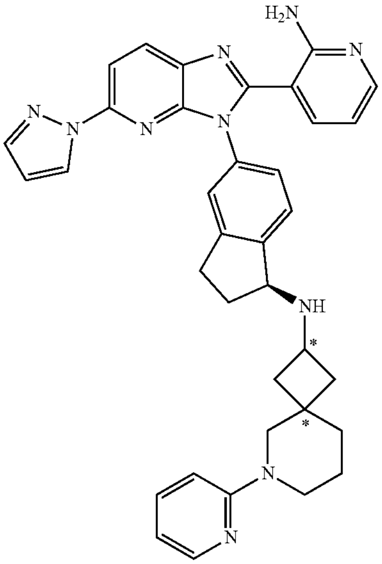 [SMILES: Nc1ncccc1-c1nc2ccc(-n3cccn3)nc2n1-c1ccc2c(c1)CC[C@@H]2NC1CC2(CCCN(c3ccccn3)C2)C1] |
| 469 | 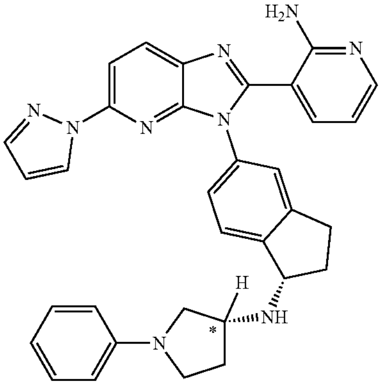 [SMILES: Nc1ncccc1-c1nc2ccc(-n3cccn3)nc2n1-c1ccc2c(c1)CC[C@@H]2N[C@@H]1CCN(c2ccccc2)C1] |
| 470 | 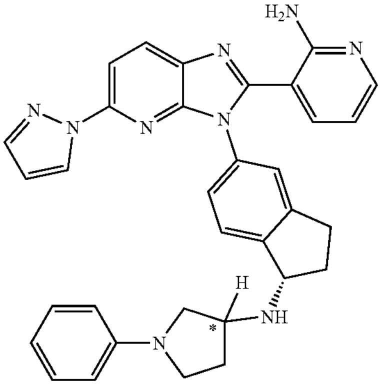 [SMILES: Nc1ncccc1-c1nc2ccc(-n3cccn3)nc2n1-c1ccc2c(c1)CC[C@@H]2NC1CCN(c2ccccc2)C1] |

TABLE 1-continued
| Chemical structures of selected compounds. | |
|---|---|
| Cpd ID | Structure |
| 471 | 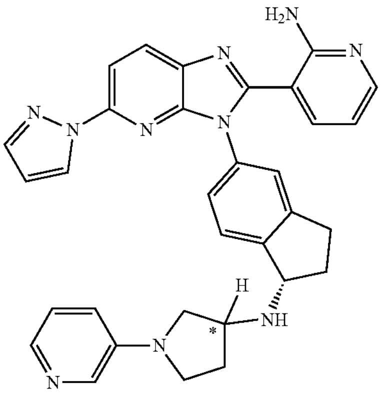 [SMILES: Nc1ncccc1-c1nc2ccc(-n3cccn3)nc2n1-c1ccc2c(c1)CC[C@@H]2NC1CCN(c2cccnc2)C1] |
| 472 | 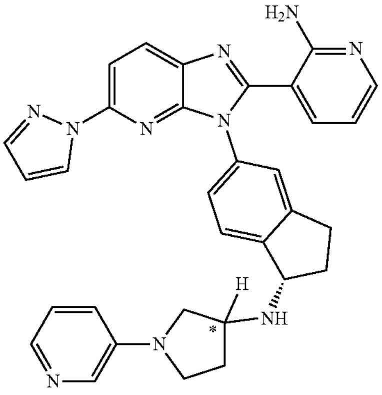 [SMILES: Nc1ncccc1-c1nc2ccc(-n3cccn3)nc2n1-c1ccc2c(c1)CC[C@@H]2NC1CCN(c2cccnc2)C1] |
| 473 | 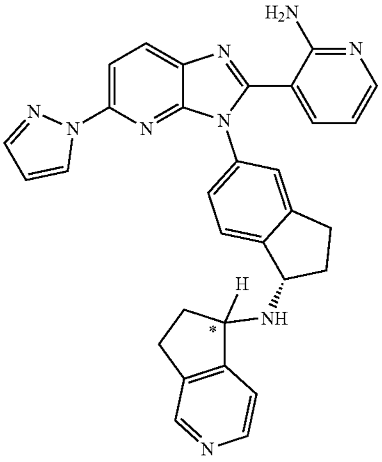 [SMILES: Nc1ncccc1-c1nc2ccc(-n3cccn3)nc2n1-c1ccc2c(c1)CC[C@@H]2NC1CCc2cnccc21] |

TABLE 1-continued
| Chemical structures of selected compounds. | |
|---|---|
| Cpd ID | Structure |
| 474 | 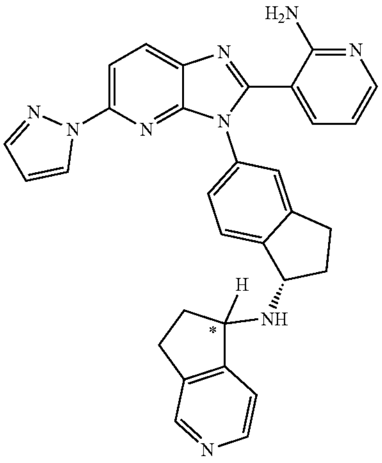 [SMILES: Nc1ncccc1-c1nc2ccc(-n3cccn3)nc2n1-c1ccc2c(c1)CC[C@@H]2NC1CCc2cnccc21] |
| 476 | 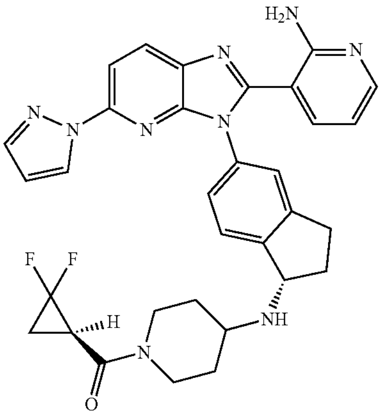 [SMILES: Nc1ncccc1-c1nc2ccc(-n3cccn3)nc2n1-c1ccc2c(c1)CC[C@@H]2NC1CCN(C(=O)[C@H]2CC2(F)F)CC1] |
| 477 | 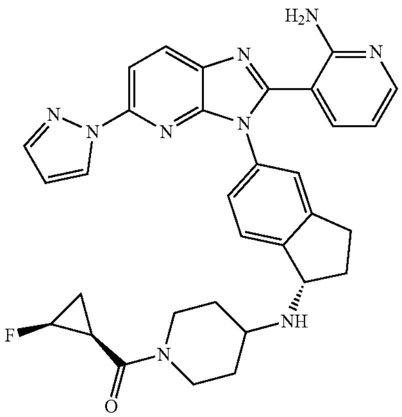 [SMILES: Nc1ncccc1-c1nc2ccc(-n3cccn3)nc2n1-c1ccc2c(c1)CC[C@@H]2NC1CCN(C(=O)[C@@H]2C[C@@H]2F)CC1] |

TABLE 1-continued
| Chemical structures of selected compounds. | |
|---|---|
| Cpd ID | Structure |
| 478 | 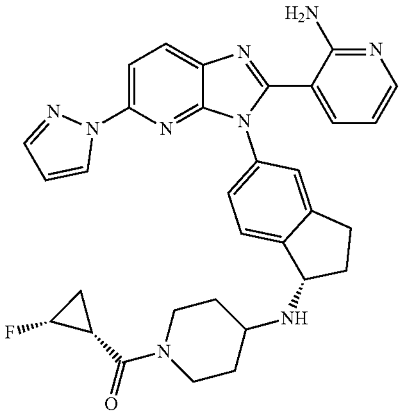 [SMILES: Nc1ncccc1-c1nc2ccc(-n3cccn3)nc2n1-c1ccc2c(c1)CC[C@@H]2NC1CCN(C(=O)[C@H]2C[C@H]2F)CC1] |
| 479 | 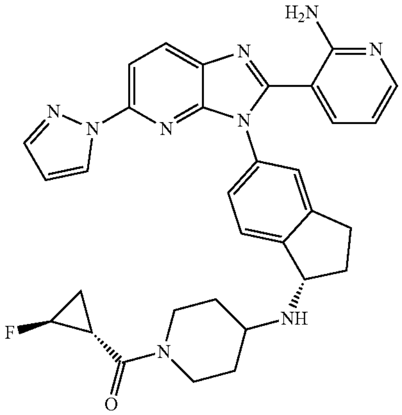 [SMILES: Nc1ncccc1-c1nc2ccc(-n3cccn3)nc2n1-c1ccc2c(c1)CC[C@@H]2NC1CCN(C(=O)[C@H]2C[C@@H]2F)CC1] |
| 480 | 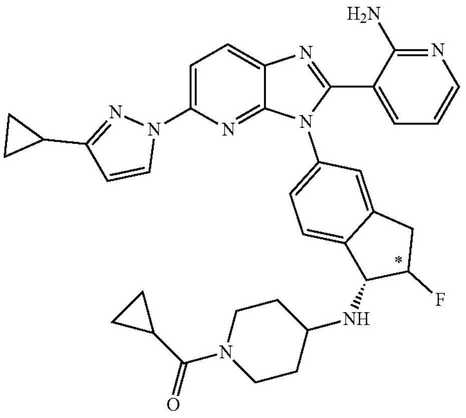 [SMILES: Nc1ncccc1-c1nc2ccc(-n3ccc(C4CC4)n3)nc2n1-c1ccc2c(c1)CC(F)[C@@H]2NC1CCN(C(=O)C2CC2)CC1] |

TABLE 1-continued
| Chemical structures of selected compounds. | |
|---|---|
| Cpd ID | Structure |
| 481 | 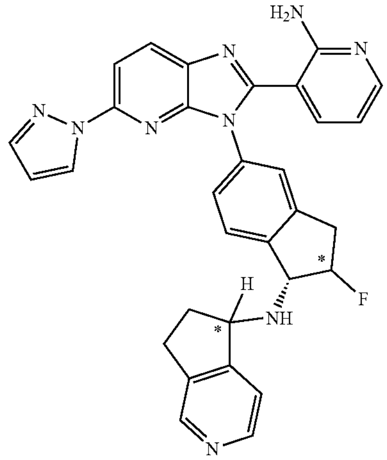 [SMILES: Nc1ncccc1-c1nc2ccc(-n3cccn3)nc2n1-c1ccc2c(c1)CC(F)[C@@H]2NC1CCc2cnccc21] |
| 482 | 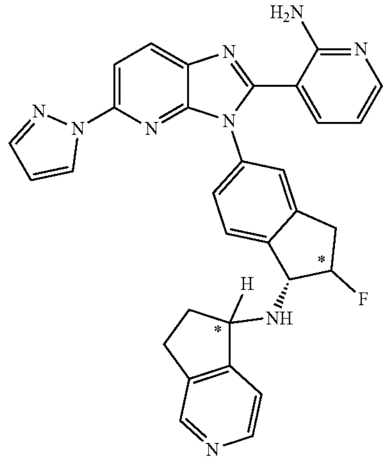 [SMILES: Nc1ncccc1-c1nc2ccc(-n3cccn3)nc2n1-c1ccc2c(c1)CC(F)[C@@H]2NC1CCc2cnccc21] |
| 483 | 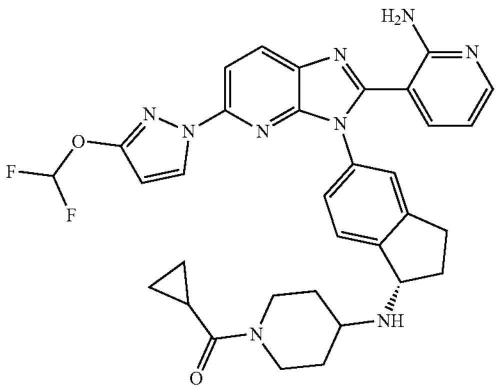 [SMILES: Nc1ncccc1-c1nc2ccc(-n3ccc(OC(F)F)n3)nc2n1-c1ccc2c(c1)CC[C@@H]2NC1CCN(C(=O)C2CC2)CC1] |

TABLE 1-continued
| Chemical structures of selected compounds. | |
|---|---|
| Cpd ID | Structure |
| 484 | 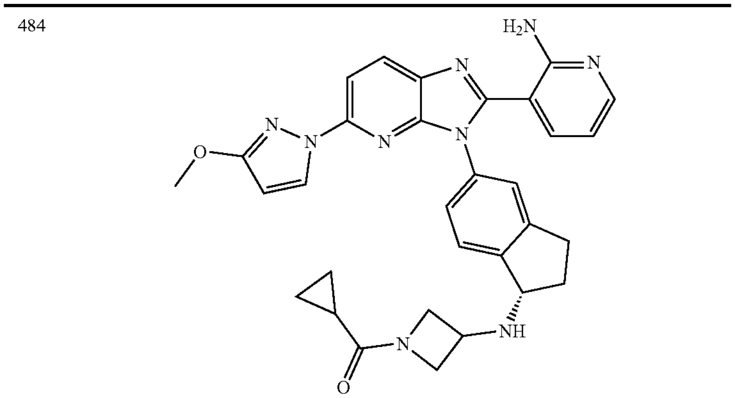 |
| 485 | 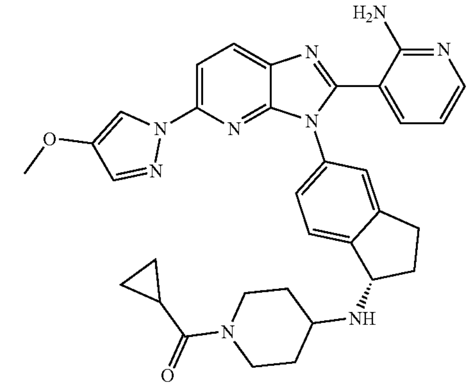 [SMILES: COc1cnn(-c2ccc3nc(-c4cccnc4N)n(-c4ccc5c(c4)CC[C@@H]5NC4CCN(C(=O)C5CC5)CC4)c3n2)c1] |
| 486 | 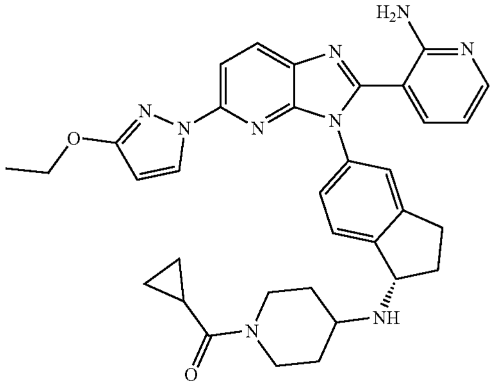 [SMILES: CCOc1ccn(-c2ccc3nc(-c4cccnc4N)n(-c4ccc5c(c4)CC[C@@H]5NC4CCN(C(=O)C5CC5)CC4)c3n2)n1] |
| 487 | 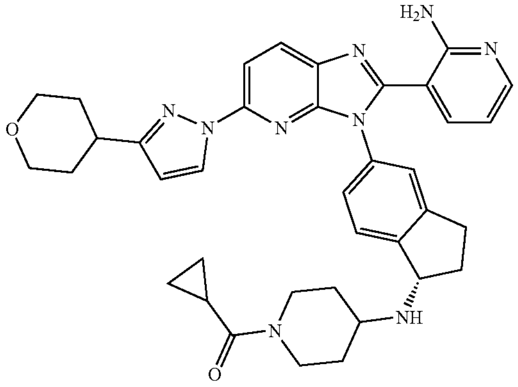 [SMILES: Nc1ncccc1-c1nc2ccc(-n3ccc(C4CCOCC4)n3)nc2n1-c1ccc2c(c1)CC[C@@H]2NC1CCN(C(=O)C2CC2)CC1] |

TABLE 1-continued
| Chemical structures of selected compounds. | |
|---|---|
| Cpd ID | Structure |
| 488 | 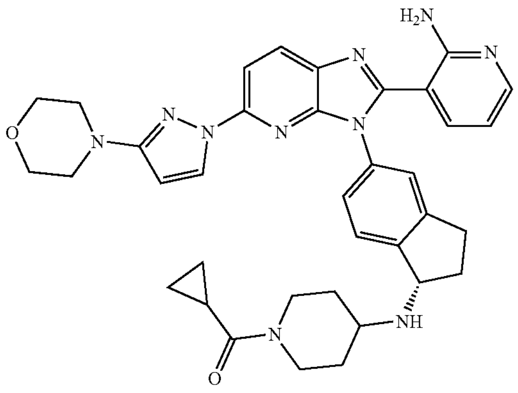 [SMILES: Nc1ncccc1-c1nc2ccc(-n3ccc(N4CCOCC4)n3)nc2n1-c1ccc2c(c1)CC[C@@H]2NC1CCN(C(=O)C2CC2)CC1] |
| 489 | 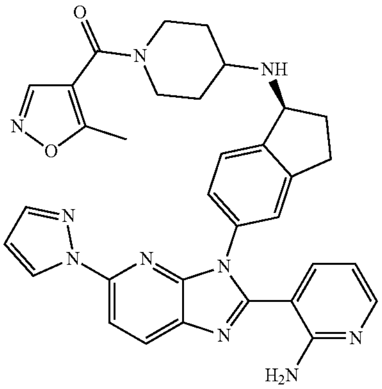 [SMILES: Cc1oncc1C(=O)N1CCC(N[C@H]2CCc3cc(-n4c(-c5cccnc5N)nc5ccc(-n6cccn6)nc54)ccc32)CC1] |
| 490 | 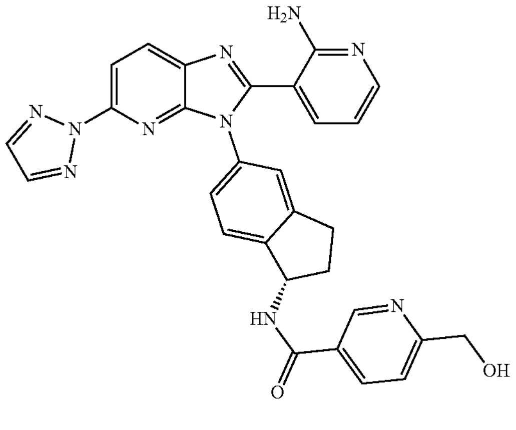 [SMILES: Nc1ncccc1-c1nc2ccc(-n3nccn3)nc2n1-c1ccc2c(c1)CC[C@@H]2NC(=O)c1ccc(CO)nc1] |

TABLE 1-continued
| Chemical structures of selected compounds. | |
|---|---|
| Cpd ID | Structure |
| 491 | 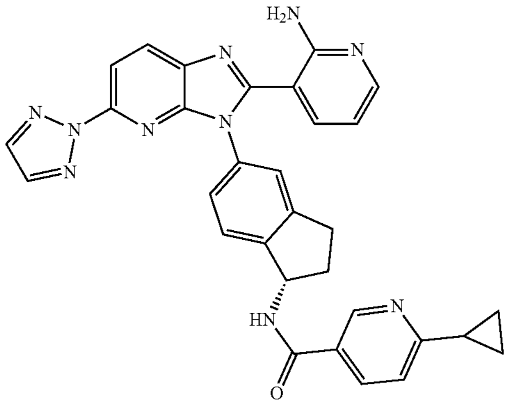 [SMILES: Nc1ncccc1-c1nc2ccc(-n3nccn3)nc2n1-c1ccc2c(c1)CC[C@@H]2NC(=O)c1ccc(C2CC2)nc1] |
| 492 | 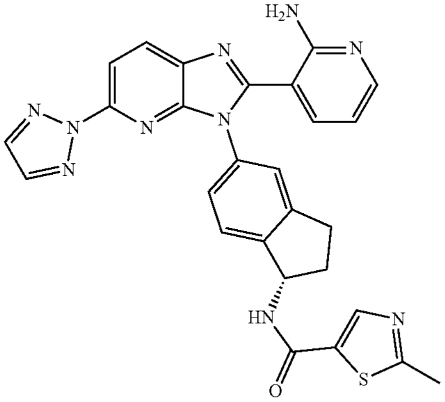 [SMILES: Cc1ncc(C(=O)N[C@H]2CCc3cc(-n4c(-c5cccnc5N)nc5ccc(-n6nccn6)nc54)ccc32)s1] |
| 493 | 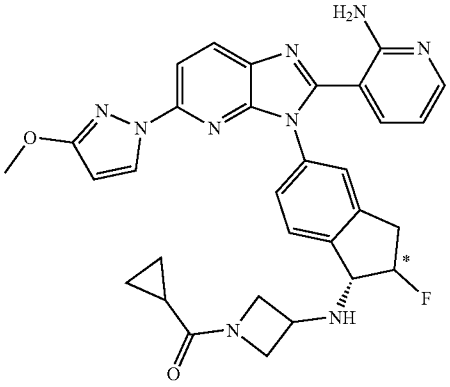 [SMILES: COc1ccn(-c2ccc3nc(-c4cccnc4N)n(-c4ccc5c(c4)CC(F)[C@@H]5NC4CN(C(=O)C5CC5)C4)c3n2)n1] |

TABLE 1-continued
| Chemical structures of selected compounds. | |
|---|---|
| Cpd ID | Structure |
| 494 | 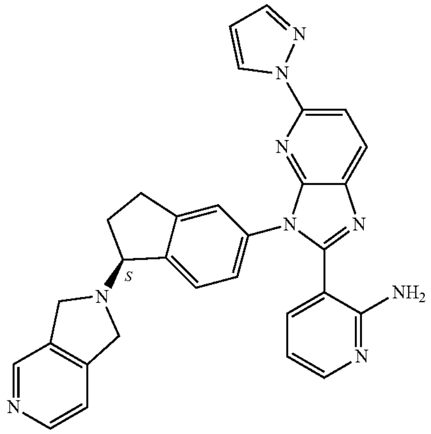 |
| 495 | 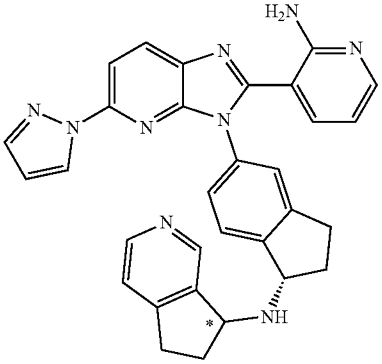 [SMILES: Nc1ncccc1-c1nc2ccc(-n3cccn3)nc2n1-c1ccc2c(c1)CC[C@@H]2NC1CCc2ccncc21] |
| 496 | 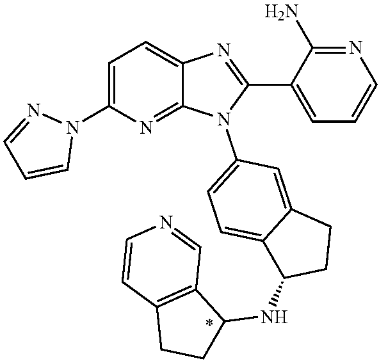 [SMILES: Nc1ncccc1-c1nc2ccc(-n3cccn3)nc2n1-c1ccc2c(c1)CC[C@@H]2NC1CCc2ccncc21] |

TABLE 1-continued
| Chemical structures of selected compounds. | |
|---|---|
| Cpd ID | Structure |
| 497 | 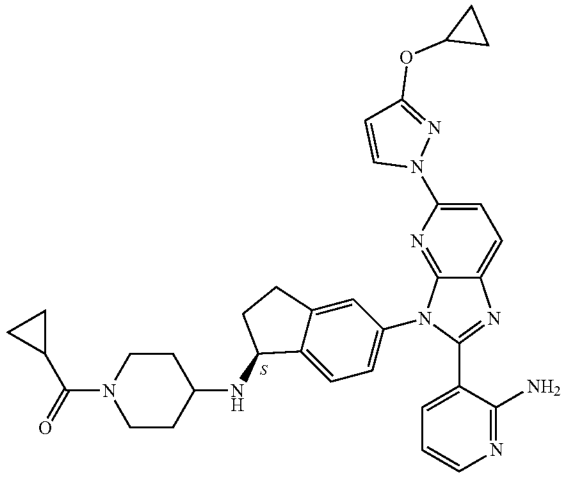 |
| 499 | 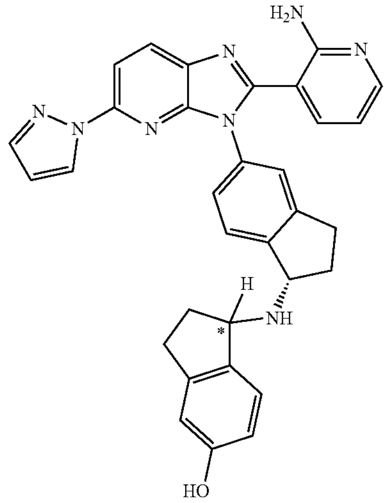 [SMILES: Nc1ncccc1-c1nc2ccc(-n3cccn3)nc2n1-c1ccc2c(c1)CC[C@@H]2NC1CCc2cc(O)ccc21] |
| 501 | 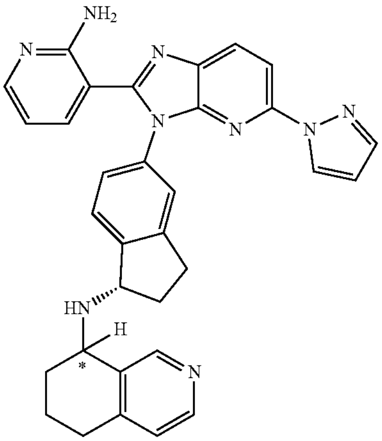 [SMILES: Nc1ncccc1-c1nc2ccc(-n3cccn3)nc2n1-c1ccc2c(c1)CC[C@@H]2NC1CCCc2ccncc21] |

TABLE 1-continued
| Chemical structures of selected compounds. | |
|---|---|
| Cpd ID | Structure |
| 503 | 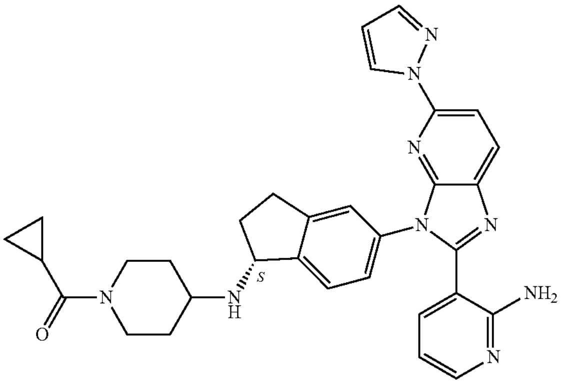 |
| 498 | 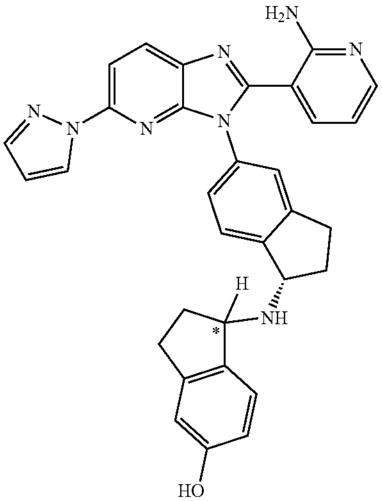 [SMILES: Nc1ncccc1-c1nc2ccc(-n3cccn3)nc2n1-c1ccc2c(c1)CC[C@@H]2NC1CCc2cc(O)ccc21] |
| 500 | 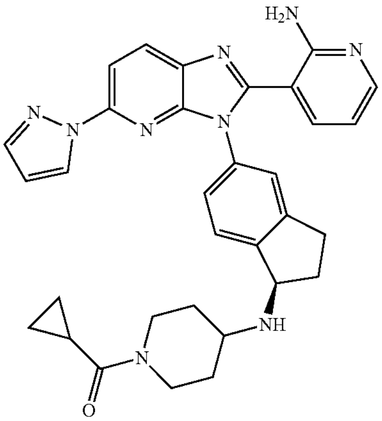 [SMILES: Nc1ncccc1-c1nc2ccc(-n3cccn3)nc2n1-c1ccc2c(c1)CC[C@H]2NC1CCN(C(=O)C2CC2)CC1] |

TABLE 1-continued
| Chemical structures of selected compounds. | |
|---|---|
| Cpd ID | Structure |
| 502 | 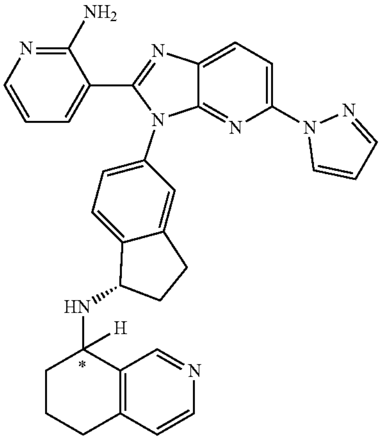 [SMILES: Nc1ncccc1-c1nc2ccc(-n3cccn3)nc2n1-c1ccc2c(c1)CC[C@@H]2NC1CCCc2ccncc21] |
| 504 | 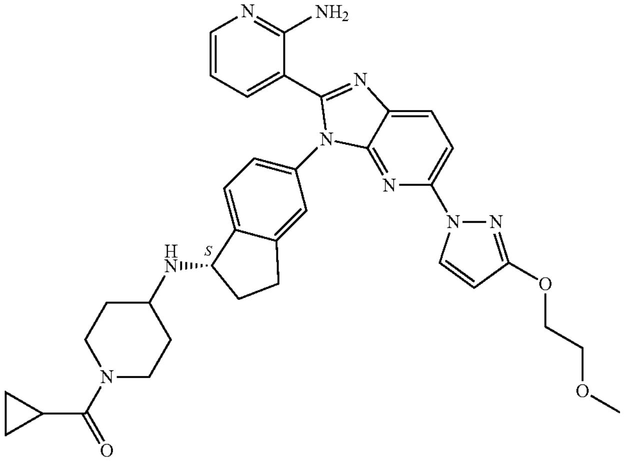 |
| 505 | 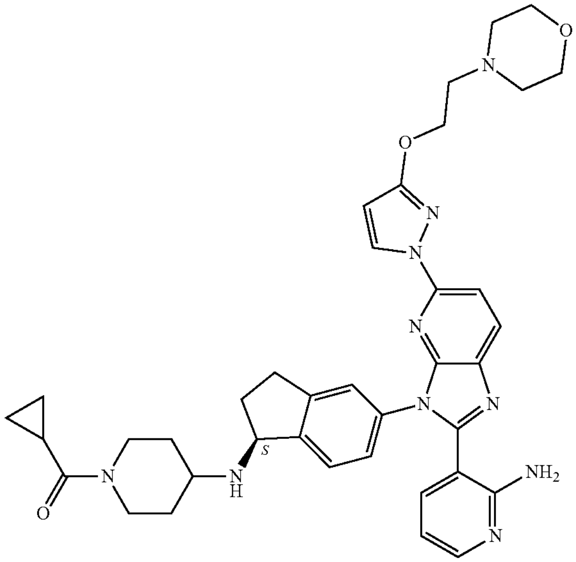 |

TABLE 1-continued
| Chemical structures of selected compounds. | |
|---|---|
| Cpd ID | Structure |
| 506 | 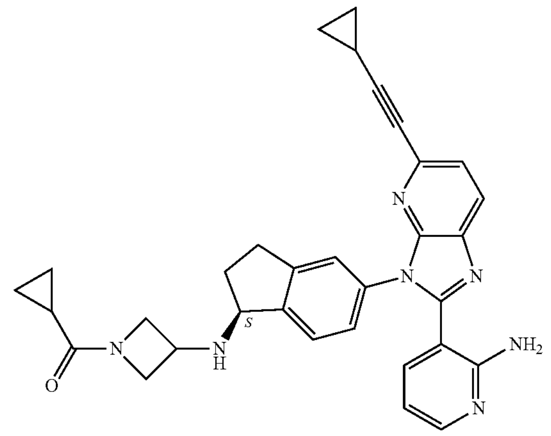 |
| 507 | 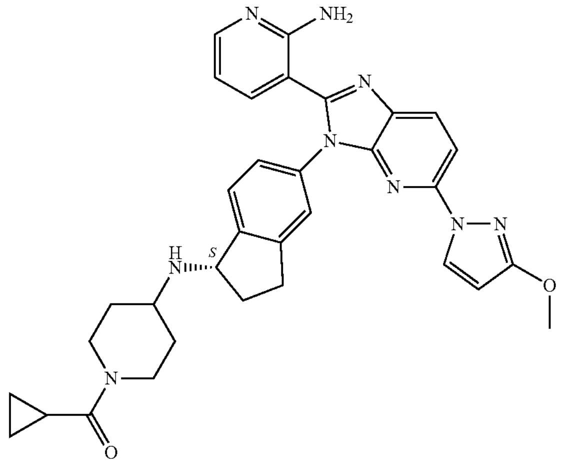 |
| 508 | 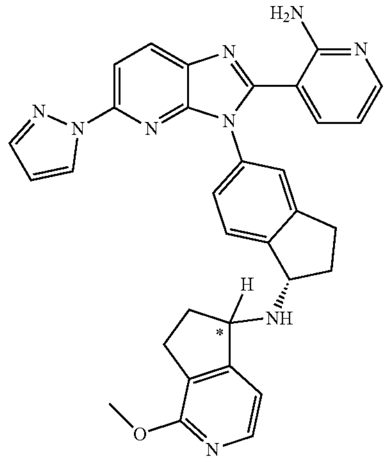 [SMILES: COc1nccc2c1CCC2N[C@H]1CCc2cc(-n3c(-c4cccnc4N)nc4ccc(-n5cccn5)nc43)ccc21] |

TABLE 1-continued
| Cpd ID | Structure |
|---|---|
| 509 | 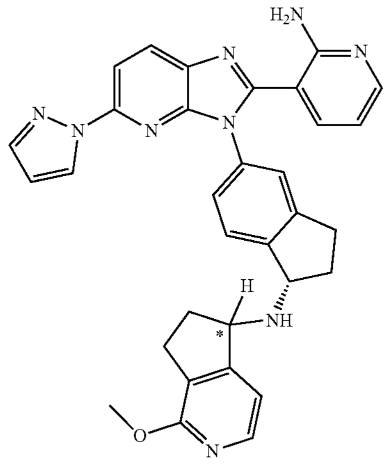 [SMILES: COc1nccc2c1CCC2N[C@H]1CCc2cc(-n3c(-c4cccnc4N)nc4ccc(-n5cccn5)nc43)ccc21] |
| 510 | 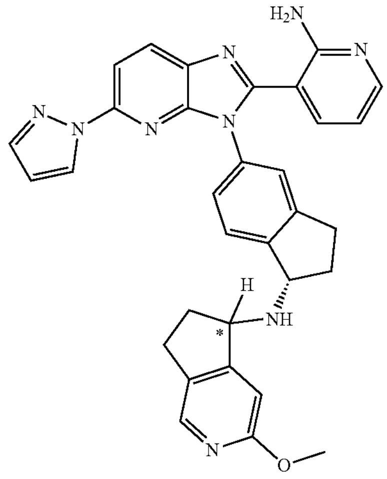 [SMILES: COc1cc2c(cn1)CCC2N[C@H]1CCc2cc(-n3c(-c4cccnc4N)nc4ccc(-n5cccn5)nc43)ccc21] |
| 511 | 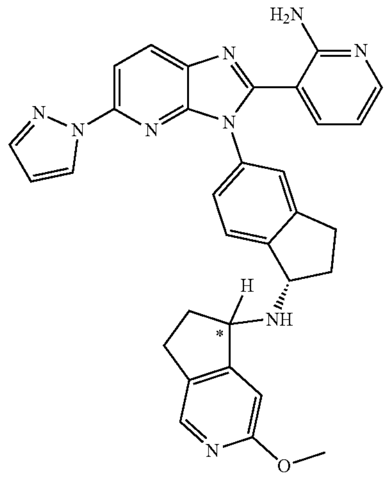 [SMILES: COc1cc2c(cn1)CCC2N[C@H]1CCc2cc(-n3c(-c4cccnc4N)nc4ccc(-n5cccn5)nc43)ccc21] |
Chemical structures of selected compounds.

TABLE 1-continued
| Chemical structures of selected compounds. | |
|---|---|
| Cpd ID | Structure |
| 512 | 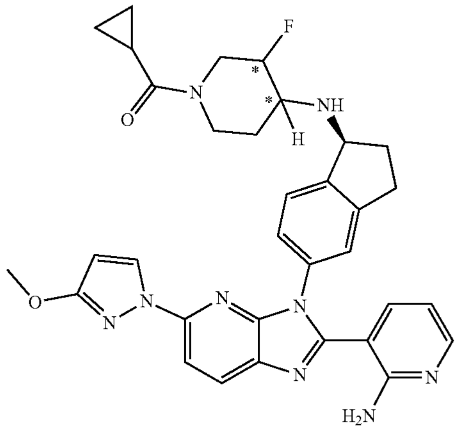 [SMILES: COc1ccn(-c2ccc3nc(-c4cccnc4N)n(-c4ccc5c(c4)CC[C@@H]5NC4CCN(C(=O)C5CC5)CC4F)c3n2)n1] |
| 513 | 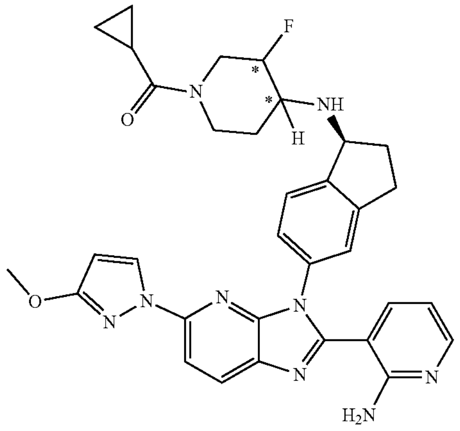 [SMILES: COc1ccn(-c2ccc3nc(-c4cccnc4N)n(-c4ccc5c(c4)CC[C@@H]5NC4CCN(C(=O)C5CC5)CC4F)c3n2)n1] |
| 514 | 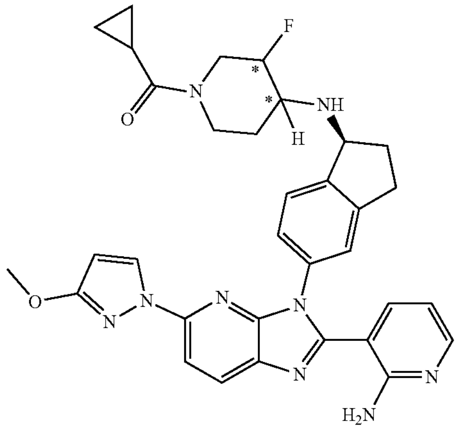 [SMILES: COc1ccn(-c2ccc3nc(-c4cccnc4N)n(-c4ccc5c(c4)CC[C@@H]5NC4CCN(C(=O)C5CC5)CC4F)c3n2)n1] |

TABLE 1-continued
| Chemical structures of selected compounds. | |
|---|---|
| Cpd ID | Structure |
| 515 | 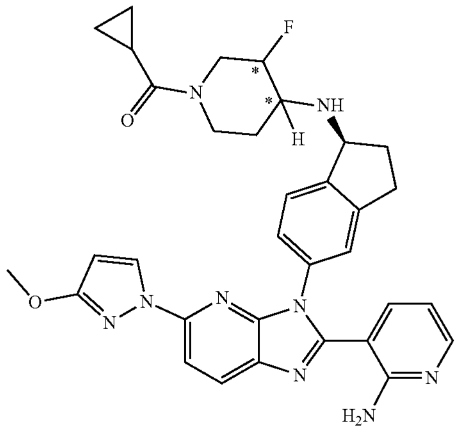 [SMILES: COc1ccn(-c2ccc3nc(-c4cccnc4N)n(-c4ccc5c(c4)CC[C@@H]5NC4CCN(C(=O)C5CC5)CC4F)c3n2)n1] |
| 516 | 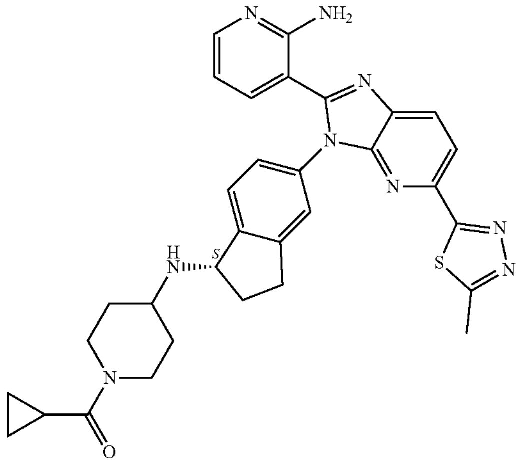 |
| 517 | 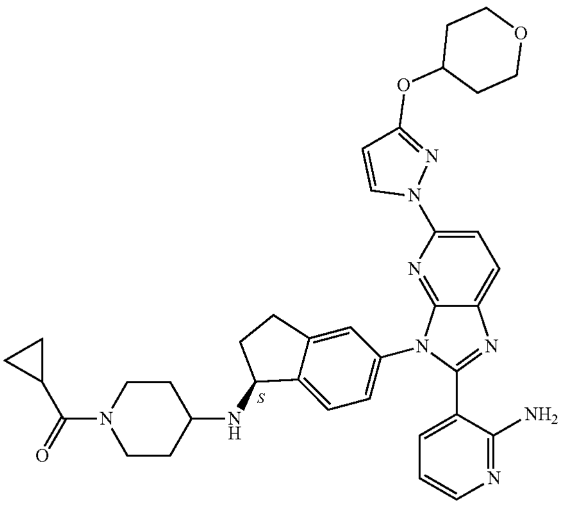 |

TABLE 1-continued
| Chemical structures of selected compounds. | |
|---|---|
| Cpd ID | Structure |
| 518 | 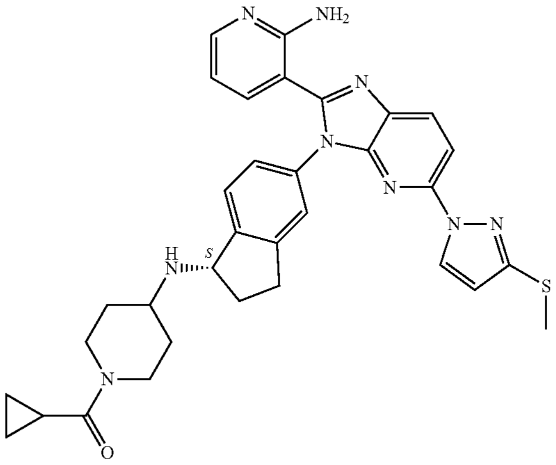 |
| 519 | 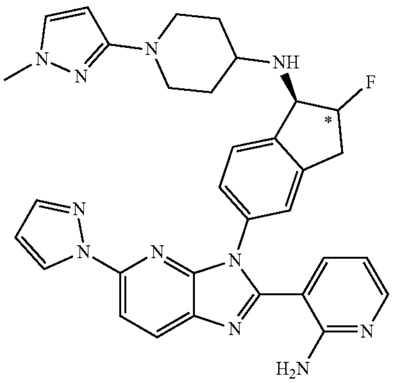 [SMILES: Cn1ccc(N2CCC(N[C@@H]3c4ccc(-n5c(-c6cccnc6N)nc6ccc(-n7cccn7)nc65)cc4CC3F)CC2)n1] |
| 520 | 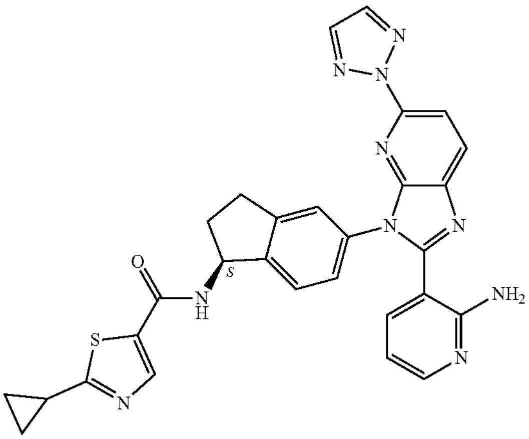 |

TABLE 1-continued
| Chemical structures of selected compounds. | |
|---|---|
| Cpd ID | Structure |
| 521 | 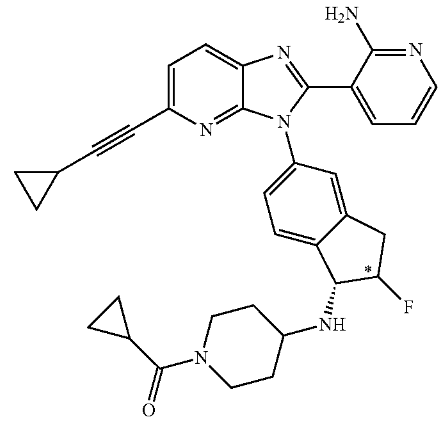 [SMILES: Nc1ncccc1-c1nc2ccc(C#CC3CC3)nc2n1-c1ccc2c(c1)CC(F)[C@@H]2NC1CCN(C(=O)C2CC2)CC1] |
| 522 | 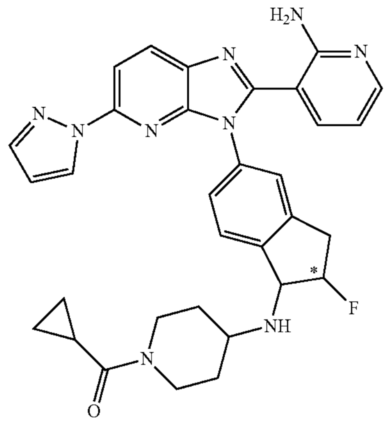 [SMILES: Nc1ncccc1-c1nc2ccc(-n3cccn3)nc2n1-c1ccc2c(c1)CC(F)C2NC1CCN(C(=O)C2CC2)CC1] |
| 523 | 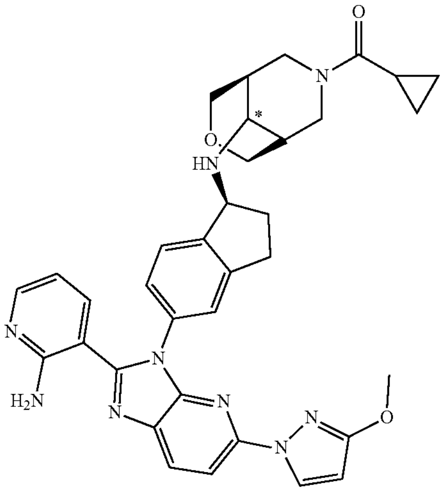 |

TABLE 1-continued
| Chemical structures of selected compounds. | |
|---|---|
| Cpd ID | Structure |
| 524 | 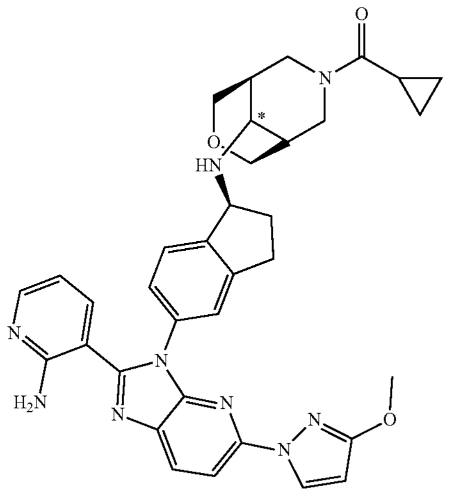 |
| 525 | 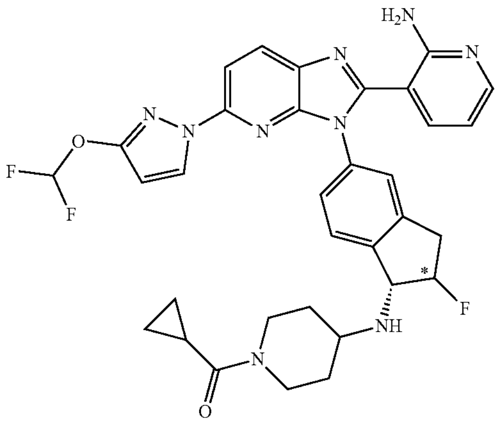 [SMILES: Nc1ncccc1-c1nc2ccc(-n3ccc(OC(F)F)n3)nc2n1-c1ccc2c(c1)CC(F)[C@@H]2NC1CCN(C(=O)C2CC2)CC1] |
| 527 | 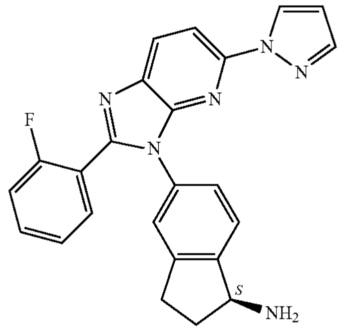 |

TABLE 1-continued
Chemical structures of selected compounds.
| Cpd ID | Structure |
| --- | --- |
| 528 | 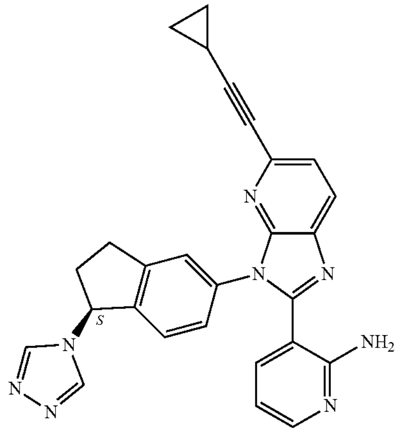 |
| 529 | 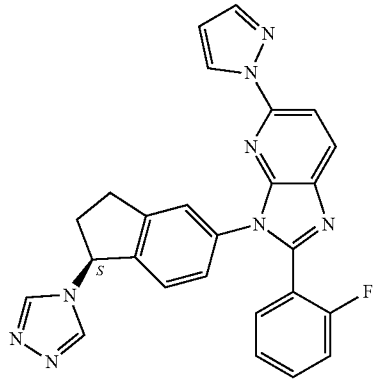 |
| 530 | 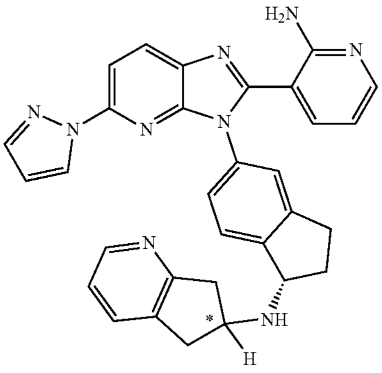 [SMILES: Nc1ncccc1-c1nc2ccc(-n3cccn3)nc2n1-c1ccc2c(c1)CC[C@@H]2NC1Cc2cccnc2C1] |

TABLE 1-continued
| Cpd ID | Structure |
|---|---|
| Chemical structures of selected compounds. | |
| 531 | 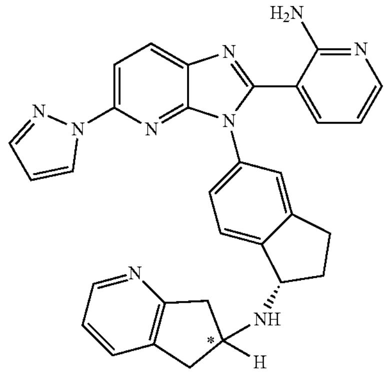 [SMILES: Nc1ncccc1-c1nc2ccc(-n3cccn3)nc2n1-c1ccc2c(c1)CC[C@@H]2NC1Cc2cccnc2C1] |
| 526 | 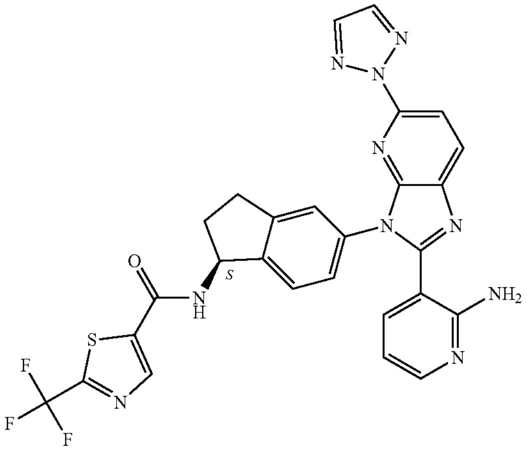 |
| 532 | 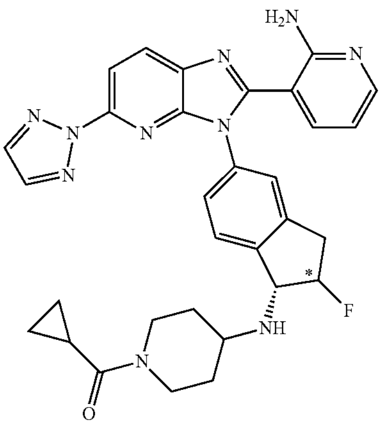 |

TABLE 1-continued
| Cpd ID | Structure |
|---|---|
| 533 | 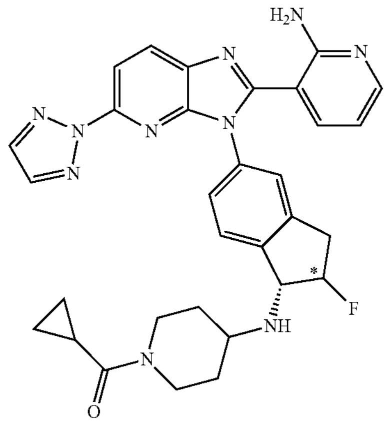 [SMILES: Nc1ncccc1-c1nc2ccc(-n3nccn3)nc2n1-c1ccc2c(c1)CC(F)[C@@H]2NC1CCN(C(=O)C2CC2)CC1] |
| 534 | 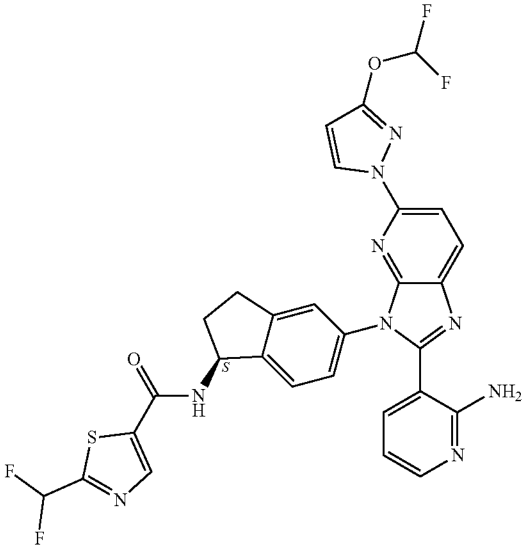 |
| 535 | 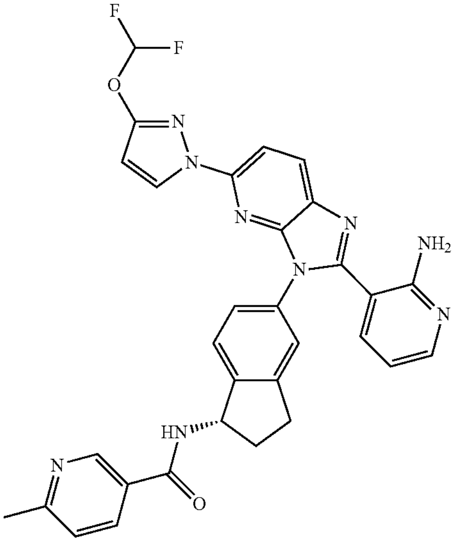 [SMILES: Cc1ccc(C(=O)N[C@H]2CCc3cc(-n4c(-c5cccnc5N)nc5ccc(-n6ccc(OC(F)F)n6)nc54)ccc32)cn1] |
Chemical structures of selected compounds.

TABLE 1-continued
Chemical structures of selected compounds.
| Cpd ID | Structure |
|---|---|
| 536 | 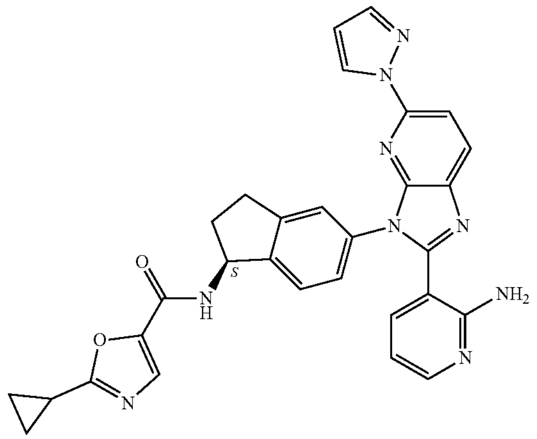 |
| 537 | 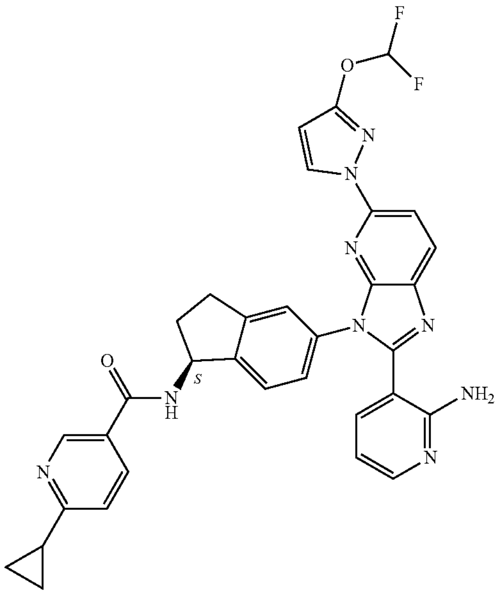 |
| 538 | 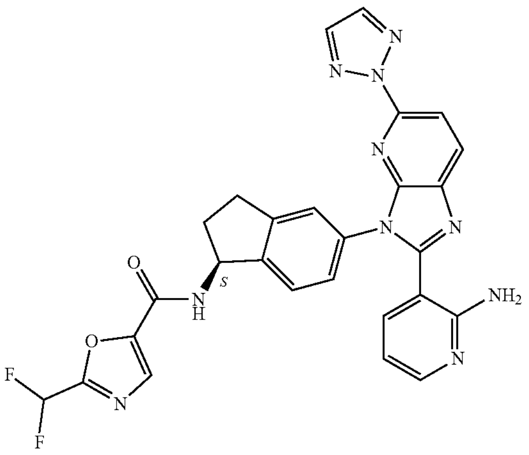 |

TABLE 1-continued
| Chemical structures of selected compounds. | |
|---|---|
| Cpd ID | Structure |
| 539 | 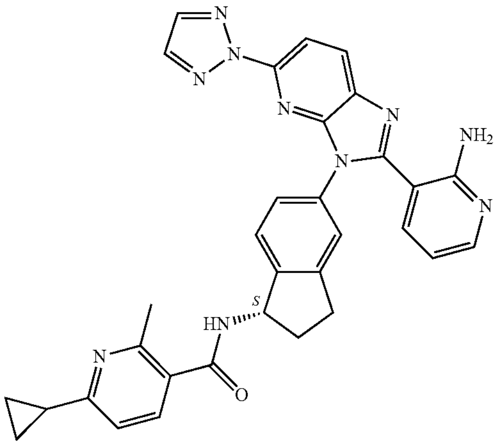 |
| 540 | 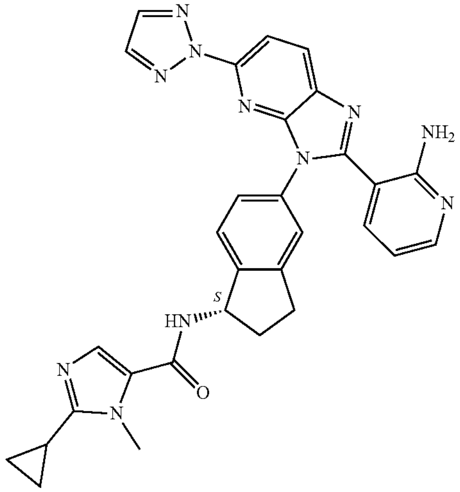 |
| 541 | 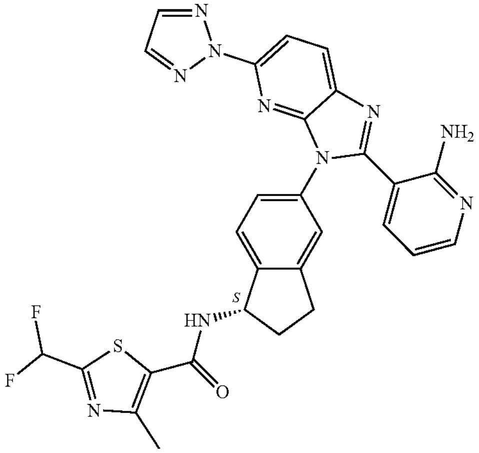 |

TABLE 1-continued
| Chemical structures of selected compounds. | |
|---|---|
| Cpd ID | Structure |
| 542 | 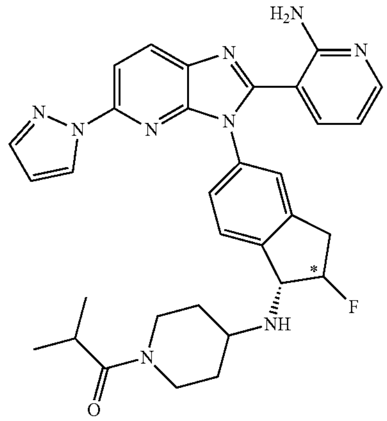 [SMILES: CC(C)C(=O)N1CCC(N[C@@H]2c3ccc(-n4c(-c5cccnc5N)nc5ccc(-n6cccn6)nc54)cc3CC2F)CC1] |
| 543 | 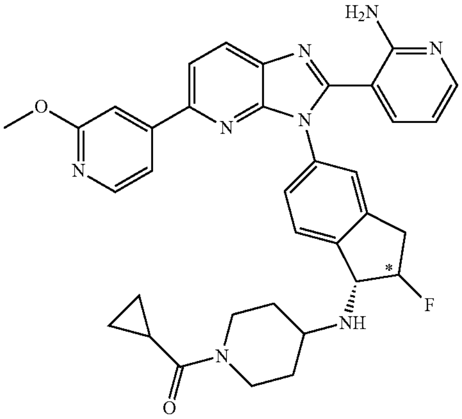 [SMILES: COc1cc(-c2ccc3nc(-c4cccnc4N)n(-c4ccc5c(c4)CC(F)[C@@H]5NC4CCN(C(=O)C5CC5)CC4)c3n2)ccn1] |
| 544 | 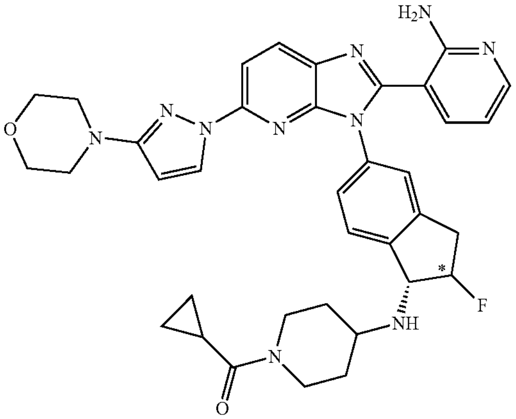 [SMILES: Nc1ncccc1-c1nc2ccc(-n3ccc(N4CCOCC4)n3)nc2n1-c1ccc2c(c1)CC(F)[C@@H]2NC1CCN(C(=O)C2CC2)CC1] |

TABLE 1-continued
| Chemical structures of selected compounds. | |
|---|---|
| Cpd ID | Structure |
| 545 | 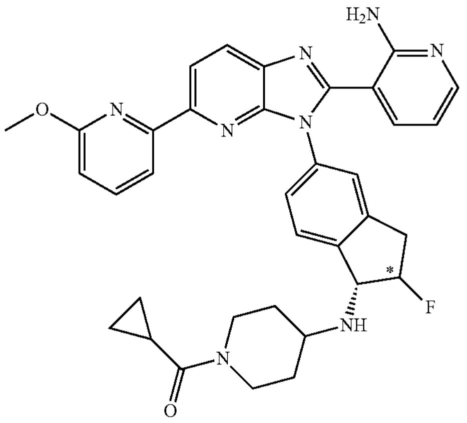 [SMILES: COc1cccc(-c2ccc3nc(-c4cccnc4N)n(-c4ccc5c(c4)CC(F)[C@@H]5NC4CCN(C(=O)C5CC5)CC4)c3n2)n1] |
| 546 | 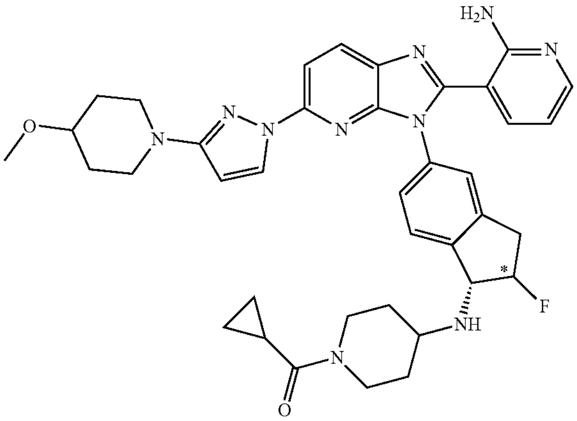 [SMILES: COC1CCN(c2ccn(-c3ccc4nc(-c5cccnc5N)n(-c5ccc6c(c5)CC(F)[C@@H]6NC5CCN(C(=O)C6CC6)CC5)c4n3)n2)CC1] |
| 547 | 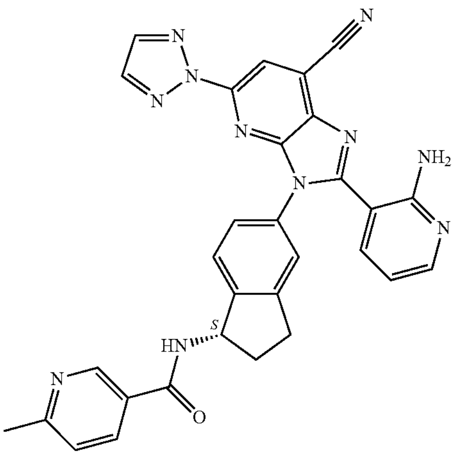 |

TABLE 1-continued
| Chemical structures of selected compounds. | |
|---|---|
| Cpd ID | Structure |
| 548 | 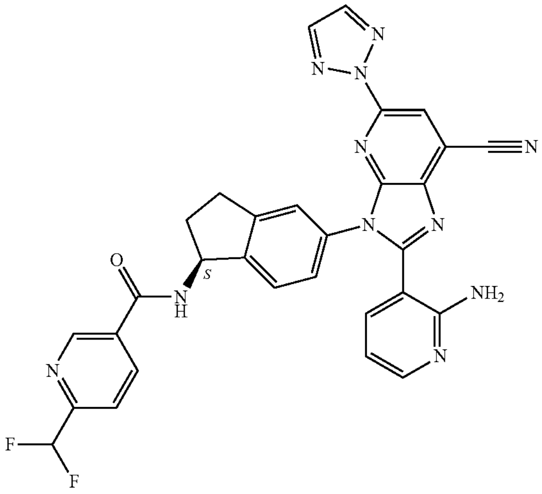 |
| 549 | 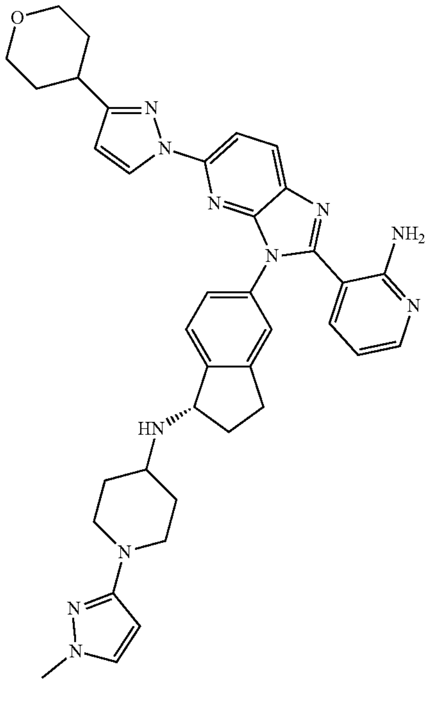 [SMILES: Cn1ccc(N2CCC(N[C@H]3CCc4cc(-n5c(-c6cccnc6N)nc6ccc(-n7ccc(C8CCOCC8)n7)nc65)ccc43)CC2)n1] |

TABLE 1-continued
| Chemical structures of selected compounds. | |
|---|---|
| Cpd ID | Structure |
| 551 | 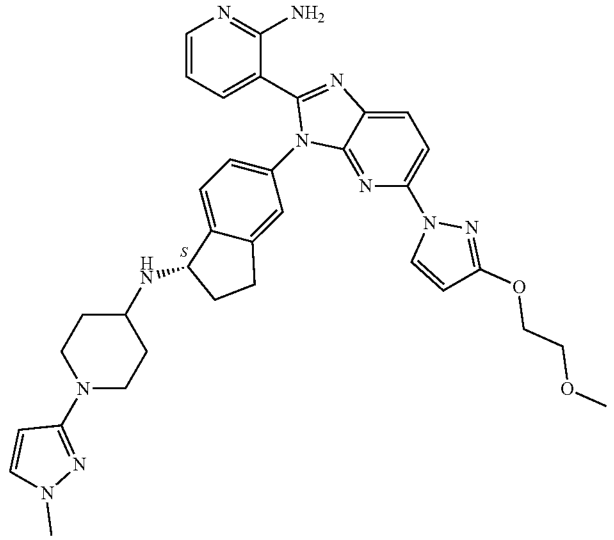 |
| 552 | 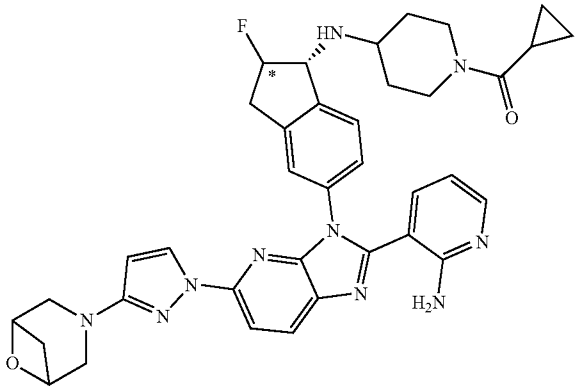 [SMILES: Nc1ncccc1-c1nc2ccc(-n3ccc(N4CC5CC(C4)O5)n3)nc2n1-c1ccc2c(c1)CC(F)[C@@H]2NC1CCN(C(=O)C2CC2)CC1] |
| 553 | 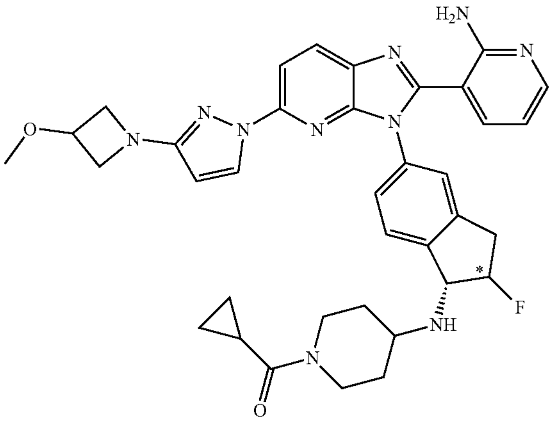 [SMILES: COC1CN(c2ccn(-c3ccc4nc(-c5cccnc5N)n(-c5ccc6c(c5)CC(F)[C@@H]6NC5CCN(C(=O)C6CC6)CC5)c4n3)n2)C1] |

TABLE 1-continued
| Chemical structures of selected compounds. | |
|---|---|
| Cpd ID | Structure |
| 554 | 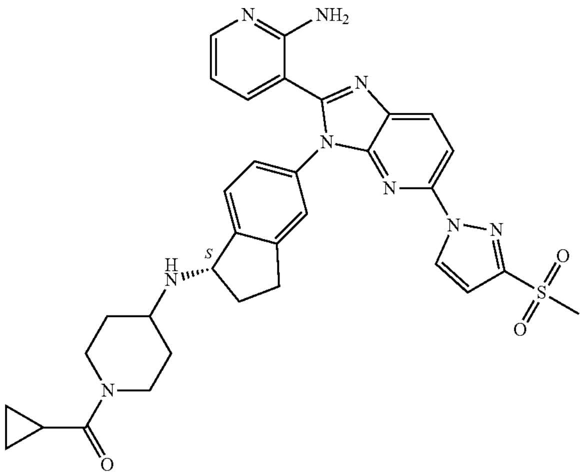 |
| 555 | 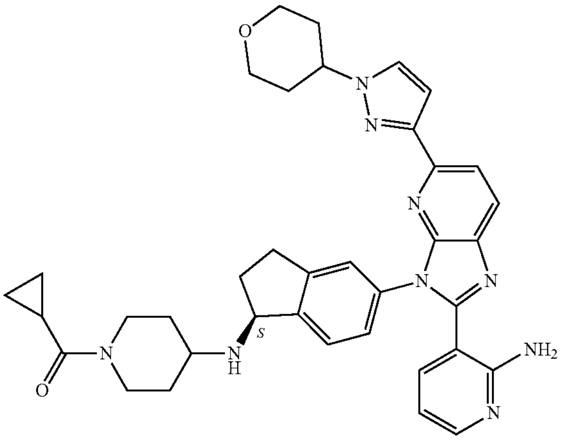 |
| 556 | 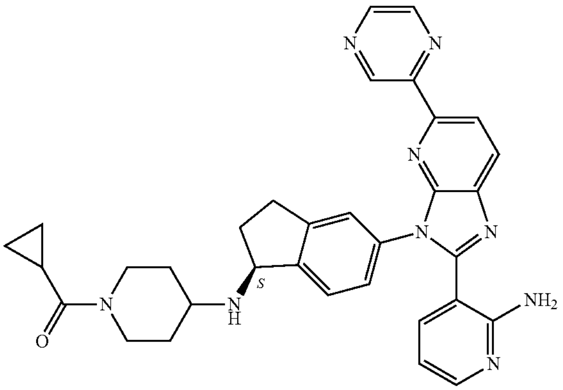 |

TABLE 1-continued
| Chemical structures of selected compounds. | |
|---|---|
| Cpd ID | Structure |
| 557 | 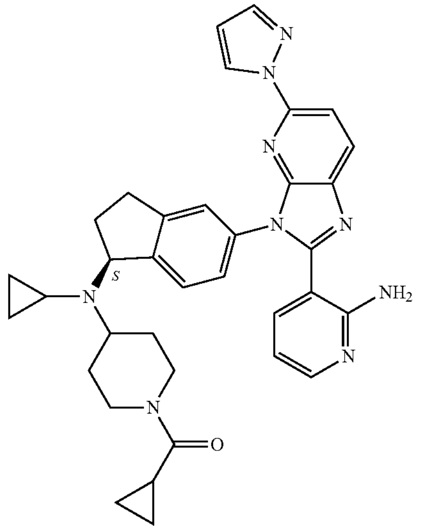 |
| 558 | 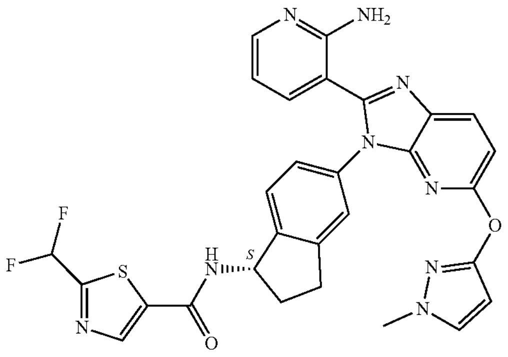 |
| 559 | 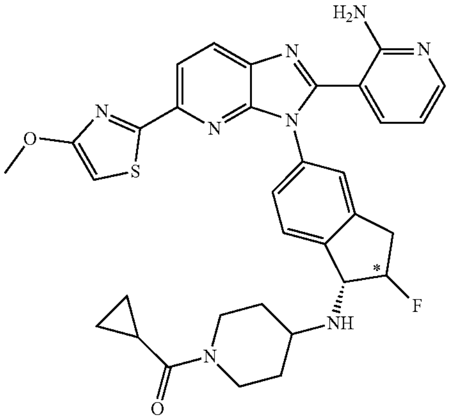 [SMILES: COc1csc(-c2ccc3nc(-c4cccnc4N)n(-c4ccc5c(c4)CC(F)[C@@H]5NC4CCN(C(=O)C5CC5)CC4)c3n2)n1] |

TABLE 1-continued
| Chemical structures of selected compounds. | |
|---|---|
| Cpd ID | Structure |
| 560 | 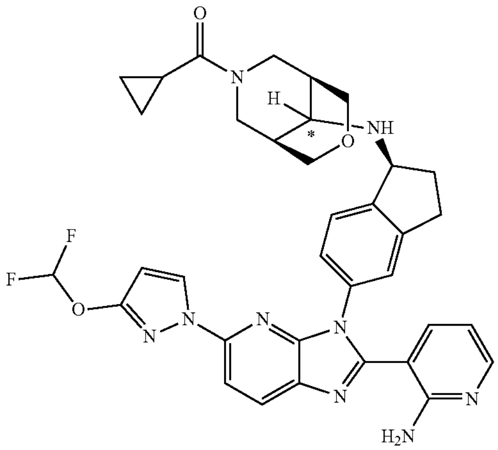 [SMILES: Nc1ncccc1-c1nc2ccc(-n3ccc(OC(F)F)n3)nc2n1-c1ccc2c(c1)CC[C@@H]2NC1[C@@H]2COC[C@H]1CN(C(=O)C1CC1)C2] |
| 561 | 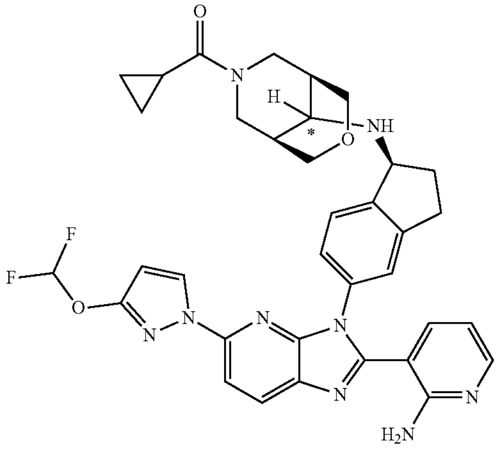 [SMILES: Nc1ncccc1-c1nc2ccc(-n3ccc(OC(F)F)n3)nc2n1-c1ccc2c(c1)CC[C@@H]2NC1[C@@H]2COC[C@H]1CN(C(=O)C1CC1)C2] |
| 562 | 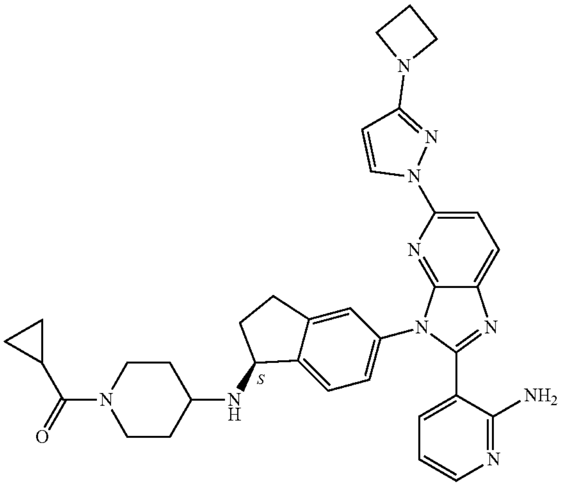 |

TABLE 1-continued
| Chemical structures of selected compounds. | |
|---|---|
| Cpd ID | Structure |
| 563 | 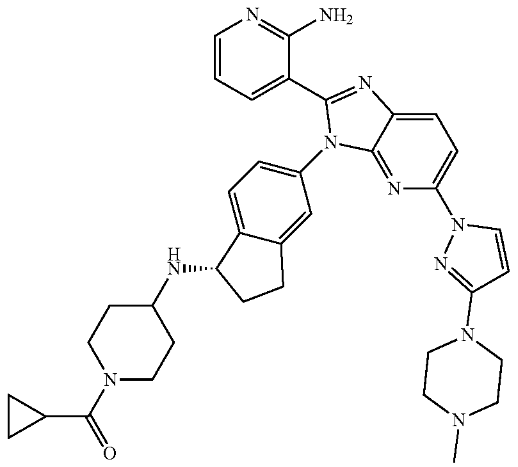 [SMILES: CN1CCN(c2ccn(-c3ccc4nc(-c5cccnc5N)n(-c5ccc6c(c5)CC[C@@H]6NC5CCN(C(=O)C6CC6)CC5)c4n3)n2)CC1] |
| 564 | 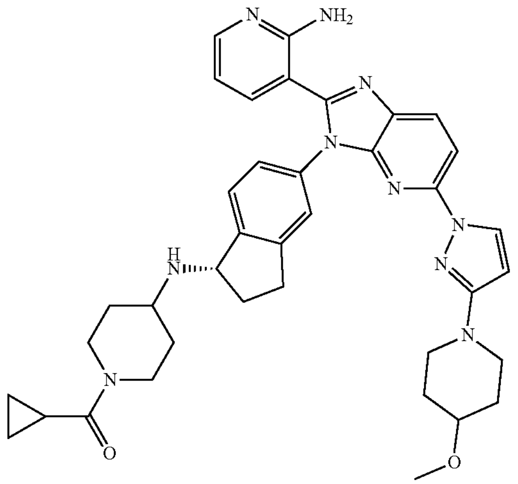 [SMILES: COC1CCN(c2ccn(-c3ccc4nc(-c5cccnc5N)n(-c5ccc6c(c5)CC[C@@H]6NC5CCN(C(=O)C6CC6)CC5)c4n3)n2)CC1] |
| 565 | 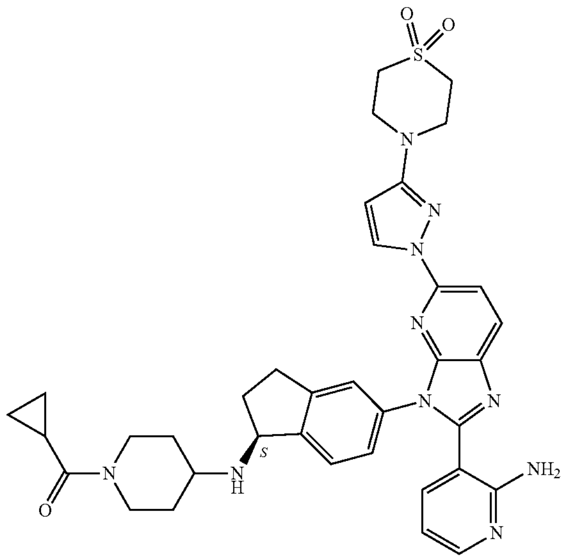 |

TABLE 1-continued
| Chemical structures of selected compounds. | |
|---|---|
| Cpd ID | Structure |
| 566 | 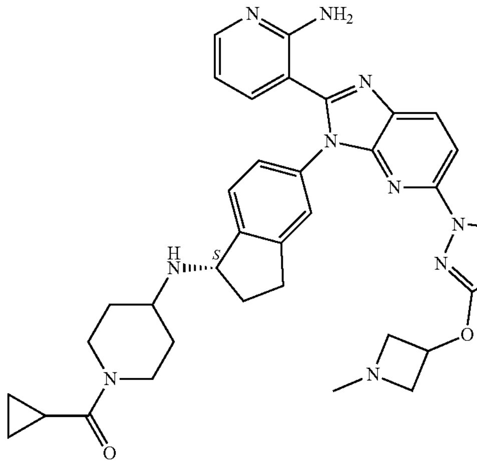 |
| 567 | 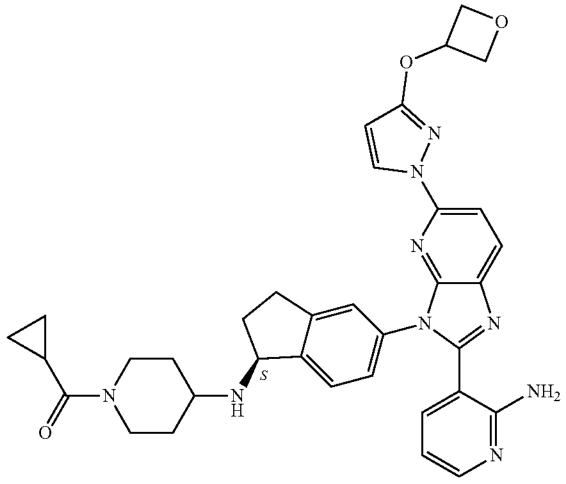 |
| 568 | 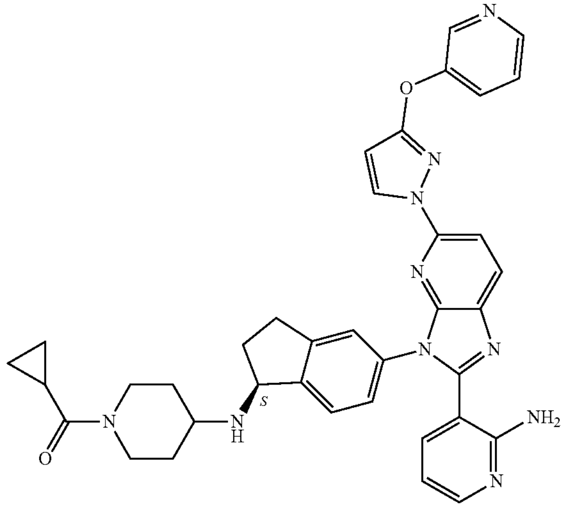 |

TABLE 1-continued
| Chemical structures of selected compounds. | |
|---|---|
| Cpd ID | Structure |
| 569 | 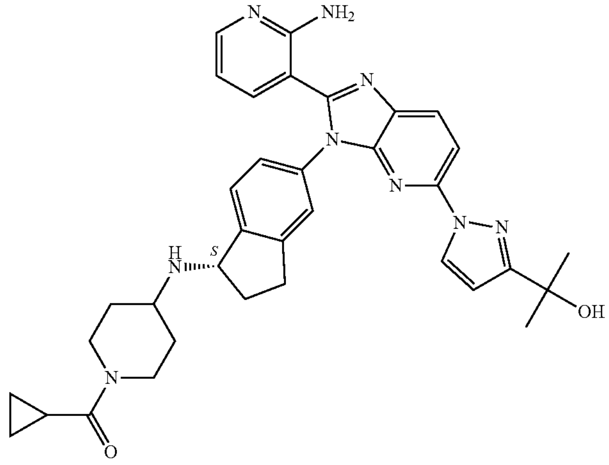 |
| 570 | 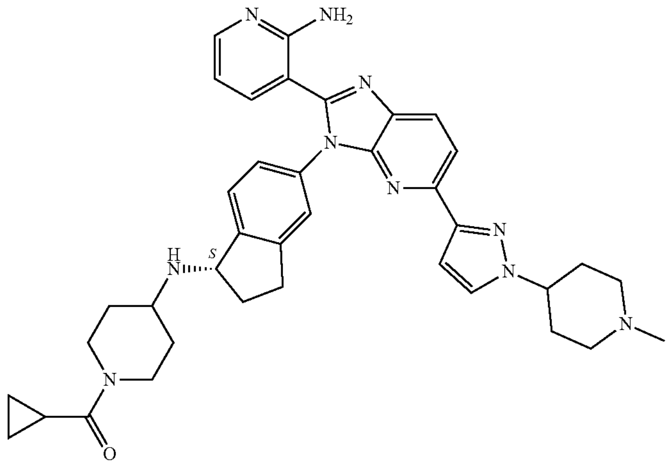 |
| 571 | 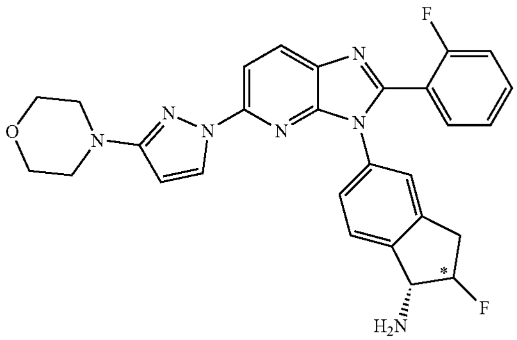 [SMILES: N[C@@H]1c2ccc(-n3c(-c4ccccc4F)nc4ccc(-n5ccc(N6CCOCC6)n5)nc43)cc2CC1F] |

TABLE 1-continued
| Chemical structures of selected compounds. | |
|---|---|
| Cpd ID | Structure |
| 572 | 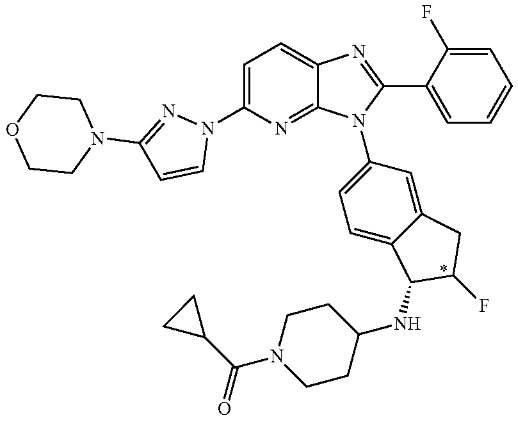 [SMILES: O=C(C1CC1)N1CCC(N[C@@H]2c3ccc(-n4c(-c5ccccc5F)nc5ccc(-n6ccc(N7CCOCC7)n6)nc54)cc3CC2F)CC1] |
| 573 | 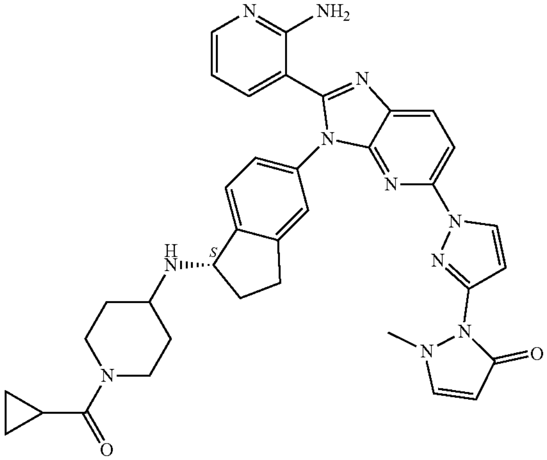 |
| 574 | 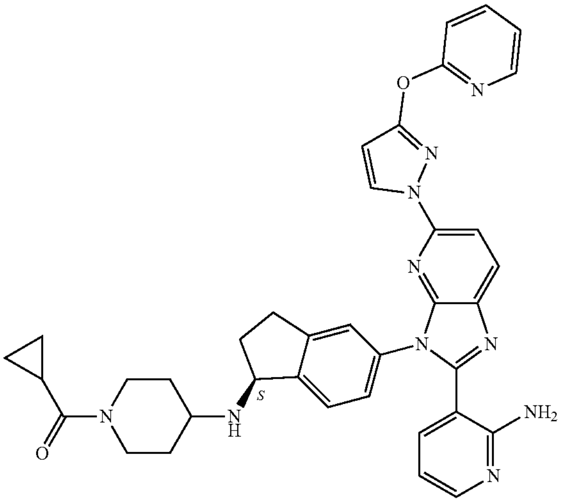 |

TABLE 1-continued
| Chemical structures of selected compounds. | |
|---|---|
| Cpd ID | Structure |
| 575 | 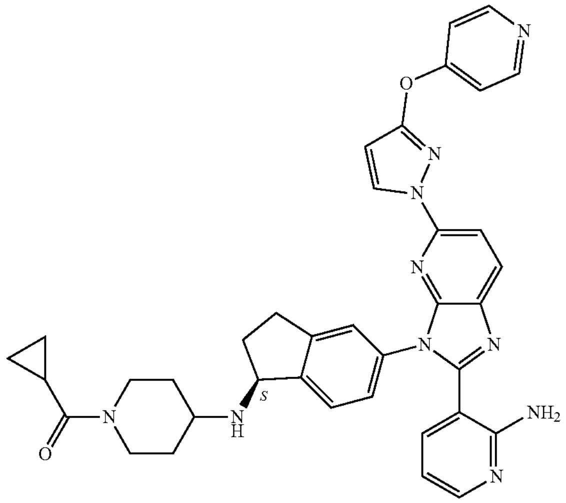 |
| 576 | 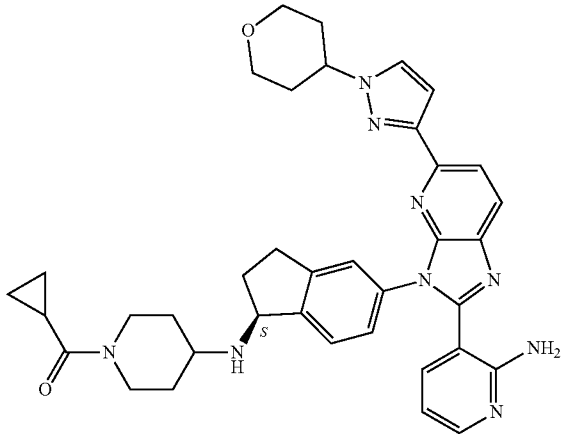 |
| 577 | 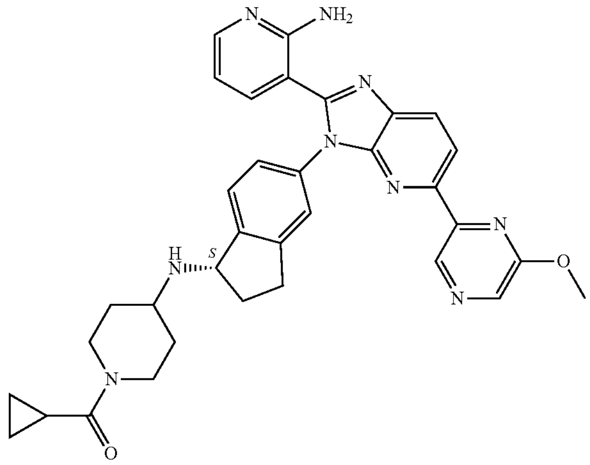 |

TABLE 1-continued
| Chemical structures of selected compounds. | |
|---|---|
| Cpd ID | Structure |
| 578 | 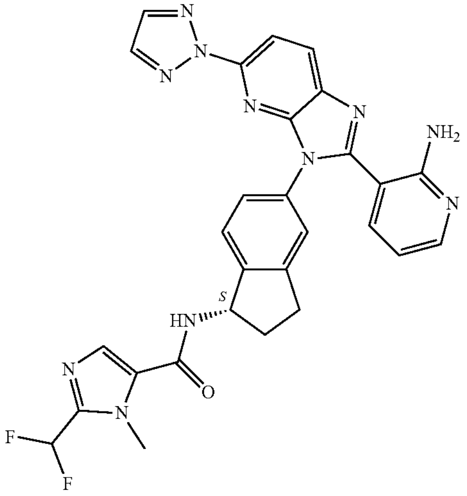 |
| 579 | 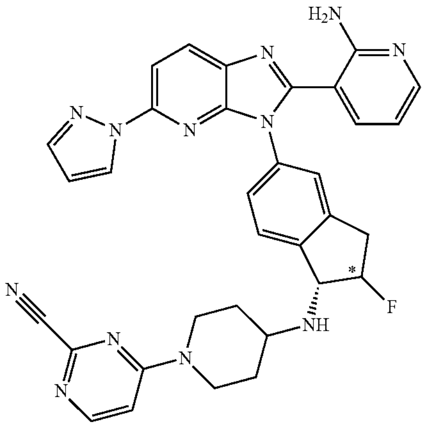 [SMILES: N#Cc1nccc(N2CCC(N[C@@H]3c4ccc(-n5c(-c6cccnc6N)nc6ccc(-n7cccn7)nc65)cc4CC3F)CC2)n1] |
| 580 | 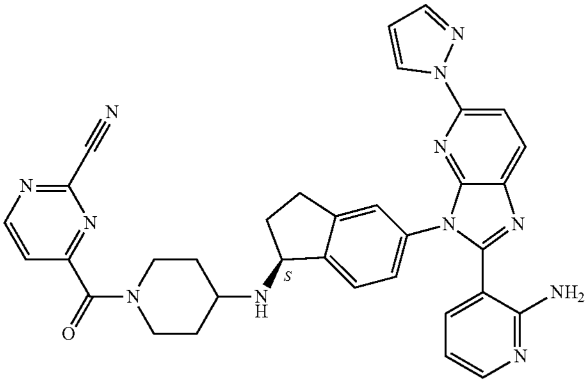 |

TABLE 1-continued
| Cpd ID | Structure |
|---|---|
| Chemical structures of selected compounds. | |
| 581 | 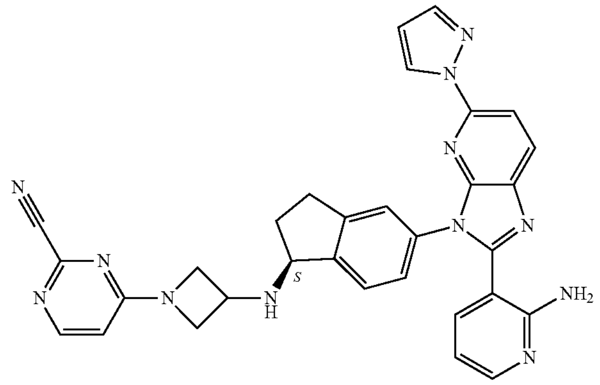 |
| 582 | 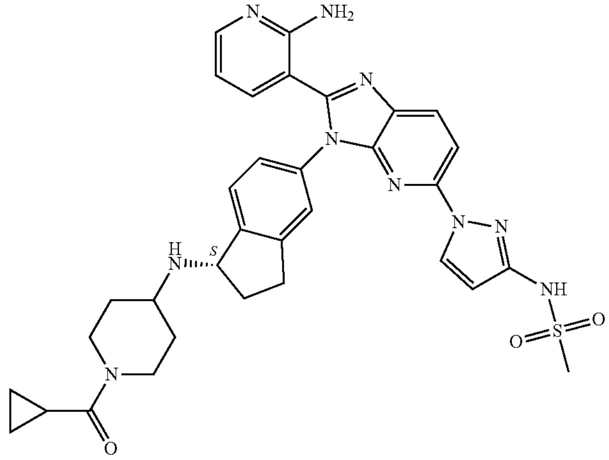 |
| 586 | 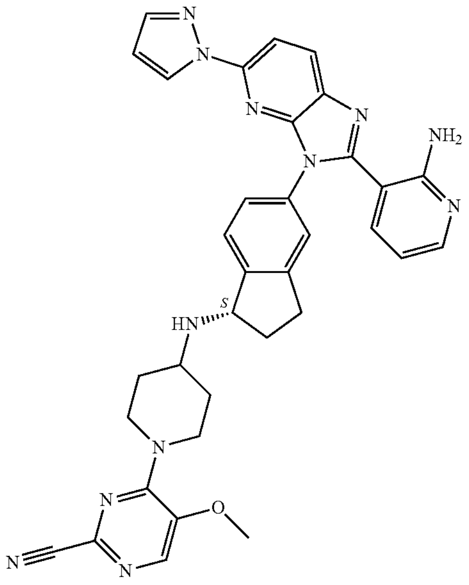 |

TABLE 1-continued
| Chemical structures of selected compounds. | |
|---|---|
| Cpd ID | Structure |
| 584 | 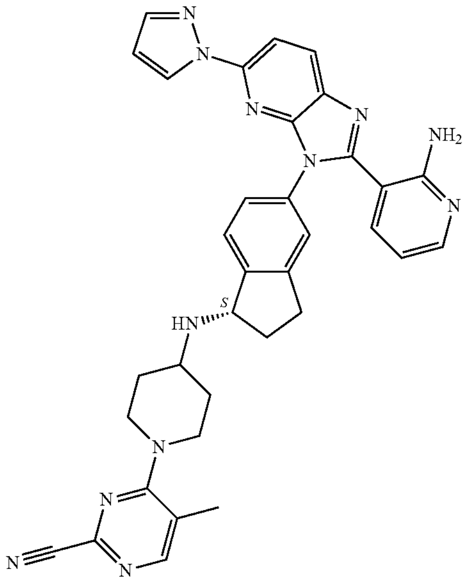 |
| 584 | 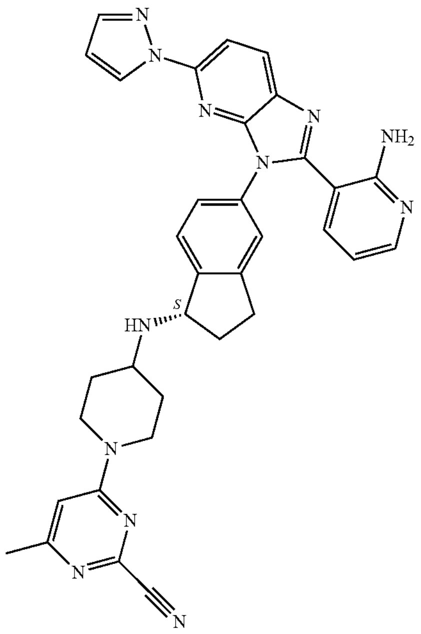 |

TABLE 1-continued
| Chemical structures of selected compounds. | |
|---|---|
| Cpd ID | Structure |
| 583 | 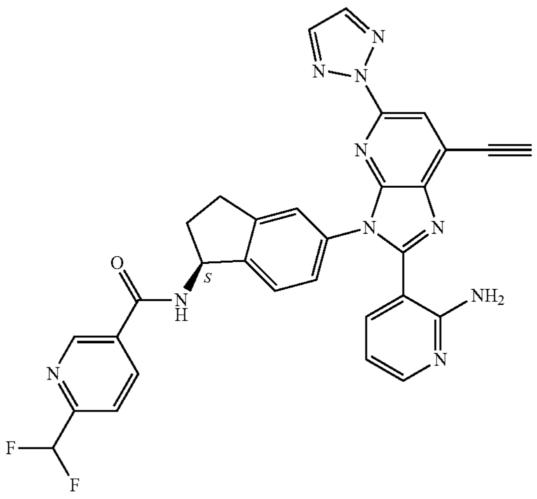 |
| 585 | 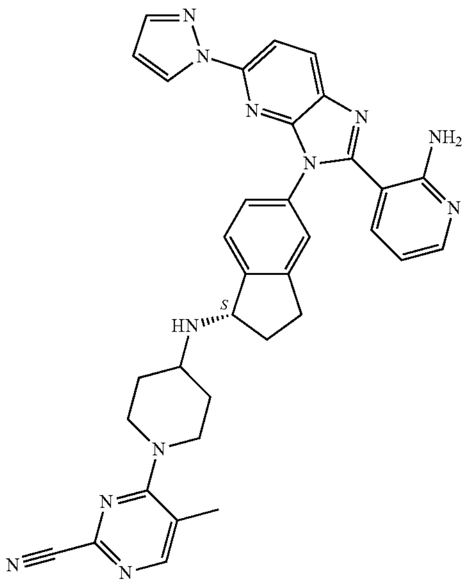 |

TABLE 1-continued
| Cpd ID | Structure |
|---|---|
| 586 | 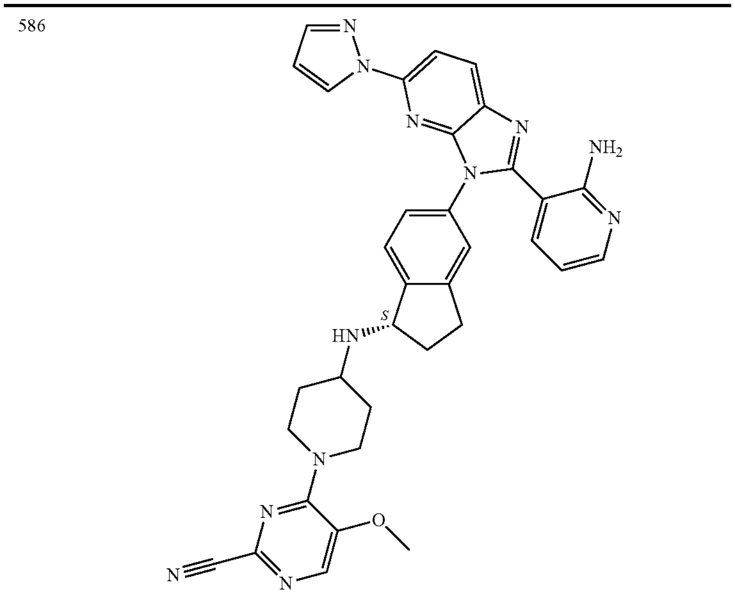 |
| 587 | 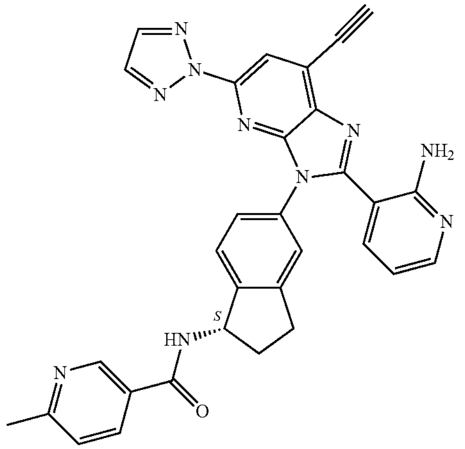 |
| 588 | 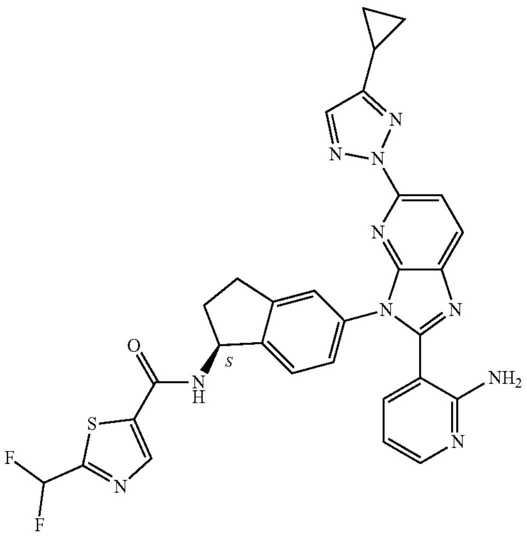 |
Chemical structures of selected compounds.

TABLE 1-continued
| Cpd ID | Structure |
|---|---|
| 589 | 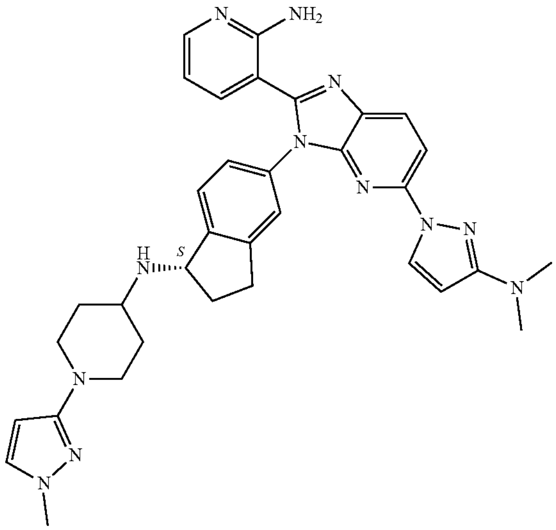 |
| 590 | 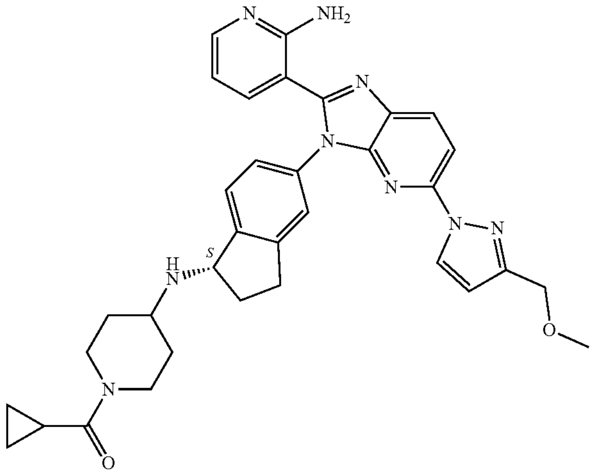 |
| 591 | 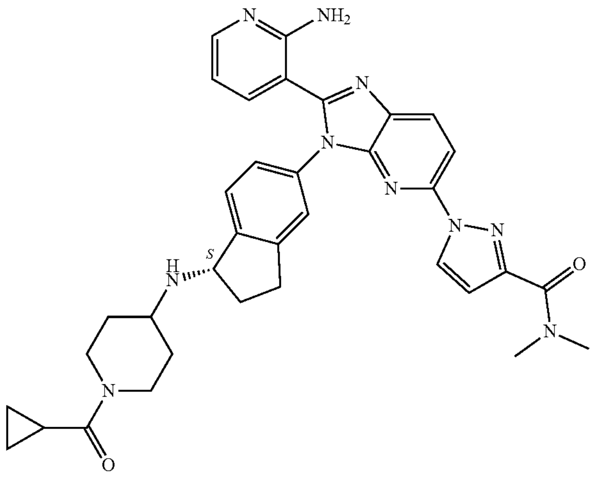 |
Chemical structures of selected compounds.

TABLE 1-continued
| Chemical structures of selected compounds. | |
|---|---|
| Cpd ID | Structure |
| 592 | 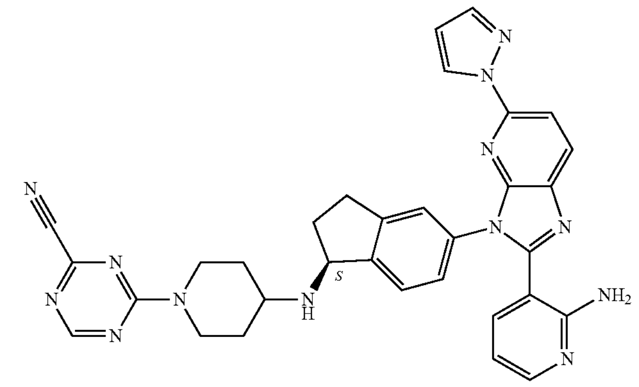 |
| 593 | 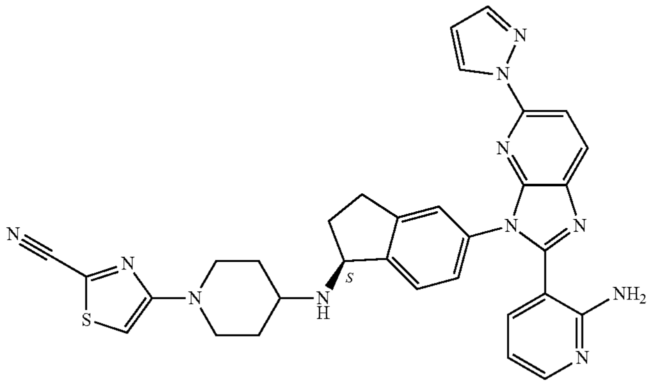 |
| 594 | 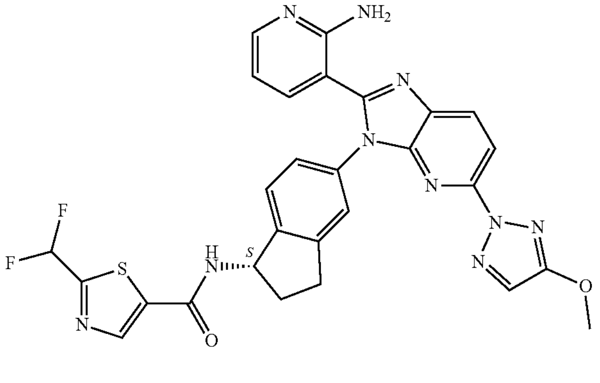 |

TABLE 1-continued
| Cpd ID | Structure |
| --- | --- |
| | Chemical structures of selected compounds. |
| 595 | 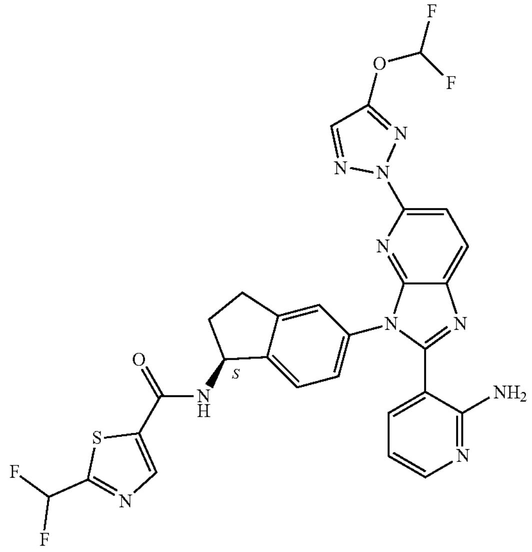 |
| 596 | 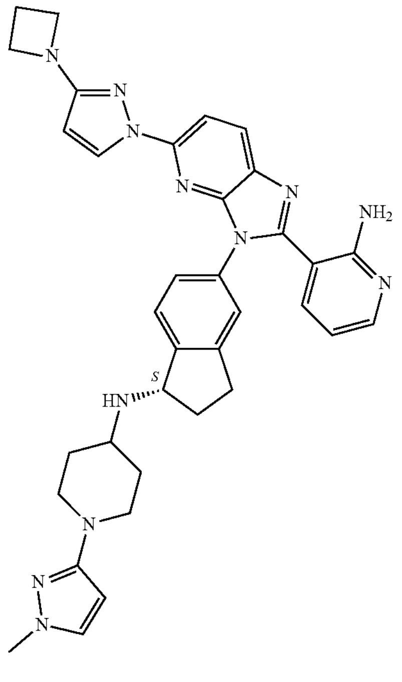 |

TABLE 1-continued
| Chemical structures of selected compounds. | |
|---|---|
| Cpd ID | Structure |
| 597 | 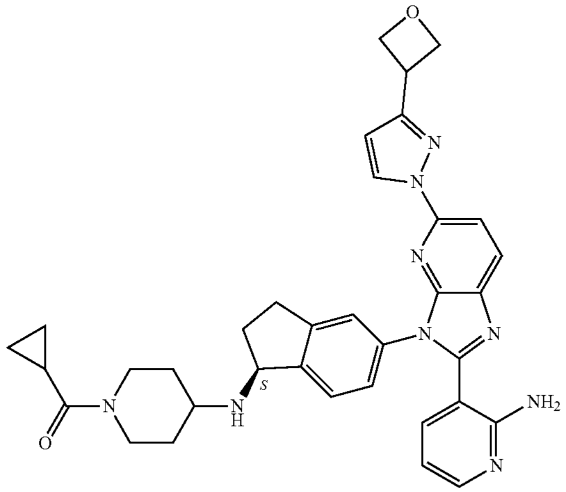 |
| 598 | 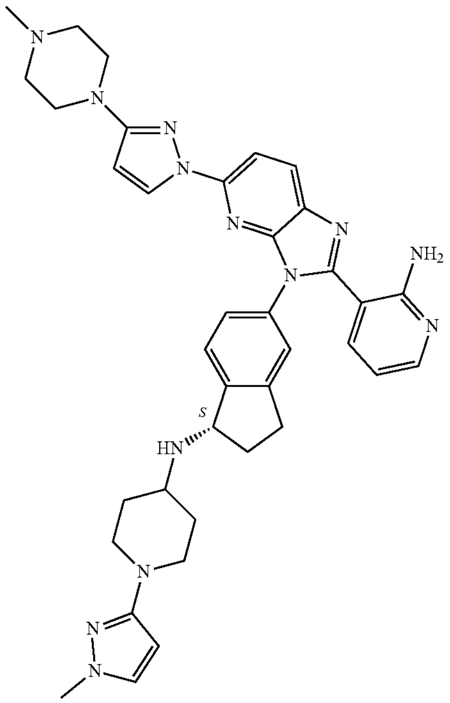 |

TABLE 1-continued
| Chemical structures of selected compounds. | |
|---|---|
| Cpd ID | Structure |
| 599 | 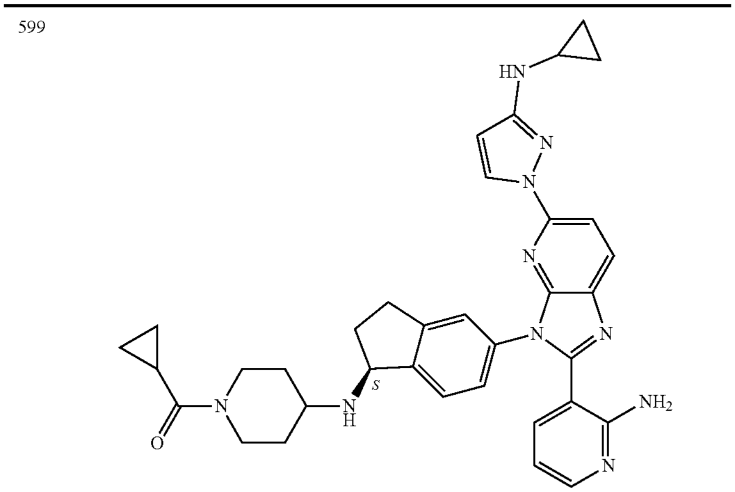 |
| 600 | 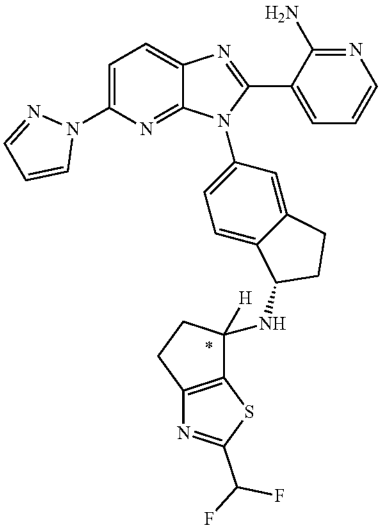 [SMILES: Nc1ncccc1-c1nc2ccc(-n3cccn3)nc2n1-c1ccc2c(c1)CC[C@@H]2NC1CCc2nc(C(F)F)sc21] |
| 601 | 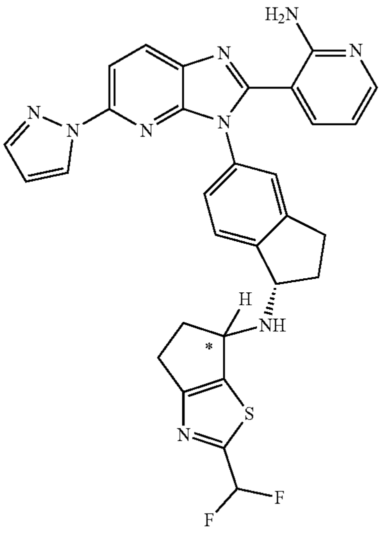 [SMILES: Nc1ncccc1-c1nc2ccc(-n3cccn3)nc2n1-c1ccc2c(c1)CC[C@@H]2NC1CCc2nc(C(F)F)sc21] |

TABLE 1-continued

| Chemical structures of selected compounds. | |
|---|---|
| Cpd ID | Structure |
| 602 | 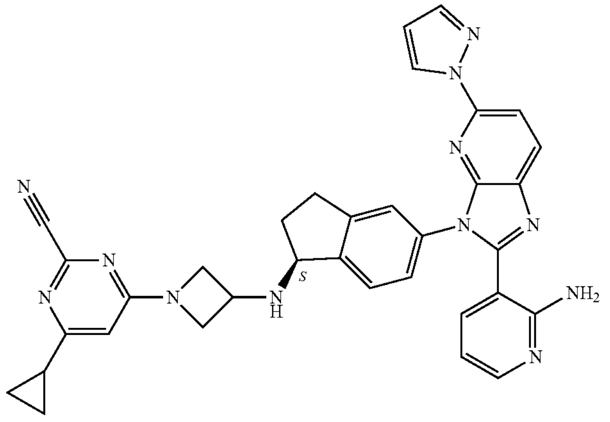 |
| 603 | 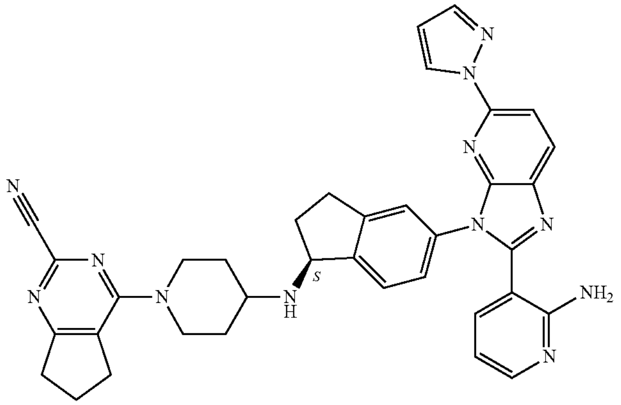 |

*Denotes a stereocenter withundetermined absolute stereochemistry of a single diastereomer.

In some aspects, the present disclosure provides a compound, wherein the compound is selected from a compound of Table 2, or a pharmaceutically acceptable salt thereof.

TABLE 2

| Chemical structures of selected compounds. | |
|---|---|
| Cpd ID | Structure |
| 109 | 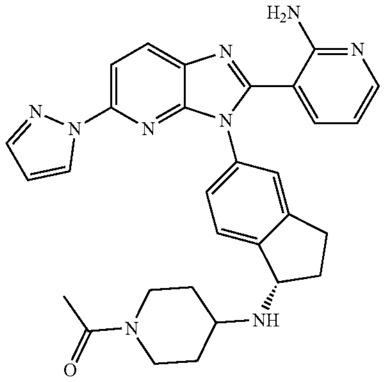 [SMILES: CC(=O)N1CCC(N[C@H]2CCc3cc(-n4c(-c5cccnc5N)nc5ccc(-n6cccn6)nc54)ccc32)CC1] |

TABLE 2-continued

| Chemical structures of selected compounds. | |
|---|---|
| Cpd ID | Structure |
| 134 | 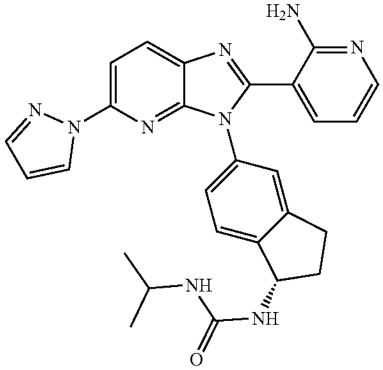 [SMILES: CC(C)NC(=O)N[C@H]1CCc2cc(-n3c(-c4cccnc4N)nc4ccc(-n5cccn5)nc43)ccc21] |

TABLE 2-continued

Chemical structures of selected compounds.

| Cpd ID | Structure |
|---|---|
| 278 | 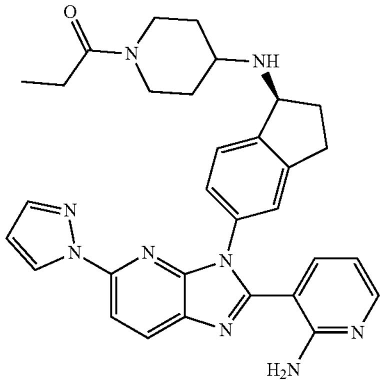 [SMILES: CCC(=O)N1CCC(N[C@H]2CCc3cc(-n4c(-c5cccnc5N)nc5ccc(-n6cccn6)nc54)ccc32)CC1] |
| 339 | 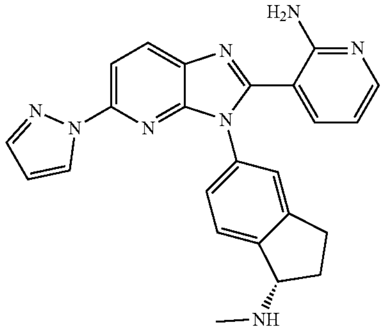 [SMILES: CN[C@H]1CCc2cc(-n3c(-c4cccnc4N)nc4ccc(-n5cccn5)nc43)ccc21] |
| 340 | 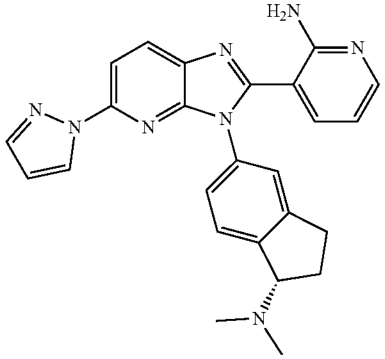 [SMILES: CN(C)[C@H]1CCc2cc(-n3c(-c4cccnc4N)nc4ccc(-n5cccn5)nc43)ccc21] |
| 457 | 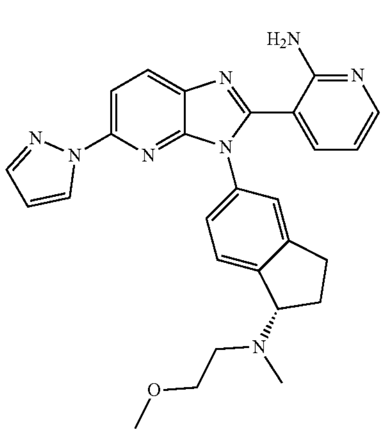 [SMILES: COCCN(C)[C@H]1CCc2cc(-n3c(-c4cccnc4N)nc4ccc(-n5cccn5)nc43)ccc21] |

TABLE 2-continued

Chemical structures of selected compounds.

| Cpd ID | Structure |
|---|---|
| 458 | 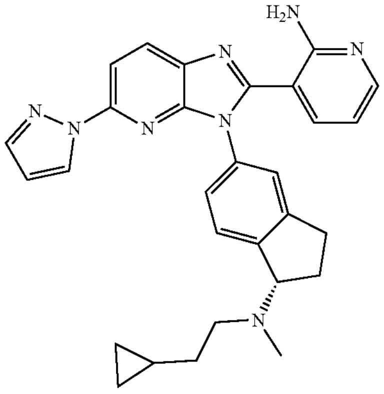 [SMILES: CN(CCC1CC1)[C@H]1CCc2cc(-n3c(-c4cccnc4N)nc4ccc(-n5cccn5)nc43)ccc21] |
| 475 | 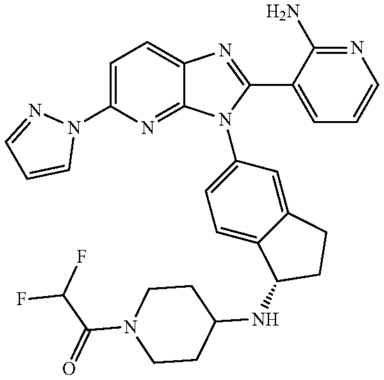 |

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

Chemical entities having carbon-carbon double bonds or carbon-nitrogen double bonds may exist in Z- or E-form (or cis- or trans-form). Furthermore, some chemical entities may exist in various tautomeric forms. Unless otherwise specified, compounds or salts of Formula (I), are intended to include all Z-, E- and tautomeric forms as well.

"Isomers" are different compounds that have the same molecular formula. "Stereoisomers" are isomers that differ only in the way the atoms are arranged in space. "Enantiomers" are a pair of stereoisomers that are non-superimposable mirror images of each other. A 1:1 mixture of a pair of enantiomers is a "racemic" mixture. The term "(±)" is used to designate a racemic mixture where appropriate. "Diastereoisomers" or "diastereomers" are stereoisomers that have at least two asymmetric atoms but are not mirror images of each other. The absolute stereochemistry is specified according to the Cahn-Ingold-Prelog R-S system. When a compound is a pure enantiomer, the stereochemistry at each chiral carbon can be specified by either R or S. Resolved compounds whose absolute configuration is unknown can be designated (+) or (−) depending on the direction (dextro- or levorotatory) in which they rotate plane polarized light at the wavelength of the sodium D line. Certain compounds described herein contain one or more asymmetric centers and can thus give rise to enantiomers, diastereomers, and other stereoisomeric forms, the asymmetric centers of which can be defined, in terms of absolute stereochemistry, as (R)- or (S)-. The present chemical entities, pharmaceutical compositions and methods are meant to include all such possible stereoisomers, including racemic mixtures, optically pure forms, mixtures of diastereomers and intermediate mixtures. Optically active (R)- and (S)-isomers can be prepared using chiral synthons or chiral reagents, or resolved using conventional techniques. The optical activity of a compound can be analyzed via any suitable method, including but not limited to chiral chromatography and polarimetry, and the degree of predominance of one stereoisomer over the other isomer can be determined.

The compounds or salts for Formula (I), (II), (II-A), (III), (III-A), (III-B), (IV), (IV-A), (IV-B), (V), (V-A), (V-B), (VI), (VI-A), or (VI-B), herein may in some cases exist as diastereomers, enantiomers, or other stereoisomeric forms. The compounds presented herein include all diastereomeric, enantiomeric, and epimeric forms as well as the racemates, mixtures of diastereomers, and other mixtures thereof, to the extent they can be made by one of ordinary skill in the art by routine experimentation. Separation of stereoisomers may be performed by chromatography or by forming diastereomers and separating by recrystallization, or chromatography, or any combination thereof. (Jean Jacques, Andre Collet, Samuel H. Wilen, "Enantiomers, Racemates and Resolutions," John Wiley And Sons, Inc., 1981, herein incorporated by reference for this disclosure). Stereoisomers may also be obtained by stereoselective synthesis. Furthermore, a mixture of two enantiomers enriched in one of the two can be purified to provide further optically enriched form of the major enantiomer by recrystallization and/or trituration.

In certain embodiments, compounds or salts for Formula (I), (II), (II-A), (III), (III-A), (III-B), (IV), (IV-A), (IV-B), (V), (V-A), (V-B), (VI), (VI-A), or (VI-B), may comprise two or more enantiomers or diatereomers of a compound wherein a single enantiomer or diastereomer accounts for at least about 70% by weight, at least about 80% by weight, at least about 90% by weight, at least about 98% by weight, or at least about 99% by weight or more of the total weight of all stereoisomers. Methods of producing substantially pure enantiomers are well known to those of skill in the art. For example, a single stereoisomer, e.g., an enantiomer, substantially free of its stereoisomer may be obtained by resolution of the racemic mixture using a method such as formation of diastereomers using optically active resolving agents (Stereochemistry of Carbon Compounds, (1962) by E. L. Eliel, McGraw Hill; Lochmuller (1975) J. Chromatogr., 113(3): 283-302). Racemic mixtures of chiral compounds can be separated and isolated by any suitable method, including, but not limited to: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions. Another approach for separation of the enantiomers is to use a Diacel chiral column and elution using an organic mobile phase such as done by Chiral Technologies (www.chiraltech.com) on a fee for service basis.

A "tautomer" refers to a molecule wherein a proton shift from one atom of a molecule to another atom of the same molecule is possible. In certain embodiments, the compounds or salts for Formula (I), (II), (II-A), (III), (III-A), (III-B), (IV), (IV-A), (IV-B), (V), (V-A), (V-B), (VI), (VI-A), or (VI-B), exist as tautomers. In circumstances where tautomerization is possible, a chemical equilibrium of the tautomers may exist. The exact ratio of the tautomers depends on several factors, including physical state, temperature, solvent, and pH. Some non-limiting examples of tautomeric equilibrium include:

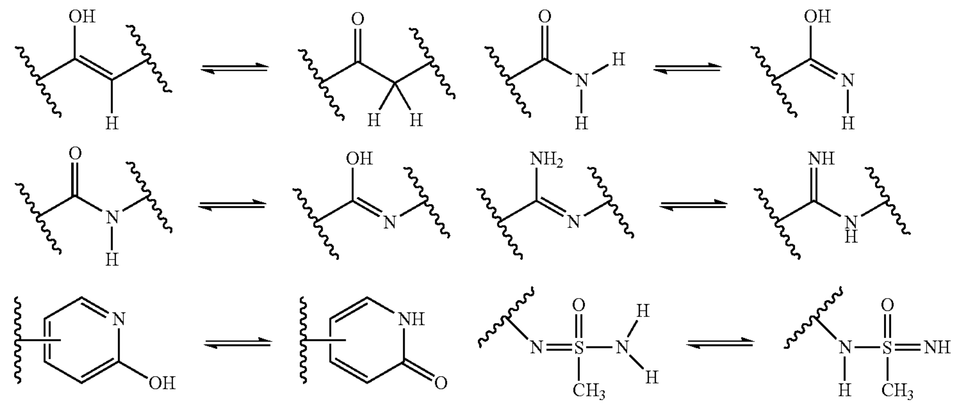

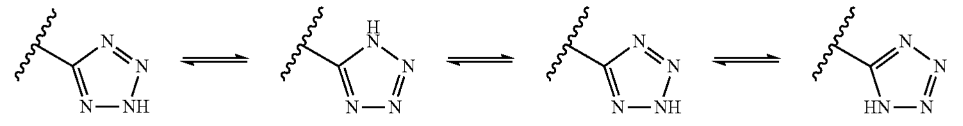

-continued

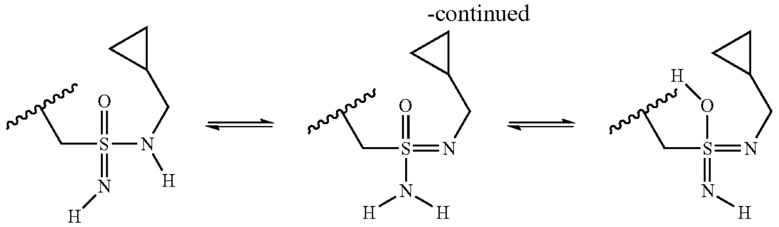

The compounds disclosed herein, in some embodiments, are used in different enriched isotopic forms, e.g., enriched in the content of $^{2}H$, $^{3}H$, $^{11}C$, $^{13}C$ and/or $^{14}C$. In one particular embodiment, the compound may be deuterated in at least one position. Such deuterated forms can be made by the procedure described in U.S. Pat. Nos. 5,846,514 and 6,334,997. As described in U.S. Pat. Nos. 5,846,514 and 6,334,997, deuteration can improve the metabolic stability and or efficacy, thus increasing the duration of action of drugs.

In certain embodiments, the compounds disclosed herein have some or all of the $^{1}H$ atoms replaced with $^{2}H$ atoms. The methods of synthesis for deuterium-containing compounds are known in the art and include, by way of non-limiting example only, the following synthetic methods.

Deuterium substituted compounds are synthesized using various methods such as described in: Dean, Dennis C.; Editor. Recent Advances in the Synthesis and Applications of Radiolabeled Compounds for Drug Discovery and Development. [In: Curr., Pharm. Des., 2000; 6(10)]2000, 110 pp; George W.; Varma, Rajender S. The Synthesis of Radiolabeled Compounds via Organometallic Intermediates, Tetrahedron, 1989, 45(21), 6601-21; and Evans, E. Anthony. Synthesis of radiolabeled compounds, J. Radioanal. Chem., 1981, 64(1-2), 9-32.

Deuterated starting materials are readily available and are subjected to the synthetic methods described herein to provide for the synthesis of deuterium-containing compounds. Large numbers of deuterium-containing reagents and building blocks are available commercially from chemical vendors, such as Aldrich Chemical Co.

Unless otherwise stated, compounds described herein are intended to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon are within the scope of the present disclosure.

The compounds of the present disclosure optionally contain unnatural proportions of atomic isotopes at one or more atoms that constitute such compounds. For example, the compounds may be labeled with isotopes, such as for example, deuterium (2H), tritium (3H), iodine-125 ($^{125}I$) or carbon-14 ($^{14}C$). Isotopic substitution with $^{2}H$, $^{11}C$, $^{13}C$, $^{14}C$, $^{15}C$, $^{12}N$, $^{13}N$, $^{15}N$, $^{16}N$, $^{16}O$, $^{17}O$, $^{14}F$, $^{15}F$, $^{16}F$ $^{17}F$, $^{18}F$, $^{33}S$, $^{34}S$, $^{35}S$, $^{36}S$, $^{35}Cl$, $^{37}Cl$, $^{79}Br$, $^{81}Br$, and $^{125}I$ are all contemplated. All isotopic variations of the compounds of the present invention, whether radioactive or not, are encompassed within the scope of the present invention.

Included in the present disclosure are salts, particularly pharmaceutically acceptable salts, of the compounds of Formula (I), (II), (II-A), (III), (III-A), (III-B), (IV), (IV-A), (IV-B), (V), (V-A), (V-B), (VI), (VI-A), or (VI-B). The compounds of the present disclosure may possess a sufficiently acidic, a sufficiently basic, or both functional groups, can react with any of a number of inorganic bases, and inorganic and organic acids, to form a salt. Alternatively, compounds that are inherently charged, such as those with a quaternary nitrogen, can form a salt with an appropriate counterion, e.g., a halide such as bromide, chloride, or fluoride, particularly bromide.

The methods and compositions of Formula (I), (II), (II-A), (III), (III-A), (III-B), (IV), (IV-A), (IV-B), (V), (V-A), (V-B), (VI), (VI-A), or (VI-B) include the use of amorphous forms as well as crystalline forms (also known as polymorphs). The compounds described herein may be in the form of pharmaceutically acceptable salts. As well, in some embodiments, active metabolites of these compounds having the same type of activity are included in the scope of the present disclosure. In addition, the compounds described herein can exist in unsolvated as well as solvated forms with pharmaceutically acceptable solvents such as water, ethanol, and the like. The solvated forms of the compounds presented herein are also considered to be disclosed herein.

Compounds of Formula (I), (II), (II-A), (III), (III-A), (III-B), (IV), (IV-A), (IV-B), (V), (V-A), (V-B), (VI), (VI-A), or (VI-B), also include crystalline and amorphous forms of those compounds, pharmaceutically acceptable salts, and active metabolites of these compounds having the same type of activity, including, for example, polymorphs, pseudopolymorphs, solvates, hydrates, unsolvated polymorphs (including anhydrates), conformational polymorphs, and amorphous forms of the compounds, as well as mixtures thereof.

Included in the present disclosure are salts, particularly pharmaceutically acceptable salts, of compounds represented by Formula (I), (II), (II-A), (III), (III-A), (III-B), (IV), (IV-A), (IV-B), (V), (V-A), (V-B), (VI), (VI-A), or (VI-B). The compounds of the present invention that possess a sufficiently acidic, a sufficiently basic, or both functional groups, can react with any of a number of inorganic bases, and inorganic and organic acids, to form a salt. Alternatively, compounds that are inherently charged, such as those with a quaternary nitrogen, can form a salt with an appropriate counterion, e.g., a halide such as bromide, chloride, or fluoride, particularly bromide.

In certain embodiments, compounds or salts of Formula (I), (II), (II-A), (III), (III-A), (III-B), (IV), (IV-A), (IV-B), (V), (V-A), (V-B), (VI), (VI-A), or (VI-B), may be prodrugs, e.g., wherein a hydroxyl in the parent compound is presented as an ester or a carbonate, or carboxylic acid present in the parent compound is presented as an ester. The term "prodrug" is intended to encompass compounds which, under physiologic conditions, are converted into pharmaceutical agents of the present disclosure. One method for making a prodrug is to include one or more selected moieties which are hydrolyzed under physiologic conditions to reveal the desired molecule.

In other embodiments, the prodrug is converted by an enzymatic activity of the host animal such as specific target cells in the host animal. For example, esters or carbonates (e.g., esters or carbonates of alcohols or carboxylic acids and esters of phosphonic acids) are preferred prodrugs of the present disclosure.

Pharmaceutical Formulations

In some aspects, the present disclosure provides a pharmaceutical composition comprising a compound or salt of Formula (I), (II), (II-A), (III), (III-A), (III-B), (IV), (IV-A), (IV-B), (V), (V-A), (V-B), (VI), (VI-A), or (VI-B) and at least one pharmaceutically acceptable excipient.

In some aspects, the present disclosure provides a pharmaceutical composition comprising a compound of Table 2.

Pharmaceutical compositions can be formulated using one or more physiologically-acceptable carriers comprising excipients and auxiliaries. Formulation can be modified depending upon the route of administration chosen. Pharmaceutical compositions comprising a compound, salt or conjugate can be manufactured, for example, by lyophilizing the compound, salt or conjugate, mixing, dissolving, emulsifying, encapsulating or entrapping the conjugate. The pharmaceutical compositions can also include the compounds, salts or conjugates in a free-base form or pharmaceutically-acceptable salt form.

A compound or salt of Formula (I), (II), (II-A), (III), (III-A), (III-B), (IV), (IV-A), (IV-B), (V), (V-A), (V-B), (VI), (VI-A), or (VI-B) may be formulated in any suitable pharmaceutical formulation. A pharmaceutical formulation of the present disclosure typically contains an active ingredient (e.g., compound or salt of any one of Formula (I), (II), (II-A), (III), (III-A), (III-B), (IV), (IV-A), (IV-B), (V), (V-A), (V-B), (VI), (VI-A), or (VI-B), and one or more pharmaceutically acceptable excipients or carriers, including but not limited to: inert solid diluents and fillers, diluents, sterile aqueous solution and various organic solvents, permeation enhancers, antioxidents, solubilizers, and adjuvants.

A compound or salt of Table 2 may be formulated in any suitable pharmaceutical formulation. A pharmaceutical formulation of the present disclosure typically contains an active ingredient (e.g., a compound or salt of Table 2), and one or more pharmaceutically acceptable excipients or carriers, including but not limited to: inert solid diluents and fillers, diluents, sterile aqueous solution and various organic solvents, permeation enhancers, antioxidents, solubilizers, and adjuvants.

Methods of Treatment

The compounds described herein can be used in the preparation of medicaments for the prevention or treatment of diseases or conditions. In addition, a method for treating any of the diseases or conditions described herein in a subject in need of such treatment, involves administration of pharmaceutical compositions containing at least one compound described herein, or a pharmaceutically acceptable salt, pharmaceutically acceptable prodrug, or pharmaceutically acceptable solvate thereof, in therapeutically effective amounts to said subject.

The compositions containing the compound(s) described herein can be administered for prophylactic and/or therapeutic treatments. In therapeutic applications, the compositions are administered to a patient already suffering from a disease or condition, in an amount sufficient to cure or at least partially arrest the symptoms of the disease or condition. Amounts effective for this use will depend on the severity and course of the disease or condition, previous therapy, the patient's health status, weight, and response to the drugs, and the judgment of the treating physician.

In prophylactic applications, compositions containing the compounds described herein are administered to a patient susceptible to or otherwise at risk of a particular disease, disorder or condition. Such an amount is defined to be a "prophylactically effective amount or dose." In this use, the precise amounts also depend on the patient's state of health, weight, and the like. When used in a patient, effective amounts for this use will depend on the severity and course of the disease, disorder or condition, previous therapy, the patient's health status and response to the drugs, and the judgment of the treating physician.

In some aspects, the present disclosure provides a method for treatment, comprising administering to a subject in need thereof an effective amount of a compound or salt of Formula (I), (II), (II-A), (III), (III-A), (III-B), (IV), (IV-A), (IV-B), (V), (V-A), (V-B), (VI), (VI-A), or (VI-B). In some aspects, the present disclosure provides a method for treating cancer in a patient in need thereof, comprising administering to the subject an effective amount of a compound or salt of Formula (I), (II), (II-A), (III), (III-A), (III-B), (IV), (IV-A), (IV-B), (V), (V-A), (V-B), (VI), (VI-A), or (VI-B). In some embodiments, the cancer is selected from breast cancer, colorectal cancer, and meningioma. In some embodiments, the cancer is breast cancer. In some embodiments, the cancer is colorectal cancer. In some embodiments, the cancer is meningioma.

In certain embodiments, the present disclosure can be used as a method of inhibiting an AKT1 protein in a subject in need thereof, comprising administering to the subject a compound or salt of Formula (I), (II), (II-A), (III), (III-A), (III-B), (IV), (IV-A), (IV-B), (V), (V-A), (V-B), (VI), (VI-A), or (VI-B) or a pharmaceutical composition of Formula (I), (II), (II-A), (III), (III-A), (III-B), (IV), (IV-A), (IV-B), (V), (V-A), (V-B), (VI), (VI-A), or (VI-B). In some embodiments, the AKT protein is wild-type AKT1. In some embodiments, the AKT protein is a mutant AKT1 protein. In some embodiments, the mutant AKT1 protein comprises an E17K mutant. In some embodiments, the administrating modulates the activity of mutant AKT1. In some embodiments, the administrating modulates the activity of wild-type AKT1.

In some aspects, the present disclosure provides a method for treatment, comprising administering to a subject in need thereof an effective amount of a compound or salt of Table 2. In some aspects, the present disclosure provides a method for treating cancer in a patient in need thereof, comprising administering to the subject an effective amount of a compound or salt of Table 2. In some embodiments, the cancer is selected from breast cancer, colorectal cancer, and meningioma. In some embodiments, the cancer is breast cancer. In some embodiments, the cancer is colorectal cancer. In some embodiments, the cancer is meningioma.

In certain embodiments, the present disclosure can be used as a method of inhibiting an AKT1 protein in a subject in need thereof, comprising administering to the subject a compound or salt of Table 2 or a pharmaceutical composition comprising a compound or salt of Table 2. In some embodiments, the AKT protein is wild-type AKT1. In some embodiments, the AKT protein is a mutant AKT1 protein. In some embodiments, the mutant AKT1 protein comprises an E17K mutant. In some embodiments, the administrating modulates the activity of mutant AKT1. In some embodiments, the administrating modulates the activity of wild-type AKT1.

EXAMPLES

The invention now being generally described, it will be more readily understood by reference to the following examples which are included merely for purposes of illustration of certain aspects and embodiments of the present invention and are not intended to limit the invention in any way.

Chemical Synthesis

The following examples describe illustrate various methods of preparation of compounds described herein. Examples are exemplary and not exhaustive. It is understood that one skilled in the art may be able to synthesize described compounds by similar methods.

Compound 1: (S)—N-(5-(2-(2-aminopyridin-3-yl)-5-(1H-pyrazol-1-yl)-3H-imidazo[4,5-b]pyridin-3-yl)-2,3-dihydro-1H-inden-1-yl)acetamide (Compound 1)

Compound 1

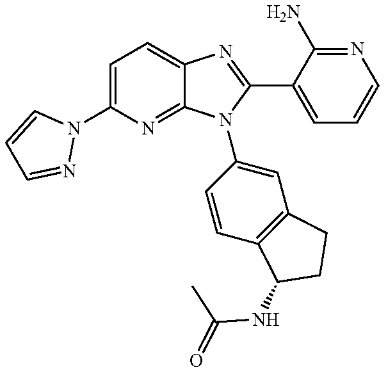

Synthetic Route:

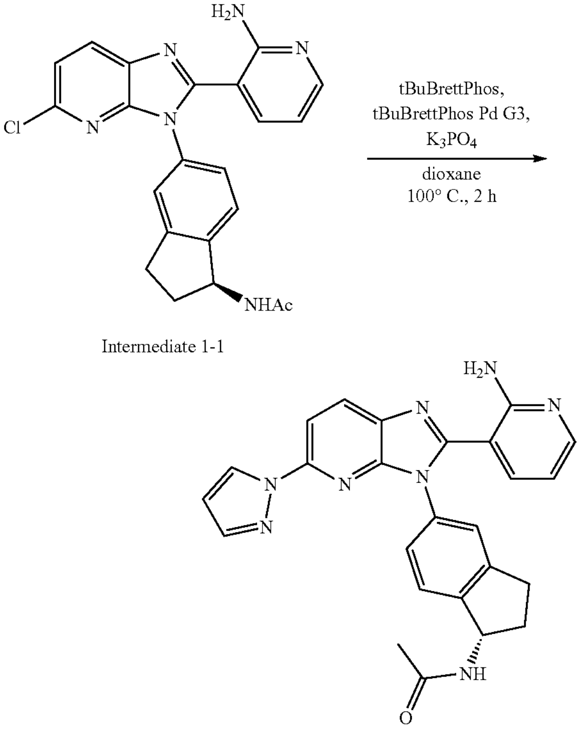

Intermediate 1-1

Compound 1

Step 1: Synthesis of (S)—N-(5-(2-(2-aminopyridin-3-yl)-5-(1H-pyrazol-1-yl)-3H-imidazo[4,5-b]pyridin-3-yl)-2,3-dihydro-1H-inden-1-yl)acetamide (Compound 1)

To a mixture of (S)—N-(5-(2-(2-aminopyridin-3-yl)-5-chloro-3H-imidazo[4,5-b]pyridin-3-yl)-2,3-dihydro-1H-inden-1-yl)acetamide (Intermediate 1-1) (200 mg, 0.477 mmol, 1 equiv), pyrazole (39 mg, 0.57 mmol, 1.5 equiv), t-BuBrettPhos Pd G3 (41 mg, 0.048 mmol, 0.1 equiv), t-BuBrettPhos (23 mg, 0.048 mmol, 0.1 equiv) and $K_3PO_4$ (304 mg, 1.43 mmol, 3 equiv) was added 1,4-dioxane (5 mL) under $N_2$ at room temperature. The resulting mixture was stirred at 100° C. for 2 h under nitrogen atmosphere. Brine was added and the mixture was extracted with ethyl acetate. The combined organic layers were dried over anhydrous sodium sulfate, filtered and concentrated under reduced pressure. The resulting residue was purified by silica gel column chromatography using a gradient of methanol in ethyl acetate. The material obtained at this stage was used in subsequent transformations vide infra. The material was further purified for characterization and assaying by preparative HPLC on a XSelect CSH Prep C18 OBD Column using a gradient of acetonitrile in water (+0.05% TFA) to afford (S)—N-(5-(2-(2-aminopyridin-3-yl)-5-(1H-pyrazol-1-yl)-3H-imidazo[4,5-b]pyridin-3-yl)-2,3-dihydro-1H-inden-1-yl)acetamide (TFA salt) (Compound 1) (84 mg, 39%) as a white solid. MS (ESI) calcd. for $C_{25}H_{22}N_8O$: 450.19 m/z, found 451.15 [M+H]+. $^1H$ NMR (300 MHz, DMSO-$d_6$) δ (ppm): 8.40-8.50 (m, 1H), 8.33-8.40 (m, 1H), 8.02-8.10 (m, 1H), 7.95-8.02 (m, 1H), 7.78-7.88 (m, 1H), 7.72-7.78 (m, 1H), 7.40-7.51 (m, 1H), 7.26-7.40 (m, 2H), 6.78-6.90 (m, 1H), 6.55-6.65 (m, 1H), 5.22-5.40 (m, 1H), 2.80-3.10 (m, 2H), 2.35-2.50 (m, 1H), 1.91-2.00 (m, 3H), 1.78-1.90 (m, 1H).

Intermediate 1-1: (S)—N-(5-(2-(2-aminopyridin-3-yl)-5-chloro-3H-imidazo[4,5-b]pyridin-3-yl)-2,3-dihydro-1H-inden-1-yl)acetamide Intermediate 1-1

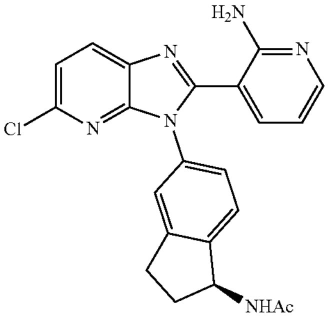

Synthetic Route:

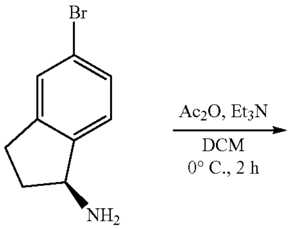

-continued

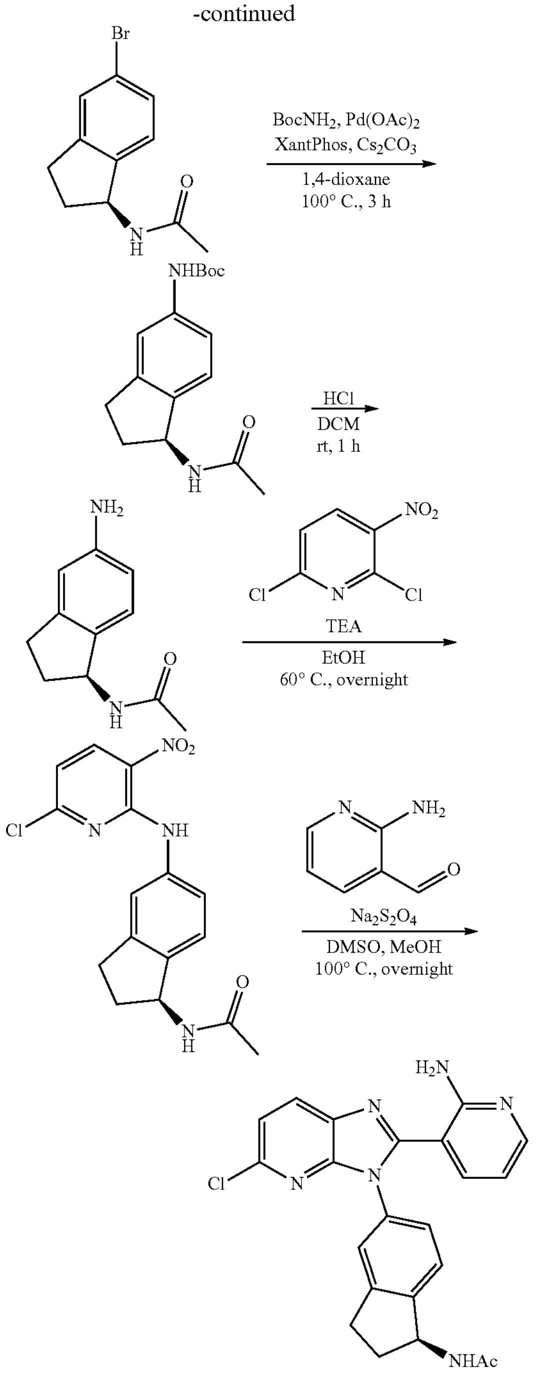

Intermediate 1-1

Step 1: Synthesis of (S)—N-(5-bromo-2,3-dihydro-1H-inden-1-yl)acetamide

To a mixture of (S)-5-bromo-2,3-dihydro-1H-inden-1-amine (74 g, 350 mmol, 1 equiv) and triethylamine (106 g, 1.05 mol, 3 equiv) in dichloromethane (1.5 L) was added acetic anhydride (55.2 g, 526 mmol, 1.5 equiv) at 0° C. and the mixture was stirred at 0° C. for 2 h. The reaction mixture was quenched by addition of water and extracted 3 times with ethyl acetate. The combined organic layers were dried over anhydrous sodium sulfate and concentrated under reduced pressure. The crude product was re-crystallized from petroleum ether to afford (S)—N-(5-bromo-2,3-dihydro-1H-inden-1-yl)acetamide (90 g, 83% yield) as a white solid. MS (ESI) calculated for $C_{11}H_{12}BrNO$: 253.01, found 254.00 $[M+H]^+$, 256.00 $[M+H+2]^+$.

Step 2: Synthesis of tert-butyl (S)-(1-acetamido-2,3-dihydro-1H-inden-5-yl)carbamate To a mixture of N-[(1S)-5-bromo-2,3-dihydro-1H-inden-1-yl]acetamide (40 g, 157 mmol, 1 equiv), tert-butyl carbamate (27.66 g, 236 mmol, 1.5 equiv), XantPhos (9.11 g, 15.7 mmol, 10 mol %), palladium (II) acetate (3.54 g, 15.7 mmol, 10 mol %), and cesium carbonate (154 g, 472 mmol, 10 mol %) was added 1,4-dioxane (300 mL) under nitrogen atmosphere. The resulting mixture was stirred for 3 h at 100° C. The reaction mixture was quenched by addition of water and extracted 3 times with ethyl acetate. The combined organic layers were dried over anhydrous sodium sulfate and concentrated under reduced pressure. The residue was purified by silica gel column chromatography using an eluent of petroleum ether/dichloromethane/methanol (70:27:3) to afford tert-butyl N-[(1S)-1-acetamido-2,3-dihydro-1H-inden-5-yl]carbamate (43.1 g, 48%). MS (ESI) calculated for $C_{16}H_{22}N_2O_3$: 290.16 m/z, found 289.05 $[M-H]^-$.

Step 3: Synthesis of (S)—N-(5-amino-2,3-dihydro-1H-inden-1-yl)acetamide

To a stirred solution of tert-butyl N-[(1S)-1-acetamido-2,3-dihydro-1H-inden-5-yl]carbamate (43.1 g, 148 mmol, 1 equiv) in dichloromethane (180 mL) was added 4N hydrochloric acid in 1,4-dioxane (185 mL, 742 mmol, 5 equiv). The reaction mixture was stirred for 1 h at room temperature. The reaction mixture was concentrated in vacuo and re-crystallized from ethyl acetate to afford N-[(1S)-5-amino-2,3-dihydro-1H-inden-1-yl]acetamide (hydrochloride salt) (23 g, 81%) as a white solid. MS (ESI) calculated for $C_{11}H_{14}N_2O$: 190.11 m/z, found 191.15 $[M+H]^+$.

Step 4: Synthesis of N-[(1S)-5-[(6-chloro-3-nitropyridin-2-yl)amino]-2,3-dihydro-1H-inden-1-yl]acetamide To a solution of N-[(1S)-5-amino-2,3-dihydro-1H-inden-1-yl]acetamide (100 g, 526 mmol, 1 equiv) in ethanol (2 L) was added triethylamine (160 g, 1.58 mol, 3 equiv) and 2,6-dichloro-3-nitropyridine (122 g, 631 mmol, 1.2 equiv). The resulting mixture was stirred at 60° C. overnight. The mixture was then cooled to room temperature and quenched with water. The resulting precipitate was collected by filtration and rinsed with ethanol/water to afford N-[(1S)-5-[(6-chloro-3-nitropyridin-2-yl)amino]-2,3-dihydro-1H-inden-1-yl]acetamide (100 g, 49%) as a red solid. MS (ESI) calculated for $C_{16}H_{15}ClN_4O_3$: 346.08 m/z, found 345.00 $[M-H]^-$.

Step 5: Synthesis of N-[(1S)-5-[2-(2-aminopyridin-3-yl)-5-chloroimidazo[4,5-b]pyridin-3-yl]-2,3-dihydro-1H-inden-1-yl]acetamide (Intermediate 1-1)

To a solution of N-[(1S)-5-[(6-chloro-3-nitropyridin-2-yl)amino]-2,3-dihydro-1H-inden-1-yl]acetamide (100 g, 288 mmol, 1 equiv) in dimethyl sulfoxide (1.8 L) and methanol (300 mL) was added 2-aminopyridine-3-carbaldehyde (38.74 g, 317.2 mmol, 1.1 equiv) and sodium dithionite (110 g, 634 mmol, 2.2 equiv). The resulting mixture was stirred at 100° C. overnight.

Water was added and the precipitated solids were collected by filtration, rinsing with water. The solid collected was purified by silica gel column chromatography eluting with dichloromethane/methanol (10:1) to afford N-[(1S)-5-[2-(2-aminopyridin-3-yl)-5-chloroimidazo[4,5-b]pyridin-3-yl]-2,3-dihydro-1H-inden-1-yl]acetamide (Intermediate 1-1) (43.2 g, 31%) as a yellow solid. MS (ESI) calculated for $C_{22}H_{19}ClN_6O$: 418.13 m/z, found 419.10 $[M+H]^+$.

Example 2: (S)-3-(3-(1-amino-2,3-dihydro-1H-inden-5-yl)-5-(1H-pyrazol-1-yl)-3H-imidazo[4,5-b]pyridin-2-yl)pyridin-2-amine (Compound 2)

Compound 2

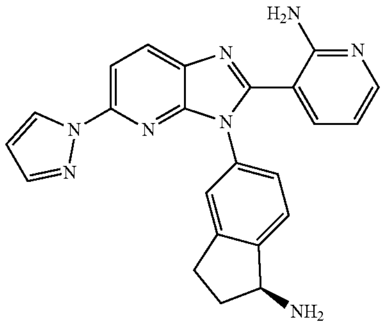

Synthetic Route:

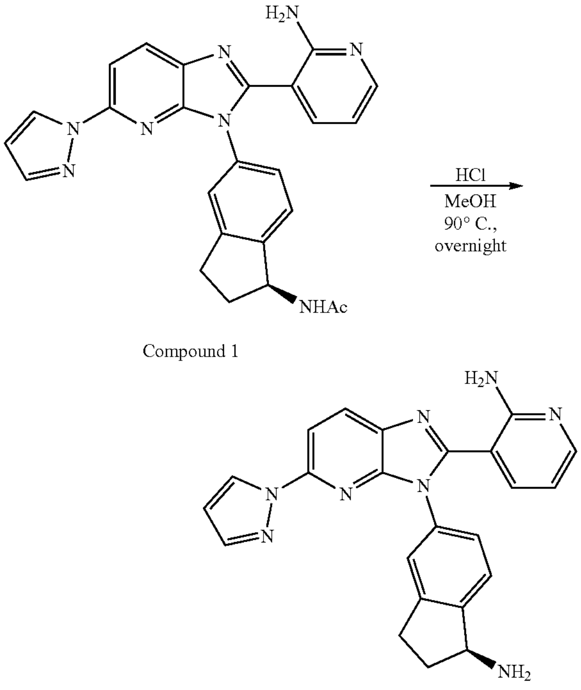

Compound 1

Compound 2

Step 1: Synthesis of (S)-3-(3-(1-amino-2,3-dihydro-1H-inden-5-yl)-5-(1H-pyrazol-1-yl)-3H-imidazo[4,5-b]pyridin-2-yl)pyridin-2-amine (Compound 2)

To a stirred suspension of (S)—N-(5-(2-(2-aminopyridin-3-yl)-5-(1H-pyrazol-1-yl)-3H-imidazo[4,5-b]pyridin-3-yl)-2,3-dihydro-1H-inden-1-yl)acetamide (Compound 1) (1.00 g, 2.22 mmol, 1 equiv) in methanol (5 mL) was added HCl (5 mL, concentrated) and the resulting solution was stirred at 90° C. overnight under nitrogen atmosphere. The solution was cooled to room temperature and diluted with dichloromethane. The solution was concentrated to dryness under reduced pressure. The crude solid was taken up into DMSO and pyrrolidine (395 mg, 5.55 mmol, 2.5 equiv) was added. The solution was stirred for 2 min followed by addition of TFA (959 mg, 6.66 mmol, 3 equiv). The solution was purified by preparative HPLC on a Phenomenex Gemini C18 Column using a gradient of acetonitrile in water (+0.05% TFA) to afford (S)-3-(3-(1-amino-2,3-dihydro-1H-inden-5-yl)-5-(1H-pyrazol-1-yl)-3H-imidazo[4,5-b]pyridin-2-yl)pyridin-2-amine (TFA salt) (Compound 2) (869 mg, 75%) as a yellow solid. MS (ESI) calcd. for $C_{23}H_{20}N_8$: 408.08 m/z, found 409.15 $[M+H]^+$. $^1H$ NMR (300 MHz, DMSO-$d_6$) δ (ppm): 8.40-8.43 (m, 1H), 8.32-8.40 (m, 1H), 8.02-8.10 (m, 1H), 7.95-8.02 (m, 1H), 7.78-7.85 (m, 1H), 7.61-7.75 (m, 2H), 7.48-7.58 (m, 1H), 7.36-7.45 (m, 1H), 6.72-6.82 (m, 1H), 6.51-6.69 (m, 1H), 4.72-4.82 (m, 1H), 3.05-3.30 (m, 1H), 2.88-3.05 (m, 1H), 2.55-2.68 (m, 1H), 2.01-2.18 (m, 1H).

Example 3: (S)—N-(5-(2-(2-aminopyridin-3-yl)-5-(1H-pyrazol-1-yl)-3H-imidazo[4,5-b]pyridin-3-yl)-2,3-dihydro-1H-inden-1-yl)-3,4-difluoro-5-methoxybenzamide (Compound 3)

Compound 3

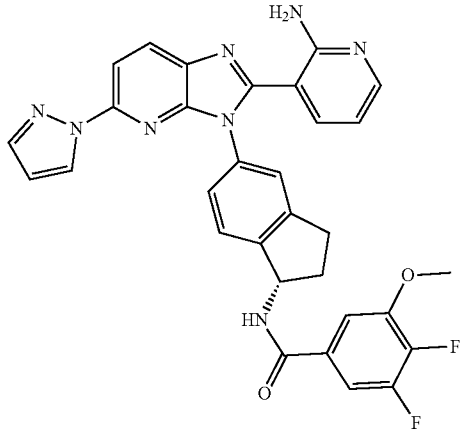

Synthetic Route:

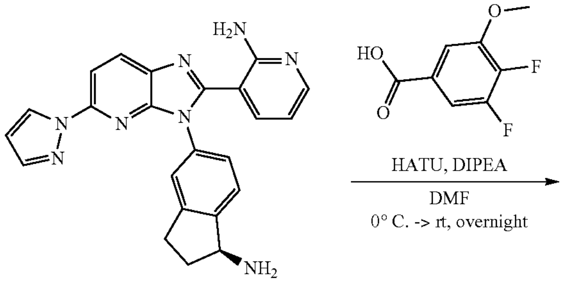

Compound 2

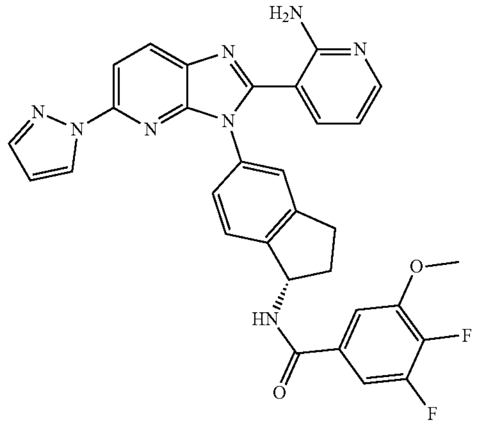

Compound 3

Step 1: Synthesis of (S)—N-(5-(2-(2-aminopyridin-3-yl)-5-(1H-pyrazol-1-yl)-3H-imidazo[4,5-b]pyridin-3-yl)-2,3-dihydro-1H-inden-1-yl)-3,4-difluoro-5-methoxybenzamide (Compound 3)

A dry vial was charged with 3,4-difluoro-5-anisic acid (37 mg, 0.20 mmol, 1 equiv) under nitrogen atmosphere. A solution of HATU (79 mg, 0.20 mmol, 1.05 equiv) in N,N-dimethylformamide (0.8 mL) was added and the solution was cooled to 0° C. N,N-diisopropylethylamine (26 mg, 0.20 mmol, 1 equiv) was added and the solution was stirred at 0° C. for 1 h. A solution of (S)-3-(3-(1-amino-2,3-dihydro-1H-inden-5-yl)-5-(1H-pyrazol-1-yl)-3H-imidazo[4,5-b]pyridin-2-yl)pyridin-2-amine (Compound 2) (126 mg, 0.24 mmol, 1.2 equiv) and N,N-diisopropylethylamine (64 mg, 0.5 mmol, 2.5 equiv) in N,N-dimethylformamide (1.2 mL) was added and the solution was stirred overnight at room temperature. The reaction mixture was purified by preparative CPLC on a Phenomenex Gemini C18 column using a gradient ofacetonitrile in water (+0.0500 TFA (or formic acid for the formic acid salts obtained using an analogous procedure or ammonium bicarbonate for free bases obtained using an analogous procedure)) to afford (S')—N-(5-(2-(2-aminopyridin-3-yl)-5-(1H-pyrazol-1-yl)-3H-imidazo[4,5-b]pyridin-3-yl)-2,3-dihydro-11H-inden-1-yl)-3,4-difluoro-5-methoxybenzamide (TFA salt) (Compound 3) (78 mg, 690%). MS (ESI) calculated for $C_{31}H_{24}F_2N_8O_2$: 578.20 m/z, found 579.25 $[M+H]^+$. $^1$H NMR (400 MHz, DMSO-$d_6$) δ (ppm) 9.00 (d, J=8.2 Hz, 1H), 8.43 (d, J=8.7 Hz, 1H), 8.38 (dd, J=2.6, 0.7 Hz, 1H), 8.09 (dd, J=5.9, 1.7 Hz, 1H), 8.01 (d, J=8.6 Hz, 1H), 7.83 (dd, J=1.8, 0.7 Hz, 1H), 7.76 (dd, J=7.5, 1.7 Hz, 1H), 7.62-7.57 (m, 2H), 7.49-7.46 (m, 1H), 7.42-7.35 (m, 2H), 6.79 (dd, J=7.6, 5.9 Hz, 1H), 6.57 (dd, J=2.6, 1.7 Hz, 1H), 5.64 (dd, J=8.2, 8.2 Hz, 1H), 3.95 (s, 3H), 3.07 (ddd, J=16.3, 8.9, 2.7 Hz, 1H), 2.93 (ddd, J=16.2, 8.4, 8.4 Hz, 1H), 2.59-2.53 (m, 1H), 2.17-2.02 (m, 1H). $^{19}$F NMR (376 MHz, DMSO$d_6$) δ (ppm) −137.55 (d, J=21.1 Hz), −156.31 (d, J=21.3 Hz).

The following compounds were prepared analogously to the synthetic preparation in Example 3 (Compound 3).

TABLE 3

Characterization data of compounds prepared analogously to compound 3.

| Cpd ID | Characterization Data |
|---|---|
| 66 | MS (ESI) calcd. for $C_{32}H_{25}F_2N_9O$, 589.22 m/z, found 590.15 $[M + H]^+$. $^1$H NMR (300 MHz, DMSO-$d_6$) δ (ppm); 8.98-9.13 (m, 1H), 8.27-8.43 (m, 3H), 7.99-8.09 (m, 1H), 7.90-7.98 (m, 1H), 7.77-7.86 (m, 1H), 7.35-7.47 (m, 2H), 7.20-7.34 (m, 2H), 6.52-6.61 (m, 1H), 6.38-6.51 (m, 1H), 5.56-5.74 (m, 1H), 2.96-3.18 (m, 3H), 2.83-2.95 (m, 1H), 2.53-2.80 (m, 3H), 2.02-2.20 (m, 1H). $^{19}$F NMR (282 MHz, DMSO-$d_6$) δ (ppm); −90.75. |
| 67 | MS (ESI) calcd. for $C_{29}H_{24}N_{10}O$, 528.21 m/z, found 529.20 $[M + H]^+$. $^1$H NMR (300 MHz, DMSO-$d_6$) δ (ppm); 9.05 (s, 1H), 8.50-8.57 (m, 2H), 8.11-8.18 (m, 3H), 8.07-8.10 (m, 1H), 7.85-7.90 (m, 1H), 7.68-7.71 (m, 1H), 7.47-7.51 (m, 2H), 7.39-7.42 (m, 1H), 6.85-6.91 (m, 1H), 5.61-5.69 (m, 1H), 2.99-3.14 (m, 1H), 2.87-2.98 (m, 1H), 2.63 (s, 3H), 2.55-2.60 (m, 1H), 2.09-2.18 (m, 1H). (2,2,2-trifluoroacetic acid salt) |
| 68 | MS (ESI) calcd. for $C_{30}H_{22}F_3N_9O_2$ 597.18 m/z, found 598.15 $[M + H]^+$. $^1$H NMR (300 MHz, DMSO-$d_6$) δ (ppm); 8.85 (s, 1H), 8.41-8.48 (m, 1H), 8.37-8.40 (m, 1H), 8.33-8.36 (m, 1H), 8.00-8.05 (m, 1H), 7.95-7.99 (m, 1H), 7.81-7.83 (m, 1H), 7.39-7.45 (m, 3H), 7.30-7.33 (m, 2H), 6.60-6.62 (m, 1H), 6.50-6.57 (m, 1H), 5.59-5.67 (m, 1H), 2.99-3.14 (m, 1H), 2.87-2.98 (m, 1H), 2.55-2.60 (m, 1H), 2.01-2.13 (m, 1H). $^{19}$F NMR (282 MHz, DMSO-$d_6$) δ (ppm); −55.21. (formic acid salt) |
| 69 | MS (ESI) calcd. for $C_{31}H_{27}N_9O$, 541.23 m/z, found 542.30 $[M + H]^+$. $^1$H NMR (300 MHz, DMSO-$d_6$) δ (ppm); 8.26-8.34 (m, 2H), 7.99-8.07 (m, 1H), 7.89-7.97 (m, 1H), 7.74-7.80 (m, 1H), 7.64-7.71 (m, 1H), 7.37-7.41 (m, 1H), 7.30-7.36 (m, 1H), 7.19-7.29 (m, 2H), 7.08-7.16 (m, 1H), 6.56-6.64 (m, 1H), 6.41-6.50 (m, 1H), 5.47-5.58 (m, 1H), 2.79-3.06 (m, 2H), 2.54-2.59 (m, 1H), 2.47-2.53 (m, 3H), 2.37-2.46 (m, 3H), 1.92-2.08 (m, 1H). |
| 71 | MS (ESI) calcd. for $C_{32}H_{26}N_{10}O$, 566.23 m/z, found 567.15 $[M + H]^+$. $^1$H NMR (300 MHz, DMSO-$d_6$) δ (ppm): 9.13-9.20 (m, 1H), 8.30-8.44 (m, 3H), 7.94-8.08 (m, 4H), 7.78-7.83 (m, 1H), 7.66-7.76 (m, 1H), 7.40-7.51 (m, 2H), 7.31-7.39 (m, 1H), 6.70-6.81 (m, 1H), 6.52-6.60 (m, 1H), 5.61-5.73 (m, 1H), 3.05-3.16 (m, 1H), 2.87-3.05 (m, 1H), 2.54-2.63 (m, 4H), 2.02-2.22 (m, 1H). |

TABLE 3-continued

Characterization data of compounds prepared analogously to compound 3.

| Cpd ID | Characterization Data |
| --- | --- |
| 72 | MS (ESI) calcd. for $C_{32}H_{26}ON_{10}$ 566.23 m/z, found, 567.15 $[M + H]^+$. $^1H$ NMR (300 MHz, DMSO-$d_6$) δ (ppm); 9.33-9.40 (m, 1H), 8.40-8.45 (m, 1H), 8.34-8.38 (m, 1H), 8.20-8.35 (m, 1H), 8.14 (s, 1H), 8.04-8.10 (m, 1H), 7.98-8.03 (m, 1H), 7.87-7.95 (m, 1H), 7.79-7.85 (m, 1H), 7.68-7.77 (m, 1H), 7.46-7.50 (m, 1H), 7.43 (s, 1H), 7.31-7.41 (m, 1H), 6.72-6.81 (m, 1H), 6.52-6.60 (m, 1H), 5.59-5.71 (m, 1H), 3.02-3.16 (m, 1H), 2.86-3.01 (m, 1H), 2.54-2.66 (m, 1H), 2.52 (s, 3H), 2.04-2.20 (m, 1H). |
| 73 | MS (ESI) calcd. for $C_{31}H_{25}F_2N_9O$, 577.22 m/z, found 578.10 $[M + H]^+$. $^1H$ NMR (300 MHz, DMSO-$d_6$) δ (ppm); 8.83-8.95 (m, 1H), 8.19-8.30 (m, 2H), 8.10-8.20 (m, 1H), 7.78-8.10 (m, 3H), 7.31-7.42 (m, 3H), 7.21-7.31 (m, 2H), 6.89-6.98 (m, 1H), 6.45-6.55 (m, 1H), 5.54-5.67 (m, 1H), 3.02-3.10 (m, 1H), 2.90-3.00 (m, 1H), 2.55-2.65 (m, 3H), 2.50-2.54 (m, 1H), 2.05-2.15 (m, 1H). $^{19}F$ NMR (282 MHz, DMSO-$d_6$) δ (ppm); −94.15. (formic acid salt) |
| 74 | MS (ESI) calcd. for $C_{31}H_{23}F_4N_9O$, 613.20 m/z, found 614.15 $[M + H]^+$. $^1H$ NMR (300 MHz, DMSO-$d_6$) δ (ppm); 9.10-9.21 (m, 1H), 8.39-8.53 (m, 1H), 8.18-8.35 (m, 2H), 7.36-8.12 (m, 6H), 7.23-7.35 (m, 2H), 6.80-7.22 (m, 2H), 6.39-6.53 (m, 1H), 5.58-5.75 (m, 1H), 2.81-3.18 (m, 2H), 2.53-2.69 (m, 1H), 1.97-2.20 (m, 1H). $^{19}F$ NMR (282 MHz, DMSO-$d_6$) δ (ppm); −94.22, −116.04. |
| 75 | MS (ESI) calcd. for $C_{30}H_{25}N_9O$, 527.22 m/z, found 528.20 $[M + H]^+$. $^1H$ NMR (300 MHz, DMSO-$d_6$) δ (ppm); 8.68-8.83 (m, 1H), 8.40-8.52 (m, 1H), 8.32-8.39 (m, 1H), 8.06-8.15 (m, 1H), 7.98-8.05 (m, 2H), 7.86-7.97 (m, 1H), 7.73-7.85 (m, 2H), 7.46-7.55 (m, 1H), 7.40-7.45 (m, 1H), 7.30-7.39 (m, 1H), 6.78-6.92 (m, 1H), 6.50-6.61 (m, 1H), 5.54-5.70 (m, 1H), 2.85-3.20 (m, 2H), 2.65 (s, 3H), 2.53-2.62 (m, 1H), 2.01-2.21 (m, 1H). (TFA salt) |
| 76 | MS (ESI) calcd. for $C_{31}H_{27}N_9O$, 541.23 m/z, found, 542.20 $[M + H]^+$. $^1H$ NMR (300 MHz, DMSO-$d_6$) δ (ppm); 8.43-8.48 (m, 1H), 8.37-8.41 (m, 1H), 8.05-8.11 (m, 1H), 8.01-8.04 (m, 1H), 7.95-7.99 (m, 2H), 7.86-7.90 (m, 1H), 7.80-7.83 (m, 1H), 7.48-7.51 (m, 1H), 7.43-7.47 (m, 1H), 7.39-7.41 (m, 1H), 6.81-6.88 (m, 1H), 6.60-6.63 (m, 1H), 5.60-5.68 (m, 1H), 3.05-3.14 (m, 1H), 2.90-3.02 (m, 1H), 2.71 (s, 6H), 2.55-2.60 (m, 1H), 2.03-2.15 (m, 1H). (TFA salt) |
| 77 | MS (ESI) calcd. for $C_{30}H_{22}F_3N_9O$, 581.19 m/z, found 582.15 $[M + H]^+$. $^1H$ NMR (300 MHz, DMSO-$d_6$) δ (ppm); 9.11-9.25 (m, 1H), 8.48-8.60 (m, 1H), 8.42-8.47 (m, 1H), 8.33-8.41 (m, 1H), 7.95-8.15 (m, 3H), 7.77-7.90 (m, 2H), 7.40-7.55 (m, 2H), 7.30-7.39 (m, 1H), 6.77-6.92 (m, 1H), 6.50-6.63 (m, 1H), 5.57-5.73 (m, 1H), 3.02-3.18 (m, 1H), 2.85-3.01 (m, 1H), 2.55-2.68 (m, 1H), 2.01-2.20 (m, 1H). $^{19}F$ NMR (282 MHz, DMSO-$d_6$) δ (ppm); −66.59. (TFA salt) |
| 78 | MS (ESI) calcd. for $C_{30}H_{22}F_3N_9O_2$ 597.18 m/z, found, 598.20 $[M + H]^+$. $^1H$ NMR (300 MHz, DMSO-$d_6$ + $D_2O$) δ (ppm); 9.16-9.20 (m, 1H), 8.42-8.46 (m, 1H), 8.33-8.41 (m, 2H), 8.13-8.16 (m, 1H), 7.92-8.06 (m, 2H), 7.79-7.82 (m, 1H), 7.53-7.57 (m, 1H), 7.45-7.49 (m, 1H), 7.25-7.41 (m, 3H), 6.55-6.58 (m, 1H), 6.48-6.50 (m, 1H), 5.50-5.65 (m, 1H), 2.88-3.09 (m, 2H), 2.55-2.60 (m, 1H), 1.91-2.10 (m, 1H). $^{19}F$ NMR (282 MHz, DMSO-$d_6$) δ (ppm); −54.65. (formic acid salt) |
| 79 | MS (ESI) calcd. for $C_{30}H_{23}F_2N_9O$, 563.20 m/z, found, 564.15 $[M + H]^+$. $^1H$ NMR (300 MHz, DMSO-$d_6$ + $D_2O$) δ (ppm); 8.80-8.82 (m, 1H), 8.42-8.47 (m, 1H), 8.39-8.41 (m, 1H), 8.03-8.11 (m, 3H), 7.84-7.88 (m, 1H), 7.81-7.83 (m, 1H), 7.68-7.73 (m, 1H), 7.50-7.57 (m, 2H), 7.15-7.42 (m, 2H), 6.80-6.88 (m, 1H), 6.59-6.61 (m, 1H), 5.59-5.63 (m, 1H), 2.90-3.11 (m, 2H), 2.55-2.60 (m, 1H), 2.00-2.13 (m, 1H). (TFA salt) |
| 80 | MS (ESI) calcd. for $C_{31}H_{27}N_9O$, 541.23 m/z, found, 542.10 $[M + H]^+$. $^1H$ NMR (300 MHz, DMSO-$d_6$ + $D_2O$) δ (ppm); 9.06-9.12 (m, 1H), 8.95-9.00 (m, 1H), 8.33-8.40 (m, 2H), 8.15-8.22 (m, 1H), 8.00-8.06 (m, 1H), 7.92-7.98 (m, 1H), 7.79-7.82 (m, 1H), 7.33-7.43 (m, 3H), 7.22-7.33 (m, 2H), 6.52-6.56 (m, 1H), 6.42-6.48 (m, 1H), 5.56-5.71 (m, 1H), 2.95-3.08 (m, 2H), 2.80-2.88 (m, 2H), 2.53-2.60 (m, 1H), 1.98-2.18 (m, 1H), 1.20-1.30 (m, 3H). (formic acid salt) |
| 85 | MS (ESI) calcd. for $C_{32}H_{30}N_{10}O$, 570.26 m/z, found, 571.20 $[M + H]^+$. $^1H$-NMR (300 MHz, DMSO-$d_6$ + $D_2O$) δ (ppm); 9.12-9.18 (m, 1H), 8.34-8.48 (m, 3H), 8.06-8.12 (m, 1H), 8.01-8.05 (m, 1H), 7.83-7.88 (m, 1H), 7.71-7.80 (m, 1H), 7.60-7.70 (m, 1H), 7.46-7.50 (m, 1H), 7.42-7.45 (m, 1H), 7.35-7.39 (m, 1H), 6.80-6.85 (m, 1H), 6.53-6.62 (m, 1H), 5.60-5.70 (m, 1H), 4.54 (s, 2H), 3.07-3.11 (m, 1H), 2.90-3.00 (m, 1H), 2.83 (s, 6H), 2.58-2.62 (m, 1H), 2.05-2.20 (m, 1H). (TFA salt) |
| 86 | MS (ESI) calcd. for $C_{31}H_{27}N_9O$, 541.23 m/z found 542.05 $[M + H]^+$. $^1H$ NMR (300 MHz, DMSO-$d_6$) δ (ppm); 8.52-8.60 (m, 1H), 8.30-8.40 (m, 2H), 8.00-8.05 (m, 1H), 7.90-8.00 (m, 1H), 7.80-7.83 (m, 1H), 7.75-7.80 (m, 1H), 7.40-7.48 (m, 1H), 7.35-7.40 (m, 1H), 7.20-7.35 (m, 3H), 6.52-6.60 (m, 1H), 6.38-6.50 (m, 1H), 5.50-5.68 (m, 1H), 2.98-3.08 (m, 1H), 2.82-2.98 (m, 3H), 2.52-2.62 (m, 1H), 1.91-2.10 (m, 1H), 1.15-1.25 (m, 3H). (formic acid salt) |
| 90 | MS (ESI) calcd. for $C_{32}H_{25}N_{11}O$, 579.22 m/z, found 580.10 $[M + H]^+$. $^1H$ NMR (300 MHz, DMSO-$d_6$) δ (ppm); 8.52-8.60 (m, 1H), 8.40-8.50 (m, 2H), 8.32-8.40 (m, 1H), 7.95-8.10 (m, 3H), 7.82-7.90 (m, 1H), 7.75-7.82 (m, 1H), 7.65-7.75 (m, 2H), 7.46-7.58 (m, 1H), 7.32-7.46 (m, 2H), 6.75-6.90 (m, 1H), 6.49-6.65 (m, 2H), 5.42-5.58 (m, 1H), 2.85-3.15 (m, 2H), 2.45-2.50 (m, 1H), 1.90-2.10 (m, 1H). (TFA salt) |
| 92 | MS (ESI) calcd. for $C_{29}H_{25}N_{11}O$, 543.22 m/z, found, 544.10 $[M + H]^+$. $^1H$ NMR (300 MHz, DMSO-$d_6$) δ (ppm); 8.66 (s, 1H), 8.50-8.53 (m, 1H), 8.15-8.19 (m, 2H), 8.11-8.13 (m, 1H), 8.05-8.10 (m, 1H), 7.85-7.88 (m, 1H), 7.51-7.53 (m, 1H), 7.47-7.50 (m, 1H), 7.38-7.42 (m, 1H), 6.80-6.90 (m, 1H), 5.59-5.64 (m, 1H), 2.90-3.10 (m, 2H), 2.61 (s, 3H), 2.58-2.60 (m, 4H), 1.94-2.09 (m, 1H). (TFA salt) |

TABLE 3-continued

| Cpd ID | Characterization Data |
|---|---|
| | Characterization data of compounds prepared analogously to compound 3. |
| 93 | MS (ESI) calcd. for $C_{29}H_{24}N_{10}O$, 528.21 m/z, found, 529.10 [M + H]$^+$. $^1$H NMR (300 MHz, DMSO-$d_6$) δ (ppm); 9.01-9.08 (m, 1H), 8.46-8.52 (m, 1H), 8.40-8.43 (m, 1H), 8.07-8.12 (m, 2H), 8.04-8.07 (m, 1H), 7.95-8.04 (m, 1H), 7.77-7.82 (m, 1H), 7.46-7.51 (m, 1H), 7.38-7.42 (m, 1H), 7.29-7.35 (m, 3H), 6.44-6.50 (m, 1H), 5.57-5.65 (m, 1H), 2.80-3.09 (m, 2H), 2.55-2.58 (m, 4H), 1.95-2.10 (m, 1H). (formic acid salt) |
| 94 | MS (ESI) calcd. for $C_{32}H_{27}N_9O$, 553.63 m/z, found 554.15 [M + H]$^+$. $^1$H NMR (400 MHz, DMSO-$d_6$) δ (ppm); 8.70-8.95 (m, 1H), 8.20-8.55 (m, 2H), 8.10-8.15 (m, 1H), 8.00-8.10 (m, 1H), 7.90-8.00 (m, 1H), 7.80-7.90 (m, 1H), 7.35-7.45 (m, 2H), 7.25-7.35 (m, 2H), 6.55-6.65 (m, 1H), 6.45-6.55 (m, 1H), 5.50-5.85 (m, 1H), 2.85-3.18 (m, 6H), 2.55-2.65 (m, 1H), 2.00-2.25 (m, 3H). (formic acid salt) |
| 95 | MS (ESI) calcd. for $C_{33}H_{30}N_{10}O_2$, 598.26 m/z, found 599.15 [M + H]$^+$. $^1$H NMR (300 MHz, DMSO-$d_6$) δ (ppm); 8.58-8.90 (m, 2H), 8.30-8.40 (m, 2H), 7.89-8.22 (m, 3H), 7.70-7.85 (m, 1H), 7.25-7.40 (m, 4H), 6.80-6.96 (m, 1H), 6.55-6.60 (m, 1H), 6.42-6.50 (m, 1H), 5.50-5.70 (m, 1H), 3.68-3.70 (m, 5H), 3.52-3.55 (m, 3H), 2.85-3.08 (m, 2H), 2.55-2.62 (m, 1H), 1.90-2.25 (m, 1H). |
| 96 | MS (ESI) calcd. for $C_{30}H_{26}N_{10}O$, 542.23 m/z, found 543.15 [M + H]$^+$. $^1$H NMR (300 MHz, DMSO-$d_6$) δ (ppm); 8.66 (s, 1H), 8.49 (s, 1H), 8.38-8.39 (m, 1H), 8.04-8.05 (m, 1H), 8.01-8.03 (m, 1H), 7.80-7.83 (m, 2H), 7.48-7.52 (m, 2H), 7.36-7.39 (m, 1H), 6.84-6.86 (m, 1H), 6.57-6.59 (m, 1H), 5.54-5.59 (m, 1H), 2.85-3.10 (m, 2H), 2.60 (s, 3H), 2.55 (s, 3H), 2.52-2.53 (m, 1H), 2.05-2.20 (m, 1H). (TFA salt) |
| 98 | MS (ESI) calcd. for $C_{30}H_{24}FN_9O$, 545.21 m/z, found 546.25 [M + H]$^+$. $^1$H NMR (300 MHz, DMSO-$d_6$) δ (ppm); 8.98-9.13 (m, 1H), 8.26-8.47 (m, 3H), 7.99-8.10 (m, 1H), 7.90-7.98 (m, 1H), 7.75-7.87 (m, 1H), 7.56-7.70 (m, 1H), 7.34-7.46 (m, 2H), 7.18-7.33 (m, 2H), 6.53-6.61 (m, 1H), 6.38-6.52 (m, 1H), 5.58-5.72 (m, 2H), 5.46 (s, 1H), 2.83-3.18 (m, 2H), 2.55-2.64 (m, 1H), 2.00-2.20 (m, 1H). $^{19}$F NMR (282 MHz, DMSO-$d_6$) δ (ppm); −217.94. |
| 99 | MS (ESI) calcd. for $C_{28}H_{23}N_9OS$ 533.17 m/z, found, 534.10 [M + H]$^+$. $^1$H NMR (400 MHz, DMSO-$d_6$) δ (ppm); 9.07 (s, 1H), 8.44-8.51 (m, 1H), 8.38-8.42 (m, 1H), 8.08-8.12 (m, 1H), 8.01-8.06 (m, 1H), 7.84-7.90 (m, 2H), 7.46-7.52 (m, 1H), 7.40-7.43 (m, 1H), 7.35-7.39 (m, 1H), 6.82-6.91 (m, 1H), 6.56-6.61 (m, 1H), 5.55 (s, 1H), 3.01-3.12 (m, 1H), 2.85-2.98 (m, 1H), 2.60-2.65 (m, 3H), 2.49-2.52 (m, 1H), 2.01-2.15 (m, 1H). |
| 100 | MS (ESI) calcd. for $C_{31}H_{27}N_9O$, 541.23 m/z, found 542.10 [M + H]$^+$. $^1$H NMR (300 MHz, DMSO-$d_6$ + $D_2O$) δ (ppm); 8.46-8.53 (m, 1H), 8.32-8.39 (m, 1H), 7.98-8.09 (m, 1H), 7.78-7.85 (m, 3H), 7.21-7.52 (m, 5H), 6.53-6.60 (m, 1H), 6.45-6.51 (m, 1H), 5.51-5.62 (m, 1H), 2.88-3.09 (m, 2H), 2.72-2.81 (m, 3H), 2.49-2.58 (m, 3H), 2.59-2.62 (m, 1H), 1.98-2.16 (m, 1H). |
| 101 | MS (ESI) calcd. for $C_{31}H_{25}F_2N_9O$, 577.22 m/z, found, 578.10[M + H]$^+$. $^1$H NMR (300 MHz, DMSO-$d_6$) δ (ppm); 9.08-9.15 (m, 1H), 8.38-8.47 (m, 1H), 8.28-8.35 (m, 1H), 7.94-8.03 (m, 1H), 7.81-7.89 (m, 1H), 7.74-7.81 (m, 2H), 7.32-7.37 (m, 1H), 7.38-7.43 (m, 1H), 7.20-7.31 (m, 2H), 6.79-7.20 (m, 1H), 6.50-6.56 (m, 1H), 6.39-6.49 (m, 1H), 5.57-5.68 (m, 1H), 2.99-3.10 (m, 1H), 2.82-2.98 (m, 1H), 2.68-2.74 (m, 3H), 2.52-2.62 (m, 1H), 1.98-2.17 (m, 1H). $^{19}$F NMR (282 MHz, DMSO-$d_6$) δ (ppm); −116.01, −116.05. |
| 103 | MS (ESI) calcd. for $C_{32}H_{27}N_9O$, 553.23 m/z, found 554.25 [M + H]$^+$. $^1$H NMR (400 MHz, DMSO-$d_6$) δ (ppm); 8.45 (m, 1H), 8.33-8.39 (m, 2H), 8.01-8.09 (m, 1H), 7.95-7.99 (m, 1H), 7.81-7.89 (m, 1H), 7.71-7.78 (m, 1H), 7.46-7.52 (m, 1H), 7.40-7.44 (m, 1H), 7.25-7.31 (m, 2H), 7.19-7.23 (m, 1H), 6.55-6.66 (m, 1H), 6.44-6.54 (m, 1H), 5.60-5.80 (m, 1H), 3.02-3.10 (m, 1H), 2.91-2.96 (m, 1H), 2.52-2.58 (m, 1H), 2.37-2.48 (m, 1H), 2.01-2.03 (m, 1H), 0.88-1.10 (m, 4H). |
| 104 | MS (ESI) calcd. for $C_{32}H_{30}N_{10}O$, 570.26 m/z, found 571.25 [M + H]$^+$. $^1$H NMR (400 MHz, DMSO-$d_6$) δ (ppm); 8.59-8.60 (m, 1H), 8.29-8.40 (m, 2H), 8.11-8.15 (m, 1H), 8.01-8.06 (m, 1H), 7.95-7.99 (m, 1H), 7.81-7.92 (m, 1H), 7.54-7.65(m, 1H), 7.48-7.50 (m, 1H), 7.42-7.44 (m, 1H), 7.32-7.39 (m, 1H), 7.25-7.28 (m, 1H), 6.55-6.75 (m, 1H), 6.40-6.50 (m, 1H), 5.55-5.68 (m, 1H), 3.70-3.75 (m, 1H), 3.49-3.60 (m, 1H), 2.88-3.09 (m, 2H), 2.61-2.68 (m, 1H), 1.96-2.05 (m, 7H). |
| 105 | MS (ESI) calcd. for $C_{31}H_{23}N_9O$, 537.20 m/z, found 538.25 [M + H]$^+$. $^1$H NMR (400 MHz, DMSO-$d_6$) δ (ppm); 9.20-9.30 (m, 1H), 8.72-8.73 (m, 1H), 8.35-8.37 (m, 2H), 8.05-8.07 (m, 2H), 7.93-7.96 (m, 1H), 7.87-7.89 (m, 1H), 7.79-7.82 (m, 1H), 7.47-7.52 (m, 2H), 7.40-7.46 (m, 1H), 7.35-7.40 (m, 1H), 6.85-6.90 (m, 2H), 6.56-6.57 (m, 1H), 6.43-6.46 (m, 1H), 5.61-5.65 (m, 1H), 4.45 (s, 1H), 3.03-3.05 (m, 1H), 2.94-2.96 (m, 1H), 2.50-2.51 (m, 1H), 2.10-2.12 (m, 1H). |
| 106 | MS (ESI) calcd. for $C_{31}H_{25}N_9O_2$, 555.21 m/z, found 556.10 [M + H]$^+$. $^1$H NMR (300 MHz, DMSO-$d_6$) δ (ppm); 8.91-8.97 (m, 1H), 8.29-8.38 (m, 2H), 8.16-8.21 (m, 1H), 8.02-8.06 (m, 1H), 7.93-8.00 (m, 1H), 7.75-7.82 (m, 1H), 7.34-7.42 (m, 2H), 7.25-7.32 (m, 2H), 6.53-6.57 (m, 1H), 6.39-6.49 (m, 1H), 5.58-5.64 (m, 1H), 5.11 (s, 2H), 4.93 (s, 2H), 2.85-3.15 (m, 2H), 2.51-2.60 (m, 1H), 1.97-2.16 (m, 1H). |
| 107 | MS (ESI) calcd. for $C_{29}H_{22}F_2N_{10}O$, 564.19 m/z, found 565.10 [M + H]$^+$. $^1$H NMR (400 MHz, DMSO-$d_6$) δ (ppm); 9.20-9.35 (m, 1H), 8.70-8.90 (m, 1H), 8.32-8.55 (m, 1H), 8.00-8.15 (m, 5H), 7.62-7.72 (m, 1H), 7.42-7.55 (m, 1H), 7.38-7.42 (m, 1H), 7.25-7.38 (m, 2H), 7.00-7.25 (m, 1H), 6.40-6.51 (m, 1H), 5.50-5.70 (m, 1H), 2.80-3.10 (m, 2H), 2.55-2.65 (m, 1H), 2.00-2.15 (m, 1H). $^{19}$F NMR (300 MHz, DMSO-$d_6$) δ (ppm); −115.30. |
| 108 | MS(ESI) calcd. for $C_{29}H_{22}ClN_9O$, 547.16 m/z, found 548.05 [M + H]$^+$. $^1$H NMR (300 MHz, DMSO-$d_6$ + $D_2O$) δ (ppm); 8.48-8.56 (m, 1H), 8.31-8.43 (m, 2H), 7.99-8.06 (m, 1H), 7.91-7.98 (m, 2H), 7.81-7.90 (m, 1H), 7.49-7.52 (m, 2H), 7.38-7.42 (m, 1H), 7.26-7.37 (m, 2H), 6.61-6.68 (m, 1H), 6.51-6.59 (m, 1H), 5.53-5.66 (m, 1H), 2.94-3.15 (m, 2H), 2.56-2.64 (m, 1H), 1.96-2.08 (m, 1H). |

TABLE 3-continued

Characterization data of compounds prepared analogously to compound 3.

| Cpd ID | Characterization Data |
|---|---|
| 110 | MS(ESI) calcd. for $C_{30}H_{22}F_3N_9O$, 581.19 m/z, found 582.05 [M + H]$^+$. $^1$H NMR (300 MHz, DMSO-$d_6$ + $D_2O$) δ (ppm); 8.78-8.85 (m, 1H), 8.31-8.42 (m, 2H), 8.08-8.13 (m, 1H), 7.99-8.06 (m, 1H), 7.91-7.98 (m, 1H), 7.78-7.86 (m, 2H), 7.49-7.52 (m, 1H), 7.38-7.43 (m, 1H), 7.29-7.37 (m, 2H), 6.58-6.60 (m, 1H), 6.49-6.57 (m, 1H), 5.51-5.60 (m, 1H), 2.92-3.14 (m, 2H), 2.53-2.66 (m, 1H), 1.98-2.06 (m, 1H). $^{19}$F NMR (282 MHz, DMSO-$d_6$ + $D_2O$) δ (ppm); −62.79, −62.84. |
| 112 | MS (ESI) calcd. for $C_{32}H_{28}N_{10}O$, 568.24 m/z, found 569.25 [M + H]$^+$. $^1$H NMR (300 MHz, DMSO-$d_6$) δ (ppm); 8.83 (s, 1H), 8.30-8.39 (m, 2H), 8.09 (s, 1H), 7.92-8.00 (m, 2H), 7.79 (s, 1H), 7.32-7.40 (m, 2H), 7.22-7.28 (m, 2H), 6.41-6.56 (m, 2H), 5.61 (s, 1H), 3.84-3.92 (m, 4H), 2.84-3.05 (m, 2H), 2.38-2.46 (m, 4H), 1.93-2.12 (m, 1H). |
| 113 | MS (ESI) calcd. for $C_{31}H_{23}N_9O$, 537.20 m/z, found 538.15 [M + H]$^+$. $^1$H NMR (300 MHz, DMSO-$d_6$) δ 8.58-8.63 (m, 1H), 8.30-8.40 (m, 2H), 7.88-8.02 (m, 3H), 7.78-7.84 (m, 1H), 7.45-7.55 (m, 2H), 7.38 (s, 1H), 7.19-7.32 (m, 2H), 6.50-6.58 (m, 1H), 6.38-6.46 (m, 1H), 5.35-5.53 (m, 1H), 4.37 (s, 1H), 2.81-3.03 (m, 2H), 2.51-2.63 (m, 1H), 1.94-2.10 (m, 1H) |
| 114 | MS (ESI) calcd. for $C_{29}H_{22}F_2N_{10}O$, 564.19 m/z, found 565.15 [M + H]$^+$. $^1$H NMR (300 MHz, DMSO-$d_6$) δ (ppm); 9.46 (s, 2H), 8.38-8.43 (m, 2H), 8.01-8.09 (m, 2H), 7.79-8.84 (m, 2H), 7.49-7.51 (m, 2H), 7.36-7.39 (m, 1H), 7.01-7.26 (m, 1H), 6.81-6.88 (m, 1H), 6.58-6.59 (m, 1H), 5.62-5.67 (m, 1H), 2.90-3.12 (m, 2H), 2.60-2.65 (m, 1H), 2.05-2.15 (m, 1H). $^{19}$F NMR (282 MHz, DMSO-$d_6$) δ (ppm); −119.00. (TFA salt) |
| 115 | MS (ESI) calcd. for $C_{31}H_{27}N_9O$, 541.23 m/z, found, 542.15 [M + H]$^+$. 1HNMR (400 MHz, DMSO-$d_6$) δ (ppm); 8.83 (s, 1H), 8.40-8.47 (m, 2H), 8.35-8.39 (m, 1H), 7.97-8.02 (m, 2H), 7.79-7.82 (m, 1H), 7.75-7.78 (m, 1H), 7.44-7.47 (m, 1H), 7.38-7.42 (m, 1H), 7.30-7.35 (m, 1H), 6.76-6.81 (m, 1H), 6.53-6.57 (m, 1H), 5.59-5.64 (m, 1H), 3.00-3.10 (m, 1H), 2.89-2.98 (m, 1H), 2.61 (s, 3H), 2.58-2.60 (m, 1H), 2.38 (s, 3H), 2.00-2.09 (m, 1H). (TFA salt) |
| 116 | MS (ESI) calcd. for $C_{29}H_{22}F_2N_{10}O$, 564.19 m/z, found 565.25 [M + H]$^+$. $^1$H NMR (300 MHz, DMSO-$d_6$) δ(ppm); 9.44 (s, 1H), 9.16 (s, 1H), 8.38-8.47 (m, 2H), 7.98-8.11 (m, 2H), 7.78-7.86 (m, 1H), 7.50-7.59 (m, 1H), 7.12-7.49 (m, 4H), 6.49-6.64 (m, 2H), 5.57-5.69 (m, 1H), 2.96-3.14 (m, 2H), 2.61-2.67 (m, 1H), 1.99-2.17 (m, 1H). |
| 117 | MS (ESI) calcd. for $C_{29}H_{24}N_{10}O$, 528.21 m/z, found 529.10 [M + H]$^+$. $^1$H NMR (400 MHz, DMSO-$d_6$) δ (ppm); 9.09 (s, 1H), 8.77-8.80 (m, 1H), 8.32-8.40 (m, 2H), 7.90-8.08 (m, 2H), 7.75-7.85 (m, 1H), 7.46-7.55 (m, 1H), 7.40-7.46 (m, 1H), 7.36-7.40 (m, 1H), 7.28-7.35 (m, 1H), 6.55-6.68 (m, 1H), 6.34-6.55 (m, 1H), 5.50-5.70 (m, 1H), 3.00-3.20 (m, 1H), 2.80-3.00 (m, 1H), 2.59-2.62 (m, 4H), 1.90-2.20 (m, 1H). (formic acid salt) |
| 118 | MS(ESI) calcd. for $C_{29}H_{24}N_{10}O$, 528.21 m/z, found 529.25 [M + H]$^+$. $^1$HNMR (300 MHz, DMSO-$d_6$) δ (ppm); 8.64-8.73 (m, 1H), 8.52-8.60 (m, 1H), 8.36-8.45 (m, 2H), 8.02-8.11 (m, 1H), 7.93-8.01 (m, 1H), 7.78-7.88 (m, 1H), 7.38-7.47 (m, 2H), 7.23-7.32 (m, 2H), 6.55-6.62 (m, 1H), 6.49-6.54 (m, 1H), 5.56-5.68 (m, 1H), 3.03-3.16 (m, 1H), 2.88-3.02 (m, 1H), 2.71-2.80 (m, 3H), 2.57-2.64 (m, 1H), 2.07-2.20 (m, 1H). (formic acid salt) |
| 119 | MS (ESI) calcd. for $C_{29}H_{22}F_2N_{10}O$, 564.19 m/z, found 565.10 [M + H]$^+$. $^1$HNMR (300 MHz, DMSO-$d_6$) δ (ppm); 8.97-8.98 (m, 1H), 8.90 (s, 1H), 8.39-8.46 (m, 2H), 8.01-8.08 (m, 2H), 7.45-7.55 (m, 3H), 7.37-7.43 (m, 2H), 7.34-7.35 (m, 1H), 6.83-6.87 (m, 1H), 6.57-6.58 (m, 1H), 5.61-5.66 (m, 1H), 3.01-3.13 (m, 1H), 2.85-2.95 (m, 1H), 2.54-2.58 (m, 1H), 2.17-2.27 (m, 1H). $^{19}$F NMR (282 MHz, DMSO-$d_6$) δ (ppm); 117.49. (TFA salt) |
| 120 | MS (ESI) calcd. for $C_{28}H_{23}N_9OS$, 533.17 m/z, found 534.05 [M + H]$^+$. $^1$H NMR (300 MHz, DMSO-$d_6$) δ (ppm); 8.30-8.49 (m, 2H), 8.15-8.30 (m, 1H), 8.00-8.15 (m, 1H), 7.90-8.00 (m, 1H), 7.71-7.90 (m, 1H), 7.32-7.45 (m, 2H), 7.22-7.32 (m, 2H), 6.55-6.70 (m, 1H), 6.35-6.55 (m, 1H), 5.42-5.70 (m, 1H), 2.85-3.10 (m, 2H), 2.68 (s, 3H), 2.58-2.60 (m, 1H), 1.90-2.20 (m, 1H). (formic acid salt) |
| 126 | MS (ESI) calcd. for $C_{29}H_{26}N_{10}O$, 530.23 m/z, found, 531.10 [M + H]$^+$. $^1$H NMR (300 MHz, DMSO-$d_6$) δ (ppm); 8.40-8.48 (m, 2H), 8.00-8.08 (m, 2H), 7.84 (s, 1H), 7.76-7.79 (m, 1H), 7.44 (s, 1H), 7.30-7.34 (m, 2H), 6.80-6.84 (m, 1H), 6.56-6.59 (m, 1H), 6.53-6.55 (m, 1H), 5.50-5.57 (m, 1H), 3.77 (s, 3H), 3.00-3.12 (m, 1H), 2.85-2.96 (m, 1H), 2.58-2.60 (m, 1H), 2.28 (s, 3H), 2.03-2.15 (m, 1H). (TFA salt) |
| 127 | MS (ESI) calcd. for $C_{29}H_{22}FN_9O$, 531.19 m/z, found 532.10 [M + H]$^+$. $^1$H NMR (400 MHz, DMSO-$d_6$) δ (ppm); 8.35-8.40 (m, 3H), 8.15-8.28 (m, 1H), 8.00-8.10 (m, 1H), 7.92-8.00 (m, 1H), 7.78-7.90 (m, 1H), 7.35-7.55 (m, 3H), 7.21-7.35 (m, 2H), 6.55-6.62 (m, 1H), 6.42-6.55 (m, 1H), 5.51-5.65 (m, 1H), 3.00-3.10 (m, 1H), 2.85-3.00 (m, 1H), 2.55-2.65 (m, 1H), 1.95-2.12 (m, 1H). $^{19}$F NMR (300 MHz, DMSO-$d_6$) δ (ppm); −68.42. (formic acid salt) |
| 128 | MS (ESI) calcd. for $C_{30}H_{25}N_9O_2$ 543.21 m/z, found, 544.10 [M + H]$^+$. $^1$H NMR (400 MHz, DMSO-$d_6$) δ (ppm); 8.44-8.48 (m, 1H), 8.34-8.44 (m, 1H), 8.28-8.34 (m, 1H), 8.11-8.15 (m, 1H), 8.05-8.09 (m, 1H), 7.99-8.05 (m, 1H), 7.76-7.86 (m, 2H), 7.41-7.51 (m, 2H), 7.33-7.40 (m, 1H), 7.12-7.19 (m, 1H), 6.80-6.90 (m, 1H), 6.55-6.61 (m, 1H), 5.53-5.63 (m, 1H), 3.95 (s, 3H), 2.88-3.11 (m, 2H), 2.53-2.63 (m, 1H), 1.97-2.15 (m, 1H). (TFA salt) |
| 129 | MS (ESI) calcd. for $C_{30}H_{27}N_7O$, 501.23 m/z, found 502.20 [M + H]$^+$. $^1$H NMR (400 MHz, DMSO-$d_6$) δ (ppm); 8.50-8.52 (m, 1H), 8.03-8.05 (m, 1H), 7.97-7.99 (m, 1H), 7.78-7.82 (m, 1H), 7.42-7.53 (m, 1H), 7.26-7.33 (m, 2H), 7.22-7.24 (m, 2H), 7.15-7.18 (m, 1H), 6.40-6.53 (m, 1H), 5.56-5.64 (m, 1H), 2.80-3.03 (m, 1H), 2.84-2.95 (m, 1H), 2.56 (s, 3H), 2.10-2.21 (m, 1H), 1.98-2.02 (m, 1H), 1.23 (s, 1H), 0.88-0.98 (m, 2H), 0.77-0.88 (m, 2H). |

TABLE 3-continued

Characterization data of compounds prepared analogously to compound 3.

| Cpd ID | Characterization Data |
|---|---|
| 130 | MS (ESI) calcd. for $C_{30}H_{25}F_2N_7O$, 537.21 m/z, found 538.25 $[M + H]^+$. $^1H$ NMR (400 MHz, DMSO-$d_6$) δ (ppm); 9.13 (s, 1H), 8.42-8.44 (m, 1H), 8.01-8.15 (m, 1H), 7.97-7.99 (m, 1H), 7.83-7.85 (m, 1H), 7.37-7.41 (m, 1H), 7.28-7.31 (m, 1H), 7.13-7.25 (m, 4H), 6.42-6.55 (m, 1H), 5.62-5.71 (m, 1H), 2.95-3.05 (m, 1H), 2.88-2.92 (m, 1H), 2.51-2.53 (m, 1H), 2.00-2.20 (m, 2H), 0.93-1.05 (m, 2H), 0.80-0.88 (m, 2H). $^{19}F$ NMR (400 MHz, DMSO-$d_6$) δ (ppm); −116.06. |
| 135 | MS (ESI) calcd. for $C_{31}H_{30}N_8O_2$, 546.25 m/z, found 547.30 $[M + H]^+$. $^1H$ NMR (400 MHz, DMSO-$d_6$) δ (ppm); 8.59-8.50 (m, 1H), 7.94-7.99 (m, 2H), 7.77-7.79 (m, 1H), 7.42-7.44 (m, 1H), 7.32-7.33 (m, 1H), 7.20-7.28 (m, 2H), 7.12-7.19 (m, 1H), 6.88-6.90 (m, 1H), 6.40-6.42 (m, 1H), 5.52-5.56 (m, 1H), 3.81-3.83 (m, 4H), 3.38-3.41 (m, 4H), 2.95-3.08 (m, 1H), 2.86-2.88 (m, 1H), 2.54-2.56 (m, 4H), 1.98-2.05 (m, 1H). |
| 136 | MS (ESI) calcd. for $C_{31}H_{28}F_2N_8O_2$, 582.23 m/z, found 583.25 $[M + H]^+$. $^1H$ NMR (400 MHz, DMSO-$d_6$) δ (ppm); 9.13 (m, 1H), 8.43-8.46 (m, 1H), 7.94-8.02 (m, 2H), 7.84-7.86 (m, 1H), 7.37-7.39 (m, 1H), 7.32-7.33 (m, 1H), 7.27-7.30 (m, 1H), 7.21-7.25 (m, 2H), 6.88-6.90 (m, 1H), 6.40-6.43 (m, 1H), 5.60-5.64 (m, 1H), 3.79-3.81 (m, 4H), 3.40-3.41 (m, 4H), 2.91-3.98 (m, 1H), 2.86-2.88 (m, 1H), 2.54-2.55 (m, 1H), 2.05-2.15 (m, 1H). $^{19}F$ NMR (376 MHz, DMSO-$d_6$) δ (ppm); −116.05. |
| 137 | MS (ESI) calcd. for $C_{31}H_{27}N_9O$, 541.23 m/z, found, 542.15 $[M + H]^+$. $^1H$ NMR (300 MHz, DMSO-$d_6$) δ (ppm); 8.58 (s, 1H), 8.43-8.49 (m, 1H), 8.40-8.42 (m, 1H), 8.25-8.27 (m, 1H), 8.01-8.09 (m, 2H), 7.80-7.85 (m, 2H), 7.52-7.54 (m, 1H), 7.49-7.51 (m, 1H), 7.36-7.39 (m, 1H), 6.85-6.88 (m, 1H), 6.57-6.59 (m, 1H), 5.54-5.59 (m, 1H), 2.90-3.15 (m, 2H), 2.69 (s, 3H), 2.52-2.53 (m, 1H), 2.44 (s, 3H), 2.01-2.11 (m, 1H). (TFA salt) |
| 138 | MS (ESI) calcd. for $C_{30}H_{22}F_3N_9O_2$, 597.18 m/z, found 598.10 $[M + H]^+$. $^1H$ NMR (300 MHz, DMSO-$d_6$) δ (ppm); 9.10-9.19 (m, 1H), 8.84-8.90 (m, 1H), 8.32-8.41 (m, 2H), 8.28-8.31 (m, 1H), 8.03-8.10 (m, 1H), 7.97-8.02 (m, 1H), 7.80-7.87 (m, 1H), 7.39-7.51 (m, 2H), 7.27-7.38 (m, 2H), 6.57-6.62 (m, 1H), 6.47-6.56 (m, 1H), 5.61-5.72 (m, 1H), 2.88-3.16 (m, 2H), 2.61-2.68 (m, 1H), 1.99-2.17 (m, 1H). |
| 143 | MS (ESI) calcd. for $C_{29}H_{24}N_{10}O$, 528.21 m/z, found, 529.15 $[M + H]^+$. $^1H$ NMR (300 MHz, DMSO-$d_6$) δ (ppm); 8.96-9.08 (m, 2H), 8.27-8.41 (m, 2H), 7.88-7.98 (m, 2H), 7.69-7.78 (m, 2H), 7.38-7.43 (m, 2H), 7.20-7.30 (m, 1H), 6.72-6.84 (m, 1H), 6.45-6.55 (m, 1H), 5.50-5.60 (m, 1H), 2.94-3.06 (m, 1H), 2.82-2.93 (m, 1H), 2.64 (s, 3H), 2.38-2.45 (m, 1H), 1.95-2.09 (m, 1H). (TFA salt) |
| 144 | MS (ESI) calcd. for $C_{28}H_{24}N_{10}O$, 516.21 m/z, found 517.10 $[M + H]^+$. $^1H$ NMR (300 MHz, DMSO-$d_6$) δ (ppm); 8.85-9.00 (m, 1H), 8.32-8.40 (m, 2H), 8.02-8.10 (m, 1H), 7.95-8.02 (m, 1H), 7.80-7.85 (m, 1H), 7.45-7.50 (m, 1H), 7.33-7.42 (m, 2H), 7.22-7.33 (m, 2H), 6.93 (s, 1H), 6.53-6.58 (m, 1H), 6.40-6.53 (m, 1H), 5.50-5.70 (m, 1H), 4.11 (s, 3H), 2.85-3.15 (m, 2H), 2.46-2.48 (m, 1H), 2.00-2.20 (m, 1H). (formic acid salt) |
| 145 | MS (ESI) calcd. for $C_{38}H_{25}N_7O$, 475.21 m/z, found 476.25 $[M + H]^+$. $^1H$ NMR (400 MHz, DMSO-$d_6$) δ (ppm); 8.69 (s, 1H), 8.04-8.28 (m, 3H), 7.62-7.79 (m, 2H), 7.32-7.50 (m, 4H), 6.82 (s, 1H), 5.57 (s, 1H), 2.85-3.12 (m, 2H), 2.60-2.71 (m, 3H), 2.52-2.53 (m, 1H), 2.49-2.51 (m, 3H), 1.98-2.08 (m, 1H). (TFA salt) |
| 146 | MS (ESI) calcd. for $C_{28}H_{23}F_2N_7O$, 511.19 m/z, found 512.25 $[M + H]^+$. $^1H$ NMR (300 MHz, DMSO-$d_6$) δ (ppm); 9.13 (m, 1H), 8.43-8.46 (m, 1H), 8.14-8.17 (m, 1H), 8.01-8.04 (m, 1H), 7.79-7.87 (m, 2H), 7.42-7.45 (m, 2H), 7.34-7.37 (m, 1H), 7.30-7.33 (m, 1H), 6.80-7.20 (m, 2H), 5.61-5.66 (m, 1H), 3.02-3.14 (m, 1H), 2.86-2.95 (m, 1H), 2.54-2.55 (m, 1H), 2.50 (s, 3H), 2.05-2.15 (m, 1H). (TFA salt) |
| 147 | MS (ESI) calcd. for $C_{30}H_{24}FN_9O$, 545.21 m/z, found, 546.10 $[M + H]^+$. $^1H$ NMR (300 MHz, DMSO-$d_6$) δ (ppm); 8.59-8.69 (m, 1H), 8.32-8.51 (m, 2H), 7.96-8.18 (m, 3H), 7.73-7.89 (m, 2H), 7.50-7.62 (m, 3H), 7.39-7.49 (m, 1H), 6.76-6.87 (m, 1H), 6.53-6.63 (m, 1H), 5.31-5.69 (m, 2H), 3.41-3.62 (m, 1H), 3.04-3.31 (m, 1H), 2.66 (s, 3H). $^{19}F$ NMR (282 MHz, DMSO-$d_6$) δ (ppm); −179.18. (TFA salt) |
| 148 | MS (ESI) calcd. for $C_{30}H_{24}FN_9O$, 545.21 m/z, found, 546.10 $[M + H]^+$. $^1H$ NMR (300 MHz, DMSO-$d_6$) δ (ppm); 8.58-8.73 (m, 1H), 8.27-8.53 (m, 2H), 7.92-8.24 (m, 3H), 7.68-7.91 (m, 2H), 7.29-7.65 (m, 4H), 6.69-6.89 (m, 1H), 6.43-6.65 (m, 1H), 5.68-5.87 (m, 1H), 5.36-5.66 (m, 1H), 3.03-3.46 (m, 2H), 2.69 (s, 3H). $^{19}F$ NMR (282 MHz, DMSO-$d_6$) δ (ppm); −192.55. (TFA salt) |
| 149 | MS (ESI) calcd. for $C_{31}H_{27}N_9O_2$, 557.23 m/z, found 558.25 $[M + H]^+$. $^1H$ NMR (300 MHz, DMSO-$d_6$) δ (ppm); 8.59-8.60 (m, 1H), 8.35-8.37 (m, 2H), 8.01-8.02 (m, 1H), 7.97-8.00 (m, 1H), 7.80-7.95 (m, 1H), 7.78-7.80 (m, 1H), 7.51-7.54 (m, 1H), 7.48-7.51 (m, 1H), 7.44-7.47 (m, 1H), 7.29-7.39 (m, 2H), 6.56-6.57 (m, 1H), 6.46-6.55 (m, 1H), 5.53-7.59 (m, 1H), 4.71-4.75 (m, 1H), 4.40-4.46 (m, 1H), 3.22-3.23 (m, 3H), 2.95-3.10 (m, 2H), 2.50-2.52 (m, 1H), 1.98-2.08 (m, 1H). |
| 150 | MS (ESI) calcd. for $C_{32}H_{29}N_9O$, 555.25 m/z, found 556.30 $[M + H]^+$. $^1H$ NMR (300 MHz, DMSO-$d_6$ + $D_2O$) δ(ppm); 8.36-8.48 (m, 2H), 8.23-8.35 (m, 1H), 7.98-8.07 (m, 2H), 7.82-7.89 (m, 1H), 7.74-7.81 (m, 1H), 7.51-7.60 (m, 1H), 7.42-7.50 (m, 1H), 7.32-7.41 (m, 1H), 6.77-6.89 (m, 1H), 6.59-6.63 (m, 1H), 5.52-5.64 (m, 1H), 2.91-3.15 (m, 2H), 2.71 (s, 3H), 2.52-2.61 (m, 4H), 2.33-2.42 (m, 3H), 2.01-2.17 (m, 1H). (TFA salt) |
| 157 | MS (ESI) calcd. for $C_{29}H_{24}N_{10}O_2$ 544.21 m/z, found, 545.20 $[M + H]^+$. $^1H$ NMR (300 MHz, DMSO-$d_6$) δ (ppm); 8.83-8.90 (m, 1H), 8.74-8.80 (m, 1H), 8.41-8.47 (m, 1H), 8.34-8.40 (m, 1H), 7.97-8.09 (m, 2H), 7.77-7.86 (m, 2H), 7.39-7.49 (m, 2H), 7.30-7.39 (m, 1H), 6.79-6.89 (m, 1H), 6.53-6.61 (m, 1H), 5.50-5.62 (m, 1H), 4.00 (s, 3H), 2.85-3.02 (m, 2H), 2.53-2.61 (m, 1H), 1.98-2.14 (m, 1H). (TFA salt) |

TABLE 3-continued

Characterization data of compounds prepared analogously to compound 3.

| Cpd ID | Characterization Data |
|---|---|
| 158 | MS (ESI) calcd. for $C_{29}H_{26}N_{10}O_2$, 546.22 m/z, found 547.25 $[M + H]^+$. $^1H$ NMR (300 MHz, DMSO-$d_6$) δ (ppm); 8.80-8.90 (m, 1H), 8.32-8.40 (m, 2H), 8.00-8.10 (m, 1H), 7.92-8.00 (m, 1H), 7.81 (s, 1H), 7.35-7.45 (m, 2H), 7.25-7.35 (m, 2H), 6.55-6.60 (m, 1H), 6.40-6.50 (m, 1H), 6.36 (s, 1H), 5.50-5.66 (m, 1H), 3.96 (s, 3H), 3.77 (s, 3H), 2.85-3.15 (m, 2H), 2.45-2.50 (m, 1H), 2.00-2.20 (m, 1H). (formic acid salt) |
| 159 | MS (ESI) calcd. for $C_{30}H_{24}FN_9O$, 545.21 m/z, found 546.25 $[M + H]^+$. $^1H$ NMR (300 MHz, DMSO-$d_6$ + $D_2O$) δ (ppm); 8.51-8.59 (m, 1H), 8.34-8.42 (m, 2H), 8.02-8.09 (m, 1H), 7.95-8.01 (m, 1H), 7.81-7.86 (m, 1H), 7.71-7.80 (m, 1H), 7.51-7.60 (m, 1H), 7.39-7.50 (m, 1H), 7.29-7.38 (m, 2H), 6.57-6.63 (m, 1H), 6.48-6.56 (m, 1H), 5.59-5.66 (m, 1H), 2.92-3.13 (m, 2H), 2.58-2.67 (m, 4H), 1.98-2.14 (m, 1H). $^{19}F$ NMR (282 MHz, DMSO-$d_6$ + $D_2O$) δ (ppm); −131.47. (TFA salt) |
| 160 | MS (ESI) calcd. for $C_{30}H_{23}N_{11}O$, 553.21 m/z, found 554.25 $[M + H]^+$. $^1H$ NMR (300 MHz, DMSO-$d_6$ + $D_2O$) δ (ppm); 9.49-9.56 (m, 1H), 8.97-9.08 (m, 1H), 8.36-8.45 (m, 2H), 8.02-8.09 (m, 2H), 7.95-8.01 (m, 1H), 7.79-7.88 (m, 2H), 7.51-7.58 (m, 1H), 7.41-7.50 (m, 1H), 7.27-7.36 (m, 2H), 6.59-6.68 (m, 1H), 6.47-6.55 (m, 1H), 5.67-5.75 (m, 1H), 2.89-3.15 (m, 2H), 2.56-2.63 (m, 1H), 2.01-2.16 (m, 1H). |
| 161 | MS (ESI) calcd. for $C_{31}H_{24}N_{10}O$, 552.21 m/z, found, 553.10 $[M + H]^+$. $^1H$ NMR (300 MHz, DMSO-$d_6$ + $D_2O$) δ (ppm); 8.79-8.83 (m, 1H), 8.36-8.43 (m, 2H), 8.10-8.18 (m, 2H), 8.02-8.09 (m, 1H), 7.95-8.01 (m, 1H), 7.85-7.88 (m, 1H), 7.71-7.73 (m, 1H), 7.41-7.50 (m, 2H), 7.27-7.36 (m, 2H), 7.15-7.21 (m, 1H), 6.57-6.60 (m, 1H), 6.47-6.55 (m, 1H), 5.67-5.75 (m, 1H), 2.93-3.15 (m, 2H), 2.69-2.80 (m, 1H), 2.01-2.13 (m, 1H). |
| 162 | MS (ESI) calcd. for $C_{30}H_{24}FN_9O_2$561.20 m/z, found, 562.10 $[M + H]^+$. $^1H$ NMR (300 MHz, DMSO-$d_6$) δ (ppm); 8.52-8.56 (m, 1H), 8.31-8.40 (m, 2H), 8.07-8.12 (m, 2H), 7.96-8.00 (m, 1H), 7.80-7.86 (m, 1H), 7.25-7.45 (m, 4H), 6.50-6.62 (m, 2H), 5.55-5.65 (m, 1H), 4.01 (s, 3H), 3.00-3.09 (m, 1H), 2.82-3.00 (m, 1H), 2.59-2.64 (m, 1H), 2.00-2.11 (m, 1H). $^{19}F$ NMR (282 MHz, DMSO-$d_6$) δ (ppm); −139.38. |
| 163 | MS (ESI) calcd. for $C_{31}H_{25}N_{11}O$, 567.22 m/z, found 568.25 $[M + H]^+$. $^1H$ NMR (300 MHz, DMSO-$d_6$ + $D_2O$) δ (ppm); 8.66-8.74 (m, 1H), 8.59-8.65 (m, 1H), 8.32-8.40 (m, 2H), 8.02-8.10 (m, 1H), 7.96-8.01 (m, 1H), 7.83-7.89 (m, 1H), 7.41-7.52 (m, 3H), 7.25-7.36 (m, 2H), 6.58-6.66 (m, 1H), 6.47-6.55 (m, 1H), 5.68-5.75 (m, 1H), 4.16 (s, 3H), 3.04-3.19 (m, 1H), 2.89-3.03 (m, 1H), 2.48-2.53 (m, 1H), 2.19-2.36 (m, 1H). |
| 166 | MS (ESI) calcd. for $C_{29}H_{24}F_2N_{10}O$, 566.21 m/z, found 567.20 $[M + H]^+$. $^1H$ NMR (300 MHz, DMSO-$d_6$) δ (ppm); 8.25-8.40 (m, 2H), 7.90-8.10 (m, 2H), 7.55-7.85 (m, 2H), 7.20-7.40 (m, 4H), 6.72-6.78 (m, 1H), 6.40-6.60 (m, 2H), 5.50-5.65 (m, 1H), 3.03-3.15 (m, 1H), 2.82-2.95 (m, 1H), 2.46 (s, 4H), 2.02-2.25 (m, 1H). $^{19}F$ NMR (282 MHz, DMSO-$d_6$) δ (ppm); −95.13. (formic acid salt) |
| 170 | MS (ESI) calcd. for $C_{28}H_{22}F_2N_{10}O$, 552.19 m/z, found 553.15 $[M + H]^+$. $^1H$ NMR (300 MHz, DMSO-$d_6$) δ (ppm); 8.15-8.60 (m, 3H), 8.00-8.10 (m, 1H), 7.92-8.00 (m, 1H), 7.85-7.90 (m, 1H), 7.70-7.85 (m, 1H), 7.35-7.49 (m, 2H), 7.20-7.32 (m, 2H), 7.02-7.20 (m, 1H), 6.50-6.60 (m, 1H), 6.30-6.50 (m, 1H), 5.50-5.65 (m, 1H), 2.80-3.10 (m, 2H), 2.52-2.60 (m, 1H), 2.00-2.18 (m, 1H). (formic acid salt) |
| 172 | MS (ESI) calcd. for $C_{29}H_{26}N_{10}O$, 530.23 m/z, found 531.30 $[M + H]^+$. $^1H$ NMR (300 MHz, DMSO-$d_6$ + $D_2O$) δ (ppm); 8.32-8.41 (m, 2H), 8.02-8.10 (m, 1H), 7.93-8.01 (m, 1H), 7.75-7.87 (m, 1H), 7.53-7.62 (m, 1H), 7.26-7.42 (m, 4H), 6.59-6.63 (m, 1H), 6.51-6.58 (m, 1H), 5.53-5.62 (m, 1H), 3.84 (s, 3H), 2.99-3.13 (m, 1H), 2.72-2.98 (m, 1H), 2.48-2.54 (m, 1H), 2.23 (s, 3H), 2.06-2.17 (m, 1H). (formic acid salt) |
| 173 | MS (ESI) calcd. for $C_{30}H_{26}N_{10}O$, 542.23 m/z, found 543.20 $[M + H]^+$. $^1H$ NMR (300 MHz, DMSO-$d_6$ + $D_2O$) δ (ppm); 8.32-8.42 (m, 2H), 8.01-8.08 (m, 1H), 7.93-7.99 (m, 1H), 7.81-7.86 (m, 1H), 7.31-7.42 (m, 1H), 7.19-7.30 (m, 3H), 6.52-6.63 (m, 1H), 6.41-6.51 (m, 2H), 5.50-5.64 (m, 1H), 4.03-4.21 (m, 2H), 2.99-3.12 (m, 1H), 2.79-2.98 (m, 3H), 2.54-2.62 (m, 2H), 2.41-2.49 (m, 1H), 2.02-2.24 (m, 1H). |
| 174 | MS (ESI) calcd. for $C_{28}H_{22}F_2N_{10}O$, 552.19 m/z, found 553.10 $[M + H]^+$. $^1H$ NMR (300 MHz, DMSO-$d_6$ + $D_2O$) δ (ppm); 8.93-8.99 (m, 1H), 8.39-8.47 (m, 2H), 8.31-8.38 (m, 1H), 7.68-8.01 (m, 4H), 7.41-7.49 (m, 1H), 7.34-7.40 (m, 1H), 7.28-7.33 (m, 2H), 6.95-7.07 (m, 1H), 6.55-6.62 (m, 1H), 6.48-6.54 (m, 1H), 5.58-5.60 (m, 1H), 2.99-3.15 (m, 1H), 2.78-2.98 (m, 1H), 2.47-2.53 (m, 1H), 2.02-2.23 (m, 1H). $^{19}F$ NMR (282 MHz, DMSO-$d_6$ + $D_2O$) δ (ppm); −94.52. |
| 175 | MS (ESI) calcd. for $C_{31}H_{24}N_{10}O$, 552.21 m/z, found, 553.15 $[M + H]^+$. $^1H$ NMR (300 MHz, DMSO-$d_6$) δ (ppm); 8.63-8.70 (m, 1H), 8.30-8.38 (m, 2H), 7.99-8.03 (m, 1H), 7.92-7.98 (m, 1H), 7.74-7.80 (m, 2H), 7.21-7.40 (m, 5H), 7.05-7.11 (m, 1H), 6.98-7.04 (m, 1H), 6.50-6.57 (m, 1H), 6.41-6.50 (m, 1H), 5.57-5.69 (m, 1H), 3.00-3.13 (m, 1H), 2.80-3.97 (m, 1H), 2.55-2.63 (m, 1H), 2.08-2.25 (m, 1H). |
| 176 | MS (ESI) calcd. for $C_{30}H_{23}N_{11}O$, 553.21 m/z, found, 554.15 $[M + H]^+$. $^1H$ NMR (300 MHz, DMSO-$d_6$) δ (ppm); 8.98-9.12 (m, 1H), 8.59-8.67 (m, 1H), 8.30-8.38 (m, 2H), 7.99-8.03 (m, 1H), 7.88-7.96 (m, 1H), 7.76-7.84 (m, 1H), 7.30-7.41 (m, 2H), 7.21-7.31 (m, 2H), 7.11-7.20 (m, 2H), 6.49-6.57 (m, 1H), 6.40-6.48 (m, 1H), 5.57-5.68 (m, 1H), 3.00-3.13 (m, 1H), 2.85-3.00 (m, 1H), 2.55-2.63 (m, 1H), 2.15-2.25 (m, 1H). |
| 183 | MS(ESI) calcd. for $C_{30}H_{26}N_{10}O$, 542.23 m/z, found 543.30 $[M + H]^+$. $^1H$ NMR (300 MHz, DMSO-$d_6$ + $D_2O$) δ (ppm); 8.55-8.64 (m, 1H), 8.23-8.54 (m, 2H), 7.95-8.22 (m, 2H), 7.68-8.21 (m, 2H), 7.23-7.67 (m, 3H), 6.78-7.00 (m, 1H), 6.44-6.77 (m, 1H), 5.44-5.76 (m, 1H), 2.88-3.14 (m, 2H), 2.73-2.87 (m, 3H), 2.57-2.62 (m, 1H), 2.49-2.51 (m, 3H), 2.07-2.26 (m, 1H). (TFA salt) |
| 184 | MS (ESI) calcd. for $C_{30}H_{25}N_9O$, 527.22 m/z, found, 528.30 $[M + H]^+$. $^1H$ NMR (300 MHz, DMSO-$d_6$ + $D_2O$) δ (ppm); 8.27-8.59 (m, 3H), 7.93-8.22 (m, 2H), 7.64-7.92 (m, 3H), 7.21-7.63 (m, 4H), 6.71-6.99 (m, 1H), 6.41-6.66 (m, 1H), 5.41-5.73 (m, 1H), 2.82-3.14 (m, 2H), 2.58-2.61 (m, 3H), 2.48-2.51 (m, 1H), 2.02-2.24 (m, 1H). (TFA salt) |

TABLE 3-continued

| Cpd ID | Characterization Data |
|---|---|
| | Characterization data of compounds prepared analogously to compound 3. |
| 185 | MS (ESI) calcd. for $C_{29}H_{24}N_{10}O$, 528.21 m/z, found 529.15 $[M + H]^+$. $^1H$ NMR (300 MHz, DMSO-$d_6$ + $D_2O$) δ (ppm); 9.09-9.18 (m, 1H), 8.61-8.70 (m, 1H), 8.37-8.46 (m, 2H), 7.93-8.08 (m, 2H), 7.82-7.89 (m, 1H), 7.24-7.49 (m, 4H), 6.49-6.60 (m, 2H), 5.58-5.60 (m, 1H), 3.07-3.19 (m, 1H), 2.89-3.05 (m, 1H), 2.61 (s, 3H), 2.51-2.58 (m, 1H), 2.12-2.26 (m, 1H). (formic acid salt) |
| 186 | MS (ESI) calcd. for $C_{29}H_{24}N_{10}O$, 528.21 m/z, found, 529.30 $[M + H]^+$. $^1H$ NMR (400 MHz, DMSO-$d_6$) δ (ppm); 9.04 (s, 1H), 8.77 (s, 1H), 8.32-8.38 (m, 2H), 7.94-8.05 (m, 2H), 7.81-7.82 (m, 1H), 7.25-7.41 (m, 4H), 6.41-6.56 (m, 2H), 5.66 (s, 1H), 3.20-3.30 (m, 2H), 2.51-2.59 (m, 3H), 2.45-2.50 (m, 1H), 2.25-2.28 (m, 1H). (formic acid salt) |
| 187 | MS (ESI) calcd. for $C_{30}H_{23}F_2N_9O$: 563.20 m/z, found: 564.30 $[M + H]^+$. $^1H$ NMR (400 MHz, DMSO-$d_6$) δ (ppm): 8.51-8.54 (m, 1H), 8.36-8.39 (m, 2H), 8.01-8.03 (m, 1H), 7.95-7.98 (m, 1H), 7.81-7.84 (m, 2H), 7.50-7.53 (m, 2H), 7.41-7.44 (m, 1H), 7.25-7.33 (m, 2H), 6.85 (s, 1H), 6.55-6.56 (m, 1 H), 6.42-6.46 (m, 1H), 5.96-5.99 (m, 1H), 3.58-3.72 (m, 2H), 2.59-2.65 (m, 3H). |
| 189 | MS (ESI) calcd. for $C_{31}H_{24}N_{10}O_2$, 568.21 m/z, found 569.15 $[M + H]^+$. $^1H$ NMR (300 MHz, DMSO-$d_6$ + $D_2O$) δ (ppm); 8.51-8.56 (m, 1H), 8.42-8.50 (m, 2H), 8.37-8.41 (m, 1H), 8.03-8.10 (m, 1H), 7.96-8.02 (m, 1H), 7.90-7.95 (m, 1H), 7.82-7.90 (m, 1H), 7.39-7.50 (m, 3H), 7.29-7.38 (m, 2H), 6.60-6.67 (m, 1H), 6.51-6.58 (m, 1H), 5.63-5.72 (m, 1H), 2.92-3.11 (m, 2H), 2.58-2.64 (m, 1H), 2.08-2.22 (m, 1H). (formic acid salt) |
| 190 | MS (ESI) calcd. for $C_{30}H_{23}N_{11}O$, 553.21 m/z, found 554.15 $[M + H]^+$. $^1H$-NMR (400 MHz, DMSO-$d_6$) δ (ppm); 8.69-8.72 (m, 1H), 8.30-8.37 (m, 2H), 7.85-8.12 (m, 4H), 7.80-7.85 (m, 1H), 7.28-7.60 (m, 4H), 6.60-6.70 (m, 1H), 6.40-6.55 (m, 1H), 5.58-5.72 (m, 1H), 3.04-3.15 (m, 1H), 2.82-2.99 (m, 1H), 2.51-2.53 (m, 1H), 2.10-2.20 (m, 1H). |
| 191 | MS (ESI) calcd. for $C_{31}H_{23}N_9O_3$ 569.19 m/z, found, 570.10 $[M + H]^+$. $^1H$-NMR (400 MHz, DMSO-$d_6$) δ (ppm); 11.95 (s, 1H), 8.85-8.89 (m, 1H), 8.39-8.43 (m, 2H), 8.05-8.09 (m, 1H), 8.00-8.03 (m, 1H), 7.53-7.90 (m, 6H), 7.41-7.43 (m, 1H), 7.30-7.38 (m, 2H), 7.19-7.21 (m, 1H), 6.69-6.74 (m, 1H), 6.57-6.59 (m, 1H), 5.60-5.66 (m, 1H), 3.01-3.10 (m, 1H), 2.89-2.98 (m, 1H), 2.54-2.57 (m, 1H), 2.05-2.13 (m, 1H). (TFA salt) |
| 192 | MS (ESI) calcd. for $C_{30}H_{23}N_{11}O$, 553.21 m/z, found, 554.25 $[M + H]^+$. $^1H$-NMR (400 MHz, DMSO-$d_6$) δ (ppm); 9.06-9.07 (m, 1H), 8.80-8.81 (m, 1H), 8.37-8.38 (m, 2H), 8.35-8.36 (m, 1H), 7.94-8.03 (m, 2H), 7.81-7.82 (m, 1H), 7.41-7.45 (m, 2H), 7.27-7.33 (m, 2H), 6.53-6.56 (m, 1H), 6.44-6.49 (m, 1H), 5.65-5.70 (m, 1H), 2.91-3.10 (m, 2H), 2.56-2.58 (m, 1H), 2.11-2.16 (m, 1H). |
| 193 | MS (ESI) calcd. for $C_{31}H_{24}N_{10}O$, 552.21 m/z, found 553.20 $[M + H]^+$. $^1H$-NMR (300 MHz, DMSO-$d_6$) δ (ppm); 8.90-9.00 (m, 1H), 8.40-8.48 (m, 1H), 8.32-8.40 (m, 2H), 8.22-8.28 (m, 1H), 8.00-8.05 (m, 1H), 7.90-8.00 (m, 2H), 7.80-7.88 (m, 1H), 7.60-7.70 (m, 1H), 7.35-7.45 (m, 2H), 7.25-7.34 (m, 2H), 6.55-6.60 (m, 1H), 6.40-6.55 (m, 1H), 5.60-5.78 (m, 1H), 2.85-3.15 (m, 2H), 2.58-2.65 (m, 1H), 2.05-2.20 (m, 1H). (formic acid salt) |
| 194 | MS (ESI) calcd. for $C_{32}H_{25}N_9O_2$, 567.21 m/z, found 568.10 $[M + H]^+$. $^1H$ NMR (300 MHz, DMSO-$d_6$ + $D_2O$) δ (ppm); 8.41-8.44 (m, 1H), 8.39-8.40 (m, 1H), 8.05-8.09 (m, 1H), 8.01-8.04 (m, 1H), 7.81-7.87 (m, 3H), 7.65-7.76 (m, 1H), 7.45-7.48 (m, 1H), 7.26-7.44 (m, 2H), 6.87-6.95 (m, 1H), 6.72-6.84 (m, 1H), 6.52-6.59 (m, 1H), 5.54-5.69 (m, 1H), 3.55-3.56 (m, 2H), 3.01-3.15 (m, 1H), 2.82-2.99 (m, 1H), 2.42-2.44 (m, 1H), 2.04-2.22 (m, 1H). (TFA salt) |
| 195 | MS (ESI) calcd. for $C_{31}H_{27}N_9O_3S$, 605.20 m/z, found 606.15 $[M + H]^+$. $^1H$ NMR (300 MHz, DMSO-$d_6$ + $D_2O$) δ (ppm); 8.35-8.44 (m, 2H), 8.02-8.09 (m, 1H), 7.96-8.02 (m, 1H), 7.87-7.95 (m, 2H), 7.79-7.85 (m, 1H), 7.41-7.48 (m, 1H), 7.36-7.40 (m, 1H), 7.24-7.35 (m, 4H), 6.56-6.64 (m, 1H), 6.44-6.54 (m, 1H), 5.65-5.72 (m, 1H), 3.02-3.19 (m, 4H), 2.90-3.01 (m, 1H), 2.50-2.58 (m, 1H), 2.05-2.18 (m, 1H). |
| 196 | MS (ESI) calcd. for $C_{32}H_{27}N_9O_2$, 569.23 m/z, found 570.15 $[M + H]^+$. $^1H$-NMR (300 MHz, DMSO-$d_6$) δ (ppm); 8.75-8.85 (m, 1H), 8.30-8.40 (m, 2H), 8.00-8.05 (m, 1H), 7.95-8.00 (m, 1H), 7.85-7.95 (m, 2H), 7.81 (s, 1H), 7.60-7.72 (m, 2H), 7.30-7.40 (m, 2H), 7.25-7.30 (m, 2H), 6.52-6.60 (m, 1H), 6.40-6.52 (m, 1H), 5.55-5.70 (m, 1H), 2.85-3.15 (m, 2H), 2.45-2.50 (m, 1H), 2.00-2.20 (m, 4H). (formic acid salt) |
| 201 | MS (ESI) calcd. for $C_{32}H_{27}N_9O_2$ 569.23 m/z, found, 570.15 $[M + H]^+$. $^1H$-NMR (400 MHz, DMSO-$d_6$) δ (ppm); 8.32-8.38 (m, 3H), 8.00-8.02 (m, 1H), 7.94-7.97 (m, 1H), 7.81-7.82 (m, 1H), 7.46-7.48 (m, 1H), 7.36-7.40 (m, 2H), 7.25-7.31 (m, 3H), 6.55-6.56 (m, 1H), 6.44-6.48 (m, 1H), 5.58-5.63 (m, 1H), 4.23-4.25 (m, 1H), 2.91-3.08 (m, 2H), 2.50-2.52 (m, 1H), 2.03-2.12 (m, 1H), 0.78-0.81 (m, 2H), 0.66-0.69 (m, 2H). |
| 202 | MS (ESI) calcd. for $C_{30}H_{23}F_2N_9O_2$, 579.19 m/z, found 580.25 $[M + H]^+$. $^1H$ NMR (300 MHz, DMSO-$d_6$ + $D_2O$) δ (ppm); 8.31-8.45 (m, 3H), 7.93-8.06 (m, 2H), 7.74-7.85 (m, 2H), 7.63-7.71 (m, 2H), 7.41-7.49 (m, 3H), 7.29-7.38 (m, 1H), 6.75-6.91 (m, 1H), 6.54-6.62 (m, 1H), 5.52-5.69 (m, 1H), 2.85-3.15 (m, 2H), 2.43-2.52 (m, 1H), 2.01-2.21 (m, 1H). (TFA salt) |
| 203 | MS (ESI) calcd. for $C_{32}H_{29}N_9O_3$ 587.24 m/z, found, 588.15 $[M + H]^+$. $^1H$-NMR (300 MHz, DMSO-$d_6$) δ (ppm); 8.35-8.39 (m, 2H), 8.29-8.32 (m, 1H), 8.01-8.05 (m, 1H), 7.96-8.00 (m, 1H), 7.82-7.85 (m, 1H), 7.39-7.44 (m, 3H), 7.27-7.33 (m, 3H), 6.59-6.61 (m, 1H), 6.47-6.52 (m, 1H), 5.57-5.63 (m, 1H), 4.40-4.43 (m, 2H), 3.69-3.72 (m, 2H), 2.29 (s, 3H), 3.01-3.10 (m, 1H), 2.89-2.98 (m, 1H), 2.54-2.57 (m, 1H), 2.01-2.12 (m, 1H). |
| 204 | MS (ESI) calcd. for $C_{31}H_{27}N_9O$, 541.23 m/z, found 542.15 $[M + H]^+$. $^1H$-NMR (400 MHz, DMSO-$d_6$) δ (ppm); 8.49-8.60 (m, 1H), 8.23-8.37 (m, 2H), 7.85-8.02 (m, 2H), 7.72-7.80 (m, 1H), 7.62-7.70 (m, 1H), 7.52-7.61 (m, 1H), 7.28-7.38 (m, 2H), 7.16-7.27 (m, 2H), 6.48-6.55 (m, 1H), 6.37-6.47 (m, 1H), 5.48-5.62 (m, 1H), 2.94-3.11 (m, 1H), 2.72-2.92 (m, 3H), 2.51-2.53 (m, 1H), 1.92-2.13 (m, 1H), 1.12-1.28 (m, 3H). |

TABLE 3-continued

Characterization data of compounds prepared analogously to compound 3.

| Cpd ID | Characterization Data |
|---|---|
| 205 | MS (ESI) calcd. for $C_{32}H_{30}N_{10}O$, 570.26 m/z, found 571.15 $[M + H]^+$. $^1H$-NMR (400 MHz, DMSO-$d_6$) δ (ppm); 8.55-8.68 (m, 1H), 8.21-8.40 (m, 2H), 7.87-8.03 (m, 2H), 7.72-7.86 (m, 2H), 7.61-7.70 (m, 1H), 7.29-7.40 (m, 2H), 7.18-7.28 (m, 2H), 6.48-6.58 (m, 1H), 6.38-6.47 (m, 1H), 5.50-5.65 (m, 1H), 3.57 (s, 2H), 2.95-3.12 (m, 1H), 2.80-2.94 (m, 1H), 2.51-2.55 (m, 1H), 2.17 (s, 6H), 1.95-2.12 (m, 1H). |
| 207 | MS (ESI) calcd. for $C_{30}H_{26}N_{10}O$, 542.23 m/z, found 543.30 $[M + H]^+$. $^1H$-NMR (300 MHz, DMSO-$d_6$ + $D_2O$) δ (ppm); 8.41-8.47 (m, 3H), 8.00-8.01 (m, 2H), 7.82-7.89 (m, 1H), 7.73-7.82 (m, 1H), 7.45-7.51 (m, 1H), 7.41-7.44 (m, 1H), 7.28-7.40 (m, 1H), 6.79-6.89 (m, 1H), 6.58-6.61 (m, 1H), 5.56-5.68 (m, 1H), 2.97-3.15 (m, 2H), 2.72-2.76 (m, 3H), 2.57-2.68 (m, 1H), 2.47-2.52 (m, 3H), 2.02-2.29 (m, 1H). (TFA salt) |
| 210 | MS (ESI) calcd. for $C_{37}H_{27}N_9O$, 613.23 m/z, found 614.15 $[M + H]^+$. $^1H$-NMR (300 MHz, DMSO-$d_6$) δ (ppm); 9.06-9.20 (m, 1H), 8.60-8.80 (m, 1H), 8.30-8.45 (m, 1H), 8.16-8.30 (m, 1H), 7.90-8.10 (m, 3H), 7.75-7.83 (m, 1H), 7.45-7.60 (m, 4H), 7.35-7.45 (m, 4H), 7.15-7.25 (m, 1H), 7.05-7.15 (m, 1H), 6.92 (s, 2H), 6.50-6.60 (m, 1H), 6.30-6.45 (m, 1H), 5.50-5.70 (m, 1H), 2.80-3.10 (m, 2H), 2.52-2.60 (m, 1H), 1.90-2.15 (m, 1H). (formic acid salt) |
| 211 | MS (ESI) calcd. for $C_{32}H_{25}N_9O$, 551.22 m/z, found 552.15 $[M + H]^+$. $^1H$ NMR (300 MHz, DMSO-$d_6$) δ (ppm); 8.90-9.02 (m, 1H), 8.50-8.65 (m, 1H), 8.25-8.45 (m, 2H), 7.90-8.08 (m, 2H), 7.85-7.90 (m, 1H), 7.70-7.85 (m, 1H), 7.45-7.60 (m, 1H), 7.35-7.45 (m, 2H), 7.30-7.35 (m, 1H), 7.15-7.30 (m, 1H), 6.91 (s, 2H), 6.50-6.58 (m, 1H), 6.30-6.48 (m, 1H), 5.50-5.70 (m, 1H), 2.80-3.15 (m, 2H), 2.50-2.60 (m, 1H), 1.85-2.20 (m, 4H). (formic acid salt) |
| 214 | MS (ESI) calcd. for $C_{29}H_{23}N_{11}O$, 541.21 m/z, found 542.15 $[M + H]^+$. $^1H$ NMR (400 MHz, DMSO-$d_6$ + $D_2O$) δ (ppm); 8.91-9.01 (m, 1H), 8.36-8.44 (m, 2H), 7.97-8.10 (m, 2H), 7.80-7.88 (m, 1H), 7.54-7.60 (m, 1H), 7.23-7.40 (m, 4H), 6.57-6.65 (m, 1H), 6.46-6.52 (m, 1H), 5.58-5.67 (m, 1H), 4.11 (s, 3H), 3.02-3.15 (m, 1H), 2.88-2.99 (m, 1H), 2.47-2.55 (m, 1H), 2.10-2.22 (m, 1H). (formic acid salt) |
| 215 | MS (ESI) calcd. for $C_{30}H_{26}N_{10}O$, 542.23 m/z, found, 543.15 $[M + H]^+$. $^1H$-NMR (400 MHz, DMSO-$d_6$) δ (ppm); 8.26-8.45 (m, 2H), 7.99-8.05 (m, 1H), 7.90-7.98 (m, 1H), 7.75-7.88 (m, 2H), 7.33-7.40 (m, 1H), 7.18-7.32 (m, 3H), 6.66-6.78 (m, 1H), 6.52-6.60 (m, 1H), 6.38-6.51 (m, 1H), 5.46-5.65 (m, 1H), 3.71-3.78 (m, 1H), 2.98-3.12 (m, 1H), 2.78-2.97 (m, 1H), 2.40-2.50 (m, 1H), 2.01-2.25 (m, 1H), 1.05-1.19 (m, 2H), 0.92-1.04 (m, 2H). |
| 216 | MS (ESI) calcd. for $C_{29}H_{26}N_{10}O_2$ 546.22 m/z, found, 547.15 $[M + H]^+$. $^1H$ NMR (300 MHz, DMSO-$d_6$) δ (ppm); 8.27-8.46 (m, 2H), 7.99-8.05 (m, 1H), 7.89-7.98 (m, 1H), 7.80-7.81 (m, 1H), 7.35-7.41 (m, 1H), 7.18-7.33 (m, 3H), 6.52-6.61 (m, 1H), 6.41-6.51 (m, 1H), 6.16 (s, 1H), 5.47-5.64 (m, 1H), 3.81-4.01 (m, 3H), 3.59-3.69 (m, 3H), 2.96-3.12 (m, 1H), 2.78-2.95 (m, 1H), 2.36-2.49 (m, 1H), 2.03-2.23 (m, 1H). (formic acid salt) |
| 223 | MS (ESI) calcd. for $C_{30}H_{24}N_8O_2$ 528.20 m/z, found, 529.15 $[M + H]^+$. $^1H$NMR (300 MHz, DMSO-$d_6$ + $D_2O$) δ (ppm); 8.33-8.73 (m, 1H), 8.32-8.45 (m, 1H), 8.16-8.31 (m, 2H), 8.03-8.15 (m, 1H), 7.83-8.02 (m, 1H), 7.66-7.82 (m, 1H), 7.25-7.59 (m, 5H), 6.53-6.86 (m, 1H), 5.42-5.74 (m, 1H), 2.83-3.11 (m, 2H), 2.58-2.67 (m, 3H), 2.53-2.57 (m, 1H), 1.92-2.27 (m, 1H). (TFA salt) |
| 224 | MS (ESI) calcd. for $C_{32}H_{26}N_{10}O_2$ 568.20 m/z, found, 569.20 $[M + H]^+$. $^1H$ NMR (300 MHz, DMSO-$d_6$) δ (ppm); 8.80 (d, J = 8.4 Hz, 1H), 8.34-8.37 (m, 2H), 7.99-8.02 (m, 1H), 7.93-7.96 (m, 1H), 7.80-7.82 (m, 1H), 7.67-7.71 (m, 2H), 7.33-7.39 (m, 1H), 7.26-7.30 (m, 1H), 7.20-7.26 (m, 2H), 7.04-7.07 (m, 1H), 6.52-6.54 (m, 1H), 6.40-6.44 (m, 1H), 5.60-5.64 (m, 1H), 3.32 (s, 3H), 3.00-3.02 (m, 1H), 2.90-2.98 (m, 1H), 2.50-2.55 (m, 1H), 2.00-2.14 (m, 1H). (formic acid salt) |
| 225 | MS (ESI) calcd. for $C_{31}H_{25}N_9O_2$, 555.21 m/z, found 556.15 $[M + H]^+$. $^1H$ NMR (400 MHz, DMSO-$d_6$ + $D_2O$) δ (ppm); 8.36-8.44 (m, 2H), 7.97-8.10 (m, 3H), 7.80-7.88 (m, 1H), 7.27-7.48 (m, 4H), 7.14-7.20 (m, 1H), 6.42-6.59 (m, 2H), 5.59-5.68 (m, 1H), 4.59-4.63 (m, 2H), 3.46-3.55 (m, 2H), 3.02-3.13 (m, 1H), 2.88-2.99 (m, 1H), 2.57-2.63 (m, 1H), 2.01-2.16 (m, 1H). |
| 229 | MS (ESI) calcd. for $C_{30}H_{24}N_8O_2$ 528.20 m/z, found, 529.15 $[M + H]^+$. $^1H$NMR (300 MHz, DMSO-$d_6$ + $D_2O$) δ (ppm); 8.33-8.73 (m, 1H), 8.32-8.45 (m, 1H), 8.16-8.31 (m, 2H), 8.03-8.15 (m, 1H), 7.83-8.02 (m, 1H), 7.66-7.82 (m, 1H), 7.25-7.59 (m, 5H), 6.53-6.86 (m, 1H), 5.42-5.74 (m, 1H), 2.83-3.11 (m, 2H), 2.58-2.67 (m, 3H), 2.53-2.57 (m, 1H), 1.92-2.27 (m, 1H). (TFA salt) |
| 230 | MS (ESI) calcd. for $C_{32}H_{26}N_{10}O_2$ 582.22 m/z, found, 583.20 $[M + H]^+$. $^1H$ NMR (300 MHz, DMSO-$d_6$) δ (ppm); 8.80 (d, J = 8.4 Hz, 1H), 8.34-8.37 (m, 2H), 7.99-8.02 (m, 1H), 7.93-7.96 (m, 1H), 7.80-7.82 (m, 1H), 7.67-7.71 (m, 2H), 7.33-7.39 (m, 1H), 7.26-7.30 (m, 1H), 7.20-7.26 (m, 2H), 7.04-7.07 (m, 1H), 6.52-6.54 (m, 1H), 6.40-6.44 (m, 1H), 5.60-5.64 (m, 1H), 3.32 (s, 3H), 3.00-3.02 (m, 1H), 2.90-2.98 (m, 1H), 2.50-2.55 (m, 1H), 2.00-2.14 (m, 1H). |
| 231 | MS (ESI) calcd. for $C_{30}H_{26}N_{10}O_3S$, 606.19 m/z, found 607.10 $[M + H]^+$. $^1H$-NMR (400 MHz, DMSO-$d_6$) δ (ppm); 8.69-8.72 (m, 1H), 8.30-8.37 (m, 2H), 8.10-8.22 (m, 1H), 7.85-8.02 (m, 2H), 7.80-7.85 (m, 1H), 7.28-7.60 (m, 4H), 6.88-7.02 (m, 1H), 6.60-6.70 (m, 1H), 6.42-6.50 (m, 1H), 5.48-5.62 (m, 1H), 3.06 (s, 3H), 2.94-3.05 (m, 1H), 2.72-2.92 (m, 1H), 2.51-2.53 (m, 1H), 1.92-2.13 (m, 1H). |
| 232 | MS (ESI) calcd. for $C_{31}H_{26}N_{10}O_2$ 570.22 m/z, found, 571.30 $[M + H]^+$. $^1H$ NMR (300 MHz, DMSO-$d_6$) δ (ppm); 8.80 (s, 1H), 8.30-8.34 (m, 2H), 8.21-8.25 (m, 1H), 8.05-8.07 (m, 1H), 7.95-7.97 (m, 1H), 7.90-7.91 (m, 1H), 7.78-7.80 (m, 1H), 7.29-7.37 (m, 2H), 7.20-7.24 (m, 2H), 6.50-6.53 (m, 1H), 6.40-6.44 (m, 1H), 5.52-5.55 (m, 1H), 2.88-3.00 (m, 2H), 2.50-2.52 (m, 1H), 2.11 (s, 3H), 2.00-2.05 (m, 1H). (formic acid salt) |

TABLE 3-continued

Characterization data of compounds prepared analogously to compound 3.

| Cpd ID | Characterization Data |
|---|---|
| 233 | MS (ESI) calcd. for $C_{31}H_{23}NO_2S$ 585.17 m/z, found, 586.25 $[M + H]^+$. $^1H$ NMR (300 MHz, DMSO-$d_6$ + $D_2O$) δ (ppm); 8.38-8.45 (m, 1H), 8.34-8.36 (m, 1H), 8.09-8.13 (m, 1H), 7.95-7.99 (m, 2H), 7.87-7.91 (m, 1H), 7.83-7.86 (m, 1H), 7.76-7.82 (m, 1H), 7.42-7.46 (m, 1H), 7.36-7.41 (m, 1H), 7.29-7.35 (m, 1H), 7.25-7.28 (m, 1H), 6.81-6.86 (m, 1H), 6.56-6.62 (m, 1H), 5.54-5.62 (m, 1H), 3.01-3.18 (m, 1H), 2.86-3.00 (m, 1H), 2.52-2.65 (m, 1H), 2.03-2.22 (m, 1H). (TFA salt) |
| 235 | MS (ESI) calcd. for $C_{32}H_{27}N_9O$, 553.23 m/z, found 554.15 $[M + H]^+$. $^1H$ NMR (300 MHz, DMSO-$d_6$ + $D_2O$) δ (ppm); 8.36-8.48 (m, 3H), 8.02-8.10 (m, 1H), 7.94-8.01 (m, 1H), 7.79-7.86 (m, 1H), 7.40-7.49 (m, 2H), 7.27-7.38 (m, 3H), 6.54-7.62 (m, 1H), 6.42-6.49 (m, 1H), 5.56-5.63 (m, 1H), 3.11-3.20 (m, 2H), 2.92-3.10 (m, 4H), 2.54-2.63 (m, 1H), 2.01-2.19 (m, 3H). |
| 236 | MS (ESI) calcd. for $C_{30}H_{23}N_{11}O$, 553.21 m/z, found 554.30 $[M + H]^+$. $^1H$ NMR (300 MHz, DMSO-$d_6$ + $D_2O$) δ (ppm); 8.40-8.52 (m, 1H), 8.34-8.39 (m, 2H), 8.25-8.33 (m, 1H), 7.96-8.13 (m, 3H), 7.66-7.95 (m, 3H), 7.54-7.65 (m, 1H), 7.36-7.53 (m, 1H), 7.29-7.35 (m, 1H), 6.73-6.99 (m, 1H), 6.45-6.72 (m, 1H), 5.52-5.81 (m, 1H), 3.06-3.27 (m, 1H), 2.87-3.05 (m, 1H), 2.55-2.69 (m, 1H), 2.15-2.37 (m, 1H). (TFA salt) |
| 237 | MS (ESI) calcd. for $C_{30}H_{23}N_{11}O$, 553.21 m/z, found, 554.15 $[M + H]^+$. $^1H$ NMR (400 MHz, DMSO-$d_6$) δ (ppm); 9.50 (s, 1H), 8.63 (s, 1H), 8.32-8.41 (m, 2H), 8.09-8.21 (m, 1H), 7.98-8.05 (m, 1H), 7.89-7.97 (m, 2H), 7.76-7.83 (m, 1H), 7.43-7.48 (m, 1H), 7.38-7.42 (m, 1H), 7.23-7.34 (m, 2H), 6.53-6.58 (m, 1H), 6.42-6.51 (m, 1H), 5.58-5.71 (m, 1H), 3.00-3.12 (m, 1H), 2.85-2.99 (m, 1H), 2.53-2.65 (m, 1H), 2.02-2.18 (m, 1H). |
| 238 | MS(ESI) calcd. for $C_{30}H_{23}N_{11}O$, 553.21 m/z, found 554.30 $[M + H]^+$. $^1H$ NMR (300 MHz, DMSO-$d_6$ + $D_2O$) δ (ppm); 9.52-9.63 (m, 1H), 8.95-9.05 (m, 1H), 8.43-8.49 (m, 1H), 8.31-8.42 (m, 2H), 7.99-8.12 (m, 2H), 7.81-7.89 (m, 1H), 7.65-7.79 (m, 1H), 7.41-7.55 (m, 2H), 7.31-7.39 (m, 1H), 6.84-6.89 (m, 1H), 6.72-6.83 (m, 1H), 6.55-6.62 (m, 1H), 5.62-5.68 (m, 1H), 2.88-3.15 (m, 2H), 2.53-2.67 (m, 1H), 2.15-2.29 (m, 1H). (TFA salt) |
| 239 | MS (ESI) calcd. for $C_{31}H_{27}N_9O_3S$ 605.20 m/z, found, 606.15 $[M + H]^+$. $^1H$ NMR (300 MHz, DMSO-$d_6$ + $D_2O$) δ (ppm); 8.32-8.41 (m, 3H), 8.20-8.25 (m, 1H), 8.05-8.10 (m, 1H), 7.98-8.01 (m, 1H), 7.92-7.95 (m, 1H), 7.80-7.83 (m, 1H), 7.72-7.78 (m, 1H), 7.60-7.65 (m, 1H), 7.47-7.49 (m, 1H), 7.39-7.45 (m, 1H), 7.30-7.34 (m, 1H), 6.60-6.65 (m, 1H), 6.53-6.57 (m, 1H), 5.62-5.67 (m, 1H), 2.84-3.11 (m, 2H), 2.48-2.53 (m, 1H), 2.40-2.43 (m, 3H), 2.05-2.20 (m, 1H). (TFA salt) |
| 240 | MS (ESI) calcd. for $C_{31}H_{26}N_8O_2$, 542.22 m/z, found 543.15 $[M + H]^+$. $^1H$ NMR (300 MHz, DMSO-$d_6$) δ (ppm); 8.90-9.00 (m, 1H), 8.30-8.45 (m, 2H), 7.90-8.10 (m, 3H), 7.82 (s, 2H), 7.30-7.60 (m, 6H), 6.57 (s, 1H), 6.42-6.50 (m, 1H), 5.60-5.78 (m, 1H), 4.56 (s, 2H), 2.85-3.15 (m, 2H), 2.55-2.60 (m, 1H), 2.05-2.25 (m, 1H). (formic acid salt) |
| 241 | MS (ESI) calcd. for $C_{31}H_{25}FN_8O_2$, 560.21 m/z, found 561.10 $[M + H]^+$. $^1H$ NMR (300 MHz, DMSO-$d_6$) δ (ppm); 8.85-8.95 (m, 1H), 8.30-8.40 (m, 2H), 8.00-8.06 (m, 1H), 7.90-8.00 (m, 1H), 7.75-7.85 (m, 3H), 7.22-7.40 (m, 5H), 6.55-6.60 (m, 1H), 6.45-6.52 (m, 1H), 5.55-5.68 (m, 1H), 3.90 (s, 3H), 2.85-3.10 (m, 2H), 2.55-2.60 (m, 1H), 2.00-2.20 (m, 1H). $^{19}F$ NMR (282 MHz, DMSO-$d_6$) δ (ppm); −135.24. (formic acid salt) |
| 242 | MS (ESI) calcd. for $C_{29}H_{24}N_{10}O_2$, 544.21 m/z, found, 545.30 $[M + H]^+$. $^1H$ NMR (400 MHz, DMSO-$d_6$) δ (ppm); 8.28-8.43 (m, 2H), 7.86-8.10 (m, 2H), 7.71-7.84 (m, 1H), 7.17-7.50 (m, 4H), 6.33-6.62 (m, 2H), 5.88 (s, 1H), 5.42-5.63 (m, 1H), 4.98-5.20 (m, 2H), 4.20-4.46 (m, 2H), 2.95-3.15 (m, 1H), 2.78-2.94 (m, 1H), 2.37-2.48 (m, 1H), 2.00-2.22 (m, 1H). |
| 244 | MS (ESI) calcd. for $C_{30}H_{25}N_9O_2$: 543.21 m/z, found: 544.15 $[M + H]^+$. $^1H$ NMR (300 MHz, DMSO-$d_6$) δ (ppm): 8.62-8.75 (m, 1H), 8.47-8.61 (m, 1H), 8.23-8.39 (m, 1H), 8.06-8.19 (m, 1H), 7.96-8.05 (m, 1H), 7.87-7.95 (m, 1H), 7.36-7.48 (m, 2H), 7.19-7.34 (m, 2H), 6.37-6.53 (m, 1H), 5.53-5.73 (m, 1H), 2.82-3.16 (m, 2H), 2.68-2.81 (m, 3H), 2.55-2.64 (m, 1H), 2.06-2.35 (m, 4H). |
| 255 | MS (ESI) calcd for $C_{31}H_{24}N_{10}O$, 552.21 m/z, found, 553.15 $[M + H]^+$. $^1H$ NMR (400 MHz, DMSO-$d_6$) δ (ppm); 8.59-8.66 (m, 1H), 8.33-8.41 (m, 2H), 8.19-8.26 (m, 1H), 8.05-8.10 (m, 1H), 7.99-8.05 (m, 1H), 7.93-7.99 (m, 1H), 7.80-7.84 (m, 1H), 7.70-7.77 (m, 1H), 7.38-7.46 (m, 3H), 7.27-7.34 (m, 2H), 6.55-6.60 (m, 1H), 6.46-6.53 (m, 1H), 5.62-5.70 (m, 1H), 3.01-3.12 (m, 1H), 2.87-3.00 (m, 1H), 2.55-2.62 (m, 1H), 2.06-2.20 (m, 1H). |
| 256 | MS (ESI) calcd. for $C_{32}H_{27}N_9O_2$ 569.23 m/z, found, 570.15 $[M + H]^+$. $^1H$ NMR (300 MHz, DMSO-$d_6$ + $D_2O$) δ (ppm); 8.43-8.52 (m, 1H), 8.37-8.42 (m, 1H), 8.07-8.13 (m, 1H), 7.98-8.06 (m, 3H), 7.86-7.97 (m, 2H), 7.82-7.86 (m, 1H), 7.76-7.81 (m, 1H), 7.47-7.51 (m, 1H), 7.40-7.46 (m, 1H), 7.32-7.39 (m, 1H), 6.79-6.88 (m, 1H), 6.56-6.62 (m, 1H), 5.60-5.70 (m, 1H), 3.01-3.18 (m, 1H), 2.84-2.99 (m, 1H), 2.84 (s, 3H), 2.45-2.51 (m, 1H), 2.09-2.19 (m, 1H). (TFA salt) |
| 257 | MS (ESI) calcd. for $C_{31}H_{23}F_3N_8O_2$, 596.19 m/z, found 597.15 $[M + H]^+$. $^1H$ NMR (400 MHz, DMSO-$d_6$) δ (ppm); 11.20-11.30 (m, 1H), 8.83-9.05 (m, 1H), 8.35-8.45 (m, 2H), 8.14-8.20 (m, 1H), 8.04-8.11 (m, 2H), 7.98-8.04 (m, 1H), 7.68-7.98 (m, 2H), 7.60-7.67 (m, 1H), 7.40-7.51 (m, 1H), 7.30-7.40 (m, 2H), 7.05-7.16 (m, 1H), 6.68-6.76 (m, 1H), 6.51-6.65 (m, 1H), 5.58-5.70 (m, 1H), 3.00-3.10 (m, 1H), 2.89-2.98 (m, 1H), 2.50-2.58 (m, 1H), 2.02-2.16 (m, 1H). $^{19}F$ NMR (376 MHz, DMSO-$d_6$) δ (ppm); −61.09, −74.07. (TFA salt) |
| 258 | MS (ESI) calcd for $C_{30}H_{23}ClN_8O_2$ 562.16 m/z, found, 563.10 $[M + H]^+$. $^1H$ NMR (300 MHz, DMSO-$d_6$) δ (ppm); 8.70-8.81 (m, 1H), 8.32-8.43 (m, 2H), 7.91-8.07 (m, 3H), 7.78-7.84 (m, 1H), 7.68-7.77 (m, 1H), 7.24-7.43 (m, 4H), 6.91-7.03 (m, 1H), 6.53-6.63 (m, 1H), 6.42-6.53 (m, 1H), 5.53-5.66 (m, 1H), 2.81-3.21 (m, 2H), 2.44-2.50 (m, 1H), 1.99-2.16 (m, 1H). (TFA salt) |

TABLE 3-continued

| Cpd ID | Characterization Data |
|---|---|
| | Characterization data of compounds prepared analogously to compound 3. |
| 259 | MS (ESI) calcd. for $C_{31}H_{23}N_9O_2$, 553.20 m/z, found 554.15 $[M + H]^+$. $^1H$ NMR (500 MHz, DMSO-$d_6$) δ (ppm); 11.57-12.66 (s, 1H), 8.72 (s, 1H), 8.32-8.41 (m, 2H), 8.16 (s, 1H), 8.01-8.06 (m, 1H), 7.95-8.00 (m, 2H), 7.78-7.86 (m, 1H), 7.34-7.42 (m, 2H), 7.28-7.31 (m, 1H), 7.23-7.29 (m, 1H), 6.91 (s, 3H), 6.54-6.58 (m, 1H), 6.40-6.51 (m, 1H), 5.48-5.66 (m, 1H), 2.98-3.06 (m, 1H), 2.85-2.95 (m, 1H), 2.45-2.51 (m, 1H), 1.98-2.15 (m, 1H). |
| 260 | MS (ESI) calcd. for $C_{31}H_{26}N_8O_3$, 558.21 m/z, found 559.15 $[M + H]^+$. $^1H$ NMR (300 MHz, DMSO-$d_6$) δ (ppm); 9.57 (brs, 1H), 8.65-8.74 (m, 1H), 8.32-8.41 (m, 2H), 7.98-8.06 (m, 1H), 7.94-7.98 (m, 1H), 7.78-7.85 (m, 1H), 7.51-7.58 (m, 1H), 7.44-7.51 (m, 1H), 7.38-7.42 (m, 1H), 7.24-7.38 (m, 3H), 6.90-6.95 (m, 2H), 6.80-6.86 (m, 1H), 6.50-6.60 (m, 1H), 6.41-6.49 (m, 1H), 5.50-5.60 (m, 1H), 3.83 (s, 3H), 2.82-3.11 (m, 2H), 2.51-2.61 (m, 1H), 2.01-2.20 (m, 1H). |
| 261 | MS (ESI) calcd. for $C_{31}H_{23}FN_{10}O$, 570.20 m/z, found 571.25 $[M + H]^+$. $^1H$ NMR (300 MHz, DMSO-$d_6$ + $D_2O$) δ (ppm); 8.46-8.51 (m, 1H), 8.35-8.45 (m, 2H), 8.31-8.35 (m, 1H), 8.01-8.09 (m, 2H), 7.72-7.89 (m, 3H), 7.42-7.51 (m, 2H), 7.32-7.41 (m, 1H), 6.82-6.89 (m, 1H), 6.55-6.62 (m, 1H), 5.52-5.81 (m, 1H), 3.02-3.37 (m, 1H), 2.83-3.01 (m, 1H), 2.55-2.63 (m, 1H), 2.08-2.22 (m, 1H). (TFA salt) |
| 262 | MS (ESI) calcd. for $C_{30}H_{22}F_2N_8O$, 548.19 m/z, found, 549.10 $[M + H]^+$. $^1H$ NMR (400 MHz, DMSO-$d_6$) δ (ppm); 8.32-8.42 (m, 2H), 8.00-8.06 (m, 1H), 7.93-8.00 (m, 2H), 7.79-7.88 (m, 2H), 7.52-7.63 (m, 1H), 7.35-7.44 (m, 2H), 7.25-7.33 (m, 2H), 6.54-7.60 (m, 1H), 6.43-6.51 (m, 1H), 5.55-5.66 (m, 1H), 2.99-3.10 (m, 1H), 2.85-2.99 (m, 1H), 2.54-2.61 (m, 1H), 2.01-2.16 (m, 1H). (TFA salt) |
| 263 | MS (ESI) calcd. for $C_{30}H_{23}ClN_8O$, 546.17 m/z, found, 547.10 $[M + H]^+$. $^1H$ NMR (400 MHz, DMSO-$d_6$) δ (ppm); 8.29-8.43 (m, 2H), 7.99-8.07 (m, 1H), 7.89-7.98 (m, 3H), 7.77 (s, 1H), 7.52-7.61 (m, 2H), 7.33-7.43 (m, 2H), 7.22-7.32 (m, 2H), 6.51-6.59 (m, 1H), 6.42-6.48 (m, 1H), 5.57-5.69 (m, 1H), 2.97-3.09 (m, 1H), 2.83-2.96 (m, 1H), 2.53-2.58 (m, 1H), 2.01-2.17 (m, 1H). |
| 264 | MS (ESI) calcd. for $C_{29}H_{22}FN_9O$, 531.19 m/z, found, 532.10 $[M + H]^+$. $^1H$ NMR (400 MHz, DMSO-$d_6$) δ (ppm); 8.76-8.80 (m, 1H), 8.43-8.51 (m, 1H), 8.34-8.40 (m, 2H), 8.00-8.34 (m, 1H), 7.93-7.99 (m, 1H), 7.79-7.84 (m, 1H), 7.39-7.45 (m, 2H), 7.27-7.35 (m, 3H), 6.54-6.59 (m, 1H), 6.44-6.50 (m, 1H), 5.60-5.68 (m, 1H), 3.00-3.10 (m, 1H), 2.87-2.99 (m, 1H), 2.54-2.62 (m, 1H), 2.03-2.15 (m, 1H). |
| 266 | MS (ESI) calcd. for $C_{29}H_{24}F_2N_{10}O$, 566.21 m/z, found 567.10 $[M + H]^+$. $^1H$ NMR (300 MHz, DMSO-$d_6$ + $D_2O$) δ(ppm); 8.32-8.41 (m, 2H), 8.02-8.10 (m, 1H), 7.94-8.01 (m, 1H), 7.78-7.84 (m, 1H), 7.28-7.49 (m, 5H), 7.03-7.12 (m, 1H), 6.57-6.62 (m, 1H), 6.47-6.53 (m, 1H), 5.59-5.67 (m, 1H), 3.98 (s, 3H), 3.03-3.17 (m, 1H), 2.84-2.99 (m, 1H), 2.45-2.51 (m, 1H), 2.11-2.27 (m, 1H). $^{19}F$ NMR (282 MHz, DMSO-$d_6$ + $D_2O$) δ (ppm); −113.93. |
| 267 | MS (ESI) calcd. for $C_{31}H_{26}N_8O_2$, 542.22 m/z, found, 543.20 $[M + H]^+$. $^1H$ NMR (400 MHz, DMSO-$d_6$) δ (ppm); 9.05 (s, 1H), 8.42-8.46 (m, 2H), 8.10-8.17 (m, 1H), 8.03-8.09 (m, 1H), 7.94-7.98 (m, 1H), 7.74-7.85 (m, 1H), 7.64-7.72 (m, 1H), 7.40-7.59 (m, 3H), 6.78-6.81 (m, 1H), 5.63-5.68 (m, 1H), 2.99-3.12 (m, 1H), 2.83-2.98 (m, 1H), 2.51-2.59 (m, 4H), 2.22-2.30 (m, 3H), 2.03-2.11 (m, 1H). |
| 268 | MS (ESI) calcd. for $C_{30}H_{26}N_{10}O$, 542.23 m/z, found, 543.15 $[M + H]^+$. $^1H$ NMR (400 MHz, DMSO-$d_6$) δ (ppm); 8.91-8.94 (m, 1H), 8.22-8.31 (m, 1H), 8.12-8.21 (m, 1H), 8.06 (s, 1H), 7.97-8.03 (m, 1H), 7.89-7.95 (m, 1H), 7.33-7.43 (m, 3H), 7.21-7.31 (m, 2H), 6.39-6.51 (m, 1H), 5.58-5.69 (m, 1H), 4.21 (s, 3H), 2.99-3.11 (m, 1H), 2.84-2.98 (m, 1H), 2.56-2.61 (m, 1H), 2.49-2.55 (m, 3H), 1.99-2.17 (m, 1H). |
| 269 | MS (ESI) calcd. for $C_{37}H_{36}N_{10}O$, 636.31 m/z, found 637.35 $[M + H]^+$. $^1H$ NMR (300 MHz, DMSO-$d_6$ + $D_2O$) δ (ppm); 8.63-8.71 (m, 1H), 8.48-8.54 (m, 1H), 8.17-8.23 (m, 1H), 7.94-8.10 (m, 2H), 7.60-7.69 (m, 1H), 7.23-7.50 (m, 6H), 6.95-7.02 (m, 1H), 6.46-6.53 (m, 1H), 5.58-5.67 (m, 1H), 3.12-3.24 (m, 4H), 2.84-3.05 (m, 2H), 2.74 (s, 3H), 2.57-2.63 (m, 2H), 2.45-2.51 (m, 3H), 2.21 (s, 3H), 2.07-2.18 (m, 1H). (formic acid salt) |
| 270 | MS (ESI) calcd. for $C_{29}H_{23}N_9O_2$: 529.20 m/z, found, 530.30 $[M + H]^+$. $^1H$ NMR (300 MHz, DMSO-$d_6$ + $D_2O$) δ (ppm); 8.66-8.73 (m, 1H), 8.49-8.56 (m, 1H), 8.28-8.39 (m, 1H), 8.20-8.28 (m, 1H), 8.11-8.19 (m, 1H), 7.98-8.07 (m, 1H), 7.38-7.49 (m, 3H), 7.23-7.37 (m, 2H), 6.46-6.52 (m, 1H), 5.60-5.71 (m, 1H), 2.86-3.15 (m, 2H), 2.78 (s, 3H), 2.53-2.60 (m, 1H), 2.09-2.20 (m, 1H). |
| 271 | MS (ESI) calcd. for $C_{29}H_{25}N_{11}O$, 543.22 m/z, found, 544.35 $[M + H]^+$. $^1H$ NMR (400 MHz, DMSO-$d_6$) δ (ppm); 8.60-8.70 (m, 1H), 8.46-8.58 (m, 1H), 8.18-8.30 (m, 1H), 8.08 (s, 1H), 7.85-8.05 (m, 2H), 7.32-7.48 (m, 2H), 7.18-7.31 (m, 2H), 6.40-6.58 (m, 1H), 5.48-5.68 (m, 1H), 4.20 (s, 3H), 2.99-3.12 (m, 1H), 2.83-2.99 (m, 1H), 2.75 (s, 3H), 2.55-2.61 (m, 1H), 2.00-2.21 (m, 1H). |
| 275 | MS (ESI) calcd for $C_{35}H_{33}N_9O$, 595.28. found, 596.20 $[M + H]^+$. $^1H$ NMR (300 MHz, DMSO-$d_6$) δ8.38-8.36 (m, 2H), 8.33-8.01 (m, 1H), 7.88-7.82 (m, 1H), 7.81-7.75 (m, 1H), 7.65-7.62 (m, 1H), 7.45 (m, 3H), 7.42-7.32 (m, 3H), 7.31-7.29 (m, 2H), 6.63 (m, 1H), 6.58-6.57 (m, 1H), 4.69 (m, 1H), 4.61-4.42 (m, 1H), 3.95-3.93 (m, 1H), 3.65-3.59 (m, 1H), 3.39-3.25 (m, 1H), 3.23-3.09 (m, 2H), 2.92-2.80 (m, 2H), 2.43-2.02 (m, 3H), 1.46 (m, 2H). |
| 278 | MS (ESI) calcd. for $C_{31}H_{33}N_9O$, 547.28 m/z, found, 548.35 $[M + H]^+$. $^1H$-NMR (400 MHz, DMSO-$d_6$) δ (ppm); 8.34-8.35 (m, 2H), 8.00-8.01 (m, 1H), 7.94-7.96 (m, 1H), 7.80-7.81 (m, 1H), 7.48-7.50 (m, 1H), 7.31-7.33 (m, 1H), 7.23-7.25 (m, 2H), 6.54-6.56 (m, 1H), 6.42-6.45 (m, 1H), 4.31-4.35 (m, 1H), 4.23-4.30 (m, 1H), 3.81-3.86 (m, 1H), 3.01-3.08 (m, 1H), 2.93-2.98 (m, 2H), 2.71-2.77 (m, 2H), 2.41-2.46 (m, 1H), 2.28-2.32 (m, 2H), 1.71-1.96 (m, 3H), 1.14-1.32 (m, 2H), 0.95-1.03 (m, 3H). |

TABLE 3-continued

| Cpd ID | Characterization Data |
|---|---|
| | Characterization data of compounds prepared analogously to compound 3. |
| 280 | MS (ESI) calcd. for $C_{31}H_{27}N_9O_2$, 557.23 m/z, found 558.20 $[M + H]^+$. $^1H$ NMR (400 MHz, DMSO-$d_6$) δ (ppm); 9.06 (d, J = 8.0 Hz, 1H), 8.33-8.40 (m, 2H), 8.00-8.03 (m, 1H), 7.95 (d, J = 8.0 Hz, 1H), 7.81 (d, J = 1.6 Hz, 1H), 7.39-7.42 (m, 1H), 7.35-7.37 (m, 1H), 7.30-7.32 (m, 2H), 7.25-7.29 (m, 1H), 7.07 (s, 1H), 6.90 (s, 2H), 6.54-6.56 (m, 1H), 6.43-6.46 (m, 1H), 5.62 (q, J = 8.0 Hz, 1H), 3.87 (s, 3H), 3.00-3.09 (m, 1H), 2.87-2.98 (m, 1H), 2.52-2.58 (m, 1H), 2.45 (s, 3H), 2.01-2.15 (m, 1H). |
| 281 | MS(ESI) calcd. for $C_{30}H_{24}ClN_9O_2$ 577.17 m/z, found 578.15 $[M + H]^+$. $^1H$ NMR (400 MHz, DMSO-$d_6$) δ (ppm); 9.12 (d, J = 8.4 Hz, 1H), 8.34-8.39 (m, 2H), 8.19 (d, J = 4.8 Hz, 1H), 8.00-8.03 (m, 1H), 7.95 (d, J = 8.8 Hz, 1H), 7.80-7.82 (m, 1H), 7.49 (d, J = 8.0 Hz, 1H), 7.41 (d, J = 2.0 Hz, 1H), 7.30-7.34 (m, 1H), 7.22-7.27 (m, 1H), 7.14 (d, J = 5.2 Hz, 1H), 6.93 (s, 2H), 6.54 (t, J = 2.0 Hz, 1H), 6.40-6.46 (m, 1H), 5.57 (q, J = 8.1 Hz, 1H), 3.97 (s, 3H), 2.98-3.05 (m, 1H), 2.87-2.95 (m, 1H), 2.52-2.58 (m, 1H), 1.95-2.05 (m, 1H). |
| 282 | MS(ESI) calcd. for $C_{31}H_{23}N_9O_2$, 553.20 m/z, found 554.20 $[M + H]^+$. $^1H$ NMR (400 MHz, DMSO-$d_6$) δ (ppm); 9.28 (d, J = 8.3 Hz, 1H), 8.45 (d, J = 5.1 Hz, 1H), 8.35-8.38 (m, 2H), 8.24 (d, J = 2.5 Hz, 1H), 8.02-8.03 (m, 1H), 7.96 (d, J = 8.6 Hz, 1H), 7.78-7.82 (m, 2H), 7.43-7.46 (m, 2H), 7.33-7.35 (m, 2H), 7.27-7.32 (m, 1H), 6.91 (s, 2H), 6.56 (t, J = 2.1 Hz, 1H), 6.44-6.47 (m, 1H), 5.71 (q, J = 8.2 Hz, 1H), 3.04-3.10 (m, 1H), 2.91-2.99 (m, 1H), 2.55-2.62 (m, 1H), 2.11-2.19 (m, 1H). |
| 283 | MS(ESI) calcd. for $C_{31}H_{27}N_9O_3$, 573.22 m/z, found 574.20 $[M + H]^+$. $^1H$ NMR (400 MHz, DMSO-$d_6$) δ (ppm); 9.05 (d, J = 8.2 Hz, 1H), 8.36-8.38 (m, 2H), 8.01-8.03 (m, 1H), 7.96 (d, J = 8.6 Hz, 1H), 7.81 (d, J = 1.7 Hz, 1H), 7.35-7.41 (m, 2H), 7.26-7.32 (m, 2H), 6.90 (s, 2H), 6.85 (s, 2H), 6.55-6.56 (m, 1H), 6.44-6.47 (m, 1H), 5.62 (q, J = 8.2 Hz, 1H), 3.90 (s, 6H), 3.01-3.08 (m, 1H), 2.87-2.96 (m, 1H), 2.52-2.56 (m, 1H), 2.04-2.14 (m, 1H). |
| 284 | MS (ESI) calcd. for $C_{31}H_{27}N_9O_2$, 557.23 m/z, found 558.20 $[M + H]^+$. $^1H$ NMR (400 MHz, DMSO-$d_6$) δ (ppm); 8.93 (d, J = 8.4 Hz,1H), 8.34-8.39 (m, 2H), 8.06 (d, J = 5.2 Hz, 1H), 8.00-8.02 (m, 1H), 7.95 (d, J = 8.4 Hz, 1H), 7.81 (d, J = 1.6 Hz, 1H), 7.45 (d, J = 8.0 Hz, 1H), 7.41 (s, 1H), 7.30-7.34 (m, 1H), 7.23-7.26 (m, 1H), 6.97 (d, J = 5.2 Hz, 1H), 6.93 (s, 2H), 6.54 (t, J = 2.0 Hz, 1H), 6.41-6.44 (m, 1H), 5.58 (q, J = 8.0 Hz, 1H), 3.90 (s, 3H), 2.98-3.05 (m, 1H), 2.86-2.94 (m, 1H), 2.53-2.58 (m, 1H), 2.18 (s, 3H), 1.95-2.07 (m, 1H). |
| 286 | MS(ESI) calcd. for $C_{30}H_{24}N_{10}O_2$, 556.21 m/z, found 557.15 $[M + H]^+$. $^1H$ NMR (400 MHz, DMSO-$d_6$) δ(ppm); 9.03-9.05 (m, 1H), 8.43-8.45 (m, 1H), 8.14 (s, 2H), 8.01-8.04 (m, 3H), 7.34-7.43 (m, 2H), 7.28-7.32 (m, 2H), 7.18-7.20 (m, 1H), 6.93 (s, 2H), 6.43-6.46 (m, 1H), 5.62-5.65 (m, 1H), 4.58-4.62 (m, 2H), 3.47-3.52 (m, 2H), 3.00-3.03 (m, 1H), 2.90-2.96 (m, 1H), 2.50-2.57 (m, 1H), 2.07-2.10 (m, 1H). |
| 288 | MS (ESI) calcd. for $C_{28}H_{21}F_2N_{11}O$, 565.19 m/z, found 566.20 $[M + H]^+$. $^1H$ NMR (400 MHz, DMSO-$d_6$) δ (ppm); 9.48 (d, J = 8.4 Hz, 1H), 9.36 (s, 1H), 9.03 (s, 1H), 8.43 (d, J = 8.4 Hz, 1H), 8.14 (s, 2H), 7.99-8.06 (m, 2H), 7.37-7.44 (m, 2H), 7.21-7.35 (m, 2H), 7.23 (t, J = 52.0 Hz, 1H) 6.94 (s, 2H), 6.45 (dd, J = 7.6, 4.8 Hz, 1H), 5.70 (q, J = 8.0 Hz, 1H), 3.01-3.11 (m, 1H), 2.85-2.98 (m, 1H), 2.52-2.56 (m, 1H), 2.19-2.31 (m, 1H). $^{19}F$ NMR (376 MHz, DMSO-$d_6$) δ (ppm); −117.98. |
| 290 | MS (ESI) calcd. for $C_{31}H_{24}N_{10}O$, 552.21 m/z, found, 553.20 $[M + H]^+$. $^1H$ NMR (400 MHz, DMSO-$d_6$) δ (ppm); 9.31 (s, 1H), 9.02-9.11 (m, 1H), 8.31-8.42 (m, 2H), 8.11-8.22 (m, 1H), 7.92-8.07 (m, 2H), 7.64-7.88 (m, 3H), 7.37-7.51 (m, 2H), 7.21-7.36 (m, 2H), 6.65-6.79 (m, 1H), 6.52-6.61 (m, 1H), 6.41-6.51 (m, 1H), 5.58-5.74 (m, 1H), 3.00-3.13 (m, 1H), 2.86-2.99 (m, 1H), 2.54-2.65 (m, 1H), 2.02-2.37 (m, 1H). (formic acid salt) |
| 291 | MS (ESI) calcd for $C_{31}H_{24}N_{10}O$, 552.21 m/z, found, 553.15 $[M + H]^+$. $^1H$ NMR (400 MHz, DMSO-$d_6$) δ (ppm); 9.18-9.28 (m, 1H), 8.49-8.57 (m, 1H), 8.34-8.45 (m, 2H), 7.96-8.07 (m, 2H), 7.80-7.87 (m, 1H), 7.59-7.66 (m, 1H), 7.49-7.57 (m, 1H), 7.39-7.49 (m, 2H), 7.29-7.38 (m, 1H), 7.07-7.15 (m, 1H), 6.54-6.71 (m, 3H), 5.59-5.70 (m, 1H), 3.01-3.14 (m, 1H), 2.87-2.99 (m, 1H), 2.58-2.65 (m, 1H), 2.03-2.16 (m, 1H). (formic acid salt) |
| 292 | MS (ESI) calcd. for $C_{32}H_{27}N_9O_2$, 569.23 m/z, found 570.15 $[M + H]^+$. $^1H$ NMR (300 MHz, DMSO-$d_6$) δ (ppm); 9.00-9.12 (m, 1H), 8.50-8.63 (m, 1H), 8.29-8.44 (m, 4H), 8.02-8.13 (m, 3H), 7.91-8.01 (m, 1H), 7.75-7.91 (m, 1H), 7.55-7.65 (m, 1H), 7.22-7.46 (m, 4H), 6.40-6.64 (m, 2H), 5.60-5.72 (m, 1H), 2.90-3.01 (m, 2H), 2.76-2.87 (m, 3H), 2.66-2.70 (m, 1H), 2.03-2.23 (m, 1H). (formic acid salt) |
| 293 | MS (ESI) calcd. for $C_{30}H_{23}FN_8O_2$, 546.19 m/z, found 547.30 $[M + H]^+$. $^1H$ NMR (300 MHz, DMSO-$d_6$) δ (ppm); 8.30-8.43 (m, 2H), 7.89-8.11 (m, 2H), 7.73-7.85 (m, 1H), 7.50-7.61 (m, 1H), 7.36-7.45 (m, 2H), 7.10-7.35 (m, 4H), 6.52-6.65 (m, 1H), 6.38-6.50 (m, 1H), 5.58-5.66 (m, 1H), 2.78-3.18 (m, 2H), 2.40-2.50 (m, 1H), 1.96-2.20 (m, 1H). $^{19}F$ NMR (282 MHz, DMSO-$d_6$) δ (ppm); −132.49. |
| 294 | MS (ESI) calcd. for $C_{33}H_{27}F_2N_9O_4$, 605.21 m/z, found 606.35 $[M + H]^+$. $^1H$ NMR (300 MHz, DMSO-$d_6$) δ (ppm); 9.05-9.20 (m, 1H), 8.30-8.45 (m, 2H), 7.90-8.15 (m, 2H), 7.78-7.85 (m, 1H), 7.60-7.78 (m, 2H), 7.35-7.50 (m, 2H), 7.25-7.35 (m, 2H), 6.40-6.60 (m, 2H), 5.50-5.70 (m, 1H), 2.82-3.15 (m, 2H), 2.55-2.65 (m, 1H), 2.00-2.25 (m, 4H). $^{19}F$ NMR (282 MHz, DMSO-$d_6$) δ (ppm); −116.21. (formic acid salt) |
| 295 | MS (ESI) calcd. for C29H22FN9O, 531.19 m/z, found 532.10 [M + H]+. 1H NMR (300 MHz, DMSO-d6) δ (ppm): 9.24-9.35 (m, 1H), 8.30-8.49 (m, 3H), 7.91-8.07 (m, 2H), 7.73-7.88 (m, 2H), 7.56-7.67 (m, 1H), 7.37-7.46 (m, 2H), 7.24-7.35 (m, 2H), 6.50-6.61 (m, 1H), 6.40-6.50 (m, 1H), 5.59-5.69 (m, 1H), 2.80-3.20 (m, 2H), 2.53-2.63 (m, 1H), 1.98-2.24 (m, 1H). 19F NMR (282 MHz, DMSO-d6) δ (ppm): −67.90. (formic acid salt) |
| 296 | MS (ESI) calcd. for $C_{29}H_{22}FN_9O_2$ 547.18 m/z, found, 548.10 $[M + H]^+$. $^1H$ NMR (400 MHz, DMSO-$d_6$) δ (ppm); 8.29-8.49 (m, 2H), 7.92-8.09 (m, 3H), 7.77-7.91 (m, 2H), 7.21-7.47 (m, 4H), 6.53-6.64 (m, 1H), 6.42-6.52 (m, 1H), 5.49-5.68 (m, 1H), 2.79-3.14 (m, 2H), 2.43-2.51 (m, 1H), 1.94-2.18 (m, 1H). $^{19}F$ NMR (376 MHz, DMSO-$d_6$) δ (ppm); −134.20. |

TABLE 3-continued

Characterization data of compounds prepared analogously to compound 3.

| Cpd ID | Characterization Data |
|---|---|
| 297 | MS (ESI) calcd. for $C_{29}H_{23}N_9O_2$ 529.20 m/z, found, 530.10 [M + H]$^+$. $^1$H-NMR (400 MHz, DMSO-$d_6$) δ (ppm); 8.33-8.40 (m, 2H), 8.05-8.15 (m, 1H), 7.90-8.00 (m, 3H), 7.79-7.83 (m, 1H), 7.20-7.40 (m, 4H), 6.53-6.59 (m, 1H), 6.32-6.50 (m, 2H), 5.50-5.65 (m, 1H), 2.80-3.15 (m, 2H), 2.55-2.60 (m, 1H), 1.90-2.15 (m, 1H). |
| 298 | MS (ESI) calcd. for $C_{29}H_{23}FN_{10}O$, 546.20 m/z, found 547.30 [M + H]$^+$. $^1$H NMR (300 MHz, DMSO-$d_6$ + $D_2O$) δ (ppm); 8.47-8.51 (m, 1H), 8.39-8.46 (m, 2H), 8.10-8.14 (m, 1H), 8.01-8.09 (m, 1H), 7.79-7.91 (m, 3H), 7.44-7.51 (m, 1H), 7.34-7.41 (m, 2H), 6.81-6.91 (m, 1H), 6.55-6.63 (m, 1H), 5.54-5.63 (m, 1H), 2.83-3.12 (m, 2H), 2.57-2.59 (m, 1H), 2.02-2.19 (m, 1H). (TFA salt) |
| 299 | MS (ESI) calcd. for $C_{30}H_{23}F_2N_9O$, 563.20 m/z, found 564.15 [M + H]$^+$. $^1$H NMR (300 MHz, DMSO-$d_6$) δ (ppm); 8.93-8.99 (m, 1H), 8.39-8.43 (m, 2H), 8.13-8.24 (m, 1H), 8.02-8.09 (m, 1H), 7.93-8.02 (m, 1H), 7.83 (s, 1H), 7.71-7.79 (m, 2H), 7.58-7.67 (m, 1H), 7.33-7.47 (m, 2H), 6.49-6.63 (m, 2H), 5.70-5.81 (m, 1H), 3.12-3.31 (m, 1H), 2.66-2.86 (m, 1H), 2.51 (s, 3H). $^{19}$F NMR (376 MHz, DMSO-$d_6$) δ (ppm); −84.70. (formic acid salt) |
| 301 | MS (ESI) calcd. for $C_{30}H_{24}F_2N_{10}O$, 578.21 m/z, found, 579.20 [M + H]$^+$. $^1$H NMR (300 MHz, DMSO-$d_6$ + $D_2O$) δ (ppm); 9.13-9.21 (m, 1H), 8.70-8.73 (m, 1H), 8.53-8.59 (m, 1H), 8.25-8.32 (m, 2H), 7.65-8.11 (m, 3H), 7.39-7.43 (m, 2H), 7.29-7.34 (m, 2H), 6.91-6.97 (m, 1H), 6.49-6.54 (m, 1H), 5.59-5.67 (m, 1H), 2.98-3.09 (m, 1H), 2.88-2.97 (m, 1H), 2.75 (s, 3H), 2.59-2.62 (m, 1H), 2.08-2.19 (m, 1H). $^{19}$H NMR (300 MHz, DMSO-$d_6$ + $D_2O$) δ (ppm); −94.18. (formic acid salt) |
| 306 | MS (ESI) calcd. for $C_{30}H_{23}N_{11}O$, 553.20 m/z, found 554.30 [M + H]$^+$. $^1$H NMR (300 MHz, DMSO-$d_6$ + $D_2O$) δ (ppm); 9.21-9.49 (m, 1H), 8.35-8.51 (m, 3H), 8.01-8.19 (m, 2H), 7.84-7.93 (m, 1H), 7.61-7.83 (m, 2H), 7.31-7.59 (m, 3H), 6.87-6.99 (m, 1H), 6.77-6.87 (m, 1H), 6.52-6.69 (m, 1H), 5.55-5.78 (m, 1H), 3.10-3.21 (m, 1H), 2.82-3.09 (m, 1H), 2.59-2.60 (m, 1H), 2.12-2.37 (m, 1H). (TFA salt) |
| 307 | MS (ESI) calcd. for $C_{30}H_{24}N_8O_2$ 528.20 m/z, found, 529.30 [M + H]$^+$. $^1$H NMR (300 MHz, DMSO-$d_6$ + $D_2O$) δ (ppm); 8.40-8.49 (m, 2H), 8.01-8.09 (m, 2H), 7.77-7.83 (m, 2H), 7.25-7.49 (m, 6H), 6.91-6.99 (m, 1H), 6.79-6.89 (m, 1H), 6.57-6.63 (m, 1H), 5.59-5.64 (m, 1H), 3.02-3.19 (m, 1H), 2.82-3.01 (m, 1H), 2.45-2.52 (m, 1H), 2.01-2.21 (m, 1H). (TFA salt) |
| 308 | MS (ESI) calcd. for $C_{31}H_{27}N_9O_3S$ 605.20 m/z, found, 606.25 [M + H]$^+$. $^1$H NMR (300 MHz, DMSO-$d_6$) δ (ppm); 8.32-8.41 (m, 2H), 7.80-8.11 (m, 7H), 7.25-7.45 (m, 4H), 6.47-6.60 (m, 2H), 5.60-5.70 (m, 1H), 2.82-3.11 (m, 2H), 2.48-2.53 (m, 1H), 2.40-2.43 (m, 3H), 2.02-2.20 (m, 1H). |
| 309 | MS (ESI) calcd. for $C_{32}H_{26}FN_9O_2$, 587.22 m/z, found 588.20 [M + H]$^+$. $^1$H NMR (300 MHz, DMSO-$d_6$) δ (ppm); 8.92 (s, 1H), 8.30-8.40 (m, 2H), 8.05-8.20 (m, 1H), 7.88-8.05 (m, 2H), 7.70-7.85 (m, 3H), 7.35-7.45 (m, 2H), 7.28-7.35 (m, 2H), 6.56 (s, 1H), 6.42-6.50 (m, 1H), 5.55-5.70 (m, 1H), 3.00-3.15 (m, 1H), 2.85-3.00 (m, 1H), 2.55-2.60 (m, 1H), 2.00-2.20 (m, 4H). $^{19}$F NMR (376 MHz, DMSO-$d_6$) δ (ppm); −124.96. (formic acid salt) |
| 310 | MS (ESI) calcd. for $C_{30}H_{23}FN_8O$, 530.20 m/z, found, 531.15 [M + H]$^+$. $^1$H NMR (300 MHz, DMSO-$d_6$ + $D_2O$) δ (ppm); 8.90-9.02 (m, 1H), 8.35-8.41 (m, 2H), 7.98-8.05 (m, 4H), 7.81-7.87 (m, 1H), 7.27-7.41 (m, 6H), 6.57-6.60 (m, 1H), 6.49-6.53 (m, 1H), 5.60-5.69 (m, 1H), 2.84-3.11 (m, 2H), 2.58-2.63 (m, 1H), 2.03-2.15 (m, 1H). $^{19}$F NMR (300 MHz, DMSO-$d_6$) δ (ppm); −109.47. |
| 311 | MS (ESI) calcd. for $C_{29}H_{24}N_{10}O$, 528.21 m/z, found, 529.15 [M + H]$^+$. $^1$H NMR (400 MHz, DMSO-$d_6$) δ (ppm); 8.48-8.60 (m, 1H), 8.30-8.41 (m, 2H), 7.86-8.06 (m, 3H), 7.77-7.86 (m, 1H), 7.21-7.42 (m, 4H), 6.51-6.60 (m, 1H), 6.39-6.50 (m, 2H), 5.52-5.65 (m, 1H), 2.96-3.10 (m, 1H), 2.79-2.96 (m, 1H), 2.41-2.49 (m, 1H), 1.98-2.14 (m, 1H). |
| 312 | MS (ESI) calcd. for $C_{30}H_{24}FN_9O$, 545.58 m/z, found 546.30 [M + H]$^+$. $^1$H NMR (400 MHz, DMSO-$d_6$) δ (ppm); 8.92-9.03 (m, 1H), 8.30-8.40 (m, 2H), 8.15-8.25 (m, 1H), 7.90-8.10 (m, 2H), 7.82 (s, 1H), 7.65 (s, 1H), 7.45-7.60 (m, 2H), 7.38-7.42 (m, 1H), 7.30-7.38 (m, 1H), 6.55-6.62 (m, 1H), 6.46-6.55 (m, 1H), 6.00-6.25 (m, 1H), 5.50-5.65 (m, 1H), 3.00-3.25 (m, 1H), 2.53 (s, 3H), 2.15-2.40 (m, 1H). $^{19}$F NMR (376 MHz, DMSO-$d_6$) δ (ppm); −163.04. |
| 313 | MS (ESI) calcd for $C_{30}H_{24}FN_9O$, 545.21 m/z, found, 546.30 [M + H]$^+$. $^1$H NMR (400 MHz, DMSO-$d_6$) δ (ppm); 8.90-8.98 (m, 1H), 8.34-8.43 (m, 2H), 8.13-8.22 (m, 1H), 7.94-8.06 (m, 2H), 7.67-7.85 (m, 2H), 7.50-7.63 (m, 2H), 7.38-7.45 (m, 1H), 7.27-7.33 (m, 1H), 6.54-6.60 (m, 1H), 6.46-6.52 (m, 1H), 6.11-6.32 (m, 1H), 5.80-5.90 (m, 1H), 2.73-2.83 (m, 1H), 2.61-2.83 (m, 3H), 2.39-2.50 (m, 1H). $^{19}$F NMR (376 MHz, DMSO-$d_6$) δ (ppm); −161.21. |
| 317 | MS (ESI) calcd. for $C_{30}H_{21}F_2N_9O_3$, 593.17 m/z, found, 594.15 [M + H]$^+$. $^1$H NMR (300 MHz, DMSO-$d_6$) δ (ppm); 8.32-8.40 (m, 2H), 8.10-8.15 (m, 1H), 8.00-8.07 (m, 1H), 7.93-8.00 (m, 1H), 7.90-7.93 (m, 1H), 7.80-7.83 (m, 1H), 7.55-7.62 (m, 1H), 7.40-7.50 (m, 2H), 7.25-7.40 (m, 2H), 6.55-6.60 (m, 1H), 6.45-6.55 (m, 1H), 5.50-5.70 (m, 1H), 2.85-3.15 (m, 2H), 2.55-2.65 (m, 1H), 2.00-2.15 (m, 1H). $^{19}$F NMR (282 MHz, DMSO-$d_6$) δ (ppm); −48.10. (formic acid salt) |
| 318 | MS (ESI) calcd. for $C_{29}H_{23}N_9O_2$, 529.20 m/z, found 530.35 [M + H]$^+$. $^1$H NMR (400 MHz, DMSO-$d_6$) δ (ppm); 11.81 (s, 1H), 9.03 (d, J = 8.0 Hz, 1H), 8.33-8.39 (m, 2H), 7.99-8.03 (m, 1H), 7.95 (d, J = 8.4 Hz, 1H), 7.81 (d, J = 1.6 Hz, 1H), 7.47 (d, J = 6.8 Hz, 1H), 7.33-7.42 (m, 2H), 7.23-7.33 (m, 2H), 6.91 (s, 2H), 6.82 (d, J = 1.6 Hz, 1H), 6.53-6.58 (m, 2H), 6.45 (dd, J = 7.6, 4.8 Hz, 1H), 5.57 (q, J = 8.4 Hz, 1H), 2.97-3.08 (m, 1H), 2.83-2.96 (m, 1H), 2.51-2.56 (m, 1H), 2.00-2.13 (m, 1H). |

TABLE 3-continued

| Cpd ID | Characterization Data |
|---|---|
| | Characterization data of compounds prepared analogously to compound 3. |
| 319 | MS(ESI) calcd. for $C_{30}H_{24}FN_9O_2$, 561.20 m/z, found 562.15 $[M + H]^+$. $^1H$ NMR (400 MHz, DMSO-$d_6$) δ (ppm); 9.15 (d, J = 8.2 Hz, 1H), 8.36-8.38 (m, 2H), 8.01-8.06 (m, 2H), 7.96 (d, J = 8.5 Hz, 1H), 7.82 (s, 1H), 7.41-7.44 (m, 2H), 7.33-7.36 (m, 1H), 7.25-7.27 (m, 1H), 7.18 (t, J = 4.6 Hz, 1H), 6.92 (s, 2H), 6.55 (t, J = 2.1 Hz, 1H), 6.43-6.46 (m, 1H), 5.58 (q, J = 8.1 Hz, 1H), 3.98 (s, 3H), 3.00-3.02 (m, 1H), 2.88-2.96 (m, 1H), 2.53-2.58 (m, 1H), 1.96-2.06 (m, 1H). |
| 321 | MS (ESI) calcd. for $C_{29}H_{24}N_{10}O_2$ 544.21 m/z, found 545.20 $[M + H]^+$. $^1H$ NMR (400 MHz, DMSO-$d_6$) δ (ppm); 9.17 (d, J = 8.4 Hz, 1H), 8.43 (d, J = 8.4 Hz, 1H), 8.30 (d, J = 5.2 Hz, 1H), 8.14 (s, 2H), 7.99-8.05 (m, 2H), 7.43-7.46 (m, 1H), 7.36-7.43 (m, 2H), 7.26-7.35 (m, 3H), 6.92 (s, 2H), 6.42-6.47 (m, 1H), 5.65 (q, J= 8.0 Hz, 1H), 3.90 (s, 3H), 2.98-3.07 (m, 1H), 2.85-2.97 (m, 1H), 2.52-2.59 (m, 1H), 2.02-2.14 (m, 1H). (formic acid salt) |
| 322 | MS (ESI) calcd. for $C_{29}H_{22}F_2N_{10}O$, 564.19 m/z, found 565.20 $[M + H]^+$. $^1H$ NMR (400 MHz, DMSO-$d_6$) δ (ppm); 9.46 (d, J = 8.8 Hz, 1H), 9.36 (s, 1H), 9.04 (s, 1H), 8.33-8.40 (m, 2H), 7.99-8.04 (m, 1H), 7.96 (d, J = 8.4 Hz, 1H), 7.81 (d, J = 1.6 Hz, 1H), 7.42 (s, 1H), 7.37 (s, 1H), 7.25-7.31 (m, 2H), 7.24 (t, J = 54.0 Hz, 1H), 6.93 (s, 2H), 6.55 (t, J = 4.0 Hz, 1H), 6.45 (dd, J = 4.8, 7.6 Hz, 1H), 5.69 (q, J = 8.4, 1H), 2.99-3.05 (m, 1H), 2.87-2.97 (m, 1H), 2.50-2.57 (m, 1H), 2.20-2.35 (m, 1H). |
| 323 | MS (ESI) calcd. for $C_{30}H_{24}N_8O_3$ 544.20 m/z, found, 545.30 $[M + H]^+$. $^1H$-NMR (400 MHz, DMSO-$d_6$) δ (ppm); 9.47 (brs, 1H), 9.13 (brs, 1H), 8.57 (d, J = 8.3 Hz, 1H), 8.36-8.38 (m, 2H), 8.01-8.03 (m, 1H), 7.96 (d, J = 8.5 Hz, 1H), 7.81 (d, J = 1.7 Hz, 1H), 7.37-7.41 (m, 2H), 7.25-7.34 (m, 4H), 6.92 (s, 2H), 6.77 (d, J = 8.3 Hz, 1H), 6.55-6.56 (m, 1H), 6.44-6.47 (m, 1H), 5.61 (q, J = 8.4 Hz, 1H), 3.00-3.06 (m, 1H), 2.85-2.93 (m, 1H), 2.44-2.49 (m, 1H), 2.07-2.15 (m, 1H). |
| 324 | MS (ESI) calcd. for $C_{29}H_{24}F_2N_{10}O_2$ 582.20 m/z, found, 583.30 $[M + H]^+$. $^1H$ NMR (300 MHz, DMSO-$d_6$ + $D_2O$) δ (ppm); 8.35-8.41 (m, 2H), 7.95-8.09 (m, 2H), 7.54-7.86 (m, 2H), 7.39-7.42 (m, 1H), 7.22-7.34 (m, 3H), 6.57-6.59 (m, 1H), 6.46-6.51 (m, 1H), 6.31-6.33 (m, 1H), 5.55-5.64 (m, 1H), 3.98 (s, 3H), 3.01-3.11 (m, 1H), 2.83-2.93 (m, 1H), 2.42-2.51 (m, 1H), 2.11-2.22 (m, 1H). |
| 328 | MS (ESI) calcd. for $C_{32}H_{25}N_9O$, 551.22 m/z, found, 552.20 $[M + H]^+$. $^1H$ NMR (400 MHz, DMSO-$d_6$) δ (ppm); 8.92 (s, 1H), 8.26-8.48 (m, 2H), 7.90-8.20 (m, 2H), 7.78-7.85 (m, 1H), 7.55-7.70 (m, 1H), 7.44-7.55 (m, 1H), 7.35-7.43 (m, 3H), 7.25-7.34 (m, 1H), 7.10-7.24 (m, 1H), 6.83-6.88 (m, 1H), 6.51-6.60 (m, 2H), 6.38-6.50 (m, 1H), 5.53-5.72 (m, 1H), 2.98-3.15 (m, 1H), 2.80-2.97 (m, 1H), 2.49-2.51 (m, 1H), 2.00-2.20 (m, 1H). (formic acid salt) |
| 331 | MS (ESI) calcd. for $C_{30}H_{22}F_2N_8O$, 548.19 m/z, found, 549.30 $[M + H]^+$. $^1H$ NMR (300 MHz, DMSO-$d_6$ + $D_2O$) δ (ppm); 8.43-8.49 (m, 1H), 8.39-8.42 (m, 1H), 8.01-8.09 (m, 2H), 7.81-7.89 (m, 1H), 7.73-7.81 (m, 1H), 7.55-7.66 (m, 2H), 7.39-7.49 (m, 3H), 7.31-7.39 (m, 1H), 6.81-6.91 (m, 1H), 6.55-6.61 (m, 1H), 5.54-5.61 (m, 1H), 2.83-3.12 (m, 2H), 2.57-2.59 (m, 1H), 2.02-2.19 (m, 1H). $^{19}F$ NMR (376 MHz, DMSO-$d_6$) δ (ppm); −112.67. (TFA salt) |
| 332 | MS (ESI) calcd for $C_{30}H_{23}FN_8O$, 530.20 m/z, found, 531.30 $[M + H]^+$. $^1H$ NMR (400 MHz, DMSO-$d_6$) δ (ppm); 8.29-8.44 (m, 2H), 7.90-8.06 (m, 2H), 7.68-7.85 (m, 3H), 7.49-7.61 (m, 1H), 7.34-7.47 (m, 3H), 7.22-7.34 (m, 2H), 6.53-6.58 (m, 1H), 6.42-6.54 (m, 1H), 5.55-5.69 (m, 1H), 2.99-3.10 (m, 1H), 2.84-2.99 (m, 1H), 2.56-2.63 (m, 1H), 2.00-2.19 (m, 1H). $^{19}F$ NMR (376 MHz, DMSO-$d_6$) δ (ppm); −112.67. |
| 333 | MS (ESI) calcd. for $C_{30}H_{23}FN_8O$, 530.20 m/z, found, 531.30 $[M + H]^+$. $^1H$ NMR (400 MHz, DMSO-$d_6$) δ (ppm); 8.32-8.41 (m, 2H), 7.93-8.04 (m, 2H), 7.81 (s, 1H), 7.60-7.71 (m, 1H), 7.37-7.59 (m, 3H), 7.21-7.36 (m, 4H), 6.52-6.61 (m, 1H), 6.41-6.49 (m, 1H), 5.54-5.64 (m, 1H), 2.83-3.09 (m, 2H), 2.49-2.52 (m, 1H), 1.94-2.14 (m, 1H). $^{19}F$ NMR (376 MHz, DMSO-$d_6$) δ (ppm); −114.53. |
| 334 | MS (ESI) calcd for $C_{31}H_{25}FN_8O_2$ 560.21 m/z, found, 561.20 $[M + H]^+$. $^1H$ NMR (400 MHz, DMSO-$d_6$) δ (ppm); 8.32-8.40 (m, 2H), 7.92-8.05 (m, 2H), 7.78-7.87 (m, 1H), 7.24-7.44 (m, 6H), 6.98-7.07 (m, 1H), 6.46-6.61 (m, 2H), 5.56-5.67 (m, 1H), 3.80 (s, 3H), 2.99-3.12 (m, 1H), 2.85-2.98 (m, 1H), 2.56-2.62 (m, 1H), 2.03-2.18 (m, 1H). $^{19}F$ NMR (376 MHz, DMSO-$d_6$) δ (ppm); −110.83. |
| 335 | MS (ESI) calcd. for $C_{31}H_{26}N_8O_2$, 542.22 m/z, found 543.30 $[M + H]^+$. $^1H$ NMR (400 MHz, DMSO-$d_6$) δ ppm 8.30-8.45 (m, 2H), 7.90-8.10 (m, 2H), 7.81 (s, 1H), 7.50-7.60 (m, 1H), 7.45-7.50 (m, 1H), 7.30-7.45 (m, 3H), 7.20-7.30 (m, 2H), 7.00-7.20 (m, 1H), 6.40-6.60 (m, 2H), 5.60-5.70 (m, 1H), 3.81 (s, 3H), 2.85-3.15 (m, 2H), 2.55-2.58 (m, 1H), 2.00-2.20 (m, 1H). |
| 336 | MS (ESI) calcd. for $C_{31}H_{25}FN_8O_2$ 560.21 m/z, found, 561.30 $[M + H]^+$. $^1H$ NMR (300 MHz, DMSO-$d_6$ + $D_2O$) δ (ppm); 8.33-8.41 (m, 2H), 7.98-8.09 (m, 2H), 7.81-7.83 (m, 1H), 7.67-7.72 (m, 1H), 7.57-7.61 (m, 1H), 7.35-7.45 (m, 1H), 7.32-7.34 (m, 1H), 7.26-7.31 (m, 3H), 6.43-6.61 (m, 2H), 5.57-5.69 (m, 1H), 3.94 (s, 3H), 2.83-3.12 (m, 2H), 2.57-2.59 (m, 1H), 2.02-2.19 (m, 1H). |
| 337 | MS (ESI) calcd. for $C_{30}H_{22}ClFN_8O$, 564.01 m/z, found 565.30 $[M + H]^+$ $^1H$ NMR (300 MHz, DMSO-$d_6$) δ (ppm); 8.30-8.45 (m, 2H), 8.10-8.25 (m, 1H), 7.90-8.10 (m, 3H), 7.81 (s, 1H), 7.50-7.65 (m, 1H), 7.35-7.50 (m, 2H), 7.15-7.35 (m, 2H), 6.40-6.60 (m, 2H), 5.50-5.70 (m, 1H), 2.85-3.15 (m, 2H), 2.55-2.58 (m, 1H), 1.90-2.20 (m, 1H). $^{19}F$ NMR (282 MHz, DMSO-$d_6$) δ (ppm); −112.20. |
| 338 | MS (ESI) calcd. for $C_{30}H_{24}ClN_9O_2$ 577.17 m/z, found, 578.10 $[M + H]^+$. $^1H$ NMR (300 MHz, DMSO-$d_6$ + $D_2O$) δ (ppm); 9.21-9.29 (m, 1H), 8.38-8.49 (m, 2H), 8.01-8.16 (m, 2H), 7.83-7.89 (m, 1H), 7.74-7.81 (m, 1H), 7.53-7.57 (m, 1H), 7.46-7.52 (m, 1H), 7.34-7.45 (m, 2H), 7.25-7.33 (m, 1H), 6.74-6.89 (m, 1H), 6.57-6.59 (m, 1H), 5.55-5.63 (m, 1H), 3.86 (s, 3H), 2.81-3.13 (m, 2H), 2.63-2.64 (m, 1H), 2.02-2.19 (m, 1H). (TFA salt) |

TABLE 3-continued

| Cpd ID | Characterization Data |
|---|---|
| | Characterization data of compounds prepared analogously to compound 3. |
| 343 | MS (ESI) calcd for $C_{30}H_{21}F_3N_8O$, 566.18 m/z, found, 567.25 [M + H]$^+$. $^1$H NMR (400 MHz, DMSO-$d_6$) δ (ppm); 8.31-8.41 (m, 2H), 7.90-8.05 (m, 2H), 7.75-7.90 (m, 3H), 7.23-7.40 (m, 4H), 6.53-6.61 (m, 1H), 6.43-6.52 (m, 1H), 5.51-5.67 (m, 1H), 2.99-3.12 (m, 1H), 2.85-2.99 (m, 1H), 2.56-2.63 (m, 1H), 2.00-2.16 (m, 1H). $^{19}$F NMR (376 MHz, DMSO-$d_6$) δ (ppm); −133.75, −156.61. |
| 344 | MS (ESI) calcd. for $C_{30}H_{24}FN_9O_2$ 561.21 m/z, found, 562.10 [M + H]$^+$. $^1$H NMR (400 MHz, DMSO-$d_6$) δ (ppm); 8.28-8.45 (m, 2H), 7.89-8.09 (m, 2H), 7.75-7.87 (m, 1H), 7.19-7.49 (m, 5H), 7.09-7.18 (m, 1H), 6.52-6.63 (m, 1H), 6.37-6.62 (m, 1H), 5.54-5.69 (m, 1H), 3.89 (s, 3H), 2.81-3.20 (m, 2H), 2.55-2.63 (m, 1H), 1.98-2.21 (m, 1H). $^{19}$F NMR (376 MHz, DMSO-$d_6$) δ (ppm); 69.79. |
| 347 | MS (ESI) calcd. for $C_{30}H_{21}F_3N_8O$, 566.18 m/z, found 567.20 [M + H]$^+$. $^1$H NMR (400 MHz, DMSO-$d_6$) δ(ppm); 8.37-8.39 (m, 1H), 8.30-8.33 (m, 1H), 7.94-8.05 (m, 2H), 7.84 (s, 1H), 7.77-7.82 (m, 1H), 7.57-7.62 (m, 1H), 7.34-7.42 (m, 2H), 7.29-7.32 (m, 2H), 6.47-6.54 (m, 1H), 6.36-6.42 (m, 1H), 5.56-5.63 (m, 1H), 3.04-3.12 (m, 1H), 2.91-2.95 (m, 1H), 2.59-2.63 (m, 1H), 2.02-2.16 (m, 1H). $^{19}$F NMR (376 MHz, DMSO-$d_6$) δ (ppm); −127.23, −134.40, −137.92. |
| 348 | MS (ESI) calcd. for $C_{29}H_{24}N_{10}O_2$ 544.57 m/z, found, 545.30 [M + H]$^+$. $^1$H NMR (300 MHz, DMSO-$d_6$ + $D_2O$) δ (ppm); 8.82-8.83 (m, 1H), 8.56-8.59 (m, 1H), 8.39-8.47 (m, 2H), 8.01-8.11 (m, 2H), 7.82-7.85 (m, 1H), 7.75-7.77 (m, 1H), 7.49-7.51 (m, 1H), 7.31-7.39 (m, 2H), 6.79-6.83 (m, 1H), 6.59-6.61 (m, 1H), 5.62-5.72 (m, 1H), 4.07 (s, 3H), 3.03-3.13 (m, 1H), 2.82-3.01 (m, 1H), 2.59-2.62 (m, 1H), 2.15-2.33 (m, 1H). (TFA salt) |
| 349 | MS (ESI) calcd. for $C_{29}H_{21}F_3N_{10}O$, 582.19 m/z, found, 583.30 [M + H]$^+$. $^1$H-NMR (400 MHz, DMSO-d6) δ (ppm); 9.44-9.46 (m, 1H), 9.24-9.25 (m, 1H), 8.51-8.56 (m, 2H), 8.15-8.17 (m, 2H), 8.09-8.11 (m, 2H), 7.80-7.86 (m, 2H), 7.50-7.58 (m, 3H), 6.93-7.20 (m, 1H), 6.77-6.80 (m, 1H), 5.80-5.89 (m, 1H), 5.43-5.58 (m, 1H), 3.17-3.47 (m, 2H), 2.50-2.52 (m, 2H). $^{19}$F-NMR (400 MHz, DMSO-d6) δ (ppm); −73.31, −116.16, −192.19. (TFA salt) |
| 350 | MS (ESI) calcd. for $C_{29}H_{21}F_3N_{10}O$, 582.19 m/z, found, 583.25 [M + H]$^+$. $^1$H-NMR (400 MHz, DMSO-d6) δ (ppm); 9.45-9.47 (m, 1H), 9.16-9.17 (m, 1H), 8.46-8.52 (m, 2H), 8.16-8.17 (m, 2H), 8.09-8.11 (m, 2H), 7.85-7.93 (m, 1H), 7.72-7.74 (m, 1H), 7.52-7.54 (m, 2H), 7.45-7.47 (m, 1H), 6.92-7.20 (m, 1H), 6.75-6.79 (m, 1H), 5.66-5.74 (m, 1H), 5.39-5.56 (m, 1H), 3.49-3.60 (m, 1H), 3.12-3.23 (m, 1H), 2.50-2.51 (m, 2H). $^{19}$F-NMR (400 MHz, DMSO-d6) δ (ppm); −74.29, −116.19, −179.20. (TFA salt) |
| 355 | MS (ESI) calcd. for $C_{31}H_{27}N_9O_3$, 573.22 m/z, found 574.15 [M + H]$^+$. $^1$H NMR (400 MHz, DMSO-$d_6$) δ (ppm); 8.84 (d, J = 8.3 Hz, 1H), 8.34-8.38 (m, 2H), 8.01 (dd, J = 4.8, 1.8 Hz, 1H), 7.93-7.97 (m, 2H), 7.80-7.82 (m, 1H), 7.44-7.47 (m, 1H), 7.41-7.43 (m, 1H), 7.30-7.34 (m, 1H), 7.25 (dd, J = 7.6, 1.9 Hz, 1H), 7.06 (d, J = 5.1 Hz, 1H), 6.93 (s, 2H), 6.55 (dd, J = 2.6, 1.6 Hz, 1H), 6.43 (dd, J = 7.7, 4.8 Hz, 1H), 5.58 (q, J = 8.1 Hz, 1H), 3.94 (s, 3H), 3.80 (s, 3H), 2.98-3.06 (m, 1H), 2.86-2.96 (m, 1H), 2.52-2.58 (m, 1H), 1.96-2.08 (m, 1H). |
| 356 | MS(ESI) calcd. for $C_{31}H_{25}N_9O_3$ 571.21 m/z, found 572.15 [M + H]$^+$. $^1$H NMR (400 MHz, DMSO-$d_6$) δ (ppm); 8.73 (d, J = 8.2 Hz, 1H), 8.34-8.39 (m, 2H), 8.02 (dd, J = 4.8, 1.9 Hz, 1H), 7.96 (d, J = 8.4 Hz, 1H), 7.78-7.83 (m, 2H), 7.40-7.44 (m, 2H), 7.29-7.33 (m, 1H), 7.24-7.28 (m, 1H), 7.15 (d, J = 5.2 Hz, 1H), 6.92 (s, 2H), 6.55-6.57 (m, 1H), 6.45 (dd, J = 7.6, 4.8 Hz, 1H), 5.59 (q, J = 8.4 Hz, 1H), 4.23-4.47 (m, 2H), 4.31-4.35 (m, 2H), 2.86-3.07 (m, 2H), 2.52-2.60 (m, 1H), 1.97-2.10 (m, 1H). |
| 357 | MS(ESI) calcd. for $C_{31}H_{27}N_9O_2$, 557.23 m/z, found 558.15 [M + H]$^+$. $^1$H NMR (400 MHz, DMSO-$d_6$) δ (ppm); 8.95 (d, J = 8.2 Hz, 1H), 8.34-8.39 (m, 2H), 8.06 (s, 1H), 8.01 (dd, J = 4.9, 1.9 Hz, 1H), 7.95 (d, J = 8.6 Hz, 1H), 7.81 (d, J = 1.6 Hz, 1H), 7.46 (d, J = 8.0 Hz, 1H), 7.40 (d, J = 1.9 Hz, 1H), 7.30-7.33 (m, 1H), 7.25 (dd, J = 7.7, 1.9 Hz, 1H), 6.93 (s, 2H), 6.81 (s, 1H), 6.55 (dd, J = 2.6, 1.7 Hz, 1H), 6.43 (dd, J = 7.6, 4.8 Hz, 1H), 5.56 (q, J = 8.1 Hz, 1H), 3.85 (s, 3H), 2.98-3.05 (m, 1H), 2.86-2.95 (m, 1H), 2.53-2.58 (m, 1H), 2.26 (s, 3H), 1.97-2.06 (m, 1H). |
| 358 | MS (ESI) calcd. for $C_{34}H_{32}N_{10}O$, 596.28 m/z, found, 597.20 [M + H]$^+$. $^1$H NMR (300 MHz, DMSO-$d_6$) δ (ppm); 8.64-8.55 (m, 1H), 8.42-8.33 (m, 2H), 8.05-7.90 (m, 3H), 7.85-7.79 (m, 1H), 7.70 (s, 1H), 7.62-7.54 (m, 1H), 7.54-7.45 (m, 1H), 7.42 (s, 1H), 7.36-7.23 (m, 3H), 6.91 (s, 2H), 6.59-6.52 (m, 1H), 6.48-6.39 (m, 1H), 4.82-4.42 (m, 2H), 3.73 (s, 1H), 3.21-2.92 (m, 4H), 2.92-2.69 (m, 1H), 2.24-1.80 (m, 3H), 1.56 (s, 2H), 1.24 (s, 1H). |
| 359 | MS (ESI) calcd. for $C_{34}H_{32}N_{10}O$, 596.28 m/z, found 597.15 [M + H]$^+$. $^1$H NMR (400 MHz, DMSO-$d_6$) δ 8.71-8.53 (m, 2H), 8.40-8.32 (m, 2H), 8.10-7.93 (m, 2H), 7.87-7.76 (m, 2H), 7.57-7.19 (m, 5H), 6.93 (s, 2H), 6.63-6.36 (m, 2H), 4.35 (s, 2H), 3.57 (s, 1H), 3.17 (s, 1H), 3.04 (s, 3H), 2.81 (s, 1H), 2.11-1.74 (m, 4H), 1.53-1.18 (m, 3H). |
| 360 | MS (ESI) calcd. for $C_{34}H_{32}N_{10}O$, 596.28 m/z, found, 597.20 [M + H]$^+$. $^1$H NMR (400 MHz, DMSO-$d_6$) δ 8.72-8.66 (m, 2H), 8.40-8.32 (m, 2H), 8.04-7.98 (m, 1H), 7.98-7.92 (m, 1H), 7.84-7.79 (m, 1H), 7.60-7.56 (m, 1H), 7.42-7.36 (m, 3H), 7.30-7.22 (m, 2H), 6.93 (s, 2H), 6.58-6.52 (m, 1H), 6.46-6.39 (m, 1H), 4.39-4.35 (m, 2H), 3.51-3.46 (m, 1H), 3.06-3.01 (m, 4H), 2.85-2.78 (m, 1H), 1.99-1.94 (m, 2H), 1.89-1.84 (m, 1H), 1.47-1.42 (m, 2H), 1.26-1.22 (m, 1H). |
| 361 | MS (ESI) calcd. for $C_{32}H_{27}N_9O_2$, 569.23 m/z, found 570.40 [M + H]$^+$. $^1$H NMR (400 MHz, DMSO-$d_6$) δ (ppm); 8.95 (d, J = 8.2 Hz, 1H), 8.36-8.37 (m, 1H), 8.35 (s, 1H), 8.06 (d, J = 4.9 Hz, 1H), 8.01-8.02 (m, 1H), 7.95 (d, J = 8.6 Hz, 1H), 7.81 (dd, J = 1.7, 0.7 Hz, 1H), 7.44-7.46 (m, 1H), 7.41 (s, 1H), 7.30-7.32 (m, 1H), 7.23-7.26 (m, 1H), 6.98 (d, J = 4.9 Hz, 1H), 6.93 (s, 2H), 6.54-6.55 (m, 1H), 6.43-6.44 (m, 1H), 5.56-5.58 (m, 1H), 4.26-4.29 (m, 2H), 2.98-3.07 (m, 1H), 2.86-2.93 (m, 1H), 2.84-2.86 (m, 2H), 2.52-2.58 (m, 1H), 1.93-2.02 (m, 1H), 1.90-1.93 (m, 2H). |

TABLE 3-continued

| Cpd ID | Characterization Data |
|---|---|
| | Characterization data of compounds prepared analogously to compound 3. |
| 363 | MS (ESI) calcd. for $C_{31}H_{23}N_9OS$ 569.17 m/z, found, 570.15 $[M + H]^+$. $^1H$ NMR (400 MHz, DMSO-$d_6$) δ (ppm); 9.29 (d, J = 8.2 Hz, 1H), 8.70 (d, J = 4.8 Hz, 1H), 8.33-8.40 (m, 2H), 8.00-8.05 (m, 2H), 7.96 (d, J = 8.6 Hz, 1H), 7.80-7.83 (m, 2H), 7.71 (d, J = 4.8 Hz, 1H), 7.49 (d, J = 8.0 Hz, 1H), 7.41-7.45 (m, 1H), 7.32-7.36 (m, 1H), 7.24-7.30 (m, 1H), 6.92 (s, 2H), 6.53-6.58 (m, 1H), 6.41-6.49 (m, 1H), 5.66-5.74 (m, 1H), 3.02-3.11 (m, 1H), 2.88-3.00 (m, 1H), 2.54-2.65 (m, 1H), 2.05-2.19 (m, 1H). |
| 364 | MS(ESI) calcd. for $C_{30}H_{24}F_2N_{10}O_2$, 594.21 m/z, found 595.15 $[M + H]^+$. $^1H$ NMR (400 MHz, DMSO-$d_6$) δ (ppm); 9.27 (d, J = 8.0 Hz, 1H), 8.74 (s, 1H), 8.43 (d, J = 8.4 Hz, 1H), 8.14 (s, 2H), 8.08 (s, 1H), 8.00-8.05 (m, 2H), 7.40-7.48 (m, 2H), 7.27-7.38 (m, 2H), 7.10 (t, J = 53.6 Hz, 1H), 6.90 (s, 2H), 6.42-6.48 (m, 1H), 5.66-5.74 (m, 1H), 3.97 (s, 3H), 3.00-3.10 (m, 1H), 2.88-3.00 (m, 1H), 2.53-2.68 (m, 1H), 2.03-2.14 (m, 1H). $^{19}F$-NMR (376 MHz, DMSO-$d_6$) δ (ppm); −118.98, −119.02. |
| 365 | MS (ESI) calcd. for $C_{30}H_{22}ClF_2N_9O$, 597.16 m/z, found 598.35 $[M + H]^+$. $^1H$ NMR (400 MHz, DMSO-$d_6$) δ (ppm); 9.32 (d, J = 8.0 Hz, 1H), 9.10 (s, 1H), 8.56 (s, 1H), 8.33-8.40 (m, 2H), 7.99-8.05 (m, 1H), 7.95 (d, J = 8.4 Hz, 1H), 7.81 (s, 1H), 7.40-7.48 (m, 2H), 7.27-7.35 (m, 2H), 7.26 (t, J = 53.2 Hz, 1H), 6.89 (s, 2H), 6.53-6.58 (m, 1H), 6.43-6.48 (m, 1H), 5.65 (q, J = 8.4 Hz, 1H), 3.00-3.11(m, 1H), 2.88-2.99 (m, 1H), 2.53-2.62 (m, 1H), 2.02-2.15 (m, 1H). $^{19}F$ NMR (376 MHz, DMSO-$d_6$) δ (ppm); −118.58, −118.63. |
| 369 | MS (ESI) calcd. for $C_{33}H_{32}N_{10}O$: 584.27. found: 585.35 $[M + H]^+$. $^1H$ NMR (400 MHz, DMSO-$d_6$) δ 8.32 (m, 3H), 8.27-8.28 (m, 1H), 7.95-7.96 (m, 1H), 7.86-7.88 (m, 1H), 7.75 (s, 1H), 7.59-7.61 (m, 1H), 7.42 (s, 1H), 7.26-7.28 (m, 2H), 6.48-6.52 (m, 2H), 4.85 (s. 1H), 4.21-4.32 (m, 2H), 3.26-3.49 (m, 1H), 3.10-3.12 (m, 1H), 3.01-3.08 (m, 1H), 2.89-2.93 (m, 1H), 2.78 (m, 1H), 2.65-2.68 (m, 1H), 1.94-2.38 (m, 3H), 1.46-1.58 (m, 6H). (formic acid salt) |
| 370 | MS (ESI) calcd. for $C_{32}H_{32}FN_9O$, 577.27. found, 578.35 $[M + H]^+$. $^1H$ NMR (400 MHz, DMSO-$d_6$) δ 8.24-8.30 (m, 2H), 7.74-8.00 (m, 2H), 7.56-7.57 (m, 2H), 7.32-7.38 (m, 1H), 7.23-7.26 (m, 2H), 6.47-6.51 (m, 2H), 4.78 (m, 1H), 4.09-4.15 (m, 3H), 3.25-3.42 (m, 1H), 2.78-3.15 (m, 4H), 1.79-2.27 (m, 3H), 1.65-1.67 (m, 2H), 1.23-1.28 (m, 2H), 1.10-1.67 (m, 2H). F NMR δ (ppm) −185.38. (TFA salt) |
| 371 | 544.21 m/z, found, 545.15 $[M + H]^+$. $^1H$ NMR (400 MHz, DMSO-d6) δ(ppm); 8.95-8.84 (m, 1H), 8.74-8.65 (m, 1H), 8.40-8.34 (m, 1H), 8.21-8.11 (m, 1H), 8.07 (s, 2H), 8.00-7.86 (m, 2H), 7.41-7.29 (m, 2H), 7.29-7.16 (m, 2H), 6.94-6.71 (m, 3H), 6.44-6.29 (m, 1H), 5.68-5.50 (m, 1H), 3.84 (s, 3H), 3.04-2.91 (m, 1H), 2.91-2.77 (m, 1H), 2.53-2.45 (m, 1H), 2.07-1.92 (m, 1H). |
| 372 | MS (ESI) calcd. for $C_{27}H_{24}N_8O_2$: 492.20 m/z, found: 493.30 $[M + H]^+$. $^1H$ NMR (400 MHz, DMSO-$d_6$) δ (ppm): 8.29-8.43 (m, 2H), 8.00-8.08 (m, 1H), 7.91-7.98 (m, 1H), 7.75-7.88 (m, 1H), 7.33-7.43 (m, 2H), 7.22-7.32 (m, 2H), 6.55-6.61 (m, 1H), 6.44-6.53 (m, 1H), 5.36-5.49 (m, 1H), 4.97-5.09 (m, 1H), 4.52-4.69 (m, 2H), 2.80-3.08 (m, 3H), 2.58-2.69 (m, 1H), 2.35-2.50 (m, 1H), 1.96-2.13 (m, 1H). |
| 373 | MS (ESI) calcd. for $C_{27}H_{24}N_8O_2$, 492.20 m/z, found 493.30 $[M + H]^+$. $^1H$ NMR (400 MHz, DMSO-$d_6$ + $D_2O$) δ (ppm); 8.33-8.40 (m, 2H), 8.00-8.01 (m, 1H), 7.92-7.94 (m, 1H), 7.83-7.84 (m, 1H), 7.26-7.36 (m, 3H), 7.24-7.25 (m, 1H), 6.55-6.59 (m, 2H), 5.42-5.44 (m, 1H), 5.07-5.11 (m, 1H), 4.61-4.69 (m, 2H), 3.01-3.09 (m, 2H), 2.99-3.00 (m, 1H), 2.59-2.60 (m, 1H), 2.54-2.55 (m, 1H), 2.04-2.05 (m, 1H). |
| 375 | MS (ESI) calcd for $C_{28}H_{23}N_9OS$ 533.17 m/z, found, 534.30 $[M + H]^+$. $^1H$ NMR (300 MHz, DMSO-$d_6$) δ (ppm); 9.21-9.30 (m, 1H), 8.32-8.42 (m, 2H), 7.99-8.06 (m, 1H), 7.90-7.98 (m, 1H), 7.74-7.87 (m, 2H), 7.23-7.45 (m, 4H), 6.88 (s, 2H), 6.52-6.59 (m, 1H), 6.40-6.50 (m, 1H), 5.51-5.65 (m, 1H), 2.82-3.20 (m, 2H), 2.45-2.63 (m, 1H), 2.46 (s, 3H), 1.97-2.16 (m, 1H). |
| 376 | MS (ESI) calcd. for $C_{28}H_{21}F_2N_9OS$ 569.16 m/z, found, 570.30 $[M + H]^+$. $^1H$ NMR (400 MHz, DMSO-$d_6$) δ (ppm); 9.40-9.50 (m, 1H), 8.50-8.66 (m, 1H), 8.27-8.43 (m, 2H), 8.00-8.05 (m, 1H), 7.92-7.99 (m, 1H), 7.79-7.85 (m, 1H), 7.21-7.50 (m, 5H), 6.56-6.61 (m, 1H), 6.47-6.54 (m, 1H), 5.51-5.64 (m, 1H), 3.00-3.12 (m, 1H), 2.85-2.96 (m, 1H), 2.56-2.65 (m, 1H), 2.01-2.16 (m, 1H). $^{19}F$ NMR (376 MHz, DMSO-$d_6$) δ (ppm); −110.16. (formic acid salt) |
| 377 | MS (ESI) calcd for $C_{29}H_{24}N_{10}O_2$ 544.21 m/z, found, 545.45 $[M + H]^+$. $^1H$ NMR (300 MHz, DMSO-$d_6$) δ (ppm); 9.31-9.40 (m, 1H), 9.24-9.31 (m, 1H), 8.32-8.41 (m, 2H), 7.91-8.08 (m, 2H), 7.78-7.84 (m, 1H), 7.57-7.63 (m, 1H), 7.39-7.48 (m, 2H), 7.23-7.36 (m, 2H), 6.88 (s, 2H), 6.52-6.59 (m, 1H), 6.40-6.50 (m, 1H), 5.56-5.70 (m, 1H), 4.09 (s, 3H), 2.84-3.17 (m, 2H), 2.52-2.63 (m, 1H), 1.98-2.17 (m, 1H). |
| 378 | MS (ESI) calcd. for $C_{29}H_{23}N_{10}O_2$, 578.17 m/z, found, 579.30 $[M + H]^+$. $^1H$ NMR (400 MHz, DMSO-$d_6$ + $D_2O$) δ (ppm); 8.41-8.42 (m, 1H), 8.00-8.19 (m, 5H), 7.48-7.50 (m, 1H), 7.26-7.40 (m, 3H), 7.12-7.13 (m, 1H), 6.42-6.45 (m, 1H), 5.54-5.58 (m, 1H), 3.97 (s, 3H), 2.85-3.02 (m, 2H), 2.51-2.59 (m, 1H), 1.99-2.07 (m, 1H). |
| 379 | MS (ESI) calcd for $C_{30}H_{22}N_{10}O_2$ 554.19 m/z, found, 555.05 $[M + H]^+$. $^1H$ NMR (300 MHz, DMSO-$d_6$) δ (ppm); 9.26-9.35 (m, 1H), 8.39-8.48 (m, 2H), 8.20-8.27 (m, 1H), 8.14 (s, 2H), 7.97-8.07 (m, 2H), 7.75-7.83 (m, 1H), 7.40-7.50 (m, 2H), 7.25-7.38 (m, 3H), 6.92 (s, 2H), 6.39-6.50 (m, 1H), 5.64-5.79 (m, 1H), 2.79-3.25 (m, 2H), 2.58-2.63 (m, 1H), 2.06-2.22 (m, 1H). |
| 380 | MS (ESI) calcd. for $C_{30}H_{26}N_{10}O_2$ 558.22 m/z, found, 559.30 $[M + H]^+$. $^1H$ NMR (300 MHz, DMSO-$d_6$ + $D_2O$) δ (ppm); 8.41-8.44 (m, 1H), 8.12-8.15 (m, 2H), 7.99-8.09 (m, 3H), 7.41-7.49 (m, 2H), 7.26-7.36 (m, 2H), 6.93-6.96 (m, 1H), 6.41-6.47 (m, 1H), 5.54-5.61 (m, 1H), 3.90 (s, 3H), 2.99-3.04 (m, 1H), 2.81-2.93 (m, 1H), 2.52-2.59 (m, 1H), 2.17 (s, 3H), 1.93-2.07 (m, 1H). |

TABLE 3-continued

Characterization data of compounds prepared analogously to compound 3.

| Cpd ID | Characterization Data |
|---|---|
| 381 | MS (ESI) calcd. for $C_{30}H_{26}N_{10}O_3$ 574.22 m/z, found, 575.15 [M + H]$^+$. $^1$H NMR (300 MHz, DMSO-d$_6$ + D$_2$O) δ (ppm); 8.47-8.52 (m, 1H), 8.03-8.19 (m, 4H), 7.74-7.79 (m, 1H), 7.31-7.51 (m, 3H), 6.77-6.84 (m, 3H), 5.55-5.62 (m, 1H), 3.81-3.95 (m, 6H), 3.01-3.09 (m, 1H), 2.80-2.94 (m, 1H), 2.57-2.59 (m, 1H), 2.02-2.17 (m, 1H). (TFA salt) |
| 382 | MS (ESI) calcd. for $C_{29}H_{23}FN_{10}O$, 546.20 m/z, found, 547.30 [M + H]$^+$. $^1$H NMR (300 MHz, DMSO-d$_6$) δ (ppm); 8.46-8.58 (m, 1H), 8.32-8.45 (m, 1H), 8.08-8.20 (m, 2H), 7.92-8.07 (m, 2H), 7.70-7.85 (m, 1H), 7.45-7.56 (m, 1H), 7.38-7.44 (m, 1H), 7.18-7.37 (m, 2H), 6.34-6.53 (m, 1H), 5.47-5.68 (m, 1H), 2.78-3.18 (m, 2H), 2.53-2.68 (m, 4H), 1.83-2.12 (m, 1H). $^{19}$F-NMR (282 MHz, DMSO-d$_6$) δ (ppm); −131.78. |
| 383 | MS (ESI) calcd. for $C_{30}H_{22}FN_{11}O$, 571.20 m/z, found, 572.30 [M + H]$^+$. $^1$H NMR (400 MHz, DMSO-d$_6$) δ (ppm); 8.40-8.48 (m, 1H), 8.27-8.39 (m, 2H), 8.13 (m, 2H), 7.98-8.09 (m, 2H), 7.67-7.89 (m, 1H), 7.37-7.47 (m, 2H), 7.24-7.36 (m, 2H), 6.42-6.52 (m, 1H), 5.59-5.74 (m, 1H), 2.99-3.12 (m, 1H), 2.81-2.98 (m, 1H), 2.55-2.64 (m, 1H), 2.03-2.33 (m, 1H). $^{19}$F NMR (376 MHz, DMSO-d$_6$) δ (ppm); −73.63, −130.61. (TFA salt) |
| 389 | MS (ESI) calcd. for $C_{31}H_{25}N_9O_2$ 555.21 m/z, found, 556.20 [M + H]$^+$. $^1$H NMR (400 MHz, DMSO-d$_6$) δ (ppm); 8.98 (d, J = 8.4 Hz, 1H), 8.47 (s, 1H), 8.34-8.39 (m, 2H), 8.22 (s, 1H), 8.00-8.04 (m, 1H), 7.96 (d, J = 8.4 Hz, 1H), 7.78-7.83 (m, 1H), 7.40-7.45 (m, 2H), 7.30-7.33 (m, 1H), 7.25-7.29 (m, 1H), 6.91 (s, 2H), 6.53-6.58 (m, 1H), 6.45 (dd, J = 7.6, 4.8 Hz, 1H), 5.64 (q, J = 8.0 Hz, 1H), 4.63 (t, J = 8.8 Hz, 2H), 3.51 (t, J = 8.4 Hz, 2H), 2.99-3.09 (m, 1H), 2.87-2.98 (m, 1H), 2.52-2.56 (m, 1H), 2.02-2.15 (m, 1H). |
| 390 | MS(ESI) calcd. for $C_{30}H_{26}N_{10}O_2$, 558.22 m/z, found 559.35 [M + H]$^+$. $^1$H NMR (400 MHz, DMSO-d$_6$) δ (ppm); 8.96 (d, J = 8.4 Hz, 1H), 8.33-8.40 (m, 2H), 7.99-8.04 (m, 1H), 7.96 (d, J = 9.6 Hz, 1H), 7.77-7.84 (m, 1H), 7.36-7.41 (m, 1H), 7.21-7.33 (m, 3H), 6.89-6.98 (m, 2H), 6.53-6.58 (m, 1H), 6.44 (dd, J = 7.6, 4.8 Hz, 1H), 5.43-5.54 (m, 1H), 3.38 (s, 3H), 3.00-3.07 (m, 1H), 2.82-2.92 (m, 1H), 2.15-2.42 (m, 4H), 1.60-1.66 (m, 2H). |
| 391 | MS (ESI) calcd. for $C_{35}H_{35}N_7O$, 569.29. found, 570.40 [M + H]$^+$. $^1$H NMR (400 MHz, DMSO-d$_6$) 8.20-8.22(m. 1H), 7.90-7.98 (m, 4H), 7.35-7.51 (m, 4H), 7.18-7.28 (m, 3H), 6.45-6.49 (m, 1H), 4.40 (m, 1H), 2.94-3.11 (m, 3H), 2.63-2.78 (m, 3H), 2.40-2.51 (m, 1H), 1.81-1.93 (m, 4H), 1.17-1.30 (m, 3H), 0.71-0.73 (m, 4H). |
| 392 | MS (ESI) calcd. for $C_{30}H_{24}F_2N_{10}O$, 578.21 m/z, found, 579.15 [M + H]$^+$. $^1$H NMR (300 MHz, DMSO-d6) δ(ppm); 9.16-9.00 (m, 1H), 8.48-8.33 (m, 1H), 8.13 (s, 2H), 8.07-7.93 (m, 3H), 7.66-7.20 (m, 5H), 7.16-6.74 (m, 3H), 6.47-6.35 (m, 1H), 5.68-5.52 (m, 1H), 3.13-2.69 (m, 2H), 2.62 (s, 3H), 2.12-1.91 (m, 1H), 1.24 (s, 1H). |
| 395 | MS (ESI) calcd. for $C_{32}H_{27}N_9O_2$ 569.23 m/z, found, 570.15 [M + H]$^+$. 1H NMR (400 MHz, DMSO-d6) δ (ppm); 8.95 (d, J = 8.4 Hz, 1H), 8.41-8.33 (m, 2H), 8.01 (dd, J = 4.9, 1.8 Hz, 1H), 7.95 (d, J = 8.6 Hz, 1H), 7.81 (s, 1H), 7.44-7.35 (m, 2H), 7.34-7.23 (m, 2H), 7.06 (s, 1H), 6.91 (s, 2H), 6.58-6.53 (m, 1H), 6.44 (dd, J = 7.6, 4.8 Hz, 1H), 5.60 (q, J = 8.2 Hz, 1H), 4.57 (t, J = 8.6 Hz, 2H), 3.42 (t, J = 8.7 Hz, 2H), 3.09-2.98 (m, 1H), 2.98-2.85 (m, 1H), 2.56-2.53 (m, 1H), 2.36 (s, 3H), 2.13-1.99 (m, 1H). |
| 396 | MS (ESI) calcd. for $C_{28}H_{23}FN_{10}O$, 534.20 m/z, found, 535.35 [M + H]$^+$. $^1$H NMR (300 MHz, DMSO-d$_6$) δ (ppm); 8.37-8.42 (m, 2H), 8.02-8.09 (m, 1H), 7.95-7.97 (m, 1H), 7.81-7.83 (m, 1H), 7.51-7.52 (m, 2H), 7.38-7.42 (m, 2H), 6.57-6.60 (m, 2H), 6.45-6.50 (m, 1H), 5.54-5.59 (m, 1H), 4.00 (s, 3H), 3.01-3.07 (m, 1H), 2.85-2.99 (m, 1H), 2.50-2.54 (m, 1H), 1.97-2.09 (m, 1H). |
| 397 | MS (ESI) calcd for $C_{30}H_{24}F_2N_{10}O$, 578.21 m/z, found, 579.30 [M + H]$^+$. $^1$H NMR (300 MHz, DMSO-d$_6$) δ (ppm); 9.07-9.15 (m, 1H), 8.66 (s, 1H), 8.39-8.48 (m, 1H), 7.91-8.17 (m, 4H), 7.68-7.62 (m, 1H), 7.59-7.18 (m, 4H), 6.64-7.17 (m, 3H), 6.39-6.49 (m, 1H), 5.55-5.69 (m, 1H), 2.80-3.10 (m, 2H), 2.52-2.67 (m, 4H), 1.93-2.12 (m, 1H). |
| 398 | MS (ESI) calcd. for $C_{31}H_{25}N_{11}O$, 567.22 m/z, found, 568.35 [M + H]$^+$. $^1$H NMR (300 MHz, DMSO-d$_6$) δ (ppm); 9.01-9.18 (m, 1H), 8.80-8.97 (m, 1H), 8.30-8.52 (m, 1H), 8.08-8.21 (m, 2H), 7.97-8.07 (m, 2H), 7.66-7.83 (m, 1H), 7.52-7.64 (m, 1H), 7.38-7.50 (m, 3H), 7.25-7.37 (m, 2H), 6.36-6.60 (m, 1H), 5.55-5.83 (m, 1H), 2.81-3.22 (m, 2H), 2.53-2.71 (m, 4H), 1.98-2.20 (m, 1H). |
| 399 | MS (ESI) calcd. for $C_{26}H_{20}N_{10}OS$, 520.15 m/z, found 521.15 [M + H]$^+$. $^1$H NMR (400 MHz, DMSO-d$_6$) δ (ppm); 9.40-9.45 (m, 1H), 8.35-8.42 (m, 2H), 8.00-8.05 (m, 1H), 7.90-8.00 (m, 1H), 7.81 (s, 1H), 7.40-7.50 (m, 2H), 7.25-7.35 (m, 2H), 6.56 (s, 1H), 6.43-6.50 (m, 1H), 5.53-5.65 (m, 1H), 3.00-3.10 (m, 1H), 2.85-3.00 (m, 1H), 2.55-2.60 (m, 1H), 2.00-2.15 (m, 1H). |
| 400 | MS (ESI) calcd. for $C_{31}H_{25}N_7O$, 511.21 m/z, found 512.20 [M + H]$^+$. $^1$H NMR (400 MHz, DMSO-d$_6$) δ (ppm); 9.01-9.07 (m, 1H), 8.91-8.97 (m, 1H), 8.34-8.41 (m, 2H), 8.16-8.18 (m, 1H), 7.91-7.96 (m, 1H), 7.81-7.85 (m, 1H), 7.56-7.64 (m, 2H), 7.36-7.52 (m, 6H), 7.28-7.31 (m, 1H), 6.56-6.58 (m, 1H), 5.65-5.71 (m, 1H), 3.05-3.14 (m, 1H), 2.83-2.98 (m, 1H), 2.61-2.63 (m, 1H), 2.56 (s, 3H), 2.06-2.21 (m, 1H). |
| 401 | MS (ESI) calcd. for $C_{31}H_{24}FN_7O$, 529.20 m/z, found, 530.30 [M + H]$^+$. $^1$H NMR (300 MHz, DMSO-d$_6$) δ (ppm); 8.85-9.12 (m, 1H), 8.30-8.50 (m, 2H), 8.08-8.21 (m, 1H), 7.90-8.07 (m, 1H), 7.80-7.89 (m, 1H), 7.70-7.79 (m, 1H), 7.51-7.68 (m, 1H), 7.12-7.45 (m, 6H), 6.45-6.61 (m, 1H), 5.50-5.72 (m, 1H), 2.72-3.20 (m, 2H), 2.52-2.61 (m, 4H), 1.90-2.20 (m, 1H). $^{19}$F-NMR (282 MHz, DMSO-d$_6$) δ (ppm); −112.56. |
| 402 | MS (ESI) calcd. for $C_{31}H_{24}FN_7O_2$, 545.20 m/z, found 546.30 [M + H]$^+$. $^1$H NMR (300 MHz, DMSO-d$_6$ + D$_2$O) δ (ppm); 8.39-8.41 (m, 2H), 8.29-8.30 (m, 1H), 7.98-8.01 (m, 1H), 7.82-7.83 (m, 1H), 7.73-7.75 (m, 1H), 7.62-7.71 (m, 1H), 7.22-7.60 (m, 7H), 6.57-6.58 (m, 1H), 5.55-5.61 (m, 1H), 3.89 (s, 3H), 2.87-3.02 (m, 2H), 2.52-2.53 (m, 1H), 2.03-2.10 (m, 1H). $^{19}$F NMR (282 MHz, DMSO-d$_6$ + D$_2$O) δ (ppm); −112.60. |

TABLE 3-continued

| Cpd ID | Characterization Data |
|---|---|
| | Characterization data of compounds prepared analogously to compound 3. |
| 403 | MS (ESI) calcd for $C_{31}H_{24}F_2N_8OS$: 594.18 m/z, found, 595.35 [M + H]$^+$. $^1$H-NMR (400 MHz, DMSO-$d_6$) δ (ppm); 9.03-9.10 (m, 1H), 8.95-9.00 (m, 1H), 8.31-8.38 (m, 1H), 8.10-8.25 (m, 3H), 7.99-8.06 (m, 1H), 7.41-7.44 (m, 1H), 7.35-7.40 (m, 2H), 7.27-7.35 (m, 2H), 6.97-7.20 (m, 1H), 6.89 (s, 2H), 6.43-6.51 (m, 1H), 5.61-5.72 (m, 1H), 2.98-3.04 (m, 1H), 2.87-2.98 (m, 1H), 2.51-2.63 (m, 4H), 2.05-2.15 (m, 1H). $^{19}$F NMR (376 MHz, DMSO-$d_6$) δ (ppm); −113.20. |
| 413 | MS (ESI) calcd. for $C_{26}H_{20}N_{10}OS$, 520.15 m/z, found, 521.25 [M + H]$^+$. $^1$H NMR (300 MHz, DMSO-$d_6$) δ (ppm); 8.70-8.73 (m, 1H), 8.45-8.49 (m, 1H), 8.11-8.17 (m, 2H), 8.00-8.10 (m, 3H), 7.41-7.47 (m, 2H), 7.30-7.38 (m, 2H), 6.49-6.52 (m, 1H), 5.57-5.64 (m, 1H), 2.87-3.10 (m, 2H), 2.60-2.62 (m, 1H), 2.00-2.16 (m, 1H). |
| 414 | MS (ESI) calcd. for $C_{33}H_{29}N_9O_3$: 599.24 m/z, found, 600.40 [M + H]$^+$. |
| 415 | MS (ESI) calcd. for $C_{34}H_{27}F_3N_8O_2$: 636.22 m/z, found, 637.40 [M + H]$^+$. $^1$H NMR (400 MHz, DMSO-$d_6$) δ (ppm); 8.30-8.42 (m, 2H), 7.99-8.05 (m, 1H), 7.92-7.98 (m, 1H), 7.87-7.92 (m, 1H), 7.79-7.85 (m, 1H), 7.49-7.57 (m, 1H), 7.35-7.38 (m, 1H), 7.21-7.34 (m, 3H), 6.55-6.60 (m, 1H), 6.47-6.54 (m, 1H), 5.54-5.65 (m, 1H), 2.97-3.09 (m, 1H), 2.83-2.97 (m, 1H), 2.45-2.52 (m, 1H), 2.00-2.13 (m, 2H), 0.86-0.96 (m, 2H), 0.56-0.66 (m, 2H). $^{19}$F NMR (376 MHz, DMSO-$d_6$) δ (ppm); −60.62. |
| 416 | MS (ESI) calcd. for $C_{32}H_{25}F_3N_8O_2$: 610.21 m/z, found, 612.30 [M + H]$^+$. $^1$H NMR (300 MHz, DMSO-$d_6$) δ (ppm); 8.33-8.45 (m, 2H), 7.92-8.11 (m, 4H), 7.91-7.87 (m, 2H), 7.41-7.49 (m, 1H), 7.31-7.39 (m, 2H), 6.82-6.89 (m, 1H), 6.55-6.63 (m, 1H), 5.57-5.63 (m, 1H), 3.02-3.13 (m, 1H), 2.83-3.01 (m, 1H), 2.58-2.59 (m, 1H), 2.29 (s, 3H), 2.02-2.19 (m, 1H). $^{19}$F NMR (282 MHz, DMSO-$d_6$) δ (ppm); −60.95, −73.96. (TFA salt) |
| 421 | MS (ESI) calcd. for $C_{31}H_{22}F_5N_9O$, 631.18 m/z, found, 632.35 [M + H]$^+$. $^1$HNMR (300 MHz, DMSO-$d_6$) δ (ppm); 9.27-9.39 (m, 1H), 8.53-8.55 (m, 1H), 8.28-8.36 (m, 2H), 8.05-8.11 (m, 3H), 7.80-7.95 (m, 2H), 7.45-7.52 (m, 2H), 7.35-7.37 (m, 1H), 6.92-6.93 (m, 1H), 6.76-6.85 (m, 1H), 5.64-5.80 (m, 1H), 2.85-3.12 (m, 2H), 2.55-2.63 (m, 1H), 2.03-2.20 (m, 1H). $^{19}$FNMR (282 MHz, DMSO-$d_6$) δ (ppm); −66.59, −73.88, −94.27. (TFA salt) |
| 422 | MS (ESI) calcd. for $C_{33}H_{35}N_9O$, 573.30. Found, 574.30 [M + H]$^+$. $^1$H-NMR (300 MHz, DMSO-$d_6$) δ (ppm); 8.35-8.50 (s, 2H), 8.00-8.10 (m, 1H), 7.89-8.00 (m, 1H), 7.7-7.89 (m, 1H), 7.40-7.55 (m, 1H), 7.30-7.40 (m, 1H), 7.10-7.30 (m, 2H), 6.82-7.10 (m, 2H), 6.55-6.75 (m, 1H), 6.40-6.52 (m, 1H), 4.15-4.30 (m, 1H), 4.30-4.45 (m, 1H), 3.65-3.75 (m, 1H), 3.10-3.20 (m, 1H), 2.90-3.10 (m, 3H), 2.70-2.80 (m, 2H), 2.40-2.50 (m, 1H), 2.10-2.20 (m, 4H), 1.70-1.95 (m, 5H), 1.10-1.30 (m, 2H). (formic acid salt) |
| 423 | MS (ESI) calcd. for $C_{32}H_{33}N_9O_2$ 575.28. Found, 576.40 [M + H]$^+$. $^1$H-NMR (300 MHz, DMSO-d6) δ (ppm); 8.20-8.50 (m, 2H), 8.00-8.10 (m, 1H), 7.89-8.00 (m, 1H), 7.80-7.89 (m, 1H), 7.60-7.80 (m, 1H), 7.35-7.60 (m, 2H), 7.20-7.35 (m, 1H), 6.80-7.00 (m, 2H), 6.55-6.75 (m, 1H), 6.30-6.52 (m, 1H), 5.35-5.55 (m, 1H), 4.70-5.10 (m, 1H), 4.50-4.70 (m, 1H), 4.25-4.45 (m, 2H), 3.60-3.80 (m, 1H), 3.10-3.20 (m, 2H), 2.70-3.00 (m, 4H), 2.50-2.60 (m, 1H), 2.00-2.25 (m, 3H), 1.40-1.60 (m, 2H), 1.15-1.25 (m, 1H). |
| 424 | MS (ESI) calcd. for $C_{32}H_{33}N_9O_2$, 575.28 m/z, found 576.20 [M + H]$^+$. $^1$H NMR (300 MHz, DMSO-$d_6$) δ (ppm); 8.32-8.43 (m, 2H), 8.27-8.31 (m, 1H), 8.00-8.08 (m, 1H), 7.94-7.99 (m, 1H), 7.81-7.90 (m, 1H), 7.54-7.69 (m, 1H), 7.41-7.49 (m, 1H), 7.21-7.34 (m, 2H), 6.60-6.67 (m, 1H), 6.51-6.58 (m, 1H), 5.46-5.53 (m, 1H), 4.69-4.78 (m, 1H), 4.52-4.61 (m, 1H), 4.29-4.47 (m, 2H), 3.63-3.77 (m, 1H), 3.21-3.42 (m, 1H), 2.93-3.14 (m, 2H), 2.83-2.92 (m, 1H), 2.67-2.82 (m, 3H), 2.41-2.49 (m, 1H), 1.83-2.18 (m, 3H), 1.37-1.52 (m, 3H). (formic acid salt) |
| 425 | MS (ESI) calcd. for $C_{32}H_{33}N_9O_2$ 575.28, found, 576.30[M + H]$^+$. $^1$H-NMR (300 MHz, DMSO-$d_6$) δ (ppm); 8.20-8.50 (m, 2H), 8.00-8.10 (m, 1H), 7.89-8.00 (m, 1H), 7.80-7.89 (m, 1H), 7.60-7.80 (m, 1H), 7.35-7.60 (m, 2H), 7.20-7.35 (m, 1H), 6.80-7.00 (m, 2H), 6.55-6.75 (m, 1H), 6.30-6.52 (m, 1H), 5.35-5.55 (m, 1H), 4.70-5.10 (m, 1H), 4.50-4.70 (m, 1H), 4.25-4.45 (m, 2H), 3.60-3.80 (m, 1H), 3.10-3.20 (m, 2H), 2.70-3.00 (m, 4H), 2.50-2.60 (m, 1H), 2.00-2.25 (m, 3H), 1.40-1.60 (m, 2H), 1.15-1.25 (m, 1H). (formic acid salt) |
| 426 | MS (ESI) calcd. for $C_{28}H_{23}N_{11}O_2$, 545.20 m/z, found, 546.30 [M + H]$^+$. $^1$H NMR (300 MHz, DMSO-$d_6$) δ (ppm); 9.25-9.26 (m, 1H), 8.41-8.44 (m, 1H), 8.12-8.15 (m, 2H), 8.00-8.06 (m, 2H), 7.59-7.60 (m, 1H), 7.41-7.46 (m, 2H), 7.30-7.35 (m, 2H), 6.45-6.49 (m, 1H), 5.60-5.65 (m, 1H), 4.05-4.12 (m, 3H), 2.95-3.12 (m, 2H), 2.55-2.62 (m, 1H), 2.03-2.20 (m, 1H). |
| 427 | MS (ESI) calcd. for $C_{27}H_{20}F_2N_{10}OS$, 570.15 m/z, found 571.30 [M + H]$^+$. $^1$H NMR (300 MHz, DMSO-$d_6$) δ (ppm); 8.61 (s, 1H), 8.42-8.45 (m, 1H), 8.13-8.14 (m, 2H), 8.01-8.06 (m, 2H), 7.18-7.53 (m, 5H), 6.44-6.48 (m, 1H), 5.58-5.63 (m, 1H), 2.89-3.08 (m, 2H), 2.74-2.78 (m, 1H), 2.03-2.10 (m, 1H). $^{19}$F NMR (282 MHz, DMSO-$d_6$) δ (ppm); −110.22. |
| 428 | MS (ESI) calcd. for $C_{28}H_{23}FN_{10}O$, 534.20 m/z, found, 535.35 [M + H]$^+$. $^1$H NMR (300 MHz, DMSO-$d_6$) δ (ppm); 8.50-8.68 (m, 1H), 8.27-8.46 (m, 2H), 7.89-8.15 (m, 2H), 7.72-7.85 (m, 1H), 7.20-7.52 (m, 4H), 6.49-6.68 (m, 2H), 6.32-6.48 (m, 1H), 5.41-5.68 (m, 1H), 3.65-3.88 (m, 3H), 2.98-3.21 (m, 1H), 2.73-2.97 (m, 1H), 2.41-2.47 (m, 1H), 1.98-2.26 (m, 1H). $^{19}$F-NMR (282 MHz, DMSO-$d_6$) δ (ppm); −132.754. |
| 429 | MS (ESI) calcd. for $C_{29}H_{23}N_9O_2S$, 549.17 m/z, found 550.20 [M + H]$^+$. $^1$H NMR (400 MHz, DMSO-$d_6$) δ (ppm); 8.30-8.40 (m, 2H), 8.00-8.10 (m, 1H), 7.90-8.00 (m, 1H), 7.75-7.85 (m, 1H), 7.35-7.45 (m, 3H), 7.25-7.35 (m, 2H), 6.55-6.60 (m, 1H), 6.45-6.55 (m, 1H), 5.50-5.60 (m, 1H), 3.95-4.00 (m, 3H), 2.85-3.15 (m, 2H), 2.60-2.65 (m, 1H), 1.95-2.10 (m, 1H). |

TABLE 3-continued

| Cpd ID | Characterization Data |
|---|---|
| | Characterization data of compounds prepared analogously to compound 3. |
| 433 | MS (ESI) calcd. for $C_{32}H_{31}F_2N_9O$, 595.26 m/z, found, 596.15 [M + H]$^+$. $^1$H-NMR (300 MHz, DMSO-$d_6$) δ (ppm); 8.35-8.40 (m, 2H), 8.23-8.25 (m, 1H), 8.05-8.10 (m, 1H), 7.97-8.00 (m, 1H), 7.83-7.90 (m, 1H), 7.51-7.55 (m, 1H), 7.37-7.40 (m, 1H), 7.28-7.30 (m, 2H), 6.93 (s, 2H), 6.53-6.55 (m, 1H), 6.42-6.50 (m, 1H), 4.41-4.45 (m, 1H), 4.13-4.28 (m, 1H), 3.83-3.99 (m, 1H), 3.13-3.31 (m, 2H), 2.89-3.02 (m, 4H), 2.45-2.50 (m, 1H), 1.78-2.01 (m, 5H), 1.34-1.57 (m, 1H), 1.18-1.31 (m, 2H). $^{19}$F NMR (282 MHz, DMSO-$d_6$) δ (ppm); −125.60, −138.21. (formic acid salt) |
| 436 | MS (ESI) calcd for $C_{25}H_{19}N_{11}OS$ 521.15 m/z, found, 522.25 [M + H]$^+$. $^1$H NMR (300 MHz, DMSO-$d_6$) δ (ppm); 9.59-9.68 (m, 1H), 9.43 (s, 1H), 8.39-8.48 (m, 1H), 8.11-8.17 (m, 2H), 7.97-8.08 (m, 2H), 7.41-7.52 (m, 2H), 7.26-7.40 (m, 2H), 6.89 (s, 2H), 6.40-6.50 (m, 1H), 5.54-5.68 (m, 1H), 2.84-3.20 (m, 2H), 2.55-2.64 (m, 1H), 1.99-2.15 (m, 1H). |
| 438 | MS (ESI) calcd. for $C_{27}H_{22}N_{10}OS$, 534.17 m/z, found, 535.15 [M + H]$^+$. $^1$H NMR (400 MHz, DMSO-$d_6$) δ (ppm); 8.35-8.39 (m, 1H), 7.95-8.13 (m, 2H), 7.81-7.83 (m, 1H), 7.41-7.48 (m, 2H), 7.30-7.35 (m, 2H), 6.50-6.59 (m, 2H), 5.54-5.58 (m, 1H), 3.02-3.10 (m, 1H), 2.90-2.99 (m, 1H), 2.81 (s, 3H), 2.55-2.60 (m, 1H), 1.99-2.15 (m, 1H). |
| 443 | MS (ESI) calcd. for $C_{32}H_{32}FN_9O$, 577.27 m/z, found, 578.20 [M + H]$^+$. $^1$H NMR (400 MHz, DMSO-d6) δ(ppm): 8.35-8.37 (m, 2H), 8.01 (s, 1H), 7.95 (d, J = 8.0 Hz, 1H), 7.81 (s, 1H), 7.49 (d, J = 8.0 Hz, 1H), 7.35 (s, 1H), 7.22-7.28 (m, 2H), 6.95 (s, 2H), 6.55 (s, 1H), 6.41-6.44 (m, 1H), 4.85-5.01 (m, 1H), 4.48-4.64 (m, 1H), 4.25-4.42 (m, 2H), 3.43-3.51 (m, 1H), 3.16-3.22 (m, 1H), 2.94-3.05 (m, 2H), 2.79-2.81 (m, 1H), 2.42-2.43 (m, 1H), 2.14-2.16 (m, 1H), 1.97-2.00 (m, 1H), 1.43-1.83 (m, 3H), 0.70-0.72 (m, 4H). |
| 444 | MS (ESI) calcd. for $C_{32}H_{32}FN_9O$, 577.27 m/z, found, 578.20 [M + H]$^+$. $^1$H NMR (400 MHz, DMSO-d6) δ(ppm): 8.35-8.37 (m, 2H), 8.00-8.01 (m, 1H), 7.95 (d, J = 8.0 Hz, 1H), 7.81 (s, 1H), 7.51 (d, J = 8.0 Hz, 1H), 7.35 (s, 1H), 7.23-7.29 (m, 2H), 6.96 (s, 2H), 6.54-6.55 (m, 1H), 6.41-6.44 (m, 1H), 4.30-4.41 (m, 2H), 3.93-4.12 (m, 2H), 3.63-3.79 (m, 1H), 3.48-3.49 (m, 2H), 3.11-3.12 (m, 1H), 2.94-2.99 (m, 1H), 2.75-2.83 (m, 1H), 2.33 2.35 (m, 1H), 1.95-2.05 (m, 2H), 1.75-1.80 (m, 1H), 1.51-1.45 (m, 1H), 0.70-0.72 (m, 4H). |
| 445 | MS (ESI) calcd. for $C_{32}H_{32}FN_9O$, 577.27 m/z, found, 578.20 [M + H]$^+$. $^1$H NMR (400 MHz, DMSO-d6) δ(ppm): 8.35-8.37 (m, 2H), 8.00 (s, 1H), 7.95 (d, J = 8.0 Hz, 1H), 7.81 (s, 1H), 7.52 (d, J = 8.0 Hz, 1H), 7.35 (s, 1H), 7.22-7.27 (m, 2H), 6.95 (s, 2H), 6.55 (s, 1H), 6.41-6.44 (m, 1H), 4.76-4.95 (m, 1H), 4.49-4.59 (m, 1H), 4.25-4.40 (m, 2H), 3.44-3.51 (m, 1H), 3.17-3.24 (m, 1H), 2.95-3.05 (m, 2H), 2.75-2.83 (m, 1H), 2.42-2.43 (m, 1H), 1.79-2.02 (m, 4H), 1.43-1.64 (m, 1H), 0.70-0.71 (m, 4H). |
| 446 | MS (ESI) calcd. for $C_{32}H_{32}FN_9O$, 577.27 m/z, found, 578.20 [M + H]$^+$. $^1$H NMR (400 MHz, DMSO-d6) δ(ppm): 8.35-8.37 (m, 2H), 8.00-8.02 (m, 1H), 7.95 (d, J = 8.0 Hz, 1H), 7.81 (s, 1H), 7.51 (d, J = 8.0 Hz, 1H), 7.35 (s, 1H), 7.22-7.29 (m, 2H), 6.96 (s, 2H), 6.54-6.55 (m, 1H), 6.41-6.44 (m, 1H), 4.36-4.59 (m, 2H), 3.82-4.18 (m, 2H), 3.51 3.60 (m, 2H), 3.11-3.15 (m, 1H), 2.90-2.96 (m, 1H), 2.80-2.85 (m, 1H), 2.43-2.45 (m, 1H), 1.78-2.02 (m, 3H), 1.43-1.45 (m, 1H), 1.23-1.26 (m, 1H), 0.69-0.71 (m, 4H). |
| 451 | MS (ESI) calcd. for $C_{28}H_{23}N_9OS$ 533.17 m/z, found, 534.30 [M + H]$^+$. $^1$H NMR (400 MHz, DMSO-$d_6$) δ (ppm); 8.41-8.50 (m, 1H), 8.31-8.41 (m, 2H), 7.98-8.06 (m, 1H), 7.92-7.98 (m, 1H), 7.77-7.86 (m, 1H), 7.36-7.46 (m, 2H), 7.25-7.35 (m, 2H), 6.55-6.65 (m, 1H), 6.43-6.55 (m, 1H), 5.51-5.60 (m, 1H), 2.99-3.11 (m, 1H), 2.86-2.98 (m, 1H), 2.43-2.51 (m, 1H), 2.42 (s, 3H), 2.02-2.15 (m, 1H). |
| 452 | MS (ESI) calcd. for $C_{28}H_{21}F_2N_9OS$, 569.16 m/z, found 570.10 [M + H]$^+$. $^1$H NMR (300 MHz, DMSO-$d_6$) δ (ppm); 8.35-8.45 (m, 3H), 8.27 (s, 1H), 8.00-8.10 (m, 1H), 7.90-8.00 (m, 1H), 7.81 (s, 1H), 7.40-7.50 (m, 2H), 7.00-7.36 (m, 3H), 6.55-6.62 (m, 1H), 6.45-6.55 (m, 1H), 5.55-5.65 (m, 1H), 3.00-3.15 (m, 1H), 2.85-3.00 (m, 1H), 2.55-2.60 (m, 1H), 2.00-2.15 (m, 1H). $^{19}$F NMR (282 MHz, DMSO-$d_6$) δ (ppm); −113.98. |
| 466 | MS (ESI) calcd. for $C_{29}H_{23}FN_{10}O$: 546.20 m/z. found: 547.15 [M + H]$^+$. $^1$H NMR (400 MHz, DMSO-d6) δ(ppm): 9.00 (d, J = 8.4 Hz, 1H), 8.94 (d, J = 2.4 Hz, 1H), 8.58 (d, J = 10.4 Hz, 1H), 8.18-8.20 (m, 2H), 8.10-8.15 (m, 1H), 7.92-8.09 (m, 1H), 7.40-7.53 (m, 1H), 7.18-7.39 (m, 4H), 6.91 (s, 2H), 6.36-6.59 (m, 1H), 5.50-5.72 (m, 1H), 2.93-3.12 (m, 1H), 2.73-2.91 (m, 1H), 2.50-2.55 (m, 4H), 1.89-2.18 (m, 1H). $^{19}$F NMR (376 MHz, DMSO-d6) δ (ppm): −134.685. |
| 475 | MS (ESI) calcd. for $C_{30}H_{29}F_2N_9O$, 569.25 m/z, found, 570.35 [M + H]$^+$. $^1$H NMR (300 MHz, DMSO-$d_6$) δ(ppm); 8.32 (d, J = 3.3 Hz, 2H), 7.92-7.95 (m, 1H), 7.91 (d, J = 4.8 Hz, 1H), 7.76 (d, J = 1.2 Hz, 1H), 7.46-7.49 (m, 1H), 7.25-7.28 (m, 1H), 7.15-7.19 (m, 2H), 6.61-6.65 (m, 2H), 6.37-6.41 (m, 1 H), 4.26-4.30 (m, 1H), 4.06-4.16 (m, 1H), 3.85-3.87 (m, 1H), 3.12-3.21 (m, 1H), 2.81-2.95 (m, 3H), 2.61-2.67 (m, 1H), 2.32-2.37 (m, 1H), 1.77-1.92 (m, 3H), 1.11-1.26 (m, 2H). $^{19}$F NMR (282 MHz, DMSO-$d_6$) δ(ppm); −124.399, −124.409. |
| 476 | MS (ESI) calcd. for $C_{32}H_{31}F_2N_9O$, 595.26. Found, 596.36 [M + H]$^+$. $^1$H-NMR (300 MHz, DMSO-d6) δ (ppm); 8.40-8.50 (m, 2H), 8.02-8.05 (m, 1H), 7.90-8.00 (m, 1H), 7.80-7.90 (m, 1H), 7.50-7.60 (m, 1H), 7.40-7.50 (m, 1H), 7.20-7.40 (m, 2H), 6.91 (s, 2H), 6.55-6.60 (m, 1H), 6.41-6.45 (m, 1H), 4.45-4.75 (m, 1H), 4.15-4.45 (m, 1H), 3.90-4.15 (m, 1H), 3.15-3.30 (m, 3H), 3.00-3.10 (m, 1H), 2.75-2.95 (m, 2H), 2.45-2.50 (m, 2H), 1.75-2.15 (m, 5H), 1.20-1.60 (m, 2H). (formic acid salt) |
| 477 | MS (ESI) calcd. for $C_{32}H_{32}FN_9O$, 577.27 m/z, found, 578.20 [M + H]$^+$. 1H-NMR (400 MHz, DMSO-d6) δ (ppm); 8.37 (m, 2H), 8.15 (m, 1H), 7.97 (m, 2H), 7.79 (m, 1H), 7.50-7.60 (m, 1H), 7.37 (m, 1H), 7.20-7.35 (m, 2H), 6.93 (s, 2H), 6.49 (m, 1H), 6.37 (m, 1H), 4.90-5.10 (m, 1H), 4.50-4.63 (m, 1H), 4.25-4.40 (m, 2H), 3.10-3.30 (m, 2H), 3.02-3.09 (m, 1H), 2.75-2.89 (m, 2H), 2.50-2.60 (m, 1H), 1.85-2.35 (m, 4H), 1.23-1.60 (m, 3H), 0.90-1.10 (m, 1H). (formic acid) |

TABLE 3-continued

| Cpd ID | Characterization Data |
|---|---|
| | Characterization data of compounds prepared analogously to compound 3. |
| 478 | MS(ESI) calcd. for $C_{32}H_{32}FN_9O$, 577.27 m/z, found 578.15 [M + H]$^+$. $^1$H NMR (300 MHz, DMSO-$d_6$) δ(ppm); 8.32-8.43 (m, 2H), 8.11-8.19 (m, 1H), 7.99-8.08 (m, 1H), 7.91-7.98 (m, 1H), 7.79-7.84 (m, 1H), 7.50-7.59 (m, 1H), 7.37-7.42 (m, 1H), 7.22-7.35 (m, 2H), 6.90-7.05 (m, 2H), 6.51-6.62 (m, 1H), 6.39-6.48 (m, 1H), 4.78-5.12 (m, 1H), 4.45-4.59 (m, 1H), 4.16-4.39 (m, 2H), 2.95-3.14 (m, 2H), 2.75-2.93 (m, 2H), 2.37-2.42 (m, 1H), 2.10-2.27 (m, 1H), 1.99-2.08 (m, 2H), 1.89-1.98 (m, 2H), 1.46-1.61 (m, 1H), 1.11-1.38 (m, 2H), 0.92-1.09 (m, 1H); $^{19}$F NMR (282 MHz, DMSO-$d_6$) δ(ppm); −218.510. (formic acid salt) |
| 479 | MS (ESI) calcd. for $C_{32}H_{32}FN_9O$, 577.27 m/z, found, 578.25 [M + H]$^+$. $^1$H-NMR (300 MHz, DMSO-d6) δ (ppm); 8.37 (m, 2H), 8.15 (m, 2H), 7.81 (m, 1H), 7.60 (m, 1H), 7.42 (m, 1H), 7.33 (m, 1H), 7.25 (m, 1H), 6.90 (s, 2H), 6.55 (m, 1H), 6.43 (m, 1H), 4.89 (m, 1H), 4.50-4.70 (m, 1H), 4.20-4.30 (m, 2H), 3.10-3.30 (m, 2H), 3.02-3.09 (m, 1H), 2.70-2.90 (m, 2H), 2.63 (m, 1H), 2.41-2.45 (m, 1H), 1.87-2.15 (m, 3H), 1.23-1.45 (m, 3H), 1.10-1.20 (m, 1H). $^{19}$F NMR (282 MHz, DMSO-d6) δ (ppm); −69.182, −71.072. (formic acid salt) |
| 484 | MS (ESI) calcd. for $C_{31}H_{31}NO_2$: 561.26 m/z. found, 562.20 [M + H]$^+$. $^1$H NMR (400 MHz, DMSO-d6) δ(ppm): 8.25-8.41 (m, 1H), 8.18 (d, J = 2.4 Hz, 1H), 7.90-8.08 (m, 1H), 7.68-7.87 (m, 1H), 7.40-7.60 (m, 1H), 7.33 (s, 1H), 7.10-7.26 (m, 2H), 6.91 (s, 1H), 6.31-6.58 (m, 1H), 6.05 (d, J = 2.4 Hz, 1H), 4.30-4.51 (m, 1H), 4.10-4.29 (m, 1H), 3.87-4.09 (m, 5H), 3.69-3.84 (m, 1H), 3.52-3.60 (m, 1H), 2.90-3.13 (m, 1H), 2.72-2.89 (m, 1H), 2.29-2.38 (m, 1H), 1.66-1.93 (m, 1H), 1.40-1.65 (m, 1H), 0.61-0.78 (m, 4H). |
| 489 | MS (ESI) clad. for $C_{33}H_{32}N_{10}O_2$ 600.27 m/z, found, 601.30 [M + H]$^+$. $^1$H-NMR (300 MHz, DMSO-d6) δ (ppm); 8.69-8.71 (m, 1H), 8.34-8.37 (m, 2H), 8.00-8.01 (m, 1H), 7.96-7.98(m, 1H), 7.81-7.83 (m, 1H), 7.47-7.49 (m, 1H), 7.34-7.37 (m, 1H), 7.24-7.27 (m, 2H), 6.95 (s, 2H), 6.44-6.46 (m, 1H), 6.40-6.41 (m, 1H), 4.34-4.37 (m, 1H), 4.27-4.32 (m, 1H), 3.34-3.69 (m, 1H), 3.17-3.22 (m, 2H), 2.96-3.06 (m, 2H), 2.78-2.84 (m, 1H), 2.50-2.73 (s, 4H), 2.23-2.26(m, 1H), 1.75-1.96 (m, 3H), 1.23-1.32 (m, 2H). |
| 490 | MS (ESI) calcd. for $C_{29}H_{24}N_{10}O_2$, 544.21 m/z, found, 545.30 [M + H]$^+$. $^1$H NMR (300 MHz, DMSO-$d_6$) δ (ppm); 8.90-9.15 (m, 1H), 8.42-8.62 (m, 1H), 8.31-8.41 (m, 1H), 8.15-8.25 (m, 2H), 8.02-8.14 (m, 2H), 7.77-7.92 (m, 1H), 7.55-7.73 (m, 1H), 7.27-7.52 (m, 3H), 6.72-6.92 (m, 1H), 5.52-5.80 (m, 1H), 4.67 (s, 2H), 2.80-3.21 (m, 2H), 2.55-2.62 (m, 1H), 1.93-2.23 (m, 1H). $^{19}$F NMR (282 MHz, DMSO-$d_6$) δ (ppm); −74.08. (TFA salt) |
| 491 | MS (ESI) calcd. for $C_{31}H_{26}N_{10}O$, 554.23 m/z, found 555.30 [M + H]$^+$. $^1$H NMR (300 MHz, DMSO-$d_6$ + $D_2O$) δ (ppm); 8.90-8.94 (m, 1H), 8.41-8.44 (m, 1H), 8.12-8.14 (m, 3H), 8.00-8.06 (m, 2H), 7.38-7.40 (m, 3H), 7.29-7.32 (m, 2H), 6.45-6.49 (m, 1H), 5.61-5.66 (m, 1H), 2.88-3.07 (m, 2H), 2.75-2.76 (m, 1H), 2.04-2.19 (m, 2H), 1.04-1.23 (m, 4H). |
| 492 | MS (ESI) calcd. for $C_{27}H_{22}N_{10}OS$ 534.17 m/z, found, 535.20 [M + H]$^+$. $^1$H NMR (400 MHz, DMSO-$d_6$) δ (ppm); 9.05-9.18 (m, 1H), 8.39-8.49 (m, 1H), 8.29 (s, 1H), 8.14 (s, 2H), 7.97-8.09 (m, 2H), 7.26-7.46 (m, 4H), 6.43-6.51 (m, 1H), 5.53-5.64 (m, 1H), 2.97-3.09 (m, 1H), 2.82-2.96 (m, 1H), 2.69 (s, 3H), 2.53-2.61 (m, 1H), 1.98-2.12 (m, 1H). |
| 520 | Observed mass (ESI): 561.2 [M + H]+. 1H NMR (300 MHz, DMSO-d6) δ (ppm): 8.43-8.46 (m, 1H), 8.24 (s, 1H), 8.13 (s, 2H), 7.97-8.09 (m, 2H), 7.26-7.44 (m, 4H), 6.35-6.67 (m, 1H), 5.47-5.69 (m, 1H), 2.82-3.19 (m, 2H), 2.39-2.41 (m, 2H), 1.91-2.03 (m, 1H), 1.12-1.24 (m, 2H), 0.88-1.31 (m, 2H). |
| 522 | Observed mass (ESI): 579.2 [M + H]+. 1H NMR (300 MHz, DMSO-d6) δ (ppm): 8.29-8.41 (m, 2H), 7.98-8.02 (m, 1H), 7.93-7.97 (m, 1H), 7.80-7.83 (m, 1H), 7.51-7.55 (m, 1H), 7.38-7.40 (m, 1H), 7.29-7.33 (m, 1H), 7.19-7.25 (m, 1H), 6.88-6.95 (m, 2H), 6.52-6.54 (m, 1H), 6.38-6.42 (m, 1H), 5.34-5.52 (m, 1H), 4.50-4.58 (m, 1H), 3.67-3.95 (m, 3H), 3.10-3.25 (m, 2H), 2.97-3.02 (m, 1H), 2.62-2.85 (m, 4H), 1.91-2.01 (m, 1H), 1.68-1.73 (m, 1H), 0.65-0.76 (m, 4H). 19F-NMR (300 MHz, DMSO-d6) δ (ppm): −195.05. (formic acid salt) |
| 526 | Observed mass (ESI): 589.3 [M + H]+. 1H NMR (300 MHz, DMSO-d6 + D2O) δ (ppm): 8.74-8.76 (m, 1H), 8.43-8.46 (m, 1H), 8.12-8.15 (m, 2H), 8.02-8.09 (m, 2H), 7.42-7.47 (m, 2H), 7.31-7.38 (m, 2H), 6.46-6.53 (m, 1H), 5.56-5.63 (m, 1H), 3.01-3.19 (m, 1H), 2.86-2.99 (m, 1H), 2.56-2.65 (m, 1H), 2.02-2.13 (m, 1H). |
| 527 | Observed mass (ESI): 411.25 [M + H]+. 1H NMR (400 MHz, DMSO-d6) δ (ppm): 8.25-8.46 (m, 2H), 7.91-8.04 (m, 1H), 7.76-7.89 (m, 1H), 7.62-7.75 (m, 1H), 7.52-7.62 (m, 1H), 7.18-7.48 (m, 5H), 6.44-6.63 (m, 1H), 4.18-4.32 (m, 1H), 2.82-2.93 (m, 1H), 2.69-2.81 (m, 1H), 2.33-2.42 (m, 1H), 1.58-1.73 (m, 1H). |
| 534 | Observed mass (ESI): 636.05 [M + H]+. 1H NMR (300 MHz, DMSO-d6) δ (ppm): 8.63 (s, 1H), 8.26-8.34 (m, 2H), 7.98-8.06 (m, 1H), 7.64-7.89 (m, 1H), 7.11-7.60 (m, 6H), 6.41-6.51 (m, 1H), 6.32-6.39 (m, 1H), 5.54-5.65 (m, 1H), 2.73-3.23 (m, 2H), 2.50-2.64 (m, 1H), 2.01-2.14 (m, 1H). |
| 535 | Observed mass (ESI): 594.3 [M + H]+. 1H NMR (400 MHz, DMSO-d6) δ 8.94 (d, J = 2.4 Hz, 1H), 8.41-8.30 (m, 2H), 8.17 (dd, J = 8.1, 2.4 Hz, 1H), 8.02 (dd, J = 4.9, 1.8 Hz, 1H), 7.82 (d, J = 8.7 Hz, 1H), 7.61-7.23 (m, 6H), 6.48 (dd, J = 7.6, 4.8 Hz, 1H), 6.35 (d, J = 2.7 Hz, 1H), 5.63-5.60 (m, 1H), 3.09-3.00 (m, 1H), 2.93 (q, J = 8.2 Hz, 1H), 2.55 (s, 3H), 2.18-2.01 (m, 2H). |
| 536 | Observed mass (ESI): 545.3 [M + H]+. 1H NMR (300 MHz, DMSO-d6 + D2O) δ (ppm): 8.43-8.45 (m, 1H), 8.11-8.14 (m, 2H), 8.01-8.09 (m, 2H), 7.65-7.69 (m, 1H), 7.29-7.41 (m, 4H), 6.45-6.49 (m, 1H), 5.52-5.57 (m, 1H), 3.01-3.07 (m, 1H), 2.82-2.98 (m, 1H), 2.49-2.52(m, 1H), 2.14-2.21 (m, 1H), 2.01-2.13 (m, 1H), 1.04-1.17 (m, 4H). |

TABLE 3-continued

| Characterization data of compounds prepared analogously to compound 3. | |
|---|---|
| Cpd ID | Characterization Data |
| 537 | Observed mass (ESI): 620.25 [M + H]+. 1H NMR (400 MHz, DMSO-d6) δ (ppm): 8.95-9.05 (m, 1H), 8.84-8.94 (m, 1H), 8.35-8.43 (m, 1H), 8.29-8.34 (m, 1H), 8.09-8.18 (m, 1H), 7.97-8.05 (m, 1H), 7.76-7.86 (m, 1H), 7.43-7.66 (m, 1H), 7.34-7.42 (m, 3H), 7.21-7.33 (m, 2H), 6.41-6.51 (m, 1H), 6.29-6.39 (m, 1H), 5.57-5.71 (m, 1H), 2.98-3.09 (m, 1H), 2.84-2.97 (m, 1H), 2.53-2.62 (m, 1H), 2.13-2.23 (m, 1H), 2.04-2.12 (m, 1H), 0.92-1.11(m, 4H). |
| 538 | Observed mass (ESI): 555.2 [M + H]+. 1H NMR (300 MHz, DMSO-d6) δ (ppm): 8.43-8.63 (m, 1H), 8.13 (s, 2H), 7.95-8.09 (m, 3H), 7.40-7.50 (m, 2H), 6.80-7.39 (3), 6.29-6.58 (m, 1H), 5.45-5.81 (m, 1H), 2.81-3.15 (m, 2H), 2.62-2.67 (m, 1H), 2.01-2.22 (m, 1H). 19F NMR (282 MHz, DMSO-d6) δ (ppm): −119.34. |
| 539 | Observed mass (ESI): 569.3 [M + H]+. 1H NMR (400 MHz, DMSO-d6) δ (ppm): 8.41-8.46 (m, 1H), 7.99-8.17 (m, 4H), 7.61-7.71 (m, 1H), 7.36-7.51 (m, 2H), 7.25-7.35 (m, 2H), 7.09-7.17 (m, 1H), 6.42-6.52 (m, 1H), 5.53-5.62 (m, 1H), 2.96-3.07 (m, 1H), 2.82-2.95 (m, 1H), 2.55-2.61 (m, 1H), 2.45-2.51 (m, 3H), 1.93-2.16 (m, 2H), 0.95-1.05 (m, 2H), 0.87-0.94 (m, 2H). |
| 540 | Observed mass (ESI): 558.25 [M + H]+. 1H NMR (400 MHz, DMSO-d6) δ (ppm): 8.65-8.70 (m, 1H), 8.43-8.50 (m, 1H), 8.13 (s, 2H), 7.98-8.07 (m, 1H), 7.40-7.52 (m, 1H), 7.33-7.42 (m, 1H), 7.19-7.48 (m, 4H), 6.36-6.67 (m, 1H), 5.40-5.70 (m, 1H), 3.93 (s, 3H), 2.95-3.06 (m, 1H), 2.73-2.88 (m, 1H), 2.49-2.50 (m, 1H), 1.85-2.13 (m, 2H), 0.96-1.09 (m, 2H), 0.84-0.91 (m, 2H). |
| 541 | Observed mass (ESI): 585.25 [M + H]+. 1H NMR (400 MHz, DMSO-d6 + D2O) δ (ppm): 8.88-9.19 (m, 1H), 8.29-8.59 (m, 1H), 8.07-8.16 (m, 2H), 7.96-8.06 (m, 2H), 7.23-7.48 (m, 5H), 6.33-6.62 (m, 1H), 5.42-5.73 (m, 1H), 2.97-3.22 (m, 1H), 2.74-2.96 (m, 1H), 2.61-2.66 (m, 3H), 2.54-2.60 (m, 1H), 1.95-2.14 (m, 1H). |
| 558 | Observed mass (ESI): 600.62 [M + H]+. 1H NMR (300 MHz, DMSO-d6) δ 9.35 (d, J = 8.2 Hz, 1H), 8.61-8.58 (m, 1H), 8.29 (d, J = 8.6 Hz, 1H), 8.10-8.01 (m, 1H), 7.73-7.64 (m, 2H), 7.59-7.16 (m, 4H), 7.03 (d, J = 8.6 Hz, 1H), 6.80-6.70 (m, 1H), 6.01 (d, J = 2.3 Hz, 1H), 5.62-5.50 (m, 1H), 3.73 (s, 3H), 3.10-2.82 (m, 2H), 2.08-2.00 (m, 1H), 1.25 (d, J = 10.0 Hz, 1H). (TFA salt) |
| 578 | Observed mass (ESI): 568.25 [M + H]+. 1H-NMR (300 MHz, DMSO-d6) δ (ppm): 8.39-8.45 (m, 1H), 7.95-8.12 (m, 4H), 7.69 (s, 1H), 7.35-7.42 (m, 2H), 7.00-7.35 (m, 3H), 6.45-6.52 (m, 1H), 4.00 (s, 3H), 3.00-3.15 (m, 1H), 2.85-3.00 (m, 1H), 2.50-2.52 (m, 1H), 2.00-2.12 (m, 1H). |
| 583 | Observed mass (ESI): 589.2 [M + H]+. 1H NMR (300 MHz, DMSO-d6) δ 9.30-9.27(m, 1H), 9.16 (m, 1H), 8.48-8.45(m, 1H), 8.16 (s,2H).8.03-8.00(m, 2H), 7.84-7.81(m, 1H), 7.45-7.43(m, 2H), 7.36-7.33(m, 2H), 7.22-7.04 (m, 3H). 6.89-6.85(m, 1H), 6.48-6.44(m, 1H), 5.04 (s, 1H). 2.94-2.91(m, 2H), 1.47-1.45(m, 2H). |
| 585 | Observed mass (ESI): 609.3 [M + H]+. 1H NMR (400 MHz, DMSO-d6) δ (ppm): 8.32-8.40 (m, 2H), 8.22 (s, 1H), 8.01 (dd, J = 5.0, 1.8 Hz, 1H), 7.95 (d, J = 8.6 Hz, 1H), 7.78-7.84 (m, 1H), 7.49 (d, J = 7.9 Hz, 1H), 7.35 (s, 1H), 7.20-7.29 (m, 2H), 6.94 (s, 2H), 6.52-6.58 (m, 1H), 6.39-6.47(m, 1H), 4.35-4.40 (m, 1H), 4.01-4.14 (m, 2H), 3.09-3.20 (m, 2H), 2.91-3.04 (m, 2H), 2.73-2.86 (m, 1H), 2.43-2.48 (m, 1H), 2.29 (s, 3H), 2.02-2.07 (m, 1H), 1.92-1.99 (m, 1H), 1.78-1.83 (m, 1H), 1.36-1.49 (m, 2H). |
| 587 | Observed mass (ESI): 553.22 [M + H]+. 1H NMR (300 MHz, DMSO-d6) δ 9.07-9.05(m, 1H), 8.97-8.96 (m, 1H), 8.18-8.16(m, 2H), 8.03-8.01 (m, 1H).7.42-7.33 (m, 4H), 7.20 (s, 1H), 6.90 (s, 1H), 6.66 (s, 1H), 6.48-6.45 (m, 1H). 6.67-6.65 (m, 1H), 5.33-5.31(m, 2H), 5.04(s, 1H), 2.92 (s, 1H).2.67 (s, 2H), 2.09-2.06 (m, 1H). 1.47-1.43 (m, 2H). |
| 588 | Observed mass (ESI): 611.2 [M + H]+. 1H NMR (300 MHz, DMSO-d6) δ (ppm): 8.61-8.75 (m, 1H), 8.39-8.59 (m, 1H), 7.92-8.05 (m, 2H), 7.87 (s, 1H), 7.11-7.65 (m, 5H), 6.46-6.54 (m, 1H), 5.45-5.65 (m, 1H), 2.85-3.15 (m, 2H), 2.61-2.72 (m, 1H), 1.83-2.22 (m, 2H), 0.98-1.10 (m, 2H), 0.77-0.88 (m, 2H). |
| 595 | Observed mass (ESI): 637.05 [M + H]+. 1H NMR (400 MHz, DMSO-d6) δ 9.40 (d, J = 8.3 Hz, 1H), 8.65-8.59 (m, 1H), 8.47-8.40 (m, 1H), 8.10 (d, J = 2.9 Hz, 1H), 8.03-7.99 (m, 1H), 7.98-7.92 (m, 1H), 7.64-7.41 (m, 3H), 7.39-7.22 (m, 3H), 6.88 (s, 1H), 6.47-6.40 (m, 1H), 5.67-5.56 (m, 1H), 3.07-2.99 (m, 1H), 2.97-2.87 (m, 1H), 2.61-2.55 (m, 1H), 2.12-2.01 (m, 1H). |

Example 4: (S)—N-(5-(2-(2-aminopyridin-3-yl)-5-(1H-pyrazol-1-yl)-3H-imidazo[4,5-b]pyridin-3-yl)-2,3-dihydro-1H-inden-1-yl)-5-methyl-11H-pyrazole-3-carboxamide (Compound 4)

Compound 4

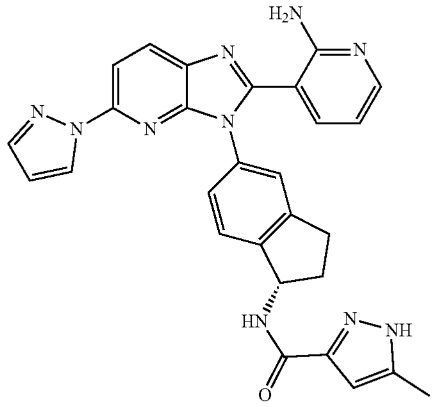

Compound 4 was prepared in a manner analogous to Compound 3 using 5-methyl-3-pyrazolecarboxylic acid in place of 3,4-difluoro-5-anisic acid. MS (ESI) calculated for $C_{28}H_{24}N_{10}O$: 516.21 m/z, found 517.30 $[M+H]^+$. $^1H$ NMR (400 MHz, DMSO-$d_6$) (ppm) δ 8.45-8.40 (m, 2H), 8.39 (d, J=2.6 Hz, 1H), 8.08 (dd, J=5.9, 1.7 Hz, 1H), 8.01 (d, J=8.6 Hz, 1H), 7.83 (d, J=1.6 Hz, 1H), 7.73 (dd, J=7.6, 1.7 Hz, 1H), 7.44 (s, 1H), 7.34 (s, 1H), 7.33 (s, 1H), 6.80 (dd, J=7.6, 5.9 Hz, 1H), 6.56 (dd, J=2.6, 1.7 Hz, 1H), 6.49 (s, 1H), 5.58 (dd, J=8.4, 8.4 Hz, 1H), 3.03 (ddd, J=16.3, 8.9, 2.7 Hz, 1H), 2.88 (ddd, J=16.4, 8.5, 8.5 Hz, 1H), 2.48-2.41 (m, 1H), 2.26 (s, 3H), 2.14 (dddd, J=12.3, 8.9, 8.9, 8.8 Hz, 1H). (TFA salt)

Example 5: (S)—N-(5-(2-(2-aminopyridin-3-yl)-5-(1H-pyrazol-1-yl)-3H-imidazo[4,5-b]pyridin-3-yl)-2,3-dihydro-1H-inden-1-yl)-2-(isoxazol-3-yloxy)acetamide (Compound 5)

Compound 5

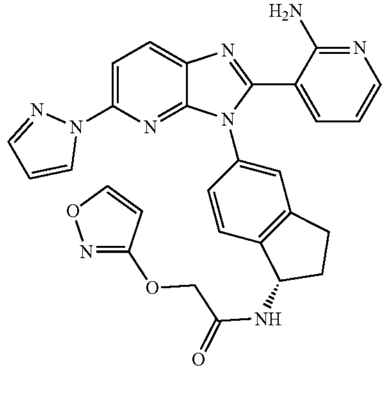

Compound 5 was prepared in a manner analogous to Compound 3 using potassium (3-isoxazolyloxy)acetate in place of 3,4-difluoro-5-anisic acid and excluding the initial addition of N,N-diisopropylethylamine. MS (ESI) calculated for $C_{28}H_{23}N_9O_3$: 533.19 m/z, found 534.25 $[M+H]^+$. $^1H$ NMR (400 MHz, DMSO-$d_6$) δ (ppm) 8.67-8.63 (m, 2H), 8.42 (d, J=8.6 Hz, 1H), 8.36 (d, J=2.5 Hz, 1H), 8.07 (dd, J=6.0, 1.7 Hz, 1H), 8.01 (d, J=8.7 Hz, 1H), 7.82 (d, J=1.7 Hz, 1H), 7.77 (dd, J=7.5, 1.7 Hz, 1H), 7.44 (s, 1H), 7.34 (s, 1H), 7.33 (s, 1H), 6.81 (dd, J=7.6, 6.0 Hz, 1H), 6.56 (dd, J=2.6, 1.7 Hz, 1H), 6.35 (d, J=1.8 Hz, 1H), 5.42 (dd, J=8.3, 8.3 Hz, 1H), 4.75 (s, 2H), 2.99 (ddd, J=16.4, 8.9, 2.9 Hz, 1H), 2.87 (ddd, J=16.4, 8.5, 8.5 Hz, 1H), 2.47-2.41 (m, 1H), 1.96 (dddd, J=12.4, 8.9, 8.9, 8.8 Hz, 1H). (TFA salt)

Example 6: (S)—N-(5-(2-(2-aminopyridin-3-yl)-5-(1H-pyrazol-1-yl)-3H-imidazo[4,5-b]pyridin-3-yl)-2,3-dihydro-1H-inden-1-yl)-5-methyl-4-oxo-4,5-dihydro-2H-pyrrolo[3,4-c]pyridine-1-carboxamide (Compound 6)

Compound 6

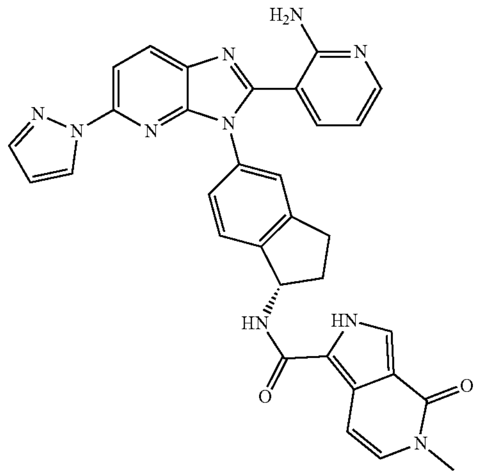

Compound 6 was prepared in a manner analogous to Compound 3 using 5-methyl-4-oxo-2,5-dihydro-2,5-diaza-1-indenecarboxylic acid in place of 3,4-difluoro-5-anisic acid. MS (ESI) calculated for $C_{32}H_{26}N_{10}O_2$: 582.22 m/z, found 583.30 $[M+H]^+$. $^1H$ NMR (400 MHz, DMSO-$d_6$) δ (ppm) 12.51 (d, J=3.4 Hz, 1H), 8.43 (d, J=8.6 Hz, 1H), 8.39 (dd, J=2.6, 0.7 Hz, 1H), 8.18 (d, J=8.0 Hz, 1H), 8.08 (dd, J=5.8, 1.7 Hz, 1H), 8.01 (d, J=8.6 Hz, 1H), 7.83 (dd, J=1.7, 0.7 Hz, 1H), 7.72-7.66 (m, 2H), 7.49-7.42 (m, 2H), 7.36 (dd, J=8.1, 2.0 Hz, 1H), 7.10 (d, J=7.4 Hz, 1H), 6.88 (dd, J=7.4, 0.7 Hz, 1H), 6.76 (dd, J=7.6, 5.8 Hz, 1H), 6.57 (dd, J=2.6, 1.7 Hz, 1H), 5.61 (q, J=8.0 Hz, 1H), 3.39 (s, 3H), 3.06 (ddd, J=16.7, 9.0, 3.3 Hz, 1H), 2.92 (ddd, J=16.3, 8.4, 8.4 Hz, 1H), 2.57 (dddd, J=12.4, 7.9, 7.9, 3.1 Hz, 1H), 2.05 (dddd, J=12.5, 8.7, 8.7, 8.7 Hz, 1H). (TFA salt)

Example 7: N—{(S)-5-[2-(2-amino-3-pyridyl)-5-(1-pyrazolyl)-3H-1,3,4-triazainden-3-yl]-1-indanyl}5-(dimethylamino)-2-fluorobenzamide (Compound 7)

Compound 7

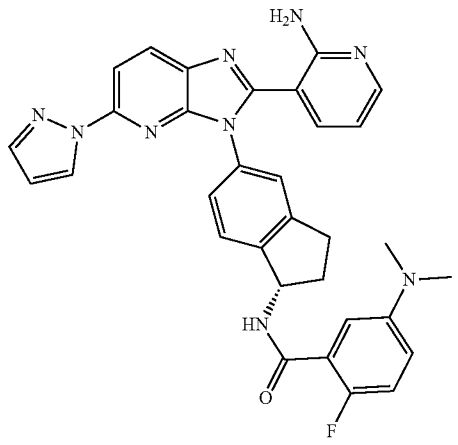

Compound 7 was prepared in a manner analogous to Compound 3 using 5-(dimethylamino)-2-fluorobenzoic acid in place of 3,4-difluoro-5-anisic acid. MS (ESI) calculated for $C_{32}H_{28}FN_9O$: 573.24 m/z, found 574.30 $[M+H]^+$. $^1H$ NMR (400 MHz, DMSO-$d_6$) δ (ppm): 8.63 (dd, J=8.2, 1.6 Hz, 1H), 8.37 (d, J=8.7 Hz, 1H), 8.31 (dd, J=2.6, 0.7 Hz, 1H), 8.04 (dd, J=6.1, 1.7 Hz, 1H), 7.95 (d, J=8.6 Hz, 1H), 7.76-7.75 (m, 1H), 7.73 (d, J=1.7 Hz, 1H), 7.41 (d, J=1.9 Hz, 1H), 7.37 (d, J=8.0 Hz, 1H), 7.31 (dd, J=8.0, 1.9 Hz, 1H), 7.09-7.02 (m, 1H), 6.89 (dd, J=5.7, 3.2 Hz, 1H), 6.82 (ddd, J=9.1, 3.6, 3.6 Hz, 1H), 6.77 (dd, J=7.5, 6.1 Hz, 1H), 6.49 (dd, J=2.6, 1.7 Hz, 1H), 5.52 (dd, J=8.2, 8.2 Hz, 1H), 3.02-2.92 (m, 1H), 2.89-2.79 (m, 7H), 2.50-2.45 (m, 1H), 2.07-1.91 (m, 1H). (TFA salt)

Example 8: N—{(S)-5-[2-(2-amino-3-pyridyl)-5-(1-pyrazolyl)-3H-1,3,4-triazainden-3-yl]-1-indanyl}-2-methyl-1-oxo-1,2-dihydro-3-isoquinolinecarboxamide (Compound 8)

Compound 8

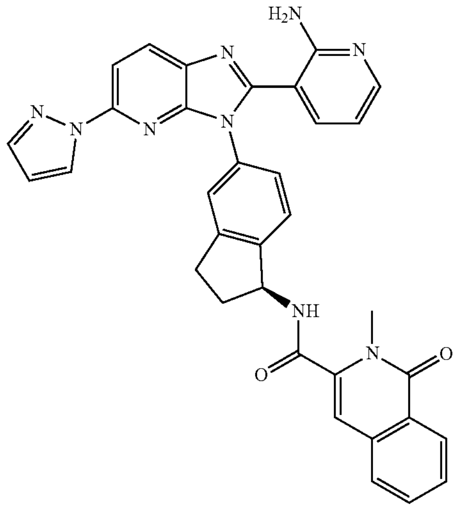

Compound 8 was prepared in a manner analogous to Compound 3 using 2-methyl-1-oxo-1,2-dihydro-3-isoquinolinecarboxylic acid in place of 3,4-difluoro-5-anisic acid. MS (ESI) calculated for $C_{34}H_{27}N_9O_2$: 593.23 m/z, found 594.25 $[M+H]^+$. $^1H$ NMR (400 MHz, DMSO-$d_6$) δ (ppm) 9.31 (d, J=8.1 Hz, 1H), 8.37 (d, J=8.6 Hz, 1H), 8.32 (dd, J=2.6, 0.7 Hz, 1H), 8.18 (dd, J=8.1, 1.1 Hz, 1H), 8.03 (dd, J=5.9, 1.7 Hz, 1H), 7.95 (d, J=8.6 Hz, 1H), 7.76 (dd, J=1.7, 0.7 Hz, 1H), 7.72-7.65 (m, 3H), 7.51 (ddd, J=8.2, 5.0, 3.4 Hz, 1H), 7.47 (d, J=8.0 Hz, 1H), 7.43 (d, J=2.0 Hz, 1H), 7.33 (dd, J=8.0, 2.0 Hz, 1H), 6.83 (s, 1H), 6.72 (dd, J=7.6, 5.9 Hz, 1H), 6.49 (dd, J=2.6, 1.6 Hz, 1H), 5.50 (dd, J=8.0, 8.0 Hz, 1H), 3.48 (s, 3H), 3.00 (ddd, J=16.4, 8.9, 3.3 Hz, 1H), 2.87 (ddd, J=16.3, 8.3, 8.3 Hz, 1H), 2.52 (dddd, J=12.6, 7.9, 7.9, 3.3 Hz, 1H), 2.07-1.96 (m, 1H). (TFA salt)

Example 9: N—{(S)-5-[2-(2-amino-3-pyridyl)-5-(1-pyrazolyl)-3H-1,3,4-triazainden-3-yl]-1-indanyl}(3-ethynyl-3-oxetanyloxy)acetamide (Compound 9)

Compound 9

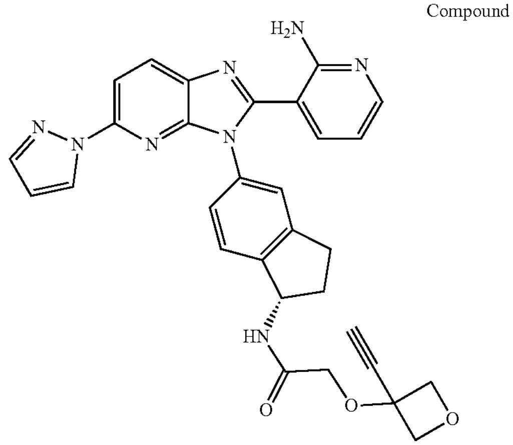

Compound 9 was prepared in a manner analogous to Compound 3 using (3-ethynyl-3-oxetanyloxy)acetic acid in place of 3,4-difluoro-5-anisic acid. MS (ESI) calculated for $C_{30}H_{26}N_8O_3$: 546.21 m/z, found 547.30 $[M+H]^+$. $^1H$ NMR (400 MHz, DMSO-$d_6$) δ (ppm) 8.42 (d, J=8.6 Hz, 1H), 8.40-8.36 (m, 2H), 8.08 (dd, J=5.8, 1.8 Hz, 1H), 8.01 (d, J=8.6 Hz, 1H), 7.83 (dd, J=1.6, 0.7 Hz, 1H), 7.70 (dd, J=7.6, 1.7 Hz, 1H), 7.44 (s, 1H), 7.34 (d, J=1.4 Hz, 2H), 6.76 (dd, J=7.6, 5.8 Hz, 1H), 6.57 (dd, J=2.6, 1.7 Hz, 1H), 5.45 (dd, J=8.4, 8.4 Hz, 1H), 4.69 (dd, J=7.4, 2.3 Hz, 2H), 4.64 (d, J=6.8 Hz, 2H), 4.06 (d, J=1.8 Hz, 2H), 3.99 (s, 1H), 3.01 (ddd, J=16.3, 8.9, 2.7 Hz, 1H), 2.88 (ddd, J=16.4, 8.5, 8.5 Hz, 1H), 2.44 (dddd, J=12.4, 8.0, 7.9, 2.8 Hz, 1H), 2.04 (dddd, J=12.4, 9.0, 9.0, 9.0 Hz, 1H). (TFA salt)

Example 10: N—{(S)-5-[2-(2-amino-3-pyridyl)-5-(1-pyrazolyl)-3H-1,3,4-triazainden-3-yl]-1-indanyl}3-(difluoromethyl)-3-methoxycyclobutanecarboxamide (Compound 10)

Compound 10

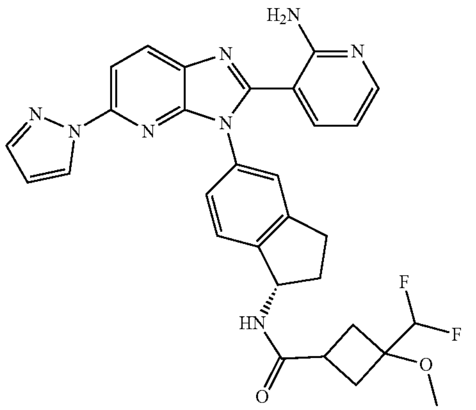

Compound 10 was prepared in a manner analogous to Compound 3 using 3-(difluoromethyl)-3-methoxycyclobutanecarboxylic acid in place of 3,4-difluoro-5-anisic acid. Note that racemic acid was used but a single unknown diastereomer was obtained. MS (ESI) calculated for $C_{30}H_{28}F_2N_8O_2$: 570.23 m/z, found 571.30 $[M+H]^+$. $^1H$ NMR (400 MHz, DMSO-$d_6$) (ppm) δ 8.42 (d, J=8.6 Hz, 1H), 8.39-8.34 (m, 2H), 8.07 (dd, J=5.8, 1.7 Hz, 1H), 8.00 (d, J=8.6 Hz, 1H), 7.83 (dd, J=1.6, 0.7 Hz, 1H), 7.67 (dd, J=7.6, 1.7 Hz, 1H), 7.43 (s, 1H), 7.34-7.29 (m, 2H), 6.74 (dd, J=7.6, 5.8 Hz, 1H), 6.56 (dd, J=2.6, 1.7 Hz, 1H), 6.15 (t, J=55.4 Hz, 1H), 5.36 (dd, J=8.1, 8.1 Hz, 1H), 3.27 (s, 3H), 2.97 (ddd, J=16.3, 8.9, 3.0 Hz, 1H), 2.86 (ddd, J=16.3, 8.4, 8.4 Hz, 1H), 2.74 (ddd, J=8.7, 8.7, 8.7 Hz, 1H), 2.47-2.39 (m, 3H), 2.35-2.25 (m, 2H), 1.87 (dddd, J=12.4, 8.9, 8.9, 8.9 Hz, 1H). 19F NMR (376 MHz, DMSO) δ (ppm): −132.55. (TFA salt)

Example 11: N—{(S)-5-[2-(2-amino-3-pyridyl)-5-(1-pyrazolyl)-3H-1,3,4-triazainden-3-yl]-1-indanyl}(1-methyl-5-oxo-2-pyrrolidinyl)acetamide (Compound 11)

Compound 11

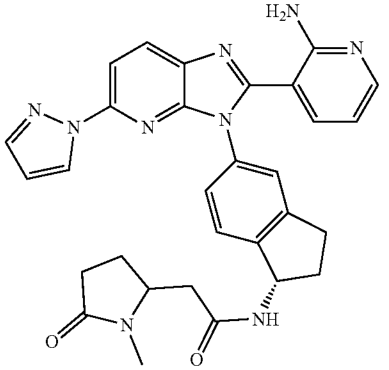

Compound 11 was prepared in a manner analogous to Compound 3 using (1-methyl-5-oxo-2-pyrrolidinyl)acetic acid in place of 3,4-difluoro-5-anisic acid. Note that racemic acid was used and a mixture of diastereomers was obtained. MS (ESI) calculated for $C_{30}H_{29}N_9O_2$: 547.24 m/z, found 548.35 $[M+H]^+$. $^1H$ NMR (400 MHz, DMSO-$d_6$) δ (ppm): 8.44 (dd, J=8.1, 3.3 Hz, 1H), 8.37 (d, J=8.6 Hz, 1H), 8.31 (dd, J=2.6, 0.7 Hz, 1H), 8.03 (dd, J=6.0, 1.7 Hz, 1H), 7.95 (d, J=8.6 Hz, 1H), 7.76 (dd, J=1.6, 0.7 Hz, 1H), 7.72-7.67 (m, 1H), 7.40-7.38 (m, 1H), 7.31-7.23 (m, 2H), 6.76-6.71 (m, 1H), 6.51-6.48 (m, 1H), 5.35-5.26 (m, 1H), 3.84-3.76 (m, 1H), 2.98-2.87 (m, 1H), 2.85-2.72 (m, 1H), 2.63 (s, 3H), 2.58-2.51 (m, 1H), 2.42-2.34 (m, 1H), 2.24-1.98 (m, 4H), 1.88-1.60 (m, 2H). (TFA salt)

Example 12: (S)—N-(5-(2-(2-aminopyridin-3-yl)-5-(1H-pyrazol-1-yl)-3H-imidazo[4,5-b]pyridin-3-yl)-2,3-dihydro-1H-inden-1-yl)-4-methoxybenzamide (Compound 12)

Compound 12

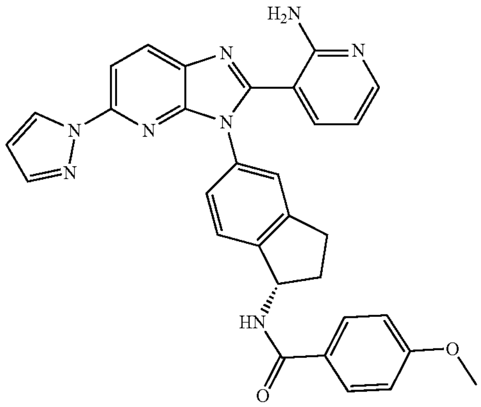

Compound 12 was prepared in a manner analogous to Compound 3 using 4-methoxybenzoic acid in place of 3,4-difluoro-5-anisic acid. MS (ESI) calcd. for $C_{31}H_{26}N_8O_2$: 542.22 m/z, found 543.30 $[M+H]^+$. $^1H$ NMR (300 MHz, DMSO-$d_6$) δ (ppm): 8.40-8.50 (m, 2H), 8.02-8.10 (m, 2H), 7.90-7.95 (m, 2H), 7.83-7.85 (m, 1H), 7.74-7.78 (m, 1H), 7.45-7.49 (m, 1H), 7.30-7.40 (m, 2H), 7.01-7.09 (m, 2H), 6.78-6.90 (m, 1H), 6.60-6.62 (m, 1H), 5.60-5.69 (m, 1H), 3.80 (s, 3H), 3.05-3.13 (m, 1H), 2.88-3.00 (m, 1H), 2.50-2.54 (m, 1H), 2.03-2.18 (m, 1H). (TFA salt)

Example 13: (S)—N-(5-(2-(2-aminopyridin-3-yl)-5-(1H-pyrazol-1-yl)-3H-imidazo[4,5-b]pyridin-3-yl)-2,3-dihydro-1H-inden-1-yl)-1-methyl-1H-pyrazole-3-carboxamide (Compound 13)

Compound 13

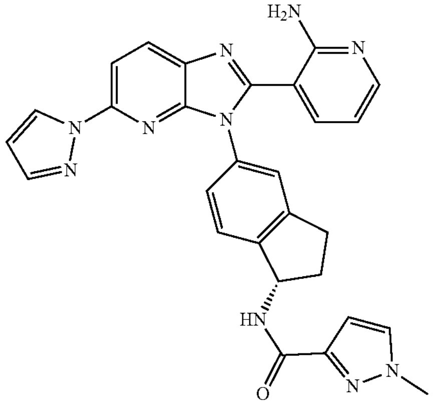

Compound 13 was prepared in a manner analogous to Compound 3 using 1-methyl-1H-pyrazole-3-carboxylic acid in place of 3,4-difluoro-5-anisic acid. MS (ESI) calcd. for $C_{28}H_{24}N_{10}O$: 516.21 m/z, found 517.20 $[M+H]^+$. $^1H$ NMR (300 MHz, DMSO-$d_6$) δ (ppm): 8.41-8.49 (m, 1H), 8.33-8.40 (m, 1H), 8.04-8.11 (m, 1H), 7.97-8.03 (m, 1H), 7.73-7.88 (m, 3H), 7.44 (s, 1H), 7.27-7.38 (m, 2H), 6.77-6.91 (m, 1H), 6.64-6.76 (m, 1H), 6.50-6.61 (m, 1H), 5.47-5.66 (m, 1H), 3.90 (s, 3H), 2.98-3.15 (m, 1H), 2.78-2.97 (m, 1H), 2.37-2.51 (m, 1H), 2.03-2.22 (m, 1H). (TFA salt)

Example 14: (S)—N-(5-(2-(2-aminopyridin-3-yl)-5-(1H-pyrazol-1-yl)-3H-imidazo[4,5-b]pyridin-3-yl)-2,3-dihydro-1H-inden-1-yl)thiazole-5-carboxamide (Compound 14)

Compound 14

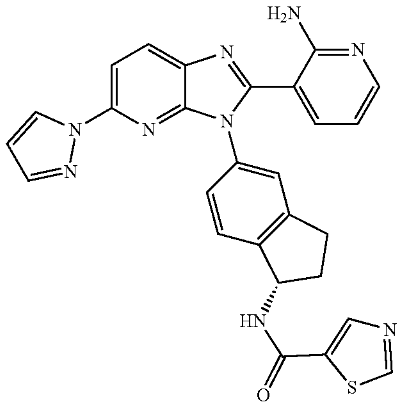

Compound 14 was prepared in a manner analogous to Compound 3 using thiazole-5-carboxylic acid in place of 3,4-difluoro-5-anisic acid. MS (ESI) calcd. for $C_{27}H_{21}N_9OS$: 519.16 m/z, found 520.20 $[M+H]^+$. $^1H$ NMR (400 MHz, DMSO-$d_6$) δ (ppm): 9.21-9.27 (m, 1H), 8.55-8.59 (m, 1H), 8.32-8.39 (m, 2H), 8.01-8.05 (m, 1H), 7.94-7.99 (m, 1H), 7.83-7.90 (m, 1H), 7.36-7.40 (m, 2H), 7.26-7.31 (m, 2H), 6.56-6.60 (m, 1H), 6.45-6.52 (m, 1H), 5.56-5.64 (m, 1H), 2.98-3.11 (m, 1H), 2.84-2.96 (m, 1H), 2.60-2.63 (m, 1H), 2.05-2.16 (m, 1H). (formic acid salt)

Example 15: (S)—N-(5-(2-(2-aminopyridin-3-yl)-5-(1H-pyrazol-1-yl)-3H-imidazo[4,5-b]pyridin-3-yl)-2,3-dihydro-1H-inden-1-yl)oxetane-3-carboxamide (Compound 15)

Compound 15

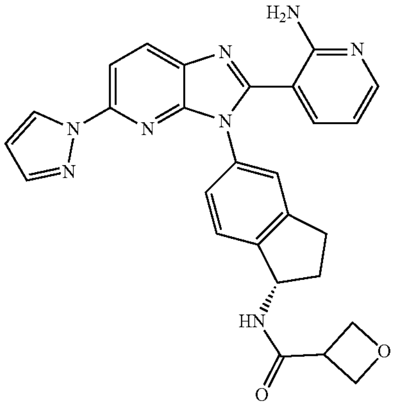

Compound 15 was prepared in a manner analogous to Compound 3 using oxetane-3-carboxylic acid in place of 3,4-difluoro-5-anisic acid. MS (ESI) calcd. for $C_{27}H_{24}N_8O_2$: 492.20 m/z, found: 493.20 $[M+H]^+$. $^1H$ NMR (300 MHz, DMSO-$d_6$) δ (ppm): 8.35-8.40 (m, 2H), 8.01-8.07 (m, 1H), 7.95-7.99 (m, 1H), 7.83-7.86 (m, 1H), 7.29-7.40 (m, 4H), 6.57-6.60 (m, 1H), 6.44-6.49 (m, 1H), 5.37-5.48 (m, 1H), 4.65-4.71 (m, 4H), 3.79-3.90 (m, 1H), 2.85-3.03 (m, 2H), 2.55-2.62 (m, 1H), 1.85-1.93 (m, 1H).

Example 16: (S)—N-(5-(2-(2-aminopyridin-3-yl)-5-(1H-pyrazol-1-yl)-3H-imidazo[4,5-b]pyridin-3-yl)-2,3-dihydro-1H-inden-1-yl)-3-fluoro-4-hydroxybenzamide (Compound 16)

Compound 16

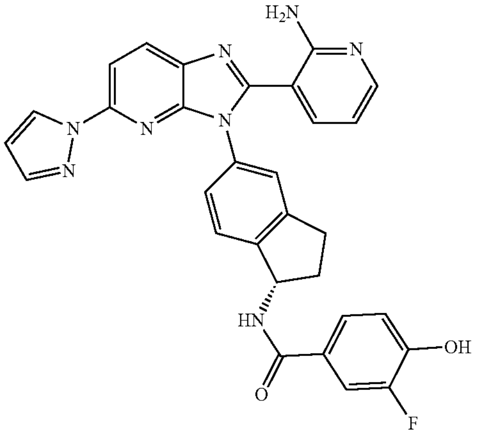

Compound 16 was prepared in a manner analogous to Compound 3 using 3-fluoro-4-hydroxybenzoic acid in place of 3,4-difluoro-5-anisic acid. MS (ESI) calcd. for $C_{30}H_{23}FN_8O_2$: 546.19 m/z, found 547.25 $[M+H]^+$. $^1H$ NMR (400 MHz, DMSO-$d_6$) δ (ppm): 8.35-8.40 (m, 2H), 8.01-8.07 (m, 1H), 7.92-7.97 (m, 1H), 7.80-7.82 (m, 1H), 7.72-7.78 (m, 1H), 7.65-7.69 (m, 1H), 7.37-7.40 (m, 1H), 7.31-7.35 (m, 1H), 7.25-7.30 (m, 2H), 6.97-7.05 (m, 1H), 6.55-6.58 (m, 1H), 6.43-6.48 (m, 1H), 5.58-5.65 (m, 1H), 2.99-3.07 (m, 1H), 2.82-2.94 (m, 1H), 2.54-2.57 (m, 1H), 2.01-2.10 (m, 1H). $^{19}F$ NMR (376 MHz, DMSO-$d_6$) δ (ppm): −136.43.

Example 17: (S)—N-(5-(2-(2-aminopyridin-3-yl)-5-(1H-pyrazol-1-yl)-3H-imidazo[4,5-b]pyridin-3-yl)-2,3-dihydro-1H-inden-1-yl)imidazo[1,2-a]pyridine-6-carboxamide (Compound 17)

Compound 17

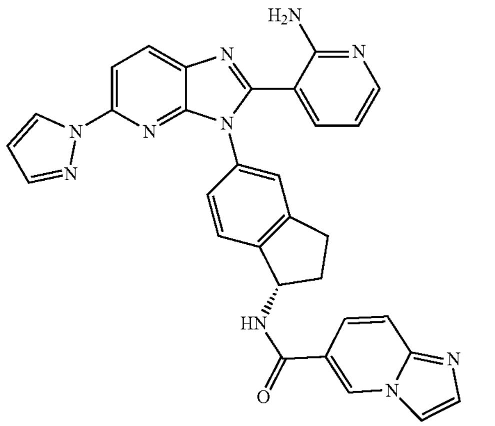

Compound 17 was prepared in a manner analogous to Compound 3 using imidazo[1,2-a]pyridine-6-carboxylic acid in place of 3,4-difluoro-5-anisic acid. MS (ESI) calcd. for $C_{31}H_{24}N_{10}O$, 552.21 m/z, found: 553.20 $[M+H]^+$. $^1H$ NMR (300 MHz, DMSO-$d_6$) δ (ppm): 9.12-9.22 (m, 1H), 8.29-8.41 (m, 2H), 8.06-8.11 (m, 1H), 7.98-8.05 (m, 1H), 7.89-7.97 (m, 1H), 7.79-7.86 (m, 1H), 7.70-7.78 (m, 1H), 7.58-7.69 (m, 2H), 7.36-7.48 (m, 2H), 7.22-7.35 (m, 2H), 6.51-6.60 (m, 1H), 6.39-6.50 (m, 1H), 5.57-5.70 (m, 1H), 3.01-3.17 (m, 1H), 2.85-3.00 (m, 1H), 2.53-2.69 (m, 1H), 2.01-2.21 (m, 1H).

Example 18: (S)—N-(5-(2-(2-aminopyridin-3-yl)-5-(1H-pyrazol-1-yl)-3H-imidazo[4,5-b]pyridin-3-yl)-2,3-dihydro-1H-inden-1-yl)-6-(difluoromethyl)nicotinamide (Compound 18)

Compound 18

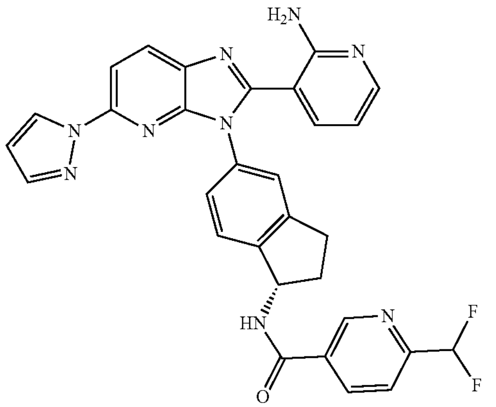

Compound 18 was prepared in a manner analogous to Compound 3 using 6-(difluoromethyl)nicotinic acid in place of 3,4-difluoro-5-anisic acid. MS (ESI) calcd. for $C_{30}H_{23}F_2N_9O$: 563.20 m/z, found: 564.15 $[M+H]^+$. $^1H$ NMR (300 MHz, DMSO-$d_6$) δ (ppm): 9.06-8.25 (m, 1H), 8.23-8.55 (m, 3H), 7.95-8.22 (m, 2H), 7.60-7.90 (m, 3H), 7.28-7.60 (m, 3H), 6.72-7.25 (m, 2H), 6.40-6.70 (m, 1H), 5.48-5.78 (m, 1H), 2.95-3.20 (m, 1H), 2.85-2.95 (m, 1H), 2.51-2.60 (m, 1H), 1.98-2.20 (m, 1H). $^{19}F$ NMR (282 MHz, DMSO-$d_6$) δ (ppm): −116.08.

Example 19: (S)—N-(5-(2-(2-aminopyridin-3-yl)-5-(1H-pyrazol-1-yl)-3H-imidazo[4,5-b]pyridin-3-yl)-2,3-dihydro-1H-inden-1-yl)pyrazine-2-carboxamide (Compound 19)

Compound 19

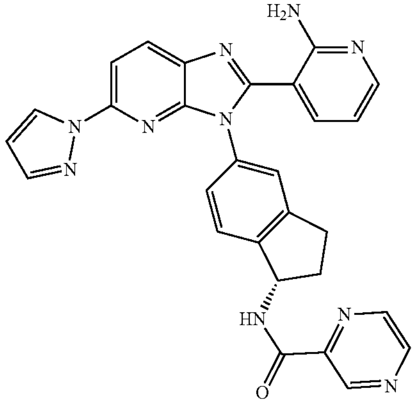

Compound 19 was prepared in a manner analogous to Compound 3 using pyrazine-2-carboxylic acid in place of 3,4-difluoro-5-anisic acid. MS (ESI) calcd. for $C_{28}H_{22}N_{10}O$: 514.20 m/z, found 515.20 $[M+H]^+$. $^1H$ NMR (400 MHz, DMSO-$d_6$) δ (ppm): 9.23-9.26 (m, 1H), 8.87-8.92 (m, 1H), 8.75-8.79 (m, 1H), 8.31-8.39 (m, 2H), 8.01-8.06 (m, 1H), 7.95-7.99 (m, 1H), 7.81-7.85 (m, 1H), 7.37-7.40 (m, 1H), 7.34-7.37 (m, 1H), 7.26-7.31 (m, 2H), 6.53-6.57 (m, 1H), 6.44-6.49 (m, 1H), 5.64-5.69 (m, 1H), 3.01-3.11 (m, 1H), 2.89-2.97 (m, 1H), 2.60-2.62 (m, 1H), 2.17-2.26 (m, 1H). (formic acid salt)

Example 20: (S)—N-(5-(2-(2-aminopyridin-3-yl)-5-(1H-pyrazol-1-yl)-3H-imidazo[4,5-b]pyridin-3-yl)-2,3-dihydro-1H-inden-1-yl)benzo[d]isoxazole-5-carboxamide (Compound 20)

Compound 20

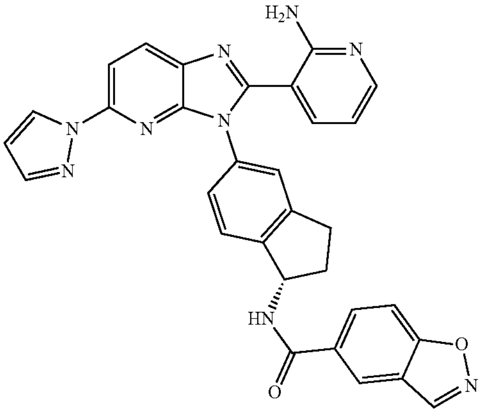

Compound 20 was prepared in a manner analogous to Compound 3 using benzo[d]isoxazole-5-carboxylic acid in place of 3,4-difluoro-5-anisic acid. MS (ESI) calcd. for $C_{31}H_{23}N_9O_2$: 553.20 m/z, found 554.15 $[M+H]^+$. $^1H$ NMR (400 MHz, DMSO-$d_6$) δ (ppm): 8.83-8.91 (m, 1H), 8.31-8.39 (m, 2H), 8.21-8.28 (m, 1H), 8.06-8.11 (m, 1H), 8.01-8.05 (m, 1H), 7.94-7.99 (m, 1H), 7.80-7.89 (m, 1H), 7.33-7.43 (m, 2H), 7.26-7.31 (m, 2H), 7.06-7.15 (m, 1H), 6.57-6.61 (m, 1H), 6.43-6.51 (m, 1H), 5.51-5.64 (m, 1H), 2.98-3.11 (m, 1H), 2.84-2.96 (m, 1H), 2.56-2.61 (m, 1H), 2.05-2.18 (m, 1H). (formic acid salt)

Example 21: (S)—N-(5-(2-(2-aminopyridin-3-yl)-5-(1H-pyrazol-1-yl)-3H-imidazo[4,5-b]pyridin-3-yl)-2,3-dihydro-1H-inden-1-yl)-5-methoxynicotinamide (Compound 21)

Compound 21

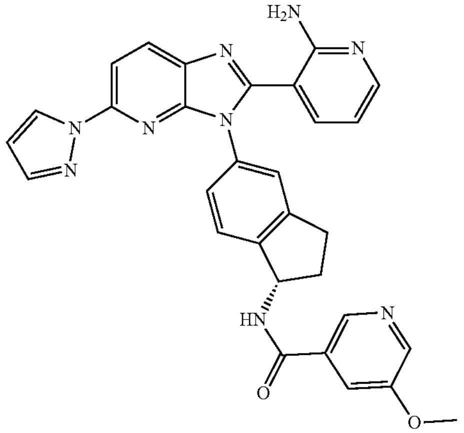

Compound 21 was prepared in a manner analogous to Compound 3 using 5-methoxynicotinic acid in place of 3,4-difluoro-5-anisic acid. MS (ESI) calcd. for $C_{30}H_{25}N_9O_2$: 543.21 m/z, found 544.20 $[M+H]^+$. $^1H$ NMR (300 MHz, DMSO-$d_6$) δ (ppm): 8.70-8.80 (m, 1H), 8.45-8.59 (m, 2H), 8.29-8.35 (m, 1H), 8.09-8.19 (m, 1H), 8.01-8.08 (m, 1H), 7.76-7.91 (m, 3H), 7.31-7.52 (m, 3H), 6.81-6.99 (m, 1H), 6.51-6.75 (m, 1H), 5.64-5.79 (m, 1H), 3.89 (s, 3H), 3.01-3.18 (m, 1H), 2.82-2.99 (m, 1H), 2.59-2.61 (m, 1H), 2.01-2.26 (m, 1H). (TFA salt)

Example 22: (S)—N-(5-(2-(2-aminopyridin-3-yl)-5-(1H-pyrazol-1-yl)-3H-imidazo[4,5-b]pyridin-3-yl)-2,3-dihydro-1H-inden-1-yl)-1H-benzo[d]imidazole-5-carboxamide (Compound 22)

Compound 22

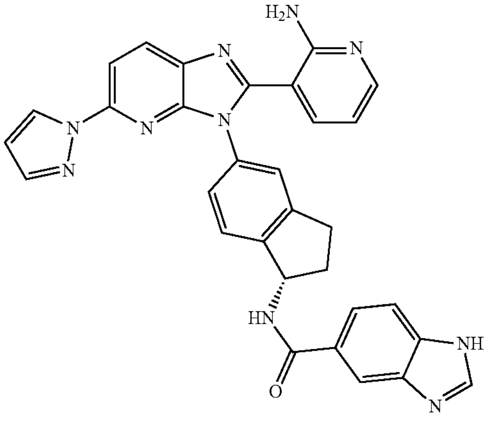

Compound 22 was prepared in a manner analogous to Compound 3 using 1H-benzo[d]imidazole-5-carboxylic acid in place of 3,4-difluoro-5-anisic acid. MS (ESI) calcd. for $C_{31}H_{24}N_{10}O$: 552.21 m/z, found 553.20 $[M+H]^+$. $^1H$ NMR (300 MHz, DMSO-$d_6$) δ (ppm): 9.26 (s, 1H), 8.25-8.46 (m, 3H), 7.95-8.12 (m, 3H), 7.69-7.88 (m, 3H), 7.30-7.51 (m, 3H), 6.79-6.83 (m, 1H), 6.51-6.60 (m, 1H), 5.55-5.68 (m, 1H), 3.09-3.21 (m, 1H), 2.88-3.02 (m, 1H), 2.58-2.68 (m, 1H), 2.03-2.23 (m, 1H). (TFA salt)

Example 23: (S)—N-(5-(2-(2-aminopyridin-3-yl)-5-(1H-pyrazol-1-yl)-3H-imidazo[4,5-b]pyridin-3-yl)-2,3-dihydro-1H-inden-1-yl)-2-methoxypyrimidine-5-carboxamide (Compound 23)

Compound 23

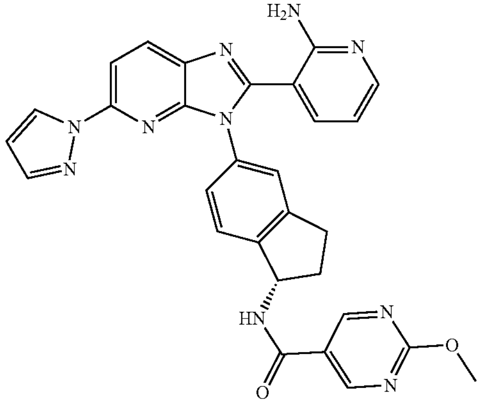

Compound 23 was prepared in a manner analogous to Compound 3 using 2-methoxypyrimidine-5-carboxylic acid in place of 3,4-difluoro-5-anisic acid. MS (ESI) calcd. for $C_{29}H_{24}N_{10}O_2$: 544.21 m/z, found 545.20 $[M+H]^+$. $^1H$ NMR (400 MHz, DMSO-$d_6$) δ (ppm): 9.08 (m, 3H), 8.35-8.37 (m, 2H), 8.01-8.02 (m, 1H), 7.94-7.96 (m, 1H), 7.81-7.82 (m, 1H), 7.41-7.44 (m, 2H), 7.31-7.33 (m, 2H), 6.88-6.89 (m, 2H), 6.55-6.56 (m, 1H), 6.46-6.47 (m, 1H), 5.63-5.65 (m, 1H), 3.99 (s, 3H), 3.05-3.06 (m, 1H), 2.93-2.95 (m, 1H), 2.50-2.51 (m, 1H), 2.06-2.09 (m, 1H).

Example 24: (S)—N-(5-(2-(2-aminopyridin-3-yl)-5-(1H-pyrazol-1-yl)-3H-imidazo[4,5-b]pyridin-3-yl)-2,3-dihydro-1H-inden-1-yl)-1-methyl-6-oxo-1,6-dihydropyridine-3-carboxamide (Compound 24)

Compound 24

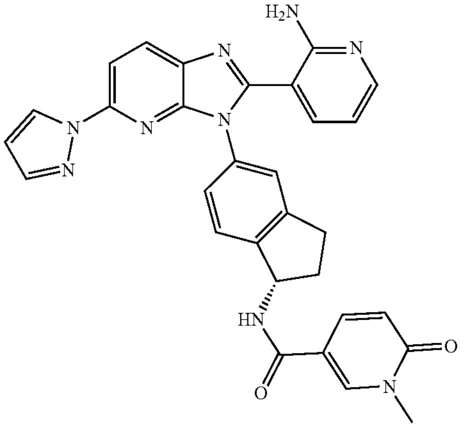

Compound 24 was prepared in a manner analogous to Compound 3 using 1-methyl-6-oxo-1,6-dihydropyridine-3-carboxylic acid in place of 3,4-difluoro-5-anisic acid. MS (ESI) calcd. for $C_{30}H_{25}N_9O_2$: 543.21 m/z, found 544.20 $[M+H]^+$. $^1H$ NMR (400 MHz, DMSO-$d_6$) δ (ppm): 8.63-8.65 (m, 1H), 8.45-8.46 (m, 1H), 8.36-8.38 (m, 2H), 8.02-8.03 (m, 1H), 7.94-7.96 (m, 2H), 7.81-7.82 (m, 1H), 7.35-7.37 (m, 1H), 7.29-7.31 (m, 1H), 7.28-7.29 (m, 2H), 6.92-6.93 (m, 2H), 6.47-6.56 (m, 1H), 6.41-6.43 (m, 2H), 5.56-5.63 (m, 1H), 3.49 (s, 3H), 3.00-3.02 (m, 1H), 2.92-2.95 (m, 1H), 2.50-2.52 (m, 1H), 2.00-2.01 (m, 1H).

Example 25: (S)—N-(5-(2-(2-aminopyridin-3-yl)-5-(1H-pyrazol-1-yl)-3H-imidazo[4,5-b]pyridin-3-yl)-2,3-dihydro-1H-inden-1-yl)-2-methoxyisonicotinamide (Compound 25)

Compound 25

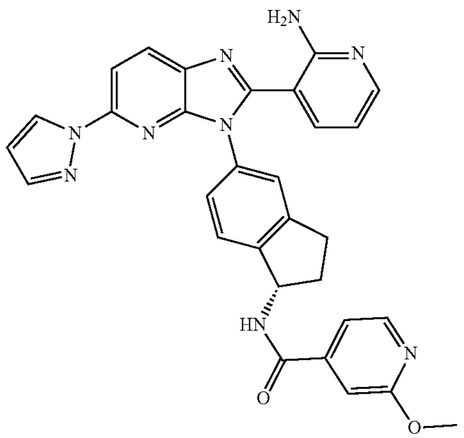

Compound 25 was prepared in a manner analogous to Compound 3 using 2-methoxyisonicotinic acid in place of 3,4-difluoro-5-anisic acid. MS (ESI) calcd. for $C_{30}H_{25}N_9O_2$, 543.21 m/z, found: 544.15 $[M+H]^+$. $^1H$ NMR (400 MHz, DMSO-$d_6$) δ (ppm): 9.13-9.15 (m, 1H), 8.37-8.38 (m, 2H), 8.30-8.31 (m, 1H), 8.01-8.02 (m, 1H), 7.94-7.96 (m, 1H), 7.81-7.82 (m, 1H), 7.39-7.45 (m, 3H), 7.28-7.32 (m, 3H), 6.90 (s, 2H), 6.55-6.56 (m, 1H), 6.43-6.45 (m, 1H), 5.62-5.64 (m, 1H), 3.90 (s, 3H), 2.96-3.05 (m, 2H), 2.50-2.55 (m, 1H), 2.09-2.12 (m, 1H).

Example 26: (S)—N-(5-(2-(2-aminopyridin-3-yl)-5-(1H-pyrazol-1-yl)-3H-imidazo[4,5-b]pyridin-3-yl)-2,3-dihydro-1H-inden-1-yl)-6-methylnicotinamide (Compound 26)

Compound 26

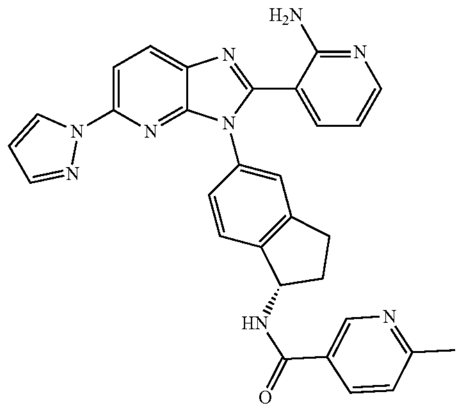

Compound 26 was prepared in a manner analogous to Compound 3 using 6-methylnicotinic acid in place of 3,4-difluoro-5-anisic acid. MS (ESI) calcd. for $C_{30}H_{25}N_9O$: 527.22 m/z, found: 528.30 $[M+H]^+$. $^1H$ NMR (300 MHz, DMSO-$d_6$) δ (ppm): 8.92-8.93 (m, 1H), 8.37-8.41 (m, 2H), 8.16-8.21 (m, 1H), 8.00-8.05 (m, 1H), 7.95-7.99 (m, 1H), 7.79-7.81 (m, 1H), 7.38-7.44 (m, 3H), 7.28-7.31 (m, 2H), 6.56-6.59 (m, 1H), 6.47-6.53 (m, 1H), 5.60-5.67 (m, 1H), 3.00-3.10 (m, 1H), 2.88-2.98 (m, 1H), 2.59-2.61 (m, 1H), 2.54 (s, 3H), 2.03-2.18 (m, 1H). (TFA salt)

Example 27: (S)—N-(5-(2-(2-aminopyridin-3-yl)-5-(1H-pyrazol-1-yl)-3H-imidazo[4,5-b]pyridin-3-yl)-2,3-dihydro-1H-inden-1-yl)morpholine-4-carboxamide (Compound 27)

Compound 27

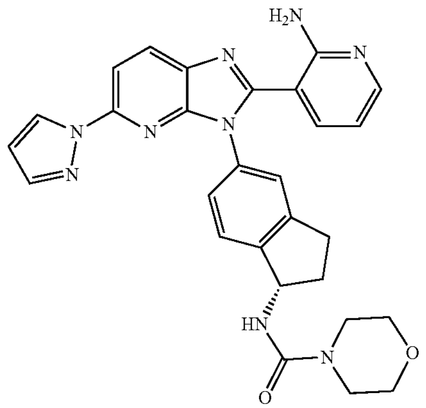

Synthetic Route:

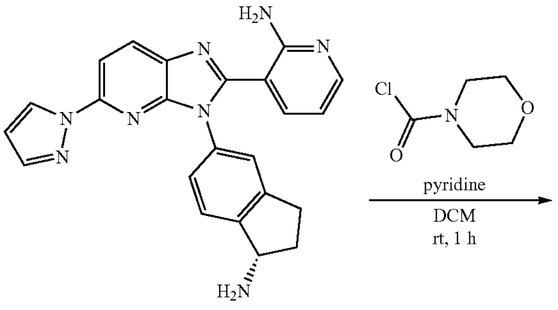

Compound 2

-continued

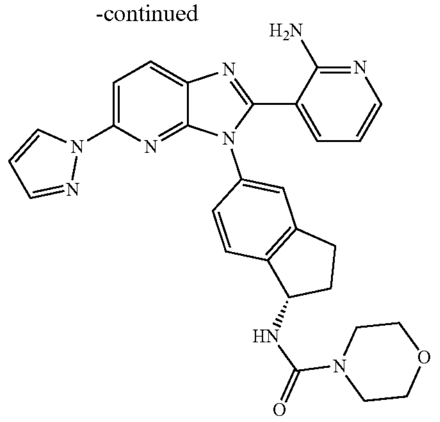

Compound 27

Step 1: Synthesis of (S)—N-(5-(2-(2-aminopyridin-3-yl)-5-(1H-pyrazol-1-yl)-3H-imidazo[4,5-b]pyridin-3-yl)-2,3-dihydro-1H-inden-1-yl)morpholine-4-carboxamide (Compound 27)

A suspension of (S)-3-(3-(1-amino-2,3-dihydro-1H-inden-5-yl)-5-(1H-pyrazol-1-yl)-3H-imidazo[4,5-b]pyridin-2-yl)pyridin-2-amine (Compound 2) (200 mg, 0.490 mmol, 1.2 equiv) in dichloromethane was treated with pyridine (484 mg, 6.12 mmol, 15 equiv) and the resulting mixture was stirred for 3 min at room temperature followed by the addition of morpholine-4-carbonyl chloride (61 mg, 0.408 mmol, 1 equiv) dropwise at room temperature. The resulting mixture was stirred for 1 h at room temperature. The reaction mixture was concentrated under reduced pressure then taken up into dichloromethane and concentrated to dryness under reduced pressure. The crude residue was purified by preparative HPLC on a YMC Triart C18 ExRs column using a gradient of acetonitrile in water (+10 mmol/L ammonium bicarbonate) to afford (S)—N-(5-(2-(2-aminopyridin-3-yl)-5-(1H-pyrazol-1-yl)-3H-imidazo[4,5-b]pyridin-3-yl)-2,3-dihydro-1H-inden-1-yl)morpholine-4-carboxamide (Compound 27) (17.5 mg, 8%) as a white solid. MS (ESI) calcd. for $C_{28}H_{27}N_9O_2$: 521.23 m/z, found 522.35 $[M+H]^+$. $^1H$ NMR (300 MHz, DMSO-$d_6$) δ (ppm): 8.35-8.47 (m, 2H), 7.93-8.09 (m, 2H), 7.81-7.89 (s, 1H), 7.29-7.48 (m, 4H), 6.52-6.64 (m, 2H), 5.21-5.33 (m, 1H), 2.55-2.68 (m, 4H), 3.32-3.43 (m, 4H), 2.92-3.06 (m, 1H), 2.78-2.89 (m, 1H), 2.46-2.51 (m, 1H), 1.89-2.03 (m, 1H).

The following compounds were prepared analogous to the synthetic preparation in Example 27 (Compound 27).

Example 28: (S)—N-(5-(2-(2-aminopyridin-3-yl)-5-(1H-pyrazol-1-yl)-3H-imidazo[4,5-b]pyridin-3-yl)-2,3-dihydro-1H-inden-1-yl)-1-methyl-1H-pyrazolo[3,4-b]pyridine-5-carboxamide (Compound 28)

Compound 28

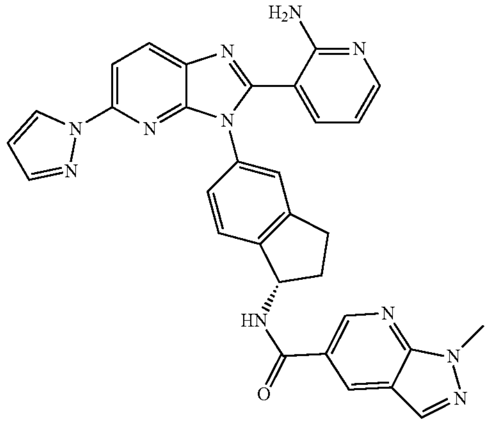

Compound 28 was prepared in a manner analogous to Compound 3 using 1-methyl-1H-pyrazolo[3,4-b]pyridine-5-carboxylic acid in place of 3,4-difluoro-5-anisic acid. MS (ESI) calcd. for $C_{31}H_{25}N_{11}O$: 567.22 m/z, found: 568.15 $[M+H]^+$. $^1H$ NMR (300 MHz, DMSO-$d_6$) δ (ppm): 9.04-9.06 (m, 1H), 8.76-8.78 (m, 1H), 8.28-8.41 (m, 3H), 8.00-8.02 (m, 1H), 7.93-7.95 (m, 1H), 7.80-7.83 (m, 1H), 7.42-7.46 (m, 1H), 7.37-7.39 (m, 1H), 7.31-7.33 (m, 2H), 6.48-6.61 (m, 2H), 5.60-5.66 (m, 1H), 4.10 (s, 3H), 2.90-3.08 (m, 2H), 2.50-2.54 (m, 1H), 2.10-2.13 (m, 1H).

TABLE 3A

Characterization data of compounds prepared analogously to compound 27.

| Cpd ID | Characterization Data |
|---|---|
| 82 | MS (ESI) calcd. for $C_{29}H_{25}N_9O_2S$: 563.19 m/z, found: 564.15 $[M + H]^+$. $^1H$ NMR (300 MHz, DMSO-$d_6$ + $D_2O$) δ (ppm): 8.85-8.92 (m, 1H), 8.32-8.36 (m, 2H), 8.15-8.20 (m, 1H), 7.96 - 8.02 (m, 1H), 7.92-7.95 (m, 1H), 7.80-7.85 (m, 1H), 7.52 -7.61 (m, 1H), 7.18-7.32 (m, 4H), 6.52-6.56 (m, 1H), 6.44-6.50 (m, 1H), 4.80-4.88 (m, 1H), 2.83-2.93 (m, 1H), 2.69-2.76 (m, 1H), 2.53-2.56 (m, 3H), 2.10-2.21 (m, 1H), 1.60-1.79 (m, 1H). |
| 139 | MS (ESI) calcd. for $C_{29}H_{25}N_9O_2S$, 563.19 m/z, found 564.10 $[M + H]^+$. $^1H$ NMR (400 MHz, DMSO-$d_6$) δ (ppm); 8.65-8.75 (m, 1H), 8.30-8.40 (m, 2H), 8.25-8.30 (m, 1H), 8.00-8.10 (m, 1H), 7.90-8.00 (m, 1H), 7.81 (m, 1H), 7.45-7.55 (m, 1H), 7.34 (s, 1H), 7.20-7.30 (m, 3H), 6.52-6.60 (m, 1H), 6.40-6.50 (m, 1H), 4.70-4.81 (m, 1H), 2.85-3.00 (m, 1H), 2.89 (s, 3H), 2.65-2.80 (m, 1H), 2.05-2.20 (m, 1H), 1.70-1.90 (m, 1H). |

Example 29: (S)—N-(5-(2-(2-aminopyridin-3-yl)-5-(1H-pyrazol-1-yl)-3H-imidazo[4,5-b]pyridin-3-yl)-2,3-dihydro-1H-inden-1-yl)-2-methylnicotinamide (Compound 29)

Compound 29

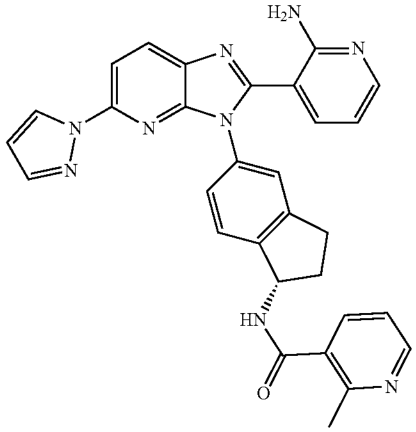

Compound 29 was prepared in a manner analogous to Compound 3 using 2-methylnicotinic acid in place of 3,4-difluoro-5-anisic acid. MS (ESI) calcd. for $C_{30}H_{25}N_9O$: 527.22 m/z, found 528.15 $[M+H]^+$. $^1H$ NMR (300 MHz, DMSO-$d_6$) δ (ppm): 8.50-8.52 (m, 1H), 8.32-8.40 (m, 2H), 8.00-8.02 (m, 1H), 7.93-7.96 (m, 1H), 7.76-7.85 (m, 2H), 7.46-7.48 (m, 1H), 7.25-7.42 (m, 4H), 6.54-6.57 (m, 1H), 6.50-6.52 (m, 1H), 5.54-5.58 (m, 1H), 2.83-3.11 (m, 2H), 2.58-2.60 (m, 1H), 2.55-3.57 (m, 3H), 1.98-2.02 (m, 1H).

Example 30: (S)—N-(5-(2-(2-aminopyridin-3-yl)-5-(1H-pyrazol-1-yl)-3H-imidazo[4,5-b]pyridin-3-yl)-2,3-dihydro-1H-inden-1-yl)-5-methylnicotinamide (Compound 30)

Compound 30

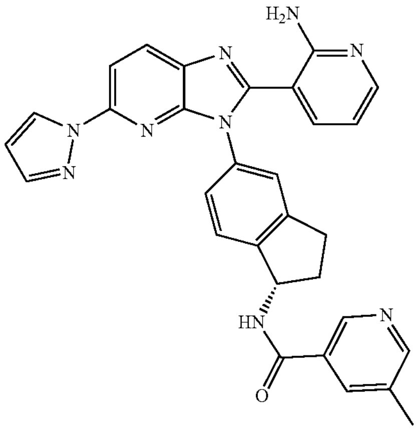

Compound 30 was prepared in a manner analogous to Compound 3 using 5-methylnicotinic acid in place of 3,4-difluoro-5-anisic acid. MS (ESI) calcd. for $C_{30}H_{25}N_9O$: 527.22 m/z, found 528.10 $[M+H]^+$. $^1H$ NMR (300 MHz, DMSO-$d_6$) δ (ppm): 8.81-8.89 (m, 1H), 8.48-8.58 (m, 1H), 8.27-8.40 (m, 2H), 8.05-8.14 (m, 1H), 7.98-8.04 (m, 1H), 7.89-7.97 (m, 1H), 7.76-7.85 (m, 1H), 7.34-7.46 (m, 2H), 7.21-7.33 (m, 2H), 6.51-6.60 (m, 1H), 6.40-6.50 (m, 1H), 5.57-5.73 (m, 1H), 2.99-3.13 (m, 1H), 2.83-2.98 (m, 1H), 2.57-2.61 (m, 1H), 2.36 (s, 3H), 1.98-2.21 (m, 1H).

Example 31: (S)—N-(5-(2-(2-aminopyridin-3-yl)-5-(1H-pyrazol-1-yl)-3H-imidazo[4,5-b]pyridin-3-yl)-2,3-dihydro-1H-inden-1-yl)-4-methylnicotinamide (Compound 31)

Compound 31

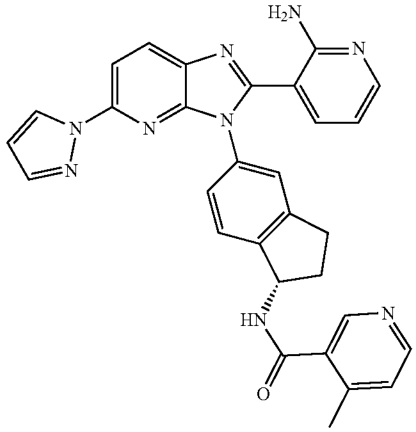

Compound 31 was prepared in a manner analogous to Compound 3 using 4-methylnicotinic acid in place of 3,4-difluoro-5-anisic acid. MS (ESI) calcd. for $C_{30}H_{25}N_9O$: 527.22 m/z, found 528.15 $[M+H]^+$. $^1H$ NMR (400 MHz, DMSO-$d_6$) δ (ppm): 8.54-8.55 (m, 1H), 8.48-8.49 (m, 1H), 8.35-8.36 (m, 2H), 8.00-8.01 (m, 1H), 7.94-7.96 (m, 1H), 7.80-7.81 (m, 1H), 7.46-7.48 (m, 1H), 7.39-7.40 (m, 1H), 7.31-7.32 (m, 2H), 7.26-7.27 (m, 1H), 6.55-6.56 (m, 1H), 6.45-6.46 (m, 1H), 5.58-5.62 (m, 1H), 2.92-3.93 (m, 2H), 2.50-2.51 (m, 1H), 2.41-2.42 (m, 3H), 2.02-2.03 (m, 1H).

Example 32: (S)—N-(5-(2-(2-aminopyridin-3-yl)-5-(1H-pyrazol-1-yl)-3H-imidazo[4,5-b]pyridin-3-yl)-2,3-dihydro-1H-inden-1-yl)-5-fluoronicotinamide (Compound 32)

Compound 32

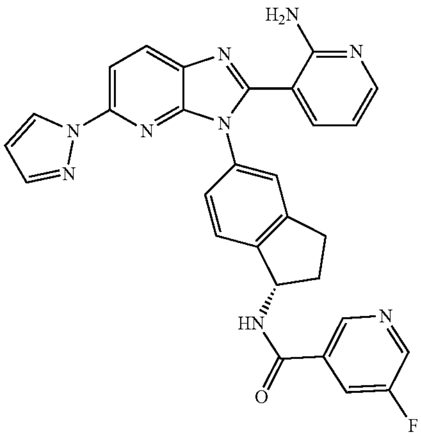

Compound 32 was prepared in a manner analogous to Compound 3 using 5-fluoronicotinic acid in place of 3,4-difluoro-5-anisic acid. MS (ESI) calcd. for $C_{29}H_{22}FN_9O$: 531.19 m/z, found 532.30 $[M+H]^+$. $^1H$ NMR (300 MHz, DMSO-$d_6$) δ (ppm): 9.15-9.23 (m, 1H), 8.89-8.96 (m, 1H), 8.68-8.75 (m, 1H), 8.30-8.39 (m, 2H), 8.03-8.17 (m, 1H), 7.97-8.01 (m, 1H), 7.87-7.96 (m, 1H), 7.73-7.79 (m, 1H), 7.32-7.41 (m, 2H), 7.19-7.31 (m, 2H), 6.50-6.56 (m, 1H), 6.38-6.48 (m, 1H), 5.53-5.66 (m, 1H), 2.86-3.09 (m, 2H), 2.56-2.61 (m, 1H), 2.01-2.16 (m, 1H). (formic acid salt)

Example 33: (S)—N-(5-(2-(2-aminopyridin-3-yl)-5-(1H-pyrazol-1-yl)-3H-imidazo[4,5-b]pyridin-3-yl)-2,3-dihydro-1H-inden-1-yl)pyridazine-4-carboxamide (Compound 33)

Compound 33

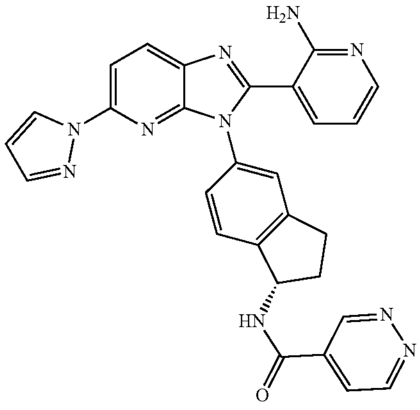

Compound 33 was prepared in a manner analogous to Compound 3 using pyridazine-4-carboxylic acid in place of 3,4-difluoro-5-anisic acid. MS (ESI) calcd. for $C_{28}H_{22}N_{10}O$: 514.20 m/z, found 515.25 $[M+H]^+$. $^1H$ NMR (400 MHz, DMSO-$d_6$) δ (ppm): 9.58-9.64 (m, 1H), 9.41-9.48 (m, 1H), 8.33-8.41 (m, 2H), 7.92-8.14 (m, 3H), 7.78-7.83 (m, 1H), 7.40-7.47 (m, 2H), 7.28-7.39 (m, 2H), 6.48-6.58 (m, 2H), 5.59-5.68 (m, 1H), 2.93-3.05 (m, 2H), 2.50-2.51 (m, 1H), 2.11-2.06 (m, 1H). (TFA salt)

Example 34: N-[(1S)-5-[2-(2-aminopyridin-3-yl)-5-(pyrazol-1-yl)imidazo[4,5-b]pyridin-3-yl]-2,3-dihydro-1H-inden-1-yl]pyridine-3-carboxamide (Compound 34)

Compound 34

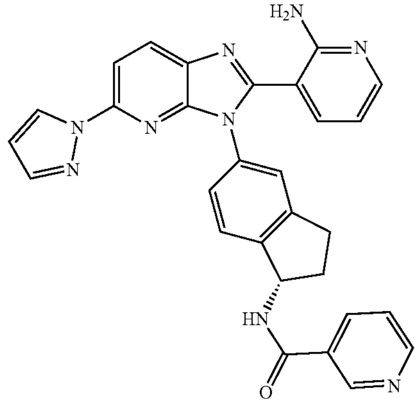

Compound 34 was prepared in a manner analogous to Compound 3 using niacin in place of 3,4-difluoro-5-anisic acid and PyBOP in place of HATU. MS (ESI) calcd. for $C_{29}H_{23}N_9O$: 513.20 m/z, found 514.25 $[M-H]^+$. $^1H$ NMR (400 MHz, DMSO-$d_6$) δ 9.14-9.16 (m, 1H), 9.05-9.08 (m, 1H), 8.71-8.72 (m, 1H), 8.33-8.36 (m, 2H), 8.25-8.28 (m, 1H), 8.16 (s, 1H), 7.93-8.02 (m, 1H), 7.80 (s, 1H), 7.51-7.54 (m, 1H), 7.38-7.40 (m, 2H), 7.26-7.31 (m, 2H), 6.54-6.55 (m, 1H), 6.44-6.47 (m, 1H), 5.62-5.68 (m, 1H), 2.87-3.08 (m, 2H), 2.53-2.58 (m, 1H), 2.09-2.14 (m, 1H).

Example 35: N-[(1S)-5-[2-(2-aminopyridin-3-yl)-5-(pyrazol-1-yl)imidazo[4,5-b]pyridin-3-yl]-2,3-dihydro-1H-inden-1-yl]pyridine-4-carboxamide (Compound 35)

Compound 35

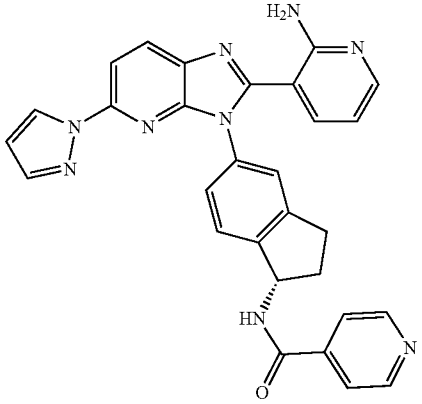

Compound 35 was prepared in a manner analogous to Compound 3 using isonicotinic acid in place of 3,4-difluoro-5-anisic acid. MS (ESI) calcd. for $C_{29}H_{23}N_9O$: 513.57 m/z, found 514.25 $[M+H]^+$. $^1H$ NMR (400 MHz, DMSO-$d_6$) δ (ppm) 8.70-8.72 (m, 2H), 8.32-8.34 (m, 2H), 7.99-8.00 (m, 1H), 7.94-7.98 (m, 1H), 7.78-7.82 (m, 3H), 7.35-7.37 (m, 2H), 7.25-7.27 (m, 2H), 6.53-6.54 (m, 1H), 6.44-6.47 (m, 1H), 5.58-5.63 (m, 1H), 3.00-3.05 (m, 1H), 2.85-2.94 (m, 1H), 2.51-2.52 (m, 1H), 2.07-2.13 (m, 1H).

Example 36: N-[(1S)-5-[2-(2-aminopyridin-3-yl)-5-(pyrazol-1-yl)imidazo[4,5-b]pyridin-3-yl]-2,3-dihydro-1H-inden-1-yl]pyridine-2-carboxamide (Compound 36)

Compound 36

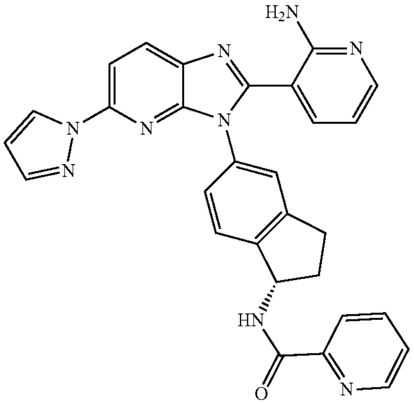

Compound 36 was prepared in a manner analogous to Compound 3 using picolinic acid in place of 3,4-difluoro-5-anisic acid and PyBOP in place of HATU. MS (ESI) calcd. for $C_{29}H_{23}N_9O$ 513.20 m/z, found: 514.15 $[M+H]^+$. $^1H$ NMR (300 MHz, DMSO-$d_6$) δ (ppm): 8.64-8.66 (m, 1H), 8.35-8.37 (m, 2H), 8.02-8.13 (m, 1H), 7.96-8.05 (m, 2H), 7.94-7.96 (m, 1H), 7.80-7.81 (m, 1H), 7.61-7.64 (m, 1H), 7.38-7.39 (m, 1H), 7.32-7.34 (m, 1H), 7.24-7.28 (m, 2H), 6.54-6.55 (m, 1H), 6.44-6.47 (m, 1H), 5.63-5.65 (m, 1H), 3.45-3.52 (m, 1H), 2.91-2.94 (m, 1H), 2.50-2.51 (m, 1H), 2.23-2.33 (m, 1H).

Example 37: N-[(1S)-5-[2-(2-aminopyridin-3-yl)-5-(pyrazol-1-yl) imidazo[4,5-b]pyridin-3-yl]-2,3-dihydro-1H-inden-1-yl]cyclopropanecarboxamide (Compound 37)

Compound 37

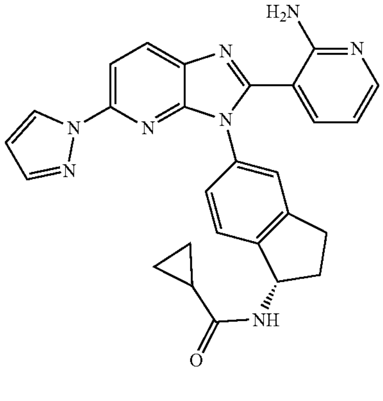

Compound 37 was prepared in a manner analogous to Compound 3 using cyclopropanecarboxylic acid in place of 3,4-difluoro-5-anisic acid. MS (ESI) calcd. for $C_{27}H_{24}N_8O$: 476.21 m/z, found 477.05 $[M+H]^+$. $^1H$NMR (400 MHz, DMSO-$d_6$) δ (ppm): 8.52-8.79 (m, 1H), 8.27-8.51 (m, 2H), 7.95-8.04 (m, 1H), 7.90-7.99 (m, 1H), 7.78-7.90 (m, 1H), 7.32-7.48 (m, 1H), 7.24-7.31 (m, 3H), 6.45-6.49 (m, 1H), 6.41-6.41 (m, 1H), 5.30-5.48 (m, 1H), 2.95-3.08 (m, 1H), 2.81-2.95 (m, 1H), 2.42-2.55 (m, 1H), 1.97-1.99 (m, 1H), 1.48-1.67 (m, 1H), 0.70-0.82 (m, 4H).

Example 38: N-[(1S)-5-[2-(2-aminopyridin-3-yl)-5-(pyrazol-1-yl)imidazo[4,5-b]pyridin-3-yl]-2,3-dihydro-1H-inden-1-yl]-6-methoxypyridine-3-carboxamide (Compound 38)

Compound 38

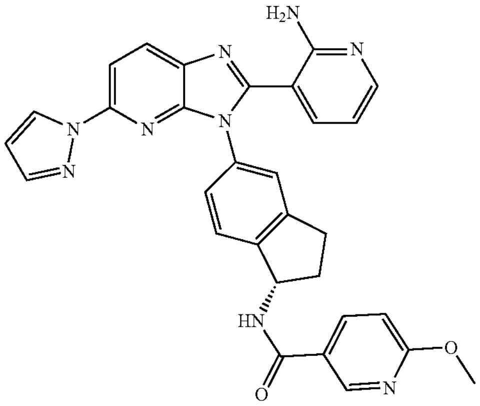

Compound 38 was prepared in a manner analogous to Compound 3 using 6-methoxynicotinic acid in place of 3,4-difluoro-5-anisic acid. MS (ESI) calcd. for $C_{30}H_{25}N_9O_2$: 543.21 m/z, found 544.25 $[M+H]^+$. $^1H$NMR (400 MHz, DMSO-$d_6$) δ (ppm): 8.85-9.09 (m, 1H), 8.61-9.85 (m, 1H), 8.42-8.49 (m, 2H), 8.09-8.27 (m, 1H), 7.98-8.10 (m, 1H), 7.89-7.95 (m, 1H), 7.56-7.89 (m, 1H), 7.14-7.44 (m, 4H), 6.85-6.92 (m, 1H), 6.55-6.70 (s, 1H), 6.35-6.55 (m, 1H), 5.55-5.70 (m, 1H), 3.85-3.99 (m, 3H), 3.08-3.14 (m, 1H), 2.81-2.99 (m, 1H), 2.52-2.61 (m, 1H), 2.01-2.15 (m, 1H).

Example 39: (S)—N-(5-(2-(2-aminopyridin-3-yl)-5-(1H-pyrazol-1-yl)-3H-imidazo[4,5-b]pyridin-3-yl)-2,3-dihydro-1H-inden-1-yl)-1-methyl-1H-pyrazole-4-carboxamide (Compound 39)

Compound 39

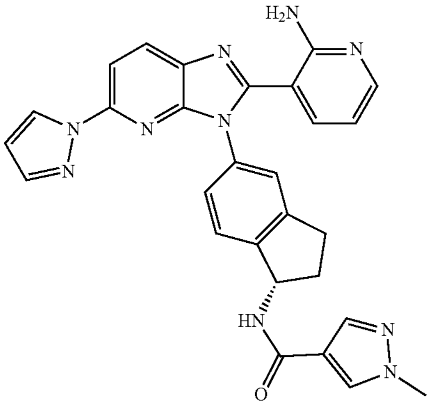

Compound 39 was prepared in a manner analogous to Compound 3 using 1-methyl-1H-pyrazole-4-carboxylic acid in place of 3,4-difluoro-5-anisic acid. MS (ESI) calcd. for $C_{28}H_{24}N_{10}O$: 516.21 m/z, found 517.15 $[M+H]^+$. $^{11}$HNMR (400 MHz, DMSO-$d_6$) δ (ppm): 8.55-8.75 (m, 1H), 8.30-8.45 (m, 2H), 8.15-8.28 (m, 1H), 8.00-8.05 (m, 1H), 7.91-8.00 (m, 2H), 7.78-7.89 (m, 1H), 7.20-7.45 (m, 4H), 6.55-6.65 (m, 1H), 6.35-6.55 (m, 1H), 3.89-3.91 (m, 3H), 2.90-3.15 (m, 1H), 2.80-2.90 (m, 1H), 2.50-2.51 (m, 1H), 1.90-2.14 (m, 1H).

Example 40: N-[(1S)-5-[2-(2-aminopyridin-3-yl)-5-(pyrazol-1-yl)imidazo[4,5-b]pyridin-3-yl]-2,3-dihydro-1H-inden-1-yl]pyrimidine-5-carboxamide (Compound 40)

Compound 40

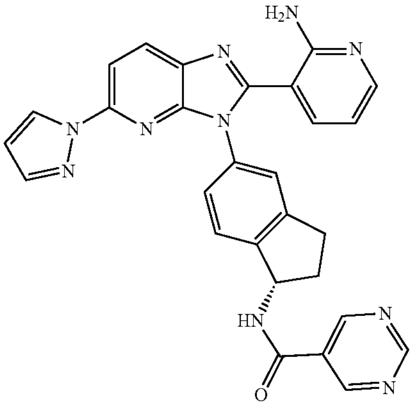

Compound 40 was prepared in a manner analogous to Compound 3 using pyrimidine-5-carboxylic acid in place of 3,4-difluoro-5-anisic acid. MS (ESI) calcd. for $C_{28}H_{22}N_{10}O$: 514.20 m/z, found 515.15 $[M+H]^+$. $^{11}$HNMR (400 MHz, DMSO-$d_6$) δ (ppm): 9.25-9.30 (m, 1H), 9.35-9.40 (m, 2H), 8.45-8.61 (m, 2H), 7.98-8.10 (m, 2H), 7.80-7.82 (s, 1H), 7.50-7.60 (m, 2H), 7.30-7.44 (m, 2H), 6.55-6.66 (m, 1H), 6.45-6.50 (m, 1H), 5.55-5.80 (m, 1H), 2.80-3.20 (m, 2H), 2.45-2.52 (m, 1H), 2.01-2.15 (m, 1H).

Example 41: N-[(1S)-5-[2-(2-aminopyridin-3-yl)-5-(pyrazol-1-yl)imidazo[4,5-b]pyridin-3-yl]-2,3-dihydro-1H-inden-1-yl]-4-cyanobenzamide (Compound 41)

Compound 41

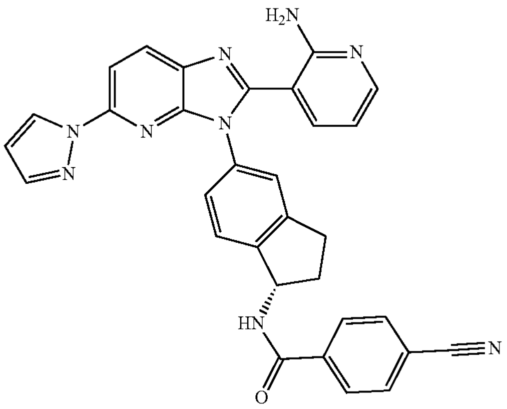

Compound 41 was prepared in a manner analogous to Compound 3 using 4-cyanobenzoic acid in place of 3,4-difluoro-5-anisic acid. MS (ESI) calcd. for $C_{31}H_{23}N_9O$: 537.20 m/z, found 538.20 $[M+H]^+$. $^1$HNMR (400 MHz, DMSO-$d_6$) δ (ppm): 8.30-8.60 (m, 2H), 7.90-8.30 (m, 6H), 7.65-7.90 (m, 1H), 7.38-7.65 (m, 2H), 7.19-7.38 (m, 2H), 6.55-6.80 (m, 1H), 6.38-6.55 (m, 1H), 5.50-5.88 (m, 1H), 2.89-3.30 (m, 2H), 2.58-2.70 (m, 1H), 1.95-2.30 (m, 1H).

Example 42: (S)—N-(5-(2-(2-aminopyridin-3-yl)-5-(1H-pyrazol-1-yl)-3H-imidazo[4,5-b]pyridin-3-yl)-2,3-dihydro-1H-inden-1-yl)-4-hydroxybenzamide (Compound 42)

Compound 42

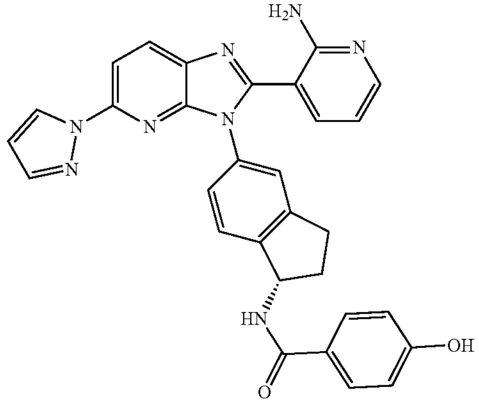

Compound 42 was prepared in a manner analogous to Compound 3 using 4-hydroxybenzoic acid in place of 3,4-difluoro-5-anisic acid. MS (ESI) calcd. for $C_{30}H_{24}N_8O_2$: 528.20 m/z, found 529.30 $[M+H]^+$. $^1$HNMR (400 MHz, DMSO-$d_6$) δ (ppm): 8.35-8.37 (m, 2H), 8.01-8.02 (m, 1H), 7.94-8.00 (m, 1H), 7.81-7.83 (m, 3H), 7.25-7.38 (m, 4H), 6.88-7.08 (m, 2H), 6.55-6.58 (m, 1H), 6.44-6.46 (m, 1H), 5.60-5.64 (m, 1H), 2.87-3.03 (m, 2H), 2.51-2.52 (m, 1H), 2.10-2.30 (m, 1H).

Example 43: (S)—N-(5-(2-(2-aminopyridin-3-yl)-5-(1H-pyrazol-1-yl)-3H-imidazo[4,5-b]pyridin-3-yl)-2,3-dihydro-1H-inden-1-yl)benzamide (Compound 43)

Compound 43

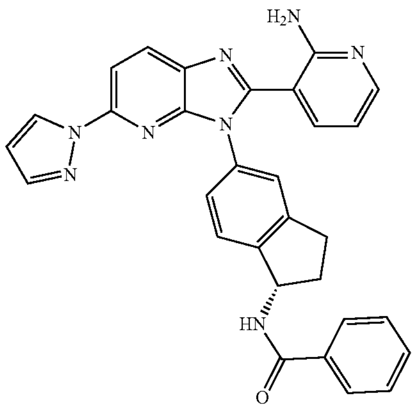

Compound 43 was prepared in a manner analogous to Compound 3 using benzoic acid in place of 3,4-difluoro-5-anisic acid and PyBOP in place of HATU. MS (ESI) calcd. for $C_{30}H_{24}N_8O$: 512.21 m/z, found 513.15 $[M+H]^+$. HNMR (400 MHz, DMSO-$d_6$) δ (ppm): 8.94 (s, 1H), 8.36-8.38 (m, 2H), 8.04 (m, 1H), 7.94-7.97 (m, 3H), 7.81-7.82 (m, 1H), 7.48-7.51 (m, 3H), 7.41 (m, 2H), 7.40 (m, 2H), 6.56-6.60 (m, 1H), 6.45-6.54 (m, 1H), 5.60-5.70 (m, 1H), 2.96-3.12 (m, 1H), 2.85-2.95 (m, 1H), 2.50-2.52 (m, 1H), 2.01-2.22 (m, 1H).

Example 44: (S)—N-(5-(2-(2-aminopyridin-3-yl)-5-(1H-pyrazol-1-yl)-3H-imidazo[4,5-b]pyridin-3-yl)-2,3-dihydro-1H-inden-1-yl)-2-(difluoromethyl)isonicotinamide (Compound 44)

Compound 44

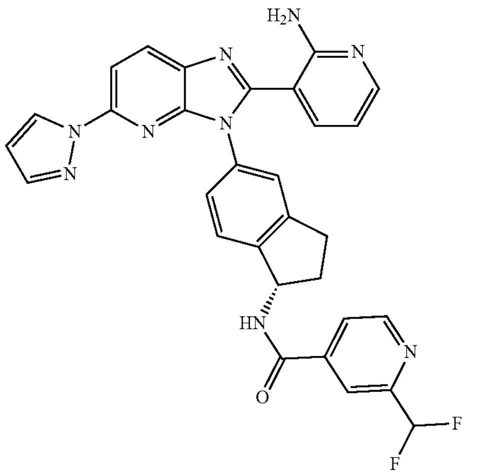

Compound 44 was prepared in a manner analogous to Compound 3 using 2-(difluoromethyl)isonicotinic acid in place of 3,4-difluoro-5-anisic acid. MS (ESI) calcd. for $C_{30}H_{23}F_2N_9O$: 563.20 m/z, found 564.25 $[M+H]^+$. $^1H$ NMR (300 MHz, DMSO-$d_6$) δ (ppm): 8.80-8.90 (m, 1H), 8.28-8.40 (m, 2H), 8.11-8.21 (m, 1H), 8.00-8.09 (m, 2H), 7.88-7.99 (m, 1H), 7.76-7.85 (m, 1H), 7.36-7.47 (m, 2H), 7.24-7.34 (m, 2H), 6.82-7.33 (m, 1H), 6.50-6.60 (m, 1H), 6.39-6.49 (m, 1H), 5.57-5.71 (m, 1H), 2.82-3.15 (m, 2H), 2.51-2.62 (m, 1H), 1.98-2.20 (m, 1H). $^{19}F$ NMR (282 MHz, DMSO-$d_6$) δ (ppm): −115.65.

Example 45: (S)—N-(5-(2-(2-aminopyridin-3-yl)-5-(1H-pyrazol-1-yl)-3H-imidazo[4,5-b]pyridin-3-yl)-2,3-dihydro-1H-inden-1-yl)-6-chloronicotinamide (Compound 45)

Compound 45

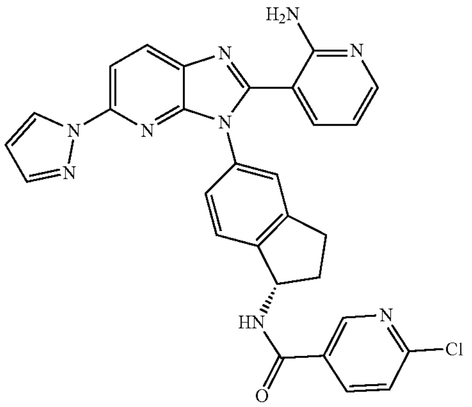

Compound 45 was prepared in a manner analogous to Compound 3 using 6-chloronicotinic acid in place of 3,4-difluoro-5-anisic acid. MS (ESI) calcd. for $C_{29}H_{22}ClN_9O$: 547.16 m/z, found 548.20 $[M+H]^+$. $^1H$ NMR (300 MHz, DMSO-$d_6$) δ (ppm): 8.78-8.84 (m, 1H), 8.22-8.43 (m, 3H), 7.89-8.06 (m, 2H), 7.82-7.87 (m, 1H), 7.62-7.68 (m, 1H), 7.23-7.49 (m, 4H), 6.54-6.62 (m, 2H), 5.57-5.64 (m, 1H), 2.85-3.11 (m, 2H), 2.61-2.69 (m, 1H), 2.04-2.16 (m, 1H).

Example 46: N-[(1S)-5-[2-(2-aminopyridin-3-yl)-5-(pyrazol-1-yl)imidazo[4,5-b]pyridin-3-yl]-2,3-dihydro-1H-inden-1-yl]-6-cyclopropylpyridine-3-carboxamide (Compound 46)

Compound 46

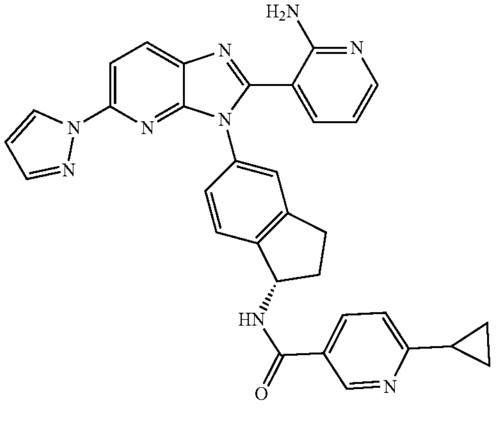

Compound 46 was prepared in a manner analogous to Compound 3 using 6-cyclopropylnicotinic acid in place of 3,4-difluoro-5-anisic acid. MS (ESI) calcd. for $C_{32}H_{27}N_9O$: 553.23 m/z, found 554.15 $[M+H]^+$. $^1H$ NMR (300 MHz, DMSO-$d_6$) δ (ppm): 8.96-9.06 (m, 1H), 8.85-8.95 (m, 1H), 8.28-8.43 (m, 2H), 8.08-8.18 (m, 1H), 7.98-8.07 (m, 1H), 7.89-7.97 (m, 1H), 7.75-7.85 (m, 1H), 7.34-7.46 (m, 3H), 7.22-7.33 (m, 2H), 6.50-6.60 (m, 1H), 6.39-6.49 (m, 1H), 5.54-5.72 (m, 1H), 2.79-3.13 (m, 2H), 2.52-2.60 (m, 1H), 1.95-2.23 (m, 2H), 0.89-1.10 (m, 4H).

Example 47: N—((S)-5-(2-(2-aminopyridin-3-yl)-5-(1H-pyrazol-1-yl)-3H-imidazo[4,5-b]pyridin-3-yl)-2,3-dihydro-1H-inden-1-yl)-2-(5-oxopyrrolidin-2-yl) acetamide (Compound 47)

Compound 47

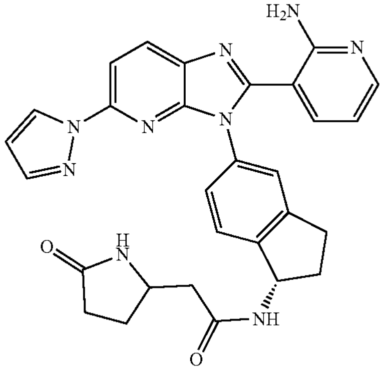

Compound 47 was prepared in a manner analogous to Compound 3 using 2-(5-oxopyrrolidin-2-yl)acetic acid in place of 3,4-difluoro-5-anisic acid. MS (ESI) calcd. for $C_{29}H_{27}N_9O_2$: 533.23 m/z, found 534.30 $[M+H]^+$. $^1$H NMR (300 MHz, DMSO-$d_6$) δ (ppm): 8.31-8.40 (m, 2H), 7.95-8.03 (m, 2H), 7.98-7.82 (m, 1H), 7.25-7.50 (m, 4H), 6.50-6.60 (m, 2H), 5.33-5.41 (m, 1H), 3.88-3.93 (m, 1H), 2.79-3.02 (m, 2H), 2.45-2.65 (m, 2H), 2.29-2.35 (m, 1H), 2.09-2.25 (m, 3H), 1.80-1.92 (m, 1H), 1.65-1.78 (m, 1H). (formic acid salt)

Example 48: (S)—N-(5-(2-(2-aminopyridin-3-yl)-5-(1H-pyrazol-1-yl)-3H-imidazo[4,5-b]pyridin-3-yl)-2,3-dihydro-1H-inden-1-yl)-2-(pyridin-3-yl)acetamide (Compound 48)

Compound 48

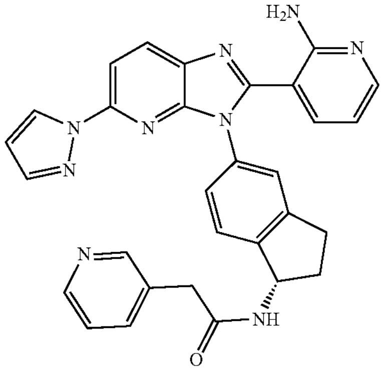

Compound 48 was prepared in a manner analogous to Compound 3 using 2-(pyridin-3-yl)acetic acid (HCl salt) in place of 3,4-difluoro-5-anisic acid and an additional equivalent of N,N-diisopropylethylamine. MS (ESI) calcd. for $C_{30}H_{25}N_9O$: 527.22 m/z, found 528.30 $[M+H]^+$. $^1$H NMR (400 MHz, DMSO-$d_6$) δ (ppm): 8.30-8.39 (m, 3H), 8.21-8.26 (m, 1H), 7.90-7.95 (m, 1H), 7.78-7.83 (m, 1H), 7.70-7.76 (m, 2H), 7.28-7.39 (m, 3H), 7.10-7.19 (m, 2H), 6.50-6.57 (m, 2H), 5.19-5.25 (m, 1H), 3.53 (s, 2H), 2.90-2.98 (m, 1H), 2.72-2.81 (m, 1H), 2.37-2.40 (m, 1H), 1.79-1.91 (m, 1H).

Example 49: N-[(1S)-5-[2-(2-aminopyridin-3-yl)-5-(pyrazol-1-yl)imidazo[4,5-b]pyridin-3-yl]-2,3-dihydro-1H-inden-1-yl]-2-(pyridin-4-yl)acetamide (Compound 49)

Compound 49

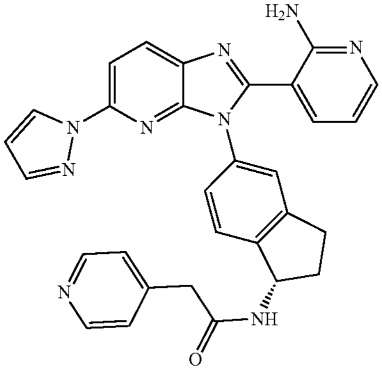

Compound 49 was prepared in a manner analogous to Compound 3 using 2-(pyridin-4-yl)acetic acid (HCl salt) in place of 3,4-difluoro-5-anisic acid and an additional equivalent of N,N-diisopropylethylaamine. MS (ESI) calcd. for $C_{30}H_{25}N_9O$: 527.22 m/z, found 528.25 $[M+H]^+$. $^1$H-NMR (400 MHz, DMSO-$d_6$) δ (ppm): 8.73-8.75 (m, 1H), 8.48-8.50 (m, 2H), 8.34-8.36 (m, 2H), 8.00-8.01 (m, 1H), 7.93-7.96 (m, 1H), 7.80-7.81 (m, 1H), 7.32-7.37 (m, 3H), 7.24-7.28 (m, 3H), 6.55-6.56 (m, 1H), 6.43-6.46 (m, 1H), 5.32-5.34 (m, 1H), 3.55 (s, 2H), 2.94-2.96 (m, 1H), 2.85-2.87 (m, 1H), 2.50-2.51 (m, 1H), 1.88-1.90 (m, 1H).

Example 50: (S)—N-(5-(2-(2-aminopyridin-3-yl)-5-(1H-pyrazol-1-yl)-3H-imidazo[4,5-b]pyridin-3-yl)-2,3-dihydro-1H-inden-1-yl)-2-(pyridin-2-yl)acetamide (Compound 50)

Compound 50

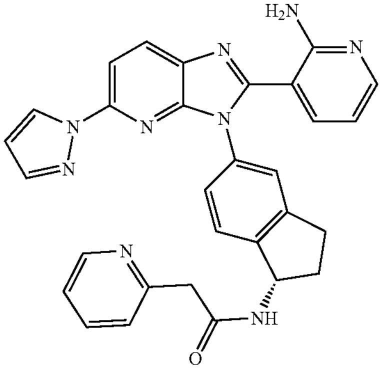

Compound 50 was prepared in a manner analogous to Compound 3 using 2-(pyridin-2-yl)acetic acid (HCl salt) in place of 3,4-difluoro-5-anisic acid and an additional equivalent of N,N-diisopropylethylamine. MS (ESI) calcd. for $C_{30}H_{25}N_9O$: 527.22 m/z, found 528.30 [M+H]$^+$. $^1$H NMR (300 MHz, DMSO-$d_6$) δ (ppm): 8.42-8.56 (m, 1H), 8.32-8.41 (m, 2H), 7.88-8.06 (m, 2H), 7.72-7.88 (m, 2H), 7.19-7.43 (m, 6H), 6.53-6.59 (m, 1H), 6.45-6.51 (m, 1H), 5.31-5.42 (m, 1H), 3.81-3.96 (m, 1H), 3.69-3.76 (m, 1H), 2.81-3.04 (m, 2H), 2.46-2.51 (m, 1H), 1.83-2.01 (m, 1H). (formic acid salt)

Example 51: (S)—N-(5-(2-(2-aminopyridin-3-yl)-5-(1H-pyrazol-1-yl)-3H-imidazo[4,5-b]pyridin-3-yl)-2,3-dihydro-1H-inden-1-yl)-2-(1H-pyrazol-5-yl)acetamide (Compound 51)

Compound 51

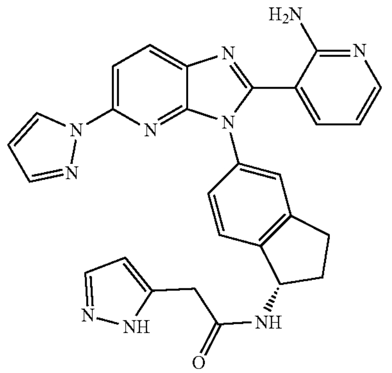

Compound 51 was prepared in a manner analogous to Compound 3 using 2-(1H-pyrazol-5-yl)acetic acid (HCl salt) in place of N,3,4-difluoro-5-anisic acid and an additional equivalent of N,N-diisopropylethylamine. MS (ESI) calcd. for $C_{28}H_{24}N_{10}O$: 516.21 m/z, found 517.15 [M+H]$^+$. $^1$H NMR (300 MHz, DMSO-$d_6$) δ (ppm): 8.32-8.41 (m, 2H), 8.00-8.02 (m, 1H), 7.92-7.96 (m, 1H), 7.81-7.83 (m, 1H), 7.60-7.62 (m, 1H), 7.21-7.35 (m, 4H), 6.52-6.56 (m, 1H), 6.42-6.46 (m, 1H), 6.18 (s, 1H), 5.33-5.35 (m, 1H), 3.57-3.59 (m, 1H), 3.55-5.57 (m, 1H), 2.78-3.05 (m, 2H), 2.44-2.47 (m, 1H), 1.90-1.92 (m, 1H).

Example 52: (S)—N-(5-(2-(2-aminopyridin-3-yl)-5-(3-fluoro-1H-pyrazol-1-yl)-3H-imidazo[4,5-b]pyridin-3-yl)-2,3-dihydro-1H-inden-1-yl)-6-methylnicotinamide (Compound 52)

Compound 52

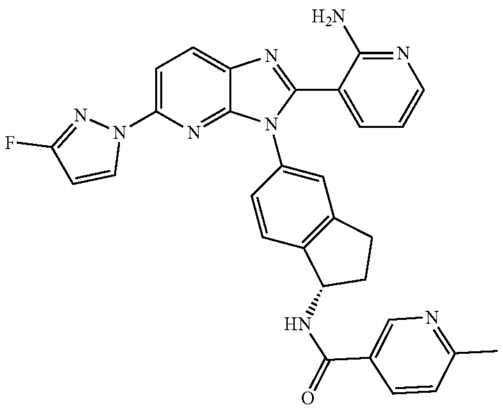

Compound 52 was prepared in a manner analogous to Compound 3 using 6-methylnicotinic acid in place of 3,4-difluoro-5-anisic acid, Intermediate 52-1 in place of Compound 2 and PyBOP in place of HATU. MS (ESI) calcd. for $C_{30}H_{24}FON_9$: 545.21, found 546.15 [M+H]$^+$. $^1$H NMR (400 MHz, DMSO-$d_6$) δ (ppm): 9.02-9.07 (m, 1H), 8.42-8.49 (m, 2H), 8.30-8.36 (m, 1H), 8.04-8.11 (m, 1H), 7.81-7.88 (m, 2H), 7.63-7.69 (m, 1H), 7.46-7.51 (m, 1H), 7.40-7.45 (m, 1H), 7.32-7.39 (m, 1H), 6.82-6.89 (m, 1H), 6.35-6.41 (m, 1H), 5.59-5.68 (m, 1H), 3.03-3.13 (m, 1H), 2.88-3.00 (m, 1H), 2.64 (s, 3H), 2.53-2.62 (m, 1H), 2.04-2.17 (m, 1H). $^{19}$F NMR (376 MHz, DMSO-$d_6$) δ (ppm): −126.82. (TFA salt)

Intermediate 52-1: (S)-3-(3-(1-amino-2,3-dihydro-1H-inden-5-yl)-5-(3-fluoro-1H-pyrazol-1-yl)-3H-imidazo[4,5-b]pyridin-2-yl)pyridin-2-amine Intermediate 52-1

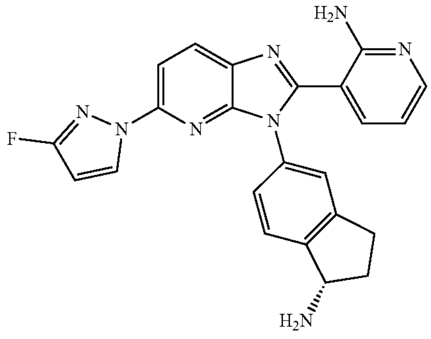

Intermediate 52-1 was prepared in a manner analogous to Compound 1 using 3-fluoropyrazole in place of pyrazole. MS (ESI) calculated for $C_{23}H_{19}FN_8$: 426.17 m/z, found 427.10 [M+H]$^+$.

Example 53: (S)—N-(5-(2-(2-aminopyridin-3-yl)-5-(3-fluoro-1H-pyrazol-1-yl)-3H-imidazo[4,5-b]pyridin-3-yl)-2,3-dihydro-1H-inden-1-yl)-6-(difluoromethyl)nicotinamide (Compound 53)

Compound 53

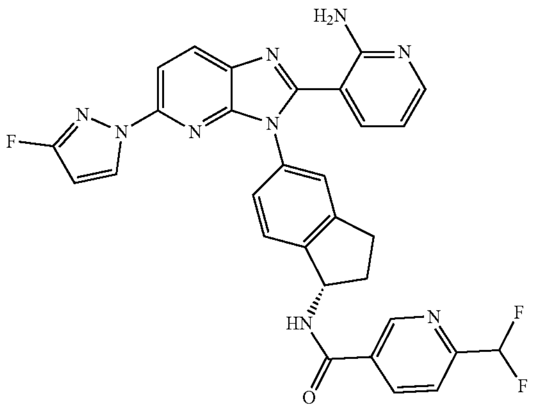

Compound 53 was prepared in a manner analogous to Compound 3 using 6-(difluoromethyl)nicotinic acid in place of 3,4-difluoro-5-anisic acid and Intermediate 52-1 in place of Compound 2. MS (ESI) calcd. for $C_{30}H_{22}F_3N_9O$: 581.19 m/z, found 582.25 $[M+H]^+$. $^1H$ NMR (300 MHz, DMSO-$d_6$) δ (ppm): 9.13-9.14 (m, 1H), 8.40-8.46 (m, 1H), 8.30-8.36 (m, 1H), 8.28-8.29 (m, 1H), 8.01-8.03 (m, 1H), 7.84-7.86 (m, 1H), 7.76-7.79 (m, 1H), 7.38-7.44 (m, 2H), 7.19-7.31 (m, 2H), 6.83-7.20 (m, 1H), 6.45-6.55 (m, 1H), 6.30-6.35 (m, 1H), 5.83-5.88 (m, 1H), 2.80-3.15 (m, 2H), 2.51-2.53 (m, 1H), 2.15-2.18 (m, 1H). $^{19}F$ NMR (300 MHz, DMSO-$d_6$) δ (ppm): −116.08, −127.28.

Example 54: (S)—N-(5-(2-(2-aminopyridin-3-yl)-5-(1H-pyrazol-1-yl)-3H-imidazo[4,5-b]pyridin-3-yl)-2,3-dihydro-1H-inden-1-yl)-6-(1H-pyrazol-1-yl)nicotinamide (Compound 54)

Compound 54

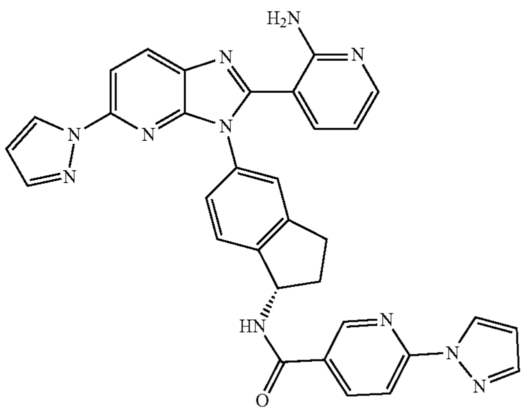

Compound 54 was prepared in a manner analogous to Compound 3 using 6-(1H-pyrazol-1-yl)nicotinic acid in place of 3,4-difluoro-5-anisic acid. MS (ESI) calcd. for $C_{32}H_{25}N_{11}O$: 579.22 m/z, found 580.30 $[M+H]^+$. $^1H$ NMR (300 MHz, DMSO-$d_6$) δ (ppm): 8.91-8.99 (m, 1H), 8.62-8.69 (m, 1H), 8.34-8.48 (m, 3H), 7.96-8.11 (m, 3H), 7.89-7.95 (m, 1H), 7.81-7.87 (m, 1H), 7.29-7.51 (m, 4H), 6.69-6.72 (m, 1H), 6.57-6.65 (m, 2H), 5.63-5.72 (m, 1H), 3.05-3.17 (m, 1H), 2.82-3.04 (m, 1H), 2.61-2.69 (m, 1H), 2.07-2.21 (m, 1H).

Example 55: (S)—N-(5-(2-(2-aminopyridin-3-yl)-5-(1H-pyrazol-1-yl)-3H-imidazo[4,5-b]pyridin-3-yl)-2,3-dihydro-1H-inden-1-yl)-6-ethynylnicotinamide (Compound 55)

Compound 55

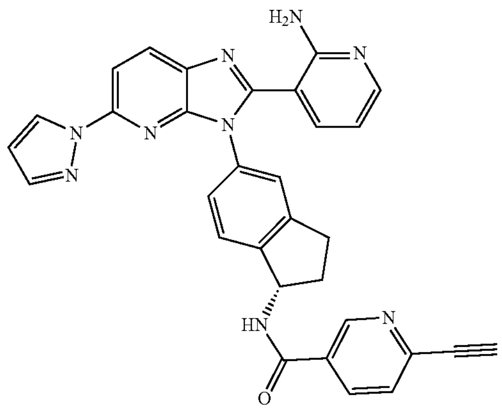

Compound 55 was prepared in a manner analogous to Compound 3 using 6-ethynylpyridine-3-carboxylic acid in place of 3,4-difluoro-5-anisic acid. MS(ESI) calcd. for $C_{31}H_{23}N_9O$: 537.20 m/z, found 538.30 $[M+H]^+$. $^1H$ NMR (300 MHz, DMSO-$d_6$) δ (ppm): 8.93-8.99 (m, 1H), 8.40-8.48 (m, 1H), 8.31-8.39 (m, 1H), 8.23-8.29 (m, 1H), 8.01-8.08 (m, 1H), 7.89-7.96 (m, 1H), 7.81-7.88 (m, 1H), 7.72-7.78 (m, 1H), 7.39-7.47 (m, 3H), 7.24-7.31 (m, 1H), 6.56-6.67 (m, 2H), 5.52-5.64 (m, 1H), 4.16-4.21 (m, 1H), 3.07-3.18 (m, 1H), 2.83-3.06 (m, 1H), 2.61-2.69 (m, 1H), 2.05-2.21 (m, 1H). (formic acid salt)

Example 56: (S)—N-(5-(2-(2-aminopyridin-3-yl)-5-(1H-pyrazol-1-yl)-3H-imidazo[4,5-b]pyridin-3-yl)-2,3-dihydro-1H-inden-1-yl)-6-(difluoromethyl)-4-methylnicotinamide (Compound 56)

Compound 56

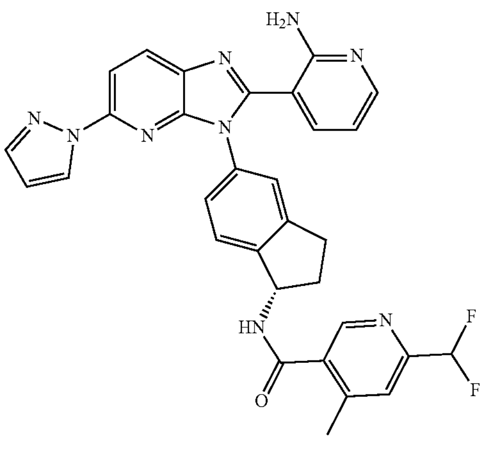

Synthetic Route:

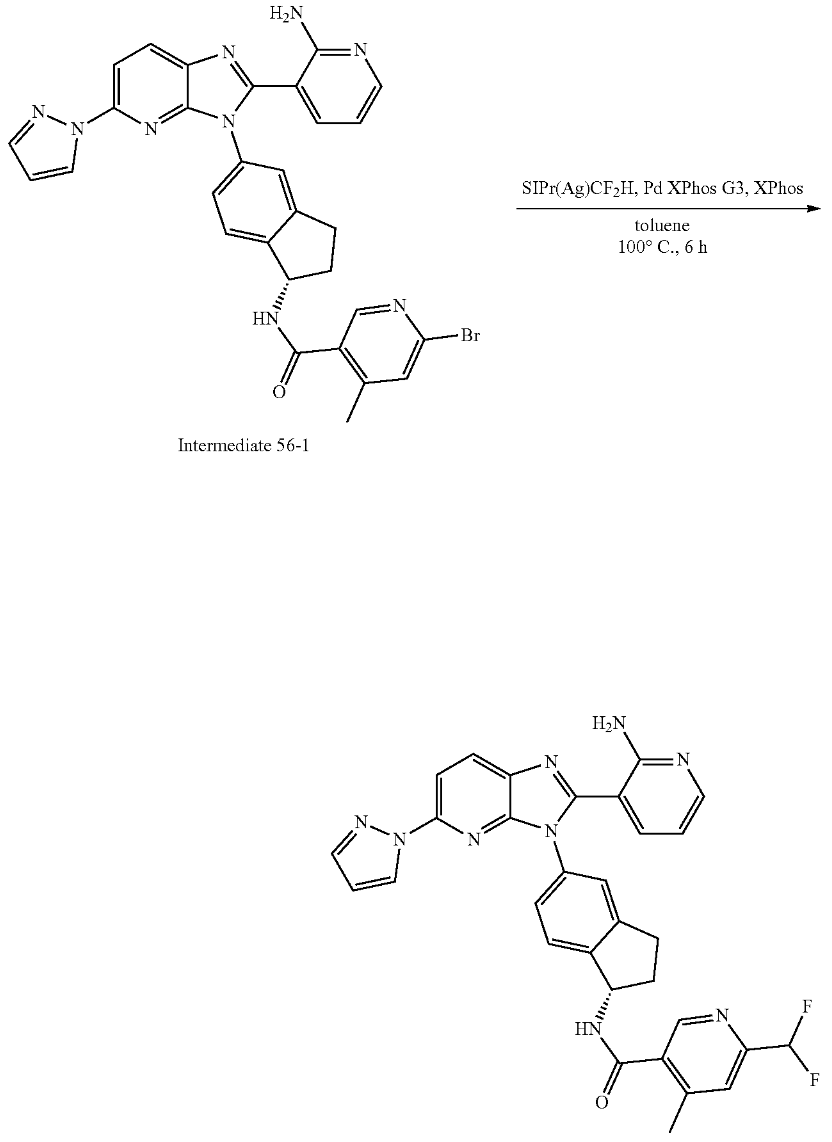

Intermediate 56-1

Compound 56

Step 2: Synthesis of (S)—N-(5-(2-(2-aminopyridin-3-yl)-5-(1H-pyrazol-1-yl)-3H-imidazo[4,5-b]pyridin-3-yl)-2,3-dihydro-1H-inden-1-yl)-6-(difluoromethyl)-4-methylnicotinamide (Compound 56)

To a solution of (S)—N-(5-(2-(2-aminopyridin-3-yl)-5-(1H-pyrazol-1-yl)-3H-imidazo[4,5-b]pyridin-3-yl)-2,3-dihydro-1H-inden-1-yl)-6-bromo-4-methylnicotinamide (Intermediate 56-1) (80 mg, 0.13 mmol, 1 equiv) and [1,3-Bis[2,6-bis(i-propyl) phenyl]-2-imidazolidinylidene] difluoromethylsilver(I) (94 mg, 0.17 mmol, 1.3 equiv) in toluene (6 mL) were added XPhos (6.3 mg, 0.013 mmol, 0.1 equiv) and XPhos Pd G3 (11 mg, 0.013 mmol, 0.1 equiv) and the resulting mixture was stirred for 6 h at 100° C. under nitrogen atmosphere. The reaction was quenched with water at room temperature. The resulting mixture was extracted with ethyl acetate 3 times. The combined organic layers were washed with brine and dried over anhydrous $Na_2SO_4$. After filtration, the filtrate was concentrated under reduced pressure. The crude product was purified by Preparative HPLC on a XSelect CSH Fluoro Phenyl column using a gradient of acetonitrile in water (+0.1% formic acid) to afford (S)—N-(5-(2-(2-aminopyridin-3-yl)-5-(1H-pyrazol-1-yl)-3H-imidazo[4,5-b]pyridin-3-yl)-2,3-dihydro-1H-inden-1-yl)-6-(difluoromethyl)-4-methylnicotinamide (Compound 56) (6.4 mg, 8%) as a white solid. MS (ESI) calcd. for $C_{31}H_{25}F_2N_9O$: 577.22 m/z, found 578.20 $[M+H]^+$. $^1H$ NMR (300 MHz, DMSO-$d_6$) δ (ppm): 8.64 (s, 1H), 8.35-8.37 (m, 2H), 7.94-8.03 (m, 2H), 7.94-7.97 (m, 1H), 7.66 (s, 1H), 7.49-7.51 (m, 1H), 7.33-7.39 (m, 1H), 7.26-7.29 (m, 2H), 6.57-7.12 (m, 1H), 6.56-7.57 (m, 1H), 6.45-6.49 (m, 1H), 5.57-5.62 (m, 1H), 2.89-3.15 (m, 2H), 2.51-2.53 (m, 1H), 2.41-2.48 (m, 3H), 1.95-2.18 (m, 1H). $^{19}F$ NMR (300 MHz, DMSO-$d_6$) δ (ppm): −115.64.

Intermediate 56-1: (S)—N-(5-(2-(2-aminopyridin-3-yl)-5-(1H-pyrazol-1-yl)-3H-imidazo[4,5-b]pyridin-3-yl)-2,3-dihydro-1H-inden-1-yl)-6-bromo-4-methylnicotinamide Intermediate 56-1

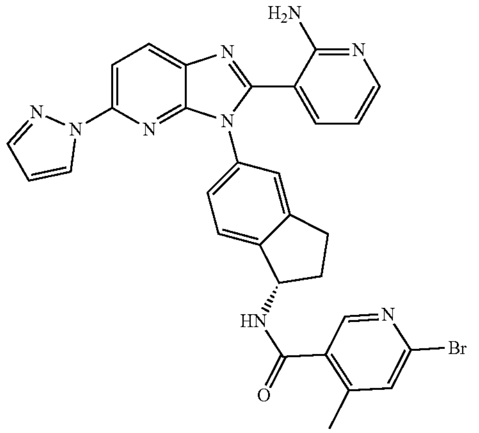

Intermediate 56-1 was prepared in a manner analogous to Compound 3 using 6-bromo-4-methylnicotinic acid in place of 3,4-difluoro-5-anisic acid. MS (ESI) calcd. for $C_{30}H_{24}BrN_9O$: 605.13 m/z, found 605.95, 607.95 [M+H, M+H+2]$^+$.

The following compounds were prepared analogous to the synthetic preparation in Example 56 (Compound 56).

Example 57: (S)—N-(5-(2-(2-aminopyridin-3-yl)-5-(1H-pyrazol-1-yl)-3H-imidazo[4,5-b]pyridin-3-yl)-2,3-dihydro-1H-inden-1-yl)-4-ethyloxazole-2-carboxamide (Compound 57)

Compound 57

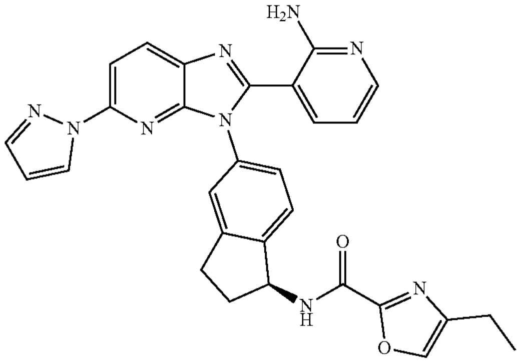

Synthetic Route:

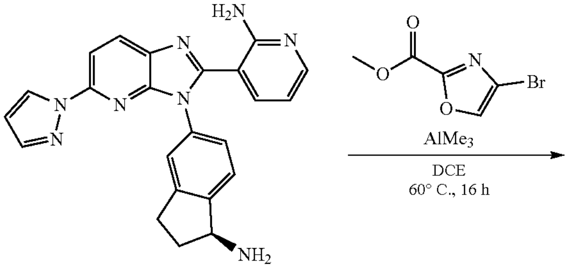

Compound 2

TABLE 4

Characterization data of compounds prepared analogously to compound 56.

| Cpd ID | Characterization Data |
|---|---|
| 97 | MS (ESI) calcd. for $C_{30}H_{22}F_3N_9O$, 581.19 m/z, found 582.10 [M + H]$^+$. $^1$H NMR (300 MHz, DMSO-d$_6$) δ (ppm); 8.78-9.01 (m, 1H), 8.22-8.50 (m, 2H), 7.88-8.13 (m, 2H), 8.68-7.87 (m, 2H), 7.23-7.55 (m, 4H), 6.80-7.22 (m, 1H), 6.37-6.79 (m, 2H), 5.45-5.70 (m, 1H), 2.80-3.18 (m, 2H), 2.60-2.68 (m, 1H), 1.83-2.14 (m, 1H). 19F NMR (282 MHz, DMSO-d$_6$) δ (ppm); −101.82, −116.64. |
| 102 | MS (ESI) calcd. for $C_{30}H_{24}F_2N_{10}O$, 578.21 m/z, found 579.10 [M + H]$^+$. $^1$H NMR (400 MHz, DMSO-d$_6$) δ (ppm); 9.20-9.45 (m, 1H), 8.92 (s, 1H), 8.40-8.59 (m, 1H), 8.20-8.35 (m, 1H), 8.08-8.20 (m, 3H), 7.95-8.08 (m, 1H), 7.55-7.70 (m, 1H), 7.40-7.50 (m, 2H), 7.30-7.40 (m, 1H), 6.90-7.28 (m, 1H), 6.62-6.75 (m, 1H), 5.40-5.78 (m, 1H), 3.00-3.15 (m, 1H), 2.18-3.00 (m, 1H), 2.45-2.50 (m, 4H), 2.00-2.20 (m, 1H). 19F NMR (300 MHz, DMSO-d$_6$) δ (ppm); −116.12. |
| 121 | MS (ESI) calcd. for $C_{29}H_{21}F_3N_{10}O$, 582.55 m/z, found 583.25 [M + H]$^+$. $^1$H NMR (400 MHz, DMSO-d$_6$) δ (ppm); 8.30-8.42 (m, 1H), 9.34 (s, 1H), 8.26-8.50 (m, 2H), 8.12 (s, 2H), 8.00 - 8.10 (m, 2H), 7.40-7.55 (m, 2H), 7.30-7.40 (m, 1H), 7.22-7.30 (m, 1H), 6.85-7.20 (m, 3H), 6.35-6.50 (m, 1H), 5.60-5.78 (m, 1H), 3.00-3.15 (m, 1H), 2.85-3.00 (m, 1H), 2.56-2.65 (m, 1H), 2.00-2.15 (m, 1H). $^{19}$F NMR (300 MHz, DMSO-d$_6$) δ (ppm); −117.74, −126.65. |

-continued

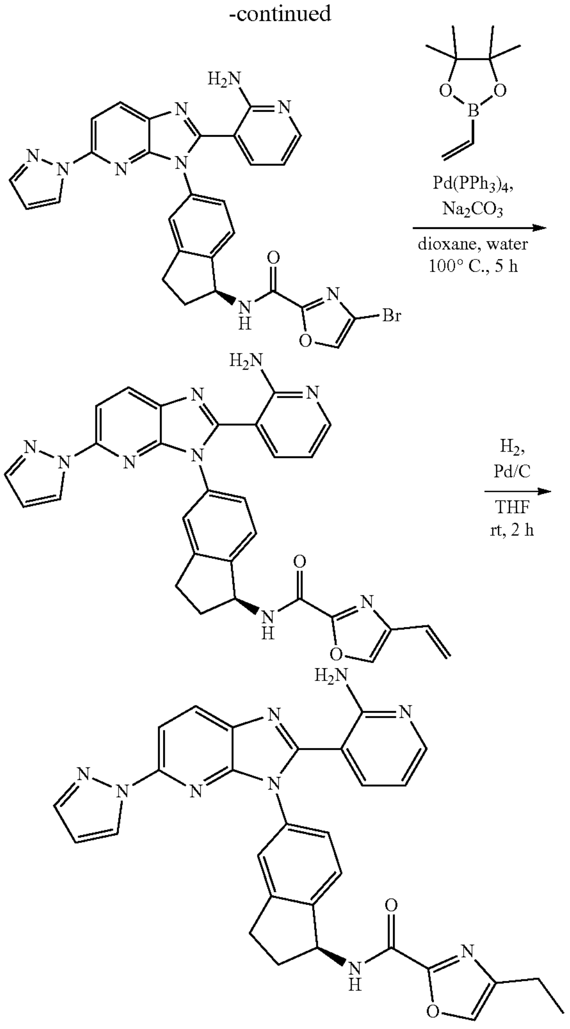

Compound 57

Step 1: Synthesis of (S)—N-(5-(2-(2-aminopyridin-3-yl)-5-(1H-pyrazol-1-yl)-3H-imidazo[4,5-b]pyridin-3-yl)-2,3-dihydro-1H-inden-1-yl)-4-bromooxazole-2-carboxamide To a solution of (S)-3-(3-(1-amino-2,3-dihydro-1H-inden-5-yl)-5-(1H-pyrazol-1-yl)-3H-imidazo[4,5-b]pyridin-2-yl)pyridin-2-amine (Compound 2) (180 mg, 0.441 mmol, 1 equiv) in DCE (5 mL) was added $AlMe_3$ (1.15 mL, 2.21 mmol, 2M in toluene, 5 equiv) at 0° C. Then methyl 4-bromooxazole-2-carboxylate (107 mg, 0.485 mmol, 1.1 equiv) was added. The resulting mixture was maintained under nitrogen and stirred at 60° C. for 16 h. After cooling to room temperature, the reaction was quenched with water. The resulting mixture was extracted with ethyl acetate 3 times. The organic layers were combined, dried over anhydrous $Na_2SO_4$, filtered and concentrated. The crude product was purified by reverse-phase flash column chromataography on C18 silica gel using a gradient of acetonitrile in water (+0.05% TFA) to afford (S)—N-(5-(2-(2-aminopyridin-3-yl)-5-(1H-pyrazol-1-yl)-3H-imidazo[4,5-b]pyridin-3-yl)-2,3-dihydro-1H-inden-1-yl)-4-bromooxazole-2-carboxamide (80 mg, 31%) as a yellow solid. MS (ESI) calcd. for $C_{27}H_{20}BrN_9O_2$: 581.09 m/z, found 582.00 $[M+H]^+$.

Step 2: Synthesis of (S)—N-(5-(2-(2-aminopyridin-3-yl)-5-(1H-pyrazol-1-yl)-3H-imidazo[4,5-b]pyridin-3-yl)-2,3-dihydro-1H-inden-1-yl)-4-vinyloxazole-2-carboxamide To a solution of (S)—N-(5-(2-(2-aminopyridin-3-yl)-5-(1H-pyrazol-1-yl)-3H-imidazo[4,5-b]pyridin-3-yl)-2,3-dihydro-1H-inden-1-yl)-4-bromooxazole-2-carboxamide (60 mg, 0.103 mmol, 1 equiv) in 1,4-dioxane (1.6 mL) and water (0.4 mL) was added 4,4,5,5-tetramethyl-2-vinyl-1,3,2-dioxaborolane (159 mg, 1.03 mmol, 1 equiv), $Pd(PPh_3)_4$ (12 mg, 0.010 mmol, 0.1 equiv) and $Na_2CO_3$ (55 mg, 0.52 mmol, 5 equiv). The resulting mixture was maintained under nitrogen atmosphere and stirred at 100° C. for 5 h. After cooling to room temperature, the reaction was quenched with water. The resulting mixture was extracted with ethyl acetate 3 times. The organic layers were combined, dried over anhydrous $Na_2SO_4$, filtered and concentrated. The crude product was purified by reverse-phase flash column chromatography on C18 silica gel using a gradient of acetonitrile in water (+0.05% TFA) to afford (S)—N-(5-(2-(2-aminopyridin-3-yl)-5-(1H-pyrazol-1-yl)-3H-imidazo[4,5-b]pyridin-3-yl)-2,3-dihydro-1H-inden-1-yl)-4-vinyloxazole-2-carboxamide (40 mg, 73%) as a yellow solid. MS (ESI) calcd. for $C_{29}H_{23}N_9O_2$: 529.20 m/z found 530.10 $[M+H]^+$.

Step 3: Synthesis of (S)—N-(5-(2-(2-aminopyridin-3-yl)-5-(1H-pyrazol-1-yl)-3H-imidazo[4,5-b]pyridin-3-yl)-2,3-dihydro-1H-inden-1-yl)-4-ethyloxazole-2-carboxamide (Compound 57)

A mixture of (S)—N-(5-(2-(2-aminopyridin-3-yl)-5-(1H-pyrazol-1-yl)-3H-imidazo[4,5-b]pyridin-3-yl)-2,3-dihydro-1H-inden-1-yl)-4-vinyloxazole-2-carboxamide (30 mg, 0.057 mmol, 1 equiv) and 10% Pd/C (30 mg, 0.026 mmol, 0.5 equiv) in THE (5 mL) was stirred for 1 h at room temperature under $H_2$ atmosphere. The mixture was filtered and concentrated. The crude product was purified by Preparative HPLC on a XSelect CSH Prep C18 OBD Column using a gradient of acetonitrile in water (+0.05% TFA) to afford (S)—N-(5-(2-(2-aminopyridin-3-yl)-5-(1H-pyrazol-1-yl)-3H-imidazo[4,5-b]pyridin-3-yl)-2,3-dihydro-1H-inden-1-yl)-4-ethyloxazole-2-carboxamide (trifluoroacetic acid salt) (Compound 57) (5.9 mg, 16%) as an off-white solid. MS (ESI) calcd. for $C_{29}H_{25}N_9O_2$: 531.21 m/z, found 532.15 $[M+H]^+$. $^1H$ NMR (300 MHz, DMSO-$d_6$) δ (ppm): 8.31-8.52 (m, 2H), 7.93-8.12 (m, 3H), 7.75-7.90 (m, 1H), 7.65-7.74 (m, 1H), 7.40-7.51 (m, 1H), 7.25-7.39 (m, 2H), 6.68-6.89 (m, 1H), 6.48-6.64 (m, 1H), 5.47-5.64 (m, 1H), 2.98-3.18 (m, 1H), 2.80-2.97 (m, 1H), 2.56-2.68 (m, 3H), 2.08-2.27 (m, 1H), 1.10-1.30 (m, 3H).

Example 58: (S)—N-(5-(2-(2-aminopyridin-3-yl)-5-(2H-1,2,3-triazol-2-yl)-3H-imidazo[4,5-b]pyridin-3-yl)-2,3-dihydro-1H-inden-1-yl)nicotinamide (Compound 58)

Compound 58

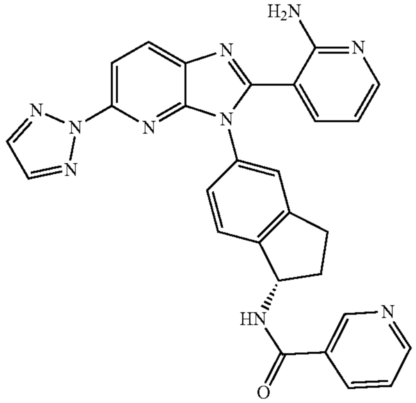

Compound 58 was prepared in a manner analogous to Compound 3 using nicotinic acid in place of 3,4-difluoro-5-anisic acid and Intermediate 58-1 in place of Compound 2. MS (ESI) calcd. for $C_{28}H_{22}N_{10}O$: 514.20 m/z, found 515.15 $[M+H]^+$. $^1H$-NMR (400 MHz, DMSO-$d_6$) δ (ppm): 9.10-9.11 (m, 1H), 8.76-8.77 (m, 1H), 8.50-8.52 (m, 1H), 8.37-8.38 (m, 1H), 8.05-8.11 (m, 4H), 7.85-7.87 (m, 1H), 7.61-7.63 (m, 1H), 7.45-7.48 (m, 2H), 7.36-7.38 (m, 1H), 6.85-6.87 (m, 1H), 5.63-5.67 (m, 1H), 3.03-3.05 (m, 1H), 2.94-2.96 (m, 1H), 2.50-2.51 (m, 1H), 2.10-2.12 (m, 1H). (TFA salt)

Intermediate 58-1: (S)-3-(3-(1-amino-2,3-dihydro-1H-inden-5-yl)-5-(2H-1,2,3-triazol-2-yl)-3H-imidazo[4,5-b]pyridin-2-yl)pyridin-2-amine Intermediate 58-1

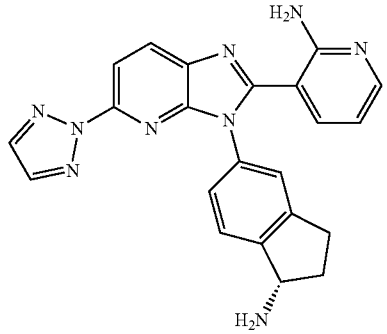

Synthetic Route:

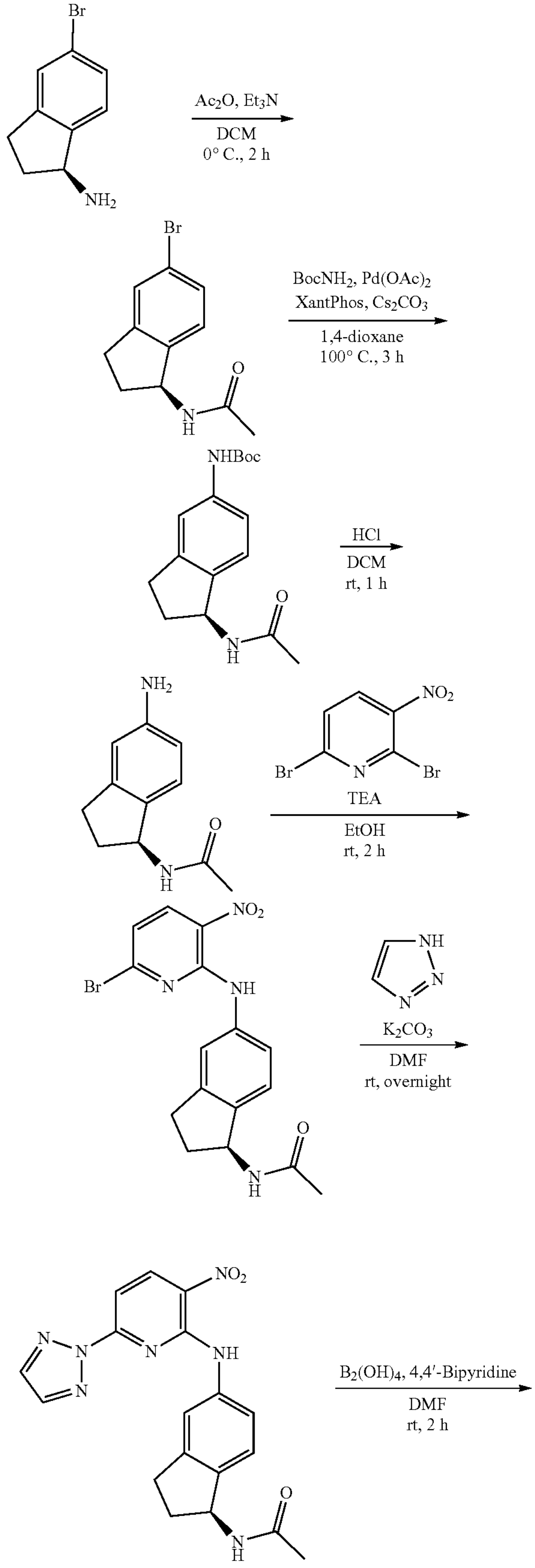

-continued

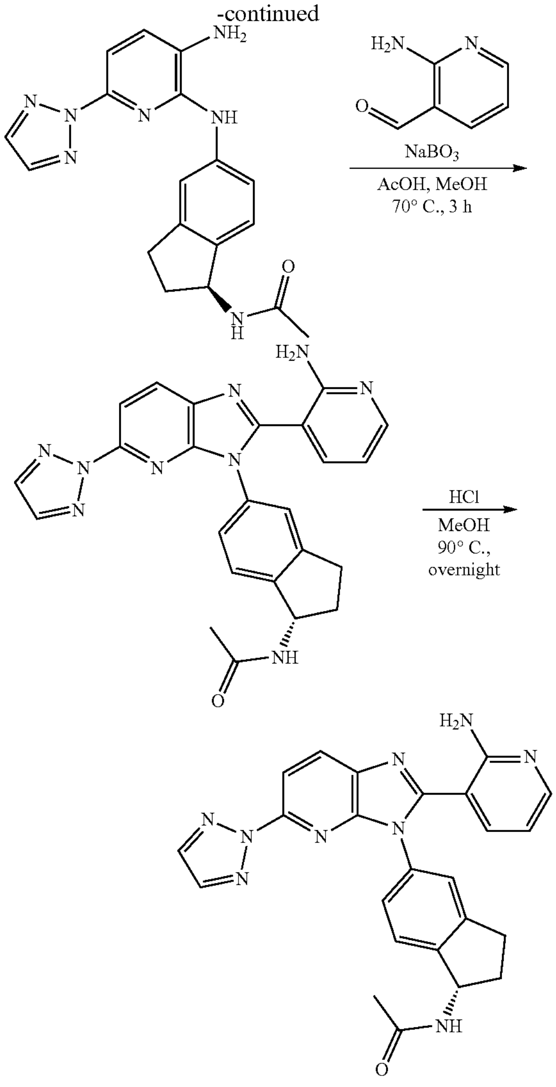

Intermediate 58-1

Step 1: Synthesis of (S)—N-(5-bromo-2,3-dihydro-1H-inden-1-yl)acetamide

To a mixture of (S)-5-bromo-2,3-dihydro-1H-inden-1-amine (74 g, 350 mmol, 1 equiv) and triethylamine (106 g, 1.05 mol, 3 equiv) in dichloromethane (1.5 L) was added acetic anhydride (55.2 g, 526 mmol, 1.5 equiv) at 0° C. and the mixture was stirred at 0° C. for 2 h. The reaction mixture was quenched by addition of water and extracted 3 times with ethyl acetate. The combined organic layers were dried over anhydrous sodium sulfate and concentrated under reduced pressure. The crude product was re-crystallized from petroleum ether to afford (S)—N-(5-bromo-2,3-dihydro-1H-inden-1-yl)acetamide (90 g, 83% yield) as a white solid. MS (ESI) calculated for $C_{11}H_{12}BrNO$: 253.01, found 254.00 $[M+H]^+$, 256.00 $[M+H+2]^+$.

Step 2: Synthesis of tert-butyl (S)-(1-acetamido-2,3-dihydro-1H-inden-5-yl)carbamate To a mixture of N-[(1S)-5-bromo-2,3-dihydro-1H-inden-1-yl]acetamide (40 g, 157 mmol, 1 equiv), tert-butyl carbamate (27.66 g, 236 mmol, 1.5 equiv), XantPhos (9.11 g, 15.7 mmol, 10 mol %), palladium (II) acetate (3.54 g, 15.7 mmol, 10 mol %), and cesium carbonate (154 g, 472 mmol, 10 mol %) was added 1,4-dioxane (300 mL) under nitrogen atmosphere. The resulting mixture was stirred for 3 h at 100° C. The reaction mixture was quenched by addition of water and extracted 3 times with ethyl acetate. The combined organic layers were dried over anhydrous sodium sulfate and concentrated under reduced pressure. The residue was purified by silica gel column chromatography using an eluent of petroleum ether/dichloromethane/methanol (70:27:3) to afford tert-butyl N-[(1S)-1-acetamido-2,3-dihydro-1H-inden-5-yl]carbamate (43.1 g, 48%). MS (ESI) calculated for $C_{16}H_{22}N_2O_3$: 290.16 m/z, found 289.05 $[M-H]^-$.

Step 3: Synthesis of (S)—N-(5-amino-2,3-dihydro-1H-inden-1-yl)acetamide

To a stirred solution of tert-butyl N-[(1S)-1-acetamido-2,3-dihydro-1H-inden-5-yl]carbamate (43.1 g, 148 mmol, 1 equiv) in dichloromethane (180 mL) was added 4N hydrochloric acid in 1,4-dioxane (185 mL, 742 mmol, 5 equiv). The reaction mixture was stirred for 1 h at room temperature. The reaction mixture was concentrated in vacuo and re-crystallized from ethyl acetate to afford N-[(1S)-5-amino-2,3-dihydro-1H-inden-1-yl]acetamide (hydrochloride salt) (23 g, 81%) as a white solid. MS (ESI) calculated for $C_{11}H_{14}N_2O$: 190.11 m/z, found 191.15 $[M+H]^+$.

Step 4: Synthesis of (S)—N-(5-((6-bromo-3-nitropyridin-2-yl)amino)-2,3-dihydro-1H-inden-1-yl)acetamide A solution of (S)—N-(5-amino-2,3-dihydro-1H-inden-1-yl)acetamide (17 g, 89 mmol), 2,6-dibromo-3-nitropyridine (25.19 g, 89.36 mmol) and triethylamine (45.21 g, 446.8 mmol) in EtOH (200 mL) was stirred at room temperature for 2 h. The reaction was quenched with water and the precipitated solids were collected by filtration, washing with $EtOH/H_2O$=1:1 to afford (S)—N-(5-((6-bromo-3-nitropyridin-2-yl)amino)-2,3-dihydro-1H-inden-1-yl)acetamide (26 g, 74.37% yield) as an orange solid. MS (ESI) calcd. for $C_{16}H_{15}BrN_4O_3$: 390.03, found 413.00 $[M+Na]^+$, 415.00 $[M+Na+2]$.

Step 5: Synthesis of (S)—N-(5-((3-nitro-6-(2H-1,2,3-triazol-2-yl)pyridin-2-yl)amino)-2,3-dihydro-1H-inden-1-yl)acetamide To a solution of (S)—N-(5-((6-bromo-3-nitropyridin-2-yl)amino)-2,3-dihydro-1H-inden-1-yl)acetamide (50.0 g, 128 mmol) in DMF (1.5 L) was added $K_2CO_3$ (52.99 g, 383.4 mmol) and 1H-1,2,3-triazole (17.65 g, 255.6 mmol). The resulting mixture was stirred at room temperature overnight. The product was precipitated by the addition of $H_2O$. The precipitated solids were collected by filtration and washed with water. The crude product was re-crystallized from petroleum ether to afford (S)—N-(5-((3-nitro-6-(2H-1,2,3-triazol-2-yl)pyridin-2-yl)amino)-2,3-dihydro-1H-inden-1-yl)acetamide (45 g, 93%) as a yellow solid. MS (ESI) calculated for $C18H_{17}N_7O_3$: 379.14 m/z, found 380.15 $[M+H]^+$. $^1H$ NMR (400 MHz, DMSO-$d_6$) δ (ppm): 7.98 (s, 2H), 7.79 (d, J=2.1 Hz, 1H), 7.68 (dd, J=8.3, 2.1 Hz, 1H), 7.17 (d, J=8.1 Hz, 1H), 7.13-7.04 (m, 2H), 5.18 (t, J=7.4 Hz, 1H), 2.93-2.85 (m, 1H), 2.80-2.70 (m, 1H), 2.43-2.31 (m, 1H), 1.87 (s, 3H), 1.82-1.71 (m, 1H).

Step 6: Synthesis of (S)—N-(5-((3-amino-6-(2H-1,2,3-triazol-2-yl)pyridin-2-yl)amino)-2,3-dihydro-1H-inden-1-yl)acetamide To a cooled (0° C.) solution of (S)—N-(5-((3-nitro-6-(2H-1,2,3-triazol-2-yl)pyridin-2-yl)amino)-2,3-dihydro-1H-inden-1-yl)acetamide (1.3 g, 3.4 mmol) and 4,4-bypyridine (27 mg, 0.17 mmol) in DMF (25 mL) was added $B_2(OH)_4$ (0.92 g, 10 mmol). The resulting mixture was stirred at room temperature for 2 h. The reaction was quenched with $H_2O$. The resulting mixture was extracted with ethyl acetate 3 times. The organic layers were combined, dried over $Na_2SO_4$, filtered and concentrated. The residue obtained was purified by silica gel column chromatography using a gradient of ethyl acetate in petroleum ether to afford (S)—N-(5-((3-amino-6-(2H-1,2,3-triazol-2-yl)pyridin-2-yl)amino)-2,3-dihydro-1H-inden-1-yl)acetamide (800 mg, 67%) as a yellow solid. MS (ESI) calcd. for $C_{18}H_{19}N_7O$: 349.17 m/z, found 350.15 $[M+H]^+$.

Step 7: Synthesis of (S)—N-(5-(2-(2-aminopyridin-3-yl)-5-(2H-1,2,3-triazol-2-yl)-3H-imidazo[4,5-b]pyridin-3-yl)-2,3-dihydro-1H-inden-1-yl)acetamide To a solution of (S)—N-(5-((3-amino-6-(2H-1,2,3-triazol-2-yl)pyridin-2-yl)amino)-2,3-dihydro-1H-inden-1-yl)acetamide (700 mg, 2.00 mmol) in AcOH (10 mL) and MeOH (2 mL) was added 2-aminonicotinaldehyde (269 mg, 2.20 mmol) and sodium perborate (328 mg, 4.00 mmol). The resulting mixture was stirred at 70° C. for 3 h. The solvent was removed by distillation under vacuum. The resulting mixture was purified by reverse-phase flash column chromatography on C18 silica gel using a gradient of acetonitrile in water (+0.05% ammonium bicarbonate) to afford (S)—N-(5-(2-(2-aminopyridin-3-yl)-5-(2H-1,2,3-triazol-2-yl)-3H-imidazo[4,5-b]pyridin-3-yl)-2,3-dihydro-1H-inden-1-yl)acetamide (520 mg, 57%) as a reddish brown solid. MS (ESI) calcd. for $C_{24}H_{21}N_9O$: 451.19 m/z, found 452.20 $[M+H]^+$.

Step 8: Synthesis of (S)-3-(3-(1-amino-2,3-dihydro-1H-inden-5-yl)-5-(2H-1,2,3-triazol-2-yl)-3H-imidazo[4,5-b]pyridin-2-yl)pyridin-2-amine (Intermediate 58-1)

A solution of (S)—N-(5-(2-(2-aminopyridin-3-yl)-5-(2H-1,2,3-triazol-2-yl)-3H-imidazo[4,5-b]pyridin-3-yl)-2,3-dihydro-1H-inden-1-yl)acetamide (520 mg, 1.152 mmol) in HCl (20 mL, concentrated) and MeOH (20 mL) was stirred at 90° C. overnight. The solvent was removed by distillation under vacuum to afford (S)-3-(3-(1-amino-2,3-dihydro-1H-inden-5-yl)-5-(2H-1,2,3-triazol-2-yl)-3H-imidazo[4,5-b]pyridin-2-yl)pyridin-2-amine (Intermediate 58-1) (400 mg, 85%) crude as a yellow solid. MS (ESI) calcd. for $C_{22}H_{19}N_9$: 409.18 m/z, found 410.20 $[M+H]^+$.

Example 59: (S)—N-(5-(2-(2-aminopyridin-3-yl)-5-(2H-1,2,3-triazol-2-yl)-3H-imidazo[4,5-b]pyridin-3-yl)-2,3-dihydro-1H-inden-1-yl)pyrimidine-5-carboxamide (Compound 59)

Compound 59

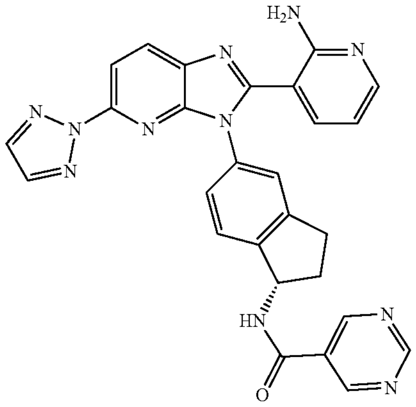

Compound 59 was prepared in a manner analogous to Compound 3 using pyrimidine-5-carboxylic acid in place of 3,4-difluoro-5-anisic acid, Intermediate 58-1 in place of Compound 2, and PyBOP in place of HATU. MS (ESI) calcd. for $C_{27}H_{21}N_{11}O$: 515.19 m/z, found 516.10 $[M+H]^+$. $^1H$ NMR (300 MHz, DMSO-$d_6$) δ (ppm): 9.23-9.33 (m, 3H), 8.49-8.52 (m, 1H), 8.04-8.15 (m, 4H), 7.80-7.83 (m, 1H), 7.37-7.51 (m, 3H), 6.80-6.84 (m, 1H), 5.62-5.67 (m, 1H), 2.89-3.15 (m, 2H), 2.51-2.53 (m, 1H), 2.06-2.13 (m, 1H). (TFA salt)

Example 60: (S)—N-(5-(2-(2-aminopyridin-3-yl)-5-(1H-pyrazol-1-yl)-3H-imidazo[4,5-b]pyridin-3-yl)-2,3-dihydro-1H-inden-1-yl)-6-(difluoromethyl)-5-methylnicotinamide (Compound 60)

Compound 60

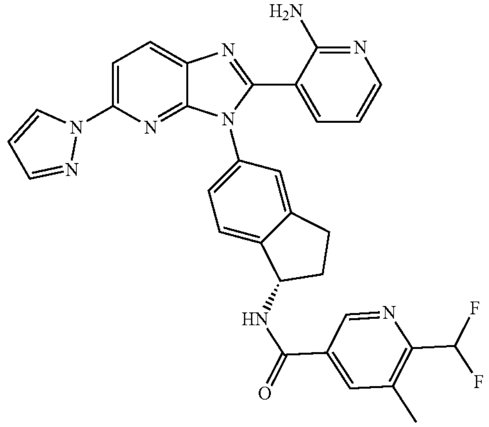

Compound 60 was prepared in a manner analogous to Compound 56 (via Intermediate 56-1) using 6-bromo-5-methylnicotinic acid in place of 6-bromo-4-methylnicotinic acid. MS (ESI) calcd. for $C_{31}H_{25}F_2N_9O$: 577.22 m/z, found 578.10 $[M+H]^+$. $^1H$ NMR (300 MHz, DMSO-$d_6$) δ (ppm):

8.88 (s, 1H), 8.24-8.40 (m, 2H), 8.19 (s, 1H), 7.95-8.02 (m, 1H), 7.82-7.94 (m, 1H), 7.67-7.81 (m, 1H), 7.31-7.45 (m, 2H), 7.12-7.30 (m, 2H), 6.65-7.11 (m, 1H), 6.47-6.56 (m, 1H), 6.37-6.46 (m, 1H), 5.48-5.68 (m, 1H), 2.77-3.13 (m, 2H), 2.52-2.61 (m, 1H), 2.38-2.48 (m, 3H), 1.90-2.15 (m, 1H). $^{19}$F NMR (282 MHz, DMSO-$d_6$) δ (ppm): −116.07.

Example 61: (S)—N-(5-(2-(2-aminopyridin-3-yl)-5-(1H-pyrazol-1-yl)-3H-imidazo[4,5-b]pyridin-3-yl)-2,3-dihydro-1H-inden-1-yl)-4-(difluoromethyl)benzamide (Compound 61)

Compound 61

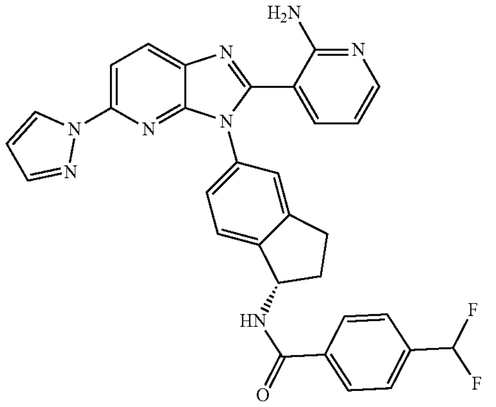

Compound 61 was prepared in a manner analogous to Compound 3 using 4-(difluoromethyl)benzoic acid in place of 3,4-difluoro-5-anisic acid. MS (ESI) calcd. for $C_{31}H_{24}F_2N_8O$: 562.20 m/z, found 563.25 [M+H]$^+$. $^1$H NMR (400 MHz, DMSO-$d_6$) δ (ppm): 8.42-8.44 (m, 1H), 8.37-8.38 (m, 1H), 8.05-8.07 (m, 4H), 7.93-7.96 (m, 2H), 7.79-7.82 (m, 2H), 7.67-7.69 (m, 1H), 7.40-7.46 (m, 2H), 7.22-7.38 (m, 1H), 6.85-6.94 (m, 1H), 6.56-6.57 (m, 1H), 5.61-5.65 (m, 1H), 3.03-3.05 (m, 1H), 2.94-2.96 (m, 1H), 2.50-2.51 (m, 1H), 2.10-2.12 (m, 1H). $^{19}$F NMR (376 MHz, DMSO-$d_6$) δ (ppm): −110.38. (TFA salt)

Example 62: (S)—N-(5-(2-(2-aminopyridin-3-yl)-5-(1H-pyrazol-1-yl)-3H-imidazo[4,5-b]pyridin-3-yl)-2,3-dihydro-1H-inden-1-yl)-6-(difluoromethyl)-5-fluoronicotinamide (Compound 62)

Compound 62

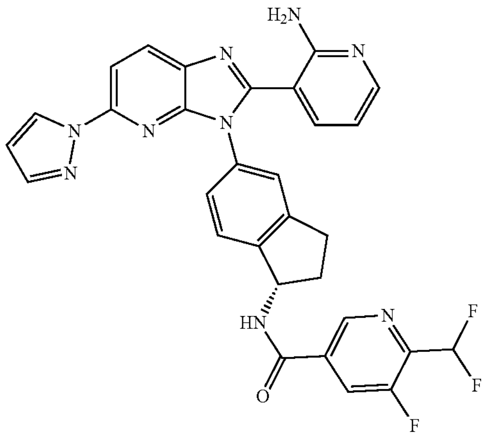

Compound 62 was prepared in a manner analogous to Compound 60 (via Intermediate 56-1) using TCFH in place of HATU, N-methyl imidazole in place of N,N-diisopropylethylamine, acetonitrile in place of N,N-dimethylformamide and 6-bromo-5-fluoronicotinic acid in place of 6-bromo-5-methylnicotinic acid. MS (ESI) calcd. for $C_{30}H_{22}F_3N_9O$: 581.19 m/z, found 582.25 [M+H]$^+$. $^1$H NMR (300 MHz, DMSO-$d_6$) δ (ppm): 9.33-9.36 (m, 1H), 9.01 (s, 1H), 8.34-8.58 (m, 3H), 8.00-8.15 (m, 2H), 7.82-7.83 (m, 1H), 7.73-7.76 (m, 1H), 7.45-7.48 (m, 2H), 7.04-7.39 (m, 2H), 6.77-6.81 (m, 1H), 6.58-6.59 (m, 1H), 5.61-5.68 (m, 1H), 2.89-3.12 (m, 2H), 2.51-2.53 (m, 1H), 2.07-2.18 (m, 1H). $^{19}$F NMR (300 MHz, DMSO-$d_6$) S (ppm): −117.82, −126.49. (TFA salt)

Example 63: (S)—N-(5-(2-(2-aminopyridin-3-yl)-5-(1H-pyrazol-1-yl)-3H-imidazo[4,5-b]pyridin-3-yl)-2,3-dihydro-1H-inden-1-yl)-2-(dimethylamino)isonicotinamide (Compound 63)

Compound 63

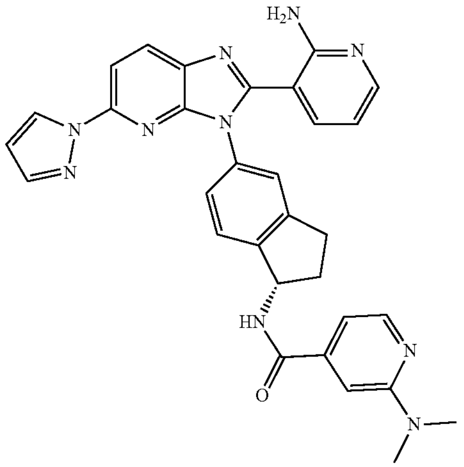

Compound 63 was prepared in a manner analogous to Compound 3 using 2-(dimethylamino)isonicotinic acid in place of 3,4-difluoro-5-anisic acid. MS (ESI) calcd. for $C_{31}H_{28}N_{10}O$: 556.24 m/z, found 557.25 [M+H]$^+$. $^1$H NMR (300 MHz, DMSO-$d_6$) δ (ppm): 8.31-8.39 (m, 2H), 8.13-8.18 (m, 1H), 7.96-8.07 (m, 2H), 7.79-7.87 (m, 1H), 7.31-7.49 (m, 4H), 6.97-7.05 (m, 2H), 6.43-6.58 (m, 2H), 5.57-5.69 (m, 1H), 2.98-3.13 (m, 6H), 2.81-2.97 (m, 2H), 2.53-2.59 (m, 1H), 2.07-2.13 (m, 1H).

Example 64: (S)—N-(5-(2-(2-aminopyridin-3-yl)-5-(1H-pyrazol-1-yl)-3H-imidazo[4,5-b]pyridin-3-yl)-2,3-dihydro-1H-inden-1-yl)-2-(trifluoromethoxy)isonicotinamide (Compound 64)

Compound 64

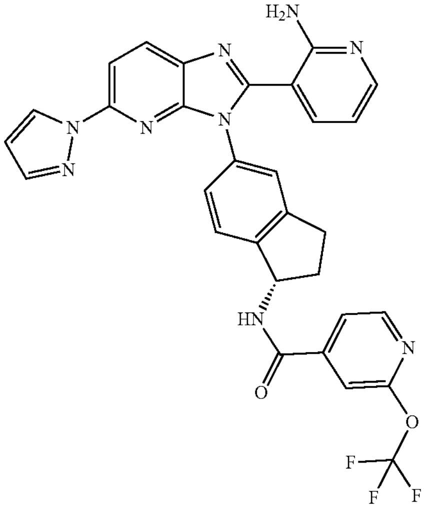

Compound 64 was prepared in a manner analogous to Compound 3 using 2-(trifluoromethoxy)isonicotinic acid in place of 3,4-difluoro-5-anisic acid and PyBOP in place of HATU. MS (ESI) calcd. for $C_{30}H_{22}F_3N_9O_2$: 597.18 m/z, found 598.10 $[M+H]^+$. $^1H$ NMR (300 MHz, DMSO-$d_6$) δ (ppm): 8.48-8.55 (m, 1H), 8.30-8.40 (m, 2H), 7.97-8.05 (m, 1H), 7.89-7.97 (m, 1H), 7.80-7.89 (m, 1H), 7.75-80 (m, 1H), 7.67 (s, 1H), 7.36-7.42 (m, 2H), 7.22-7.33 (m, 2H), 6.51-6.58 (m, 1H), 6.41-6.50 (m, 1H), 5.55-5.66 (m, 1H), 2.82-3.11 (m, 2H), 2.53-2.61 (m, 1H), 2.00-2.17 (m, 1H). $^{19}F$ NMR (282 MHz, DMSO-$d_6$) δ (ppm): −55.18. (formic acid salt)

Example 65: (S)—N-(5-(2-(2-aminopyridin-3-yl)-5-(2H-1,2,3-triazol-2-yl)-3H-imidazo[4,5-b]pyridin-3-yl)-2,3-dihydro-1H-inden-1-yl)-6-(difluoromethyl)nicotinamide (Compound 65)

Compound 65

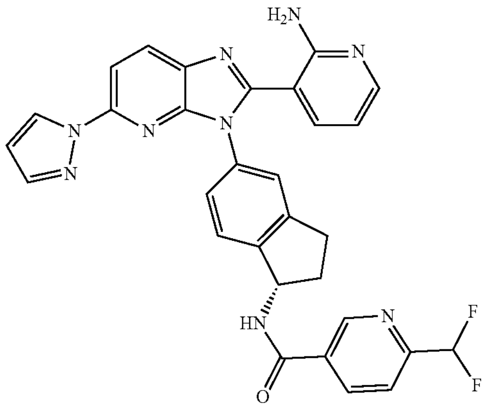

Compound 65 was prepared in a manner analogous to Compound 3 using 6-(difluoromethyl)nicotinic acid in place of 3,4-difluoro-5-anisic acid, PyBOP in place of HATU and Intermediate 58-1 in place of Compound 2. MS (ESI) calcd. for $C_{29}H_{22}F_2N_{10}O$: 564.19 m/z, found 565.25 $[M+H]^+$. $^1H$ NMR (300 MHz, DMSO-$d_6$) δ (ppm): 9.15-9.25 (m, 1H), 8.38-8.52 (m, 2H), 8.13 (s, 2H), 7.97-8.08 (m, 2H), 7.78-7.85 (m, 1H), 7.39-7.48 (m, 2H), 7.24-7.35 (m, 2H), 7.85-7.03 (m, 1H), 6.40-6.50 (m, 1H), 5.61-5.72 (m, 1H), 2.85-3.15 (m, 2H), 2.52-2.64 (m, 1H), 2.00-2.19 (m, 1H). $^{19}F$ NMR (282 MHz, DMSO-$d_6$) δ (ppm): −116.04. (formic acid salt).

Example 66: (S)-3-(5-(2-(2-aminopyridin-3-yl)-5-(1H-pyrazol-1-yl)-3H-imidazo[4,5-b]pyridin-3-yl)-2,3-dihydro-1H-inden-1-yl)-6-methylpyrido[3,4-d]pyrimidin-4(3H)-one (Compound 81)

Compound 81

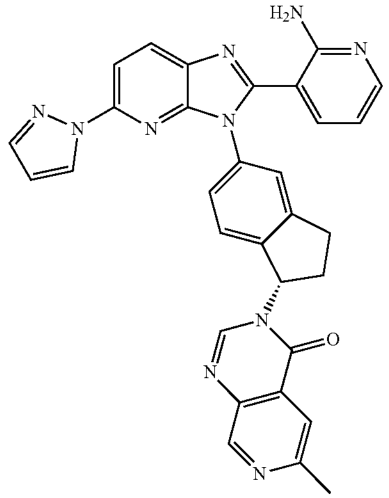

Synthetic Route:

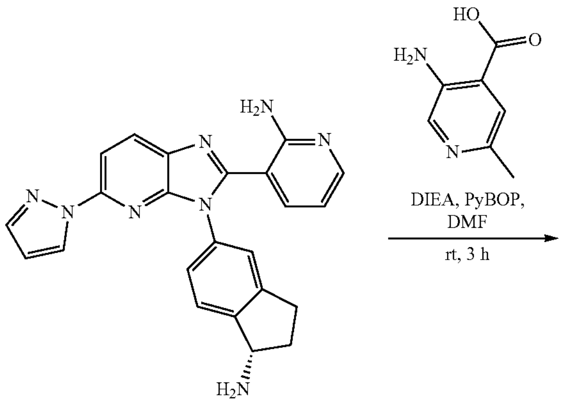

Compound 2

-continued

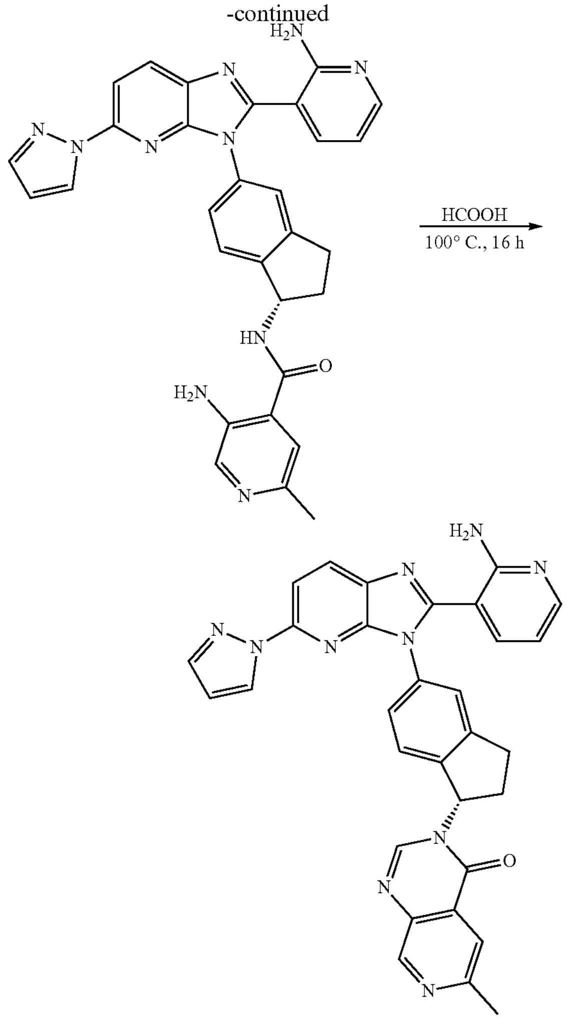

Compound 81

Step 1: Synthesis of (S)-5-amino-N-(5-(2-(2-aminopyridin-3-yl)-5-(1H-pyrazol-1-yl)-3H-imidazo[4,5-b]pyridin-3-yl)-2,3-dihydro-1H-inden-1-yl)-2-methylisonicotinamide To a solution of 5-amino-2-methylpyridine-4-carboxylic acid hydrochloride (41.6 mg, 0.220 mmol) in DMF (1 mL) was added DIEA (85.4 mg, 0.660 mmol), 3-{3-[(1S)-1-amino-2,3-dihydro-1H-inden-5-yl]-5-(pyrazol-1-yl)imidazo[4,5-b]pyridin-2-yl}pyridin-2-amine (Compound 2) (90 mg, 0.22 mmol) and HATU (101 mg, 0.264 mmol). The resulting mixture was maintained under nitrogen and stirred at room temperature for 3 h. The reaction was quenched with water (100 mL). The resulting mixture was extracted with ethyl acetate (3×100 mL). The organic layers were combined, dried over anhydrous $Na_2SO_4$, filtered and concentrated. The crude product was purified by reverse-phase flash column chromatography on C18 silica gel using a gradient of acetonitrile in water (+0.05% TFA) to afford (S)-5-amino-N-(5-(2-(2-aminopyridin-3-yl)-5-(1H-pyrazol-1-yl)-3H-imidazo[4,5-b]pyridin-3-yl)-2,3-dihydro-1H-inden-1-yl)-2-methylisonicotinamide (90 mg, 75% yield) as a yellow solid. MS (ESI) calcd. for $C_{30}H_{26}N_{10}O$, 542.23 m/z, found: 543.15 $[M+H]^+$.

Step 2: Synthesis of (S)-3-(5-(2-(2-aminopyridin-3-yl)-5-(1H-pyrazol-1-yl)-3H-imidazo[4,5-b]pyridin-3-yl)-2,3-dihydro-1H-inden-1-yl)-6-methylpyrido[3,4-d]pyrimidin-4(3H)-one (Compound 81)

A solution of 5-amino-N-[(1S)-5-[2-(2-aminopyridin-3-yl)-5-(pyrazol-1-yl)imidazo[4,5-b]pyridin-3-yl]-2,3-dihydro-1H-inden-1-yl]-2-methylpyridine-4-carboxamide (80 mg, 0.15 mmol) in formic acid (2 mL) was stirred for 16 h at 100° C. The reaction mixture was cooled to room temperature and purified by Prep-HPLC on a XBridge Prep OBD C18 Column using a gradient of acetonitrile in water (+0.05% TFA) to afford (S)-3-(5-(2-(2-aminopyridin-3-yl)-5-(1H-pyrazol-1-yl)-3H-imidazo[4,5-b]pyridin-3-yl)-2,3-dihydro-1H-inden-1-yl)-6-methylpyrido[3,4-d]pyrimidin-4(3H)-one (Compound 81) (TFA salt) (16.2 mg, 16% yield) as a yellow solid. MS (ESI) calcd. for $C_{31}H_{24}N_{10}O$, 552.21 m/z, found 553.15 $[M+H]^+$. $^1H$ NMR (300 MHz, DMSO-$d_6$+$D_2O$) δ (ppm): 8.96-9.04 (m, 1H), 8.37-8.52 (m, 2H), 8.15-8.25 (m, 1H), 8.04-8.12 (m, 1H), 8.00-8.03 (m, 1H), 7.88-7.95 (m, 1H), 7.80-7.87 (m, 1H), 7.74-7.86 (m, 1H), 7.53-7.64 (m, 1H), 7.28-7.42 (m, 2H), 6.80-6.93 (m, 1H), 6.53-6.62 (m, 1H), 6.26-6.40 (m, 1H), 3.19-3.37 (m, 1H), 2.98-3.17 (m, 1H), 2.68-2.87 (m, 1H), 2.60-2.67 (m, 3H), 2.25-2.50 (m, 1H).

Example 67: (S)-1-(5-(2-(2-aminopyridin-3-yl)-5-(1H-pyrazol-1-yl)-3H-imidazo[4,5-b]pyridin-3-yl)-2,3-dihydro-1H-inden-1-yl)pyridin-4(1H)-one (Compound 83)

Compound 83

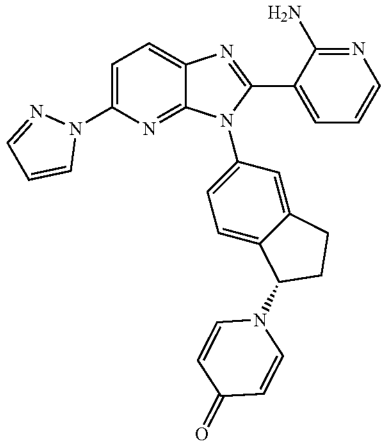

Synthetic Route:

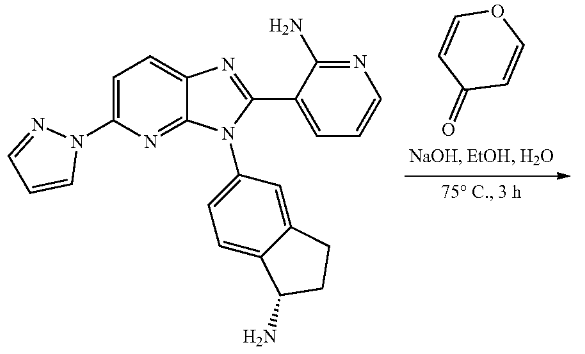

Compound 2

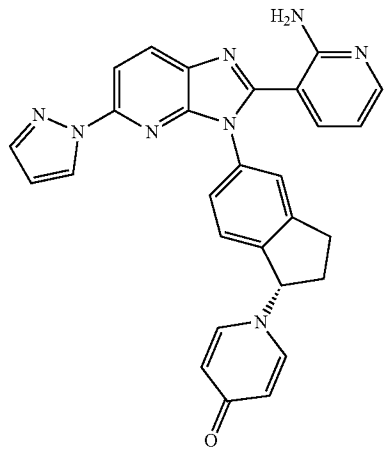

Compound 83

Step 1: Synthesis of (S)-1-(5-(2-(2-aminopyridin-3-yl)-5-(1H-pyrazol-1-yl)-3H-imidazo[4,5-b]pyridin-3-yl)-2,3-dihydro-1H-inden-1-yl)pyridin-4(1H)-one (Compound 83)

A mixture of 3-{3-[(1S)-1-amino-2,3-dihydro-1H-inden-5-yl]-5-(pyrazol-1-yl)imidazo[4,5-b]pyridin-2-yl}pyridin-2-amine (Compound 2) (100 mg, 0.245 mmol) and pyran-4-one (25.9 mg, 0.270 mmol) in EtOH (5 mL) was treated with NaOH (14.7 mg, 0.367 mmol) in water (2 mL) at room temperature. The resulting mixture was stirred for 3 h at 75° C. The reaction was quenched by the addition of water (20 mL), extracted with EtOAc (3x30 mL) and dried over anhydrous $Na_2SO_4$. After filtration, the filtrate was concentrated under reduced pressure. The residue was purified by Prep-HPLC on a YMC-Actus Triart C18 ExRS column using a gradient of acetonitrile in water (+10 mmol/L $NH_4HCO_3$) to (S)-1-(5-(2-(2-aminopyridin-3-yl)-5-(1H-pyrazol-1-yl)-3H-imidazo[4,5-b]pyridin-3-yl)-2,3-dihydro-1H-inden-1-yl)pyridin-4(1H)-one (Compound 83) (19.2 mg, 16% yield) as an off-white solid. MS (ESI) calcd. for $C_{28}H_{22}N_8O$, 486.19 m/z, found 487.25 $[M+H]^+$. $^1H$ NMR (400 MHz, DMSO-$d_6$+$D_2O$) δ (ppm): 8.33-8.42 (m, 2H), 8.02-8.10 (m, 1H), 7.96-8.01 (m, 1H), 7.80-7.88 (m, 1H), 7.67-7.73 (m, 2H), 7.52-7.58 (m, 1H), 7.31-7.38 (m, 1H), 7.25-7.30 (m, 1H), 7.19-7.24 (m, 1H), 6.54-6.60 (m, 1H), 6.46-6.51 (m, 1H), 6.18-6.25 (m, 2H), 5.77-5.86 (m, 1H), 3.15-3.27 (m, 1H), 2.94-3.08 (m, 1H), 2.73-2.86 (m, 1H), 2.19-2.28 (m, 1H).

Example 68: (S)-3-(3-(1-(azetidin-1-yl)-2,3-dihydro-1H-inden-5-yl)-5-(1H-pyrazol-1-yl)-3H-imidazo[4,5-b]pyridin-2-yl)pyridin-2-amine (Compound 87)

Compound 87

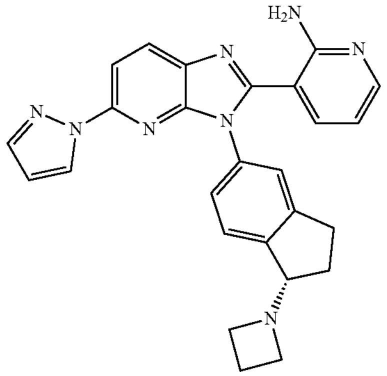

Synthetic Route:

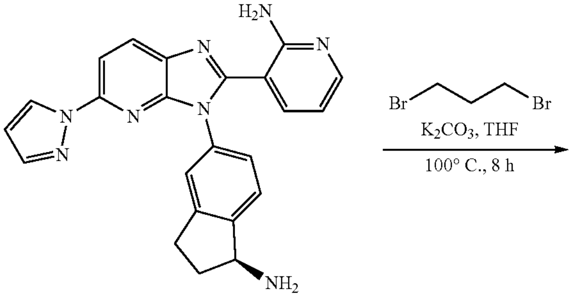

Compound 2

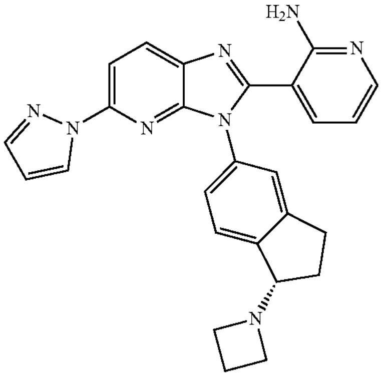

Compound 87

Step 1: Synthesis of (S)-3-(3-(1-(azetidin-1-yl)-2,3-dihydro-1H-inden-5-yl)-5-(1H-pyrazol-1-yl)-3H-imidazo[4,5-b]pyridin-2-yl)pyridin-2-amine (Compound 87)

To a solution of (S)-3-(3-(1-amino-2,3-dihydro-1H-inden-5-yl)-5-(1H-pyrazol-1-yl)-3H-imidazo[4,5-b]pyridin-2-yl)pyridin-2-amine (Compound 2) (100 mg, 0.245 mmol) in THE (2 mL) was added $K_2CO_3$ (102 mg, 0.735 mmol) and 1,3-dibromopropane (98.9 mg, 0.490 mmol). Then the reaction mixture was stirred at 100° C. for 8 h. After cooling to room temperature the reaction was quenched with water (50 mL). The resulting mixture was extracted with ethyl acetate (3×50 mL). The organic layers were combined and dried over anhydrous $Na_2SO_4$. After filtration, the filtrate was concentrated under reduced pressure. The crude product was purified by Prep-HPLC on a YMC Triart C18 ExRs column using a gradient of acetonitrile in water (+10 mmol/L $NH_4HCO_3$) to afford (S)-3-(3-(1-(azetidin-1-yl)-2,3-dihydro-1H-inden-5-yl)-5-(1H-pyrazol-1-yl)-3H-imidazo[4,5-b]pyridin-2-yl)pyridin-2-amine (Compound 87) (6.3 mg, 6% yield) as a white solid. MS (ESI) calcd. for $C_{26}H_{24}N_8$, 448.21, found 449.20. $[M+H]^+$. $^1H$ NMR (300 MHz, DMSO-$d_6$) δ (ppm): 8.30-8.40 (m, 2H), 7.90-8.03 (m, 2H), 7.75-7.85 (m, 1H), 7.38-7.44 (m, 1H), 7.31-7.37 (m, 1H), 7.15-7.19 (m, 2H), 6.50-6.57 (m, 1H), 6.38-6.45 (m, 1H), 3.83-3.89 (m, 1H), 3.31-3.39 (Sm, 2H), 3.15-3.25 (m, 2H), 2.91-3.01 (m, 1H), 2.69-2.84 (m, 1H), 2.02-2.17 (m, 1H), 1.92-2.07 (m, 2H), 1.83-1.90 (m, 1H).

The following compounds were prepared analogous to the synthetic preparation in Example 68 (Compound 87).

TABLE 4A

| Characterization data of compounds prepared analogously to compound 87. | |
|---|---|
| Cpd ID | Characterization Data |
| 330 | MS (ESI) calcd. for $C_{27}H_{26}N_8$: 462.22 m/z, found, 463.30 $[M + H]^+$. $^1H$ NMR (400 MHz, DMSO-$d_6$) δ (ppm); 8.28-8.45 (m, 2H), 7.89-8.09 (m, 2H), 7.75-7.87 (m, 1H), 7.45-7.58 (m, 1H), 7.33-7.42 (m, 1H), 7.22-7.32 (m, 1H), 7.13-7.21 (m, 1H), 6.51-6.61 (m, 1H), 6.35-6.45 (m, 1H), 4.18-4.41 (m, 1H), 2.93-3.15 (m, 1H), 2.73-2.92 (m, 1H), 2.57-2.72 (m, 4H), 1.99-2.35 (m, 2H), 1.61-1.83 (m, 4H). |
| 457 | MS (ESI) calcd. for $C_{27}H_{28}N_8O$, 480.24 m/z, found, 481.30 $[M + H]^+$. $^1H$ NMR (400 MHz, DMSO-$d_6$) δ (ppm); 8.30-8.40 (m, 2H), 7.98-8.04 (m, 1H), 7.92-7.98 (m, 1H), 7.79-7.85 (m, 1H), 7.43-7.51 (m, 1H), 7.29-7.36 (m, 1H), 7.16-7.28 (m, 2H), 6.53-6.61 (m, 1H), 6.40-6.49 (m, 1H), 4.41-4.49 (m, 1H), 3.40-3.51 (m, 2H), 3.23 (s, 3H), 2.77-2.96 (m, 2H), 2.49-2.54 (m, 2H), 2.19 (s, 3H), 2.09-2.18 (m, 1H), 1.97-2.10 (m, 1H). |

Example 69: (S)-3-(3-(1-(cyclobutylamino)-2,3-dihydro-1H-inden-5-yl)-5-(1H-pyrazol-1-yl)-3H-imidazo[4,5-b]pyridin-2-yl)pyridin-2-amine (Compound 88)

Compound 88

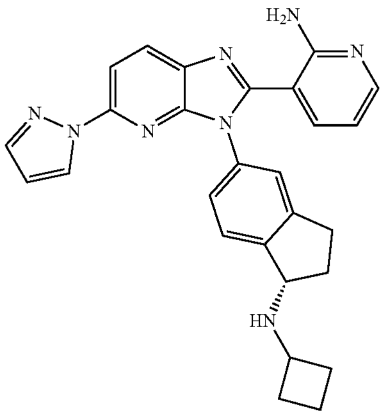

Synthetic Route:

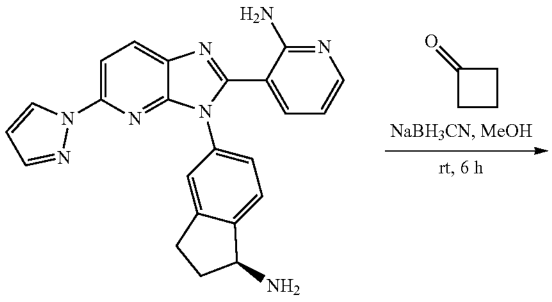

Compound 2

-continued

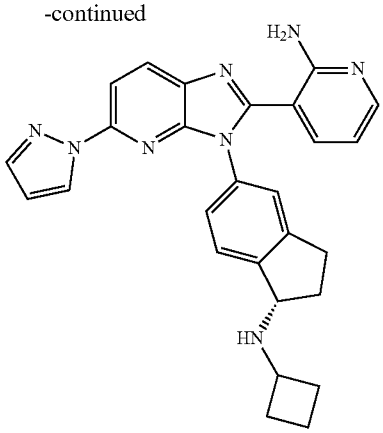

Compound 88

Step 1: Synthesis of (S)-3-(3-(1-(cyclobutylamino)-2,3-dihydro-1H-inden-5-yl)-5-(1H-pyrazol-1-yl)-3H-imidazo[4,5-b]pyridin-2-yl)pyridin-2-amine To a cooled (0° C.) solution of (S)-3-(3-(1-amino-2,3-dihydro-1H-inden-5-yl)-5-(1H-pyrazol-1-yl)-3H-imidazo[4,5-b]pyridin-2-yl)pyridin-2-amine (Example 2) (60 mg, 0.15 mmol) and cyclobutanone (20.7 mg, 0.294 mmol) in MeOH (2 mL) was added $NaBH_3CN$ (18.6 mg, 0.294 mmol). The resulting mixture was stirred at room temperature for 3 h. The reaction was quenched by the addition of water (30 mL) at room temperature. The resulting mixture was extracted with ethyl acetate (3×50 mL) and dried over anhydrous $Na_2SO_4$. The organic layers were combined and dried over anhydrous $Na_2SO_4$. After filtration, the filtrate was concentrated under reduced pressure. The residue was purified by Prep-HPLC on XSelect CSH Fluoro Phenyl column using a gradient of acetonitrile in water (+0.05% TFA) to afford (S)-3-(3-(1-(cyclobutylamino)-2,3-dihydro-1H-inden-5-yl)-5-(1H-pyrazol-1-yl)-3H-imidazo[4,5-b]pyridin-2-yl)pyridin-2-amine (TFA salt) (32.7 mg, 48% yield) as an off-white solid. MS (ESI) calcd. for $C_{27}H_{26}N_8$: 462.23 m/z, found: 463.20 $[M+H]^+$.

$^1H$ NMR (300 MHz, DMSO-$d_6$) δ (ppm): 8.38-8.46 (m, 1H), 8.31-8.37 (m, 1H), 8.02-8.09 (m, 1H), 7.96-8.01 (m, 1H), 7.79-7.85 (m, 1H), 7.64-7.76 (m, 2H), 7.52-7.59 (m, 1H), 7.37-7.47 (m, 1H), 6.66-6.76 (m, 1H), 6.53-6.60 (m, 1H), 4.71-4.81 (m, 1H), 3.81-3.94 (m, 1H), 3.07-3.23 (m, 1H), 2.86-3.03 (m, 1H), 2.45-2.50 (m, 1H), 2.06-2.25 (i, 5H), 1.72-1.88 (i, 2H).

The following compounds were prepared analogous to the synthetic preparation in Example 69 (Compound 88).

TABLE 5A

Characterization data of compounds prepared analogously to compound 88.

| Cpd ID | Characterization Data |
|---|---|
| 70 | MS (ESI) calcd. for $C_{30}H_{27}N_9$, 513.24 m/z, found 514.30 $[M + H]^+$. $^1H$ NMR (400 MHz, DMSO-$d_6$) δ (ppm); 8.33-8.46 (m, 3H), 7.99-8.07 (m, 1H), 7.92-7.98 (m, 1H), 7.82-7.88 (m, 1H), 7.74-7.81 (m, 1H), 7.49-7.55 (m, 1H), 7.27-7.36 (m, 3H), 7.18-7.26 (m, 1H), 6.55-6.62 (m, 1H), 6.49-6.54 (m, 1H), 4.28-4.31 (m, 1H), 3.72-3.86 (m, 2H), 2.94-3.06 (m, 1H), 2.71-2.88 (m, 1H), 2.36-2.47 (m, 4H), 1.88-2.04 (m, 1H). |
| 84 | MS (ESI) calcd. for $C_{30}H_{25}F_2N_9$, 549.22 m/z, found 550.30 $[M + H]^+$. $^1H$ NMR (300 MHz, DMSO-$d_6$ + $D_2O$) δ (ppm); 8.69-8.72 (m, 1H), 8.31-8.42 (m, 2H), 7.96-8.10 (m, 3H), 7.78-7.83 (m, 1H), 7.64-7.73 (m, 1H), 7.46-7.55 (m, 1H), 7.31-7.39 (m, 1H), 7.09-7.24 (m, 2H), 6.77-6.92 (m, 1H), 6.53-6.60 (m, 1H), 6.44-6.51 (m, 1H), 4.12-4.26 (m, 1H), 3.81-3.96 (m, 2H), 2.91-3.08 (m, 1H), 2.73-2.88 (m, 1H), 2.34-2.43 (m, 1H), 1.82-1.98 (m, 1H). $^{19}F$ NMR (282 MHz, DMSO-$d_6$) δ (ppm); −114.54. |
| 89 | MS (ESI) calcd. for $C_{28}H_{28}N_8O_2S$, 540.21 m/z, found 541.05 $[M + H]^+$. $^1H$ NMR (300 MHz, DMSO-$d_6$) δ (ppm); 8.31-8.41 (m, 2H), 8.00-8.08 (m, 1H), 7.89-8.00 (m, 1H), 7.76-7.85 (m, 1H), 7.50-7.58 (m, 1H), 7.30-7.38 (m, 1H), 7.22-7.30 (m, 2H), 6.52-6.60 (m, 1H), 6.40-6.50 (m, 1H), 4.20-4.35 (m, 1H), 3.15-3.30 (m, 2H), 2.90-3.15 (m, 4H), 2.70-2.88 (m, 1H), 2.35-2.50 (m, 1H), 2.10-2.25 (m, 2H), 1.90-2.10 (m, 2H), 1.68-1.85 (m, 1H). |
| 109 | MS (ESI) calcd. for $C_{30}H_{31}N_90$, 533.27 m/z, found, 534.10 $[M + H]^+$. $^1H$ NMR (300 MHz, DMSO-$d_6$) δ (ppm); 8.38-8.47 (m, 1H), 8.32-8.37 (m, 1H), 7.96-8.08 (m, 2H), 7.79-7.85 (m, 1H), 7.66-7.79 (m, 2H), 7.52-7.59 (m, 1H), 7.37-7.47 (m, 1H), 6.71-6.81 (m, 1H), 6.53-6.61 (m, 1H), 4.93-5.01 (m, 1H), 4.40-4.51 (m, 1H), 3.45-3.52 (m, 2H), 3.08-3.25 (m, 2H), 2.85 - 3.02 (m, 1H), 2.55-2.63 (m, 2H), 2.45-2.54 (m, 2H), 2.15-2.25 (m, 1H), 2.00-2.06 (m, 3H), 1.35-1.65 (m, 2H). |
| 111 | MS (ESI) calcd. for $C_{26}H_{24}N_8O$, 464.21 m/z, found, 465.15 $[M + H]^+$. $^1H$ NMR (400 MHz, DMSO-$d_6$ + $D_2O$) δ (ppm); 8.31-8.39 (m, 2H), 7.98-8.01 (m, 1H), 7.92-7.97 (m, 1H), 7.80 (s, 1H), 7.41-7.48 (m, 1H), 7.32-7.34 (m, 1H), 7.20-7.28 (m, 2H), 6.54 (s, 1H), 6.39-6.45 (m, 1H), 4.58-4.69 (m, 2H), 4.30-4.40 (m, 2H), 4.13-4.18 (m, 1H), 4.00-4.10 (m, 1H), 2.95-3.01 (m, 1H), 2.70-2.80 (m, 1H), 2.21-2.31 (m, 1H), 1.69-1.75 (m, 1H). |
| 131 | MS (ESI) calcd. for $C_{29}H_{25}N_9$, 499.22 m/z, found 500.20 $[M + H]^+$. $^1H$ NMR (400 MHz, DMSO-$d_6$) δ (ppm): 8.50-8.58 (m, 1H), 8.32-8.46 (m, 2H), 7.90-8.10 (m, 2H), 7.80-7.90 (m, 2H), 7.50 - 7.65 (m, 2H), 7.30-7.45 (m, 2H), 7.22-7.30 (m, 2H), 6.57 (s, 1H), 6.45-6.55 (m, 1H), 4.25 - 4.37 (m, 1H), 3.92-4.00 (m, 2H), 2.90-3.15 (m, 1H), 2.75-2.90 (m, 1H), 2.35-2.45 (m, 1H), 1.82-2.00 (m, 1H). (formic acid salt) |
| 140 | MS (ESI) calcd. for $C_{30}H_{27}N_9$: 513.24 m/z, found, 514.10 $[M + H]^+$. $^1H$ NMR (300 MHz, DMSO-$d_6$) δ (ppm): 8.31-8.39 (m, 2H), 8.25-8.30 (m, 1H), 7.96-8.03 (m, 1H), 7.90-7.96 (m, 1H), 7.78-7.83 (m, 1H), 7.72-7.78 (m, 1H), 7.49-7.57 (m, 1H), 7.30-7.37 (m, 1H), 7.15-7.29 (m, 3H), 6.49-6.56 (m, 1H), 6.37-6.48 (m, 1H), 4.20-4.30 (m, 1H), 3.79 (s, 2H), 2.91-3.05 (m, 1H), 2.73-2.86 (m, 1H), 2.49 (s, 3H), 2.28-2.44 (m, 1H),1.80-1.98 (m, 1H). |
| 141 | MS (ESI) calcd. for $C_{29}H_{25}N_9$: 499.22 m/z, found, 500.05 $[M + H]^+$. $^1H$ NMR (300 MHz, DMSO-$d_6$) δ (ppm); 8.55-8.63 (m, 1H), 8.40-8.48 (m, 1H), 8.31-8.40 (m, 2H), 7.97-8.04 (m, 1H), 7.90-7.96 (m, 1H), 7.82-7.89 (m, 1H), 7.77-7.82 (m, 1H), 7.49-7.57 (m, 1H), 7.30-7.41 (m, 2H), 7.18-7.30 (m, 2H), 6.50-6.57 (m, 1H), 6.36-6.47 (m, 1H), 4.15-4.16 (m, 1H), 3.75-3.92 (m, 2H), 2.89-3.05 (m, 1H), 2.70-2.87 (m, 1H), 2.31-2.47 (m, 1H), 1.77-1.96 (m, 1H). |
| 142 | MS (ESI) calcd. for $C_{29}H_{25}N_9$: 499.22 m/z, found, 500.20 $[M + H]^+$. $^1H$ NMR (300 MHz, DMSO-$d_6$) δ (ppm); 8.50-8.54 (m, 2H), 8.34-8.38 (m, 2H), 8.00-8.05 (m, 1H), 7.93-7.96 (m, 1H), 7.81-7.82 (m, 1H), 7.53-7.55 (m, 1H), 7.46-7.49 (m, 2H), 7.33-7.35 (m, 1H), 7.22-7.27 (m, 2H), 6.57-6.59 (m, 1H), 6.42-6.48 (m, 1H), 4.21-4.27 (m, 1H), 3.85 (s, 2H), 2.98-3.08 (m, 1H), 2.71-2.81 (m, 1H), 2.38-2.45 (m, 1H), 1.82-2.00 (m, 1H). |
| 153 | MS (ESI) calcd. for $C_{31}H_{29}N_9$, 527.25 m/z, found 528.30 $[M + H]^+$. $^1H$ NMR (300 MHz, DMSO-$d_6$) δ (ppm); 8.45-8.47 (s, 1H), 8.28-8.38 (m, 2H), 7.99-8.02 (m, 1H), 7.91-7.95 (m, 1H), 7.81 - 7.86 (m, 1H), 7.72-7.76 (m, 1H), 7.48-7.51 (m, 1H), 7.16-7.28 (m, 4H), 6.53-6.68 (m, 1H), 6.41-6.51 (m, 1H), 4.02-4.15 (m, 2H), 2.89-2.96 (m, 1H), 2.67-2.69 (m, 1H), 2.45 (s, 3H), 2.05-2.29 (m, 1H), 1.65-1.80 (m, 1H), 1.25-1.40 (m, 3H). |
| 154 | MS (ESI) calcd. for $C_{31}H_{29}N_9$, 527.25 m/z, found 528.30 $[M + H]^+$. $^1H$ NMR (300 MHz, DMSO-$d_6$) δ (ppm); 8.47-8.45 (s, 1H), 8.28-8.38 (m, 2H), 7.89-8.02 (m, 2H), 7.75-7.86 (m, 2H), 7.48-7.51 (m, 1H), 7.16-7.28 (m, 4H), 6.53-6.68 (m, 1H), 6.41-6.51 (m, 1H), 3.95-4.02 (m, 1H), 3.68-3.72 (m, 1H), 2.90-2.92 (m, 1H), 2.67-2.69 (m, 1H), 2.43 (s, 3H), 2.36-2.39 (m, 1H), 1.70-1.88 (m, 1H), 1.30-1.40 (m, 3H). |

TABLE 5A-continued

Characterization data of compounds prepared analogously to compound 88.

| Cpd ID | Characterization Data |
|---|---|
| 168 | MS (ESI) calcd. for $C_{31}H_{29}N_9$ 527.25 m/z, found, 528.10 [M + H]$^+$. $^1$H NMR (300 MHz, DMSO-$d_6$) δ (ppm); 8.25-8.39 (m, 3H), 7.88-7.99 (m, 2H), 7.73-7.80 (m, 1H), 7.60-7.70 (m, 1H), 7.45-7.53 (m, 1H), 7.30-7.34 (m, 1H), 7.19-7.28 (m, 2H), 7.08-7.18 (m, 1H), 6.47-6.54 (m, 1H), 6.28-6.36 (m, 1H), 4.41-4.52 (m, 1H), 3.49 (s, 2H), 2.80-3.01 (m, 2H), 2.40 (s, 3H), 2.08-2.0 (m, 2H), 2.08 (s, 3H). |
| 206 | MS (ESI) calcd. for $C_{28}H_{26}N_{10}$ 502.23 m/z, found, 503.30 [M + H]+. 1H-NMR (400 MHz, DMSO-$d_6$) δ (ppm); 8.43-8.45 (m, 1H), 8.37-8.38 (m, 1H), 8.07-8.09 (m, 1H), 8.01-8.02 (m, 1H), 7.83-7.84 (m, 1H), 7.81-7.82 (m, 1H), 7.77-7.78 (m, 1H), 7.61-7.63 (m, 1H), 7.57-7.58 (m, 1H), 7.43-7.46 (m, 1H), 6.68-6.71 (m, 1H), 6.57-6.58 (m, 1H), 6.41-6.42 (m, 1H), 4.86-4.89 (m, 1H), 4.20-4.22 (m, 2H), 3.86-3.88 (m, 3H), 3.18-3.20 (m, 1H), 2.96-2.98 (m, 1H), 2.58 - 2.61 (m, 1H), 2.25-2.33 (m, 1H). (TFA salt) |
| 208 | MS (ESI) calcd. for $C_{31}H_{27}FN_{10}$ 558.24 m/z. found, 559.30 [M + H]+. $^1$H NMR (400 MHz, DMSO-d6) δ(ppm) 8.30-8.46 (m, 2H), 8.01-8.12 (m, 2H), 7.90-8.00 (m, 1H), 7.81 (d, J = 1.2 Hz, 1H), 7.45-7.60 (m, 2H), 7.38-7.44 (m, 1H), 7.31-7.37 (m, 1H), 7.19-7.30 (m, 1H), 6.59-6.70 (m, 1H), 6.51-6.58 (m, 1H), 6.35-6.48 (m, 2H), 5.21-5.50 (m, 1H), 4.25-4.43 (m, 1H), 4.11-4.24 (m, 2H), 3.97-4.10 (m, 1H), 3.75-3.85 (m, 1H), 3.65-3.73 (m, 1H), 3.15-3.30 (m, 1H), 3.12 (s, 1H). $^{19}$F NMR (376 MHz, DMSO-d6) δ (ppm); −194.779. |
| 234 | MS (ESI) calcd. for $C_{29}H_{24}F_2N_{10}$, 550.22 m/z, found 551.20 [M + H]$^+$. $^1$H NMR (300 MHz, DMSO-$d_6$ + $D_2O$) δ (ppm); 8.80-8.91 (m, 1H), 8.49-8.57 (m, 1H), 8.19-8.26 (m, 3H), 8.12-8.18 (m, 1H), 8.06-8.11 (m, 1H), 7.81-7.92 (m, 2H), 7.71-7.80 (m, 1H), 7.62-7.69 (m, 1H), 7.45-7.54 (m, 1H), 6.84-7.20 (m, 1H), 6.73-6.81 (m, 1H), 4.94-5.09 (m, 1H), 4.39-4.57 (m, 2H), 3.16 - 3.30 (m, 1H), 2.97-3.11 (m, 1H), 2.62-2.74 (m, 1H), 2.35-2.49 (m, 1H). $^{19}$F NMR (282 MHz, DMSO-$d_6$+ $D_2O$) δ (ppm); −115.51. (TFA salt) |
| 274 | MS (ESI) calcd. for $C_{29}H_{31}N_9$, 505.27. found, 506.35 [M + H]$^+$, $^1$H NMR (300 MHz, DMSO-$d_6$) δ 8.37-8.00 (m, 2H), 7.93-7.99 (m, 2H), 7.80 (s, 1H), 7.47 -7.44 (m, 1H), 7.25-7.32 (m, 1H), 7.23-7.20 (m. 2H), 6.97 (s, 2H), 6.53 (s, 1H), 6.43-6.39 (m, 1H), 4.32-4.23 (m, 1H), 2.97- 2.90 (m, 1H), 2.89-2.71 (m, 3H), 2.57-2.50 (m, 1H), 2.39 -2.49 (m, 1H), 2.14 (s, 3H), 1.91-1.80 (m, 4H), 1.78-1.71 (m, 2H), 1.40-1.29 (m, 2H). (formic acid salt) |
| 276 | MS (ESI) calcd. for $C_{32}H_{33}N_{11}$, 571.29 m/z, found 572.15 [M + H]$^+$. $^1$H NMR (400 MHz, DMSO-d6) δ 8.41-8.30 (m, 2H), 8.03-7.91 (m, 2H), 7.81 (d, J = 1.6 Hz, 1H), 7.50-7.31 (m, 3H), 7.31-7.18 (m, 2H), 6.95 (s, 2H), 6.54 (t, J = 2.1 Hz, 1H), 6.48-6.38 (m, 1H), 5.65 (d, J = 2.3 Hz, 1H), 4.41-4.28 (m, 1H), 3.75-3.49 (m, 5H), 3.01-2.87 (m, 1H), 2.87-2.71 (m, 2H), 2.71 - 2.55 (m, 2H), 2.47-2.41 (m, 1H), 2.08-1.93 (m, 2H), 1.91-1.80 (m, 1H), 1.80-1.72 (m, 1H), 1.50-1.32 (m, 2H). |
| 277 | MS (ESI) calcd. for $C_{33}H_{32}N_{10}$, 568.28 m/z, found, 569.40 [M + H]$^+$; 1H NMR (400 MHz, DMSO-d6) δ 8.41-8.32 (m, 2H), 8.13-8.06 (m, 1H), 8.03-7.91 (m, 2H), 7.81 (d, J = 1.6 Hz, 1H), 7.54 - 7.44 (m, 2H), 7.33 (d, J = 1.9 Hz, 1H), 7.29-7.19 (m, 2H), 6.94 (s, 2H), 6.83 (d, J = 8.6 Hz, 1H), 6.62-6.51 (m, 2H), 6.43 (dd, J = 7.6, 4.8 Hz, 1H), 4.41-4.33 (m, 1H), 4.27-4.16 (m, 2H), 2.99 - 2.86 (m, 4H), 2.85-2.72 (m, 1H), 2.50-2.52 (m, 1H), 2.09-1.96 (m, 2H), 1.92-1.85 (m, 1H), 1.85-1.72 (m, 1H), 1.40-1.24 (m, 2H). |
| 279 | MS (ESI) calcd for $C_{32}H_{33}N_9O$ 559.68 m/z, found 560.35 [M + H]$^+$. 1H NMR (500 MHz, DMSO-d6) δ 9.10 (s, 1H), 8.92 (s, 1H), 8.43 (d, J = 8.6 Hz, 1H), 8.36 (d, J = 2.6 Hz, 1H), 8.07 (dd, J = 5.3, 1.8 Hz, 1H), 8.00 (d, J = 8.5 Hz, 1H), 7.84 (d, J = 1.7 Hz, 1H), 7.77 (d, J = 8.1 Hz, 1H), 7.59 (d, J = 1.9 Hz, 1H), 7.51 (d, J = 7.6 Hz, 1H), 7.45 (dd, J = 8.1, 2.0 Hz, 1H), 6.64-6.56 (m, 2H), 5.04 (s, 1H), 4.48 (s, 1H), 4.41 (s, 1H), 3.50-3.58 (m, 1H), 3.23-3.17 (m, 2H), 3.01-2.95 (m, 1H), 2.67 (s, 2H), 2.63-2.56 (m, 2H), 2.26-2.20 (m, 1H), 2.05 (s, 2H), 1.59 (s, 1H), 1.47 (s, 1H), 0.74 (s, 4H). |
| 305 | MS (ESI) calcd for $C_{30}H_{24}F_3N_9O$: 583.21 m/z, found: 584.15 [M + H]$^+$. $^1$H NMR (300 MHz, DMSO-$d_6$) δ (ppm): 8.36-8.41 (m, 1H), 8.33-8.36 (m, 1H), 8.26-8.32 (m, 1H), 7.93-8.04 (m, 2H), 7.79-7.84 (m, 1H), 7.45-7.59 (m, 2H), 7.31-7.37 (m, 2H), 7.21-7.28 (m, 2H), 6.51-6.62 (m, 1H), 6.40-6.50 (m, 1H), 4.14-4.30 (m, 1H), 3.92 (s, 2H), 2.88-3.04 (m, 1H), 2.66-2.88 (m, 1H), 2.30-2.43 (m, 1H), 1.77-1.93 (m, 1H). $^{19}$F NMR (282 MHz, DMSO-$d_6$) 8 (ppm): −54.93. |
| 339 | MS (ESI) calcd. for $C_{24}H_{22}N_8$, 422.20 m/z, found, 423.20 [M + H]$^+$. $^1$H NMR (400 MHz, DMSO-$d_6$) δ (ppm); 8.35-8.38 (m, 2H), 8.02-8.06 (m, 1H), 7.94-7.99 (m, 1H), 7.82-7.84 (m, 1H), 7.65-7.68 (m, 1H), 7.45-7.48 (m, 1H), 7.31-7.34 (m, 1H), 7.22-7.28 (m, 1H), 6.92 (s, 2H), 6.52-6.54 (m, 1H), 6.40-6.45 (m, 1H), 4.42-4.49 (m, 1H), 3.02-3.10 (m, 1H), 2.82-2.91 (m, 1H), 2.50-2.52 (m, 3H), 2.39-2.42 (m, 1H), 2.00-2.09 (m, 1H). |
| 340 | MS (ESI) calcd. for $C_{25}H_{24}N_8$, 436.21 m/z, found, 437.25 [M + H]$^+$. $^1$H NMR (400 MHz, DMSO-$d_6$) δ (ppm); 8.34-8.37 (m, 2H), 7.94-8.10 (m, 2H), 7.77-7.82 (m, 1H), 7.38-7.49 (m, 2H), 7.31-7.36 (m, 1H), 7.19-7.28 (m, 1H), 6.95-7.11 (m, 2H), 6.54 (s, 1H), 6.35-6.38 (m, 1H), 4.30-4.39 (m, 1H), 2.82-3.00 (m, 2H), 1.90-2.30 (m, 8H). |
| 366 | MS (ESI) calcd. for $C_{32}H_{31}N_{11}$ 569.28 m/z, found, 570.20 [M + H]$^-$. $^1$H-NMR (400 MHz, DMSO) δ (ppm); 8.45-8.55 (m, 1H), 8.05-8.20 (m, 5H), 7.81-7.95 (m, 1H), 7.72-7.80 (m, 2H), 7.52 - 7.60 (m, 1H), 7.41-7.50 (m, 1H), 7.21-7.30 (m, 1H), 6.85-6.95 (m, 1H), 6.72-6.81 (m, 1H), 5.00-5.10 (m, 1H), 4.30-4.41 (m, 2H), 3.60-3.69 (m, 1H), 3.11-3.23 (m, 3H), 2.90-3.05 (m, 1H), 2.58-2.70 (m, 1H), 2.12-2.35 (m, 3H), 1.61-1.78 (m, 2H). (TFA salt) |
| 367 | MS (ESI) calcd. for $C_{33}H_{31}FN_{10}$ 586.27 m/z, found, 587.20 [M + H]$^+$. $^1$H-NMR (400 MHz, DMSO) δ (ppm); 8.40-8.48 (m, 1H), 8.25-8.35 (m, 1H), 8.02-8.13 (m, 2H), 7.81-7.92 (m, 2H), 7.71 - 7.80 (m, 2H), 7.55-7.61 (m, 1H), 7.40-7.48 (m, 1H), 7.25-7.32 (m, 1H), 6.85-6.95 (m, 1H), 6.75-6.84 (m, 1H), 6.35-6.41 (m, 1H), 4.98-5.06 (m, 1H), 4.27-4.42 (m, 2H), 3.60-3.65 (m, 1H), 3.12-3.26 (m, 3H), 2.91-3.05 (m, 1H), 2.55-2.70 (m, 1H), 2.14-2.35 (m, 3H), 1.61-1.80 (m, 2H). $^{19}$F NMR (376 MHz, DMSO-$d_6$) δ (ppm); −126.83, −74.05. (TFA salt) |

TABLE 5A-continued

| Cpd ID | Characterization data of compounds prepared analogously to compound 88. Characterization Data |
|---|---|
| 368 | MS (ESI) calcd. for $C_{33}H_{32}N_{10}$ 568.28m/z, found, 569.20[M + H]$^+$. $^1$H NMR (300 MHz, DMSO-$d_6$) δ (ppm); 8.29-8.37 (m, 3H), 7.93-8.02 (m, 3H), 7.79-7.81 (m, 1H), 7.48-7.51 (m, 1H), 7.18 - 7.35 (m, 5H), 6.52-6.55 (m, 1H), 6.40-6.45 (m, 1H), 4.30-4.38 (m, 1H), 3.65-3.78 (m, 2H), 2.91-2.99 (m, 1H), 2.72-2.88 (m, 4H), 2.39-2.43 (m, 1H), 1.99-2.06 (m, 1H), 1.89-1.98 (m, 1H), 1.72-1.83 (m, 1H), 1.34-1.50 (m, 2H). |
| 387 | MS (ESI) calcd. For $C_{32}H_{30}N_{10}$, 554.27 m/z, found 555.20 [M + H]$^+$. $^1$H NMR (400 MHz, DMSO-$d_6$ + $CF_3COOD$) δ (ppm); 8.49 (d, J = 8.8 MHz, 1H), 8.37-8.38 (m, 1H), 8.05-8.15 (m, 4H), 7.81-7.94 (m, 3H), 7.66 (s, 1H), 7.47-7.50 (m, 1H), 7.19 (d, J = 9.2 MHz, 1H), 6.99-7.02 (m, 1H), 6.87-6.90 (m, 1H), 6.57-6.58 (m, 1H), 5.02-5.05 (m, 1H), 4.29-4.30 (m, 1H), 4.01-4.04 (m, 1H), 3.81-3.91 (m, 2H), 3.68-3.70 (m, 1H), 3.19-3.27 (m, 1H), 2.95-3.03 (m, 1H), 2.55 - 2.62 (m, 3H), 2.30-2.35 (m, 1H). |
| 388 | MS (ESI) calcd. For $C_{32}H_{30}N_{10}$, 554.27 m/z, found 555.20 [M + H]$^+$. $^1$H NMR (400 MHz, DMSO-$d_6$ + $CF_3COOD$) δ (ppm); 8.49 (d, J = 8.8 MHz, 1H), 8.37-8.38 (m, 1H), 8.05-8.15 (m, 4H), 7.81-7.94 (m, 3H), 7.66 (s, 1H), 7.47-7.50 (m, 1H), 7.19 (d, J = 9.2 MHz, 1H), 6.99-7.02 (m, 1H), 6.87-6.90 (m, 1H), 6.57-6.58 (m, 1H), 5.02-5.05 (m, 1H), 4.29-4.30 (m, 1H), 4.01-4.04 (m, 1H), 3.81-3.91 (m, 2H), 3.68-3.70 (m, 1H), 3.19-3.27 (m, 1H), 2.95-3.03 (m, 1H), 2.55 - 2.62 (m, 3H), 2.30-2.35 (m, 1H). |
| 393 | MS (ESI) calcd. for $C_{31}H_{33}N_9O_2S$, 595.25 m/z, found, 596.35 [M + H]$^+$. $^1$H NMR (400 MHz, DMSO-d6) δ 8.43-8.22 (m, 2H), 8.08-7.91 (m, 2H), 7.81 (s, 1H), 7.60-7.41 (m, 1H), 7.36 - 7.31 (m, 1H), 7.27-7.18 (m, 2H), 6.95 (s, 2H), 6.55 (s, 1H), 6.45-6.39 (m, 1H), 4.43-4.16 (m, 1H), 3.63-3.54 (m, 2H), 3.01-2.89 (m, 3H), 2.86-2.73 (m, 2H), 2.61-2.57 (m, 1H), 2.49-2.25 (m, 1H), 2.20-2.04 (m, 1H), 2.03-1.89 (m, 2H), 1.82-1.69 (m, 1H), 1.42 (s, 2H), 1.03-0.88 (m, 4H). |
| 394 | MS (ESI) calcd. for $C_{31}H_{34}N_{10}O$, 562.29 m/z, found, 563.40 [M + H]$^+$. $^1$H NMR (400 MHz, DMSO-d6) δ 8.44-8.24 (m, 2H), 8.05-7.91 (m, 2H), 7.85-7.74 (m, 1H), 7.56-7.43 (m, 1H), 7.37-7.30 (m, 1H), 7.28-7.19 (m, 2H), 6.99-6.89 (m, 2H), 6.59-6.51 (m, 1H), 6.45-6.38 (m, 1H), 4.36 (s, 1H), 3.59-3.44 (m, 2H), 3.04-2.87 (m, 1H), 2.85-2.71 (m, 10H), 2.50-2.30 (m, 2H), 2.00-1.89 (m, 1H), 1.87-1.70 (m, 2H), 1.38-1.20 (m, 2H). |
| 434 | MS (ESI) calcd. for $C_{33}H_{33}F_2N_9O$, 609.28 m/z, found 610.20 [M + H]$^+$. $^1$H NMR (300 MHz, DMSO-$d_6$) δ (ppm); 8.68-8.74 (m, 1H), 8.25-8.33 (m, 1H), 8.19-8.24 (m, 1H), 7.68-8.04 (m, 3H), 7.44-7.51 (m, 1H), 7.29-7.35 (m, 1H), 7.19-7.27 (m, 2H), 6.96-7.05 (m, 2H), 6.39-6.48 (m, 1H), 4.32-4.46 (m, 1H), 4.12-4.29 (m, 2H), 3.16-3.27 (m, 1H), 2.88-3.01 (m, 2H), 2.72 - 2.86 (m, 2H), 2.41-2.49 (m, 1H), 1.78-2.13 (m, 5H), 1.15-1.36 (m, 2H), 0.67-0.74 (m, 4H). $^{19}$F NMR (282 MHz, DMSO-$d_6$) δ(ppm) −94.38. |
| 437 | MS (ESI) calcd. for $C_{28}H_{28}N_8$, 476.24 m/z, found, 477.30 [M + H]$^+$. $^1$H NMR (300 MHz, DMSO-$d_6$) δ (ppm); 8.33-8.38 (m, 2H), 7.93-8.01 (m, 2H), 7.81-7.83 (m, 1H), 7.43-7.46 (m, 1H), 7.31-7.33 (m, 1H), 7.22-7.25 (m, 1H), 7.16-7.19 (m, 1H), 6.57-6.58 (m, 1H), 6.33-6.39 (m, 1H), 4.51-4.56 (m, 1H), 2.73-2.92 (m, 2H), 2.22-2.32 (m, 2H), 2.21 (s, 3H), 2.01-2.14 (m, 2H), 0.81-0.89 (m, 1H), 0.39-0.56 (m, 2H), 0.02-0.13 (m, 2H). |
| 439 | MS (ESI) calcd. For $C_{31}H_{28}N_{10}$, 540.25 m/z, found 541.40 [M + H]$^+$. $^1$H NMR NMR (300 MHz, DMSO-$d_6$) δ 8.35-8.37 (m, 2H), 8.04-8.06 (m, 1H), 8.00-8.02 (m, 1H), 7.95 (d, J = 8.4 Hz, 1H), 7.80-7.81 (m, 1H), 7.46-7.51 (m, 2H), 7.35-7.36 (m, 1H), 7.21-7.28 (m, 2H), 6.98 (s, 2H), 6.58-6.62 (m, 1H), 6.52-6.53 (m, 1H), 6.44-6.48 (m, 1H), 6.34-6.37 (m, 1H), 4.23-4.27 (m, 1H), 4.07-4.13 (m, 2H), 3.87-3.91 (m, 1H), 3.60-3.65 (m, 2H), 2.95-3.05 (m, 1H), 2.74 - 2.85 (m, 1H), 2.31-2.42 (m, 1H), 1.77-1.89 (m, 1H). |
| 440 | MS (ESI) calcd. for $C_{33}H_{35}N_9O_2$, 589.29 m/z, found, 590.20 [M + H]$^+$. $^1$H NMR (400 MHz, DMSO-$d_6$) δ(ppm) 8.34-8.26 (m, 1H), 8.20-8.14 (m, 1H), 8.03-7.96 (m, 1H), 7.82-7.72 (m, 1H), 7.52-7.42 (m, 1H), 7.32 (s, 1H), 7.28-7.16 (m, 2H), 6.95 (s, 2H), 6.46-6.35 (m, 1H), 6.13-5.98 (m, 1H), 4.34 (s, 1H), 4.19 (s, 2H), 3.92 (s, 3H), 3.22 (s, 1H), 2.92 (s, 2H), 2.86-2.69 (m, 2H), 2.48-2.36 (m, 1H), 2.08 (s, 1H), 2.04-1.69 (m, 4H), 1.39-1.22 (m, 1H), 1.19 (s, 1H), 0.77-0.62 (m, 4H). |
| 442 | MS (ESI) calcd. for $C_{35}H_{37}N_9O$, 599.31 m/z, found 600.30 [M + H]$^+$. $^1$H NMR (300 MHz, DMSO-d6) δ (ppm); 8.24-8.37 (m, 2H), 7.78-8.04 (m, 2H), 7.48-7.60 (m, 1H), 7.16-7.38 (m, 3H), 6.38-6.49 (m, 1H), 6.20-6.30 (m, 1H), 4.40-4.53 (m, 1H), 4.25 (s, 2H), 3.15-3.28 (m, 1H), 2.91-3.12 (m, 2H), 2.75-2.87 (m, 2H), 2.40-2.51 (m, 1H), 1.69-2.14 (m, 5H), 1.20-1.36 (m, 2H), 0.87-1.03 (m, 2H), 0.62-0.87 (m, 6H). |
| 458 | MS (ESI) calcd. for $C_{29}H_{30}N_8$, 490.26 m/z, found, 491.20 [M + H]$^+$. $^1$H NMR (300 MHz, DMSO-$d_6$ + $D_2O$) δ (ppm); 8.32-8.39 (m, 2H), 7.96-8.03 (m, 2H), 7.79-7.82 (m, 1H), 7.43-7.47 (m, 1H), 7.34-7.36 (m, 1H), 7.17-7.29 (m, 2H), 6.56-6.58 (m, 1H), 6.35-6.39 (m, 1H), 4.43-4.51 (m, 1H), 2.77-2.94 (m, 2H), 2.41-2.49 (m, 2H), 2.21 (s, 3H), 1.95-2.13 (m, 2H), 1.31-1.41 (m, 2H), 0.64-0.72 (m, 1H), 0.32-0.41 (m, 2H), 0.01-0.03 (m, 2H). |
| 461 | MS (ESI) calcd. for $C_{31}H_{31}N_9O$, 545.26 m/z, found, 546.25 [M + H]$^+$. $^1$H NMR (300 MHz, DMSO-$d_6$) δ (ppm); 8.30-8.40 (m, 2H), 7.93-8.02 (m, 2H), 7.79-7.81 (m, 1H), 7.42-7.48 (m, 1H), 7.30-7.39 (m, 1H), 7.20-7.29 (m, 2H), 6.89-6.99 (m, 2H), 6.50-6.52 (m, 1H), 6.38-6.42 (m, 1H), 4.18-4.31 (m, 1H), 3.71-3.88 (m, 1H), 3.38-3.62 (m, 3H), 3.10-3.18 (m, 1H), 2.89-2.98 (m, 1H), 2.70-2.81 (m, 1H), 2.40-2.45 (m, 1H), 1.91-2.10 (m, 1H), 1.79-1.88 (m, 1H), 1.69 - 1.75 (m, 2H), 1.13-1.25 (m, 1H), 0.65-0.73 (m, 4H). |
| 462 | MS (ESI) calcd. for $C_{31}H_{31}N_9O$, 545.26 m/z, found, 546.20 [M + H]$^+$ $^1$H NMR (300 MHz, DMSO-$d_6$) δ (ppm); 8.30-8.40 (m, 2H), 7.93-8.02 (m, 2H), 7.79-7.83 (m, 1H), 7.55-7.62 (m, 1H), 7.31-7.36 (m, 1H), 7.18-7.26 (m, 2H), 6.92-7.00 (m, 2H), 6.53-6.56 (m, 1H), 6.39-6.46 (m, 1H), 4.21-4.31 (m, 1H), 3.70-3.86 (m, 1H), 3.45-3.65 (m, 3H), 3.09-3.15 (m, 1H), 2.90-3.00 (m, 1H), 2.71-2.81 (m, 1H), 2.40- 2.45 (m, 1H), 1.64-2.10 (m, 4H), 1.12-1.25 (m, 1H), 0.65 - 0.73 (m, 4H). |

TABLE 5A-continued

Characterization data of compounds prepared analogously to compound 88.

| Cpd ID | Characterization Data |
|---|---|
| 463 | MS (ESI) calcd. for $C_{32}H_{29}N_9$, 539.25 m/z, found, 540.40 $[M + H]^+$. $^1H$ NMR (300 MHz, DMSO-$d_6$) δ ppm 8.34-8.36 (m, 2H), 8.28-8.33 (m, 1H), 8.21-8.22 (m, 1H), 7.99 (d, J = 4.8 Hz, 1H), 7.94 (d, J = 8.4 Hz, 1H), 7.79 (d, J = 1.2 Hz, 1H), 7.45 (d, J = 7.8 Hz, 1H), 7.29-7.33 (m, 1H), 7.20-7.25 (m, 2H), 7.08 (d, J = 5.1 Hz, 1H), 6.94 (s, 2H), 6.53 (d, J = 2.4 Hz, 1H), 6.40(d, J = 7.5, 1H), 4.30-4.45 (m, 1H), 3.07-3.20 (m, 2H), 2.91-2.93 (m, 1H), 2.80-2.85 (m, 1H), 2.73 - 2.78 (m, 2H), 2.57-2.59 (m, 1H), 2.00-2.10 (m, 1H), 1.72-1.89 (m, 1H), 1.55-1.66 (m, 1H), 1.15-1.22 (m, 1H). |
| 464 | MS (ESI) calcd. for $C_{32}H_{29}N_9$, 539.25 m/z, found, 540.40 $[M + H]^+$. $^1H$ NMR (300 MHz, DMSO-$d_6$) δ ppm 8.34-8.37 (m, 2H), 8.28-8.33 (m, 1H), 8.21-8.23 (m, 1H), 8.00 (d, J = 4.8 Hz, 1H), 7.95 (d, J = 8.7 Hz, 1H), 7.79 (d, J = 1.2 Hz, 1H), 7.46 (d, J = 8.1 Hz, 1H), 7.36-7.45 (m, 1H), 7.22-7.27 (m, 2H), 7.08 (d, J = 5.1 Hz, 1H), 6.94 (s, 2H), 6.54 (d, J = 4.2 Hz, 1H), 6.42(d, J = 7.5, 1H), 4.36-4.47 (m, 1H), 3.10-3.21 (m, 1H), 2.91-3.00 (m, 3H), 2.76-2.85 (m, 2H), 2.55 - 2.71 (m, 2H), 2.01-2.16 (m, 1H), 1.75-1.92 (m, 1H), 1.60-1.74 (m, 1H), 1.20-1.28 (m, 1H). |
| 469 | MS (ESI) calcd. for $C_{33}H_{31}N_9$, 553.27 m/z, found, 554.35 $[M + H]^+$/$^1H$ NMR (400 MHz, DMSO-$d_6$) δ (ppm); 8.33-8.35 (m, 2H), 7.95-8.01 (m, 2H), 7.81 (s, 1H), 7.52 (d, J = 5.2 Hz, 1H), 7.34 (s, 1H), 7.25 (d, J = 5.2 Hz, 2H), 7.15-7.18 (m, 2H), 6.52-6.60 (m, 4H), 6.43-6.46 (m, 1H), 4.30-4.31 (m, 1H), 3.59-3.62 (m, 1H), 3.51-3.55 (m, 1H), 3.33-3.37 (m, 1H), 3.22-3.27 (m, 1H), 2.96-3.07 (m, 2H), 2.76-2.84 (m, 1H), 2.48-2.49 (m, 1H), 2.20-2.22 (m, 1H), 1.85-1.89 (m, 2H). |
| 470 | MS (ESI) calcd. for $C_{33}H_{31}N_9$, 553.27 m/z, found, 554.35 $[M + H]^+$/$^1H$ NMR (400 MHz, DMSO-$d_6$) δ (ppm); 8.33-8.35 (m, 2H), 7.95-8.01 (m, 2H), 7.81 (s, 1H), 7.53 (d, J = 8.0 Hz, 1H), 7.34 (s, 1H), 7.23-7.27 (m, 2H), 7.14-7.18 (m, 2H), 6.51-6.60 (m, 4H), 6.42-6.45 (m, 1H), 4.30 - 4.33 (m, 1H), 3.59-3.62 (m, 1H), 3.49-3.52 (m, 1H), 3.35-3.37 (m, 1H), 3.23-3.26 (m, 1H), 2.96-3.07 (m, 2H), 2.76-2.83 (m, 1H), 2.48-2.49 (m, 1H), 2.20-2.22 (m, 1H), 1.84-1.90 (m, 2H). |
| 471 | MS (ESI) calcd. for $C_{32}H_{30}N_{10}$ 8.33-8.36 (m, 2H), 7.92-8.10 (m, 3H), 7.70 -7.80 (m, 2H), 7.47 (d, J = 7.8 Hz, 1H), 7.34 (s, 1H), 7.24 (t, J = 8.0 Hz, 2H), 7.11-715 (m, 1H), 6.85-6.94 (m, 3H), 6.53 (s, 1H), 6.38-6.42 (m, 1H), 4.30 (s, 1H), 3.51-3.86 (m, 2H), 3.32-3.39 (m, 1H), 3.23 - 3.28 (m, 1H), 3.10-3.12 (m, 1H), 2.93-2.95 (m, 1H), 2.73-2.81 (m, 1H), 2.58-2.69 (m, 2H), 2.18-2.20 (m, 1H), 1.83-1.90 (m, 2H).554.27 m/z, found, 555.20 $[M + H]^+$. $^1H$ NMR (300 MHz, DMSO-d6) δ(ppm) |
| 472 | MS (ESI) calcd. for $C_{32}H_{30}N_{10}$ 554.27 m/z, found, 555.20 $[M + H]^+$. $^1H$ NMR (300 MHz, DMSO-d6) δ(ppm) 8.33-8.36 (m, 2H), 7.98-8.00 (m, 1H), 7.90 -7.97 (m, 2H), 7.79-7.81 (m, 2H), 7.49 - 7.51 (m, 1H), 7.34 (s, 1H), 7.20-7.26 (m, 2H), 711-715 (m, 1H), 6.94 (s, 2H), 6.84-6.87 (m, 1H), 6.51-6.53 (m, 1H), 6.38-6.42 (m, 1H), 4.29-4.32 (m, 1H), 3.60-3.64 (m, 1H), 3.50-3.55 (m, 1H), 3.40-3.41 (m, 1H), 3.26-3.29 (m, 1H), 2.94-3.08 (m, 2H), 2.73-2.84 (m, 1H), 2.41 - 2.43 (m, 2H), 2.13-2.23 (m, 1H), 1.79-1.98 (m, 2H). |
| 473 | MS (ESI) calcd. for $C_{31}H_{27}N_9$, 525.24. Found, 526.35 $[M + H]^+$. $^1H$-NMR (300 MHz, DMSO-d6) δ (ppm); 8.50-8.60 (m, 1H),8.50-8.40 (m, 2H), 8.40-8.30 (m, 1H), 8.20-8.30 (m, 1H), 8.00-8.10 (m, 1H), 7.90-8.00 (m, 1H),7.75-7.90 (m, 1H), 7.60- 7.70 (m, 1H), 7.50-7.60 (m, 1H), 7.35 - 7.40 (m, 2H), 6.90-7.05 (m, 2H), 6.50-6.60 (m, 1H), 6.30-6.50 (m, 1H), 4.30-4.70 (m, 2H), 3.00-3.10 (m, 2H), 2.80-2.95 (m, 2H), 2.50-2.55 (m, 1H), 1.80-2.15 (m, 2H), 1.20-1.30 (m, 1H) |
| 474 | MS (ESI) calcd. for $C_{31}H_{27}N_9$, 525.24. Found, 526.35 $[M + H]^+$. $^1H$-NMR (300 MHz, DMSO-d6) δ (ppm); 8.50-8.60 (m, 1H),8.50-8.40 (m, 1H), 8.40-8.30 (m, 2H), 8.20-8.30 (m, 1H), 8.00-8.10 (m, 1H), 7.90-8.00 (m, 1H), 7.75-7.90 (m, 1H), 7.60- 7.70 (m, 1H), 7.50-7.60 (m, 1H), 7.40 - 7.50 (m, 1H), 7.35-7.40 (m, 2H), 6.90-7.05 (m, 2H), 6.60-6.70 (m, 1H), 6.50-6.60 (m, 1H), 4.40-4.65 (m, 2H), 3.00-3.10 (m, 2H), 2.75-2.95 (m, 2H), 2.50-2.60 (m, 1H), 2.40-2.50 (m, 1H), 1.80-2.00 (m, 2H). |
| 480 | MS (ESI) calcd. for $C_{35}H_{36}FN_9O$, 617.30 m/z, found 618.30 $[M + H]^+$. $^1H$ NMR (300 MHz, DMSO-$d_6$) δ(ppm) 8.38-8.40 (m, 1H), 8.18-8.19 (m, 1H), 8.05-8.07 (m, 1H), 7.91-7.94 (m, 1H), 7.75-7.77 (m, 2H), 7.59-7.60 (m, 1H), 7.51-7.53 (m, 1H), 6.74-6.78 (m, 1H), 6.27-6.28 (m, 1H), 5.79-5.92 (m, 1H), 5.20-5.26 (m, 1H), 4.41-4.48 (m, 2H), 3.78-3.80 (m, 3H), 3.20 - 3.38 (m, 3H), 2.67-2.71 (m, 1H), 2.29-2.38 (m, 1H), 2.12-2.20 (m, 1H), 1.99-2.09 (m, 2H), 1.45-1.55 (m, 2H), 0.99-1.00 (m, 2H), 0.75-0.80 (m, 4H). $^{19}F$ NMR (376 MHz, DMSO-$d_6$) δ (ppm); −74.01, −195.70. (TFA salt) |
| 481 | MS (ESI) calcd. for $C_{31}H_{26}FN_9$, 543.23 m/z, found, 544.20 $[M + H]^+$. $^1H$-NMR (400 MHz, DMSO-d6) δ (ppm); 8.42-8.59 (m, 1H), 8.21-8.42 (m, 3H), 7.89-8.15 (m, 2H), 7.68-7.89 (m, 1H), 7.45-7.68(m, 2H), 7.15-7.45 (m, 3H), 6.51-6.69 (m, 1H), 6.35-6.51 (m, 1H), 5.42-5.73 (m, 1H),4.52-4.69 (m, 1H), 4.22-4.52 (m, 1H), 2.95-3.38 (m, 3H), 2.78-2.95 (m, 1H), 2.42-2.52 (m, 1H), 1.85-2.15 (m, 1H). |
| 482 | MS (ESI) calcd. for $C_{31}H_{26}FN_9$, 543.23 m/z, found, 544.20 $[M + H]^+$. $^1H$-NMR (400 MHz, DMSO-d6) δ (ppm); 8.42-8.58 (m, 1H), 8.22-8.42 (m, 3H), 7.89-8.15 (m, 2H), 7.71-7.89 (m, 1H), 7.49-7.71(m, 2H), 7.31-7.49 (m, 2H), 7.15-7.31 (m, 1H), 6.51-6.69 (m, 1H), 6.33-6.51 (m, 1H), 5.22-5.73 (m, 1H),4.37-4.54 (m, 2H), 3.09-3.33 (m, 2H), 2.95-3.33 (m, 1H), 2.79-2.95 (m, 1H), 2.56-2.62 (m, 1H), 1.71-2.03 (m, 1H). |
| 493 | MS (ESI) calcd. for $C_{31}H_{30}FN_9O_2$: 579.25 m/z, found, 580.40 $[M + H]^+$. $^1H$-NMR (400 MHz, DMSO) δ (ppm); 8.35-8.42 (m, 1H), 8.18-8.22 (m, 1H), 8.03-8.08 (m, 1H), 7.82-7.88 (m, 1H), 7.75-7.80 (m, 1H), 7.65-7.73 (m, 1H), 7.59-7.65 (m, 1H), 7.48-7.55 (m, 1H), 6.70-6.80 (m, 1H), 6.08-6.12 (m, 1H), 5.62-5.82 (m, 1H), 4.98-5.10 (m, 1H), 4.58-4.70 (m, 1H), 4.35 - 4.50 (m, 2H), 4.15-4.25 (m, 1H), 3.99-4.06 (m, 1H), 3.87-3.95 (m, 3H), 3.28-3.42 (m, 2H), 1.50-1.62 (m, 1H), 0.70-0.85 (m, 4H). $^{19}F$ NMR (376 MHz, DMSO-$d_6$) δ (ppm); −194.96, −73.88. (TFA salt) |

TABLE 5A-continued

| Cpd ID | Characterization Data |
|---|---|
| | Characterization data of compounds prepared analogously to compound 88. |
| 500 | Observed mass (ESI): 560.2 [M + H]+. 1H-NMR (400 MHz, DMSO) δ (ppm): 8.32-8.50 (m, 2H), 7.98-8.15 (m, 2H), 7.70-7.88 (m, 3H), 7.53-7.65 (m, 1H), 7.40-7.50 (m, 1H), 6.75-6.85 (m, 1H), 6.52-6.63 (m, 1H), 4.96-5.10 (m, 1H), 4.32-4.55 (m, 2H), 3.55-3.65 (m, 1H), 3.11-3.30 (m, 2H), 2.90-3.08 (m, 1H), 2.55-2.75 (m, 2H), 1.99-2.40 (m, 4H), 1.37-1.65 (m, 2H), 1.65 - 1.85 (m, 4H). |
| 501 | Observed mass (ESI): 540.4 [M + H]+. 1H NMR (400 MHz, DMSO-d6) δ (ppm): 8.35-8.38 (m, 3H), 8.00-8.01 (m, 1H), 7.95-7.99 (m, 1H), 7.80-7.81 (m, 1H), 7.51-7.54 (m, 2H), 7.36-7.37 (m, 1H), 7.18-7.28 (m, 3H), 6.53-6.54 (m, 1H), 6.40-6.43 (m, 1H), 4.44-4.48 (m, 1H), 3.98 - 4.00 (m, 1H), 2.98-3.05 (m, 1H), 2.77-2.84 (m, 3H), 2.52-2.53 (m, 1H), 2.12-2.18 (m, 1H), 1.94-2.05 (m, 1H), 1.85-1.93 (m, 1H), 1.74-1.76 (m, 2H). |
| 502 | Observed mass (ESI): 540.4 [M + H]+. 1H NMR (400 MHz, DMSO-d6) δ (ppm): 8.35-8.38 (m, 3H), 8.00-8.01 (m, 1H), 7.95-7.97 (m, 1H), 7.81-7.82 (m, 1H), 7.54-7.56 (m, 1H), 7.49-7.50 (m, 1H), 7.34-7.35 (m, 1H), 7.20-7.27 (m, 3H), 6.55-6.56 (m, 1H), 6.45-6.48 (m, 1H), 4.45 - 4.48 (m, 1H), 3.94-3.97 (m, 1H), 2.91-3.01 (m, 1H), 2.75-2.86 (m, 3H), 2.61-2.64 (m, 1H), 2.15-2.20 (m, 1H), 2.00-2.05 (m, 1H), 1.77-1.85 (m, 3H). |
| 503 | Observed mass (ESI): 561.2 [M + H]+. 1H NMR (400 MHz, DMSO-d6) δ (ppm): 8.30-8.32 (m, 1H), 8.13-8.17 (m, 2H), 7.98-7.99 (m, 1H), 7.49-7.51 (m, 1H), 7.39 (s, 1H), 7.29-7.30 (m, 1H), 7.22-7.26 (m, 2H), 6.41-6.44 (m, 1H), 4.32-4.35 (m, 1H), 4.20-4.29 (m, 2H), 3.17-3.20 (m, 1H), 2.87-2.97 (m, 2H), 2.73-2.80 (m, 2H), 2.50-2.51 (m, 1H), 1.91-2.04 (m, 3H), 1.81 - 1.83 (m, 1H), 1.21-1.31 (m, 1H), 1.08-1.18 (m, 1H), 0.60-0.75 (m, 4H). |
| 506 | Observed mass (ESI): 530.3 [M + H]+. 1H NMR (300 MHz, DMSO-d6) δ (ppm): 8.06-8.24 (m, 1H), 7.87-8.05 (m, 1H), 7.35-7.62 (m, 2H), 7.05-7.34 (m, 3H), 6.30-6.57 (m, 1H), 4.30-4.55 (m, 1H), 4.09-4.28 (m, 1H), 3.86-4.08 (m, 2H), 3.71-3.85 (m, 1H), 3.45-3.70 (m, 1H), 2.88 - 3.12 (m, 1H), 2.65-2.87 (m, 1H), 2.20-2.43 (m, 1H), 1.70-1.95 (m, 1H), 1.40-1.65 (m, 2H), 0.84-1.02 (m, 2H), 0.55-0.83 (m, 6H). |
| 507 | Observed mass (ESI): 608.35 [M + H]+. 1H NMR (400 MHz, DMSO-d6) δ(ppm): 8.41 (d, J = 11.2 Hz, 1H), 7.89-8.12 (m, 2H), 7.48 (d, J = 8.0 Hz, 1H), 7.33 (s, 1H), 7.10-7.30 (m, 2H), 6.29 - 6.58 (m, 1H), 6.08 (d, J = 2.8 Hz, 1H), 4.37 (t, J = 7.2 Hz, 1H), 4.11-4.30 (m, 2H), 3.84 (s, 3H), 3.10-3.30 (m, 1H), 2.89-3.02 (m, 2H), 2.70-2.81 (m, 2H), 2.39-2.49 (m, 1H), 1.76-2.06 (m, 4H), 1.07-1.42 (m, 2H), 0.50-0.98 (m, 4H). 19F NMR (376 MHz, DMSO-d6) δ (ppm): −73.527, −112.623. (TFA salt) |
| 508 | Observed mass (ESI): 556.15 [M + H]+. 1H-NMR (400 MHz, DMSO-d6) δ (ppm): 8.33-8.35 (m, 2H), 7.93-8.00 (m, 3H), 7.79 (s, 1H), 7.51-7.53 (m, 1H), 7.32 (s, 1H), 7.22-7.24 (m, 2H), 7.09-7.10 (m, 1H), 6.52-6.54 (m, 1H), 6.40-6.44 (m, 1H), 4.33-4.36 (m, 2H), 3.66-3.67 (m, 3H), 2.78-3.03 (m, 2H), 2.63-2.67 (m, 1H), 2.44-2.52 (m, 2H), 1.86-1.93 (m, 4H). |
| 509 | Observed mass (ESI): 556.15 [M + H]+. 1H-NMR (400 MHz, DMSO-d6) δ (ppm): 8.33-8.35 (m, 2H), 7.93-8.00 (m, 3H), 7.79 (s, 1H), 7.51-7.53 (m, 1H), 7.32 (s, 1H), 7.22-7.24 (m, 2H), 7.07-7.09 (m, 1H), 6.52-6.53 (m, 1H), 6.38-6.43 (m, 1H), 4.31-4.38 (m, 2H), 3.86 (s, 3H), 2.93 - 2.96 (m, 1H), 2.76-2.86 (m, 2H), 2.60-2.64 (m, 1H), 2.38-2.51 (m, 2H), 1.77-1.88 (m, 2H). |
| 510 | Observed mass (ESI): 556.35 [M + H]+. 1H NMR (400 MHz, DMSO-d6) δ (ppm): 8.34-8.35 (m, 2H), 7.99-8.01 (m, 2H), 7.94-7.96 (m, 1H), 7.80-7.81 (m, 1H), 7.53-7.55 (m, 1H), 7.32-7.33 (m, 1H), 7.23-7.25 (m, 2H), 6.86 (s, 1H), 6.52-6.57 (m, 1H), 6.42-6.45 (m, 1H), 4.30-4.37 (m, 1H), 4.26-4.28 (m, 1H), 3.74-3.81 (s, 3H), 2.88-3.00 (m, 2H), 2.69-2.83 (m, 2H), 2.47 - 2.54 (m, 2H), 1.84-1.93(m, 2H). |
| 511 | Observed mass (ESI): 556.35 [M + H]+. 1H NMR (400 MHz, DMSO-d6) δ (ppm): 8.35-8.37 (m, 2H), 7.95-8.01 (m, 3H), 7.81 (s, 1H), 7.54-7.56 (m, 1H), 7.33-7.34 (s, 1H), 7.24-7.26 (m, 2H), 6.83 (s, 1H), 6.55 (s, 1H), 6.42-6.45 (m, 1H), 4.36-4.39 (m, 1H), 4.25-4.29 (m, 1H), 3.81 (s, 3H), 2.91-3.01 (m, 1H), 2.77-2.88 (m, 2H), 2.65-2.73 (m, 1H), 2.40-2.53 (m, 2H), 1.75 - 1.92 (m, 2H). |
| 512 | Observed mass (ESI): 608.2 [M + H]+. 1H NMR (400 MHz, DMSO-d6) δ (ppm): 8.28-8.42 (m, 1H), 8.09-8.28 (m, 1H), 7.89-8.09 (m, 1H), 7.65-7.89 (m, 1H), 7.41-7.65 (m, 1H), 7.07-7.41 (m, 3H), 6.36-6.63 (m, 1H), 5.95-6.21 (m, 1H), 4.75-4.99 (m, 1H), 4.48-4.75 (m, 1H),4.23 - 4.48 (m, 2H), 3.85-4.02 (m, 3H), 3.14-3.49 (m, 1H), 2.91-3.12 (m, 2H), 2.61-2.91 (m, 2H), 2.26-2.49 (m, 1H), 1.78-2.12 (m, 3H), 1.37-1.71 (m, 1H), 0.55-0.98 (m, 4H). |
| 513 | Observed mass (ESI): 608.2 [M + H]+. 1H NMR (400 MHz, DMSO-d6) δ (ppm): 8.28-8.42 (m, 1H), 8.09-8.28 (m, 1H), 7.89-8.09 (m, 1H), 7.68-7.89 (m, 1H), 7.39-7.65 (m, 1H), 7.07-7.39 (m, 3H), 6.35-6.61 (m, 1H), 5.95-6.19 (m, 1H), 4.85-5.11 (m, 1H), 4.46-4.73 (m, 1H),4.16 - 4.46 (m, 2H), 3.87-3.95 (m, 3H), 3.12-3.49 (m, 1H), 2.89-3.12 (m, 2H), 2.61-2.89 (m, 2H), 2.40-2.49 (m, 1H), 1.91-2.15 (m, 1H), 1.79-1.91 (m, 1H), 1.37-1.79 (m, 2H), 0.55-0.98 (m, 4H). |
| 514 | Observed mass (ESI): 608.15 [M + H]+. 1H NMR (400 MHz, DMSO-d6) δ (ppm): 8.28-8.42 (m, 1H), 8.09-8.28 (m, 1H), 7.89-8.09 (m, 1H), 7.65-7.89 (m, 1H), 7.42-7.65 (m, 1H), 7.08-7.42 (m, 3H), 6.36-6.61 (m, 1H), 5.95-6.21 (m, 1H), 4.22-4.65 (m, 2H), 4.08-4.19 (m, 1H),4.01 - 4.08 (m, 1H), 3.88-3.93 (m, 3H), 3.66-3.82 (m, 1H), 3.41-3.59 (m, 1H),3.22-3.41 (m, 1H), 3.06-3.22 (m, 1H), 2.88-3.06 (m, 1H), 2.75-2.88 (m, 1H), 2.42-2.52 (m, 1H), 1.88-2.22 (m, 2H), 1.75-1.88 (m, 1H), 1.32-1.65 (m, 1H), 0.65-0.85 (m, 4H). |
| 515 | Observed mass (ESI): 608.2 [M + H]+. 1H NMR (400 MHz, DMSO-d6) δ (ppm): 8.09-8.42 (m, 2H), 7.89-8.09 (m, 1H), 7.65-7.89 (m, 1H), 7.41-7.65 (m, 1H), 7.07-7.41 (m, 3H), 6.36-6.61 (m, 1H), 5.95-6.21 (m, 1H), 4.28-4.69 (m, 2H), 4.08-4.19 (m, 1H),3.88-3.93 (m, 3H), 3.61 - 3.82 (m, 1H), 3.23-3.58 (m, 2H), 3.06-3.23 (m, 1H), 2.88-3.06 (m, 1H), 2.67-2.88 (m, 1H), 2.48-2.52 (m, 1H), 1.93-2.18 (m, 2H), 1.68-1.93 (m, 2H), 1.32-1.65 (m, 1H), 1.06-1.32 (m, 1H), 0.69-0.89 (m, 4H). |

TABLE 5A-continued

| Characterization data of compounds prepared analogously to compound 88. | |
|---|---|
| Cpd ID | Characterization Data |
| 519 | Observed mass (ESI): 590.25 [M + H]+. 1H NMR (400 MHz, DMSO-d6) δ (ppm): 8.35-8.38 (m, 2H), 8.00-8.02 (m, 1H), 7.94-7.96 (m, 1H), 7.81 (s, 1H), 7.48-7.50 (m, 1H), 7.41-7.42 (m, 1H), 7.33-7.37 (m, 2H), 7.22-7.25 (m, 1H), 6.93 (s, 2H), 6.54-6.55 (m, 1H), 6.41-6.44 (m, 1H), 5.66-5.67 (m, 1H), 5.40-5.54 (m, 1H), 4.42-4.50 (m, 1H), 3.59-3.65 (m, 5H), 309-3.16 (m, 2H), 2.90 (s, 1H), 2.67-2.73 (m, 2H), 2.12-2.15 (m, 1H), 2.03-2.08 (m, 1H), 1.86-1.89 (m, 1H), 1.43-1.49 (m, 2H). |
| 521 | Observed mass (ESI): 576.3 [M + H]+. 1H NMR (300 MHz, DMSO-d6 + D2O) δ (ppm): 8.19-8.22 (m, 1H), 8.05-8.09 (m, 1H), 7.74-7.79 (m, 1H), 7.65-7.72 (m, 1H), 7.45-7.59 (m, 3H),6.66 - 6.71 (m, 1H), 5.77-5.97 (m, 1H), 5.21-5.29 (m, 1H), 4.35-4.57 (m, 2H), 3.61-3.62 (m, 1H), 3.35-3.38 (m, 1H), 3.32-3.34 (m, 1H), 3.15-3.31 (m, 1H), 2.63-2.81 (m, 1H), 2.28-2.45 (m, 1H), 2.11-2.23 (m, 1H), 2.01-2.09 (m, 1H), 1.41-1.73 (m, 3H), 0.89-0.94 (m, 2H), 0.71-0.83 (m, 6H). (TFA salt) |
| 523 | Observed mass (ESI): 632.25 [M + H]+. 1H NMR (300 MHz, DMSO-d6) δ ppm: 8.29-8.32 (m, 1H), 8.17 (s, 1H), 8.00-8.01 (m, 1H), 7.77 (d, J = 8.7 Hz, 1H), 7.54 (d, J = 7.8 Hz, 1H), 7.33 (s, 1H), 7.26-7.29 (m, 1H), 7.22-7.25 (m, 1H), 6.93 (s, 2H), 6.40-6.44 (m, 1H), 6.05 (s, 1H), 4.61 - 4.68 (m, 1H), 4.42-4.49 (m, 1H), 4.27-4.31 (m, 1H), 4.13-4.25 (m, 2H), 3.92 (s, 3H), 3.65 - 3.67 (m, 1H), 3.42-3.51 (m, 2H), 3.15-3.17 (m, 1H), 2.75-3.01 (m, 3H), 2.28-2.36 (m, 1H), 1.96-2.03 (m, 1H), 1.78-1.82 (m, 2H), 1.62-1.69 (m, 1H), 0.67-0.74 (m, 4H). |
| 524 | Observed mass (ESI): 632.25 [M + H]+. 1H NMR (300 MHz, DMSO-d6) δ ppm: 8.29-8.32 (m, 1H), 8.17 (s, 1H), 8.00-8.01 (m, 1H), 7.77 (d, J = 8.7 Hz, 1H), 7.54 (d, J = 8.1 Hz, 1H), 7.33 (s, 1H), 7.26-7.28 (m, 1H), 7.21-7.25 (m, 1H), 6.93 (s, 2H), 6.40-6.44 (m, 1H), 6.05 (s, 1H), 4.22-4.36 (m, 2H), 4.08-4.15 (m, 1H), 3.98-4.06 (m, 1H), 3.92 (s, 3H), 3.82-3.88 (m, 2H), 3.51 - 3.66 (m, 2H), 3.28-3.33 (m, 1H), 3.12-3.14 (m, 1H), 2.93-3.01 (m, 1H), 2.73-2.84 (m, 1H), 2.26-2.38 (m, 1H), 1.74-1.95 (m, 4H), 0.66-0.73 (m, 4H). |
| 530 | Observed mass (ESI): 526.3 [M + H]+. 1H NMR (300 MHz, DMSO-d6) δ(ppm): 8.30-8.41 (m, 2H), 8.21-8.29 (m, 1H), 7.89-8.05 (m, 2H), 7.76-7.82 (m, 1H), 7.55-7.64 (m, 1H), 7.43-7.54 (m, 1H), 7.34-7.40 (m, 1H), 7.19-7.30 (m, 2H), 7.08-7.18 (m, 1H), 6.92-6.99 (m, 2H), 6.50 - 6.58 (m, 1H), 6.40-6.49 (m, 1H), 4.30-4.49 (m, 1H), 4.20-4.16 (m, 1H), 3.78-3.91 (m, 1H), 3.10-3.26 (m, 2H), 2.77-3.09 (m, 5H), 1.88-1.97 (m, 1H). |
| 531 | Observed mass (ESI): 526.3 [M + H]+. 1H NMR (300 MHz, DMSO-d6) δ(ppm): 8.22-8.41 (m, 3H), 7.89-8.05 (m, 2H), 7.76-7.82 (m, 1H), 7.55-7.64 (m, 1H), 7.43-7.54 (m, 1H), 7.34-7.40 (m, 1H), 7.19-7.30 (m, 2H), 7.08-7.18 (m, 1H), 6.92-6.99 (m, 2H), 6.50-6.58 (m, 1H), 6.40 - 6.49 (m, 1H), 4.30-4.49 (m, 1H), 4.16-4.20 (m, 1H), 3.78-3.91 (m, 1H), 3.10-3.26 (m, 2H), 2.77-3.09 (m, 5H), 1.88-1.97 (m, 1H). |
| 532 | Observed mass (ESI): 579.3 [M + H]+. 1H NMR (300 MHz, DMSO-d6 + D2O) δ (ppm): 8.33-8.46 (m, 1H), 8.01-8.13 (m, 3H), 7.91-7.99 (m, 1H), 7.53-7.61 (m, 1H), 7.21-7.44 (m, 3H), 6.44 - 6.51 (m, 1H), 5.45-5.69 (m, 1H), 4.55-4.69 (m, 1H), 4.18-4.41 (m, 2H), 3.07-3.31 (m, 4H), 2.64-2.82 (m, 1H), 1.82-2.19 (m, 3H), 1.35-1.48 (m, 1H), 1.25-1.34 (m, 1H), 0.65-0.79 (m, 4H). |
| 533 | Observed mass (ESI): 579.3 [M + H]+. 1H NMR (300 MHz, DMSO-d6 + D2O) δ (ppm): 8.43-8.46 (m, 1H), 8.01-8.19 (m, 4H), 7.55-7.59 (m, 1H), 7.36-7.42 (m, 1H), 7.24-7.34 (m, 2H), 6.45 - 6.49 (m, 1H), 5.17-5.38 (m, 1H), 4.39-4.44 (m, 1H), 4.15-4.32 (m, 2H), 3.41-3.55 (m, 1H), 3.12-3.23 (m, 1H), 2.95-3.11 (m, 2H), 2.71-2.84 (m, 1H), 1.82-2.11 (m, 3H), 1.25-1.37 (m, 1H), 1.15-1.19 (m, 1H), 0.72-0.89 (m, 4H). |
| 542 | Observed mass (ESI): 580.29 [M + H]+. 1H NMR (400 MHz, DMSO-d6) δ 9.35 (s, 1H), 9.34-9.29 (m, 1H), 8.38 (d, J = 2.6 Hz, 1H), 8.08 (d, J = 2.0 Hz, 1H), 8.01 (d, J = 8.6 Hz, 1H), 7.84 (d, J = 1.6 Hz, 1H), 7.76 (d, J = 8.0 Hz, 1H), 7.63 (s, 1H), 7.57 (d, J = 7.4 Hz, 1H), 7.50 (d, J = 2.0 Hz, 1H), 6.69-6.55 (m, 1H), 5.91-5.70 (m, 1H), 5.30-5.26 (m, 1H), 5.92-5.74 (m, 1H), 5.38-5.21 (m, 1H), 4.55-4.26 (m, 1H), 4.19-4.11 (m, 2H), 4.00-3.64(m, 2H), 3.29-3.10 (m, 1H), 2.94-2.91 (m, 1H), 3.18-3.11 (m, 1H), 2.94-2.91 (m, 1H), 2.23-2.18 (m, 2H), 1.70-1.42 (m, 2H), 1.03-1.01 (m, 6H). |
| 543 | Observed mass (ESI): 619.35 [M + H]+. 1H NMR (300 MHz, DMSO-d6) δ (ppm): 8.32 (d, J = 8.3 Hz, 1H), 8.25 (d, J = 5.4 Hz, 1H), 8.14 (d, J = 4.0 Hz, 1H), 8.02 (dd, J = 4.8, 1.9 Hz, 1H), 7.61 (dd, J = 5.5, 1.5 Hz, 1H), 7.54 (d, J = 8.1 Hz, 1H), 7.36-7.43 (m, 3H), 7.26 (dd, J = 7.7, 1.9 Hz, 1H), 6.97 (s, 2H), 6.43 (dd, J = 7.7, 4.8 Hz, 1H), 5.34-5.61 (m, 1H), 4.41-4.58 (m, 1H), 4.12 - 4.29 (m, 2H), 3.89 (s, 3H), 3.19-3.25 (m, 2H), 3.13-3.19 (m, 1H), 3.01-3.11 (m, 2H), 2.80 - 2.97 (m, 1H), 1.81-2.10 (m, 3H), 1.23-1.52 (m, 2H), 0.65-0.81 (m, 4H). |
| 545 | Observed mass (ESI): 619.2 [M + H]+. 1H NMR (300 MHz, DMSO-d6) δ (ppm) 8.47 (d, J = 8.4 Hz, 1H), 8.31 (d, J = 8.4 Hz, 1H), 7.94-8.09 (m, 1H), 7.72-7.87 (m, 2H), 7.53 (d, J = 7.8 Hz, 1H), 7.39 (d, J = 8.5 Hz, 2H), 7.16-7.29 (m, 1H), 6.98 (s, 2H), 6.77-6.86 (m, 1H), 6.37-6.47 (m, 1H), 5.31-5.61 (m, 1H), 4.36-4.57 (m, 1H), 4.10-4.27 (m, 2H), 4.01 (s, 3H), 3.15-3.31 (m, 2H), 2.68-2.98 (m, 3H), 2.14-2.28 (m, 1H), 1.73-2.11 (m, 3H), 1.20-1. 49 (m, 2H), 0.58 - 0.82 (m, 4H). |
| 557 | Observed mass (ESI): 600.2 [M + H]+. 1H NMR (300 MHz, DMSO-d6) δ (ppm): 8.37-8.39 (m, 1H), 8.31-8.33 (m, 1H), 8.00-8.06 (m, 1H), 7.92-7.95 (m, 1H), 7.81-7.85 (m, 1H), 7.28-7.37 (m, 2H), 7.20-7.26 (m, 2H), 6.54-6.68 (m, 1H), 6.24-6.42 (m, 1H), 4.21-4.60 (m, 3H), 3.56 - 3.60 (m, 2H), 2.83-3.14 (m, 4H), 2.21-2.32 (m, 2H), 1.92-2.09 (m, 2H), 1.37-1.82 (m, 3H), 0.60-0.89 (m, 4H), 0.31-0.45 (m, 1H), 0.15-0.29 (m, 2H),-0.09-0.00 (m, 1H). |
| 560 | Observed mass (ESI): 668.25 [M + H]+. 1H NMR (300 MHz, DMSO-d6) δ ppm: 8.36 (d, J = 8.6 Hz, 1H), 8.29 (d, J = 2.7 Hz, 1H), 7.99 (dd, J = 4.9, 1.8 Hz, 1H), 7.79 (d, J = 8.6 Hz, 1H), 7.20 - 7.73 (m, 5H), 6.90 (s, 2H), 6.38-6.47 (m, 1H), 6.30-6.37 (m, 1H), 4.18-4.38 (m, 2H), 3.95 - 4.16 (m, 2H), 3.76-3.93 (m, 2H), 3.51-3.69 (m, 2H), 3.21-3.29 (m, 2H), 3.10-3.20 (m, 1H), 2.70-3.04 (m, 2H), 2.24-2.38 (m, 1H ), 1.70-1.98 (m, 4H), 0.60-0.75 (m, 4H). |

TABLE 5A-continued

| Characterization data of compounds prepared analogously to compound 88. | |
|---|---|
| Cpd ID | Characterization Data |
| 561 | Observed mass (ESI): 668.2 [M + H]+. 1H NMR (300 MHz, DMSO-d6) δ (ppm): 8.36 (d, J = 8.6 Hz, 1H), 8.30 (d, J = 2.7 Hz, 1H), 7.99 (dd, J = 4.8, 1.9 Hz, 1H), 7.79 (d, J = 8.6 Hz, 1H), 7.70 - 7.21 (m, 5H), 6.90 (s, 2H), 6.38-6.47 (m, 1H), 6.34 (d, J = 2.7 Hz, 1H), 4.57-4.71 (m, 1H), 4.42 - 4.55 (m, 1H), 4.26-4.38 (m, 1H), 4.03-4.24 (m, 2H), 3.57-3.70 (m, 1H), 3.39-3.52 (m, 2H), 3.21-3.25 (m, 1H), 3.08-3.19 (m, 1H), 2.74-3.01 (m, 3H), 2.28-2.38 (m, 1H), 1.91-2.03 (m, 1H), 1.72-1.88 (m, 2H), 1.60-1.70 (m, 1H), 0.60-0.76 (m, 4H). |
| 579 | Observed mass (ESI): 613.25 [M + H]+. 1H NMR (400 MHz, DMSO-d6) δ(ppm): 8.30-8.43 (m, 2H), 8.24 (d, J = 6.5 Hz, 1H), 7.91-8.06 (m, 2H), 7.80-7.83 (m, 1H), 7.50 (d, J = 7.8 Hz, 1H), 7.32-7.40 (m, 2H), 7.24 (dd, J = 7.7, 1.9 Hz, 1H), 7.16 (d, J = 6.5 Hz, 1H), 6.92 (s, 2H), 6.52 - 6.58 (m, 1H), 6.38-6.47 (m, 1H), 5.35-5.63 (m, 1H), 4.38-4.56 (m, 1H), 3.97-4.37 (m, 1H), 3.19-3.33 (m, 4H), 3.06-3.18 (m, 2H), 2.23-2.36 (m, 1H), 2.02-2.13 (m, 1H), 1.76-2.01 (m, 1H), 1.34-1.54 (m, 2H). |
| 580 | Observed mass (ESI): 623.4 [M + H]+. 1H NMR (300 MHz, DMSO-d6) δ (ppm): 8.99-9.20 (m, 1H), 8.21-8.46 (m, 2H), 7.84-8.08 (m, 3H), 7.70-8.84 (m, 1H), 7.40-7.56 (m, 1H), 7.26-7.36 (m, 1H), 7.11-7.26 (m, 2H), 6.43-6.60 (m, 1H), 6.34-6.43 (m, 1H), 4.20-4.40 (m, 2H), 3.54 - 3.57 (m, 1H), 3.01-3.18 (m, 2H), 2.84-3.00 (m, 2H), 2.66-2.84 (m, 1H), 2.41-2.45 (m, 1H), 1.70-2.11 (m, 3H), 1.33-1.37 (m, 2H). |
| 581 | Observed mass (ESI): 567.35 [M + H]+. 1H NMR (300 MHz, DMSO-d6) δ(ppm): 8.35-8.38 (m, 2H), 8.22 (d, J = 6.3 Hz, 1H), 7.94-8.03 (m, 2H), 7.81 (s, 1H), 7.49 (d, J = 8.1 Hz, 1H), 7.38 (s, 1H), 7.22-7.28 (m, 2H), 6.98 (s, 2H), 6.64 (d, J = 6.3 Hz, 1H), 6.53-6.54 (m, 1H), 6.45-6.48 (m, 1H), 4.22-4.31 (m, 3H), 3.93-3.95 (m, 1H), 3.79-3.84 (m, 2H), 2.95-3.05 (m, 1H), 2.80 - 2.82 (m, 1H), 2.49-2.51 (m, 1H), 1.72-1.80 (m, 1H). |
| 586 | Observed mass (ESI): 625.35 [M + H]+. 1H NMR (300 MHz, DMSO-d6) δ (ppm): 8.32-8.40 (m, 2H), 8.08 (s, 1H), 7.92-8.04 (m, 2H), 7.78-7.84 (m, 1H), 7.48 (d, J = 8.0 Hz, 1H), 7.34 (d, J = 1.9 Hz, 1H), 7.18-7.29 (m, 2H), 6.94 (s, 2H), 6.52-6.58 (m, 1H), 6.43 (dd, J = 7.7, 4.8 Hz, 1H), 4.32-4.50 (m, 3H), 3.93 (s, 3H), 3.18-3.25 (m, 2H), 2.90-3.04 (m, 2H), 2.73-2.84 (m, 1H), 2.39-2.46 (m, 1H), 2.00-2.10 (m, 1H), 1.91-1.99 (m, 1H), 1.76-1.90 (m, 2H), 1.32-1.47 (m, 2H). |
| 589 | Observed mass (ESI): 615.3 [M + H]+. 1H NMR (300 MHz, DMSO-d6) δ 8.24 (d, J = 8.6 Hz, 1H), 8.10 (d, J = 2.7 Hz, 1H), 8.01-7.93 (m, 1H), 7.75 (d, J = 8.6 Hz, 1H), 7.46 (d, J = 7.8 Hz, 1H), 7.39 (d, J = 2.1 Hz, 1H), 7.29 (d, J = 1.8 Hz, 1H), 7.25-7.14 (m, 2H), 6.94 (s, 2H), 6.44-6.35 (m, 1H), 6.05 (d, J = 2.7 Hz, 1H), 5.64 (d, J = 2.1 Hz, 1H), 4.36 (s, 1H), 3.63 (s, 5H), 2.87 (s, 7H), 2.83-2.71 (m, 2H), 2.71-2.57 (m, 2H), 2.43 (d, J = 8.1 Hz, 1H), 1.97 (d, J = 12.0 Hz, 1H), 1.90-1.68 (m, 2H), 1.48-1.30 (m, 2H). |
| 592 | Observed mass (ESI): 596.2 [M + H]+. 1H NMR (300 MHz, DMSO-d6) δ (ppm): 8.70 (s, 1H), 8.31-8.40 (m, 2H), 7.92-8.04 (m, 2H), 7.81 (d, J = 1.6 Hz, 1H), 7.48 (d, J = 8.0 Hz, 1H), 7.34 (s, 1H), 7.19-7.30 (m, 2H), 6.94 (s, 2H), 6.52-6.58 (m, 1H), 6.38-6.46 (m, 1H), 4.29-4.51 (m, 3H), 3.26-3.31 (m, 2H), 2.91-3.09 (m, 2H), 2.73-2.84 (m, 1H), 2.40-2.45 (m, 1H), 1.91-2.08 (m, 2H), 1.75-1.84 (m, 1H), 1.30- 1.45 (m, 2H). |
| 596 | Observed mass (ESI): 627.3 [M + H]+. 1H NMR (300 MHz, DMSO-d6) δ 8.26 (d, J = 8.6 Hz, 1H), 8.10 (d, J = 2.7 Hz, 1H), 8.03-7.94 (m, 1H), 7.73 (d, J = 8.6 Hz, 1H), 7.50 (d, J = 8.1 Hz, 1H), 7.41 (d, J = 2.2 Hz, 1H), 7.32 (s, 1H), 7.28-7.16 (m, 2H), 6.94 (s, 2H), 6.45-6.37 (m, 1H), 5.86 (d, J = 2.7 Hz, 1H), 5.66 (d, J = 2.3 Hz, 1H), 4.48-4.32 (m, 1H), 4.16-4.07 (m, 1H), 3.93-3.81 (m, 4H), 3.69-3.55 (m, 5H), 3.17 (d, J = 5.1 Hz, 4H), 2.99-2.90 (m, 1H), 2.86-2.77 (m, 1H), 2.74-2.64 (m, 1H), 2.40-2.29 (m, 2H), 2.04-1.93 (m, 1H), 1.92-1.79 (m, 1H), 1.51-1.35 (m, 1H). |
| 602 | Observed mass (ESI): 635.45 [M + H]+. 1H NMR (300 MHz, DMSO-d6) δ (ppm): 8.32- 8.42 (m, 2H), 8.02 (dd, J = 4.9, 1.9, 1H), 7.96 (d, J = 8.6, 1H), 7.82 (d, J = 1.6 Hz, 1H), 7.57 (d, J = 8.0 Hz, 1H), 7.41 (s, 1H), 7.21- 7.33 (m, 2H), 7.12 (s, 1H), 6.92 (s, 2H), 6.56 (dd, J = 2.6, 1.7 Hz, 1H), 6.44 (dd, J = 7.6, 4.8 Hz, 1H), 4.26- 4.59 (m, 3H), 3.00- 3.22 (m, 4H), 2.78- 2.92 (m, 1H), 2.40 - 2.45 (m, 1H),2.05- 2.16 (m, 1H), 1.84- 2.05 (m, 3H), 1.36- 1.45 (m, 2H), 0.94- 1.07 (m, 4H). (formic acid salt) |
| 603 | Observed mass (ESI): 635.3 [M + H]+. 1H NMR (300 MHz, DMSO-d6) δ(ppm): 8.35-8.38 (m, 2H), 8.00-8.02 (m, 1H), 7.94-7.97 (m, 1H), 7.81 (s, 1H), 7.48-7.51 (m, 1H), 7.33 (s, 1H), 7.23-7.25 (m, 2H), 6.56 (s, 1H), 6.42-6.46 (m, 1H), 4.32-4.37 (m, 3H), 3.23-3.30 (m, 2H), 3.07 - 3.13 (m, 2H), 2.95-3.01 (m, 2H), 2.81-2.93 (m, 3H), 2.47-2.53 (m, 1H), 1.97-2.06 (m, 4H), 1.79-1.91 (m, 1H), 1.36-1.47 (m, 2H). |

Example 70: (S)-3-(5-(2-(2-aminopyridin-3-yl)-5-(1H-pyrazol-1-yl)-3H-imidazo[4,5-b]pyridin-3-yl)-2,3-dihydro-1H-inden-1-yl)-7-methylpyrido[4,3-d]pyrimidin-4(3H)-one (Compound 91)

Compound 91

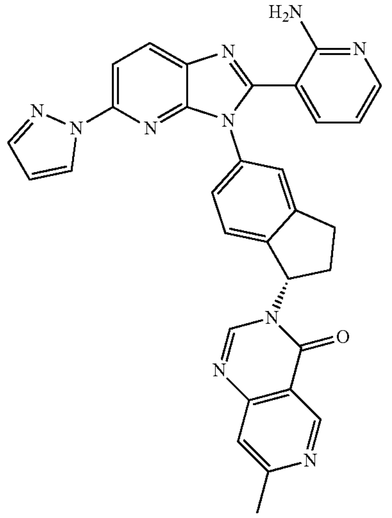

Synthetic Route:

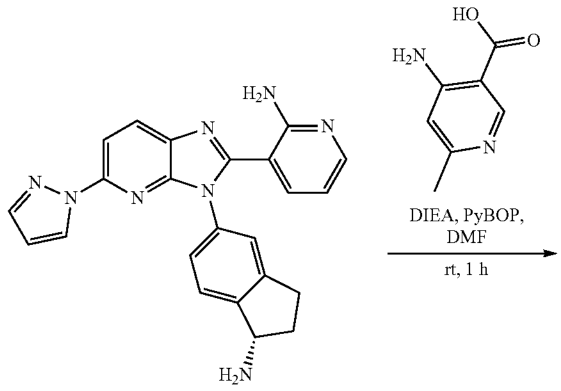

Compound 2

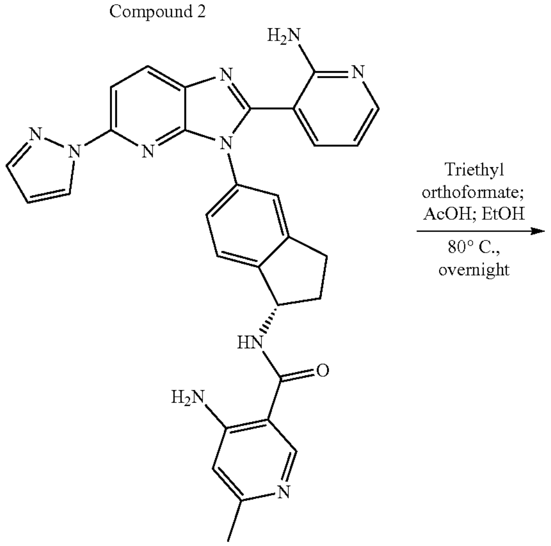

-continued

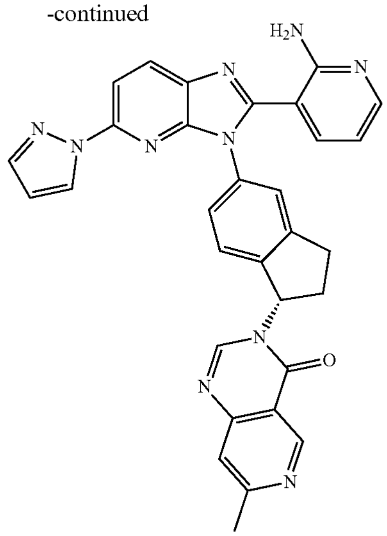

Compound 91

Step 1: Synthesis of (S)-4-amino-N-(5-(2-(2-amino-pyridin-3-yl)-5-(1H-pyrazol-1-yl)-3H-imidazo[4,5-b]pyridin-3-yl)-2,3-dihydro-1H-inden-1-yl)-6-methylnicotinamide To a solution of (S)-3-(3-(1-amino-2,3-dihydro-1H-inden-5-yl)-5-(1H-pyrazol-1-yl)-3H-imidazo[4,5-b]pyridin-2-yl)pyridin-2-amine (Compound 2) (100 mg, 0.245 mmol), 4-amino-6-methylpyridine-3-carboxylic acid (37.3 mg, 0.245 mmol) and N,N-diisopropylethylamine (94.9 mg, 0.735 mmol) in DMF (3 mL) was added PyBOP (127 mg, 0.245 mmol) at 0° C. The resulting mixture was stirred at room temperature for 1 h. The reaction was quenched by the addition of $H_2O$ (20 ml). The precipitated solids were collected by filtration and washed with $H_2O$ (3×20 ml). The solids were purified by reverse phase column chromatography on C18 silica gel using a gradient of acetonitrile in water (+0.05% TFA) to afford (S)-4-amino-N-(5-(2-(2-aminopyridin-3-yl)-5-(1H-pyrazol-1-yl)-3H-imidazo[4,5-b]pyridin-3-yl)-2,3-dihydro-1H-inden-1-yl)-6-methylnicotinamide (100 mg, 74% yield) as an off-white solid. MS (ESI) calcd. For $C_{30}H_{26}N_{10}O$: 542.23 m/z, found: 543.20 $[M+H]^+$.

Step 2: Synthesis of (S)-3-(5-(2-(2-aminopyridin-3-yl)-5-(1H-pyrazol-1-yl)-3H-imidazo[4,5-b]pyridin-3-yl)-2,3-dihydro-1H-inden-1-yl)-7-methylpyrido[4,3-d]pyrimidin-4(3H)-one (Compound 91)

A solution of (S)-4-amino-N-(5-(2-(2-aminopyridin-3-yl)-5-(1H-pyrazol-1-yl)-3H-imidazo[4,5-b]pyridin-3-yl)-2,3-dihydro-1H-inden-1-yl)-6-methylnicotinamide (80 mg, 0.15 mmol), triethyl orthoformate (0.4 mL) and AcOH (0.2 mL) in EtOH (2 mL) was maintained under nitrogen and stirred overnight at 80° C. The solvent was evaporated under vacuum. The residue was purified by Prep-HPLC on a XBridge Prep OBD C18 Column using a gradient of acetonitrile in water (+0.05% TFA) to afford (S)-3-(5-(2-(2-aminopyridin-3-yl)-5-(1H-pyrazol-1-yl)-3H-imidazo[4,5-b]pyridin-3-yl)-2,3-dihydro-1H-inden-1-yl)-7-methylpyrido[4,3-d]pyrimidin-4(3H)-one (TFA salt) (12.1 mg, 15% yield) as an off-white solid. MS (ESI) calcd. for $C_{31}H_{24}N_{10}O$, 552.21 m/z, found 553.20 $[M+H]^+$. $^1H$ NMR (300 MHz, DMSO-$d_6$) δ (ppm): 9.26-9.32 (m, 1H), 8.35-8.47 (m, 3H), 7.96-8.08 (m, 2H), 7.81-7.85 (m, 1H), 7.70-7.78 (m, 1H), 7.56-7.60 (m, 2H), 7.25-7.45 (m, 2H), 6.80-6.88 (m, 1H), 6.56-6.61 (m, 1H), 6.25-6.34 (m, 1H), 3.23-3.31 (m, 1H), 2.98-3.11 (m, 1H), 2.69-2.83 (m, 1H), 2.63 (s, 3H), 2.36-2.45 (m, 1H).

Example 71: (S)—N-(5-(2-(2-aminopyridin-3-yl)-7-methoxy-5-(1H-pyrazol-1-yl)-3H-imidazo[4,5-b]pyridin-3-yl)-2,3-dihydro-1H-inden-1-yl)-6-(difluoromethyl)nicotinamide (Compound 122); (S)—N-(5-(2-(2-aminopyridin-3-yl)-7-cyano-5-(1H-pyrazol-1-yl)-3H-imidazo[4,5-b]pyridin-3-yl)-2,3-dihydro-1H-inden-1-yl)-6-(difluoromethyl)nicotinamide (Compound 123); (S)—N-(5-(2-(2-aminopyridin-3-yl)-7-fluoro-5-(1H-pyrazol-1-yl)-3H-imidazo[4,5-b]pyridin-3-yl)-2,3-dihydro-1H-inden-1-yl)-6-(difluoromethyl)nicotinamide (Compound 165); and (S)—N-(5-(2-(2-aminopyridin-3-yl)-7-(difluoromethyl)-5-(1H-pyrazol-1-yl)-3H-imidazo[4,5-b]pyridin-3-yl)-2,3-dihydro-1H-inden-1-yl)-6-(difluoromethyl)nicotinamide Compound 122

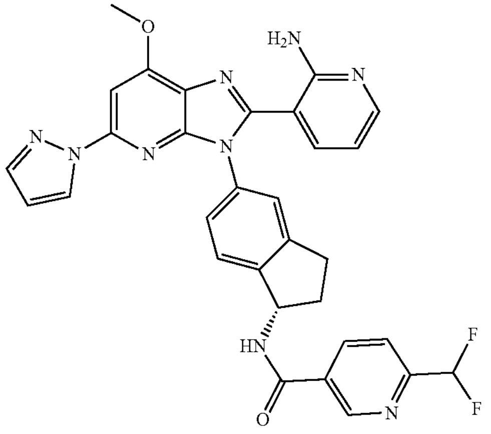

Synthetic Route:

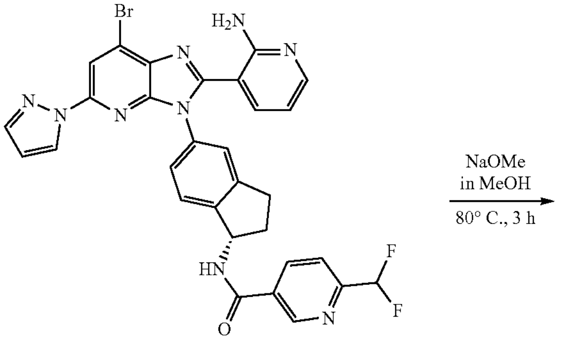

Intermediate 122-2

-continued

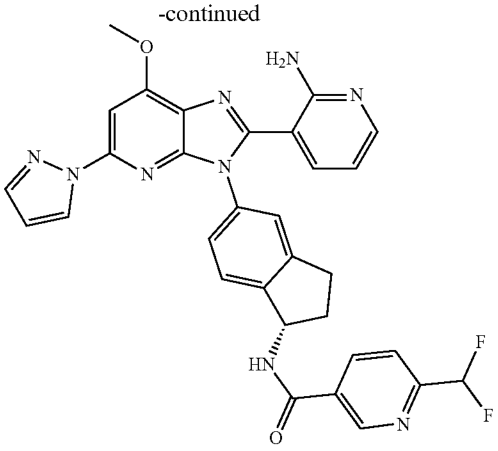

Compound 122

Step 1: Synthesis of (S)—N-(5-(2-(2-aminopyridin-3-yl)-7-methoxy-5-(1H-pyrazol-1-yl)-3H-imidazo[4,5-b]pyridin-3-yl)-2,3-dihydro-1H-inden-1-yl)-6-(difluoromethyl)nicotinamide (Compound 122)

To a solution of (S)—N-(5-(2-(2-aminopyridin-3-yl)-7-bromo-5-(1H-pyrazol-1-yl)-3H-imidazo[4,5-b]pyridin-3-yl)-2,3-dihydro-1H-inden-1-yl)-6-(difluoromethyl)nicotinamide (Intermediate 122-2) (100 mg, 0.156 mmol) in MeOH (5 mL) was added $CH_3ONa$ (42.0 mg, 0.780 mmol) and the resulting mixture was stirred for 3 h at 80° C. The reaction was quenched by the addition of $H_2O$ (5 ml) at room temperature. The resulting mixture was extracted with ethyl acetate (3x30 ml). The combined organic layers were dried over anhydrous $Na_2SO_4$. After filtration, the filtrate was concentrated under reduced pressure. The residue was purified by reverse-phase flash chromatography on C18 silica gel using a gradient of acetonitrile in water (+0.05 mmol/L formic acid) to afford (S)—N-(5-(2-(2-aminopyridin-3-yl)-7-methoxy-5-(1H-pyrazol-1-yl)-3H-imidazo[4,5-b]pyridin-3-yl)-2,3-dihydro-1H-inden-1-yl)-6-(difluoromethyl)nicotinamide (Compound 122) (5 mg, 5% yield) as an off-white solid. MS (ESI) calcd. for $C_{31}H_{25}F_2N_9O_2$, 593.21 m/z, found 594.10 $[M+H]^+$. $^1H$ NMR (400 MHz, DMSO-$d_6$) δ (ppm): 9.13 (s, 1H), 8.42-8.50 (m, 1H), 8.32-8.40 (m, 1H), 7.95-8.05 (m, 1H), 7.80-7.90 (m, 2H), 7.50 (s, 1H), 7.40-7.45 (m, 1H), 7.30-7.40 (m, 1H), 7.22-7.30 (m, 2H), 6.85-7.20 (m, 1H), 6.55-6.60 (m, 1H), 6.40-6.52 (m, 1H), 5.60-5.70 (m, 1H), 4.18 (s, 3H), 3.00-3.15 (m, 1H), 2.85-3.00 (m, 1H), 2.58-2.63 (m, 1H), 2.00-2.20 (m, 1H). $^{19}F$ NMR (300 MHz, DMSO-$d_6$) δ (ppm): −116.05. (formic acid salt)

(S)—N-(5-(2-(2-aminopyridin-3-yl)-7-cyano-5-(1H-pyrazol-1-yl)-3H-imidazo[4,5-b]pyridin-3-yl)-2,3-dihydro-1H-inden-1-yl)-6-(difluoromethyl)nicotinamide (Compound 123)

Compound 123

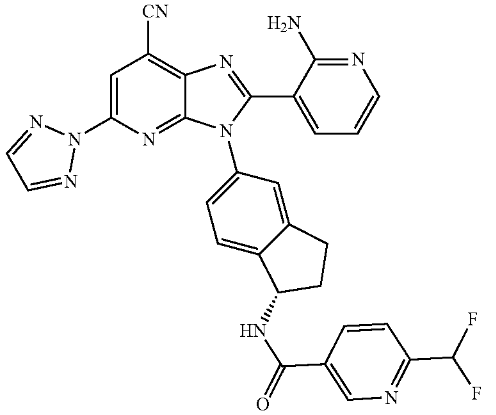

Synthetic Route:

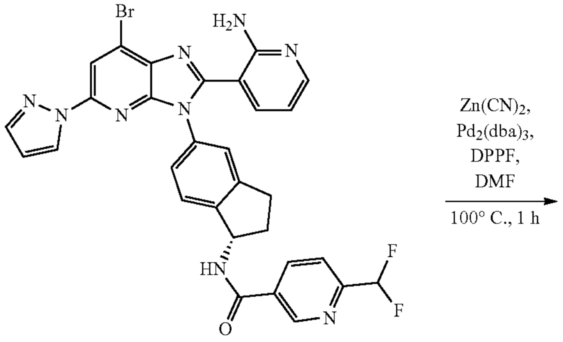

Intermediate 122-2

-continued

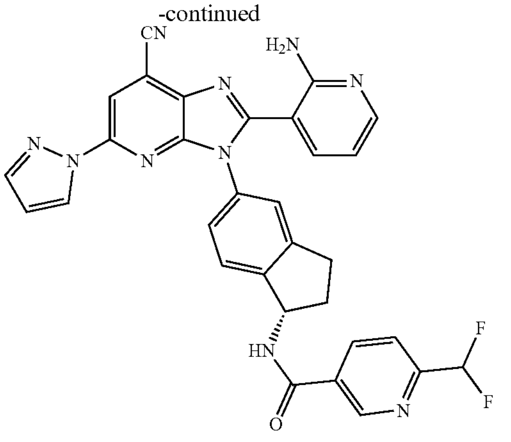

Compound 123

Step 1: Synthesis of (S)—N-(5-(2-(2-aminopyridin-3-yl)-7-cyano-5-(1H-pyrazol-1-yl)-3H-imidazo[4,5-b]pyridin-3-yl)-2,3-dihydro-1H-inden-1-yl)-6-(difluoromethyl)nicotinamide (Example 123)

A mixture of (S)—N-(5-(2-(2-aminopyridin-3-yl)-7-bromo-5-(1H-pyrazol-1-yl)-3H-imidazo[4,5-b]pyridin-3-yl)-2,3-dihydro-1H-inden-1-yl)-6-(difluoromethyl)nicotinamide (Intermediate 122-2) (80 mg, 0.125 mmol), $Zn(CN)_2$ (29.2 mg, 0.250 mmol), DPPF (14 mg, 0.025 mmol) and $Pd_2(dba)_3$ (23 mg, 0.025 mmol) in DMF (2 mL) was stirred for 1 h at 100° C. The resulting mixture was diluted with water (30 mL). The mixture was extracted with ethyl acetate (3×50 mL) and dried over anhydrous $Na_2SO_4$. After filtration, the filtrate was concentrated under reduced pressure. The residue was purified by Prep-HPLC on a XBridge Prep Shield RP OBD C18 Column using a gradient of acetonitrile in water to afford (S)—N-(5-(2-(2-aminopyridin-3-yl)-7-cyano-5-(1H-pyrazol-1-yl)-3H-imidazo[4,5-b]pyridin-3-yl)-2,3-dihydro-1H-inden-1-yl)-6-(difluoromethyl)nicotinamide (21.2 mg, 28% yield) as a yellow solid. MS (ESI) calcd. for $C_{31}H_{22}F_2N_{10}O$, 588.19 m/z, found 589.30 $[M+H]^+$. $^1H$ NMR (300 MHz, DMSO-$d_6$) δ (ppm): 9.28-9.34 (m, 1H), 9.12-9.21 (m, 1H), 8.43-8.52 (m, 1H), 8.33-8.42 (m, 1H), 8.28-8.32 (m, 1H), 8.05-8.11 (m, 1H), 7.82-7.93 (m, 2H), 7.33-7.54 (m, 4H), 6.88-7.22 (m, 1H), 6.61-6.69 (m, 1H), 6.50-6.58 (m, 1H), 5.64-5.73 (m, 1H), 2.91-3.12 (m, 2H), 2.57-2.63 (m, 1H), 2.08-2.20 (m, 1H).

The following compounds were prepared analogously to the synthetic preparation of Compound 123.

TABLE 5B

Characterization data of compounds prepared analogously to compound 325.

| Cpd ID | Characterization Data |
|---|---|
| 547 | Observed mass (ESI): 554.2 [M + H]+. 1H NMR (400 MHz, DMSO-d6) δ (ppm): 8.89-8.94 (m, 1H), 8.42-8.45 (m, 1H), 8.12-8.18 (m, 3H), 8.02-8.05 (m, 1H), 7.37-7.44 (m, 3H), 7.30-7.37 (m, 2H), 6.46-6.54 (m, 1H), 5.56-5.67 (m, 1H), 2.96-3.07 (m, 1H), 2.82-2.96 (m, 1H), 2.54-2.59 (m, 1H), 2.51 (s, 3H), 2.00-2.13 (m, 1H). |
| 548 | Observed mass (ESI): 590.2 [M + H]+. 1H NMR (400 MHz, DMSO-d6) δ (ppm): 9.11-9.16 (m, 1H), 8.42-8.47 (m, 2H), 8.17 (s, 2H), 8.01-8.07 (m, 1H), 7.80-7.85 (m, 1H), 7.41-7.46 (m, 2H), 7.32-7.41 (m, 2H), 6.85-7.18 (m, 1H), 6.47-6.54 (m, 1H), 5.59-5.69 (m, 1H), 2.97-3.08 (m, 1H), 2.83-2.97 (m, 1H), 2.55-2.62 (m, 1H), 2.01-2.14 (m, 1H). |

(S)—N-(5-(2-(2-aminopyridin-3-yl)-7-fluoro-5-(1H-pyrazol-1-yl)-3H-imidazo[4,5-b]pyridin-3-yl)-2,3-dihydro-1H-inden-1-yl)-6-(difluoromethyl)nicotinamide (Compound 165)

Compound 165

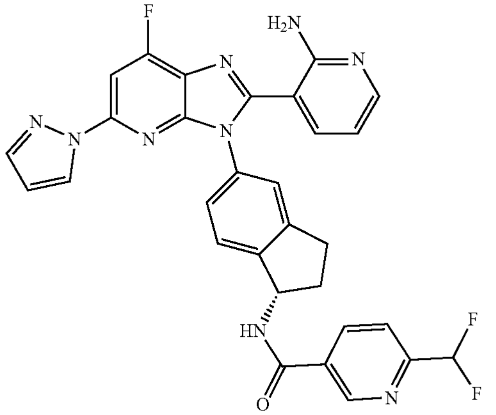

Synthetic Route:

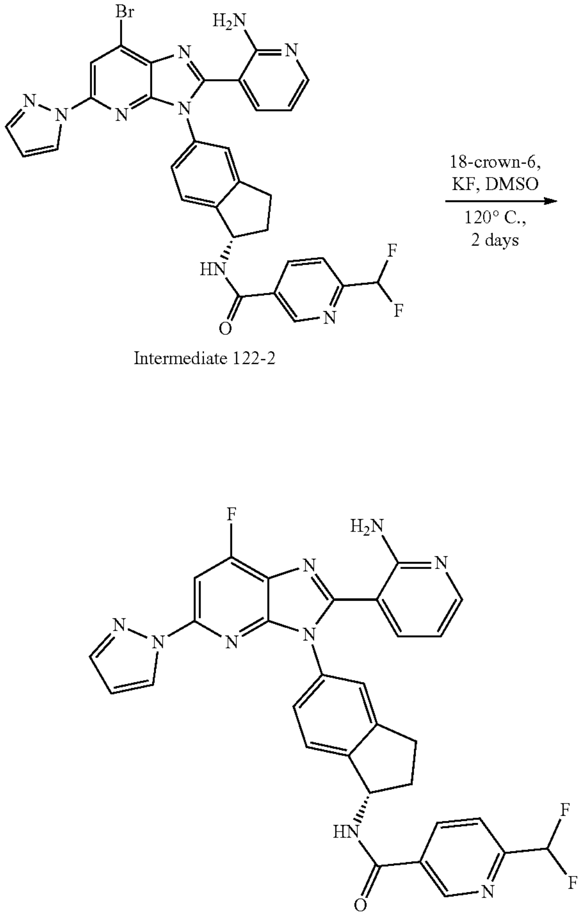

Intermediate 122-2

Compound 165

Step 1: Synthesis of (S)—N-(5-(2-(2-aminopyridin-3-yl)-7-fluoro-5-(1H-pyrazol-1-yl)-3H-imidazo[4,5-b]pyridin-3-yl)-2,3-dihydro-1H-inden-1-yl)-6-(difluoromethyl)nicotinamide A solution of (S)—N-(5-(2-(2-aminopyridin-3-yl)-7-bromo-5-(1H-pyrazol-1-yl)-3H-imidazo[4,5-b]pyridin-3-yl)-2,3-dihydro-1H-inden-1-yl)-6-(difluoromethyl)nicotinamide (Intermediate 122-2) (150 mg, 0.233 mmol) in DMSO (3 mL) was treated with 18-crown-6 (61.7 mg, 0.233 mmol) and KF (135.6 mg, 2.330 mmol) at room temperature. The resulting mixture was stirred for 2 days at 120° C. under $N_2$ atmosphere. The residue was purified by reverse-phase flash chromatography on C18 silica gel using a gradient of acetonitrile in water (+0.05% $NH_4HCO_3$). The product was further purified by Prep-HPLC on a Xselect CSH Prep Fluoro-Phenyl Column using a gradient of acetonitrile in water (+10 mmol/L ammonium bicarbonate) to afford (S)—N-(5-(2-(2-aminopyridin-3-yl)-7-fluoro-5-(1H-pyrazol-1-yl)-3H-imidazo[4,5-b]pyridin-3-yl)-2,3-dihydro-1H-inden-1-yl)-6-(difluoromethyl)nicotinamide (Compound 165) (11.4 mg, 8% yield) as an off-white solid. MS (ESI) calcd. for $C_{30}H_{22}F_3N_9O$, 581.19 m/z, found 582.15 $[M+H]^+$. $^1H$ NMR (300 MHz, DMSO-$d_6$) δ (ppm): 9.14 (s, 1H), 8.40-8.50 (m, 1H), 8.32-8.40 (m, 1H), 8.00-8.10 (m, 1H), 7.82-7.85 (m, 2H), 7.75-7.80 (m, 1H), 7.37-7.45 (m, 2H), 7.30-7.37 (m, 2H), 6.80-7.20 (m, 1H), 6.55-6.60 (m, 1H), 6.45-6.52 (m, 1H), 5.60-5.70 (m, 1H), 2.85-3.10 (m, 2H), 2.58-2.63 (m, 1H), 2.00-2.18 (m, 1H). $^{19}F$ NMR (282 MHz, DMSO-$d_6$) δ (ppm): −114.41, −116.05.

(S)—N-(5-(2-(2-aminopyridin-3-yl)-7-(difluoromethyl)-5-(1H-pyrazol-1-yl)-3H-imidazo[4,5-b]pyridin-3-yl)-2,3-dihydro-1H-inden-1-yl)-6-(difluoromethyl)nicotinamide (Compound 177)

Compound 177

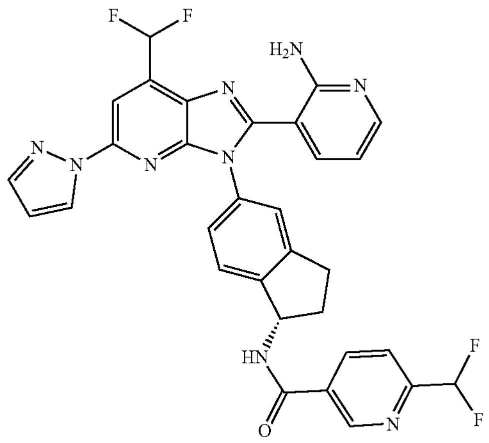

Synthetic Route:

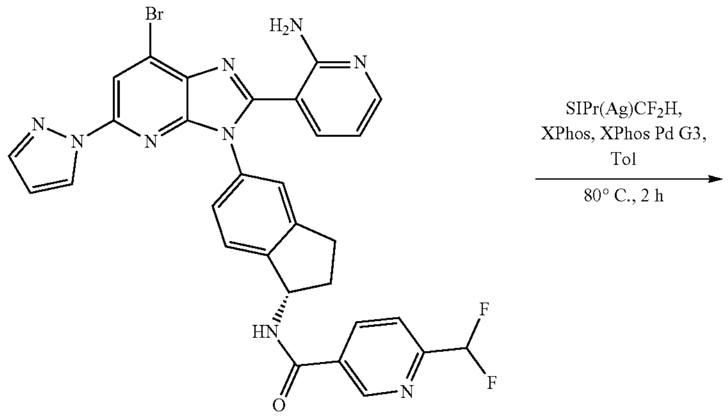

Intermediate 122-2

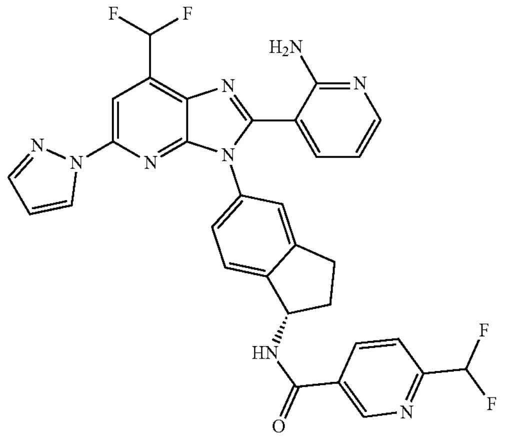

Compound 177

Step 1: Synthesis of (S)—N-(5-(2-(2-aminopyridin-3-yl)-7-(difluoromethyl)-5-(1H-pyrazol-1-yl)-3H-imidazo[4,5-b]pyridin-3-yl)-2,3-dihydro-1H-inden-1-yl)-6-(difluoromethyl)nicotinamide (Compound 177)

A mixture of (S)—N-(5-(2-(2-aminopyridin-3-yl)-7-bromo-5-(1H-pyrazol-1-yl)-3H-imidazo[4,5-b]pyridin-3-yl)-2,3-dihydro-1H-inden-1-yl)-6-(difluoromethyl)nicotinamide (Intermediate 122-2) (100 mg, 0.156 mmol, 1 equiv), XPhos (7.4 mg, 0.016 mmol, 0.1 equiv), XPhos Pd $G_3$ (13 mg, 0.016 mmol, 0.1 equiv) and {1,3-bis[2,6-bis(propan-2-yl)phenyl]imidazolidin-2-ylidene}(difluoromethyl)silver (120 mg, 0.218 mmol, 1.4 equiv) in toluene (2 mL) was stirred for 2 h at 80° C. under nitrogen atmosphere. The resulting mixture was diluted with water (20 mL) at room temperature. The resulting mixture was extracted with ethyl acetate (3×50 mL) and dried over anhydrous $Na_2SO_4$. After filtration, the filtrate was concentrated under reduced pressure. The residue was purified by reverse-phase flash chromatography on C18 silica gel using a gradient of acetonitrile in water (+0.05% $NH_4HCO_3$). The product was further purified by Prep-HPLC on a XSelect CSH Fluoro Phenyl column using a gradient of acetonitrile in water (+0.1% formic acid) to afford (S)—N-(5-(2-(2-aminopyridin-3-yl)-7-(difluoromethyl)-5-(1H-pyrazol-1-yl)-3H-imidazo[4,5-b]pyridin-3-yl)-2,3-dihydro-1H-inden-1-yl)-6-(difluoromethyl)nicotinamide (Compound 177, formic acid salt) (5.1 mg, 5% yield) as an off-white solid. MS (ESI) calcd. for $C_{31}H_{23}F_4N_9O$, 613.20 m/z, found 614.25 $[M+H]^+$. $^1H$ NMR (300 MHz, DMSO-$d_6$+$D_2O$) δ (ppm): 9.13-9.20 (m, 1H), 8.39-8.52 (m, 2H), 8.06-8.15 (m, 2H), 7.85-7.96 (m, 2H), 7.67-7.74 (m, 1H), 7.41-7.54 (m, 2H), 7.31-7.40 (m, 2H), 6.84-7.19 (m, 1H), 6.59-6.70 (m, 1H), 6.49-6.57 (m, 1H), 5.67-5.78 (m, 1H), 4.38-4.52 (m, 3H), 2.89-3.13 (m, 2H), 2.61-2.68 (m, 1H), 2.09-2.20 (m, 1H); $^{19}F$ NMR (282 MHz, DMSO-$d_6$+$D_2O$) δ (ppm): −115.49, −116.04.

Intermediate 122-2: (S)—N-(5-(2-(2-aminopyridin-3-yl)-7-bromo-5-(1H-pyrazol-1-yl)-3H-imidazo[4,5-b]pyridin-3-yl)-2,3-dihydro-1H-inden-1-yl)-6-(difluoromethyl)nicotinamide Intermediate 122-2

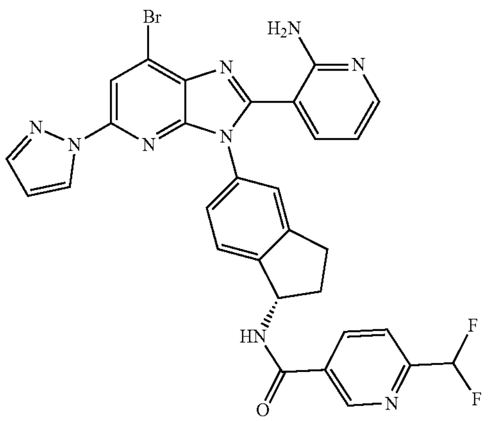

Intermediate 122-2 was prepared in a manner analogous to Compound 3 using Intermediate 122-1 in place of Compound 2, 6-(difluoromethyl)nicotinic acid in place of 3,4-difluoro-5-anisic acid and PyBOP in place of HATU. MS (ESI) calcd. for $C_{30}H_{22}BrF_2N_9O$: 641.11 m/z, found: 642.15 [M+H]*. (formic acid salt)

Intermediate 122-1: (S)-3-(3-(1-amino-2,3-dihydro-1H-inden-5-yl)-7-bromo-5-(1H-pyrazol-1-yl)-3H-imidazo[4,5-b]pyridin-2-yl)pyridin-2-amine Intermediate 122-1

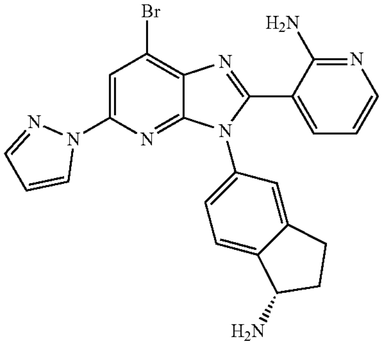

Intermediate 122-1 was prepared in a manner analogous to Intermediate 122-0 using copper (I) bromide in place of copper (I) chloride. MS (ESI) calculated for MS (ESI) calculated for $C_{23}H_{19}BrN_8$: 486.09, 488.09, found 487.11, 489.15 $[M+H]^+$.

Intermediate 122-0: (S)-3-(3-(1-amino-2,3-dihydro-1H-inden-5-yl)-7-chloro-5-(1H-pyrazol-1-yl)-3H-imidazo[4,5-b]pyridin-2-yl)pyridin-2-amine Intermediate 122-0

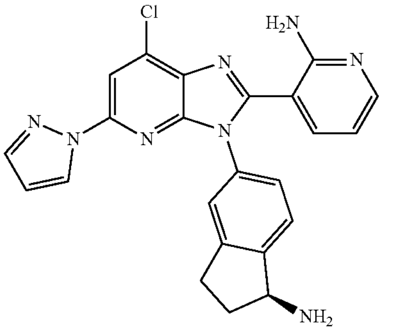

Synthetic Route:

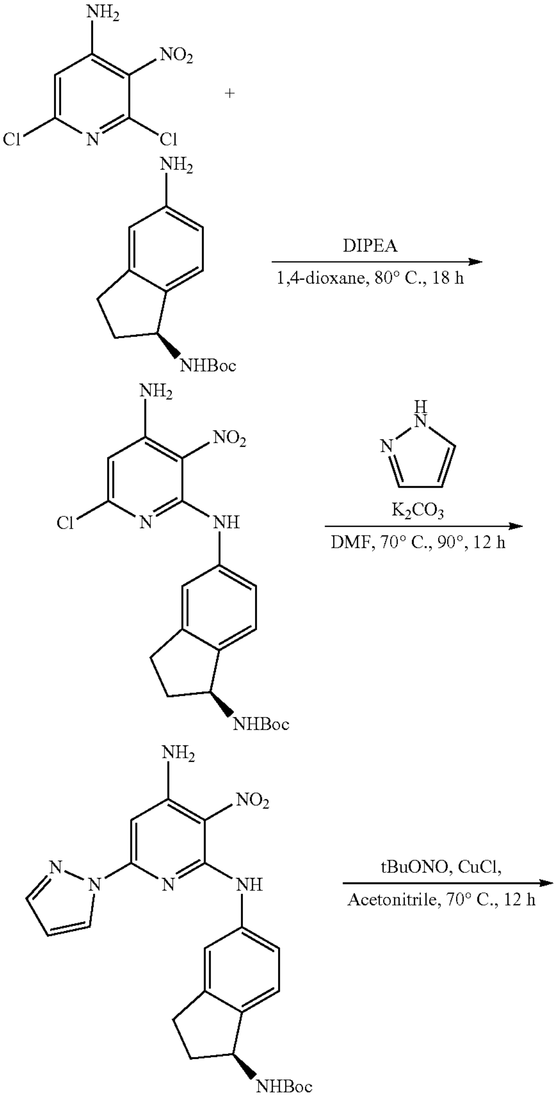

-continued

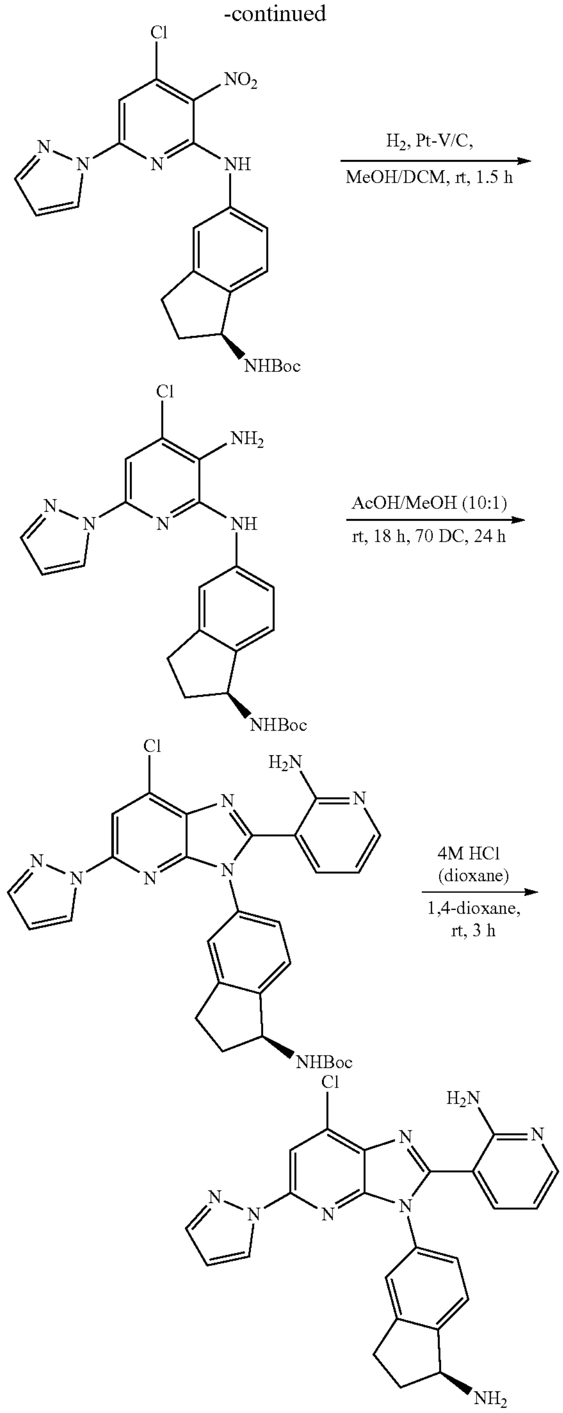

Intermediate 122-0

Step 1: Synthesis of (S)-tert-butyl (5-((4-amino-6-chloro-3-nitropyridin-2-yl)amino)-2,3-dihydro-1H-inden-1-yl)carbamate To a solution of 2,6-dichloro-3-nitropyridin-4-amine (3.51 g, 16.4 mmol, 1.05 equiv) and (S)-tert-butyl (5-amino-2,3-dihydro-1H-inden-1-yl)carbamate (4.26 mg, 15.6 mmol, 1 equiv) in 1,4-dioxane (35 mL) was added N,N-diisopropylethylamine (8.23 mL, 46.8 mmol, 3 equiv) and the mixture was stirred at 80° C. for 18 h. The reaction mixture was concentrated in vacuo and the residue was purified by silica gel column chromatography (0-15% methanol in dichloromethane) to obtain (S)-tert-butyl (5-((4-amino-6-chloro-3-nitropyridin-2-yl)amino)-2,3-dihydro-1H-inden-1-yl)carbamate (6.25 g, 95%) as an orange solid. MS (ESI) calculated for $C_{19}H_{22}ClN_5O_4$: 419.14 found 420.20 $[M+H]^+$.

Step 2: Synthesis of (S)-tert-butyl (5-((4-amino-3-nitro-6-(1H-pyrazol-1-yl)pyridin-2-yl)amino)-2,3-dihydro-1H-inden-1-yl)carbamate To a solution of (S)-tert-butyl (5-((4-amino-6-chloro-3-nitropyridin-2-yl)amino)-2,3-dihydro-1H-inden-1-yl)carbamate (4.88 g, 11.6 mmol, 1 equiv) and pyrazole (1.67 g, 23.2 mmol, 2 equiv) in N,N-dimethylformamide (23 mL) was added potassium carbonate (4.92 g, 34.9 mmol, 3 equiv) and the resulting suspension was stirred at 70° C. for 18 h and then at 90° C. for 12 h. The reaction was allowed to cool to room temperature and was diluted with diethyl ether (20 mL) followed by water (50 mL) dropwise, during which an orange solid precipitated. The solid was filtered through a Buchner funnel. The crude solid was purified by silica gel column chromatography (5-15% methanol in dichloromethane) to obtain (S)-tert-butyl (5-((4-amino-3-nitro-6-(1H-pyrazol-1-yl)pyridin-2-yl)amino)-2,3-dihydro-1H-inden-1-yl)carbamate (3.18 g, 60%) as an orange solid. MS (ESI) calculated for $C_{22}H_{25}N_7O_4$: 451.20, found 452.26 $[M+H]^+$.

Step 3: Synthesis of (S)-tert-butyl (5-((4-chloro-3-nitro-6-(1H-pyrazol-1-yl)pyridin-2-yl)amino)-2,3-dihydro-1H-inden-1-yl)carbamate To a solution of (S)-tert-butyl (5-((4-amino-3-nitro-6-(1H-pyrazol-1-yl)pyridin-2-yl)amino)-2,3-dihydro-1H-inden-1-yl)carbamate (680 mg, 1.11 mmol, 1 equiv) in acetonitrile (4.1 mL) was added tert-butyl nitrite (172 mg, 1.67 mmol, 1.5 equiv) followed by copper (I) chloride (171 mg, 1.67 mmol, 1.5 equiv) and the resulting mixture was stirred at 70° C. for 12 h. The reaction mixture was concentrated and purified by silica gel column chromatography (15-20% ethyl acetate in heptanes) to obtain (S)-tert-butyl (5-((4-chloro-3-nitro-6-(1H-pyrazol-1-yl)pyridin-2-yl)amino)-2,3-dihydro-1H-inden-1-yl)carbamate (177 mg, 34%) as a yellow solid. MS (ESI) calculated for $C_{22}H_{23}ClN_6O_4$: 470.15, found 471.16.

Step 4: Synthesis of (S)-tert-butyl (5-((3-amino-4-chloro-6-(1H-pyrazol-1-yl)pyridin-2-yl)amino)-2,3-dihydro-1H-inden-1-yl)carbamate To a solution of (S)-tert-butyl (5-((4-chloro-3-nitro-6-(1H-pyrazol-1-yl)pyridin-2-yl)amino)-2,3-dihydro-1H-inden-1-yl)carbamate (87 mg, 0.18 mmol, 1 equiv) in methanol (1.8 mL) and dichloromethane (1.8 mL) was added platinum on carbon (contains 1 wt % platinum, 2 wt % vanadium) (20 mg, 1.02 μmol, 0.5 mol %) and the mixture was stirred at room temperature for 1.5 h under hydrogen atmosphere. The reaction mixture was filtered through celite washing with dichloromethane (5 mL). The filtrate was concentrated in vacuo to obtain (S)-tert-butyl (5-((3-amino-4-chloro-6-(1H-pyrazol-1-yl)pyridin-2-yl)amino)-2,3-dihydro-1H-inden-1-yl)carbamate (79.8 mg, 100%) as a pale-yellow oil, which was used without further purification in the next step.

MS (ESI) calculated for $C_{22}H_{25}ClN_6O_2$: 440.17, found 441.24 $[M+H]^+$.

Step 5: Synthesis of (S)-tert-butyl (5-(2-(2-amino-pyridin-3-yl)-7-chloro-5-(1H-pyrazol-1-yl)-3H-imidazo[4,5-b]pyridin-3-yl)-2,3-dihydro-1H-inden-1-yl) carbamate To a solution of (S)-tert-butyl (5-((3-amino-4-chloro-6-(1H-pyrazol-1-yl)pyridin-2-yl)amino)-2,3-dihydro-1H-inden-1-yl)carbamate (79.8 mg, 0.181 mmol, 1 equiv) in acetic acid (650 μL) and methanol (65.0 μL) was added 2-aminopyridine-3-carboxaldehyde (24.8 mg, 0.199 mmol, 1.1 equiv) and the reaction was stirred at room temperature for 18 h, then at 70° C. for 24 h. The reaction mixture was then cooled to 0° C. and quenched with 2N aqueous sodium hydroxide (until pH ~9-10), then extracted with dichloromethane (3×5 mL). The organic layers were combined, washed with brine (3 mL), dried over sodium sulfate, and concentrated in vacuo. The residue was purified by silica gel column chromatography (60-70% ethyl acetate in heptanes) to obtain (S)-tert-butyl (5-(2-(2-aminopyridin-3-yl)-7-chloro-5-(1H-pyrazol-1-yl)-3H-imidazo[4,5-b]pyridin-3-yl)-2,3-dihydro-1H-inden-1-yl)carbamate (87 mg, 89%) as a pale-yellow solid. MS (ESI) calculated for $C_{28}H_{27}ClN_8O_2$: 542.19, found 543.22 $[M+H]^+$.

Step 6: Synthesis of (S)-3-(3-(1-amino-2,3-dihydro-1H-inden-5-yl)-5-(1H-pyrazol-1-yl)-3H-imidazo[4,5-b]pyridin-2-yl)pyridin-2-amine hydrochloride (Intermediate 122-0)

To a solution of (S)-tert-butyl (5-(2-(2-aminopyridin-3-yl)-7-chloro-5-(1H-pyrazol-1-yl)-3H-imidazo[4,5-b]pyridin-3-yl)-2,3-dihydro-1H-inden-1-yl)carbamate (87 mg, 0.16 mmol) in 1,4-dioxane (1.0 mL) was added a 4N solution of hydrochloric acid in 1,4-dioxane (0.8 mL) and the mixture was stirred at room temperature for 3 h. The reaction mixture was concentrated in vacuo co-evaporating with dichloromethane (3×5 mL) to obtain (S)-3-(3-(1-amino-2,3-dihydro-1H-inden-5-yl)-7-chloro-5-(1H-pyrazol-1-yl)-3H-imidazo[4,5-b]pyridin-2-yl)pyridin-2-amine (Intermediate 122-0) (76.8 mg, 100%) as a beige solid, which was used in subsequent transformations without further purification. MS (ESI) calculated for $C_{23}H_{19}ClN_8$: 442.14, found 443.05 $[M+H]^+$.

TABLE 6

Characterization data of compounds prepared analogously to compounds 122, 123, 165, and 177.

| Cpd ID | Characterization Data |
|---|---|
| 124 | MS (ESI) calcd. for $C_{31}H_{27}N_9O_2$, 557.23 m/z, found 558.25 $[M + H]^+$. $^1H$ NMR (300 MHz, DMSO-$d_6$) δ (ppm): 8.50-8.56 (m, 1H), 8.29-8.36 (m, 1H), 7.98-8.06 (m, 1H), 7.74 -7.85 (m, 2H), 7.50-7.56 (m, 1H), 7.43-7.49 (m, 1H), 7.34-7.39 (m, 1H), 7.25-7.33 (m, 2H), 7.19-7.24 (m, 1H), 6.54-6.61 (m, 1H), 6.41-6.49 (m, 1H), 5.56-5.63 (m, 1H), 4.19 (s, 3H), 2.86-3.10 (m, 2H), 2.56-2.62 (m, 4H), 1.97-2.12 (m, 1H) |
| 125 | MS (ESI) calcd. for $C_{31}H_{24}N_{10}O$, 552.21 m/z, found 553.10 $[M + H]^+$. $^1H$ NMR (400 MHz, DMSO-$d_6$) δ (ppm): 8.50-8.60 (m, 1H), 8.35-8.40 (m, 1H), 8.29 (s, 1H), 8.02-8.10 (m, 1H), 7.85-7.92 (m, 1H), 7.75-7.85 (m, 1H), 7.46-7.55 (m, 1H), 7.40-7.45 (m, 1H), 7.25-7.40 (m, 3H), 6.60 - 6.65 (m, 1H), 6.45-6.55 (m, 1H), 6.50-6.52 (m, 1H), 3.00-3.10 (m, 1H), 2.85-3.00 (m, 1H), 2.55-2.62 (m, 4H), 1.90-2.12 (m, 1H). (formic acid salt) |
| 212 | MS (ESI) calcd. for $C_{30}H_{24}FN_9O$: 545.21 m/z, found: 546.25 $[M + H]^+$. $^1H$-NMR (400 MHz, DMSO-$d_6$) δ (ppm): 8.63-8.64 (m, 1H), 8.36-8.37 (m, 1H), 8.08-8.10 (m, 2H), 7.84-7.86 (m, 3H), 7.47-7.58 (m, 3H), 7.47-7.48 (m, 1H), 6.80-6.85 (m, 1H), 6.59-6.60 (m, 1H), 5.55-5.59 (m, 1H), 3.01-3.07 (m, 1H), 2.90-2.96 (m, 1H), 2.65-2.69 (m, 3H), 2.53-2.57 (m, 1H), 2.00 - 2.06 (m, 1H). (TFA salt) |
| 213 | MS (ESI) calcd. for $C_{31}H_{25}F_2N_9O$, 577.22 m/z, found 578.10 [M + H]+. 1H NMR (300 MHz, DMSO-$d_6$ + $D_2O$) 8 (ppm): 8.49-8.57 (m, 1H), 8.38-8.41 (m, 1H), 8.12-8.19 (m, 1H), 8.05 - 8.11 (m, 1H), 7.85-7.93 (m, 1H), 7.76-7.84 (m, 1H), 7.50-7.69 (m, 2H), 7.41-7.48 (m, 1H), 7.29-7.40 (m, 3H), 6.59-6.67 (m, 1H), 6.46-6.53 (m, 1H), 5.58-5.64 (m, 1H), 2.93-3.16 (m, 3H), 2.58-2.69 (m, 3H), 2.50-2.58 (m, 1H), 2.01-2.18 (m, 1H). 19F NMR (282 MHz, DMSO-$d_6$ + $D_2O$) δ (ppm): −114.742, −115.521. |
| 329 | MS (ESI) calcd. for C31H21F3N10O, 606.19 m/z, found 607.10 [M + H]+. 1H NMR (400 MHz, DMSO-d6) 8 (ppm): 9.10-9.18 (m, 1H), 8.39-8.49 (m, 1H), 8.27-8.35 (m, 1H), 8.09-8.14 (m, 1H), 8.02-8.08 (m, 1H), 7.81-7.88 (m, 1H), 7.28-7.48 (m, 4H), 6.83-7.17 (m, 1H), 6.48-6.56 (m, 1H), 6.34-6.44 (m, 1H), 5.56-5.70 (m, 1H), 3.00-3.10 (m, 1H), 2.86-2.99 (m, 1H), 2.57 - 2.62 (m, 1H), 2.02-2.17 (m, 1H). 19F NMR (376 MHz, DMSO-d6) δ (ppm): −116.06, −126.04. |

Example 72: (S)-3-(5-(2-(2-aminopyridin-3-yl)-5-(1H-pyrazol-1-yl)-3H-imidazo[4,5-b]pyridin-3-yl)-2,3-dihydro-1H-inden-1-yl)-1-methyl-1-phenylurea (Compound 132)

Compound 132

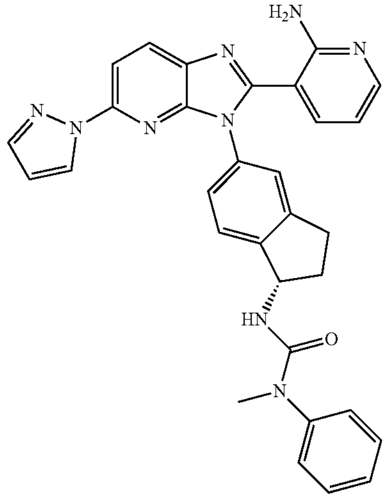

Synthetic Route:

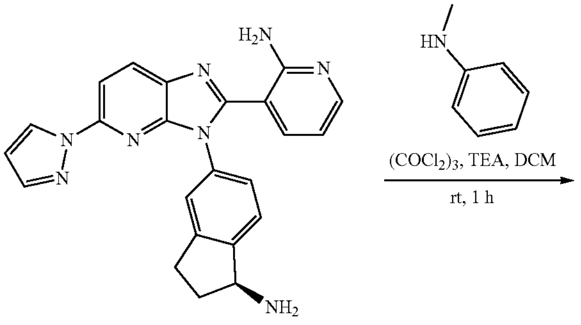

Compound 2

-continued

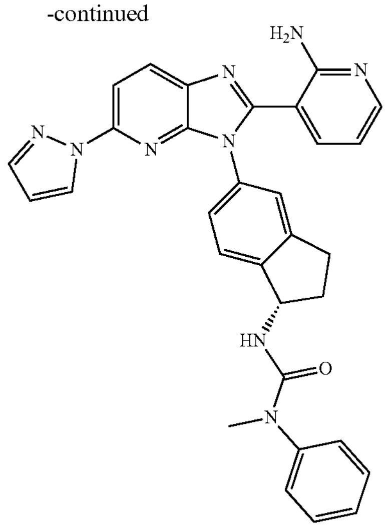

Compound 132

Step 1: Synthesis of (S)-3-(5-(2-(2-aminopyridin-3-yl)-5-(1H-pyrazol-1-yl)-3H-imidazo[4,5-b]pyridin-3-yl)-2,3-dihydro-1H-inden-1-yl)-1-methyl-1-phenylurea (Compound 132)

To a solution of 3-{3-[(1S)-1-amino-2,3-dihydro-1H-inden-5-yl]-5-(pyrazol-1-yl)imidazo[4,5-b]pyridin-2-yl}pyridin-2-amine (Compound 2) (100 mg, 0.245 mmol) and triethylamine (74.3 mg, 0.735 mmol) in DCM (2.00 mL) was added triphosgene (24 mg, 0.081 mmol) and the mixture was stirred for 20 min at room temperature followed by addition of N-methylaniline (31.5 mg, 0.294 mmol). Stirring was continued for 1 h at room temperature. The resulting mixture was concentrated under reduced pressure and the residue was purified by Prep-HPLC on a XSelect CSH Fluoro Phenyl column using a gradient of acetonitrile in water (+0.1% TFA) to afford (S)-3-(5-(2-(2-aminopyridin-3-yl)-5-(1H-pyrazol-1-yl)-3H-imidazo[4,5-b]pyridin-3-yl)-2,3-dihydro-1H-inden-1-yl)-1-methyl-1-phenylurea (Compound 132) (2 mg, 1% yield) as a yellow solid. MS (ESI) calcd. for $C_{31}H_{27}N_9O$, 541.23 m/z, found 542.20 $[M+H]^+$. $^1$H NMR (300 MHz, DMSO-$d_6$) δ (ppm): 8.47-8.50 (m, 1H), 8.42-8.45 (m, 1H), 8.35-8.36 (m, 1H), 8.03-8.06 (m, 1H), 7.85-7.86 (m, 1H), 7.70-7.74 (m, 1H), 7.43-7.44 (m, 1H), 7.22-7.23 (m, 6H), 7.06-7.08 (m, 1H), 6.79-6.82 (m, 1H), 6.59-6.60 (m, 1H), 4.79-4.84 (m, 1H), 3.48-3.53 (m, 3H), 3.11-3.12 (m, 1H), 2.96-2.98 (m, 1H), 2.51-2.52 (m, 1H), 2.06-2.08 (m, 1H). (TFA salt)

The following compounds were prepared analogous to the synthetic preparation in Example 72 (Compound 132).

TABLE 7

Characterization data of compounds prepared analogously to compound 132.

| Cpd ID | Characterization Data |
|---|---|
| 133 | MS (ESI) calcd. for $C_{30}H_{25}N_9O$, 527.22 m/z, found 528.20 $[M + H]^+$. $^1$H NMR (300 MHz, DMSO-$d_6$) δ (ppm): 8.36-8.38 (m, 2H), 8.02-8.03 (m, 1H), 7.94-7.97 (m, 1H), 7.81-7.82 (m, 1H), 7.42-7.44 (m, 4H), 7.32-7.38 (m, 4H), 6.92-6.95 (m, 1H), 6.55-6.56 (m, 1H), 6.44-6.45 (m, 1H), 5.26-5.29 (m, 1H), 2.96-2.97 (m, 2H), 2.51-2.52 (m, 1H), 1.89-1.90 (m, 1H). |

Example 73: (S)-1-(5-(2-(2-aminopyridin-3-yl)-5-(1H-pyrazol-1-yl)-3H-imidazo[4,5-b]pyridin-3-yl)-2,3-dihydro-1H-inden-1-yl)-3-isopropylurea (Compound 134)

Compound 134

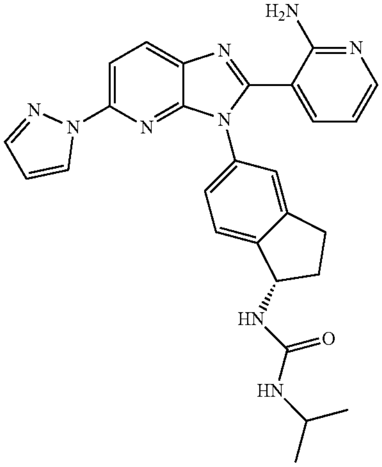

Synthetic Route:

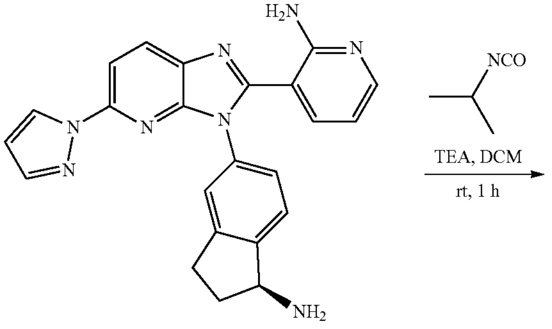

Compound 2

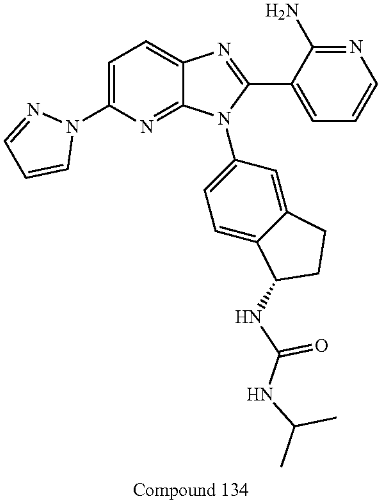

Compound 134

Step 1: Synthesis of (S)-1-(5-(2-(2-aminopyridin-3-yl)-5-(1H-pyrazol-1-yl)-3H-imidazo[4,5-b]pyridin-3-yl)-2,3-dihydro-1H-inden-1-yl)-3-isopropylurea To a solution of 3-{3-[(1S)-1-amino-2,3-dihydro-1H-inden-5-yl]-5-(pyrazol-1-yl)imidazo[4,5-b]pyridin-2-yl}pyridin-2-amine (Compound 2) (100 mg, 0.245 mmol) and triethylamine (74.3 mg, 0.735 mmol) in DCM (2.00 mL) was added 2-isocyanato-propane (20.8 mg, 0.245 mmol) and the mixture was stirred for 1 h at room temperature. The resulting mixture was concentrated under reduced pressure and the residue was purified by Prep-HPLC on a XSelect CSH Fluoro Phenyl column using a gradient of acetonitrile in water (+0.05% TFA) to afford (S)-1-(5-(2-(2-aminopyridin-3-yl)-5-(1H-pyrazol-1-yl)-3H-imidazo[4,5-b]pyridin-3-yl)-2,3-dihydro-1H-inden-1-yl)-3-isopropylurea (Compound 134) (25.3 mg, 17% yield) as an off-white solid. MS (ESI) calcd. for $C_{27}H_{27}N_9O$, 493.23 m/z, found 494.25 $[M+H]^+$. $^1H$ NMR (300 MHz, DMSO-$d_6$) δ (ppm): 8.42-8.44 (m, 1H), 8.38-8.39 (m, 1H), 8.06-8.08 (m, 1H), 8.00-8.03 (m, 1H), 7.76-7.77 (m, 1H), 7.73-7.74 (m, 1H), 7.35-7.38 (m, 1H), 7.33-7.34 (m, 2H), 6.80-6.81 (m, 1H), 5.57-6.58 (m, 1H), 5.17-5.19 (m, 1H), 3.74-3.76 (m, 1H), 2.82-2.85 (m, 2H), 2.46-2.47 (m, 1H), 1.77-1.80 (m, 1H), 1.01-1.02 (m, 6H). (TFA salt)

Example 74: (S)—N-(5-(2-(2-aminopyridin-3-yl)-5-(1H-pyrazol-1-yl)-3H-imidazo[4,5-b]pyridin-3-yl)-2,3-dihydro-1H-inden-1-yl)-4-(difluoromethyl)-2-methylpyrimidine-5-carboxamide (Compound 151)

Compound 151

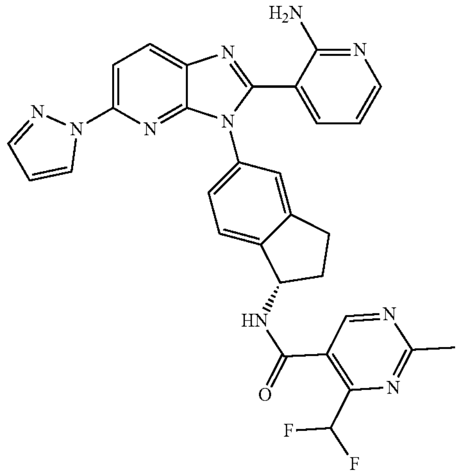

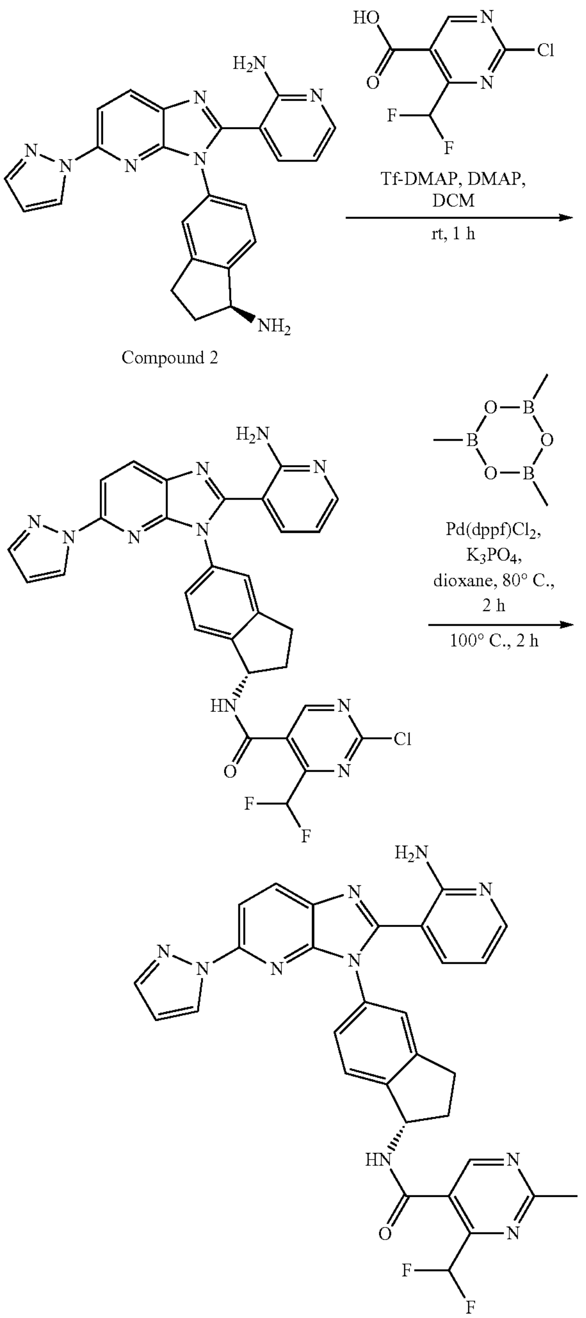

Compound 2

Compound 151

Step 1: Synthesis of (S)—N-(5-(2-(2-aminopyridin-3-yl)-5-(1H-pyrazol-1-yl)-3H-imidazo[4,5-b]pyridin-3-yl)-2,3-dihydro-1H-inden-1-yl)-2-chloro-4-(difluoromethyl)pyrimidine-5-carboxamide A solution of 3-{3-[(1S)-1-amino-2,3-dihydro-1H-inden-5-yl]-5-(pyrazol-1-yl)imidazo[4,5-b]pyridin-2-yl}pyridin-2-amine (Compound 2) (200 mg, 0.490 mmol), 2-chloro-4-(difluoromethyl)pyrimidine-5-carboxylic acid (102 mg, 0.490 mmol) and DMAP (190 mg, 1.47 mmol) in DCM (10 mL) was treated with Tf-DMAP (107 mg, 0.490 mmol) at room temperature The resulting mixture was stirred for 1 h at room temperature. The reaction was quenched with water at room temperature and the resulting mixture was extracted with ethyl acetate (3×20 ml). The combined organic layers were dried over anhydrous $Na_2SO_4$. After filtration, the filtrate was concentrated under reduced pressure. The residue was purified by silica gel column chromatography using a gradient of ethyl acetate in petroleum ether to afford (S)—N-(5-(2-(2-aminopyridin-3-yl)-5-(1H-pyrazol-1-yl)-3H-imidazo[4,5-b]pyridin-3-yl)-2,3-dihydro-1H-inden-1-yl)-2-chloro-4-(difluoromethyl)pyrimidine-5-carboxamide (100 mg, 34% yield) as a yellow solid: MS (ESI) calcd. for $C_{29}H_{21}ClF_2N_{10}O$, 598.16 m/z, found 599.15 $[M+H]^+$.

Step 2: Synthesis of (S)—N-(5-(2-(2-aminopyridin-3-yl)-5-(1H-pyrazol-1-yl)-3H-imidazo[4,5-b]pyridin-3-yl)-2,3-dihydro-1H-inden-1-yl)-4-(difluoromethyl)-2-methylpyrimidine-5-carboxamide (Compound 151)

A solution of (S)—N-(5-(2-(2-aminopyridin-3-yl)-5-(1H-pyrazol-1-yl)-3H-imidazo[4,5-b]pyridin-3-yl)-2,3-dihydro-1H-inden-1-yl)-2-chloro-4-(difluoromethyl)pyrimidine-5-carboxamide (150 mg, 0.250 mmol), methylboronic acid (75 mg, 1.3 mmol) and $K_3PO_4$ (160 mg, 0.750 mmol) in 1,4-dioxane (5 mL) was added $Pd(dppf)Cl_2$ (36.7 mg, 0.050 mmol) at room temperature The resulting mixture was stirred for 3 h at 100° C. under $N_2$ atmosphere. The reaction was quenched with water at room temperature The resulting mixture was extracted with ethyl acetate (3×20 ml). The combined organic layers were dried over anhydrous $Na_2SO_4$. After filtration, the filtrate was concentrated under reduced pressure. The crude product was purified by Prep-HPLC on a XSelect CSH Fluoro Phenyl column using a gradient of acetonitrile in water (+0.1% formic acid) to afford (S)—N-(5-(2-(2-aminopyridin-3-yl)-5-(1H-pyrazol-1-yl)-3H-imidazo[4,5-b]pyridin-3-yl)-2,3-dihydro-1H-inden-1-yl)-4-(difluoromethyl)-2-methylpyrimidine-5-carboxamide (Compound 151, formic acid salt) (3.2 mg, 2% yield) as a yellow green solid: MS (ESI) calcd. for $C_{30}H_{24}F_2N_{10}O$, 578.21 m/z, found 579.10 $[M+H]^+$. $^1H$ NMR (300 MHz, DMSO-$d_6$) δ (ppm); 9.03 (m, 1H), 8.30-8.40 (m, 2H), 8.00-8.06 (m, 1H), 7.95-8.00 (m, 1H), 7.81 (s, 1H), 7.45-7.52 (m, 1H), 7.05-7.43 (m, 4H), 6.55-6.60 (m, 1H), 6.43-6.50 (m, 1H), 5.50-5.62 (m, 1H), 2.85-3.10 (m, 2H), 2.75 (s, 3H), 2.58-2.62 (m, 1H), 1.95-2.15 (m, 1H). $^{19}F$ NMR (282 MHz, DMSO-$d_6$) δ (ppm); −119.54.

The following compounds were prepared analogous to the synthetic preparation in Example 74 (Compound 151).

TABLE 8

Characterization data of compounds prepared analogously to compound 151.

| Cpd ID | Characterization Data |
|---|---|
| 167 | MS (ESI) calcd. for $C_{31}H_{25}F_2N_9O$, 577.22 m/z, found, 578.20 [M + H]$^+$. $^1$H NMR (300 MHz, DMSO-$d_6$) δ (ppm); 8.30-8.38 (m, 2H), 7.95-8.05 (m, 1H), 7.88-7.95 (m, 2H), 7.74-7.81 (m, 1H), 7.46-7.53 (m, 2H), 7.00-7.41 (m, 4H), 6.50-6.57 (m, 1H), 6.39-6.50 (m, 1H), 5.47-5.59 (m, 1H), 2.82-3.08 (m, 2H), 2.50-2.61 (m, 4H), 1.95-2.08 (m, 1H). $^{19}$F NMR (282 MHz, DMSO-$d_6$) δ (ppm); −115.13. |

Example 75: (S)—N-(5-(2-(2-aminopyridin-3-yl)-5-(1H-pyrazol-1-yl)-3H-imidazo[4,5-b]pyridin-3-yl)-2,3-dihydro-1H-inden-1-yl)-2-(hydroxymethyl)nicotinamide (Compound 152)

Compound 152

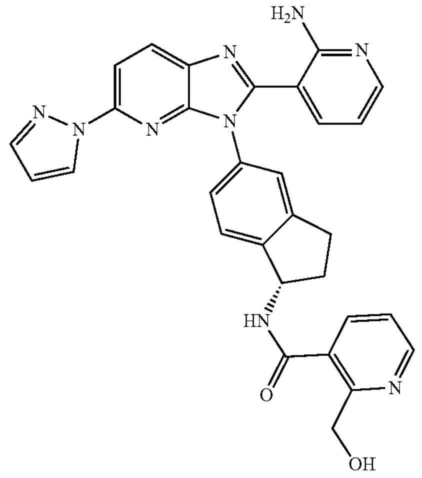

Synthetic Route:

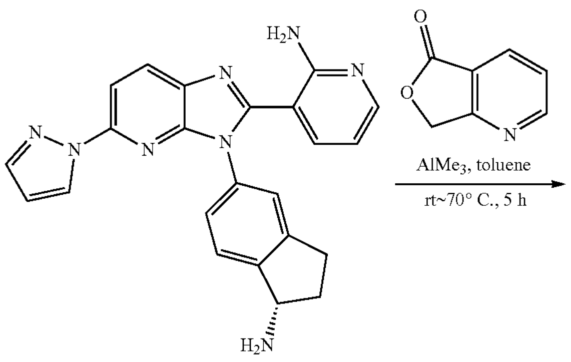

Compound 2

-continued

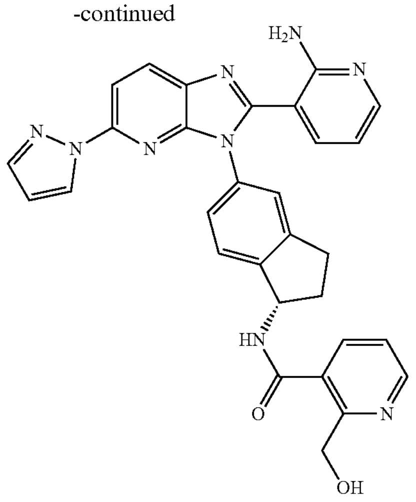

Compound 152

Step 1: Synthesis of (S)—N-(5-(2-(2-aminopyridin-3-yl)-5-(1H-pyrazol-1-yl)-3H-imidazo[4,5-b]pyridin-3-yl)-2,3-dihydro-1H-inden-1-yl)-2-(hydroxymethyl)nicotinamide (Compound 152)

To a solution of (S)-3-(3-(1-amino-2,3-dihydro-1H-inden-5-yl)-5-(1H-pyrazol-1-yl)-3H-imidazo[4,5-b]pyridin-2-yl)pyridin-2-amine (Compound 2) (120 mg, 0.294 mmol) and 7H-furo[3,4-b]pyridin-5-one (79.4 mg, 0.588 mmol) in toluene (3 mL) was added $AlMe_3$ (0.44 mL, 0.882 mmol, 2M in Toluene) at 0° C. under $N_2$ atmosphere. The resulting mixture was stirred for 5 h at 70° C. The reaction was quenched by the addition of water (100 mL) at room temperature. The resulting mixture was extracted with ethyl acetate (3×30 mL). The combined organic layers were dried over anhydrous $Na_2SO_4$, filtered and concentrated. The residue was purified by reverse phase column chromatography on C18 silica gel using a gradient of acetonitrile in water (+0.05% TFA) to afford (S)—N-(5-(2-(2-aminopyridin-3-yl)-5-(1H-pyrazol-1-yl)-3H-imidazo[4,5-b]pyridin-3-yl)-2,3-dihydro-1H-inden-1-yl)-2-(hydroxymethyl)nicotinamide (Compound 152—TFA salt) (38.2 mg, 23% yield) as a brown solid: MS (ESI) calcd. for $C_{30}H_{25}N_9O_2$: 543.21 m/z, found, 544.15 [M+H]$^+$. $^1$H NMR (300 MHz, DMSO-$d_6$) δ (ppm); 8.68-8.78 (m, 1H), 8.41-8.48 (m, 2H), 8.31-8.40 (m, 1H), 8.05-8.10 (m, 1H), 8.01-8.05 (m, 1H), 7.75-7.88 (m, 3H), 7.50-7.56 (m, 1H), 7.44-7.50 (m, 1H), 7.35-7.40 (m, 1H), 6.82-6.88 (m, 1H), 6.56-6.60 (m, 1H), 5.56-5.62 (m, 1H), 4.95 (s, 2H), 2.90-3.11 (m, 2H), 2.55-2.62 (m, 1H), 2.00-2.11 (m, 1H).

Example 76: (S)-3-(3-(1-(4-phenyl-1H-1,2,3-triazol-1-yl)-2,3-dihydro-1H-inden-5-yl)-5-(1H-pyrazol-1-yl)-3H-imidazo[4,5-b]pyridin-2-yl)pyridin-2-amine (Compound 155)

Compound 155

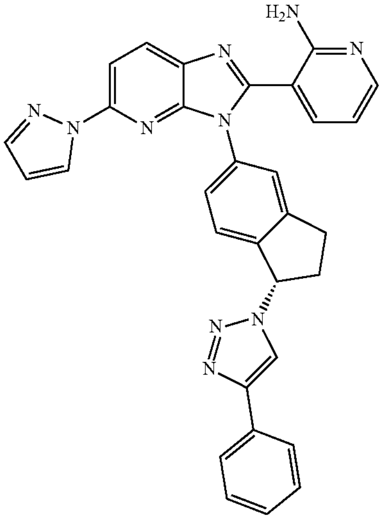

Synthetic Route:

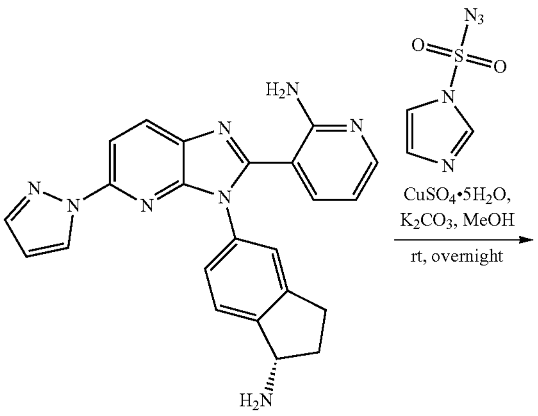

Compound 2

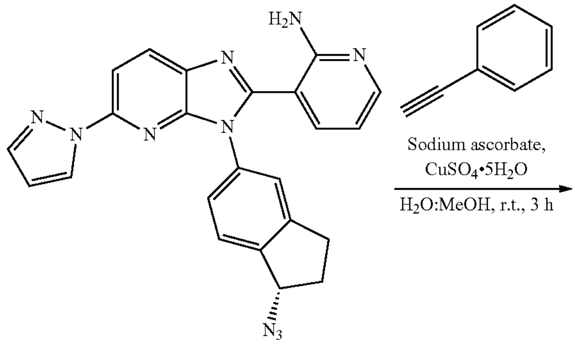

Intermediate 155-1

-continued

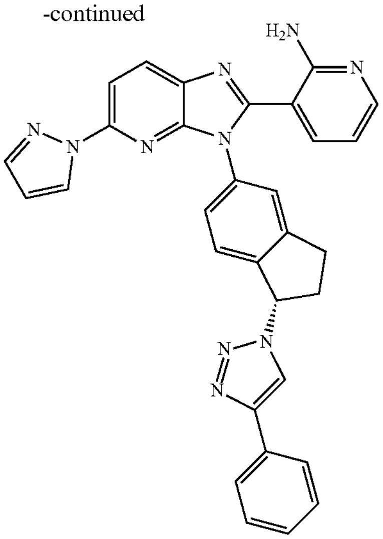

Compound 155

Step 1: Synthesis of (S)-3-(3-(1-(4-phenyl-1H-1,2,3-triazol-1-yl)-2,3-dihydro-1H-inden-5-yl)-5-(1H-pyrazol-1-yl)-3H-imidazo[4,5-b]pyridin-2-yl)pyridin-2-amine (Compound 155)

A mixture of 3-{3-[(1S)-1-azido-2,3-dihydro-1H-inden-5-yl]-5-(pyrazol-1-yl)imidazo[4,5-b]pyridin-2-yl}pyridin-2-amine (Intermediate 155-1) (200 mg, 0.460 mmol), phenylacetylene (940.3 mg, 9.200 mmol), copper(II) sulfate pentahydrate (23 mg, 0.092 mmol) and sodium ascorbate (36.7 mg, 0.184 mmol) in MeOH (1 mL) and $H_2O$ (1 mL) was stirred for 3 h at room temperature. The resulting mixture was concentrated under reduced pressure. The residue was purified by Prep-HPLC on a XSelect CSH Fluoro Phenyl column using a gradient of acetonitrile in water (+0.05% TFA) to afford (S)-3-(3-(1-(4-phenyl-1H-1,2,3-triazol-1-yl)-2,3-dihydro-1H-inden-5-yl)-5-(1H-pyrazol-1-yl)-3H-imidazo[4,5-b]pyridin-2-yl)pyridin-2-amine (Compound 155, trifluoroacetic acid salt) (31.0 mg, 10% yield) as an off-white solid: MS (ESI) calcd. for $C_{31}H_{24}N_{11}$, 536.22 m/z, found 537.15 $[M+H]^+$. $^1H$ NMR (300 MHz, DMSO-$d_6$) δ (ppm); 8.63 (s, 1H), 8.39-8.42 (m, 2H), 8.03-8.05 (m, 2H), 7.83-7.89 (m, 3H), 7.69-7.70 (m, 1H), 7.44-7.46 (m, 1H), 7.41-7.44 (m, 2H), 7.31-7.32 (m, 3H), 6.31-6.76 (m, 3H), 3.30-3.31 (m, 1H), 3.08-3.10 (m, 1H), 2.83-2.86 (m, 1H), 2.58-2.61 (m, 1H).

Intermediate 155-1: (S)-3-(3-(1-azido-2,3-dihydro-1H-inden-5-yl)-5-(1H-pyrazol-1-yl)-3H-imidazo[4,5-b]pyridin-2-yl)pyridin-2-amine Step 1: (S)-3-(3-(1-azido-2,3-dihydro-8H-inden-5-yl)-5-(1H-pyrazol-1-yl)-3H-imidazo[4,5-b]pyridin-2-yl)pyridin-2-amine (Intermediate 155-1)

A solution of 3-{3-[(1S)-1-amino-2,3-dihydro-1H-inden-5-yl]-5-(pyrazol-1-yl)imidazo[4,5-b]pyridin-2-yl}pyridin-2-amine (Compound 2) (300 mg, 0.734 mmol), imidazole-1-sulfonyl azide (153 mg, 0.881 mmol), potassium carbonate (409 mg, 2.94 mmol) and $CuSO_4 \cdot 5H_2O$ (9.2 mg, 0.037 mmol) in MeH (5 mL) was stirred overnight at room temperature. The resulting mixture was concentrated under reduced pressure. The residue was purified by reverse-phase flash chromatography on C18 silica gel using a gradient of acetonitrile in water (+0.050M TFA) to afford (S)-3-(3-(1-azido-2,3-dihydro-7H-inden-5-yl)-5-(1H-pyrazol-1-yl)-3H-imidazo[4,5-b]pyridin-2-yl)pyridin-2-amine (Intermediate 155-1) (200 mg, 630 yield) as a yellow solid: MS (ESI) calcd. for $C_{23}H_{18}N_{12}$, 434.17 m/z, found 435.15 $[M+H]^+$.

The following compounds were prepared analogous to the synthetic preparation in Example 76 (Compound 155).

TABLE 9

Characterization data of compounds prepared analogously to compound 155.

| Cpd ID | Characterization Data |
|---|---|
| 156 | MS (ESI) calcd. for $C_{32}H_{26}N_{10}$, 550.23 m/z, found 551.15 $[M + H]^+$. $^1H$ NMR (300 MHz, DMSO-$d_6$) δ (ppm); 8.39-8.42 (m, 2H), 8.03-8.04 (m, 2H), 7.90-7.98 (m, 1H), 7.70-7.81 (m, 1H), 7.67-7.70 (m, 1H), 7.55-7.56 (m, 1H), 7.16-7.28 (m, 7H), 6.73-6.75 (m, 1H), 6.54-6.55 (m, 1H), 6.20-6.23 (m, 1H), 3.98-3.99 (m, 2H), 3.19-3.21 (m, 1H), 3.02-3.04 (m, 1H), 2.77-2.79 (m, 1H), 2.48-2.49 (m, 1H). (TFA salt) |
| 188 | MS (ESI) calcd. for $C_{25}H_{20}N_{10}$, 460.19 m/z, found 461.15 $[M + H]^+$. $^1H$ NMR (400 MHz, DMSO-$d_6$) δ (ppm): 8.36-8.37 (m, 2H), 8.17-8.18 (m, 1H), 8.01-8.02 (m, 2H), 7.80-7.81 (m, 2H), 7.53-7.54 (m, 1H), 7.28-7.30 (m, 1H), 7.23-7.24 (m, 2H), 6.56-6.57 (m, 1H), 6.43-6.44 (m, 1H), 6.33-6.35 (m, 1H), 3.56-3.58 (m, 1H), 3.06-3.08 (m, 1H), 2.83-2.84 (m, 1H), 2.53-2.56 (m, 1H). |
| 197 | MS (ESI) calcd. for $C_{29}H_{24}N_{12}$, 540.22 m/z, found, 541.15 $[M + H]^+$. $^1H$ NMR (300 MHz, DMSO-$d_6$) δ (ppm); 8.28-8.45 (m, 3H), 7.91-8.09 (m, 2H), 7.71-7.86 (m, 2H), 7.54 (s, 1H), 7.27-7.37 (m, 2H), 7.18-7.26 (m, 1H), 6.52-6.65 (m, 2H), 6.42-6.51 (m, 1H), 6.29-6.39 (m, 1H), 3.87 (s, 3H), 3.21-3.37 (m, 1H), 2.99-3.14 (m, 1H), 2.78-2.91 (m, 1H), 2.55-2.67 (m, 1H). |
| 198 | MS (ESI) calcd. for $C_{30}H_{23}N_{11}$, 537.21 m/z, found, 538.15 $[M + H]^+$. $^1H$ NMR (400 MHz, DMSO-$d_6$) δ (ppm); 8.90 (s, 1H), 8.63-8.65 (m, 2H), 8.36-8.40 (m, 2H), 8.01-8.03 (m, 1H), 7.96-7.98 (m, 1H), 7.81-7.86 (m, 3H), 7.57 (s, 1H), 7.29-7.35 (m, 2H), 7.24-7.27 (m, 1H), 6.55-6.56 (m, 1H), 6.38-6.47 (m, 2H), 3.27-3.38 (m, 1H), 3.04-3.17 (m, 1H), 2.80-2.96 (m, 1H), 2.56-2.67 (m, 1H). |
| 199 | MS (ESI) calcd. for $C_{30}H_{23}N_{11}$, 537.21 m/z, found, 538.15 $[M + H]^+$. $^1H$ NMR (400 MHz, DMSO-$d_6$) δ (ppm); 9.04-9.12 (m, 1H), 8.79 (s, 1H), 8.52-8.58 (m, 1H), 8.36 (s, 2H), 8.20-8.30 (m, 1H), 7.96-8.05 (m, 1H), 7.90-7.96 (m, 1H), 7.79-7.83 (m, 1H), 7.57 (s, 1H), 7.45-7.56 (m, 1H), 7.28-7.35 (m, 2H), 7.22-7.28 (m, 1H), 6.53-6.59 (m, 1H), 6.38-6.47 (m, 2H), 3.28-3.38 (m, 1H), 3.01-3.19 (m, 1H), 2.78-2.97 (m, 1H), 2.56-2.69 (m, 1H). |
| 200 | MS (ESI) calcd. for $C_{30}H_{23}N_{11}$, 537.21 m/z, found, 538.15 $[M + H]^+$. $^1H$ NMR (300 MHz, DMSO-$d_6$) δ (ppm); 8.53-8.71 (m, 2H), 8.31-8.45 (m, 2H), 7.87-8.16 (m, 4H), 7.78-7.85 (m, 1H), 7.53-7.61 (m, 1H), 7.18-7.45 (m, 4H), 6.54-6.63 (m, 1H), 6.33-6.52 (m, 2H), 3.21-3.41 (m, 1H), 2.99-3.19 (m, 1H), 2.78-2.97 (m, 1H), 2.85-2.71 (m, 1H). |
| 218 | MS (ESI) calcd. for $C_{28}H_{27}N_{11}$, 517.25 m/z, found 518.20 $[M + H]^+$. $^1H$ NMR (400 MHz, DMSO-$d_6$ + $D_2O$) δ (ppm); 8.38-8.43 (m, 2H), 7.97-8.11 (m, 3H), 7.80-7.88 (m, 1H), 7.52-7.59 (m, 1H), 7.22-7.37 (m, 3H), 6.54-6.61 (m, 1H), 6.42-6.51 (m, 1H), 6.28-6.34 (m, 1H), 3.55 (s, 2H), 3.23-3.35 (m, 1H), 3.04-3.16 (m, 1H), 2.78-2.89 (m, 1H), 2.58-2.65 (m, 1H), 2.12 (s, 6H). |
| 219 | MS (ESI) calcd. for $C_{28}H_{26}N_{10}O$, 518.23 m/z, found, 519.15 $[M + H]^+$. $^1H$-NMR (400 MHz, DMSO-$d_6$) δ (ppm); 8.28-8.32 (m, 2H), 7.90-8.00 (m, 2H), 7.78-7.82 (m, 1H), 7.69-7.77 (m, 1H), 7.44 (s, 1H), 7.17-7.20 (m, 3H), 6.44-6.55 (m, 2H), 6.16-6.19 (m, 1H), 3.04-3.15 (m, 1H), 2.99-3.02 (m, 1H), 2.71-2.76 (m, 1H), 2.43-2.49 (m, 1H), 1.45 (s, 6H). |
| 220 | MS (ESI) calcd. for $C_{28}H_{24}N_{10}O$, 516.21 m/z, found, 517.30 $[M + H]^+$. $^1H$ NMR (300 MHz, DMSO-$d_6$ + $D_2O$) δ (ppm); 8.34-8.59 (m, 2H), 8.02-8.15 (m, 1H), 7.96-8.01 (m, 2H), 7.73-7.95 (m, 2H), 7.42-7.71 (m, 1H), 7.13-7.41 (m, 2H), 6.73-6.97 (m, 1H), 6.45-6.72 (m, 1H), 6.12-6.42 (m, 1H), 4.83-5.11 (m, 2H), 4.59-4.82 (m, 2H), 4.26-4.58 (m, 1H), 3.22-3.45 (m, 1H), 3.00-3.21 (m, 1H), 2.69-2.99 (m, 1H), 2.43-2.61 (m, 1H). (TFA salt) |
| 221 | MS (ESI) calcd. for $C_{28}H_{24}N_{10}$, 500.22 m/z, found, 501.30 $[M + H]^+$. $^1H$ NMR (300 MHz, DMSO-$d_6$ + $D_2O$) δ (ppm); 8.29-8.55 (m, 2H), 7.79-8.15 (m, 2H), 7.68-7.78 (m, 1H), 7.47-7.67 (m, 1H), 7.30-7.46 (m, 1H), 7.12-7.29 (m, 1H), 6.70-6.95 (m, 1H), 6.48-6.69 (m, 1H), 6.05-6.33 (m, 1H), 3.16-3.42 (m, 1H), 2.94-3.15 (m, 1H), 2.66-2.93 (m, 1H), 2.41-2.52 (m, 1H), 2.29-2.34 (m, 1H), 1.81-2.12 (m, 1H), 0.85-1.11 (m, 2H), 0.58-0.84 (m, 2H). (TFA salt) |
| 227 | MS (ESI) calcd. for $C_{25}H_{20}N_{10}$, 460.19 m/z, found 461.10 $[M + H]^+$. $^1H$ NMR (400 MHz, DMSO-$d_6$) δ (ppm); 8.36-8.37 (m, 2H), 8.17-8.18 (m, 1H), 8.01-8.02 (m, 2H), 7.80-7.81 (m, 2H), 7.53-7.54 (m, 1H), 7.28-7.30 (m, 1H), 7.23-7.24 (m, 2H), 6.56-6.57 (m, 1H), 6.43-6.44 (m, 1H), 6.33-6.35 (m, 1H), 3.56-3.58 (m, 1H), 3.06-3.08 (m, 1H), 2.83-2.84 (m, 1H), 2.53-2.56 (m, 1H). |
| 250 | MS (ESI) calcd. for $C_{28}H_{25}N_{11}$, 515.23 m/z, found, 516.30 $[M + H]^+$. $^1H$-NMR (400 MHz, DMSO-$d_6$) δ (ppm); 8.31-8.51 (m, 2H), 8.16 (s, 1H), 7.93-8.10 (m, 2H), 7.78-7.88 (m, 1H), 7.64-7.76 (m, 1H), 7.60 (s, 1H), 7.30-7.40 (m, 1H), 7.21-7.29 (m, 1H), 6.68-6.82 (m, 1H), 6.50-6.63 (m, 1H), 6.21-6.38 (m, 1H), 4.02-4.40 (m, 5H), 3.18-3.38 (m, 1H), 2.95-3.15 (m, 1H), 2.73-2.90 (m, 1H), 2.46-2.50 (m, 1H). |
| 251 | MS (ESI) calcd. for $C_{29}H_{27}N_{11}$, 529.25 m/z, found, 530.35 $[M + H]^+$. $^1H$ NMR (400 MHz, DMSO-$d_6$) δ (ppm); 8.28-8.35 (m, 2H), 7.90-8.09 (m, 2H), 7.83-7.88 (m, 1H), 7.70-7.75 (m, 1H), 7.40-7.52 (m, 1H), 7.13-7.35 (m, 3H), 6.62-6.65 (m, 2H), 6.09-6.20 (m, 1H), 3.57-3.65 (m, 3H), 3.10-3.19 (m, 3H), 2.97-3.02 (m, 1H), 2.73-2.76 (m, 1H), 2.51-2.59 (m, 1H), 2.22-2.30 (m, 3H). |

TABLE 9-continued

| Characterization data of compounds prepared analogously to compound 155. | |
|---|---|
| Cpd ID | Characterization Data |
| 254 | MS (ESI) calcd. for $C_{31}H_{25}N_{11}$, 551.23 m/z, found 552.30 $[M + H]^+$. $^1$H NMR (300 MHz, DMSO-$d_6$) δ (ppm); 8.76-8.81 (m, 1H), 8.66-8.67 (m, 1H), 8.64-8.65 (m, 1H), 8.45-8.46 (m, 1H), 8.41-8.42 (m, 1H), 8.08-8.09 (m, 1H), 8.06-8.07 (m, 1H), 7.83-7.84 (m, 1H), 7.72-7.77 (m, 2H), 7.69-7.70 (m, 1H), 7.36-7.40 (m, 2H), 6.76-6.78 (m, 1H), 6.56-6.57 (m, 1H), 6.41-6.43 (m, 1H), 3.31-3.33 (m, 1H), 3.12-3.15 (m, 1H), 2.88-2.91 (m, 1H), 2.64-2.66 (m, 3H), 2.51-2.52 (m, 1H). (TFA salt) |
| 285 | MS (ESI) calcd. for $C_{27}H_{24}N_{10}$, 488.22 m/z, found 489.15 $[M + H]^+$. $^1$H NMR (400 MHz, DMSO-$d_6$) δ (ppm); 8.36-8.38 (m, 2H), 8.01-8.03 (m, 1H), 7.97 (d, J = 8.6 Hz, 1H), 7.89 (s, 1H), 7.81-7.82 (m, 1H), 7.54 (d, J = 1.9 Hz, 1H), 7.29-7.32 (m, 1H), 7.21-7.25 (m, 2H), 6.92 (s, 2H), 6.55-6.56 (m, 1H), 6.42-6.45 (m, 1H), 6.25-6.28 (m, 1H), 3.21-3.29 (m, 1H), 3.01-3.09 (m, 1H), 2.75-2.84 (m, 1H), 2.65 (q, J = 7.6 Hz, 2H), 2.52-2.56 (m, 1H), 1.21 (t, J = 7.6 Hz, 3H). |
| 287 | MS (ESI) calcd. for $C_{29}H_{26}N_{10}$, 514.23 m/z, found 515.20 $[M + H]^+$. $^1$H NMR (300 MHz, DMSO-$d_6$) δ (ppm); 8.36-8.37 (m, 2H), 8.01-8.02 (m, 1H), 7.94-7.97 (m, 2H), 7.81 (s, 1H), 7.53 (s, 1H), 7.28-7.31 (m, 1H), 7.22-7.24 (m, 2H), 6.92 (s, 2H), 6.54-6.55 (m, 1H), 6.42-6.44 (m, 1H), 6.24-6.27 (m, 1H), 3.51-3.60 (m, 1H), 3.21-3.28 (m, 1H), 3.02-3.08 (m, 1H), 2.74-2.83 (m, 1H), 2.51-2.56 (m, 1H), 2.27-2.31 (m, 2H), 2.14-2.19 (m, 2H), 1.96-1.98 (m, 1H), 1.80-1.98 (m, 1H). |
| 304 | MS (ESI) calcd. for $C_{26}H_{22}N_{10}$: 474.20 m/z, found: 475.10 $[M + H]^+$. $^1$H NMR (400 MHz, DMSO-$d_6$) δ (ppm): 8.38-8.48 (m, 2H), 7.99-8.10 (m, 2H), 7.81-7.90 (m, 2H), 7.68-7.73 (m, 1H), 7.55-7.61 (m, 1H), 7.21-7.39 (m, 2H), 6.73-6.82 (m, 1H), 6.55-6.62 (m, 1H), 6.19-6.30 (m, 1H), 3.18-3.31 (m, 1H), 3.01-3.11 (m, 1H), 2.73-2.86 (m, 1H), 2.43-2.51 (m, 1H), 2.26 (s, 3H) |
| 320 | MS (ESI) calcd. for $C_{29}H_{28}N_{10}$, 516.25 m/z, found 517.20 $[M + H]^+$. $^1$H NMR (300 MHz, DMSO-$d_6$) δ (ppm); 8.36-8.38 (m, 2H), 8.01-8.02 (m, 1H), 7.96 (d, J = 8.6 Hz, 1H), 7.88 (s, 1H), 7.81 (d, J = 1.7 Hz, 1H), 7.54 (d, J = 2.0 Hz, 1H), 7.29-7.31 (m, 1H), 7.21-7.23 (m, 2H), 6.94 (s, 2H), 6.54 (t, J = 2.1 Hz, 1H), 6.40-6.43 (m, 1H), 6.25 (t, J = 7.1 Hz, 1H), 3.21-3.29 (m, 1H), 3.00-3.08 (m, 1H), 2.74-2.83 (m, 1H), 2.53-2.57 (m, 1H), 1.29 (s, 9H). |
| 326 | MS (ESI) calcd. for $C_{26}H_{20}F_2N_{10}$: 510.18 m/z, found, 511.30 $[M + H]^+$. $^1$H-NMR (300 MHz, DMSO-$d_6$) δ (ppm); 8.63-8.65 (m, 1H), 8.32-8.38 (m, 2H), 7.90-8.09 (m, 2H), 7.78-7.85 (m, 1H), 7.63-7.69 (m, 1H), 7.02-7.45 (m, 4H), 6.90-6.99 (m, 2H), 6.52-6.59 (m, 1H), 6.32-6.49 (m, 2H), 3.15-3.22 (m, 1H), 2.99-3.10 (m, 1H), 2.75-2.85 (m, 1H), 2.50-2.60 (m, 1H). $^{19}$F-NMR (282 MHz, DMSO-$d_6$) δ (ppm); −111.74. |
| 345 | MS (ESI) calcd. for $C_{29}H_{22}N_{10}$, 510.20 m/z, found, 511.10 $[M + H]^+$. $^1$H NMR (400 MHz, DMSO-$d_6$) δ (ppm); 8.32-8.35 (m, 1H), 8.36-8.38 (m, 1H), 8.03-8.07 (m, 1H), 8.01-8.02 (m, 1H), 7.95-7.97 (m, 1H), 7.81-7.85 (m, 1H), 7.71-7.75 (m, 1H), 7.43-7.52 (m, 3H), 7.22-7.27 (m, 2H), 7.09-7.18 (m, 1H), 6.99-7.05 (m, 2H), 6.85-6.87 (m, 1H), 6.51-6.60 (m, 1H), 6.42-6.45 (m, 1H), 3.26-3.33 (m, 1H), 3.11-3.28 (m, 1H), 2.85-3.08 (m, 1H), 2.52-2.60 (m, 1H). |
| 352 | MS (ESI) calcd. for $C_{27}H_{23}N_{11}$, 501.21 m/z, found 502.15 $[M + H]^+$. $^1$H NMR (400 MHz, DMSO-$d_6$) δ (ppm); 8.44 (d, J = 8.5 Hz, 1H), 8.14 (s, 2H), 8.01-8.06 (m, 2H), 7.90 (s, 1H), 7.52 (d, J = 1.9 Hz, 1H), 7.31-7.35 (m, 1H), 7.21-7.25 (m, 2H), 6.92 (s, 2H), 6.43 (dd, J = 7.7, 4.8 Hz, 1H), 6.23 (t, J = 7.2 Hz, 1H), 3.18-3.25 (m, 1H), 2.98-3.06 (m, 1H), 2.74-2.82 (m, 1H), 2.45-2.49 (m, 1H), 1.92-1.98 (m, 1H), 0.88-0.92 (m, 2H), 0.72-0.77 (m, 2H). |
| 353 | MS (ESI) calcd. for $C_{28}H_{24}N_{10}O$, 516.21 m/z, found 517.35 $[M + H]^+$. $^1$H NMR (400 MHz, DMSO-$d_6$) δ (ppm); 8.36-8.40 (m, 2H), 8.32 (s, 1H), 8.02 (dd, J = 4.8, 1.8 Hz, 1H), 7.97 (d, J = 8.6 Hz, 1H), 7.81-7.82 (m, 1H), 7.55 (d, J = 1.8 Hz, 1H), 7.30-7.33 (m, 1H), 7.25-7.28 (m, 1H), 7.22-7.24 (m, 1H), 6.92 (s, 2H), 6.54-6.56 (m, 1H), 6.44 (dd, J = 7.7, 4.8 Hz, 1H), 6.31-6.36 (m, 1H), 5.80 (t, J = 7.6 Hz, 1H), 4.59-4.65 (m, 1H), 4.50-4.55 (m, 1H), 3.24-3.29 (m, 1H), 3.02-3.10 (m, 1H), 2.91-3.00 (m, 2H), 2.79-2.87 (m, 1H), 2.54-2.59 (m, 1H). |
| 354 | MS (ESI) calcd. for $C_{28}H_{24}N_{10}O$, 516.21 m/z, found 517.30 $[M + H]^+$. $^1$H NMR (400 MHz, DMSO-$d_6$) δ (ppm); 8.36-8.40 (m, 2H), 8.31 (s, 1H), 8.02 (dd, J = 4.9, 1.9 Hz, 1H), 7.97 (d, J = 8.5 Hz, 1H), 7.82 (d, J = 1.6 Hz, 1H), 7.55 (d, J = 1.9 Hz, 1H), 7.29-7.34 (m, 1H), 7.26-7.28 (m, 1H), 7.24-7.25 (m, 1H), 6.92 (s, 2H), 6.54-6.57 (m, 1H), 6.43 (dd, J = 7.7, 4.8 Hz, 1H), 6.31-6.36 (m, 1H), 5.80 (t, J = 7.5 Hz, 1H), 4.60-4.65 (m, 1H), 4.51-4.56 (m, 1H), 3.23-3.30 (m, 1H), 3.03-3.11 (m, 1H), 2.92-2.99 (m, 2H), 2.78-2.87 (m, 1H), 2.54-2.59 (m, 1H). |
| 362 | MS (ESI) calcd. for $C_{28}H_{22}F_2N_{10}$: 536.20 m/z, found, 537.30 $[M + H]^+$. $^1$H-NMR (400 MHz, DMSO-$d_6$) δ (ppm); 8.31-8.44 (m, 2H), 8.10 (d, J = 8.8 Hz, 1H), 7.99-8.06 (m, 1H), 7.97 (d, J = 1.7 Hz, 1H), 7.81-7.83 (m, 1H), 7.54 (s, 1H), 7.29-7.37 (m, 1H), 7.18-7.28 (m, 2H), 6.93 (s, 2H), 6.50-6.58 (m, 1H), 6.37-6.48 (m, 1H), 6.31 (t, J = 7.0 Hz, 1H), 3.20-3.30 (m, 1H), 2.97-3.12 (m, 2H), 2.75-2.88 (m, 1H), 2.53-2.60 (m, 1H), 1.99-2.12 (m, 1H), 1.85-1.99 (m, 1H). $^{19}$F-NMR (376 MHz, DMSO-$d_6$) δ (ppm); −127.24, −120.28. |

Example 77: (S)—N-(5-(2-(2-aminopyridin-3-yl)-5-(1H-pyrazol-1-yl)-3H-imidazo[4,5-b]pyridin-3-yl)-2,3-dihydro-1H-inden-1-yl)-2-(oxetan-3-yloxy)isonicotinamide (Compound 164)

Compound 164

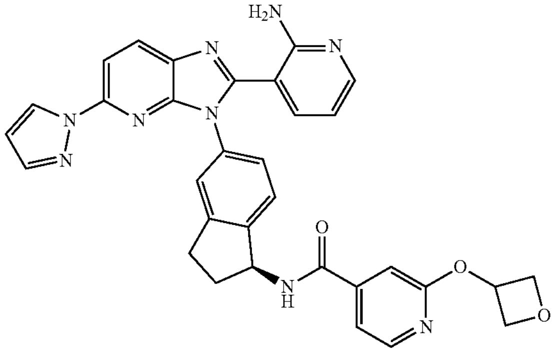

Synthetic Route:

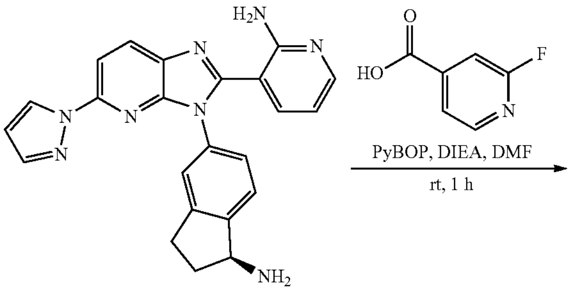

Compound 2

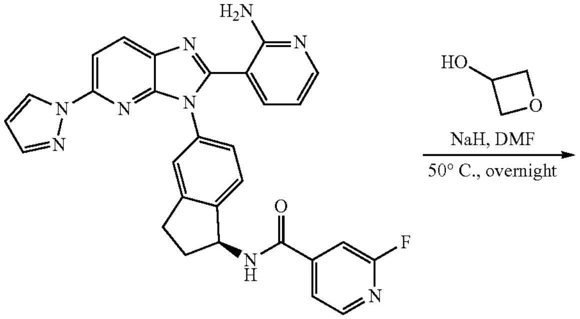

Intermediate 164-1

-continued

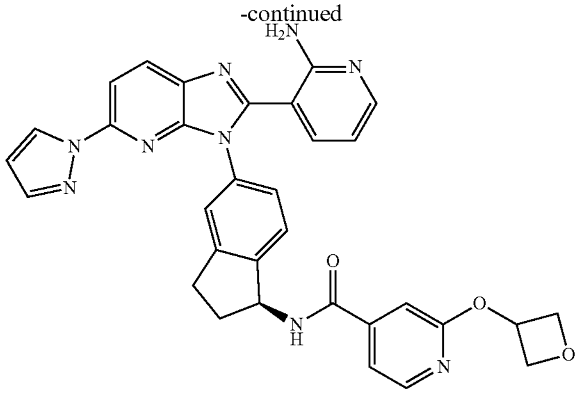

Compound 164

Step 1: (S)—N-(5-(2-(2-aminopyridin-3-yl)-5-(1H-pyrazol-1-yl)-3H-imidazo[4,5-b]pyridin-3-yl)-2,3-dihydro-1H-inden-1-yl)-2-(oxetan-3-yloxy)isonicotinamide (Compound 164)

To a solution of oxetan-3-ol (43.5 mg, 0.588 mmol) in DMF (4 mL) was added NaH (29.4 mg, 1.23 mmol, 60% purity) and the reaction mixture was stirred for 0.5 h at room temperature. To the mixture was added (S)—N-(5-(2-(2-aminopyridin-3-yl)-5-(1H-pyrazol-1-yl)-3H-imidazo[4,5-b]pyridin-3-yl)-2,3-dihydro-1H-inden-1-yl)-2-fluoroisonicotinamide (Intermediate 164-1) (130 mg, 0.245 mmol). The resulting mixture was stirred at 50° C. overnight. The reaction was quenched with $H_2O$ (50 mL). The resulting mixture was extracted with ethyl acetate (3×50 mL). The organic layers were combined, dried over $Na_2SO_4$, and concentrated under vacuum. The resulting mixture was purified by Prep-HPLC on a XBridge Prep OBD C18 Column using a gradient of acetonitrile in water (+0.05% TFA) to afford (S)—N-(5-(2-(2-aminopyridin-3-yl)-5-(1H-pyrazol-1-yl)-3H-imidazo[4,5-b]pyridin-3-yl)-2,3-dihydro-1H-inden-1-yl)-2-(oxetan-3-yloxy)isonicotinamide (Compound 164) (9.0 mg, 6% yield) as an off-white solid: MS (ESI) calcd. for $C_{32}H_{27}N_9O_3$: 585.22 m/z, found, 586.20 $[M+H]^+$. $^1H$ NMR (300 MHz, DMSO-$d_6$) δ (ppm); 8.31-8.43 (m, 2H), 8.19-8.30 (m, 1H), 8.01-8.06 (m, 1H), 7.91-8.00 (m, 1H), 7.75-7.85 (m, 1H), 7.17-7.55 (m, 6H), 6.52-6.59 (m, 1H), 6.42-6.51 (m, 1H), 5.45-5.69 (m, 2H), 4.82-5.01 (m, 2H), 4.47-4.62 (m, 2H), 3.00-3.15 (m, 1H), 2.78-2.99 (m, 1H), 2.54-2.64 (m, 1H), 1.98-2.21 (m, 1H). (TFA salt).

The following compounds were prepared analogous to the synthetic preparation in Example 77 (Compound 164).

TABLE 10

Characterization data of compounds prepared analogously to compound 164.

| Cpd ID | Characterization Data |
|---|---|
| 179 | MS (ESI) calcd. for $C_{33}H_{30}N_{10}O_2$: 598.25 m/z, found, 599.30 $[M + H]^+$. $^1H$ NMR (300 MHz, DMSO-$d_6$) δ (ppm); 8.09-8.40 (m, 3H), 7.87-8.01 (m, 1H), 7.76-7.86 (m, 1H), 7.68-7.77 (m, 1H), 7.23-7.41 (m, 4H), 7.09-7.22 (m, 2H), 6.43-6.57 (m, 2H), 5.38-5.56 (m, 1H), 5.07-5.23 (m, 1H), 3.88-4.11 (m, 2H), 3.41-3.61 (m, 2H), 2.91-3.07 (m, 1H), 2.71-2.90 (m, 1H), 2.42-2.49 (m, 3H), 2.31-2.48(m, 1H), 1.83-2.15 (m, 1H). (formic acid salt) |

Example 78: (S)-3-(3-(1-(3-benzyl-4H-1,2,4-triazol-4-yl)-2,3-dihydro-1H-inden-5-yl)-5-(1H-pyrazol-1-yl)-3H-imidazo[4,5-b]pyridin-2-yl)pyridin-2-amine (Compound 169)

Compound 169

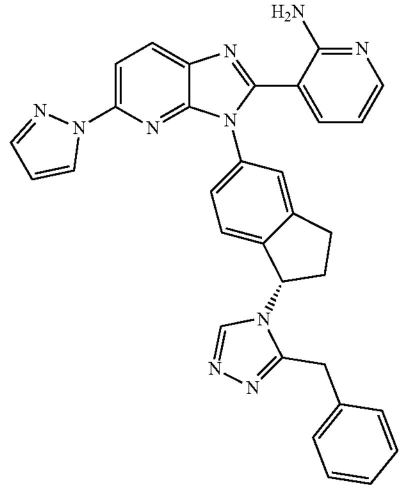

Synthetic Route:

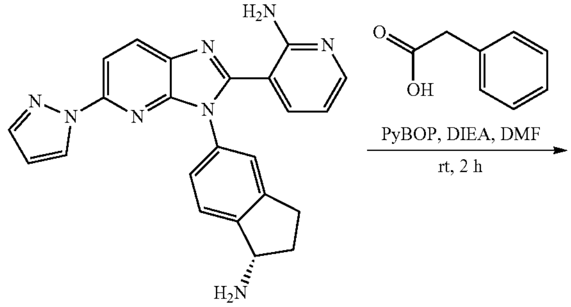

Compound 2

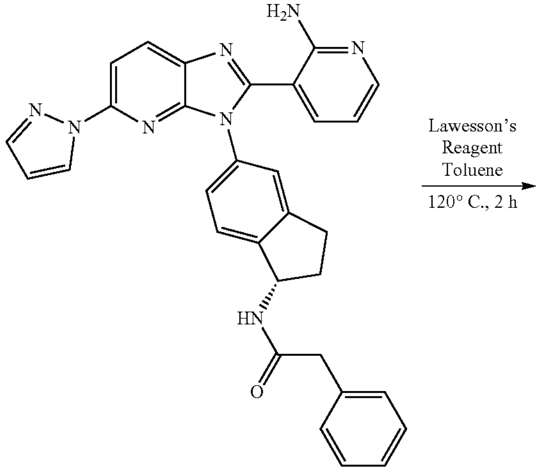

-continued

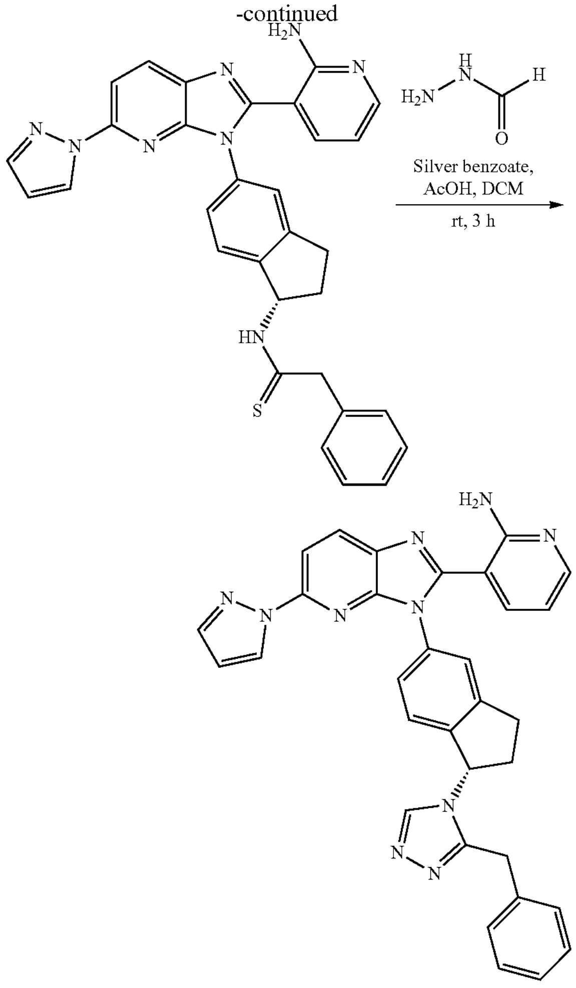

Compound 169

Step 1: (S)—N-(5-(2-(2-aminopyridin-3-yl)-5-(1H-pyrazol-1-yl)-3H-imidazo[4,5-b]pyridin-3-yl)-2,3-dihydro-1H-inden-1-yl)-2-phenylacetamide A solution of (S)-3-(3-(1-amino-2,3-dihydro-1H-inden-5-yl)-5-(1H-pyrazol-1-yl)-3H-imidazo[4,5-b]pyridin-2-yl) pyridin-2-amine (Compound 2) (400 mg, 0.979 mmol), phenylacetic acid (160 mg, 1.18 mmol), PyBOP (611.5 mg, 1.175 mmol) and DIEA (316.4 mg, 2.447 mmol) in DMF (4 mL) was stirred for 2 h at room temperature. The reaction mixture was purified by reverse-phase flash chromatography on C18 silica gel using a gradient of acetonitrile in water (+0.05% $NH_4HCO_3$) to afford (S)—N-(5-(2-(2-aminopyridin-3-yl)-5-(1H-pyrazol-1-yl)-3H-imidazo[4,5-b]pyridin-3-yl)-2,3-dihydro-1H-inden-1-yl)-2-phenylacetamide (300 mg, 58% yield) as a yellow solid: MS (ESI) calcd. for $C_{31}H_{26}N_8O$, 526.22 m/z, found 527.30 $[M+H]^+$.

Step 2: (S)—N-(5-(2-(2-aminopyridin-3-yl)-5-(1H-pyrazol-1-yl)-3H-imidazo[4,5-b]pyridin-3-yl)-2,3-dihydro-1H-inden-1-yl)-2-phenylethanethioamide A solution of (S)—N-(5-(2-(2-aminopyridin-3-yl)-5-(1H-pyrazol-1-yl)-3H-imidazo[4,5-b]pyridin-3-yl)-2,3-dihydro-1H-inden-1-yl)-2-phenylacetamide (400 mg, 0.760 mmol) and Lawesson's Reagent (338 mg, 0.836 mmol) in toluene (4 mL) was stirred for 2 h at 120° C. The resulting mixture was concentrated under reduced pressure. The residue was purified by reverse-phase flash chromatography on C18 silica gel using a gradient of acetonitrile in water (+0.05% $NH_4HCO_3$) to afford (S)—N-(5-(2-(2-aminopyridin-3-yl)-5-(1H-pyrazol-1-yl)-3H-imidazo[4,5-b]pyridin-3-yl)-2,3-dihydro-1H-inden-1-yl)-2-phenylethanethioamide (200 mg, 49% yield) as a yellow solid: MS (ESI) calcd. for $C_{31}H_{26}N_8S$, 542.20 m/z, found 543.15 [M+H].

Step 3: (S)-3-(3-(1-(3-benzyl-4H-1,2,4-triazol-4-yl)-2,3-dihydro-1H-inden-5-yl)-5-(1H-pyrazol-1-yl)-3H-imidazo[4,5-b]pyridin-2-yl)pyridin-2-amine (Compound 169)

A solution of (S)—N-(5-(2-(2-aminopyridin-3-yl)-5-(1H-pyrazol-1-yl)-3H-imidazo[4,5-b]pyridin-3-yl)-2,3-dihydro-1H-inden-1-yl)-2-phenylethanethioamide (500 mg, 0.921 mmol), N-formylhydrazine (66.4 mg, 1.11 mmol), silver benzoate (422 mg, 1.84 mmol) and AcOH (166 mg, 2.76 mmol) in DCM (5 mL) was stirred for 3 h at room temperature. The resulting mixture was concentrated under reduced pressure. The residue was purified by Prep-HPLC on a XSelect CSH OBD Column using a gradient of acetonitrile in water (+0.1% formic acid) to afford (S)-3-(3-(1-(3-benzyl-4H-1,2,4-triazol-4-yl)-2,3-dihydro-1H-inden-5-yl)-5-(1H-pyrazol-1-yl)-3H-imidazo[4,5-b]pyridin-2-yl)pyridin-2-amine (Compound 169) (6.9 mg, 1.4% yield) as a white solid: MS (ESI) calcd. for $C_{32}H_{26}N_{11}$, 550.23 m/z, found 551.20 $[M+H]^+$. $^1H$ NMR (300 MHz, DMSO-$d_6$) δ (ppm); 8.31-8.34 (m, 3H), 7.97-7.99 (m, 2H), 7.78-7.79 (m, 1H), 7.46-7.47 (m, 1H), 7.15-7.30 (m, 7H), 6.76-6.79 (m, 1H), 6.52-6.53 (m, 1H), 6.40-6.41 (m, 1H), 5.88-5.90 (m, 1H), 4.21-4.25 (m, 2H), 3.02-3.04 (m, 1H), 2.88-2.91 (m, 1H), 2.43-2.44 (m, 1H), 1.93-1.96 (m, 1H).

The following compounds were prepared analogous to the synthetic preparation in Example 78 (Compound 169).

Example 79: (S)—N-(5-(2-(2-aminopyridin-3-yl)-5-(1H-pyrazol-1-yl)-3H-imidazo[4,5-b]pyridin-3-yl)-2,3-dihydro-1H-inden-1-yl)-2-(prop-1-yn-1-yl)isonicotinamide (Compound 171)

Compound 171

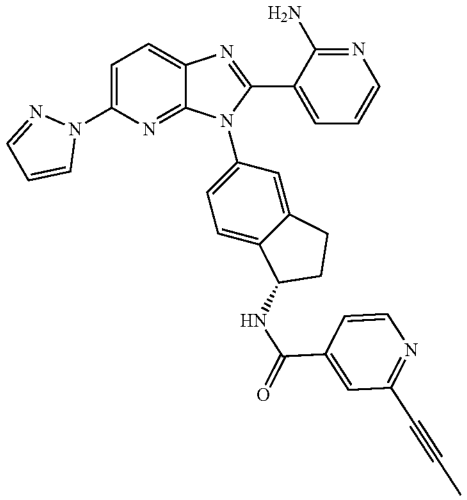

TABLE 11

Characterization data of compounds prepared analogously to compound 169.

| Cpd ID | Characterization Data |
|---|---|
| 178 | MS (ESI) calcd. for $C_{31}H_{24}N_{10}$, 536.22 m/z, found 537.15 $[M + H]^+$. $^1H$ NMR (300 MHz, DMSO-$d_6$) δ (ppm); 8.52-8.53 (m, 1H), 8.39-8.40 (m, 2H), 7.98-8.00 (m, 2H), 7.81-7.82 (m, 1H), 7.68-7.69 (m, 2H), 7.59-7.65 (m, 3H), 7.57-7.58 (m, 1H), 7.23-7.32 (m, 3H), 6.56-6.57 (m, 1H), 6.46-6.47 (m, 1H), 5.89-5.92 (m, 1H), 3.03-3.05 (m, 2H), 2.77-2.80 (m, 1H), 2.51-2.52 (m, 1H). (formic acid salt) |
| 222 | MS (ESI) calcd. for $C_{30}H_{26}N_{12}$: 554.24 m/z, found, 555.15 $[M + H]^+$. $^1H$ NMR (300 MHz, DMSO-$d_6$) δ (ppm); 8.35-8.58 (m, 2H), 8.27-8.34 (m, 1H), 8.00-8.12 (m, 1H), 7.87-8.00 (m, 1H), 7.76-7.85 (m, 1H), 7.54-7.59 (m, 1H), 7.27-7.41 (m, 1H), 7.18-7.27 (m, 2H), 7.01-7.10 (m, 1H), 6.53-6.62 (m, 1H), 6.32-6.49 (m, 1H), 6.05-6.16 (m, 1H), 5.88-6.04 (m, 1H), 4.36-4.38 (m, 2H), 3.79 (s, 3H), 3.07-3.21 (m, 1H), 2.84-3.06 (m, 1H), 2.58-2.79 (m, 1H), 1.98-2.13 (m, 1H) |
| 228 | MS (ESI) calcd. for $C_{30}H_{26}N_{12}$: 554.24 m/z, found: 555.15 $[M + H]^+$. $^1H$ NMR (300 MHz, DMSO-$d_6$) δ (ppm): 8.32-8.44 (m, 2H), 8.19-8.30 (m, 1H), 7.91-8.07 (m, 2H), 7.77-7.86 (m, 1H), 7.44-7.67 (m, 2H), 7.17-7.38 (m, 3H), 6.83-7.04 (m, 2H), 6.56-6.62 (m, 1H), 6.36-6.51 (m, 1H), 5.84-6.01 (m, 1H), 3.99-4.10 (m, 2H), 3.69-3.88 (m, 3H), 3.06-3.25 (m, 1H), 2.87-3.05 (m, 1H), 2.56-2.71 (m, 1H), 1.95-2.21 (m, 1H) |
| 384 | MS (ESI) calcd. for $C_{29}H_{26}N_{10}$: 514.23 m/z, found, 515.20 $[M + H]^+$. $^1H$ NMR (300 MHz, DMSO-$d_6$) δ (ppm); 8.58-8.65 (m, 1H), 8.38-8.49 (m, 2H), 7.99-8.16 (m, 1H), 7.89-7.98 (m, 1H), 7.72-7.88 (m, 1H), 7.64-7.71 (m, 1H), 7.57-7.63 (m, 1H), 7.46-7.56 (m, 1H), 7.35-7.46 (m, 1H), 7.25-7.34 (m, 1H), 6.51-7.01 (m, 2H), 5.93-6.16 (m, 1H), 3.13-3.33 (m, 1H), 2.94-3.12 (m, 1H), 2.67-2.93 (m, 3H), 2.18-2.38 (m, 1H), 1.05-1.29 (m, 1H), 0.49-0.68 (m, 2H), 0.25-0.36 (m, 2H). (TFA salt) |

Synthetic Route:

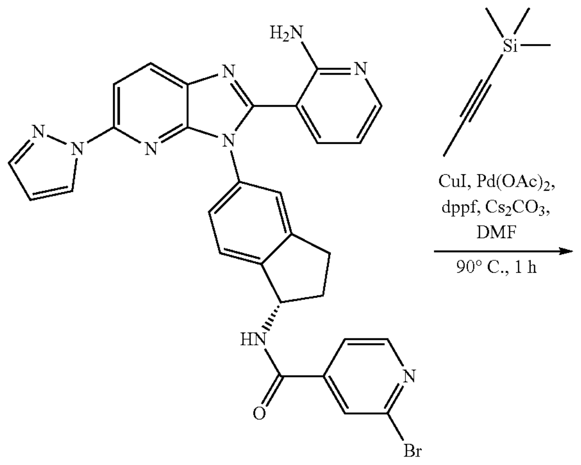

Intermediate 171-1

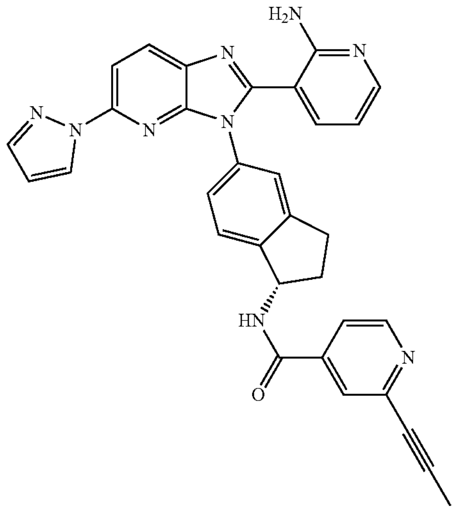

Compound 171

Step 1: Synthesis of (S)—N-(5-(2-(2-aminopyridin-3-yl)-5-(1H-pyrazol-1-yl)-3H-imidazo[4,5-b]pyridin-3-yl)-2,3-dihydro-1H-inden-1-yl)-2-(prop-1-yn-1-yl)isonicotinamide (Compound 171)

A mixture of (S)—N-(5-(2-(2-aminopyridin-3-yl)-5-(1H-pyrazol-1-yl)-3H-imidazo[4,5-b]pyridin-3-yl)-2,3-dihydro-1H-inden-1-yl)-2-bromoisonicotinamide (Intermediate 171-1) (100 mg, 0.190 mmol), trimethyl(prop-1-yn-1-yl)silane (31.9 mg, 0.285 mmol), CuI (36.1 mg, 0.190 mmol), $Pd(OAc)_2$ (6.4 mg, 0.028 mmol), dppf (16 mg, 0.028 mmol) and $Cs_2CO_3$ (185 mg, 0.570 mmol) in DMF (3 mL) was stirred for 1 h at 90° C. under $N_2$. The reaction was quenched by the addition of water (100 mL) at room temperature. The resulting mixture was extracted with ethyl acetate (3×50 mL) and the combined organic layers were dried over anhydrous sodium sulfate, filtered and concentrated in vacuo. The residue was purified by Prep-HPLC on a XBridge Prep OBD C18 Column using a gradient of acetonitrile in water (+10 mmol/L TFA) to afford (S)—N-(5-(2-(2-aminopyridin-3-yl)-5-(1H-pyrazol-1-yl)-3H-imidazo[4,5-b]pyridin-3-yl)-2,3-dihydro-1H-inden-1-yl)-2-(prop-1-yn-1-yl)isonicotinamide (Compound 171, trifluoroacetic acid salt) (31.5 mg, 39% yield) as an off-white solid: MS (ESI) calcd. for $C_{32}H_{25}N_9O$, 551.22 m/z, found, 552.20 $[M+H]^+$. $^1H$ NMR (300 MHz, DMSO-$d_6$+$D_2O$) δ (ppm); 8.65-8.69 (m, 1H), 8.38-8.45 (m, 1H), 8.33-8.38 (m, 1H), 7.95-8.05 (m, 2H), 7.85-7.88 (m, 1H), 7.79-7.83 (m, 2H), 7.69-7.77 (m, 1H), 7.43-7.48 (m, 1H), 7.36-7.43 (m, 1H), 7.27-7.36 (m, 1H), 6.78-6.88 (m, 1H), 6.52-6.60 (m, 1H), 5.51-5.63 (m, 1H), 3.00-3.10 (m, 1H), 2.85-3.00 (m, 1H), 2.55-2.63 (m, 1H), 2.00-2.15 (m, 4H).

Intermediate 171-1: (S)—N-(5-(2-(2-aminopyridin-3-yl)-5-(1H-pyrazol-1-yl)-3H-imidazo[4,5-b]pyridin-3-yl)-2,3-dihydro-1H-inden-1-yl)-2-bromoisonicotinamide Intermediate 171-1

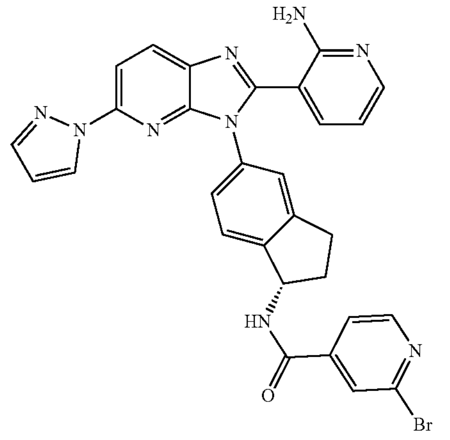

Synthetic Route:

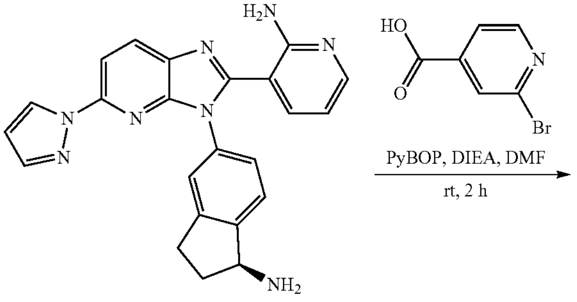

Compound 2

-continued

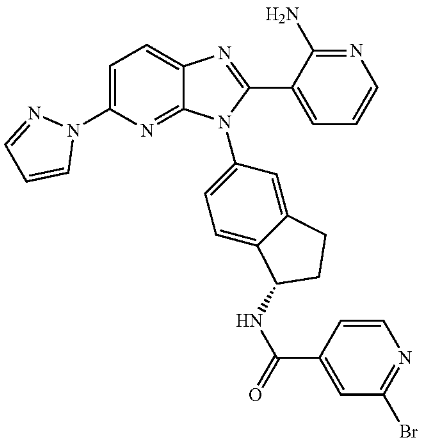

Intermediate 171-1

Step 1: Synthesis of (S)—N-(5-(2-(2-aminopyridin-3-yl)-5-(1H-pyrazol-1-yl)-3H-imidazo[4,5-b]pyridin-3-yl)-2,3-dihydro-1H-inden-1-yl)-2-bromoisonicotinamide (Intermediate 171-1)

To a solution of 2-bromoisonicotinic acid (250 mg, 1.24 mmol), (S)-3-(3-(1-amino-2,3-dihydro-1H-inden-5-yl)-5-(1H-pyrazol-1-yl)-3H-imidazo[4,5-b]pyridin-2-yl)pyridin-2-amine (Compound 2) (505.5 mg, 1.238 mmol) and DIEA (479.9 mg, 3.714 mmol) in DMF (8 mL) was added PyBOP (644 mg, 1.238 mmol) at 0° C. The resulting mixture was stirred for 2 h at room temperature. The product was precipitated by the addition of water (80 mL). The precipitated solids were collected by filtration and washed with water (3×10 mL) to afford (S)—N-(5-(2-(2-aminopyridin-3-yl)-5-(1H-pyrazol-1-yl)-3H-imidazo[4,5-b]pyridin-3-yl)-2,3-dihydro-1H-inden-1-yl)-2-bromoisonicotinamide (Intermediate 171-1) (600 mg, 82% yield) as a brown solid: MS (ESI) calcd. for $C_{29}H_{22}BrN_9O$, 591.11 m/z, found, 592.20 $[M+H]^+$.

The following compounds were prepared analogous to the synthetic preparation in Example 79 (Compound 171).

TABLE 12

Characterization data of compounds prepared analogously to compound 171.

| Cpd ID | Characterization Data |
|---|---|
| 180 | MS (ESI) calcd. for $C_{32}H_{25}N_9O$, 551.22 m/z, found 552.10 $[M + H]^+$. $^1H$ NMR (300 MHz, DMSO-$d_6$) δ (ppm); 8.85-8.93 (m, 1H), 8.32-8.40 (m, 2H), 8.18-8.30 (m, 1H), 8.00-8.08 (m, 1H), 7.95-8.00 (m, 1H), 7.80-7.83 (m, 1H), 7.50-7.60 (m, 1H), 7.49 (s, 1H), 7.20-7.30 (m, 3H), 7.05-7.20 (m, 2H), 6.55-6.58 (m, 1H), 6.40-6.48 (m, 1H), 6.20-6.40 (m, 1H), 3.10-3.25 (m, 2H), 2.55-2.65 (m, 1H), 2.30-2.45 (m, 4H). (formic acid salt). |
| 181 | MS (ESI) calcd. for $C_{35}H_{27}N_{11}O$, 617.24 m/z, found 618.10 $[M + H]^+$. $^1H$ NMR (300 MHz, DMSO-$d_6$) δ (ppm); 9.08-9.19 (m, 1H), 8.63-8.72 (m, 1H), 8.30-8.47 (m, 2H), 7.89-8.06 (m, 3H), 7.80-7.88 (m, 1H), 7.69-7.78 (m, 1H), 7.57-7.67 (m, 1H), 7.49-7.56 (m, 1H), 7.41-7.48 (m, 1H), 7.09-7.26 (m, 2H), 6.88-7.06 (m, 2H), 6.38-6.54 (m, 3H), 5.58-5.60 (m, 1H), 3.78 (s, 3H), 2.83-3.12 (m, 2H), 2.53-2.66 (m, 1H), 1.97-2.14 (m, 1H). (formic acid salt) |
| 182 | .: MS (ESI) calcd. for $C_{35}H_{27}N_{11}O$, 617.24 m/z, found, 618.35 $[M + H]^+$. $^1H$ NMR (400 MHz, DMSO-$d_6$) δ (ppm); 8.75-8.77 (m, 1H), 8.35-8.38 (m, 2H), 8.08-8.09 (m, 1H), 8.01-8.02 (m, 2H), 7.81-7.97 (m, 3H), 7.41-7.43 (m, 2H), 7.26-7.32 (m, 2H), 6.44-6.62 (m, 3H), 5.61-5.66 (m, 1H), 3.89 (s, 3H), 2.95-3.15 (m, 2H), 2.49-2.58 (m, 1H), 2.05-2.19 (m, 1H). |
| 209 | MS (ESI) calcd. for $C_{37}H_{27}N_9O$, 613.23 m/z, found 614.15 $[M + H]^+$. $^1H$ NMR (300 MHz, DMSO-$d_6$ + $D_2O$) δ (ppm); 8.81-8.89 (m, 1H), 8.51-8.58 (m, 1H), 8.42-8.50 (m, 1H), 8.11-8.19 (m, 1H), 8.01-8.10 (m, 2H), 7.83-7.94 (m, 3H), 7.62-7.71 (m, 3H), 7.51-7.60 (m, 4H), 7.45-7.50 (m, 1H), 7.36-7.44 (m, 1H), 6.88-6.97 (m, 1H), 6.56-6.63 (m, 1H), 5.68-5.75 (m, 1H), 3.07-3.20 (m, 1H), 2.91-3.06 (m, 1H), 2.58-2.69 (m, 1H), 2.07-2.20 (m, 1H). (TFA salt) |
| 226 | MS (ESI) calcd. for $C_{33}H_{27}F_2N_7O$, 575.22 m/z, found 576.30 $[M + H]^+$. $^1H$ NMR (300 MHz, DMSO-$d_6$) δ (ppm); 9.14-9.15 (m, 1H), 8.43-8.44 (m, 1H), 8.00-8.39 (m, 2H), 7.82-7.85 (m, 1H), 7.67-7.70 (m, 1H), 7.41-7.49 (m, 3H), 7.27-7.29 (m, 1H), 6.84-7.21 (m, 1H), 6.50-6.79 (m, 1H), 5.64-5.66 (m, 1H), 3.31-3.34 (m, 1H), 2.90-3.04 (m, 2H), 2.51-2.52 (m, 1H), 2.31-2.34 (m, 2H), 2.00-2.19 (m, 3H), 1.89-1.99 (m, 2H). $^{19}F$ NMR (282 MHz, DMSO-$d_6$) δ (ppm); −116.08, −73.26. (TFA salt) |
| 265 | MS (ESI) calcd. for $C_{30}H_{25}N_7O$, 499.21 m/z, found 500.15 $[M + H]^+$. $^1H$ NMR (300 MHz, DMSO-$d_6$ + $D_2O$) δ (ppm); 8.89-9.03 (m, 1H), 8.11-8.23 (m, 2H), 8.02-8.10 (m, 1H), 7.15-7.52 (m, 6H), 6.41-6.53 (m, 1H), 5.59-5.68 (m, 1H), 2.89-3.18 (m, 2H), 2.56-2.64 (m, 1H), 2.45-2.51 (m, 3H), 2.01-2.21 (m, 4H). |
| 327 | MS (ESI) calcd. for $C_{32}H_{28}N_8O_2$, 556.23 m/z, found 557.15 $[M + H]^+$. $^1H$ NMR (300 MHz, DMSO-$d_6$) δ (ppm); 8.93-9.02 (m, 1H), 8.11-8.38 (m, 2H), 7.89-8.10 (m, 1H), 7.14-7.57 (m, 6H), 6.37-6.56 (m, 1H), 5.55-5.72 (m, 1H), 4.11 (s, 2H), 2.81-3.15 (m, 2H), 2.56-2.65 (m, 1H), 2.49 (s, 3H), 2.01-2.21 (m, 1H), 1.86 (s, 3H). |
| 341 | MS (ESI) calcd. for $C_{32}H_{24}N_8O_2$: 552.20 m/z, found, 553.30 $[M + H]^+$. $^1H$ NMR (300 MHz, DMSO-$d_6$ + $D_2O$) δ (ppm); 8.91-9.15 (m, 1H), 8.32-8.48 (m, 2H), 8.25-8.27 (m, 1H), 8.04-8.19 (m, 1H), 7.81-7.92 (m, 2H), 7.61-7.72 (m, 2H), 7.41-7.51 (m, 3H), 7.31-7.36 (m, 1H), 6.79-6.89 (m, 1H), 5.62-5.72 (m, 1H), 3.03-3.16 (m, 1H), 2.82-2.99 (m, 1H), 2.63-2.69 (m, 4H), 2.03-2.18 (m, 1H). |

TABLE 12-continued

| Cpd ID | Characterization Data |
|---|---|
| | Characterization data of compounds prepared analogously to compound 171. |
| 404 | MS (ESI) calcd. for $C_{29}H_{21}F_2N_7O$, 521.18 m/z, found, 522.30 $[M + H]^+$. $^1H$ NMR (300 MHz, DMSO-$d_6$ + $D_2O$) δ (ppm); 9.12-9.16 (m, 1H), 8.44-8.47 (m, 1H), 8.26-8.28 (m, 1H), 8.03-8.07 (m, 1H), 7.82-7.85 (m, 1H), 7.74-7.76 (m, 1H), 7.61-7.63 (m, 1H), 7.44-7.47 (m, 2H), 7.29-7.31 (m, 1H), 6.84-7.19 (m, 1H), 6.74-6.78 (m, 1H), 5.61-5.69 (m, 1H), 4.32 (s, 1H), 3.01-3.12 (m, 1H), 2.86-2.99 (m, 1H), 2.57-2.61 (m, 1H), 2.02-2.13 (m, 1H). $^{19}F$ NMR (282 MHz, DMSO-$d_6$) δ (ppm); −74.06, −116.08. (TFA salt) |
| 405 | MS (ESI) calcd. for $C_{30}H_{23}F_2N_7O$, 535.19 m/z, found 536.35 $[M + H]^+$. $^1H$ NMR (400 MHz, DMSO-$d_6$) δ (ppm); 9.25-9.35 (m, 1H), 9.14 (s, 1H), 8.42-8.50 (m, 1H), 8.10-8.20 (m, 1H), 8.00-8.06 (m, 1H), 7.83-7.90 (m, 1H), 7.40-7.50 (m, 2H), 7.35-7.40 (m, 1H), 7.25-7.35 (m, 1H), 7.20-7.35 (m, 1H), 6.90-7.20 (m, 1H), 6.40-6.50 (m, 1H), 5.60-5.75 (m, 1H), 3.00-3.15 (m, 1H), 2.85-3.00 (m, 1H), 2.55-2.65 (m, 1H), 2.00-2.20 (m, 4H). $^{19}F$ NMR (376 MHz, DMSO-$d_6$) δ (ppm); −116.06. (formic acid salt) |
| 406 | MS (ESI) calcd. for $C_{32}H_{25}F_2N_7O$, 561.21 m/z, found 562.40 $[M + H]^+$. $^1H$ NMR (400 MHz, DMSO-$d_6$) δ (ppm); 9.25-9.35 (m, 1H), 9.14 (s, 1H), 8.42-8.50 (m, 1H), 8.10-8.20 (m, 1H), 8.00-8.06 (m, 1H), 7.83-7.90 (m, 1H), 7.40-7.45 (m, 2H), 7.35-7.40 (m, 1H), 7.25-7.35 (m, 1H), 7.20-7.25 (m, 1H), 6.90-7.20 (m, 1H), 6.40-6.50 (m, 1H), 5.50-5.60 (m, 1H), 3.00-3.15 (m, 1H), 2.88-3.00 (m, 1H), 2.55-2.65 (m, 1H), 2.00-2.15 (m, 1H), 1.50-1.60 (m, 1H), 0.85-0.93 (m, 2H), 0.73-0.80 (m, 2H). $^{19}F$ NMR (376 MHz, DMSO-$d_6$) δ (ppm); −116.07. (formic acid salt) |
| 407 | MS (ESI) calcd. for $C_{32}H_{28}F_2N_8O$, 578.24 m/z, found, 579.35 $[M + H]^+$. $^1H$ NMR (300 MHz, DMSO-$d_6$) δ (ppm); 9.30-9.32 (m, 1H), 8.97-9.13 (m, 1H), 8.44-8.52 (m, 1H), 8.12-8.16 (m, 1H), 7.97-8.07 (m, 1H), 7.76-7.85 (m, 1H), 7.15-7.69 (m, 6H), 6.83-7.08 (m, 1H), 6.45-6.55 (m, 1H), 5.64-5.80 (m, 1H), 3.46-3.56 (m, 2H), 2.85-3.12 (m, 2H), 2.23-2.49 (m, 7H), 2.03-2.20 (m, 1H). $^{19}F$-NMR (282 MHz, DMSO-$d_6$) δ (ppm); −116.04. |
| 408 | MS (ESI) calcd. for $C_{32}H_{25}F_2N_7O_2$, 577.20 m/z, found, 578.30 $[M + H]^+$. $^1H$ NMR (300 MHz, DMSO-$d_6$ + $D_2O$) δ (ppm); 9.14 (s, 1H), 8.44-8.46 (m, 1H), 8.10-8.19 (m, 1H), 8.00-8.01 (m, 1H), 7.82-7.85 (m, 1H), 7.51-7.54 (m, 1H), 7.41-7.44 (m, 1H), 7.31-7.37 (m, 1H), 7.20-7.29 (m, 2H), 6.84-6.85 (m, 1H), 6.42-6.47 (m, 1H), 5.62-5.67 (m, 1H), 4.78-4.83 (m, 2H), 4.58-4.62 (m, 2H), 4.13-4.18 (m, 1H), 2.90-3.06 (m, 2H), 2.52-2.59 (m, 1H), 2.06-2.12 (m, 1H). $^{19}F$ NMR (282 MHz, DMSO-$d_6$ + $D_2O$) δ (ppm); −116.06. |
| 409 | MS (ESI) calcd. for $C_{31}H_{25}F_2N_7O_2$: 565.20 m/z, found, 566.20 $[M + H]^+$. $^1H$ NMR (400 MHz, DMSO-$d_6$) δ (ppm); 9.04-9.15 (m, 1H), 8.38-8.45 (m, 1H), 8.14-8.26 (m, 1H), 7.94-8.12 (m, 1H), 7.81-7.92 (m, 1H), 7.52-7.64 (m, 1H), 7.40-7.46 (m, 1H), 7.31-7.39 (m, 2H), 7.16-7.28 (m, 1H), 6.80-7.14 (m, 1H), 6.44-6.58 (m, 1H), 5.57-5.67 (m, 1H), 4.28-4.39 (m, 2H), 3.27-3.40 (m, 3H), 3.01-3.14 (m, 1H), 2.86-3.00 (m, 1H), 2.58-2.66 (m, 1H), 2.01-2.18 (m, 1H). $^{19}F$ NMR (376 MHz, DMSO-$d_6$) δ (ppm); −116.09. |
| 412 | MS (ESI) calcd. for $C_{31}H_{25}F_2N_7O$, 549.20 m/z, found, 550.30 $[M + H]^+$. $^1H$ NMR (300 MHz, DMSO-$d_6$ + $D_2O$) δ (ppm); 9.26-9.33 (m, 1H), 9.12-9.18 (m, 1H), 8.41-8.47 (m, 1H), 7.88-8.22 (m, 2H), 7.79-7.87 (m, 1H), 7.35-7.48 (m, 3H), 7.22-7.33 (m, 2H), 6.84-7.03 (m, 1H), 6.20-6.51 (m, 1H), 5.59-5.79 (m, 1H), 2.99-3.12 (m, 1H), 2.83-2.98 (m, 1H), 2.59-2.62 (m, 1H), 2.37-2.47 (m, 2H), 2.01-2.16 (m, 1H), 1.08-2.25 (m, 3H). $^{19}F$ NMR (282 MHz, DMSO-$d_6$) δ (ppm); −116.07. |
| 435 | MS (ESI) calcd. for $C_{32}H_{27}N_7O$, 525.23 m/z, found 526.35 $[M + H]^+$. $^1H$ NMR (400 MHz, DMSO-$d_6$) δ (ppm); 9.05-9.15 (m, 1H), 8.85-8.98 (m, 1H), 8.10-8.22 (m, 2H), 7.90-8.10 (m, 1H), 7.30-7.46 (m, 4H), 7.25-7.30 (m, 1H), 7.15-7.25 (m, 1H), 6.40-6.55 (m, 1H), 5.60-5.70 (m, 1H), 2.85-3.15 (m, 2H), 2.55-2.63 (m, 4H), 2.00-2.15 (m, 1H), 1.47-1.60 (m, 1H), 0.90-1.00 (m, 2H), 0.70-0.80 (m, 2H). |
| 453 | MS (ESI) calcd. for $C_{32}H_{25}F_2N_7O_2$: 577.20 m/z, found, 578.20 $[M + H]^+$. $^1H$ NMR (400 MHz, DMSO-$d_6$) δ (ppm); 9.02-9.20 (m, 1H), 8.37-8.54 (m, 1H), 8.11-8.29 (m, 1H), 7.95-8.08 (m, 1H), 7.77-7.91 (m, 1H), 7.51-7.65 (m, 1H), 7.40-7.50 (m, 1H), 7.30-7.39 (m, 2H), 7.18-7.28 (m, 1H), 6.80-7.17 (m, 1H), 6.40-6.60 (m, 1H), 5.60-5.75 (m, 1H), 5.49-5.59 (m, 1H), 4.46-4.70 (m, 2H), 2.86-3.15 (m, 3H), 2.70-2.85 (m, 1H), 2.61-2.68 (m, 1H), 2.02-2.18 (m, 1H). $^{19}F$ NMR (376 MHz, DMSO-$d_6$) δ (ppm); −116.07. |
| 454 | MS (ESI) calcd. for $C_{32}H_{25}F_2N_7O_2$: 577.20 m/z, found, 578.20 $[M + H]^+$. $^1H$ NMR (400 MHz, DMSO-$d_6$) δ (ppm); 9.27-9.40 (m, 1H), 9.02-9.20 (m, 1H), 8.37-8.54 (m, 1H), 8.11-8.29 (m, 1H), 7.96-8.08 (m, 1H), 7.77-7.91 (m, 1H), 7.51-7.65 (m, 1H), 7.41-7.64 (m, 1H), 7.30-7.39 (m, 2H), 7.18-7.28 (m, 1H), 6.80-7.17 (m, 1H), 6.40-6.60 (m, 1H), 5.60-5.75 (m, 1H), 5.49-5.59 (m, 1H), 4.46-4.70 (m, 2H), 2.86-3.15 (m, 3H), 2.70-2.85 (m, 1H), 2.61-2.68 (m, 1H), 2.02-2.18 (m, 1H). $^{19}F$ NMR (376 MHz, DMSO-$d_6$) δ (ppm); −116.05. |
| 459 | MS (ESI) calcd. for $C_{32}H_{24}F_2N_6O$, 546.58 m/z, found, 547.30 $[M + H]^+$. $^1H$ NMR (300 MHz, DMSO-$d_6$) δ (ppm); 8.19-8.22 (m, 1H), 7.94-8.05 (m, 2H), 7.81-7.84 (m, 1H), 7.73-7.76 (m, 1H), 7.47-7.59 (m, 2H), 7.36-7.42 (m, 2H), 7.22-7.24 (m, 1H), 6.73-6.81 (m, 1H), 5.55-5.62 (m, 1H), 3.02-3.11 (m, 1H), 2.82-2.95 (m, 1H), 2.55-2.57 (m, 1H), 2.01-2.11 (m, 1H), 1.51-1.59 (m, 1H), 0.91-0.94 (m, 2H), 0.72-0.75 (m, 2H). $^{19}F$ NMR (282 MHz, DMSO-$d_6$) δ (ppm); −73.88, −134.20, −137.77. (TFA salt) |
| 460 | MS (ESI) calcd. for $C_{34}H_{29}F_2N_7O$, 589.24 m/z, found 590.35 $[M + H]^+$. $^1H$ NMR (300 MHz, DMSO-$d_6$) δ (ppm); 9.14 (s, 1H), 8.40-8.55 (m, 1H), 8.10-8.30 (m, 1H), 7.90-8.10 (m, 1H), 7.75-7.90 (m, 1H), 7.40-7.50 (m, 2H), 7.35-7.40 (m, 1H), 7.15-7.35 (m, 2H), 6.80-7.10 (m, 1H), 6.45 (s, 1H), 5.55-5.75 (m, 1H), 2.85-3.15 (m, 3H), 2.60-2.65 (m, 1H), 1.85-2.20 (m, 3H), 1.50-1.80 (m, 6H). $^{19}F$ NMR (282 MHz, DMSO-$d_6$) δ (ppm); −116.05. |

Example 80: (S)-3-(3-(1-(3-methyl-4H-1,2,4-triazol-4-yl)-2,3-dihydro-1H-inden-5-yl)-5-(1H-pyrazol-1-yl)-3H-imidazo[4,5-b]pyridin-2-yl)pyridin-2-amine (Compound 217)

Compound 217

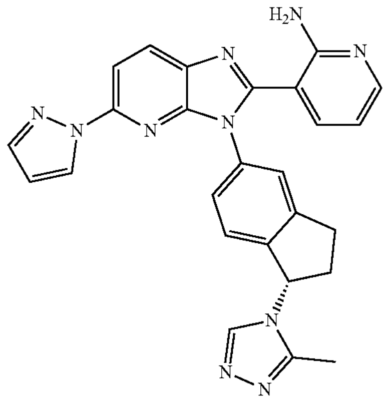

Synthetic Route:

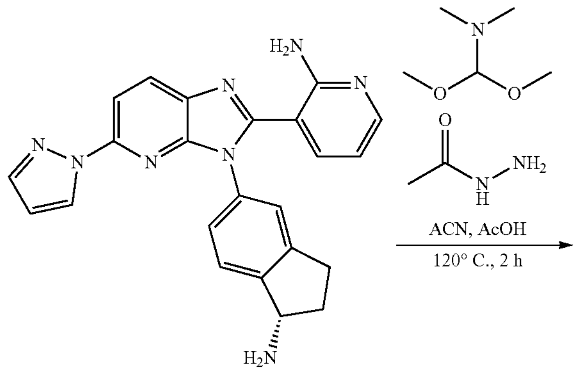

Compound 2

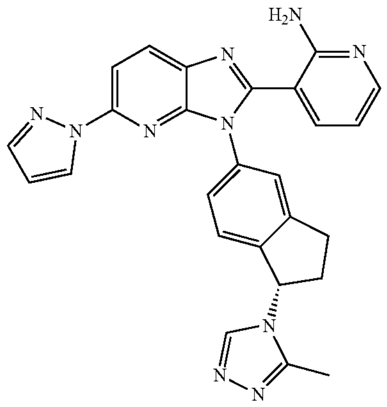

Compound 217

Step 1: (S)-3-(3-(1-(3-methyl-4H-1,2,4-triazol-4-yl)-2,3-dihydro-1H-inden-5-yl)-5-(1H-pyrazol-1-yl)-3H-imidazo[4,5-b]pyridin-2-yl)pyridin-2-amine To a solution of acetohydrazide (36.3 mg, 0.490 mmol, 2 equiv) in ACN (5 mL) was added (dimethoxymethyl)dimethylamine (58.4 mg, 0.490 mmol, 2 equiv). The resulting mixture was stirred for 2 h at 60° C. To the reaction mixture was added AcOH (29.4 mg, 0.490 mmol, 2 equiv) and 3-{3-[(1S)-1-amino-2,3-dihydro-1H-inden-5-yl]-5-(pyrazol-1-yl)imidazo[4,5-b]pyridin-2-yl}pyridin-2-amine (Compound 2) (100 mg, 0.245 mmol, 1 equiv) and the reaction mixture was stirred at 120° C. for 2 h. The reaction mixture was purified by Prep-HPLC on a Xselect CSH Fluoro Phenyl column using a gradient of acetonitrile in water (+0.05% TFA) to afford (S)-3-(3-(1-(3-methyl-4H-1,2,4-triazol-4-yl)-2,3-dihydro-1H-inden-5-yl)-5-(1H-pyrazol-1-yl)-3H-imidazo[4,5-b]pyridin-2-yl)pyridin-2-amine (Compound 217) (25.5 mg, 20.04% yield) as an off-white solid: MS (ESI) calcd. for $C_{26}H_{22}N_{10}$: 474.20 m/z, found, 475.30 $[M+H]^+$. $^1H$ NMR (300 MHz, DMSO-$d_6$+$D_2O$) δ (ppm): 8.52-8.85 (m, 1H), 8.38-8.49 (m, 2H), 7.98-8.11 (m, 2H), 7.82-7.97 (m, 1H), 7.68-7.81 (m, 1H), 7.52-7.67 (m, 1H), 7.22-7.51 (m, 2H), 6.72-6.95 (m, 1H), 6.45-6.71 (m, 1H), 5.91-6.19 (m, 1H), 3.16-3.29 (m, 1H), 2.93-3.15 (m, 1H), 2.75-2.89 (m, 1H), 2.52-2.53 (m, 3H), 2.19-2.39 (m, 1H). (TFA salt)

Example 81: (S)—N-(5-(2-(2-aminopyridin-3-yl)-5-(5-methylthiazol-2-yl)-3H-imidazo[4,5-b]pyridin-3-yl)-2,3-dihydro-1H-inden-1-yl)-3-methylpyrazine-2-carboxamide (Compound 243)

Compound 243

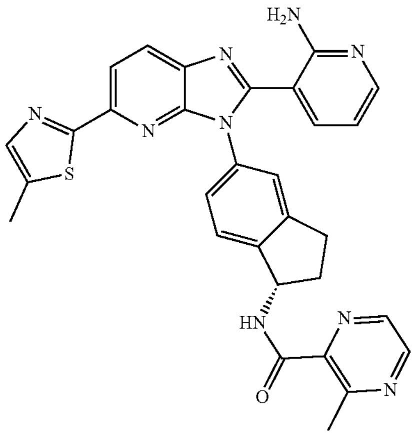

Synthetic Route:

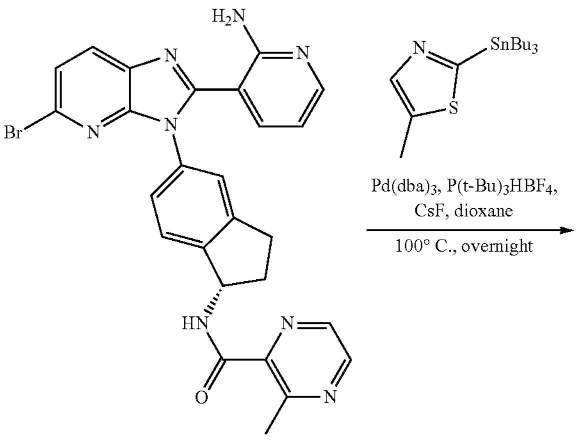

Intermediate 243-1

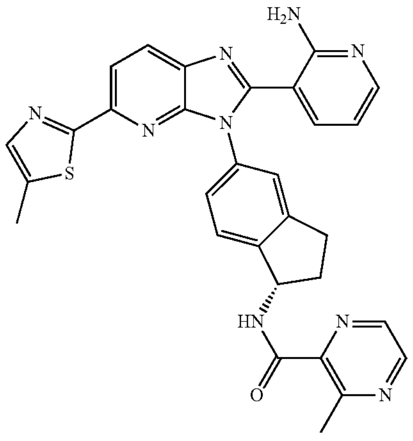

Compound 243

Step 1: Synthesis of (S)—N-(5-(2-(2-aminopyridin-3-yl)-5-(5-methylthiazol-2-yl)-3H-imidazo[4,5-b]pyridin-3-yl)-2,3-dihydro-1H-inden-1-yl)-3-methylpyrazine-2-carboxamide (Compound 243)

A mixture of N-[(1S)-5-[2-(2-aminopyridin-3-yl)-5-bromoimidazo[4,5-b]pyridin-3-yl]-2,3-dihydro-1H-inden-1-yl]-3-methylpyrazine-2-carboxamide (Intermediate 243-1) (100 mg, 0.185 mmol, 1 equiv), $Pd_2(dba)_3$ (16.9 mg, 0.018 mmol, 0.1 equiv) and CsF (140 mg, 0.925 mmol, 5 equiv) in dioxane (3 mL) was treated with 5-methyl-2-(tributylstannyl)-1,3-thiazole (143.4 mg, 0.370 mmol, 2 equiv) at room temperature under nitrogen atmosphere. The resulting mixture was stirred overnight at 100° C. under nitrogen atmosphere. The reaction was quenched with water (50 mL) at room temperature. The resulting mixture was extracted with ethyl acetate (3×50 mL) and dried over anhydrous $Na_2SO_4$. After filtration, the filtrate was concentrated under reduced pressure. The residue was purified by reverse-phase flash chromatography on C18 silica gel using a gradient of acetonitrile in water (+10 mmol/L ammonium bicarbonate) to afford (S)—N-(5-(2-(2-aminopyridin-3-yl)-5-(5-methylthiazol-2-yl)-3H-imidazo[4,5-b]pyridin-3-yl)-2,3-dihydro-1H-inden-1-yl)-3-methylpyrazine-2-carboxamide (Compound 243) (29.8 mg, 28% yield) as a light yellow solid: MS (ESI) calcd. for $C_{30}H_{25}N_9OS$, 559.19 m/z, found 560.15 $[M+H]^+$. $^1H$ NMR (300 MHz, DMSO-$d_6$+$D_2O$) δ (ppm); 8.67-8.75 (m, 1H), 8.52-8.60 (m, 1H), 8.29-8.37 (m, 1H), 8.11-8.21 (m, 1H), 8.01-8.09 (m, 1H), 7.64-7.70 (m, 1H), 7.40-7.59 (m, 2H), 7.22-7.38 (m, 2H), 6.48-6.57 (m, 1H), 5.61-5.70 (m, 1H), 2.89-3.15 (m, 2H), 2.78 (s, 3H), 2.53-2.60 (m, 1H), 2.42-2.50 (m, 3H), 2.12-2.24 (m, 1H).

Intermediate 243-1: (S)—N-(5-(2-(2-aminopyridin-3-yl)-5-bromo-3H-imidazo[4,5-b]pyridin-3-yl)-2,3-dihydro-1H-inden-1-yl)-3-methylpyrazine-2-carboxamide Intermediate 243-1

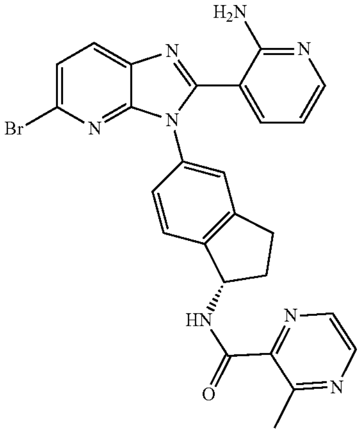

Intermediate 243-1 was prepared in a manner analogous to Compound 3 using PyBOP in place of HATU, Intermediate 245-3 in place of Compound 2 and 3-methylpyrazine-2-carboxylic acid in place of 3,4-difluoro-5-anisic acid: MS (ESI) calcd. for $C_{26}H_{21}BrN_8O$, 540.10 m/z, found, 541.15 $[M+H]^+$.

The following compounds were prepared analogous to the synthetic preparation in Example 81 (Compound 243).

TABLE 13A

Characterization data of compounds prepared analogously to compound 243.

| Cpd ID | Characterization Data |
|---|---|
| 300 | MS(ESI) calcd. for $C_{31}H_{26}N_8OS$, 558.20 m/z, found 589.10 $[M + H]^+$. $^1H$ NMR (300 MHz, DMSO-$d_6$ + $D_2O$) δ (ppm); 9.03-9.08 (m, 1H), 8.38-8.45 (m, 2H), 8.25-8.28 (m, 1H), 8.07-8.12 (m, 1H), 7.82-7.87 (m, 1H), 7.61-7.64 (m, 1H), 7.42-7.49. (m, 2H), 7.31-7.37 (m, 2H), 6.83-6.89 (m, 1H), 5.61-5.70 (m, 1H), 3.03-3.16 (m, 1H), 2.87-2.99 (m, 1H), 2.63 (s, 3H), 2.57-2.59 (m, 1H), 2.45 (s, 3H), 2.02-2.19 (m, 1H). (TFA salt) |

TABLE 13A-continued

Characterization data of compounds prepared analogously to compound 243.

| Cpd ID | Characterization Data |
|---|---|
| 302 | MS (ESI) calcd. for $C_{30}H_{25}N_9OS$, 559.19 m/z, found 560.20 $[M + H]^+$. $^1H$ NMR (300 MHz, DMSO-$d_6$ + $D_2O$) δ (ppm); 8.68-8.71 (m, 1H), 8.52-8.59 (m, 1H), 8.33-8.39 (m, 1H), 8.17-8.23 (m, 1H), 8.06-8.11 (m, 1H), 7.69-7.72 (m, 1H), 7.31-7.49 (m, 4H), 6.72-6.83 (m, 1H), 5.55-5.67 (m, 1H), 2.83-3.09 (m, 2H), 2.75 (s, 3H), 2.55-2.61 (m, 1H), 2.44 (s, 3H), 2.03-2.29 (m, 1H). (TFA salt) |
| 303 | MS (ESI) calcd. for C26H21N9S, 491.16 m/z, found 492.20 [M + H]+. 1H NMR (300 MHz, DMSO-$d_6$) δ (ppm): 8.20-8.40 (m, 2H), 8.05-8.20 (m, 2H), 7.90-8.05 (m, 1H), 7.70-7.82 (m, 1H), 7.61 (s, 1H), 7.35-7.50 (m, 1H), 7.05-7.30 (m, 3H), 6.40-6.58 (m, 1H), 6.20-6.40 (m, 1H), 3.15-3.30 (m, 1H), 2.95-3.15 (m, 1H), 2.65-2.90 (m, 1H), 2.35-2.45 (m, 4H) |
| 314 | MS (ESI) calcd. for $C_{31}H_{26}N_8OS$, 558.20 m/z, found 559.10 $[M + H]^+$. $^1H$ NMR (300 MHz, DMSO-$d_6$ + $D_2O$) δ (ppm); 8.89-8.95 (m, 1H), 8.29-8.35 (m, 1H), 8.20-8.28 (m, 1H), 8.12-8.19 (m, 1H), 8.01-8.10 (m, 1H), 7.61-7.69 (m, 1H), 7.45-7.61 (m, 2H), 7.35-7.44 (m, 2H), 7.26-7.34 (m, 1H), 6.57-6.64 (m, 1H), 5.61-5.70 (m, 1H), 3.03-3.18 (m, 1H), 2.89-3.02 (m, 1H), 2.62-2.69 (m, 1H), 2.53-2.59 (m, 3H), 2.48 (s, 3H), 2.02-2.19 (m, 1H). |
| 316 | MS (ESI) calcd for $C_{26}H_{21}N_9S$: 491.16 m/z, found, 492.20 $[M + H]^+$. $^1H$ NMR (300 MHz, DMSO-$d_6$) δ (ppm); 8.27-8.34 (m, 1H), 8.13-8.20 (m, 2H), 7.99-8.06 (m, 1H), 7.78-7.84 (m, 1H), 7.48-7.54 (m, 1H), 7.18-7.35 (m, 4H), 6.41-6.52 (m, 1H), 6.30-6.39 (m, 1H), 3.17-3.31 (m, 1H), 2.97-3.12 (m, 1H), 2.72-2.91 (m, 1H), 2.55-2.62 (m, 1H), 2.44 (s, 3H). |
| 556 | Observed mass (ESI): 572.45 [M + H]+. 1H NMR (400 MHz, DMSO-d6 + D2O) δ (ppm): 9.11-9.42 (m, 1H), 8.72-8.83 (m, 1H), 8.56-8.71 (m, 1H), 8.28-8.53 (m, 2H), 7.93-8.12 (m, 1H), 7.42-7.62 (m, 1H), 7.33-7.41 (m, 1H), 7.17-7.32 (m, 2H), 6.35-6.56 (m, 1H), 4.29-4.45 (m, 1H), 4.08-4.28 (m, 2H), 3.09-3.32 (m, 1H), 2.87-3.05 (m, 2H), 2.72-2.86 (m, 2H), 2.39-2.48 (m, 1H), 1.73-2.12 (m, 4H), 1.06-1.42 (m, 2H), 0.64-0.82 (m, 4H). |
| 559 | Observed mass (ESI): 625.25 [M + H]+. 1H NMR (300 MHz, DMSO-d6) δ (ppm): 8.30 (d, J = 8.3 Hz, 1H), 7.98-8.12 (m, 2H), 7.50 (d, J = 8.0 Hz, 1H), 7.30-7.40 (m, 2H), 7.25 (dd, J = 7.7, 1.9 Hz, 1H), 6.91 (s, 2H), 6.64 (s, 1H), 6.43 (dd, J = 7.7, 4.8 Hz, 1H), 5.34-5.59 (m, 1H), 4.40-4.55 (m, 1H), 4.15-4.23 (m, 2H), 3.87 (s, 3H), 3.14-3.22 (m, 2H), 3.05-3.11 (m, 2H), 2.86-2.93 (m, 1H), 2.25-2.31 (m, 1H), 1.90-2.06 (m, 3H), 1.28-1.48 (m, 2H), 0.68-1.48 (m, 4H). |

Example 82: (S)-3-(3-(1-(1H-1,2,3-triazol-1-yl)-2,3-dihydro-1H-inden-5-yl)-5-(4-methyloxazol-2-yl)-3H-imidazo[4,5-b]pyridin-2-yl)pyridin-2-amine (Compound 245)

Compound 245

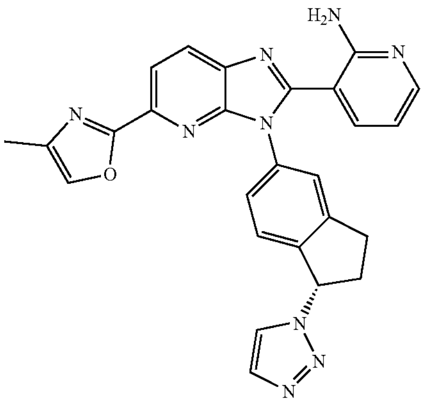

Synthetic Route:

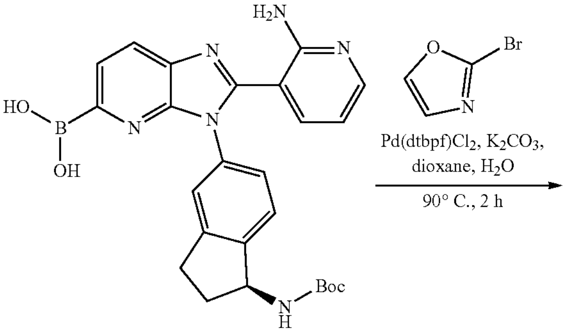

Intermediate 223-1

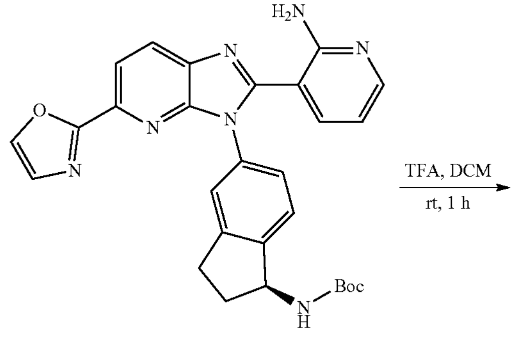

-continued

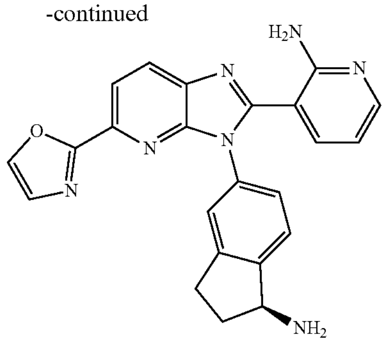

Intermediate 223-2

Compound 245 was prepared by Suzuki coupling of Intermediate 245-1 and 2-bromo-4-methyloxazole using a procedure analogous to Step 1 of Intermediate 223-2: MS (ESI) calcd. for $C_{26}H_{21}N_9O$, 475.19 m/z, found 476.10 $[M+H]^+$. $^1H$ NMR (300 MHz, DMSO-$d_6$) δ (ppm); 8.30-8.36 (m, 1H), 8.22-8.30 (m, 1H), 8.10-8.18 (m, 1H), 8.00-8.06 (m, 1H), 7.86-7.90 (m, 1H), 7.80-7.85 (m, 1H), 7.50 (s, 1H), 7.20-7.35 (m, 3H), 6.42-6.55 (m, 1H), 6.30-6.40 (m, 1H), 3.20-3.35 (m, 1H), 3.00-3.15 (m, 1H), 2.75-2.98 (m, 1H), 2.55-2.60 (m, 1H), 2.19 (s, 3H).

Intermediate 245-1: (S)-(3-(1-(1H-1,2,3-triazol-1-yl)-2,3-dihydro-1H-inden-5-yl)-2-(2-aminopyridin-3-yl)-3H-imidazo[4,5-b]pyridin-5-yl)boronic acid Intermediate 245-1

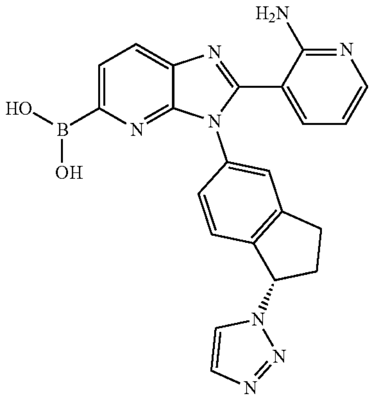

Intermediate 245-1 was prepared in a manner analogous to Intermediate 223-1 using Intermediate 245-2 in place of Intermediate 129-1: MS (ESI) calcd. for $C_{22}H_{19}BN_8O_2$, 438.17 m/z, found 439.10 $[M+H]^+$.

Intermediate 245-2: (S)-3-(3-(1-(1H-1,2,3-triazol-1-yl)-2,3-dihydro-1H-inden-5-yl)-5-bromo-3H-imidazo[4,5-b]pyridin-2-yl)pyridin-2-amine Intermediate 245-2

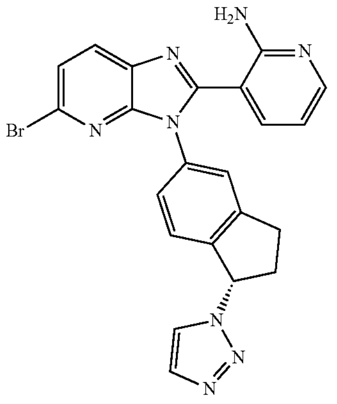

Synthetic Route:

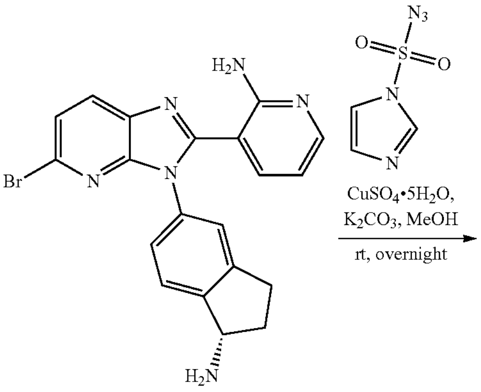

Intermediate 245-3

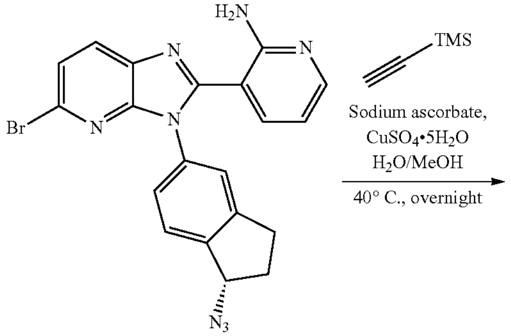

-continued

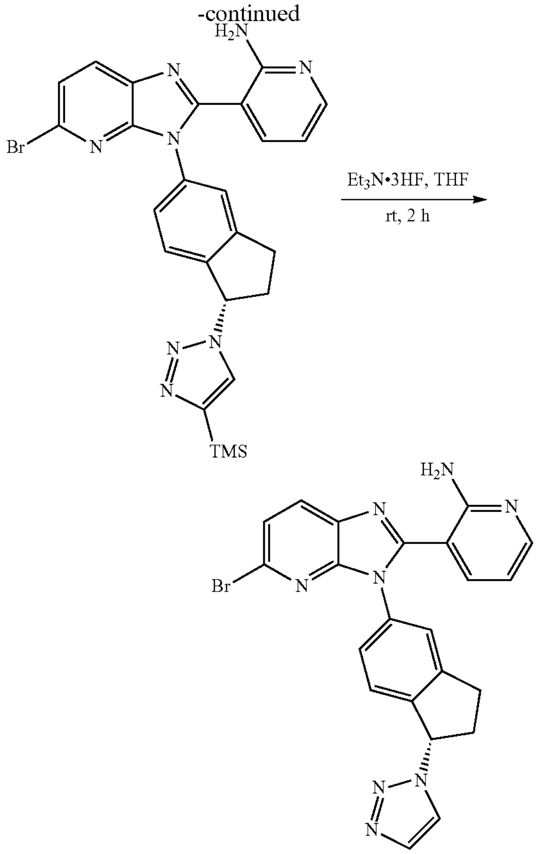

Intermediate 245-2

Step 1: Synthesis of (S)-3-(3-(1-azido-2,3-dihydro-1H-inden-5-yl)-5-bromo-3H-imidazo[4,5-b]pyridin-2-yl)pyridin-2-amine A mixture of 3-{3-[(1S)-1-amino-2,3-dihydro-1H-inden-5-yl]-5-bromoimidazo[4,5-b]pyridin-2-yl}pyridin-2-amine (Intermediate 245-3) (3 g, 7.12 mmol, 1 equiv), imidazole-1-sulfonyl azide (1.48 g, 8.55 mmol, 1.2 equiv), $K_2CO_3$ (3.94 g, 28.5 mmol, 4 equiv) and $CuSO_4 \cdot 5H_2O$ (88.9 mg, 0.356 mmol, 0.05 equiv) in MeOH (30 mL) was stirred overnight at room temperature. The resulting mixture was concentrated under reduced pressure. The residue was purified by reverse-phase flash chromatography on C18 silica gel using a gradient of acetonitrile in water (+0.05% $NH_4HCO_3$) to afford (S)-3-(3-(1-azido-2,3-dihydro-1H-inden-5-yl)-5-bromo-3H-imidazo[4,5-b]pyridin-2-yl)pyridin-2-amine (1.8 g, 57% yield) as a yellow solid: MS (ESI) calcd. for $C_{20}H_{15}BrN_8$, 446.06 m/z, found 447.15 $[M+H]^+$.

Step 2: Synthesis of (S)-3-(5-bromo-3-(1-(4-(trimethylsilyl)-1H-1,2,3-triazol-1-yl)-2,3-dihydro-1H-inden-5-yl)-3H-imidazo[4,5-b]pyridin-2-yl)pyridin-2-amine A mixture of (S)-3-(3-(1-azido-2,3-dihydro-1H-inden-5-yl)-5-bromo-3H-imidazo[4,5-b]pyridin-2-yl)pyridin-2-amine (1.8 g, 4.0 mmol, 1 equiv), trimethylsilylacetylene (7.91 g, 80.5 mmol, 20 equiv), $CuSO_4 \cdot 5H_2O$ (0.20 g, 0.81 mmol, 0.2 equiv) and sodium ascorbate (0.32 g, 1.6 mmol, 0.4 equiv) in MeOH (10 mL) and $H_2O$ (10 mL) was stirred overnight at 40° C. The reaction was quenched by addition of water (100 mL). The resulting mixture was extracted with ethyl acetate (3×200 mL). The organic layers were combined, dried over $Na_2SO_4$ and concentrated under vacuum to afford (S)-3-(5-bromo-3-(1-(4-(trimethylsilyl)-1H-1,2,3-triazol-1-yl)-2,3-dihydro-1H-inden-5-yl)-3H-imidazo[4,5-b]pyridin-2-yl)pyridin-2-amine (1.2 g, crude) as a yellow solid: MS (ESI) calcd. for $C_{25}H_{25}BrN_8Si$, 544.12 m/z, found 545.10 $[M+H]^+$.

Step 3: Synthesis of (S)-3-(3-(1-(1H-1,2,3-triazol-1-yl)-2,3-dihydro-1H-inden-5-yl)-5-bromo-3H-imidazo[4,5-b]pyridin-2-yl)pyridin-2-amine (Intermediate 254-2)

(S)-3-(5-bromo-3-(1-(4-(trimethylsilyl)-1H-1,2,3-triazol-1-yl)-2,3-dihydro-1H-inden-5-yl)-3H-imidazo[4,5-b]pyridin-2-yl)pyridin-2-amine (1.2 g, 2.2 mmol, 1 equiv) was dissolved in THF (12 mL) and $Et_3N \cdot 3HF$ (0.71 g, 4.4 mmol, 2 equiv) was added. The mixture was stirred for 2 h at room temperature. The resulting mixture was concentrated under reduced pressure. The residue was purified by reverse-phase flash chromatography on C18 silica gel using a gradient of acetonitrile in water (+0.05% $NH_4HCO_3$) to afford (S)-3-(3-(1-(1H-1,2,3-triazol-1-yl)-2,3-dihydro-1H-inden-5-yl)-5-bromo-3H-imidazo[4,5-b]pyridin-2-yl)pyridin-2-amine (Intermediate 245-2) (1 g, 96% yield) as a yellow solid: MS (ESI) calcd. for $C_{22}H_{17}BrN_8$, 472.08 m/z, found 473.15 $[M+H]^+$.

Intermediate 245-3: (S)-3-(3-(1-amino-2,3-dihydro-1H-inden-5-yl)-5-bromo-3H-imidazo[4,5-b]pyridin-2-yl)pyridin-2-amine Intermediate 245-3

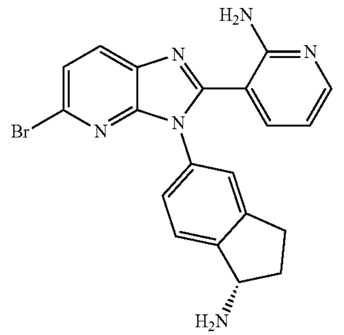

Synthetic Route:

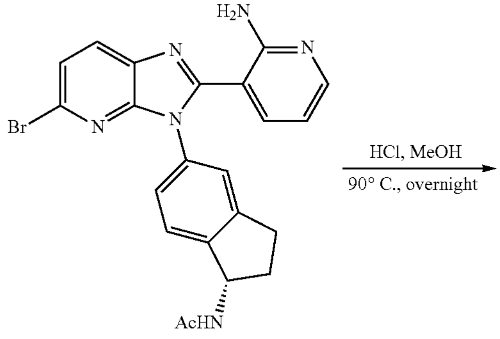

Intermediate 245-4

-continued

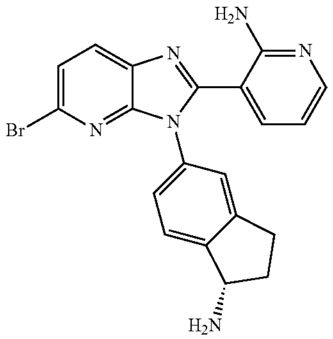

Intermediate 245-3

Step 1: Synthesis of (S)-3-(3-(1-amino-2,3-dihydro-1H-inden-5-yl)-5-bromo-3H-imidazo[4,5-b]pyridin-2-yl)pyridin-2-amine (Intermediate 245-3)

To a solution of N-[(1S)-5-[2-(2-aminopyridin-3-yl)-5-bromoimidazo[4,5-b]pyridin-3-yl]-2,3-dihydro-1H-inden-1-yl]acetamide (Intermediate 245-4) (40 g, 86 mmol, 1 equiv) in methanol (200 mL) was added conc. HCl (200 mL) and the resulting mixture was stirred overnight at 90° C. The mixture was allowed to cool to room temperature. The resulting mixture was concentrated under reduced pressure. The residue was neutralized to pH 7-8 with saturated aqueous sodium bicarbonate. The precipitated solids were collected by filtration and washed with $H_2O$ (3×100 mL). The resulting solid was air-dried to afford 3-{3-[(1S)-1-amino-2,3-dihydro-1H-inden-5-yl]-5-bromoimidazo[4,5-b]pyridin-2-yl}pyridin-2-amine (Intermediate 245-3) (33 g, 91%) as a brown solid: MS (ESI) calcd. for $C_{20}H_{17}BrN_6$, 421.07 m/z, found, 422.15 $[M+H]^+$.

Intermediate 245-4: (S)—N-(5-(2-(2-aminopyridin-3-yl)-5-bromo-3H-imidazo[4,5-b]pyridin-3-yl)-2,3-dihydro-1H-inden-1-yl)acetamide Intermediate 245-4

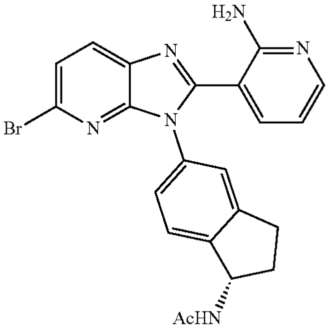

Synthetic Route:

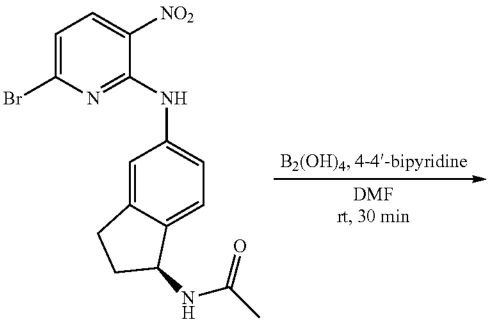

Intermediate 245-5

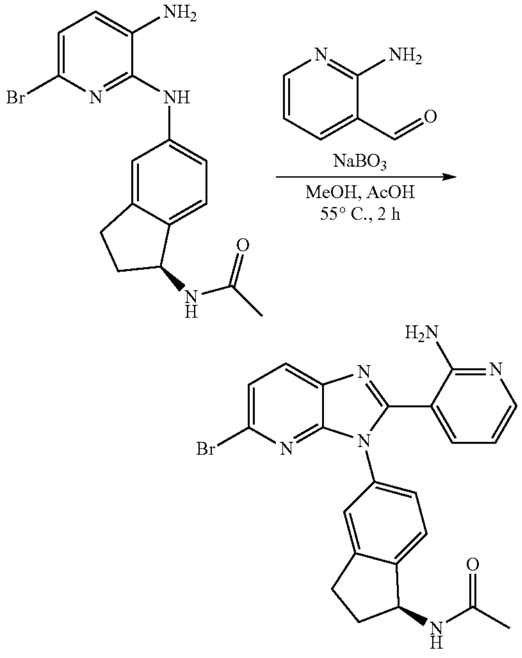

Intermediate 245-4

Step 1: Synthesis of (S)—N-(5-((3-amino-6-bromopyridin-2-yl)amino)-2,3-dihydro-1H-inden-1-yl)acetamide To a cooled (0° C.) solution of N-[(1S)-5-[(6-bromo-3-nitropyridin-2-yl)amino]-2,3-dihydro-1H-inden-1-yl]acetamide (Intermediate 245-5) (25 g, 64 mmol, 1 equiv) in N,N-dimethylformamide (250 mL) was added 4,4'-bpyridine (0.5 g, 2 mmol, 3 mol %), followed by hypodiboric acid (17.3 g, 0.192 mol, 3 equiv). The resulting mixture was stirred at 0° C. for 0.5 h. The reaction mixture was quenched by addition of 500 mL saturated aqueous ammonium chloride. The aqueous layer was extracted with ethyl acetate (3×250 mL). The combined organic layers were dried over anhydrous sodium sulfate, filtered and concentrated in vacuo. The resulting residue was purified by silica gel column chromatography, eluting with petroleum ether/dichloromethane/methanol (70:27:3) to afford N-[(1S)-5-[(3-amino-6-bromopyridin-2-yl)amino]-2,3-dihydro-1H-inden-1-yl]acetamide (16 g, 69%): MS (ESI) calculated for $C_{16}H_{17}BrN_4O$, $_{360.06}$, found 361.00 $[M+H]^+$, 363.00 $[M+2+H]^+$.

Step 2: Synthesis of (S)—N-(5-(2-(2-aminopyridin-3-yl)-5-bromo-3H-imidazo[4,5-b]pyridin-3-yl)-2,3-dihydro-1H-inden-1-yl)acetamide (Intermediate 245-4)

A solution of N-[(1S)-5-[(3-amino-6-bromopyridin-2-yl) amino]-2,3-dihydro-1H-inden-1-yl]acetamide (15.5 g, 42.9 mmol, 1 equiv) in methanol (72 mL) and acetic acid (14 mL) was treated with 2-aminopyridine-3-carbaldehyde (6.29 g, 51.5 mmol, 1.2 equiv) followed by the addition of sodium perborate tetrahydrate (26.41 g, 172 mmol, 4 equiv) portion wise. The resulting mixture was stirred at 55° C. for 2 h. The reaction mixture was concentrated under reduced pressure and then brought to pH 8-9 with saturated aqueous sodium bicarbonate. The resulting precipitate was filtered. The filter cake was then washed with ethyl acetate (3×100 mL). The resulting filtrate was concentrated under reduced pressure and the residue was purified by silica gel column chromatography using a 0 to 20% gradient of ethyl acetate in petroleum ether followed by a 0 to 10% gradient of dichloromethane in methanol to provide (S)—N-(5-(2-(2-aminopyridin-3-yl)-5-bromo-3H-imidazo[4,5-b]pyridin-3-yl)-2,3-dihydro-1H-inden-1-yl)acetamide (Intermediate 245-4) (4 g, 18% yield): MS (ESI) calculated for $C_{22}H_{19}BrN_6O$, 462.08, found 463.00 $[M+H]^+$, 465.00 $[M+H+2]^+$.

Intermediate 245-5: (S)—N-(5-((6-bromo-3-nitropyridin-2-yl)amino)-2,3-dihydro-1H-inden-1-yl)acetamide Intermediate 245-5

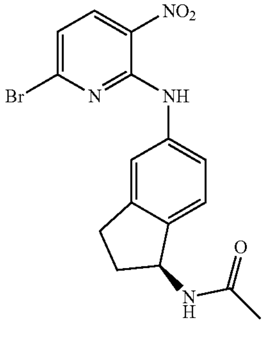

Synthetic Route:

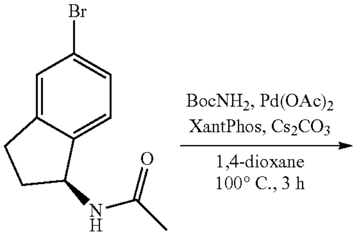

Intermediate 245-6

-continued

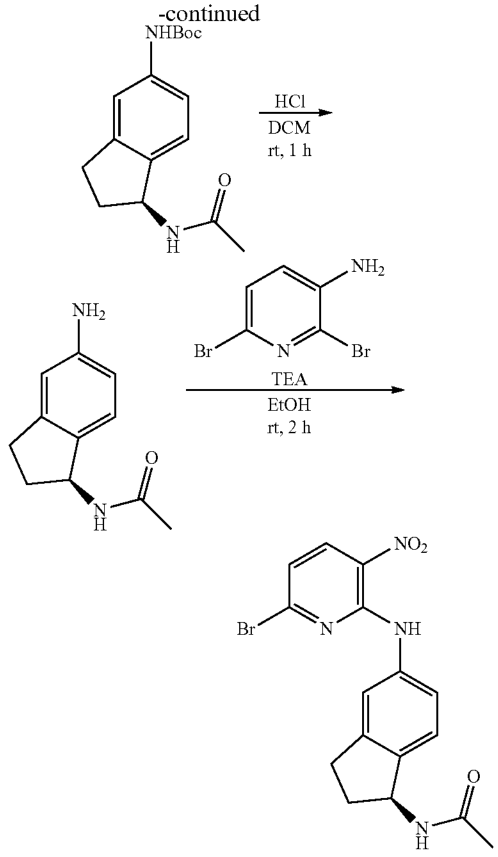

Intermediate 245-4

Step 1: Synthesis of tert-butyl (S)-(1-acetamido-2,3-dihydro-1H-inden-5-yl)carbamate To a mixture of N-[(1S)-5-bromo-2,3-dihydro-1H-inden-1-yl]acetamide (Intermediate 245-6) (40 g, 157 mmol, 1 equiv), tert-butyl carbamate (27.66 g, 236 mmol, 1.5 equiv), XantPhos (CAS: 161265-03-8) (9.11 g, 15.7 mmol, 10 mol %), $Pd(OAc)_2$ (3.54 g, 15.7 mmol, 10 mol %), and cesium carbonate (154 g, 472 mmol, 10 mol %) was added 1,4-dioxane (300 mL) under nitrogen atmosphere. The resulting mixture was stirred for 3 h at 100° C. The reaction mixture was quenched by addition of water (50 mL) and extracted with ethyl acetate (3×50 mL). The combined organic layers were dried over anhydrous sodium sulfate and concentrated under reduced pressure. The residue was purified by silica gel column chromatography using an eluent of petroleum ether/dichloromethane/methanol (70:27:3) to afford tert-butyl N-[(1S)-1-acetamido-2,3-dihydro-1H-inden-5-yl]carbamate (43.1 g, 48% yield): MS (ESI) calculated for $C_{16}H_{22}N_2O_3$: 290.16, found 289.05 $[M-H]^-$.

Step 2: Synthesis of (S)—N-(5-amino-2,3-dihydro-1H-inden-1-yl)acetamide

To a stirred solution of tert-butyl N-[(1S)-1-acetamido-2,3-dihydro-1H-inden-5-yl]carbamate (43.1 g, 148 mmol, 1 equiv) in dichloromethane (180 mL) was added 4N HCl in 1,4-dioxane (185 mL, 742 mmol, 5 equiv). The reaction mixture was stirred for 1 h at room temperature. The reaction mixture was concentrated in vacuo and re-crystallized from ethyl acetate to afford N-[(1S)-5-amino-2,3-dihydro-1H- inden-1-yl]acetamide (hydrochloride salt) (23 g, 81% yield) as a white solid: MS (ESI) calculated for $C_{11}H_{14}N_2O$, 190.11, found 191.15 $[M+H]^+$.

Step 3: (S)—N-(5-((6-bromo-3-nitropyridin-2-yl) amino)-2,3-dihydro-1H-inden-1-yl)acetamide (Intermediate 245-5)

N-[(1S)-5-amino-2,3-dihydro-1H-inden-1-yl]acetamide (17 g, 89 mmol), 2,6-dibromo-3-nitropyridine (25.19 g, 89.36 mmol) was dissolved in triethylamine (45.21 g, 446.8 mmol, 5 equiv) and ethanol (200 mL). The reaction mixture was stirred at room temperature for 2 h. The reaction mixture was quenched with 400 mL water and the precipitate was rinsed with 1:1 ethanol/water (800 mL:800 mL) to afford N-[(1S)-5-[(6-bromo-3-nitropyridin-2-yl)amino]-2,3-dihydro-1H-inden-1-yl]acetamide (Intermediate 245-5) (26 g, 74% yield) as an orange solid: MS (ESI) calculated for $C_{16}H_{15}BrN_4O_3$: 390.03, found 413.00 $[M+Na]^+$, 415.00 $[M+Na+2]^+$.

Intermediate 245-6: (S)—N-(5-bromo-2,3-dihydro-1H-inden-1-yl)acetamide

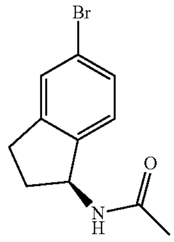

Intermediate 245-6

Synthetic route:

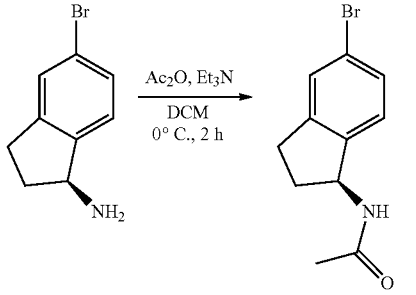

Intermedaite 245-6

Step 1: Synthesis of (S)—N-(5-bromo-2,3-dihydro-1H-inden-1-yl)acetamide (Intermediate 245-6)

To a mixture of (S)-5-bromo-2,3-dihydro-1H-inden-1-amine (74 g, 350 mmol, 1 equiv) and triethylamine (106 g, 1.05 mol, 3 equiv) in dichloromethane (1.5 L) was added acetic anhydride (55.2 g, 526 mmol, 1.5 equiv) at 0° C. and the mixture was stirred at 0° C. for 2 h. The reaction mixture was quenched by addition of water (500 mL) and extracted with ethyl acetate (3×500 mL). The combined organic layers were dried over anhydrous sodium sulfate and concentrated under reduced pressure. The crude product was re-crystallized from petroleum ether to afford (S)—N-(5-bromo-2,3-dihydro-1H-inden-1-yl)acetamide (Intermediate 245-6) (90 g, 83% yield) as a white solid: MS (ESI) calculated for $C_{11}H_{12}BrNO$, 253.01, found 254.00 $[M+H]^+$, 256.00 $[M+H+2]^+$.

The following compounds were prepared analogously to the synthetic preparation of Compound 245.

TABLE 13B

Characterization data of compounds prepared analogously to compound 245.

| Cpd ID | Characterization Data |
|---|---|
| 570 | Observed mass (ESI): 657.37 [M + H]+. 1H NMR (300 MHz, DMSO-d6) δ (ppm): 8.18-8.23 (m, 1H), 7.99-8.02 (m, 1H), 7.91-8.01 (m, 1H), 7.81-7.89 (m, 1H), 7.47-7.53 (m, 1H), 7.29-7.38 (m, 1H), 7.18-7.22 (m, 2H), 6.61-6.71 (m, 1H), 6.37-6.45 (m, 1H), 4.35-4.45 (m, 1H), 4.25-4.31 (m, 3H), 3.17-3.37 (m, 1H), 2.89-2.99 (m, 2H), 2.81-2.97 (m, 2H), 2.70-2.71 (m, 2H), 2.41-2.60 (m, 1H), 2.16-2.37 (m, 3H), 1.91-2.18 (m, 9H), 1.77-1.91 (m, 1H), 1.24-1.38 (m, 1H), 1.15-1.24 (m, 1H), 0.65-0.79 (m, 4H). |
| 576 | Observed mass (ESI): 616.35 [M + H]+. 1H NMR (300 MHz, DMSO-d6 + D2O) δ (ppm): 8.21-8.24 (m, 1H), 8.05-8.06 (m, 2H), 7.93-8.01 (m, 1H), 7.51-7.52 (m, 1H), 7.34-7.35 (m, 1H), 7.23-7.25 (m, 2H), 6.69-6.70 (m, 1H), 6.44-6.45 (m, 1H), 5.63-5.64 (m, 1H), 4.95-4.97 (m, 4H), 4.41-4.52 (m, 1H), 4.23-4.24 (m, 2H), 3.21-3.22 (m, 1H), 2.96-2.97 (m, 2H), 2.75-2.79 (m, 2H), 1.98-2.10 (m, 4H), 1.23-1.83 (m, 3H), 0.72-0.82 (m, 4H). |
| 577 | Observed mass (ESI): 602.35 [M + H]+. 1H NMR (500 MHz, DMSO-d6) δ (ppm): 8.83 (s, 1H), 8.34-8.43 (m, 1H), 8.26-8.34 (m, 1H), 8.24 (s, 1H), 7.93-8.03 (m, 1H), 7.44-7.58 (m, 1H), 7.30 (s, 1H), 7.20-7.27 (m, 2H), 6.37-6.50 (m, 1H), 4.23-4.44 (m, 1H), 4.11-4.27 (m, 2H), 4.02 (s, 3H), 3.07-3.23 (m, 1H), 2.82-3.00 (m, 2H), 2.59-2.82 (m, 2H), 2.35-2.47 (m, 1H), 1.61-2.09 (m, 4H), 1.08-1.38 (m, 2H), 0.60-0.76 (m, 4H). |

Intermediate 223-2: 3-{3-[(1S)-1-amino-2,3-dihydro-1H-inden-5-yl]-5-(1,3-oxazol-2-yl)imidazo[4,5-b]pyridin-2-yl}pyridin-2-amine Intermediate 223-2

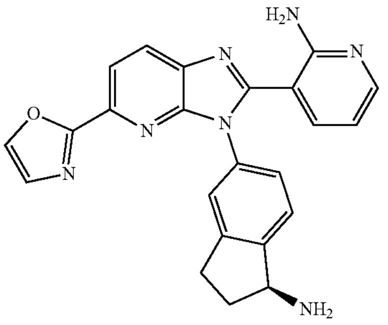

Synthetic Route:

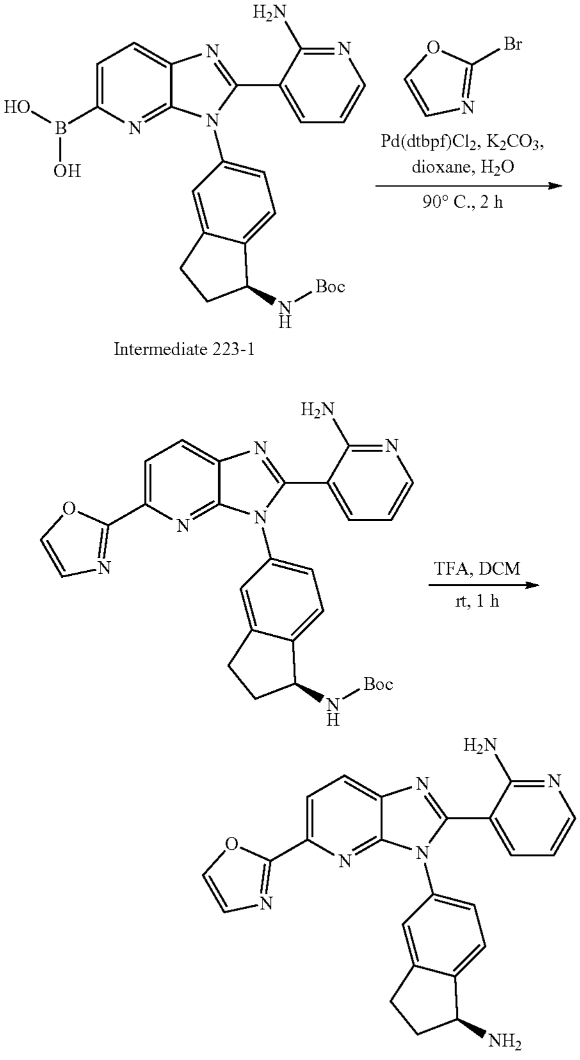

Step 1: Synthesis of tert-butyl N-[(1S)-5-[2-(2-aminopyridin-3-yl)-5-(1,3-oxazol-2-yl)imidazo[4,5-b]pyridin-3-yl]-2,3-dihydro-1H-inden-1-yl]carbamate To a stirred mixture of 2-(2-aminopyridin-3-yl)-3-[(1S)-1-[(tert-butoxycarbonyl)amino]-2,3-dihydro-1H-inden-5-yl]imidazo[4,5-b]pyridin-5-ylboronic acid (Intermediate 223-1) (300 mg, 0.617 mmol, 1 equiv) in dioxane (6 mL) was added 2-bromo-1,3-oxazole (109.5 mg, 0.740 mmol, 1.2 equiv), $Pd(dtbpf)Cl_2$ (40 mg, 0.062 mmol, 0.1 equiv), $K_2CO_3$ (170.5 mg, 1.234 mmol, 2 equiv) and $H_2O$ (1.5 mL). The resulting mixture was stirred at 90° C. for 2 h under a nitrogen atmosphere. The mixture was purified by reverse phase flash chromatography on C18 silica gel using a gradient of acetonitrile in water (+0.05% $NH_4HCO_3$) to afford tert-butyl N-[(1S)-5-[2-(2-aminopyridin-3-yl)-5-(1,3-oxazol-2-yl)imidazo[4,5-b]pyridin-3-yl]-2,3-dihydro-1H-inden-1-yl]carbamate (230 mg, 73%) as a yellow solid. MS (ESI) calcd. for $C_{28}H_{27}N_7O_3$: 509.22 m/z, found: 510.20 $[M+H]^+$.

Step 2: Synthesis of 3-{3-[(1S)-1-amino-2,3-dihydro-1H-inden-5-yl]-5-(1,3-oxazol-2-yl)imidazo[4,5-b]pyridin-2-yl}pyridin-2-amine (Intermediate 223-2)

To a solution of tert-butyl N-[(1S)-5-[2-(2-aminopyridin-3-yl)-5-(1,3-oxazol-2-yl)imidazo[4,5-b]pyridin-3-yl]-2,3-dihydro-1H-inden-1-yl]carbamate (220 mg, 0.432 mmol, 1 equiv) in DCM (6 mL) was added TFA (2 mL) and the resulting mixture was stirred at r.t for 1 h. The mixture was basified to pH 8 with aq. NaOH (2 mol/L). The resulting mixture was extracted with ethyl acetate (2×20 ml). The combined organic layers were concentrated under reduced pressure to afford 3-{3-[(1S)-1-amino-2,3-dihydro-1H-inden-5-yl]-5-(1,3-oxazol-2-yl)imidazo[4,5-b]pyridin-2-yl}pyridin-2-amine (Intermediate 223-2) (200 mg, crude) as a yellow solid. MS (ESI) calcd. for $C_{23}H_{19}N_7O$: 409.17 m/z, found: 410.20 $[M+H]^+$.

Intermediate 223-1: (S)-(2-(2-aminopyridin-3-yl)-3-(1-((tert-butoxycarbonyl)amino)-2,3-dihydro-1H-inden-5-yl)-3H-imidazo[4,5-b]pyridin-5-yl)boronic acid Intermediate 223-1

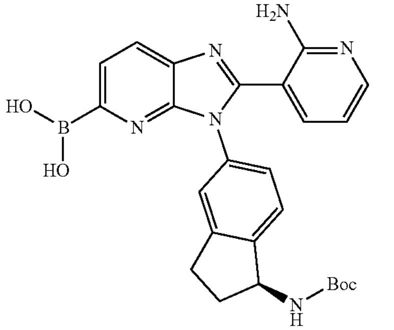

Synthetic Route:

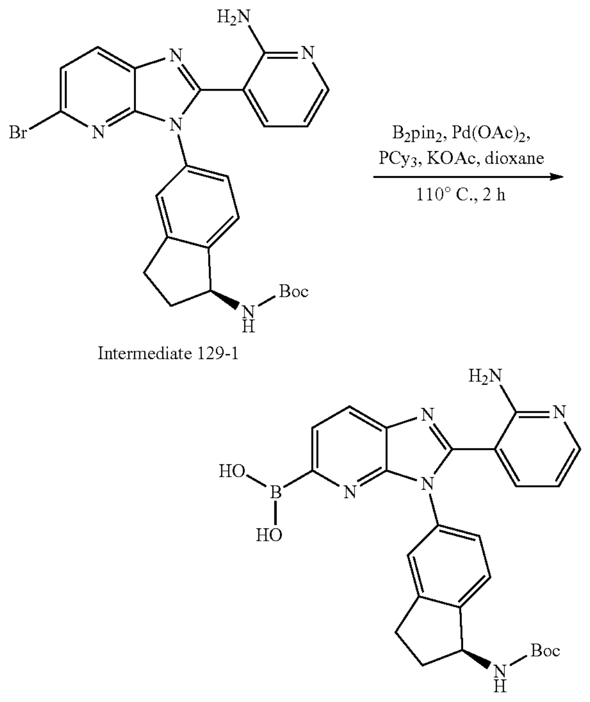

Intermediate 129-1

Intermediate 223-1

Step 1: Synthesis of (S)-(2-(2-aminopyridin-3-yl)-3-(1-((tert-butoxycarbonyl)amino)-2,3-dihydro-1H-inden-5-yl)-3H-imidazo[4,5-b]pyridin-5-yl)boronic acid (Intermediate 223-1)

To a solution of tert-butyl (S)-(5-(2-(2-aminopyridin-3-yl)-5-bromo-3H-imidazo[4,5-b]pyridin-3-yl)-2,3-dihydro-1H-inden-1-yl)carbamate (Intermediate 129-1) (3 g, 5.8 mmol) and 4,4,5,5-tetramethyl-2-(4,4,5,5-tetramethyl-1,3,2-dioxaborolan-2-yl)-1,3,2-dioxaborolane (1.753 g, 6.905 mmol) in dioxane (30 mL) were added $Pd(OAc)_2$ (77.5 mg, 0.345 mmol), $PCy_3$ (193.6 mg, 0.690 mmol) and KOAc (1.412 g, 14.39 mmol) and the mixture was stirred for 2 h at 110° C. under a nitrogen atmosphere. After cooling to room temperature, the mixture was quenched with water (200 mL). The resulting mixture was extracted with ethyl acetate (3×200 mL). The organic layers were combined, dried over anhydrous sodium sulfate, filtered and concentrated. The crude product was purified by silica gel flash column chromatography (0-15%, MeOH/DCM) to afford (S)-(2-(2-aminopyridin-3-yl)-3-(1-((tert-butoxycarbonyl)amino)-2,3-dihydro-1H-inden-5-yl)-3H-imidazo[4,5-b]pyridin-5-yl) boronic acid (Intermediate 223-1) (1.7 g, 61% yield) as a white solid.

MS (ESI) calcd. for $C_{25}H_{27}N_6BO_4$: 486.21 m/z, found 487.25 $[M+H]^+$.

Intermediate 129-1: tert-butyl (S)-(5-(2-(2-aminopyridin-3-yl)-5-bromo-3H-imidazo[4,5-b]pyridin-3-yl)-2,3-dihydro-1H-inden-1-yl)carbamate Intermediate 129-1

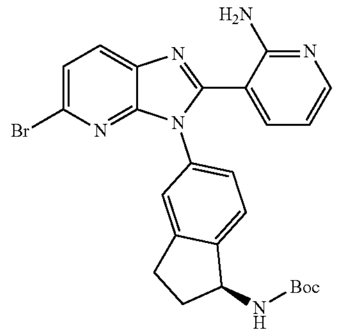

Synthetic Route:

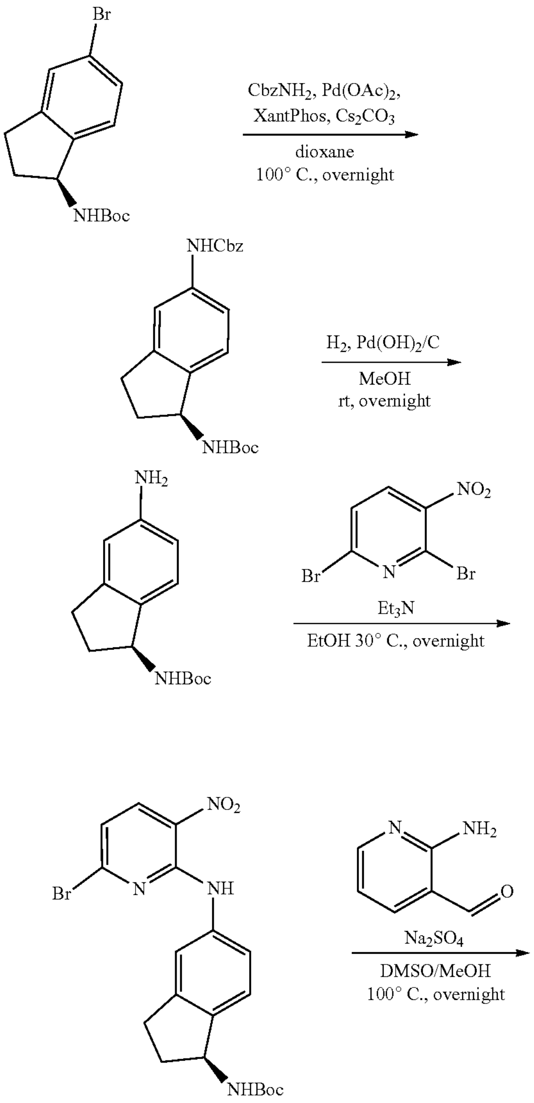

-continued

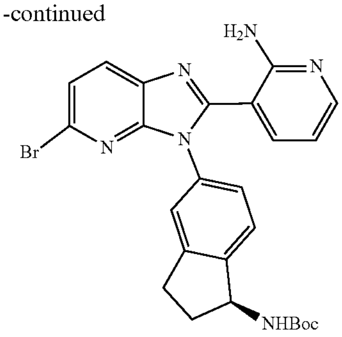

Intermediate 129-1

Step 1: Synthesis of benzyl N-[(1S)-1-[(tert-butoxycarbonyl)amino]-2,3-dihydro-1H-inden-5-yl]carbamate To a solution of tert-butyl N-[(1S)-5-bromo-2,3-dihydro-1H-inden-1-yl]carbamate (60.00 g, 192.2 mmol, 1 equiv), benzyl carbamate (34.63 g, 230.6 mmol, 1.2 equiv) and XantPhos (22.24 g, 38.44 mmol, 0.2 equiv) in 1,4-dioxane (1.2 L) were added $Cs_2CO_3$ (125.23 g, 384.36 mmol, 2 equiv) and $Pd(OAc)_2$ (4.31 g, 19.2 mmol, 0.1 equiv). After stirring overnight at 100° C. under nitrogen atmosphere the mixture was cooled to room temperature and the product was precipitated by the addition of $H_2O$. The precipitated solids were collected by filtration and washed with $H_2O$ (3×400 ml). The solids were suspended in ethyl acetate and filtered, washing with ethyl acetate. The filtrate was concentrated under reduced pressure to afford benzyl N-[(1S)-1-[(tert-butoxycarbonyl)amino]-2,3-dihydro-1H-inden-5-yl]carbamate (50 g, 46%) as a grey solid. MS (ESI) calcd. for $C_{22}H_{26}N_2O_4$, 382.19 m/z, found: 381.10 $[M-H]^-$.

Step 2: Synthesis of tert-butyl N-[(1S)-5-amino-2,3-dihydro-1H-inden-1-yl]carbamate To a solution of benzyl N-[(1S)-1-[(tert-butoxycarbonyl)amino]-2,3-dihydro-1H-inden-5-yl]carbamate (50.00 g, 130.7 mmol, 1 equiv) in 500 ml $CH_3OH$ was added 10% $Pd(OH)_2/C$ (5.00 g, 35.6 mmol, 0.27 equiv) in a pressure tank. The mixture was hydrogenated at room temperature under 30 psi of hydrogen overnight then filtered through a Celite pad and concentrated under reduced pressure to afford tert-butyl N-[(1S)-5-amino-2,3-dihydro-1H-inden-1-yl]carbamate (40 g, 73%) as a brown solid. MS (ESI) calcd. for $C_{1-4}H_2ON_2O_2$, 248.15 m/z, found: 249.15 $[M+H]^+$.

Step 3: Synthesis of tert-butyl N-[(1S)-5-[(6-bromo-3-nitropyridin-2-yl)amino]-2,3-dihydro-1H-inden-1-yl]carbamate A mixture of tert-butyl N-[(1S)-5-amino-2,3-dihydro-1H-inden-1-yl]carbamate (40.0 g, 161 mmol, 1 equiv) and triethylamine (48.90 g, 483.2 mmol, 3 equiv) in EtOH (800 mL) was stirred at room temperature until dissolved. 2,6-dibromo-3-nitropyridine (54.49 g, 193.3 mmol, 1.2 equiv) was added and the mixture was stirred at 30° C. overnight. The mixture was allowed to cool to room temperature and the precipitated solids were collected by filtration and washed with EtOH (3×100 mL) to afford tert-butyl N-[(1S)-5-[(6-bromo-3-nitropyridin-2-yl)amino]-2,3-dihydro-1H-inden-1-yl]carbamate (30 g, 27%) as a red solid. MS (ESI) calcd. for $C_{19}H_{21}BrN_4O_4$, 448.07 m/z, found: 447.00 $[M-H]^-$.

Step 4: Synthesis of tert-butyl N-[(1S)-5-[2-(2-aminopyridin-3-yl)-5-bromoimidazo[4,5-b]pyridin-3-yl]-2,3-dihydro-1H-inden-1-yl]carbamate (Intermediate 129-1)

To a solution of tert-butyl N-[(1S)-5-[(6-bromo-3-nitropyridin-2-yl)amino]-2,3-dihydro-1H-inden-1-yl]carbamate (30.0 g, 66.8 mmol, 1 equiv) in DMSO (600 mL) and MeOH (100 mL) was added 2-aminopyridine-3-carbaldehyde (8.97 g, 73.4 mmol, 1.1 equiv) and the mixture was stirred until the solids were dissolved. $Na_2S_2O_4$ (25.57 g, 146.9 mmol, 2.2 equiv) was added and the mixture was stirred at 100° C. overnight. The product was precipitated by the addition of $H_2O$. The precipitated solids were collected by filtration and washed with $H_2O$ (3×500 ml). The residue was purified by silica gel column chromatography eluting with $CH_2Cl_2$/MeOH (10:1) to afford tert-butyl N-[(1S)-5-[2-(2-aminopyridin-3-yl)-5-bromoimidazo[4,5-b]pyridin-3-yl]-2,3-dihydro-1H-inden-1-yl]carbamate (Intermediate 129-1) (15 g, 36%) as a yellow solid. MS (ESI) calcd. for $C_{25}H_{25}BrN_6O_2$, 520.12 m/z, found: 521.20 $[M+H]^+$.

The following compounds were prepared analogous to the synthetic preparation in Example 82 (Compound 245).

TABLE 14A

Characterization data of compounds prepared analogously to compound 245.

| Cpd ID | Characterization Data |
|---|---|
| 246 | MS (ESI) calcd. for $C_{25}H_{19}N_9O$, 461.17 m/z, found 462.20 $[M + H]^+$. $^1H$ NMR (300 MHz, DMSO-$d_6$) δ (ppm); 8.32-8.38 (m, 1H), 8.19-8.26 (m, 2H), 8.13-8.19 (m, 1H), 7.98-8.05 (m, 1H), 7.77-7.83 (m, 1H), 7.49-7.54 (m, 1H), 7.39-7.45 (m, 1H), 7.28-7.36 (m, 1H), 7.19-7.27 (m, 2H), 6.32-6.47 (m, 2H), 3.17-3.33 (m, 1H), 2.97-3.12 (m, 1H), 2.72-2.90 (m, 1H), 2.54-2.64 (m, 1H). |
| 247 | MS (ESI) calcd. for $C_{25}H_{21}N_{11}$, 475.20 m/z, found 476.30 $[M + H]^+$. $^1H$ NMR (300 MHz, DMSO-$d_6$) δ (ppm); 8.26-8.28 (m, 1H), 8.17-8.18 (m, 1H), 8.07-8.08 (m, 1H), 7.93-7.95 (m, 2H), 7.80-7.81 (m, 1H), 7.52-7.53 (m, 1H), 7.20-7.28 (m, 3H), 6.44-6.45 (m, 1H), 6.41-6.43 (m, 1H), 4.21-4.22 (m, 3H), 3.21-3.24 (m, 1H), 3.09-3.11 (m, 1H), 2.85-2.88 (m, 1H), 2.56-2.59 (m, 1H). |
| 315 | MS (ESI) calcd for $C_{26}H_{20}F_2N_{10}$: 510.18 m/z, found, 511.10 $[M + H]^+$. $^1H$ NMR (400 MHz, DMSO-$d_6$) δ (ppm); 8.24-8.35 (m, 2H), 8.13-8.20 (m, 1H), 7.97-8.09 (m, 2H), 7.66-7.97 (m, 2H), 7.47-7.56 (m, 1H), 7.15-7.39 (m, 3H), 6.87-6.98 (m, 1H), 6.42-6.51 (m, 1H), 6.30-6.39 (m, 1H), 3.19-3.31 (m, 1H), 3.00-3.13 (m, 1H), 2.76-2.88 (m, 1H), 2.57-2.67 (m, 1H). $^{19}F$ NMR (376 MHz, DMSO-$d_6$) δ (ppm); −94.20. (formic acid salt). |

Example 83: (S)-3-(3-(1-(4H-1,2,4-triazol-4-yl)-2,3-dihydro-1H-inden-5-yl)-5-(1H-pyrazol-1-yl)-3H-imidazo[4,5-b]pyridin-2-yl)pyridin-2-amine (Compound 248)

Compound 248

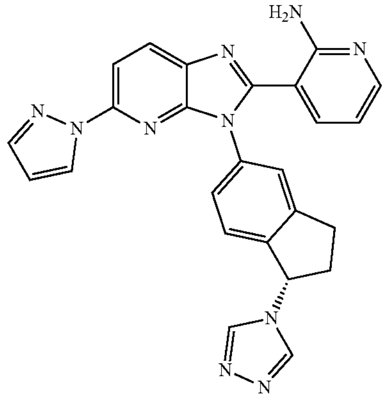

Synthetic Route:

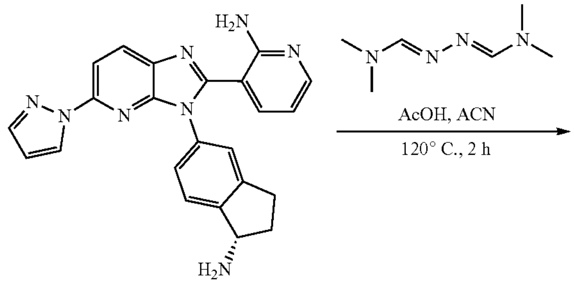

Compound 2

-continued

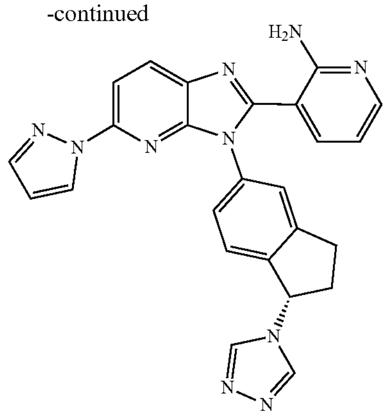

Compound 248

Compound 2 Compound 248

Step 1: Synthesis of (S)-3-(3-(1-(4H-1,2,4-triazol-4-yl)-2,3-dihydro-1H-inden-5-yl)-5-(1H-pyrazol-1-yl)-3H-imidazo[4,5-b]pyridin-2-yl)pyridin-2-amine (Compound 248)

A mixture of (S)-3-(3-(1-amino-2,3-dihydro-1H-inden-5-yl)-5-(1H-pyrazol-1-yl)-3H-imidazo[4,5-b]pyridin-2-yl) pyridin-2-amine (Compound 2) (80 mg, 0.196 mmol, 1 equiv), AcOH (0.1 mL) and (E)-N'—((E)-(dimethylamino) methylene)-N,N-dimethylformohydrazonamide (111 mg, 0.784 mmol, 4 equiv) in ACN (2 mL) was stirred for 2 h at 120° C. The resulting mixture was diluted with water (20 mL). The mixture was extracted with ethyl acetate (3×50 mL) and dried over anhydrous $Na_2SO_4$. After filtration, the filtrate was concentrated under reduced pressure. The crude product was purified by Prep-HPLC on a XBridge Prep Shield RP OBD C18 Column using a gradient of acetonitrile in water (+10 mmol/L $NH_4HCO_3$) to afford (S)-3-(3-(1-(4H-1,2,4-triazol-4-yl)-2,3-dihydro-1H-inden-5-yl)-5-(1H-pyrazol-1-yl)-3H-imidazo[4,5-b]pyridin-2-yl)pyridin-2-amine (Compound 248) (31.8 mg, 40% yield) as a white solid: MS (ESI) calcd. for $C_{25}H_{20}N_{11}$, 460.19 m/z, found 461.10 $[M+H]^+$. $^1H$ NMR (300 MHz, DMSO-d+$D_2O$) δ (ppm); 8.63 (s, 21H), 8.39-8.47 (m, 2H), 8.02-8.10 (m, 1H), 7.96-8.01 (m, 1H), 7.78-7.86 (m, 1H), 7.51-7.59 (m, 1H), 7.23-7.39 (m, 3H), 6.57-6.63 (m, 1H), 6.43-6.54 (m, 1H), 5.97-6.09 (m, 1H), 3.20-3.36 (m, 1H), 2.98-3.13 (m, 1H), 2.77-2.89 (m, 1H), 2.31-2.44 (m, 1H).

The following compounds were prepared analogously to the synthetic preparation of Compound 248.

TABLE 14B

Characterization data of compounds prepared analogously to compound 248.

| Cpd ID | Characterization Data |
|---|---|
| 528 | Observed mass (ESI): 459.3 [M + H]+. 1H NMR (400 MHz, DMSO-d6) δ (ppm): 8.62-8.71 (m, 2H), 8.08-8.18 (m, 1H), 7.90-8.01 (m, 1H), 7.58-7.62 (m, 1H), 7.35-7.49 (m, 1H), 7.15-7.25 (m, 3H), 6.89-7.08 (m, 2H), 6.32-6.45 (m, 1H), 5.92-6.10 (m, 1H), 3.15-3.28 (m, 1H), 2.89-3.19 (m, 1H), 2.69-2.82 (m, 1H), 2.25-2.49 (m, 1H), 1.49-1.62 (m, 1H), 0.85-0.95 (m, 2H), 0.69-0.79 (m, 2H). |
| 529 | Observed mass (ESI): 463.25 [M + H]+. 1H NMR (300 MHz, DMSO-d6) δ (ppm): 8.46-8.78 (m, 2H), 8.25-8.45 (m, 2H), 7.91-8.14 (m, 1H), 7.77-7.90 (m, 1H), 7.62-7.76 (m, 1H), 7.51-7.61 (m, 1H), 7.43-7.61 (m, 1H), 7.29-7.42 (m, 1H), 7.03-7.28 (m, 3H), 6.42-6.71 (m, 1H), 5.83-6.14 (m, 1H), 3.12-3.27 (m, 1H), 2.89-3.04 (m, 1H), 2.64-2.82 (m, 1H), 2.24-2.44 (m, 1H). |

Example 84: (S)-3-(3-(1-(4,5-dimethyl-1H-1,2,3-triazol-1-yl)-2,3-dihydro-1H-inden-5-yl)-5-(1H-pyrazol-1-yl)-3H-imidazo[4,5-b]pyridin-2-yl)pyridin-2-amine (Compound 249)

Compound 249

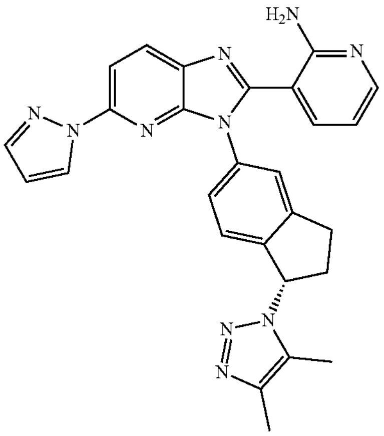

Synthetic Route:

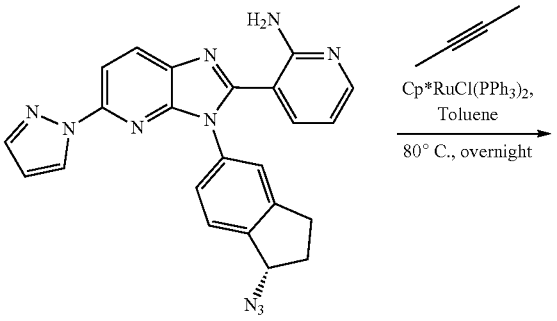

Intermediate 155-1

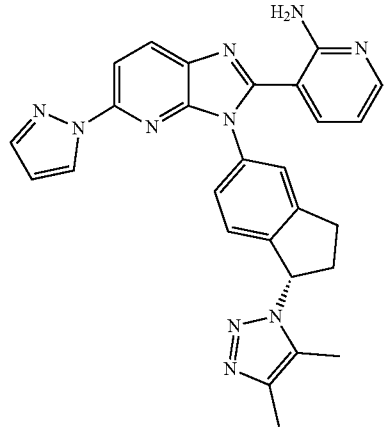

Compound 249

-continued

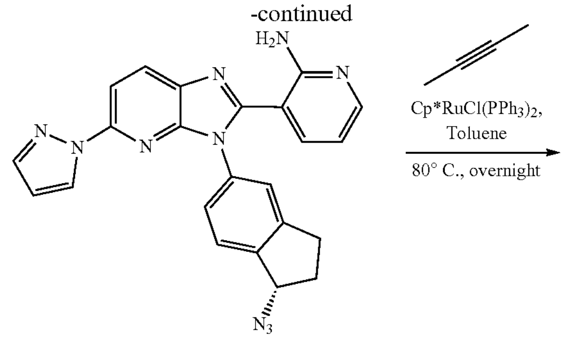

Intermediate 155-1

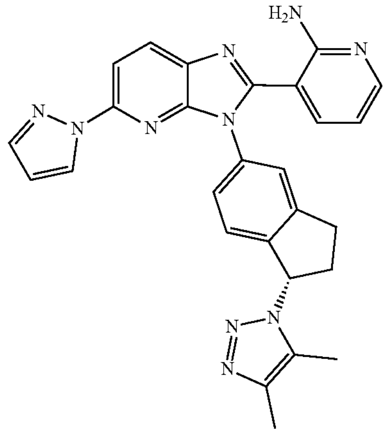

Example 249

Step 1: Synthesis of (S)-3-(3-(1-(4,5-dimethyl-1H-1,2,3-triazol-1-yl)-2,3-dihydro-1H-inden-5-yl)-5-(1H-pyrazol-1-yl)-3H-imidazo[4,5-b]pyridin-2-yl) pyridin-2-amine (Compound 249)

To a solution of 3-{3-[(1S)-1-azido-2,3-dihydro-1H-inden-5-yl]-5-(pyrazol-1-yl)imidazo[4,5-b]pyridin-2-yl}pyridin-2-amine (Intermediate 155-1) (80 mg, 0.18 mmol, 1 equiv) and Cp*RuCl($PPh_3$)$_2$ (220 mg, 0.276 mmol, 1.5 equiv) in toluene (5 mL) was added but-2-yne (99.5 mg, 1.84 mmol, 10 equiv) under $N_2$ atmosphere. The resulting mixture was stirred overnight at 80° C. The reaction was quenched with $H_2O$ (50 mL) at room temperature. The resulting mixture was extracted with ethyl acetate (100 mL×3) and dried over anhydrous $Na_2SO_4$. After filtration, the filtrate was concentrated under reduced pressure. The residue was purified by Prep-HPLC on a XSelect CSH Fluoro Phenyl column using a gradient of acetonitrile in water (+0.05% TFA) to afford (S)-3-(3-(1-(4,5-dimethyl-1H-1,2,3-triazol-1-yl)-2,3-dihydro-1H-inden-5-yl)-5-(1H-pyrazol-1-yl)-3H-imidazo[4,5-b]pyridin-2-yl)pyridin-2-amine (4.2 mg, 5% yield) as a white solid: MS (ESI) calcd. for $C_{27}H_{24}N_{11}$, 488.21 m/z, found 489.30 $[M+H]^+$. $^1H$ NMR (300 MHz, DMSO-$d_6$+$D_2O$) δ (ppm); 8.39-8.51 (m, 2H), 7.95-8.11 (m, 2H), 7.79-7.91 (m, 2H), 7.52-7.63 (m, 1H), 7.31-7.42 (m, 1H), 7.16-7.21 (m, 1H), 6.77-6.91 (m, 1H), 6.55-6.62 (m, 1H), 6.13-6.25 (m, 1H), 3.20-3.41 (m, 1H), 2.99-3.19 (m, 1H), 2.71-2.91 (m, 1H), 2.35-2.51 (m, 1H), 2.15-2.29 (m, 6H). (TFA salt)

Example 85: (*)-3-(3-(1-(((2-methylpyridin-3-yl)oxy)methyl)-2,3-dihydro-1H-inden-5-yl)-5-(1H-pyrazol-1-yl)-3H-imidazo[4,5-b]pyridin-2-yl)pyridin-2-amine (Compound 252) and (*)-3-(3-(1-(((2-methylpyridin-3-yl)oxy)methyl)-2,3-dihydro-1H-inden-5-yl)-5-(1H-pyrazol-1-yl)-3H-imidazo[4,5-b]pyridin-2-yl)pyridin-2-amine (Compound 253)
Compouns 252
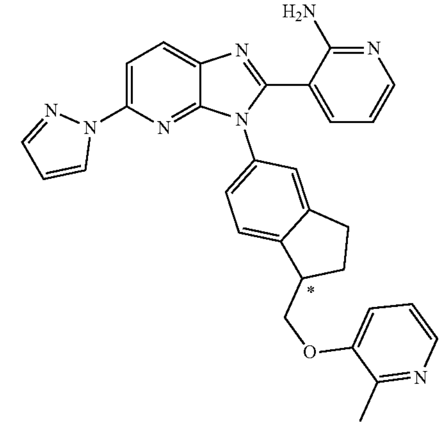
-continued
Compound 253
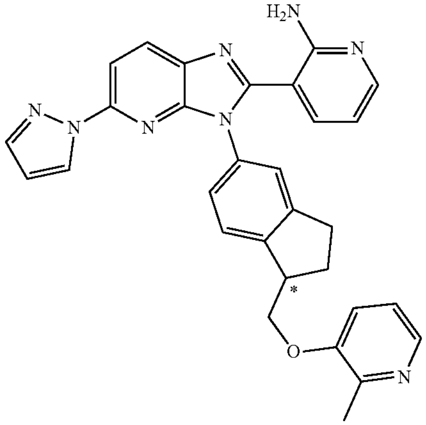
Synthetic Route:
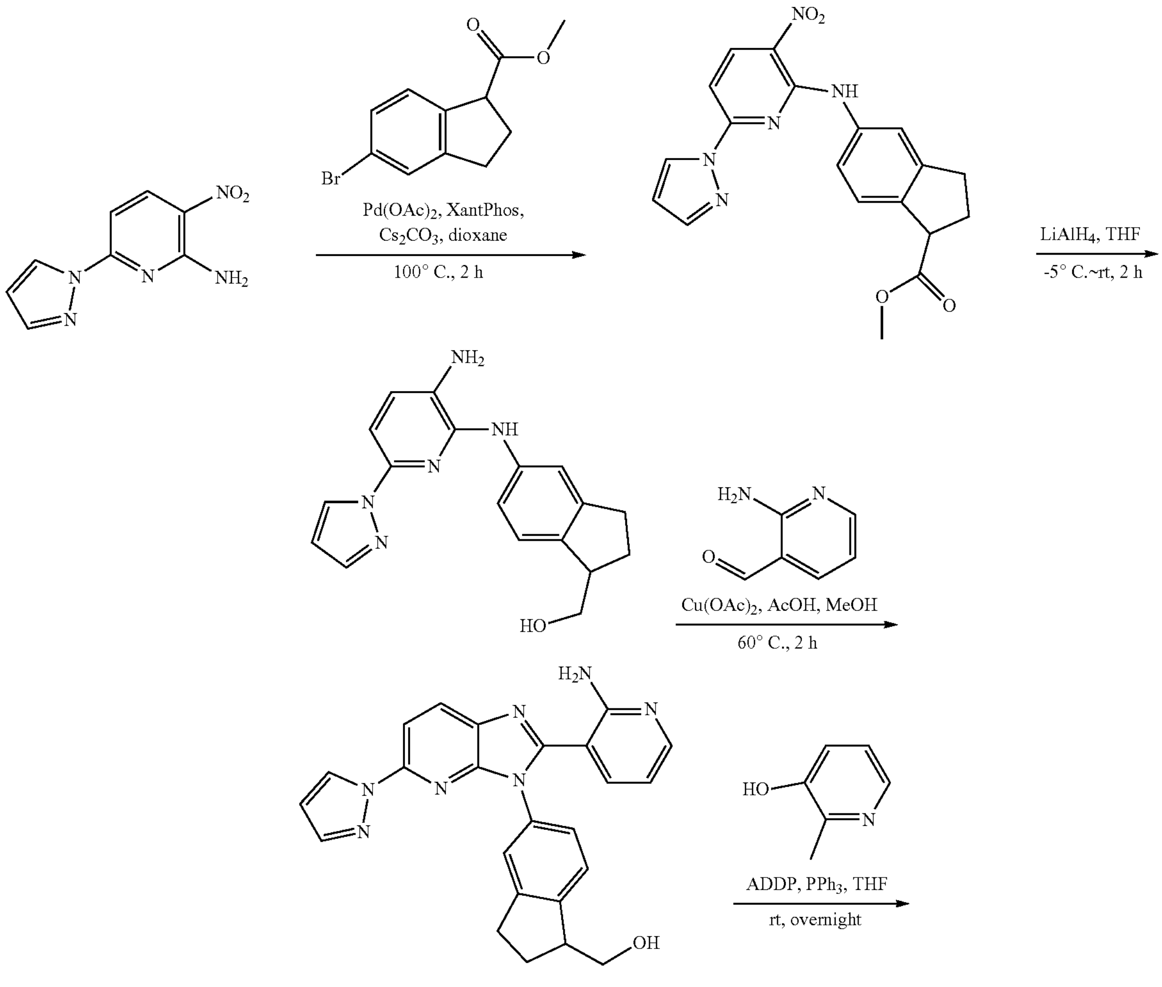

-continued

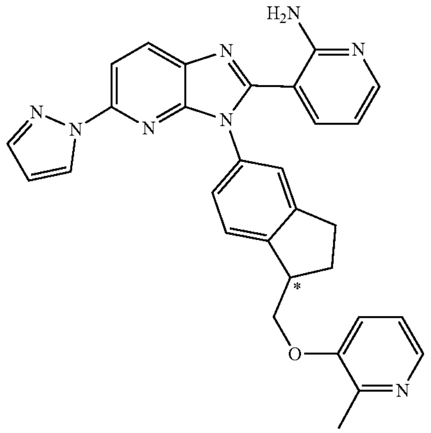

Compouns 252

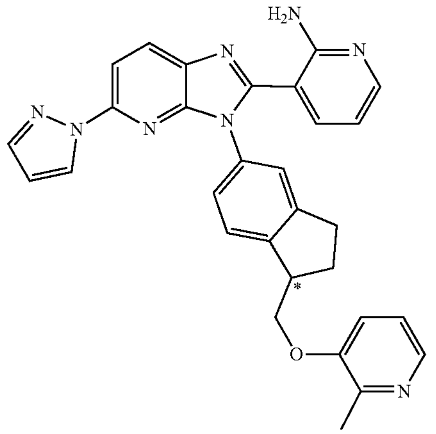

Compound 253

Step 1: Synthesis of methyl 5-((3-nitro-6-(1H-pyrazol-1-yl)pyridin-2-yl)amino)-2,3-dihydro-1H-indene-1-carboxylate To a solution of methyl 5-bromo-2,3-dihydro-1H-indene-1-carboxylate (2.86 g, 11.2 mmol, 1 equiv) in dioxane (50 mL) was added $Cs_2CO_3$ (10.96 g, 33.63 mmol, 3 equiv), $Pd(OAc)_2$ (251.7 mg, 1.121 mmol, 0.1 equiv), XantPhos (648.7 mg, 1.121 mmol, 0.1 equiv) and 3-nitro-6-(pyrazol-1-yl)pyridin-2-amine (2.53 g, 12.3 mmol, 1.1 equiv) and the resulting mixture was stirred at 100° C. for 2 h under nitrogen atmosphere. The resulting mixture was quenched with HCl (1M, 100 mL) and extracted with DCM (3x200 mL). The organic layers were combined, dried over $Na_2SO_4$ and concentrated under vacuum to afford methyl 5-((3-nitro-6-(1H-pyrazol-1-yl)pyridin-2-yl)amino)-2,3-dihydro-1H-indene-1-carboxylate (2 g, 47% yield): MS (ESI) calcd. for $C_{19}H_{17}N_5O_4$: 379.13 m/z, found, 380.15 $[M+H]^+$.

Step 2: Synthesis of (5-((3-amino-6-(1H-pyrazol-1-yl)pyridin-2-yl)amino)-2,3-dihydro-1H-inden-1-yl) methanol To a solution of methyl 5-((3-nitro-6-(1H-pyrazol-1-yl) pyridin-2-yl)amino)-2,3-dihydro-1H-indene-1-carboxylate (2.0 g, 5.3 mmol, 1 equiv) in THE (50 mL) was added $LiA1H_4$ (1.00 g, 26.4 mmol, 5 equiv) in portions at 0° C. The resulting mixture was stirred at room temperature for 2 h. The resulting mixture was diluted with ethyl acetate (500 mL) and then poured into (1:1) ice/saturated $NH_4Cl$ solution (500 mL). The resulting mixture was extracted with ethyl acetate (3x500 mL). The separated organic layers were combined, dried over sodium sulfate, filtered and concentrated under vacuum. The crude product was purified by silica gel flash chromatography (0-10% MeOH/DCM) to afford (5-((3-amino-6-(1H-pyrazol-1-yl)pyridin-2-yl) amino)-2,3-dihydro-1H-inden-1-yl)methanol (1.4 g, 74% yield) as a purple solid: MS (ESI) calcd. for $C18H_{19}N_{50}$, 321.16 m/z, found, 322.10 $[M+H]^+$.

Step 3: Synthesis of (5-(2-(2-aminopyridin-3-yl)-5-(1H-pyrazol-1-yl)-3H-imidazo[4,5-b]pyridin-3-yl)-2,3-dihydro-1H-inden-1-yl)methanol To a solution of (5-((3-amino-6-(1H-pyrazol-1-yl)pyridin-2-yl)amino)-2,3-dihydro-1H-inden-1-yl)methanol (1.4 g, 4.36 mmol, 1 equiv) in AcOH (32 mL) and MeOH (8 mL) was added 2-aminopyridine-3-carbaldehyde (0.80 g, 6.53 mmol, 1.5 equiv) and $Cu(OAc)_2$ (0.79 g, 4.36 mmol, 1 equiv). The resulting mixture was stirred at 60° C. for 2 h. The reaction was then quenched by addition of water (200 mL). The resulting mixture was extracted with ethyl acetate (3x200 mL). The organic layers were combined, dried over sodium sulfate, filtered and concentrated under a vacuum. The residue obtained was purified by silica gel chromatography (0-100% ethyl acetate in petroleum ether) to afford (5-(2-(2-aminopyridin-3-yl)-5-(1H-pyrazol-1-yl)-3H-imidazo[4,5-b]pyridin-3-yl)-2,3-dihydro-1H-inden-1-yl)methanol (380 mg, 19% yield) as a purple solid: MS (ESI) calcd. for $C_{24}H_{21}N_7O$, 423.18 m/z, found, 424.15 $[M+H]^+$.

Step 4: Synthesis of 3-(3-(1-(((2-methylpyridin-3-yl)oxy)methyl)-2,3-dihydro-1H-inden-5-yl)-5-(1H-pyrazol-1-yl)-3H-imidazo[4,5-b]pyridin-2-yl)pyridin-2-amine (Compounds 252 and 253)

A solution of (5-(2-(2-aminopyridin-3-yl)-5-(1H-pyrazol-1-yl)-3H-imidazo[4,5-b]pyridin-3-yl)-2,3-dihydro-1H-inden-1-yl)methanol (100 mg, 0.223 mmol, 1 equiv) in THE (5 mL) was treated with 2-methylpyridin-3-ol (51.5 mg, 0.472 mmol, 2 equiv) and $PPh_3$ (186 mg, 0.708 mmol, 3 equiv) and the resulting mixture was stirred for 5 min at room temperature under nitrogen atmosphere followed by the addition of a solution of 1,1-(azodicarbonyl)dipiperidine (177 mg, 0.708 mmol, 3 equiv) in THE dropwise at −5° C. The resulting mixture was stirred overnight at room temperature. The residue was quenched with $H_2O$ (100 mL) and extracted with ethyl acetate (3x50 mL). The combined organic layers were dried over anhydrous $Na_2SO_4$. After filtration, the filtrate was concentrated under reduced pressure. The residue was purified by chiral Prep-HPLC on a CHIRALPAK ID-3 column using a mixture of [Hexanes/DCM 3:1+0.1% diethylamine] and ethanol to afford (*)-3-(3-(1-(((2-methylpyridin-3-yl)oxy)methyl)-2,3-dihydro-1H-inden-5-yl)-5-(1H-pyrazol-1-yl)-3H-imidazo[4,5-b]pyridin-2-yl)pyridin-2-amine (Compound 252) (24 mg, 20% yield) as an off-white solid (eluting first) and (*)-3-(3-(1-(((2-methylpyridin-3-yl)oxy)methyl)-2,3-dihydro-1H-inden-5-yl)-5-(1H-pyrazol-1-yl)-3H-imidazo[4,5-b]pyridin-2-yl) pyridin-2-amine (Compound 253) (25.0 mg, 21% yield) as an off-white solid (eluting second). *Denotes a stereocenter with undetermined absolute stereochemistry of a single diastereomer.

Compound 252: MS (ESI) calcd. for $C_{30}H_{26}N_8O$, 514.22 m/z, found, 515.15 $[M+H]^+$. $^1H$ NMR (300 MHz, DMSO-$d_6$) δ (ppm); 8.25-8.43 (m, 2H), 7.88-8.06 (m, 3H), 7.73-7.85 (m, 1H), 7.45-7.59 (m, 1H), 7.31-7.44 (m, 2H), 7.11-7.30 (m, 3H), 6.46-6.59 (m, 1H), 6.31-6.45 (m, 1H), 4.24-4.37 (m, 1H), 4.11-4.23 (m, 1H), 3.59-3.79 (m, 1H), 2.79-3.15 (m, 2H), 2.35-2.44 (m, 1H), 2.21-2.33 (m, 3H), 1.91-2.16 (m, 1H).

Compound 253: MS (ESI) calcd. for $C_{30}H_{26}N_8O$, 514.22 m/z, found, 515.15 $[M+H]^+$. $^1H$ NMR (300 MHz, DMSO-$d_6$) δ (ppm); 8.24-8.44 (m, 2H), 7.89-8.08 (m, 3H), 7.75-7.87 (m, 1H), 7.34-7.62 (m, 3H), 7.17-7.31 (m, 3H), 6.51-6.62 (m, 1H), 6.35-6.45 (m, 1H), 4.11-4.44 (m, 2H), 3.63-3.82 (m, 1H), 2.78-3.18 (m, 2H), 2.35-2.47 (m, 1H), 2.22-2.34 (m, 3H), 1.92-2.17 (m, 1H).

Example 86: (S)-3-(3-(1-(3,5-dimethyl-4H-1,2,4-triazol-4-yl)-2,3-dihydro-1H-inden-5-yl)-5-(1H-pyrazol-1-yl)-3H-imidazo[4,5-b]pyridin-2-yl)pyridin-2-amine (Compound 272)

Compound 272

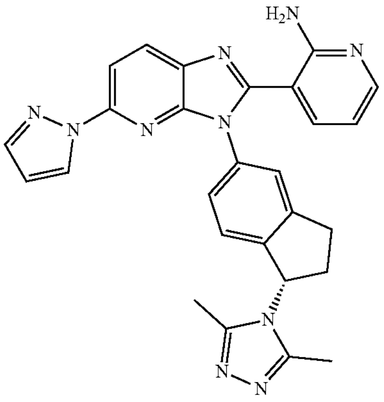

Synthetic Route:

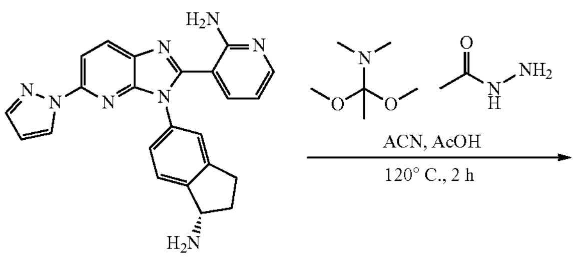

Compound 2

-continued

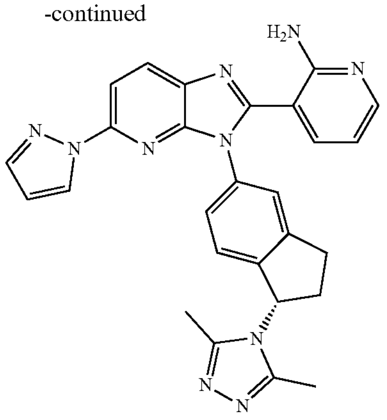

Compound 272

Step 1: Synthesis of (S)-3-(3-(1-(3,5-dimethyl-4H-1,2,4-triazol-4-yl)-2,3-dihydro-1H-inden-5-yl)-5-(1H-pyrazol-1-yl)-3H-imidazo[4,5-b]pyridin-2-yl)pyridin-2-amine (Compound 272)

A solution of (1,1-dimethoxyethyl)dimethylamine (48.9 mg, 0.367 mmol, 1.5 equiv) and acetohydrazide (27.2 mg, 0.367 mmol, 1.5 equiv) in ACN (1 mL) was stirred for 2 h at 60° C. 3-{3-[(1S)-1-amino-2,3-dihydro-1H-inden-5-yl]-5-(pyrazol-1-yl)imidazo[4,5-b]pyridin-2-yl}pyridin-2-amine (Compound 2) (100 mg, 0.245 mmol, 1 equiv) was added and the mixture was stirred for 2 h at 120° C. The reaction mixture was purified by Prep-HPLC on a XSelect CSH F-Phenyl OBD Column using a gradient of acetonitrile in water (+0.05% TFA) to afford (S)-3-(3-(1-(3,5-dimethyl-4H-1,2,4-triazol-4-yl)-2,3-dihydro-1H-inden-5-yl)-5-(1H-pyrazol-1-yl)-3H-imidazo[4,5-b]pyridin-2-yl)pyridin-2-amine (31 mg, 25% yield) as a white solid: MS (ESI) calcd. for $C_{27}H_{24}N_{11}$, 488.22 m/z, found 489.30 $[M+H]^+$. $^1H$ NMR (300 MHz, DMSO-$d_6$+$D_2O$) δ (ppm); 8.42-8.52 (m, 1H), 8.37-8.41 (m, 1H), 8.01-8.11 (m, 2H), 7.84-7.87 (m, 1H), 7.71-7.81 (m, 1H), 7.57-7.63 (m, 1H), 7.39-7.49 (m, 2H), 6.72-6.81 (m, 1H), 6.57-6.62 (m, 1H), 6.18-6.29 (m, 1H), 3.02-3.31 (m, 2H), 2.81-3.01 (m, 1H), 2.57-2.58 (m, 1H), 2.19-2.49 (m, 6H). (TFA salt)

Example 87: (S)-3-(3-(1-(1H-imidazol-1-yl)-2,3-dihydro-1H-inden-5-yl)-5-(1H-pyrazol-1-yl)-3H-imidazo[4,5-b]pyridin-2-yl)pyridin-2-amine (Compound 273)

Compound 273

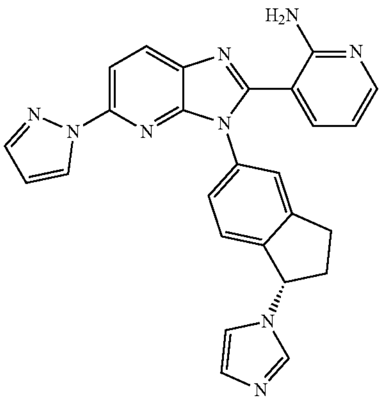

Synthetic Route:

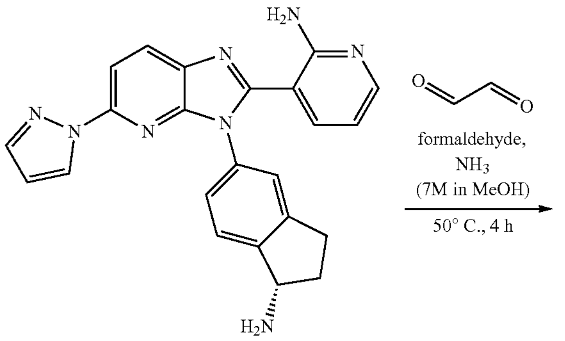

Compound 2

-continued

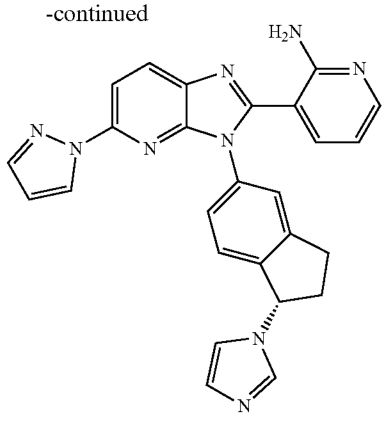

Compound 273

Step 1: Synthesis of (S)-3-(3-(1-(1H-imidazol-1-yl)-2,3-dihydro-1H-inden-5-yl)-5-(1H-pyrazol-1-yl)-3H-imidazo[4,5-b]pyridin-2-yl)pyridin-2-amine To a stirred solution of glyoxal (42.6 mg, 0.735 mmol, 3 equiv) and formaldehyde (7.4 mg, 0.245 mmol, 1 equiv) were added 3-{3-[(1S)-1-amino-2,3-dihydro-1H-inden-5-yl]-5-(pyrazol-1-yl)imidazo[4,5-b]pyridin-2-yl}pyridin-2-amine (Compound 2) (100 mg, 0.245 mmol, 1 equiv) and $NH_3$ in MeOH (2 mL, 7M) in portions. The resulting mixture was stirred for 4 h at 50° C.

The resulting mixture was concentrated under reduced pressure. The crude product was purified by reverse-phase flash chromatography on C18 silica gel using a gradient of acetonitrile in water (+10 mmol/L $NH_4HCO_3$) to (S)-3-(3-(1-(1H-imidazol-1-yl)-2,3-dihydro-1H-inden-5-yl)-5-(1H-pyrazol-1-yl)-3H-imidazo[4,5-b]pyridin-2-yl)pyridin-2-amine (Compound 273) (37.6 mg, 33% yield) as an off-white solid: MS (ESI) calcd. for $C_{26}H_{21}N_9$, 459.19 m/z, found, 458.15 $[M-H]^-$. $^1H$ NMR (400 MHz, DMSO-$d_6$) δ (ppm); 9.25 (s, 1H), 8.42-8.46 (m, 2H), 8.03-8.09 (m, 2H), 7.84-7.85 (m, 1H), 7.64-7.72 (m, 4H), 7.40-7.42 (m, 2H), 6.78-6.81 (m, 1H), 6.58-6.62 (m, 1H), 6.18-6.21 (m, 1H), 3.32-3.40 (m, 1H), 2.99-3.12 (m, 1H), 2.83-3.00 (m, 1H), 2.45-2.61 (m, 1H). (TFA salt)

The following compounds were prepared analogously to the synthetic preparation in Example 87 (Compound 273).

TABLE 14C

Characterization data of compounds prepared analogously to compound 273.

| Cpd ID | Characterization Data |
|---|---|
| 494 | Observed mass (ESI): 512.2 [M + H]+. 1H NMR (400 MHz, DMSO-d6) δ (ppm): 8.60-8.72 (m, 2H), 8.40-8.50 (m, 2H), 8.00-8.15 (m, 2H), 7.80-7.90 (m, 2H), 7.55-7.70 (m, 3H), 7.45-7.52 (m, 1H), 6.70-6.80 (m, 1H), 6.57-6.63 (m, 1H), 5.25-5.35 (m, 1H), 4.70-4.96 (m, 4H), 3.20-3.35 (m, 1H), 2.90-3.10 (m, 1H), 2.60-2.65 (m, 1H), 2.40-2.50 (m, 1H). (TFA salt) |

Example 88: 3-(3-(1-(1H-pyrazol-1-yl)-2,3-dihydro-1H-inden-5-yl)-5-(1H-pyrazol-1-yl)-3H-imidazo[4,5-b]pyridin-2-yl)pyridin-2-amine (compound 325)

Compound 325

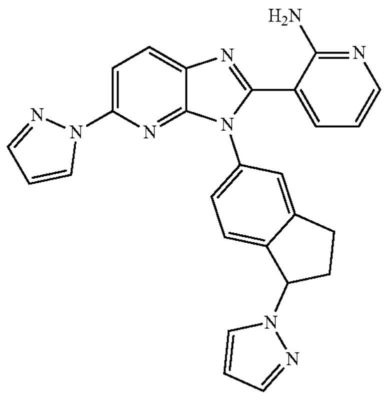

Synthetic Route:

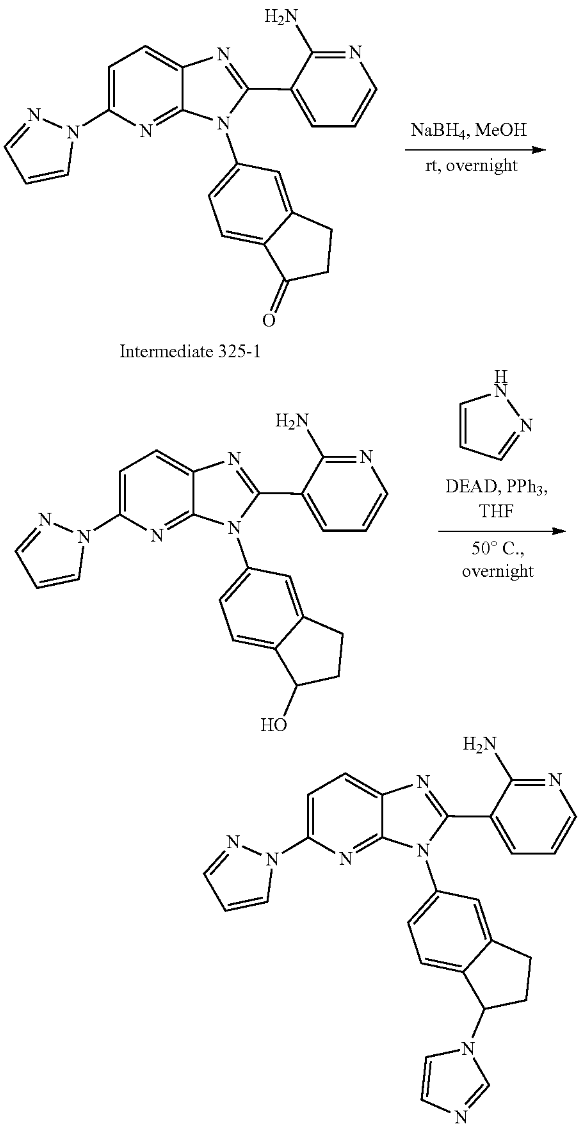

Intermediate 325-1

Compound 325

Step 1: 5-(2-(2-aminopyridin-3-yl)-5-(1H-pyrazol-1-yl)-3H-imidazo[4,5-b]pyridin-3-yl)-2,3-dihydro-1H-inden-1-ol A solution of 5-(2-(2-aminopyridin-3-yl)-5-(1H-pyrazol-1-yl)-3H-imidazo[4,5-b]pyridin-3-yl)-2,3-dihydro-1H-inden-1-one (Intermediate 325-1) (500.0 mg, 1.225 mmol, 1 equiv) in MeOH (25 mL) was treated with $NaBH_4$ (139.3 mg, 3.675 mmol, 3 equiv) at 0° C. The resulting mixture was stirred overnight at rt. The reaction was quenched with water (30 mL) at rt. The resulting mixture was extracted with ethyl acetate (3x20 ml). The combined organic layers were dried over anhydrous $Na_2SO_4$. After filtration, the filtrate was concentrated under reduced pressure. The residue was purified by silica gel column chromatography, eluting with MeOH/DCM (0-10%) to afford 5-(2-(2-aminopyridin-3-yl)-5-(1H-pyrazol-1-yl)-3H-imidazo[4,5-b]pyridin-3-yl)-2,3-dihydro-1H-inden-1-ol (300 mg, 60% yield) as a brown solid: MS (ESI) calcd. for $C_{23}H_{19}N_7O$, 409.17 m/z, found 410.25 $[M+H]^+$.

Step 2: 3-(3-(1-(1H-pyrazol-1-yl)-2,3-dihydro-1H-inden-5-yl)-5-(1H-pyrazol-1-yl)-3H-imidazo[4,5-b]pyridin-2-yl)pyridin-2-amine (Compound 325)

To a stirred solution of 5-(2-(2-aminopyridin-3-yl)-5-(1H-pyrazol-1-yl)-3H-imidazo[4,5-b]pyridin-3-yl)-2,3-dihydro-1H-inden-1-ol (100.0 mg, 0.244 mmol, 1.00 equiv), pyrazole (50.0 mg, 0.734 mmol, 3.00 equiv) and $PPh_3$ (192.8 mg, 0.734 mmol, 3.00 equiv) in THF (5.0 mL) was added DEAD (128.0 mg, 0.734 mmol, 3.00 equiv) in portions at 0° C. under nitrogen atmosphere. The resulting mixture was stirred overnight at 50° C. under nitrogen atmosphere. The reaction was quenched with water (30 mL) at rt. The resulting mixture was extracted with ethyl acetate (3x20 ml). The combined organic layers were dried over anhydrous $Na_2SO_4$. After filtration, the filtrate was concentrated under reduced pressure. The residue was purified by Prep-HPLC on a XSelect CSH OBD Column using a gradient of acetonitrile in water (+0.1% formic acid) to afford 3-(3-(1-(1H-pyrazol-1-yl)-2,3-dihydro-1H-inden-5-yl)-5-(1H-pyrazol-1-yl)-3H-imidazo[4,5-b]pyridin-2-yl)pyridin-2-amine (Compound 325, formic acid salt) (7.4 mg, 6% yield) as a white solid: MS (ESI) calcd for $C_{26}H_{21}N_9$: 459.19 m/z, found, 460.40 $[M+H]^+$. $^1H$ NMR (400 MHz, DMSO-$d_6$) δ (ppm); 8.27-8.45 (m, 2H), 7.90-8.06 (m, 2H), 7.68-7.85 (m, 2H), 7.43-7.57 (m, 2H), 7.18-7.31 (m, 2H), 7.06-7.18 (m, 1H), 6.83-6.97 (m, 2H), 6.48-6.59 (m, 1H), 6.36-6.47 (m, 1H), 6.26-6.36 (m, 1H), 5.93-6.08 (m, 1H), 3.09-3.25 (m, 1H), 2.91-3.06 (m, 1H), 2.63-2.77 (m, 1H), 2.52-2.59 (m, 1H).

Intermediate 325-1: 5-(2-(2-aminopyridin-3-yl)-5-(1H-pyrazol-1-yl)-3H-imidazo[4,5-b]pyridin-3-yl)-2,3-dihydro-1H-inden-1-one Intermediate 325-1

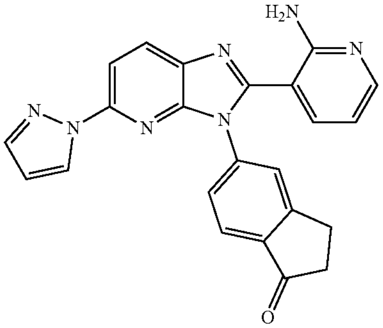

Synthetic Route:

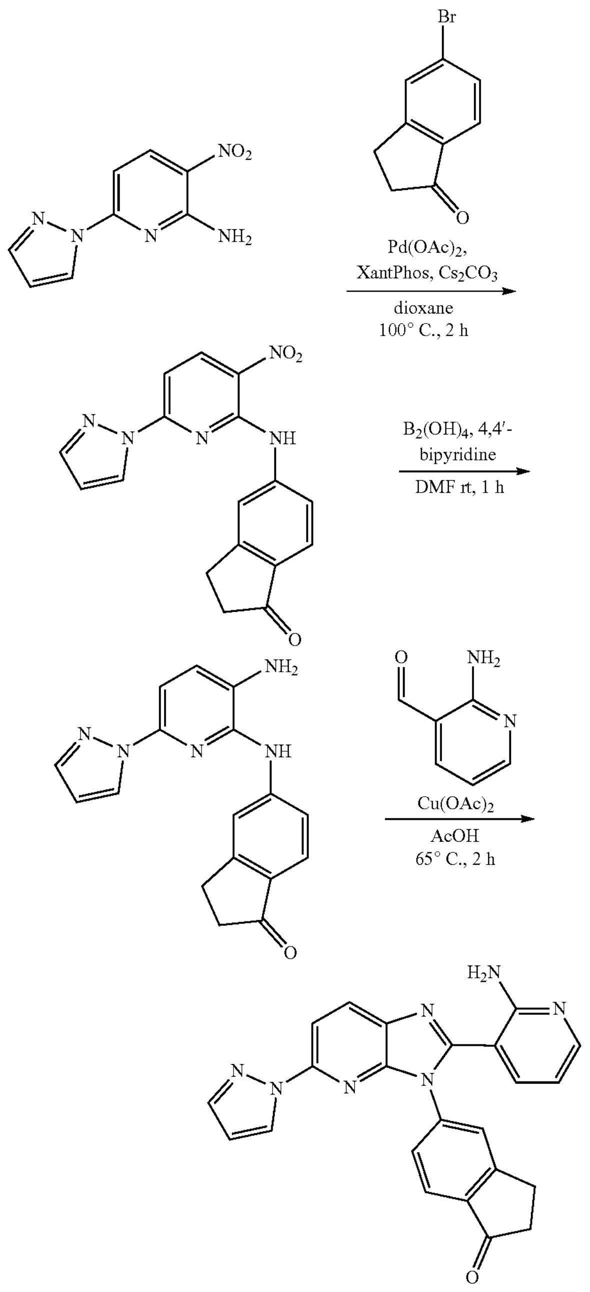

Intermediate 325-1

Step 1: Synthesis of 5-((3-nitro-6-(1H-pyrazol-1-yl) pyridin-2-yl)amino)-2,3-dihydro-1H-inden-1-one To a solution of 3-nitro-6-(pyrazol-1-yl)pyridin-2-amine (15.0 g, 73.1 mmol, 1 equiv) and 5-bromo-2,3-dihydroinden-1-one (15.43 g, 73.11 mmol, 1 equiv) in 1,4-dioxane (400 mL) were added $Pd(OAc)_2$ (1.64 g, 7.31 mmol, 0.1 equiv), XantPhos (4.23 g, 7.31 mmol, 0.1 equiv) and $Cs_2CO_3$ (71.46 g, 219.3 mmol, 3 equiv). The resulting mixture was maintained under nitrogen and stirred for 1 h at 100° C. The mixture was allowed to cool to room temperature. Water was added and the precipitated solids were collected by filtration to afford 5-((3-nitro-6-(1H-pyrazol-1-yl)pyridin-2-yl)amino)-2,3-dihydro-1H-inden-1-one (37 g, 91%) as a black solid. MS (ESI) calcd. for $C_{17}H_{13}N_5O_3$: 335.10 m/z, found: 336.00 $[M+H]^+$.

Step 2: Synthesis of 5-((3-amino-6-(1H-pyrazol-1-yl)pyridin-2-yl)amino)-2,3-dihydro-1H-inden-1-one To a cooled (0° C.) solution of 5-((3-nitro-6-(1H-pyrazol-1-yl)pyridin-2-yl)amino)-2,3-dihydro-1H-inden-1-one (10.00 g, 29.82 mmol, 1 equiv) in DMF (100 mL) were added $B_2(OH)_4$ (8.02 g, 89.5 mmol, 3 equiv) and 4-(pyridin-4-yl)pyridine (232.9 mg, 1.491 mmol, 0.05 equiv). The resulting mixture was stirred for 1 h at room temperature. Water was added and the precipitated solids were collected by filtration to afford 5-((3-amino-6-(1H-pyrazol-1-yl)pyridin-2-yl)amino)-2,3-dihydro-1H-inden-1-one (8.5 g, 50%) as a black solid. MS (ESI) calcd. for $C_{17}H_{15}N_5O$: 305.13 m/z, found: 306.15 $[M+H]^+$.

Step 3: Synthesis of 5-[2-(2-aminopyridin-3-yl)-5-(pyrazol-1-yl)imidazo[4,5-b]pyridin-3-yl]-2,3-dihydroinden-1-one (Intermediate 77-1)

To a solution of 5-((3-amino-6-(1H-pyrazol-1-yl)pyridin-2-yl)amino)-2,3-dihydro-1H-inden-1-one (8.5 g, 28 mmol, 1 equiv) in AcOH (400 mL) were added 2-aminopyridine-3-carbaldehyde (4.05 g, 33.2 mmol, 1.2 equiv) and $Cu(OAc)_2$ (1.00 g, 5.53 mmol, 0.2 equiv). The resulting mixture was stirred for 12 h at 65° C. The resulting mixture was concentrated under reduced pressure. The residue was purified by silica gel column chromatography, eluting with MeOH/DCM (0-10%) to afford 5-[2-(2-aminopyridin-3-yl)-5-(pyrazol-1-yl)imidazo[4,5-b]pyridin-3-yl]-2,3-dihydroinden-1-one (Intermediate 325-1) (2.5 g, 16%) as a black solid. MS (ESI) calcd. for $C_{23}H_{17}N_7O$: 407.15 m/z, found: 408.15 $[M+H]^+$.

Example 89: (S)-3-(3-(1-(piperidin-1-yl)-2,3-dihydro-1H-inden-5-yl)-5-(1H-pyrazol-1-yl)-3H-imidazo[4,5-b]pyridin-2-yl)pyridin-2-amine (Compound 342)

Compound 342

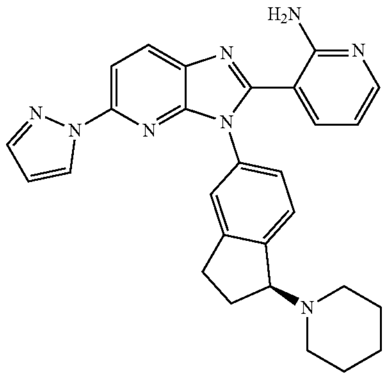

Synthetic Route:

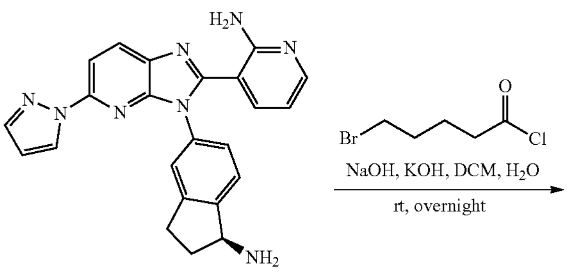

Compound 2

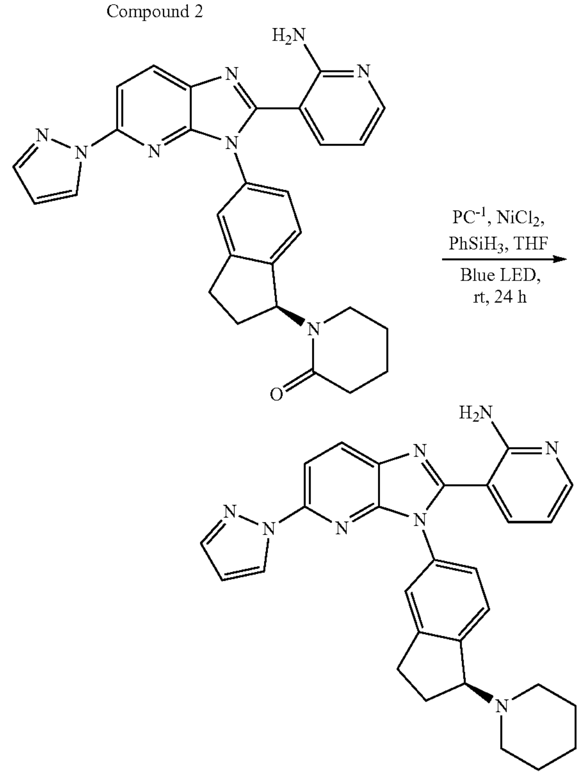

Compound 342

Step 1: Synthesis of (S)-1-(5-(2-(2-aminopyridin-3-yl)-5-(1H-pyrazol-1-yl)-3H-imidazo[4,5-b]pyridin-3-yl)-2,3-dihydro-1H-inden-1-yl)piperidin-2-one To a solution of (S)-3-(3-(1-amino-2,3-dihydro-1H-inden-5-yl)-5-(1H-pyrazol-1-yl)-3H-imidazo[4,5-b]pyridin-2-yl)pyridin-2-amine (Compound 2) (200 mg, 0.490 mmol, 1 equiv) in DCM (50 mL) and $H_2O$ (2 mL) was added a solution of NaOH (19.58 mg, 0.490 mmol, 1 equiv) in $H_2O$, TBAB (189.41 mg, 0.588 mmol, 1.2 equiv) and 5-bromopentanoyl chloride (112.32 mg, 0.564 mmol, 1.15 equiv) in DCM (50 mL) dropwise at 0° C. The mixture was stirred for 1 h at 0-5° C. The reaction mixture was allowed to warm to room temperature and a solution of KOH (329.65 mg, 5.880 mmol, 12 equiv) in $H_2O$ (0.01M) was added dropwise following by stirring overnight. The reaction was quenched with $H_2O$ (100 mL). The resulting mixture was extracted with DCM (3×100 mL). The organic layers were combined, dried over $Na_2SO_4$, filtered and concentrated under reduced pressure. The crude product was purified by reverse-phase flash chromatography on C18 silica gel using a gradient of acetonitrile in water (+0.05% TFA) to afford (S)-1-(5-(2-(2-aminopyridin-3-yl)-5-(1H-pyrazol-1-yl)-3H-imidazo[4,5-b]pyridin-3-yl)-2,3-dihydro-1H-inden-1-yl)piperidin-2-one (trifluoroacetic acid salt) (28.4 mg, 11.54% yield) as an off-white solid: MS (ESI) calcd. for $C_{28}H_{26}N_8O$, 490.22 m/z, found, 491.20 $[M+H]^+$.

Step 2: Synthesis of (S)-3-(3-(1-(piperidin-1-yl)-2,3-dihydro-1H-inden-5-yl)-5-(1H-pyrazol-1-yl)-3H-imidazo[4,5-b]pyridin-2-yl)pyridin-2-amine (Compound 342)

To a mixture of (S)-1-(5-(2-(2-aminopyridin-3-yl)-5-(1H-pyrazol-1-yl)-3H-imidazo[4,5-b]pyridin-3-yl)-2,3-dihydro-1H-inden-1-yl)piperidin-2-one (100 mg, 0.204 mmol, 1 equiv) and $NiCl_2$ (7.92 mg, 0.061 mmol, 0.3 equiv) in THE (5 mL) was added phenylsilane (1.10 g, 10.200 mmol, 50 equiv) and 4,4'-di-tert-butyl-2,2'-bpyridine; bis[2-(pyridin-2-yl)phenyl]iridiumylium; hexafluorophosphate (55.89 mg, 0.061 mmol, 0.3 equiv) under nitrogen atmosphere. The resulting mixture was stirred overnight at room temperature under $N_2$ atmosphere and blue LED light (425 nm). The reaction was quenched with $H_2O$ (100 mL). The resulting mixture was extracted with ethyl acetate (3×100 mL). The organic layers were combined, dried over $Na_2SO_4$, filtered and concentrated under reduced pressure. The crude product was purified by reverse-phase flash chromatography on C18 silica gel using a gradient of acetonitrile in water (+0.05% ammonium bicarbonate) to afford (S)-3-(3-(1-(piperidin-1-yl)-2,3-dihydro-1H-inden-5-yl)-5-(1H-pyrazol-1-yl)-3H-imidazo[4,5-b]pyridin-2-yl)pyridin-2-amine (Compound 342) (15.2 mg, 15.50% yield) as an off-white solid: MS (ESI) calcd. for $C_{28}H_{28}N_8$: 476.20 m/z, found, 477.30 $[M+H]^+$. $^1H$ NMR (400 MHz, DMSO-$d_6$) δ (ppm); 8.27-8.43 (m, 2H), 7.89-8.09 (m, 2H), 7.75-7.84 (m, 1H), 7.38-7.49 (m, 1H), 7.19-7.37 (m, 2H), 7.08-7.18 (m, 1H), 6.48-6.59 (m, 1H), 6.29-6.43 (m, 1H), 4.26-4.43 (m, 1H), 2.72-3.01 (m, 2H), 2.43-2.50 (m, 2H), 2.27-2.49 (m, 2H), 1.97-2.19 (m, 2H), 1.29-1.78 (m, 6H).

Example 90: N-[(1S)-5-[2-(2-aminopyridin-3-yl)-5-(pyrazol-1-yl)imidazo[4,5-b]pyridin-3-yl]-2,3-dihydro-1H-inden-1-yl]-2-fluoro-4,5-dihydroxybenzamide (Compound 351)

Compound 351

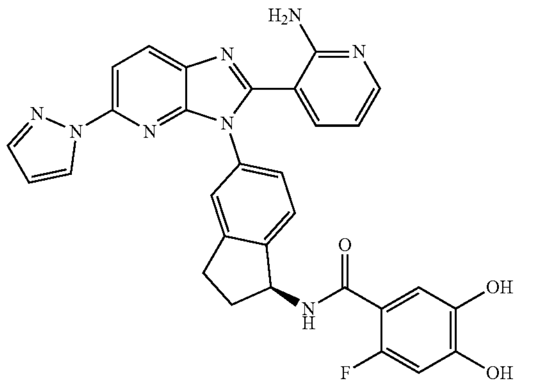

Synthetic Route:

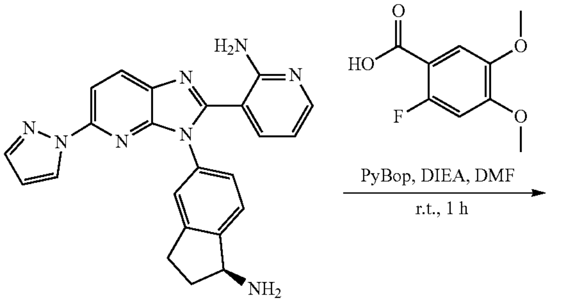

Compound 2

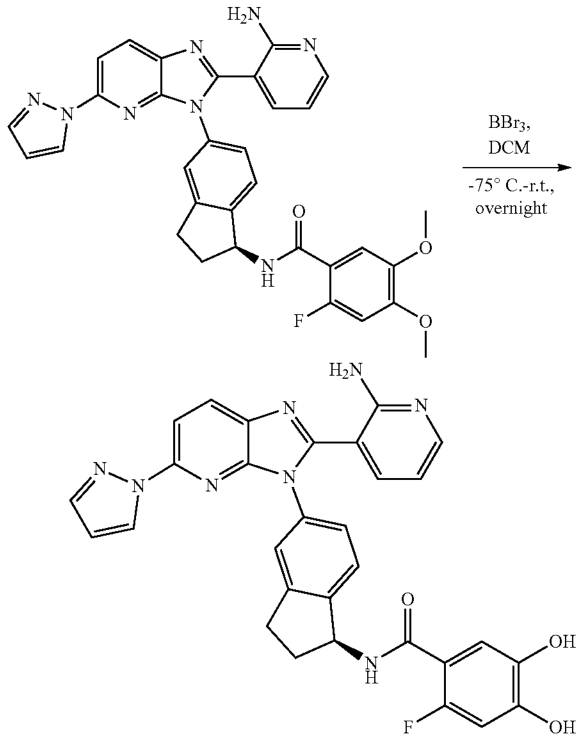

Compound 351

Step 1: Synthesis of N-[(1S)-5-[2-(2-aminopyridin-3-yl)-5-(pyrazol-1-yl)imidazo[4,5-b]pyridin-3-yl]-2,3-dihydro-1H-inden-1-yl]-2-fluoro-4,5-dimethoxy-benzamide To a solution of 3-{3-[(1S)-1-amino-2,3-dihydro-1H-inden-5-yl]-5-(pyrazol-1-yl)imidazo[4,5-b]pyridin-2-yl}pyridin-2-amine (Compound 2) (150 mg, 0.367 mmol, 1 equiv) in DMF (3 mL) was added DIEA (142.39 mg, 1.101 mmol, 3 equiv), PyBOP (191.10 mg, 0.367 mmol, 1 equiv) and 2-fluoro-4,5-dimethoxybenzoic acid (73.51 mg, 0.367 mmol, 1 equiv). The resulting mixture was stirred at room temperature for 1 h. The mixture was purified by reverse-phase flash chromatography on C18 silica gel using a gradient of acetonitrile in water (+0.05% TFA) to afford N-[(1S)-5-[2-(2-aminopyridin-3-yl)-5-(pyrazol-1-yl)imidazo[4,5-b]pyridin-3-yl]-2,3-dihydro-1H-inden-1-yl]-2-fluoro-4,5-dimethoxybenzamide (163 mg, 75.3%) as a yellow solid: MS (ESI) calcd. for $C_{32}H_{27}FN_8O_3$:590.22. found, 591.25 $[M+H]^+$.

Step 2: Synthesis of N-[(1S)-5-[2-(2-aminopyridin-3-yl)-5-(pyrazol-1-yl)imidazo[4,5-b]pyridin-3-yl]-2,3-dihydro-1H-inden-1-yl]-2-fluoro-4,5-dihydroxy-benzamide (Compound 351)

To a solution of N-[(1S)-5-[2-(2-aminopyridin-3-yl)-5-(pyrazol-1-yl)imidazo[4,5-b]pyridin-3-yl]-2,3-dihydro-1H-inden-1-yl]-2-fluoro-4,5-dimethoxybenzamide (163 mg, 0.276 mmol, 1 equiv) in DCM (10 mL) under nitrogen atmosphere was added $BBr_3$ (345.69 mg, 1.380 mmol, 5 equiv) at −78° C. The mixture was stirred at r.t. overnight. The solvent was removed by distillation under vacuum. The residue was purified by reverse-phase flash chromatography on C18 silica gel using a gradient of acetonitrile in water (+0.05% TFA). The product was further purified by Prep-HPLC on a XSelect CSH Fluoro Phenyl column using a gradient of acetonitrile in water (+0.1% TFA) to afford N-[(1S)-5-[2-(2-aminopyridin-3-yl)-5-(pyrazol-1-yl)imidazo[4,5-b]pyridin-3-yl]-2,3-dihydro-1H-inden-1-yl]-2-fluoro-4,5-dihydroxybenzamide (Compound 351) (7.1 mg, 4.50%) as a white solid: MS (ESI) calcd. for $C_{30}H_{23}FN_8O3$: 562.19. found, 585.25 $[M+Na]^+$. $^1H$ NMR (400 MHz, DMSO-$d_6$) δ(ppm) 8.29-8.33 (m. 2H), 7.91-7.96 (m, 2H), 7.76-7.89 (m, 1H), 7.23-7.32 (m, 4H), 7.04-7.06 (m, 1H), 6.52-6.62 (m, 1H), 6.45-6.48 (m, 2H), 5.49-5.40 (m, 1H), 2.84-2.96 (m, 2H), 2.33-2.44 (m, 1H), 1.92-1.99 (m, 1H), 1.02-1.99 (m, 1H). F NMR δ (ppm) −122.24.

Example 91: (S)—N-(5-(2-(2-aminopyridin-3-yl)-5-(4-methylthiazol-2-yl)-3H-imidazo[4,5-b]pyridin-3-yl)-2,3-dihydro-1H-inden-1-yl)-1-methyl-1H-pyrazole-3-carboxamide (Compound 374)

Compound 374

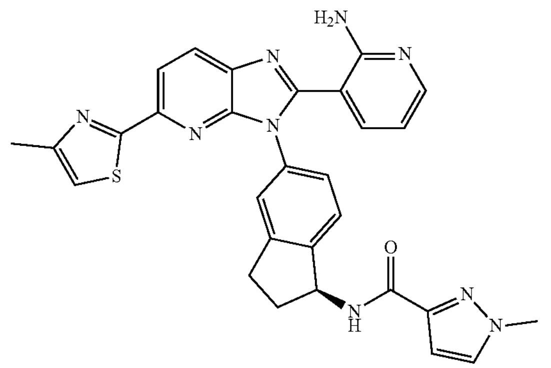

Synthetic Route:

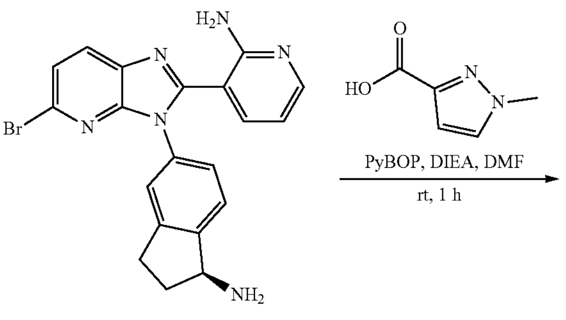

Intermediate 245-3

-continued

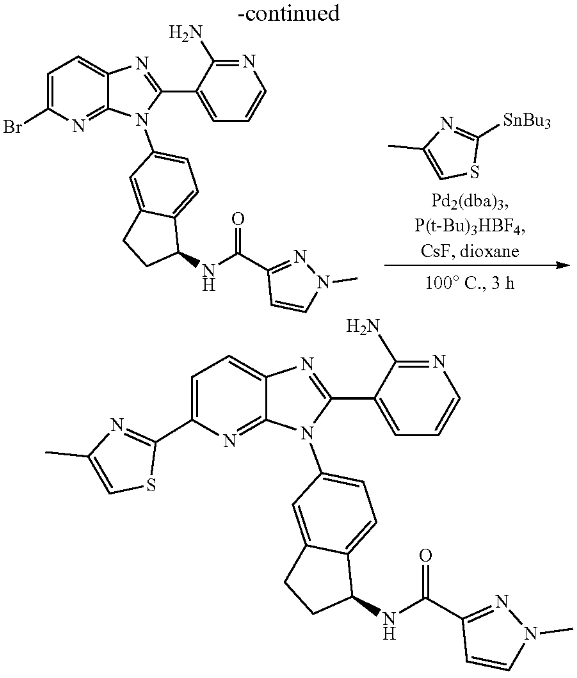

Compound 374

Step 1: Synthesis of (S)—N-(5-(2-(2-aminopyridin-3-yl)-5-bromo-3H-imidazo[4,5-b]pyridin-3-yl)-2,3-dihydro-1H-inden-1-yl)-1-methyl-1H-pyrazole-3-carboxamide A solution of 3-{3-[(1S)-1-amino-2,3-dihydro-1H-inden-5-yl]-5-bromoimidazo[4,5-b]pyridin-2-yl}pyridin-2-amine (Intermediate 245-3) (600 mg, 1.424 mmol, 1 equiv), 1-methylpyrazole-3-carboxylic acid (179.61 mg, 1.424 mmol, 1 equiv), PyBOP (741.13 mg, 1.424 mmol, 1 equiv) and DIEA (552.20 mg, 4.272 mmol, 3 equiv) in DMF (5 mL) was stirred for 1 h at room temperature. The reaction mixture was purified by reverse-phase flash chromatography on C18 silica gel using a gradient of acetonitrile in water (+0.05% ammonium bicarbonate) to afford (S)—N-(5-(2-(2-amino-pyridin-3-yl)-5-bromo-3H-imidazo[4,5-b]pyridin-3-yl)-2,3-dihydro-1H-inden-1-yl)-1-methyl-1H-pyrazole-3-carboxamide (600 mg, 71.62% yield) as a white solid: MS (ESI) calcd. for $C_{25}H_{21}BrN_8O$, 528.10 m/z, found, 529.20 $[M+H]^+$.

Step 2: Synthesis of (S)—N-(5-(2-(2-aminopyridin-3-yl)-5-(4-methylthiazol-2-yl)-3H-imidazo[4,5-b]pyridin-3-yl)-2,3-dihydro-1H-inden-1-yl)-1-methyl-1H-pyrazole-3-carboxamide (Compound 374)

To a solution of N-[(1S)-5-[2-(2-aminopyridin-3-yl)-5-bromoimidazo[4,5-b]pyridin-3-yl]-2,3-dihydro-1H-inden-1-yl]-1-methylpyrazole-3-carboxamide (200 mg, 0.378 mmol, 1 equiv) in dioxane (3 mL) was added 4-methyl-2-(tributylstannyl)-1,3-thiazole (733.28 mg, 1.890 mmol, 5 equiv), $Pd_2(dba)_3$ (34.59 mg, 0.038 mmol, 0.1 equiv), P(t-Bu)$_3$HBF$_4$ (21.92 mg, 0.076 mmol, 0.2 equiv), and CsF (172.16 mg, 1.134 mmol, 3 equiv). The resulting mixture was maintained under nitrogen and stirred at 100° C. for 3 h. After cooling to room temperature, the reaction was quenched with water (100 mL). The resulting mixture was extracted with ethyl acetate (3×100 mL). The organic layers were combined, dried over anhydrous $Na_2SO_4$, filtered and concentrated. The residue was purified by reverse-phase flash chromatography on C18 silica gel using a gradient of acetonitrile in water (+0.05% ammonium bicarbonate) to afford (S)—N-(5-(2-(2-aminopyridin-3-yl)-5-(4-methylthiazol-2-yl)-3H-imidazo[4,5-b]pyridin-3-yl)-2,3-dihydro-1H-inden-1-yl)-1-methyl-1H-pyrazole-3-carboxamide (Compound 374) (19.6 mg, 9.27% yield) as a yellow solid: MS (ESI) calcd. for $C_{29}H_{25}N_9OS$, 547.19 m/z, found, 548.30 $[M+H]^+$. $^1H$ NMR (300 MHz, DMSO-$d_6$) δ (ppm); 8.21-8.35 (m, 1H), 8.10-8.20 (m, 1H), 7.90-8.08 (m, 1H), 7.68-7.85 (m, 1H), 7.10-7.51 (m, 5H), 6.62-6.81 (m, 1H), 6.35-6.55 (m, 1H), 5.43-5.70 (m, 1H), 3.78-4.00 (m, 3H), 2.73-3.15 (m, 2H), 2.35-2.50 (m, 4H), 2.00-2.30 (m, 1H).

Example 92: 3-{3-[(1R,2*)-1-[(1-cyclopropanecarbonylpiperidin-4-yl)amino]-2-fluoro-2,3-dihydro-1H-inden-5-yl]-5-(pyrazol-1-yl)imidazo[4,5-b]pyridin-2-yl}pyridin-2-amine (Compound 385)

Compound 385

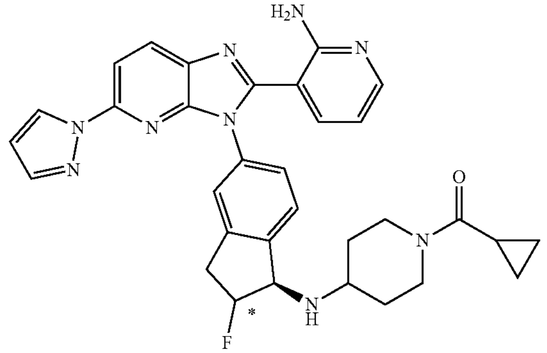

Synthetic Route:

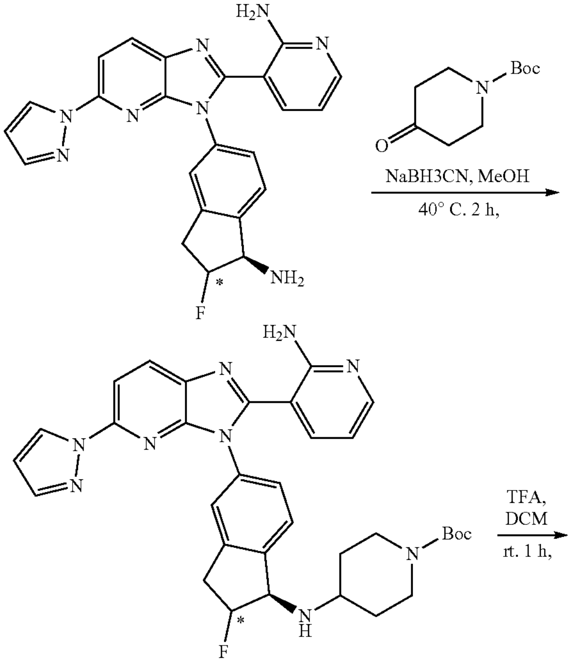

-continued

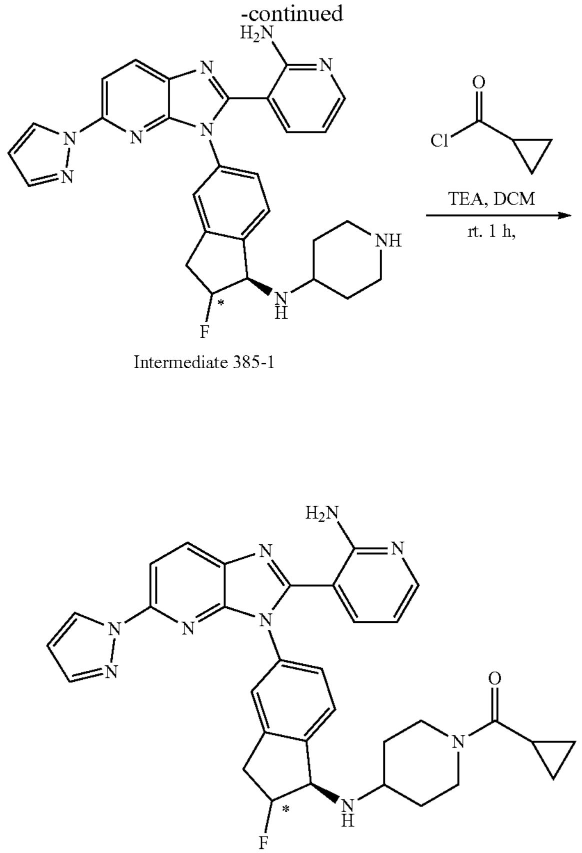

Intermediate 385-1

Compound 385

Step 1: Synthesis of 3-{3-[(1R,2*)-1-[(1-cyclopropanecarbonylpiperidin-4-yl)amino]-2-fluoro-2,3-dihydro-1H-inden-5-yl]-5-(pyrazol-1-yl)imidazo[4,5-b]pyridin-2-yl}pyridin-2-amine (Compound 385)

To a solution of 3-{3-[(1R,2R)-2-fluoro-1-(piperidin-4-ylamino)-2,3-dihydro-1H-inden-5-yl]-5-(pyrazol-1-yl)imidazo[4,5-b]pyridin-2-yl}pyridin-2-amine (Intermediate 385-1) (50 mg, 0.098 mmol, 1 equiv) in DCM (4 mL) was added TEA (49.64 mg, 0.490 mmol, 5 equiv) and cyclopropanecarbonyl chloride (11.28 mg, 0.108 mmol, 1.1 equiv) and the mixture was stirred at rt for 1 h. The solvent was removed under vacuum and the resulting crude was purified by Prep-HPLC on a XSelect CSH OBD Column using a gradient of acetonitrile in water (+0.1% FA) to 3-{3-[(1R, 2*)-1-[(1-cyclopropanecarbonylpiperidin-4-yl)amino]-2-fluoro-2,3-dihydro-1H-inden-5-yl]-5-(pyrazol-1-yl)imidazo[4,5-b]pyridin-2-yl}pyridin-2-amine (Compound 385) (14.9 mg, 25.70%) as white solid: MS (ESI) calcd. for $C_{32}H_{32}FN_9O$, 577.27 m/z, found 578.35 $[M+H]^+$. $^1H$ NMR (400 MHz, DMSO-$d_6$) δ (ppm); 8.14-&3.52 (m, 2H), 7.89-<3.14 (m, 2H), 7.74-7.89 (m, 1H), 7.52-7.74 (m, 1H), 7.29-7.52 (m, 2H), 6.38-6.74 (m, 2H), 5.18-5.58 (m, 1H), 4.42-4.54 (m, 1H), 4.18-4.42 (m, 2H), 4.11-4.18 (m, 1H), 3.45-3.62 (m, 1H), 3.12-3.31 (m, 1H), 2.95-3.12 (m, 2H), 2.68-2.85 (m, 1H), 1.74-2.24 (m, 3H), 1.08-1.48 (m, 2H), 0.68-0.94 (m, 4H). (formic acid salt) *Denotes a stereocenter with undetermined absolute stereochemistry of a single diastereomer.

Intermediate 385-1: 3-(3-((1R,2*)-2-fluoro-1-(piperidin-4-ylamino)-2,3-dihydro-1H-inden-5-yl)-5-(1H-pyrazol-1-yl)-3H-imidazo[4,5-b]pyridin-2-yl)pyridin-2-amine Intermediate 385-1

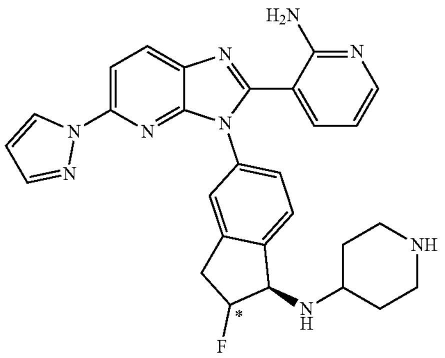

Intermediate 385-1 was prepared in a manner analogous to Intermediate 275-1 using Intermediate 147-2 in place of Example 2. *Denotes a stereocenter with undetermined absolute stereochemistry of a single diastereomer. MS (ESI) calcd. for $C_{28}H_{28}FN_9$: 509.25 m/z, found: 510.15 $[M+H]^+$.

25 (m, 1H), 3.23-3.09 (m, 2H), 2.92-2.80 (m, 2H), 2.43-2.02 (m, 3H), 1.46 (m, 2H).

Intermediate 275-1: (S)-3-(3-(1-(piperidin-4-ylamino)-2,3-dihydro-1H-inden-5-yl)-5-(1H-pyrazol-1-yl)-3H-imidazo[4,5-b]pyridin-2-yl)pyridin-2-amine Intermediate 275-1

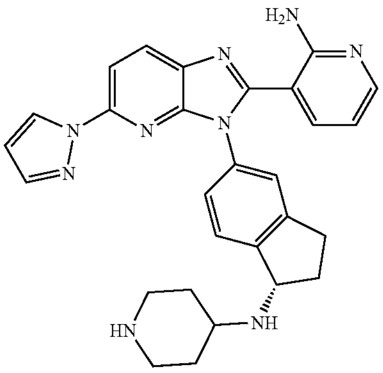

Synthetic Route:

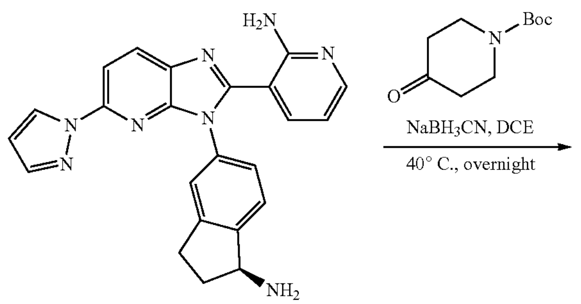

Compound 2

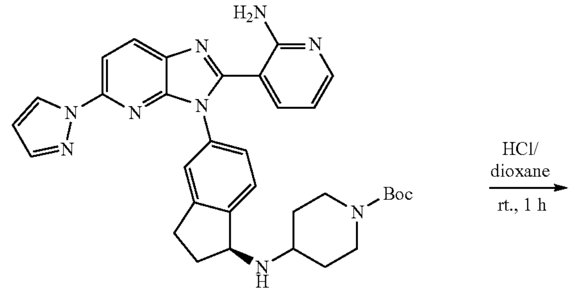

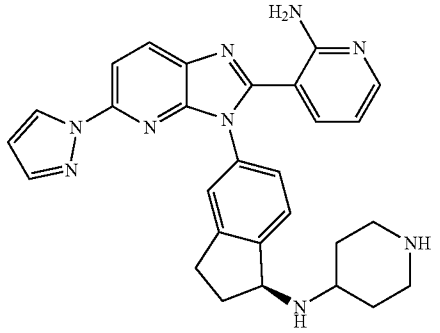

Intermediate 275-1

Step 1: Synthesis of tert-butyl 4-{[(1S)-5-[2-(2-aminopyridin-3-yl)-5-(pyrazol-1-yl)imidazo[4,5-b]pyridin-3-yl]-2,3-dihydro-1H-inden-1-yl]amino}piperidine-1-carboxylate To a solution of 3-{3-[(1S)-1-amino-2,3-dihydro-1H-inden-5-yl]-5-(pyrazol-1-yl)imidazo[4,5-b]pyridin-2-yl}pyridin-2-amine (Compound 2) (410 mg, 1.00 mmol) in DCE (10 mL) was added tert-butyl 4-oxopiperidine-1-carboxylate (200 mg, 1.00 mmol). The resulting mixture was stirred at 40° C. for 1 h. To the above mixture was added $NaBH_3CN$ (252 mg, 4.02 mmol). The resulting mixture was stirred overnight at 40° C. The mixture was filtered and the filter cake was washed with acetonitrile (3×5 mL). The filtrate was concentrated under reduced pressure. The resulting mixture was purified by reverse-phase flash column chromatography on C18 silica gel using a gradient of acetonitrile in water (+0.05% ammonium bicarbonate) to afford tert-butyl 4-{[(1S)-5-[2-(2-aminopyridin-3-yl)-5-(pyrazol-1-yl)imidazo[4,5-b]pyridin-3-yl]-2,3-dihydro-1H-inden-1-yl]amino}piperidine-1-carboxylate (260 mg, 44% yield) as a yellow solid. MS (ESI) calcd. for $C_{33}H_{37}N_9O_2$: 591.31 m/z, found: 592.40 $[M+H]^+$.

Step 2: Synthesis of 3-{3-[(1S)-1-(piperidin-4-ylamino)-2,3-dihydro-1H-inden-5-yl]-5-(pyrazol-1-yl)imidazo[4,5-b]pyridin-2-yl}pyridin-2-amine (Intermediate 275-1)

A solution of tert-butyl 4-{[(1S)-5-[2-(2-aminopyridin-3-yl)-5-(pyrazol-1-yl)imidazo[4,5-b]pyridin-3-yl]-2,3-dihydro-1H-inden-1-yl]amino}piperidine-1-carboxylate (260 mg, 0.439 mmol) in 4N HCl in 1,4-dioxane (10 mL) was stirred at room temperature for 1 h. The solvent was removed by distillation under vacuum to afford 3-{3-[(1S)-1-(piperidin-4-ylamino)-2,3-dihydro-1H-inden-5-yl]-5-(pyrazol-1-yl)imidazo[4,5-b]pyridin-2-yl}pyridin-2-amine HCl (Intermediate 275-1) (220 mg) as a yellow solid, which was used directly in subsequent steps without further purification. MS (ESI) calcd. for $C_{28}H_{29}N_9$: 491.25 m/z, found: 492.25 $[M+H]^+$.

The following compounds were prepared analogous to the synthetic preparation in Compound 275-1's Buchwald intermediate.

TABLE 15A

Characterization data of compounds prepared analogously to Compound 275-1's Buchwald intermediate.

| Cpd ID | Characterization Data |
|---|---|
| 593 | Observed mass (ESI): 600.15 [M + H]+. 1H NMR (300 MHz, DMSO-d6) δ(ppm): 8.34-8.37 (m, 2H), 7.99-8.01 (m, 2H), 7.88 (s, 1H), 7.49-7.80 (m, 1H), 7.47 (s, 1H), 7.22-7.46 (m, 2H), 6.88-6.94 (m, 3H), 6.54 (s, 1H), 6.42-6.44 (m, 1H), 4.37 (t, J = 6.9 Hz, 1H), 3.83-3.87 (m, 2H), 2.78-2.98 (m, 5H), 2.42-2.45 (m, 1H), 2.07-2.11 (m, 2H), 1.85-1.99 (m, 1H), 1.65-1.80 (m, 1H), 1.34-1.56 (m, 2H). |

The following compounds were prepared analogous to the synthetic preparation in Example 92 (Compound 385).

TABLE 15B

Characterization data of compounds prepared analogously to compound 385.

| Cpd ID | Characterization Data |
|---|---|
| 386 | MS (ESI) calcd. for $C_{32}H_{32}FN_9O$, 577.27 m/z, found 577.90 $[M + H]^+$. $^1H$ NMR (400 MHz, DMSO-$d_6$) δ (ppm); 8.18-8.52 (m, 2H), 7.89-8.18 (m, 2H), 7.72-7.89 (m, 1H), 7.47-7.72 (m, 1H), 7.12-7.42 (m, 3H), 6.36-6.74 (m, 2H), 5.34-5.69 (m, 1H), 4.42-4.62 (m, 1H), 4.18-4.36 (m, 2H), 4.12-4.14 (m, 1H), 3.18-3.34 (m, 2H), 3.06-3.18 (m, 2H), 2.76-2.98 (m, 1H), 1.82-2.22 (m, 3H), 1.18-1.59 (m, 2H), 0.68-0.95 (m, 4H). (formic acid salt) |
| 441 | .: MS (ESI) calcd. for $C_{30}H_{29}N_9O$, 531.25 m/z, found, 532.35 [M + H]+. $^1H$ NMR (400 MHz, DMSO-$d_6$) δ (ppm); 8.35-8.37 (m, 2H), 8.00-8.01 (m, 1H), 7.95-7.97 (m, 1H), 7.81-7.82 (m, 1H), 7.50-7.53 (m, 1H), 7.34-7.35 (m, 1H), 7.23-7.27 (m, 2H), 6.55-6.56 (m, 1H), 6.47-6.49 (m, 1H), 4.39-4.41 (m, 1H), 4.20-4.21 (m, 1H), 3.86-3.99 (m, 2H), 3.77-3.80 (m, 1H), 3.50-3.63 (m, 1H), 2.94-3.00 (m, 1H), 2.79-2.81 (m, 1H), 2.28-2.41 (m, 1H), 1.53-1.54 (m, 1H), 1.51-1.52 (m, 1H), 0.70-0.74 (m, 4H). |

Example 93: (S)—N-(5-(2-(2-aminopyridin-3-yl)-5-(1H-pyrazol-1-yl)-3H-imidazo[4,5-b]pyridin-3-yl)-2,3-dihydro-1H-inden-1-yl)-4-hydroxy-3-(methoxymethyl)benzamide (Compound 410)

Compound 410

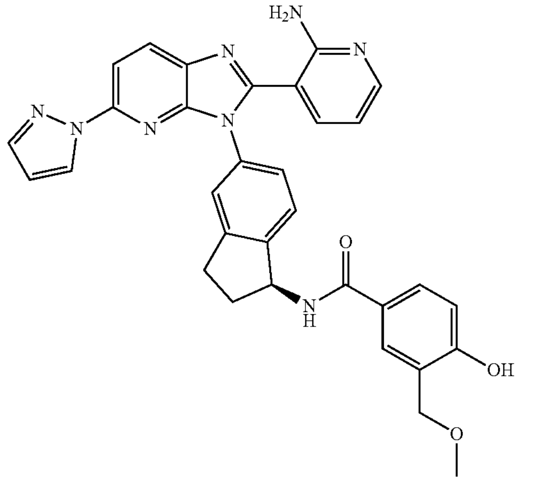

Synthetic Route:

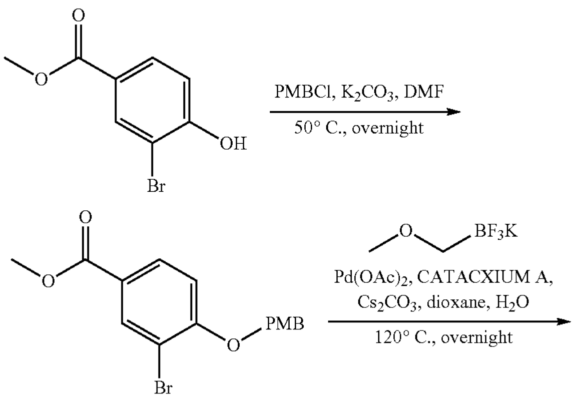

-continued

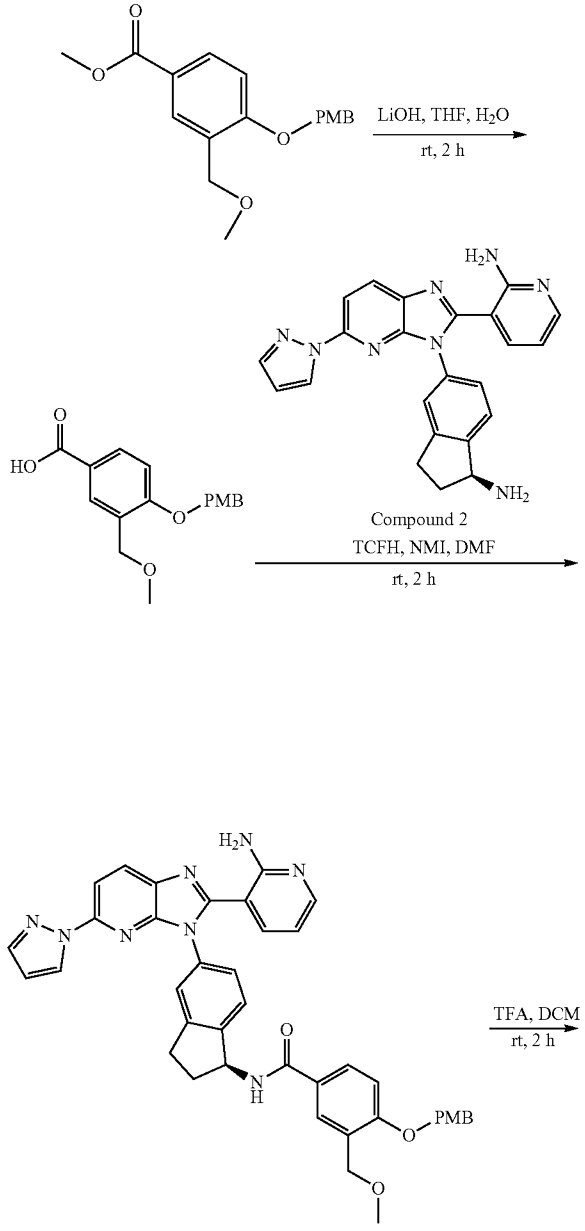

-continued

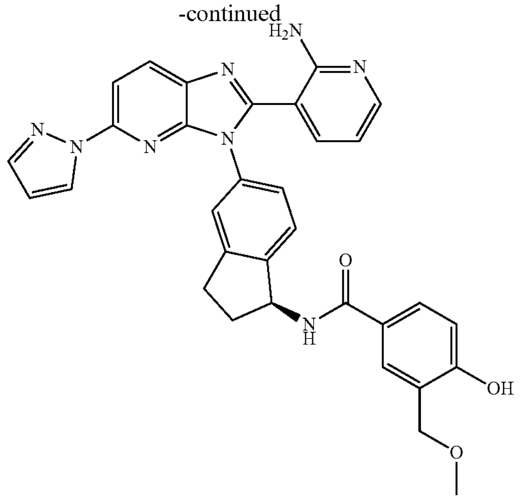

Compound 410

Step 1: Synthesis of methyl 3-bromo-4-((4-methoxybenzyl)oxy)benzoate

To a solution of methyl 3-bromo-4-hydroxybenzoate (1 g, 4.328 mmol, 1 equiv) and $K_2CO_3$ (0.90 g, 6.492 mmol, 1.5 equiv) in DMF (15 mL) was added PMBCl (1.01 g, 6.492 mmol, 1.5 equiv) at room temperature and the mixture was stirred at 50° C. overnight. After cooling to room temperature, the reaction was quenched with water (100 mL). The resulting mixture was extracted with ethyl acetate (3×150 mL). The organic layers were combined, dried over anhydrous $Na_2SO_4$, filtered and concentrated. The residue obtained was purified by silica gel chromatography (0-20% ethyl acetate/petroleum ether) to afford methyl 3-bromo-4-[(4-methoxyphenyl)methoxy]benzoate (1.5 g, 90.79% yield) as a white solid. Structure confirmed by TLC (Rf=0.3, PE:EA=10:1) and NMR/MS of downstream derivatives.

Step 2: Synthesis of methyl 4-((4-methoxybenzyl)oxy)-3-(methoxymethyl)benzoate

To a solution of methyl 3-bromo-4-[(4-methoxyphenyl)methoxy]benzoate (1 g, 2.847 mmol, 1 equiv) in dioxane (8 mL) and $H_2O$ (2 mL) was added potassium trifluoro(methoxymethyl)borate (0.87 g, 5.694 mmol, 2 equiv), $Pd(OAc)_2$ (0.06 g, 0.285 mmol, 0.1 equiv), bis(adamantan-1-yl)(butyl)phosphane (0.20 g, 0.569 mmol, 0.2 equiv) and $Cs_2CO_3$ (2.78 g, 8.541 mmol, 3 equiv). The resulting mixture was maintained under nitrogen and stirred at 120° C. overnight. After cooling to room temperature, the reaction was quenched with water (100 mL). The resulting mixture was extracted with ethyl acetate (3×150 mL). The organic layers were combined, dried over anhydrous $Na_2SO_4$, filtered and concentrated. The residue obtained was purified by silica gel chromatography (0~20% ethyl acetate/petroleum ether) to afford methyl 4-((4-methoxybenzyl)oxy)-3-(methoxymethyl)benzoate (400 mg, 41.30% yield) as a yellow solid. 1H NMR (300 MHz, DMSO-$d_6$) δ (ppm); 7.86-7.92 (m, 2H), 7.38-7.41 (m, 2H), 7.19-7.22 (m, 1H), 6.94-6.97 (m, 2H), 5.14 (s, 2H), 4.43 (s, 2H), 3.81-3.89 (m, 6H), 3.31-3.34 (m, 3H).

Step 3: Synthesis of 3-(methoxymethyl)-4-[(4-methoxyphenyl)methoxy]benzoic acid

To a solution of methyl 4-((4-methoxybenzyl)oxy)-3-(methoxymethyl)benzoate (600 mg, 1.897 mmol, 1 equiv) in THE (3 mL) was added LiOH (136.27 mg, 5.691 mmol, 3 equiv) in $H_2O$ (3 mL). The resulting mixture was stirred at room temperature for 2 h. The resulting mixture was concentrated under reduced pressure to afford 3-(methoxymethyl)-4-[(4-methoxyphenyl)methoxy]benzoic acid (550 mg, crude) as a yellow solid: MS (ESI) calcd. for $C_{17}H_{18}O_5$, 302.12 m/z, found, 301.10 $[M-H]^-$.

Step 4: Synthesis of (S)—N-(5-(2-(2-aminopyridin-3-yl)-5-(1H-pyrazol-1-yl)-3H-imidazo[4,5-b]pyridin-3-yl)-2,3-dihydro-1H-inden-1-yl)-4-((4-methoxybenzyl)oxy)-3-(methoxymethyl)benzamide To a solution of 3-(methoxymethyl)-4-[(4-methoxyphenyl)methoxy]benzoic acid (300 mg, 0.992 mmol, 1 equiv) in DMF (5 mL) was added 3-{3-[(1S)-1-amino-2,3-dihydro-1H-inden-5-yl]-5-(pyrazol-1-yl)imidazo[4,5-b]pyridin-2-yl}pyridin-2-amine (Compound 2) (405.33 mg, 0.992 mmol, 1 equiv), TCFH (278.42 mg, 0.992 mmol, 1 equiv) and NMI (244.42 mg, 2.976 mmol, 3 equiv). The resulting mixture was maintained under nitrogen and stirred at room temperature for 2 h. the reaction was quenched with water (100 mL). The resulting mixture was extracted with ethyl acetate (3×150 mL). The organic layers were combined, dried over anhydrous $Na_2SO_4$, filtered and concentrated. The residue was purified by reverse-phase flash chromatography on C18 silica gel using a gradient of acetonitrile in water (+0.05% ammonium bicarbonate) to afford (S)—N-(5-(2-(2-aminopyridin-3-yl)-5-(1H-pyrazol-1-yl)-3H-imidazo[4,5-b]pyridin-3-yl)-2,3-dihydro-1H-inden-1-yl)-4-((4-methoxybenzyl)oxy)-3-(methoxymethyl)benzamide (450 mg, 58.91% yield) as a yellow solid: MS (ESI) calcd. for $C_{40}H_{36}N_8O_4$, 692.29 m/z, found, 693.35 $[M+H]^+$.

Step 5: Synthesis of (S)—N-(5-(2-(2-aminopyridin-3-yl)-5-(1H-pyrazol-1-yl)-3H-imidazo[4,5-b]pyridin-3-yl)-2,3-dihydro-1H-inden-1-yl)-4-hydroxy-3-(methoxymethyl)benzamide (Compound 410)

A solution of (S)—N-(5-(2-(2-aminopyridin-3-yl)-5-(1H-pyrazol-1-yl)-3H-imidazo[4,5-b]pyridin-3-yl)-2,3-dihydro-1H-inden-1-yl)-4-((4-methoxybenzyl)oxy)-3-(methoxymethyl)benzamide (250 mg, 0.361 mmol, 1 equiv) in TFA (4 mL) and DCM (12 mL) was stirred at room temperature for 2 h. The resulting mixture was concentrated under reduced pressure. The residue was purified by reverse-phase flash chromatography on C18 silica gel using a gradient of acetonitrile in water (+0.05% ammonium bicarbonate) to afford (S)—N-(5-(2-(2-aminopyridin-3-yl)-5-(1H-pyrazol-1-yl)-3H-imidazo[4,5-b]pyridin-3-yl)-2,3-dihydro-1H-inden-1-yl)-4-hydroxy-3-(methoxymethyl)benzamide (Compound 410) (82.8 mg, 39.31% yield) as an off-white solid: MS (ESI) calcd. for $C_{32}H_{28}N_8O_3$, 572.22 m/z, found, 573.35 $[M+H]^+$. $^1H$ NMR (300 MHz, DMSO-$d_6$) S (ppm); 10.06-10.20 (m, 1H), 8.57-8.80 (m, 1H), 8.20-8.46 (m, 2H), 7.98-8.08 (m, 1H), 7.90-7.97 (m, 1H), 7.85-7.89 (m, 1H), 7.81-7.84 (m, 1H), 7.66-7.80 (m, 1H), 7.18-7.45 (m, 4H), 6.72-7.01 (m, 3H), 6.48-6.60 (m, 1H), 6.35-6.47 (m, 1H), 5.48-5.72 (m, 1H), 4.40 (s, 2H), 3.32-3.36 (m, 3H), 2.80-3.15 (m, 2H), 2.41-2.50 (m, 1H), 1.98-2.23 (m, 1H).

Example 94: (S)—N-(5-(2-(2-aminopyridin-3-yl)-5-((1-methylazetidin-3-yl)ethynyl)-3H-imidazo[4,5-b]pyridin-3-yl)-2,3-dihydro-1H-inden-1-yl)-6-(difluoromethyl)nicotinamide (Compound 411)
Compound 411
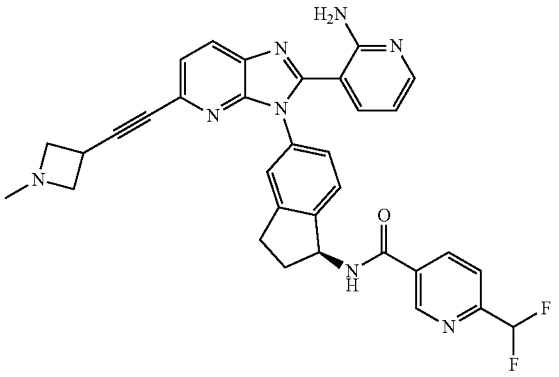
Synthetic Route:
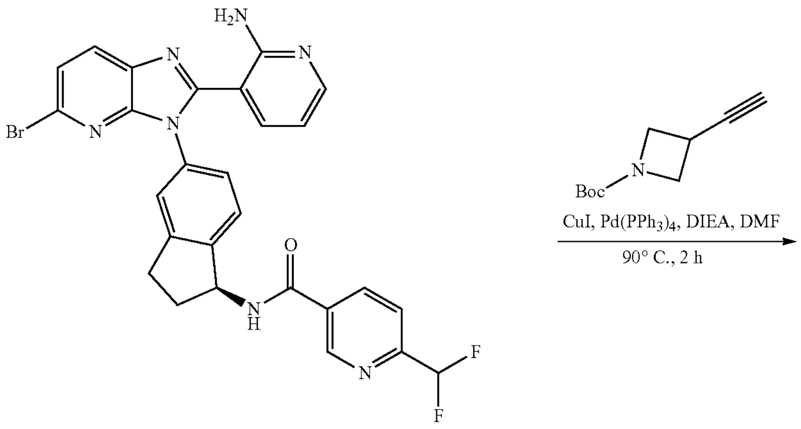
Intermediate 404-1
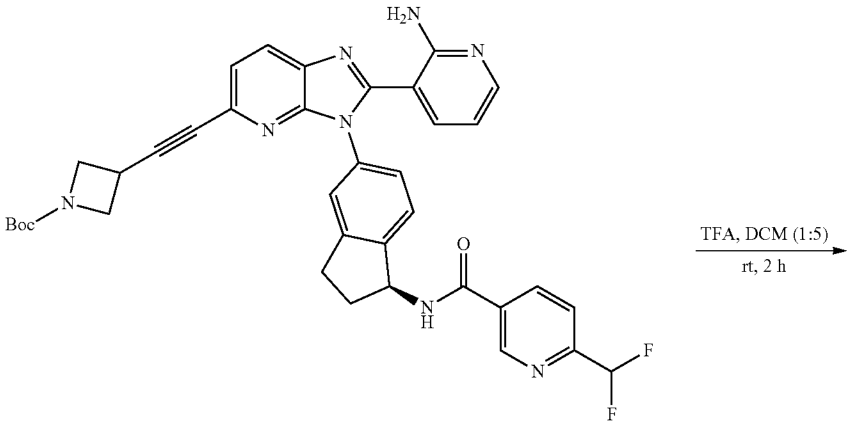

-continued

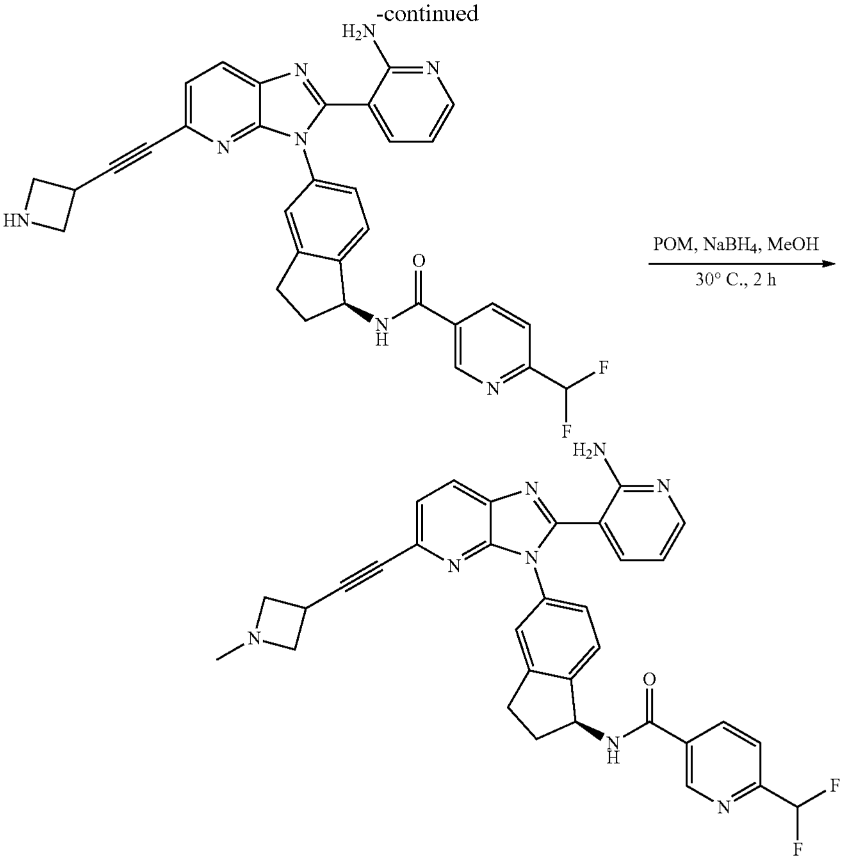

Compound 411

Step 1: Synthesis of tert-butyl (S)-3-((2-(2-aminopyridin-3-yl)-3-(1-(6-(difluoromethyl)nicotinamido)-2,3-dihydro-1H-inden-5-yl)-3H-imidazo[4,5-b]pyridin-5-yl)ethynyl)azetidine-1-carboxylate To a stirred mixture of (S)—N-(5-(2-(2-aminopyridin-3-yl)-5-bromo-3H-imidazo[4,5-b]pyridin-3-yl)-2,3-dihydro-1H-inden-1-yl)-6-(difluoromethyl)nicotinamide (Intermediate 404-1) (150 mg, 0.260 mmol, 1 equiv), CuI (9.91 mg, 0.052 mmol, 0.20 equiv), $Pd(PPh_3)_4$ (60.14 mg, 0.052 mmol, 0.2 equiv) and DIEA (100.90 mg, 0.780 mmol, 3 equiv) in DMF (5 mL) was added tert-butyl 3-ethynylazetidine-1-carboxylate (70.75 mg, 0.390 mmol, 1.50 equiv) under $N_2$ atmosphere. The reaction mixture was stirred at 90° C. for 2 h. After cooling to room temperature, the reaction was quenched with water (50 mL). The resulting mixture was extracted with ethyl acetate (3×50 mL). The organic layers were combined, dried over anhydrous $Na_2SO_4$, filtered and concentrated. The residue was purified by reverse-phase flash chromatography on C18 silica gel using a gradient of acetonitrile in water (+0.05% ammonium bicarbonate) to afford tert-butyl (S)-3-((2-(2-aminopyridin-3-yl)-3-(1-(6-(difluoromethyl)nicotinamido)-2,3-dihydro-1H-inden-5-yl)-3H-imidazo[4,5-b]pyridin-5-yl)ethynyl)azetidine-1-carboxylate (110 mg, 70.98% yield) as a yellow solid: MS (ESI) calcd. for $C_{37}H_{34}F_2N_8O_3$: 676.27 m/z, found, 677.30 $[M+H]^+$.

Step 2: Synthesis of (S)—N-(5-(2-(2-aminopyridin-3-yl)-5-(azetidin-3-ylethynyl)-3H-imidazo[4,5-b]pyridin-3-yl)-2,3-dihydro-1H-inden-1-yl)-6-(difluoromethyl)nicotinamide A solution of tert-butyl (S)-3-((2-(2-aminopyridin-3-yl)-3-(1-(6-(difluoromethyl)nicotinamido)-2,3-dihydro-1H-inden-5-yl)-3H-imidazo[4,5-b]pyridin-5-yl)ethynyl)azetidine-1-carboxylate (100 mg, 0.147 mmol, 1 equiv) in TFA (1 mL) and DCM (5 mL) was stirred at room temperature for 2 h. The resulting mixture was concentrated to afford (S)—N-(5-(2-(2-aminopyridin-3-yl)-5-(azetidin-3-ylethynyl)-3H-imidazo[4,5-b]pyridin-3-yl)-2,3-dihydro-1H-inden-1-yl)-6-(difluoromethyl)nicotinamide (80 mg, crude) as a yellow solid: MS (ESI) calcd. for $C_{32}H_{26}F_2N_8O$, 576.22 m/z, found, 577.35 $[M+H]^+$.

Step 3: (S)—N-(5-(2-(2-aminopyridin-3-yl)-5-((1-methylazetidin-3-yl)ethynyl)-3H-imidazo[4,5-b]pyridin-3-yl)-2,3-dihydro-1H-inden-1-yl)-6-(difluoromethyl)nicotinamide (Compound 411)

A mixture of (S)—N-(5-(2-(2-aminopyridin-3-yl)-5-(azetidin-3-ylethynyl)-3H-imidazo[4,5-b]pyridin-3-yl)-2,3-dihydro-1H-inden-1-yl)-6-(difluoromethyl)nicotinamide (80 mg, 0.139 mmol, 1 equiv) and paraformaldehyde (37.49 mg, 0.417 mmol, 3 equiv) in MeOH (4 mL) was stirred for 2 h at 30° C. To the reaction mixture was added Sodium borohydride (15.75 mg, 0.417 mmol, 3.00 equiv). The reaction was quenched with water (50 mL). The resulting mixture was extracted with ethyl acetate (3×50 mL). The organic layers were combined, dried over anhydrous $Na_2SO_4$, filtered and concentrated. The residue was purified by reverse-phase flash chromatography on C18 silica gel using a gradient of acetonitrile in water (+0.05% ammonium bicarbonate) to afford (S)—N-(5-(2-(2-aminopyridin-3-yl)-5-((1-methylazetidin-3-yl)ethynyl)-3H-imidazo[4,5-b]pyridin-3-yl)-2,3-dihydro-1H-inden-1-yl)-6-(difluoromethyl) nicotinamide (Compound 411) (15.6 mg, 16.79% yield) as a white solid: MS (ESI) calcd. for $C_{33}H_{28}F_2N_8O$, 590.24 m/z, found, 591.30 $[M+H]^+$. $^1H$ NMR (300 MHz, DMSO-$d_6$) δ (ppm); 9.12-9.17 (m, 1H), 8.42-8.46 (m, 1H), 8.12-8.17 (m, 1H), 7.97-8.02 (m, 1H), 7.81-7.85 (m, 1H), 7.45-7.51 (m, 1H), 7.41-7.44 (m, 1H), 7.34-7.39 (m, 1H), 7.30-7.32 (m, 1H), 7.22-7.24 (m, 1H), 6.87-7.19 (m, 1H), 6.42-6.46 (m, 1H), 5.61-5.68 (m, 1H), 3.51-3.55 (m, 2H), 3.32-3.44 (m, 1H), 3.01-3.11 (m, 3H), 2.85-2.99 (m, 1H), 2.61-2.62 (m, 1H), 2.21 (s, 3H), 2.01-2.13 (m, 1H). $^{19}F$ NMR (282 MHz, DMSO-$d_6$) δ (ppm); −116.05.

Intermediate 404-1: (S)—N-(5-(2-(2-aminopyridin-3-yl)-5-bromo-3H-imidazo[4,5-b]pyridin-3-yl)-2,3-dihydro-1H-inden-1-yl)-6-(difluoromethyl)nicotinamide Intermediate 404-1

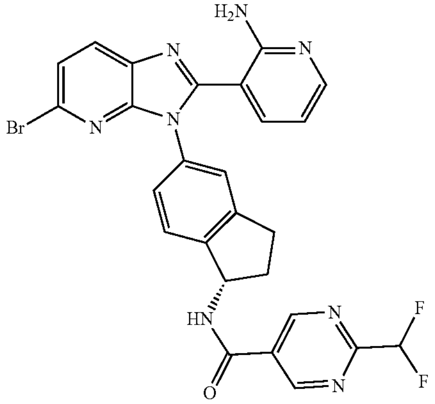

Intermediate 404-1 was prepared in a manner analogous to Example 3 using PyBOP in place of HATU, Intermediate 245-3 in place of Example 2 and 6-(difluoromethyl)nicotinic acid in place of 3,4-difluoro-5-anisic acid. MS data. MS (ESI) calcd. for $C_{27}H_{20}BrF_2N_7O$: 575.09 m/z, found: 576.30 $[M+H]^+$.

Example 95: (S)—N-(5-(2-(2-aminopyridin-3-yl)-5-(3-methyl-1H-1,2,4-triazol-1-yl)-3H-imidazo[4,5-b]pyridin-3-yl)-2,3-dihydro-1H-inden-1-yl)-6-methylnicotinamide (Compound 417) and (S)—N-(5-(2-(2-aminopyridin-3-yl)-5-(5-methyl-11H-1,2,4-triazol-1-yl)-3H-imidazo[4,5-b]pyridin-3-yl)-2,3-dihydro-1H-inden-1-yl)-6-methylnicotinamide (Compound 418)

Compouns 417

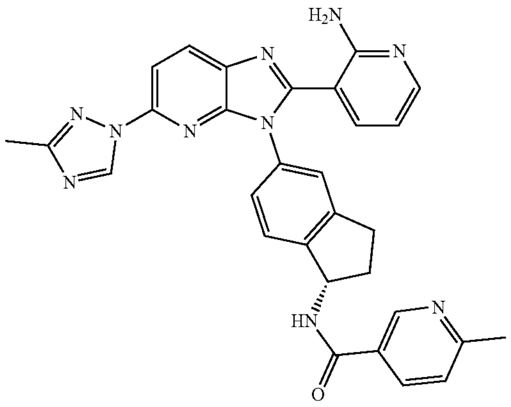

Compound 418

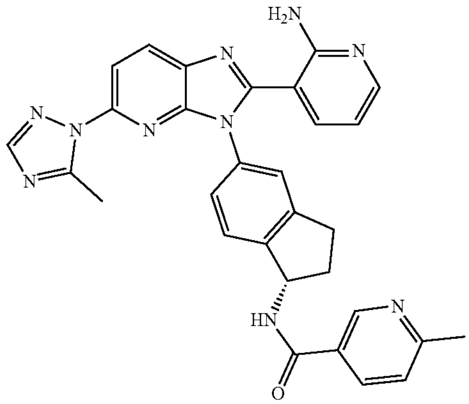

Synthetic Route:

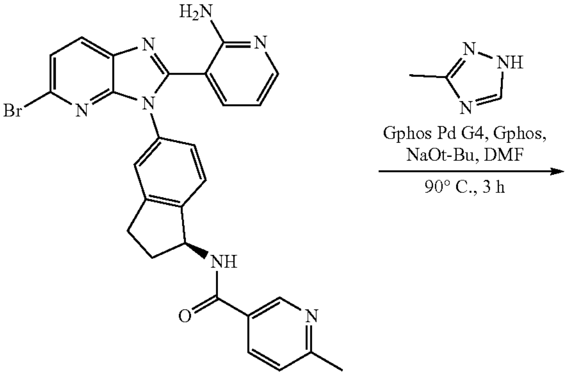

Intermediate 265-1

-continued

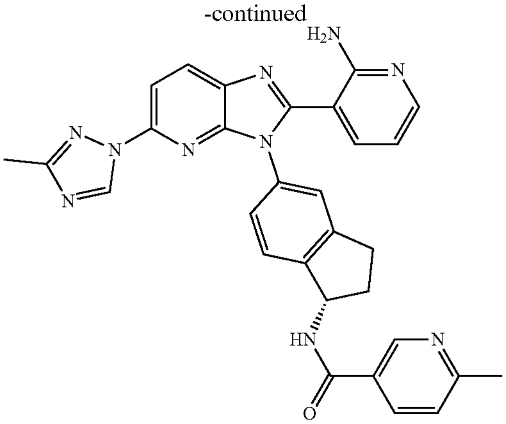

Compound 417

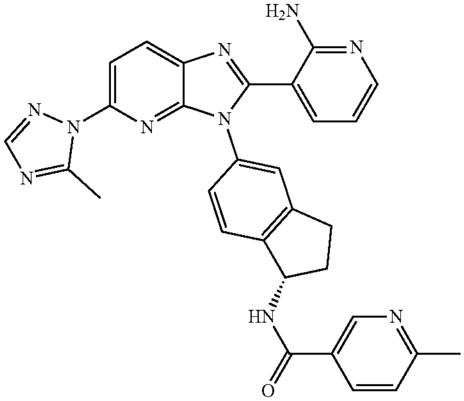

Compound 418

Step 1: Synthesis of (S)—N-(5-(2-(2-aminopyridin-3-yl)-5-(3-methyl-1H-1,2,4-triazol-1-yl)-3H-imidazo [4,5-b]pyridin-3-yl)-2,3-dihydro-1H-inden-1-yl)-6-methylnicotinamide (Compound 417) and (S)—N-(5-(2-(2-aminopyridin-3-yl)-5-(5-methyl-11H-1,2,4-triazol-1-yl)-3H-imidazo[4,5-b]pyridin-3-yl)-2,3-dihydro-1H-inden-1-yl)-6-methylnicotinamide (Compound 418)

To a stirred solution of (S)—N-(5-(2-(2-aminopyridin-3-yl)-5-bromo-3H-imidazo[4,5-b]pyridin-3-yl)-2,3-dihydro-1H-inden-1-yl)-6-methylnicotinamide (Intermediate 265-1) (200 mg, 0.370 mmol, 1 equiv), 3-methyl-1H-1,2,4-triazole (61.50 mg, 0.740 mmol, 2 equiv), GPhos (39.73 mg, 0.074 mmol, 0.2 equiv) and GPhos Pd G4 (69.98 mg, 0.074 mmol, 0.2 equiv) in DMF (3 mL) was added sodium tert-butylate (1.5 M, 0.5 mL, 2 equiv) under $N_2$ atmosphere. The reaction mixture was stirred at 90° C. for 3 h. After cooling to room temperature, the reaction was quenched with water (50 mL). The resulting mixture was extracted with ethyl acetate (3×50 mL). The organic layers were combined, dried over anhydrous $Na_2SO_4$, filtered and concentrated to afford crude product. The crude product was purified by Prep-HPLC on a XSelect CSH Fluoro Phenyl column using a gradient of acetonitrile in water (+0.05% TFA) to afford (S)—N-(5-(2-(2-aminopyridin-3-yl)-5-(3-methyl-1H-1,2,4-triazol-1-yl)-3H-imidazo[4,5-b]pyridin-3-yl)-2,3-dihydro-1H-inden-1-yl)-6-methylnicotinamide (Compound 417, TFA salt, 18.1 mg, 8.98% yield) as a white solid and (S)—N-(5-(2-(2-aminopyridin-3-yl)-5-(5-methyl-1H-1,2,4-triazol-1-yl)-3H-imidazo[4,5-b]pyridin-3-yl)-2,3-dihydro-1H-inden-1-yl)-6-methylnicotinamide (Compound 418, TFA salt, 8.1 mg, 3.52% yield) as a white solid.

Compound 417: MS (ESI) calcd. for $C_{30}H_{26}N_{10}O$, 542.23 m/z, found, 543.30 $[M+H]^+$. $^1H$ NMR (300 MHz, DMSO-$d_6$) δ (ppm); 9.26-9.33 (m, 1H), 9.12-9.18 (m, 1H), 8.41-8.47 (m, 1H), 7.88-8.22 (m, 2H), 7.79-7.87 (m, 1H), 7.35-7.48 (m, 3H), 7.22-7.33 (m, 2H), 6.84-7.03 (m, 1H), 6.20-6.51 (m, 1H), 5.59-5.79 (m, 1H), 2.99-3.12 (m, 1H), 2.83-2.98 (m, 1H), 2.59-2.62 (m, 1H), 2.37-2.47 (m, 2H), 2.01-2.16 (m, 1H), 1.08-2.25 (m, 3H).

Compound 418: MS (ESI) calcd. for $C_{30}H_{26}N_{10}O$, 542.23 m/z, found, 543.30 $[M+H]^+$. $^1H$ NMR (300 MHz, DMSO-$d_6$) δ (ppm); 8.97-9.04 (m, 1H), 8.47-8.54 (m, 2H), 8.04-8.11 (m, 2H), 7.88-7.93 (m, 2H), 7.71-7.77 (m, 1H), 7.52-7.54 (m, 1H), 7.41-7.43 (m, 1H), 7.29-7.31 (m, 1H), 6.85-6.91 (m, 1H), 5.56-5.63 (m, 1H), 3.01-3.12 (m, 1H), 2.83-2.99 (m, 1H), 2.66-2.73 (m, 6H), 2.63-2.65 (m, 1H), 2.02-2.14 (m, 1H).

The following compounds were prepared analogously to the synthetic preparation of Compound 417 and 418.

TABLE 15C

Characterization data of compounds prepared analogously to compound 417 and 418.

| Cpd ID | Characterization Data |
|---|---|
| 544 | Observed mass (ESI): 663.25 [M + H]+. 1H NMR (300 MHz, DMSO-d6) δ (ppm): 8.27 (d, J = 8.6 Hz, 1H), 8.15 (d, J = 2.7 Hz, 1H), 7.96-8.03 (m, 1H), 7.77 (d, J = 8.6 Hz, 1H), 7.49 (d, J = 7.8 Hz, 1H), 7.28-7.38 (m, 2H), 7.25-7.14 (m, 1H), 6.92 (s, 2H), 6.47-6.35 (m, 1H), 6.16 (d, J = 2.8 Hz, 1H), 5.28-5.59 (m, 1H), 4.33-4.54 (m, 1H), 3.91-4.31 (m, 2H), 3.65-3.81 (m, 4H), 3.02-3.29 (m, 8H), 2.81-2.98 (m, 1H), 2.11-2.29 (m, 1H), 1.61-2.08 (m, 3H), 1.16-1.49 (m, 2H), 0.60-0.81 (m, 4H). |
| 546 | Observed mass (ESI): 691.3 [M + H]+. 1H NMR (300 MHz, DMSO-d6) δ (ppm): 8.26 (d, J = 8.6 Hz, 1H), 8.12 (d, J = 2.7 Hz, 1H), 7.99 (dd, J = 4.8, 1.8 Hz, 1H), 7.76 (d, J = 8.6 Hz, 1H), 7.49 (d, J = 7.9 Hz, 1H), 7.26-7.39 (m, 2H), 7.18-7.21(m, 1H), 6.92 (s, 2H), 6.38-6.42 (m, 1H), 6.14 (d, J = 2.8 Hz, 1H), 5.31-5.46 (m, 1H), 4.32-4.45 (m, 1H), 4.19-4.25 (m, 2H), 3.52-3.63 (m, 2H), 3.32-3.35(m, 1H), 3.27 (s, 3H), 3.11-3.18 (m, 1H), 2.93-3.10 (m, 6H), 2.13-2.22 (m, 1H), 1.91-2.00 (m, 5H), 1.35-1.47 (m, 3H), 1.23-1.32 (m, 1H), 0.65-0.75 (m, 4H). |

TABLE 15C-continued

| Characterization data of compounds prepared analogously to compound 417 and 418. | |
|---|---|
| Cpd ID | Characterization Data |
| 549 | Observed mass (ESI): 656.3 [M + H]+. 1H NMR (300 MHz, DMSO-d6) δ 8.33 (d, J = 8.4 Hz, 1H), 8.25 (d, J = 2.7 Hz, 1H), 8.03-7.99 (m, 1H), 7.90 (d, J = 8.7 Hz, 1H), 7.48 (s, 1H), 7.41 (d, J = 2.1 Hz, 1H), 7.34 (s, 1H), 7.28-7.20 (m, 2H), 6.94 (s, 2H), 6.46-6.39 (m, 2H), 5.66 (d, J = 2.4 Hz, 1H), 4.38 (s, 1H), 3.93 (d, J = 11.4 Hz, 2H), 3.65 (s, 5H), 3.52-3.41 (m, 2H), 3.00-2.89 (m, 2H), 2.80 (d, J = 7.8 Hz, 2H), 2.65 (d, J = 12.3 Hz, 2H), 1.98 (s, 1H), 1.88 (d, J = 12.6 Hz, 3H), 1.78-1.65 (m, 3H), 1.42 (s, 2H), 1.24 (s, 1H). |
| 550 | Observed mass (ESI): 657.45 [M + H]+. 1H NMR (300 MHz, DMSO-d6) δ 9.03 (s, 1H), 8.86 (s, 1H), 8.35 (d, J = 8.6 Hz, 1H), 8.17 (d, J = 2.7 Hz, 1H), 8.07 (d, J = 5.6, 1.8 Hz, 1H), 7.82 (d, J = 8.6 Hz, 1H), 7.75 (d, J = 8.2 Hz, 1H), 7.62 (d, J = 7.6 Hz, 1H), 7.57 (d, J = 1.9 Hz, 1H), 7.47-7.35 (m, 2H), 6.68 (d, J = 6.6 Hz, 1H), 6.21 (d, J = 2.8 Hz, 1H), 5.73 (d, J = 2.3 Hz, 1H), 5.02 (s, 1H), 3.87-3.56 (m, 9H), 3.44 (s, 1H), 3.30-3.10 (m, 5H), 3.02-2.88 (m, 1H), 2.76 (d, 2H), 2.59 (s, 1H), 2.28-1.93 (m, 3H), 1.71 (d, J = 11.0 Hz, 2H), 1.23 (s, 1H). |
| 551 | Observed mass (ESI): 646.35 [M + H]+. 1H NMR (400 MHz, DMSO-d6) δ (ppm): 8.32-8.30 (m, 1H), 8.17-8.16 (m, 1H), 8.00-7.99 (m, 1H), 7.76-7.74 (m, 1H), 7.46-7.41 (m, 2H), 7.32 (s, 1H), 7.31-7.22 (m, 2H), 6.94 (s, 2H), 6.43-6.40 (m, 1H), 6.07-6.06 (m, 1H), 5.66 (s, 1H), 4.34-4.32 (m, 3H), 3.68-3.64 (m, 7H), 3.34-3.31 (m, 3H), 3.31 (s, 1H), 2.76 (s, 2H), 2.67-2.66 (m, 2H), 2.50-2.49 (m, 1H), 2.00-1.98 (m, 2H), 1.98-1.84(m, 2H), 1.50-1.32 (m, 2H). |
| 552 | Observed mass (ESI): 675.3 [M + H]+. 1H NMR (300 MHz, DMSO-d6) δ (ppm): 8.25 (d, J = 8.6 Hz, 1H), 8.15 (d, J = 2.7 Hz, 1H), 7.98 (dd, J = 4.9, 1.9 Hz, 1H), 7.78 (d, J = 8.6 Hz, 1H), 7.49 (d, J = 7.9 Hz, 1H), 7.39-7.50 (m, 2H), 7.16-7.24 (m, 1H), 6.91 (s, 2H), 6.35-6.40 (m, 1H), 6.03 (d, J = 2.8 Hz, 1H), 5.34-5.58 (m, 1H), 4.63-4.70 (m, 2H), 4.38-4.54 (m, 1H), 4.10-4.27 (m, 2H), 3.48-3.65 (m, 4H), 2.98-3.25 (m, 5H), 2.78-2.96 (m, 1H), 1.81-2.29 (m, 5H), 1.25-1.47 (m, 2H), 0.62-0.77 (m, 4H). |
| 553 | Observed mass (ESI): 663.3 [M + H]+. 1H NMR (400 MHz, DMSO-d6) δ (ppm): 8.26 (d, J = 8.6 Hz, 1H), 8.10 (d, J = 2.6 Hz, 1H), 7.99 (dd, J = 4.8, 1.9 Hz, 1H), 7.73 (d, J = 8.6 Hz, 1H), 7.49 (d, J = 7.8 Hz, 1H), 7.28-7.36 (m, 2H), 7.20 (dd, J = 7.7, 1.9 Hz, 1H), 6.91 (s, 2H), 6.40 (dd, J = 7.7, 4.8 Hz, 1H), 5.89 (d, J = 2.7 Hz, 1H), 5.36-5.55 (m, 1H), 4.39-4.50 (m, 1H), 4.27-4.37 (m, 1H), 4.13-4.24 (m, 2H), 4.05-4.12 (m, 2H), 3.61-3.75 (m, 2H), 3.23 (s, 3H), 3.19-3.22 (m, 1H), 3.14-3.16 (m, 1H), 3.02-3.11 (m, 3H), 2.84-2.93 (m, 1H), 1.83-2.06 (m, 3H), 1.22-1.43 (m, 2H), 0.65-0.77 (m, 4H). (formic acid salt) |
| 554 | Observed mass (ESI): 638.35 [M + H]+. 1H NMR (300 MHz, DMSO-d6) δ (ppm): 8.49-8.58 (m, 1H), 8.39.-8.48 (m, 1H), 7.95-8.04 (m, 2H), 7.45-7.54 (m, 1H), 7.31-7.34 (m, 1H), 7.21-7.29 (m, 2H), 7.03-7.06 (m, 1H), 6.41-6.51 (m, 1H), 4.31-4.35 (m, 1H), 4.15-4.28 (m, 2H), 3.31-3.35 (m, 3H), 3.09-3.29 (m, 1H), 2.89-3.01 (m, 2H), 2.72-2.88 (m, 2H), 2.41-2.45 (m, 1H), 1.78-2.03 (m, 4H), 1.15-1.30 (m, 2H), 0.71-0.78 (m, 4H). |
| 562 | Observed mass (ESI): 615.25 [M + H]+. 1H NMR (300 MHz, DMSO-d6) δ (ppm): 8.25 (d, J = 8.6 Hz, 1H), 8.09 (d, J = 2.7 Hz, 1H), 7.99 (dd, J = 4.8, 1.9 Hz, 1H), 7.73 (d, J = 8.6 Hz, 1H), 7.47 (d, J = 8.0 Hz, 1H), 7.30 (s, 1H), 7.27-7.15 (m, 2H), 6.94 (s, 2H), 6.41 (dd, J = 7.7, 4.8 Hz, 1H), 5.85 (d, J = 2.7 Hz, 1H), 4.31-4.38 (m, 1H), 4.10-4.15 (m, 2H), 3.93-3.82 (m, 4H), 2.88-2.98 (m, 2H), 2.86-2.71 (m, 2H), 2.41-2.27 (m, 2H), 2.15-1.86 (m, 4H), 1.86-1.71 (m, 2H), 1.26-1.38 (m, 2H), 1.00-1.18 (m, 2H), 0.67-0.71 (m, 3H). |
| 563 | Observed mass (ESI): 658.3 [M + H]+. 1H NMR (300 MHz, DMSO-d6) δ ppm: 8.26 (d, J = 8.6 Hz, 1H), 8.13 (d, J = 2.7 Hz, 1H), 7.92-8.05 (m, 1H), 7.76 (d, J = 8.6 Hz, 1H), 7.47 (d, J = 8.0 Hz, 1H), 7.31 (s, 1H), 7.13-7.30 (m, 2H), 6.94 (s, 2H), 6.35-6.48 (m, 1H), 6.08-6.20 (m, 1H), 4.31-4.50 (m, 1H), 4.06-4.30 (m, 2H), 3.15-3.28 (m, 5H), 2.88-3.04 (m, 2H), 2.68-2.85 (m, 2H), 2.33-2.47 (m, 5H), 2.22 (s, 3H), 1.68-2.10 (m, 5H), 1.21-1.32 (m, 1H), 1.08-1.19 (m, 1H), 0.59-0.79 (m, 4H). |
| 564 | Observed mass (ESI): 673.25 [M + H]+. 1H NMR (400 MHz, DMSO-d6) δ ppm: 8.21-8.26 (m, 1H), 8.12 (d, J = 2.8 Hz, 1H), 7.98-7.99 (m, 1H), 7.72-7.80 (m, 1H), 7.47 (d, J = 8.0 Hz, 1H), 7.30-7.31 (m, 1H), 7.15-7.26 (m, 2H), 6.95 (s, 2H), 6.36-6.46 (m, 1H), 6.14 (d, J = 2.7 Hz, 1H), 4.30-4.41 (m, 1H), 4.12-4.29 (m, 2H), 3.56-3.68 (m, 2H), 3.31-3.35 (m, 1H), 3.27 (s, 3H), 3.18-3.24 (m, 1H), 2.87-3.01 (m, 4H), 2.72-2.87 (m, 2H), 2.40-2.48 (m, 1H), 1.71-2.13 (m, 7H), 1.44-1.57 (m, 2H), 1.14-1.36 (m, 2H), 0.64-0.77 (m, 4H). |
| 565 | Observed mass (ESI): 693.35 [M + H]+. 1H NMR (400 MHz, DMSO-d6) δ (ppm) 8.28 (d, J = 8.7 Hz, 1H), 8.18 (d, J = 2.7 Hz, 1H), 8.00 (m, J = 4.9, 1.8 Hz, 1H), 7.78 (d, J = 8.6 Hz, 1H), 7.50 (d, J = 8.0 Hz, 1H), 7.33 (d, J = 1.9 Hz, 1H), 7.16-7.26 (m, 2H), 6.96 (s, 2H), 6.38-6.45 (m, 1H), 6.28 (d, J = 2.8 Hz, 1H), 4.35-4.42 (m, 1H), 4.11-4.31 (m, 2H), 3.79-3.92 (m, 5H), 3.11-3.30 (m, 5H), 2.90-3.04 (m, 2H), 2.70-2.86 (m, 2H), 2.38-2.48 (m, 1H), 1.74-2.09 (m, 4H), 1.12-1.41 (m, 2H), 0.61-0.77 (m, 4H). (formic acid salt) |
| 566 | Observed mass (ESI): 645.3 [M + H]+. 1H NMR (300 MHz, DMSO-d6) δ (ppm) 8.31 (d, J = 8.6 Hz, 1H), 8.16 (d, J = 2.7 Hz, 1H), 7.95-8.05 (m, 1H), 7.74 (d, J = 8.6 Hz, 1H), 7.47 (d, J = 8.0 Hz, 1H), 7.32 (d, J = 1.9 Hz, 1H), 7.13-7.27 (m, 2H), 6.96 (s, 2H), 6.37-6.47 (m, 1H), 6.04 (d, J = 2.7 Hz, 1H), 4.89-5.02 (m, 1H), 4.30-4.41 (m, 1H), 4.11-4.30 (m, 2H), 3.64-3.82 (m, 2H), 3.10-3.29 (m, 1H), 3.00-3.09 (m, 2H), 2.86-2.95 (m, 2H), 2.65-2.85 (m, 2H), 2.39-2.49 (m, 1H), 2.30 (s, 3H), 1.86-2.13 (m, 3H), 1.62-1.83 (m, 2H), 1.10-1.39 (m, 2H), 0.60-0.78 (m, 4H). |
| 567 | Observed mass (ESI): 632.3 [M + H]+. 1H NMR (400 MHz, DMSO-d6) δ ppm: 8.32 (d, J = 8.4 Hz, 1 H), 8.18 (s, 1H), 8.00 (d, J = 4.8 Hz, 1H), 7.73 (d, J = 8.4 Hz, 1H), 7.47 (d, J = 8.0 Hz, 1H), 7.31 (s, 1H), 7.19-7.24 (m, 2H), 6.96 (s, 2H), 6.42 (d, J = 8.0 Hz, 1H), 6.08 (s, 1H), 5.47-5.50 (m, 1H), 4.91-4.94 (m, 2H), 4.60-4.63 (m, 2H), 4.32-4.34 (m, 1H), 4.17-4.23 (m, 2H), 3.17-3.24 (m, 1H), 2.91-2.99 (m, 2H), 2.78-2.81 (m, 2H), 2.43-2.45 (m, 1H), 1.74-2.11 (m, 5H), 1.26-1.33 (m, 1H), 1.17-1.22 (m, 1H), 0.68-0.72 (m, 4H). |

TABLE 15C-continued

| Characterization data of compounds prepared analogously to compound 417 and 418. | |
|---|---|
| Cpd ID | Characterization Data |
| 568 | Observed mass (ESI): 653.3 [M + H]+. MS (ESI) calcd. for C37H36N10O2: 652.30 m/z, found: 653.30 [M + H]+ /1H NMR (300 MHz, DMSO-d6) δ (ppm): 8.54-8.62 (m, 1H), 8.43 (dd, J = 4.7, 1.3 Hz, 1H), 8.28-8.37 (m, 2H), 8.00 (dd, J = 4.8, 1.9 Hz, 1H), 7.69-7.80 (m, 2H), 7.43-7.54 (m, 2H), 7.33 (s, 1H), 7.18-7.30 (m, 2H), 6.95 (s, 2H), 6.37-6.47 (m, 1H), 6.27 (d, J = 2.7 Hz, 1H), 4.29-4.40 (m, 1H), 4.15-4.20 (m, 2H), 3.16-3.24(m, 1H), 2.88-2.97 (m, 2H), 2.72-2.86 (m, 2H), 2.40-2.47 (m, 1H), 1.70-2.06 (m, 5H), 1.27-1.37(m, 1H), 1.10-1.21(m, 1H), 0.67-0.71 (m, 4H). |
| 569 | Observed mass (ESI): 618.45 [M + H]+. 1H NMR (400 MHz, DMSO-d6) δ ppm: 8.33 (d, J = 8.6 Hz, 1H), 8.21 (d, J = 2.5 Hz, 1H), 7.96-8.02 (m, 1H), 7.90 (d, J = 8.6 Hz, 1H), 7.48 (d, J = 8.0 Hz, 1H), 7.29-7.35 (m, 1H), 7.18-7.28 (m, 2H), 6.94 (s, 2H), 6.51 (d, J = 2.6 Hz, 1H), 6.34-6.46 (m, 1H), 5.11 (s, 1H), 4.31-4.41 (m, 1H), 4.11-4.29 (m, 2H), 3.12-3.27 (m, 2H), 2.87-3.00 (m, 2H), 2.73-2.83 (m, 2H), 1.76-2.12 (m, 5H), 1.50 (s, 6H), 1.15-1.34 (m, 2H), 0.65-0.76 (m, 4H). |
| 571 | Observed mass (ESI): 514.35 [M + H]+. 1H NMR (300 MHz, DMSO-d6) δ (ppm): 8.32 (d, J = 8.7 Hz, 1H), 8.21 (d, J = 2.7 Hz, 1H), 7.81 (d, J = 8.6 Hz, 1H), 7.65-7.76 (m, 1H), 7.49-7.62 (m, 1H), 7.44 (d, J = 7.9 Hz, 1H), 7.19-7.40 (m, 4H), 6.19 (d, J = 2.8 Hz, 1H), 5.06-5.30 (m, 1H), 4.22-4.35 (m, 1H), 3.68-3.77 (m, 4H), 3.19-3.28 (m, 4H), 3.08-3.10 (m, 1H), 2.98-3.07 (m, 1H), 2.01-2.30 (m, 2H). |
| 572 | Observed mass (ESI): 665.3 [M + H]+. 1H NMR (300 MHz, DMSO-d6) δ (ppm): 8.32 (d, J = 8.6 Hz, 1H), 8.17-8.25 (m, 1H), 7.80 (d, J = 8.6 Hz, 1H), 7.66-7.76 (m, 1H), 7.49-7.63 (m, 1H), 7.42 (d, J = 8.0 Hz, 1H), 7.36 (d, J = 7.6 Hz, 1H), 7.29-7.33 (m, 1H), 7.20-7.28 (m, 2H), 6.19 (d, J = 2.8 Hz, 1H), 5.29-5.55 (m, 1H), 4.33-4.48 (m, 1H), 4.11-4.24 (m, 2H), 3.68-3.77 (m, 4H), 3.21-3.26 (m, 5H), 3.12-3.18 (m, 1H), 2.96-3.08 (m, 3H), 2.79-2.93 (m, 1H), 1.74-2.09 (m, 3H), 1.16-1.45 (m, 2H), 0.62-0.78 (m, 4H). |
| 573 | Observed mass (ESI): 656.25 [M + H]+. 1H NMR (300 MHz, DMSO-d6) δ (ppm): 8.31-8.42(m, 2H), 7.97 (d, J = 4.9, 1H), 7.85-7.93 (m, 2H), 7.48 (d, J = 8.0 Hz, 1H), 7.30 (s, 1H), 7.22 (dd, J = 7.7, 2.1 Hz, 2H), 6.77 (d, J = 2.7 Hz, 1H), 6.42 (dd, J = 7.7, 4.9 Hz, 1H), 5.40 (d, J = 3.5 Hz, 1H), 4.29-4.38 (m, 1H), 4.15-4.20 (m, 2H), 3.46 (s, 3H), 3.16-3.20 (m, 1H), 2.91-2.96 (m, 2H), 2.77-2.80 (m, 2H), 2.40-2.42 (m, 1H), 1.72-2.00 (m, 4H), 1.17-1.30 (m, 2H), 0.69-0.72 (m, 4H). |
| 574 | Observed mass (ESI): 653.3 [M + H]+. 1H NMR (300 MHz, DMSO-d6) δ (ppm): 8.34-8.45 (m, 2H), 8.13-8.20 (m, 1H), 7.93-8.05 (m, 2H), 7.43-7.60 (m, 2H), 7.35 (s, 1H), 7.19-7.31 (m, 2H), 7.02 (d, J = 2.7 Hz, 1H), 6.94 (s, 2H), 6.55 (d, J = 9.3 Hz, 1H), 6.36-6.47 (m, 2H), 4.29-4.44 (m, 1H), 4.08-4.29 (m, 2H), 3.14-3.29 (m, 1H), 2.87-3.03 (m, 2H), 2.67-2.87 (m, 2H), 2.39-2.42 (m, 1H), 1.68-2.25 (m, 5H), 1.10-1.41 (m, 2H), 0.60-0.79 (m, 4H). |
| 575 | Observed mass (ESI): 653.4 [M + H]+. 1H NMR (300 MHz, DMSO-d6) δ (ppm): 8.46 (d, J = 2.8 Hz, 1H), 8.36-8.44 (m, 3H), 8.02 (dd, J = 4.8, 1.8 Hz, 1H), 7.98 (d, J = 8.6 Hz, 1H), 7.49 (d, J = 8.0 Hz, 1H), 7.35 (d, J = 1.9 Hz, 1H), 7.21-7.31 (m, 2H), 6.98 (d, J = 2.8 Hz, 1H), 6.94 (s, 2H), 6.43 (dd, J = 7.7, 4.8 Hz, 1H), 6.27-6.32 (m, 2H), 4.30-4.41 (m, 1H), 4.12-4.27 (m, 2H), 3.12-3.29 (m, 1H), 2.87-3.04 (m, 2H), 2.71-2.85 (m, 2H), 2.40-2.46 (m, 1H), 1.90-2.18 (m, 3H), 1.71-1.87 (m, 2H), 1.10-1.39 (m, 2H), 0.65-0.76 (m, 4H). |
| 582 | Observed mass (ESI): 653.15 [M + H]+. 1H NMR (300 MHz, DMSO-d6) δ (ppm): 8.28-8.37 (m, 1H), 8.21-8.27 (m, 1H), 7.95-8.05 (m, 1H), 7.71-7.81 (m, 1H), 7.45-7.51 (m, 1H), 7.31-7.35 (m, 1H), 7.19-7.28 (m, 2H), 6.93-7.01 (m, 2H), 6.42-6.45 (m, 1H), 6.22-6.25 (m, 1H), 4.33-4.40 (m, 1H), 4.25-4.29 (m, 2H), 3.20-3.25 (m, 1H), 3.15 (s, 3H), 2.89-3.01 (m, 2H), 2.72-2.89 (m, 2H), 2.45-2.50 (m, 1H), 1.91-2.08 (m, 2H), 1.85-1.91 (m, 1H), 1.75-1.85 (m, 2H), 1.23-1.37 (m, 1H), 1.13-1.20 (m, 1H), 0.80-0.85 (m, 1H), 0.63-0.75 (m, 4H). |
| 590 | Observed mass (ESI): 604.45 [M + H]+. 1H NMR (300 MHz, DMSO-d6) δ (ppm): 8.30-8.36 (m, 2H), 8.01 (d, J = 1.5 Hz, 1H), 7.99 (d, J = 1.5 Hz, 1H), 7.49 (d, J = 8.1 Hz, 1H), 7.34 (s, 1H), 7.22-7.28 (m, 2H), 6.94 (s, 2H), 6.52 (s, 1H), 6.41-6.45 (m, 1H), 4.46 (s, 2H), 4.41-4.45 (m, 1H), 4.20-4.23 (m, 2H), 3.25 (s, 3H), 3.18-3.22 (m, 1H), 2.93-2.97 (m, 2H), 2.76-2.81 (m, 2H), 2.41-2.42 (m, 1H), 1.70-2.00 (m, 4H), 1.15-1.30 (m, 2H), 0.68-0.72 (m, 4H) (formic acid salt). |
| 591 | Observed mass (ESI): 631.25 [M + H]+. 1H NMR (400 MHz, DMSO-d6) δ(ppm): 8.31-8.50 (m, 2H), 8.01 (dd, J = 4.8, 1.9 Hz, 1H), 7.95 (d, J = 8.6 Hz, 1H), 7.48 (d, J = 8.0 Hz, 1H), 7.32-7.38 (m, 1H), 7.22-7.30 (m, 2H), 6.95 (s, 2H), 6.80 (d, J = 2.6 Hz, 1H), 6.39-6.48 (m, 1H), 4.35 (t, J = 7.2 Hz, 1H), 4.11-4.27 (m, 2H), 3.28-3.33 (m, 3H), 3.16-3.27 (m, 1H), 2.97-3.09 (m, 3H), 2.87-2.96 (m, 2H), 2.72-2.86 (m, 2H), 2.41-2.49 (m, 1H), 1.70-2.14 (m, 5H), 1.11-1.37 (m, 2H), 0.64-0.75 (m, 4H). |
| 597 | Observed mass (ESI): 616.25 [M + H]+. 1H NMR (400 MHz, DMSO-d6) δ (ppm): 8.29-8.37 (m, 2H), 8.00 (dd, J = 4.8, 1.8 Hz, 1H), 7.92 (d, J = 8.6 Hz, 1H), 7.48 (d, J = 8.0 Hz, 1H), 7.33 (d, J = 1.9 Hz, 1H), 7.19-7.29 (m, 2H), 6.93 (s, 2H), 6.63 (d, J = 2.6 Hz, 1H), 6.38-6.46 (m, 1H), 4.92 (dd, J = 8.5, 5.7 Hz, 2H), 4.70-4.78 (m, 2H), 4.31-4.41 (m, 2H), 4.18-4.22 (m, 2H), 3.22-3.25 (m, 1H), 2.86-3.00 (m, 2H), 2.72-2.84 (m, 2H), 2.40-2.46 (m, 1H), 2.08-2.10 (m, 1H), 1.95-2.04 (m, 2H), 1.86-1.95 (m, 1H), 1.75-1.83 (m, 1H), 1.14-1.35 (m, 2H), 0.62-0.75 (m, 4H). |
| 598 | Observed mass (ESI): 670.45 [M + H]+. 1H NMR (300 MHz, DMSO-d6 + D2O)δ(ppm): 8.24-8.27 (m, 1H), 8.13-8.14 (m, 1H), 7.99-8.00 (m, 1H), 7.97-7.98 (m, 1H), 7.75-7.78 (m, 1H), 7.50-7.69 (m, 1H),<br>7.40-7.47 (m, 1H), 7.20-7.30 (m, 2H), 6.40-6.45 (m, 1H), 6.13-6.14 (m, 1H), 5.66-5.67 (m, 1H), 4.35-4.37 (m, 1H), 4.14-4.32 (m, 4H), 3.58-3.64 (s, 3H), 3.23-3.25 (m, 4H), 2.91-2.99 (m, 1H), 2.64-2.80 (m, 4H), 2.43-2.53 (m, 4H), 2.21 (s, 3H), 1.92-1.97 (m, 1H), 1.72-1.80 (m, 2H), 1.31-1.35 (m, 2H), |

TABLE 15C-continued

| Characterization data of compounds prepared analogously to compound 417 and 418. | |
|---|---|
| Cpd ID | Characterization Data |
| 599 | Observed mass (ESI): 615.4 [M + H]+. 1H-NMR (400 MHz, DMSO-d6) δ (ppm): 8.30-8.40 (m, 1H), 8.00-8.08 (m, 1H), 7.81-7.90 (m, 1H), 7.41-7.60 (m, 3H), 7.32-7.40 (m, 1H), 7.20-7.32 (m, 2H), 7.00-7.15 (m, 2H), 6.32-6.50 (m, 1H), 5.61 (s, 1H), 4.30-4.45 (m, 1H), 4.10-4.30 (m, 2H), 3.10-3.30 (m, 2H), 2.90-3.10 (m, 2H), 2.73-2.90 (m, 2H), 2.22-2.36 (m, 1H), 1.90-2.05 (m, 3H), 1.70-1.90 (m, 2H), 1.25-1.40 (m, 2H), 0.60-0.80 (m, 6H), 0.23 (s, 2H). |

Intermediate 265-1: (S)—N-(5-(2-(2-aminopyridin-3-yl)-5-bromo-3H-imidazo[4,5-b]pyridin-3-yl)-2,3-dihydro-1H-inden-1-yl)-6-methylnicotinamide Intermediate 265-1

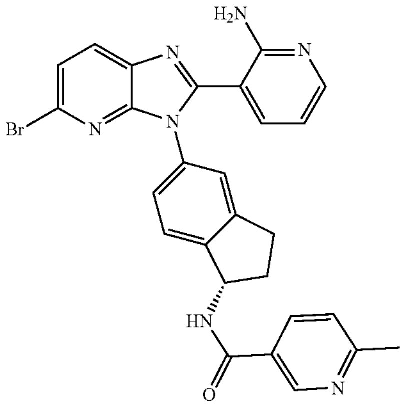

Intermediate 265-1 was prepared in a manner analogous to Example 3 using PyBOP in place of HATU, Intermediate 245-3 in place of Example 2 and 6-methylpyridine-3-carboxylic acid in place of 3,4-difluoro-5-ani sic acid. MS (ESI) calcd. for $C_{27}H_{22}BrN_7O$: 539.11 m/z, found: 540.20 $[M+H]^+$.

The following compounds were prepared analogous to the synthetic preparation in Example 95 (Compounds 417 and 418).

TABLE 16

| Characterization data of compounds prepared analogously to compound 417/418. | |
|---|---|
| Cpd ID | Characterization Data |
| 419 | MS (ESI) calcd. for $C_{32}H_{28}N_{10}O$, 568.24 m/z, found, 569.40 $[M + H]^+$. $^1$HNMR (400 MHz, DMSO-$d_6$) δ (ppm); 9.00-9.09 (m, 1H), 8.91-8.97 (m, 1H), 8.44-8.58 (m, 2H), 8.02-8.10 (m, 1H), 7.88-7.93 (m, 1H), 7.80-7.82 (m, 1H), 7.69-7.76 (m, 1H), 7.47-7.52 (m, 1H), 7.40-7.46 (m, 1H), 7.32-7.39 (m, 1H), 6.81-6.92 (m, 1H), 5.56-5.68 (m, 1H), 3.03-3.15 (m, 1H), 2.88-3.02 (m, 1H), 2.67 (s, 3H), 2.58-2.63 (m, 1H), 2.02-2.18 (m, 2H), 1.00-1.10 (m, 2H), 0.86-0.95 (m, 2H). $^{19}$FNMR (376 MHz, DMSO-$d_6$) δ (ppm); −73.98. (TFA salt) |
| 420 | MS (ESI) calcd. for $C_{32}H_{28}N_{10}O$, 568.24 m/z, found, 569.40 $[M + H]^+$. $^1$HNMR (400 MHz, DMSO-$d_6$) δ (ppm); 8.94-9.01 (m, 1H), 8.48-8.56 (m, 1H), 8.37-8.47 (m, 1H), 8.03-8.10 (m, 1H), |

TABLE 16-continued

| Characterization data of compounds prepared analogously to compound 417/418. | |
|---|---|
| Cpd ID | Characterization Data |
| | 7.99-8.02 (m, 1H), 7.83-7.92 (m, 2H), 7.62-7.71 (m, 1H), 7.50-7.54 (m, 1H), 7.38-7.46 (m, 1H), 7.24-7.34 (m, 1H), 6.81-6.90 (m, 1H), 5.52-5.65 (m, 1H), 2.98-3.10 (m, 1H), 2.86-2.98 (m, 1H), 2.70-2.81 (m, 1H), 2.65 (s, 3H), 2.58-2.63 (m, 1H), 2.02-2.18 (m, 1H), 0.98-1.10 (m, 4H). $^{19}$FNMR (376 MHz, DMSO-$d_6$) δ (ppm); −73.95. (TFA salt) |
| 430 | MS (ESI) calcd. for $C_{30}H_{24}F_2N_{10}O$, 578.21 m/z, found, 579.35 $[M + H]^+$. $^1$H NMR (400 MHz, DMSO-$d_6$) δ (ppm); 9.21-9.34 (m, 1H), 8.83-8.99 (m, 1H), 8.39-8.52 (m, 1H), 8.11-8.21 (m, 1H), 7.99-8.09 (m, 1H), 7.85-7.96 (m, 1H), 7.37-7.49 (m, 3H), 7.33-7.36 (m, 1H), 7.02-7.32 (m, 2H), 6.47-6.59 (m, 1H), 5.54-5.68 (m, 1H), 3.01-3.11 (m, 1H), 2.87-2.99 (m, 1H), 2.58-2.63 (m, 1H), 2.51-2.55 (m, 3H), 2.04-2.16 (m, 1H). $^{19}$F NMR (376 MHz, DMSO-$d_6$) δ (ppm); −116.80. |

Example 96: (S)—N-(5-(5-(1-cyclopropyl-1H-pyrazol-3-yl)-2-phenyl-3H-imidazo[4,5-b]pyridin-3-yl)-2,3-dihydro-1H-inden-1-yl)-6-methylnicotinamide (Compound 431)

Compound 431

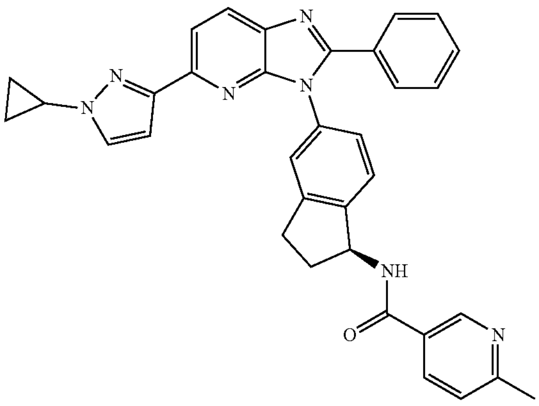

Synthetic Route:

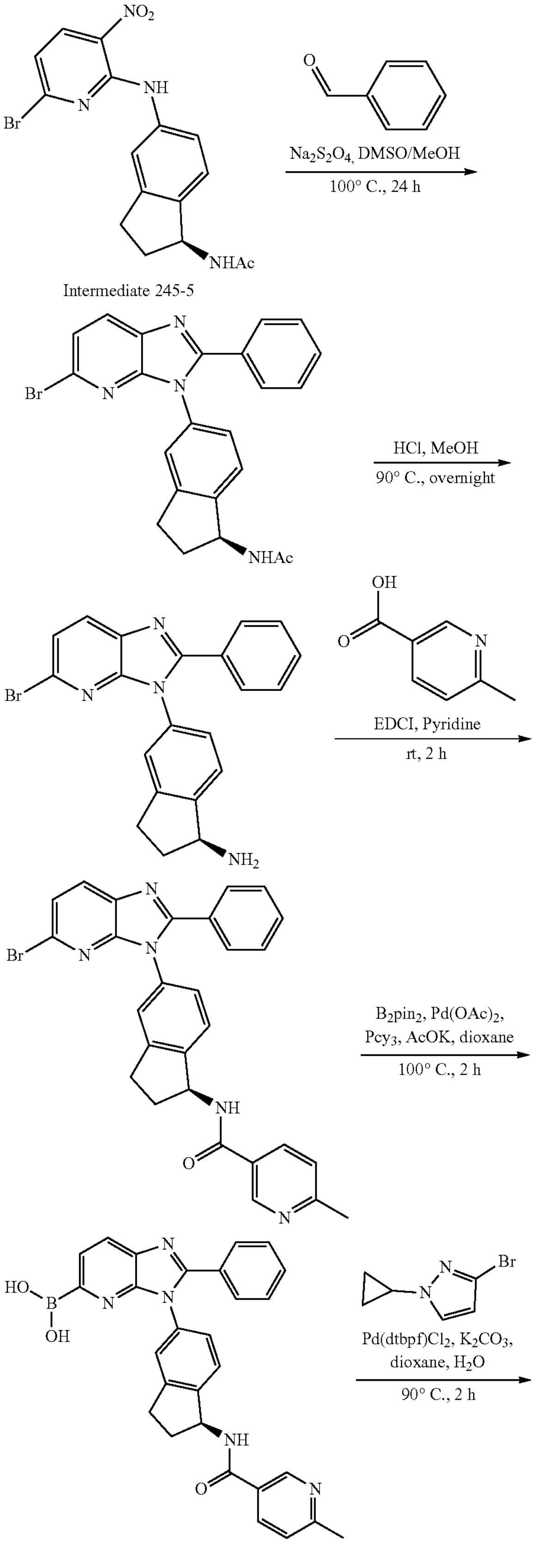

Intermediate 245-5

-continued

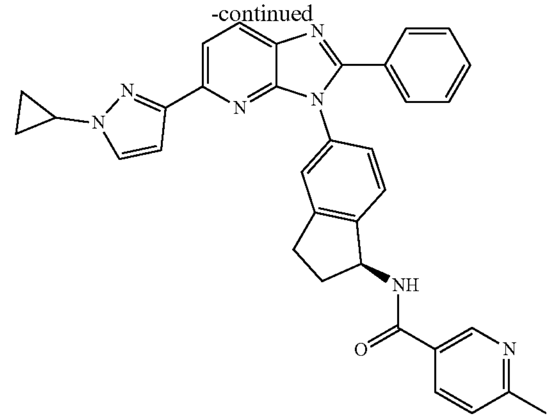

Compound 431

Step 1: Synthesis of (S)—N-(5-(5-bromo-2-phenyl-3H-imidazo[4,5-b]pyridin-3-yl)-2,3-dihydro-1H-inden-1-yl)acetamide To a stirred solution of (S)—N-(5-((6-bromo-3-nitropyridin-2-yl)amino)-2,3-dihydro-1H-inden-1-yl)acetamide (Intermediate 245-5) (3 g, 7.668 mmol, 1 equiv) in DMSO (30 mL, 422.373 mmol, 55.08 equiv) and MeOH (5 mL, 123.494 mmol, 16.10 equiv) were added benzaldehyde (3.26 g, 30.672 mmol, 4 equiv) and $Na_2S_2O_4$ (3.34 g, 19.170 mmol, 2.5 equiv) and the resulting mixture was stirred for 24 h at 100° C. The mixture was allowed to cool to room temperature. The mixture was concentrated. To this mixture, sodium bicarbonate (150 mL) solution was added. After separation of phases, the aqueous phase was extracted with ethyl acetate (200 mL×2). The combined organic layers were washed with brine (2×200 mL) and dried over anhydrous $Na_2SO_4$. After filtration, the filtrate was concentrated under reduced pressure. The residue was purified by silica gel column chromatography, eluted with petroleum ether/ethyl acetate (1:1) to afford (S)—N-(5-(5-bromo-2-phenyl-3H-imidazo[4,5-b]pyridin-3-yl)-2,3-dihydro-1H-inden-1-yl)acetamide (1.4 g, 33.45% yield) as yellow solid: MS (ESI) calcd. for $C_{23}H_{19}BrN_4O$, 446.07 m/z, found 447.00 $[M+H]^+$.

Step 2: Synthesis of (S)-5-(5-bromo-2-phenyl-3H-imidazo[4,5-b]pyridin-3-yl)-2,3-dihydro-1H-inden-1-amine A solution of (S)—N-(5-(5-bromo-2-phenyl-3H-imidazo[4,5-b]pyridin-3-yl)-2,3-dihydro-1H-inden-1-yl)acetamide (10 g, 22.355 mmol, 1 equiv) in HCl (70 mL) and MeOH (70 mL) was stirred at 100° C. overnight. The mixture was allowed to cool to room temperature. The resulting mixture was concentrated under reduced pressure. The mixture was basified to pH 8-9 with $NaHCO_3/H_2O$. The precipitated solids were collected by filtration and washed with $H_2O$ (500 mL×3) to afford (S)-5-(5-bromo-2-phenyl-3H-imidazo[4,5-b]pyridin-3-yl)-2,3-dihydro-1H-inden-1-amine (7.5 g, 74.50% yield) as a red solid. The crude product was used in the next step directly without further purification: MS (ESI) calcd. for $C_{21}H_{17}BrN_4$, 404.06 m/z, found, 405.10 $[M+H]^+$.

Step 3: Synthesis of (S)—N-(5-(5-bromo-2-phenyl-3H-imidazo[4,5-b]pyridin-3-yl)-2,3-dihydro-1H-inden-1-yl)-6-methylnicotinamide A solution of (S)-5-(5-bromo-2-phenyl-3H-imidazo[4,5-b]pyridin-3-yl)-2,3-dihydro-1H-inden-1-amine (3 g, 7.402 mmol, 1 equiv), 6-methylpyridine-3-carboxylic acid (1.22 g, 8.882 mmol, 1.2 equiv) and EDCI (2.13 g, 11.103 mmol, 1.5 equiv) in Pyridine (30 mL) was stirred at room temperature for 1 h. The reaction was quenched with water (100 mL). The resulting mixture was extracted with ethyl acetate (3×100 mL). The organic layers were combined, dried over anhydrous $Na_2SO_4$, filtered and concentrated. The crude product was purified by reverse-phase flash chromatography on C18 silica gel using a gradient of acetonitrile in water (+0.05% ammonium bicarbonate) to afford (S)—N-(5-(5-bromo-2-phenyl-3H-imidazo[4,5-b]pyridin-3-yl)-2,3-dihydro-1H-inden-1-yl)-6-methylnicotinamide (2.5 g, 59.25% yield) as a yellow solid: MS (ESI) calcd. for $C_{28}H_{22}BrN_5O$, 523.10 m/z, found, 524.10 $[M+H]^+$.

Step 4: Synthesis of (S)-(3-(1-(6-methylnicotinamido)-2,3-dihydro-1H-inden-5-yl)-2-phenyl-3H-imidazo[4,5-b]pyridin-5-yl)boronic acid To a solution of (S)—N-(5-(5-bromo-2-phenyl-3H-imidazo[4,5-b]pyridin-3-yl)-2,3-dihydro-1H-inden-1-yl)-6-methylnicotinamide (1.4 g, 2.670 mmol, 1 equiv) in dioxane (15 mL) were added 4,4,5,5-tetramethyl-2-(4,4,5,5-tetramethyl-1,3,2-dioxaborolan-2-yl)-1,3,2-dioxaborolane (1.36 g, 5.340 mmol, 2 equiv), $Pd(OAc)_2$ (0.12 g, 0.534 mmol, 0.2 equiv) and $PCy_3$ (0.15 g, 0.534 mmol, 0.2 equiv). The resulting mixture was maintained under nitrogen and stirred at 100° C. for 2 h. After cooling to room temperature, the reaction was quenched with water (100 mL). The resulting mixture was extracted with ethyl acetate (3×100 mL). The organic layers were combined, dried over anhydrous $Na_2SO_4$, filtered and concentrated. The crude product was purified by reverse-phase flash chromatography on C18 silica gel using a gradient of acetonitrile in water (+0.05% ammonium bicarbonate) to afford (S)-(3-(1-(6-methylnicotinamido)-2,3-dihydro-1H-inden-5-yl)-2-phenyl-3H-imidazo[4,5-b]pyridin-5-yl)boronic acid (760 mg, 54.11% yield) as a yellow solid: MS (ESI) calcd. for $C_{28}H_{24}BN_5O_3$, 489.19 m/z, found, 490.25 $[M+H]^+$.

Step 5: Synthesis of (S)—N-(5-(5-(1-cyclopropyl-1H-pyrazol-3-yl)-2-phenyl-3H-imidazo[4,5-b]pyridin-3-yl)-2,3-dihydro-1H-inden-1-yl)-6-methylnicotinamide (Compound 431)

To a solution of (S)-(3-(1-(6-methylnicotinamido)-2,3-dihydro-1H-inden-5-yl)-2-phenyl-3H-imidazo[4,5-b]pyridin-5-yl)boronic acid (200 mg, 0.409 mmol, 1 equiv) in dioxane (4 mL) was added 3-bromo-1-cyclopropylpyrazole (114.67 mg, 0.613 mmol, 1.5 equiv), $Pd(dtbpf)Cl_2$ (53.28 mg, 0.082 mmol, 0.2 equiv) and $K_2CO_3$ (169.46 mg, 1.227 mmol, 3 equiv). The resulting mixture was maintained under nitrogen and stirred at 90° C. for 2 h. After cooling to room temperature, the reaction was quenched with water (100 mL). The resulting mixture was extracted with ethyl acetate (3×100 mL). The organic layers were combined, dried over anhydrous $Na_2SO_4$, filtered and concentrated. The crude product was purified by reverse-phase flash chromatography on C18 silica gel using a gradient of acetonitrile in water (+0.05% ammonium bicarbonate) to afford (S)—N-(5-(5-(1-cyclopropyl-1H-pyrazol-3-yl)-2-phenyl-3H-imidazo[4,5-b]pyridin-3-yl)-2,3-dihydro-1H-inden-1-yl)-6-methylnicotinamide (Compound 431) (58.6 mg, 25.81% yield) as a yellow solid: MS (ESI) calcd. for $C_{34}H_{29}N_7O$, 551.24 m/z, found, 552.35 $[M+H]^+$. $^1H$ NMR (300 MHz, DMSO-$d_6$) δ (ppm); 8.80-9.13 (m, 1H), 8.05-8.31 (m, 2H), 7.88-8.02 (m, 1H), 7.70-7.85 (m, 1H), 7.52-7.65 (m, 2H), 7.31-7.51 (m, 6H), 7.12-7.30 (m, 1H), 6.50-6.63 (m, 1H), 5.53-5.82 (m, 1H), 3.72-3.92 (m, 1H), 2.80-3.20 (m, 2H), 2.53-2.60 (m, 4H), 1.96-2.23 (m, 1H), 0.81-1.28 (m, 4H).

The following compounds were prepared analogous to the synthetic preparation in Example 96 (Compound 431).

TABLE 17

Characterization data of compounds prepared analogously to compound 431.

| Cpd ID | Characterization Data |
|---|---|
| 432 | .: MS (ESI) calcd. for $C_{34}H_{27}F_2N_7O$, 587.22 m/z, found 588.40 $[M + H]^+$. $^1H$ NMR (400 MHz, DMSO-$d_6$) δ (ppm); 9.15 (s, 1H), 8.40-8.50 (m, 1H), 8.15-8.25 (m, 1H), 7.90-8.00 (m, 1H), 7.82-7.90 (m, 1H), 7.75-7.82 (m, 1H), 7.55-7.70 (m, 2H), 7.35-7.50 (m, 5H), 7.20-7.30 (m, 1H), 6.85-7.20 (m, 1H), 6.63 (s, 1H), 5.60-5.70 (m, 1H), 3.70-3.80 (m, 1H), 2.85-3.15 (m, 2H), 2.55-2.65 (m, 1H), 2.00-2.20 (m, 1H), 0.95-1.15 (m, 4H). $^{19}F$ NMR (376 MHz, DMSO-$d_6$) δ −116.05. |
| 555 | Observed mass (ESI): 644.35 [M + H]+. 1H NMR (400 MHz, DMSO-d6) δ (ppm): 8.20-8.24 (m, 1H), 7.97-8.02 (m, 2H), 7.85-7.87 (m, 1H), 7.45-7.53 (m, 1H), 7.29-7.34 (m, 1H), 7.19-7.28 (m, 2H), 6.93-7.01 (m, 2H), 6.62-6.65 (m, 1H), 6.42-6.45 (m,1H), 4.45-4.52 (m, 1H), 4.33-4.40 (m,1H), 4.25-4.29 (m, 2H), 3.95-4.04 (m, 2H), 3.43-3.52 (m, 2H), 3.17-3.37 (m, 1H), 2.89-3.01 (m, 2H), 2.72-2.89 (m, 2H), 2.35-2.65 (m, 2H), 1.71-2.08 (m, 8H), 1.13-1.37 (m, 2H), 0.63-0.75 (m, 4H). |
| 516 | Observed mass (ESI): 592.2 [M + H]+. 1H NMR (400 MHz, DMSO + D2O)8.29-8.32 (m, 1H), 8.21-8.19 (m, 1H), 8.10 (m, 1H), 7.55-7.60 (m, 1H), 7.30-7.35 (s, 1H), 7.21-7.26 (m, 2H), 6.51 (m, 1H), 4.62 (m, 1H), 4.25-4.31 (m, 2H), 3.14 (m, 2H), 2.94-3.09 (m, 1H), 2.81-2.90 (m, 1H), 2.65-2.71 (m, 4H), 2.44-2.49 (m, 1H), 1.92-2.15 (m, 4H), 1.23-1.45 (m, 2H), 0.75-0.80 (m, 4H). |

Example 97: N-[(1S)-5-[2-(2-aminopyridin-3-yl)-5-(pyrazol-1-yl)imidazo[4,5-b]pyridin-3-yl]-2,3-dihydro-1H-inden-1-yl]-6-(pyridin-2-yl)-6-azaspiro[3.4]octan-2-amine (Compound 447)

Compound 447

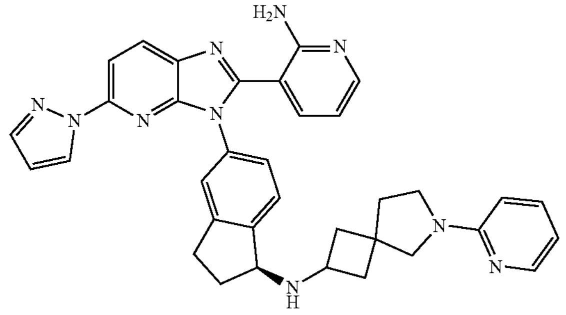

Synthetic Route:

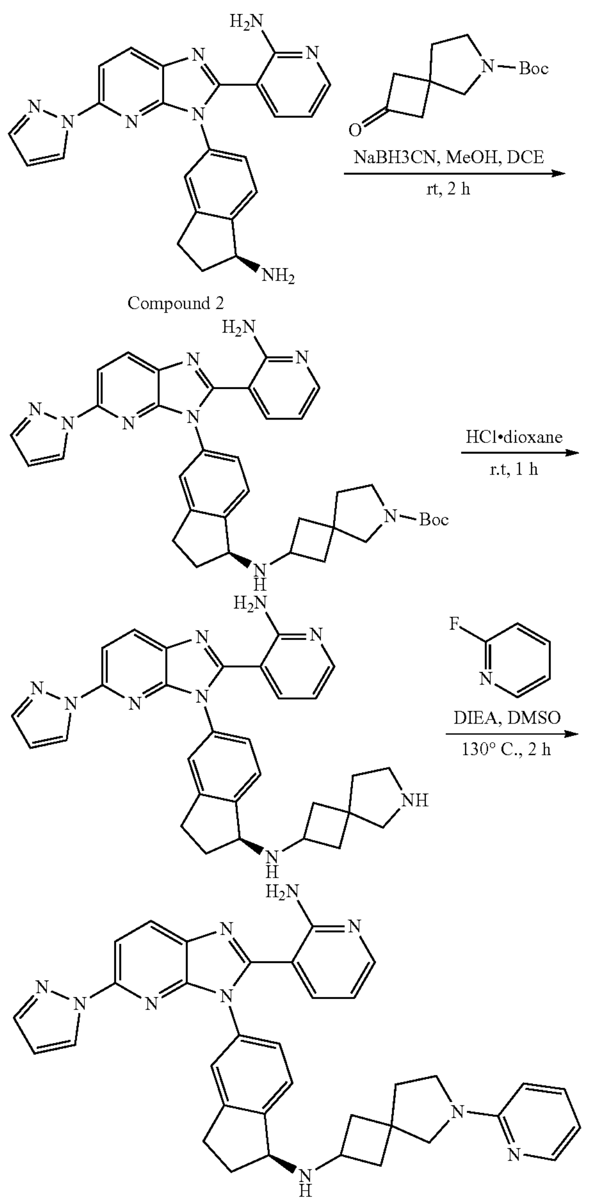

Compound 2

Compound 447

Step 1: Synthesis of tert-butyl 2-{[(1S)-5-[2-(2-aminopyridin-3-yl)-5-(pyrazol-1-yl)imidazo[4,5-b]pyridin-3-yl]-2,3-dihydro-1H-inden-1-yl]amino}-6-azaspiro[3.4]octane-6-carboxylate A solution of (S)-3-(3-(1-amino-2,3-dihydro-1H-inden-5-yl)-5-(1H-pyrazol-1-yl)-3H-imidazo[4,5-b]pyridin-2-yl)pyridin-2-amine (Compound 2) (300 mg, 0.761 mmol, 1 equiv) and tert-butyl 2-oxo-6-azaspiro[3.4]octane-6-carboxylate (171.35 mg, 0.761 mmol, 1 equiv) in DCE (3 mL) and MeOH (0.3 mL) was stirred for 1 h at 40° C. Then, $NaBH_3CN$ (191.18 mg, 3.044 mmol, 4 equiv) was added to the reaction mixture. The obtained suspension was stirred at 40° C. for 1 h. The mixture was purified by reverse-phase flash chromatography on C18 silica gel using a gradient of acetonitrile in water (+0.05% ammonium bicarbonate) to afford tert-butyl 2-{[(1S)-5-[2-(2-aminopyridin-3-yl)-5-(pyrazol-1-yl)imidazo[4,5-b]pyridin-3-yl]-2,3-dihydro-1H-inden-1-yl]amino}-6-azaspiro[3.4]octane-6-carboxylate (200 mg, 42.57%) as a yellow solid. MS (ESI) calcd. for $C_{35}H_{39}N_9O_2$: 617.32 m/z, found, 616.30 $[M+H]^-$.

Step 2: Synthesis of N-[(1S)-5-[2-(2-aminopyridin-3-yl)-5-(pyrazol-1-yl)imidazo[4,5-b]pyridin-3-yl]-2,3-dihydro-1H-inden-1-yl]-6-azaspiro[3.4]octan-2-amine A solution of tert-butyl 2-{[(1S)-5-[2-(2-aminopyridin-3-yl)-5-(pyrazol-1-yl)imidazo[4,5-b]pyridin-3-yl]-2,3-dihydro-1H-inden-1-yl]amino}-6-azaspiro[3.4]octane-6-carboxylate (200 mg, 0.324 mmol, 1 equiv) in HCl (5 mL, 4 M in 1,4-dioxane) was stirred at room temperature for 1 h. The solvent was removed by distillation under vacuum to afford N-[(1S)-5-[2-(2-aminopyridin-3-yl)-5-(pyrazol-1-yl)imidazo[4,5-b]pyridin-3-yl]-2,3-dihydro-1H-inden-1-yl]-6-azaspiro[3.4]octan-2-amine (100 mg, crude) as a yellow solid: MS (ESI) calcd. for $C_{30}H_{31}N_9$: 517.27 m/z, found, 518.35 $[M+H]^+$.

Step 3: Synthesis of N-[(1S)-5-[2-(2-aminopyridin-3-yl)-5-(pyrazol-1-yl)imidazo[4,5-b]pyridin-3-yl]-2,3-dihydro-1H-inden-1-yl]-6-(pyridin-2-yl)-6-azaspiro[3.4]octan-2-amine (Compound 447)

To a solution of N-[(1S)-5-[2-(2-aminopyridin-3-yl)-5-(pyrazol-1-yl)imidazo[4,5-b]pyridin-3-yl]-2,3-dihydro-1H-inden-1-yl]-6-azaspiro[3.4]octan-2-amine (90 mg, 0.174 mmol, 1 equiv) in DMSO (5 mL) was added DIEA (112.36 mg, 0.870 mmol, 5 equiv) and 2-fluoropyridine (18.57 mg, 0.191 mmol, 1.1 equiv). The resulting mixture was stirred at 130° C. for 2 h. The residue was purified by reverse-phase flash chromatography on C18 silica gel using a gradient of acetonitrile in water (+0.05% ammonium bicarbonate). The material was further purified by Prep-HPLC on a XSelect CSH OBD Column using a gradient of acetonitrile in water (+0.05% TFA) to afford N-[(1S)-5-[2-(2-aminopyridin-3-yl)-5-(pyrazol-1-yl)imidazo[4,5-b]pyridin-3-yl]-2,3-dihydro-1H-inden-1-yl]-6-(pyridin-2-yl)-6-azaspiro[3.4]octan-2-amine (Compound 447) (16.7 mg, 15.84%) as a light yellow solid: MS (ESI) calcd. for $C_{35}H_{34}N_{10}$: 594.30 m/z, found, 595.20 $[M+H]^+$. $^1$H-NMR (400 MHz, DMSO) δ (ppm); 8.40-8.48 (m, 1H), 8.30-8.39 (m, 1H), 7.91-8.10 (m, 4H), 7.80-7.85 (m, 1H), 7.65-7.78 (m, 2H), 7.55-7.61 (m, 1H), 7.40-7.45 (m, 1H), 6.98-7.10 (m, 1H), 6.88-6.95 (m, 1H), 6.65-6.75 (m, 1H), 6.52-6.60 (m, 1H), 4.75-4.85 (m, 1H), 3.90-4.10 (m, 2H), 3.48-3.60 (m, 3H), 3.11-83.25 (m, 1H), 2.90-3.05 (m, 1H), 2.55-2.70 (m, 1H), 2.26-2.43 (m, 4H), 2.15-2.25 (m, 2H), 2.05-2.14 (m, 1H).

The following compounds were prepared analogous to the synthetic preparation in Example 97 (Compound 447).

TABLE 18

Characterization data of compounds prepared analogously to compound 447.

| Cpd ID | Characterization Data |
|---|---|
| 448 | MS (ESI) calcd. for $C_{34}H_{32}N_{10}$: 580.28 m/z, found, 581.40 $[M + H]^+$. $^1$H NMR (300 MHz, DMSO-$d_6$) δ (ppm); 8.32-8.39 (m, 2H), 8.00-8.02 (m, 1H), 7.92-7.99 (m, 2H), 7.79- |

TABLE 18-continued

Characterization data of compounds prepared analogously to compound 447.

| Cpd ID | Characterization Data |
|---|---|
| | 7.81 (m, 1H), 7.44-7.51 (m, 2H), 7.30-7.33 (m, 1H), 7.19-7.28 (m, 2H), 6.97-7.01 (m, 2H), 6.58-6.62 (m, 1H), 6.53-6.55 (m, 1H), 6.37-6.41 (m, 1H), 6.31-6.36 (m, 1H), 4.12-4.19 (m, 1H), 3.88-3.96 (m, 1H), 3.79-3.87 (m, 1H), 3.20-3.21 (m, 1H), 2.88-2.95 (m, 1H), 2.70-2.81 (m, 1H), 2.29-2.34 (m, 4H), 1.91-1.99 (m, 2H), 1.71-1.82 (m, 1H). |
| 449 | MS (ESI) calcd. for $C_{36}H_{36}N_{10}$, 608.31 m/z, found 609.20 $[M + H]^+$. $^1H$ NMR (400 MHz, DMSO-$d_6$) δ (ppm); 8.28-8.47 (m, 2H), 8.07-8.18 (m, 1H), 7.91-8.07 (m, 2H), 7.70-7.87(m, 1H), 7.38-7.63 (m, 2H), 7.12-7.38 (m, 3H), 6.71-6.88 (m, 1H), 6.56-6.71 (m, 1H), 6.49-6.54 (m, 1H),6.32-6.48 (m, 1H), 4.16-4.23 (m, 1H), 3.31-3.54 (m, 5H), 2.92-3.08 (m, 1H), 2.71-2.84 (m, 1H), 2.26-2.42 (m, 1H), 2.09-2.21 (m, 1H), 1.98-2.11 (m, 1H), 1.76-1.92 (m, 1H), 1.41-1.68 (m, 6H). |
| 450 | MS (ESI) calcd. for $C_{36}H_{36}N_{10}$: 608.31 m/z, found, 609.45 $[M + H]^+$. $^1H$-NMR (400 MHz, DMSO-$d_6$) δ (ppm); 8.31-8.46 (m, 2H), 7.92-8.23 (m, 3H), 7.77-7.82 (m, 1H), 7.44-7.56 (m, 2H), 7.37-7.39 (m, 1H), 7.22-7.29 (m, 2H), 6.52-6.61 (m, 2H), 6.31-6.45 (m, 2H), 4.51-4.55 (m, 1H), 3.61-3.72 (m, 3H), 2.95-3.05 (m, 1H), 2.75-2.83 (m, 2H), 2.39-2.48 (m, 1H), 1.72-2.01 (m, 5H), 1.43-1.58 (m, 3H), 1.22-1.33 (m, 2H). |
| 465 | MS (ESI) calcd. for $C_{35}H_{34}N_{10}$: 594.30 m/z, found, 595.20 $[M + H]^+$. $^1H$-NMR (400 MHz, DMSO) δ (ppm); 8.45-8.55 (m, 2H), 8.35-8.41 (m, 1H), 8.23-8.30 (m, 1H), 8.01-8.15 (m, 2H), 7.80-7.90 (m, 2H), 7.70-7.79 (m, 1H), 7.55-7.65 (m, 2H), 7.32-7.40 (m, 1H), 7.20-7.30 (m, 1H), 7.11-7.19 (m, 1H), 6.55-6.62 (m, 1H), 4.62-4.72 (m, 1H), 3.75-4.05 (m, 1H), 3.05-3.25 (m, 3H), 2.79-2.92 (m, 1H), 2.62-2.78 (m, 2H), 2.32-2.50 (m, 2H), 2.09-2.20 (m, 1H), 2.00-2.08 (m, 2H), 1.85-1.99 (m, 3H). |
| 467 | MS (ESI) calcd. for $C_{36}H_{36}N_{10}$, 608.31 m/z, found 609.25 $[M + H]^+$. $^1H$ NMR (400 MHz, DMSO-d6) δ (ppm); 8.24-8.56 (m, 2H), 7.88-8.16 (m, 4H), 7.79-7.88 (m, 1H), 7.62-7.79 (m, 2H), 7.49-7.62 (m, 1H), 7.29-7.49 (m, 2H), 6.82-7.05 (m, 1H), 6.55-6.82 (m, 1H), 6.48-6.55 (m, 1H), 4.68-4.91 (m, 1H), 4.08-4.15 (m, 1H), 3.57-3.81 (m, 2H), 3.38-3.57 (m, 2H), 3.09-3.33 (m, 1H), 2.85-3.09 (m, 1H), 2.48-2.56 (m, 1H), 2.15-2.38 (m, 2H), 2.06-2.15 (m, 1H), 1.85-2.06 (m, 2H), 1.71-1.85 (m, 2H), 1.46-1.71 (m, 2H). |
| 468 | MS (ESI) calcd. for $C_{36}H_{36}N_{10}$, 608.31 m/z, found 609.25 $[M + H]^+$. $^1H$ NMR (400 MHz, DMSO-d6) δ (ppm); 8.41-8.58 (m, 1H), 8.25-8.41 (m, 1H), 7.98-8.16 (m, 2H), 7.89-7.98 (m, 2H), 7.77-7.89 (m, 1H), 7.66-7.77 (m, 2H), 7.48-7.66 (m, 1H), 7.38-7.48 (m, 1H), 7.20-7.38 (m, 1H), 6.83-7.05 (m, 1H), 6.65-6.83 (m, 1H), 6.48-6.65 (m, 1H), 4.62-4.92 (m, 1H), 3.86-4.02 (m, 1H), 3.55-3.75 (m, 2H),3.35-3.75 (m, 2H), 3.09-3.32 (m, 1H), 2.85-3.09 (m, 1H), 2.49-2.53 (m, 1H), 2.09-2.36 (m, 3H), 1.91-2.09 (m, 2H), 1.75-1.91 (m, 2H), 1.51-1.75 (m, 2H). |

Example 98: (S)—N-(5-(2-(2-aminopyridin-3-yl)-5-(1-methyl-11H-1,2,4-triazol-3-yl)-3H-imidazo[4,5-b]pyridin-3-yl)-2,3-dihydro-1H-inden-1-yl)-6-methyl-nicotinamide (Compound 455)

Compound 455

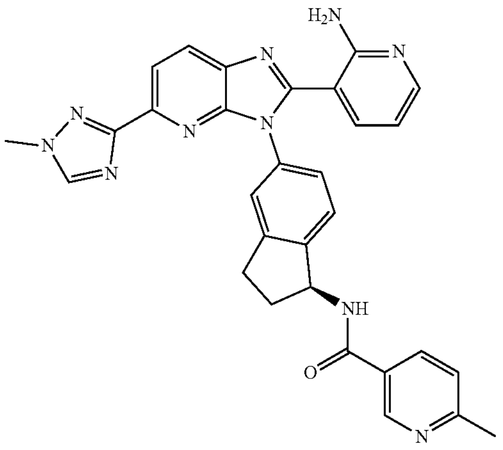

Synthetic Route:

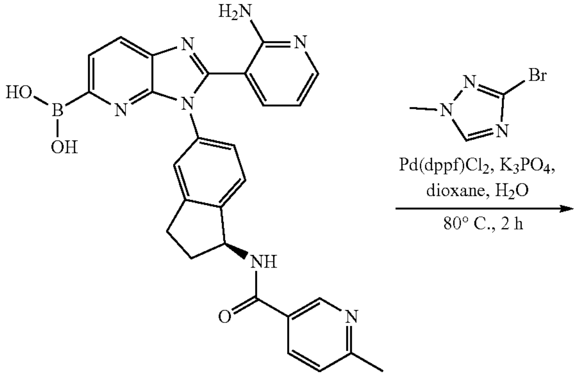

Intermediate 267-1

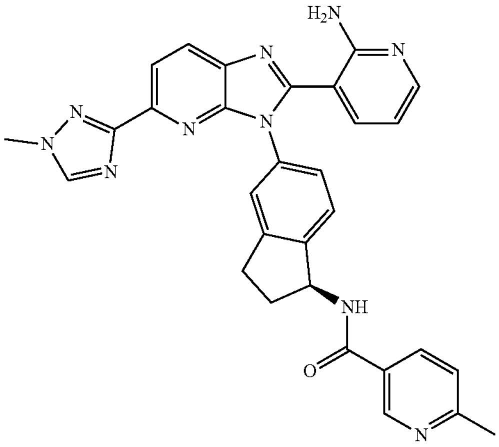

Compound 455

Step 1: Synthesis of (S)—N-(5-(2-(2-aminopyridin-3-yl)-5-(1-methyl-1H-1,2,4-triazol-3-yl)-3H-imidazo[4,5-b]pyridin-3-yl)-2,3-dihydro-1H-inden-1-yl)-6-methylnicotinamide (Compound 455)

A mixture of 2-(2-aminopyridin-3-yl)-3-[(1S)-1-(6-methylpyridine-3-amido)-2,3-dihydro-1H-inden-5-yl]imidazo[4,5-b]pyridin-5-ylboronic acid (Intermediate 267-1) (100 mg, 0.198 mmol, 1 equiv), 3-bromo-1-methyl-1,2,4-triazole (32.06 mg, 0.198 mmol, 1 equiv), $K_3PO_4$ (126.01 mg, 0.594 mmol, 3 equiv) and $Pd(dppf)Cl_2$ (14.48 mg, 0.020 mmol, 0.1 equiv) in water (0.5 mL) and dioxane (2 mL) was stirred overnight at 80° C. under $N_2$ atmosphere. The reaction was quenched with $H_2O$ (10 mL). The resulting mixture was extracted with ethyl acetate (3×10 mL). The combined organic layers were washed with NaCl/$H_2O$ (3×20 mL) and dried over anhydrous $Na_2SO_4$. After filtration, the filtrate was concentrated under reduced pressure. The residue was purified by silica gel column chromatography, eluting with MeOH/DCM (0-10%) to afford crude product. The crude product was purified by Prep-HPLC on a XBridge Prep Shield RP OBD C18 Column using gradient of acetonitrile in water (+0.05% ammonium bicarbonate) to afford N-[(1S)-5-[2-(2-aminopyridin-3-yl)-5-(1-methyl-1,2,4-triazol-3-yl)imidazo[4,5-b]pyridin-3-yl]-2,3-dihydro-1H-inden-1-yl]-6-methylpyridine-3-carboxamide (Compound 455) (16.5 mg, 15.29%) as a white solid. MS (ESI) calcd. for $C_{30}H_{26}N_{10}O$, 542.23 m/z, found 543.20 $[M+H]^+$. $^1H$ NMR (400 MHz, DMSO-$d_6$) δ (ppm); 8.97 (s, 1H), 8.53 (s, 1H), 8.08-8.29 (m, 3H), 8.00-8.06 (m, 1H), 7.15-7.55 (m, 5H), 6.34-6.67 (m, 1H), 5.57-5.82 (m, 1H), 3.91 (s, 3H), 3.01-3.15 (m, 1H), 2.83-2.98 (m, 1H), 2.55-2.63 (m, 1H), 2.53 (s, 3H), 2.02-2.17 (m, 1H).

Example 99: (S)—N-(5-(2-(2-aminopyridin-3-yl)-5-(3-methoxy-1H-1,2,4-triazol-1-yl)-3H-imidazo[4,5-b]pyridin-3-yl)-2,3-dihydro-1H-inden-1-yl)-6-methylnicotinamide (Compound 456)

Compound 456

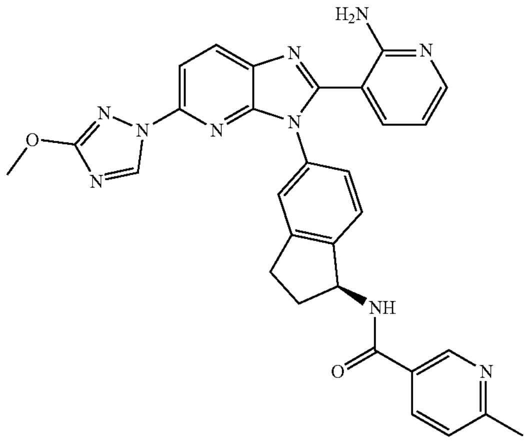

Synthetic Route:

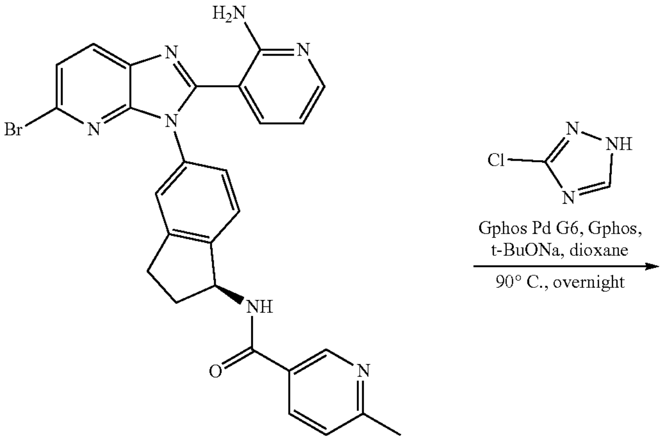

Intermediate 265-1

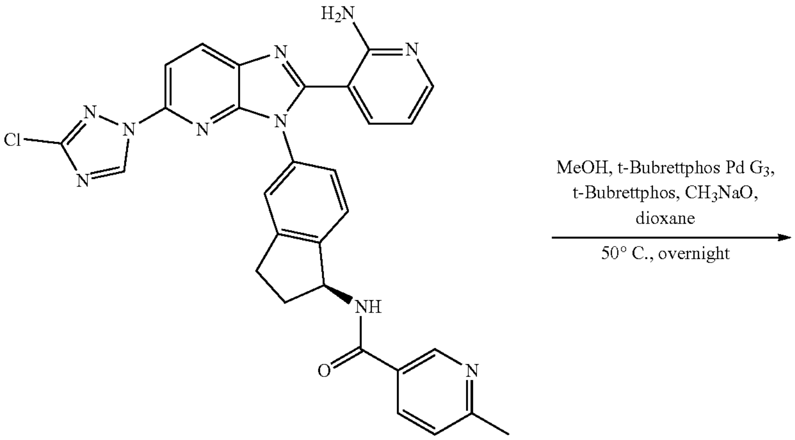

-continued

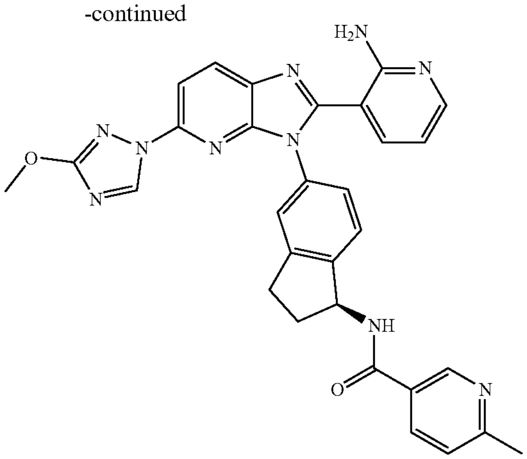

Compound 456

Step 1: Synthesis of (S)—N-(5-(2-(2-aminopyridin-3-yl)-5-(3-chloro-1H-1,2,4-triazol-1-yl)-3H-imidazo[4,5-b]pyridin-3-yl)-2,3-dihydro-1H-inden-1-yl)-6-methylnicotinamide To a solution of N-[(1S)-5-[2-(2-aminopyridin-3-yl)-5-bromoimidazo[4,5-b]pyridin-3-yl]-2,3-dihydro-1H-inden-1-yl]-6-methylpyridine-3-carboxamide (Intermediate 265-1) (200 mg, 0.370 mmol, 1 equiv) in dioxane (5 mL) was added 3-chloro-1H-1,2,4-triazole (76.61 mg, 0.740 mmol, 2 equiv), GPhos (19.86 mg, 0.037 mmol, 0.1 equiv), GPhos Pd G6 TES (34.99 mg, 0.037 mmol, 0.1 equiv) and t-BuONa (88.91 mg, 0.925 mmol, 2.5 equiv). The resulting mixture was maintained under nitrogen and stirred at 90° C. overnight. After cooling to room temperature, the reaction was quenched with water (100 mL). The resulting mixture was extracted with ethyl acetate (3×100 mL). The organic layers were combined, dried over anhydrous $Na_2SO_4$, filtered and concentrated. The residue was purified by reverse-phase flash chromatography on C18 silica gel using a gradient of acetonitrile in water (+0.05% ammonium bicarbonate) to afford (S)—N-(5-(2-(2-aminopyridin-3-yl)-5-(3-chloro-1H-1,2,4-triazol-1-yl)-3H-imidazo[4,5-b]pyridin-3-yl)-2,3-dihydro-1H-inden-1-yl)-6-methylnicotinamide (100 mg, 43.19% yield) as a yellow solid: MS (ESI) calcd. for $C_{29}H_{23}ClN_{10}O$, 562.17 m/z, found, 563.25 $[M+H]^+$.

Step 2: Synthesis of (S)—N-(5-(2-(2-aminopyridin-3-yl)-5-(3-methoxy-1H-1,2,4-triazol-1-yl)-3H-imidazo[4,5-b]pyridin-3-yl)-2,3-dihydro-1H-inden-1-yl)-6-methylnicotinamide (Compound 456)

To a solution of (S)—N-(5-(2-(2-aminopyridin-3-yl)-5-(3-chloro-1H-1,2,4-triazol-1-yl)-3H-imidazo[4,5-b]pyridin-3-yl)-2,3-dihydro-1H-inden-1-yl)-6-methylnicotinamide (60 mg, 0.107 mmol, 1 equiv) in dioxane (2 mL) was added MeOH (17.07 mg, 0.535 mmol, 5 equiv), tBuBrettPhos (5.17 mg, 0.011 mmol, 0.1 equiv), tBuBrettPhos Pd G3 (9.25 mg, 0.011 mmol, 0.1 equiv) and t-BuONa (14.34 mg, 0.150 mmol, 1.4 equiv). The resulting mixture was maintained under nitrogen and stirred at 50° C. overnight. After cooling to room temperature, the reaction was quenched with water (10 mL). The resulting mixture was extracted with ethyl acetate (3×10 mL). The organic layers were combined, dried over anhydrous $Na_2SO_4$, filtered and concentrated. The residue was purified by reverse-phase flash chromatography on C18 silica gel using a gradient of acetonitrile in water (+0.05% ammonium bicarbonate) to afford (S)—N-(5-(2-(2-aminopyridin-3-yl)-5-(3-methoxy-1H-1,2,4-triazol-1-yl)-3H-imidazo[4,5-b]pyridin-3-yl)-2,3-dihydro-1H-inden-1-yl)-6-methylnicotinamide (Compound 456) (10.7 mg, 17.97% yield) as an off-white solid: MS (ESI) calcd. for $C_{30}H_{26}N_{10}O_2$, 558.22 m/z, found, 559.35 $[M+H]^+$. $^1$H-NMR (300 MHz, DMSO-$d_6$) S (ppm); 9.94-9.95 (m, 1H), 8.83-8.85 (m, 1H), 8.39-8.41 (m, 1H), 8.18-8.21 (m, 1H), 8.00-8.05 (m, 1H), 7.75-7.78 (m, 1H), 7.36-7.40 (m, 3H), 7.30-7.33 (m, 2H), 6.45-6.49 (m, 1H), 5.60-5.65 (m, 1H), 3.99 (s, 3H), 3.02-3.04 (m, 1H), 2.91-2.97 (m, 1H), 2.55-2.62 (m, 4H), 2.03-2.20 (m, 1H).

The following compounds were prepared analogous to the synthetic preparation in Example 99 (Compound 456).

TABLE 19A

Characterization data of compounds prepared analogously to compound 456.

| Cpd ID | Characterization Data |
|---|---|
| 346 | MS (ESI) calcd. for $C_{29}H_{24}N_{10}O$: 528.21 m/z, found: 529.15 $[M + H]^+$. $^1$H NMR (300 MHz, DMSO-$d_6$ + $D_2O$) δ (ppm): 9.13 (s, 1H), 8.92-8.98 (m, 1H), 8.42-8.49 (m, 1H), 8.29-8.32 (m, 1H), 8.15-8.19 (m, 1H), 8.03-8.07 (m, 1H), 7.88-7.91 (m, 1H), 7.36-7.45 (m, 3H), 7.26-7.31 (m, 2H), 6.46-6.71 (m, 1H), 5.61-5.69 (m, 1H), 3.01-3.13 (m, 1H), 2.85-2.97 (m, 1H), 2.58-2.61 (m, 1H), 2.55 (s, 3H), 2.02-2.19 (m, 1H) |
| 483 | MS (ESI) calcd. for $C_{33}H_{33}F_2N_9O_2$: 625.27 m/z, found, 626.20 $[M + H]^+$. $^1$H NMR (400 MHz, DMSO-d6) δ(ppm): 8.37 (d, J = 8.8 Hz, 1H), 8.30 (s, 1H), 8.00-8.01 (m, 1H), 7.80 (d, J = 8.4 Hz, 1H), 7.33-7.65 (m, 3H), 7.21-7.30 (m, 2H), 6.93 (s, 2H), 6.41-6.44 (m, 1H), 6.34-6.35 (m, 1H), 4.35-4.37 (m, 1H), 4.19-4.21 (m, 2H), 3.22-3.23 (m, 1H), 2.92-2.94 (m, 2H), 2.76-2.82 (m, 2H), 2.42-2.47 (m, 1H), 1.77-2.02 (m, 5H), 1.18-1.30 (m, 2H), 0.68-0.72 (m, 4H). |
| 485 | MS (ESI) calcd. for $C_{33}H_{35}N_9O_2$: 589.29 m/z, found, 590.25 $[M + H]^+$. $^1$H NMR (300 MHz, DMSO-$d_6$) δ(ppm): 8.30 (d, J = 8.4 Hz, 1H), 8.17-8.18 (m, 1H), 7.98-8.00 (m, 1H), 7.77 (d, J = 8.7 Hz, 1H), 7.74 (d, J = 7.8 Hz, 1H), 7.31 (s, 1H), 7.19-7.25 (m, 2H), 6.94 (s, 2H), 6.39-6.44 (m, 1H), 6.04-6.05 (m, 1H), 4.33-4.35 (m, 1H), 4.19-4.22 (m, 2H), 3.92 (s, 3H), 3.15-3.23 |

TABLE 19A-continued

Characterization data of compounds prepared analogously to compound 456.

| Cpd ID | Characterization Data |
|---|---|
| | (m, 1H), 2.75-2.93 (m, 4H), 2.43-2.46 (m, 1H), 1.77-2.07 (m, 5H), 1.23-1.28 (m, 2H), 0.67-0.72 (m, 4H). |
| 486 | MS (ESI) calcd. for $C_{34}H_{37}N_9O_2$: 603.31 m/z, found, 604.25[M + H]$^+$. $^1$H NMR (300 MHz, DMSO-d6) δ(ppm): 8.30 (d, J = 8.7 Hz, 1H), 8.15 (s, 1H), 7.98-8.00 (m, 1H), 7.75 (d, J = 8.4 Hz, 1H), 7.46 (d, J = 8.4 Hz, 1H), 7.31 (s, 1H), 7.19-7.24 (m, 2H), 6.94 (s, 2H), 6.39-6.43 (m, 1H), 6.03-6.04 (m, 1H), 4.20-4.35 (m, 5H), 3.15-3.23 (m, 1H), 2.80-2.93 (m, 2H), 2.75-2.77 (m, 2H), 2.42-2.46 (m, 1H), 1.78-2.06 (m, 5H), 1.23-1.38 (m, 5H), 0.67-0.72 (m, 4H). |
| 487 | MS (ESI) calcd. for $C_{37}H_{41}N_9O_2$, 643.34 m/z, found 644.45 [M + H]$^+$.$^1$H NMR (300 MHz, DMSO-d6) δ ppm: 8.32 (d, J = 8.7 Hz, 1H), 8.24 (d, J = 2.7 Hz, 1H), 8.00 (d, J = 1.5 Hz, 1H), 7.87-7.99 (m, 1H), 7.48 (d, J = 8.1 Hz, 1H), 7.33 (s, 1H), 7.20-7.25 (m, 2H), 6.93 (s, 2H), 6.39-6.44 (m, 2H), 4.36 (s, 1H), 4.20 (s, 2H), 3.92 (d, J = 9.9 Hz, 2H), 3.42-3.49 (m, 2H), 3.22-3.32 (m, 2H), 2.92-2.98 (m, 3H), 2.80-2.90 (m, 2H), 2.35-2.45 (m, 1H), 1.98-2.00 (m, 2H), 1.84-1.89 (m, 3H), 1.60-1.75 (m, 3H), 1.10-1.41 (m, 2H), 0.63-0.71 (m, 4H). |
| 488 | MS (ESI) calcd. for $C_{36}H_{40}N_{10}O_2$, 644.33 m/z, found 645.20 [M + H]$^+$. $^1$H NMR (400 MHz, DMSO-d6) δ (ppm); 8.27 (d, J = 8.6 Hz, 1H), 8.15 (d, J = 2.7 Hz, 1H), 7.99 (dd, J = 4.8, 1.9 Hz, 1H), 7.77 (d, J = 8.6 Hz, 1H), 7.47 (d, J = 8.0 Hz, 1H), 7.31 (s, 1H), 7.16-7.25 (m, 2H), 6.96 (s, 2H), 6.41 (dd, J = 7.6, 4.8 Hz, 1H), 6.16 (d, J = 2.7 Hz, 1H), 4.27-4.40 (m, 1H), 4.11-4.26 (m, 2H), 3.66-3.78 (m, 4H), 3.16-3.26 (m, 5H), 2.86-3.01 (m, 2H), 2.72-2.85 (m, 2H), 2.40-2.48 (m, 1H), 2.10-2.22 (m, 1H), 1.71-2.05 (m, 4H), 1.09-1.40 (m, 2H), 0.64-0.76 (m, 4H). |
| 497 | Observed mass (ESI): 616.25 [M + H]+. 1H NMR (300 MHz, DMSO-d6) δ ppm: 8.31 (d, J = 8.7 Hz, 1H), 8.18 (d, J = 2.7 Hz, 1H), 8.00 (d, J = 4.8 Hz, 1H), 7.76 (d, J = 8.7 Hz, 1H), 7.47 (d, J = 8.1 Hz, 1H), 7.31 (s, 1H), 7.19-7.25 (m, 2H), 6.94 (s, 2H), 6.41 (d, J = 7.5 Hz, 1H), 6.14 (s, 1H), 4.33-4.35 (m, 1H), 4.19 (s, 2H), 4.09-4.14 (m, 1H), 3.20-3.26 (m, 1H), 2.91-2.94 (m, 2H), 2.75-2.83 (m, 2H), 2.43-2.46 (m, 1H), 1.77-2.10 (m, 5H), 1.19-1.30 (m, 2H), 0.67-0.76 (m, 8H). |
| 504 | Observed mass (ESI): 634.25 [M + H]+. 1H NMR (400 MHz, DMSO-d6) δ (ppm): 8.31 (d, J = 8.6 Hz, 1H), 8.17 (d, J = 2.7 Hz, 1H), 8.00 (dd, J = 4.8, 1.9 Hz, 1H), 7.76 (d, J = 8.6 Hz, 1H), 7.47 (d, J = 8.0 Hz, 1H), 7.32 (d, J = 1.9 Hz, 1H), 7.19-7.25 (m, 2H), 6.95 (s, 2H), 6.42 (dd, J = 7.7, 4.8 Hz, 1H), 6.06 (d, J = 2.7 Hz, 1H), 4.30-4.38 (m, 3H), 4.13-4.26 (m, 2H), 3.65-3.71 (m, 2H), 3.31 (s, 3H), 3.16-3.27 (m, 1H), 2.86-2.99 (m, 2H), 2.72-2.85 (m, 2H), 2.40-2.48 (m, 1H), 1.73-2.11 (m, 5H), 1.11-1.36 (m, 2H), 0.66-0.75 (m, 4H). |
| 505 | Observed mass (ESI): 689.3 [M + H]+. 1H NMR (300 MHz, DMSO-d6) δ(ppm): 8.29-8.32 (m, 1H), 8.16-8.17 (m, 1H), 7.99-8.01 (m, 1H), 7.76 (d, J = 8.7 Hz, 1H), 7.46 (d, J = 7.8 Hz, 1H), 7.31 (s, 1H), 7.19-7.24 (m, 2H), 6.95 (s, 2H), 6.39-6.43 (m, 1H), 6.06-6.07 (m, 1H), 4.31-4.34 (m, 3H), 4.19-4.25 (m, 2H), 3.56-3.59 (m, 4H), 3.21-3.23 (m, 1H), 2.91-2.93 (m, 2H), 2.71-2.80 (m, 4H), 2.46-2.47 (m, 5H), 1.78-2.06 (m, 5H), 1.20-1.30 (m, 2H), 0.67-0.72 (m, 4H). |
| 517 | Observed mass (ESI): 660.45 [M + H]+. 1H NMR (400 MHz, DMSO-d6) δ ppm: 8.30 (d, J = 8.4 Hz, 1H), 8.16 (s, 1H), 8.00 (s, 1H), 7.75 (d, J = 8.0 Hz, 1H), 7.46 (d, J = 8.0 Hz, 1H), 7.31 (s, 1H), 7.19-7.24 (m, 2H), 6.95-6.98 (m, 2H), 6.42 (d, J = 7.6 Hz, 1H), 6.08 (s, 1H), 4.77-4.81 (m, 1H), 4.32-4.36 (m, 1H), 4.13-4.24 (m, 2H), 3.86-3.89 (m, 2H), 3.47-3.53 (m, 2H), 3.18-3.23 (m, 1H), 2.92-2.98 (m, 2H), 2.78-2.82 (m, 2H), 2.47-2.48 (m, 1H), 1.99-2.09 (m, 4H), 1.88-1.93 (m, 1H), 1.75-1.85 (m, 2H), 1.64-1.68 (m, 2H), 1.15-1.35 (m, 2H), 0.68-0.72 (m, 4H). |
| 518 | Observed mass (ESI): 606.15 [M + H]+. 1H NMR (400 MHz, DMSO-d6) δ(ppm): 8.25-8.52 (m, 2H), 7.96-8.09 (m, 1H), 7.89 (d, J = 8.4 Hz, 1H), 7.48 (d, J = 8.0 Hz, 1H), 7.32 (s, 1H), 7.16-7.30 (m, 2H), 6.55 (d, J = 2.8 Hz, 1H), 6.38-6.50 (m, 1H), 4.33 (t, J = 7.2 Hz, 1H), 4.10-4.30 (m, 2H), 3.11-3.31 (m, 1H), 2.86-3.03 (m, 2H), 2.70-2.85 (m, 2H), 2.55-2.59 (m, 3H), 2.40-2.49 (m, 1H), 1.70-2.09 (m, 4H), 1.06-1.41 (m, 2H), 0.62-0.80 (m, 4H). |
| 525 | Observed mass (ESI): 644.25 [M + H]+. 1H-NMR (400 MHz, DMSO + D2O) δ (ppm): 8.33-8.45 (m, 1H), 8.25-8.32 (m, 1H), 7.97-8.10 (m, 1H), 7.72-7.88 (m, 1H), 7.20-7.70 (m, 5H), 6.40-6.50 (m, 1H), 6.30-6.39 (m, 1H), 5.40-5.70 (m, 1H), 4.15-4.65 (m, 3H), 3.00-3.35 (m, 4H), 2.72-2.90 (m, 1H), 1.80-2.20 (m, 3H), 1.15-1.55 (m, 2H), 0.60-0.85 (m, 4H). 19F NMR (376 MHz, DMSO-d6) δ (ppm): −196.84, −84.19. |

Example 101: Synthetic Procedures for Intermediates

Intermediate 147-1: 3-(3-((1R,2*)-1-amino-2-fluoro-2,3-dihydro-1H-inden-5-yl)-5-(1H-pyrazol-1-yl)-3H-imidazo[4,5-b]pyridin-2-yl)pyridin-2-amine and

Intermediate 147-2: 3-(3-((1R,2*)-1-amino-2-fluoro-2,3-dihydro-1H-inden-5-yl)-5-(1H-pyrazol-1-yl)-3H-imidazo[4,5-b]pyridin-2-yl)pyridin-2-amine Intermediate 147-1

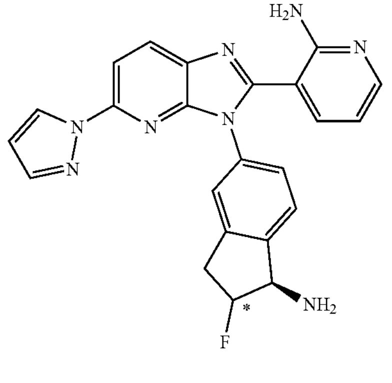

-continued
Intermediate 147-2
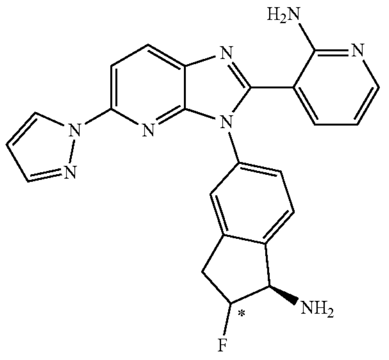
Synthetic Route:
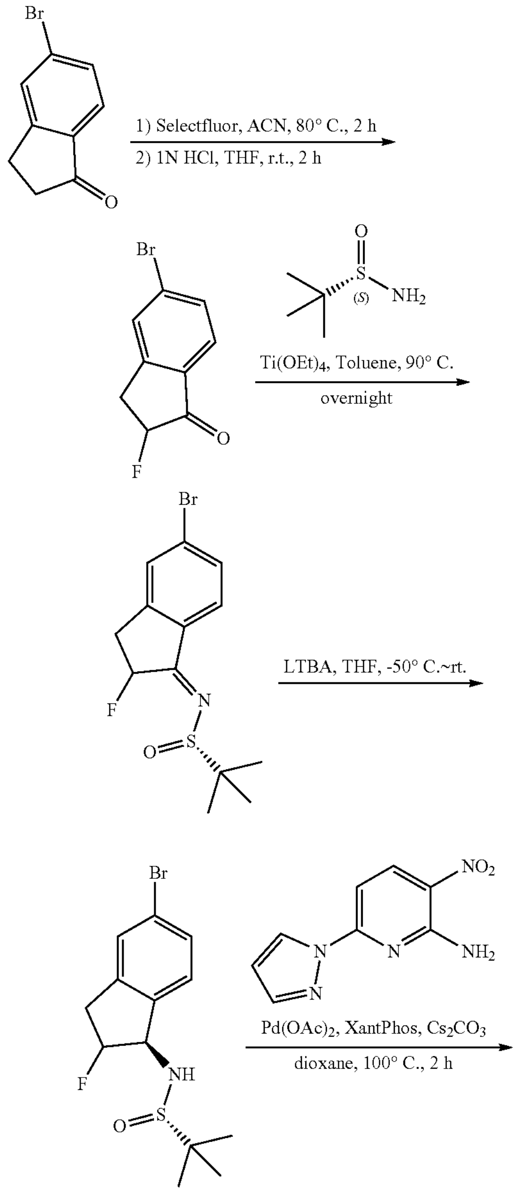
-continued
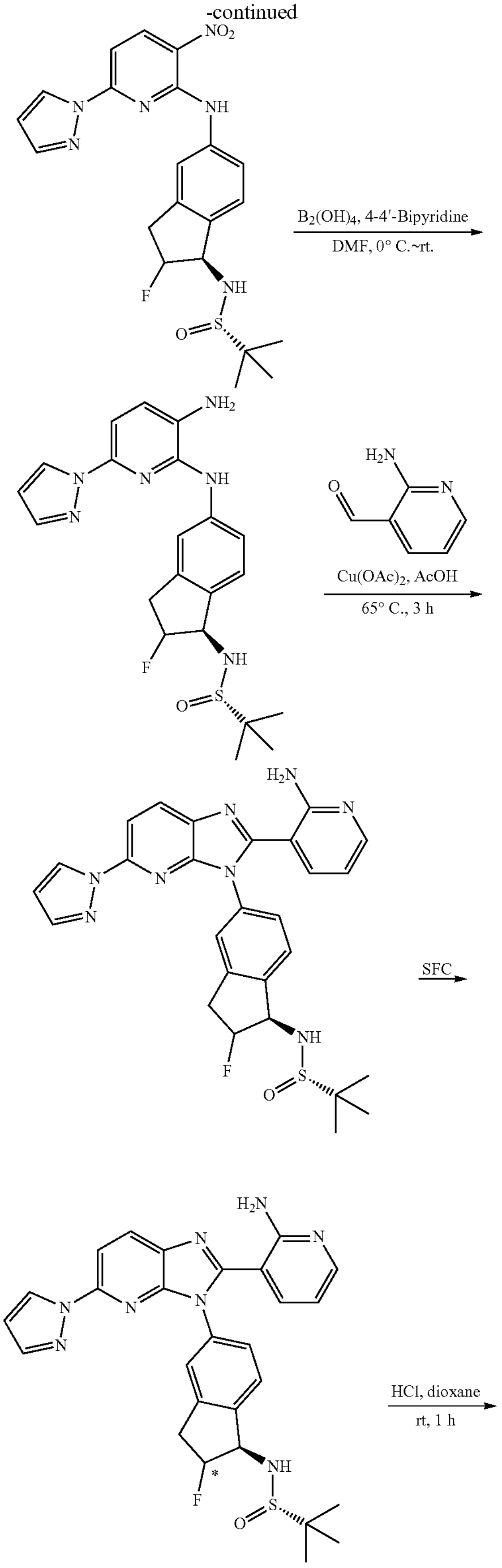

-continued

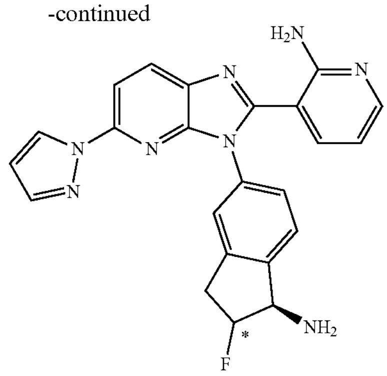

Intermediate 147-1

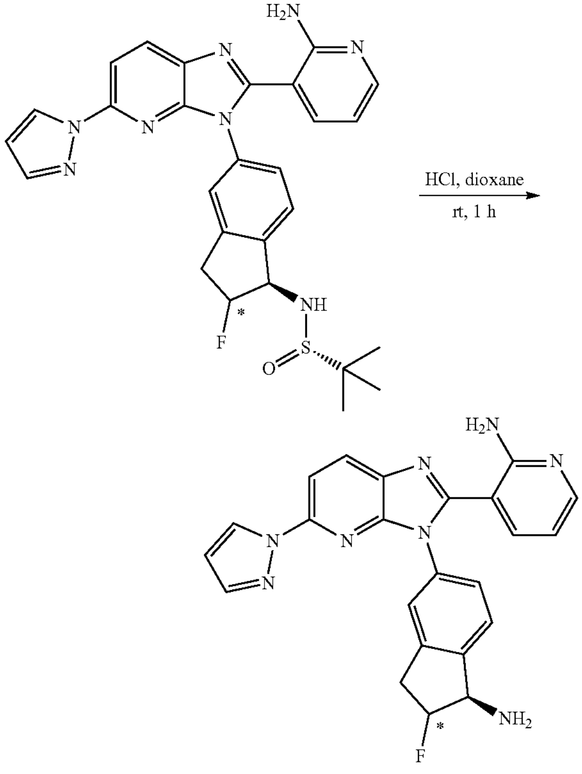

Intermediate 147-2

Step 1: Synthesis of 5-bromo-2-fluoro-2,3-dihydro-1H-inden-1-one

To a solution of 5-bromo-1-indanone (5.00 g, 23.8 mmol) in methanol (50 mL) was added SelectFluor (10.0 g, 28.2 mmol) and the resulting mixture was stirred under reflux for 2 hours. The reaction mixture was filtered through Celite, and the filtrate was concentrated under reduced pressure. The resulting residue was dissolved in tetrahydrofuran (50 mL) and 1 N hydrochloric acid (50 mL) was added followed by stirring at room temperature for 3 hours. To the reaction mixture, a 2 N aqueous sodium hydroxide solution (50 mL) was added, and the mixture was diluted with a saturated aqueous sodium bicarbonate solution. The mixture was extracted with ethyl acetate. The organic layer was washed with brine, dried over anhydrous magnesium sulfate, and then concentrated under reduced pressure to afford 5-bromo-2-fluoro-2,3-dihydroinden-1-one (4.0 g, 74% yield) as a white solid. MS (ESI) calcd. for $C_9H_6BrFO$, 227.96 m/z, found: 229.00 $[M+H]^+$.

Step 2: Synthesis of (S)—N—((Z)-5-bromo-2-fluoro-2,3-dihydro-1H-inden-1-ylidene)-2-methylpropane-2-sulfinamide To a solution of 5-bromo-2-fluoro-2,3-dihydroinden-1-one (3.0 g, 13 mmol) in toluene (5 mL) was added (S)-2-methylpropane-2-sulfinamide (1.90 g, 15.7 mmol) and $Ti(OEt)_4$ (5.08 g, 22.2 mmol). The mixture was stirred at 90° C. for 2 h. After cooling to room temperature, the reaction was quenched by the addition of 2M Rochelle's salt (30 mL). The resulting mixture was diluted with brine (50 mL) and extracted with ethyl acetate (3×50 mL). The combined organic layers were dried over anhydrous $Na_2SO_4$. After filtration, the filtrate was concentrated under reduced pressure. The residue was purified by silica gel column chromatography using a gradient of ethyl acetate in petroleum ether to afford (S)—N-(5-bromo-2-fluoro-2,3-dihydro-1H-inden-1-ylidene)-2-methylpropane-2-sulfinamide (3.0 g, 69% yield) as a yellow solid. MS (ESI) calcd. for $C_{13}H_{15}BrFNOS$: 331.00 m/z, found: 332.10 $[M+H]^+$. Note that the (S)- applies to the sulfur stereocenter and not the C—F bond for this and all instances vide infra.

Step 3: Synthesis of (S)—N-((1R)-5-bromo-2-fluoro-2,3-dihydro-1H-inden-1-yl)-2-methylpropane-2-sulfinamide To a cooled (−50° C.) solution of (S)—N—((Z)-5-bromo-2-fluoro-2,3-dihydro-1H-inden-1-ylidene)-2-methylpropane-2-sulfinamide (3.0 g, 9.0 mmol) in THF was added LTBA (3.90 g, 15.4 mmol) and the resulting mixture was stirred at room temperature for 2 h. The reaction was quenched by the addition of 2M Rochelle's salt (30 mL). The mixture was diluted with brine (50 mL) and extracted with ethyl acetate (3×50 mL). The combined organic layers were dried over anhydrous $Na_2SO_4$. After filtration, the filtrate was concentrated under reduced pressure. The residue was purified by silica gel column chromatography using a gradient of ethyl acetate in petroleum ether to afford (S)—N-((1R)-5-bromo-2-fluoro-2,3-dihydro-1H-inden-1-yl)-2-methylpropane-2-sulfinamide (2.0 g, 66% yield) as a yellow solid. MS (ESI) calcd. for $C_{13}H_{17}BrFNOS$: 333.02 m/z, found: 334.10 $[M+H]^+$.

Step 4: Synthesis of (S)—N-((1R)-2-fluoro-5-((3-nitro-6-(1H-pyrazol-1-yl)pyridin-2-yl)amino)-2,3-dihydro-1H-inden-1-yl)-2-methylpropane-2-sulfinamide A mixture of (S)—N-((1R)-5-bromo-2-fluoro-2,3-dihydro-1H-inden-1-yl)-2-methylpropane-2-sulfinamide (2.0 g, 6.0 mmol), 3-nitro-6-(pyrazol-1-yl)pyridin-2-amine (1.35 g, 6.58 mmol), $Pd(OAc)_2$ (0.13 g, 0.60 mmol), $Cs_2CO_3$ (5.86 g, 18.0 mmol) and XantPhos (0.35 g, 0.60 mmol) in dioxane (4.0 mL) was stirred at 100° C. for 2 h under nitrogen atmosphere. The reaction was quenched with water (100 mL) and the mixture was extracted with ethyl acetate (3×100 mL). The combined organic extracts were washed with brine (100 mL) and dried over anhydrous $Na_2SO_4$. After filtration, the filtrate was concentrated under reduced pressure. The crude product was purified by silica gel column chromatography using a gradient of methanol in dichloromethane to afford (S)—N-((1R)-2-fluoro-5-((3-nitro-6-(1H-pyrazol-1-yl yl)pyridin-2-yl)amino)-2,3-dihydro-1H-inden-1-yl)-2-methylpropane-2-sulfinamide (2.5 g, 91% yield) as a yellow solid. MS (ESI) calcd. for $C_{21}H_{23}FN_6O_3S$, 458.15 m/z, found: 459.10 $[M+H]^+$.

Step 5: Synthesis of (S)—N-((1R)-5-((3-amino-6-(1H-pyrazol-1-yl)pyridin-2-yl)amino)-2-fluoro-2,3-dihydro-1H-inden-1-yl)-2-methylpropane-2-sulfinamide To a solution of (S)—N-[(1R)-2-fluoro-5-{[3-nitro-6-(pyrazol-1-yl)pyridin-2-yl]amino}-2,3-dihydro-1H-inden-1-yl]-2-methylpropane-2-sulfinamide (2.5 g, 5.5 mmol) in DMF (30 mL) was added $B_2(OH)_4$ (1.47 g, 16.4 mmol) and 4-(pyridin-4-yl)pyridine (25.0 mg, 0.163 mmol). The resulting mixture was stirred at room temperature for 1 h. The reaction was quenched by the addition of water (200 mL) and then the mixture was extracted with ethyl acetate (3×100 mL). The combined organic extracts were washed with brine (100 mL) and dried over anhydrous $Na_2SO_4$. After filtration, the filtrate was concentrated under reduced pressure to afford (S)—N-((1R)-5-((3-amino-6-(1H-pyrazol-1-yl)pyridin-2-yl)amino)-2-fluoro-2,3-dihydro-1H-inden-1-yl)-2-methylpropane-2-sulfinamide (2.0 g, 86% yield) as a yellow solid. MS (ESI) calcd. for $C_{21}H_{25}FN_6OS$: 428.17 m/z. found: 429.15 $[M+H]^+$.

Step 6: Synthesis of (S)—N-((1R)-5-(2-(2-amino-pyridin-3-yl)-5-(1H-pyrazol-1-yl)-3H-imidazo[4,5-b]pyridin-3-yl)-2-fluoro-2,3-dihydro-1H-inden-1-yl)-2-methylpropane-2-sulfinamide To a solution of (S)—N-[(1R)-5-{[3-amino-6-(pyrazol-1-yl)pyridin-2-yl]amino}-2-fluoro-2,3-dihydro-1H-inden-1-yl]-2-methylpropane-2-sulfinamide (2.0 g, 4.7 mmol) and 2-aminopyridine-3-carbaldehyde (0.68 g, 5.6 mmol) in AcOH (60 mL) was added $Cu(OAc)_2$ (171 mg, 0.94 mmol). The mixture was stirred at 65° C. for 1.0 h. After cooling to room temperature, the mixture was concentrated and the residue obtained was purified by reverse phase flash column chromatography on C18 silica gel using a gradient of acetonitrile in water (+0.05 mmol/L $NH_4HCO_3$) to afford (S)—N-((1R)-5-(2-(2-aminopyridin-3-yl)-5-(1H-pyrazol-1-yl)-3H-imidazo[4,5-b]pyridin-3-yl)-2-fluoro-2,3-dihydro-1H-inden-1-yl)-2-methylpropane-2-sulfinamide (1.47 g, 59% yield). MS (ESI) calcd. for $C_{27}H_{27}FN_8OS$, 530.20 m/z, found: 531.25 $[M+H]^+$. The two diastereomers were separated by chiral SFC on a (S,S)-Whelk-O 1 5 μm Kromasil column using a 2:1 mix of $CO_2$ and [acetonitrile/methanol 4:1]. The first eluting peak was carried through step 7 below to afford Intermediate 147-1 and the second eluting peak was converted to Intermediate 147-2. *Denotes a stereocenter with undetermined absolute stereochemistry of a single diastereomer.

Step 7: Synthesis of 3-(3-((1R)-1-amino-2-fluoro-2,3-dihydro-1H-inden-5-yl)-5-(1H-pyrazol-1-yl)-3H-imidazo[4,5-b]pyridin-2-yl)pyridin-2-amine (Intermediates 147-1 and 147-2)

The two diastereomers of (S)—N-((1R)-5-(2-(2-amino-pyridin-3-yl)-5-(1H-pyrazol-1-yl)-3H-imidazo[4,5-b]pyridin-3-yl)-2-fluoro-2,3-dihydro-1H-inden-1-yl)-2-methylpropane-2-sulfinamide (500 mg, 0.754 mmol) were dissolved separately in 4N HCl in dioxane (8 mL) and the resulting mixtures were stirred at room temperature for 1 h under nitrogen atmosphere. The solvent was removed under vacuum to afford 3-(3-((1R)-1-amino-2-fluoro-2,3-dihydro-1H-inden-5-yl)-5-(1H-pyrazol-1-yl)-3H-imidazo[4,5-b]pyridin-2-yl)pyridin-2-amine (400 mg, crude) as a light yellow solid. MS (ESI) calcd. For $C_{23}H_{19}FN_8$: 426.17 m/z, found: 427.30 $[M+H]^+$.

The following compounds were prepared analogous to the synthetic preparation in Compound 147-1.

TABLE 19B

Characterization data of compounds prepared analogously to Compound 147-1.

| Cpd ID | Characterization Data |
|---|---|
| 527 | Observed mass (ESI): 411.25 [M + H]+. 1H NMR (400 MHz, DMSO-d6) δ (ppm): 8.25-8.46 (m, 2H), 7.91-8.04 (m, 1H), 7.76-7.89 (m, 1H), 7.62-7.75 (m, 1H), 7.52-7.62 (m, 1H), 7.18-7.48 (m, 5H), 6.44-6.63 (m, 1H), 4.18-4.32 (m, 1H), 2.82-2.93 (m, 1H), 2.69-2.81 (m, 1H), 2.33-2.42 (m, 1H), 1.58-1.73 (m, 1H). |

Intermediate 187-1: 5-bromo-2,2-difluoro-2,3-dihydro-1H-inden-1-one

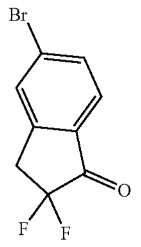

Intermendiate 187-1

Synthetic Route:

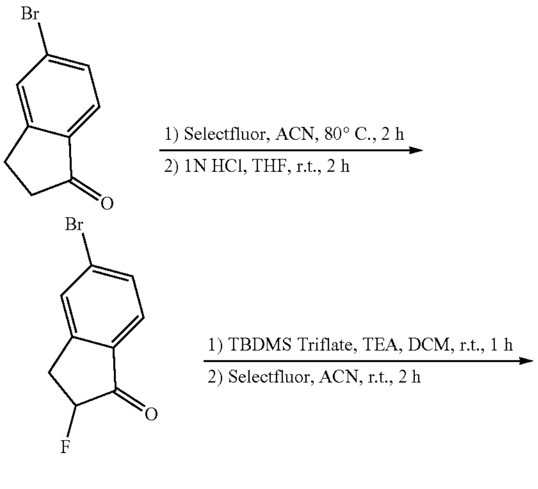

-continued

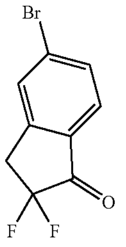

Intermediate 187-1

Step 1: Synthesis of 5-bromo-2-fluoro-2,3-dihydro-1H-inden-1-one

To a solution of 5-bromo-1-indanone (5.00 g, 23.8 mmol) in methanol (50 mL) was added SelectFluor (10.0 g, 28.2 mmol) and the resulting mixture was stirred under reflux for 2 hours. The reaction mixture was filtered through Celite, and the filtrate was concentrated under reduced pressure. The resulting residue was dissolved in tetrahydrofuran (50 mL), and 1 N hydrochloric acid (50 mL) was added followed by stirring at room temperature for 3 hours. To the reaction mixture, a 2 N aqueous sodium hydroxide solution (50 mL) was added, and the mixture was diluted with a saturated aqueous sodium bicarbonate solution. The mixture was extracted with ethyl acetate. The organic layer was washed with brine, dried over anhydrous magnesium sulfate, and then concentrated under reduced pressure to afford 5-bromo-2-fluoro-2,3-dihydroinden-1-one (4.0 g, 74% yield) as a white solid. MS (ESI) calcd. for $C_9H_6BrFO$, 227.96 m/z, found: 229.00 $[M+H]^+$.

Step 2: 5-bromo-2,2-difluoro-2,3-dihydro-1H-inden-1-one (Intermediate 187-1)

To a solution of 5-bromo-2-fluoro-2,3-dihydro-1H-inden-1-one (3.0 g, 13 mmol, 1 equiv) in DCM (30 mL) was added tert-butyldimethylsilyl trifluoromethanesulfonate (5.16 mL, 988 mmol, 70 equiv) and triethylamine (9.1 mL, 65.5 mmol, 5.0 equiv) and the resulting mixture was stirred at room temperature for 1 hour. The reaction mixture was diluted with saturated aqueous sodium bicarbonate and extracted with ethyl acetate. The organic layer was dried over anhydrous sodium sulfate and concentrated under reduced pressure. The resulting residue was dissolved in acetonitrile (30 mL) and Selectfluor (5.57 g, 15.7 mmol, 1.2 equiv) was added. The resulting mixture was stirred at room temperature for 2 hours. The reaction mixture was diluted with saturated aqueous sodium bicarbonate and extracted with ethyl acetate. The organic layer was washed with brine, dried over anhydrous magnesium sulfate, and concentrated under reduced pressure. To the resulting residue, hexane was added, and the precipitate was collected by filtration to afford 5-bromo-2,2-difluoro-2,3-dihydro-1H-inden-1-one (Intermediate 187-1) (2.3 g, 71%). MS (ESI) calcd. for $C_9H_5BrF_2O$, 245.95 m/z, found: 247.00 $[M+H]^+$.

Intermediate 299-1: (S)-3-(3-(1-amino-3,3-difluoro-2,3-dihydro-1H-inden-5-yl)-5-(1H-pyrazol-1-yl)-3H-imidazo[4,5-b]pyridin-2-yl)pyridin-2-amine Intermediate 299-1

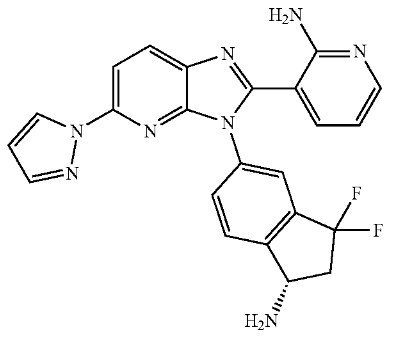

Synthetic Route:

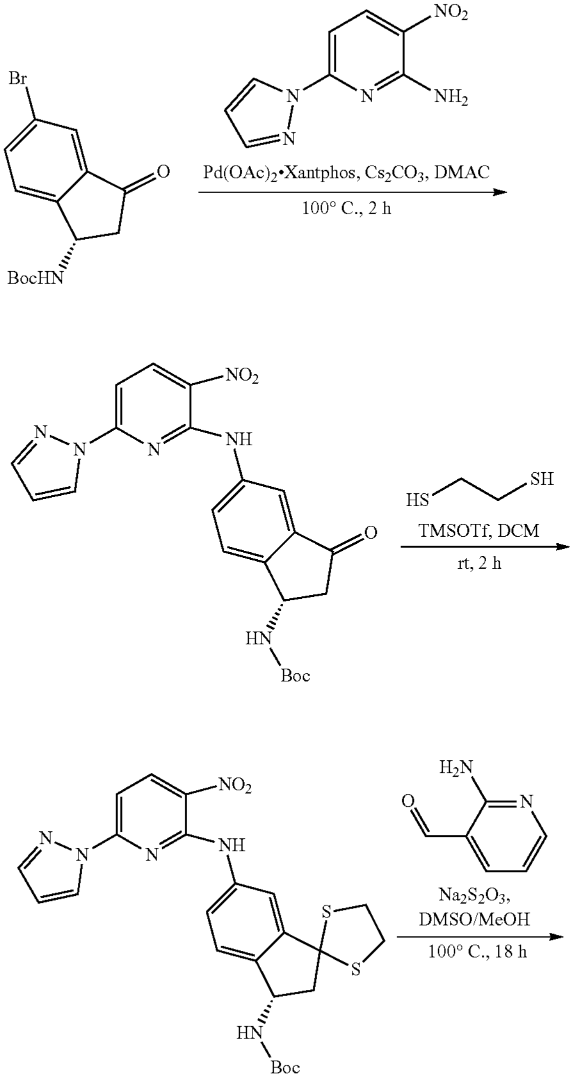

-continued

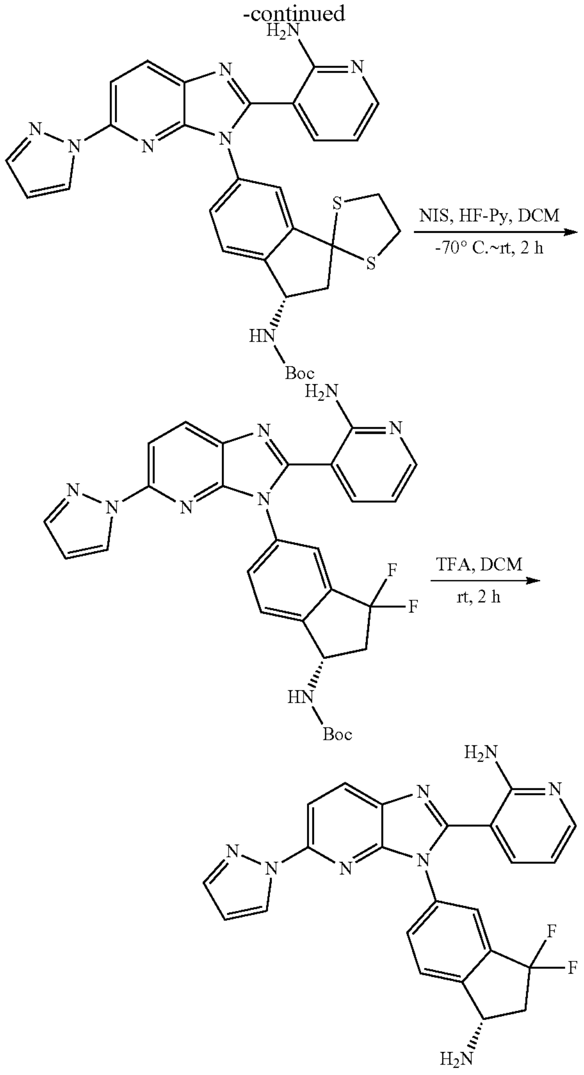

Intermediate 299-1

Step 1: Synthesis of tert-butyl (S)-(5-((3-nitro-6-(1H-pyrazol-1-yl)pyridin-2-yl)amino)-3-oxo-2,3-dihydro-1H-inden-1-yl)carbamate To a solution of tert-butyl (S)-(5-bromo-3-oxo-2,3-dihydro-1H-inden-1-yl)carbamate (product of Step 4 of Intermediate 312-2) (1 g, 3.066 mmol, 1 equiv) and 3-nitro-6-(1H-pyrazol-1-yl)pyridin-2-amine (0.69 g, 3.4 mmol, 1.1 equiv) in 1,4-dioxane (15 mL) were added $Cs_2CO_3$ (2.00 g, 6.13 mmol, 2 equiv), $Pd(OAc)_2$ (0.07 g, 0.3 mmol, 0.1 equiv) and XantPhos (0.35 g, 0.61 mmol, 0.2 equiv) at room temperature under $N_2$ atmosphere. After stirring for 2 h at 100° C. under a nitrogen atmosphere, the mixture was allowed to cool to room temperature. The resulting mixture was filtered, the filter cake was washed with ethyl acetate (3×50 mL). The filtrate was concentrated under reduced pressure. The residue was purified by reverse-phase flash chromatography on C18 silica gel using a gradient of acetonitrile in water (+0.05% ammonium bicarbonate) to afford tert-butyl (S)-(5-((3-nitro-6-(1H-pyrazol-1-yl)pyridin-2-yl)amino)-3-oxo-2,3-dihydro-1H-inden-1-yl)carbamate (1 g, 72%) as a brown solid. MS (ESI) calcd. for $C_{22}H_{22}N_6O_5$, 450.17 m/z, found 451.15 $[M+H]^+$.

Step 2: Synthesis of tert-butyl (S)-(6-((3-nitro-6-(1H-pyrazol-1-yl)pyridin-2-yl)amino)-2,3-dihydrospiro[indene-1,2'-[1,3]dithiolan]-3-yl)carbamate To a stirred solution of tert-butyl (S)-(5-((3-nitro-6-(1H-pyrazol-1-yl)pyridin-2-yl)amino)-3-oxo-2,3-dihydro-1H-inden-1-yl)carbamate (1 g, 2.2 mmol, 1 equiv) and ethane-1,2-dithiol (0.42 g, 4.4 mmol, 2 equiv) in DCM (30 mL) was added TMSOTf (0.10 g, 0.44 mmol, 0.2 equiv) dropwise at 0° C. The resulting mixture was stirred for 2 h at room temperature. The reaction was quenched with water (100 mL). The resulting mixture was extracted with ethyl acetate (3×200 mL). The combined organic layers were washed with brine (200 mL) and dried over anhydrous $Na_2SO_4$. After filtration, the filtrate was concentrated under reduced pressure. The residue was purified by silica gel column chromatography, eluting with ethyl acetate in petroleum ether (0~50%) to afford tert-butyl (S)-(6-((3-nitro-6-(1H-pyrazol-1-yl)pyridin-2-yl)amino)-2,3-dihydrospiro[indene-1,2'-[1,3]dithiolan]-3-yl)carbamate (900 mg, 77% yield) as a brown solid. MS (ESI) calcd. for $C_{24}H_{26}N_6O_4S_2$, 526.15 m/z, found 527.10 $[M+H]^+$.

Step 3: Synthesis of tert-butyl (S)-(6-(2-(2-aminopyridin-3-yl)-5-(1H-pyrazol-1-yl)-3H-imidazo[4,5-b]pyridin-3-yl)-2,3-dihydrospiro[indene-1,2'-[1,3]dithiolan]-3-yl)carbamate To a stirred solution of tert-butyl (S)-(6-((3-nitro-6-(1H-pyrazol-1-yl)pyridin-2-yl)amino)-2,3-dihydrospiro[indene-1,2'-[1,3]dithiolan]-3-yl)carbamate (900 mg, 1.709 mmol, 1 equiv) and 2-aminonicotinaldehyde (229.58 mg, 1.880 mmol, 1.1 equiv) in DMSO (24 mL) and MeOH (4 mL) was added $Na_2S_2O_4$ (654.57 mg, 3.760 mmol, 2.2 equiv) at room temperature. The resulting mixture was stirred for 18 h at 100° C. The mixture was allowed to cool to room temperature. The mixture was basified to pH 7 with sat. $NaHCO_3$. The resulting mixture was extracted with ethyl acetate (3×200 mL). The combined organic layers were washed with brine (200 mL) and dried over anhydrous $Na_2SO_4$. After filtration, the filtrate was concentrated under reduced pressure. The residue was purified by reverse-phase flash chromatography on C18 silica gel using a gradient of acetonitrile in water (+0.05% ammonium bicarbonate) to afford tert-butyl (S)-(6-(2-(2-aminopyridin-3-yl)-5-(1H-pyrazol-1-yl)-3H-imidazo[4,5-b]pyridin-3-yl)-2,3-dihydrospiro[indene-1,2'-[1,3]dithiolan]-3-yl)carbamate (500 mg, 48.86% yield) as a yellow solid.

MS (ESI) calcd. for $C_{30}H_{30}N_8O_2S_2$, 598.19 m/z, found 599.20 $[M+H]^+$.

Step 4: Synthesis of tert-butyl (S)-(5-(2-(2-aminopyridin-3-yl)-5-(1H-pyrazol-1-yl)-3H-imidazo[4,5-b]pyridin-3-yl)-3,3-difluoro-2,3-dihydro-1H-inden-1-yl)carbamate To a solution of NIS (338.19 mg, 1.503 mmol, 3 equiv) in DCM (5 mL) was added dropwise pyridine hydrofluoride (993.15 mg, 10.020 mmol, 20 equiv) (70% in Pyridine) at −78° C. under $N_2$ atmosphere. The reaction mixture was stirred at −78° C. for 30 mins. Then a solution of tert-butyl (S)-(6-(2-(2-aminopyridin-3-yl)-5-(1H-pyrazol-1-yl)-3H-imidazo[4,5-b]pyridin-3-yl)-2,3-dihydrospiro[indene-1,2'-[1,3]dithiolan]-3-yl)carbamate (300 mg, 0.501 mmol, 1 equiv) in 2 mL DCM was added dropwise and the mixture was stirred for another 10 mins at −78° C. The resulting mixture was stirred for 2 h at room temperature. The reaction was quenched with sat. $NaHCO_3$ (50 mL), and the mixture was extracted with ethyl acetate (2*50 mL). The combined organic extracts were washed with brine (50 mL), dried over anhydrous $Na_2SO_4$, filtered and concentrated under vacuum. The residue was purified by reverse-phase flash chromatography on C18 silica gel using a gradient of acetonitrile in water (+0.05% ammonium bicarbonate) to afford tert-butyl (S)-(5-(2-(2-aminopyridin-3-yl)-5-(1H-pyrazol-1-yl)-3H-imidazo[4,5-b]pyridin-3-yl)-3,3-difluoro-2,3-dihydro-1H-inden-1-yl)carbamate (110 mg, 40.31% yield) as a yellow solid. MS (ESI) calcd. for $C_{28}H_{26}F_2N_8O_2$, 544.21 m/z, found 545.20 $[M+H]^+$.

Step 5: Synthesis of (S)-3-(3-(1-amino-3,3-difluoro-2,3-dihydro-1H-inden-5-yl)-5-(1H-pyrazol-1-yl)-3H-imidazo[4,5-b]pyridin-2-yl)pyridin-2-amine (Intermediate 299-1)

A solution of tert-butyl (S)-(5-(2-(2-aminopyridin-3-yl)-5-(1H-pyrazol-1-yl)-3H-imidazo[4,5-b]pyridin-3-yl)-3,3-difluoro-2,3-dihydro-1H-inden-1-yl)carbamate (50 mg, 0.092 mmol, 1 equiv) in DCM (1.5 mL) was treated with TFA (0.5 mL) at room temperature. The resulting mixture was stirred for 2 h at room temperature. The mixture was concentrated under vacuum and the residue was purified by reverse-phase flash chromatography on C18 silica gel using a gradient of acetonitrile in water (+0.05% ammonium bicarbonate) to afford (S)-3-(3-(1-amino-3,3-difluoro-2,3-dihydro-1H-inden-5-yl)-5-(1H-pyrazol-1-yl)-3H-imidazo[4,5-b]pyridin-2-yl)pyridin-2-amine (Intermediate 299-1) (9.5 mg, 22% yield) as a white solid. MS (ESI) calcd. for $C_{23}H_{18}F_2N_8$, 444.16 m/z, found 445.10 $[M+H]^+$.

Intermediate 312-2: tert-butyl ((1S)-5-bromo-3-fluoro-2,3-dihydro-1H-inden-1-yl)carbamate Intermediate 312-2

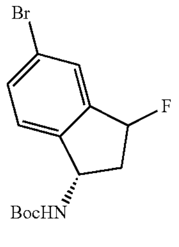

Synthetic Route:

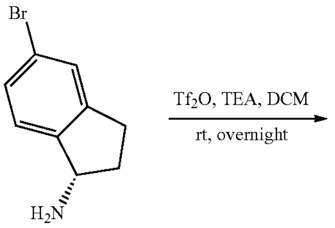

-continued

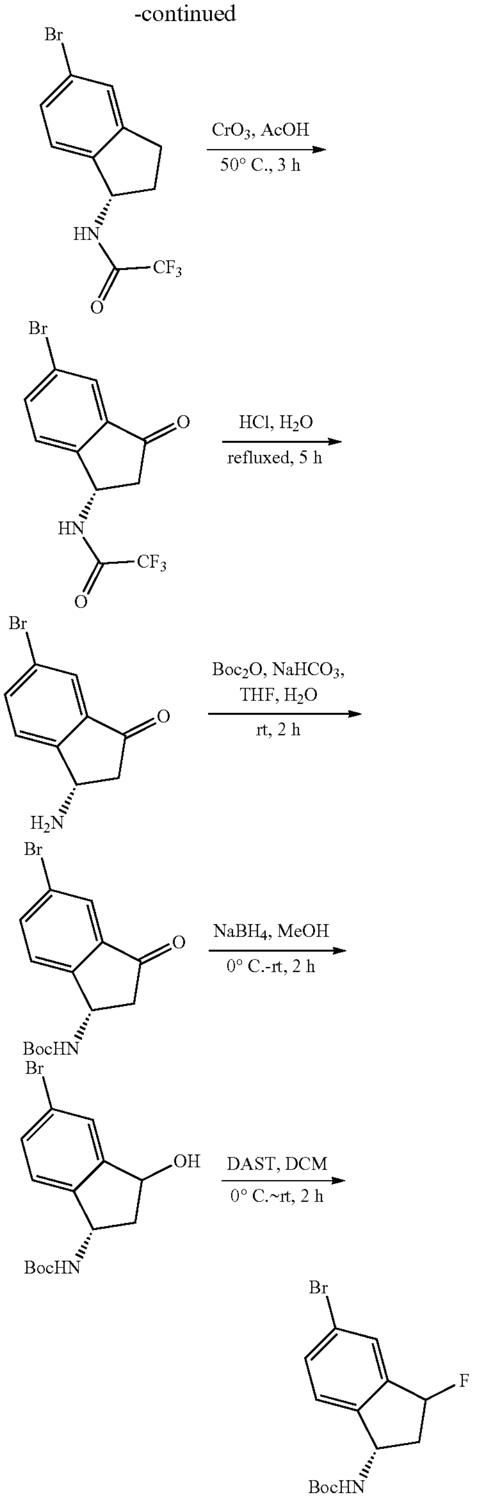

Intermediate 312-2

Step 1: Synthesis of (S)—N-(5-bromo-2,3-dihydro-1H-inden-1-yl)-2,2,2-trifluoroacetamide A solution of (1S)-5-bromo-2,3-dihydro-1H-inden-1-amine (50 g, 236 mmol, 1 equiv) and TEA (55.7 g, 550 mmol, 2 equiv) in DCM (750 mL) was added TFAA (63.25 g, 301.1 mmol, 1.3 equiv) at 0° C. The resulting mixture was stirred overnight at room temperature. The reaction was quenched with $H_2O$ (500 mL) at room temperature. The aqueous layer was extracted with DCM (2×500 mL). The combined organic layers were dried over anhydrous $Na_2SO_4$. After filtration, the filtrate was concentrated under reduced pressure to afford crude (S)—N-(5-bromo-2,3-dihydro-1H-inden-1-yl)-2,2,2-trifluoroacetamide (86 g) as a white solid. MS (ESI) calcd. for $C_{11}H_9BrF_3NO$, 306.98 m/z, found: 306.10 $[M-H]^-$.

Step 2: Synthesis of (S)—N-(5-bromo-3-oxo-2,3-dihydro-1H-inden-1-yl)-2,2,2-trifluoroacetamide A solution of (S)—N-(5-bromo-2,3-dihydro-1H-inden-1-yl)-2,2,2-trifluoroacetamide (50 g, 162 mmol, 1.00 equiv) and $CrO_3$ (48.8 g, 488 mmol, 3.00 equiv) in AcOH (600 mL) was stirred for 2 h at 50° C. under air atmosphere. The mixture was allowed to cool to room temperature. The resulting mixture was concentrated under reduced pressure. The residue was purified by silica gel column chromatography, eluting with ethyl acetate in petroleum ether (0~20%) to afford (S)—N-(5-bromo-3-oxo-2,3-dihydro-1H-inden-1-yl)-2,2,2-trifluoroacetamide (11.5 g, 22%) as a white solid. MS (ESI) calcd. for $C_{11}H_7BrF_3NO_2$, 320.96 m/z, found: 319.90 $[M-H]^-$.

Step 3: Synthesis of (S)-3-amino-6-bromo-2,3-dihydro-1H-inden-1-one

A solution of (S)—N-(5-bromo-3-oxo-2,3-dihydro-1H-inden-1-yl)-2,2,2-trifluoroacetamide (10 g, 31 mmol, 1 equiv) in 6M aqueous HCl (200 mL) was refluxed 5 h. The resulting mixture was concentrated under reduced pressure and the residue was triturated with $Et_2O$ (200 mL). The residue was filtered and dried to afford (S)-3-amino-6-bromo-2,3-dihydro-1H-inden-1-one (7 g, crude quant.) as a white solid. MS (ESI) calcd. for $C_9H_8BrNO$, 224.98 m/z, found 224.05 $[M-H]^-$.

Step 4: Synthesis of tert-butyl (S)-(5-bromo-3-oxo-2,3-dihydro-1H-inden-1-yl)carbamate To a stirred solution of (S)-3-amino-6-bromo-2,3-dihydro-1H-inden-1-one (7 g, 31 mmol, 1 equiv) in THE (60 mL) and $H_2O$ (15 mL) were added $NaHCO_3$ (5.20 g, 61.9 mmol, 2 equiv) and $Boc_2O$ (8.11 g, 37.2 mmol, 1.2 equiv) in portions at 0° C. The resulting mixture was stirred for 2 h at room temperature. The reaction was quenched with water (100 mL). The resulting mixture was extracted with ethyl acetate (3×200 mL). The combined organic layers were washed with brine (200 mL) and dried over anhydrous $Na_2SO_4$. After filtration, the filtrate was concentrated under reduced pressure. The residue was purified by silica gel column chromatography, eluting with ethyl acetate in petroleum ether (0~50%) to afford tert-butyl (S)-(5-bromo-3-oxo-2,3-dihydro-1H-inden-1-yl)carbamate (7 g, 69% yield) as an off-white solid. MS (ESI) calcd. for $C_{1-4}H_{16}BrNO_3$, 325.03 m/z, found 324.10 $[M-H]^-$.

Step 5: Synthesis of tert-butyl ((1S)-5-bromo-3-hydroxy-2,3-dihydro-1H-inden-1-yl)carbamate To a stirred solution of tert-butyl (S)-(5-bromo-3-oxo-2,3-dihydro-1H-inden-1-yl)carbamate (7 g, 21 mmol, 1 equiv) in MeOH (100 mL) was added $NaBH_4$ (1.62 g, 42.9 mmol, 2 equiv) in portions at 0° C. The resulting mixture was stirred for 2 h at room temperature. The reaction was quenched by the addition of water (200 mL) at room temperature. The resulting mixture was extracted with ethyl acetate (3×300 mL). The combined organic layers were washed with brine (200 mL) and dried over anhydrous $Na_2SO_4$. After filtration, the filtrate was concentrated under reduced pressure. The residue was purified by silica gel column chromatography, eluting with ethyl acetate in petroleum ether (0~50%) to afford tert-butyl ((1S)-5-bromo-3-hydroxy-2,3-dihydro-1H-inden-1-yl)carbamate (5 g, 71%) as a white solid. MS (ESI) calcd. for $C_{14}H_{18}BrNO_3$, 327.05 m/z, found 326.10 $[M-H]^-$.

Step 6: Synthesis of tert-butyl ((1S)-5-bromo-3-fluoro-2,3-dihydro-1H-inden-1-yl)carbamate (Intermediate 312-2)

To a stirred solution of tert-butyl ((1S)-5-bromo-3-hydroxy-2,3-dihydro-1H-inden-1-yl)carbamate (5 g, 15 mmol, 1 equiv) in DCM (100 mL) was added DAST (4.91 g, 30.5 mmol, 2 equiv) in portions at 0° C. The resulting mixture was stirred for 2 h at room temperature. The reaction was quenched by the addition of saturated aqueous sodium bicarbonate (200 mL) at room temperature. The resulting mixture was extracted with ethyl acetate (3×300 mL). The combined organic layers were washed with brine (300 mL) and dried over anhydrous $Na_2SO_4$. After filtration, the filtrate was concentrated under reduced pressure. The residue was purified by silica gel column chromatography, eluted with ethyl acetate in petroleum ether (0~30%) to afford tert-butyl ((1S)-5-bromo-3-fluoro-2,3-dihydro-1H-inden-1-yl)carbamate (Intermediate 312-2) (4 g, 80% yield) as a white solid. MS (ESI) calcd. for $C_{1-4}H_{17}BrFNO_2$, 329.04 m/z, found 310.15 [M-F]*.

Intermediate 329-1: (S)—N-(5-(2-(2-aminopyridin-3-yl)-7-bromo-5-(3-fluoro-1H-pyrazol-1-yl)-3H-imidazo[4,5-b]pyridin-3-yl)-2,3-dihydro-1H-inden-1-yl)-6-(difluoromethyl)nicotinamide Intermediate 329-1

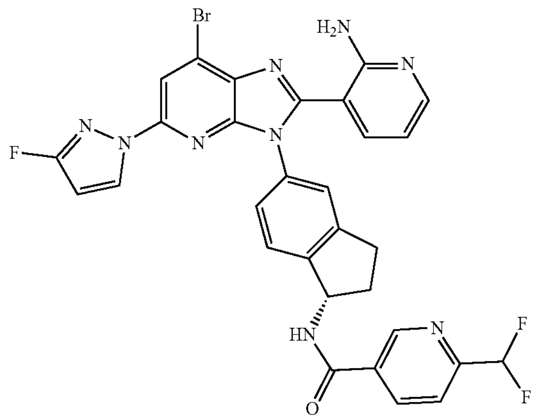

Intermediate 329-1 was prepared in a manner analogous to Intermediate 122-2 (via Intermediate 122-1) using 3-fluoropyrazole in place of pyrazole. MS (ESI) calcd. for $C_{30}H_{21}BrF_3N_9O$, 659.10 m/z, found 660.08 $[M+H]^+$.

Intermediate 341-1: (S)—N-(5-(2-(2-aminopyridin-3-yl)-5-ethynyl-3H-imidazo[4,5-b]pyridin-3-yl)-2,3-dihydro-1H-inden-1-yl)-6-methylnicotinamide Intermediate 341-1

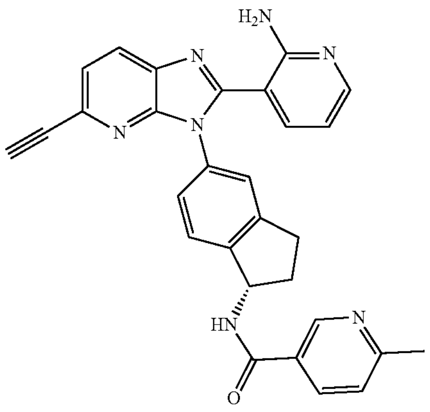

Synthetic Route:

Step 1: Synthesis of (S)—N-(5-(2-(2-aminopyridin-3-yl)-5-((trimethylsilyl)ethynyl)-3H-imidazo[4,5-b]pyridin-3-yl)-2,3-dihydro-1H-inden-1-yl)-6-methylnicotinamide To a stirred solution of (S)—N-(5-(2-(2-aminopyridin-3-yl)-5-bromo-3H-imidazo[4,5-b]pyridin-3-yl)-2,3-dihydro-1H-inden-1-yl)-6-methylnicotinamide (Intermediate 265-1) (300 mg, 0.431 mmol, 1 equiv), CuI (16.41 mg, 0.086 mmol, 0.2 equiv), $Pd(PPh_3)_4$ (99.57 mg, 0.086 mmol, 0.2 equiv) and DIEA (167.04 mg, 1.293 mmol, 3 equiv) in DMF (2 mL) was added trimethylsilylacetylene (211.58 mg, 2.155 mmol, 5 equiv) under $N_2$ atmosphere. The reaction mixture was stirred at 90° C. for 2 h. The crude product was purified by reverse-phase flash chromatography on C18 silica gel using a gradient of acetonitrile in water (+0.05% ammonium bicarbonate) to afford (S)—N-(5-(2-(2-aminopyridin-3-yl)-5-((trimethylsilyl)ethynyl)-3H-imidazo[4,5-b]pyridin-3-yl)-2,3-dihydro-1H-inden-1-yl)-6-methylnicotinamide (147 mg, 11.37% yield) as an off-white solid. MS (ESI) calcd. for $C_{32}H_{31}N_7OSi$: 557.20 m/z, found: 558.30 $[M+H]^+$.

Step 2: Synthesis of (S)—N-(5-(2-(2-aminopyridin-3-yl)-5-ethynyl-3H-imidazo[4,5-b]pyridin-3-yl)-2,3-dihydro-1H-inden-1-yl)-6-methylnicotinamide (Intermediate 341-1)

To a solution of N-[(1S)-5-[2-(2-aminopyridin-3-yl)-5-[2-(trimethylsilyl)ethynyl]imidazo[4,5-b]pyridin-3-yl]-2,3-dihydro-1H-inden-1-yl]-6-methylpyridine-3-carboxamide (200 mg, 0.359 mmol, 1 equiv) in DMF (2 mL) was added triethylamine trihydrofluoride (173.43 mg, 1.077 mmol, 3 equiv) at rt. The resulting mixture was stirred for 2 h at rt. The crude product was purified by reverse-phase flash chromatography on C18 silica gel using a gradient of acetonitrile in water (+0.05% ammonium bicarbonate) to afford (S)—N-(5-(2-(2-aminopyridin-3-yl)-5-ethynyl-3H-imidazo[4,5-b]pyridin-3-yl)-2,3-dihydro-1H-inden-1-yl)-6-methylnicotinamide (Intermediate 341-1) (135 mg, 77.52% yield) as yellow oil. MS (ESI) calcd. for $C_{29}H_{23}N_7O$: 485.20 m/z, found: 486.30 $[M+H]^+$.

Example 495: (S*)—N—((S)-5-(2-(2-aminopyridin-3-yl)-5-(1H-pyrazol-1-yl)-3H-imidazo[4,5-b]pyridin-3-yl)-2,3-dihydro-1H-inden-1-yl)-6,7-dihydro-5H-cyclopenta[c]pyridin-7-amine and Example 496: (R*)—N—((S)-5-(2-(2-aminopyridin-3-yl)-5-(1H-pyrazol-1-yl)-3H-imidazo[4,5-b]pyridin-3-yl)-2,3-dihydro-1H-inden-1-yl)-6,7-dihydro-5H-cyclopenta[c]pyridin-7-amine Example 495

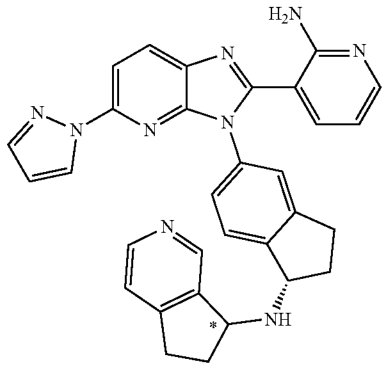

Example 496

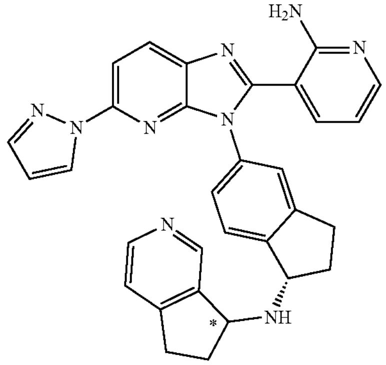

Synthetic Route:

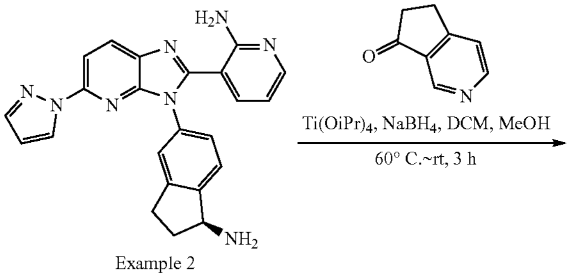

Example 2

-continued

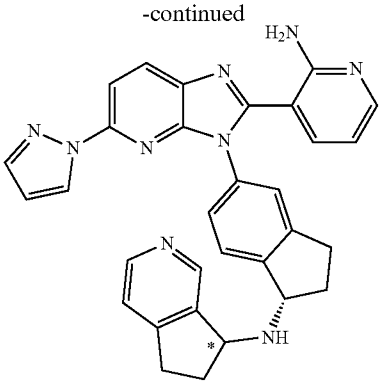

Example 495

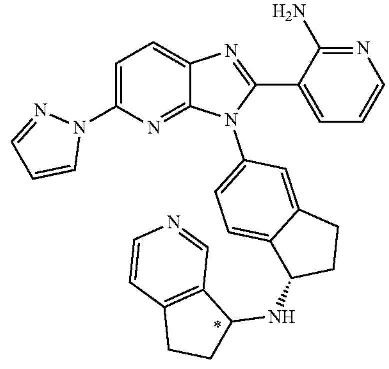

Example 496

Step 1: Synthesis of N—((S)-5-(2-(2-aminopyridin-3-yl)-5-(1H-pyrazol-1-yl)-3H-imidazo[4,5-b]pyridin-3-yl)-2,3-dihydro-1H-inden-1-yl)-6,7-dihydro-5H-cyclopenta[c]pyridin-7-amine A solution of (S)-3-(3-(1-amino-2,3-dihydro-1H-inden-5-yl)-5-(1H-pyrazol-1-yl)-3H-imidazo[4,5-b]pyridin-2-yl) pyridin-2-amine (Example 2) (500 mg, 1.224 mmol, 1 equiv), 5H,6H-cyclopenta[c]pyridin-7-one (325.9 mg, 2.448 mmol, 2 equiv) and tetrakis(propan-2-yloxy)titanium (1739.5 mg, 6.120 mmol, 5 equiv) in DCM (10 mL) and MeOH (2 mL) was stirred at 60° C. for 1 h. Then to the mixture was added $NaBH_4$ (92.6 mg, 2.448 mmol, 2 equiv) at 0° C. The resulting mixture was stirred at room temperature for 2 h. The reaction was quenched with water (20 ml) at 0° C. The resulting mixture was extracted with DCM (3×50 ml). The combined organic layers were dried over anhydrous $Na_2SO_4$. After filtration, the filtrate was concentrated under reduced pressure. The residue was purified by reverse-phase flash chromatography on C18 silica gel using a gradient of acetonitrile in water (+0.05% ammonium bicarbonate) to afford crude product. The diastereomers were separated by Chiral-HPLC on a CHIRALPAK IA column using a mixture of [Hex/DCM (3:1) (+0.5% 2M $NH_3$-MeOH)] and IPA to afford Example 496 (39.0 mg, 6.06% yield) as an off-white solid and Example 495 (59.7 mg, 9.28% yield) as an off-white solid. * Note that the stereochemistry of the newly formed stereocenter was assumed.

Example 495: MS (ESI) calcd. for $C_{31}H_{27}N_9$, 525.24 m/z, found 526.30 $[M+H]^+$. $^1H$ NMR (400 MHz, DMSO-$d_6$) δ (ppm): 8.55-8.68 (m, 1H), 8.30-8.40 (m, 3H), 7.90-8.10 (m, 2H), 7.80-7.90 (m, 1H), 7.50-7.60 (m, 1H), 7.30-7.40 (m, 1H), 7.26-7.30 (m, 1H), 7.20-7.26 (m, 2H), 6.50-6.60 (m, 1H), 6.40-6.50 (m, 1H), 4.41-4.50 (m, 1H), 4.30-4.41 (m, 1H), 2.90-3.10 (m, 2H), 2.72-2.90 (m, 2H), 2.40-2.52 (m, 2H), 1.80-2.00 (m, 2H).

Example 496: MS (ESI) calcd. for $C_{31}H_{27}N_9$, 525.24 m/z, found 526.30 $[M+H]^+$. $^1H$ NMR (400 MHz, DMSO-$d_6$) δ (ppm): 8.50-8.68 (m, 1H), 8.30-8.40 (m, 3H), 8.00-8.10 (m, 1H), 7.90-8.00 (m, 1H), 7.80-7.90 (m, 1H), 7.50-7.60 (m, 1H), 7.30-7.40 (m, 2H), 7.20-7.28 (m, 2H), 6.50-6.60 (m, 1H), 6.40-6.50 (m, 1H), 4.30-4.50 (m, 2H), 2.90-3.10 (m, 2H), 2.72-2.90 (m, 2H), 2.45-2.50 (m, 1H), 2.30-2.45 (m, 1H), 1.75-1.95 (m, 2H).

The following compounds were prepared analogous to the synthetic preparation in Example Compounds 495 and 496.

TABLE 19C

Characterization data of compounds prepared analogously to Compound 495 and Compound 496.

| Cpd ID | Characterization Data |
|---|---|
| 498 | Observed mass (ESI): 541.15 [M + H]+. 1H NMR (300 MHz, DMSO-d6) δ (ppm): 8.31-8.38 (m, 2H), 8.16-8.20 (m, 1H), 7.99-8.02 (m, 1H), 7.95-7.98 (m, 1H), 7.78-7.82 (m, 1H), 7.57-7.62 (m, 1H), 7.38-7.40 (m, 1H), 7.19-7.30 (m, 3H), 6.84-6.96 (m, 2H), 6.64-6.68 (m, 1H), 6.54-6.62 (m, 1H), 6.50-6.53 (m, 1H), 6.38-6.46 (m, 1H), 4.50-4.61 (m, 1H), 4.35-4.47 (m, 1H), 2.96-3.06 (m, 1H), 2.79-2.92 (m, 2H), 2.65-2.76 (m, 1H), 2.48-2.53 (m, 1H), 2.38-2.46 (m, 1H), 1.91-2.05 (m, 2H). |
| 499 | Observed mass (ESI): 541.2 [M + H]+. 1H NMR (300 MHz, DMSO-d6) δ (ppm): 8.31-8.39 (m, 2H), 8.17-8.22 (m, 1H), 7.91-8.03 (m, 2H), 7.78-7.82 (m, 1H), 7.53-7.59 (m, 1H), 7.34-7.39 (m, 1H), 7.17-7.30 (m, 3H), 6.91-7.01 (m, 2H), 6.65-6.68 (m, 1H), 6.55-6.62 (m, 1H), 6.50-6.53 (m, 1H), 6.39-6.46 (m, 1H), 4.42-4.50 (m, 1H), 4.30-4.40 (m, 1H), 2.92-3.02 (m, 1H), 2.73-2.91 (m, 2H), 2.61-2.71 (m, 1H), 2.50-2.53 (m, 1H), 2.30-2.41 (m, 1H), 1.82-1.99 (m, 2H) |

Intermediate 522-1: N-(5-(2-(2-aminopyridin-3-yl)-5-(1H-pyrazol-1-yl)-3H-imidazo[4,5-b]pyridin-3-yl)-2-fluoro-2,3-dihydro-1H-inden-1-yl)piperazin-1-amine Intermediate 522-1

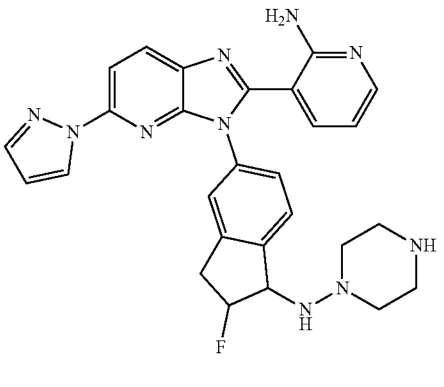

Synthetic Route:

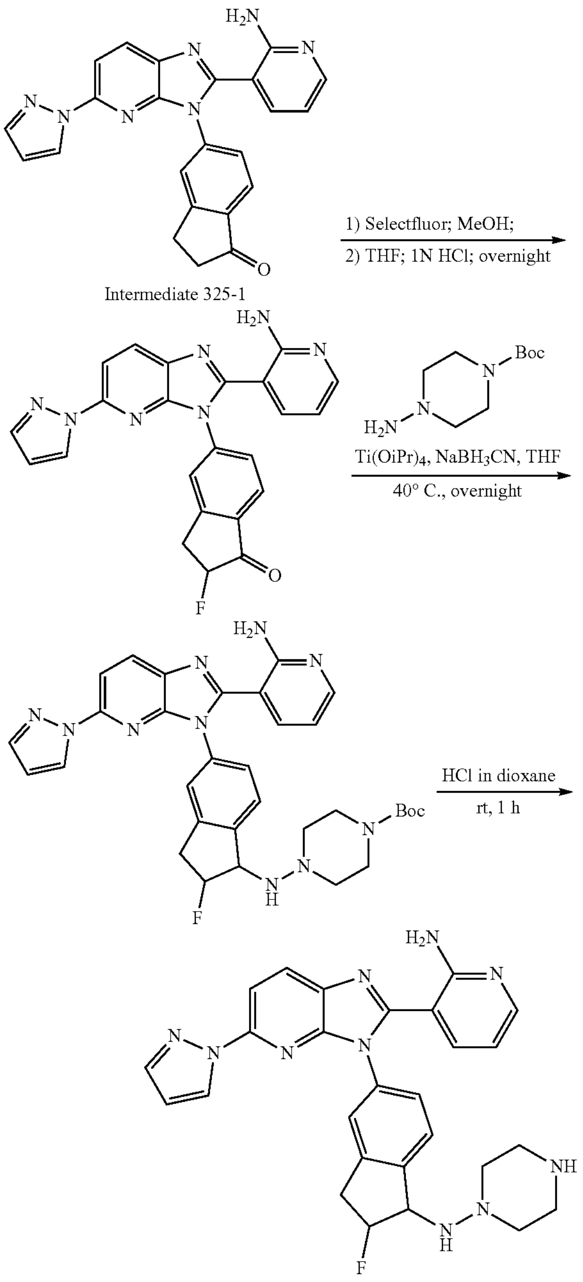

Intermediate 325-1

Intermediate 522-1

Step 1: Synthesis of 5-[2-(2-aminopyridin-3-yl)-5-(pyrazol-1-yl)imidazo[4,5-b]pyridin-3-yl]-2-fluoro-2,3-dihydroinden-1-one A mixture of 5-[2-(2-aminopyridin-3-yl)-5-(pyrazol-1-yl) imidazo[4,5-b]pyridin-3-yl]-2,3-dihydroinden-1-one (Intermediate 325-1) (500 mg, 1.227 mmol, 1 equiv) and Select-Fluor (1 g, 2.823 mmol, 2.30 equiv) in MeOH was stirred for 2 hours under reflux. The reaction mixture was filtered through Celite and the filtrate was concentrated under reduced pressure. The resulting residue was dissolved in tetrahydrofuran (30 mL), and 1 N hydrochloric acid (30 mL) was added. The mixture was stirred at room temperature for 3 hours. To the reaction mixture, a 2 N aqueous sodium hydroxide solution (20 mL) was added, and the mixture was diluted with saturated aqueous sodium bicarbonate then extracted with ethyl acetate. The organic layer was washed with brine and dried over anhydrous magnesium sulfate, filtered and concentrated under reduced pressure to afford 5-[2-(2-aminopyridin-3-yl)-5-(pyrazol-1-yl)imidazo[4,5-b] pyridin-3-yl]-2-fluoro-2,3-dihydroinden-1-one as a white solid. MS (ESI) calcd. for $C_{23}H_{16}FN_7O$, 425.14 m/z, found: 426.10 $[M+H]^+$.

Step 2: Synthesis of tert-butyl 4-({5-[2-(2-amino-pyridin-3-yl)-5-(pyrazol-1-yl)imidazo[4,5-b]pyridin-3-yl]-2-fluoro-2,3-dihydro-1H-inden-1-yl}amino) piperazine-1-carboxylate To a solution of 5-[2-(2-aminopyridin-3-yl)-5-(pyrazol-1-yl)imidazo[4,5-b]pyridin-3-yl]-2-fluoro-2,3-dihydroinden-1-one (450 mg, 1.058 mmol, 1 equiv) in THE (20 mL) was added tetrakis(propan-2-yloxy)titanium (600 mg, 2.111 mmol, 2.00 equiv) and tert-butyl 4-aminopiperazine-1-carboxylate (320 mg, 1.590 mmol, 1.50 equiv). The resulting mixture was stirred at 40° C. for 4 h then cooled to 0° C. $NaBH_3CN$ (300 mg, 4.774 mmol, 4.51 equiv) was added and the resulting mixture was stirred at 40° C. overnight. The reaction was quenched with $H_2O$ (2 mL). The resulting mixture was concentrated under reduced pressure. The residue was purified by reverse phase column chromatography on C18 silica gel (0-41% ACN/0.05% TFA in water) to afford tert-butyl 4-({5-[2-(2-aminopyridin-3-yl)-5-(pyrazol-1-yl)imidazo[4,5-b]pyridin-3-yl]-2-fluoro-2,3-dihydro-1H-inden-1-yl}amino)piperazine-1-carboxylate (70 mg, 87% purity) as a yellow solid. MS (ESI) calcd. for $C_{32}H_{35}FN_{10}O_2$: 610.29 m/z, found: 611.30 $[M+H]^+$.

Step 3: Synthesis of N-{5-[2-(2-aminopyridin-3-yl)-5-(pyrazol-1-yl)imidazo[4,5-b]pyridin-3-yl]-2-fluoro-2,3-dihydro-1H-inden-1-yl}piperazin-1-amine (Intermediate 522-1)

A solution of tert-butyl 4-({5-[2-(2-aminopyridin-3-yl)-5-(pyrazol-1-yl)imidazo[4,5-b]pyridin-3-yl]-2-fluoro-2,3-dihydro-1H-inden-1-yl}amino)piperazine-1-carboxylate (70 mg, 0.115 mmol, 1 equiv) in 4N HCl in 1,4-dioxane (3 mL) was stirred at r.t for 1 h. The residue was adjusted to pH 8 with saturated $NaHCO_3$ and extracted with MeOH:DCM (1:10). The combined organic layers were washed with water and brine then dried over $Na_2SO_4$. After filtration, the filtrate was concentrated to afford N-{5-[2-(2-aminopyridin-3-yl)-5-(pyrazol-1-yl)imidazo[4,5-b]pyridin-3-yl]-2-fluoro-2,3-dihydro-1H-inden-1-yl}piperazin-1-amine (Intermediate 522-1) (50 mg, 90% purity) as a yellow solid. MS (ESI) calcd. for $C_{27}H_{27}FN_{10}$: 510.24 m/z, found: 511.30 $[M+H]^+$.

Example 584: (S)-4-(4-((5-(2-(2-aminopyridin-3-yl)-5-(1H-pyrazol-1-yl)-3H-imidazo[4,5-b]pyridin-3-yl)-2,3-dihydro-1H-inden-1-yl)amino)piperidin-1-yl)-6-methylpyrimidine-2-carbonitrile

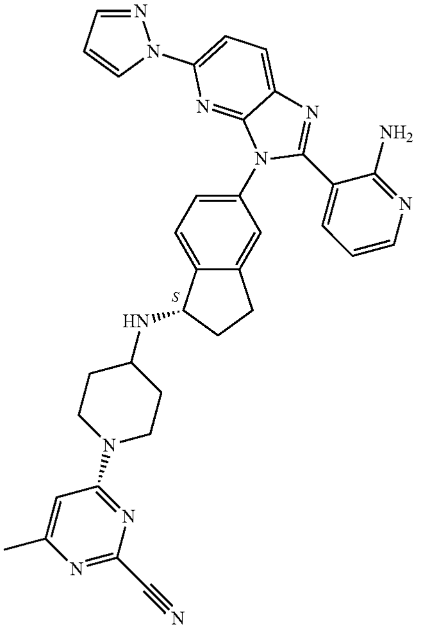

Synthetic Route:

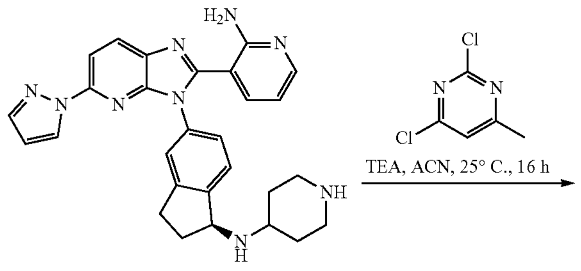

Intermediate 275-1

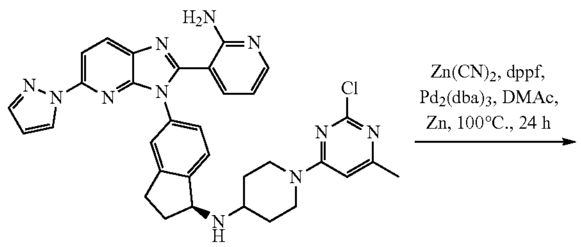

-continued

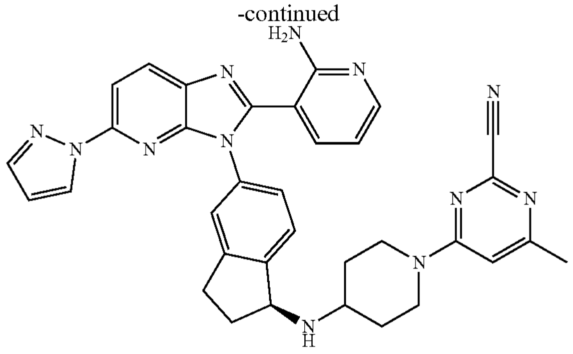

Example 584

Step 1: Synthesis of 3-{3-[(1S)-1-{[1-(2-chloro-6-methylpyrimidin-4-yl)piperidin-4-yl]amino}-2,3-dihydro-1H-inden-5-yl]-5-(pyrazol-1-yl)imidazo[4,5-b]pyridin-2-yl}pyridin-2-amine To a stirred solution of 3-{3-[(1S)-1-(piperidin-4-ylamino)-2,3-dihydro-1H-inden-5-yl]-5-(pyrazol-1-yl)imidazo[4,5-b]pyridin-2-yl}pyridin-2-amine (Intermediate 275-1) (510 mg, 1.037 mmol, 1 equiv) and 2,4-dichloro-6-methylpyrimidine (338.20 mg, 2.074 mmol, 2 equiv) in MeCN (30 mL) was added $Et_3N$ (839.84 mg, 8.296 mmol, 8 equiv) at 25° C. The resulting mixture was stirred at 25° C. for 16 h. The residue was purified by silica gel column chromatography, eluting with $CH_2Cl_2$/MeOH (10:1) to afford 3-{3-[(1S)-1-{[1-(2-chloro-6-methylpyrimidin-4-yl)piperidin-4-yl]amino}-2,3-dihydro-1H-inden-5-yl]-5-(pyrazol-1-yl)imidazo[4,5-b]pyridin-2-yl}pyridin-2-amine (306 mg, 47.72% yield, 98% purity) as a yellow solid. Observed mass (ESI): 618.35 $[M+H]^+$.

Step 2: Synthesis of 4-(4-{[(1S)-5-[2-(2-aminopyridin-3-yl)-5-(pyrazol-1-yl)imidazo[4,5-b]pyridin-3-yl]-2,3-dihydro-1H-inden-1-yl]amino}piperidin-1-yl)-6-methylpyrimidine-2-carbonitrile (TER-6308)

To a stirred solution of 3-{3-[(1S)-1-{[1-(2-chloro-6-methylpyrimidin-4-yl)piperidin-4-yl]amino}-2,3-dihydro-1H-inden-5-yl]-5-(pyrazol-1-yl)imidazo[4,5-b]pyridin-2-yl}pyridin-2-amine (260 mg, 0.421 mmol, 1 equiv) and $Zn(CN)_2$ (74.08 mg, 0.631 mmol, 1.5 equiv) in N,N-dimethylacetamide (5 mL) were added Dppf (46.64 mg, 0.084 mmol, 0.2 equiv) and $Pd_2(dba)_3$ (77.03 mg, 0.084 mmol, 0.2 equiv) at 25° C. To the above mixture was added Zn (13.75 mg, 0.210 mmol, 0.5 equiv) at 25° C. The resulting mixture was stirred at 100° C. for 24 h under $N_2$ atmosphere. The residue was purified by Prep-TLC ($CH_2Cl_2$/MeOH 10:1) to afford crude product.

The crude product (200 mg) was purified by Prep-HPLC on a XBridge Prep OBD C18 Column using a gradient of acetonitrile in water (+10 mmol/L ammonium bicarbonate) to afford 4-(4-{[(1S)-5-[2-(2-aminopyridin-3-yl)-5-(pyrazol-1-yl)imidazo[4,5-b]pyridin-3-yl]-2,3-dihydro-1H-inden-1-yl]amino}piperidin-1-yl)-6-methylpyrimidine-2-carbonitrile (Example 584) (96.8 mg, 37.81% yield, 99.3% purity) as a white solid. Observed mass (ESI): 609.35 $[M+H]^+$. $^1H$ NMR (400 MHz, DMSO-d6) δ (ppm): 8.32-8.39 (m, 2H), 7.98-8.04 (m, 1H), 7.95 (d, J=8.6 Hz, 1H), 7.81 (s, 1H), 7.48 (d, J=8.0 Hz, 1H), 7.34 (s, 1H), 7.20-7.29 (m, 2H), 7.04 (s, 1H), 6.94 (s, 2H), 6.53-6.57 (m, 1H), 6.39-6.47 (m, 1H), 4.11-4.41 (m, 3H), 3.12-3.23 (m, 2H), 2.92-3.03 (m, 2H), 2.71-2.85 (m, 1H), 2.44-2.47 (m, 1H), 2.30 (s, 3H), 2.08-2.17 (m, 1H), 1.98-2.06 (m, 1H), 1.88-1.96 (m, 1H), 1.72-1.85 (m, 1H), 1.21-1.39 (m, 2H).

TABLE 19D

Characterization data of Compounds 594, 600, and 601.

| Cpd ID | Characterization Data |
|---|---|
| 594 | Observed mass (ESI): 601.2 [M + H]+. 1H NMR (400 MHz, DMSO-d6) δ 9.41 (d, J = 8.3 Hz, 1H), 8.64-8.59 (m, 1H), 8.42 (d, J = 8.6 Hz, 1H), 8.04 (s, 1H), 7.96-7.91 (m, 1H), 7.81 (d, J = 0.9 Hz, 1H), 7.55-7.40 (m, 4H), 7.39-7.31 (m, 2H), 7.24 (s, 1H), 6.65-6.54 (m, 1H), 5.64-5.55 (m, 1H), 3.98 (s, 3H), 3.05-3.00 (m, 1H), 2.97-2.87 (m, 1H), 2.78-2.75 (m, 1H), 2.62-2.56 (m, 1H), 2.11-2.00 (m, 1H). |
| 600 | Observed mass (ESI): 582.35 [M + H]+. 1H NMR (300 MHz, DMSO-d6) δ (ppm): 8.33-8.41 (m, 2H), 8.02-8.06 (m, 1H), 7.98-8.01 (m, 1H), 7.82-7.85 (m, 1H), 7.51-7.59 (m, 1H), 7.39-7.42 (m, 1H), 7.32-7.37 (m, 1H), 7.20-7.29 (m, 2H), 6.55-6.59 (m, 1H), 6.51-6.57 (m, 1H), 4.59-4.65 (m, 1H), 4.30-4.41 (m, 1H), 2.97-3.07 (m, 2H), 2.74-2.90 (m, 3H), 2.48-2.51 (m, 1H), 2.30-2.38 (m, 1H), 1.89-1.99 (m, 1H). |
| 601 | Observed mass (ESI): 582.35 [M + H]+. 1H NMR (300 MHz, DMSO-d6) δ (ppm): 8.33-8.41 (m, 2H), 7.98-8.06 (m, 2H), 7.82-7.85 (m, 1H), 7.51-7.59 (m, 1H), 7.05-7.40 (m, 4H), 6.58-6.61 (m, 1H), 6.46-6.51 (m, 1H), 4.59-4.65 (m, 1H), 4.30-4.38 (m, 1H), 2.98-3.09 (m, 2H), 2.74-2.90 (m, 3H), 2.48-2.51 (m, 1H), 2.30-2.38 (m, 1H), 1.89-1.99 (m, 1H). |

Example 102: AKT1 Inhibition Data

Antiproliferative Effects in LAPC4 Cells.

LAPC4 prostate cancer cells (Klein, K. A. et al. Nat Med 1997, 3, 402-408), which express the AKT1 E17K allele, were grown in IMDM media (Hyclone) supplemented with 12% FBS+1% P/S. To assess compound effects on growth, 1,000 cells/well were seeded in 384 well assay plates, incubated with compound dilutions dissolved in DMSO. After 72 h, intracellular ATP content was assessed with CellTiter Glo reagent (Promega) according to the manufacturer's instructions. $IC_{50}$ values were calculated by fitting luminescence values to a log(inhibitor) vs. response Hill equation.

Determining live cell AKT1 E17K, AKT1 WT, and AKT2 target engagement by NanoBRET competitive probe displacement. Live cell target engagement assays were performed as described (Vasta, J. D. et al. *Cell Chem Biol* 2018, 25(11), 206-214). Briefly, HEK293 cells were transfected with plasmids encoding kinase-NanoLuciferase fusion proteins overnight. Cells were then treated with serial dilutions of compound and an ~$EC_{50}$ concentration of fluorescently-tagged ATP-competitive tracer (Promega). After incubation for 2 h at 37° C., luciferase substrate and extracellular luciferase inhibitor were added to all wells, and luminescent intensity at 460 nm and 600 nm were measured on a multimode plate-reader. The ratio of $E_{600}/E_{460}$ was calculated to give the tracer engagement signal (BRET). $IC_{50}$ values were calculated by fitting BRET values to a log (inhibitor) vs. response Hill equation.

TABLE 20 provides $IC_{50}$ values for selected compounds of the present disclosure.

| Cpd ID | AKT1 WT IC50 (nM) | AKT1 E17K IC50 (nM) | AKT2 IC50 (nM) | LAPC4 proliferation IC50 (nM) |
|---|---|---|---|---|
| 1 | >737 | >1.00E+03 | 4310 | |
| 2 | 61.9 | >1.00E+03 | 858 | 8980 |
| 3 | 7.21 | 120 | 132 | 1710 |
| 4 | 19.7 | 172 | 295 | 1770 |
| 5 | 129 | >1.00E+03 | 1410 | 9300 |
| 6 | 10.8 | 179 | 307 | 1660 |
| 7 | 7.29 | 320 | 118 | 2600 |
| 8 | 2.97 | 10.8 | 55.8 | 523 |
| 9 | >1.00E+03 | >1.00E+03 | 8890 | |
| 10 | 390 | >1.00E+03 | >10.0E+03 | >10.0E+03 |
| 11 | >1.00E+03 | >1.00E+03 | >10.0E+03 | |
| 12 | 7.56 | 10.5 | 38.1 | 740 |
| 13 | 49.4 | 329 | 1270 | 3480 |
| 14 | 14.5 | 22.9 | 264 | 1290 |
| 15 | 215 | >1.00E+03 | 4030 | >10.0E+03 |
| 16 | 2.41 | 10.2 | 66.5 | 560 |
| 17 | 5.78 | 41.2 | 90.6 | 1020 |
| 18 | 10.5 | 44.4 | 55.5 | 733 |
| 19 | 43.5 | 167 | 2120 | 8030 |
| 20 | 126 | 137 | 713 | 8490 |
| 21 | 4.46 | 20.9 | 30.2 | 1050 |
| 22 | 11.2 | 31.9 | 67.6 | 1260 |
| 23 | 4.61 | 390 | 46.6 | 1200 |
| 24 | 55.1 | 232 | 846 | 6360 |
| 25 | 2.11 | 7.43 | 9.84 | 576 |
| 26 | 6.46 | 26.8 | 69.6 | 1060 |
| 27 | >1.00E+03 | | >10.0E+03 | |
| 28 | 2.53 | 12.1 | 6.6 | 225 |
| 29 | 15.9 | 78.6 | 153 | 3650 |
| 30 | 10.6 | 51.1 | 127 | 721 |
| 31 | 33.9 | 366 | 470 | 7880 |
| 32 | 11 | 49 | 123 | 914 |
| 33 | 19.6 | >1.00E+03 | 321 | 3750 |
| 34 | 6.27 | 24.1 | 64 | 555 |
| 35 | 14.2 | 143 | 98.6 | 1750 |
| 36 | 58.6 | 164 | 1250 | 3460 |
| 37 | 175 | >1.00E+03 | 7720 | >10.0E+03 |
| 38 | 4.07 | 25.6 | 19 | 585 |
| 39 | 49.2 | 211 | 754 | 5190 |
| 40 | 9.21 | 36 | 179 | 1770 |
| 41 | 6.36 | 30.1 | 57.4 | 1170 |
| 42 | 2.84 | 14.4 | 40.7 | 631 |
| 43 | 14.1 | 44.2 | 139 | 1160 |
| 44 | 9.55 | 74.1 | 141 | 1400 |
| 45 | 17.4 | 170 | 139 | 1340 |
| 46 | 6.94 | 15 | 17 | 331 |
| 47 | >1.00E+03 | | >10.0E+03 | |
| 48 | 155 | >1.00E+03 | 2850 | >10.0E+03 |
| 49 | 199 | >1.00E+03 | 2840 | >10.0E+03 |
| 50 | 279 | >1.00E+03 | 3740 | >10.0E+03 |
| 51 | 137 | >1.00E+03 | 4560 | >10.0E+03 |
| 52 | 11.6 | 357 | 128 | 915 |
| 53 | 18.1 | 142 | 118 | 1120 |
| 54 | 12 | 17.4 | 10.7 | 207 |
| 55 | 16.2 | 107 | 49.2 | 1510 |
| 56 | 12.2 | 143 | 43.3 | 1630 |
| 57 | 23.4 | 192 | 52.8 | 1320 |
| 58 | 30.7 | 157 | 2040 | 1900 |
| 59 | 48.8 | 261 | 3430 | 3620 |
| 60 | 2.5 | 62.1 | 31.5 | 741 |
| 61 | 4.75 | 72.6 | 49.7 | 921 |
| 62 | 4.97 | 64 | 59.5 | 692 |
| 63 | 2.57 | 73.9 | 12.6 | 970 |
| 64 | 4.63 | 159 | 183 | 2620 |
| 65 | 19.4 | 292 | 1070 | 925 |
| 66 | 8.95 | | 15 | |
| 67 | 15 | 229 | 636 | 1140 |
| 68 | 5.29 | | 15.2 | |
| 69 | 10.9 | | 71.6 | |
| 70 | 49.4 | | 576 | |
| 71 | 4.63 | | 69.7 | |
| 72 | 7.95 | | 28.1 | |
| 73 | 9.03 | | 49.8 | |

TABLE 20-continued provides $IC_{50}$ values for selected compounds of the present disclosure.

| Cpd ID | AKT1 WT IC50 (nM) | AKT1 E17K IC50 (nM) | AKT2 IC50 (nM) | LAPC4 proliferation IC50 (nM) |
|---|---|---|---|---|
| 74 | 4.94 | | 34.8 | |
| 75 | 5.99 | | 73.6 | |
| 76 | 6.86 | | 39.4 | |
| 77 | 13.6 | | 50.1 | |
| 78 | 106 | | 1910 | |
| 79 | 19.5 | | 540 | |
| 80 | 8.65 | | 28.4 | |
| 81 | 121 | | 2900 | |
| 82 | 65.8 | | 2140 | |
| 83 | 139 | | 867 | |
| 84 | 113 | | 1960 | |
| 85 | 36.3 | | 169 | |
| 86 | 46.8 | | 427 | |
| 87 | 149 | | 1900 | |
| 88 | 155 | | 1810 | |
| 89 | 459 | | >10.0E+03 | |
| 90 | 228 | | 5850 | |
| 91 | 198 | | 763 | |
| 92 | 42.8 | | 1140 | |
| 93 | 38.8 | | 1790 | |
| 94 | 7.33 | | 18.8 | |
| 95 | 6.98 | | 9.41 | |
| 96 | 18.6 | | 94.7 | |
| 97 | 21.9 | | 83.5 | |
| 98 | 13.2 | | 52.6 | |
| 99 | 28.4 | | 260 | |
| 100 | 17.2 | | 24.9 | |
| 101 | 11.9 | | 8.02 | |
| 102 | 31.5 | | 836 | |
| 103 | 25.2 | | 316 | |
| 104 | 317 | | >10.0E+03 | |
| 105 | 11.2 | | 109 | |
| 106 | 6.39 | | 36 | |
| 107 | 118 | | >10.0E+03 | |
| 108 | 18.8 | | 223 | |
| 109 | 257 | | 5830 | |
| 110 | 46.2 | | 963 | |
| 111 | 178 | | 4500 | |
| 112 | 9.53 | | 52.7 | |
| 113 | 21 | | 537 | |
| 114 | 9.15 | | 102 | |
| 115 | 5.16 | | 31.7 | |
| 116 | 10.2 | 157 | 303 | 5240 |
| 117 | 5.32 | | 103 | |
| 118 | 66.2 | | 3230 | |
| 119 | 90.8 | | 3160 | |
| 120 | 5.61 | | 103 | |
| 121 | 36.6 | | 1590 | |
| 122 | 10.6 | | 34.6 | |
| 123 | 9.84 | | 114 | |
| 124 | 13.9 | | 54.8 | |
| 125 | 13.3 | | 201 | |
| 126 | 721 | | 532 | |
| 127 | 12.6 | | 126 | |
| 128 | 34.4 | | 442 | |
| 129 | 111 | | >10.0E+03 | |
| 130 | 46.4 | | 2290 | |
| 131 | 42.5 | | 785 | |
| 132 | >1.00E+03 | | 2550 | |
| 133 | 76.2 | | 1340 | |
| 134 | >1.00E+03 | | >10.0E+03 | |
| 135 | 83.1 | | 1110 | |
| 136 | 19.8 | | 284 | |
| 137 | 21.5 | | 174 | |
| 138 | 13.5 | | 284 | |
| 139 | 89.6 | | 5850 | |
| 140 | 31.5 | | 576 | |
| 141 | 52.6 | | 734 | |
| 142 | 43.8 | | 886 | |
| 143 | 24.9 | | 138 | |
| 144 | 43.6 | | 520 | |
| 145 | 170 | | >10.0E+03 | |
| 146 | 508 | | >10.0E+03 | |
| 147 | 19.6 | | 131 | |
| 148 | 16.7 | | 107 | |
| 149 | 50.3 | | 1580 | |
| 150 | 18.2 | | 107 | |
| 151 | 22.8 | | 366 | |
| 152 | 61.7 | | 984 | |
| 153 | 120 | | 2220 | |
| 154 | 508 | | 3180 | |
| 155 | 16.5 | | 197 | |
| 156 | 39.3 | | 722 | |
| 157 | 40.5 | | 521 | |
| 158 | 13.5 | | 124 | |
| 159 | 4.65 | | 22.1 | |
| 160 | 53.5 | | 560 | |
| 161 | 94.6 | | 1910 | |
| 162 | 9.12 | | 37.8 | |
| 163 | 20.4 | | 363 | |
| 164 | 15.3 | | 180 | |
| 165 | 11.6 | | 100 | |
| 166 | 29.9 | | 687 | |
| 167 | 40.9 | | 830 | |
| 168 | 41.1 | | 1010 | |
| 169 | 12 | | 228 | |
| 170 | 69.6 | | 1380 | |
| 171 | 7.74 | | 82.9 | |
| 172 | 203 | | 2390 | |
| 173 | 30.2 | | 226 | |
| 174 | 13.2 | 52 | 431 | 1440 |
| 175 | 13 | | 79.7 | |
| 176 | 24.7 | | 315 | |
| 177 | 10.6 | | 47.2 | |
| 178 | 88.2 | | 3520 | |
| 179 | 80 | | 1270 | |
| 180 | 91.8 | | 1150 | |
| 181 | 78.4 | | 3680 | |
| 182 | 11.5 | | 219 | |
| 183 | 330 | | >10.0E+03 | |
| 184 | 114 | | 4740 | |
| 185 | 65.3 | | 1540 | |
| 186 | 76.3 | | 3270 | |
| 187 | 6.73 | | 21.3 | |
| 188 | 20 | | 650 | |
| 189 | 554 | | 2850 | |
| 190 | 25.5 | | 122 | |
| 191 | 9.23 | | 78.6 | |
| 192 | 9.54 | | 86.4 | |
| 193 | 6.71 | | 42.3 | |
| 194 | 9.37 | | 39.5 | |
| 195 | 12.4 | | 48.9 | |
| 196 | 9.31 | | 72.4 | |
| 197 | 14.7 | | 95.3 | |
| 198 | 9.5 | | 113 | |
| 199 | 10.6 | | 83.1 | |
| 200 | 14.7 | | 212 | |
| 201 | 9.27 | | 66.5 | |
| 202 | 5.59 | | 29.4 | |
| 203 | 10.5 | | 99.6 | |
| 204 | 9.42 | | 53.1 | |
| 205 | 168 | | 2340 | |
| 206 | 121 | | 1780 | |
| 207 | 151 | | 2520 | |
| 208 | 32.4 | | 1030 | |
| 209 | 37.7 | | 316 | |
| 210 | 95.8 | | 596 | |
| 211 | 32.1 | | 824 | |
| 212 | 57.8 | | 158 | |
| 213 | 13.8 | | 60.6 | |
| 214 | 56.9 | | 2690 | |
| 215 | 21.5 | | 381 | |
| 216 | 58.4 | | 1390 | |
| 217 | 38.9 | | 328 | |
| 218 | 643 | | 4400 | |
| 219 | 119 | | 6640 | |

TABLE 20-continued provides $IC_{50}$ values for selected compounds of the present disclosure.

| Cpd ID | AKT1 WT IC50 (nM) | AKT1 E17K IC50 (nM) | AKT2 IC50 (nM) | LAPC4 proliferation IC50 (nM) |
|---|---|---|---|---|
| 220 | 68.2 | | 6260 | |
| 221 | 10.9 | 5.8 | 449 | 1280 |
| 222 | 146 | | 1400 | |
| 223 | 38.7 | | 586 | |
| 224 | 32.1 | | 342 | |
| 225 | 11.3 | 408 | 343 | 8430 |
| 226 | 45.5 | | 2020 | |
| 227 | >1.00E+03 | | >10.0E+03 | |
| 228 | 586 | | 2030 | |
| 229 | 95.9 | | 2850 | |
| 230 | 13.6 | | 68.2 | |
| 231 | 504 | | 3870 | |
| 232 | 13.5 | | 46.6 | |
| 233 | 12.3 | | 24.2 | |
| 234 | 168 | | 4550 | |
| 235 | 22.8 | | 111 | |
| 236 | 12.1 | | 158 | |
| 237 | 7.29 | | 28.1 | |
| 238 | 9.1 | | 57.7 | |
| 239 | 117 | | 1090 | |
| 240 | 5.82 | | 59.3 | |
| 241 | 4.06 | | 15.7 | |
| 242 | 70 | | 3220 | |
| 243 | 75 | | 8230 | |
| 244 | 221 | | >10.0E+03 | |
| 245 | 41.8 | | 1960 | |
| 246 | 65.5 | | 2370 | |
| 247 | 60.4 | | 1570 | |
| 248 | 20.2 | | 107 | |
| 249 | 21.8 | | 368 | |
| 250 | >1.00E+03 | | >10.0E+03 | |
| 251 | 363 | | 5810 | |
| 252 | 599 | | 2610 | |
| 253 | 65.8 | | 2120 | |
| 254 | 23.9 | | 753 | |
| 255 | 3.42 | | 30.4 | |
| 256 | 5.19 | | 73.8 | |
| 257 | 8.26 | 16.5 | 273 | 1430 |
| 258 | 3.06 | | 60.3 | |
| 259 | 204 | | 1210 | |
| 260 | 7.55 | | 164 | |
| 261 | 4.75 | | 46.7 | |
| 262 | 8.14 | 68.1 | 211 | 2340 |
| 263 | 9.18 | | 120 | |
| 264 | 9.54 | | 163 | |
| 265 | 35.9 | | 1870 | |
| 266 | 18.3 | | 468 | |
| 267 | 14.6 | | 286 | |
| 268 | 7.96 | | 100 | |
| 269 | 3.21 | | 9.39 | |
| 270 | 535 | | >10.0E+03 | |
| 271 | 285 | | >10.0E+03 | |
| 272 | 38.6 | | 604 | |
| 273 | 11.6 | | 165 | |
| 274 | 593 | >1.00E+03 | 5000 | >10.0E+03 |
| 275 | 51 | 570 | 1070 | 4380 |
| 276 | 47.4 | >1.00E+03 | 1200 | >10.0E+03 |
| 277 | 25.1 | 365 | 486 | 2440 |
| 278 | 93 | >1.00E+03 | 3290 | >10.0E+03 |
| 279 | 45.4 | >1.00E+03 | 2400 | 9360 |
| 280 | 2.75 | 33.7 | 7.09 | 516 |
| 281 | 3.63 | 75.5 | 18.3 | 950 |
| 282 | 5.86 | 84.2 | 68.9 | 1310 |
| 283 | 2.75 | 10.6 | 2.91 | 264 |
| 284 | 5.1 | 143 | 10.5 | 1070 |
| 285 | 23.7 | 39.5 | 608 | 2230 |
| 286 | 40.5 | 897 | 589 | 4810 |
| 287 | 16.9 | 259 | 636 | 3000 |
| 288 | 112 | >1.00E+03 | >10.0E+03 | 3680 |
| 289 | 69.9 | 283 | 2990 | 4780 |
| 290 | 3.83 | | 18.9 | |
| 291 | 5.14 | | 56.5 | |
| 292 | 12.9 | | 73.2 | |
| 293 | 12.3 | | 83.8 | |
| 294 | 5.27 | | 29.1 | |
| 295 | 5.59 | | 81.3 | |
| 296 | 56.2 | | 660 | |
| 297 | 163 | | 4220 | |
| 298 | 7.16 | | 51.6 | |
| 299 | >1.00E+03 | | >10.0E+03 | |
| 300 | 3.32 | | 8.47 | |
| 301 | 189 | | 2050 | |
| 302 | 20.9 | | 456 | |
| 303 | 45.6 | | 1720 | |
| 304 | 80.8 | | 4750 | |
| 305 | 32.1 | | 1160 | |
| 306 | 34.5 | | 132 | |
| 307 | 10.8 | | 123 | |
| 308 | 15.1 | | 296 | |
| 309 | 10.8 | | 8.38 | |
| 310 | 22.1 | | 351 | |
| 311 | 19.1 | | 191 | |
| 312 | 80.5 | | 1870 | |
| 313 | 11.2 | | 41.1 | |
| 314 | 10.5 | | 70.4 | |
| 315 | 23.9 | | 617 | |
| 316 | 16.9 | | 201 | |
| 317 | 131 | | 1730 | |
| 318 | 149 | 181 | 931 | 3600 |
| 319 | 7.5 | 22.1 | 28.5 | 571 |
| 320 | 83.7 | 472 | 2330 | 2250 |
| 321 | 6.84 | 127 | 207 | 628 |
| 322 | 63.5 | 274 | 1330 | 2550 |
| 323 | 45.6 | 112 | 594 | 713 |
| 324 | 23.1 | | 502 | |
| 325 | 120 | | 4290 | |
| 326 | 18.2 | | 1320 | |
| 327 | 526 | | 6850 | |
| 328 | 17.9 | | 181 | |
| 329 | 14.7 | | 143 | |
| 330 | 55.1 | | 1190 | |
| 331 | 19.1 | | 41.3 | |
| 332 | 7.58 | | 60.2 | |
| 333 | 6.14 | | 58.7 | |
| 334 | 8.16 | | 21.4 | |
| 335 | 5.88 | | 31.5 | |
| 336 | 17.7 | | 305 | |
| 337 | 8.65 | | 82.2 | |
| 338 | 5.01 | | 13.2 | |
| 339 | 126 | | 5170 | |
| 340 | 37.7 | | 1010 | |
| 341 | 391 | | 2850 | |
| 342 | 43.9 | | 979 | |
| 343 | 16.6 | | 240 | |
| 344 | 7.97 | | 19.6 | |
| 345 | 51.6 | | 752 | |
| 346 | 24.7 | | 987 | |
| 347 | 23.7 | | 824 | |
| 348 | 58.2 | | 2600 | |
| 349 | 10.3 | 49.6 | 222 | 408 |
| 350 | 11.5 | 94.4 | 423 | 885 |
| 351 | 20.3 | 82.5 | 497 | 1140 |
| 352 | 141 | | 4290 | |
| 353 | 25 | | 1270 | |
| 354 | 39.8 | | 900 | |
| 355 | 16.8 | 734 | 74.4 | 2770 |
| 356 | 52.3 | >1.00E+03 | 1070 | >10.0E+03 |
| 357 | 5.79 | 23.8 | 20 | 875 |
| 358 | 208 | >1.00E+03 | 4640 | 7530 |
| 359 | 231 | >1.00E+03 | >10.0E+03 | >10.0E+03 |
| 360 | 483 | >1.00E+03 | 8140 | >10.0E+03 |
| 361 | 24.7 | 486 | 411 | 4290 |
| 362 | 36.1 | 138 | 1270 | 6960 |
| 363 | 7.74 | 57.9 | 67.2 | 1420 |
| 364 | 20.7 | 260 | 1110 | 2320 |
| 365 | 8.58 | 26.5 | 24.9 | 444 |

TABLE 20-continued provides $IC_{50}$ values for selected compounds of the present disclosure.

| Cpd ID | AKT1 WT IC50 (nM) | AKT1 E17K IC50 (nM) | AKT2 IC50 (nM) | LAPC4 proliferation IC50 (nM) |
|---|---|---|---|---|
| 366 | 70.9 | 818 | 4380 | >10.0E+03 |
| 367 | 74.4 | 735 | 2520 | 6330 |
| 368 | 36.8 | 406 | 768 | 6620 |
| 369 | 117 | >1.00E+03 | 5590 | >10.0E+03 |
| 370 | 58.4 | 810 | 1720 | >10.0E+03 |
| 371 | 15.4 | 47.8 | 1280 | 1050 |
| 372 | >1.00E+03 | | >10.0E+03 | |
| 373 | 704 | | 9910 | |
| 374 | 27.8 | | 389 | |
| 375 | 7.52 | | 68.9 | |
| 376 | 8.07 | | 151 | |
| 377 | 2.9 | | 22.2 | |
| 378 | 16.9 | | 392 | |
| 379 | 12.6 | 248 | 1280 | 4240 |
| 380 | 13.9 | | 312 | |
| 381 | 3.48 | 15.8 | 90.1 | 687 |
| 382 | 13.1 | 92.3 | 546 | 4150 |
| 383 | 12.8 | | 214 | |
| 384 | 13.2 | 93.9 | 525 | 1260 |
| 385 | 34.3 | >856 | 1790 | >7.50E+03 |
| 386 | 17.6 | >487 | 1310 | >7.16E+03 |
| 387 | 9.48 | 376 | 351 | 4430 |
| 388 | 28.7 | 247 | 674 | 3140 |
| 389 | 7.01 | 55.9 | 63.3 | 1710 |
| 390 | 15.8 | 31.8 | 105 | >10.0E+03 |
| 391 | 19.7 | 257 | 103 | 2250 |
| 392 | 41.3 | >1.00E+03 | 5530 | >10.0E+03 |
| 393 | 125 | >1.00E+03 | 3850 | >10.0E+03 |
| 394 | 101 | >1.00E+03 | 1480 | >10.0E+03 |
| 395 | 7.78 | 120 | 137 | 1650 |
| 396 | 14.7 | | 250 | |
| 397 | 16.5 | | 1440 | |
| 398 | 17.8 | | 1090 | |
| 399 | 15 | 177 | 656 | 2730 |
| 400 | 14.4 | | 2100 | |
| 401 | 10.9 | 108 | 2730 | 4210 |
| 402 | 7.99 | 53.3 | 477 | 3000 |
| 403 | 6.13 | | 20.1 | |
| 404 | 33.7 | | 2820 | |
| 405 | 46.2 | | 1580 | |
| 406 | 20.4 | | 903 | |
| 407 | 421 | | 3550 | |
| 408 | 91.1 | | 2300 | |
| 409 | 36 | | 1290 | |
| 410 | 7.43 | | 57.6 | |
| 411 | 976 | | >10.0E+03 | |
| 412 | 26.4 | | 686 | |
| 413 | 21.7 | | 1470 | |
| 414 | 26.1 | | 562 | |
| 415 | 2.96 | | 70 | |
| 416 | 1.43 | | 34 | |
| 417 | 19.6 | | 561 | |
| 418 | 76 | | 2680 | |
| 419 | 35.9 | | 540 | |
| 420 | 336 | | 3100 | |
| 421 | 3.52 | | 37.9 | |
| 422 | 67.9 | | 2080 | |
| 423 | 188 | | 2620 | |
| 424 | 122 | | 5380 | |
| 425 | 109 | | 3090 | |
| 426 | 3.17 | 59 | 360 | 1510 |
| 427 | 9.56 | 101 | 1080 | 1710 |
| 428 | 58.9 | | 1730 | |
| 429 | 5.64 | | 57 | |
| 430 | 83.5 | | 2490 | |
| 431 | 16.7 | | 900 | |
| 432 | 14.6 | 145 | 1450 | 3500 |
| 433 | 190 | | 3530 | |
| 434 | 57.7 | | 1300 | |
| 435 | 19.6 | | 1390 | |
| 436 | 40 | | 4660 | |
| 437 | 80.7 | | 1570 | |
| 438 | 25.3 | | 795 | |

TABLE 20-continued provides $IC_{50}$ values for selected compounds of the present disclosure.

| Cpd ID | AKT1 WT IC50 (nM) | AKT1 E17K IC50 (nM) | AKT2 IC50 (nM) | LAPC4 proliferation IC50 (nM) |
|---|---|---|---|---|
| 439 | 15 | 655 | 794 | 3820 |
| 440 | 24.3 | >1.00E+03 | 1750 | 5270 |
| 441 | 21.7 | >1.00E+03 | 1340 | 3710 |
| 442 | 72.6 | | 1600 | |
| 443 | 23.2 | | 940 | |
| 444 | 23.5 | | 499 | |
| 445 | 20.2 | | 980 | |
| 446 | 31.9 | | 1330 | |
| 447 | 78.5 | | 1490 | |
| 448 | 47.8 | | 1760 | |
| 449 | 79.7 | | 1200 | |
| 450 | 198 | | 4470 | |
| 451 | 8.14 | | 198 | |
| 452 | 6.63 | | 131 | |
| 453 | 28 | | 3770 | |
| 454 | 37.5 | | >10.0E+03 | |
| 455 | 195 | | 3020 | |
| 456 | 52.3 | | 715 | |
| 457 | 235 | | 6740 | |
| 458 | 93.4 | | 2800 | |
| 459 | 26.6 | | 782 | |
| 460 | 33.6 | | 6180 | |
| 461 | 109 | | 3030 | |
| 462 | 225 | | 2370 | |
| 463 | 27 | | 1080 | |
| 464 | 19.2 | | 167 | |
| 465 | >1.00E+03 | | >10.0E+03 | |
| 466 | 25.9 | | 1570 | |
| 467 | 358 | | 3560 | |
| 468 | 74.7 | | 1960 | |
| 469 | 93.4 | | 1130 | |
| 470 | 68.2 | | 777 | |
| 471 | 39 | | 1040 | |
| 472 | 18 | | 404 | |
| 473 | 19 | | 28 | |
| 474 | 14.9 | 196 | 423 | 2730 |
| 475 | 130 | | 2780 | |
| 476 | 209 | | >10.0E+03 | |
| 477 | 170 | | 4360 | |
| 478 | 126 | | 3170 | |
| 479 | 89.3 | | >10.0E+03 | |
| 480 | 38.9 | | 3140 | |
| 481 | 13.9 | | 278 | |
| 482 | 5.39 | 140 | 194 | 827 |
| 483 | 30.9 | | 7440 | |
| 484 | 28.4 | | 3850 | |
| 485 | 50.9 | | 997 | |
| 486 | 25.1 | | 1070 | |
| 487 | 42.8 | | >10.0E+03 | |
| 488 | 7.99 | 30.6 | 98 | 624 |
| 489 | 92.6 | | 5410 | |
| 490 | 74.3 | | 3200 | |
| 491 | 5.37 | 23.6 | 351 | 285 |
| 492 | 24.1 | | 2120 | |
| 493 | 57.6 | | 973 | |
| 494 | 199 | | 6860 | |
| 495 | 9.4 | | 197 | |
| 496 | 28.2 | | 1070 | |
| 497 | 18.9 | | 1280 | |
| 498 | 43 | | 620 | |
| 499 | 45.6 | | 897 | |
| 500 | 81.5 | | >10.0E+03 | |
| 501 | 20.5 | | 695 | |
| 502 | 134 | | 2090 | |
| 503 | 74.1 | | 2930 | |
| 504 | 14.3 | >1.00E+03 | 665 | 4410 |
| 505 | 17.6 | 485 | 547 | 4360 |
| 506 | 96.9 | | 8940 | |
| 507 | 125 | | 3760 | |
| 508 | 75.9 | | 627 | |
| 509 | 28.7 | | 928 | |
| 510 | 14.6 | | 262 | |
| 511 | 10.4 | | 196 | |

TABLE 20-continued provides $IC_{50}$ values for selected compounds of the present disclosure.

| Cpd ID | AKT1 WT IC50 (nM) | AKT1 E17K IC50 (nM) | AKT2 IC50 (nM) | LAPC4 proliferation IC50 (nM) |
|---|---|---|---|---|
| 512 | 19.7 | | 409 | |
| 513 | 13.9 | | 240 | |
| 514 | 26.4 | | 1130 | |
| 515 | 12.1 | | 452 | |
| 516 | 102 | | 6240 | |
| 517 | 31.6 | | 973 | |
| 518 | 32 | | 1290 | |
| 519 | 39.2 | | 1220 | |
| 520 | 9.92 | | 198 | |
| 521 | 105 | | >10.0E+03 | |
| 522 | 524 | | >10.0E+03 | |
| 523 | 48.4 | | 1740 | |
| 524 | 48.4 | | 1740 | |
| 525 | 33.5 | | 1330 | |
| 526 | 20.2 | | 1260 | |
| 527 | 19.5 | | 1150 | |
| 528 | 17.2 | | 320 | |
| 529 | 8.2 | | 621 | |
| 530 | 21.2 | | 422 | |
| 531 | 50.6 | | 1280 | |
| 532 | 177 | | >10.0E+03 | |
| 533 | >1.00E+03 | | 7230 | |
| 534 | 38.9 | | 507 | |
| 535 | 6.42 | | 42.1 | |
| 536 | 26.2 | | 1570 | |
| 537 | 2.77 | | 15.3 | |
| 538 | 25.1 | | 2910 | |
| 539 | 5.11 | | 430 | |
| 540 | 107 | | 3180 | |
| 541 | 5.46 | | 556 | |
| 542 | 117 | | 2330 | |
| 543 | 81 | 526 | 1210 | |
| 544 | 6.24 | | 130 | |
| 545 | 20.8 | | 730 | |
| 546 | 9.86 | | 221 | |
| 547 | 28.3 | | 1740 | |
| 548 | 27.4 | | 4080 | |
| 549 | 27.6 | | 723 | |
| 550 | 7.1 | | 75.7 | |
| 551 | 13.1 | | 296 | |
| 552 | 9.18 | | 166 | |
| 553 | 7.04 | | 344 | |
| 554 | 339 | | 9260 | |
| 555 | 64.4 | | 1570 | |
| 556 | 124 | | 1330 | |
| 557 | 15.9 | | 1760 | |
| 558 | 71.5 | | 7510 | |
| 559 | 5.67 | | 268 | |
| 560 | 249 | | 2520 | |
| 561 | 93.3 | | 3090 | |
| 562 | 9.77 | | 430 | |
| 563 | 1.83 | | 37.8 | |
| 564 | 2.28 | | 84.4 | |
| 565 | 9.86 | | 274 | |
| 566 | 10.5 | | 246 | |
| 567 | 11.3 | | 455 | |
| 568 | 8.72 | | 458 | |
| 569 | 77.4 | | 808 | |
| 570 | 47.5 | | 679 | |
| 571 | 2.22 | | 176 | |
| 572 | 16.1 | | 945 | |
| 573 | 318 | | 5640 | |
| 574 | 52.4 | | 2420 | |
| 575 | 221 | | 3300 | |
| 576 | 133 | | 4300 | |
| 577 | 87.9 | | 904 | |
| 578 | 74.9 | | 1690 | |
| 579 | 5.42 | 9.88 | 26.6 | |
| 580 | 11.2 | 11.4 | 24.4 | |
| 581 | 6.51 | 20.8 | 38.4 | |
| 582 | >1.00E+03 | | >10.0E+03 | |
| 583 | 805 | | 3780 | |
| 584 | 6.1 | 11.8 | 62.5 | |
| 585 | 4.77 | 8.23 | 10.7 | |
| 586 | 6.98 | 17.3 | 43 | |
| 587 | 116 | | 1010 | |
| 588 | 27 | | 764 | |
| 589 | 16.8 | | 650 | |
| 590 | 45.2 | | 1540 | |
| 591 | 25.2 | | 962 | |
| 592 | 4.32 | 5.5 | 11 | |
| 593 | 4.56 | 22 | 23.7 | |
| 594 | 27.6 | | 2690 | |
| 595 | 15 | | 520 | |
| 596 | 12.9 | | 689 | |
| 597 | 66.1 | | 3780 | |
| 598 | 3.8 | | 40.5 | |
| 599 | 25.4 | | 1280 | |
| 600 | 418 | | 7070 | |
| 601 | 102 | | 2500 | |
| 602 | 34 | 61.4 | 351 | |
| 603 | 7.65 | 16.5 | 76.8 | |

What is claimed is:

1. A compound represented by the structure of Formula (I):

(I)

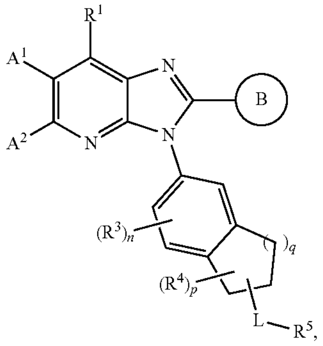

or a pharmaceutically acceptable salt thereof, wherein:

Ring B is selected from:

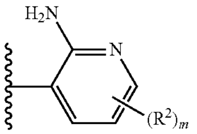 and 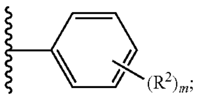

$R^1$ is selected from hydrogen, halogen, —$OR^{10}$, —$SR^{10}$, —$N(R^{10})_2$, —$NO_2$, —CN, optionally substituted $C_{3-8}$ carbocycle, optionally substituted 4- to 8-membered heterocycle, and optionally substituted $C_{1-6}$ alkyl, each of which is optionally substituted with one or more substituents independently selected from: halogen, —$OR^{10}$, —$SR^{10}$, —$N(R^{10})_2$, —$NO_2$, and —CN;

$A^1$ and $A^2$ are each independently selected from (i), (ii), and (iii):

(i) hydrogen, halogen, $C_{1-4}$ haloalkyl, —$OR^{11}$, —$SR^{11}$, —$N(R^{11})_2$, —$C(O)N(R^{11})_2$, —$N(R^{11})C(O)R^{11}$, —$C(O)OR^{11}$, —$OC(O)R^{11}$, —$N(R^{11})C(O)OR^{11}$, —OC(O)N($R^{11}$)$_2$, —N($R^{11}$)C(O)N($R^{11}$)$_2$, —S(O)$R^{11}$, —S(O)$_2R^{11}$, —N($R^{11}$)S(O)$_2R^{11}$, —S(O)$_2$N($R^{11}$)$_2$, —$NO_2$, and —CN;

(ii) $C_{1-6}$ alkyl, $C_{2-6}$ alkenyl, and $C_{2-6}$ alkynyl, any of which is optionally substituted with one or more substituents independently selected from:

halogen, —$OR^{10}$, —$SR^{10}$, —N($R^{10}$)$_2$, —$NO_2$, and —CN;

$C_{3-10}$ carbocycle and 4- to 10-membered heterocycle, any of which is optionally substituted with one or more substituents independently selected from:

halogen, —$OR^{11A}$, —N($R^{11A}$)$_2$, —C(O)$R^{11A}$, —C(O)N($R^{11A}$)$_2$, —N($R^{11A}$)C(O)$R^{11A}$, —C(O)$OR^{11A}$, —OC(O)$R^{11A}$, —$NO_2$, ═O, ═S, ═N($R^{11A}$), and —CN; and $C_{1-6}$ alkyl, $C_{2-6}$ alkenyl, and $C_{2-6}$ alkynyl, any one of which is optionally substituted with one or more substituents independently selected from:

halogen, —$OR^{11A}$, —$SR^{11A}$, —N($R^{11A}$)$_2$, —C(O)$R^{11A}$, —C(O)N($R^{11A}$)$_2$, —N($R^{11A}$)C(O)$R^{11A}$, —N($R^{11A}$)S(O)$_2R^{11A}$, —C(O)$OR^{11A}$, —OC(O)$R^{11A}$, —$NO_2$, ═O, ═S, ═N($R^{11A}$), and —CN; and (iii) 5- to 10-membered heterocycle and $C_{3-10}$ carbocycle, any of which is optionally substituted with one or more substituents independently selected from:

halogen, —$OR^{11}$, —$SR^{11}$, —N($R^{11}$)$_2$, —C(O)$R^{11}$, —C(O)N($R^{11}$)$_2$, —N($R^{11}$)C(O)$R^{11}$, —N($R^{11}$)S(O)$_2R^{11}$, —NS(O)$_2$N($R^{11}$)$_2$, —C(O)$OR^{11}$, —OC(O)$R^{11}$, —N($R^{11}$)C(O)$OR^{11}$, —OC(O)N($R^{11}$)$_2$, —N($R^{11}$)C(O)N($R^{11}$)$_2$, —S(O)$R^{11}$, —S(O)$_2R^{11}$, —S(O)$_2$N($R^{11}$)$_2$, —$NO_2$, ═O, ═S, =N($R^{11}$), and —CN;

$C_{1-6}$ alkyl, $C_{2-6}$ alkenyl, and $C_{3-6}$ alkynyl, any one of which is optionally substituted with one or more substituents independently selected from:

halogen, —$OR^{11}$, —$SR^{11}$, —N($R^{11}$)$_2$, —C(O)$R^{11}$, —C(O)N($R^{11}$)$_2$, —N($R^{11}$)C(O)$R^{11}$, —C(O)$OR^{11}$, —OC(O)$R^{11}$, —N($R^{11}$)C(O)$OR^{11}$, —OC(O)N($R^{11}$)$_2$, —N($R^{11}$)C(O)N($R^{11}$)$_2$, —S(O)$R^{11}$, —S(O)$_2R^{11}$, —N($R^{11}$)S(O)$_2R^{11}$, —S(O)$_2$N($R^{11}$)$_2$, —$NO_2$, ═O, =S, =N($R^{11}$), and —CN; and $C_{3-10}$ carbocycle and 4- to 10-membered heterocycle, any of which is optionally substituted with one or more substituents independently selected from:

halogen, —$OR^{11}$, —N($R^{11}$)$_2$, —C(O)$R^{11}$, —C(O)N($R^{11}$)$_2$, —N($R^{11}$)C(O)$R^{11}$, —C(O)$OR^{11}$, —OC(O)$R^{11}$, —$NO_2$, ═O, =S, =N($R^{11}$), and —CN; and $C_{1-6}$ alkyl, $C_{2-6}$ alkenyl, $C_{3-6}$ alkynyl, $C_{3-8}$ carbocycle, and 4- to 8-membered heterocycle, any one of which is optionally substituted with one or more substituents independently selected from:

halogen, —$OR^{11}$, —$SR^{11}$, —N($R^{11}$)$_2$, —C(O)$R^{11}$, —C(O)N($R^{11}$)$_2$, —N($R^{11}$)C(O)$R^{11}$, —N($R^{11}$)S(O)$_2R^{11}$, —C(O)$OR^{11}$, —OC(O)$R^{11}$, —$NO_2$, ═O, ═S, ═N($R^{11}$), and —CN;

q is selected from 1, 2, and 3;

m and n are each independently selected from 0, 1, 2, and 3;

$R^2$ is independently selected at each instance from halogen, $C_{1-4}$ alkyl, $C_{1-4}$ haloalkyl, —$OR^{12}$, —$SR^{12}$, —N($R^{12}$)$_2$, —$NO_2$, and —CN;

$R^3$ is independently selected at each instance from:

halogen, —$OR^{13}$, —$SR^{13}$, —N($R^{13}$)$_2$, —C(O)$R^{13}$, —C(O)N($R^{13}$)$_2$, —N($R^{13}$)C(O)$R^{13}$, —C(O)$OR^{13}$, —OC(O)$R^{13}$, —$NO_2$, and —CN; and $C_{1-6}$ alkyl optionally substituted with one or more substituents independently selected from: halogen, —$OR^{13}$, —$SR^{13}$, —N($R^{13}$)$_2$, —C(O)$R^{13}$, —C(O)N($R^{13}$)$_2$, —N($R^{13}$)C(O)$R^{13}$, —C(O)$OR^{13}$, —OC(O)$R^{13}$, —$NO_2$, ═O, ═S, =N($R^{13}$), and —CN;

p is selected from 0, 1, 2, 3, 4, and 5;

$R^4$ is independently selected at each instance from:

halogen, —$OR^{14}$, —$SR^{14}$, —N($R^{14}$)$_2$, —C(O)$R^{14}$, —C(O)N($R^{14}$)$_2$, —N($R^{14}$)C(O)$R^{14}$, —C(O)$OR^{14}$, —OC(O)$R^{14}$, —$NO_2$, and —CN; and $C_{1-6}$ alkyl, $C_{2-6}$ alkenyl, $C_{2-6}$ alkynyl, any one of which is optionally substituted with one or more substituents independently selected from halogen, —$OR^{14}$, —$SR^{14}$, —N($R^{14}$)$_2$, —C(O)$R^{14}$, —C(O)N($R^{14}$)$_2$, —N($R^{14}$)C(O)$R^{14}$, —C(O)$OR^{14}$, —OC(O)$R^{14}$, —$NO_2$, —O, —S, —N($R^{14}$), and —CN; or two $R^4$ attached to the same atom are taken together to form a group selected from: ═O, ═S, and =N($R^{14}$); or two $R^4$ attached to the same atom or to adjacent atoms are taken together with the carbons to which they are attached to form a group selected from 4- to 8-membered heterocycle and $C_{3-8}$ carbocycle, any of which is optionally substituted with one or more substituents independently selected from: halogen, $C_{1-4}$ alkyl, $C_{1-4}$ haloalkyl, —$OR^{14}$, —$SR^{14}$, —N($R^{14}$)$_2$, —$NO_2$, and —CN;

L is represented by —$L^1$—$L^2$—$L^3$—$L^4$—, wherein $L^1$, $L^2$, $L^3$, and $L^4$ are each independently selected from (a) and (b):

(a) —O—, —N($R^{15}$)—, —S—, —S(O)—, —S(O)$_2$—, —S(O)($NR^{15}$)—, —N($R^{15}$)C(O)—, —N($R^{15}$)C(O)O—, —N($R^{15}$)S(O)$_2$—, and —($R^{15}$)NC(O)N($R^{15}$)N($R^{15}$)N($r^{15}$)—; and (b) $C_{1-6}$ alkylene, $C_{2-6}$ alkenylene, $C_{2-6}$ alkynylene, $C_{3-8}$ carbocyclene, and 4- to 8-membered heterocyclene, any of which is optionally substituted with one or more substituents independently selected from halogen, —$OR^{15}$, —$SR^{15}$, ═O, ═S, and —CN;

wherein $L^1$, $L^2$, $L^3$, and $L^4$ are each optionally absent;

wherein no more than two of $L^1$, $L^2$, $L^3$, and $L^4$ are selected from (a) and the two selected are not adjacent;

$R^5$ is selected from 4- to 10-membered heterocycle and $C_{3-10}$ carbocycle, any of which is optionally substituted with one or more substituents independently selected from:

halogen, —$OR^{16}$, —$SR^{16}$, —N($R^{16}$)$_2$, —C(O)N($R^{16}$)$_2$, —C(O)$OR^{16}$, —OC(O)$R^{16}$, —N($R^{16}$)C(O)$R^{16}$, —N($R^{16}$)S(O)$_2R^{16}$, —S(O)$_2$N($R^{16}$)$_2$, —N($R^{16}$)C(O)N($R^{16}$)$_2$, —N($R^{16}$)C(O)$OR^{16}$, —OC(O)N($R^{16}$)$_2$, —S(O)$R^{16}$, —S(O)$_2R^{16}$, —$NO_2$, —O, ═S, and =N($R^{16}$), and CN;

$C_{1-6}$ alkyl optionally substituted with one or more substituents independently selected from: halogen, —$OR^{16}$, —$SR^{16}$, —N($R^{16}$)$_2$, and —$NO_2$, and CN; and 4- to 6-membered heterocycle and $C_{3-8}$ carbocycle, each of which is optionally substituted with one or more substituents independently selected from:

halogen, $C_{1-4}$ alkyl, $C_{1-4}$ haloalkyl, —$OR^{16}$, —$SR^{16}$, —N($R^{16}$)$_2$, and —$NO_2$;

$R^{10}$, $R^{11}$, $R^{11A}$, $R^{12}$, $R^{13}$, $R^{14}$, and $R^{15}$ are each independently selected at each occurrence from:

hydrogen, $C_{1-4}$ alkyl, $C_{3-8}$ carbocycle, 4- to 8-membered heterocycle, and $C_{1-4}$ haloalkyl;

$R^{16}$ is independently selected at each occurrence from (iv), (v), and (vi):

(iv) hydrogen;

(v) $C_{1-4}$ alkyl optionally substituted with one or more substituents independently selected from:

halogen, —$OR^{20}$, —$SR^{20}$, —$N(R^{20})_2$, —$C(O)R^{20}$, —$C(O)OR^{20}$, —$OC(O)R^{20}$, —$C(O)N(R^{20})_2$, —$N(R^{20})C(O)R^{20}$, —$N(R^{20})C(O)N(R^{20})_2$, —$N(R^{20})C(O)OR^{20}$, —$OC(O)N(R^{20})_2$, —$S(O)R^{20}$, —$S(O)_2R^{20}$, —$N(R^{20})S(O)_2R^{20}$, —$S(O)_2N(R^{20})_2$, and —$NO_2$; and $C_{3-8}$ carbocycle and 4- to 8-membered heterocycle, either of which is optionally substituted with one or more substituents independently selected from: halogen, $C_{1-4}$ alkyl, $C_{1-4}$ haloalkyl, —$OR^{20}$, —$SR^{20}$, —$N(R^{20})_2$, —$C(O)R^{20}$, —$C(O)OR^{20}$, —$OC(O)R^{20}$, —$C(O)N(R^{20})_2$, —$N(R^{20})C(O)R^{20}$, —$N(R^{20})C(O)N(R^{20})_2$, —$N(R^{20})C(O)OR^{20}$, —$OC(O)N(R^{20})_2$, —$S(O)R^{20}$, —$S(O)_2R^{20}$, —$N(R^{20})S(O)_2R^{20}$, —$S(O)_2N(R^{20})_2$, and —$NO_2$; and (vi) $C_{3-8}$ carbocycle and 4- to 8-membered heterocycle, either of which is optionally substituted with one or more substituents independently selected from halogen, $C_{1-4}$ alkyl, $C_{1-4}$ haloalkyl, —$OR^{20}$, —$SR^{20}$, —$N(R^{20})_2$, —$C(O)R^{20}$, —$C(O)N(R^{20})_2$, —$C(O)OR^{20}$, —$OC(O)R^{20}$, —$N(R^{20})C(O)R^{20}$, —$N(R^{20})S(O)_2R^{20}$, —$N(R^{20})C(O)N(R^{20})_2$, —$N(R^{20})C(O)OR^{20}$, —$OC(O)N(R^{20})_2$, —$S(O)R^{20}$, —$S(O)_2R^{20}$, —$NO_2$, $C_{3-8}$ carbocycle, and 4- to 8-membered heterocycle, wherein the $C_{3-8}$ carbocycle and 4- to 8-membered heterocycle are each optionally further substituted with one or more substituents independently selected from halogen, $C_{1-4}$ alkyl, $C_{1-4}$ haloalkyl, —$OR^{20}$, —$SR^{20}$, —$N(R^{20})_2$, —$C(O)R^{20}$, —$C(O)N(R^{20})_2$, —$C(O)OR^{20}$, —$OC(O)R^{20}$, —$N(R^{20})C(O)R^{20}$, —$N(R^{20})S(O)_2R^{20}$, —$N(R^{20})C(O)N(R^{20})_2$, —$N(R^{20})C(O)OR^{20}$, —$OC(O)N(R^{20})_2$, —$S(O)R^{20}$, —$S(O)_2R^{20}$, and —$NO_2$; and $R^{20}$ is independently selected at each occurrence from hydrogen, $C_{1-4}$ alkyl, $C_{1-4}$ haloalkyl, $C_{3-8}$ carbocycle, and 4- to 8-membered heterocycle.

2. The compound or salt of claim 1, wherein Ring B is

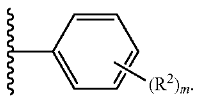

3. The compound or salt of claim 1, wherein Ring B is

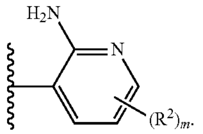

4. The compound or salt of claim 1, wherein the structure of Formula (I) is represented by the structure of Formula (II):

(II)

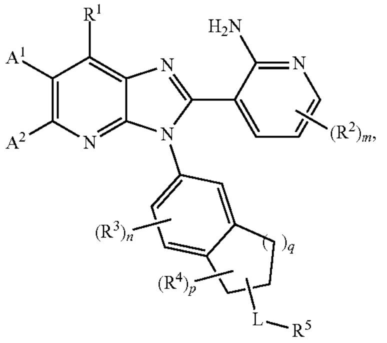

or a pharmaceutically acceptable salt thereof, wherein:

$R^1$ is selected from hydrogen, halogen, —$OR^{10}$, —$SR^{10}$, —$N(R^{10})_2$, —$NO_2$, and —CN; and $C_{1-6}$ alkyl optionally substituted with one or more substituents independently selected from:

halogen, —$OR^{10}$, —$SR^{10}$, —$N(R^{10})_2$, —$NO_2$, and —CN;

$A^1$ and $A^2$ are each independently selected from (i), (ii), and (iii):

(i) hydrogen, halogen, $C_{1-4}$ haloalkyl, —$OR^{11}$, —$SR^{11}$, —$N(R^{11})_2$, —$C(O)N(R^{11})_2$, —$N(R^{11})C(O)R^{11}$, —$C(O)OR^{11}$, —$OC(O)R^{11}$, —$N(R^{11})C(O)OR^{11}$, —$OC(O)N(R^{11})_2$, —$N(R^{11})C(O)N(R^{11})_2$, —$S(O)R^{11}$, —$S(O)_2R^{11}$, —$N(R^{11})S(O)_2R^{11}$, —$S(O)_2N(R^{11})_2$, —$NO_2$, and —CN;

(ii) $C_{1-6}$ alkyl, $C_{2-6}$ alkenyl, and $C_{2-6}$ alkynyl, any of which is optionally substituted with one or more substituents independently selected from halogen, —$OR^{11}$, —$SR^{11}$, —$N(R^{11})_2$, —$C(O)N(R^{11})_2$, —$N(R^{11})C(O)R^{11}$, —$C(O)OR^{11}$, —$OC(O)R^{11}$, —$N(R^{11})C(O)OR^{11}$, —$OC(O)N(R^{11})_2$, —$N(R^{11})C(O)N(R^{11})_2$, —$S(O)R^{11}$, —$S(O)_2R^{11}$, —$N(R^{11})S(O)_2R^{11}$, —$S(O)_2N(R^{11})_2$, —$NO_2$, =O, =S, =$N(R^{11})$, and —CN; and (iii) 5- to 10-membered heterocycle and $C_{3-10}$ carbocycle, any of which is optionally substituted with one or more substituents independently selected from:

halogen, —$OR^{11}$,—$SR^{11}$, —$N(R^{11})_2$, —$C(O)R^{11}$, —$C(O)N(R^{11})_2$, —$N(R^{11})C(O)^{11}$, —$N(R^{11})S(O)_2R^{11}$, —$C(O)OR^{11}$, —$OC(O)R^{11}$, —$N(^{11})C(O)OR^{11}$, —$OC(O)N(R^{11})_2$, —$N(R^{11})C(O)N(R^{11})_2$, —$S(O)R^{11}$, —$S(O)_2R^{11}$, —$S(O)_2N(R^{11})_2$, —$NO_2$, =O, =S, =$N(R^{11})$, and —CN;

$C_{1-6}$ alkyl, $C_{2-6}$ alkenyl, and $C_{3-6}$ alkynyl, any one of which is optionally substituted with one or more substituents independently selected from:

halogen, —$OR^{11}$,—$SR^{11}$, —$N(R^{11})_2$, —$C(O)R^{11}$, —$C(O)N(R^{11})_2$, —$N(R^{11})C(O)^{11}$, —$C(O)OR^{11}$, —$OC(O)R^{11}$, —$N(^{11})C(O)OR^{11}$, —$OC(O)N(R^{11})_2$, —$N(R^{11})C(O)N(R^{11})_2$, —$S(O)R^{11}$, —$S(O)_2R^{11}$, —$N(R^{11})S(O)_2R^{11}$, —$S(O)_2N(R^{11})_2$, —$NO_2$, =O, =S, =$N(R^{11})$, and —CN; and $C_{3-10}$ carbocycle and 4- to 10-membered heterocycle, any of which is optionally substituted with one or more substituents independently selected from:

halogen, —$OR^{11}$, —$N(R^{11})_2$, —$C(O)R^{11}$, —$C(O)N(R^{11})_2$, —$N(R^{11})C(O)R^{11}$, $C(O)OR^{11}$—$OC(O)R^{11}$—$NO_2$, =O, =S, =$N(R^{11})$, and —CN; and $C_{1-6}$ alkyl, $C_{2-6}$ alkenyl, and $C_{3-6}$ alkynyl, any one of which is optionally substituted with one or more substituents independently selected from: halogen, —$OR^{11}$, —$N(R^{11})_2$, —$C(O)R^{11}$, —$C(O)N(R^{11})_2$, —$N(R^{11})C(O)R^{11}$, —$N(R^{11})S(O)_2R^{11}$, —$C(O)OR^{11}$, —$OC(O)R^{11}$, —$NO_2$, =O, =S, =$N(R^{11})$, and —CN;

q is selected from 1, 2, and 3;

m and n are each independently selected from 0, 1, 2, and 3;

$R^2$ is independently selected at each instance from halogen, $C_{1-4}$ alkyl, $C_{1-4}$ haloalkyl, —$OR^{12}$, —$SR^{12}$, —$N(R^{12})_2$, —$NO_2$, and —CN;

$R^3$ is independently selected at each instance from:

halogen, —$OR^{13}$, —$SR^{13}$—$N(R^{13})_2$, —$C(O)R^{13}$, —$C(O)N(R^{13})_2$, —$N(R^{13})C(O)R^{13}$, —$C(O)OR^{13}$, —$OC(O)R^{13}$, —$NO_2$, and —CN; and $C_{1-6}$ alkyl optionally substituted with one or more substituents independently selected from: halogen, —$OR^{13}$, —$SR^{13}$, —$N(R^{13})_2$, —$C(O)R^{13}$, —$C(O)N(R^{13})_2$, —$N(R^{13})C(O)R^{13}$, —$C(O)OR^{13}$, —$OC(O)R^{13}$, —$NO_2$, =O, =S, =$N(R^{13})$, and —CN;

p is selected from 0, 1, 2, 3, 4, and 5;

$R^4$ is independently selected at each instance from:

halogen, —$OR^{14}$, —$SR^{14}$, —$N(R^{14})_2$, —$C(O)R^{14}$, —$C(O)N(R^{14})_2$, —$N(R^{14})C(O)R^{14}$, —$C(O)OR^{14}$, —$OC(O)R^{14}$, —$NO_2$, and —CN; and $C_{1-6}$ alkyl, $C_{2-6}$ alkenyl, $C_{2-6}$ alkynyl, any one of which is optionally substituted with one or more substituents independently selected from halogen, —$OR^{14}$, —$SR^{14}$, —$N(R^{14})_2$, —$C(O)R^{14}$, —$C(O)N(R^{14})_2$, —$N(R^{14})C(O)R^{14}$, —$C(O)OR^{14}$, —$OC(O)R^{14}$—$NO_2$, =O, =S, =$N(R^{14})$, and —CN; or two $R^4$ attached to the same atom are taken together to form a group selected from: =O, =S, and =$N(R^{14})$; or two $R^4$ attached to the same atom or to adjacent atoms are taken together with the carbons to which they are attached to form a group selected from 4- to 8-membered heterocycle and $C_{3-8}$ carbocycle, any of which is optionally substituted with one or more substituents independently selected from: halogen, $C_{1-4}$ alkyl, $C_{1-4}$ haloalkyl, —$OR^{14}$, —$SR^{14}$, —$N(R^{14})_2$, —$NO_2$, and —CN;

L is represented by —$L^1$—$L^2$—$L^3$—$L^4$—, wherein $L^1$, $L^2$, $L^3$, and $L^4$ are each independently selected from (a) and (b):

(a) —O—, —$N(R^{15})$—, —S—, —S(O)—, —$S(O)_2$, —$S(O)(NR^{15})$—, —$N(R^{15})C(O)$—, —$N(R^{15})C(O)O$—, —$N(R^{15})S(O)_2$—, —$N(R^{15})S(O)_2N(R^{15})$—, —$S(O)(NR^{15})N(R^{15})$—, —$N(R^{15})N(R^{15})$—, —$(R^{15})NC(O)N(R^{15})$—, and —$(R^{15})NC(O)N(R^{15})N(R^{15})$—; and (b) $C_{1-6}$ alkylene, $C_{2-6}$ alkenylene, $C_{2-6}$ alkynylene, $C_{3-8}$ carbocyclene, and 4- to 8-membered heterocyclene, any of which is optionally substituted with one or more substituents independently selected from halogen, —$OR^{15}$, —$SR^{15}$, =O, and =S, and —CN;

wherein $L^2$, $L^3$, and $L^4$ are each optionally absent;

wherein no more than two of $L^1$, $L^2$, $L^3$, and $L^4$ are selected from (a) and the two selected are not adjacent;

$R^5$ is selected from 4- to 10-membered heterocycle and $C_{3-10}$ carbocycle, any of which is optionally substituted with one or more substituents independently selected from:

halogen, —$OR^{16}$, —$SR^{16}$, —$N(R^{16})_2$, —$C(O)N(R^{16})_2$, —$C(O)OR^{16}$, —$OC(O)R^{16}$, —$N(R^{16})C(O)R^{16}$, —$N(R^{16})S(O)_2R^{16}$, —$S(O)_2N(R^{16})_2$, —$N(R^{16})C(O)N(R^{16})_2$, —$N(R^{16})C(O)OR^{16}$, —$OC(O)N(R^{16})_2$, —$S(O)R^{16}$, —$S(O)_2R^{16}$, —$NO_2$, =O, =S, and —$N(R^{16})$;

$C_{1-4}$ alkyl optionally substituted with one or more substituents independently selected from: halogen, —$OR^{16}$, —$SR^{16}$, —$N(R^{16})_2$, and —$NO_2$; and 4- to 6-membered heterocycle and $C_{3-8}$ carbocycle, each of which is optionally substituted with one or more substituents independently selected from: halogen, $C_{1-4}$ alkyl, $C_{1-4}$ haloalkyl, —$OR^{16}$, —$SR^{16}$, —$N(R^{16})_2$, and —$NO_2$;

$R^{10}$, $R^{11}$, $R^{12}$, $R^{13}$, $R^{14}$, and $R^{15}$ are each independently selected at each occurrence from:

hydrogen, $C_{1-4}$ alkyl, $C_{3-8}$ carbocycle, 4- to 8-membered heterocycle, and $C_{1-4}$ haloalkyl;

$R^{16}$ is independently selected at each occurrence from (iv), (v), and (vi):

(iv) hydrogen;

(v) $C_{1-4}$ alkyl optionally substituted with one or more substituents independently selected from:

halogen, —$OR^{20}$, —$SR^{20}$, —$N(R^{20})_2$, —$C(O)R^{20}$, —$C(O)OR^{20}$, —$OC(O)R^{20}$, —$C(O)N(R^{20})_2$, —$N(R^{20})C(O)R^{20}$, —$N(R^{20})C(O)N(R^{20})_2$, —$N(R^{20})C(O)OR^{20}$, —$OC(O)N(R^{20})_2$, —$S(O)R^{20}$, —$S(O)_2R^{20}$, —$N(R^{20})S(O)_2R^{20}$, —$S(O)_2N(R^{20})_2$, and —$NO_2$; and $C_{3-8}$ carbocycle and 4- to 8-membered heterocycle, either of which is optionally substituted with one or more substituents independently selected from: halogen, $C_{1-4}$ alkyl, $C_{1-4}$ haloalkyl, —$OR^{20}$, —$SR^{20}$, —$N(R^{20})_2$, —$C(O)R^{20}$, —$C(O)OR^{20}$, —$OC(O)R^{20}$, —$C(O)N(R^{20})_2$, —$N(R^{20})C(O)R^{20}$, —$N(R^{20})C(O)N(R^{20})_2$, —$N(R^{20})C(O)OR^{20}$, —$OC(O)N(R^{20})_2$, —$S(O)R^{20}$, —$S(O)_2R^{20}$, —$N(R^{20})S(O)_2R^{20}$, —$S(O)_2N(R^{20})_2$, and —$NO_2$; and (vi) $C_{3-8}$ carbocycle and 4- to 8-membered heterocycle, either of which is optionally substituted with one or more substituents independently selected from halogen, $C_{1-4}$ alkyl, $C_{1-4}$ haloalkyl, —$OR^{20}$, —$SR^{20}$, —$N(R^{20})_2$, —$C(O)R^{20}$, —$C(O)N(R^{20})_2$, —$C(O)OR^{20}$, —$OC(O)R^{20}$, —$N(R^{20})C(O)R^{20}$, —$N(R^{20})S(O)_2R^{20}$, —$N(R^{20})C(O)N(R^{20})_2$, —$N(R^{20})C(O)OR^{20}$, —$OC(O)N(R^{20})_2$, —$S(O)R^{20}$, —$S(O)_2R^{20}$, and —$NO_2$; and $R^{20}$ is independently selected at each occurrence from hydrogen, $C_{1-4}$ alkyl, $C_{1-4}$ haloalkyl, $C_{3-8}$ carbocycle, and 4- to 8-membered heterocycle.

5. The compound or salt of claim 1, wherein $A^1$ is selected from hydrogen, halogen, $C_{1-4}$ alkyl, $C_{1-4}$ haloalkyl, —$OR^{11}$, —$N(R^{11})_2$, and —CN.

6. The compound or salt of claim 1, wherein $A^2$ is selected from:

$C_{1-6}$ alkyl, $C_{2-6}$ alkenyl, and $C_{2-6}$ alkynyl, any of which is optionally substituted with one or more substituents independently selected from halogen, —$OR^{11}$, —$N(R^{11})_2$, —$C(O)N(R^{11})_2$, —$N(R^{11})C(O)R^{11}$, —$N(R^{11})S(O)_2R^{11}$, —$S(O)_2N(R^{11})_2$, —$NO_2$, =O, and —CN; and 5- to 10-membered heterocycle and $C_{3-10}$ carbocycle, any of which is optionally substituted with one or more substituents independently selected from:

halogen, —$OR^{11}$, —$N(R^{11})_2$, —$C(O)R^{11}$, —$C(O)N(R^{11})_2$, —$N(R^{11})C(O)R^{11}$, —$N(R^{11})S(O)_2R^{11}$, —$NO_2$, =O, and —CN;

$C_{1-6}$ alkyl, $C_{2-6}$ alkenyl, and $C_{3-6}$ alkynyl, any one of which is optionally substituted with one or more substituents independently selected from:

halogen, —$OR^{11}$, —$N(R^{11})_2$, —$C(O)R^{11}$, —$C(O)N(R^{11})_2$, —$N(R^{11})C(O)R^{11}$, —$N(R^{11})S(O)_2R^{11}$, —$NO_2$, —$NO_2$, =O, and —CN; and $C_{3-10}$ carbocycle and 4- to 10-membered heterocycle, any of which is optionally substituted with one or more substituents independently selected from halogen, —$OR^{11}$, —$N(R^{11})_2$, —$C(O)R^{11}$, —$C(O)N(R^{11})_2$, —$N(R^{11})C(O)R^{11}$, —$NO_2$, =O, —CN, $C_{1-6}$ alkyl, $C_{2-6}$ alkenyl, and $C_{2-6}$ alkynyl, the $C_{1-6}$ alkyl, $C_{2-6}$ alkenyl, and $C_{3-6}$ alkynyl are each optionally substituted with one or more substituents independently selected from: halogen, —$OR^{11}$, —$N(R^{11})_2$, —$C(O)R^{11}$, —$C(O)N(R^{11})_2$, —$N(R^{11})C(O)R^{11}$, —$N(R^{11})S(O)_2R^{11}$, —$NO_2$, =O, and —CN.

7. The compound or salt of claim 1, wherein $A^2$ is selected from pyrazolyl, triazolyl, oxazolyl, thiazolyl, morpholinyl, phenyl, and cyclopropyl, each of which is optionally substituted with one or more substituents independently selected from:

halogen, —$OR^{11}$, —$N(R^{11})_2$, —$C(O)R^{11}$, —$C(O)N(R^{11})_2$, —$N(R^{11})C(O)R^{11}$, —$N(R^{11})S(O)_2R^{11}$, —$NO_2$, =O, and —CN;

$C_{1-6}$ alkyl, $C_{2-6}$ alkenyl, and $C_{3-6}$ alkynyl, any one of which is optionally substituted with one or more substituents independently selected from: halogen, —$OR^{11}$, —$N(R^{11})_2$, —$C(O)R^{11}$, —$C(O)N(R^{11})_2$, —$N(R^{11})C(O)R^{11}$, —$N(R^{11})S(O)_2R^{11}$, —$NO_2$; =O, and —CN; and $C_{3-10}$ carbocycle and 4- to 10-membered heterocycle, any of which is optionally substituted with one or more substituents independently selected from halogen, —$OR^{11}$, —$N(R^{11})_2$, —$C(O)R^{11}$, —$C(O)N(R^{11})_2$, —$N(R^{11})C(O)R^{11}$, —$NO_2$, =O, —CN, $C_{1-6}$ alkyl, $C_{2-6}$ alkenyl, and $C_{2-6}$ alkynyl, the $C_{1-6}$ alkyl, $C_{2-6}$ alkenyl, and $C_{3-6}$ alkynyl are each optionally substituted with one or more substituents independently selected from: halogen, —$OR^{11}$, —$N(R^{11})_2$, —$C(O)R^{11}$, —$C(O)N(R^{11})_2$, —$N(R^{11})C(O)R^{11}$, —$N(R^{11})S(O)_2R^{11}$, —$NO_2$, =O, and —CN.

8. The compound or salt of claim 1, wherein $A^2$ is selected from:

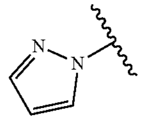 , 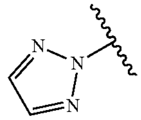 , 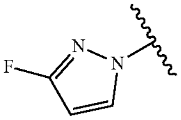 ,

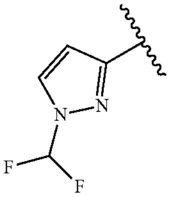 , 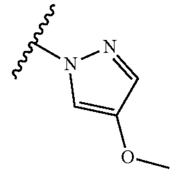 ,

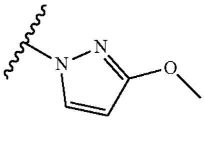 , 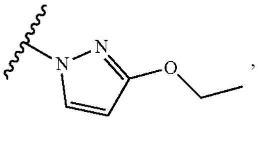 ,

-continued

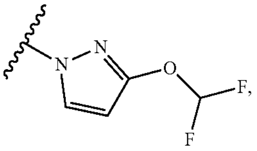 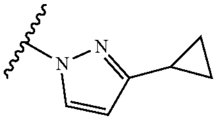 ,

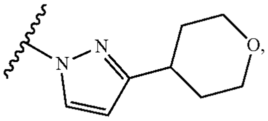 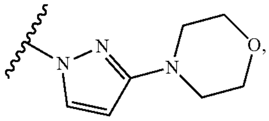

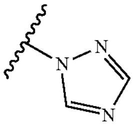 , 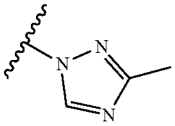 ,

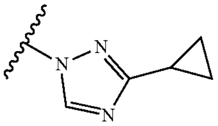 , 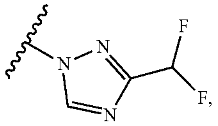

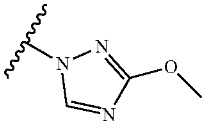 , 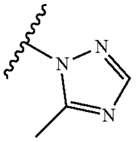 , 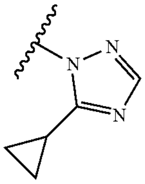 ,

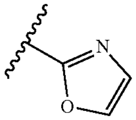 , 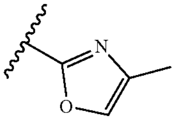 , 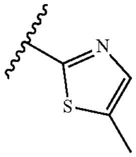 ,

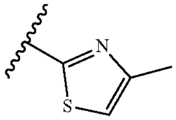 , 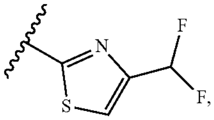

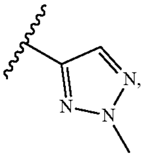 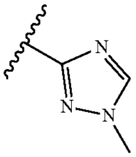 , 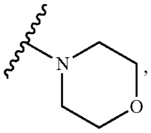 ,

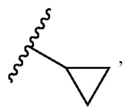 , 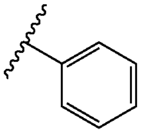 ,

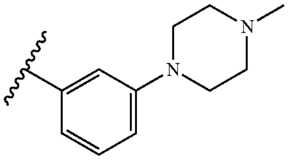 , —$CH_3$, 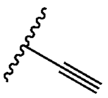 ,

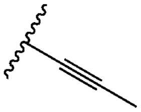 , 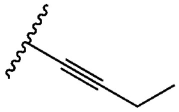 ,

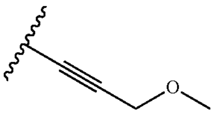 , 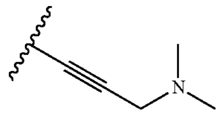 ,

-continued

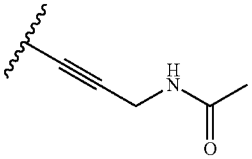,
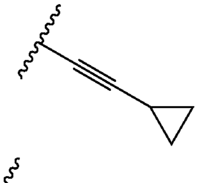,
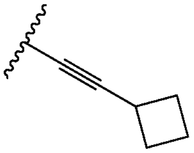,
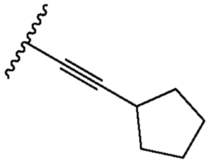,
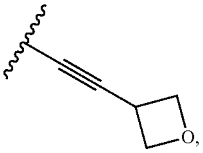
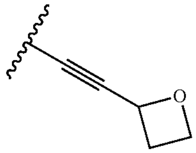,
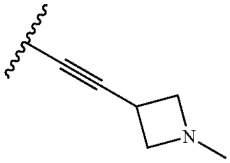, and
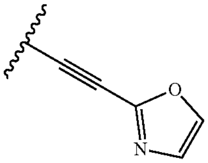.

9. The compound or salt of claim 1, wherein $R^1$ is selected from hydrogen, halogen, —$OR^{10}$, —$N(R^{10})_2$, —$NO_2$, —CN, and $C_{1-6}$ alkyl optionally substituted with one or more substituents independently selected from halogen, —$OR^{10}$, and —$N(R^{10})_2$.

10. The compound or salt of claim 1, wherein $R^1$ is selected from hydrogen, fluoro, methoxy, —CN, methyl, ethyl, (methoxy) methyl, and

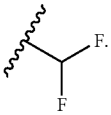 [SMILES: *C(F)F]

11. The compound or salt of claim 1, wherein q is 1.

12. The compound or salt of claim 1, wherein n is 0.

13. The compound or salt of claim 1, wherein p is selected from 0, 1, and 2.

14. The compound or salt of claim 1, wherein $R^4$ is independently selected at each instance from halogen, —$OR^{14}$, —$SR^{14}$, —$N(R^{14})_2$, —$C(O)R^{14}$, —$C(O)N(R^{14})_2$, —$N(R^{14})C(O)R^{14}$, —$C(O)OR^{14}$, —$OC(O)R^{14}$, —$NO_2$, and —CN.

15. The compound or salt of claim 1, wherein $L^1$, $L^2$, $L^3$, and $L^4$ are each independently selected from (a) and (b):

(a) —O—, —$N(R^{15})$—, —S—, —$N(R^{15})C(O)$—, —$N(R^{15})C(O)O$—, —$N(R^{15})S(O)_2$, —$N(R^{15})N(R^{15})$—, and —$(R^{15})NC(O)N(R^{15})$—; and (b) $C_{1-6}$ alkylene, $C_{2-6}$ alkenylene, $C_{2-6}$ alkynylene, $C_{3-6}$ carbocyclene, and 4- to 6-membered heterocyclene, any of which is optionally substituted with one or more substituents independently selected from halogen, —$OR^{15}$, —O, and —CN;

wherein $L^2$, $L^3$, and $L^4$ are each optionally absent;

wherein no more than two of $L^1$, $L^2$, $L^3$, and $L^4$ are selected from (a) and the two selected are not adjacent; and $R^{15}$ is selected from hydrogen and $C_{1-4}$ alkyl.

16. The compound or salt of claim 1, wherein $L^4$ is absent.

17. The compound or salt of claim 1, wherein $L^3$ is absent, —O—, ethynyl, or methylene substituted with ═O.

18. The compound or salt of claim 1, wherein $L^2$ is absent, methylene, (methyl)methylene, ethylene, or —O—.

19. The compound or salt of claim 1, wherein $L^1$ is selected from —$N(R^{15})C(O)$—, —$N(R^{15})$—, —$N(R^{15})S(O)_2$—, —$(R^{15})NC(O)N(R^{15})$—, and 4- to 6-membered heterocyclene optionally substituted with one or more halogen atoms.

20. The compound or salt of claim 1, wherein L is selected from

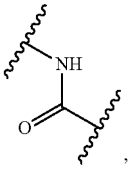,
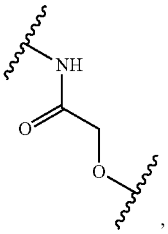,
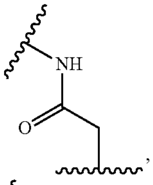,
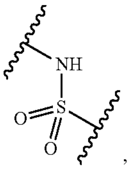,
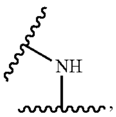,
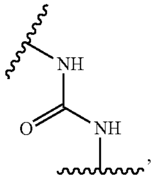,
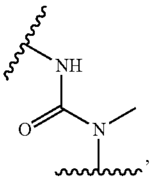,
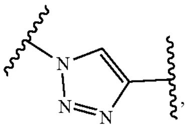,
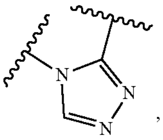,
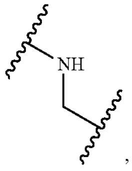,
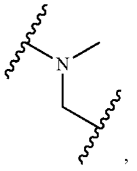,
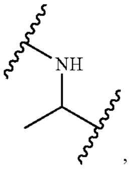,
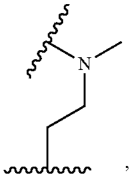,
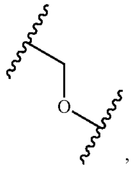,
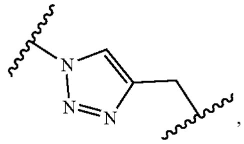,
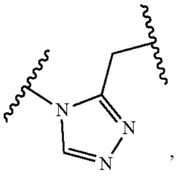,
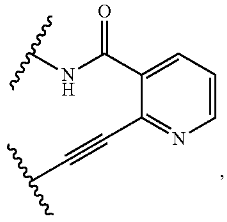, -continued

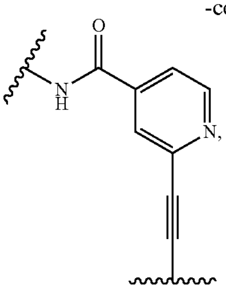

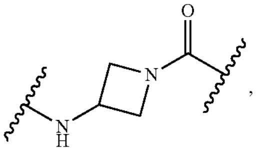,

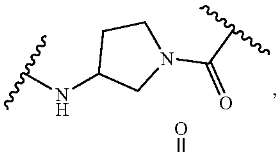,

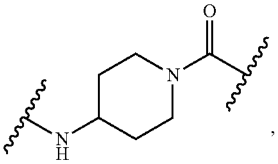, and

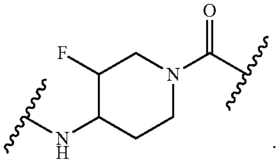 [SMILES: *NC1CCN(C(*)=O)CC1F].

21. The compound or salt of claim 1, wherein $R^5$ is selected from 4- to 10-membered heterocycle and $C_{3-10}$ carbocycle, any of which is optionally substituted with one or more substituents independently selected from:

halogen, $—OR^{16}$, $—SR^{16}$, $—N(R^{16})_2$, $—C(O)N(R^{16})_2$, $—C(O)OR^{16}$, $—OC(O)R^{16}$, $—N(R^{16})C(O)R^{16}$, $—N(R^{16})S(O)_2R^{16}$, $—S(O)_2N(R^{16})_2$, $—N(R^{16})C(O)N(R^{16})_2$, $—N(R^{16})C(O)OR^{16}$, $—OC(O)N(R^{16})_2$, $—S(O)R^{16}$, $—S(O)_2R^{16}$, $—NO_2$, =O, =S, and $=N(R^{16})$;

$C_{1-4}$ alkyl optionally substituted with one or more substituents independently selected from: halogen, $—OR^{16}$, $—SR^{16}$, $—N(R^{16})_2$, and $—NO_2$; and 4- to 6-membered heterocycle and $C_{3-8}$ carbocycle, each of which is optionally substituted with one or more substituents independently selected from:

halogen, $C_{1-4}$ alkyl, $C_{1-4}$ haloalkyl, $—OR^{16}$, $—SR^{16}$, $—N(R^{16})_2$, and $—NO_2$.

22. The compound or salt of claim 1, wherein $R^5$ is 4- to 10-membered heterocycle optionally substituted with one or more substituents independently selected from:

halogen, $—OR^{16}$, $—SR^{16}$, $—N(R^{16})_2$, $—C(O)N(R^{16})_2$, $—C(O)OR^{16}$, $—OC(O)R^{16}$, $—N(R^{16})C(O)R^{16}$, $—N(R^{16})S(O)_2R^{16}$, $—S(O)_2N(R^{16})_2$, $—N(R^{16})C(O)N(R^{16})_2$, $—N(R^{16})C(O)OR^{16}$, $—OC(O)N(R^{16})_2$, $—S(O)R^{16}$, $—S(O)_2R^{16}$, $—NO_2$, =O, =S, and $—N(R^{16})$;

$C_{1-4}$ alkyl optionally substituted with one or more substituents independently selected from: halogen, $—OR^{16}$, $—SR^{16}$, $—N(R^{16})_2$, and $—NO_2$; and 4- to 6-membered heterocycle and $C_{3-8}$ carbocycle, each of which is optionally substituted with one or more substituents independently selected from:

halogen, $C_{1-4}$ alkyl, $C_{1-4}$ haloalkyl, $—OR^{16}$, $—SR^{16}$, $—N(R^{16})_2$, and $—NO_2$.

23. The compound or salt of claim 1, wherein $R^5$ is selected from 4- to 10-membered heterocycle and $C_{3-10}$ carbocycle, any of which is optionally substituted with one or more substituents independently selected from: fluoro, chloro, methyl, ethyl, fluoromethyl, difluoromethyl, trifluoromethyl, hydroxy, $—CH_2OH$, methoxy, $—CH_2OCH_3$,

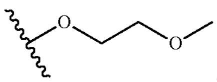, 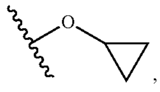, 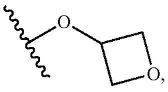

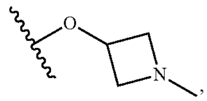, difluoromethoxy, trifluoromethoxy, $—NH_2$, dimethylamino, $—CH_2N(CH_3)_2$,

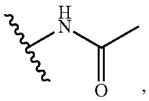, 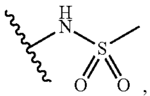, 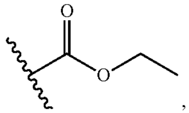,

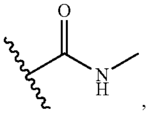, 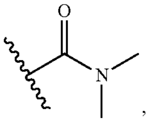, 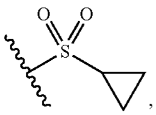,

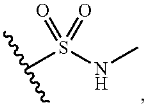,

=O, cyclopropyl, phenyl, morpholinyl, pyrazolyl,

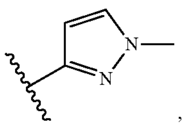 [SMILES: *c1ccn(C)n1], and pyridinyl.

24. The compound or salt of claim 1, wherein $R^5$ is selected from optionally substituted pyrazolyl, optionally substituted thiazolyl, optionally substituted oxazolyl, optionally substituted pyridyl, optionally substituted pyrimidyl, optionally substituted pyrazinyl, optionally substituted pyridazinyl, optionally substituted benzo[d]isoxazolyl, optionally substituted imidazo[1,2-a]pyridinyl, optionally substituted 1H-benzo[d]imidazolyl, optionally substituted 1H-pyrazolo[3,4-b]pyridinyl, optionally substituted 2H-pyrrolo[3,4-c]pyridinyl, and optionally substituted isoquinolinyl, optionally substituted isoxazolyl, optionally substituted isothiazole, optionally substituted 1,2,3-thiadiazolyl, optionally substituted 5,6-dihydro-4H-pyrrolo[1,2-b]pyrazolyl, optionally substituted 2,3-dihydropyrazolo[5,1-b]oxazolyl, optionally substituted 5,6-dihydro-3H-furo[2,3-d]imidazolyl, optionally substituted indolizinyl, optionally substituted pyrazolo[1,5-a]pyridinyl, optionally substituted pyrrolo[1,2-a]pyrimidinyl, optionally substituted pyrazolo[1,5-a]pyrimidinyl, optionally substituted imidazo[1,2-a]pyrimidinyl, optionally substituted imidazo[1,2-b]pyridazinyl, optionally substituted [1,2,4]triazolo[1,5-a]pyridinyl, optionally substituted 6,7-dihydro-5H-cyclopenta[b]pyridinyl, optionally substituted 6,7-dihydro-5H-cyclopenta[c]pyridinyl, optionally substituted 5,6,7,8-tetrahydroisoquinolinyl, optionally substituted 3,4-dihydro-2H-pyrano[2,3-b]pyridinyl, optionally substituted 2,3- dihydro-[1,4]dioxino[2,3-b]pyridinyl, optionally substituted 5,7-dihydrofuro[3,4-b]pyridinyl, optionally substituted 2,3-dihydrofuro[2,3-c]pyridinyl, optionally substituted 2,3-dihydrofuro[2,3-b]pyridinyl, optionally substituted [1,3]dioxolo[4,5-b]pyridinyl, optionally substituted furo[2,3-b]pyridinyl, optionally substituted thieno[2,3-b]pyridinyl, optionally substituted 1,2-dihydro-3H-indazol-3-onyl, optionally substituted 1H-benzo[d][1,2,3]triazolyl, optionally substituted 1,3-dihydro-2H-benzo[d]imidazol-2-onyl, optionally substituted benzo[d]oxazol-2(3H)-onyl, optionally substituted benzo[d]thiazol-2(3H)-onyl, optionally substituted 1H-indazolyl, optionally substituted indolin-2-onyl, optionally substituted 1,3-dihydro-2H-pyrrolo[2,3-b]pyridin-2-onyl, 2-azaspiro[3.3]heptanyl, optionally substituted 6-azaspiro[3.4]octanyl, optionally substituted 5-azaspiro[3.4]octanyl, optionally substituted 2-azaspiro[3.5]nonanyl, optionally substituted 7-azaspiro[3.5]nonanyl, optionally substituted 6-azaspiro[3.5]nonanyl, optionally substituted oxetanyl, optionally substituted pyrrolyl, optionally substituted morpholinyl, optionally substituted azetidinyl, optionally substituted pyrrolidinyl, optionally substituted tetrahydro-2H-thiopyranyl, optionally substituted piperidinyl, optionally substituted cyclopropyl, optionally substituted cyclobutyl, and optionally substituted phenyl.

25. The compound or salt of claim 1, wherein $R^5$ is selected from;

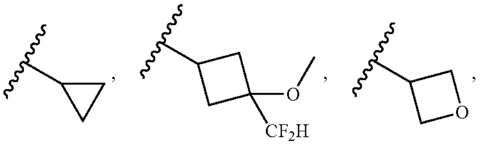

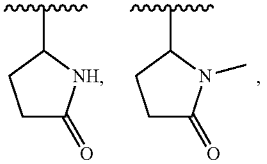

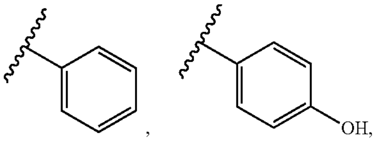

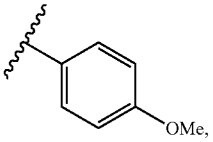

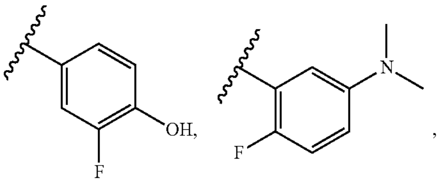

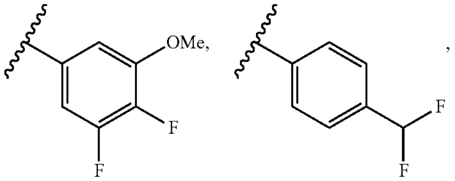

-continued

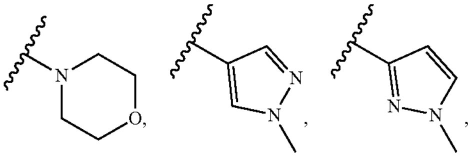

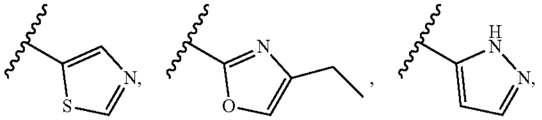

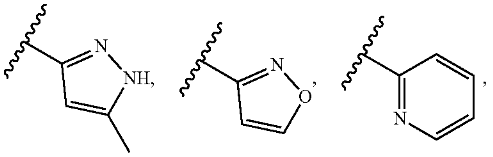

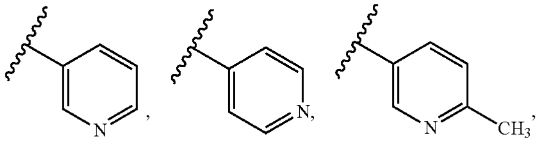

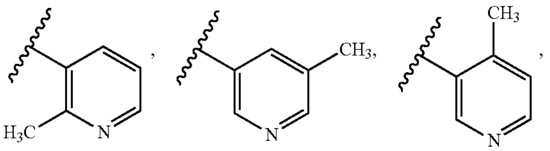

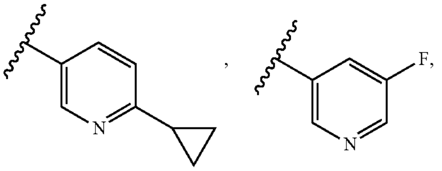

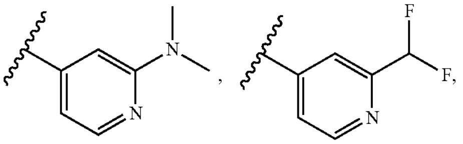

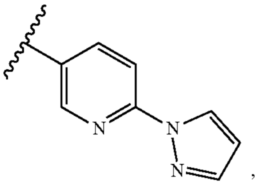

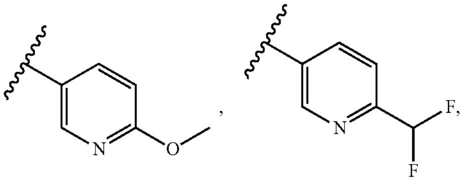

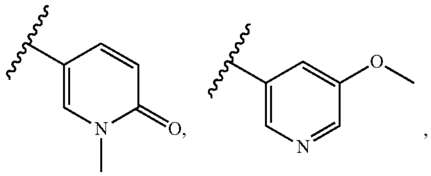

-continued
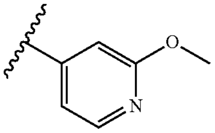 , 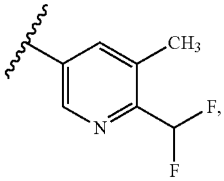
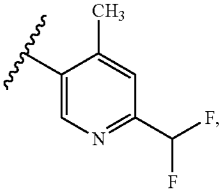 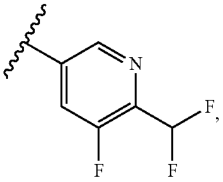
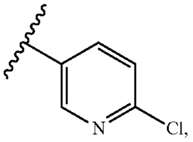 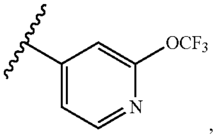 ,
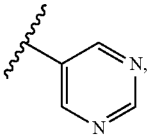 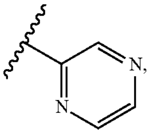 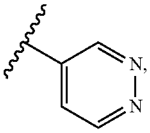
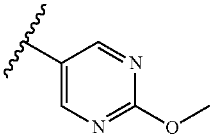 , 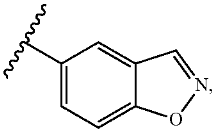
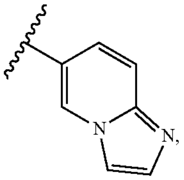 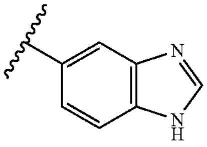 ,
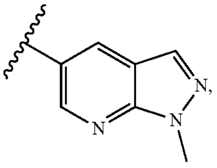 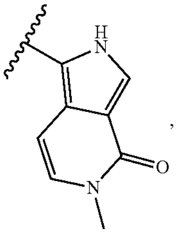 ,
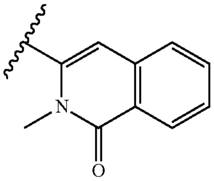 , 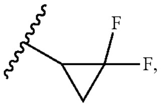
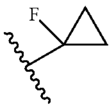 , 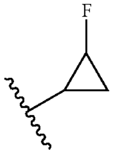 ,
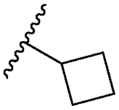 , 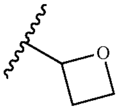 , 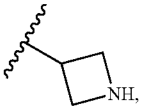
-continued
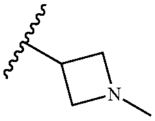 , 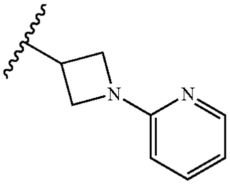 ,
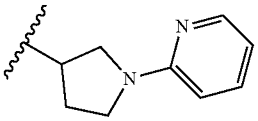 , 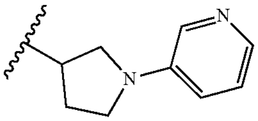 ,
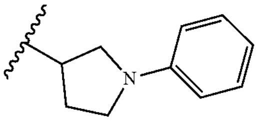 , 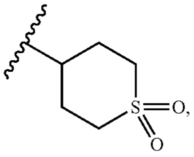
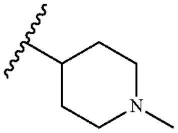 , 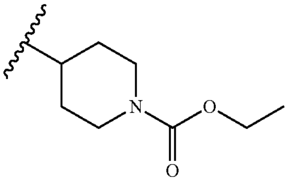 ,
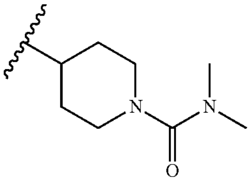 , 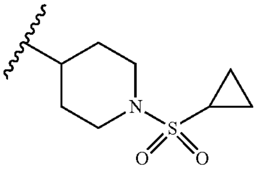 ,
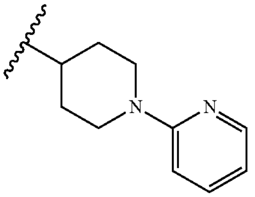 , 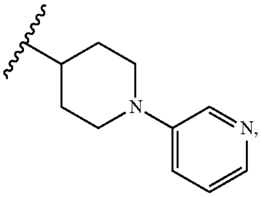
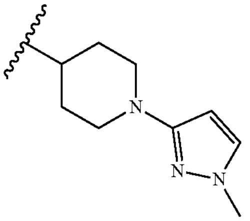 , 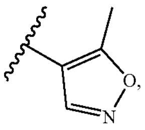
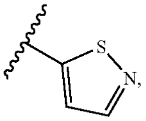 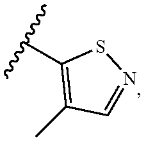 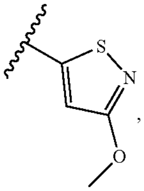 ,
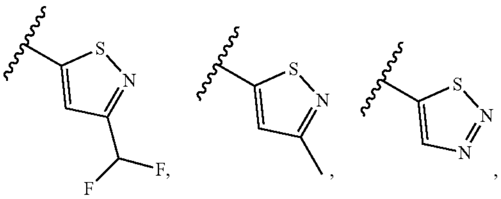

-continued
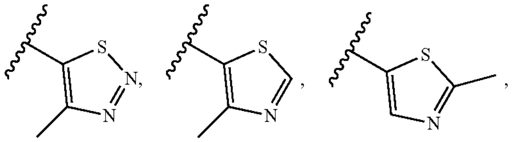
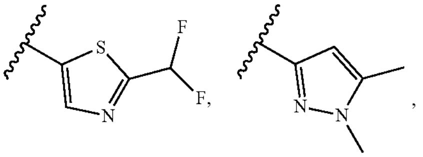
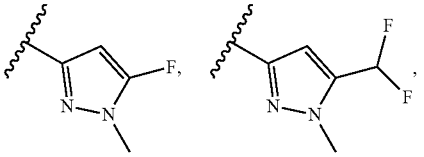
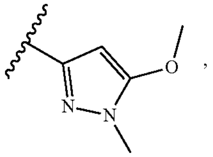
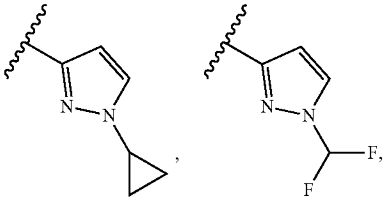
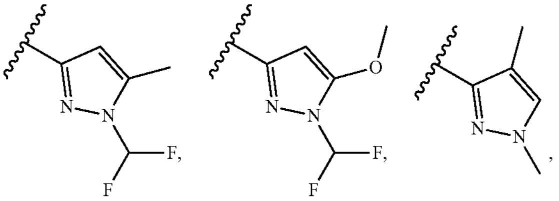
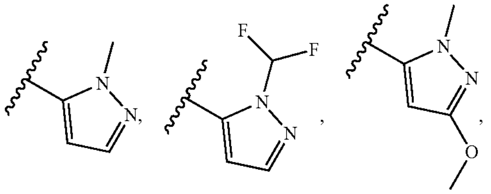
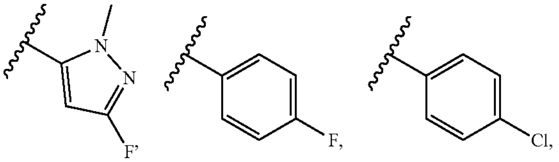
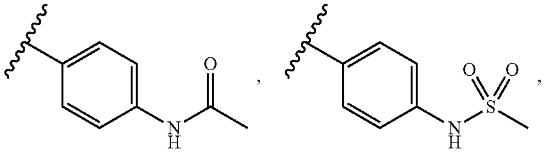
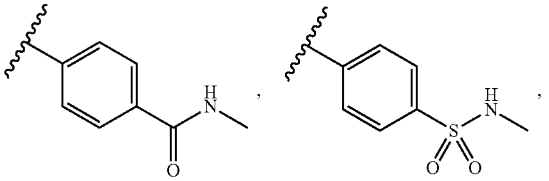
-continued
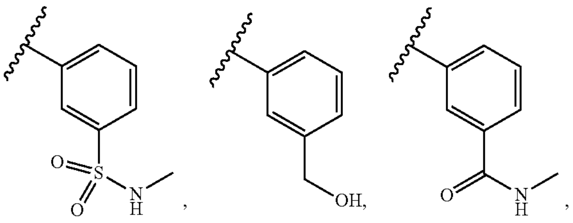
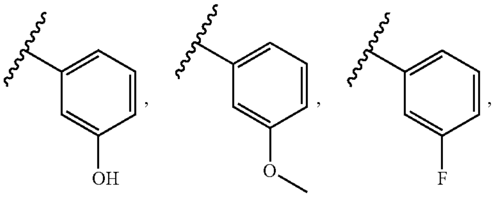
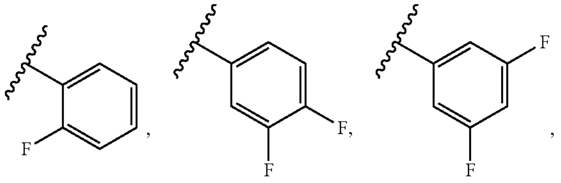
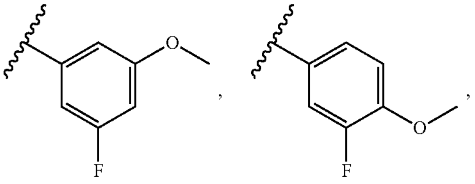
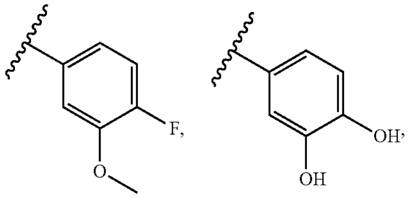
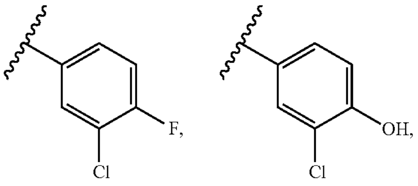
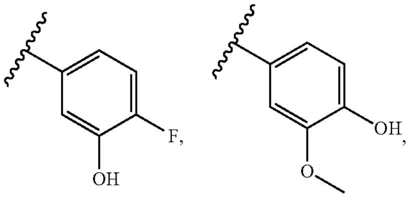
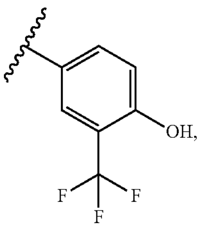

-continued
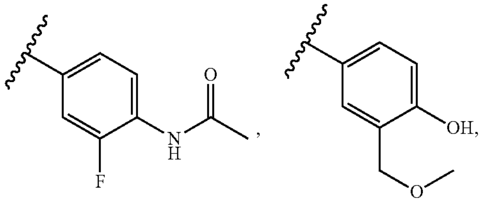
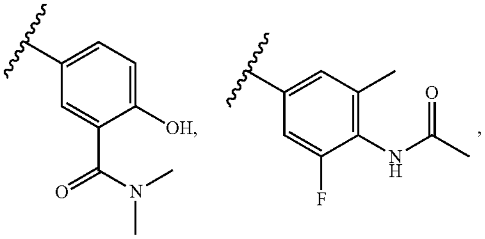
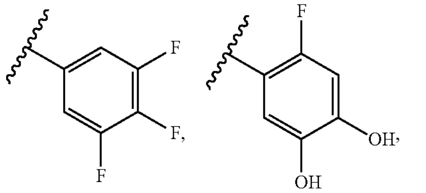
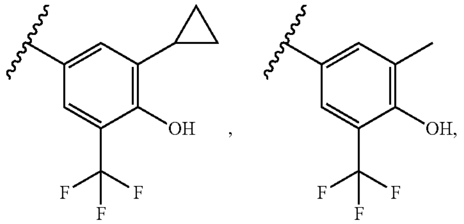
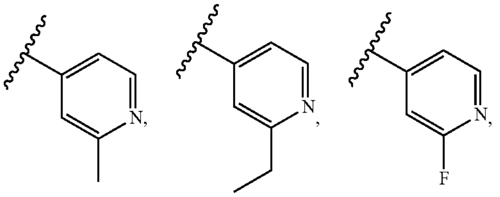
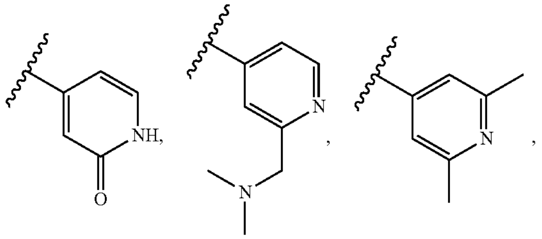
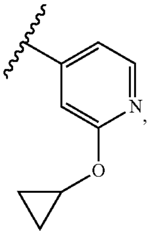
-continued
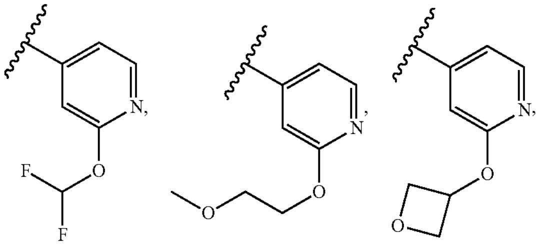
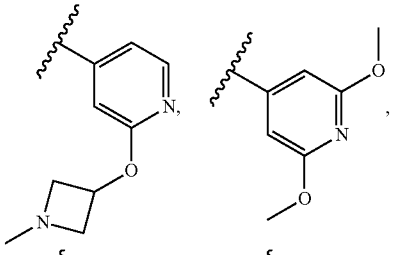
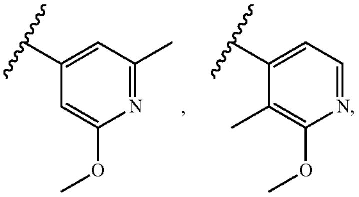
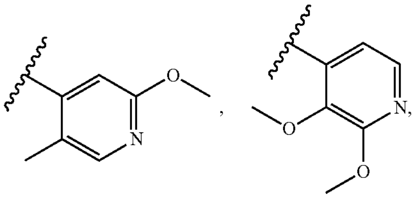
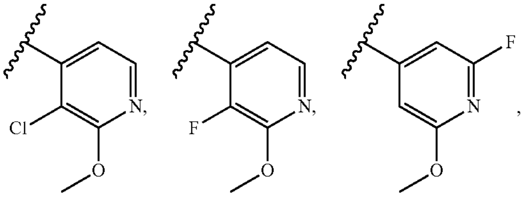
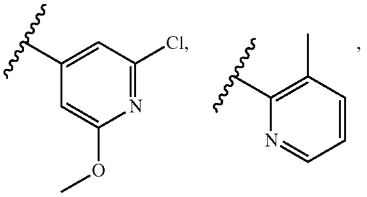
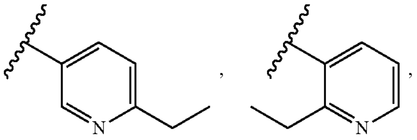
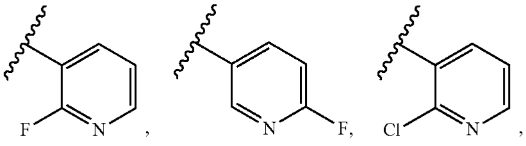
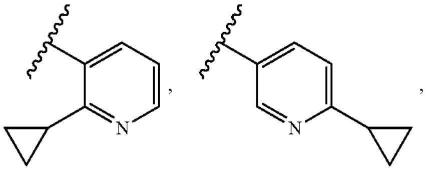

-continued
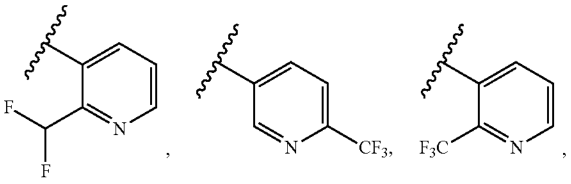
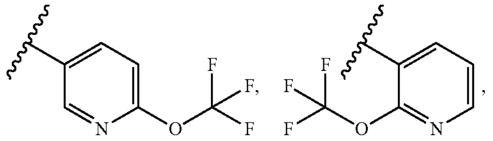
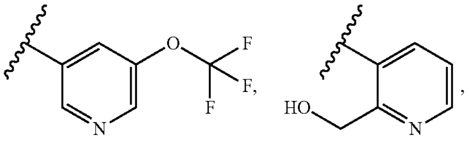
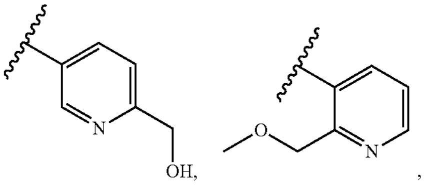
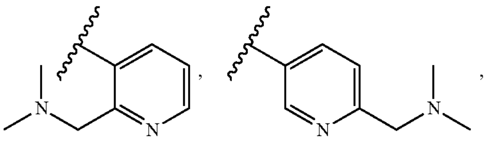
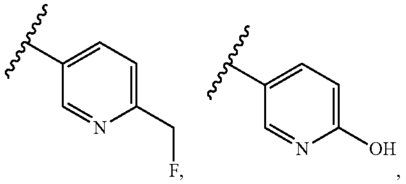
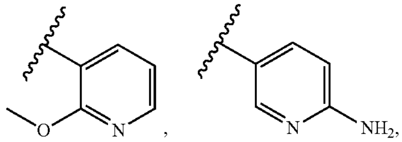
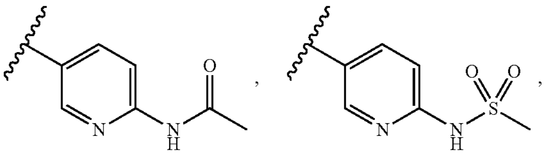
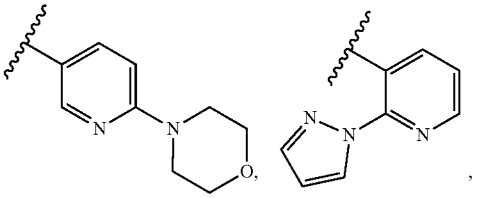
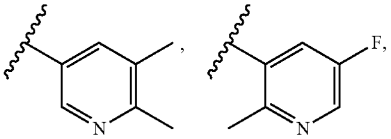
-continued
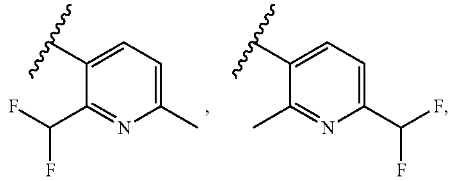
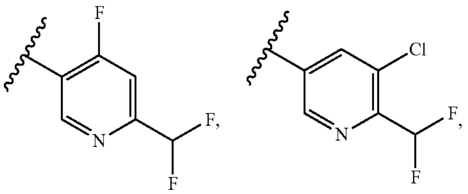
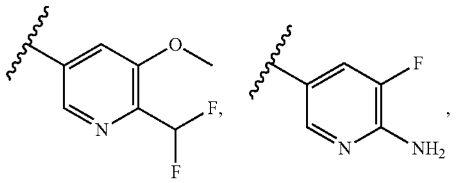
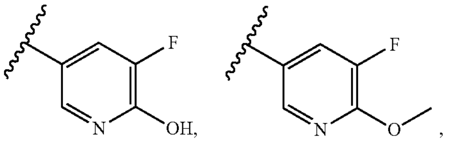
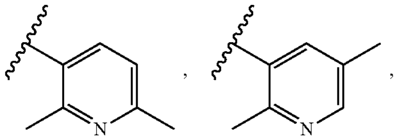
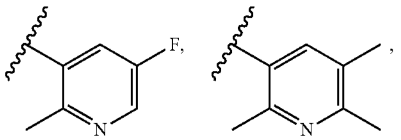
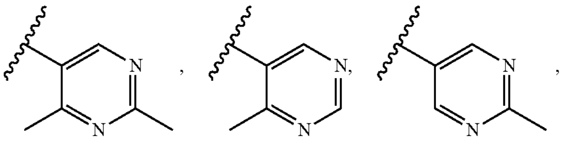
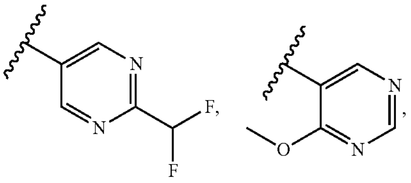
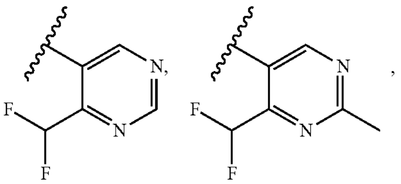
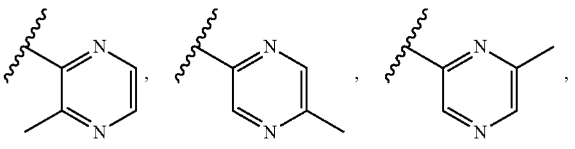

-continued
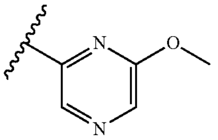 , 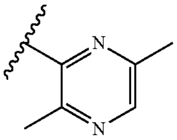 ,
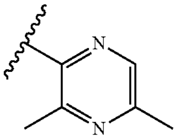 , 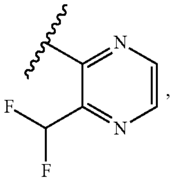 ,
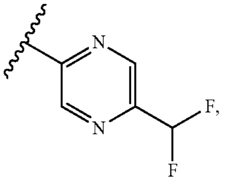 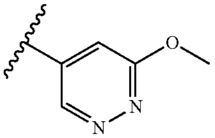 ,
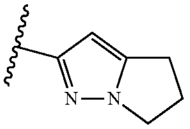 , 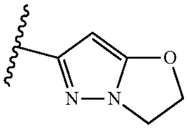 ,
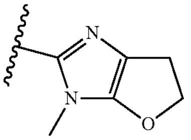 , 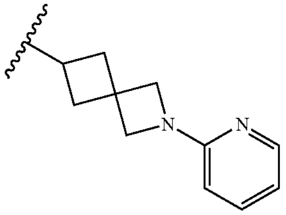 ,
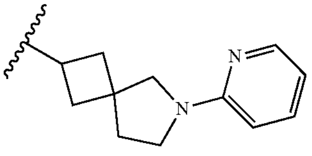 , 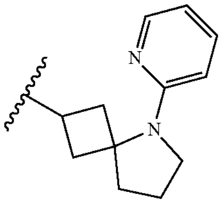 ,
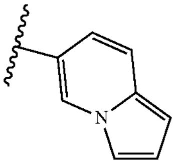 , 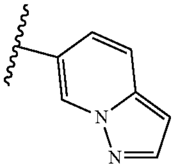 ,
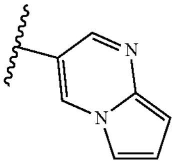 , 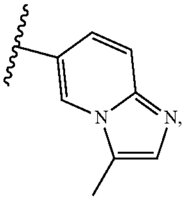
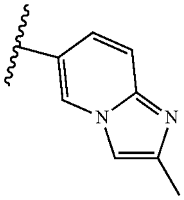 , 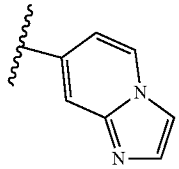 ,
-continued
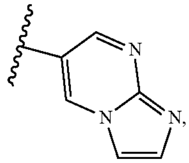 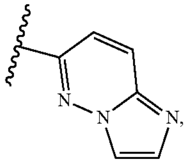
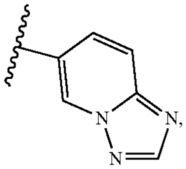 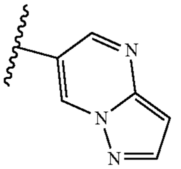 ,
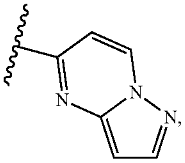 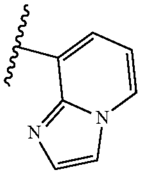 , 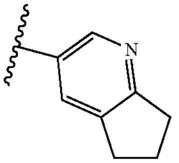 ,
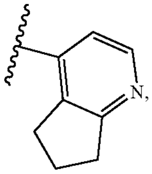 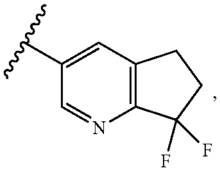 ,
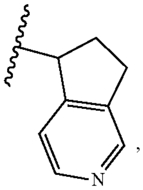 , 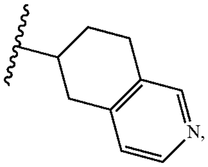 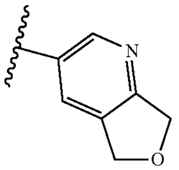 ,
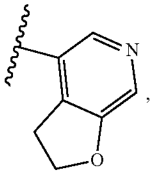 , 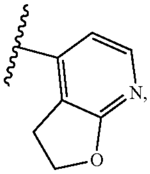 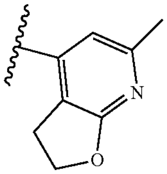 ,
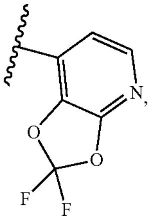 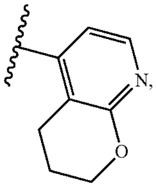 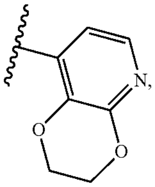
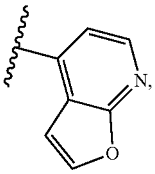 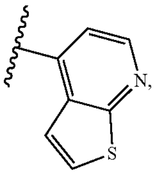 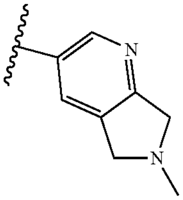 ,
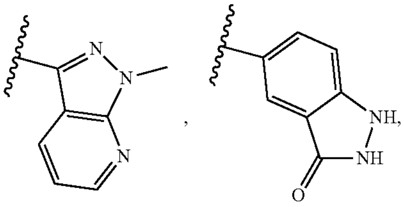

-continued
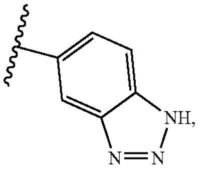, 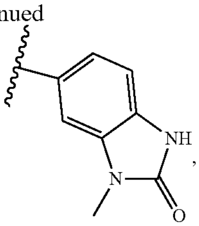,
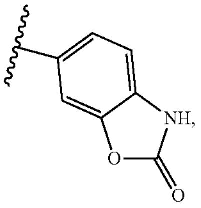, 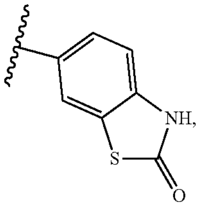,
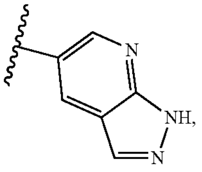, 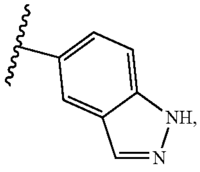,
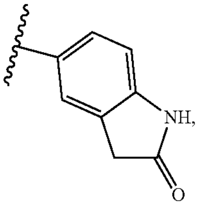, 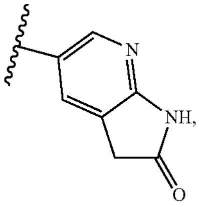,
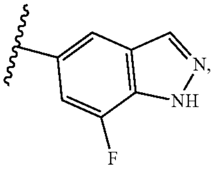, 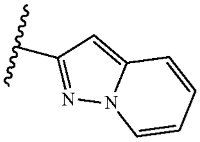,
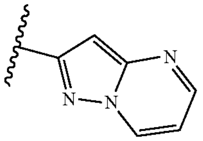, 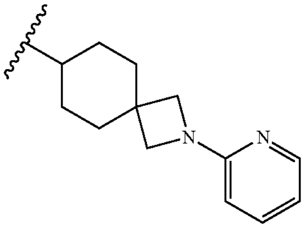,
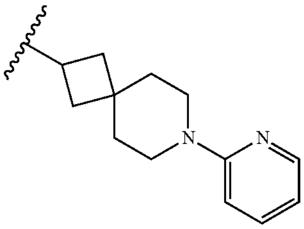,
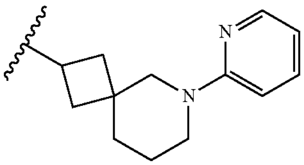, 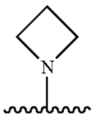, 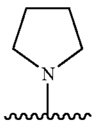,
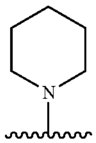, 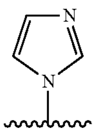, 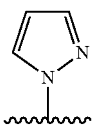, 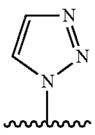,
-continued
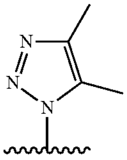, 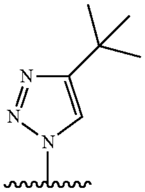, 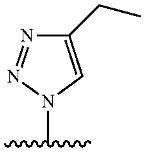,
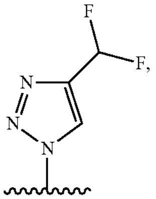, 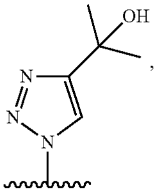, 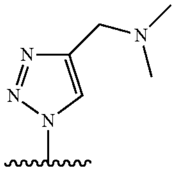,
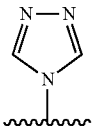, 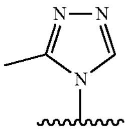, 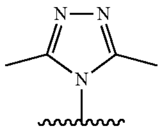,
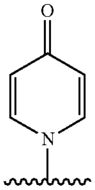, 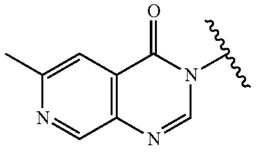, and
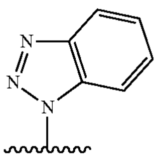.
26. The compound or salt of claim 1, wherein the compound of Formula (I) is selected from:
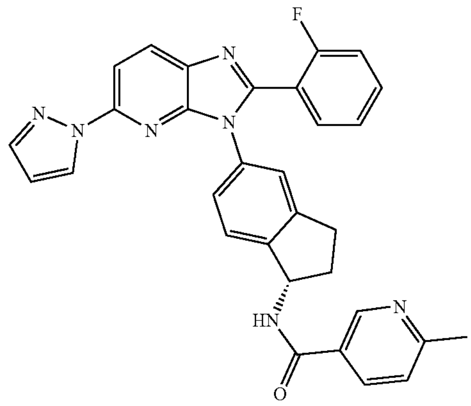, -continued
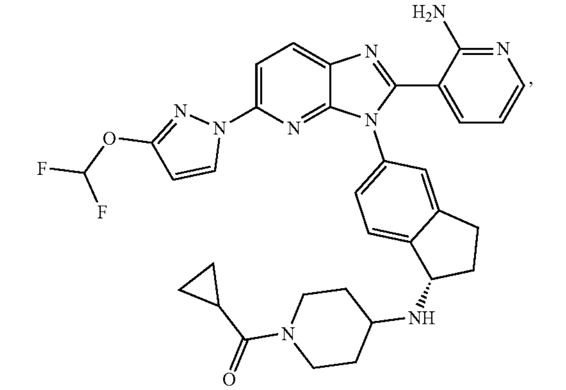
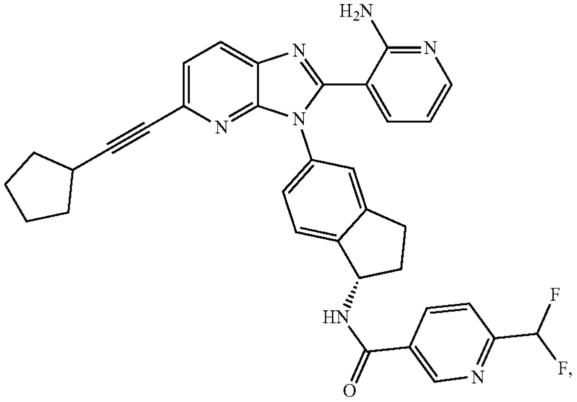
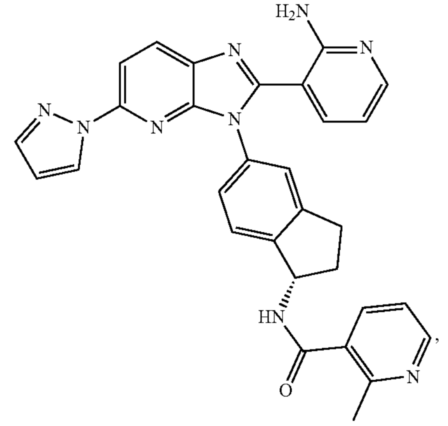
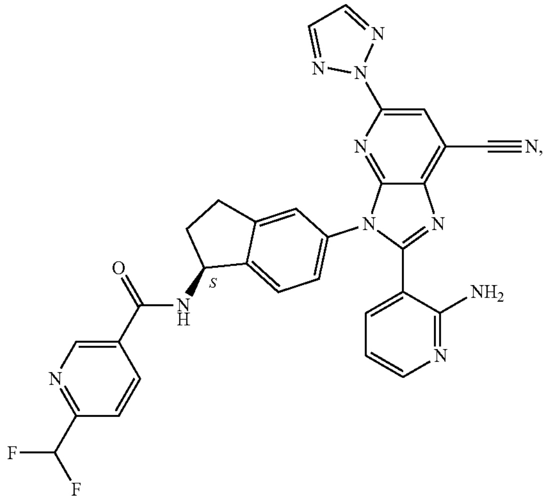
-continued
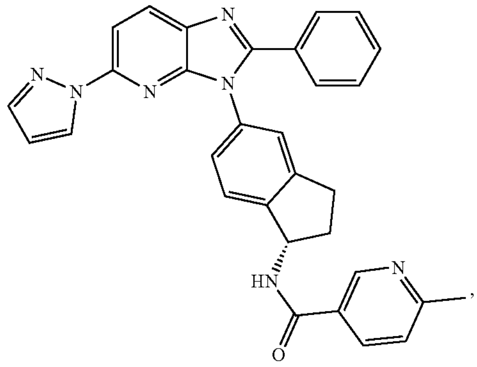
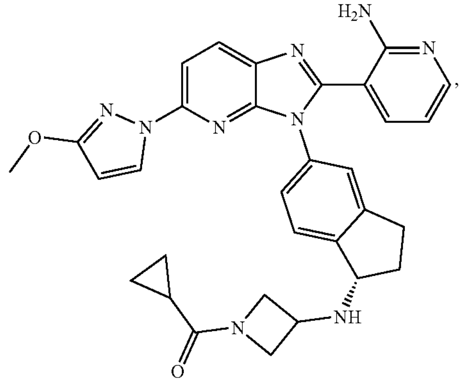
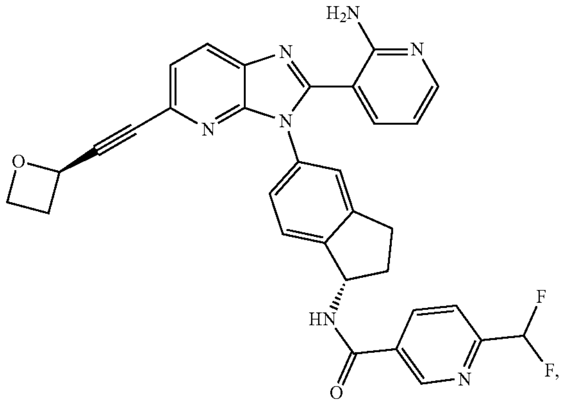
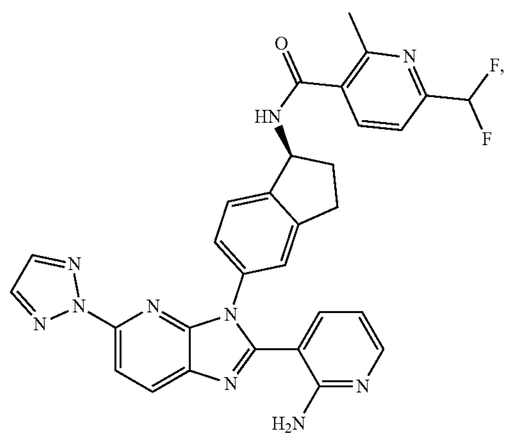

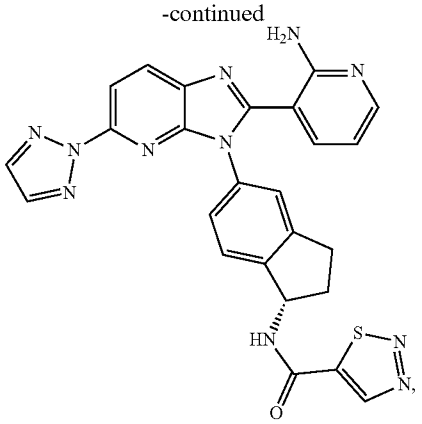
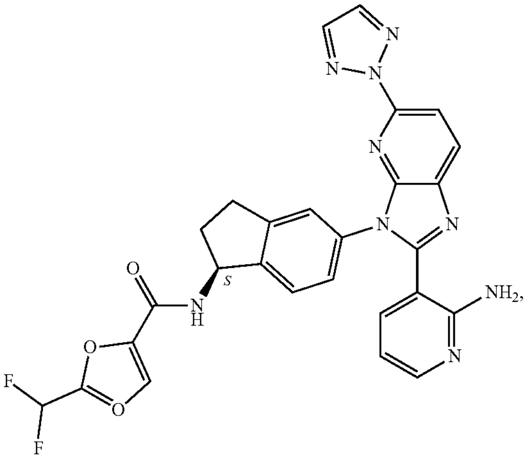
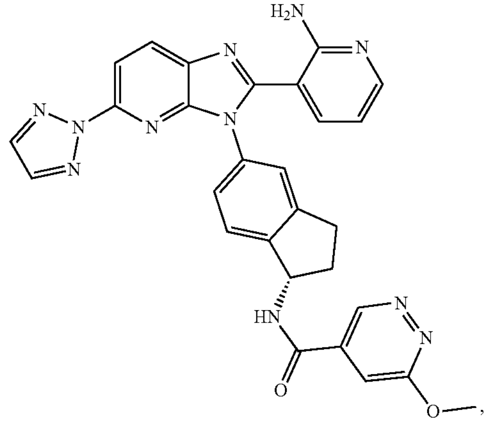
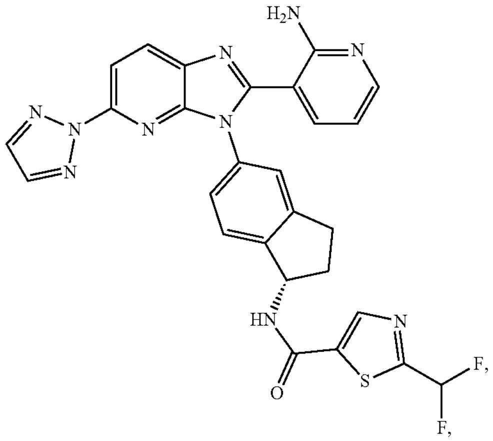
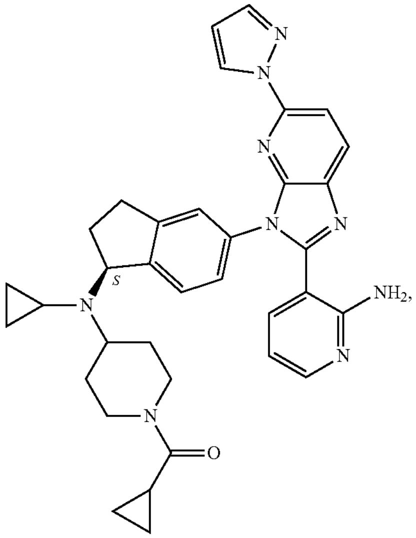
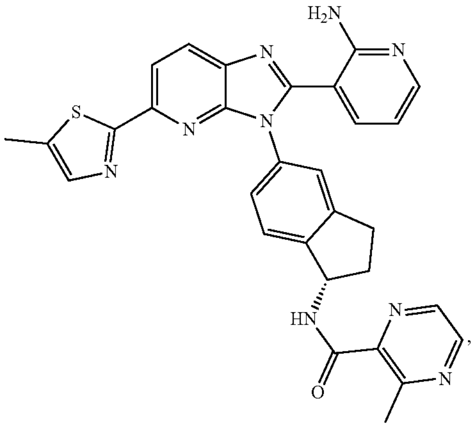
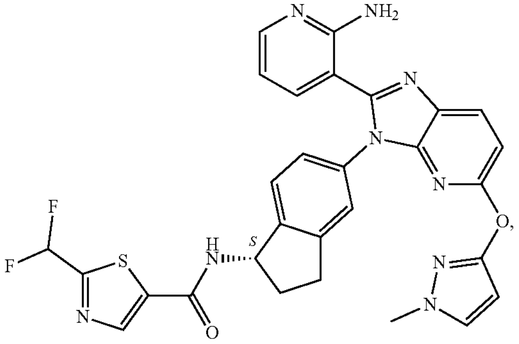

-continued
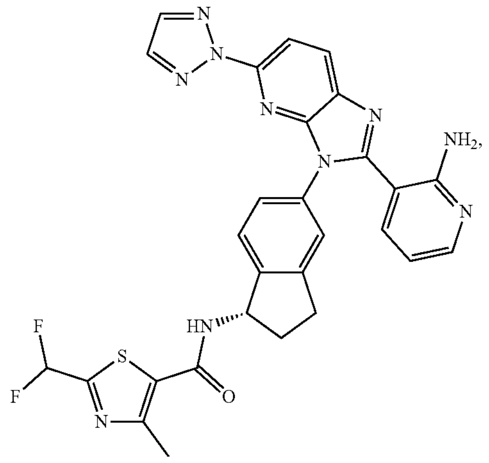
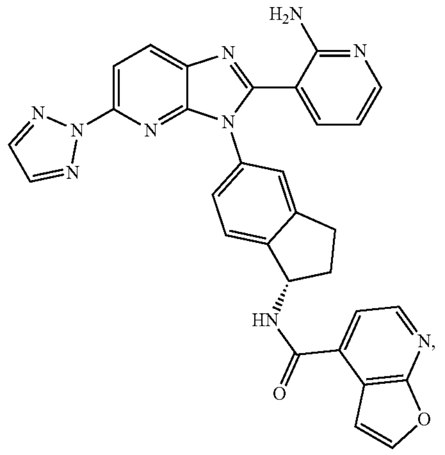
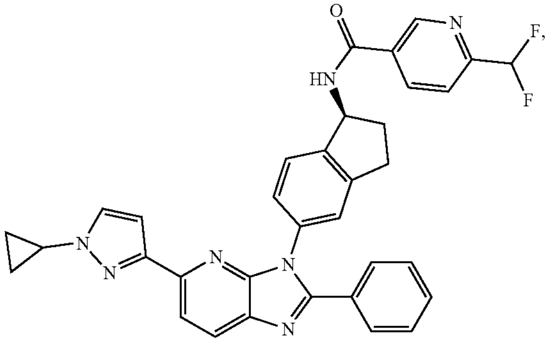
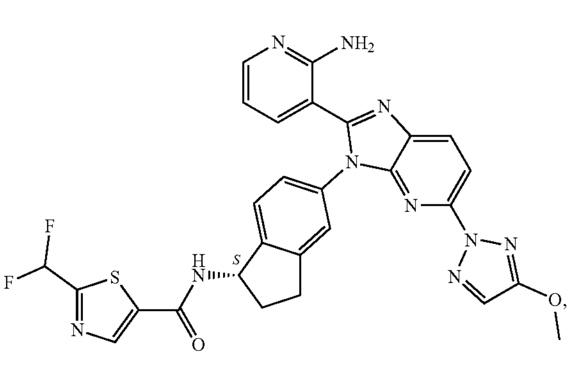
-continued
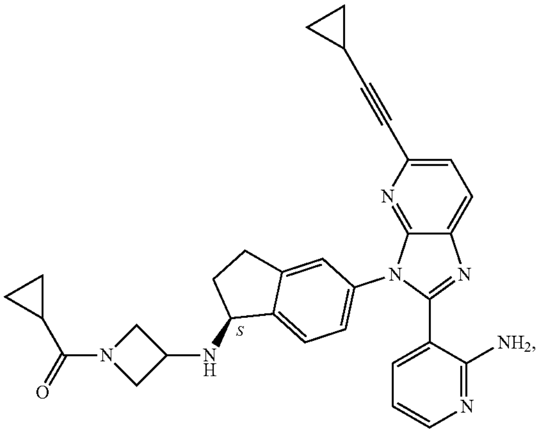
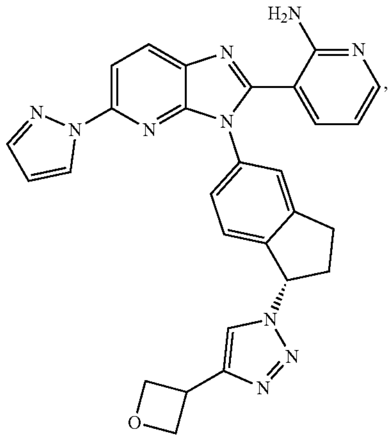
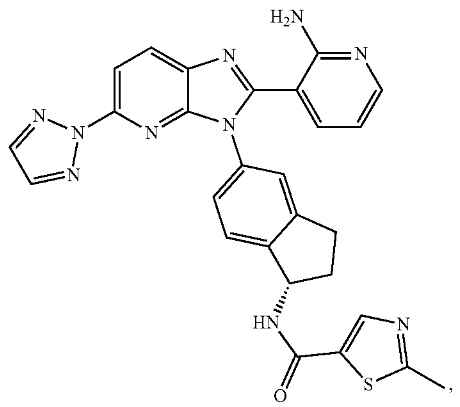
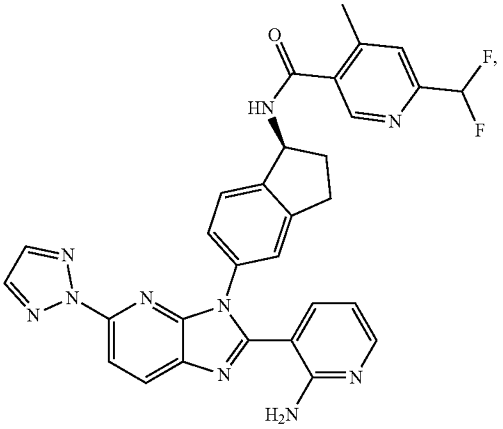

-continued
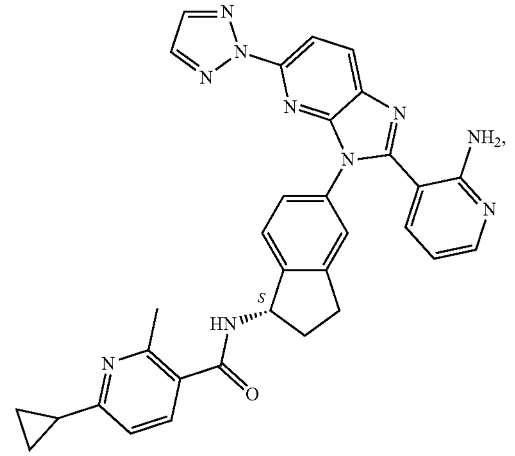
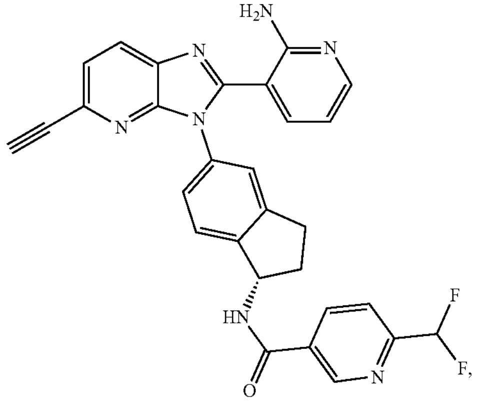
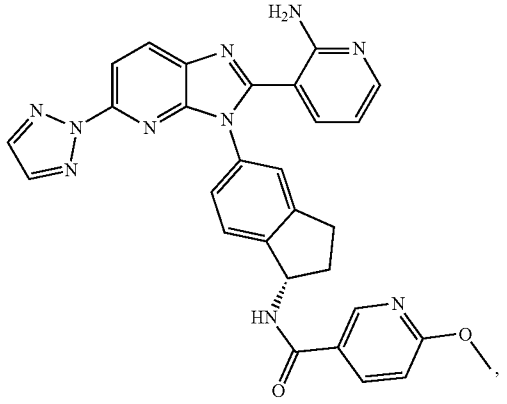
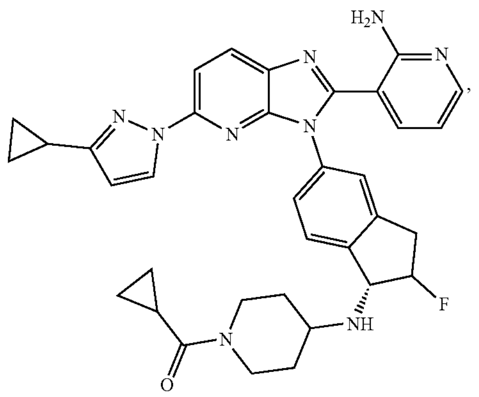
-continued
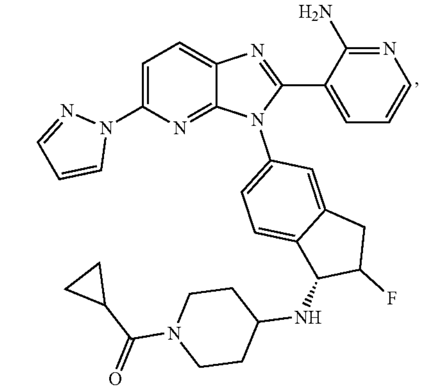
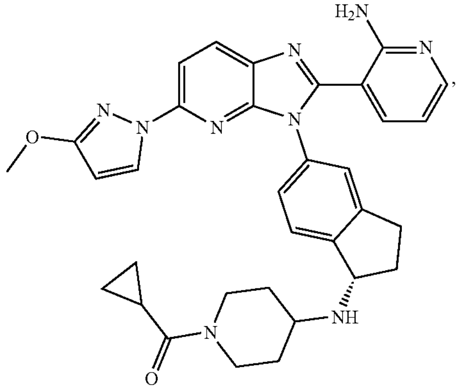
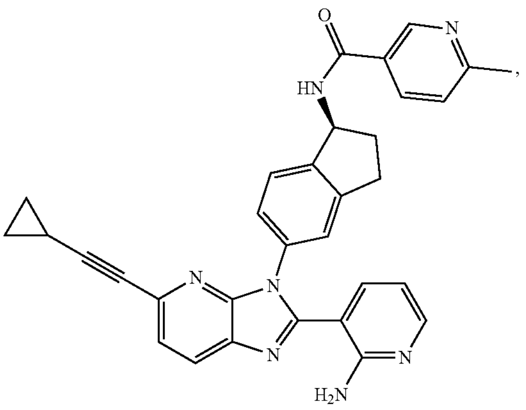
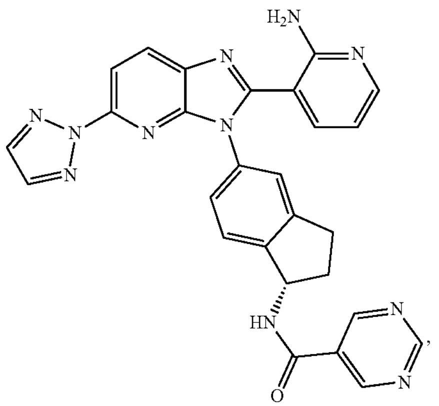

-continued
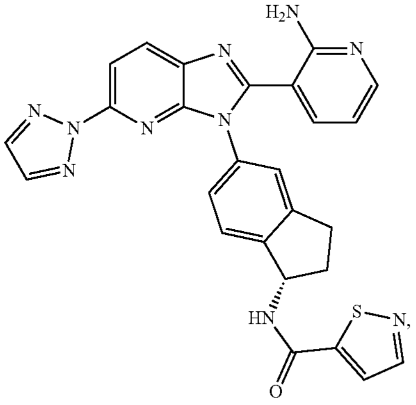
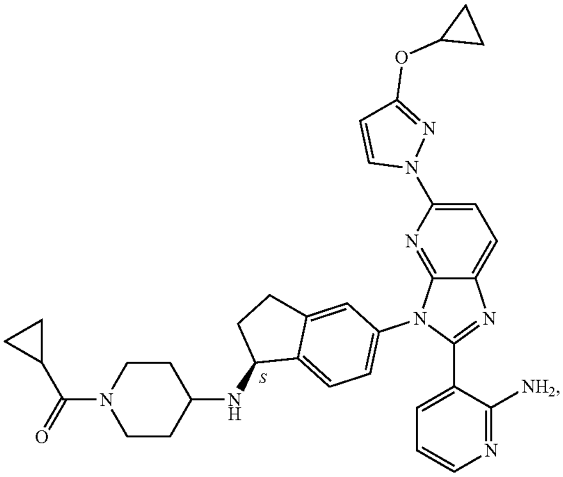
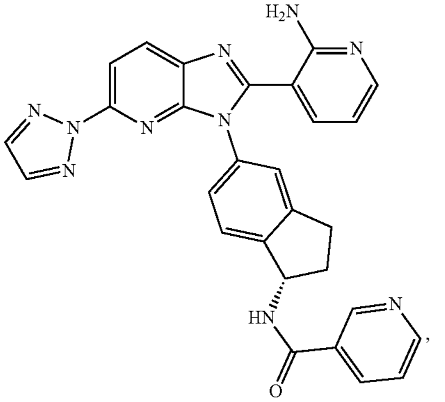
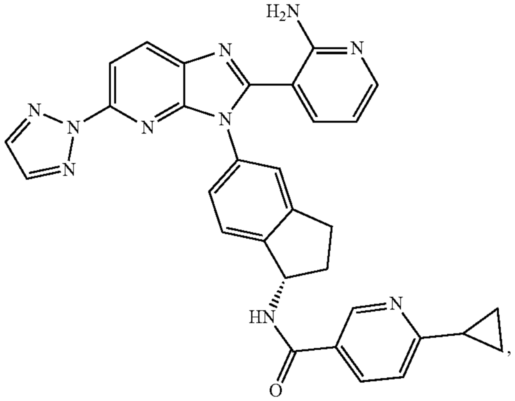
-continued
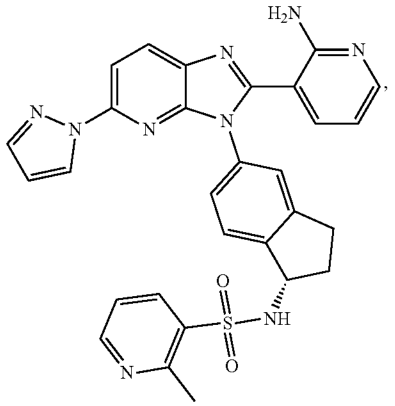
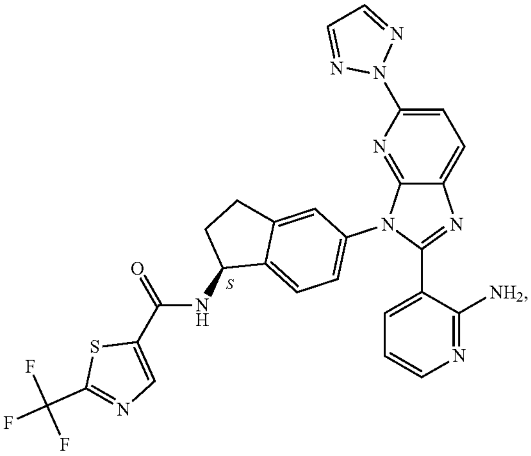
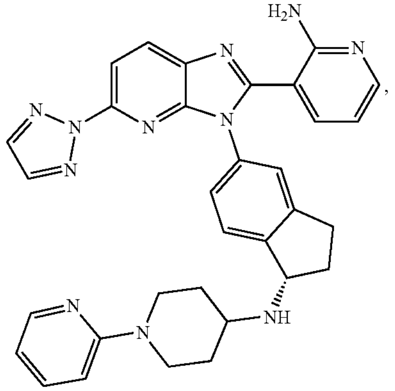
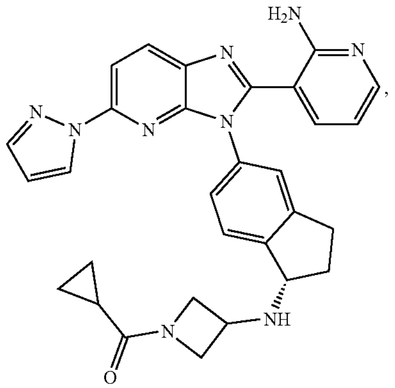

-continued
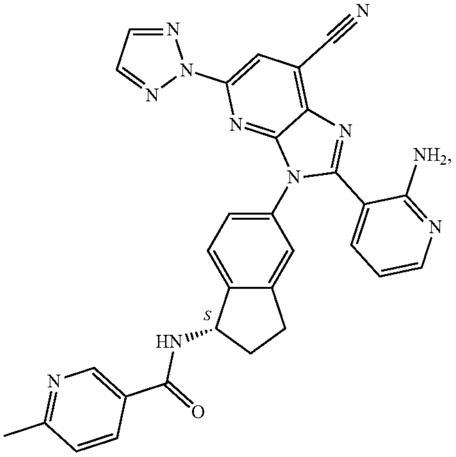
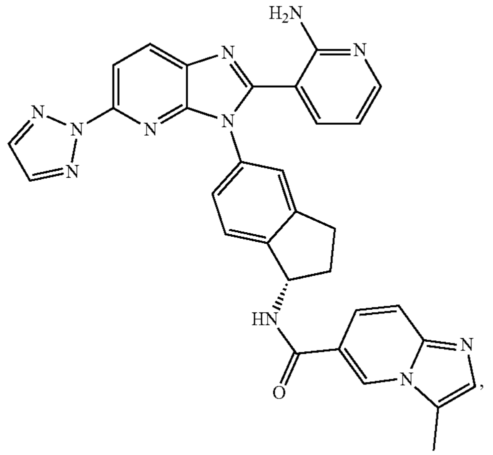
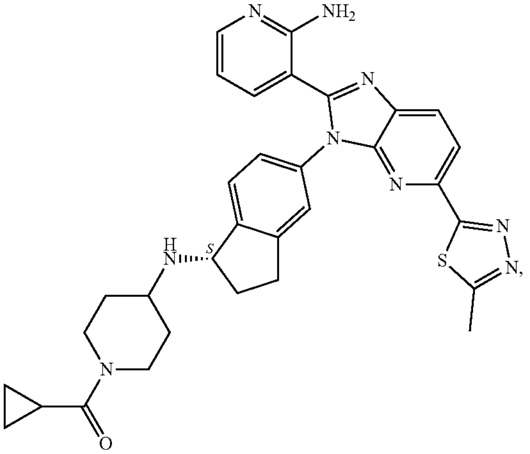
-continued
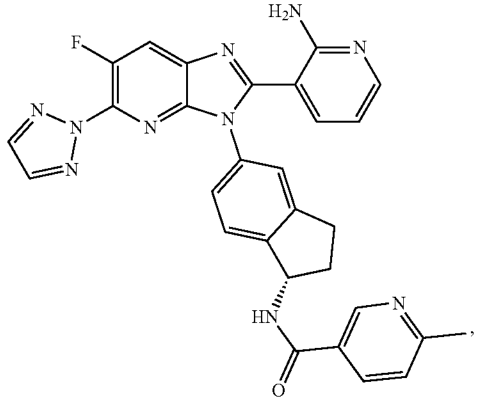
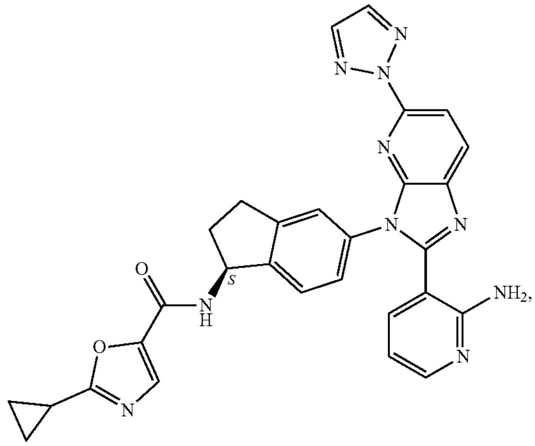
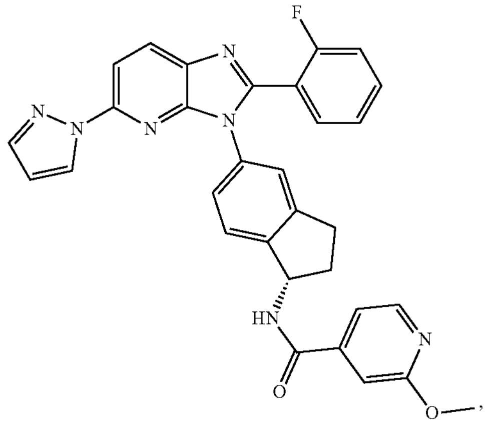
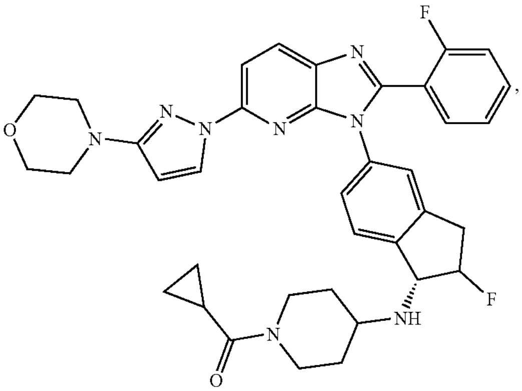

-continued

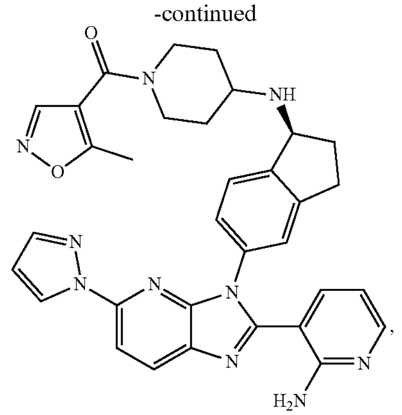

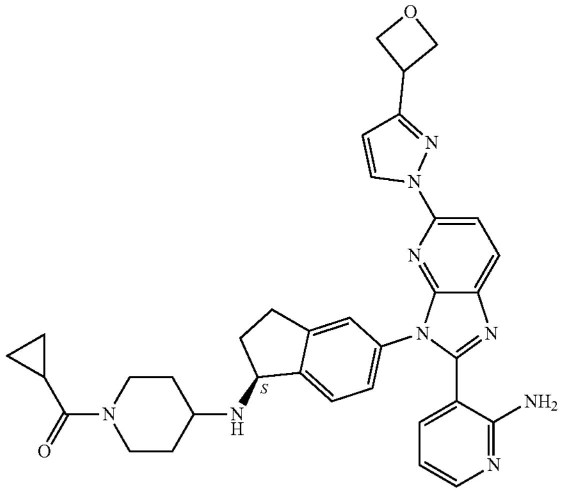

and

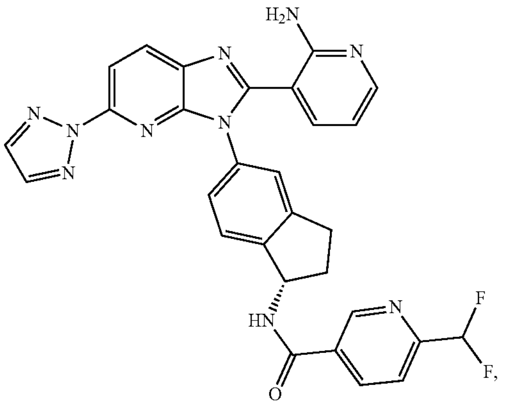 [SMILES: Nc1ncccc1-c1nc2ccc(-n3nccn3)nc2n1-c1ccc2c(c1)CC[C@@H]2NC(=O)c1ccc(C(F)F)nc1]

or a pharmaceutically acceptable salt of any one thereof.

27. A pharmaceutical composition comprising a pharmaceutically acceptable excipient and a compound or salt of claim 1.

28. A method of treating cancer in a subject in need thereof, the method comprising administering to the subject a compound or salt of claim 1, or a pharmaceutical composition comprising a compound or salt of claim 1 and a pharmaceutically acceptable excipient.

29. The method of claim 28, wherein the cancer is selected from breast cancer, colorectal cancer, and meningioma.

30. The method of claim 28, wherein the administration modulates activity of a mutant AKT1.

31. The compound or salt of claim 1, wherein the compound or salt of Formula (I) is

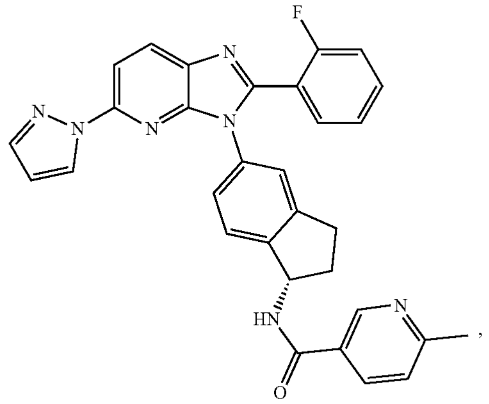 [SMILES: Cc1ccc(C(=O)N[C@H]2CCc3cc(-n4c(-c5ccccc5F)nc5ccc(-n6cccn6)nc54)ccc32)cn1]

or a pharmaceutically acceptable salt thereof.

32. The compound or salt of claim 1, wherein the compound or salt of Formula (I) is

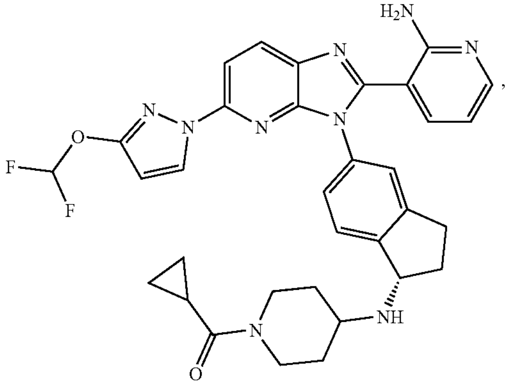 [SMILES: Nc1ncccc1-c1nc2ccc(-n3ccc(OC(F)F)n3)nc2n1-c1ccc2c(c1)CC[C@@H]2NC1CCN(C(=O)C2CC2)CC1]

or a pharmaceutically acceptable salt thereof.

33. The compound or salt of claim 1, wherein the compound or salt of Formula (I) is

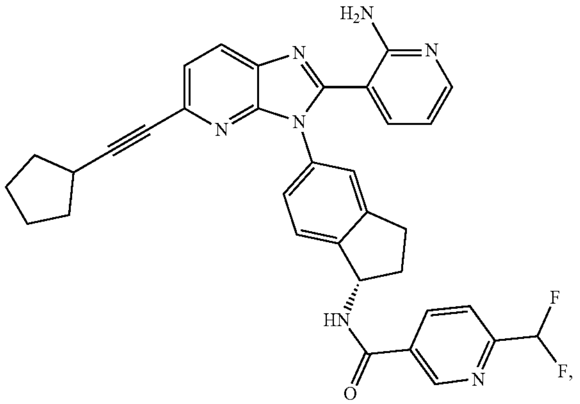 [SMILES: Nc1ncccc1-c1nc2ccc(C#CC3CCCC3)nc2n1-c1ccc2c(c1)CC[C@@H]2NC(=O)c1ccc(C(F)F)nc1]

or a pharmaceutically acceptable salt thereof.

34. The compound or salt of claim 1, wherein the compound or salt of Formula (I) is,

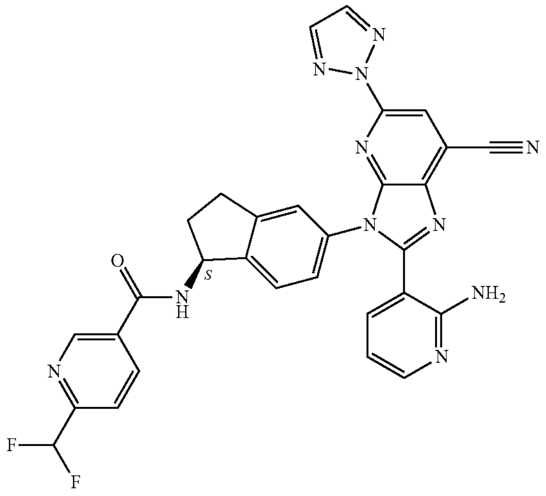

or a pharmaceutically acceptable salt thereof.

35. The compound or salt of claim 1, wherein the compound or salt of Formula (I) is

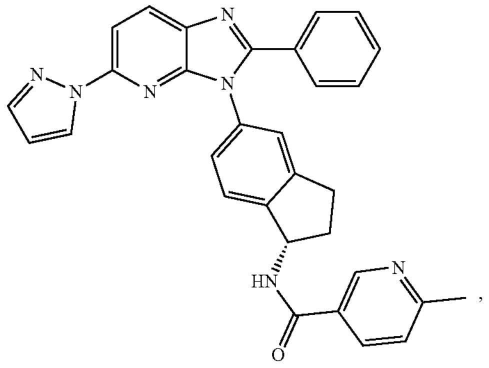 [SMILES: Cc1ccc(C(=O)N[C@H]2CCc3cc(-n4c(-c5ccccc5)nc5ccc(-n6cccn6)nc54)ccc32)cn1]

or a pharmaceutically acceptable salt thereof.

36. The compound or salt of claim 1, wherein the compound or salt of Formula (I) is

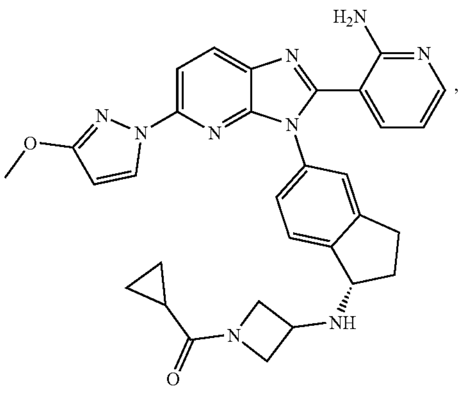 [SMILES: COc1ccn(-c2ccc3nc(-c4cccnc4N)n(-c4ccc5c(c4)CC[C@@H]5NC4CN(C(=O)C5CC5)C4)c3n2)n1]

or a pharmaceutically acceptable salt thereof.

37. The compound or salt of claim 1, wherein the compound or salt of Formula (I) is

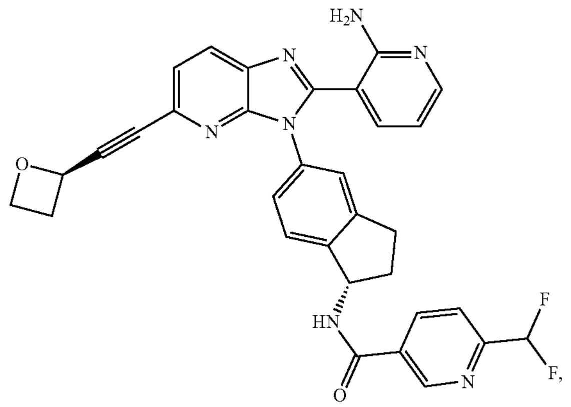 [SMILES: Nc1ncccc1-c1nc2ccc(C#C[C@H]3CCO3)nc2n1-c1ccc2c(c1)CC[C@@H]2NC(=O)c1ccc(C(F)F)nc1]

or a pharmaceutically acceptable salt thereof.

38. The compound or salt of claim 1, wherein the compound or salt of Formula (I) is

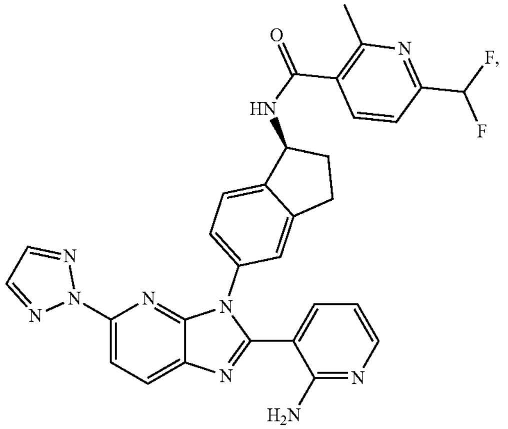 [SMILES: Cc1nc(C(F)F)ccc1C(=O)N[C@H]1CCc2cc(-n3c(-c4cccnc4N)nc4ccc(-n5nccn5)nc43)ccc21]

or a pharmaceutically acceptable salt thereof.

39. The compound or salt of claim 1, wherein the compound or salt of Formula (I) is

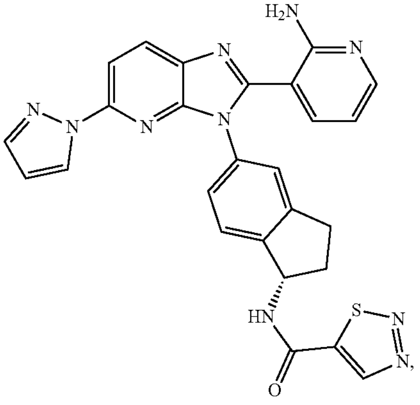 [SMILES: Nc1ncccc1-c1nc2ccc(-n3cccn3)nc2n1-c1ccc2c(c1)CC[C@@H]2NC(=O)c1cnns1]

or a pharmaceutically acceptable salt thereof.

40. The compound or salt of claim 1, wherein the compound or salt of Formula (I) is

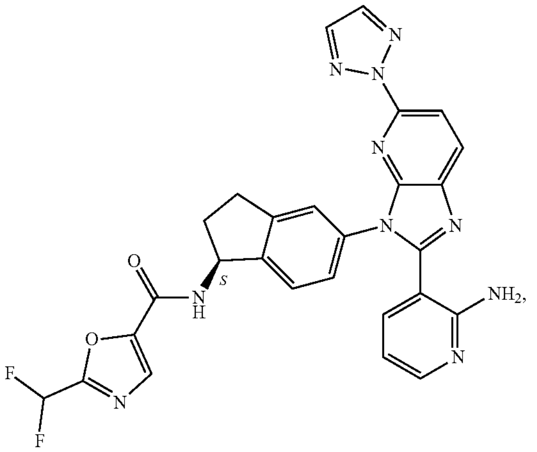

or a pharmaceutically acceptable salt thereof.

41. The compound or salt of claim 1, wherein the compound or salt of Formula (I) is

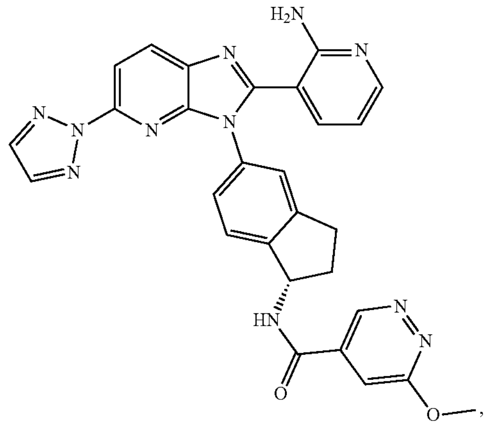 [SMILES: COc1cc(C(=O)N[C@H]2CCc3cc(-n4c(-c5cccnc5N)nc5ccc(-n6nccn6)nc54)ccc32)cnn1]

or a pharmaceutically acceptable salt thereof.

42. The compound or salt of claim 1, wherein the compound or salt of Formula (I) is

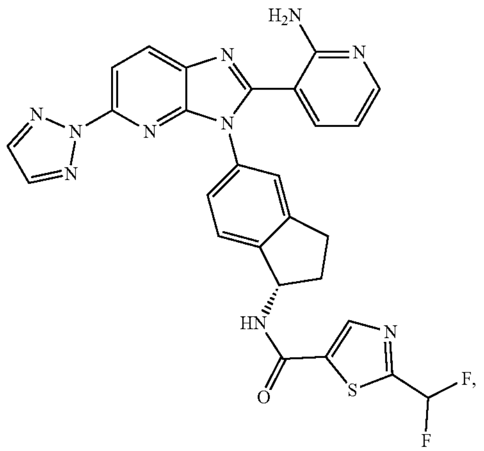 [SMILES: Nc1ncccc1-c1nc2ccc(-n3nccn3)nc2n1-c1ccc2c(c1)CC[C@@H]2NC(=O)c1cnc(C(F)F)s1]

or a pharmaceutically acceptable salt thereof.

43. The compound or salt of claim 1, wherein the compound or salt of Formula (I) is

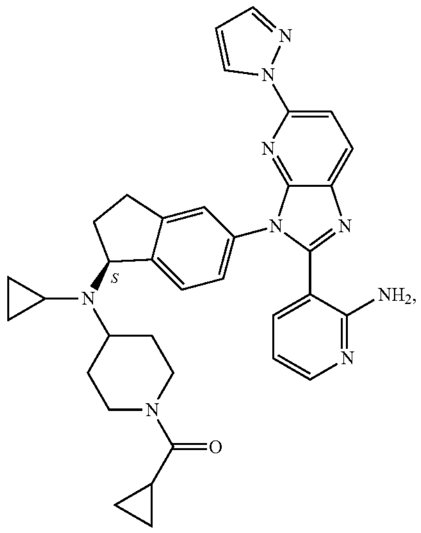

or a pharmaceutically acceptable salt thereof.

44. The compound or salt of claim 1, wherein the compound or salt of Formula (I) is

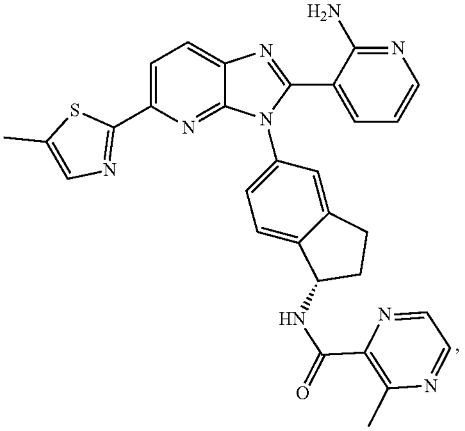 [SMILES: Cc1cnc(-c2ccc3nc(-c4cccnc4N)n(-c4ccc5c(c4)CC[C@@H]5NC(=O)c4nccnc4C)c3n2)s1]

or a pharmaceutically acceptable salt thereof.

45. The compound or salt of claim 1, wherein the compound or salt of Formula (I) is

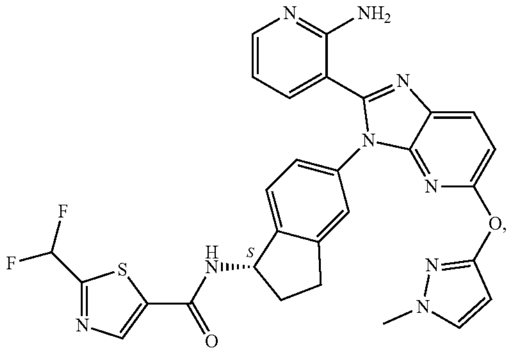

or a pharmaceutically acceptable salt thereof.

46. The compound or salt of claim 1, wherein the compound or salt of Formula (I) is

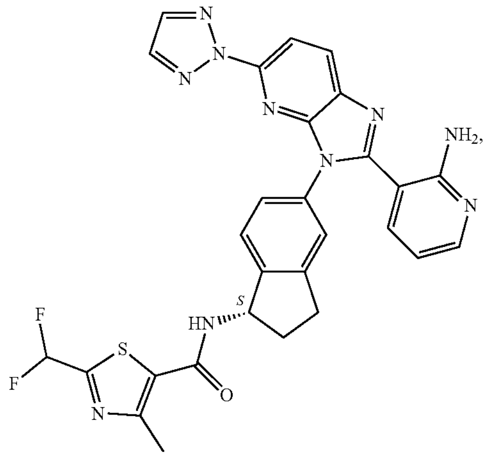

or a pharmaceutically acceptable salt thereof.

47. The compound or salt of claim 1, wherein the compound or salt of Formula (I) is

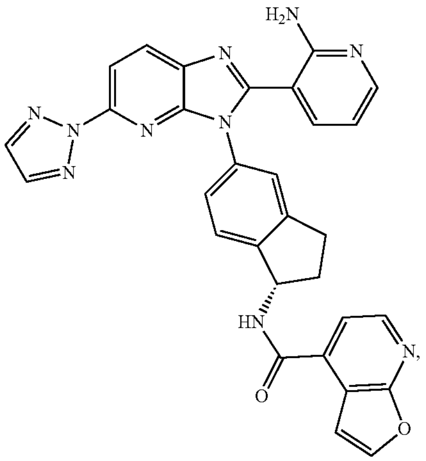 [SMILES: Nc1ncccc1-c1nc2ccc(-n3nccn3)nc2n1-c1ccc2c(c1)CC[C@@H]2NC(=O)c1ccnc2occc12]

or a pharmaceutically acceptable salt thereof.

48. The compound or salt of claim 1, wherein the compound or salt of Formula (I) is

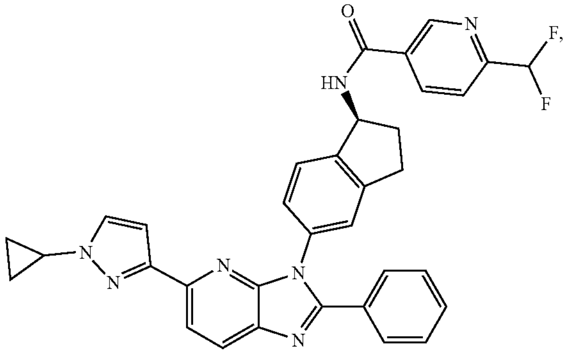 [SMILES: O=C(N[C@H]1CCc2cc(-n3c(-c4ccccc4)nc4ccc(-c5ccn(C6CC6)n5)nc43)ccc21)c1ccc(C(F)F)nc1]

or a pharmaceutically acceptable salt thereof.

49. The compound or salt of claim 1, wherein the compound or salt of Formula (I) is

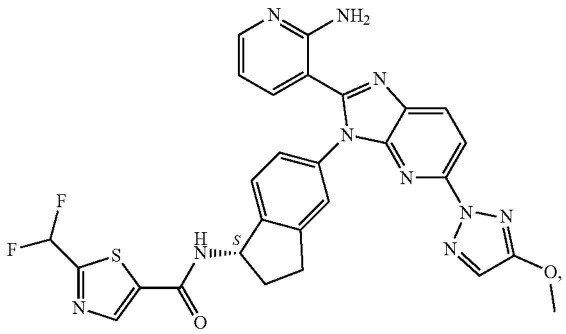

or a pharmaceutically acceptable salt thereof.

50. The compound or salt of claim 1, wherein the compound or salt of Formula (I) is

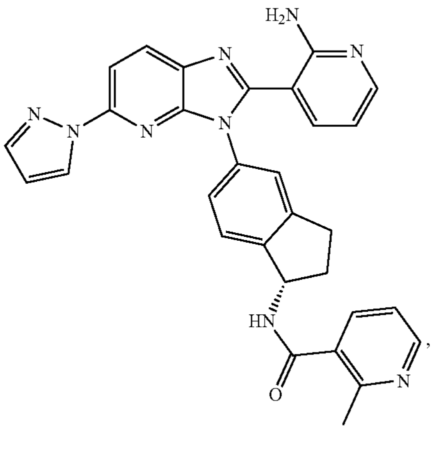 [SMILES: Cc1ncccc1C(=O)N[C@H]1CCc2cc(-n3c(-c4cccnc4N)nc4ccc(-n5cccn5)nc43)ccc21]

or a pharmaceutically acceptable salt thereof.

51. The compound or salt of claim 1, wherein the compound or salt of Formula (I) is

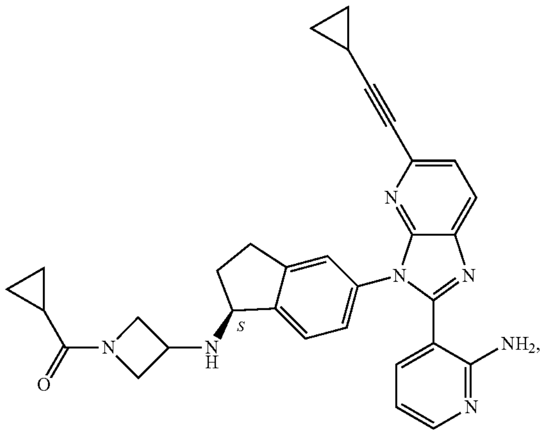

or a pharmaceutically acceptable salt thereof.

52. The compound or salt of claim 1, wherein the compound or salt of Formula (I) is

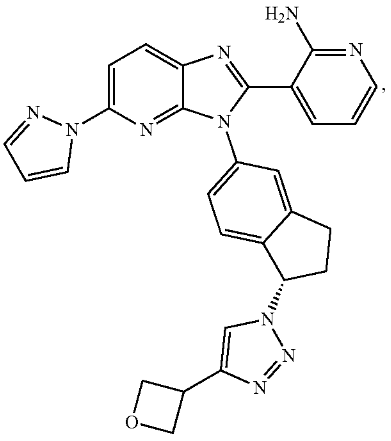 [SMILES: Nc1ncccc1-c1nc2ccc(-n3cccn3)nc2n1-c1ccc2c(c1)CC[C@@H]2n1cc(C2COC2)nn1]

or a pharmaceutically acceptable salt thereof.

53. The compound or salt of claim 1, wherein the compound or salt of Formula (I) is

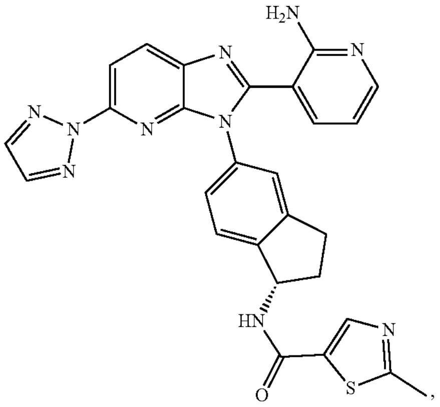 [SMILES: Cc1ncc(C(=O)N[C@H]2CCc3cc(-n4c(-c5cccnc5N)nc5ccc(-n6nccn6)nc54)ccc32)s1]

or a pharmaceutically acceptable salt thereof.

54. The compound or salt of claim 1, wherein the compound or salt of Formula (I) is

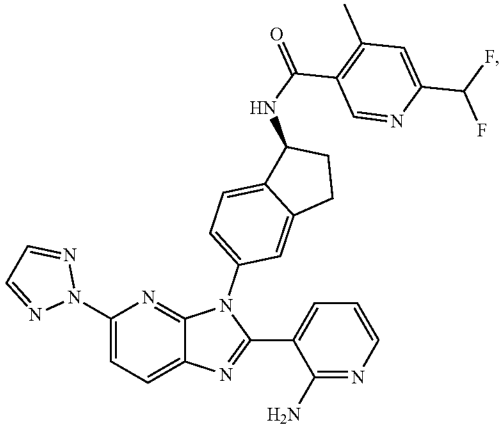 [SMILES: Cc1cc(C(F)F)ncc1C(=O)N[C@H]1CCc2cc(-n3c(-c4cccnc4N)nc4ccc(-n5nccn5)nc43)ccc21]

or a pharmaceutically acceptable salt thereof.

55. The compound or salt of claim 1, wherein the compound or salt of Formula (I) is

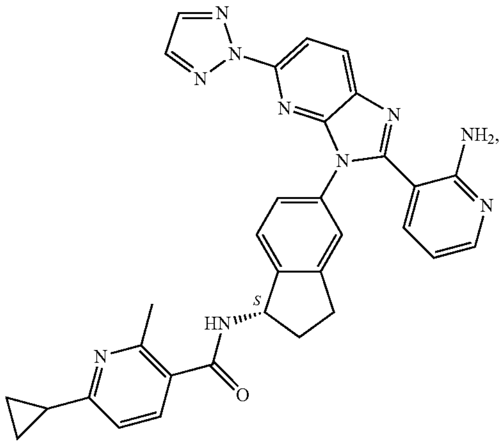

or a pharmaceutically acceptable salt thereof.

* * * * *